US012595251B2

(12) United States Patent
Wang et al.

(10) Patent No.: US 12,595,251 B2
(45) Date of Patent: Apr. 7, 2026

(54) AMIDINES AND AMIDINE ANALOGS FOR THE TREATMENT OF BACTERIAL INFECTIONS AND POTENTIATION ANTIBIOTICS

(71) Applicant: GEORGIA STATE UNIVERSITY RESEARCH FOUNDATION, INC., Atlanta, GA (US)

(72) Inventors: Binghe Wang, Marietta, GA (US); David W. Boykin, Atlanta, GA (US); Manjusha Roy Choudhary, Atlanta, GA (US); Arvind Kumar, Lilburn, GA (US); Bingchen Yu, Atlanta, GA (US); Mengyuan Zhu, Cary, NC (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 1360 days.

(21) Appl. No.: 17/251,658

(22) PCT Filed: Jun. 13, 2019

(86) PCT No.: PCT/US2019/037065

§ 371 (c)(1),
(2) Date: Dec. 11, 2020

(87) PCT Pub. No.: WO2019/241566

PCT Pub. Date: Dec. 19, 2019

(65) Prior Publication Data

US 2021/0309641 A1 Oct. 7, 2021

Related U.S. Application Data

(60) Provisional application No. 62/825,701, filed on Mar. 28, 2019, provisional application No. 62/685,142, filed on Jun. 14, 2018.

(51) Int. Cl.

| | |
|---|---|
| *C07D 403/12* | (2006.01) |
| *A61K 31/155* | (2006.01) |
| *A61K 45/06* | (2006.01) |
| *A61P 31/04* | (2006.01) |
| *C07C 217/58* | (2006.01) |
| *C07C 257/18* | (2006.01) |
| *C07C 259/18* | (2006.01) |
| *C07C 279/18* | (2006.01) |
| *C07C 321/28* | (2006.01) |
| *C07C 323/62* | (2006.01) |
| *C07D 213/30* | (2006.01) |
| *C07D 231/06* | (2006.01) |
| *C07D 235/18* | (2006.01) |
| *C07D 239/06* | (2006.01) |
| *C07D 401/06* | (2006.01) |
| *C07D 403/10* | (2006.01) |
| *C07D 409/04* | (2006.01) |
| *C07D 409/10* | (2006.01) |
| *C07D 409/14* | (2006.01) |

(52) U.S. Cl.

CPC ............ *C07D 403/12* (2013.01); *A61K 45/06* (2013.01); *C07C 217/58* (2013.01); *C07C 257/18* (2013.01); *C07C 321/28* (2013.01); *C07D 409/04* (2013.01)

(58) Field of Classification Search

CPC .. C07D 403/12; C07D 409/04; C07D 213/30; C07D 231/06; C07D 235/18; C07D 239/06; C07D 401/06; C07D 403/10; C07D 409/10; C07D 409/14; A61K 45/06; A61K 31/155; A61K 2300/00; C07C 217/58; C07C 257/18; C07C 321/28; C07C 323/62; C07C 259/18; C07C 279/18; A61P 31/04

See application file for complete search history.

(56) References Cited

U.S. PATENT DOCUMENTS

| | | | |
|---|---|---|---|
| 4,034,010 | A | 7/1977 | Hamano et al. |
| 4,064,169 | A | 12/1977 | Hamano et al. |
| 4,619,942 | A | 10/1986 | Tidwell et al. |
| 7,994,225 | B2 | 8/2011 | Bostian et al. |
| 9,960,588 | B2 | 5/2018 | Kreuter et al. |
| 2007/0021483 | A1 | 1/2007 | Chalifour et al. |
| 2007/0088067 | A1 | 4/2007 | Tidwell et al. |
| 2008/0132457 | A1 | 6/2008 | Bostian et al. |

FOREIGN PATENT DOCUMENTS

| | | |
|---|---|---|
| DE | 2833135 | 2/1980 |
| WO | 9628427 | 9/1996 |
| WO | 9729067 | 8/1997 |
| WO | 0031068 | 6/2000 |
| WO | 03017994 | 3/2003 |
| WO | 03103598 | 12/2003 |
| WO | 2005033065 | 4/2005 |
| WO | 2005089738 | 9/2005 |
| WO | 2006021833 | 3/2006 |
| WO | 2008090831 | 7/2008 |
| WO | 2009105691 | 8/2009 |
| WO | 2010133748 | 11/2010 |
| WO | 2021127452 | 6/2021 |

OTHER PUBLICATIONS

Liang et al., 2012, caplus an 2012:323481.*
RN67833-99-2, 1984, registry database compound.*
"WHO Publishes List of Bacteria for Which New Antibiotics Are Urgently Needed", Available online at: https://www.who.int/news/item/27-02-2017-who-publishes-list-of-bacteria-for-which-new-antibiotics-are-urgently-needed, Feb. 27, 2017, 4 pages.
Balusek et al., "Role of the Native Outer-Membrane Environment on the Transporter BtuB", Biophysical Journal, vol. 111, Oct. 4, 2016, pp. 1409-1417.

(Continued)

*Primary Examiner* — Sun Jae Yoo
(74) *Attorney, Agent, or Firm* — Kilpatrick Townsend & Stockton LLP

(57) ABSTRACT

Compounds and methods for the treatment of a bacterial infection or the potentiation of an antibiotic in treating a bacterial infection are described herein.

10 Claims, 15 Drawing Sheets

(56) References Cited

OTHER PUBLICATIONS

Bazydlo et al., “Calcium, Magnesium, and Phosphate”, Laboratory Medicine, vol. 45, No. 1, Feb. 1, 2014, pp. e44-e50.
Bean et al., “Pentamidine: A Drug to Consider Re-Purposing in the Targeted Treatment of Multi-Drug Resistant Bacterial Infections?”, Journal of Laboratory and Precision Medicine, vol. 2, No. 49, Jul. 27, 2017, pp. 1-4.
Blair et al., “Molecular Mechanisms of Antibiotic Resistance”, Nature Reviews Microbiology, vol. 13, No. 1, Jan. 2015, pp. 42-51.
Boekema et al., “The Effect of a Honey Based Gel and Silver Sulphadiazine on Bacterial Infections of in Vitro Burn Wounds”, Burns, vol. 39, No. 4, Jun. 2013, pp. 754-759.
Brochado et al., “Species-Specific Activity of Antibacterial Drug Combinations”, Nature, vol. 559, No. 7713, Jul. 2018, pp. 259-263.
Brown et al., “Antibacterial Drug Discovery In the Resistance Era”, Nature, vol. 529, Jan. 21, 2016, pp. 336-343.
Chew et al., “Colistin and Polymyxin B Susceptibility Testing for Carbapenem-resistant and Mcr-Positive Enterobacteriacea: Comparison of Sensititre, MicroScan, Vitek 2, and Etest with Broth Microdilution”, Journal of Clinical Microbiology, vol. 55, No. 9, Sep. 2017, pp. 2609-2616.
Clifton et al., “Effect of Divalent Cation Removal on the Structure of Gram-Negative Bacterial Outer Membrane Models”, Langmuir, vol. 31, No. 1, 2015, pp. 404-412.
Codjoe et al., “Carbapenem Resistance: A Review”, Medical Sciences (Basel), vol. 6, No. 1, Dec. 21, 2017, 28 pages.
Corbett et al., “Potentiation of Antibiotic Activity by a Novel Cationic Peptide: Potency and Spectrum of Activity of SPR741”, Antimicrobial Agents and Chemotherapy, vol. 61, No. 8, Aug. 2017, pp. 1-10.
Davies et al., “Annual Report of the Chief Medical Officer: Infection and the Rise of Antimicrobial Resistance”, Lancet, vol. 381, No. 9878, Mar. 11, 2013, pp. 1606-1609.
De Breij et al., “The Antimicrobial Peptide Saap-148 Combats Drug-Resistant Bacteria and Biofilms”, Science Translational Medicine, vol. 10, 2018, pp. 1-14.
De La Cruz et al., “Click, Release, and Fluoresce: A Chemical Strategy for a Cascade Prodrug System for Codelivery of Carbon Monoxide, a Drug Payload, and a Fluorescent Reporter”, Organic Letters, vol. 20, 2018, pp. 897-900.
Fischer et al., “In Vitro Cytotoxicity Testing of Polycations: Influence of Polymer Structure on Cell Viability and Hemolysis”, Biomaterials, vol. 24, No. 7, Mar. 2003, pp. 1121-1131.
Geratz et al., “Novel Bis(Benzamidino) Compounds With an Aromatic Central Link. Inhibitors of Thrombin, Pancreatic Kallikrein, Trypsin, and Complement”, Journal of Medicinal Chemistry, vol. 19, No. 5, May 1, 1976, pp. 634-639.
Guo et al., “Compound Shape Effects in Minor Groove Binding Affinity and Specificity for Mixed Sequence DNA”, Journal of the American Chemical Society, vol. 140, No. 44, Nov. 7, 2018, pp. 14761-14769.
Hall et al., “The Fractional Inhibitory Concentration (FIC) Index as a Measure of Synergy”, Journal of Antimicrobial Chemotherapy, vol. 11, No. 5, May 1983, pp. 427-433.
Holmes et al., “Understanding the Mechanisms and Drivers of Antimicrobial Resistance”, Lancet, vol. 387, No. 10014, Jan. 9, 2016, pp. 176-187.
Jahnen-Dechent et al., “Magnesium Basics”, Clinical Kidney Journal, vol. 5, No. 1, Feb. 1, 2012, pp. i3-i14.
King et al., “Aspergillomarasmine a Overcomes Metallo-β-lactamase Antibiotic Resistance”, Nature, vol. 510, No. 7506, Jun. 26, 2014, pp. 503-506.
Koebnik et al., “Structure and Function of Bacterial Outer Membrane Proteins: Barrels in a Nutshell”, Molecular Microbiology, vol. 37, No. 2, Jul. 2000, pp. 239-523.
Laxminarayan et al., “Achieving Global Targets for Antimicrobial Resistance”, Science, vol. 353, No. 6302, Aug. 26, 2016, 3 pages.
Li et al., “The Challenge of Efflux-Mediated Antibiotic Resistance in Gram-Negative Bacteria”, Clinical Microbiology Reviews, vol. 28, No. 2, Apr. 2015, pp. 337-418.
Liu et al., “Emergence of Plasmid-mediated Colistin Resistance Mechanism Mcr-1 in Animals and Human Beings in China: A Microbiological and Molecular Biological Study”, The Lancet Infectious Diseases, vol. 16, No. 2, Feb. 2016, pp. 161-168.
Macnair et al., “Overcoming MCR-1 Mediated Colistin Resistance With Colistin in Combination With Other Antibiotics”, Nature Communications, vol. 9, No. 458, Jan. 2018, pp. 1-8.
May et al., “The Bacterial Outer Membrane Is an Evolving Antibiotic Barrier”, Proceedings of the National Academy of Sciences, vol. 115, No. 36, Sep. 4, 2018, pp. 8852-8854.
Moellering , “NDM-1—A Cause for Worldwide Concern”, The New England Journal of Medicine, vol. 363, No. 25, Dec. 16, 2010, pp. 2377-2379.
Moison et al., “A Fluorescent Probe Distinguishes between Inhibition of Early and Late Steps of Lipopolysaccharide Biogenesis in Whole Cells”, ACS Chemical Biology, vol. 12, 2017, pp. 1-9.
Munde et al., “DNA Minor Groove Induced Dimerization of Heterocyclic Cations: Compound Structure, Binding Affinity, and Specificity for a TTAA Site”, Journal of Molecular Biology, vol. 402, No. 5, Oct. 8, 2010, pp. 847-864.
Ni et al., “Inhibitors and Antagonists of Bacterial Quorum Sensing”, Medicinal Research Reviews, vol. 29, No. 1, 2009, pp. 65-124.
Parrish et al., “Structure-Activity Relationships for the Inhibition of Acrosin by Benzamidine Derivatives”, Journal of Medicinal Chemistry, vol. 21, No. 11, Nov. 1978, pp. 1132-1136.
Patrick et al., “Synthesis and Antiprotozoal Activities of Dicationic Bis(Phenoxymethyl)benzenes, Bis(Phenoxymethyl)Naphthalenes, and Bis(Benzyoxy)naphthalenes”, European Journal of Medicinal Chemistry, vol. 44, No. 9, Sep. 2009, pp. 3543-3551.
Pavlova et al., “Living on the Edge: Simulations of Bacterial Outer-Membrane Proteins”, Biochimica et Biophysica Acta, vol. 1858, No. 7, Part B, Jul. 2016, pp. 1753-1759.
Application No. PCT/US2019/037065 , International Preliminary Report on Patentability, Mailed On Dec. 24, 2020, 8 pages.
Application No. PCT/US2019/037065 , International Search Report and Written Opinion, Mailed On Oct. 18, 2019, 11 pages.
Rice , “Progress and Challenges in Implementing the Research on ESKAPE Pathogens”, Infection Control & Hospital Epidemiology, vol. 31, No. 1, Nov. 2010, pp. S7-S10.
Ruiz et al., “Chemical Conditionality: A Genetic Strategy to Probe Organelle Assembly”, Cell, vol. 121, No. 2, Apr. 22, 2005, pp. 307-317.
Rutherford et al., “Bacterial Quorum Sensing: Its Role in Virulence and Possibilities for Its Control”, Cold Spring Harbor Perspectives in Medicine, vol. 2, No. 11, 2012, pp. 1-25.
Sands et al., “Pentamidine: A Review”, Reviews of Infectious Diseases, vol. 7, No. 5, Sep.-Oct. 1985, pp. 625-634.
Schmalstig et al., “Noncatalytic Antioxidant Role for Helicobacter pylori Urease”, Journal of Bacteriology, vol. 200, No. 17, e00124-18, Sep. 2018, pp. 1-11.
Silhavy et al., “The Bacterial Cell Envelope”, Cold Spring Harbor Perspectives in Biology, vol. 2, No. 5, May 2010, 16 pages.
Smith et al., “Optimized Arylomycins are a New Class of Gram-Negative Antibiotics”, Nature, vol. 561, Sep. 13, 2018, pp. 189-194.
Soeiro et al., “Novel Amidines and Analogues as Promising Agents Against Intracellular Parasites: a Systematic Review”, Parasitology, vol. 140, No. 8, Jul. 2013, 40 pages.
Steimle et al., “Structure and function: Lipid A Modifications in Commensals and Pathogens”, International Journal of Medical Microbiology, vol. 306, No. 5, Aug. 2016, pp. 290-301.
Stoesser et al., “Colistin Resistance Gene mcr-1and pHNSHP45 Plasmid in Human Isolates of *Escherichia coli* and Klebsiella Pneumoniae”, The Lancet Infectious Diseases, vol. 16, No. 3, Mar. 2016, pp. 285-286.
Stokes et al., “Pentamidine Sensitizes Gram-Negative Pathogens to Antibiotics and Overcomes Acquired Colistin Resistance”, Nature Microbiology, vol. 2, No. 5, Mar. 6, 2017, 21 pages.
Tsubery et al., “Structure-Function Studies of Polymyxin B Nonapeptide: Implications to Sensitization of Gram-Negative Bacteria”, Journal of Medicinal Chemistry, vol. 43, No. 16, 2000, pp. 3085-3092.

(56) References Cited

OTHER PUBLICATIONS

Vaara , "New Polymyxin Derivatives That Display Improved Efficacy in Animal Infection Models as Compared to Polymyxin B and Colistin", Medicinal Research Reviews, vol. 38, No. 5, Sep. 2018, pp. 1661-1673.
Van Meer et al., "Membrane Lipids: Where They are and How They Behave", Nature Reviews Molecular Cell Biology, vol. 9, No. 2, Feb. 2008, pp. 112-124.
Ventola , "The Antibiotic Resistance Crisis: Part 1: Causes and Threats", Pharmacology & Therapeutics, vol. 40, No. 4, Apr. 2015, pp. 277-283.
Wang et al., "Prevalence, Risk Factors, Outcomes, and Molecular Epidemiology of Mcr-1-positive Enterobacteriaceae in Patients and Healthy Adults From China: An Epidemiological and Clinical Study", The Lancet Infectious Diseases, vol. 17, No. 4, Apr. 2017, pp. 390-399.
Yorke , "Recent Work on the Chemotherapy of Protozoal Infections", Transactions of The Royal Society of Tropical Medicine and Hygiene, vol. 33, No. 5, Mar. 20, 1940, pp. 463-476.
CN201980053282.2, "Office Action", Feb. 29, 2024, 14 pages.
Chinese Patent Application No. 201980053282.2, First Office Action mailed Mar. 22, 2023, 25 pages with translation.
CN201980053282.2, "Office Action", Oct. 18, 2023, 8 pages.
Chauhan et al., "Antiparasitic Agents Part VI. Synthesis of 1 2-1 3 and 1 4 Bis(4-Substituted-Aryloxy) Benzenes and their Biological Activities", Indian Journal of Chemistry, Council of Scientific and Industrial Research (CSIR), vol. 27, No. 1, Jan. 1, 1988, pp. 38-42.
EP19819942.4 , "Partial Supplementary European Search Report", Mar. 16, 2022, 12 pages.

* cited by examiner

Compound M-1 and Compound B can decrease the bacteria resistant frequency towards antibiotics

| | Resistance frequency | resistance frequency with 25 µM Compound M-1 | Resistance to Compound M-1 |
|---|---|---|---|
| Trovafloxacin (100 ng/mL) | 173/$10^8$ | 13/$10^8$ | 0/$10^8$ |
| Novobiocin (600 µg/mL) | 688/$10^8$ | 260/$10^8$ | 0/$10^8$ |
| Chloramphenicol (12 µg/mL) | 25/108 | 1/$10^8$ | 0/$10^8$ |
| Polymycin B (4.8 µg/mL) | 2688/$10^8$ | 2/$10^8$ | 0/$10^8$ |

AMIDINES AND AMIDINE ANALOGS FOR THE TREATMENT OF BACTERIAL INFECTIONS AND POTENTIATION ANTIBIOTICS

CROSS-REFERENCE TO RELATED APPLICATIONS

This application claims the benefit of provisional U.S. Application Nos. 62/685,142 filed Jun. 14, 2018 and 62/825,701 filed Mar. 28, 2019. The entirety of these applications is incorporated by reference.

FIELD OF THE INVENTION

The invention is directed to compounds and their use in the treatment of medical disorders caused by bacteria or to potentiate the effect of an antibiotic in the treatment of medical disorders caused by bacteria.

BACKGROUND OF THE INVENTION

Despite the overall success of antibiotics in diminishing the effects of infectious disease in the modern world, their ease of access has led to overuse, resulting in the development of bacterial resistance. Antibiotic resistance is on the rise globally, leading the World Health Organization to classify antibiotic resistance as a "serious threat [that] is no longer a prediction for the future" ("Antimicrobial resistance: global report on surveillance 2014" The World Health Organization, April 2014). Antibiotic resistance is linked to inappropriate prescribing of antibiotics, incorrect dosing, and missing doses. In the United States, approximately two million people become infected with antibiotic resistant bacteria each year and roughly 23,000 die as a result ("Antibiotic/Antimicrobial Resistance" Centers for Disease Control and Prevention, https://www.cdc.gov/drugresistance/). Some bacteria harbor a natural resistance to certain types of antibiotics, while others may gain resistance by genetic mutation or horizontal gene transfer from already-resistant species. Bacteria diminish the effectiveness of antibiotics by modifying or inactivating the drug, altering the target or binding site, altering the metabolic pathways that propagate the drug's effects, or reducing accumulation of the drug within the cell by decreasing drug permeability or increasing efflux. Certain bacteria, colloquially known as "superbugs", may eventually develop resistance to multiple types of antibiotics, requiring alternative medications at higher doses, often with higher cost and greater toxicity.

Several preventative measures have been proposed to slow bacterial resistance to currently available antibiotics. Proper antibiotic stewardship along with increased hygiene provides significant strides in preventing future resistance. Despite this, new therapeutics are necessary to treat infections caused by currently resistant bacterial strains. The period from the 1950s untill the 1970s represented the peak of antibiotic discovery, but since that time no new classes of antibiotics have been discovered, and development of new antibiotics within existing classes has been low. Alternative strategies, such as the development of bacterial vaccines and phage therapy, have not seen the success necessary to become widely used.

Investigators in the 1920s discovered that an anti-diabetic drug, Synthalin, had therapeutic activity against *Trypanosoma brucei* infections in mice. Out of a series of subsequently developed analogs, pentamidine was found to be curative of murine *T. rhodesiense* infections (Yorke W.

"Recent work on the chemotherapy of protozoal infections", Trans. R., Soc. Trop. Med. Hyg. 1940, 33:463). It was not until the 1960s that pentamidine became available on a restricted basis for use in the treatment of protozoal infections, and only in the 1980s did it see more extensive use as a treatment of pnuemocystis pneumonia in immunocompromised individuals such as HIV patients (Sands et al. "Pentamidine: A Review", Reviews of Infectious Diseases 1985, 7 (5): 625-634). In recent years, pentamidine has received renewed interest as a possible therapeutic in the treatment of infections by antibiotic resistant bacteria. For example, pentamidine has been demonstrated to sensitize resistant bacteria to colistin, one of the antibiotics of last resort (Stokes et al. "Pentamidine sensitizes Gram-negative pathogens to antibiotics and overcomes acquired colistin resistance", Nat. Microbiol. 2017, 2:17028; Bean et al. "Pentamidine: a drug to consider re-purposing in the targeted treatment of multi-drug resistant bacterial infections?" J. Lab. Precis. Med. 2017, 2:49).

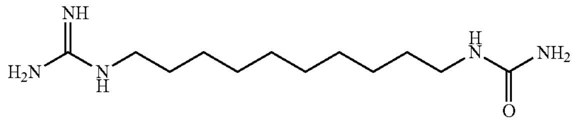

Synthalin

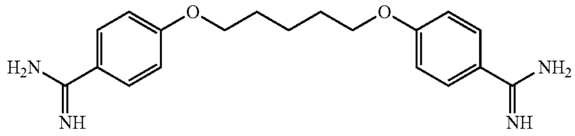

Pentamidine

The use of amidine compounds for biological applications is described in Geratz et al. "Novel Bis(benzamidino) Compounds with an Aromatic Central Link. Inhibitors of Thrombin, Pancreatic Kallikrein, Trypsin, and Complement" J. Med. Chem. 1976, 19 (5): 634-639; Parrish et al. "Structure-Activity Relationships for the Inhibition of Acrosin by Benzamidine Derivatives" J. Med. Chem. 1978, 21 (11) 1132-1136; and Patrick et al. "Synthesis and antiprotozoal activities of dicationic bis(phenoxymethyl)benzenes, bis (phenoxymethyl) naphthalenes, and bis(benzyoxy)naphthalenes" Eur. J. Med. Chem. 2009, 44:3543-3551.

University of North Carolina describes the use of amidine compounds to inhibit RSV-induced cell fusion in U.S. Pat. No. 4,619,942 titled "Inhibition of Respiratory Syncytial Virus-Induced Cell Fusion by Amidino Compounds".

Eisai Co., Ltd. describes the use of amidine compounds as antifungal, antibacterial, and anti-trichomonal therapeutics in "U.S. Pat. No. 4,034,010 titled "Bis-(Meta-Amidinophenoxy)-Compounds and Pharmacologically Acceptable Acid Addition Salts Thereof".

Berlex Laboratories describes the use of amidine compounds as anticoagulants in International Patent Application Publication Nos. WO96/28427 titled "Benzamidine Derivatives Their Preparation and Their Use as Anti-Coagulants"; WO97/29067 titled "Benzamidine Derivatives Substituted by Amino Acid and Hydroxy Acid Derivatives and Their Use as Anti-Coagulants"; and WO00/31068 titled "Polyhydroxylated Heterocyclic Derivatives as Anticoagulants".

University of North Carolina and the Georgia State University Research Foundation, Inc., jointly disclosed the use of amidine compounds in amyloidosis and the treatment of microbial infections in International Patent Application Publication Nos. WO03/103598 titled "Amidine Derivatives for Treating Amyloidosis" and WO2005/033065 titled "Novel Amidine Compounds for Treating Microbial Infections".

Neurochem, Inc. describes the use of amidine compounds in the treatment of amyloidosis in International Patent Application Publication No. WO03/017994 titled "Amidine Derivatives for Treating Amyloidosis".

Altana Pharma AG describes compounds including amidine derivatives for use as tryptase inhibitors in U.S. Pat. No. 9,960,588 titled "Tryptase Inhibitors".

Mpex Pharmaceuticals describes the use of amidine compounds as bacterial efflux inhibitors in International Patent Application Publication No. WO2005/089738 title "Use and Administration of Bacterial Efflux Inhibitors". Bostian et al. also describe a similar use of amidine compounds as bacterial efflux inhibitors in the treatment of ophthalmic and otic infections in U.S. Patent Application Publication No. US2008/0132457 titled "Bacterial Efflux Inhibitors for the Treatment of Ophthalmic and Otic Infections".

The University of Cincinnati describes the use of amidine compounds for the treatment of pneumonia in International Patent Application Publication No. WO2006/021833 titled "Bisbenzamidines for the Treatment of Pneumonia". Xavier University of Louisiana describes the use of amidine compounds for the treatment of trypanosomiasis in International Patent Application Publication No. WO2008/090831 titled "Bisbenzamidines and Bisbenzamidoximes for the Treatment of Human African Trypanosomiasis".

The University of Oregon describes the use of pentamidine and related compounds in the treatment of myotonic dystrophy in International Patent Application Publication No. WO2009/105691 titled "Use of Pentamidine and Related Compounds".

Orion Corporation describes the use of amidine compounds as protease inhibitors in Internationla Patent Application Publication No. WO2010/133748 titled "Protease Inhibitors".

There is a clear need for the development of novel therapeutics and pharmaceutical compositions and their use for the treatment of bacterial infections, including therapeutics that might potentiate the effect of antibiotics on bacterial strains already resistant to these antibiotics.

SUMMARY OF THE INVENTION

The present invention provides compounds and their uses and manufacture for the treatment of bacterial infections. Compounds are described of Formula IA, Formula IB, Formula IC, Formula I', Formula II, Formula II', Formula III, Formula IV, Formula V, Formula V', Formula VI, Formula VII, Formula VIII, Formula VIII', Formula IX, Formula X, Formula XIII, and Formula XIV or pharmaceutically acceptable salts thereof, for the treatment of bacterial infections as well as the potentiation of the therapeutic effect of antibiotics in the treatment of bacterial infections. A compound can be selected from these formulas that can be used predominantly against gram-negative bacteria, predominantly gram-positive bacteria, predominantly against both gram-negative and gram-positive bacteria, or that can be used against mycobacteria.

In some embodiments, a method to treat a host with a bacterial infection is provided that comprises administering an effective amount of a compound of Formula IA, Formula IB, Formula IC, Formula I', Formula II, Formula II', Formula III, Formula IV, Formula V, Formula V', Formula VI, Formula VII, Formula VIII, Formula VIII', Formula IX, Formula X, Formula XIII, or Formula XIV or a pharmaceutically acceptable salt thereof to the host, typically a human, optionally as a pharmaceutically acceptable composition. In one embodiment, the bacterial infection is caused by a gram-positive bacterium. In one embodiment, the bacterial infection is caused by a gram-negative bacterium. In one embodiment, the bacterial infection is caused by a mycobacterium.

The present invention also provides topical compositions containing, either alone or in combination with an effective amount of an antibiotic, an effective amount of a compound of Formula IA, Formula IB, Formula IC, Formula I', Formula II, Formula II', Formula III, Formula IV, Formula V, Formula V', Formula VI, Formula VII, Formula VIII, Formula VIII', Formula IX, Formula X, Formula XI, Formula XI', Formula XII, Formula XIII, or Formula XIV or a pharmaceutically acceptable salt thereof for the treatment of acne vulgaris. The compounds used in the topical compositions and methods provided herein have an anti-microbial effect that helps alleviate the symptoms of acne vulgaris and treats the underlying overgrowth of bacterial that cause acne, for example, the bacterium *Propionibacterium acnes* or *Staphylococcus epidermidis*. The present invention provides treatment options that may complement or replace those currently available in the treatment of this highly common dermatological condition.

In some embodiments a compound provided herein or its pharmaceutically acceptable salt can be used to potentiate the effect of an antibiotic in the treatment of a bacterial infection. In some embodiments, a method is provided to potentiate the effect of an antibiotic in the treatment of a bacterial infection in a host in need thereof comprising administering an effective amount of a compound of Formula IA, Formula IB, Formula IC, Formula I', Formula II, Formula II', Formula III, Formula IV, Formula V, Formula V', Formula VI, Formula VII, Formula VIII, Formula VIII', Formula IX, Formula X, Formula XI, Formula XI', Formula XII, Formula XIII, or Formula XIV or a pharmaceutically acceptable salt thereof, in combination with an effective amount of an antibiotic to the host, typically a human, optionally as a pharmaceutically acceptable composition. In one embodiment, the bacterial infection is caused by a gram-positive bacterium. In one embodiment, the bacterial infection is caused by a gram-negative bacterium. In one embodiment, the bacterial infection is caused by a mycobacterium.

In one aspect, a compound is provided of Formula IA, Formula IB, or Formula IC:

(IA)

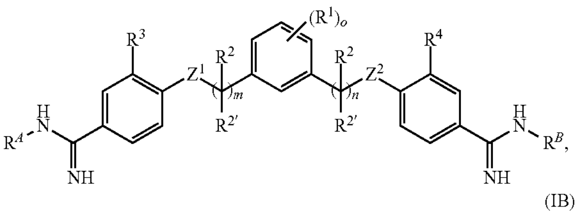

, (IB)

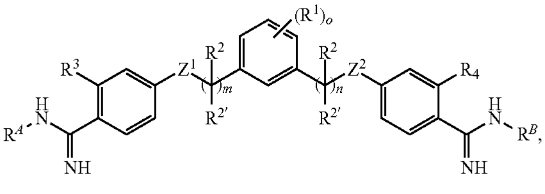

, or

-continued (IC)

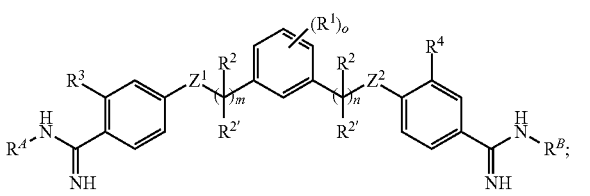

or a pharmaceutically acceptable salt thereof;

wherein:

$R^1$ is independently selected at each occurrence from halogen, hydroxyl, $C_1$-$C_6$alkoxy, $C_1$-$C_6$haloalkoxy, $C_1$-$C_6$alkanoyl, cyano, azido, nitro, —COOH, —$CONH_2$, —$P(O)(OH)_2$, —$N(R^5)(R^{5'})$, —$S(O)R^5$, —$SO_2R^5$, —$SO_3R^5$, —$SO_2N(R^5)(R^{5'})$, —$OSO_2R^5$, —$N(R^{5'})SO_2R'$, $C_1$-$C_6$alkyl, $C_3$-$C_6$cycloalkyl, $C_2$-$C_6$alkenyl, $C_2$-$C_6$alkynyl, $C_1$-$C_6$haloalkyl, $C_1$-$C_6$aliphatic, thiol, $C_1$-$C_6$alkylthiol, and ($C_1$-$C_6$haloalkyl)thiol;

$Z^1$ and $Z^2$ are independently selected from O, S, $N(R^5)$, and C═O;

$R^2$ and $R^{2'}$ are independently selected at each occurrence from hydrogen, $C_1$-$C_6$alkyl, $C_3$-$C_6$cycloalkyl, $C_1$-$C_6$haloalkyl, and $C_1$-$C_6$aliphatic;

$R^3$ and $R^4$ are independently selected from halogen, —$S(O)R^5$, —$SO_2R^5$, —$SO_3R^5$, —$SO_2N(R^5)(R^{5'})$, —$OSO_2R^5$, —$N(R^{5'})SO_2R^5$, $C_1$-$C_6$alkyl, and $C_1$-$C_6$alkoxy;

$R^5$ and $R^{5'}$ are independently selected at each occurrence from hydrogen, $C_1$-$C_6$alkyl, $C_3$-$C_6$cycloalkyl, $C_1$-$C_6$haloalkyl, and $C_1$-$C_6$aliphatic;

$R^A$ and $R^B$ are independently selected from hydrogen and $C_1$-$C_6$alkyl; and m, n, and o are independently selected from 1, 2, 3, and 4.

In one aspect, a compound is provided of Formula I':

(I')

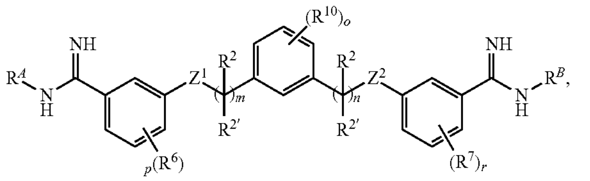

or a pharmaceutically acceptable salt thereof;

wherein:

$R^{10}$ is independently selected at each occurrence from hydroxyl, $C_1$-$C_6$alkoxy, $C_1$-$C_6$haloalkoxy, $C_1$-$C_6$alkanoyl, cyano, azido, nitro, —COOH, —$CONH_2$, —$P(O)(OH)_2$, —$N(R^5)(R^{5'})$, —$S(O)R^5$, —$SO_2R^5$, —$SO_3R$, —$SO_2N(R^5)(R^{5'})$, —$OSO_2R^5$, —$N(R^{5'})SO_2R^5$, $C_1$-$C_6$alkyl, $C_3$-$C_6$cycloalkyl, $C_2$-$C_6$alkenyl, $C_2$-$C_6$alkynyl, $C_1$-$C_6$haloalkyl, $C_1$-$C_6$aliphatic, thiol, $C_1$-$C_6$alkylthiol, and ($C_1$-$C_6$haloalkyl)thiol;

$Z^1$ and $Z^2$ are independently selected from O, S, $N(R^5)$, and C═O;

$R^2$ and $R^{2'}$ are independently selected at each occurrence from hydrogen, $C_1$-$C_6$alkyl, $C_3$-$C_6$cycloalkyl, $C_1$-$C_6$haloalkyl, and $C_1$-$C_6$aliphatic;

$R^6$ and $R^7$ is independently selected at each occurrence from hydrogen, halogen, hydroxyl, $C_1$-$C_6$alkoxy, $C_1$-$C_6$haloalkoxy, $C_1$-$C_6$alkanoyl, cyano, azido, nitro, —COOH, —$CONH_2$, —$P(O)(OH)_2$, —$N(R^5)(R^{5'})$, —$S(O)R^5$, —$SO_2R^5$, —$SO_3R^5$, —$SO_2N(R^5)(R^{5'})$, —$OSO_2R^5$, —$N(R^{5'})SO_2R^5$, $C_1$-$C_6$alkyl, $C_3$-$C_6$cycloalkyl, $C_2$-$C_6$alkenyl, $C_2$-$C_6$alkynyl, $C_1$-$C_6$haloalkyl, $C_1$-$C_6$aliphatic, thiol, $C_1$-$C_6$alkylthiol, and ($C_1$-$C_6$haloalkyl)thiol;

$R^A$ and $R^B$ are independently selected from hydrogen and $C_1$-$C_6$alkyl;

p and r are independently selected from 1, 2, 3, and 4; and $R^5$, $R^{5'}$, m n, and o are defined as herein.

In another aspect, a compound is provided of Formula II:

(II)

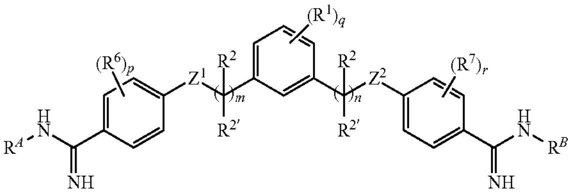

or a pharmaceutically acceptable salt thereof;

wherein $R^1$, $R^2$, $R^{2'}$, $R^5$, $R^{5'}$, $R^A$, $R^B$, $Z^1$, $Z^2$, m, and n are defined as above;

$R^6$ and $R^7$ is independently selected at each occurrence from hydrogen, halogen, hydroxyl, $C_1$-$C_6$alkoxy, $C_1$-$C_6$haloalkoxy, $C_1$-$C_6$alkanoyl, cyano, azido, nitro, —COOH, —$CONH_2$, —$P(O)(OH)_2$, —$N(R^5)(R^{5'})$, —$S(O)R^5$, —$SO_2R^5$, —$SO_3R^5$, —$SO_2N(R^5)(R^{5'})$, —$OSO_2R^5$, —$N(R^5)SO_2R^5$, $C_1$-$C_6$alkyl, $C_3$-$C_6$cycloalkyl, $C_2$-$C_6$alkenyl, $C_2$-$C_6$alkynyl, $C_1$-$C_6$haloalkyl, $C_1$-$C_6$aliphatic, thiol, $C_1$-$C_6$alkylthiol, and ($C_1$-$C_6$haloalkyl)thiol;

wherein at least one of $R^6$ and $R^7$ is not hydrogen in Formula II;

p and r are independently selected from 1, 2, 3, and 4; and q is 0, 1, 2, 3, or 4;

wherein if q is 0 in Formula II, then p is 1 and $R^6$ is hydrogen.

In another aspect, a compound is provided of Formula II':

(II')

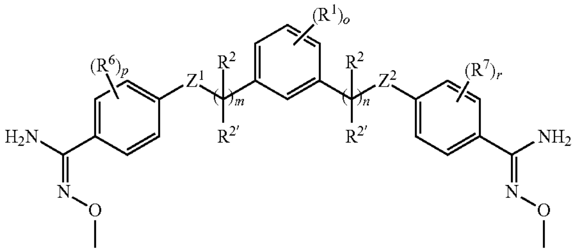

or a pharmaceutically acceptable salt thereof;

wherein $R^1$, $R^2$, $R^{2'}$, $R^5$, $R^{5'}$, $R^6$, $R^7$, $Z^1$, $Z^2$, m, n, p, q, and o are defined as above.

In another aspect, a compound is provided of Formula III:

(III)

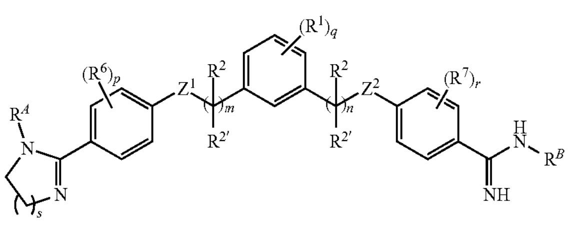

or a pharmaceutically acceptable salt thereof;

wherein $R^1$, $R^2$, $R^{2'}$, $R^5$, $R^{5'}$, $R^6$, $R^7$, $R^A$, $R^B$, $Z^1$, $Z^2$, m, n, p, q, and r are defined as above;

and s is 1 or 2.

In another aspect, a compound is provided of Formula IV:

(IV)

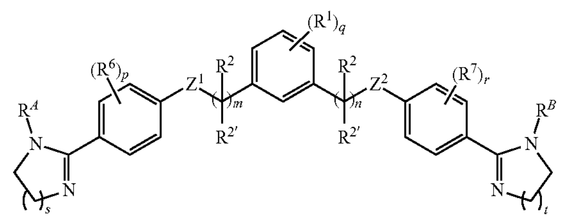

or a pharmaceutically acceptable salt thereof, wherein $R^1$, $R^2$, $R^{2'}$, $R^5$, $R^{5'}$, $R^6$, $R^7$, $R^A$, $R^B$, $Z^1$, $Z^2$, m, n, p, q, and r are defined as above;

and s and t are independently selected from 1 and 2;

wherein if q is 0 in Formula IV, at least one of $R^6$ and $R^7$ is not hydrogen.

In another aspect, a compound is provided of Formula V:

(V)

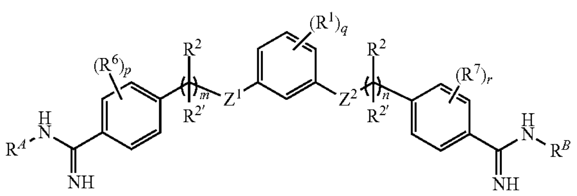

or a pharmaceutically acceptable salt thereof;

wherein $R^1$, $R^2$, $R^{2'}$, $R^5$, $R^{5'}$, $R^6$, $R^7$, $R^A$, $R^B$, $Z^1$, $Z^2$, m, n, p, q, and r are defined as above;

and wherein if q is 0 in Formula V, then at least one of $R^6$ and $R^7$ is not hydrogen.

In another aspect, a compound is provided of Formula V':

(V')

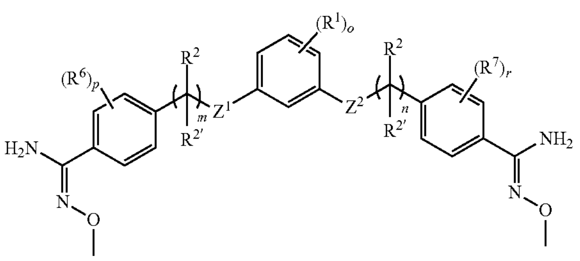

or a pharmaceutically acceptable salt thereof;

wherein $R^1$, $R^2$, $R^{2'}$, $R^5$, $R^{5'}$, $R^6$, $R^7$, $Z^1$, $Z^2$, m, n, p, o, and r are defined as above.

In another aspect, a compound is provided of Formula VI or Formula VII:

(VI)

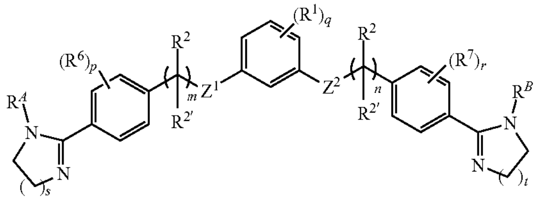

or (VII)

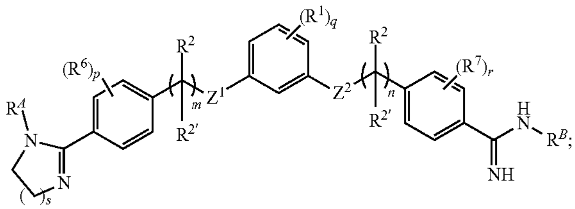

;

or a pharmaceutically acceptable salt thereof, wherein R, $R^1$, $R^2$, $R^{2'}$, $R^5$, $R^{5'}$, $R^6$, $R^7$, $R^A$, $R^B$, $Z^1$, $Z^2$ m, n, p q, r, s, and t are defined as above.

In another aspect, a compound is provided of Formula VIII, VIII', Formula IX, or Formula X:

(VIII)

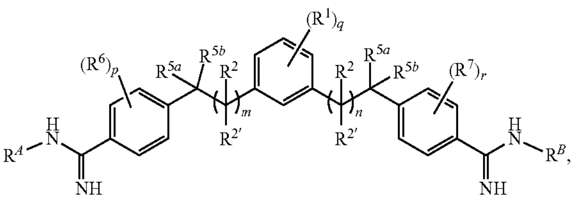

,

-continued (VIII')

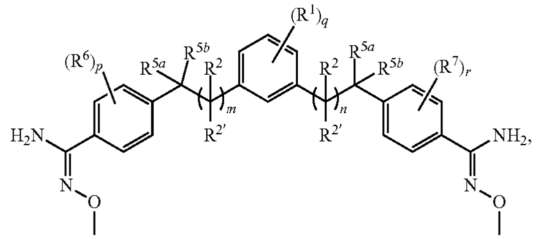

(IX)

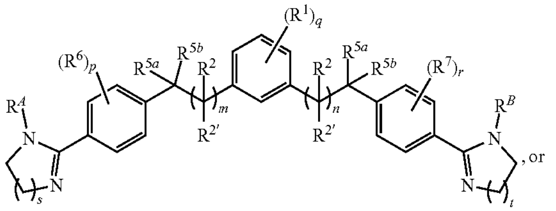

(X)

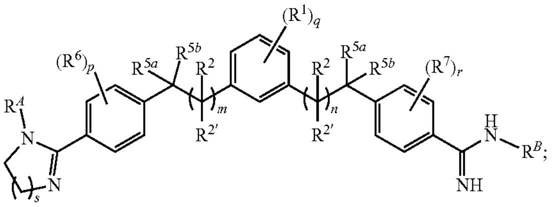

or a pharmaceutically acceptable salt thereof;

wherein $R^1$, $R^2$, $R^{2'}$, $R^5$, $R^{5'}$, $R^6$, $R^7$, $R^6$, $R^7$, $R^A$, $R^B$, m, n, p, q, r, s, and t are defined as above; and $R^{5a}$ and $R^{5b}$ are independently selected at each occurrence from hydrogen, $C_1$-$C_6$alkyl, $C_3$-$C_6$cycloalkyl, $C_1$-$C_6$haloalkyl, and $C_1$-$C_0$aliphatic; or $R^{5a}$ is taken together with an $R^2$ group present on an alpha carbon to form a carbon-carbon double bond; or $R^{5a}$ and $R^{5b}$ are taken together with a respective $R^2$ group and $R^{2'}$ group present on an alpha carbon to form a carbon-carbon triple bond.

A pharmaceutical composition is also provided comprising an effective amount of a compound of Formula I-X, or its pharmaceutically acceptable salt, in a pharmaceutically acceptable carrier either alone or in combination with an effective amount of an antibiotic.

In another aspect, a method is provided for treating a bacterial infection in a host, typically a human, comprising administering to the host an effective amount of an antibiotic in combination with an effective amount of a compound of Formula XI or Formula XI':

(XI)

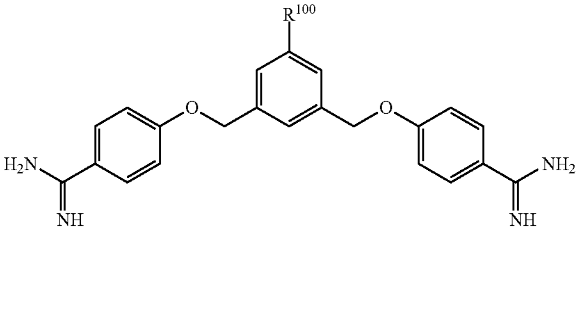

-continued (XI')

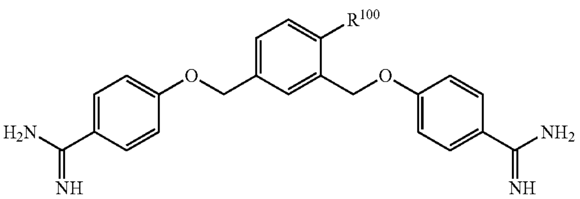

or a pharmaceutically acceptable salt thereof, optionally in a pharmaceutically acceptable carrier to form a pharmaceutical composition;

wherein $R^{100}$ is selected from halogen, cyano, —COOH, —COO($C_1$-$C_6$alkyl), trifluoromethyl, —$SO_3H$, $C_1$-$C_6$alkyl, hydroxyl, $C_1$-$C_6$alkoxy, amino, and —N($C_1$-$C_6$alkyl). In one embodiment, the bacterial infection is caused by a gram-positive bacterium. In one embodiment, $R^{100}$ is $C_{1-6}$alkyl, including methyl, ethyl, isopropyl, propyl, butyl, sec-butyl, isobutyl, and tert-butyl. In one embodiment, the bacterial infection is caused by a gram-negative bacterium. In one embodiment, the bacterial infection is caused by a mycobacterium.

In another aspect, a method is provided for treating a bacterial infection in a host, typically a human, comprising administering to the host an effective amount of an antibiotic in combination with an effective amount of a compound of Formula XII:

(XII)

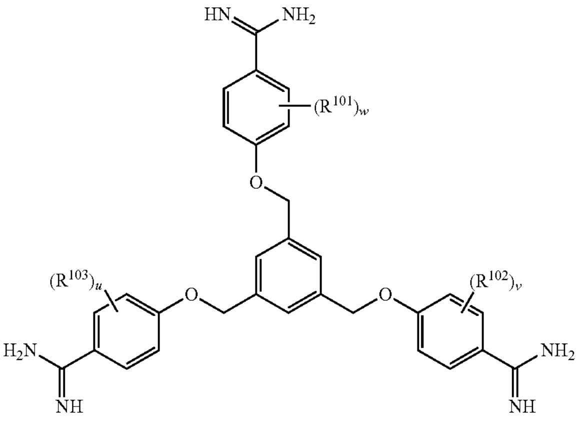

or a pharmaceutically acceptable salt thereof, optionally in a pharmaceutically acceptable carrier to form a pharmaceutical composition;

wherein $R^{101}$, $R^{102}$, and $R^{103}$ are independently selected from hydrogen and halogen; and u, v, and w are independently selected from 1, 2, 3, or 4.

In yet another aspect, provided is a method for potentiating the effect of an antibiotic in the treatment of a bacterial infection in a host, typically a human, comprising administering to the host an effective amount of the antibiotic in combination with an effective amount of a compound of Formula XI, Formula XI', or Formula XII or a pharmaceutically acceptable salt thereof, optionally in a pharmaceutically acceptable carrier to form a pharmaceutical composition. In one embodiment, the bacterial infection is caused by a gram-negative bacterium. In one embodiment, the bacterial infection is caused by a gram-positive bacterium. In one embodiment, the bacterial infection is caused by a mycobacterium.

In yet another aspect, a topical pharmaceutical composition comprising a compound of Formula I-Formula XII is provided. The topical composition can include any carrier or carriers that do not adversely interact with the active agent and achieve the desired effect. For example, the topical carrier can be water-based or anhydrous. Water-based topical compositions are well known, and described further below. Anhydrous pharmaceutically acceptable topical materials are also well known, and include silicon-based oils, aliphatic-based compositions, oleaginous materials, jellies, mineral oil, dimethicone, and other substantially anhydrous lipophilic carriers.

In yet another aspect, a compound is provided of Formula XIII or Formula XIV:

(XIII)

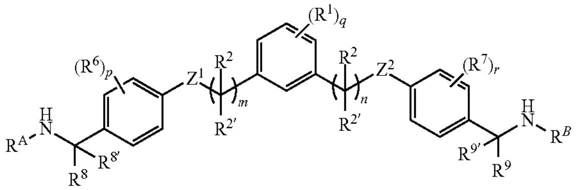

(XIV)

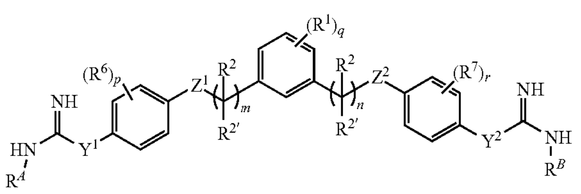

or a pharmaceutically acceptable salt thereof;

wherein:

$R^1$ is independently selected at each occurrence from halogen, hydroxyl, $C_1$-$C_6$alkoxy, $C_1$-$C_6$haloalkoxy, $C_1$-$C_6$alkanoyl, cyano, azido, nitro, —COOH, —$CONH_2$, —$P(O)(OH)_2$, —$N(R^5)(R^{5'})$, —$S(O)R^5$, —$SO_2R^5$, —$SO_3R^5$, —$SO_2N(R^5)(R^{5'})$, —$OSO_2R^5$, —$N(R^{5'})SO_2R^5$, $C_1$-$C_6$alkyl, $C_3$-$C_6$cycloalkyl, $C_2$-$C_6$alkenyl, $C_2$-$C_6$alkynyl, $C_1$-$C_6$haloalkyl, $C_1$-$C_6$aliphatic, thiol, $C_1$-$C_6$alkylthiol, and ($C_1$-$C_6$haloalkyl)thiol;

$Z^1$ and $Z^2$ are independently selected from O, S, $N(R^5)$, and C═O;

$R^2$ and $R^{2'}$ are independently selected at each occurrence from hydrogen, $C_1$-$C_6$alkyl, $C_3$-$C_6$cycloalkyl, $C_1$-$C_6$haloalkyl, and $C_1$-$C_6$aliphatic;

$R^5$ and $R^{5'}$ are independently selected at each occurrence from hydrogen, $C_1$-$C_6$alkyl, $C_3$-$C_6$cycloalkyl, $C_1$-$C_6$haloalkyl, and $C_1$-$C_6$aliphatic;

$R^A$ and $R^B$ are independently selected from hydrogen and $C_1$-$C_6$alkyl;

$R^6$ and $R^7$ is independently selected at each occurrence from hydrogen, halogen, hydroxyl, $C_1$-$C_6$alkoxy, $C_1$-$C_6$haloalkoxy, $C_1$-$C_6$alkanoyl, cyano, azido, nitro, —COOH, —$CONH_2$, —$P(O)(OH)_2$, —$N(R^5)(R^{5'})$, —$S(O)R^5$, —$SO_2R^5$, —$SO_3R^5$, —$SO_2N(R^5)(R^{5'})$, —$OSO_2R^5$, —$N(R^{5'})SO_2R^5$, $C_1$-$C_6$alkyl, $C_3$-$C_6$cycloalkyl, $C_2$-$C_6$alkenyl, $C_2$-$C_6$alkynyl, $C_1$-$C_6$haloalkyl, $C_1$-$C_6$aliphatic, thiol, $C_1$-$C_6$alkylthiol, and ($C_1$-$C_6$haloalkyl)thiol;

$R^8$, $R^{8'}$, $R^9$, and $R^{9'}$ are independently selected at from hydrogen, $C_1$-$C_6$alkyl, $C_3$-$C_6$cycloalkyl, $C_1$-$C_6$haloalkyl, and $C_1$-$C_6$aliphatic;

m and n are independently selected from 1, 2, 3, and 4;

p and r are independently selected from 1, 2, 3, and 4; and q is 0, 1, 2, 3, or 4.

The active compound of Formula I-Formula XII can be provided in the topical formulation in any amount that achieves the desired effect. In certain non-limiting examples, the weight percentage of the active compound in the topical formulation is from about 0.1% to about 50%, or from about 0.1% to about 40%, or about 1% to about 30%, or from about 2, 3, 4 or 5% to about 20%, or between about 5% to about 10%. Examples include at least about 0.5, 1, 2, 3, 4, 5, 10 or 15% by weight. In one embodiment, the topical formulation contains a compound of Formula I-XII in combination with an additional active agent, for example benzoyl peroxide, a retinoid, azelaic acid, an antibiotic, or salicylic acid, as long as it does not adversely affect the active agent.

In one aspect, a method is provided for the treatment of acne vulgaris in a human comprising administering a topical formulation containing, either alone or in combination with an effective amount of an antibiotic, an effective amount of a compound of Formula IA, Formula IB, Formula IC, Formula I', Formula II, Formula II', Formula III, Formula IV, Formula V, Formula V', Formula VI, Formula VII, Formula VIII, Formula VIII', Formula IX, Formula X, Formula XI, Formula XI', Formula XII, Formula XIII, or Formula XIV.

In one embodiment, at least one hydrogen within a compound of Formula IA, Formula IB, Formula ICFormula I', Formula II, Formula II', Formula III, Formula IV, Formula V, Formula V', Formula VI, Formula VII, Formula VIII, Formula VIII', Formula IX, Formula X, Formula XI, Formula XI', Formula XII, Formula XIII, or Formula XIV is replaced with a deuterium. In one aspect, the deuterium is at a location of metabolism.

Thus, the present invention includes at least the following features:

(a) a compound of Formula I-X as described herein or a pharmaceutically salt thereof;

(b) a compound of Formula I-X as described herein, or a pharmaceutically acceptable salt thereof, for use in the treatment of a bacterial infection;

(c) a compound of Formula I-X as described herein, or a pharmaceutically acceptable salt thereof, either alone or in combination with an antibiotic, for use in the treatment of acne vulgaris;

(d) use of a compound of Formula I-X in the manufacture of a medicament for the treatment of a bacterial infection;

(e) use of a compound of Formula I-X in the manufacture of a medicament for the treatment of acne vulgaris;

(f) a method of manufacturing a medicament for the treatment of a bacterial infection characterized in that a compound of Formula I-X as described herein, or a pharmaceutically acceptable salt thereof, is used in the manufacture;

(g) a method of manufacturing a medicament for the treatment of acne vulgaris characterized in that a compound of Formula I-X as described herein, or a pharmaceutically acceptable salt thereof, is used in the manufacture;

(h) a compound of Formula I-X as described herein, or a pharmaceutically acceptable salt thereof, for use in the potentiation of the effect of an antibiotic in the treatment of a bacterial infection;

(i) a compound of Formula I-X as described herein, or a pharmaceutically acceptable salt thereof, for use in the potentiation of the effect of an antibiotic in the treatment of acne vulgaris;

(j) a compound of Formula I-X as described herein, or a pharmaceutically acceptable salt thereof, for use in the treatment of an infection caused by a gram-positive bacterium;

(k) use of a compound of Formula I-X in the manufacture of a medicament for the treatment of an infection caused by a gram-positive bacterium;

(l) a method of manufacturing a medicament for the treatment of an infection caused by a gram-positive bacterium characterized in that a compound of Formula I-X as described herein, o a pharmaceutically acceptable salt thereof, is used in the manufacture;

(m) a compound of Formula I-X as described herein, or a pharmaceutically acceptable salt thereof, for use in the potentiation of the effect of an antibiotic in the treatment of an infection caused by a gram-positive bacterium;

(n) a compound of Formula I-X as described herein, or a pharmaceutically acceptable salt thereof, for use in the treatment of an infection caused by a gram-negative bacterium;

(o) use of a compound of Formula I-X in the manufacture of a medicament for the treatment of an infection caused by a gram-negative bacterium;

(p) a method of manufacturing a medicament for the treatment of an infection caused by a gram-negative bacterium characterized in that a compound of Formula I-X as described herein, or a pharmaceutically acceptable salt thereof, is used in the manufacture;

(q) a compound of Formula I-X as described herein, or a pharmaceutically acceptable salt thereof, for use in the potentiation of the effect of an antibiotic in the treatment of an infection caused by a gram-negative bacterium;

(r) a compound of Formula I-X as described herein, or a pharmaceutically acceptable salt thereof, for use in the treatment of an infection caused by a mycobacterium;

(s) use of a compound of Formula I-X in the manufacture of a medicament for the treatment of an infection caused by a mycobacterium;

(t) a method of manufacturing a medicament for the treatment of an infection caused by a mycobacterium characterized in that a compound of Formula I-X as described herein, o a pharmaceutically acceptable salt thereof, is used in the manufacture;

(u) a compound of Formula I-X as described herein, or a pharmaceutically acceptable salt thereof, for use in the potentiation of the effect of an antibiotic in the treatment of an infection caused by a mycobacterium;

(v) a pharmaceutical composition comprising an effective amount of a compound of Formula I-X as described herein, or its pharmaceutically acceptable salt, in a pharmaceutically acceptable carrier either alone or in combination with an effective amount of an antibiotic;

(w) a topical formulation comprising an effective amount of a compound Formula I-X in a topically acceptable carrier for the treatment of acne;

(x) a method for the treatment of a bacterial infection in a host comprising administering to the host an effective amount of an antibiotic in combination with an effective amount of a compound of Formula XI, Formula XI', or Formula XII as described herein, or its pharmaceutically acceptable salt;

(y) a method for the potentiation of the effect of an antibiotic in the treatment of a bacterial infection in a host comprising administering to the host an effective amount of an antibiotic in combination with an effective amount of a compound of Formula XI, Formula XI', or Formula XII as described herein, or its pharmaceutically acceptable salt;

(z) a method for the treatment of an infection caused by a gram-positive bacterium in a host comprising administering to the host an effective amount of an antibiotic in combination with an effective amount of a compound of Formula XI, Formula XI', or Formula XII as described herein, or its pharmaceutically acceptable salt;

(aa) a method for the potentiation of the effect of an antibiotic in the treatment of an infection caused by a gram-positive bacterium in a host comprising administering to the host an effective amount of an antibiotic in combination with an effective amount of a compound of Formula XI, Formula XI', or Formula XII as described herein, or its pharmaceutically acceptable salt;

(bb) a method for the treatment of an infection caused by a gram-negative bacterium in a host comprising administering to the host an effective amount of an antibiotic in combination with an effective amount of a compound of Formula XI, Formula XI', or Formula XII as described herein, or its pharmaceutically acceptable salt;

(cc) a method for the potentiation of the effect of an antibiotic in the treatment of an infection caused by a gram-negative bacterium in a host comprising administering to the host an effective amount of an antibiotic in combination with an effective amount of a compound of Formula XI, Formula XI', or Formula XII as described herein, or its pharmaceutically acceptable salt;

(dd) a method for the treatment of an infection caused by a mycobacterium in a host comprising administering to the host an effective amount of an antibiotic in combination with an effective amount of a compound of Formula XI, Formula XI', or Formula XII as described herein, or its pharmaceutically acceptable salt;

(ee) a method for the potentiation of the effect of an antibiotic in the treatment of an infection caused by a mycobacterium in a host comprising administering to the host an effective amount of an antibiotic in combination with an effective amount of a compound of Formula XI, Formula XI', or Formula XII as described herein, or its pharmaceutically acceptable salt;

(ff) a method for the treatment of acne vulgaris in a host comprising administering to the host an effective amount of an antibiotic in combination with an effective amount of a compound of Formula XI, Formula XI', or Formula XII as described herein, or its pharmaceutically acceptable salt;

(gg) a pharmaceutical composition comprising an effective amount of an antibiotic in combination with an effective amount of a compound of Formula XI, Formula XI', or Formula XII as described herein, or its pharmaceutically acceptable salt, in a pharmaceutically acceptable carrier;

(hh) a compound of Formula I-XII or a pharmaceutically acceptable salt thereof as a mixture of enantiomers or diastereomers (as relevant), including as a racemate or including at least one atom that is isotopically enriched;

(ii) a compound Formula I-XII or a pharmaceutically acceptable salt thereof in enantiomerically or diastereomerically (as relevant) enriched form, including as an isolated enantiomer or diastereomer (i.e., greater than 85, 90, 95, 97, or 99% pure);

(jj) a topical composition or method described herein for acne wherein the compound of the composition is in enantiomerically or diastereomerically (as relevant) enriched form, including as an isolated enantiomer or diastereomer (i.e., greater than 85, 90, 95, 97, or 99% pure);

(kk) a topical composition or method as used herein for acne wherein in the compound is a mixture of enantiomers or diastereomers (as relevant), including as a racemate or including at least one atom that is isotopically enriched;

(ll) a process for the preparation of a therapeutic product that contains an effective amount of a compound of Formula I-X, or its pharmaceutically acceptable salt, either alone or in combination with an effective amount of an antibiotic; and (mm) a process for the preparation of a therapeutic product that contains an effective amount of a compound of Formula XI, Formula XI', or Formula XII, or its pharmaceutically acceptable salt, in combination with an effective amount of an antibiotic.

DETAILED DESCRIPTION OF THE INVENTION

Definitions

Figure 1:
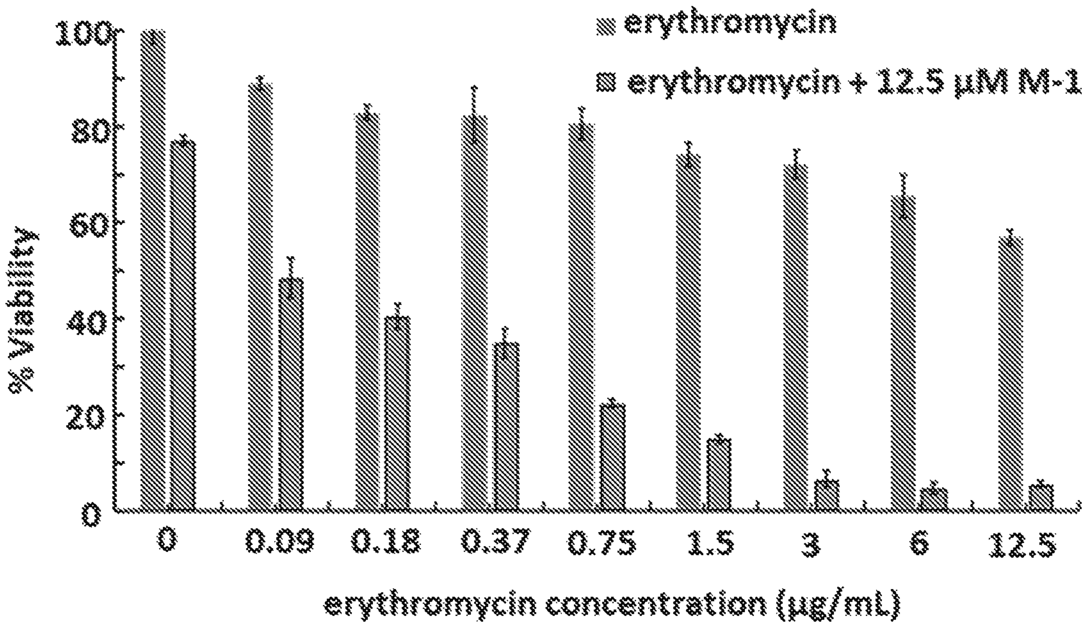
FIG. 1 is a bar graph showing the growth inhibitory effect on *B. subtilus* by the combination of 12.5 μM compound M-1 with erythromycin. *B. subtilis* was cultured with erythromycin at varying concentrations (0, 0.09, 0.18, 0.37, 0.75, 1.5, 3, 6 or 12.5 μg/mL) either alone or in combination with 12.5 μM M-1. The y-axis is bacterial viability measured in percent. The x-axis is erythromycin concentration measured in micrograms per milliliter.

Compounds are described using standard nomenclature. Unless defined otherwise, all technical and scientific terms used herein have the same meaning as is commonly understood by one of skill in the art to which the invention belongs.

The terms "a" and "an" do not denote a limitation of quantity, but rather denote the presence of at least one of the referenced item. The term "or" means "and/or". Recitation of ranges of values merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of example, or exemplary language (e.g. "such as"), is intended merely to better illustrate the invention and does not pose a limitation on the scope of the invention unless otherwise claimed.

A dash ("—") that is not between two letters or symbols is used to indicate a point of attachment for a substituent. For example, $-(C{=}O)NH_2$ is attached through the carbon of the keto (C═O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "Alkyl" also encompasses cycloalkyl or carbocyclic groups. For example, when a term is used that includes "alk" then "cycloalkyl" or "carbocyclic" can be considered part of the definition, unless unambiguously excluded by the context. For example, and without limitation, the terms alkyl, alkoxy, haloalkyl, etc. can all be considered to include the cyclic forms of alkyl, unless unambiguously excluded by context.

"Alkenyl" is a linear or branched aliphatic hydrocarbon groups having one or more carbon-carbon double bonds that may occur at a stable point along the chain. In one embodiment, "alkenyl" is used to indicate those alkenyl groups having 2-12 carbons. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. In one embodiment, "alkynyl" is used to indicate those alkenyl groups having 2-12 carbons. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or carbocyclic groups possessing at least one point of unsaturation.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly, an "alkylthio" or "thioalkyl" group is an alkyl group as defined above with the indicated number of carbon atoms covalently bound through a sulfur bridge (—S—).

"Alkanoyl" is an alkyl group as defined above covalently bound through a carbonyl (C═O) bridge. The carbonyl carbon is included in the number of carbons, that is $C_2$alkanoyl is a $-(C{=}O)CH_3$ group.

"Aliphatic" refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-12 carbon atoms. The aliphatic group can be for example, alkyl, mono-unsaturated, di-unsaturated, tri-unsaturated, or polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$, or $C_1$-$C_6$. The specified ranges as used herein indicate an aliphatic group having each member of the range described as an independent species. For example, the term $C_1$-$C_6$aliphatic as used herein indicates a straight or branched alkyl, alkenyl, or alkynyl group having 1, 2, 3, 4, 5, or 6 carbon atoms and is intended to mean that each of these is described as an independent species. For example, the term $C_1$-$C_4$aliphatic as used herein indicates a straight or branched alkyl, alkenyl, or alkynyl group having from 1, 2, 3, or 4 carbon atoms and is intended to mean that each of these is described as an independent species.

As used herein, "carbocyclyl", "carbocyclic", "carbocycle" or "cycloalkyl" is a saturated or partially unsaturated (i.e., not aromatic) group containing all carbon ring atoms and from 3 to 14 ring carbon atoms ("$C_{3-14}$ cycloalkyl") and zero heteroatoms in the non-aromatic ring system. In some embodiments, a cycloalkyl group has 3 to 10 ring carbon atoms ("$C_{3-10}$ cycloalkyl"). In some embodiments, a cycloalkyl group has 3 to 9 ring carbon atoms ("$C_{3-9}$ cycloalkyl"). In some embodiments, a cycloalkyl group has 3 to 8 ring carbon atoms ("$C_{3-8}$ cycloalkyl"). In some embodiments, a cycloalkyl group has 3 to 7 ring carbon atoms ("$C_{3-7}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Exemplary $C_{3-6}$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-8 cycloalkyl groups include, without limitation, the aforementioned C3-6 cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), and the like. Exemplary $C_{3-10}$ cycloalkyl groups include, without limitation, the aforementioned $C_{3-8}$ cycloalkyl groups as well as cyclononyl ($C_9$), cyclononenyl ($C_9$), cyclodecyl ($C_{10}$), cyclodecenyl ($C_{10}$), and the like. As the foregoing examples illustrate, in certain embodiments, the cycloalkyl group can be saturated or can contain one or more carbon-carbon double or triple bonds. In an alternative embodiment, "cycloalkyl" also includes ring systems wherein the cycloalkyl ring, as defined above, is fused with one heterocycle, aryl or heteroaryl ring wherein the point of attachment is on the cycloalkyl ring, and in such instances, the number of carbons continue to designate the number of carbons in the carbocyclic ring system. In an alternative embodiment, each instance of cycloalkyl is optionally substituted with one or more substituents. In certain embodiments, the cycloalkyl group is an unsubstituted $C_{3-14}$ cycloalkyl.

"Halo" and "halogen" refer to fluorine, chlorine, bromine, or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

"Haloalkoxy" indicates a haloalkyl group as defined herein attached through an oxygen bridge (—O—). Similarly, a "haloalkylthio" or "thio(haloalkyl)" group is an alkyl group as defined above with the indicated number of carbon atoms covalently bound through a sulfur bridge (—S—).

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein means an amount which provides a therapeutic or prophylactic benefit.

"Parenteral" administration of a pharmaceutical composition includes, e.g., subcutaneous (s.c.), intravenous (i.v.), intramuscular (i.m.), intrasternal injection, or infusion techniques.

To "treat" a disease as the term is used herein means to reduce the frequency or severity of at least one sign or symptom of a disease or disorder experienced by a subject (i.e. palliative treatment) or to decrease a cause or effect of the disease or disorder (i.e. disease-modifying treatment).

As used herein, "pharmaceutical compositions" are compositions comprising at least one active agent and at least one other substance, such as a carrier. "Pharmaceutical combinations" are combinations of at least two active agents which may be combined in a single dosage form or provided together in separate dosage forms with instructions that the active agents are to be used together to treat any disorder described herein.

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders specifically described herein. Typically, the host is a human. A "host" may alternatively refer to for example, a mammal, primate (e.g. human), cow, sheep, goat, horse, dog, cat, rabbit, rat, mice, fish, bird, and the like.

A "therapeutically effective amount" of a pharmaceutical composition/combination of this invention means an amount effective, when administered to a host, to provide a therapeutic benefit such as an amelioration of symptoms or reduction or dimunition of the disease itself.

Compounds of the Present Invention

A compound is provided in the present invention of Formula IA, IB, IC, ID, IE, I', II, II', III, IV, V. V', VI, VII, VIII, VIII', IX, or X, or a pharmaceutically acceptable salt thereof, optionally in a pharmaceutically acceptable carrier to form a pharmaceutical composition.

The compounds in any of the Formulas described herein may be in the form of a racemate, enantiomer, mixture of enantiomers, diastereomer, mixture of diastereomers, tautomer, N-oxide, or other isomer, such as a rotamer, as if each is specifically described unless specifically excluded by context.

The present invention includes compounds of Formula IA, Formula IB, Formula IC, Formula I', Formula II, Formula II', Formula III, Formula IV, Formula V, Formula V', Formula VI, Formula VII, Formula VIII, Formula VIII', Formula IX, Formula X, Formula XI, Formula XI', Formula XII, Formula XIII, or Formula XIV with at least one desired isotopic substitution of an atom, at an amount above the natural abundance of the isotope, i.e. enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine, and iodine such as $^{2}H$, $^{3}H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$, and $^{125}I$, respectively. In one non-limiting embodiment, isotopically labeled compounds can be used in metabolic studies (with for example $^{14}C$), reaction kinetic studies (with for example $^{2}H$ or $^{3}H$), detection or imaging techniques, such as positron emission tomography (PET) or single-photon emission computed tomography (SPECT) including drug or substrate tissue distribution assays. In particular, an $^{18}F$ labeled compound may be particularly desirable for PET or SPECT studies. Isotopically labeled compounds of this invention can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95, or 99% or more enriched in an isotope at any location of interest. In one non-limiting embodiment, deuterium is 90, 95, or 99% enriched at a desired location.

In one non-limiting embodiment, the substitution of one or more hydrogen atoms for a deuterium atom can be provided in any one of Formula IA, Formula IB, Formula IC, Formula II, Formula II', Formula III, Formula IV, Formula V, Formula V', Formula VI, Formula VII, Formula VIII, Formula VIII', Formula IX, Formula X, Formula XI, Formula XI', Formula XII, Formula XIII, or Formula XIV. In one non-limiting embodiment, the substitution of a hydrogen atom for a deuterium atom occurs within a group selected from any of $R^1$, $R^2$, $R^{2'}$, $R^3$, $R^4$, $R^5$, $R^{5'}$, $R^{5a}$, $R^{5b}$, $R^6$, $R^7$, $R^{10}$, $R^{100}$, $R^{101}$, $R^{102}$, $R^{103}$, $R^A$, $R^B$, $Y^1$, $Y^2$, $Z^1$, and $Z^2$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$, etc.). In certain other embodiments, when two substituents are combined to form a cycle the unsubstituted carbons may be deuterated.

A compound of the present invention may form a solvate with one or more solvent (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, dimethyl sulfoxide, acetone, and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, and do-DMSO. A solvate can be in a liquid or solid form.

As used herein, "pharmaceutically acceptable salt" is a derivative of the disclosed compound in which the parent compound is modified by making inorganic or organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reactive free base forms of these compounds with a stoichiometric amount of the appropriate acid. Such reactions are typically carrier out in water or in an organic solvent, or in a mixture of the two. Generally, non-aqueous media like ether, ethyl acetate, ethanol, isopropanol, or acetonitrile are typical, where practical. Salts of the present compounds further include solvates of the compound and the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)$n-COOH where n is 0-4, and the like, or using a different acid that produces the same counterion. Lists of additional suitable salts may be found, e.g., in Remington's *Pharmaceutical Sciences,* 17$^{th}$ ed., Mack Publishing Company, Easton, Pa., p. 1418 (1985).

Embodiments of "Alkyl"

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.

In one embodiment "alkyl" has two carbons.

In one embodiment "alkyl" has three carbons.

In one embodiment "alkyl" has four carbons.

In one embodiment "alkyl" has five carbons.

In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In one embodiment "alkyl" is "substituted alkyl"

In one embodiment "alkenyl" is "substituted alkenyl"

In one embodiment "alkynyl" is "substituted alkynyl"

Embodiments of "Haloalkyl"

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.

In one embodiment "haloalkyl" has one carbon and one halogen.

In one embodiment "haloalkyl" has one carbon and two halogens.

In one embodiment "haloalkyl" has one carbon and three halogens.

In one embodiment "haloalkyl" has two carbons.

In one embodiment "haloalkyl" has three carbons.

In one embodiment "haloalkyl" has four carbons.

In one embodiment "haloalkyl" has five carbons.

In one embodiment "haloalkyl" has six carbons.

Non-limiting examples of "haloalkyl" include:

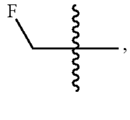, 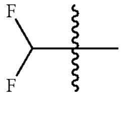, and 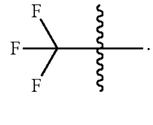.

Additional non-limiting examples of "haloalkyl" include:

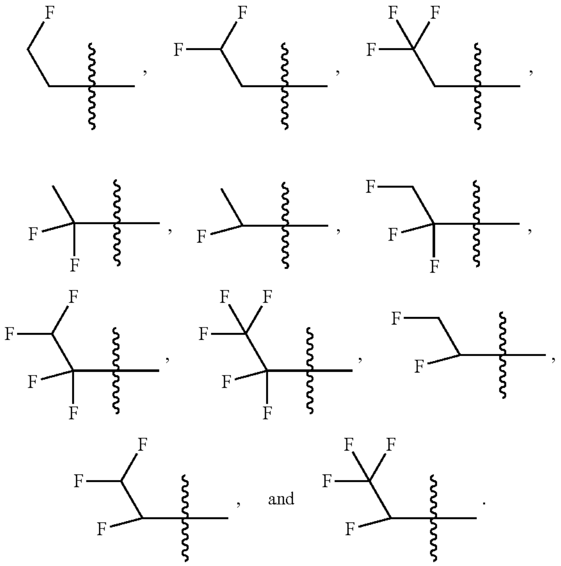

and

Additional non-limiting examples of "haloalkyl" include:

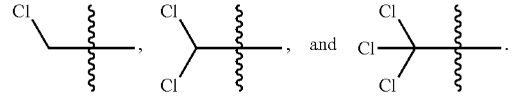

and

Additional non-limiting examples of "haloalkyl" include:

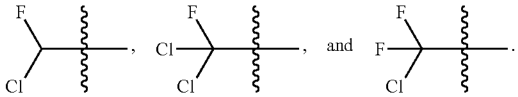

and

Additional non-limiting examples of "haloalkyl" include

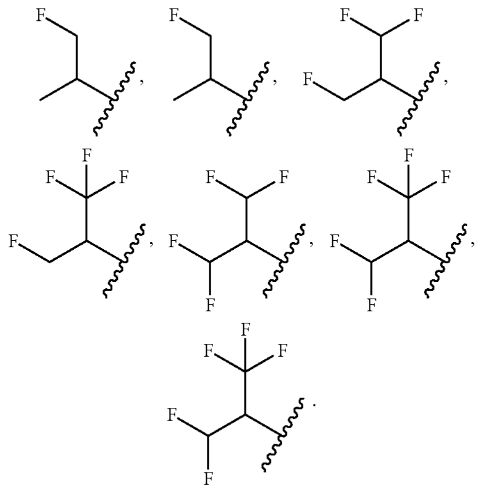

Embodiments of "Cycloalkyl"

In one embodiment "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In one embodiment "cycloalkyl" has three carbons.

In one embodiment "cycloalkyl" has four carbons.

In one embodiment "cycloalkyl" has five carbons.

In one embodiment "cycloalkyl" has six carbons.

In one embodiment "cycloalkyl" has seven carbons.

In one embodiment "cycloalkyl" has eight carbons.

In one embodiment "cycloalkyl" has nine carbons.

In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

Additional non-limiting examples of "cycloalkyl" include dihydro-indene and tetrahydronaphthalene wherein the point of attachment for each group is on the cycloalkyl ring.

For example

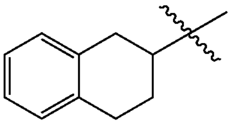 [SMILES: *C1CCc2ccccc2C1]

is an "cycloalkyl" group.

However,

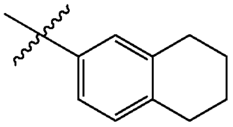 [SMILES: *c1ccc2c(c1)CCCC2]

is an "aryl" group.

In one embodiment "cycloalkyl" is a "substituted cycloalkyl"

In one embodiment of any one of Formula IA, Formula IB, Formula IC, Formulas III-X, and Formulas XIII-XIV above, $R^1$ is halogen. In one embodiment of any one of Formula IA, Formula IB, Formula IC, Formulas III-X, and Formulas XIII-XIV above, $R^1$ is hydroxy. In one embodiment of any one of Formula IA, Formula IB, Formula IC, Formulas III-X, and Formulas XIII-XIV above, R' is halogen. In one embodiment of any one of Formula IA, Formula IB, Formula IC, Formulas III-X, and Formulas XIII-XIV, $R^1$ is $C_1$-$C_6$alkoxy. In one embodiment of any one of Formula IA, Formula IB, Formula IC, Formulas III-X, and Formulas XIII-XIV above, R' is halogen. In one embodiment of any one of Formula IA, Formula IB, Formula IC, Formulas III-X, and Formulas XIII-XIV above, $R^1$ is $C_1$-$C_6$haloalkoxy. In one embodiment of any one of Formula IA, Formula IB, Formula IC, Formulas III-X, and Formulas XIII-XIV above, $R^1$ is halogen. In one embodiment of any one of Formula IA, Formula IB, Formula IC, Formulas III-X, and Formulas XIII-XIV above, $R^1$ is $C_1$-$C_6$alkanoyl. In one embodiment of any one of Formula IA, Formula IB, Formula IC, Formulas III-X, and Formulas XIII-XIV above, $R^1$ is halogen. In one embodiment of any one of Formula IA, Formula IB, Formula IC, Formulas III-X, and Formulas XIII-XIV above, $R^1$ is cyano. In one embodiment of any one of Formula IA, Formula IB, Formula IC, Formulas III-X, and Formulas XIII-XIV above, $R^1$ is halogen. In one embodiment of any one of Formula IA, Formula IB, Formula IC, Formulas III-X, and Formulas XIII-XIV above, $R^1$ is azido. In one embodiment of any one of Formula IA, Formula IB, Formula IC, Formulas III-X, and Formulas XIII-XIV above, $R^1$ is halogen. In one embodiment of any one of Formula IA, Formula IB, Formula IC, Formulas III-X, and Formulas XIII-XIV above, $R^1$ is halogen. In one embodiment of any one of Formula IA, Formula IB, Formula IC, Formulas III-X, and Formulas XIII-XIV above, $R^1$ is nitro. In one embodiment of any one of Formula IA, Formula IB, Formula IC, Formulas III-X, and Formulas XIII-XIV above, $R^1$ is —COOH. In one embodiment of any one of Formula IA, Formula IB, Formula IC, Formulas III-X, and Formulas XIII-XIV above, R' is —$CONH_2$. In one embodiment of any one of Formulas Formula IA, Formula IB, Formula IC, Formulas III-X, and Formulas XIII-XIV above, $R^1$ is —$P(O)(OH)_2$. In one embodiment, of any one of Formula IA, Formula IB, Formula IC, Formulas III-X, and Formulas XIII-XIV above $R^1$ is —$N(R^5)(R^{5'})$. In one embodiment of any one of Formula IA, Formula IB, Formula IC, Formulas III-X, and Formulas XIII-XIV above, $R^1$ is —$S(O)R^5$. In one embodiment of any one of Formula IA, Formula IB, Formula IC, Formulas III-X, and Formulas XIII-XIV above, $R^1$ is —$SO_2R^5$. In one embodiment of any one of Formula IA, Formula IB, Formula IC, Formulas III-X, and Formulas XIII-XIV above, $R^1$ is —$SO_3R^5$. In one embodiment of any one of Formula IA, Formula IB, Formula IC, Formulas III-X, and Formulas XIII-XIV above, $R^1$ is —$SO_2N(R^5)(R^{5'})$. In one embodiment of any one of Formula IA, Formula IB, Formula IC, Formulas III-X, and Formulas XIII-XIV above, $R^1$ is —$OSO_2R^5$. In one embodiment of any one of Formula IA, Formula IB, Formula IC, Formulas III-X, and Formulas XIII-XIV above, $R^1$ is —$N(R^{5'})SO_2R^5$. In one embodiment of any one of Formula IA, Formula IB, Formula IC, Formulas III-X, and Formulas XIII-XIV above, $R^1$ is $C_1$-$C_6$alkyl. In one embodiment of any one of Formula IA, Formula IB, Formula IC, Formulas III-X, and Formulas XIII-XIV above, $R^1$ is $C_3$-$C_6$cycloalkyl. In one embodiment of any one of Formula IA, Formula IB, Formula IC, Formulas III-X, and Formulas XIII-XIV above, $R^1$ is $C_2$-$C_6$alkenyl. In one embodiment of any one of Formula IA, Formula IB, Formula IC, Formulas III-X, and Formulas XIII-XIV above, $R^1$ is $C_2$-$C_6$alkynyl. In one embodiment of any one of Formula IA, Formula IB, Formula IC, Formulas III-X, and Formulas XIII-XIV above, $R^1$ is $C_1$-$C_6$haloalkyl. In one embodiment of any one of Formula IA, Formula IB, Formula IC, Formulas III-X, and Formulas XIII-XIV above, $R^1$ is $C_1$-$C_6$aliphatic. In one embodiment of any one of Formula IA, Formula IB, Formula IC, Formulas III-X, and Formulas XIII-XIV above, R' is thiol. In one embodiment of any one of Formula IA, Formula IB, Formula IC, Formulas III-X, and Formulas XIII-XIV above, $R^1$ is $C_1$-$C_6$alkylthiol. In one embodiment of any one of Formula IA, Formula IB, Formula IC, Formulas III-X, and Formulas XIII-XIV above, $R^1$ is ($C_1$-$C_6$haloalkyl)thiol.

In one embodiment of Formula I' above, $R^{10}$ is hydroxy. In one embodiment of Formula I', $R^{10}$ is $C_1$-$C_6$alkoxy. In one embodiment of Formula I' above, $R^{10}$ is $C_1$-$C_6$haloalkoxy. In one embodiment of Formula I' above, $R^{10}$ is $C_1$-$C_6$alkanoyl. In one embodiment of Formula I' above, $R^{10}$ is cyano. In one embodiment of Formula I' above, $R^{10}$ is azido. In one embodiment of Formula I' above, $R^{10}$ is nitro. In one embodiment of Formula I' above, $R^{10}$ is —COOH. In one embodiment of Formula I' above, $R^{10}$ is —$CONH_2$. In one embodiment of Formula I' above, $R^{10}$ is —$P(O)(OH)_2$. In one embodiment, of Formula I' above $R^{10}$ is —$N(R^5)(R^{5'})$. In one embodiment of Formula I' above, $R^{10}$ is —$S(O)R^5$. In one embodiment of Formula I' above, $R^{10}$ is —$SO_2R^5$. In one embodiment of Formula I' above, $R^{10}$ is —$SO_3R^5$. In one embodiment of Formula I' above, $R^{10}$ is —$SO_2N(R^5)(R^{5'})$. In one embodiment of Formula I' above, $R^{10}$ is —$OSO_2R^5$. In one embodiment of Formula I' above, $R^{10}$ is —$N(R^{5'})$ $SO_2R^5$. In one embodiment of Formula I' above, $R^{10}$ is $C_1$-$C_6$alkyl. In one embodiment of Formula I' above, $R^{10}$ is $C_3$-$C_6$cycloalkyl. In one embodiment of Formula I' above, $R^{10}$ is $C_2$-$C_6$alkenyl. In one embodiment of Formula I' above, $R^{10}$ is $C_2$-$C_6$alkynyl. In one embodiment of Formula I' above, $R^{10}$ is $C_1$-$C_6$haloalkyl. In one embodiment of Formula I' above, $R^{10}$ is $C_1$-$C_6$aliphatic. In one embodiment of Formula I' above, $R^{10}$ is thiol. In one embodiment of Formula I' above, $R^{10}$ is $C_1$-$C_6$alkylthiol. In one embodiment of Formula I' above, $R^{10}$ is ($C_1$-$C_6$haloalkyl)thiol.

In one embodiment of any one of Formulas IA-VII above, $Z^1$ is O. In one embodiment of any one of Formulas IA-VII above, $Z^1$ is S. In one embodiment of any one of Formulas IA-VII above, $Z^1$ is $N(R^5)$. In one embodiment of any one of Formulas IA-VII above, $Z^1$ is C═O.

In one embodiment of any one of Formulas IA-VII above, $Z^2$ is O. In one embodiment of any one of Formulas IA-VII above, $Z^2$ is S. In one embodiment, $Z^2$ is $N(R^5)$. In one embodiment of any one of Formulas IA-VII above, $Z^2$ is C═O.

In one embodiment of any one of Formulas IA-X above, $R^2$ is hydrogen. In one embodiment of any one of Formulas IA-X above, $R^2$ is $C_1$-$C_6$alkyl. In one embodiment of any one of Formulas IA-X above, $R^2$ is methyl. In one embodiment of any one of Formulas IA-X above, $R^2$ is ethyl. In one embodiment of any one of Formulas IA-X above, $R^2$ is propyl. In one embodiment of any one of Formulas IA-X above, $R^2$ is isopropyl. In one embodiment of any one of Formulas IA-X above, $R^2$ is butyl. In one embodiment of any one of Formulas IA-X above, $R^2$ is isobutyl. In one embodiment of any one of Formulas IA-X above, $R^2$ is sec-butyl. In one embodiment of any one of Formulas IA-X above, $R^2$ is tert-butyl. In one embodiment of any one of Formulas IA-X above, $R^2$ is pentyl. In one embodiment of any one of Formulas IA-X above, $R^2$ is hexyl. In one embodiment of any one of Formulas IA-X above, $R^2$ is $C_3$-$C_6$cycloalkyl. In one embodiment of any one of Formulas IA-X above, $R^2$ is cyclopropyl. In one embodiment of any one of Formulas IA-X above, $R^2$ is cyclobutyl. In one embodiment of any one of Formulas IA-X above, $R^2$ is cyclopentyl. In one embodiment of any one of Formulas IA-X above, $R^2$ is cyclohexyl. In one embodiment of any one of Formulas IA-X above, $R^2$ is $C_1$-$C_6$haloalkyl. In one embodiment of any one of Formulas IA-X above, $R^2$ is trifluoromethyl. In one embodiment of any one of Formulas IA-X above, $R^2$ is trifluoroethyl. In one embodiment of any one of Formulas IA-X above, $R^2$ is hexafluoroisopropyl. In one embodiment of any one of Formulas IA-X above, $R^2$ is $C_1$-$C_6$aliphatic.

In one embodiment of any one of Formulas IA-X above, $R^{2'}$ is hydrogen. In one embodiment of any one of Formulas IA-X above, $R^{2'}$ is $C_1$-$C_6$alkyl. In one embodiment of any one of Formulas IA-X above, $R^{2'}$ is methyl. In one embodiment of any one of Formulas IA-X above, $R^{2'}$ is ethyl. In one embodiment of any one of Formulas IA-X above, $R^{2'}$ is propyl. In one embodiment of any one of Formulas IA-X above, $R^{2'}$ is isopropyl. In one embodiment of any one of Formulas IA-X above, $R^{2'}$ is butyl. In one embodiment of any one of Formulas IA-X above, $R^{2'}$ is isobutyl. In one embodiment of any one of Formulas IA-X above, $R^{2'}$ is sec-butyl. In one embodiment of any one of Formulas IA-X above, $R^{2'}$ is tert-butyl. In one embodiment of any one of Formulas IA-X above, $R^{2'}$ is pentyl. In one embodiment of any one of Formulas IA-X above, $R^{2'}$ is hexyl. In one embodiment of any one of Formulas IA-X above, $R^{2'}$ is $C_3$-$C_6$cycloalkyl. In one embodiment of any one of Formulas IA-X above, $R^{2'}$ is cyclopropyl. In one embodiment of any one of Formulas IA-X above, $R^{2'}$ is cyclobutyl. In one embodiment of any one of Formulas IA-X above, $R^{2'}$ is cyclopentyl. In one embodiment of any one of Formulas IA-X above, $R^{2'}$ is cyclohexyl. In one embodiment of any one of Formulas IA-X above, $R^{2'}$ is $C_1$-$C_6$haloalkyl. In one embodiment of any one of Formulas IA-X above, $R^{2'}$ is trifluoromethyl. In one embodiment of any one of Formulas IA-X above, $R^{2'}$ is trifluoroethyl. In one embodiment of any one of Formulas IA-X above, $R^2$ is hexafluoroisopropyl. In one embodiment of any one of Formulas IA-X above, $R^2$ is $C_1$-$C_6$aliphatic.

In one embodiment of any one of Formulas IA-IC above, $R^3$ is halogen. In one embodiment of any one of Formulas IA-IC above, $R^3$ is fluoro. In one embodiment of any one of Formulas IA-IC above, $R^3$ is chloro. In one embodiment of any one of Formulas IA-IC above, $R^3$ is bromo. In one embodiment of any one of Formulas IA-IC above, $R^3$ is iodo. In one embodiment of any one of Formulas IA-IC above, $R^3$ is $S(O)R^5$. In one embodiment of any one of Formulas IA-IC above, $R^3$ is $—SO_2R^5$. In one embodiment of any one of Formulas IA-IC above, $R^3$ is $—SO_3R^5$. In one embodiment of any one of Formulas IA-IC above, $R^3$ is $—SO_2N(R^5)(R^{5'})$. In one embodiment of any one of Formulas IA-IC above, $R^3$ is $—OSO_2R^5$. In one embodiment of any one of Formulas IA-IC above, $R^3$ is $N(R^{5'})SO_2R^5$. In one embodiment of any one of Formulas IA-IC above, $R^3$ is $C_1$-$C_6$alkyl. In one embodiment of any one of Formulas IA-IC above, $R^3$ is methyl. In one embodiment of any one of Formulas IA-IC above, $R^3$ is ethyl. In one embodiment of any one of Formulas IA-IC above, $R^3$ is propyl. In one embodiment of any one of Formulas IA-IC above, $R^3$ is isopropyl. In one embodiment of any one of Formulas IA-IC above, $R^3$ is butyl. In one embodiment of any one of Formulas IA-IC above, $R^3$ is isobutyl. In one embodiment of any one of Formulas IA-IC above, $R^3$ is sec-butyl. In one embodiment of any one of Formulas IA-IC above, $R^3$ is tert-butyl. In one embodiment of any one of Formulas IA-IC above, $R^3$ is pentyl. In one embodiment of any one of Formulas IA-IC above, $R^3$ is hexyl. In one embodiment of any one of Formulas IA-IC above, $R^3$ is $C_1$-$C_6$alkoxy. In one embodiment of any one of Formulas IA-IC above, $R^3$ is methoxy. In one embodiment of any one of Formulas IA-IC above, $R^3$ is ethoxy. In one embodiment of any one of Formulas IA-IC above, $R^3$ is propoxy. In one embodiment of any one of Formulas IA-IC above, $R^3$ is isopropoxy. In one embodiment of any one of Formulas IA-IC above, $R^3$ is butoxy. In one embodiment of any one of Formulas IA-IC above, $R^3$ is isobutoxy. In one embodiment of any one of Formulas IA-IC above, $R^3$ is sec-butoxy. In one embodiment of any one of Formulas IA-IC above, $R^3$ is tert-butoxy.

In one embodiment of any one of Formulas IA-IC above, $R^4$ is halogen. In one embodiment of any one of Formulas IA-IC above, $R^4$ is fluoro. In one embodiment of any one of Formulas IA-IC above, $R^4$ is chloro. In one embodiment of any one of Formulas IA-IC above, $R^4$ is bromo. In one embodiment of any one of Formulas IA-IC above, $R^4$ is iodo. In one embodiment of any one of Formulas IA-IC above, $R^4$ is $S(O)R^5$. In one embodiment of any one of Formulas IA-IC above, $R^4$ is $—SO_2R^5$. In one embodiment of any one of Formulas IA-IC above, $R^4$ is $—SO_3R^5$. In one embodiment of any one of Formulas IA-IC above, $R^4$ is $—SO_2N(R^5)(R^{5'})$. In one embodiment of any one of Formulas IA-IC above, $R^4$ is $—OSO_2R^5$. In one embodiment of any one of Formulas IA-IC above, $R^4$ is $N(R^5)$ $SO_2R^5$. In one embodiment of any one of Formulas IA-IC above, $R^4$ is $C_1$-$C_6$alkyl. In one embodiment of any one of Formulas IA-IC above, $R^4$ is methyl. In one embodiment of any one of Formulas IA-IC above, $R^4$ is ethyl. In one embodiment of any one of Formulas IA-IC above, $R^4$ is propyl. In one embodiment of any one of Formulas IA-IC above, $R^4$ is isopropyl. In one embodiment of any one of Formulas IA-IC above, $R^4$ is butyl. In one embodiment of any one of Formulas IA-IC above, $R^4$ is isobutyl. In one embodiment of any one of Formulas IA-IC above, $R^4$ is sec-butyl. In one embodiment of any one of Formulas IA-IC above, $R^4$ is tert-butyl. In one embodiment of any one of Formulas IA-IC above, $R^4$ is pentyl. In one embodiment of any one of Formulas IA-IC above, $R^4$ is hexyl. In one embodiment of any one of Formulas IA-IC above, $R^4$ is $C_1$-$C_6$alkoxy. In one embodiment of any one of Formulas IA-IC above, $R^4$ is methoxy. In one embodiment of any one of Formulas IA-IC above, $R^4$ is ethoxy. In one embodiment of any one of Formulas IA-IC above, $R^4$ is propoxy. In one embodiment of any one of Formulas IA-IC above, $R^4$ is isopropoxy. In one embodiment of any one of Formulas IA-IC above, $R^4$ is butoxy. In one embodiment of any one of Formulas IA-IC above, $R^4$ is isobutoxy. In one embodiment of any one of Formulas IA-IC above, $R^4$ is sec-butoxy. In one embodiment of any one of Formulas IA-IC above, $R^4$ is tert-butoxy.

In one embodiment of any one of Formulas IA-X above, $R^5$ is hydrogen. In one embodiment of any one of Formulas IA-X above, $R^5$ is $C_1$-$C_6$alkyl. In one embodiment of any one of Formulas IA-X above, $R^5$ is methyl. In one embodiment of any one of Formulas IA-X above, R$ is ethyl. In one embodiment of any one of Formulas IA-X above, $R^5$ is propyl. In one embodiment of any one of Formulas IA-X above, $R^5$ is isopropyl. In one embodiment of any one of Formulas IA-X above, $R^5$ is butyl. In one embodiment of any one of Formulas IA-X above, R$ is isobutyl. In one embodiment of any one of Formulas IA-X above, $R^5$ is sec-butyl. In one embodiment of any one of Formulas IA-X above, $R^5$ is tert-butyl. In one embodiment of any one of Formulas IA-X above, $R^5$ is pentyl. In one embodiment of any one of Formulas IA-X above, $R^5$ is hexyl. In one embodiment of any one of Formulas IA-X above, $R^5$ is $C_3$-$C_6$cycloalkyl. In one embodiment of any one of Formulas IA-X above, $R^5$ is cyclopropyl. In one embodiment of any one of Formulas IA-X above, $R^5$ is cyclobutyl. In one embodiment of any one of Formulas IA-X above, $R^5$ is cyclopentyl. In one embodiment of any one of Formulas IA-X above, $R^5$ is cyclohexyl. In one embodiment of any one of Formulas IA-X above, $R^5$ is $C_1$-$C_6$haloalkyl. In one embodiment of any one of Formulas IA-X above, $R^5$ is trifluoromethyl. In one embodiment of any one of Formulas IA-X above, $R^5$ is trifluoroethyl. In one embodiment of any one of Formulas IA-X above, $R^5$ is hexafluoroisopropyl. In one embodiment of any one of Formulas IA-X above, $R^5$ is $C_1$-$C_6$aliphatic.

In one embodiment of any one of Formulas IA-X above, $R^{5'}$ is hydrogen. In one embodiment of any one of Formulas IA-X above, $R^{5'}$ is $C_1$-$C_6$alkyl. In one embodiment of any one of Formulas IA-X above, $R^{5'}$ is methyl. In one embodiment of any one of Formulas IA-X above, $R^{5'}$ is ethyl. In one embodiment of any one of Formulas IA-X above, $R^{5'}$ is propyl. In one embodiment of any one of Formulas IA-X above, $R^{5'}$ is isopropyl. In one embodiment of any one of Formulas IA-X above, $R^{5'}$ is butyl. In one embodiment of any one of Formulas IA-X above, $R^{5'}$ is isobutyl. In one embodiment of any one of Formulas IA-X above, $R^{5'}$ is sec-butyl. In one embodiment of any one of Formulas IA-X above, $R^{5'}$ is tert-butyl. In one embodiment of any one of Formulas IA-X above, $R^{5'}$ is pentyl. In one embodiment of any one of Formulas IA-X above, $R^{5'}$ is hexyl. In one embodiment of any one of Formulas IA-X above, $R^{5'}$ is $C_3$-$C_6$cycloalkyl. In one embodiment of any one of Formulas IA-X above, $R^{5'}$ is cyclopropyl. In one embodiment of any one of Formulas IA-X above, $R^{5'}$ is cyclobutyl. In one embodiment of any one of Formulas IA-X above, $R^{5'}$ is cyclopentyl. In one embodiment of any one of Formulas IA-X above, $R^{5'}$ is cyclohexyl. In one embodiment of any one of Formulas IA-X above, $R^{5'}$ is $C_1$-$C_6$haloalkyl. In one embodiment of any one of Formulas IA-X above, $R^{5'}$ is trifluoromethyl. In one embodiment of any one of Formulas IA-X above, $R^{5'}$ is trifluoroethyl. In one embodiment of any one of Formulas IA-X above, $R^{5'}$ is hexafluoroisopropyl. In one embodiment of any one of Formulas IA-X above, $R^{5'}$ is $C_1$-$C_6$aliphatic.

In one embodiment of any one of Formulas II-X above, $R^6$ is hydrogen. In one embodiment of any one of Formulas II-X above, $R^6$ is halogen. In one embodiment of any one of Formulas II-X above, $R^6$ is hydroxy. In one embodiment of any one of Formulas II-X above, Reis $C_1$-$C_6$alkoxy. In one embodiment of any one of Formulas II-X above, $R^6$ is $C_1$-$C_6$haloalkoxy. In one embodiment of any one of Formulas II-X above, $R^6$ is $C_2$-$C_6$alkanoyl. In one embodiment of any one of Formulas II-X above, $R^6$ is cyano. In one embodiment of any one of Formulas II-X above, $R^6$ is azido. In one embodiment of any one of Formulas II-X above, $R^6$ is nitro. In one embodiment of any one of Formulas II-X above, $R^6$ is —COOH. In one embodiment of any one of Formulas II-X above, $R^6$ is —$CONH_2$. In one embodiment of any one of Formulas II-X above, $R^6$ is —$P(O)(OH)_2$. In one embodiment of any one of Formulas II-X above, $R^6$ is —$N(R^5)(R^{5'})$. In one embodiment of any one of Formulas II-X above, $R^6$ is —$S(O)R^5$. In one embodiment of any one of Formulas II-X above, $R^6$ is —$SO_2R^5$. In one embodiment of any one of Formulas II-X above, $R^6$ is —$SO_3R^5$. In one embodiment of any one of Formulas II-X above, $R^6$ is —$SO_2N(R^5)(R^{5'})$. In one embodiment of any one of Formulas II-X above, $R^6$ is —$OSO_2R^5$. In one embodiment of any one of Formulas II-X above, $R^6$ is —$N(R^{5'})SO_2R^5$. In one embodiment of any one of Formulas II-X above, $R^6$ is $C_1$-$C_6$alkyl. In one embodiment of any one of Formulas II-X above, $R^6$ is $C_3$-$C_6$cycloalkyl. In one embodiment of any one of Formulas II-X above, $R^6$ is $C_2$-$C_6$alkenyl. In one embodiment of any one of Formulas II-X above, $R^6$ is $C_2$-$C_6$alkynyl. In one embodiment of any one of Formulas II-X above, $R^6$ is $C_1$-$C_6$haloalkyl. In one embodiment of any one of Formulas II-X above, $R^6$ is $C_1$-$C_6$aliphatic. In one embodiment of any one of Formulas II-X above, $R^6$ is thiol. In one embodiment of any one of Formulas II-X above, $R^6$ is $C_1$-$C_6$alkylthiol. In one embodiment of any one of Formulas IA-X above, $R^6$ is ($C_1$-$C_6$haloalkyl)thiol.

In one embodiment of any one of Formulas II-X above, $R^7$ is hydrogen. In one embodiment of any one of Formulas II-X above, $R^7$ is halogen. In one embodiment of any one of Formulas II-X above, $R^7$ is hydroxy. In one embodiment of any one of Formulas II-X above, $R^7$ is $C_1$-$C_6$alkoxy. In one embodiment of any one of Formulas II-X above, $R^7$ is $C_1$-$C_6$haloalkoxy. In one embodiment of any one of Formulas II-X above, $R^7$ is $C_2$-$C_6$alkanoyl. In one embodiment of any one of Formulas II-X above, $R^7$ is cyano. In one embodiment of any one of Formulas II-X above, $R^7$ is azido. In one embodiment of any one of Formulas II-X above, $R^7$ is nitro. In one embodiment of any one of Formulas II-X above, $R^7$ is —COOH. In one embodiment of any one of Formulas II-X above, $R^7$ is —$CONH_2$. In one embodiment of any one of Formulas II-X above, $R^7$ is —$P(O)(OH)_2$. In one embodiment of any one of Formulas II-X above, $R^7$ is —$N(R^5)(R^{5'})$. In one embodiment of any one of Formulas II-X above, $R^7$ is —$S(O)R^5$. In one embodiment of any one of Formulas II-X above, $R^7$ is —$SO_2R^5$. In one embodiment of any one of Formulas II-X above, $R^7$ is —$SO_3R^5$. In one embodiment of any one of Formulas II-X above, $R^7$ is —$SO_2N(R^5)(R^{5'})$. In one embodiment of any one of Formulas II-X above, $R^7$ is —$OSO_2R^5$. In one embodiment of any one of Formulas II-X above, $R^7$ is —$N(R^5)$ $SO_2R^5$. In one embodiment of any one of Formulas II-X above, $R^7$ is $C_1$-$C_6$alkyl. In one embodiment of any one of Formulas II-X above, $R^7$ is $C_3$-$C_6$cycloalkyl. In one embodiment of any one of Formulas II-X above, $R^7$ is $C_2$-$C_6$alkenyl. In one embodiment of any one of Formulas II-X above, $R^7$ is $C_2$-$C_6$alkynyl. In one embodiment of any one of Formulas II-X above, $R^7$ is $C_1$-$C_6$haloalkyl. In one embodiment of any one of Formulas II-X above, $R^7$ is $C_1$-$C_6$aliphatic. In one embodiment of any one of Formulas II-X above, $R^7$ is thiol. In one embodiment of any one of Formulas II-X above, $R^7$ is $C_1$-$C_6$alkylthiol. In one embodiment of any one of Formulas II-X above, $R^7$ is ($C_1$-$C_6$haloalkyl)thiol.

In one embodiment of any one of Formulas IA-X above, $R^A$ is hydrogen. In one embodiment of any one of Formulas IA-X above, $R^A$ is $C_1$-$C_6$alkyl. In one embodiment of any one of Formulas IA-X above, $R^B$ is hydrogen. In one embodiment of any one of Formulas IA-X above, $R^A$ is $C_1$-$C_6$alkyl.

In one embodiment of any one of Formulas VIII-X above, $R^{5a}$ is hydrogen. In one embodiment of any one of Formulas VIII-X above, $R^{5a}$ is $C_1$-$C_6$alkyl. In one embodiment of any one of Formulas VIII-X above, $R^{5a}$ is methyl. In one embodiment of any one of Formulas VIII-X above, $R^{5a}$ is ethyl. In one embodiment of any one of Formulas VIII-X above, $R^{5a}$ is propyl. In one embodiment of any one of Formulas VIII-X above, $R^{5a}$ is isopropyl. In one embodiment of any one of Formulas VIII-X above, $R^{5a}$ is butyl. In one embodiment of any one of Formulas VIII-X above, $R^{5a}$ is isobutyl. In one embodiment of any one of Formulas VIII-X above, $R^{5a}$ is sec-butyl. In one embodiment of any one of Formulas VIII-X above, $R^{5a}$ is tert-butyl. In one embodiment of any one of Formulas VIII-X above, $R^{5a}$ is pentyl. In one embodiment of any one of Formulas VIII-X above, $R^{5a}$ is hexyl. In one embodiment of any one of Formulas VIII-X above, $R^{5a}$ is $C_3$-$C_6$cycloalkyl. In one embodiment of any one of Formulas VIII-X above, $R^{5a}$ is cyclopropyl. In one embodiment of any one of Formulas VIII-X above, $R^{5a}$ is cyclobutyl. In one embodiment of any one of Formulas VIII-X above, $R^{5a}$ is cyclopentyl. In one embodiment of any one of Formulas VIII-X above, $R^{5a}$ is cyclohexyl. In one embodiment of any one of Formulas VIII-X above, $R^{5a}$ is $C_1$-$C_6$haloalkyl. In one embodiment of any one of Formulas VIII-X above, $R^{5a}$ is trifluoromethyl. In one embodiment of any one of Formulas VIII-X above, $R^{5a}$ is trifluoroethyl. In one embodiment of any one of Formulas VIII-X above, $R^{5a}$ is hexafluoroisopropyl. In one embodiment of any one of Formulas VIII-X above, $R^{5a}$ is $C_1$-$C_6$aliphatic.

In one embodiment of any one of Formulas VIII-X above, $R^{5b}$ is hydrogen. In one embodiment of any one of Formulas VIII-X above, $R^{5b}$ is $C_1$-$C_6$alkyl. In one embodiment of any one of Formulas VIII-X above, $R^{5b}$ is methyl. In one embodiment of any one of Formulas VIII-X above, $R^{5b}$ is ethyl. In one embodiment of any one of Formulas VIII-X above, $R^{50}$ is propyl. In one embodiment of any one of Formulas VIII-X above, $R^{5b}$ is isopropyl. In one embodiment of any one of Formulas VIII-X above, $R^{5b}$ is butyl. In one embodiment of any one of Formulas VIII-X above, $R^{5b}$ is isobutyl. In one embodiment of any one of Formulas VIII-X above, $R^{5b}$ is sec-butyl. In one embodiment of any one of Formulas VIII-X above, $R^{5b}$ is tert-butyl. In one embodiment of any one of Formulas VIII-X above, $R^{5b}$ is pentyl. In one embodiment of any one of Formulas VIII-X above, $R^{5b}$ is hexyl. In one embodiment of any one of Formulas VIII-X above, $R^{5b}$ is $C_3$-$C_6$cycloalkyl. In one embodiment of any one of Formulas VIII-X above, $R^{5b}$ is cyclopropyl. In one embodiment of any one of Formulas VIII-X above, $R^{5b}$ is cyclobutyl. In one embodiment of any one of Formulas VIII-X above, $R^{5b}$ is cyclopentyl. In one embodiment of any one of Formulas VIII-X above, $R^{5b}$ is cyclohexyl. In one embodiment of any one of Formulas VIII-X above, $R^{5b}$ is $C_1$-$C_6$haloalkyl. In one embodiment of any one of Formulas VIII-X above, $R^{5b}$ is trifluoromethyl. In one embodiment of any one of Formulas VIII-X above, $R^{5b}$ is trifluoroethyl. In one embodiment of any one of Formulas VIII-X above, Rob is hexafluoroisopropyl. In one embodiment of any one of Formulas VIII-X above, $R^{5b}$ is $C_1$-$C_6$aliphatic.

In one embodiment of any one of Formulas IA-X above, m is 1. In one embodiment of any one of Formulas IA-X above, m is 2. In one embodiment of any one of Formulas IA-X above, m is 3. In one embodiment of any one of Formulas IA-X above, m is 4. In one embodiment of any one of Formulas IA-X above, n is 1. In one embodiment of any one of Formulas IA-X above, nis 2. In one embodiment of any one of Formulas IA-X above, n is 3. In one embodiment of any one of Formulas IA-X above, n is 4.

In one embodiment of any one of Formulas IA-X above, m is 1 and n is 1. In one embodiment of any one of Formulas IA-X above, m is 1 and n is 2. In one embodiment of any one of Formulas IA-X above, m is 1 and n is 3. In one embodiment of any one of Formulas IA-X above, mis 1 and n is 4. In one embodiment of any one of Formulas IA-X above, m is 2 and n is 1. In one embodiment of any one of Formulas IA-X above, m is 2 and n is 2. In one embodiment of any one of Formulas IA-X above, m is 2 and n is 3. In one embodiment of any one of Formulas IA-X above, m is 2 and n is 4. In one embodiment of any one of Formulas IA-X above, m is 3 and n is 1. In one embodiment of any one of Formulas IA-X above, m is 3 and n is 2. In one embodiment of any one of Formulas IA-X above, m is 3 and n is 3. In one embodiment of any one of Formulas IA-X above, m is 3 and n is 4. In one embodiment of any one of Formulas IA-X above, m is 4 and n is 1. In one embodiment of any one of Formulas IA-X above, m is 4 and n is 2. In one embodiment of any one of Formulas IA-X above, m is 4 and n is 3. In one embodiment of any one of Formulas IA-X above, m is 4 and n is 4.

In one embodiment of any one of Formulas IA-IC above, o is 1. In one embodiment of any one of Formulas IA-IC above, o is 2. In one embodiment of any one of Formulas IA-IC above, o is 3. In one embodiment of any one of Formulas IA-IC above, o is 4.

In one embodiment of any one of Formulas II-X above, p is 1. In one embodiment of any one of Formulas II-X above, p is 2. In one embodiment of any one of Formulas II-X above, p is 3. In one embodiment of any one of Formulas II-X above, p is 4.

In one embodiment of any one of Formulas II-X above, q is 0. In one embodiment of any one of Formulas II-X above, q is 1. In one embodiment of any one of Formulas II-X above, q is 2. In one embodiment of any one of Formulas II-X above, q is 3. In one embodiment of any one of Formulas II-X above, q is 4.

In one embodiment of any one of Formulas II-X above, r is 1. In one embodiment of any one of Formulas II-X above, r is 2. In one embodiment of any one of Formulas II-X above, r is 3. In one embodiment of any one of Formulas II-X above, r is 4.

In one embodiment of any one of Formulas II-X above, q is 0, p is 1, and r is 1. In one embodiment of any one of Formulas II-X above, q is 0, p is 1, and r is 2. In one embodiment of any one of Formulas II-X above, q is 0, p is 1, and r is 3. In one embodiment of any one of Formulas II-X above, q is 0, p is 1, and r is 4. In one embodiment of any one of Formulas II-X above, q is 0, p is 2, and r is 1. In one embodiment of any one of Formulas II-X above, q is 0, p is 2, and r is 2. In one embodiment of any one of Formulas II-X above, q is 0, p is 2, and r is 3. In one embodiment of any one of Formulas II-X above, q is 0, p is 2, and r is 4. In one embodiment of any one of Formulas II-X above, q is 0, p is 3, and r is 1. In one embodiment of any one of Formulas II-X above, q is 0, p is 3, and r is 2. In one embodiment of any one of Formulas II-X above, q is 0, p is 3, and r is 3. In one embodiment of any one of Formulas II-X above, q is 0, p is 3, and r is 4. In one embodiment of any one of Formulas II-X above, q is 0, p is 4, and r is 1. In one embodiment of any one of Formulas II-X above, q is 0, p is 4, and r is 2. In one embodiment of any one of Formulas II-X above, q is 0, p is 4, and r is 3. In one embodiment of any one of Formulas II-X above, q is 0, p is 4, and r is 4.

In one embodiment of any one of Formulas II-X above, q is 1, p is 1, and r is 1. In one embodiment of any one of Formulas II-X above, q is 1, p is 1, and r is 2. In one embodiment of any one of Formulas II-X above, q is 1, p is 1, and r is 3. In one embodiment of any one of Formulas II-X above, q is 1, p is 1, and r is 4. In one embodiment of any one of Formulas II-X above, q is 1, p is 2, and r is 1. In one embodiment of any one of Formulas II-X above, q is 1, p is 2, and r is 2. In one embodiment of any one of Formulas II-X above, q is 1, p is 2, and r is 3. In one embodiment of any one of Formulas II-X above, q is 1, p is 2, and r is 4. In one embodiment of any one of Formulas II-X above, q is 1, p is 3, and r is 1. In one embodiment of any one of Formulas II-X above, q is 1, p is 3, and r is 2. In one embodiment of any one of Formulas II-X above, q is 1, p is 3, and r is 3. In one embodiment of any one of Formulas II-X above, q is 1, p is 3, and r is 4. In one embodiment of any one of Formulas II-X above, q is 1, p is 4, and r is 1. In one embodiment of any one of Formulas II-X above, q is 1, p is 4, and r is 2. In one embodiment of any one of Formulas II-X above, q is 1, p is 4, and r is 3. In one embodiment of any one of Formulas II-X above, q is 1, p is 4, and r is 4.

In one embodiment of any one of Formulas II-X above, q is 2, p is 1, and r is 1. In one embodiment of any one of Formulas II-X above, q is 2, p is 1, and r is 2. In one embodiment of any one of Formulas II-X above, q is 2, p is 1, and r is 3. In one embodiment of any one of Formulas II-X above, q is 2, p is 1, and r is 4. In one embodiment of any one of Formulas II-X above, q is 2, p is 2, and r is 1. In one embodiment of any one of Formulas II-X above, q is 2, p is 2, and r is 2. In one embodiment of any one of Formulas II-X above, q is 2, p is 2, and r is 3. In one embodiment of any one of Formulas II-X above, q is 2, p is 2, and r is 4. In one embodiment of any one of Formulas II-X above, q is 2, p is 3, and r is 1. In one embodiment of any one of Formulas II-X above, q is 2, p is 3, and r is 2. In one embodiment of any one of Formulas II-X above, q is 2, p is 3, and r is 3. In one embodiment of any one of Formulas II-X above, q is 2, p is 3, and r is 4. In one embodiment of any one of Formulas II-X above, q is 2, p is 4, and r is 1. In one embodiment of any one of Formulas II-X above, q is 2, p is 4, and r is 2. In one embodiment of any one of Formulas II-X above, q is 2, p is 4, and r is 3. In one embodiment of any one of Formulas II-X above, q is 2, p is 4, and r is 4.

In one embodiment of any one of Formulas II-X above, q is 3, p is 1, and r is 1. In one embodiment of any one of Formulas II-X above, q is 3, p is 1, and r is 2. In one embodiment of any one of Formulas II-X above, q is 3, p is 1, and r is 3. In one embodiment of any one of Formulas II-X above, q is 3, p is 1, and r is 4. In one embodiment, q is 3, p is 2, and r is 1. In one embodiment of any one of Formulas II-X above, q is 3, p is 2, and r is 2. In one embodiment of any one of Formulas II-X above, q is 3, p is 2, and r is 3. In one embodiment of any one of Formulas II-X above, q is 3, p is 2, and r is 4. In one embodiment of any one of Formulas II-X above, q is 3, p is 3, and r is 1. In one embodiment of any one of Formulas II-X above, q is 3, p is 3, and r is 2. In one embodiment of any one of Formulas II-X above, q is 3, p is 3, and r is 3. In one embodiment of any one of Formulas II-X above, q is 3, p is 3, and r is 4. In one embodiment of any one of Formulas II-X above, q is 3, p is 4, and r is 1. In one embodiment of any one of Formulas II-X above, q is 3, p is 4, and r is 2. In one embodiment of any one of Formulas II-X above, q is 3, p is 4, and r is 3. In one embodiment of any one of Formulas II-X above, q is 3, p is 4, and r is 4.

In one embodiment of any one of Formulas II-X above, q is 4, p is 1, and r is 1. In one embodiment of any one of Formulas II-X above, q is 4, p is 1, and r is 2. In one embodiment of any one of Formulas II-X above, q is 4, p is 1, and r is 3. In one embodiment of any one of Formulas II-X above, q is 4, p is 1, and r is 4. In one embodiment of any one of Formulas II-X above, q is 4, p is 2, and r is 1. In one embodiment of any one of Formulas II-X above, q is 4, p is 2, and r is 2. In one embodiment of any one of Formulas II-X above, q is 4, p is 2, and r is 3. In one embodiment of any one of Formulas II-X above, q is 4, p is 2, and r is 4. In one embodiment of any one of Formulas II-X above, q is 4, p is 3, and r is 1. In one embodiment of any one of Formulas II-X above, q is 4, p is 3, and r is 2. In one embodiment of any one of Formulas II-X above, q is 4, p is 3, and r is 3. In one embodiment of any one of Formulas II-X above, q is 4, p is 3, and r is 4. In one embodiment of any one of Formulas II-X above, q is 4, p is 4, and r is 1. In one embodiment of any one of Formulas II-X above, q is 4, p is 4, and r is 2. In one embodiment of any one of Formulas II-X above, q is 4, p is 4, and r is 3. In one embodiment of any one of Formulas II-X above, q is 4, p is 4, and r is 4.

In one embodiment of any one of Formulas III, IV, VI, VII, IX, or X above, sis 1. In one embodiment of any one of Formulas III, IV, VI, VII, IX, or X above, s is 2. In one embodiment of any one of Formulas IV, VI, or X above, t is 1. In one embodiment of any one of Formulas IV, VI, or X above, t is 2.

In one embodiment of any one of Formulas IV, VI, or X above, s is 1 and t is 1. In one embodiment of any one of Formulas IV, VI, or X above, s is 1 and t is 2. In one embodiment of any one of Formulas IV, VI, or X above, s is 2 and t is 1. In one embodiment of any one of Formulas IV, VI, or X above, s is 2 and t is 2.

In one embodiment,

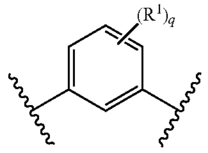

is selected from:

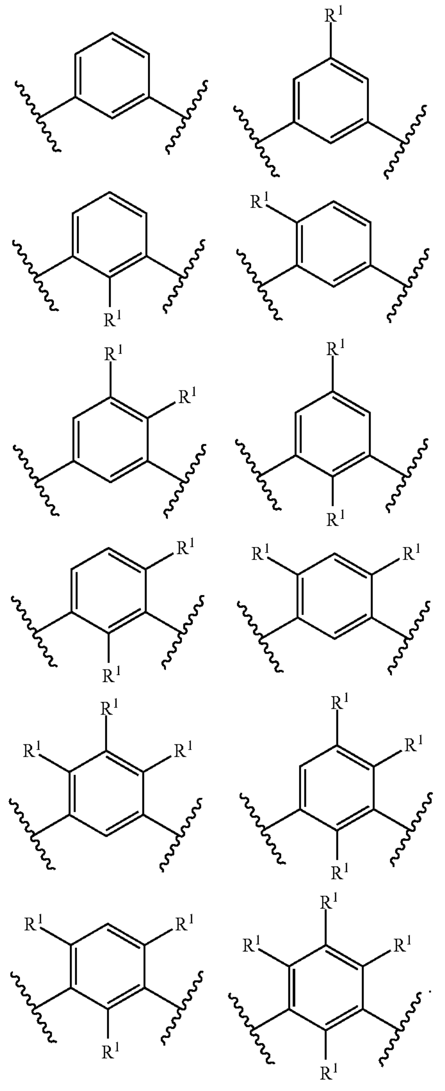

Additional non-limiting examples of

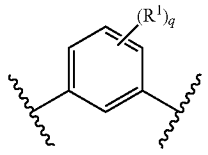

include:
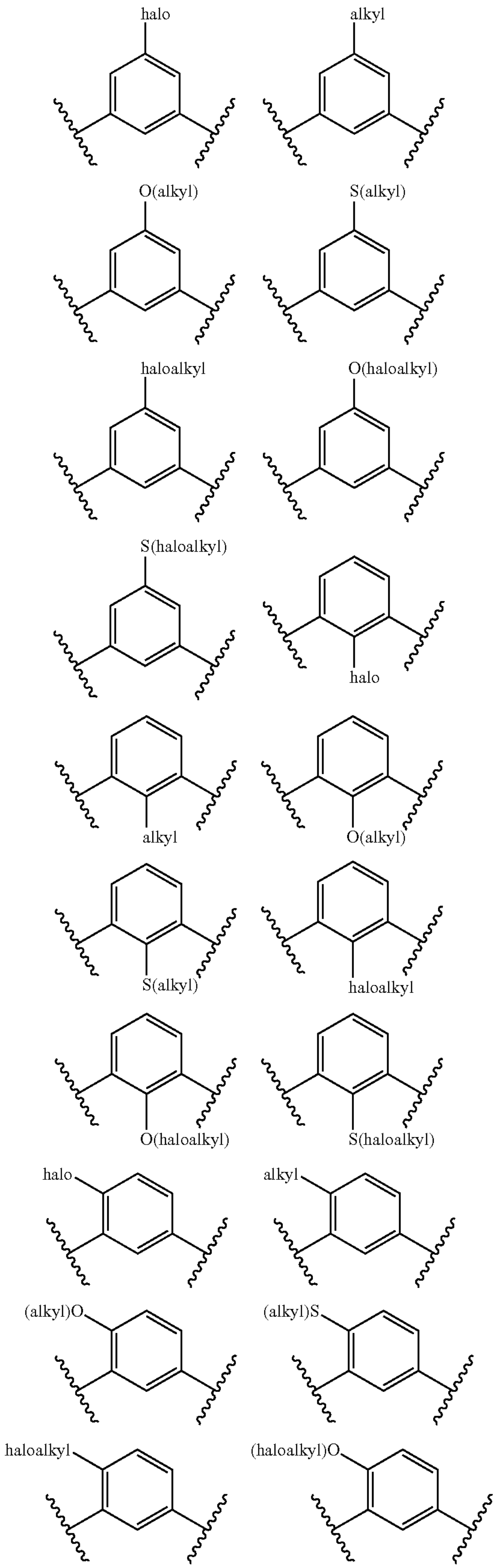
-continued
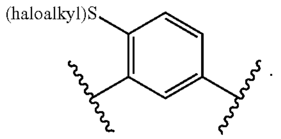
Additional non-limiting examples
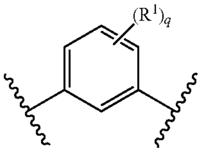
of include:
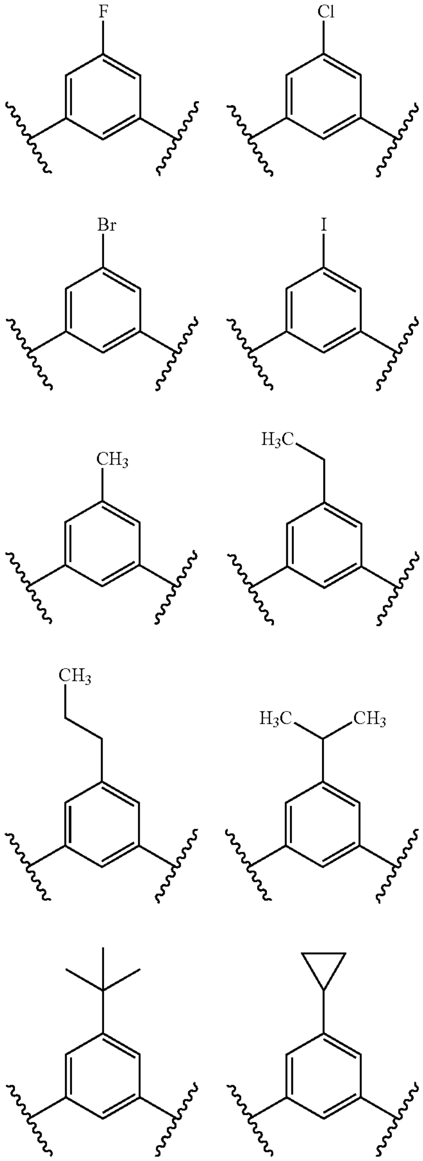

-continued
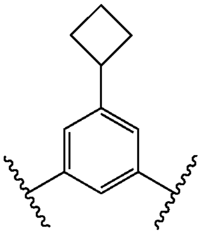
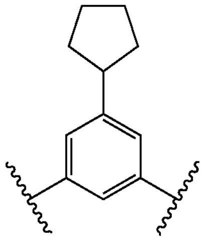
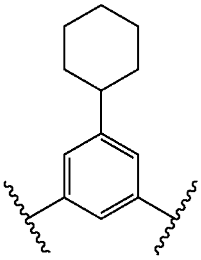
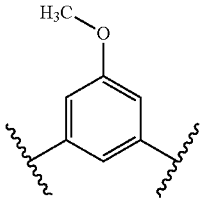
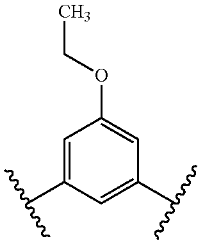
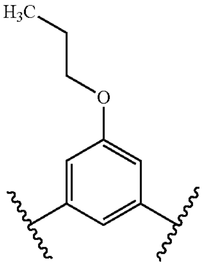
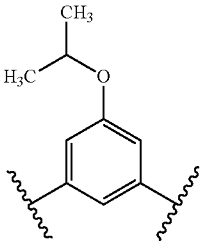
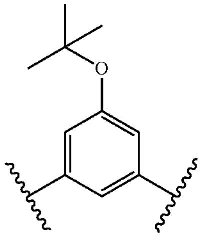
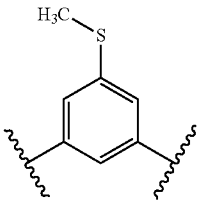
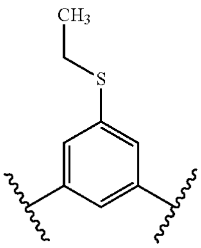
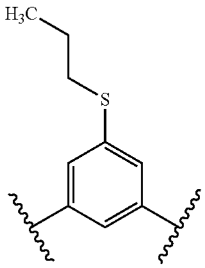
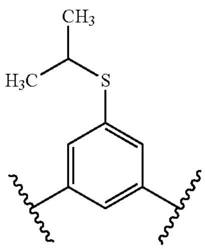
-continued
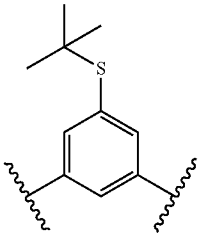
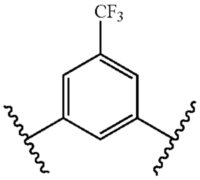
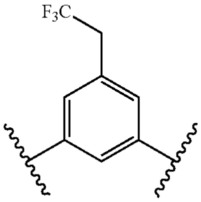
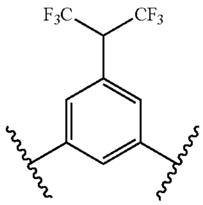
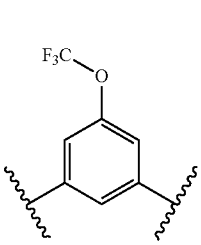
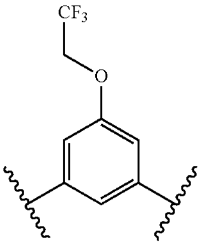
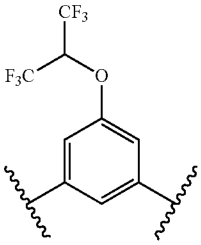
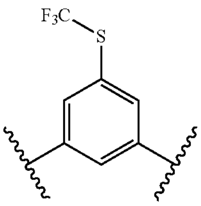
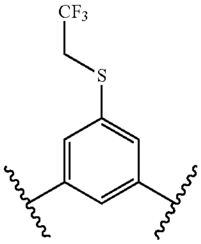
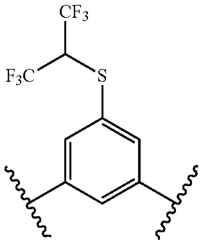
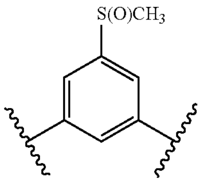
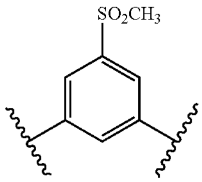
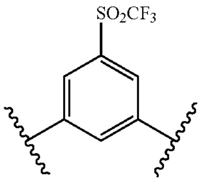
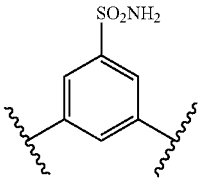

-continued
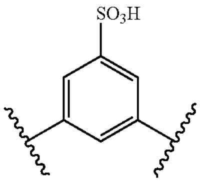
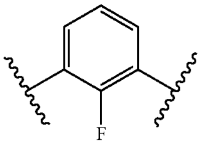
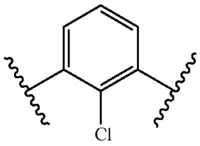
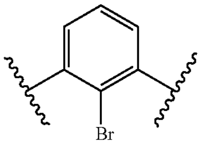
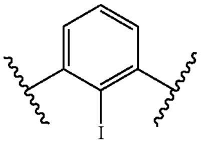
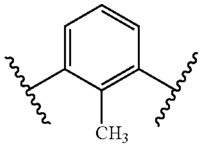
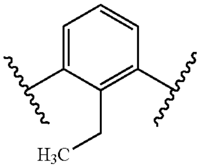
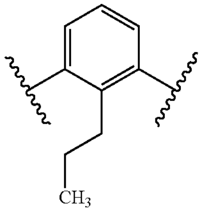
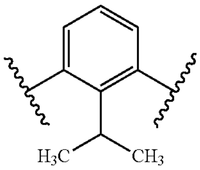
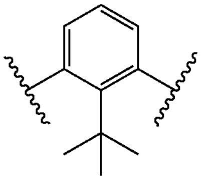
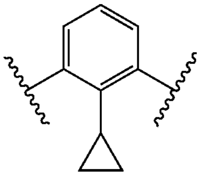
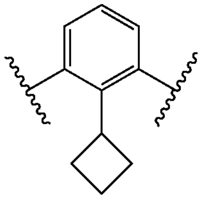
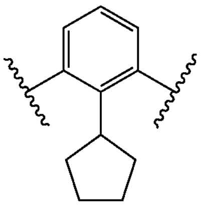
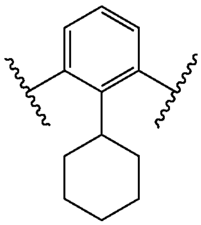
-continued
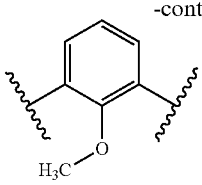
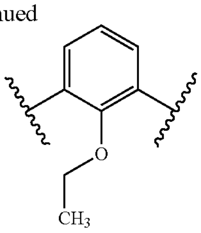
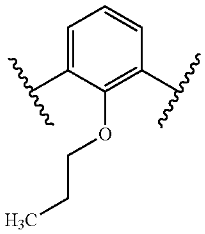
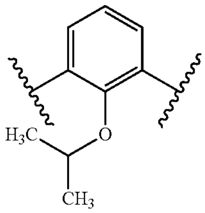
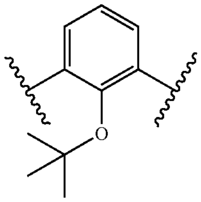
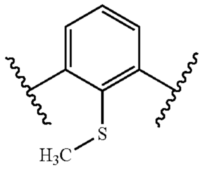
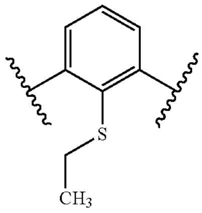
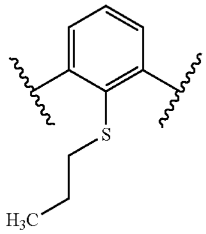
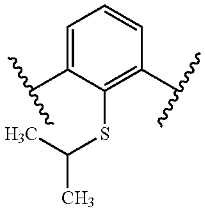
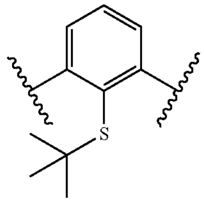
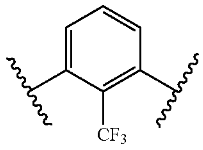
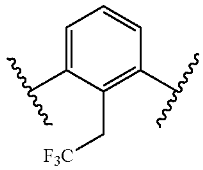
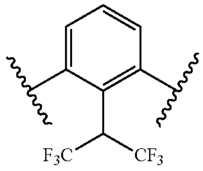
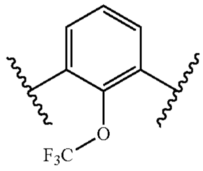
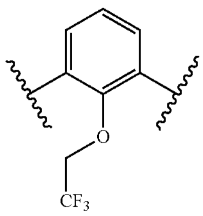
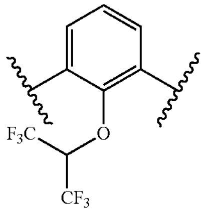

-continued
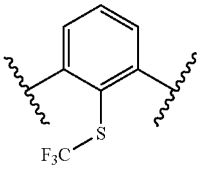
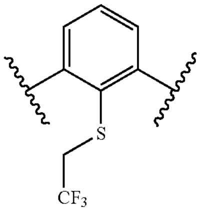
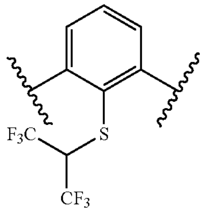
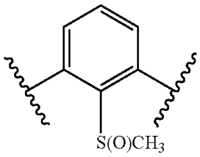
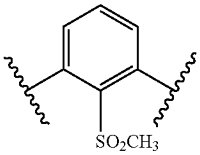
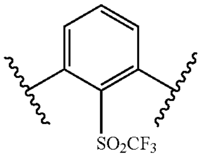
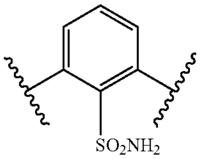
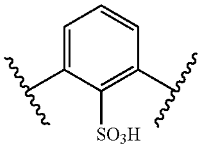
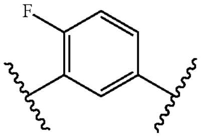
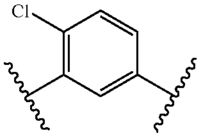
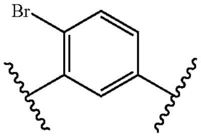
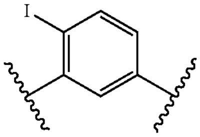
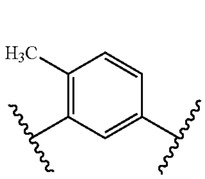
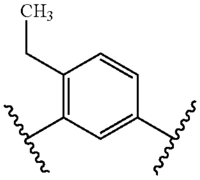
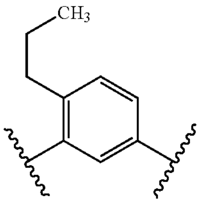
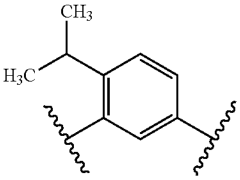
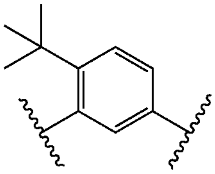
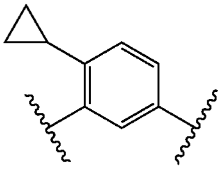
-continued
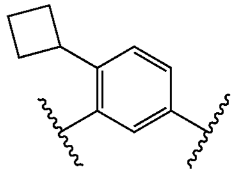
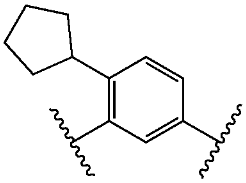
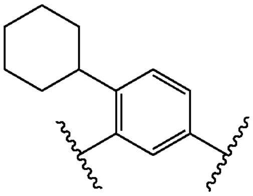
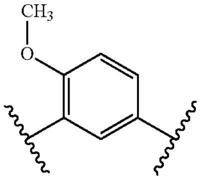
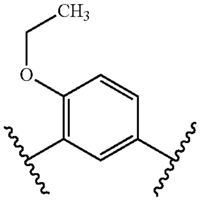
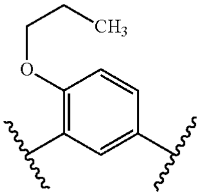
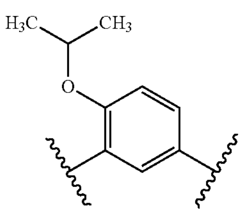
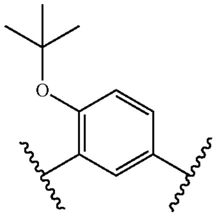
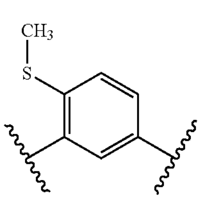
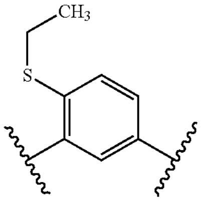
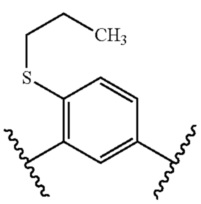
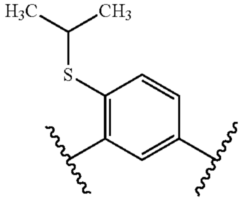
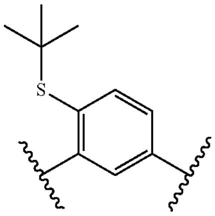
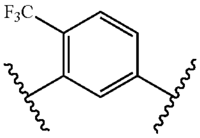
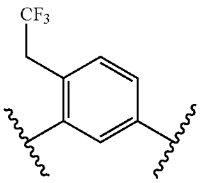
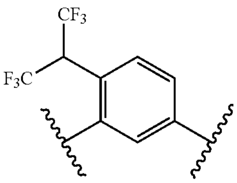

-continued
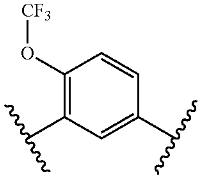
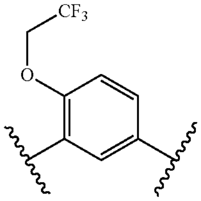
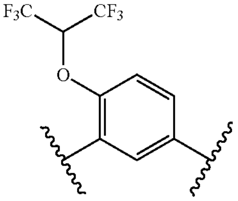
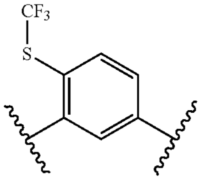
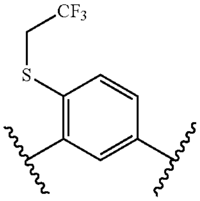
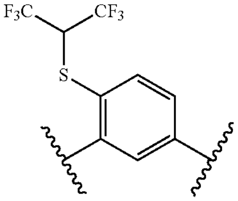
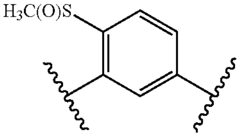
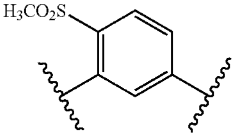
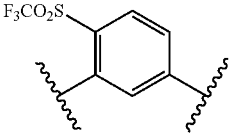
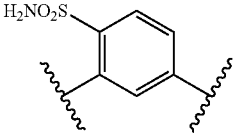
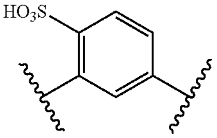
.
Additional non-limiting examples of
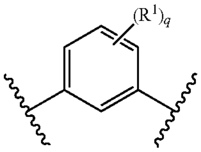
include:
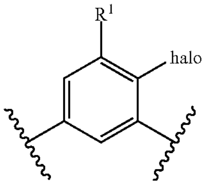
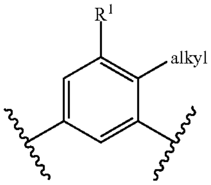
-continued
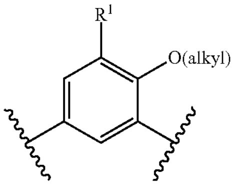
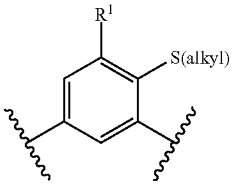
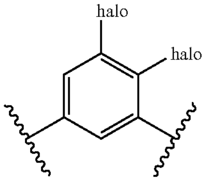
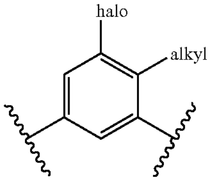
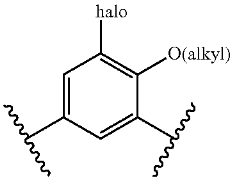
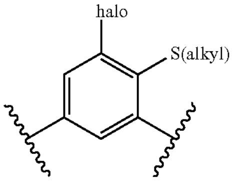
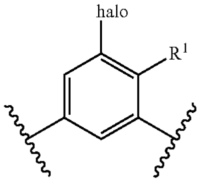
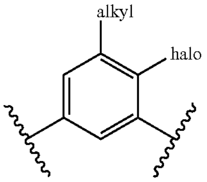
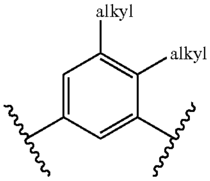
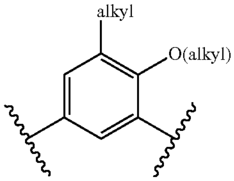
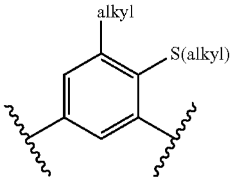
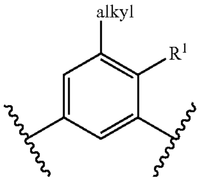
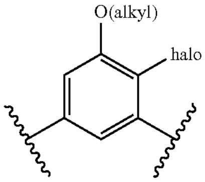
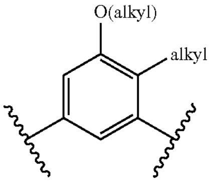
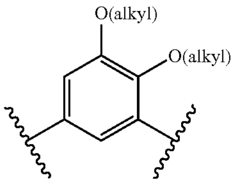
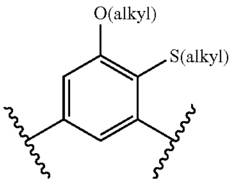
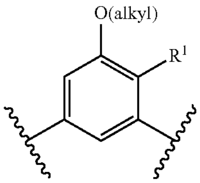
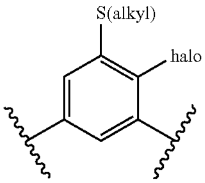

-continued
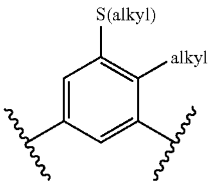
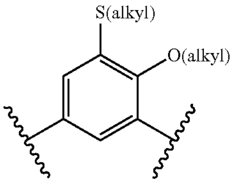
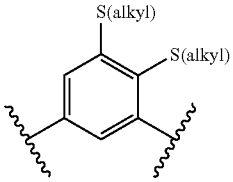
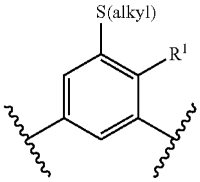
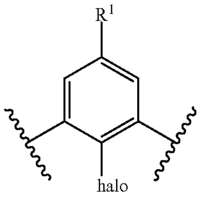
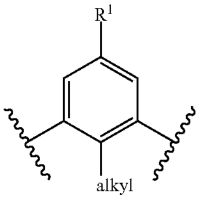
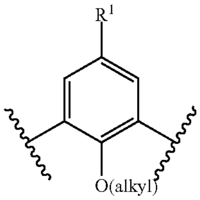
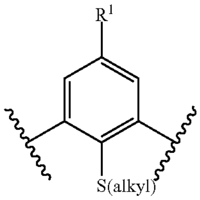
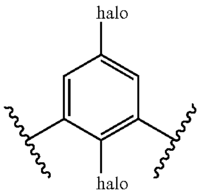
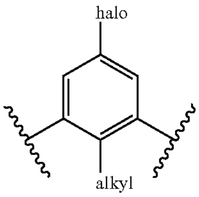
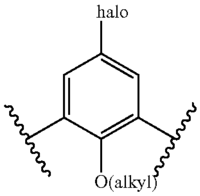
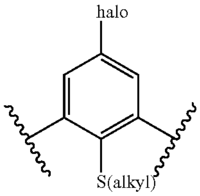
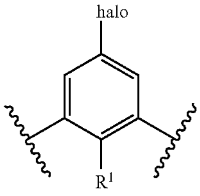
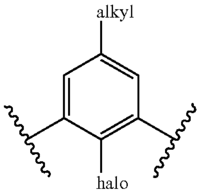
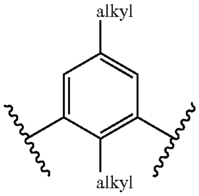
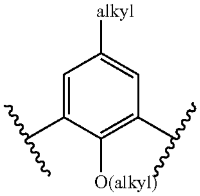
-continued
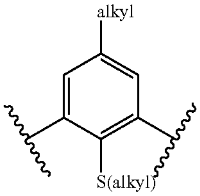
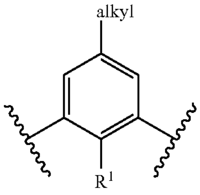
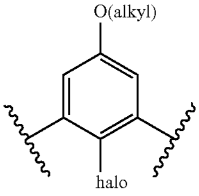
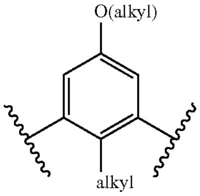
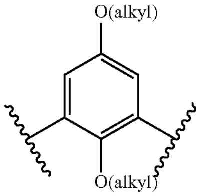
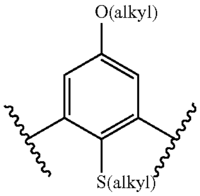
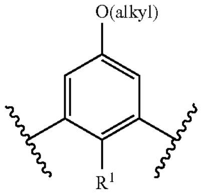
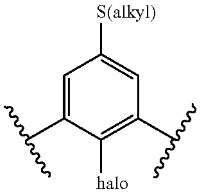
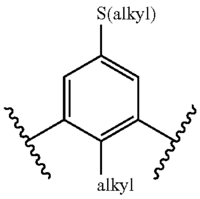
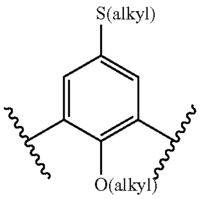
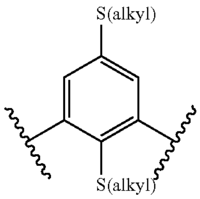
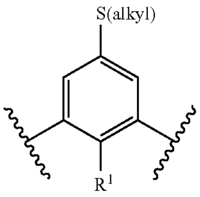
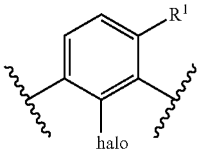
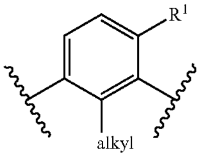
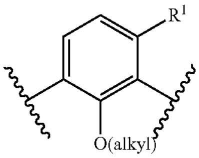
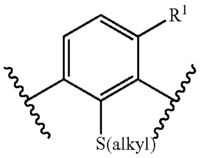
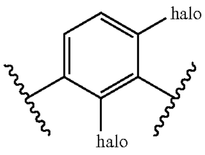
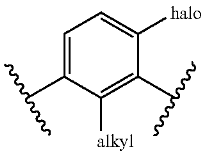

-continued
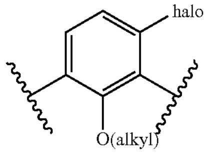
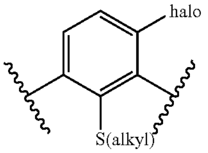
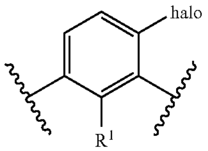
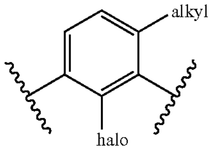
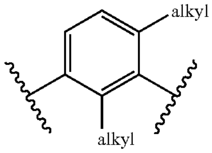
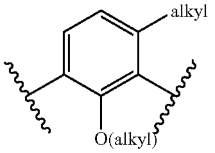
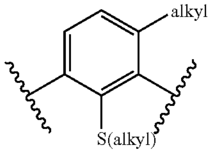
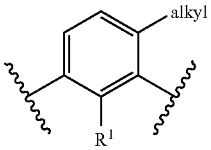
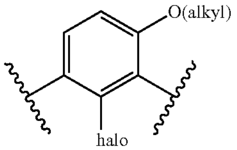
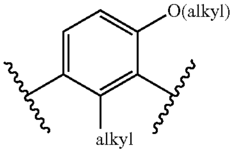
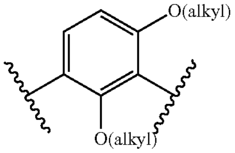
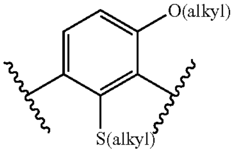
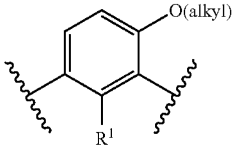
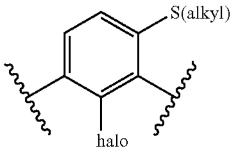
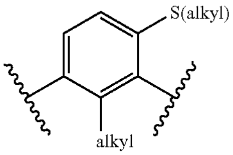
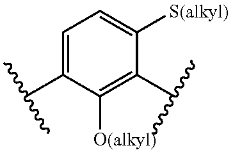
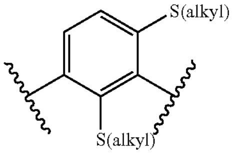
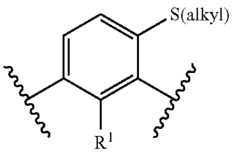
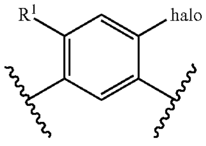
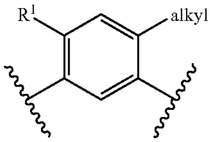
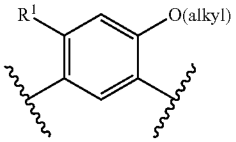
-continued
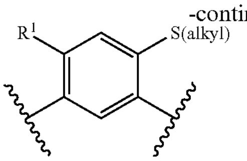
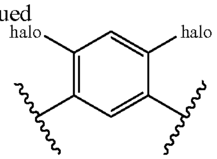
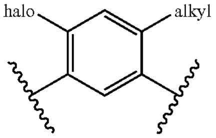
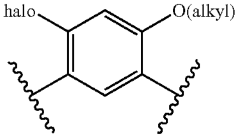
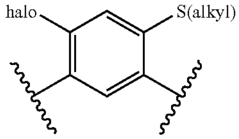
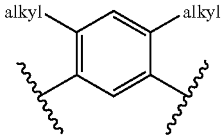
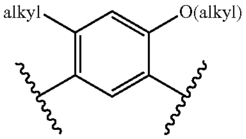
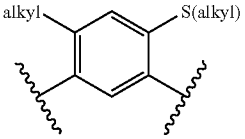
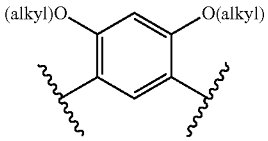
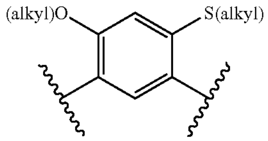
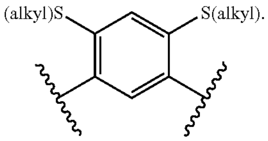
Additional non-limiting examples of
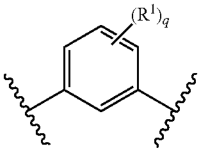
include:
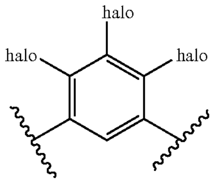
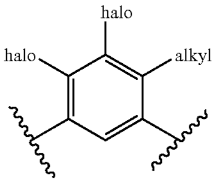
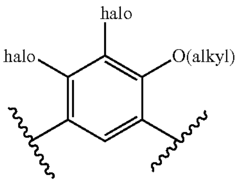
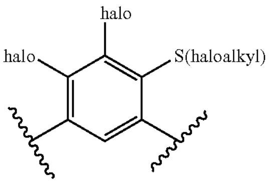

-continued
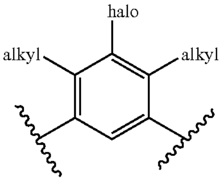
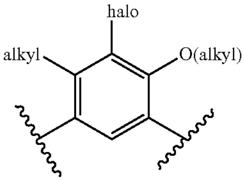
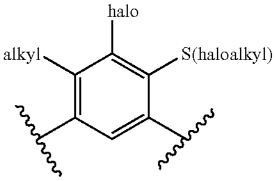
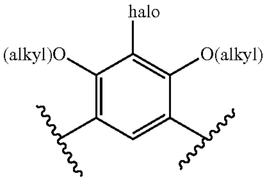
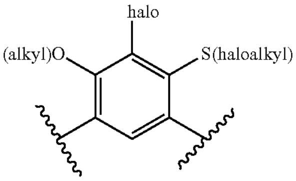
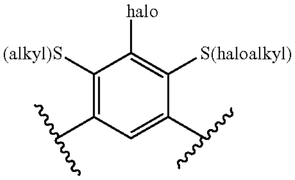
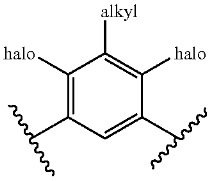
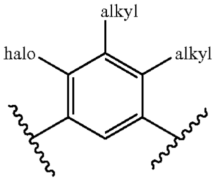
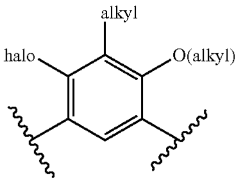
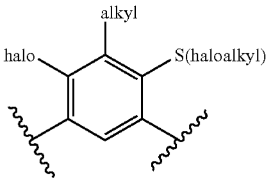
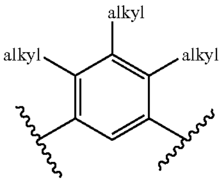
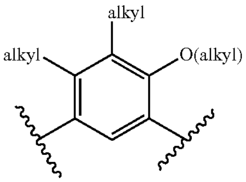
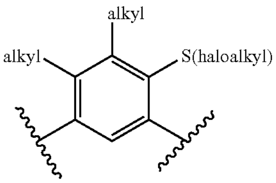
-continued
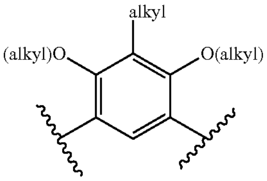
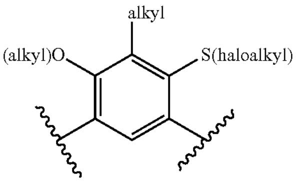
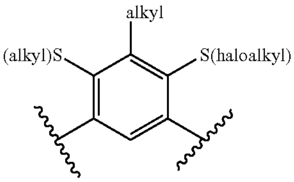
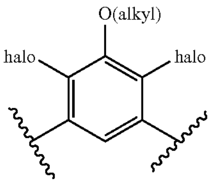
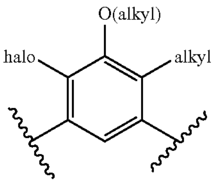
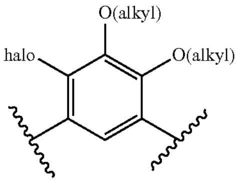
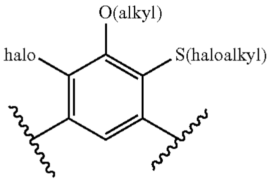
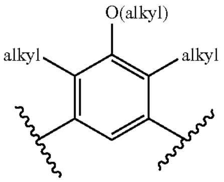
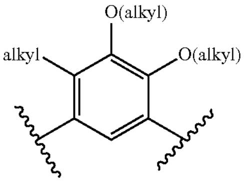
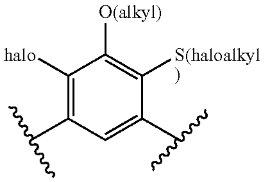
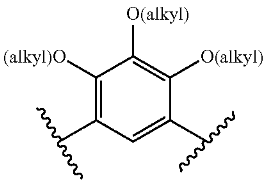
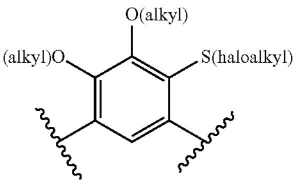

-continued
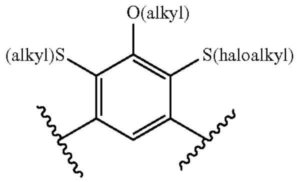
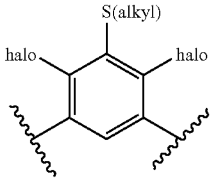
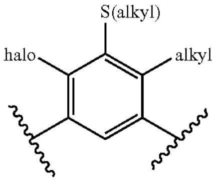
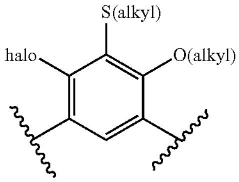
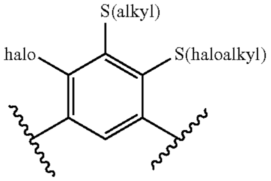
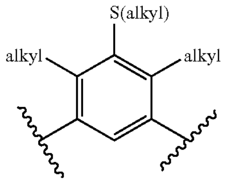
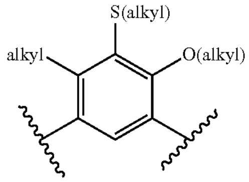
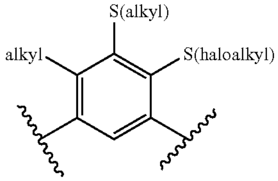
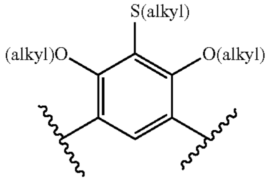
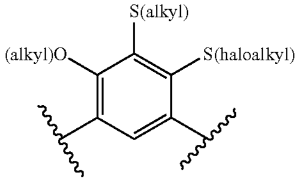
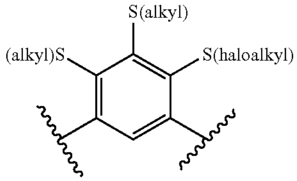
-continued
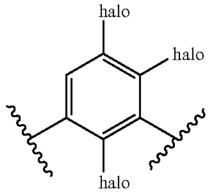
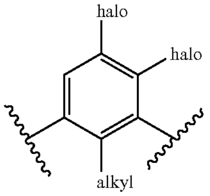
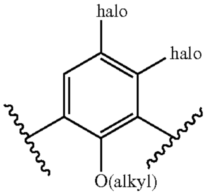
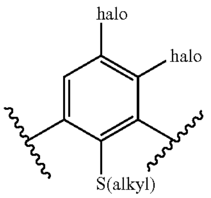
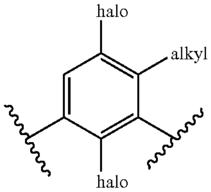
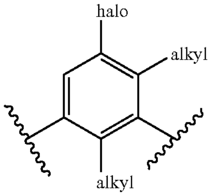
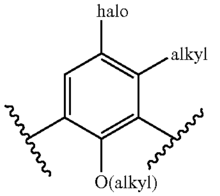
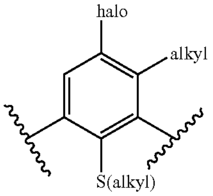
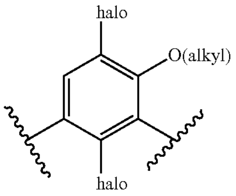
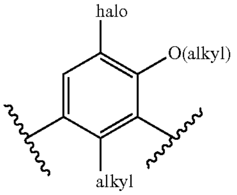
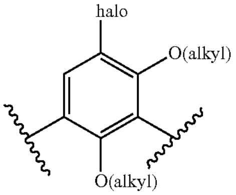
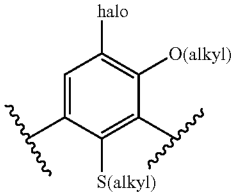
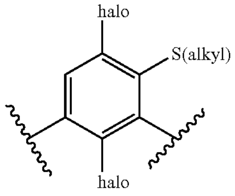
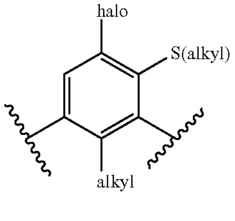
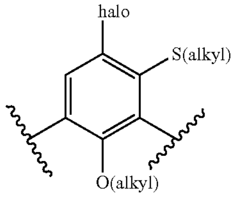

-continued
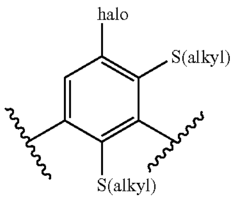
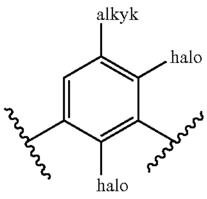
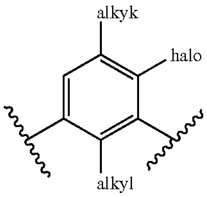
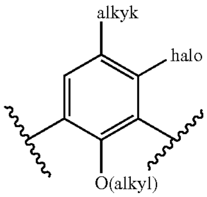
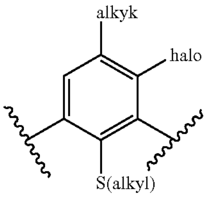
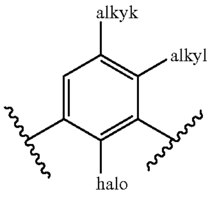
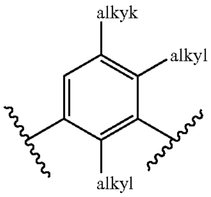
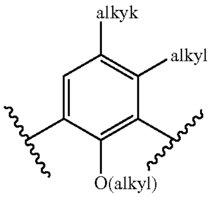
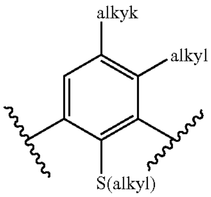
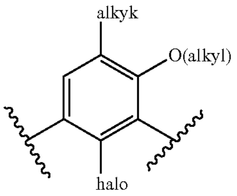
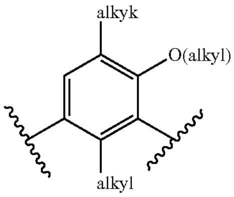
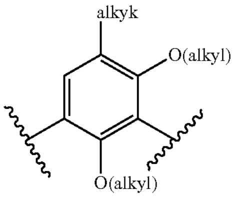
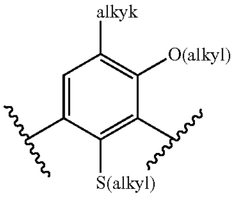
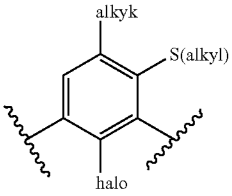
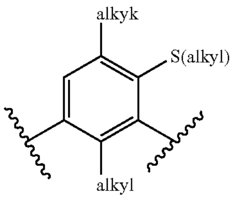
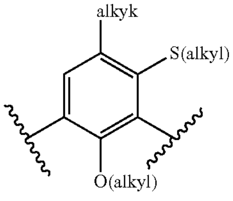
-continued
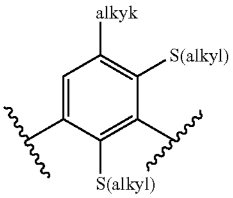
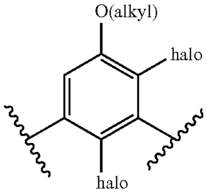
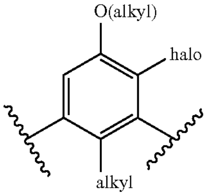
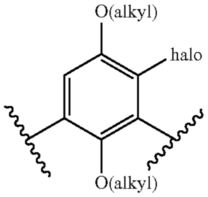
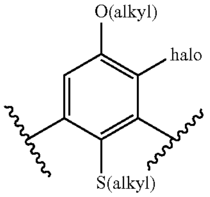
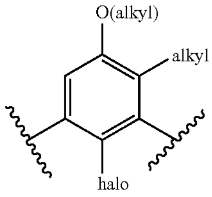
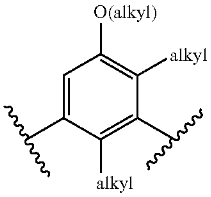
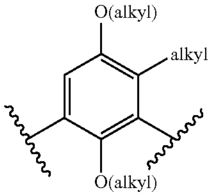
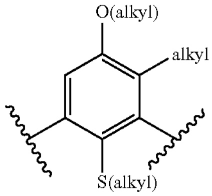
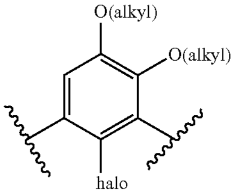
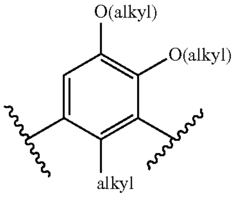
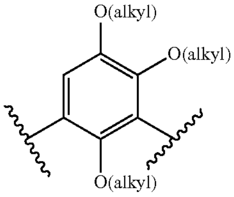
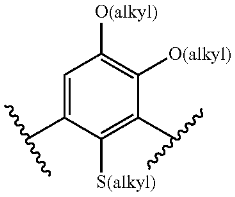
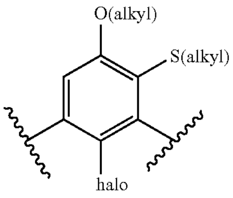
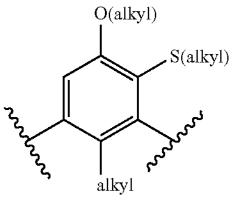

-continued
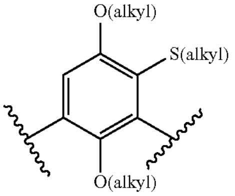
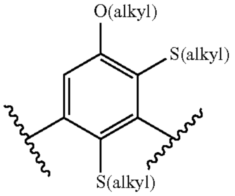
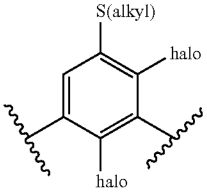
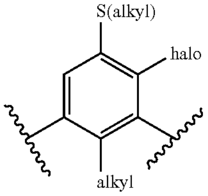
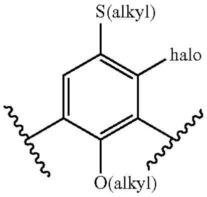
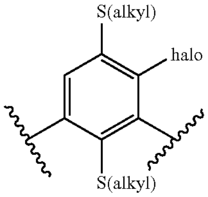
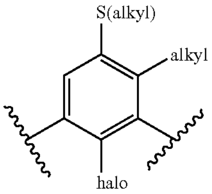
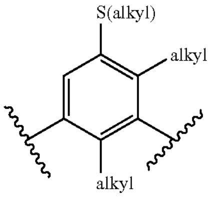
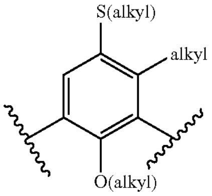
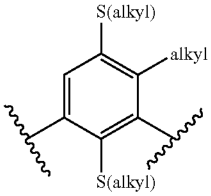
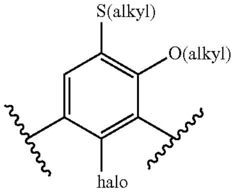
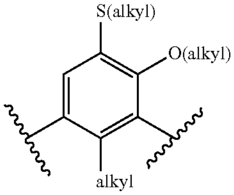
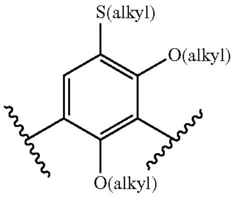
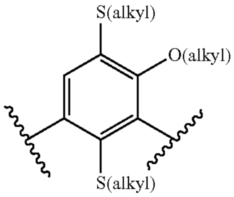
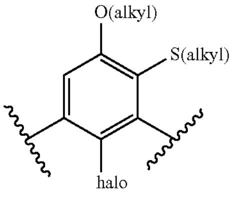
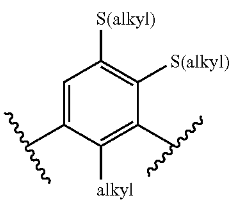
-continued
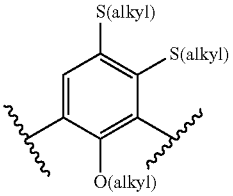
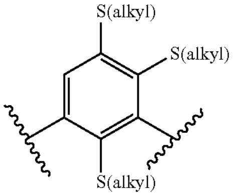
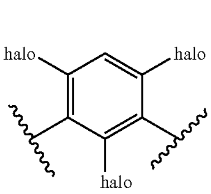
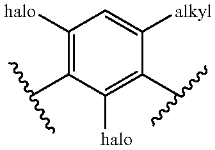
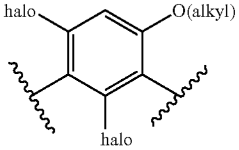
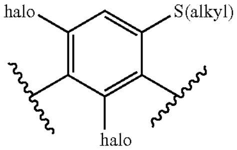
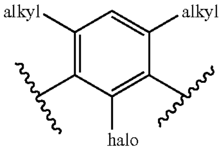
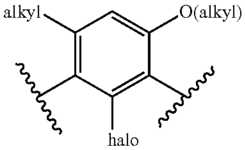
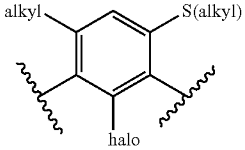
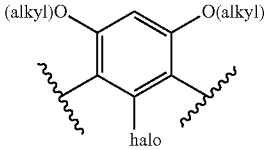
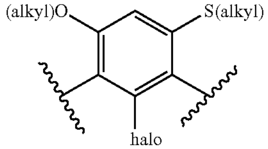
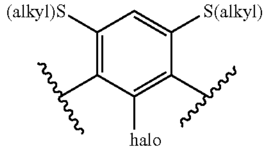
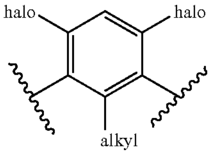
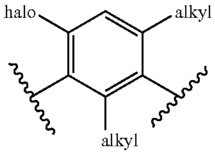
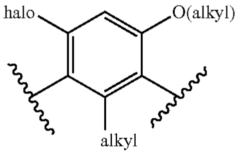
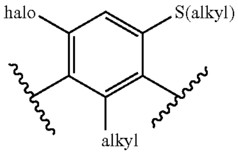

-continued
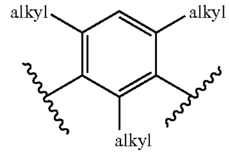
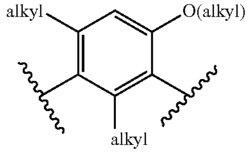
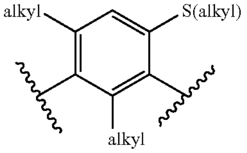
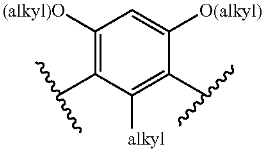
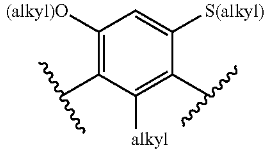
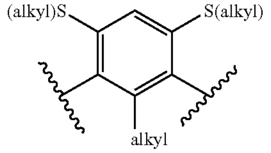
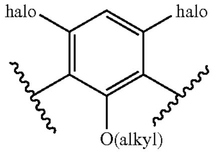
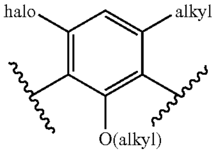
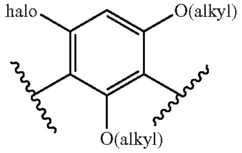
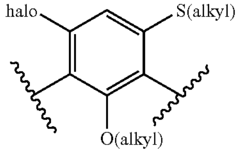
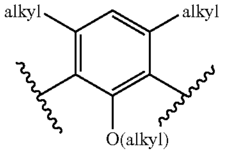
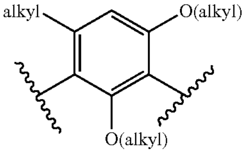
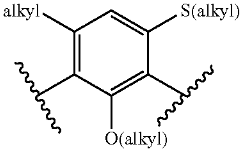
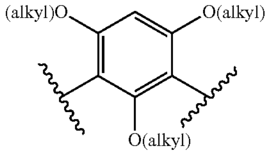
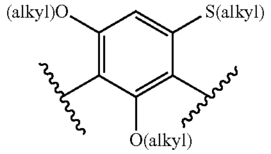
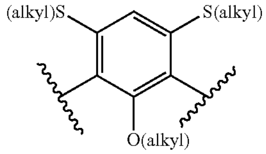
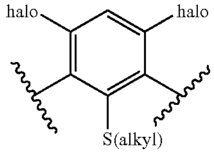
-continued
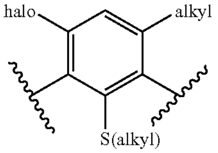
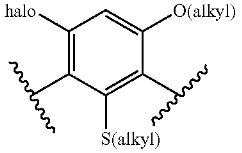
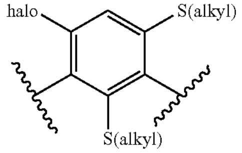
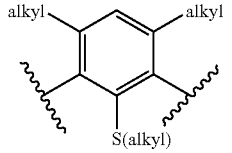
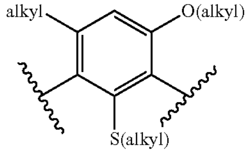
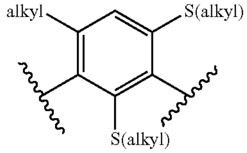
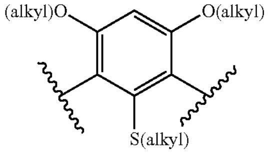
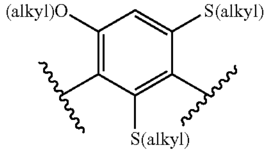
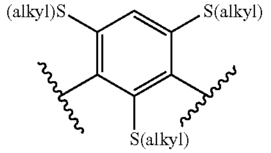
In one embodiment,
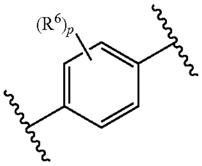
is selected from:
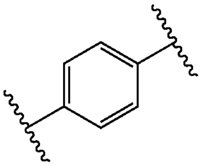
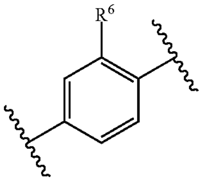
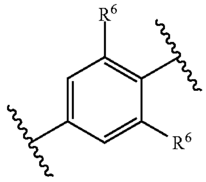
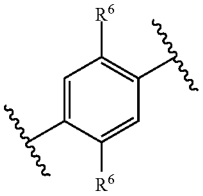

-continued
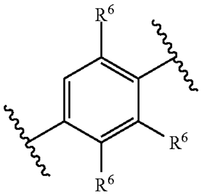
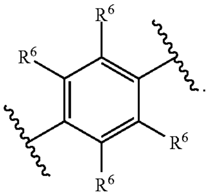
.
Additional non-limiting examples of
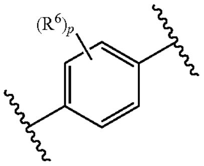
include:
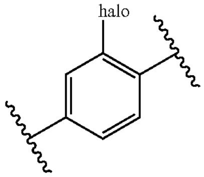
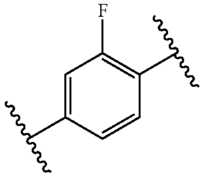
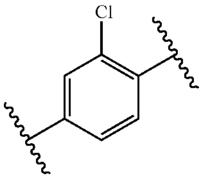
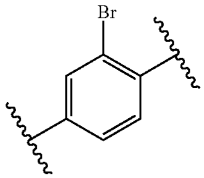
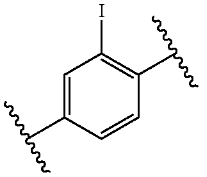
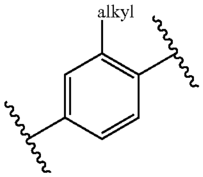
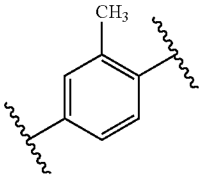
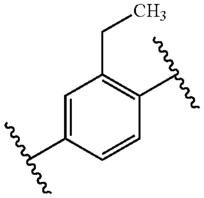
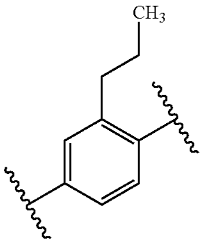
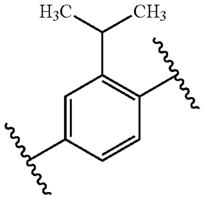
-continued
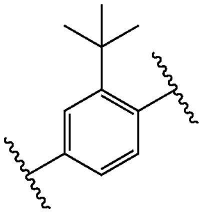
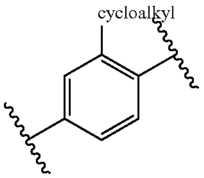
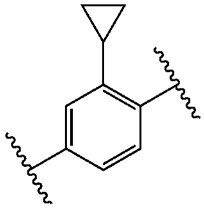
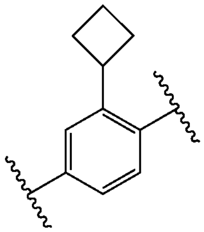
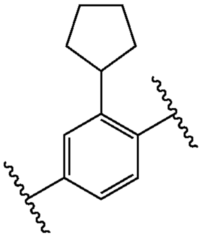
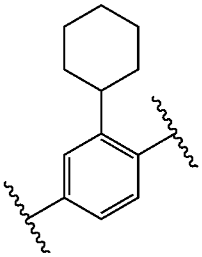
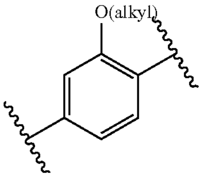
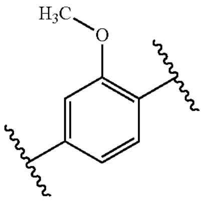
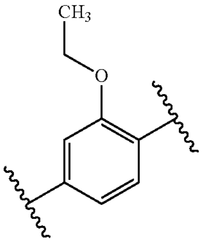
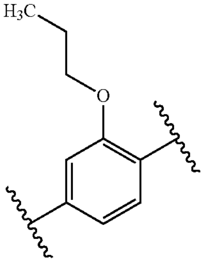
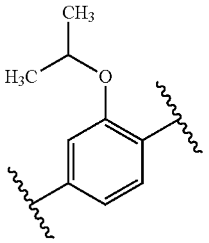
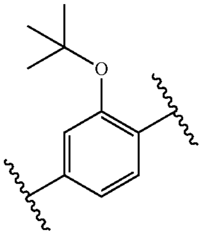
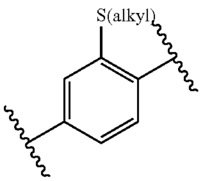
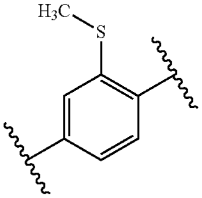

-continued
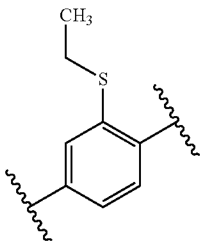
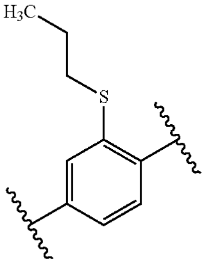
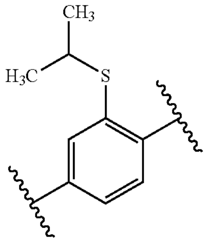
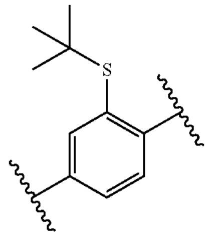
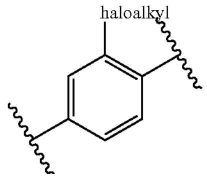
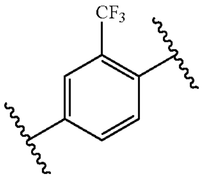
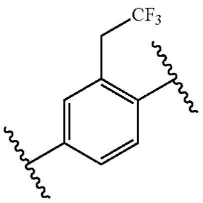
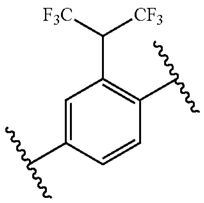
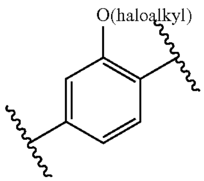
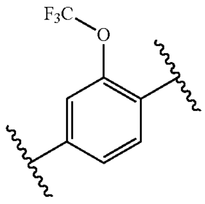
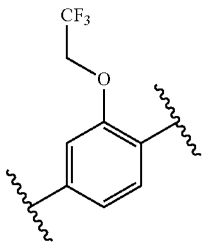
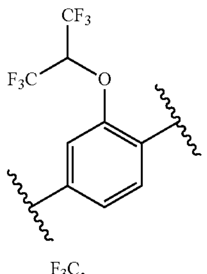
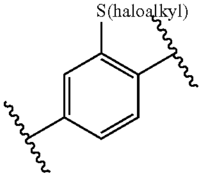
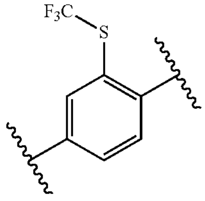
-continued
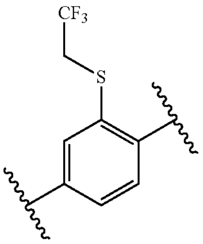
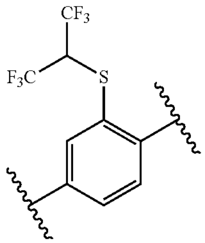
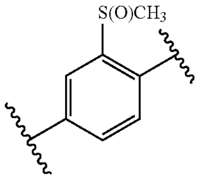
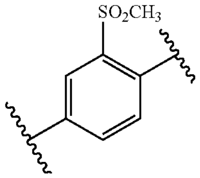
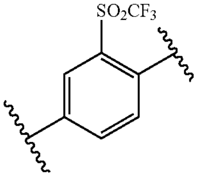
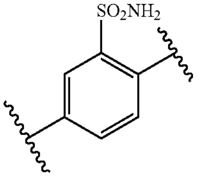
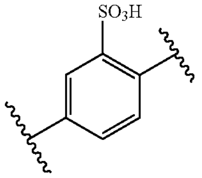
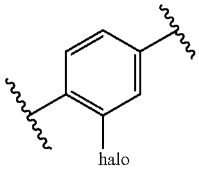
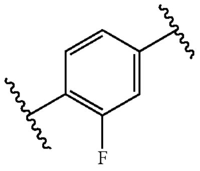
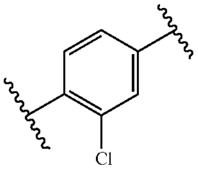
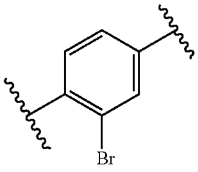
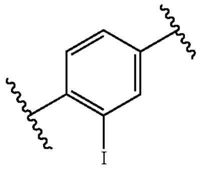
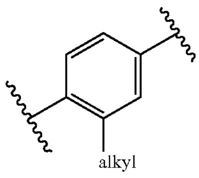
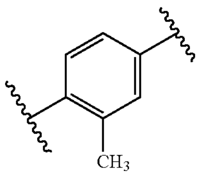
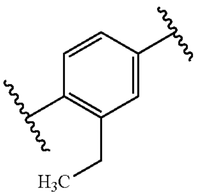
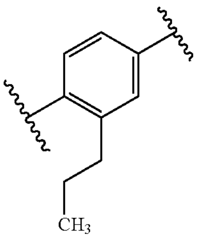

-continued
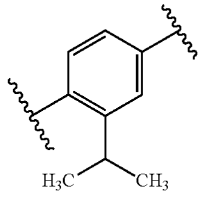
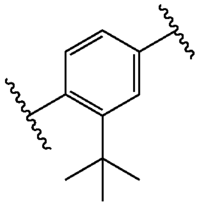
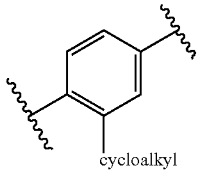
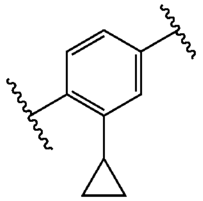
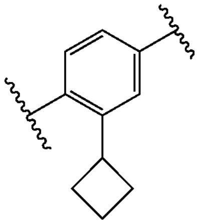
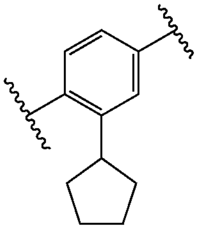
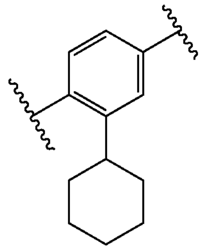
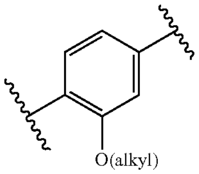
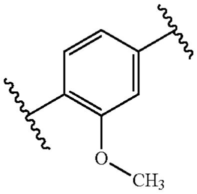
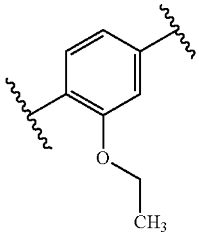
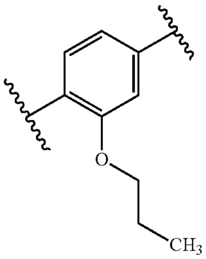
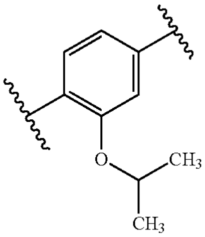
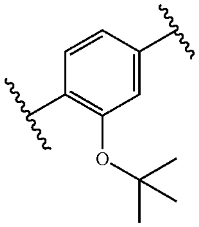
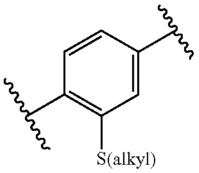
-continued
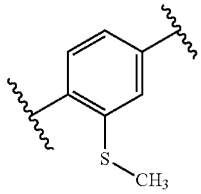
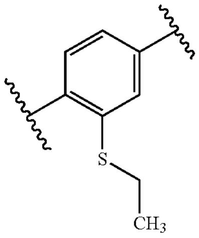
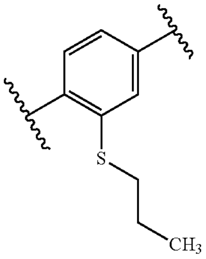
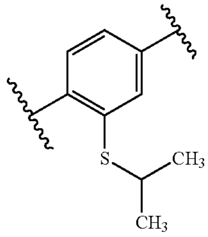
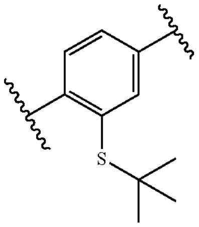
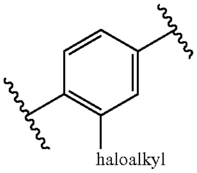
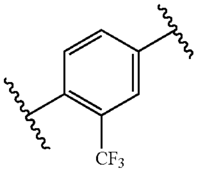
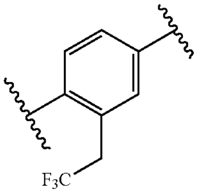
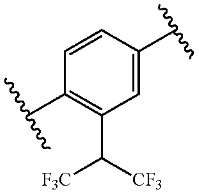
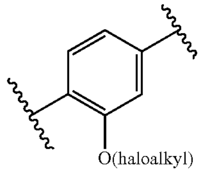
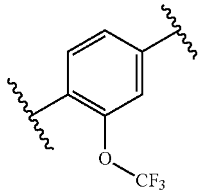
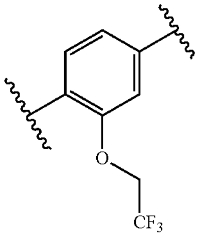
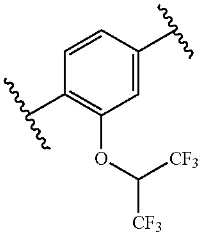
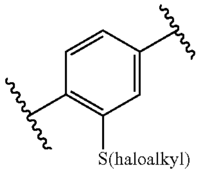

-continued
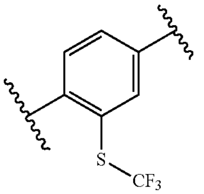
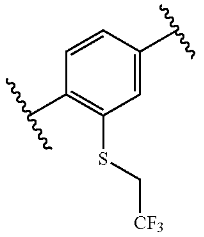
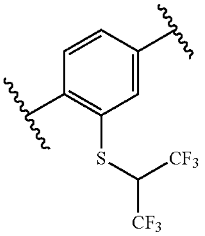
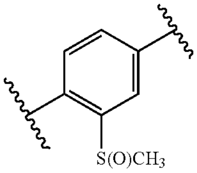
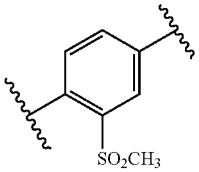
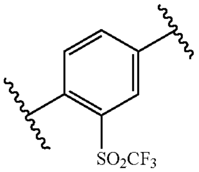
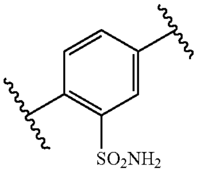
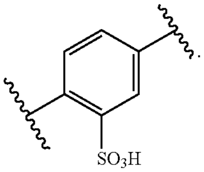
Additional non-limiting examples of
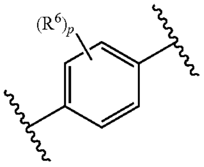
include:
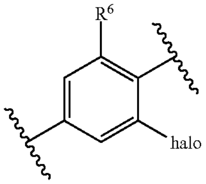
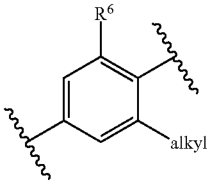
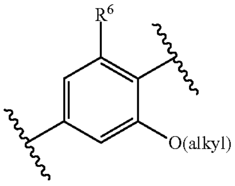
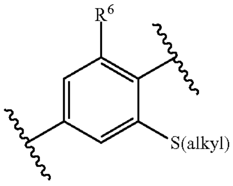
-continued
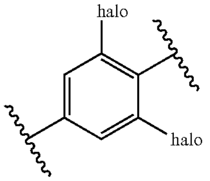
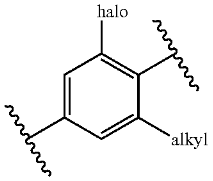
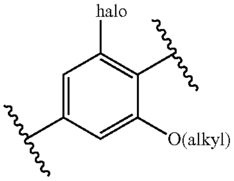
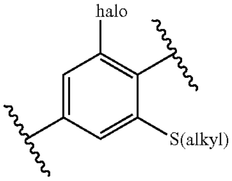
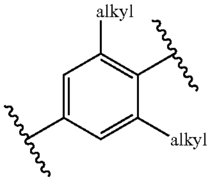
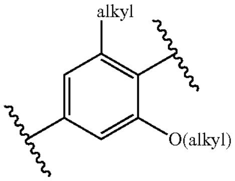
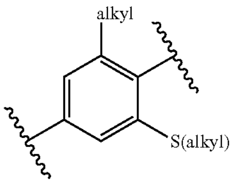
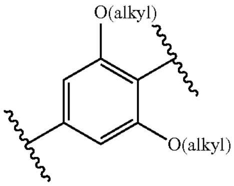
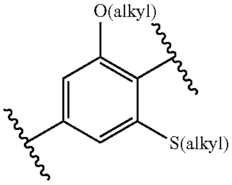
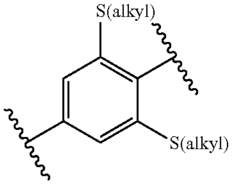
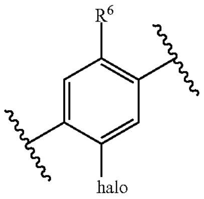
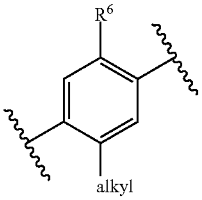
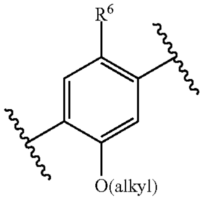
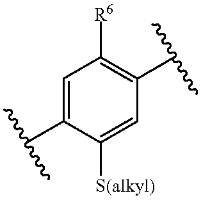
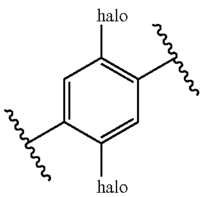
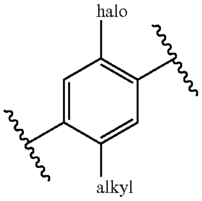
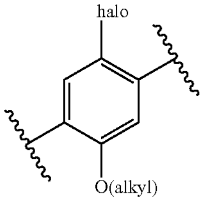
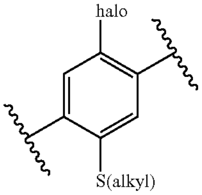

-continued
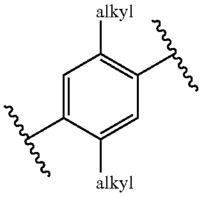
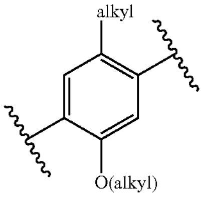
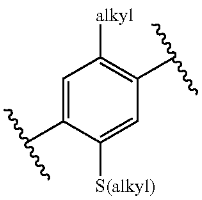
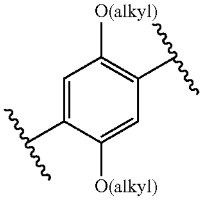
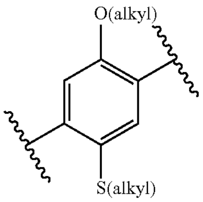
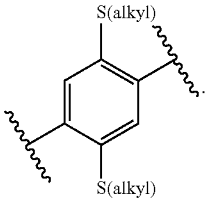
Additional non-limiting examples of
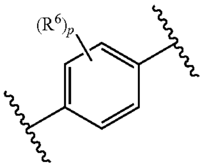
include:
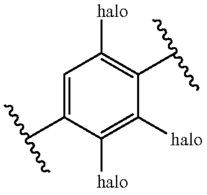
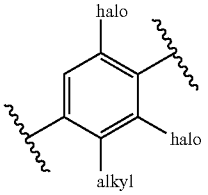
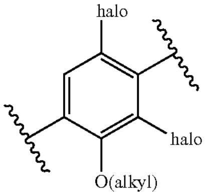
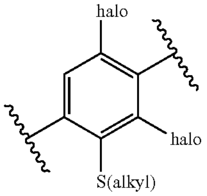
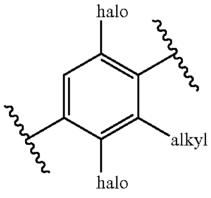
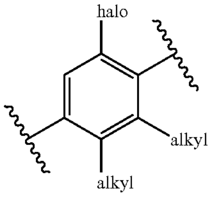
-continued
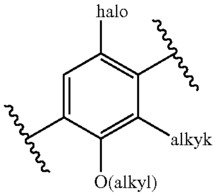
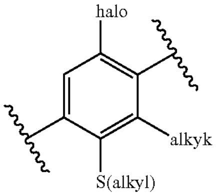
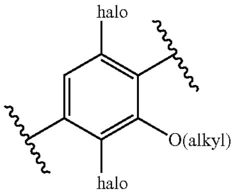
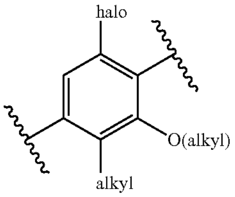
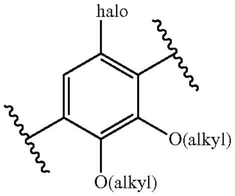
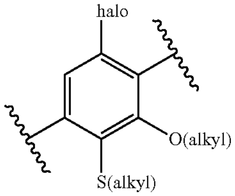
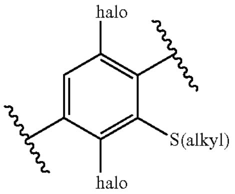
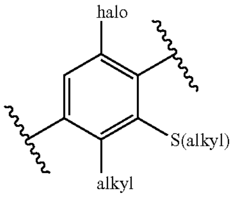
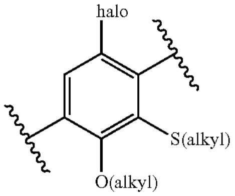
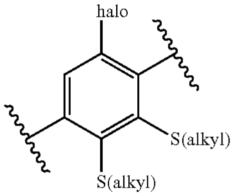
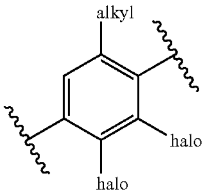
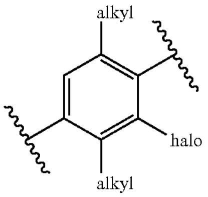
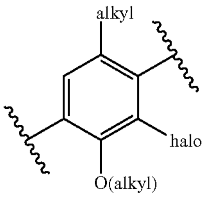
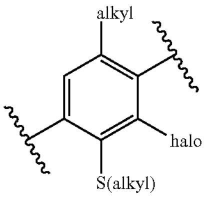
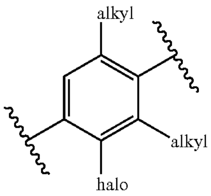
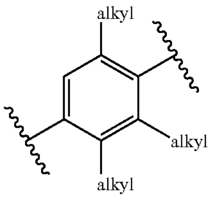

-continued
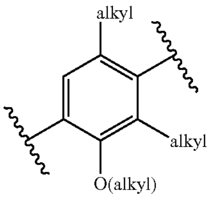
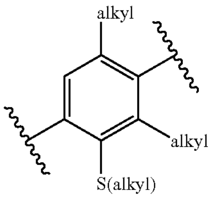
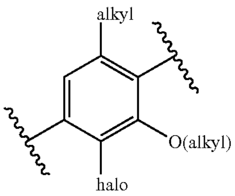
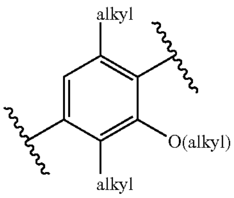
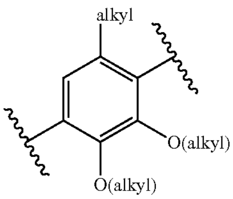
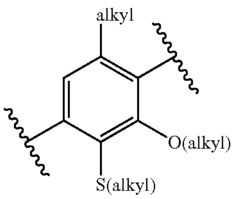
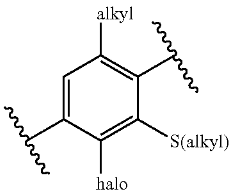
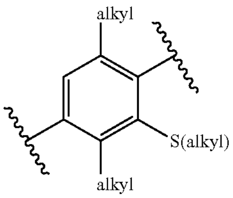
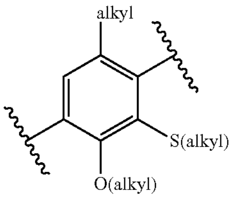
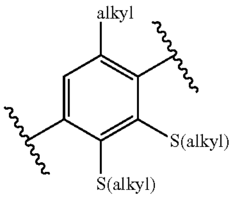
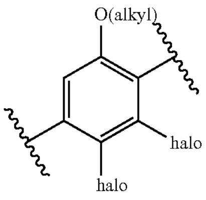
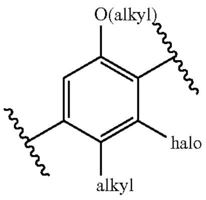
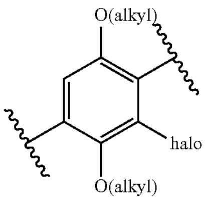
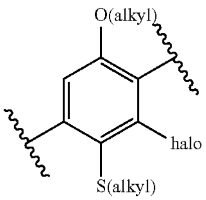
-continued
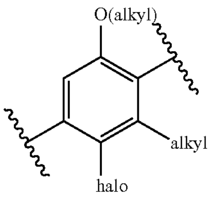
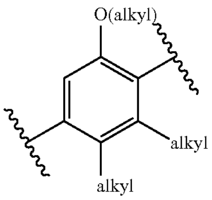
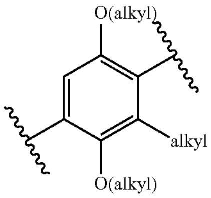
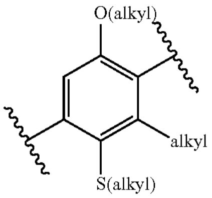
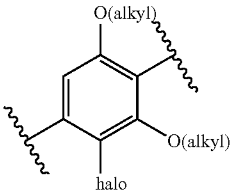
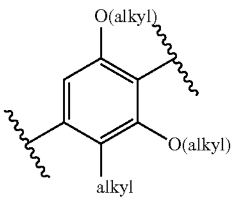
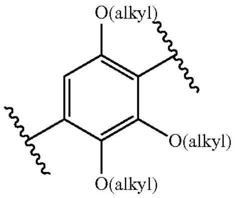
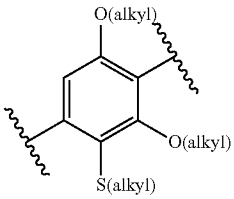
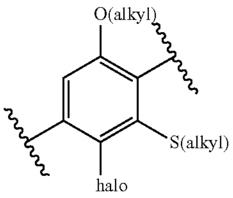
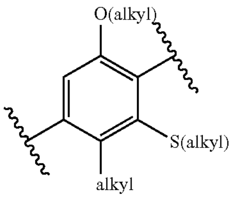
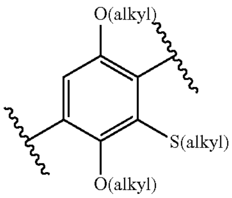
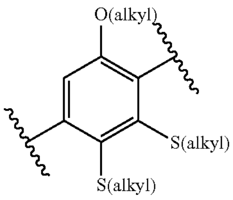
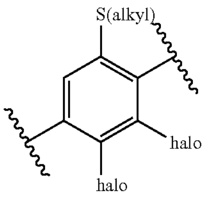
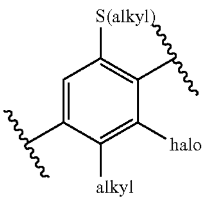
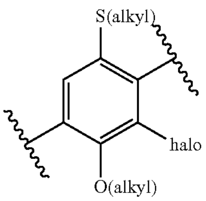

-continued
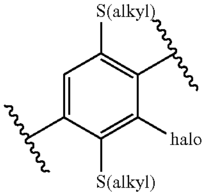
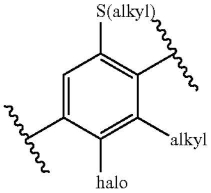
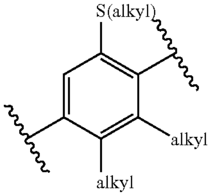
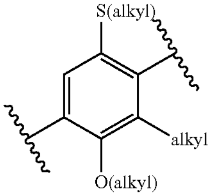
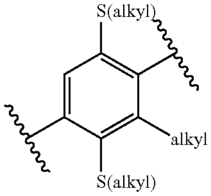
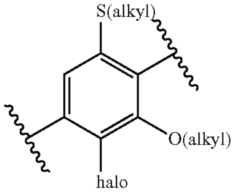
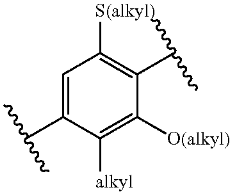
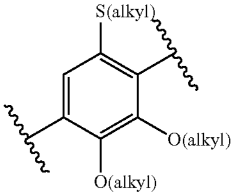
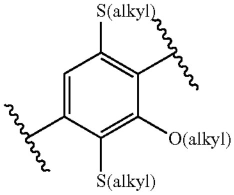
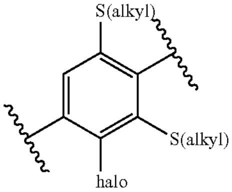
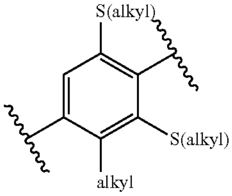
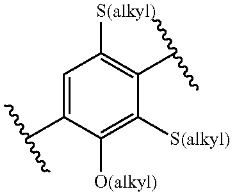
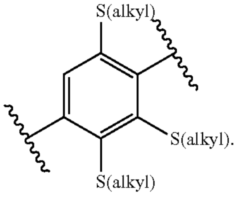
In one embodiment,
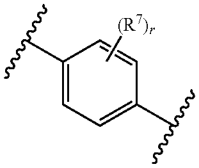
is selected from:
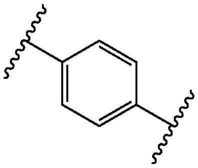
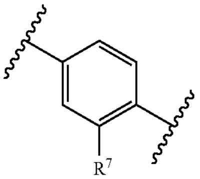
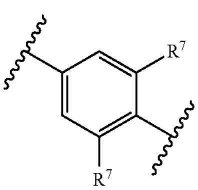
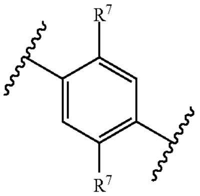
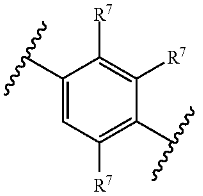
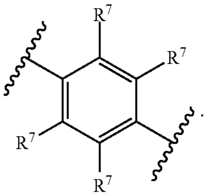
Additional non-limiting examples of
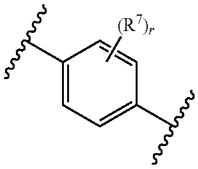
include:
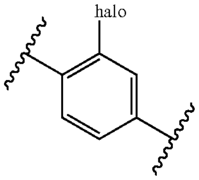
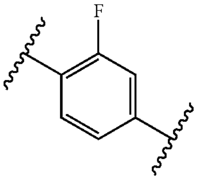
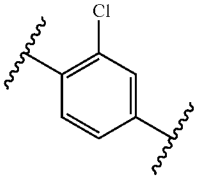
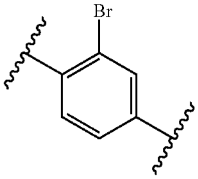
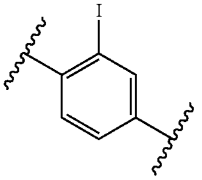
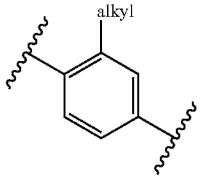
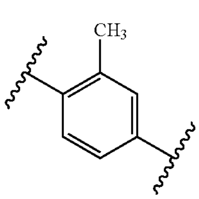
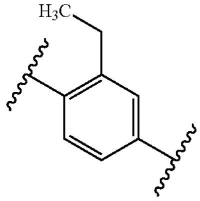

-continued
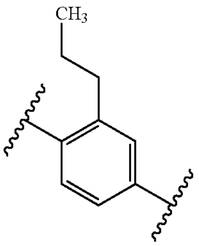
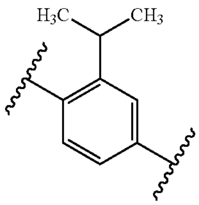
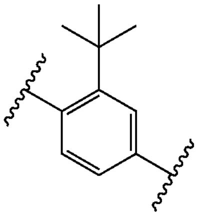
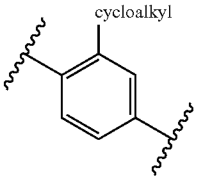
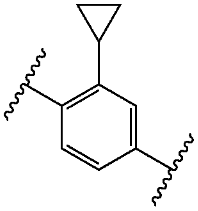
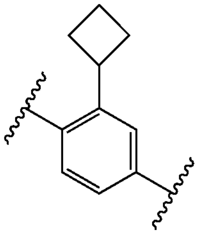
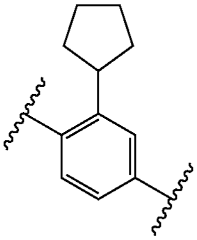
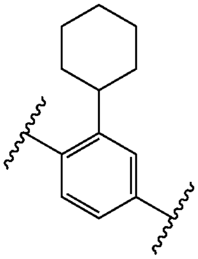
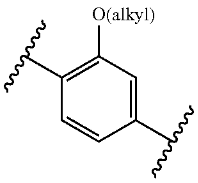
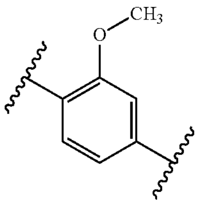
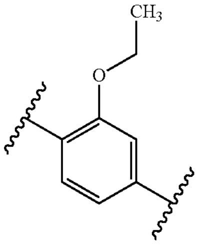
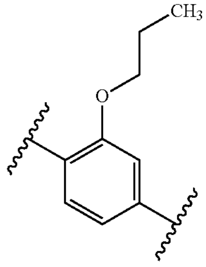
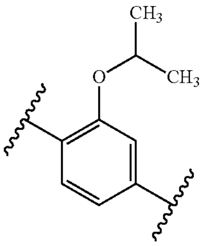
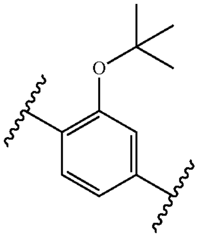
-continued
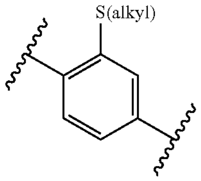
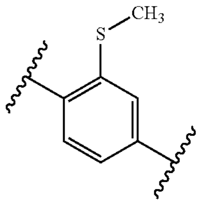
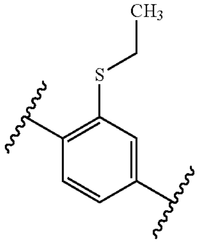
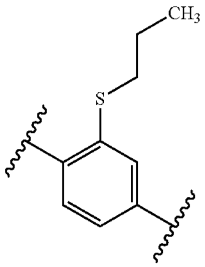
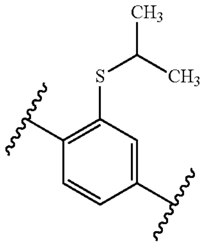
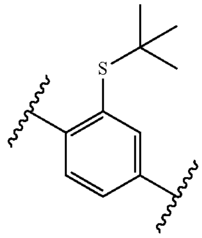
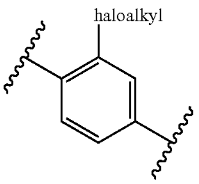
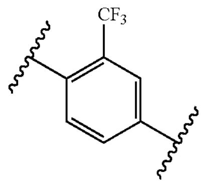
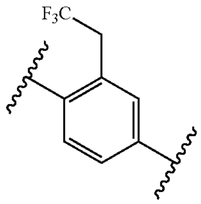
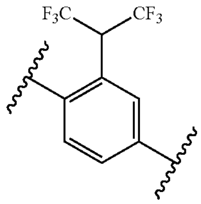
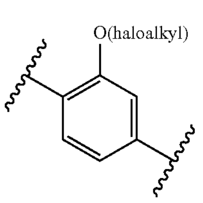
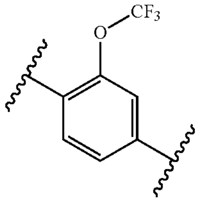
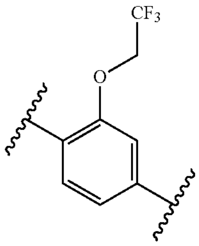
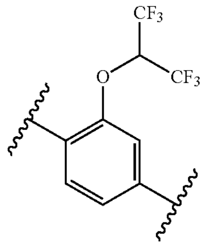

-continued
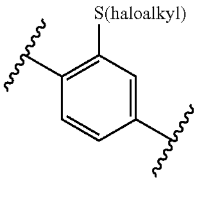
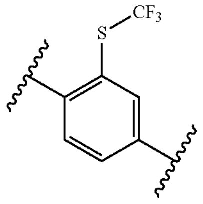
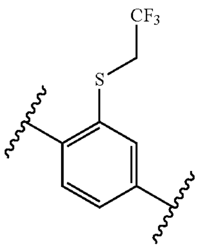
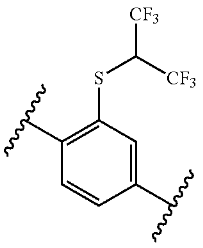
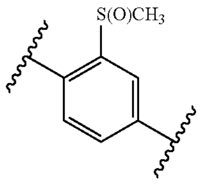
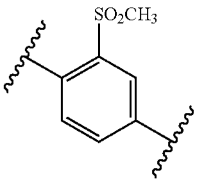
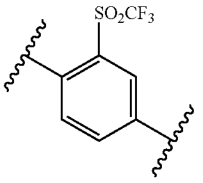
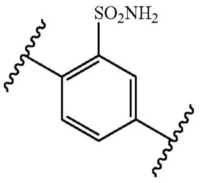
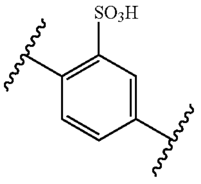
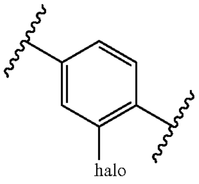
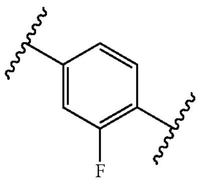
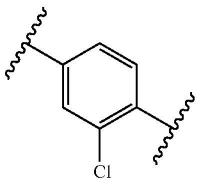
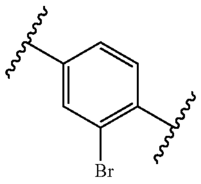
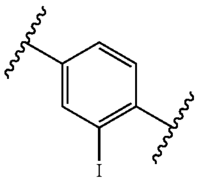
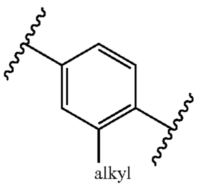
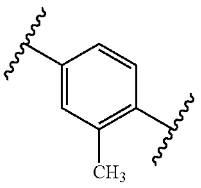
-continued
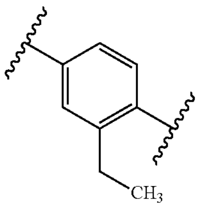
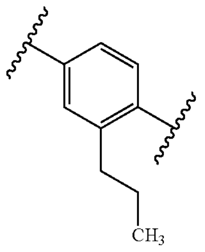
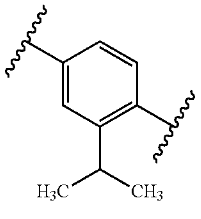
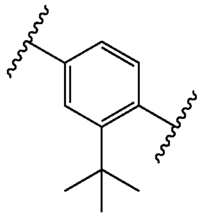
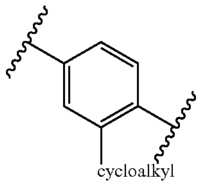
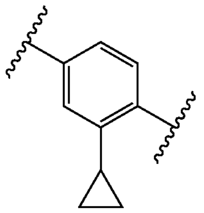
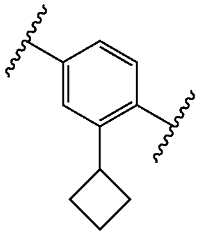
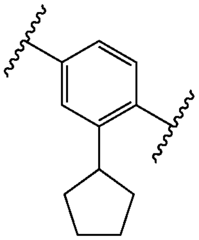
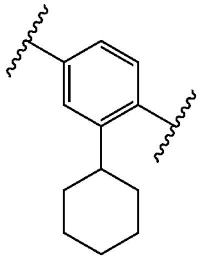
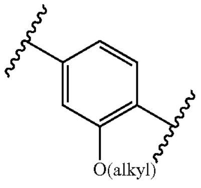
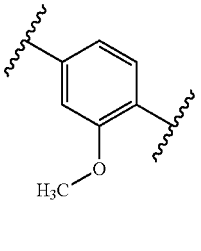
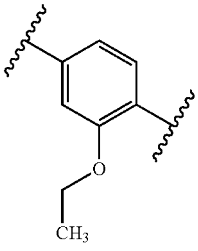
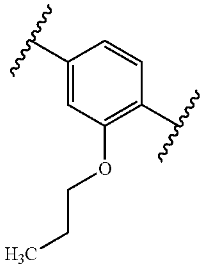
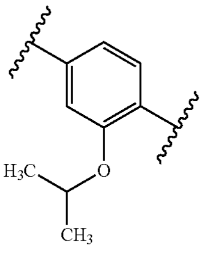

-continued
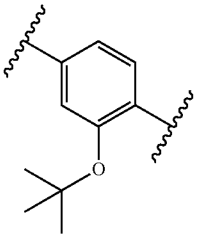
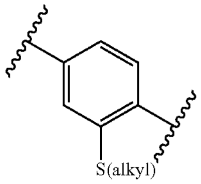
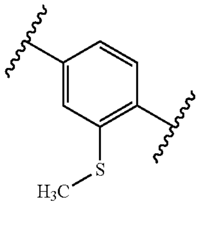
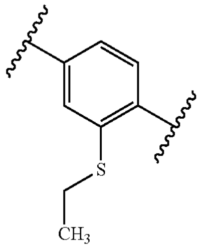
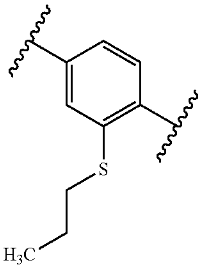
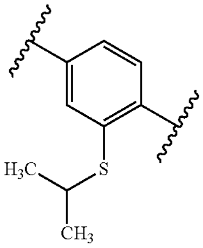
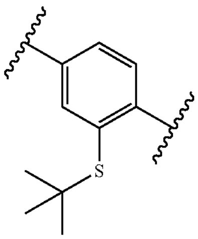
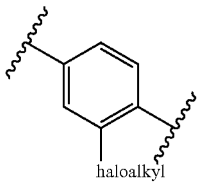
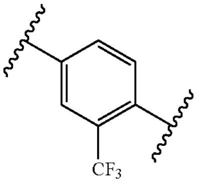
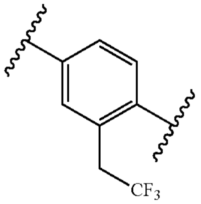
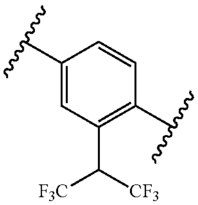
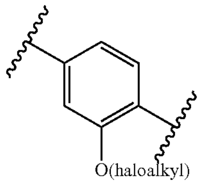
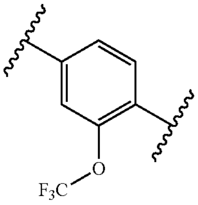
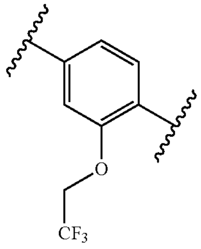
-continued
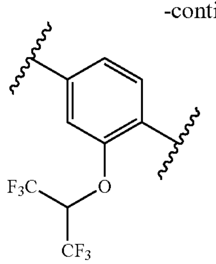
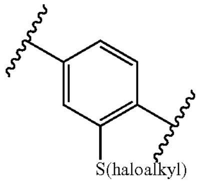
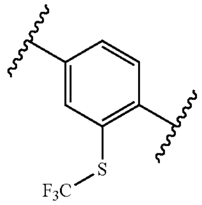
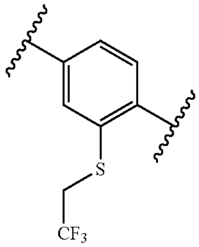
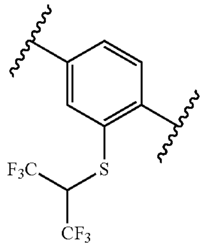
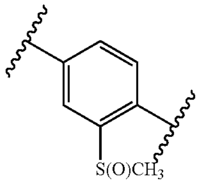
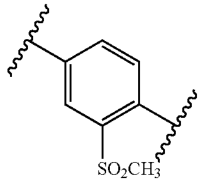
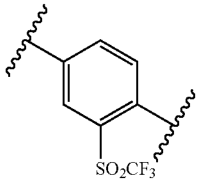
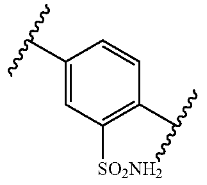
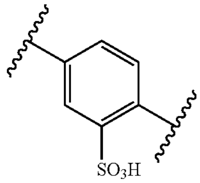.
Additional non-limiting examples of
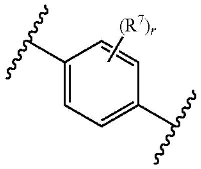
include:
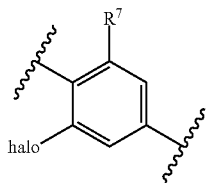
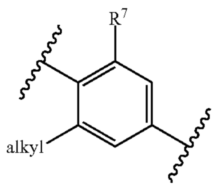

-continued
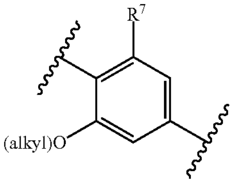
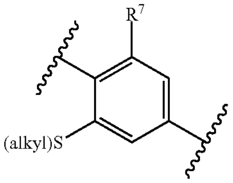
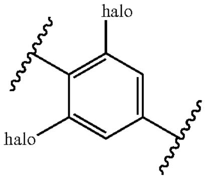
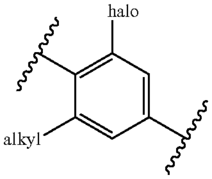
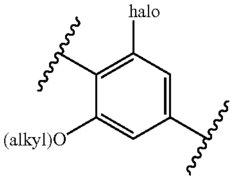
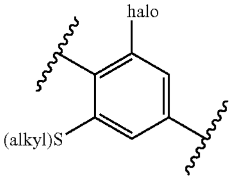
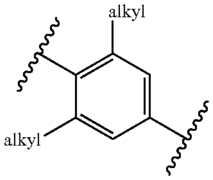
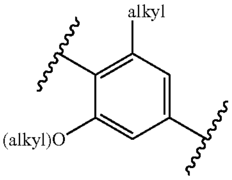
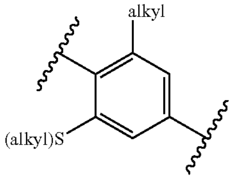
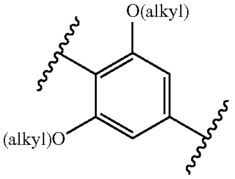
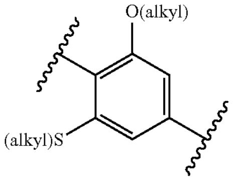
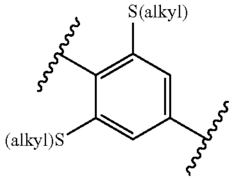
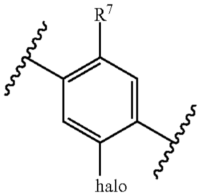
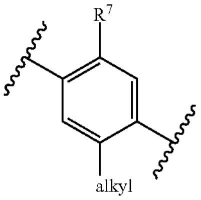
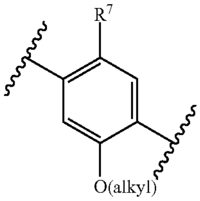
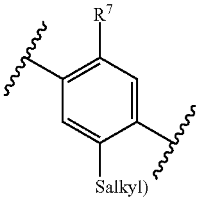
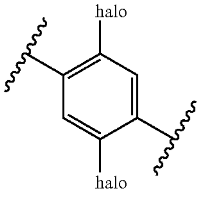
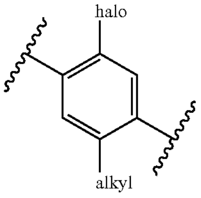
-continued
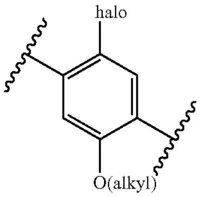
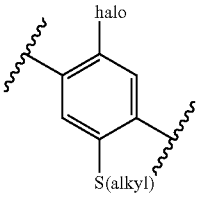
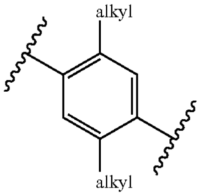
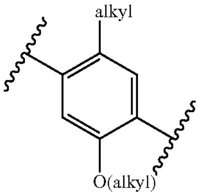
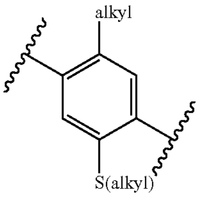
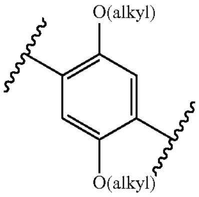
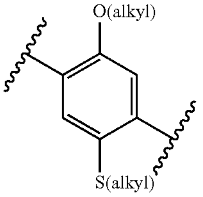
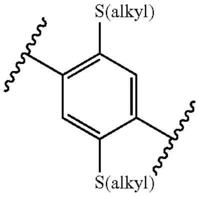.
Additional non-limiting examples of
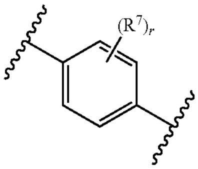
include:
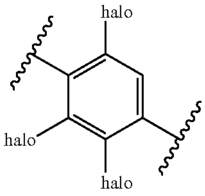
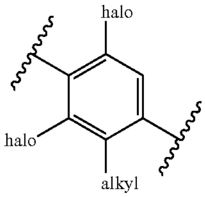
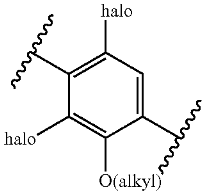
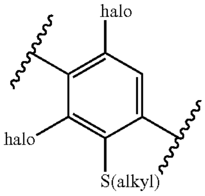

-continued
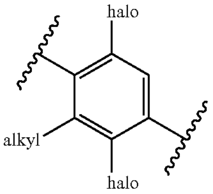
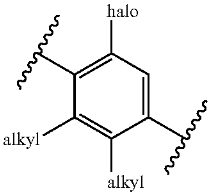
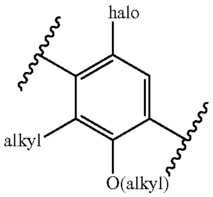
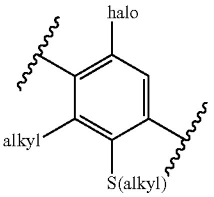
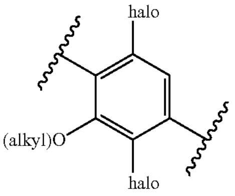
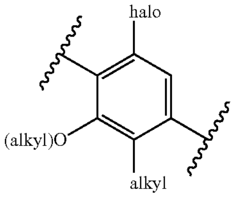
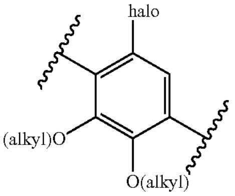
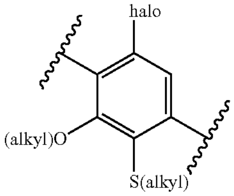
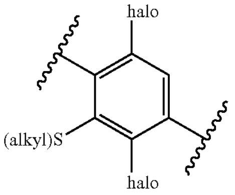
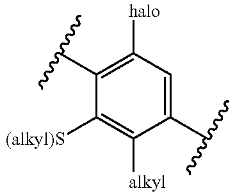
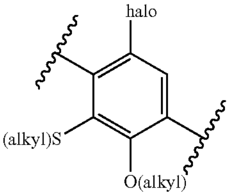
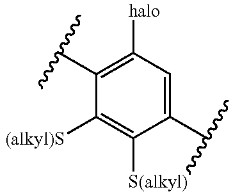
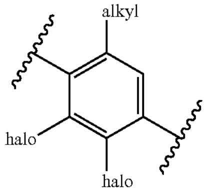
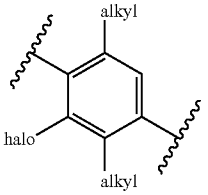
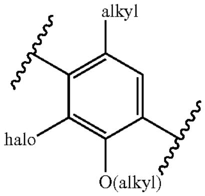
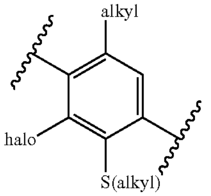
-continued
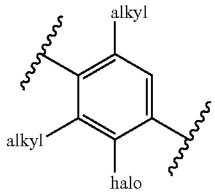
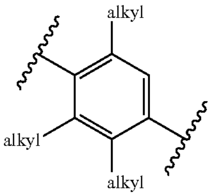
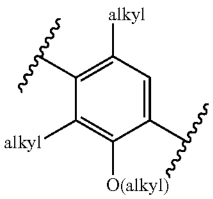
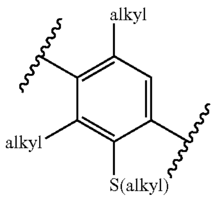
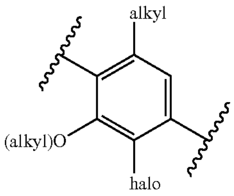
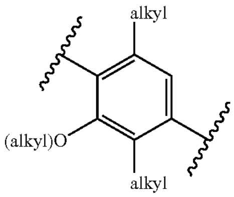
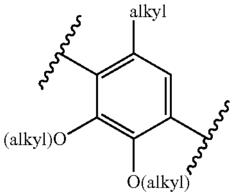
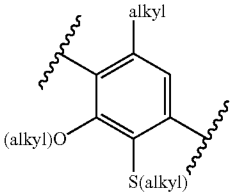
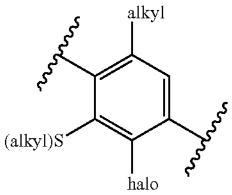
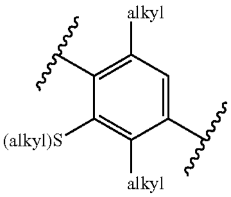
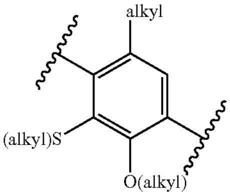
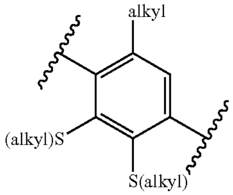
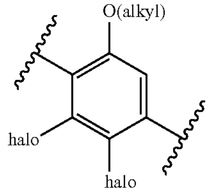
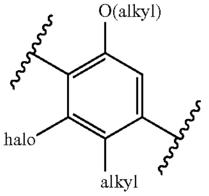
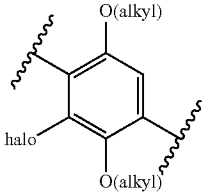

-continued
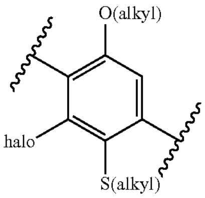
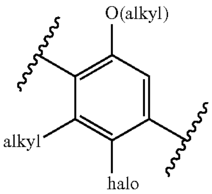
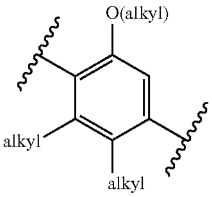
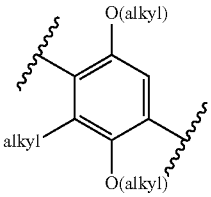
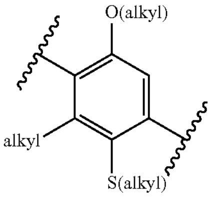
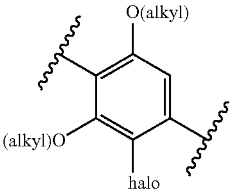
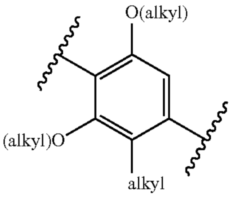
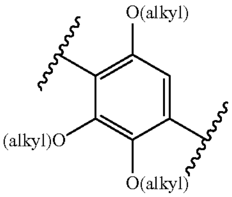
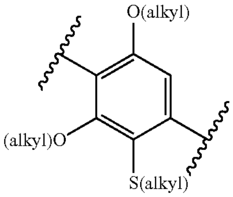
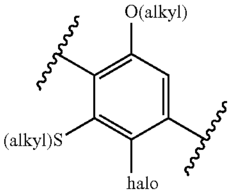
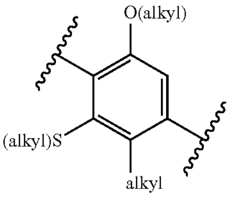
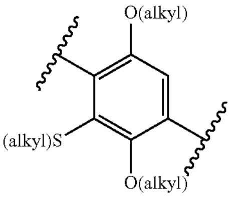
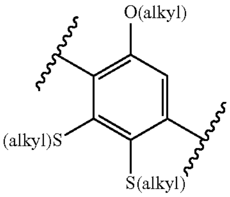
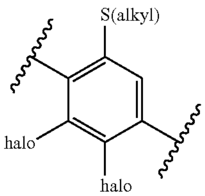
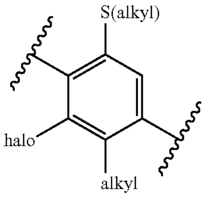
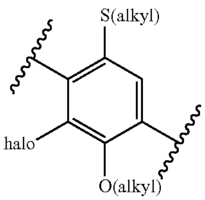
-continued
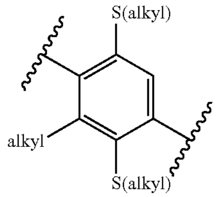
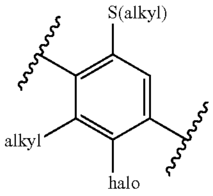
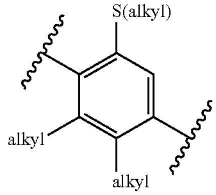
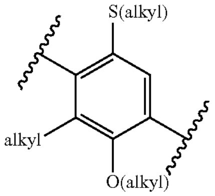
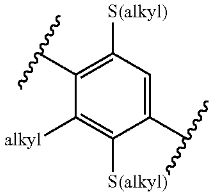
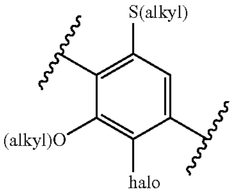
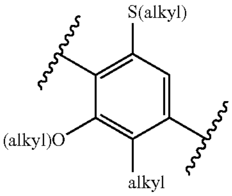
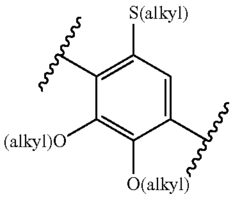
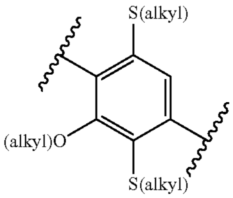
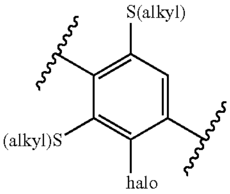
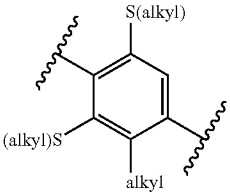
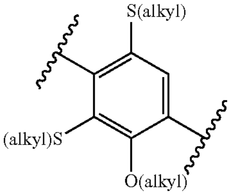
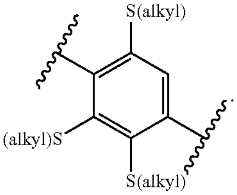
Additional non-limiting examples of $R^1$, $R^6$, and $R^7$ include:
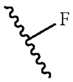
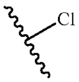
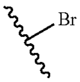
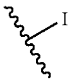
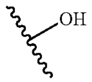
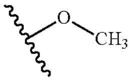
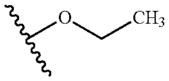

-continued
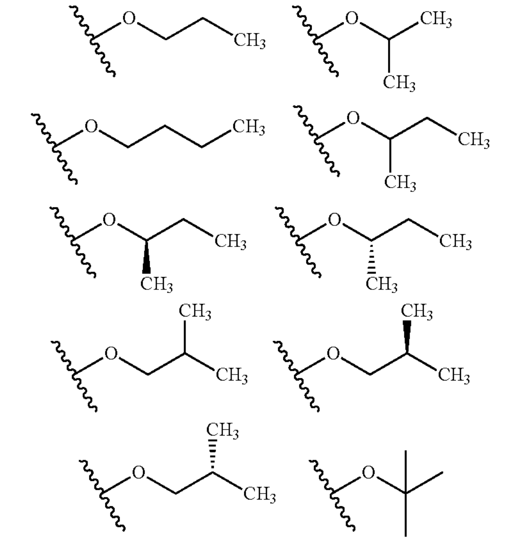
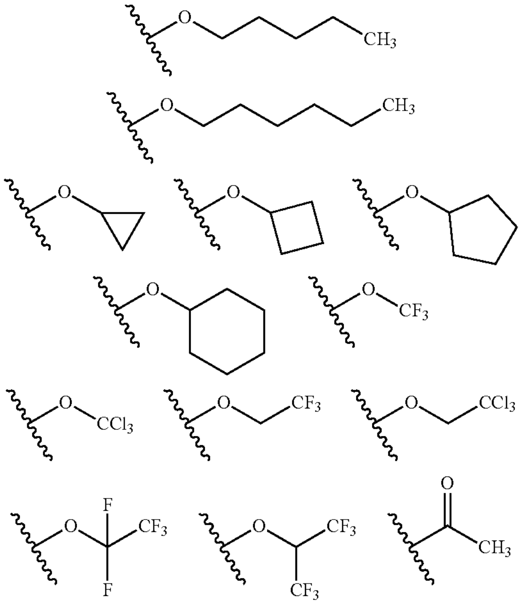
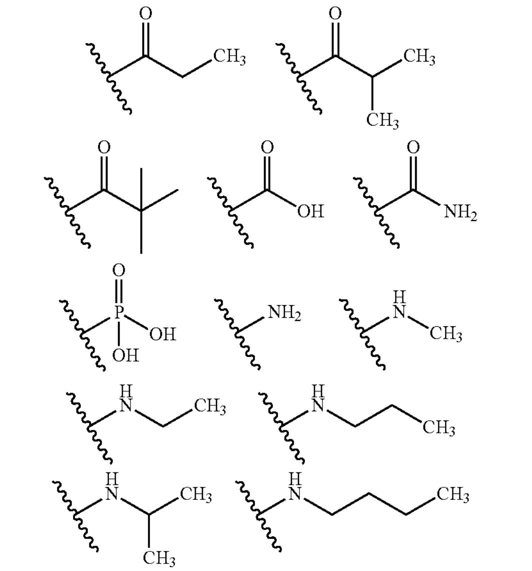
-continued
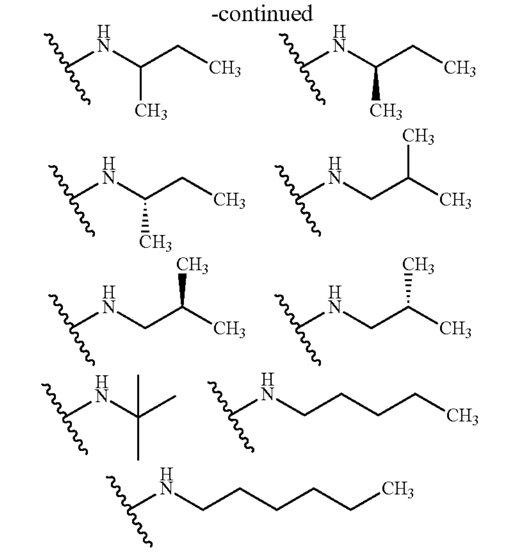
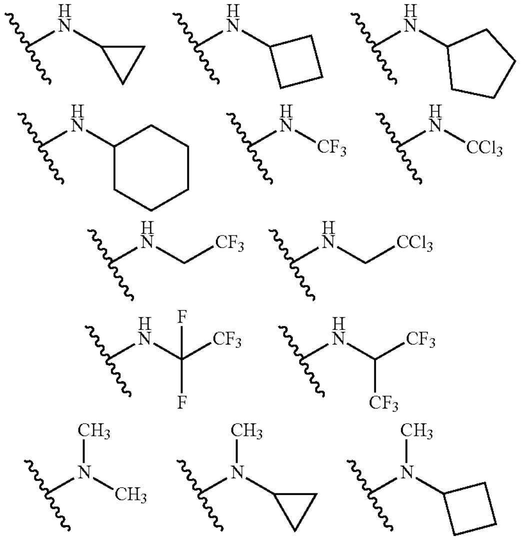
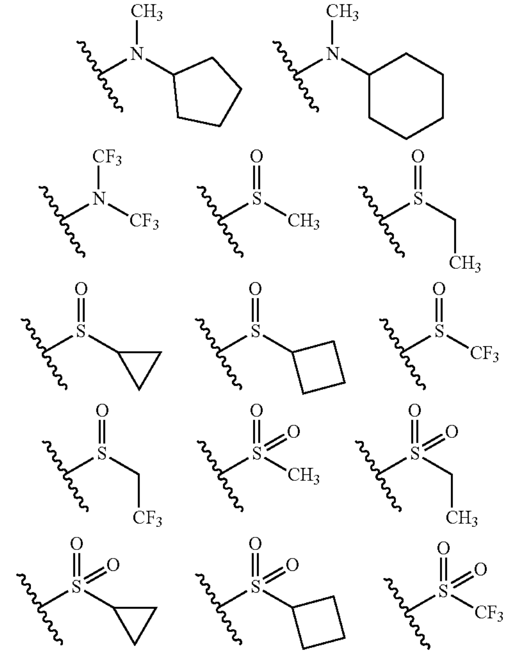

-continued
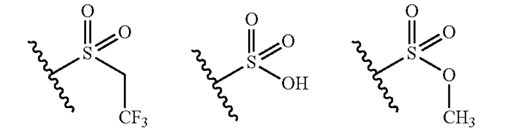
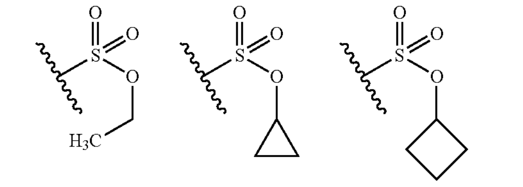
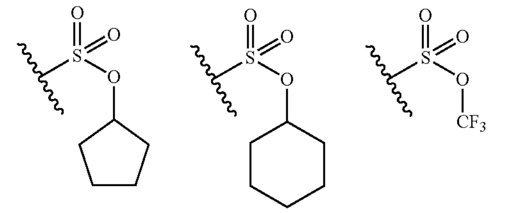
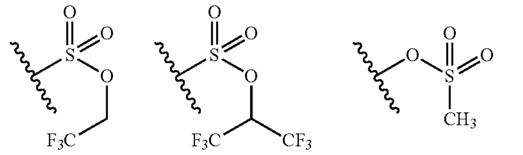
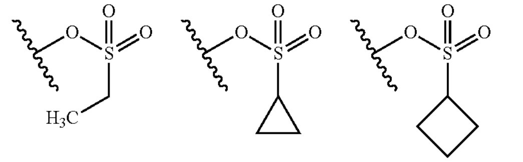
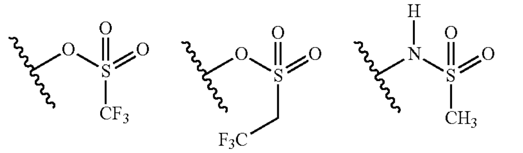
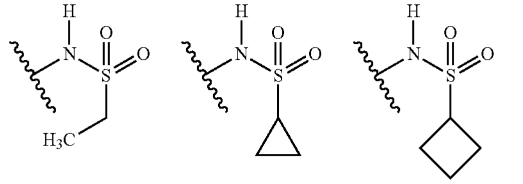
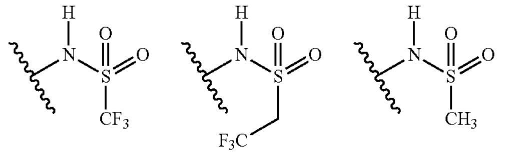
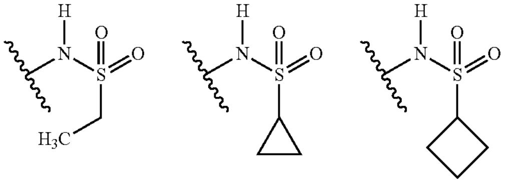
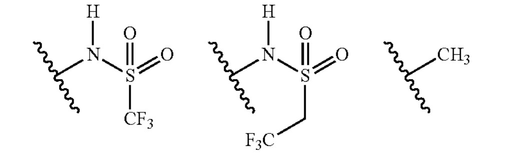
-continued
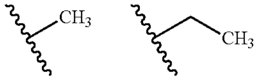
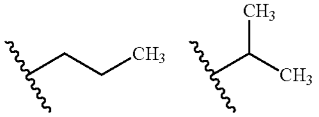
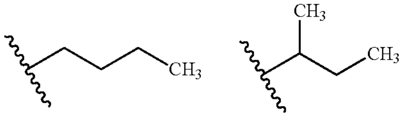
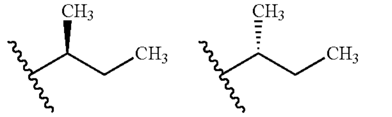
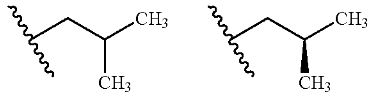
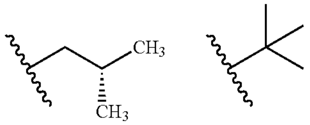
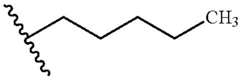
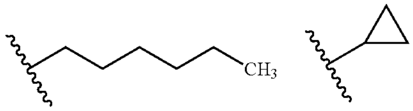
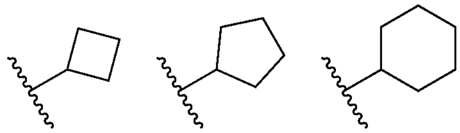
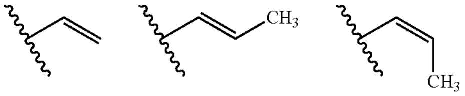
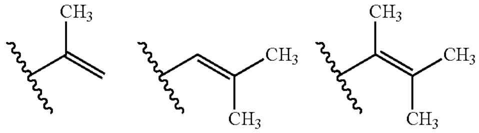
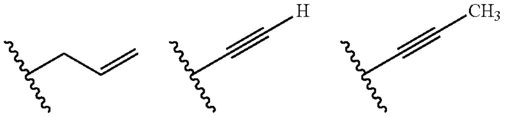
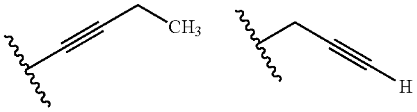
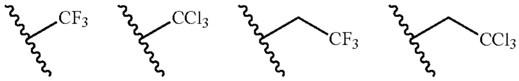
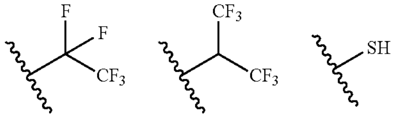
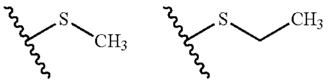

-continued
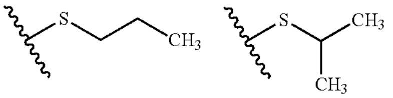
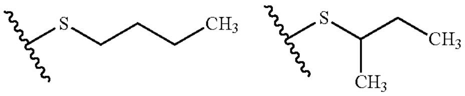
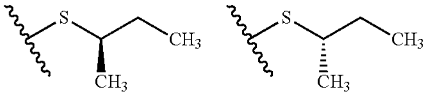
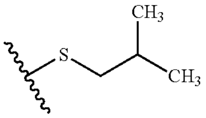
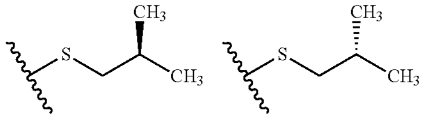
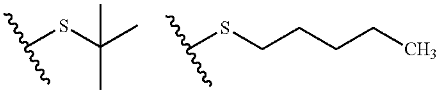
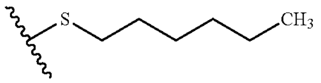
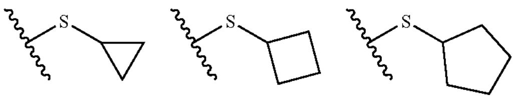
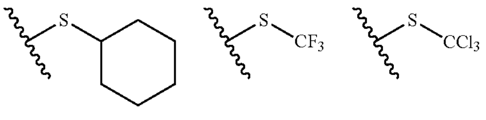
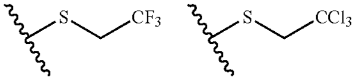
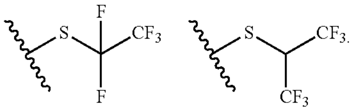
In one embodiment,
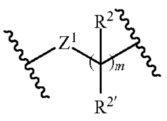
is selected from:
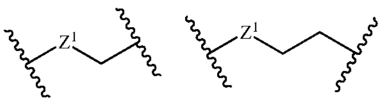
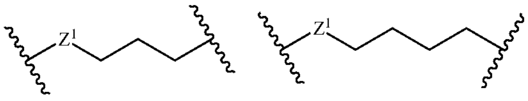
-continued
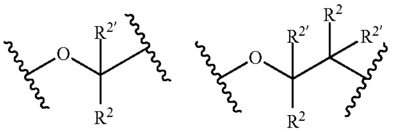
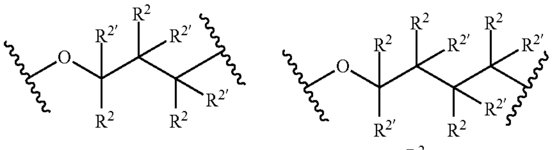
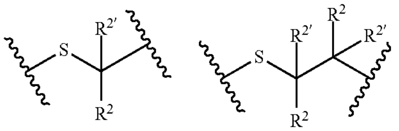
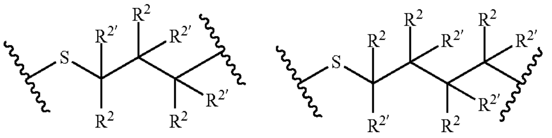
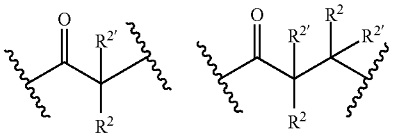
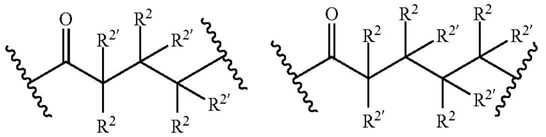
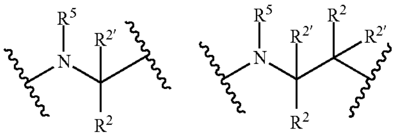
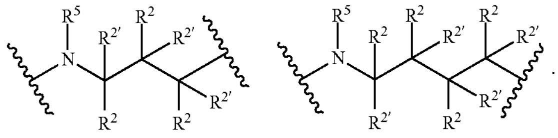
Additional non-limiting examples of
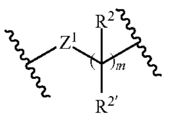
include:
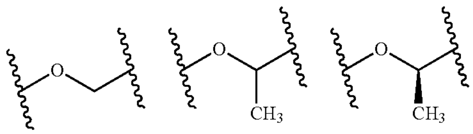
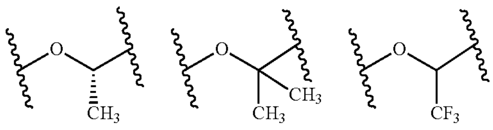

-continued
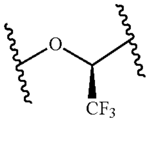
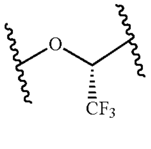
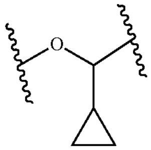
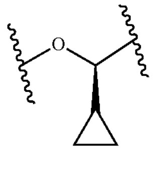
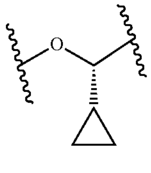
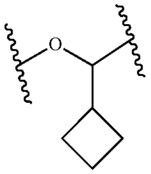
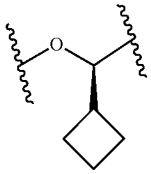
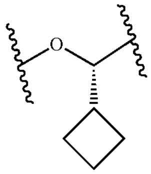
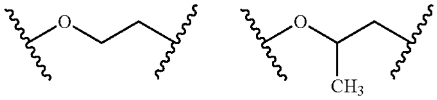
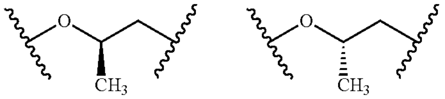
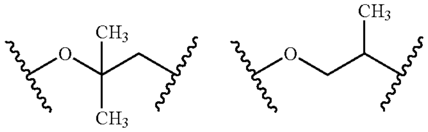
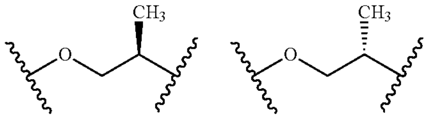
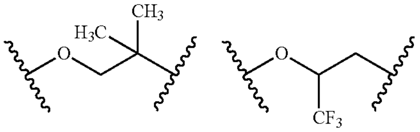
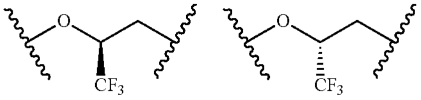
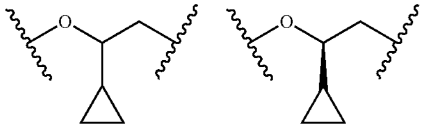
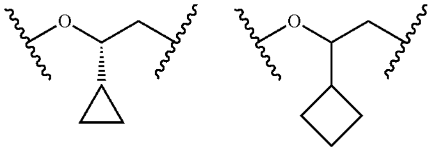
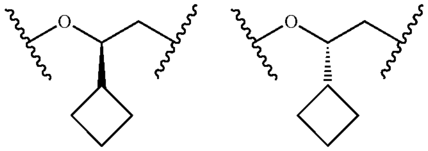
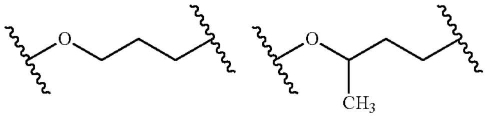
-continued
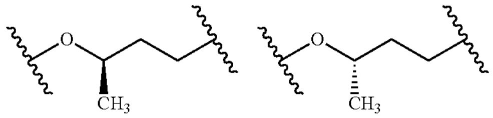
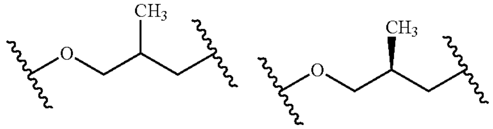
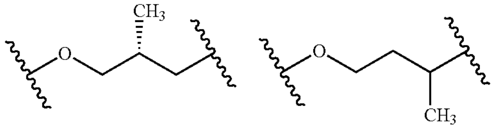
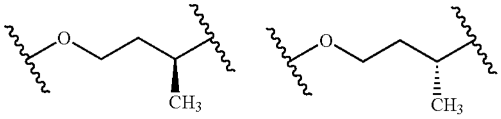
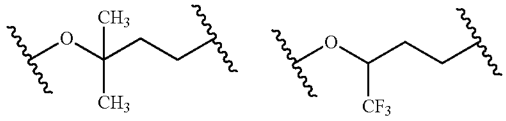
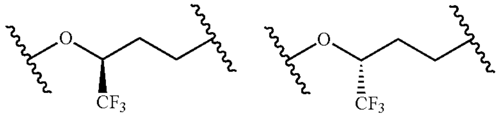
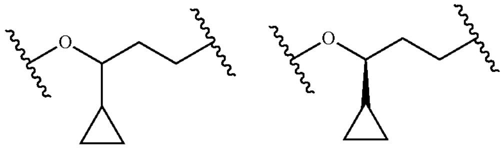
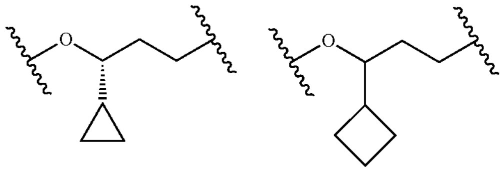
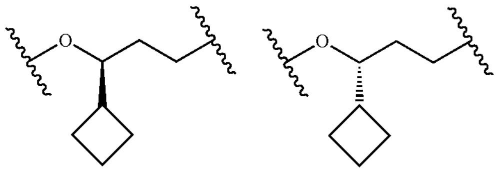
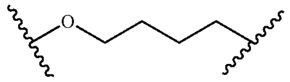
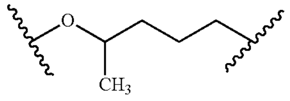
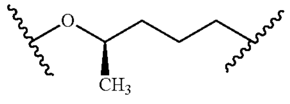
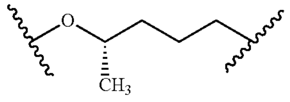

-continued
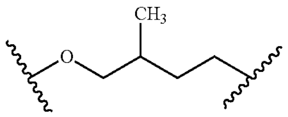
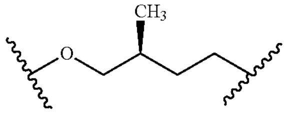
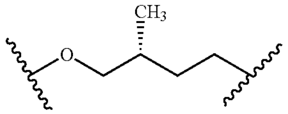
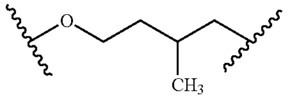
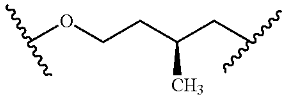
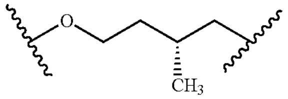
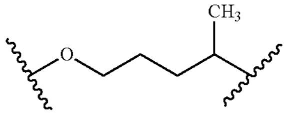
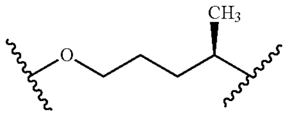
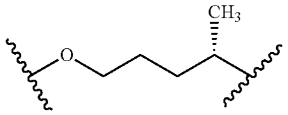
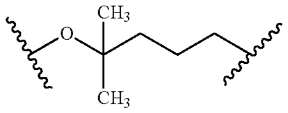
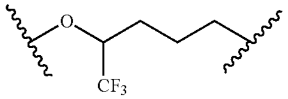
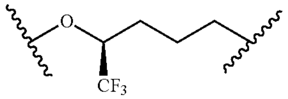
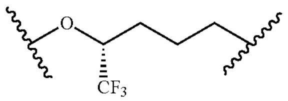
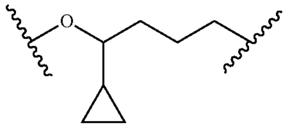
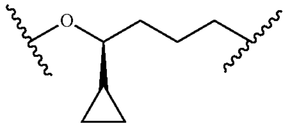
-continued
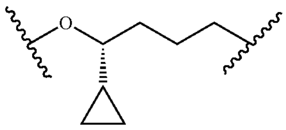
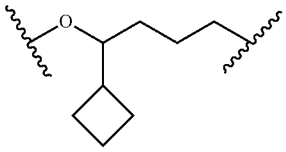
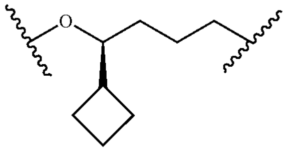
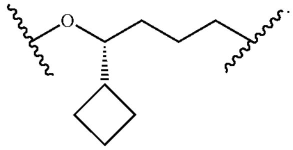
Additional non-limiting examples of
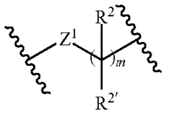
include:
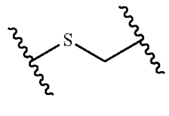 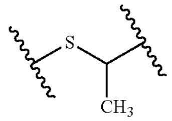 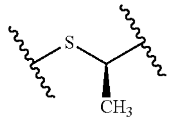
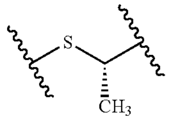 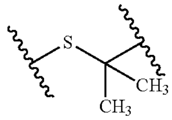 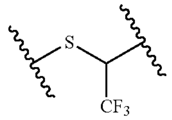
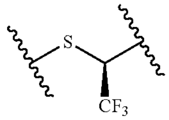 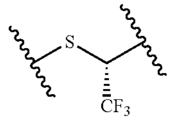 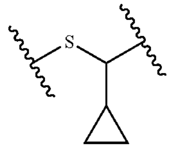
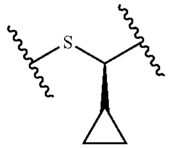 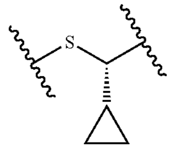 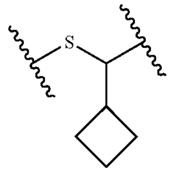
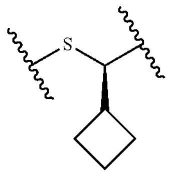 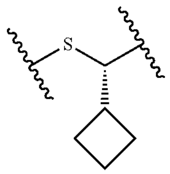 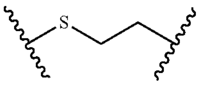

-continued
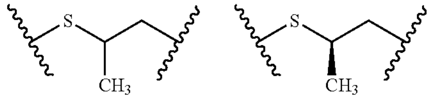
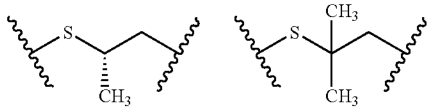
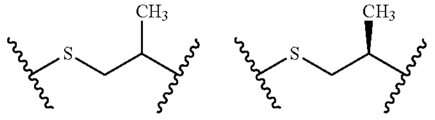
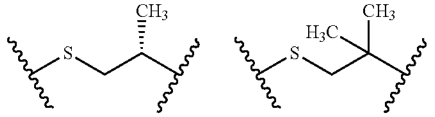
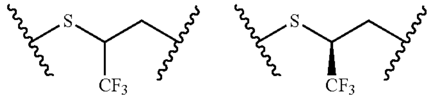
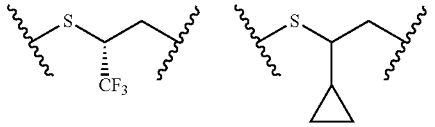
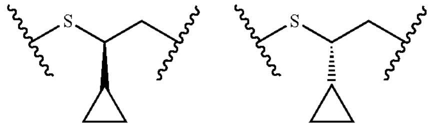
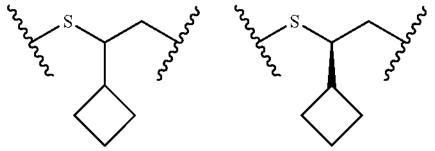
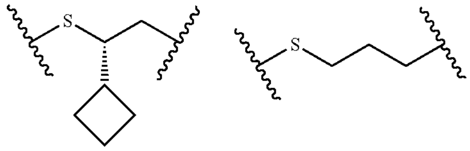
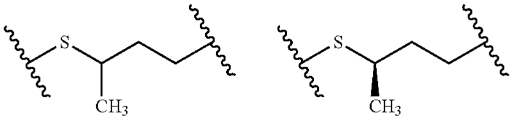
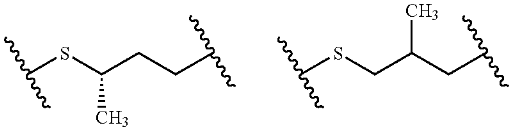
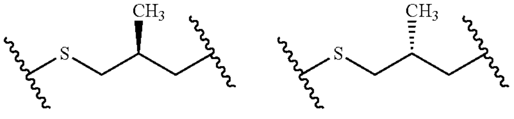
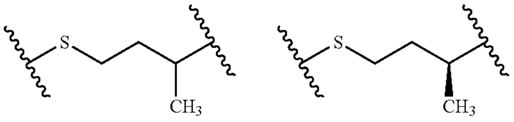
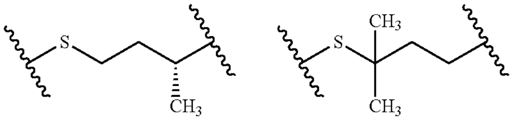
-continued
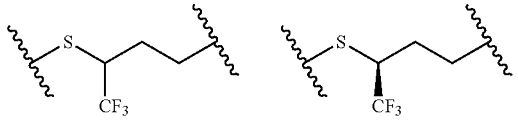
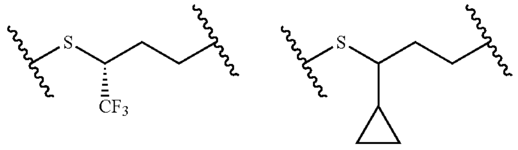
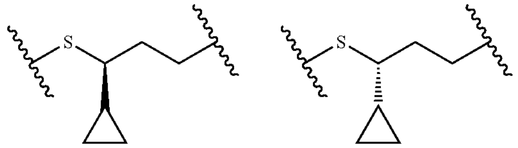
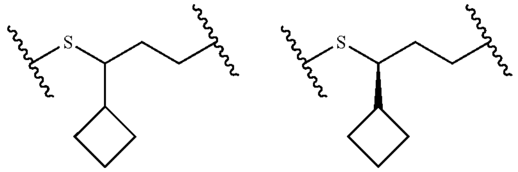
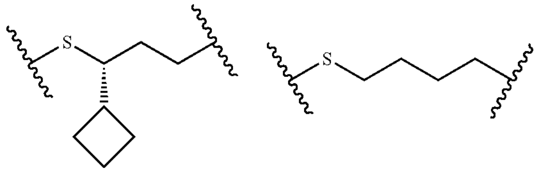
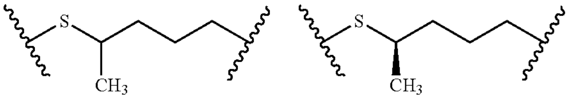
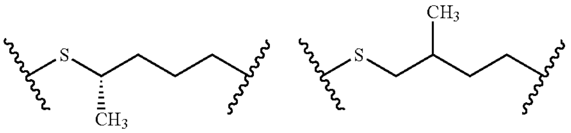
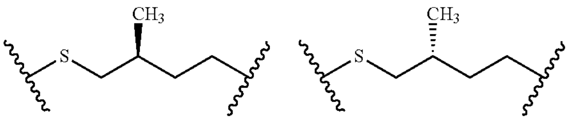
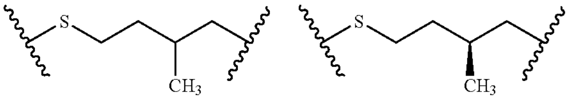
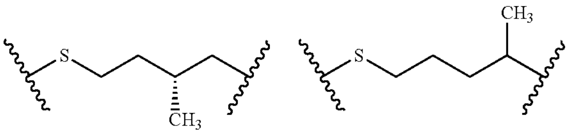
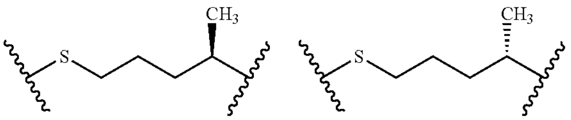
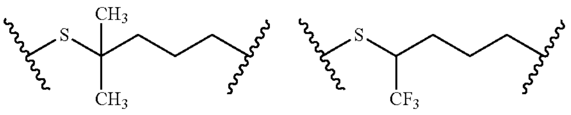
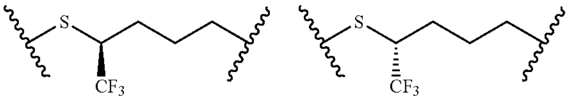

-continued
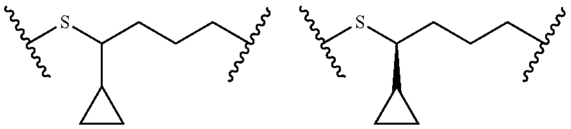
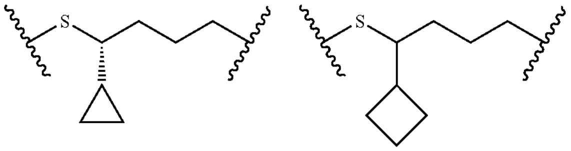
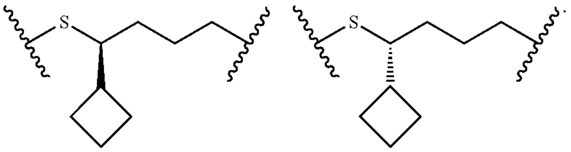
Additional non-limiting examples of
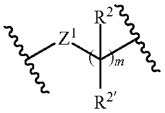
include:
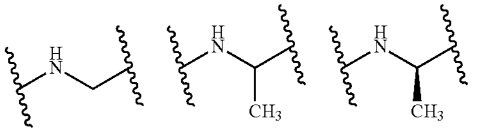
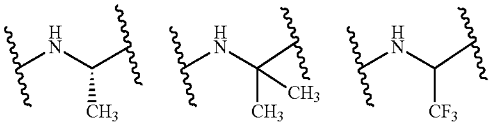
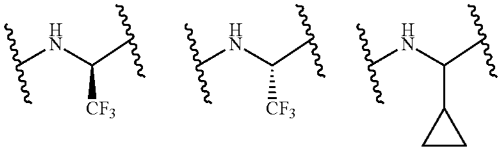
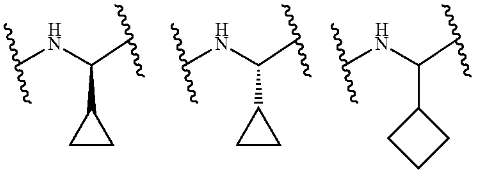
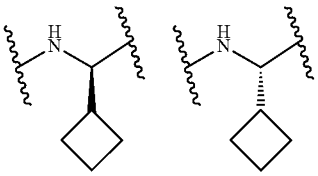
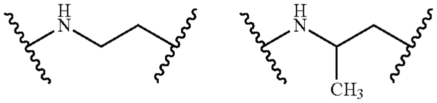
-continued
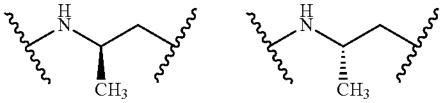
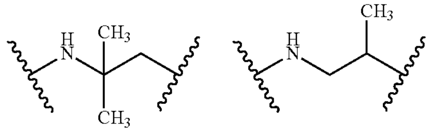
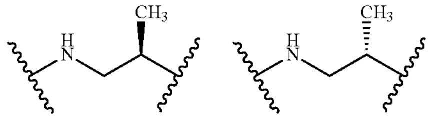
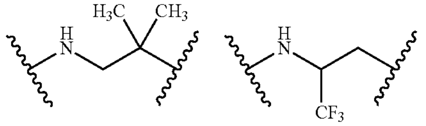
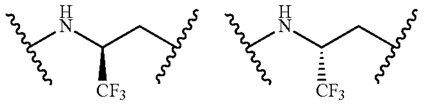
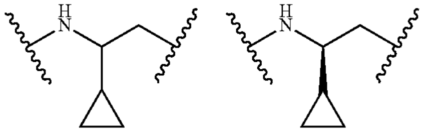
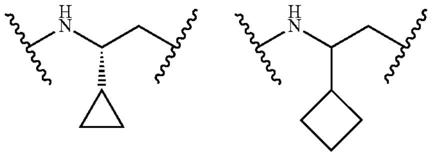
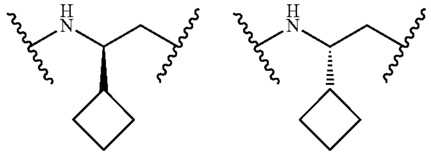
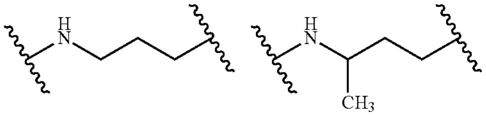
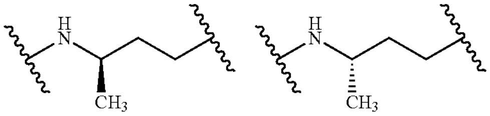
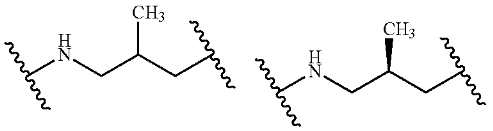
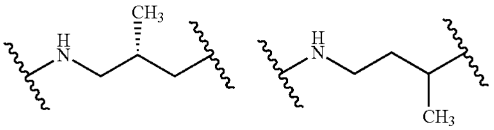
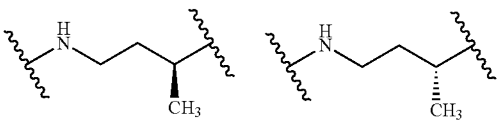

-continued
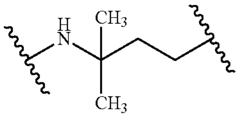
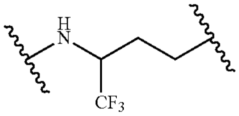
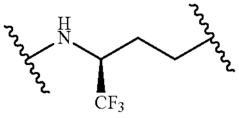
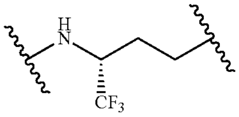
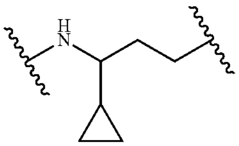
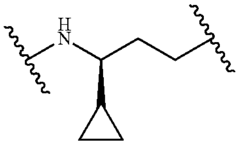
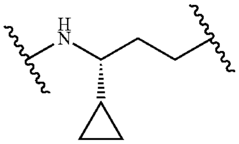
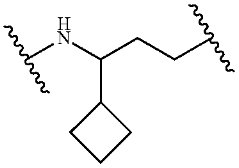
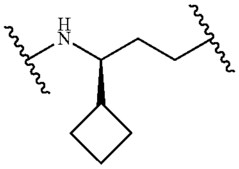
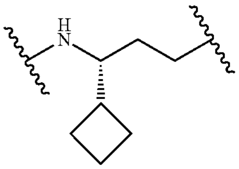
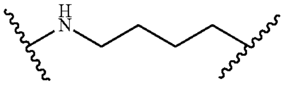
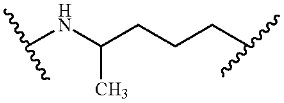
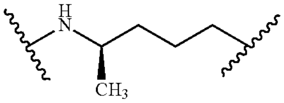
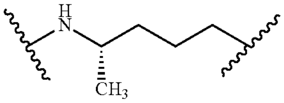
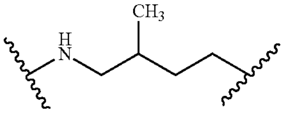
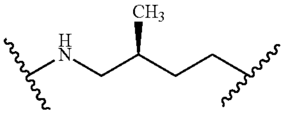
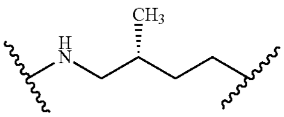
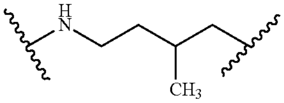
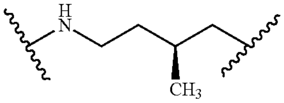
-continued
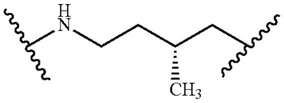
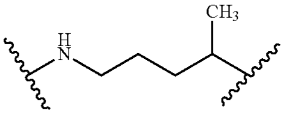
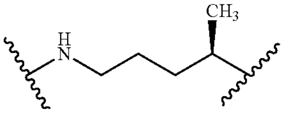
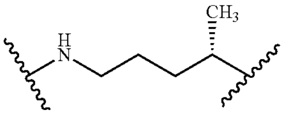
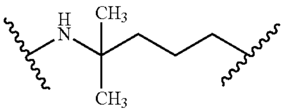
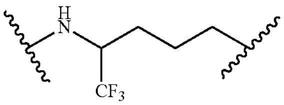
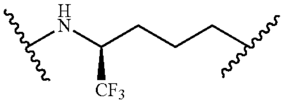
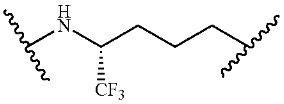
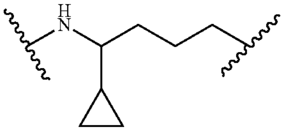
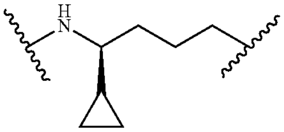
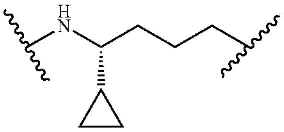
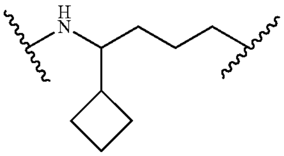
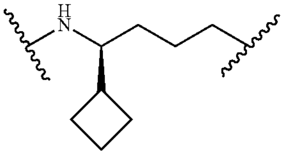

-continued
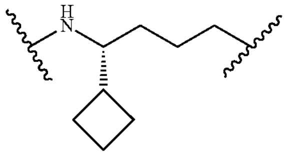
Additional non-limiting examples of
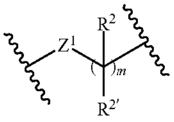
include:
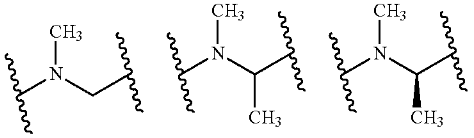
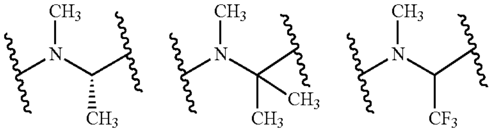
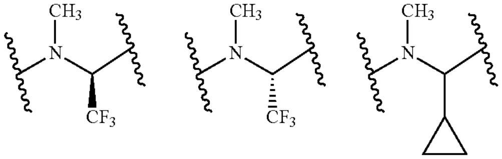
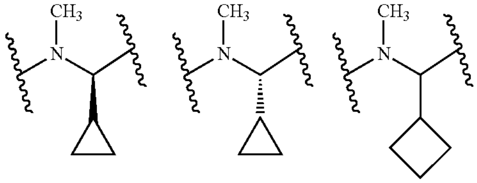
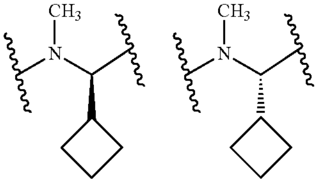
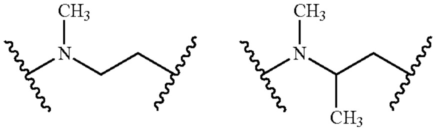
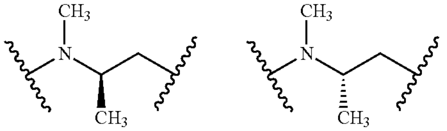
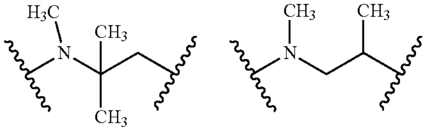
-continued
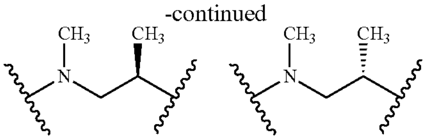
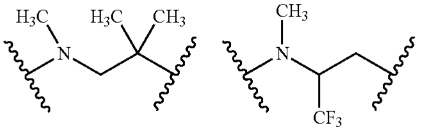
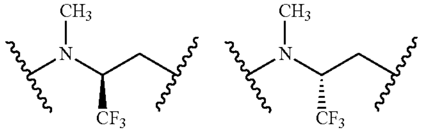
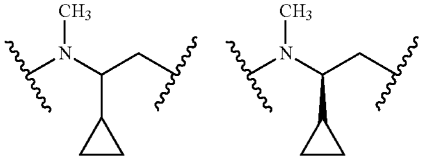
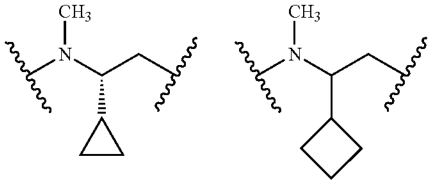
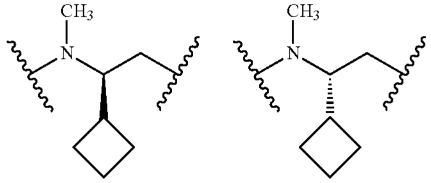
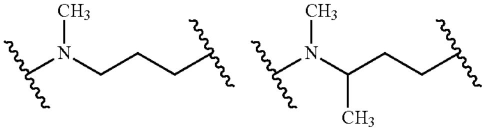
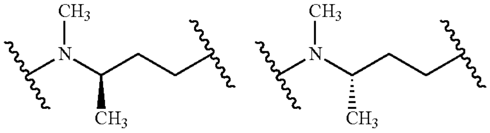
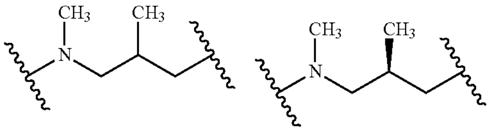
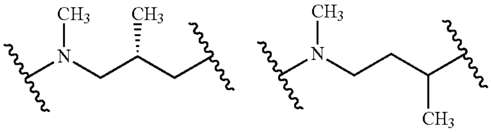
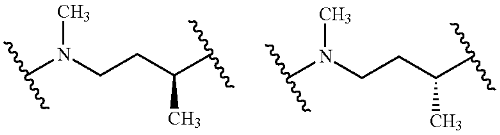
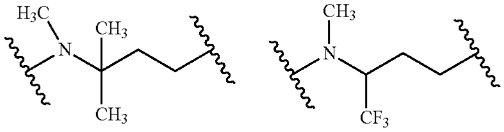

-continued
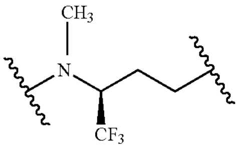
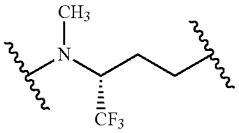
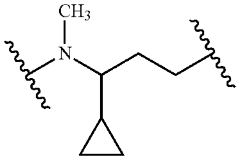
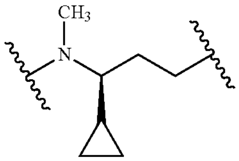
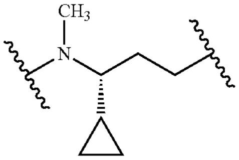
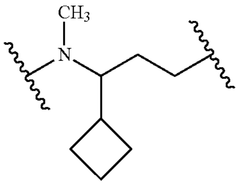
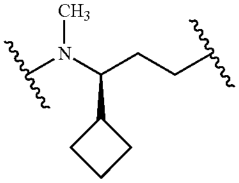
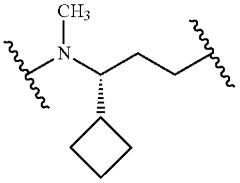
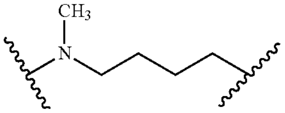
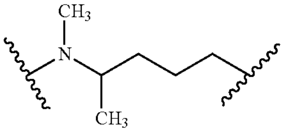
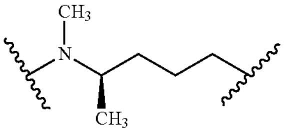
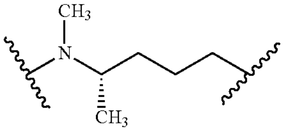
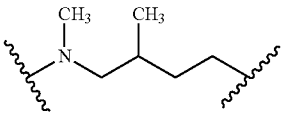
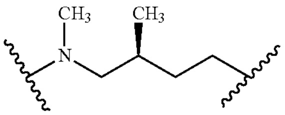
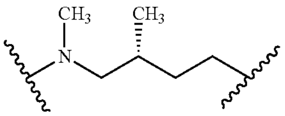
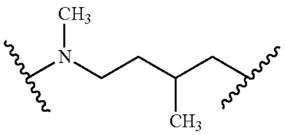
-continued
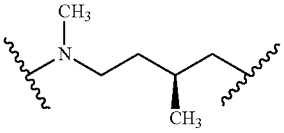
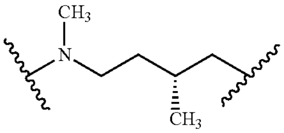
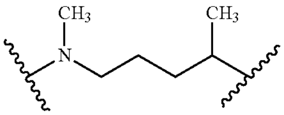
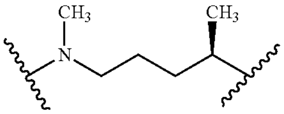
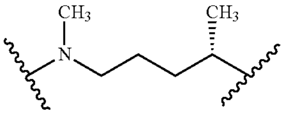
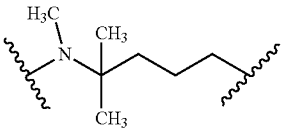
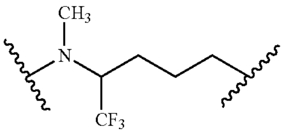
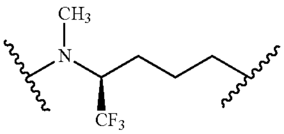
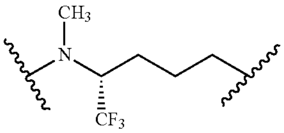
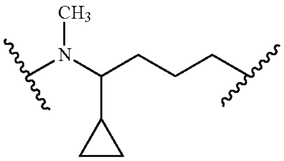
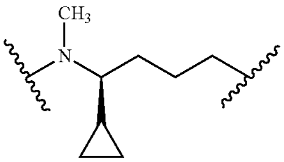
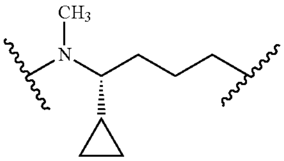

-continued
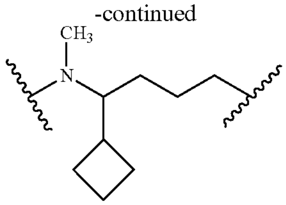
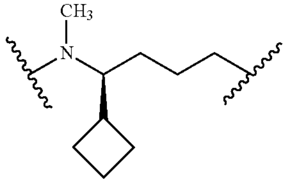
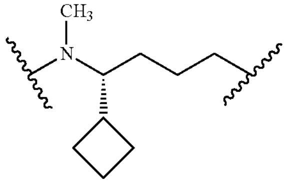
Additional non-limiting examples of
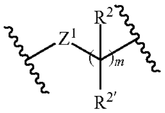
include:
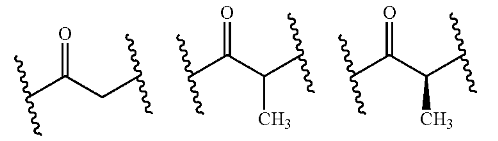
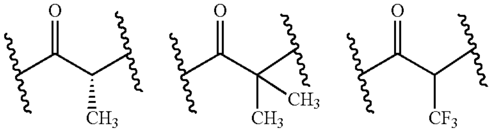
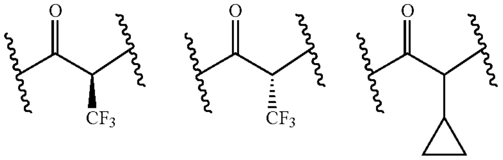
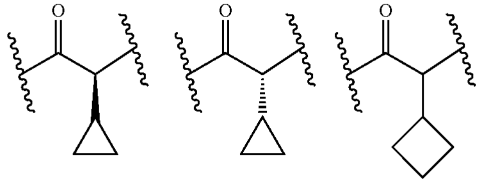
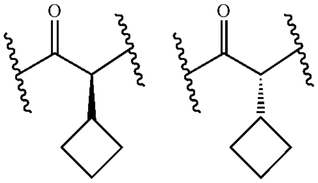
-continued
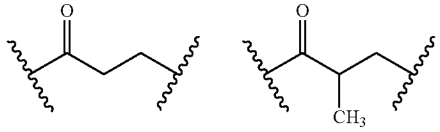
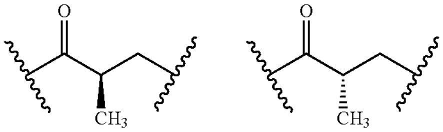
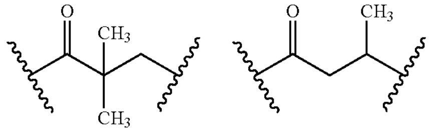
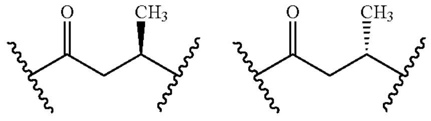
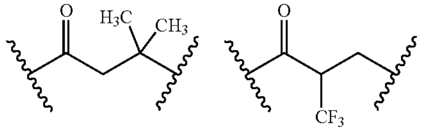
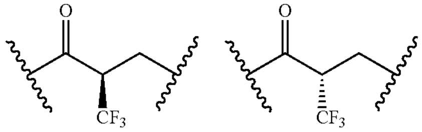
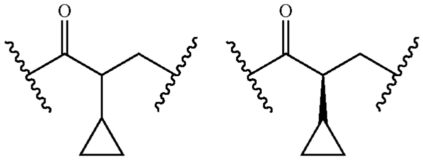
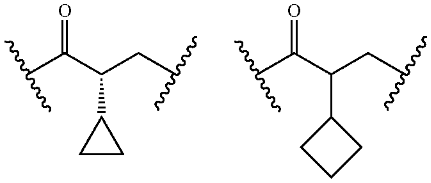
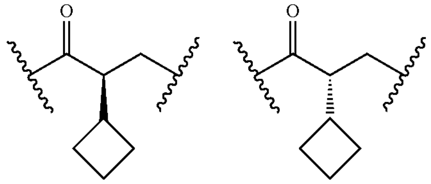
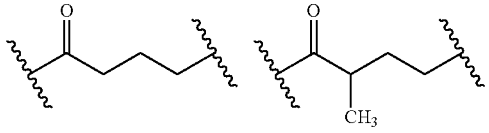
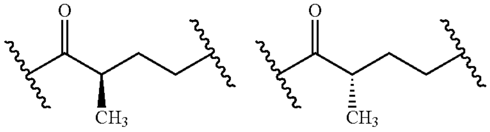
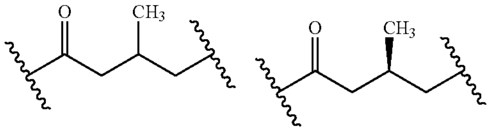

-continued
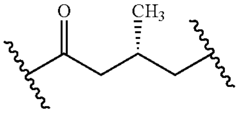
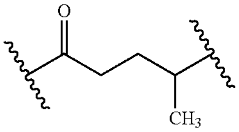
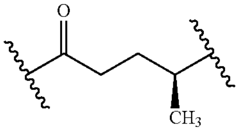
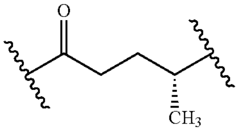
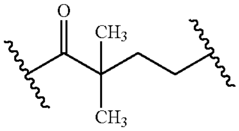
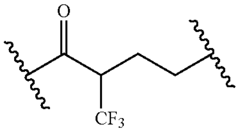
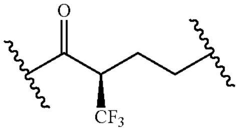
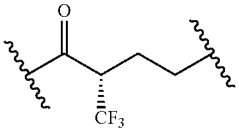
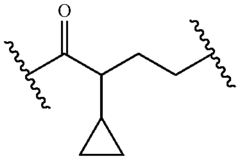
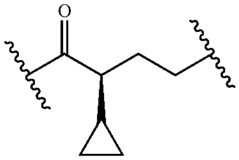
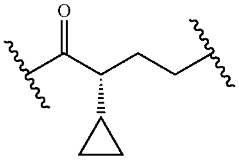
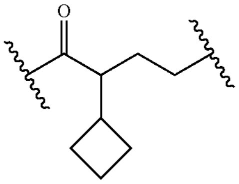
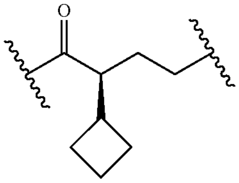
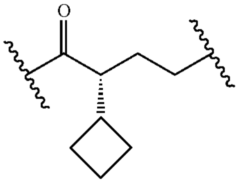
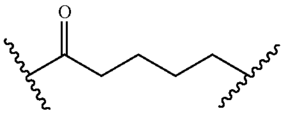
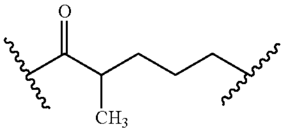
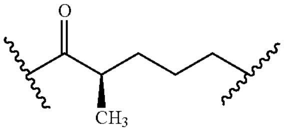
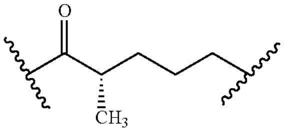
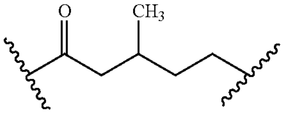
-continued
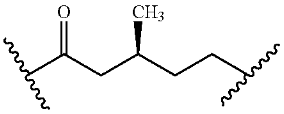
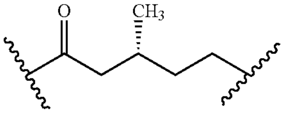
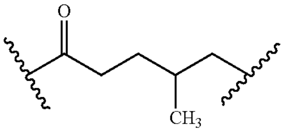
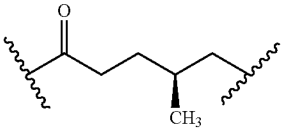
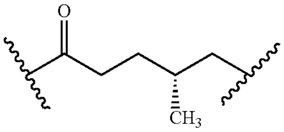
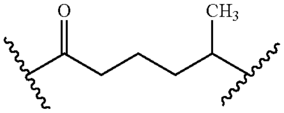
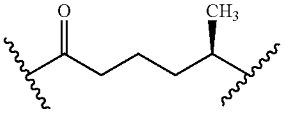
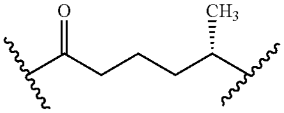
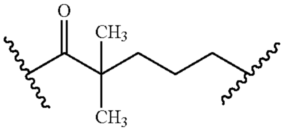
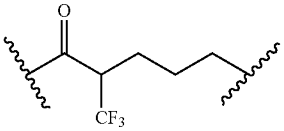
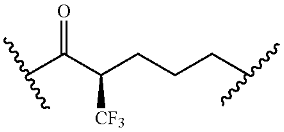
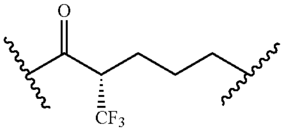
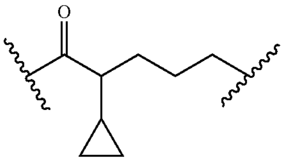

-continued
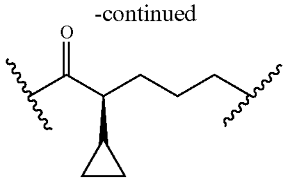
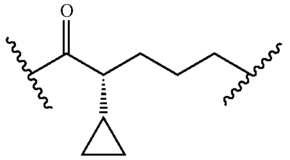
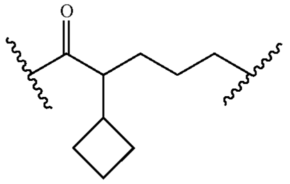
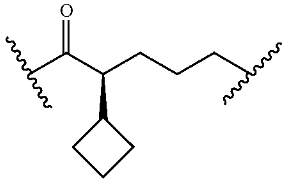
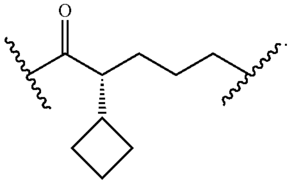
In one embodiment,
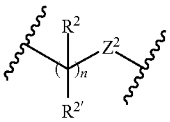
is selected from:
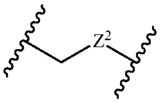
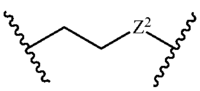
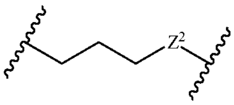
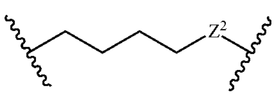
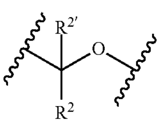
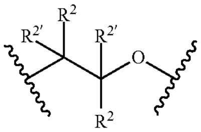
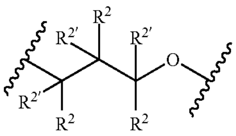
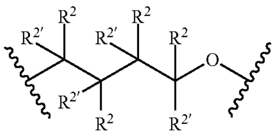
-continued
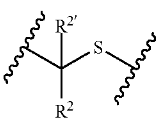
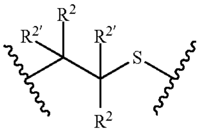
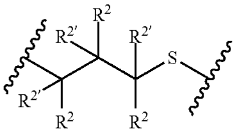
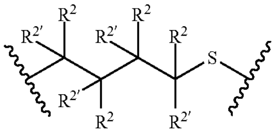
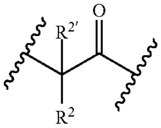
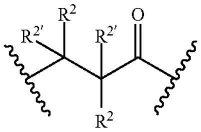
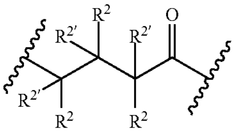
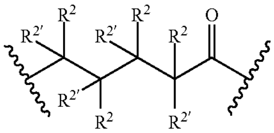
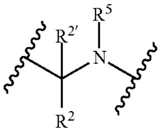
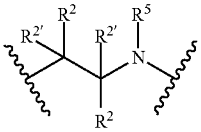
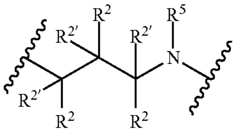
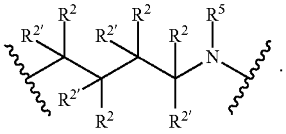
Additional non-limiting examples of
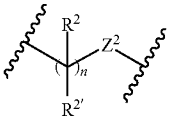
include:
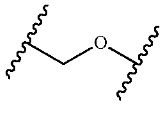
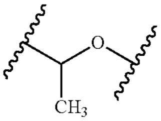
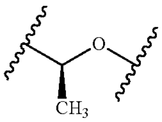
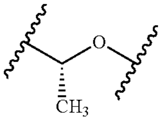
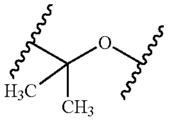
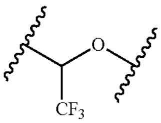
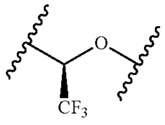
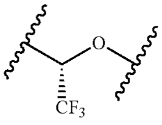

-continued
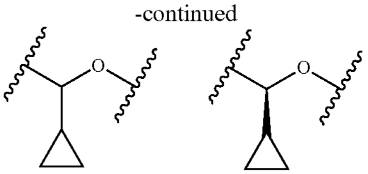
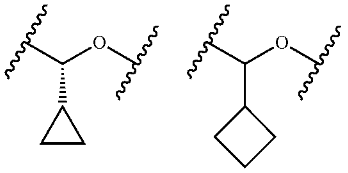
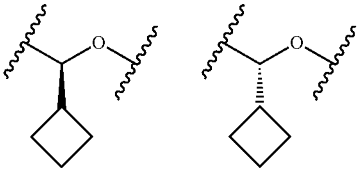
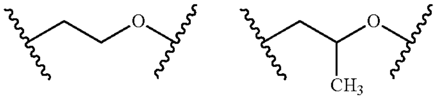
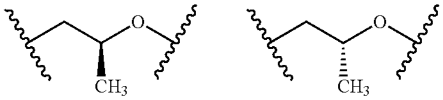
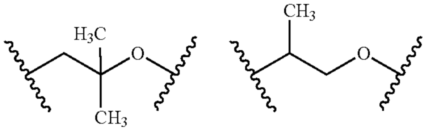
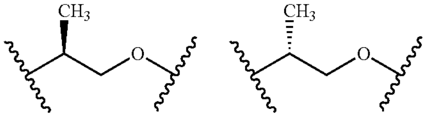
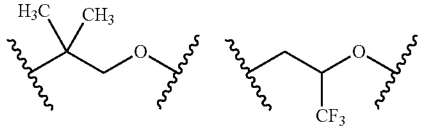
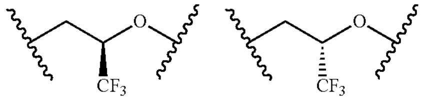
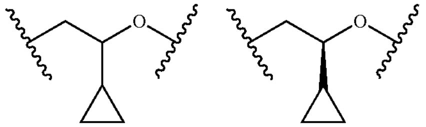
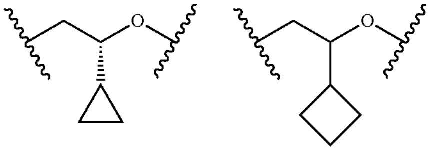
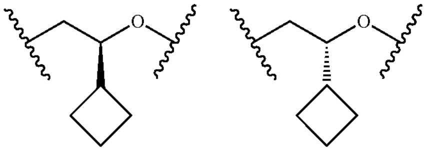
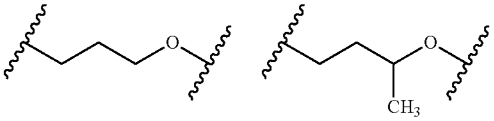
-continued
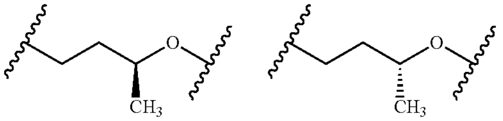
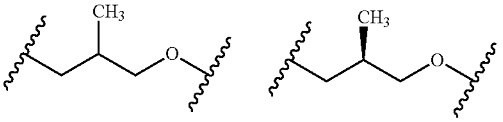
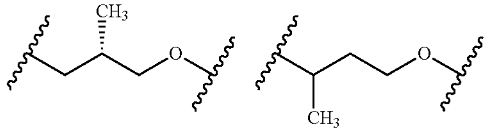
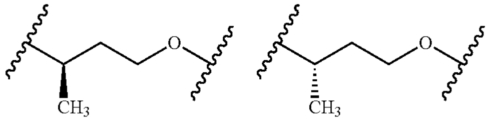
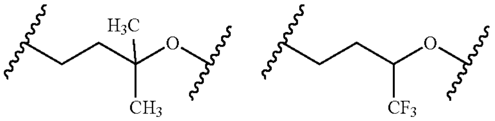
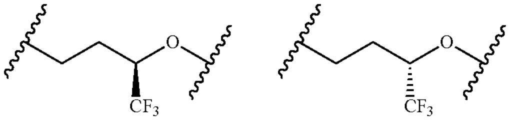
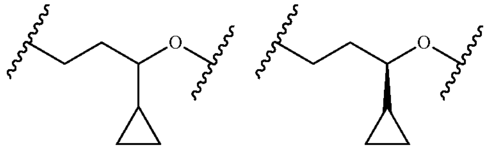
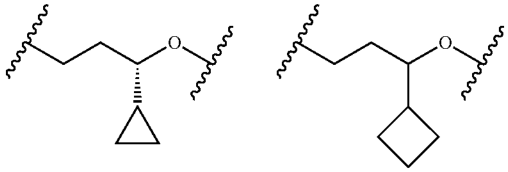
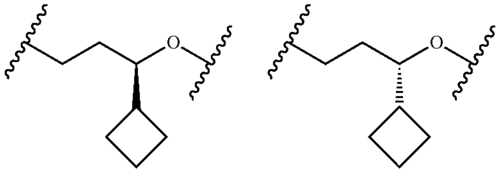
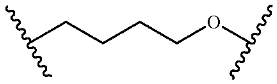
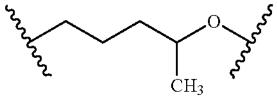
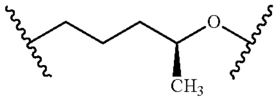
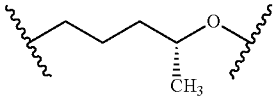

-continued
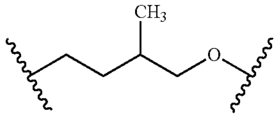
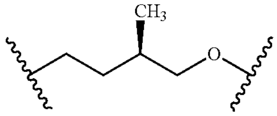
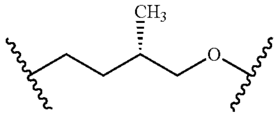
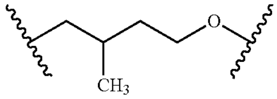
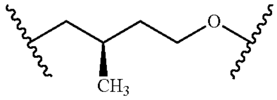
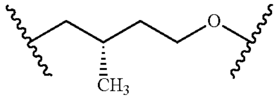
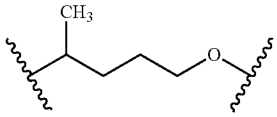
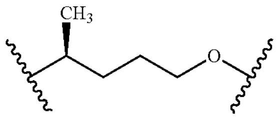
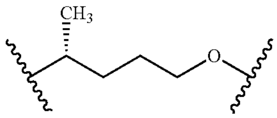
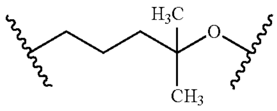
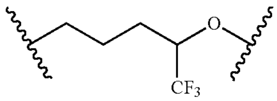
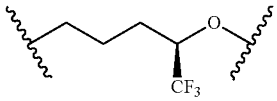
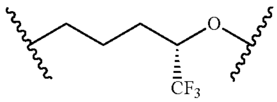
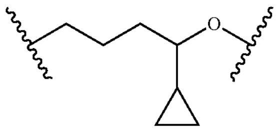
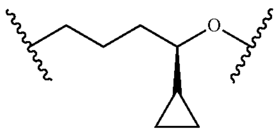
-continued
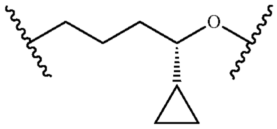
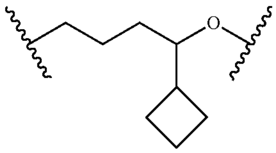
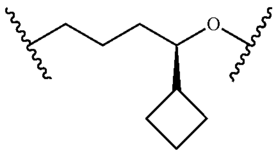
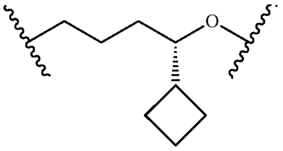
Additional non-limiting examples of
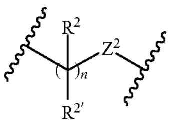
include:
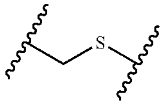
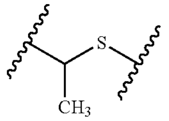
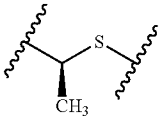
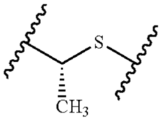
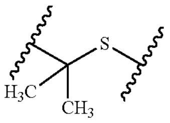
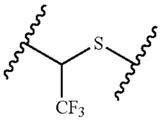
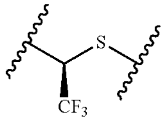
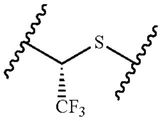
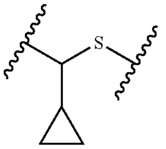
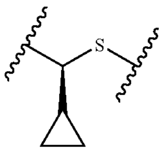

-continued
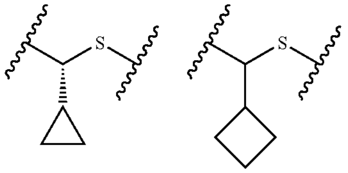
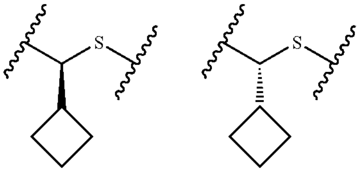
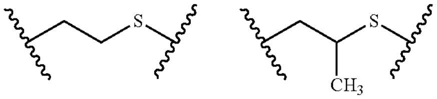
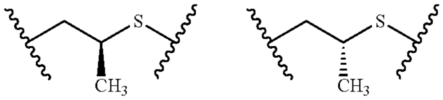
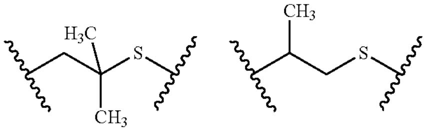
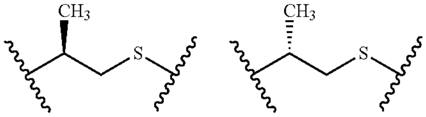
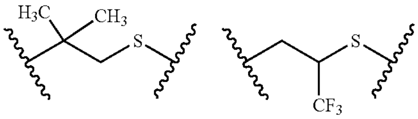
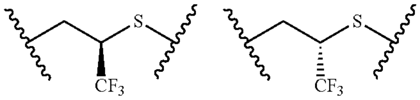
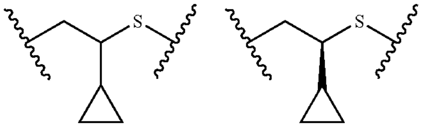
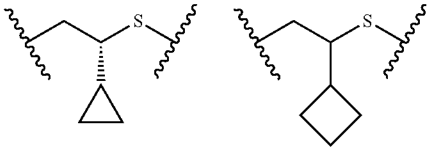
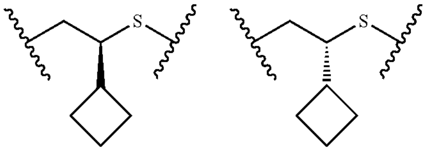
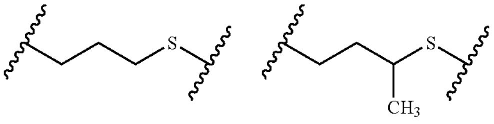
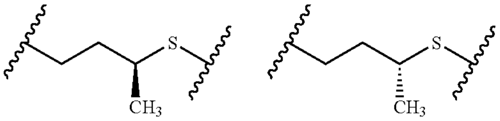
-continued
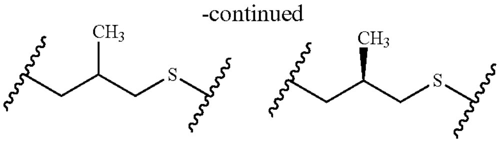
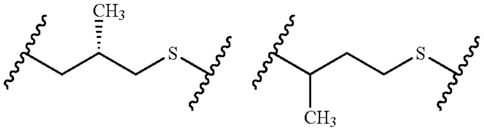
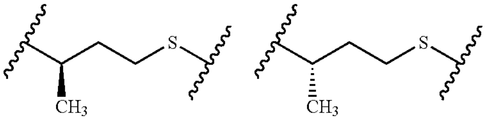
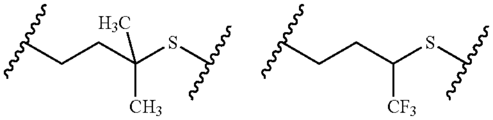
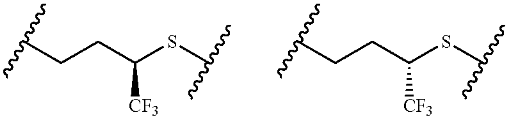
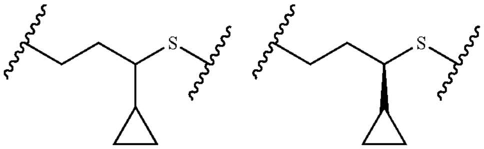
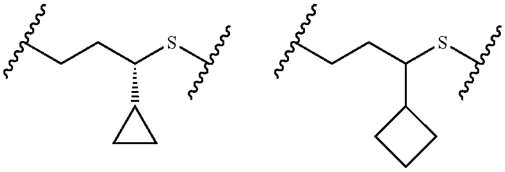
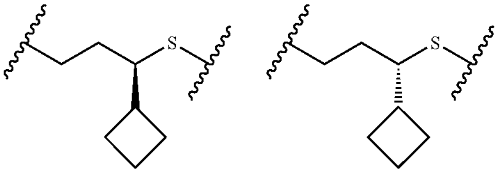
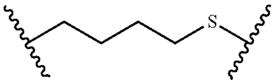
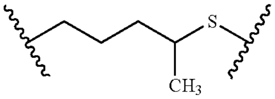
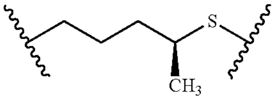
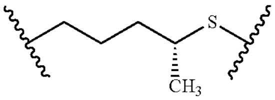
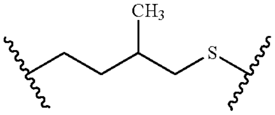
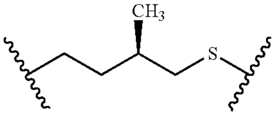

-continued
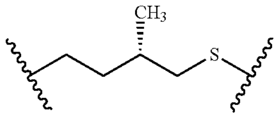
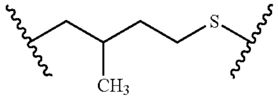
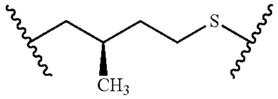
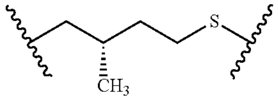
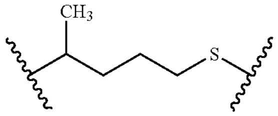
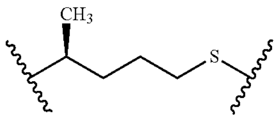
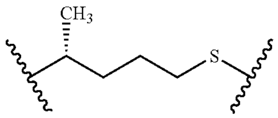
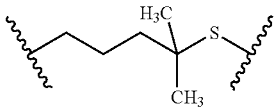
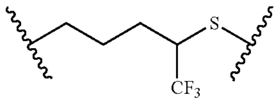
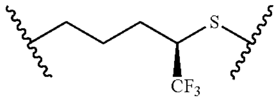
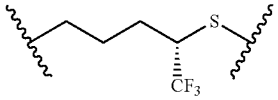
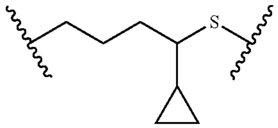
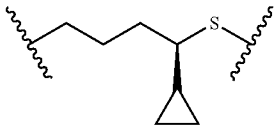
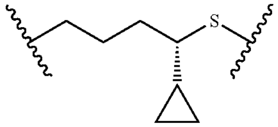
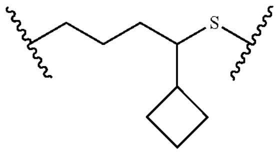
-continued
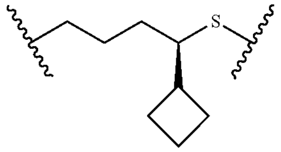
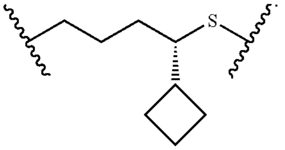
Additional non-limiting examples of
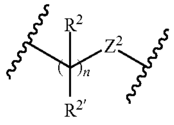
include:
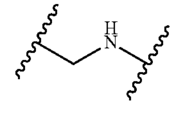 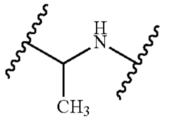
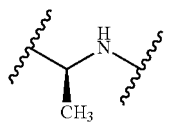 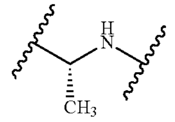
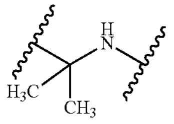 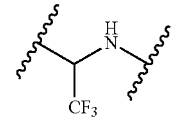
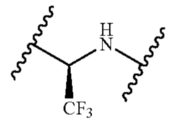 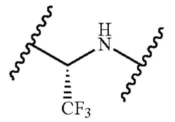
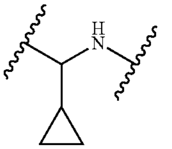 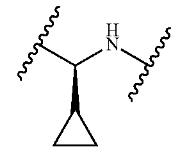
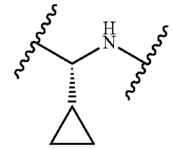 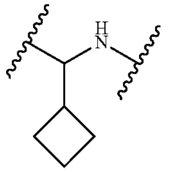
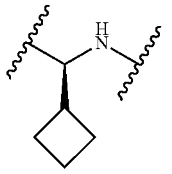 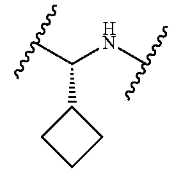

-continued
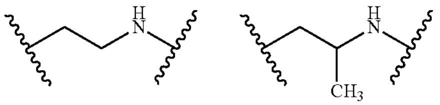
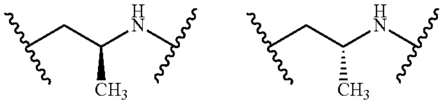
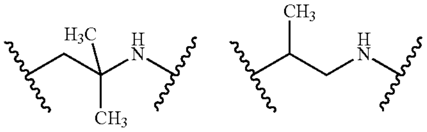
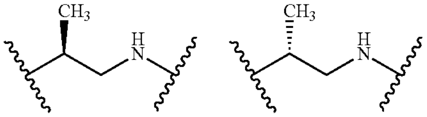
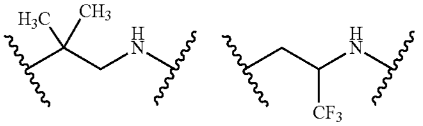
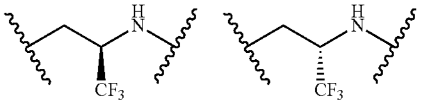
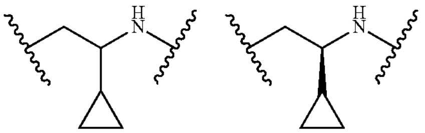
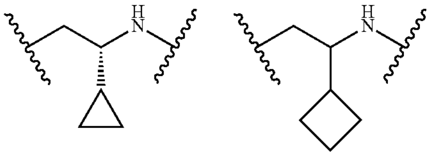
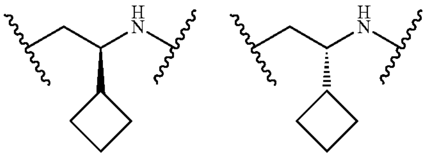
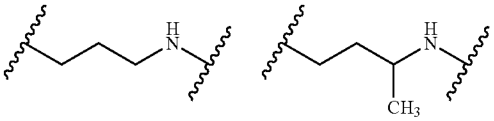
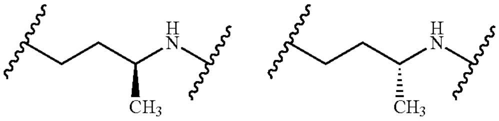
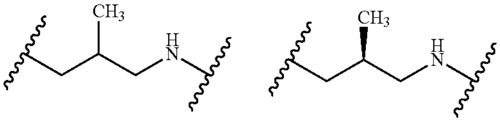
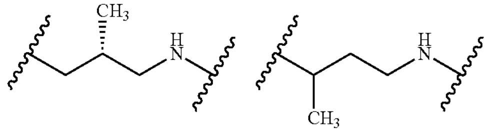
-continued
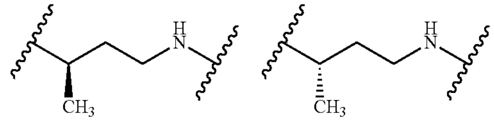
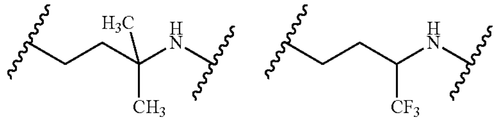
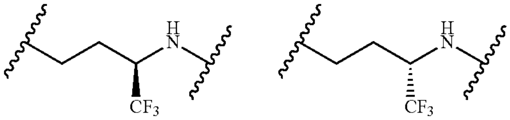
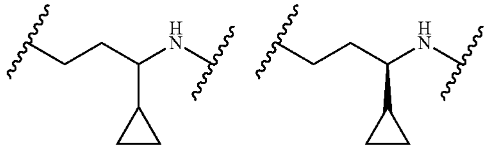
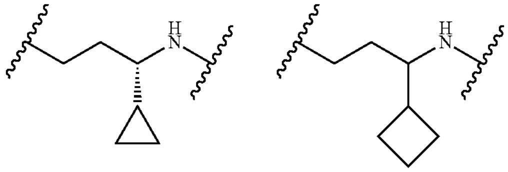
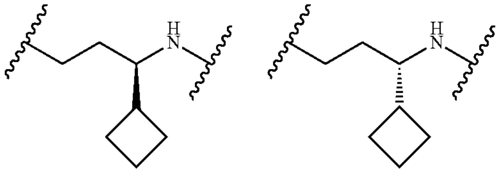
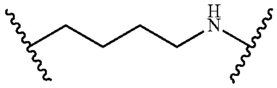
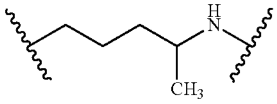
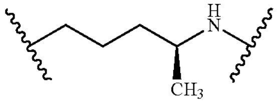
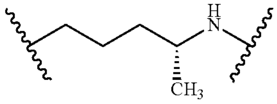
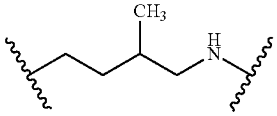
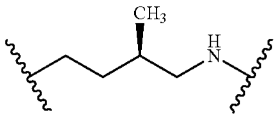
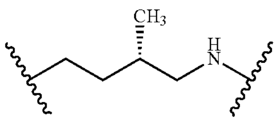
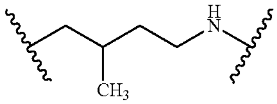

-continued
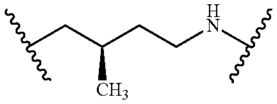
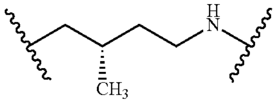
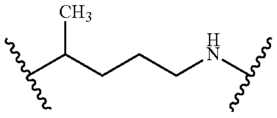
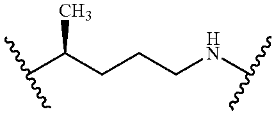
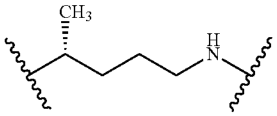
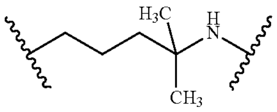
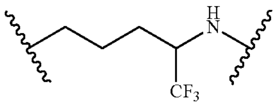
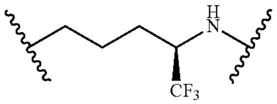
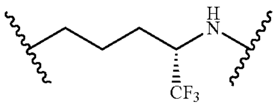
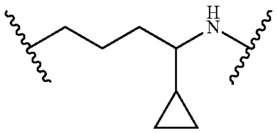
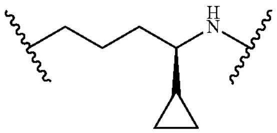
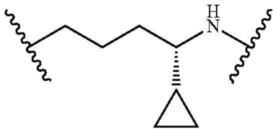
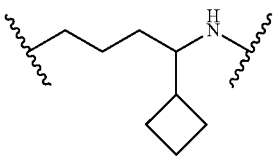
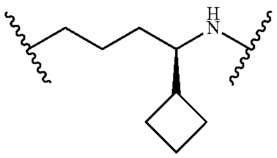
-continued
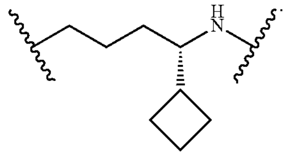
Additional non-limiting examples of
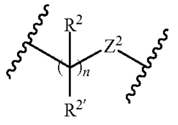
include:
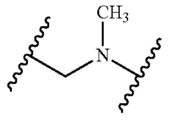 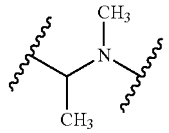
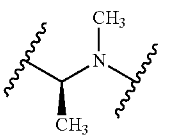 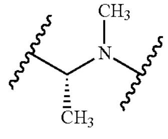
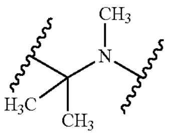 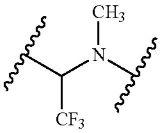
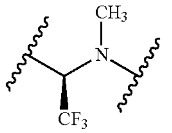 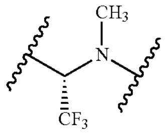
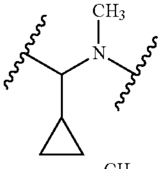 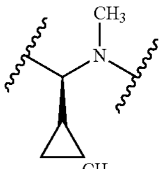
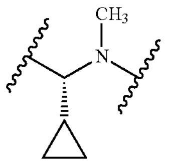 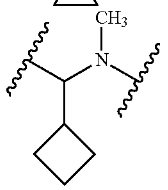
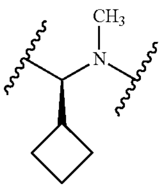 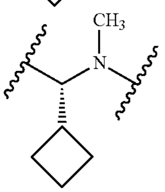
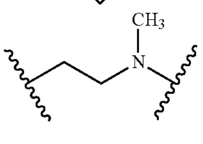 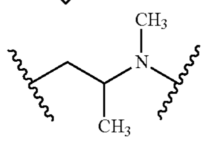

-continued
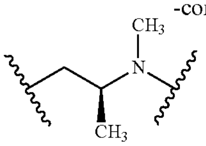
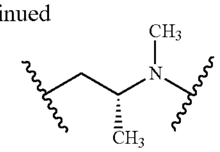
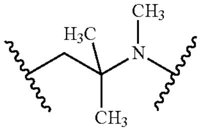
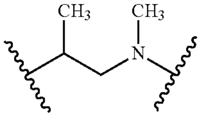
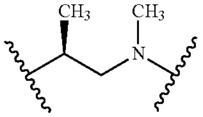
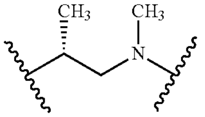
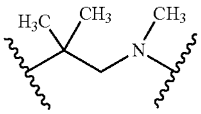
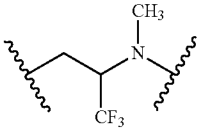
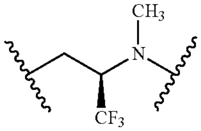
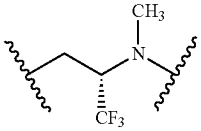
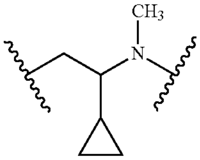
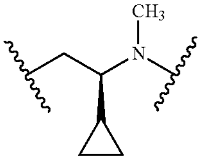
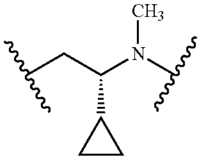
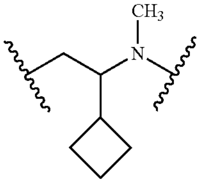
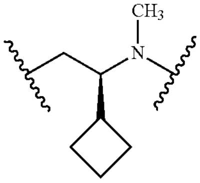
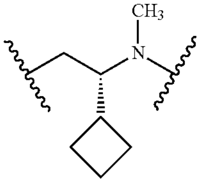
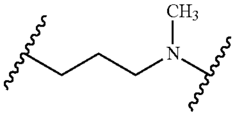
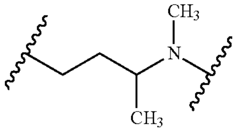
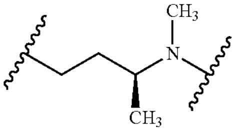
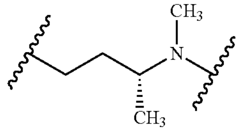
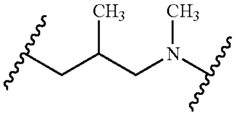
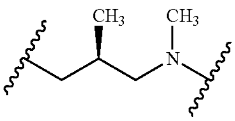
-continued
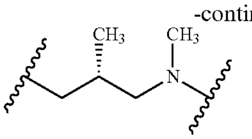
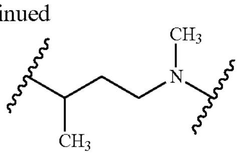
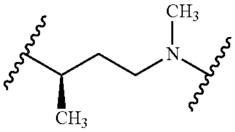
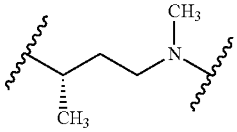
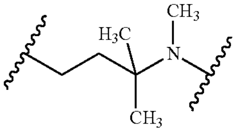
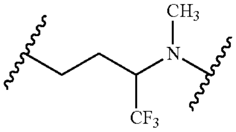
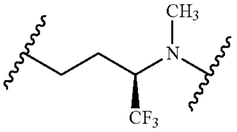
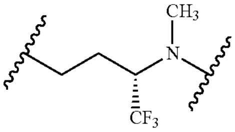
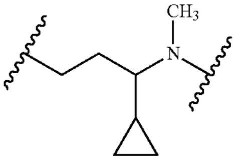
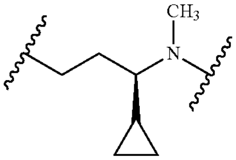
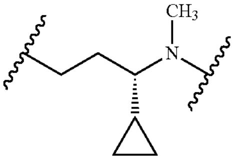
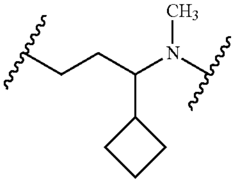
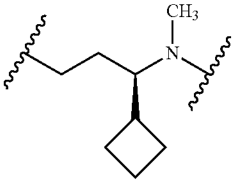
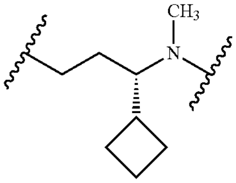
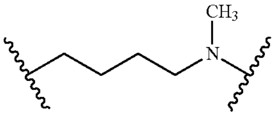
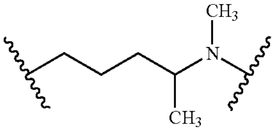
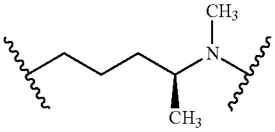
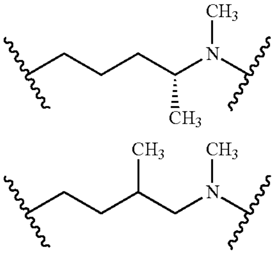

-continued
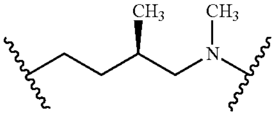
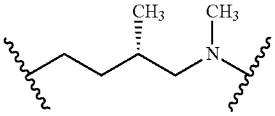
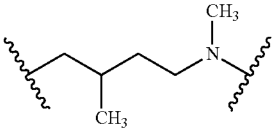
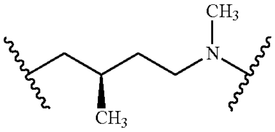
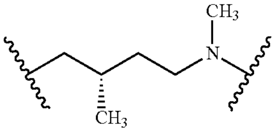
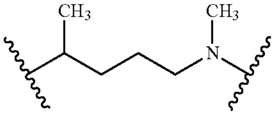
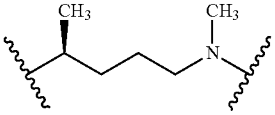
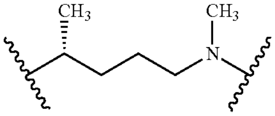
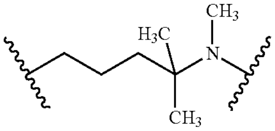
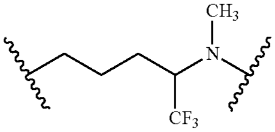
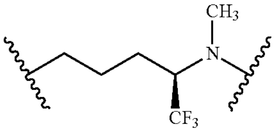
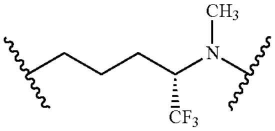
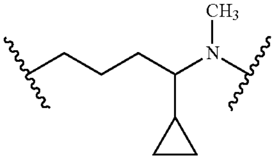
-continued
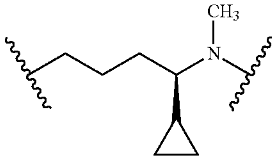
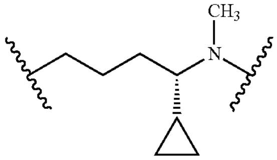
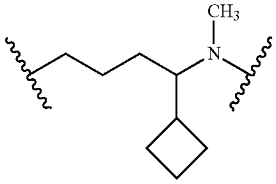
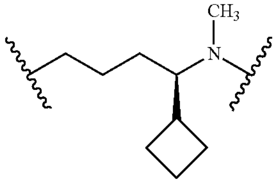
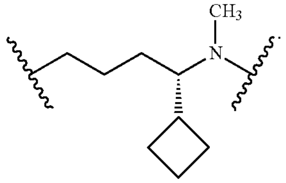
Additional non-limiting examples of
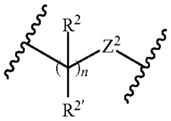
include:
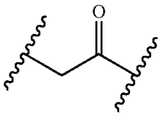
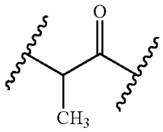
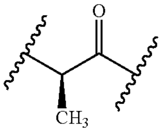
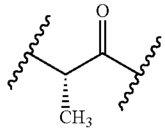
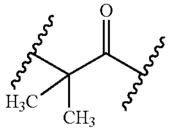
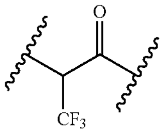

-continued
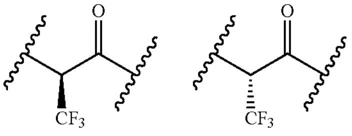
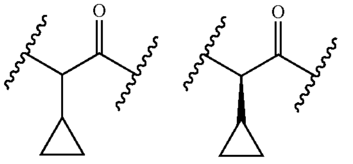
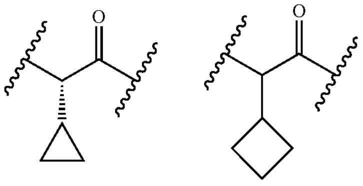
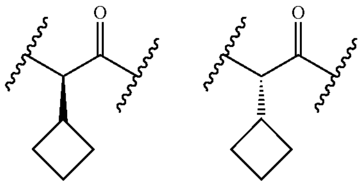
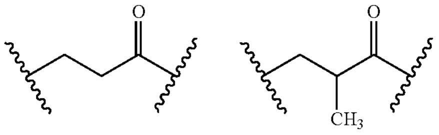
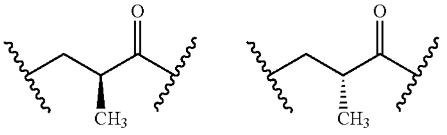
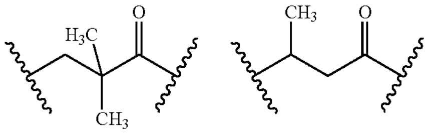
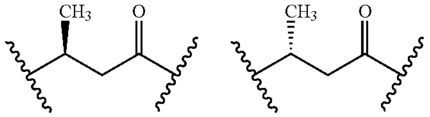
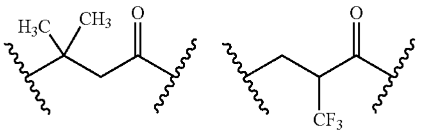
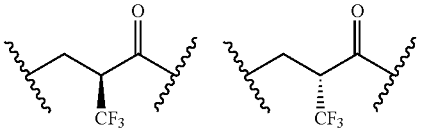
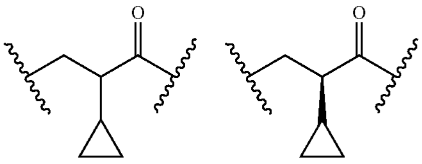
-continued
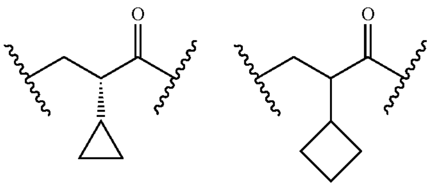
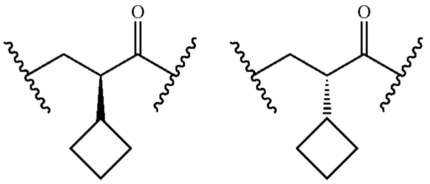
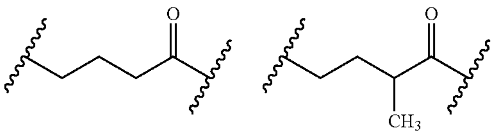
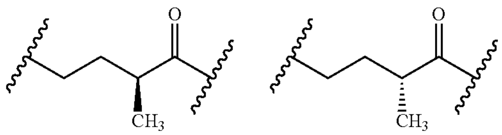
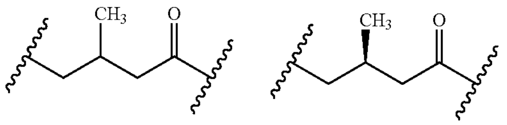
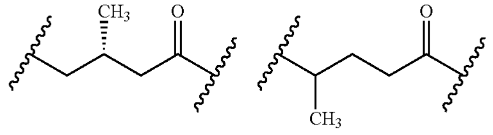
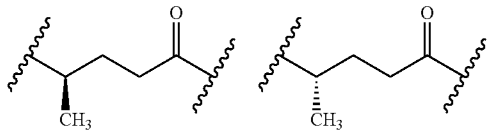
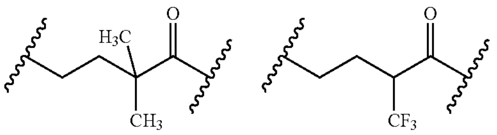
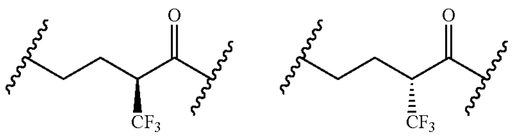
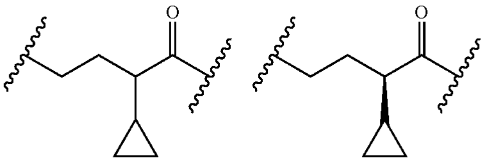
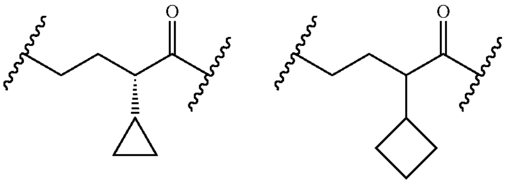

-continued
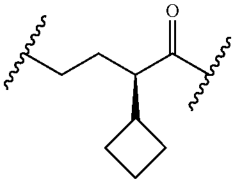
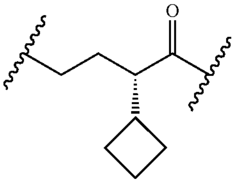
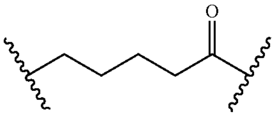
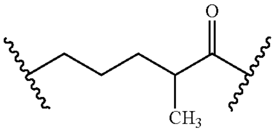
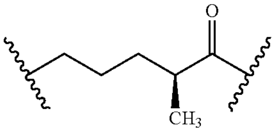
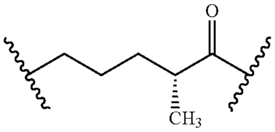
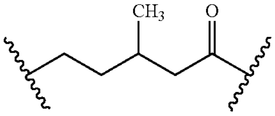
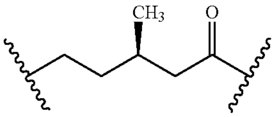
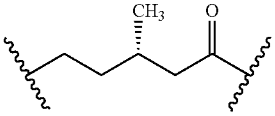
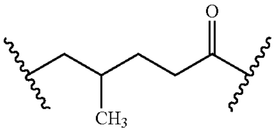
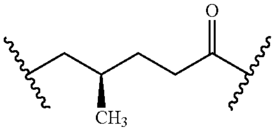
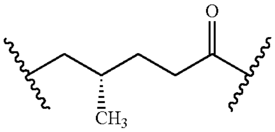
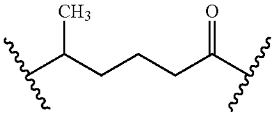
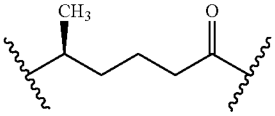
-continued
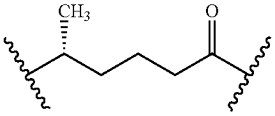
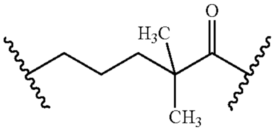
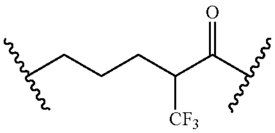
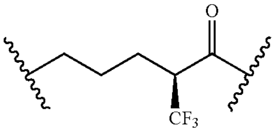
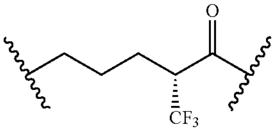
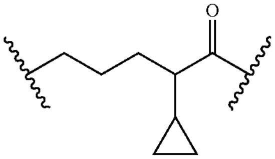
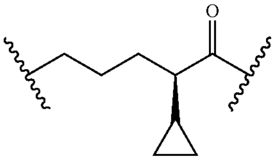
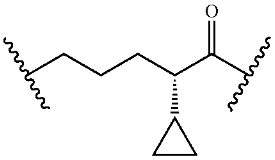
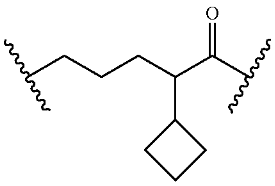
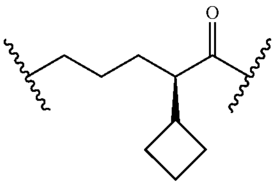
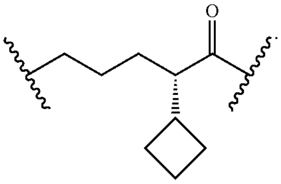
.

Additional non-limiting examples of $Z^1$ and $Z^2$ include:
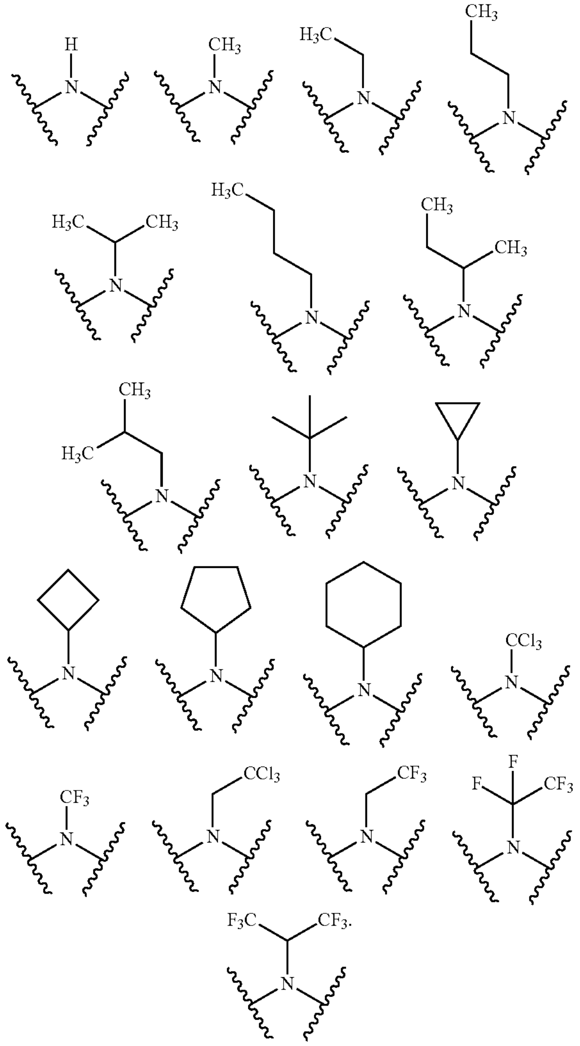
In one embodiment,
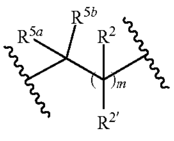
is selected from:
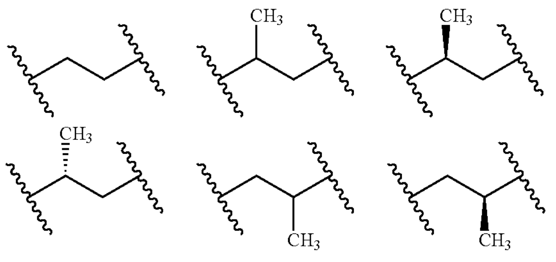
-continued
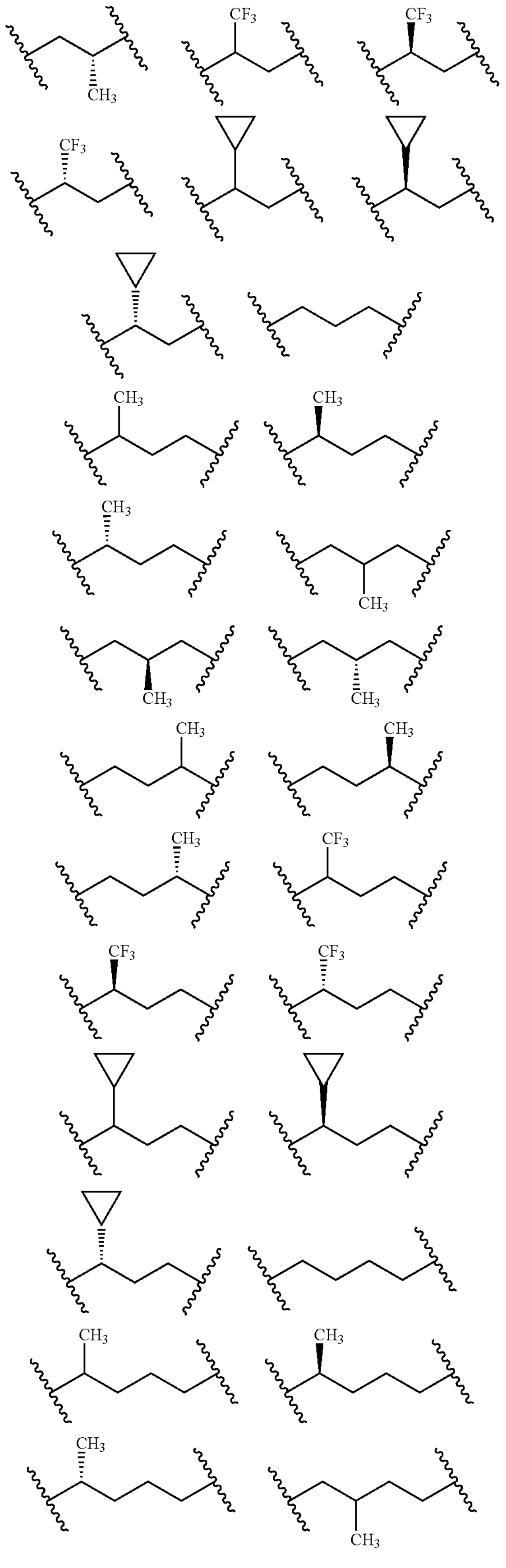

-continued
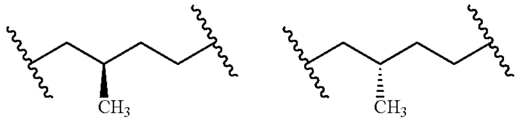
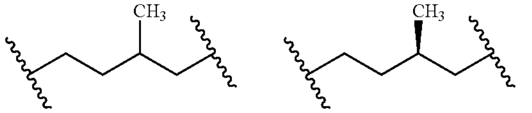
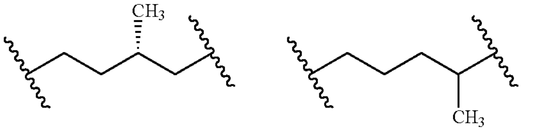
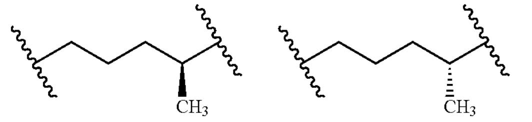
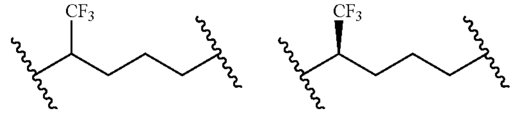
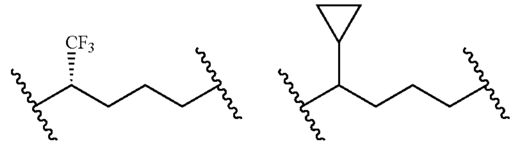
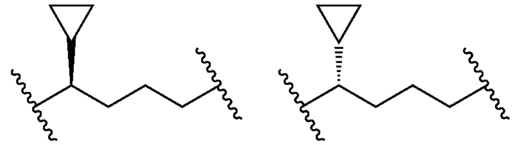
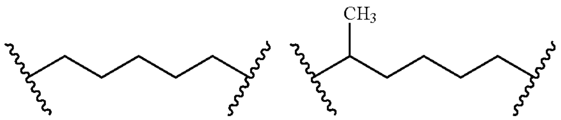
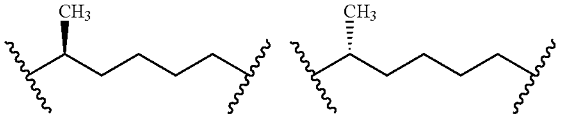
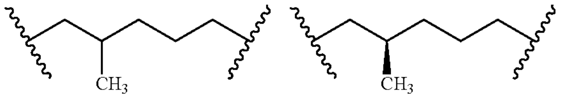
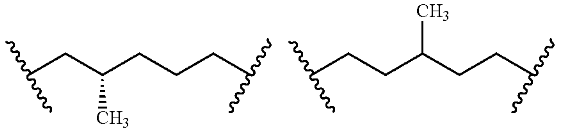
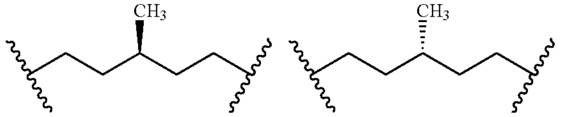
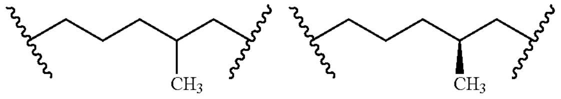
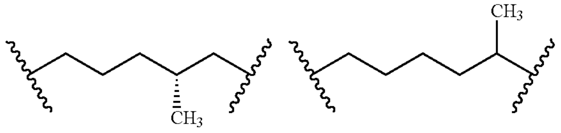
-continued
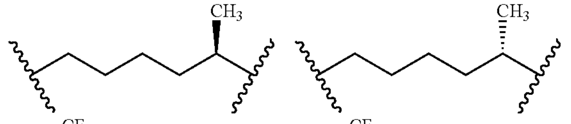
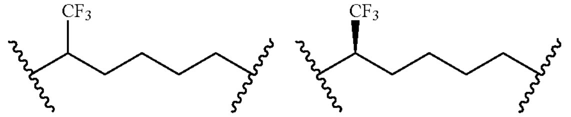
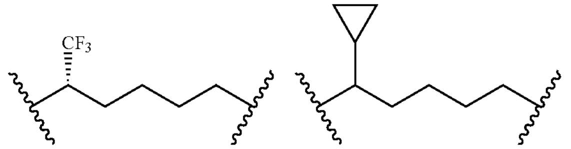
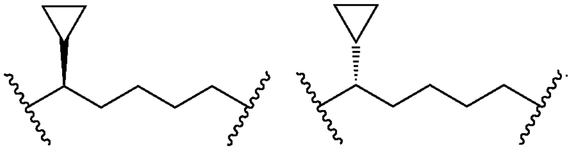
Additional examples of
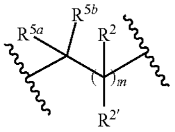
include:
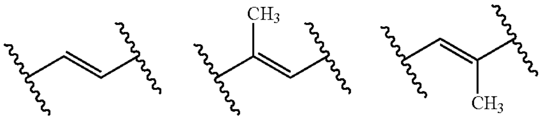
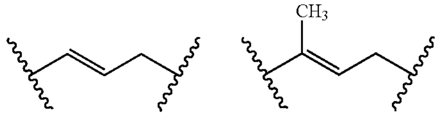
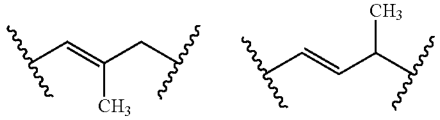
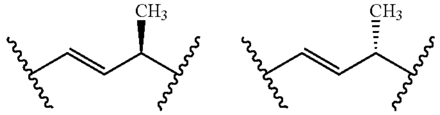
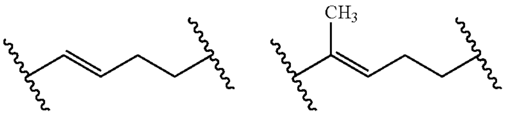
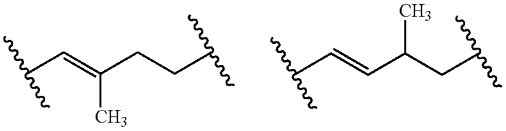
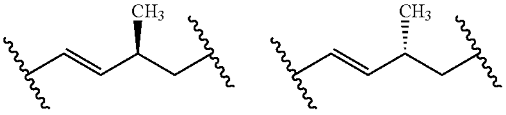

-continued
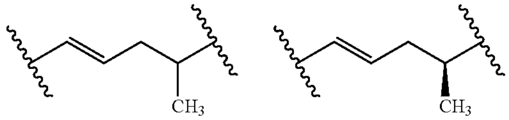
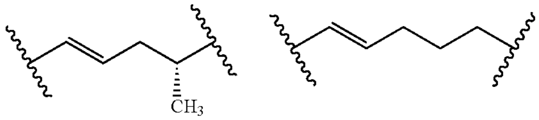
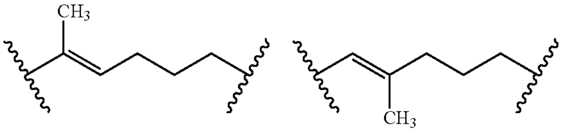
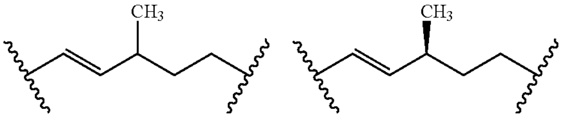
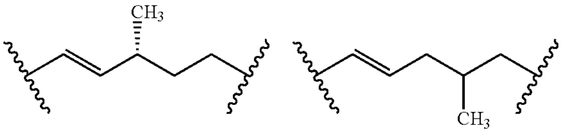
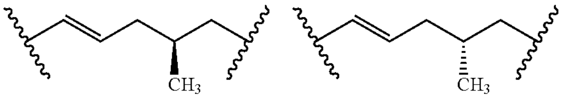
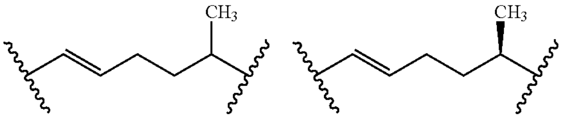
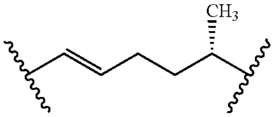
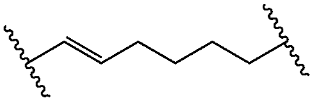
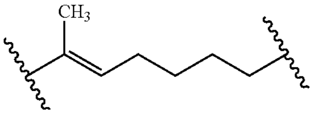
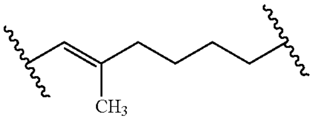
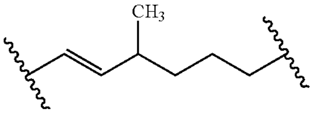
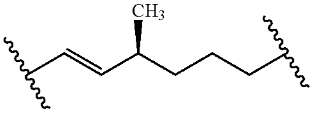
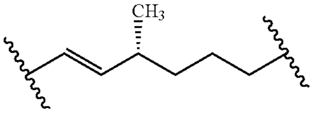
-continued
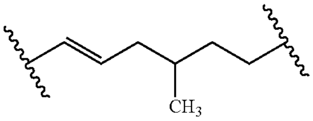
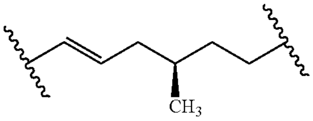
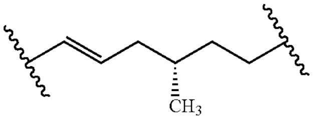
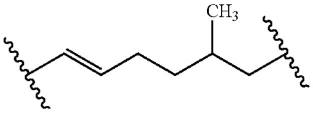
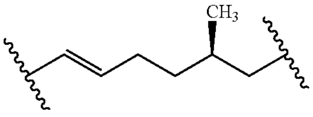
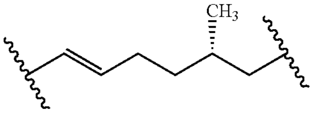
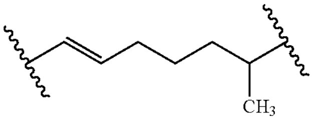
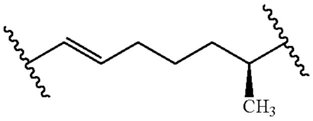
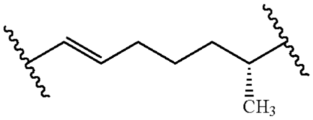
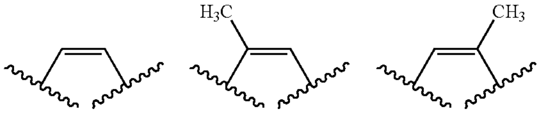
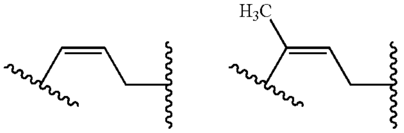
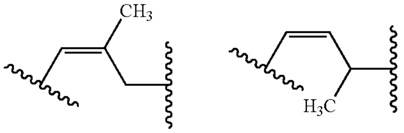
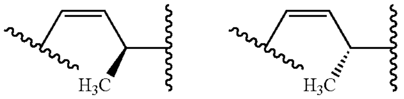
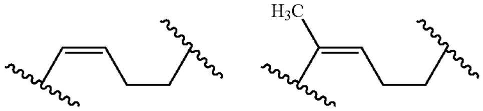

-continued
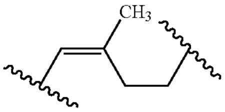
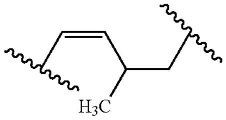
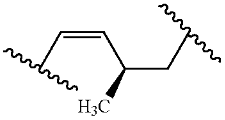
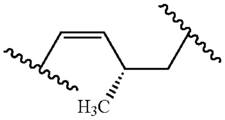
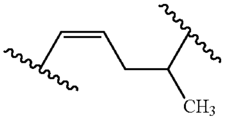
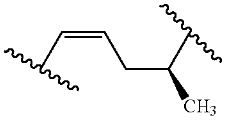
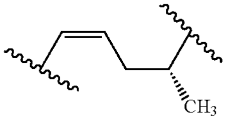
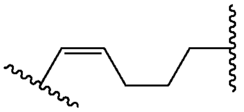
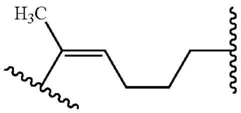
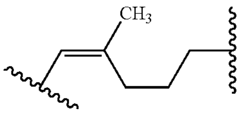
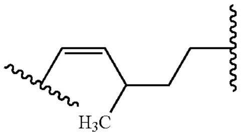
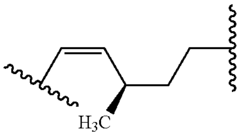
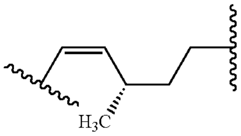
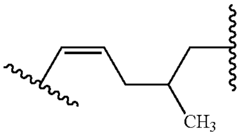
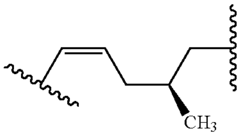
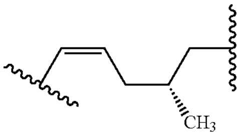
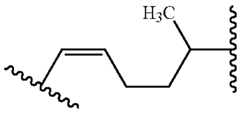
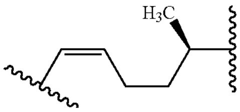
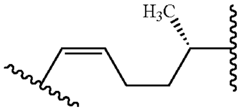
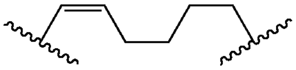
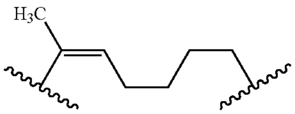
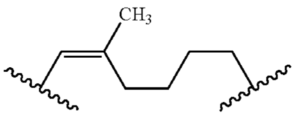
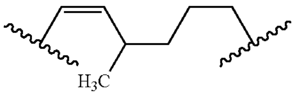
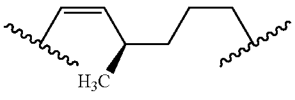
-continued
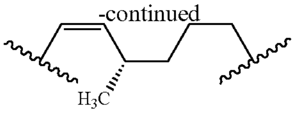
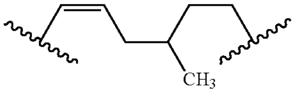
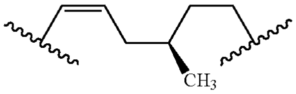
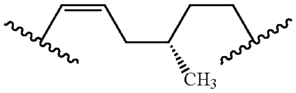
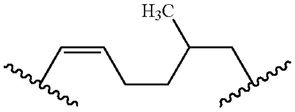
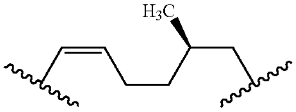
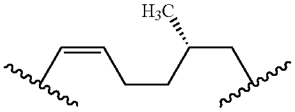
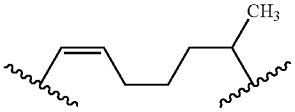
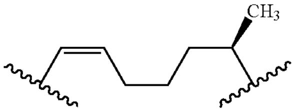
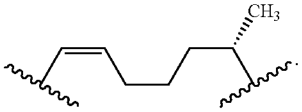
Additional examples of
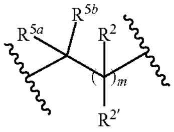
include:
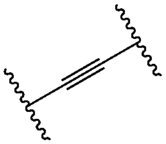
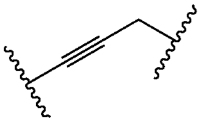
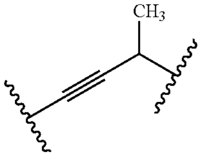
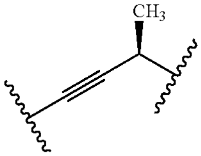

-continued
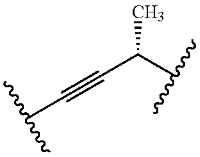
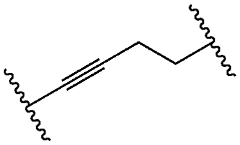
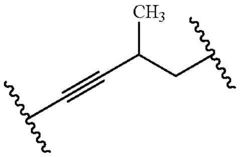
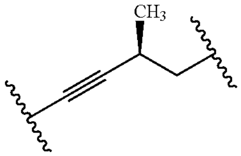
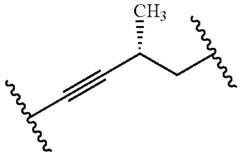
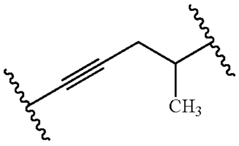
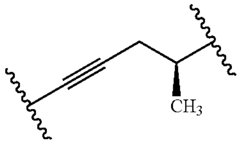
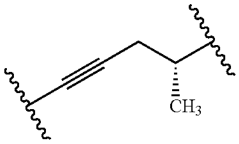
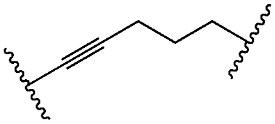
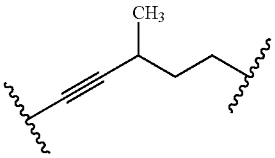
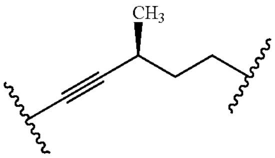
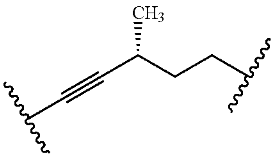
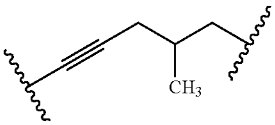
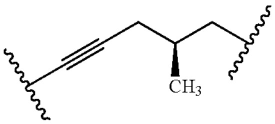
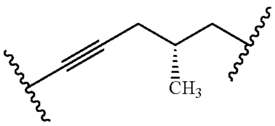
-continued
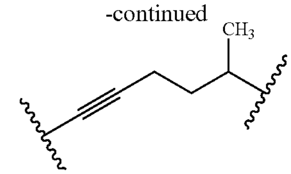
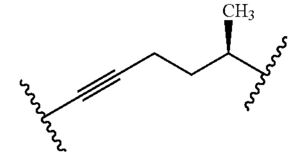
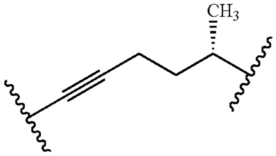
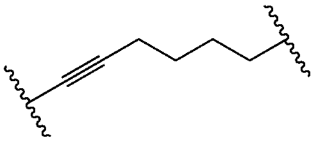
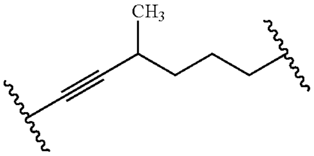
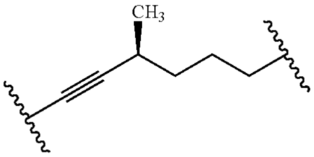
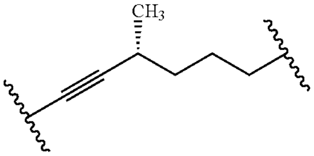
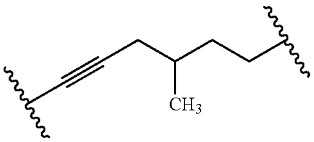
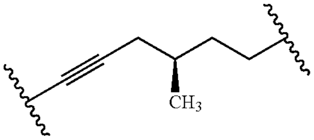
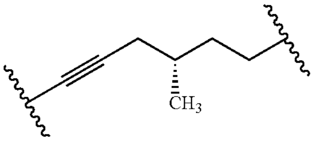
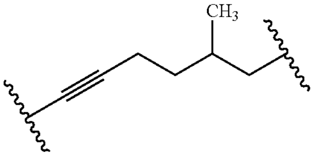

-continued
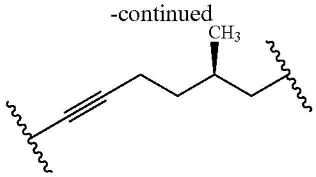
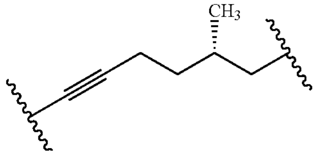
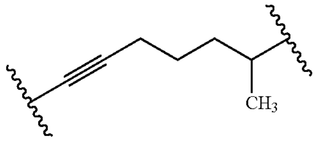
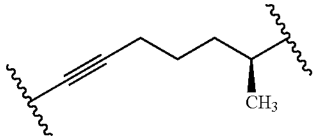
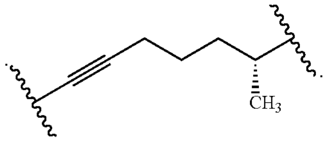
In one embodiment,
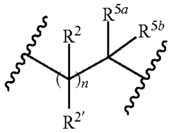
is selected from:
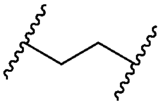
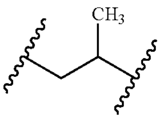
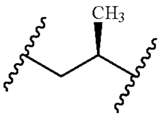
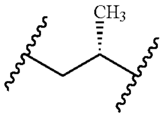
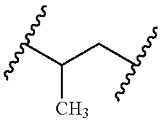
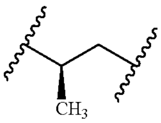
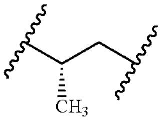
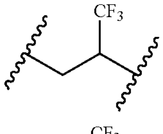
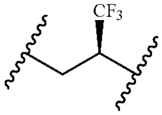
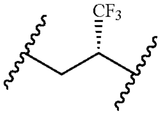
-continued
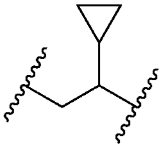
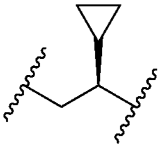
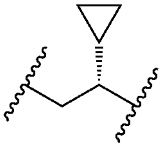
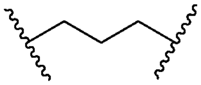
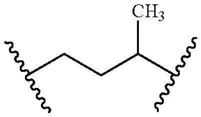
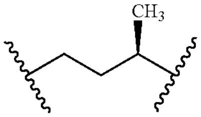
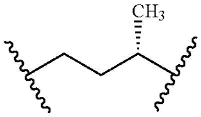
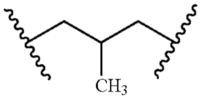
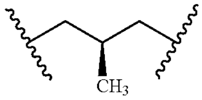
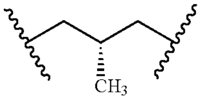
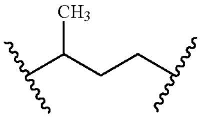
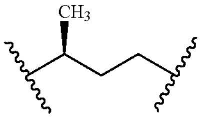
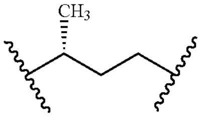
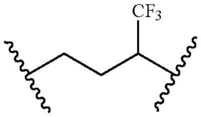
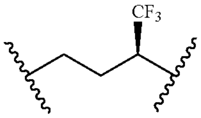
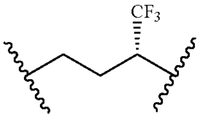
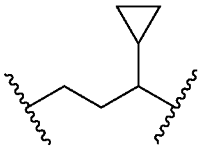
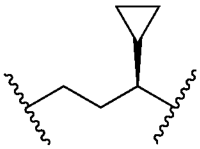
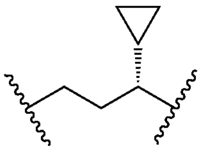
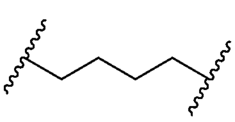
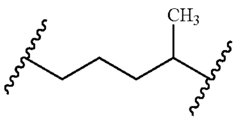
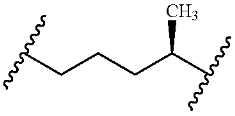
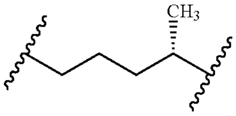
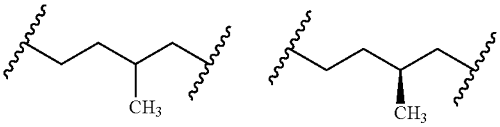

-continued
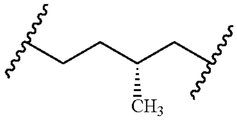
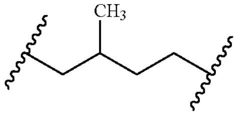
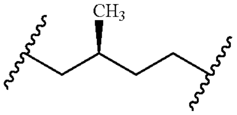
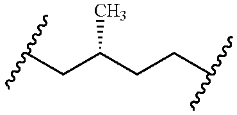
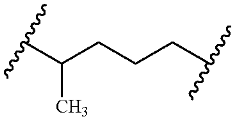
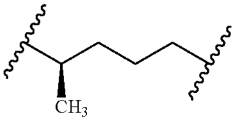
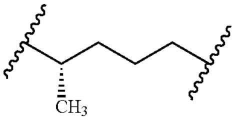
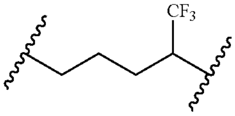
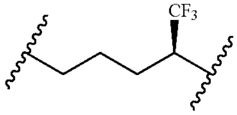
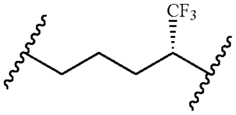
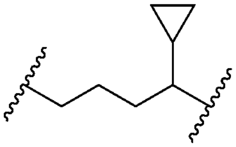
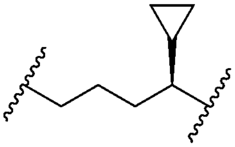
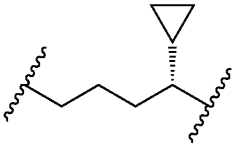
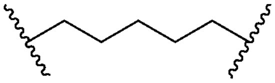
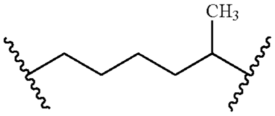
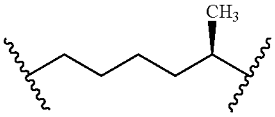
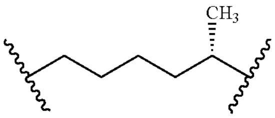
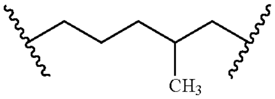
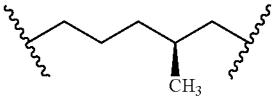
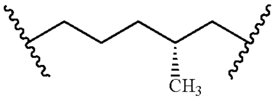
-continued
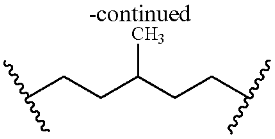
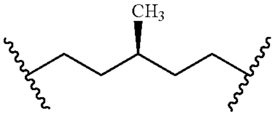
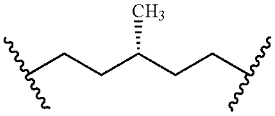
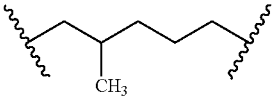
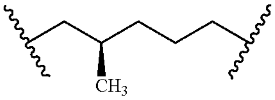
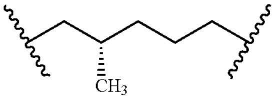
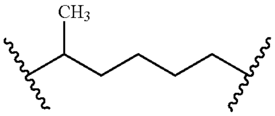
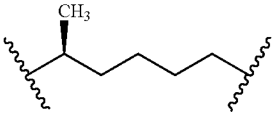
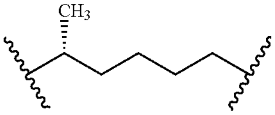
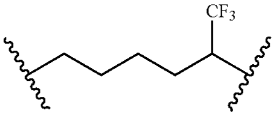
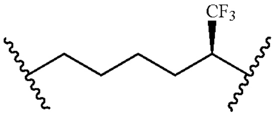
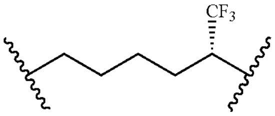
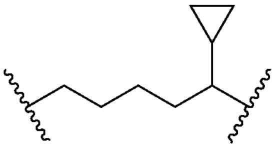
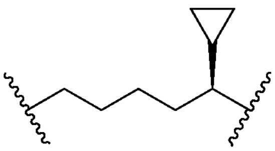

-continued
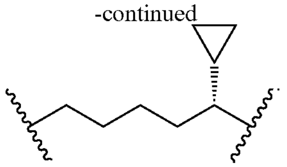
Additional examples of
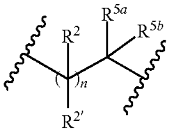
include:
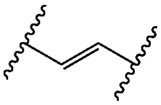
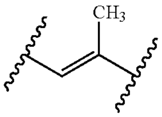
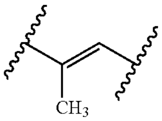
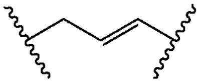
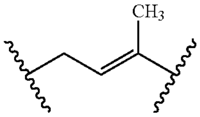
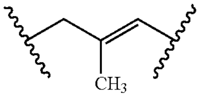
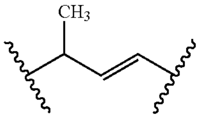
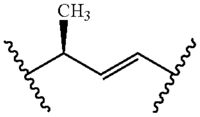
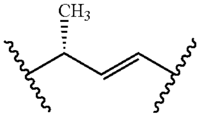
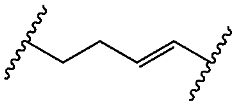
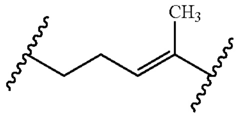
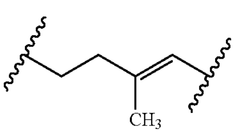
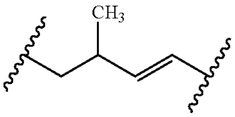
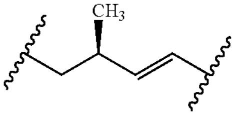
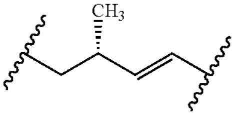
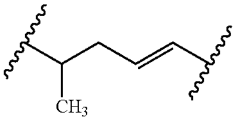
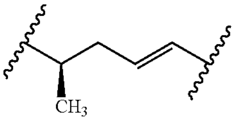
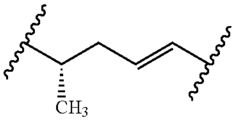
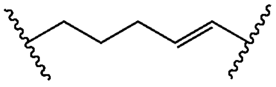
-continued
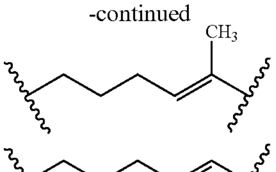
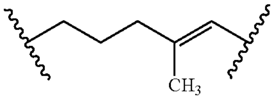
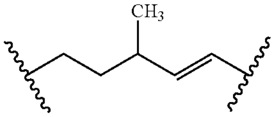
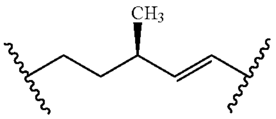
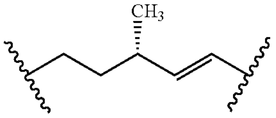
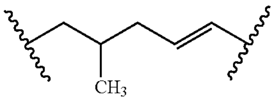
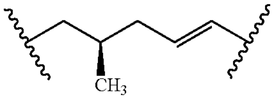
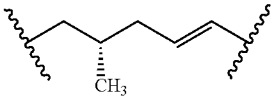
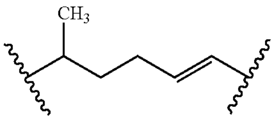
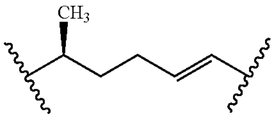
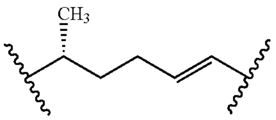
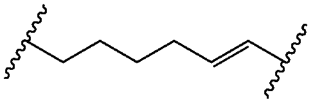
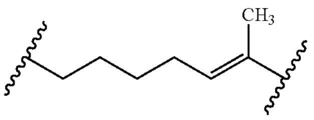
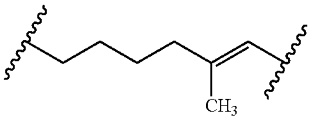
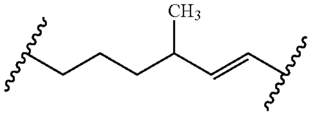

-continued
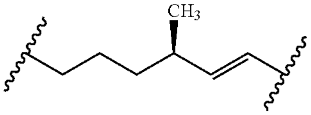
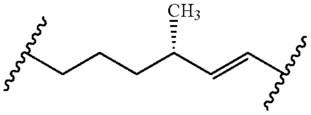
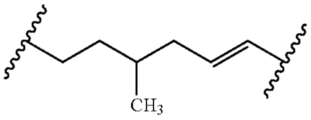
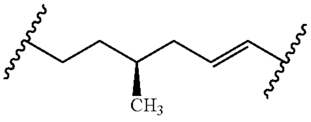
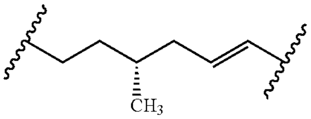
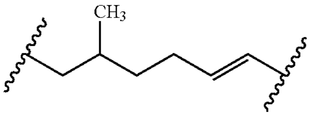
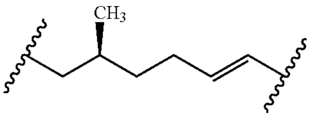
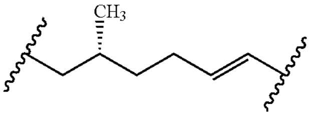
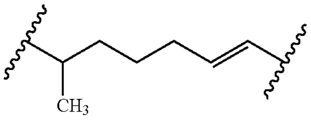
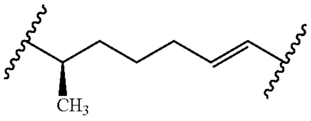
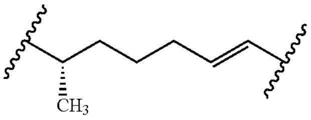
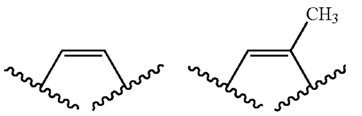
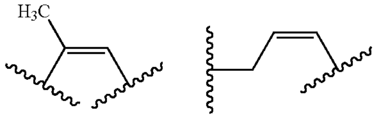
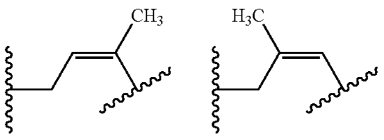
-continued
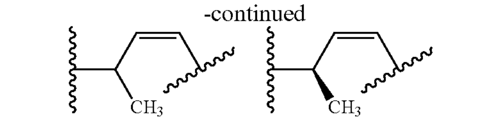
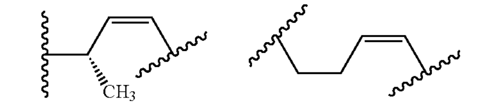
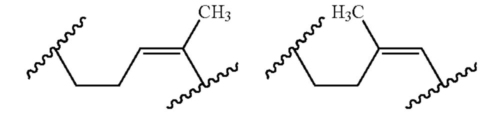
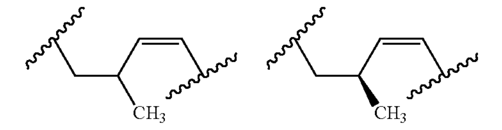
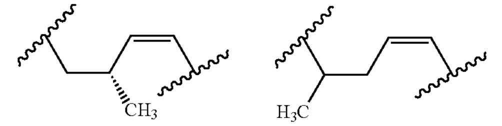
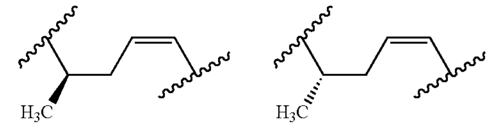
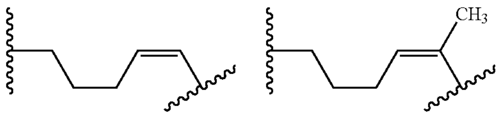
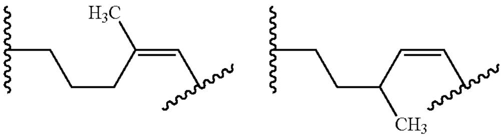
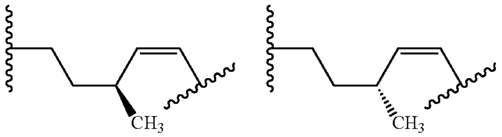
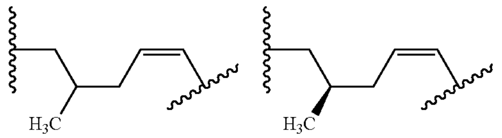
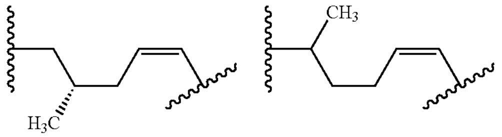
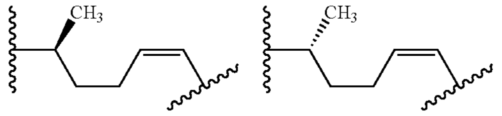
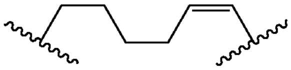
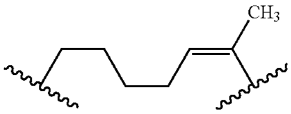

-continued
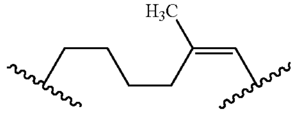
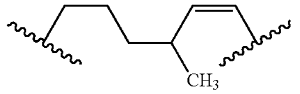
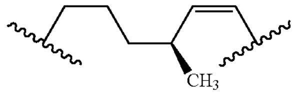
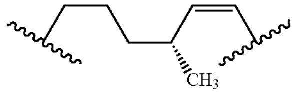
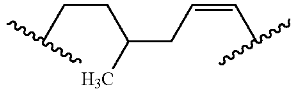
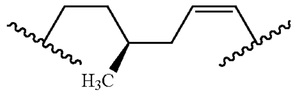
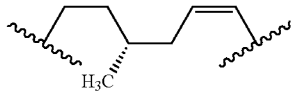
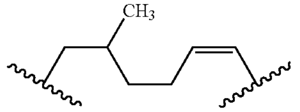
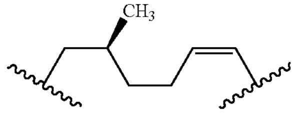
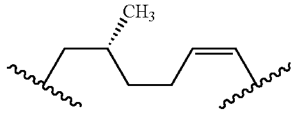
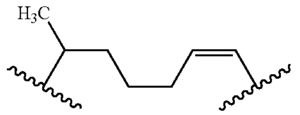
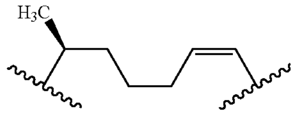
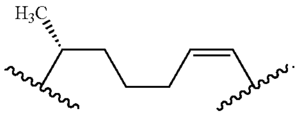
Additional examples of
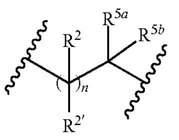
include:
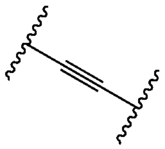
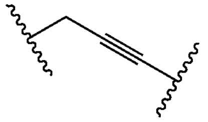
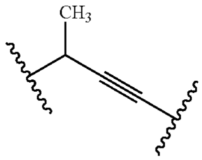
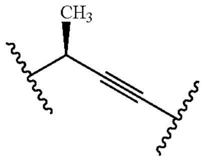
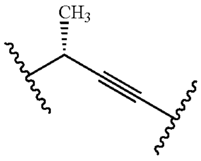
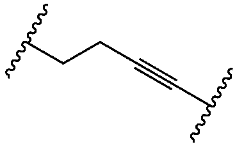
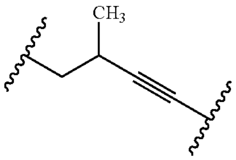
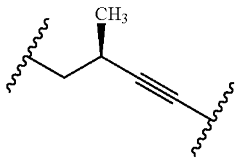
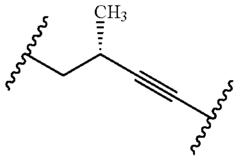
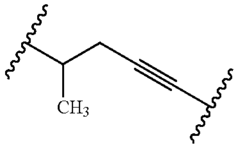
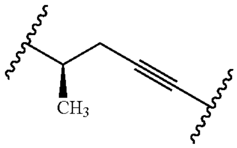
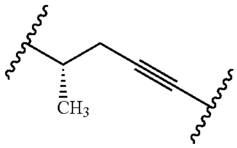
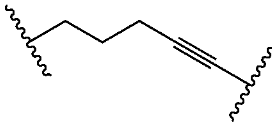
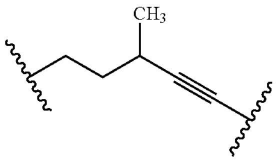
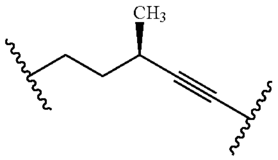
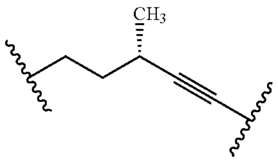
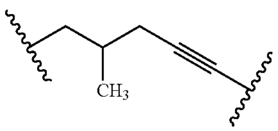

-continued
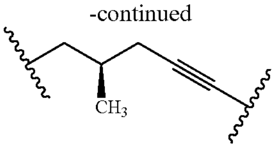
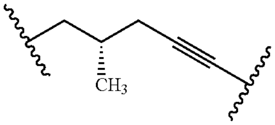
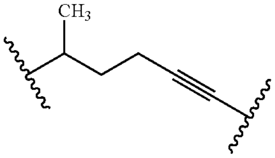
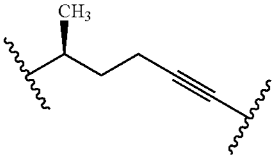
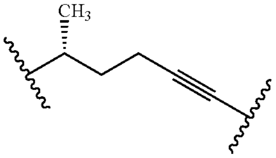
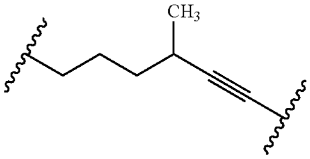
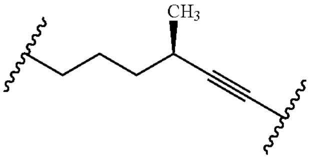
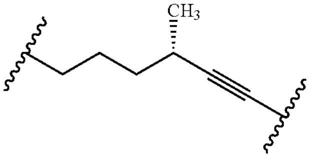
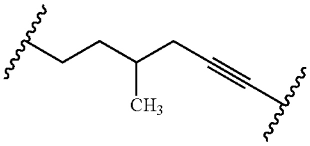
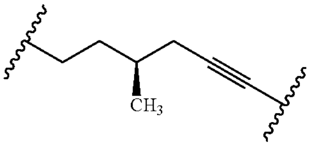
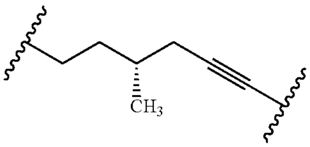
-continued
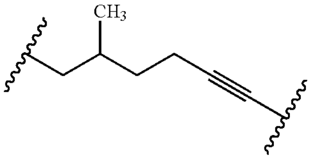
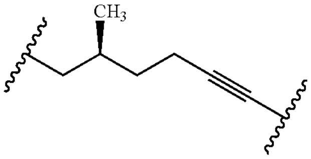
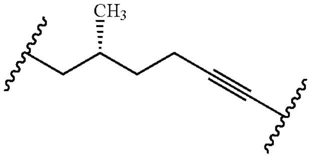
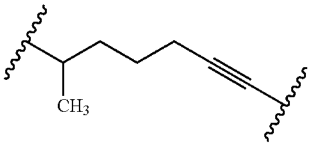
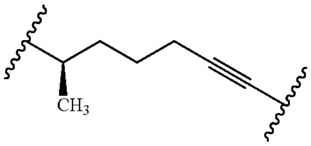
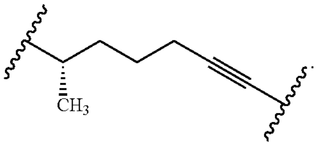
.
In one embodiment,
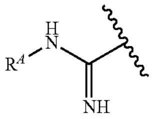
or
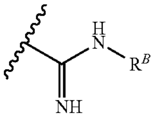
is selected from:
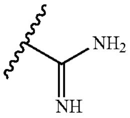
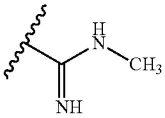
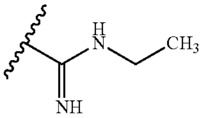
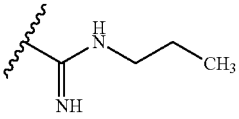
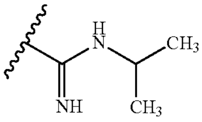
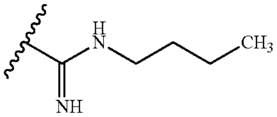
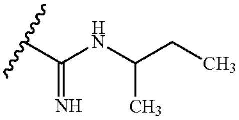

-continued
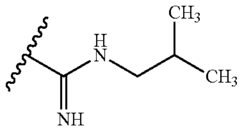
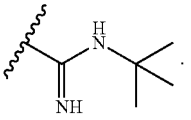
In one embodiment,
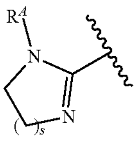
or
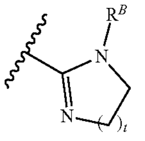
is selected from:
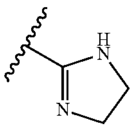
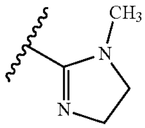
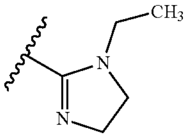
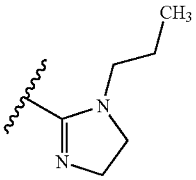
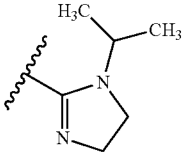
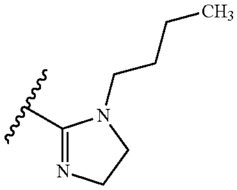
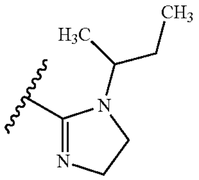
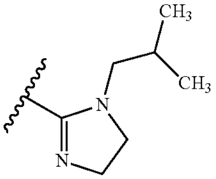
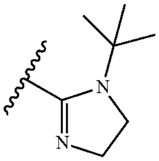
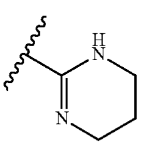
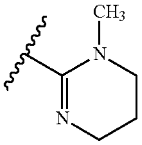
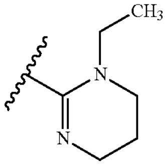
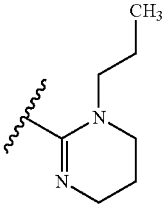
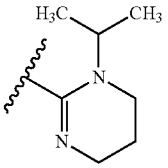
-continued
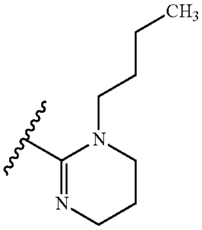
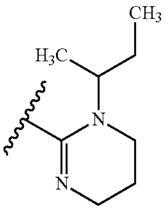
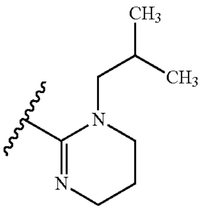
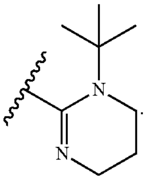
Non-limiting examples of compounds of Formula IA include:
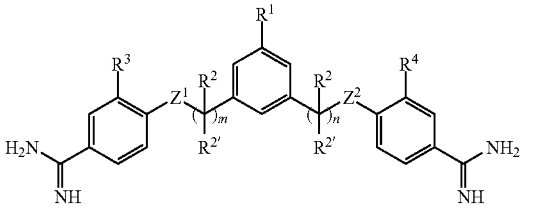
and
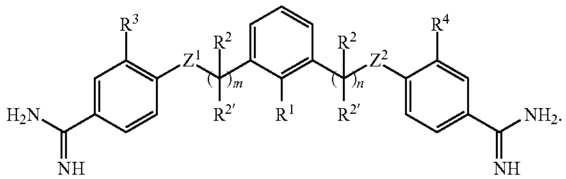
Non-limiting examples of compounds of Formula IA include.
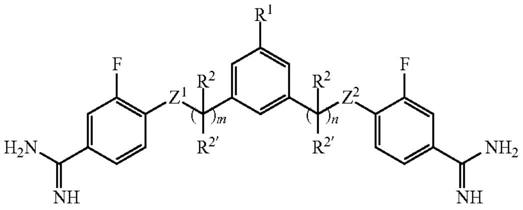
and
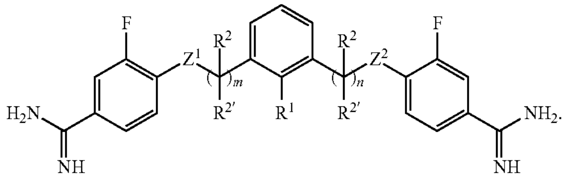

Non-limiting examples of compounds of Formula IA include:
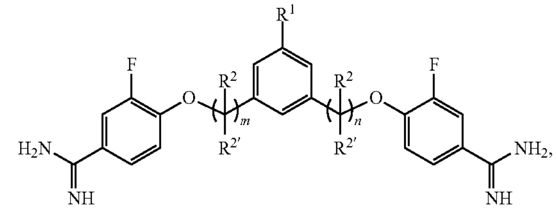
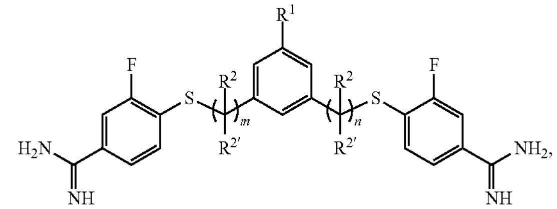
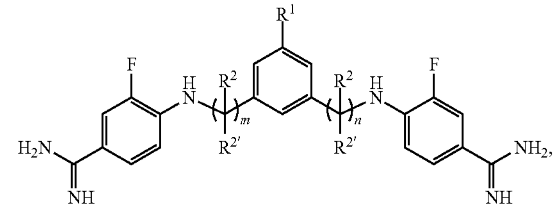
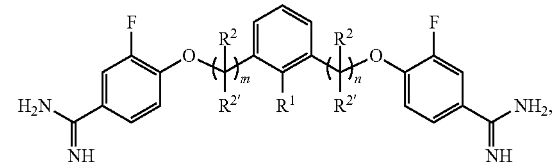
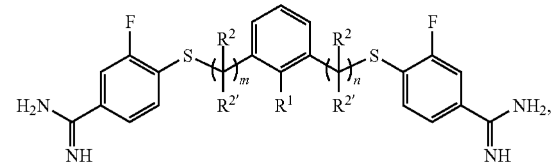
and
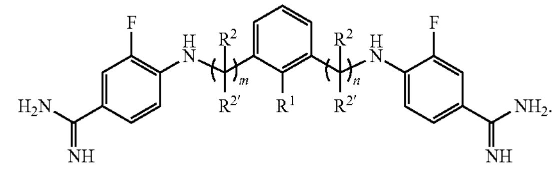
Non-limiting examples of compounds of Formula IB include.
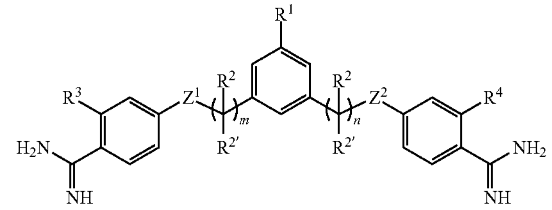
and
-continued
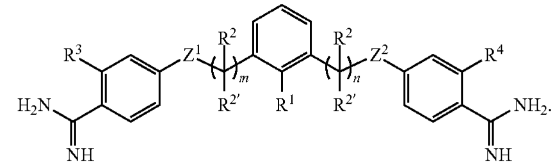
Non-limiting examples of compounds of Formula IB include:
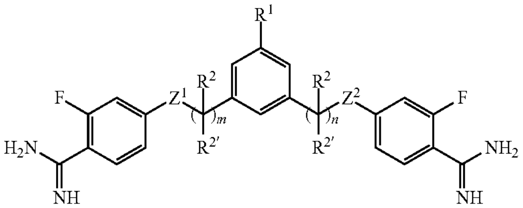
and
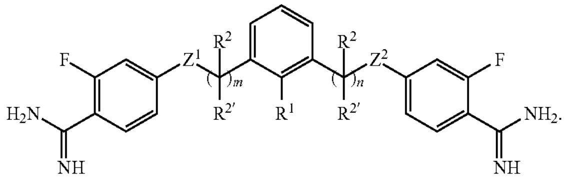
Non-limiting examples of compounds of Formula IB include.
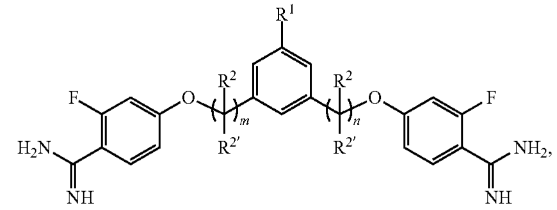
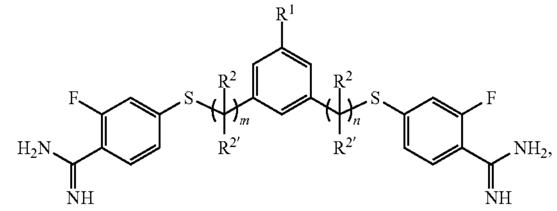
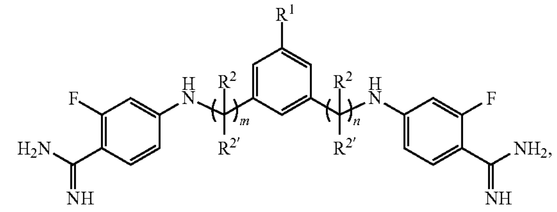
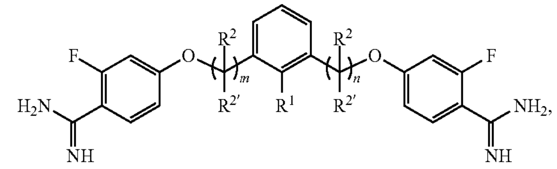

-continued
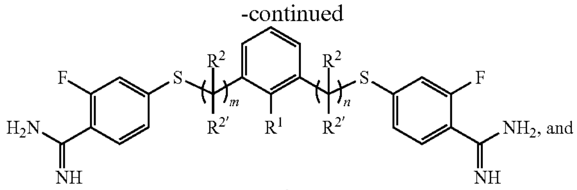
and
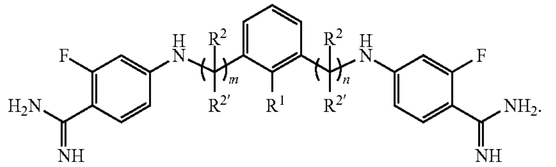
Non-limiting examples of compounds of Formula IC include:
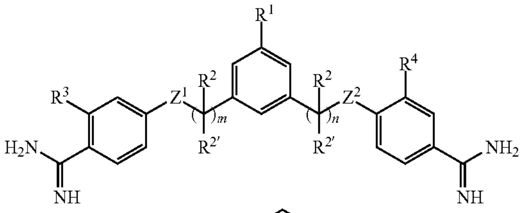
and
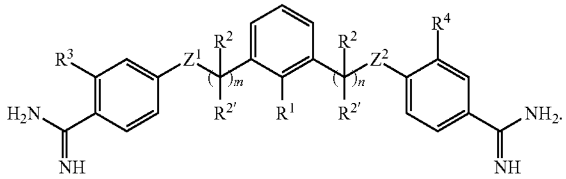
Non-limiting examples of compounds of Formula IC include:
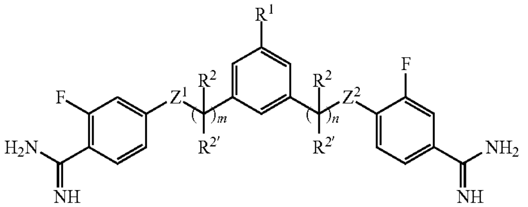
and
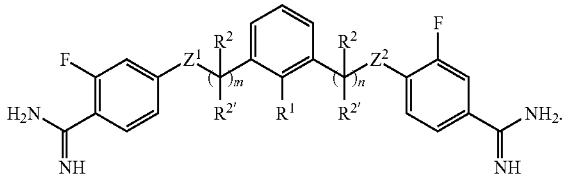
Non-limiting examples of compounds of Formula IC include:
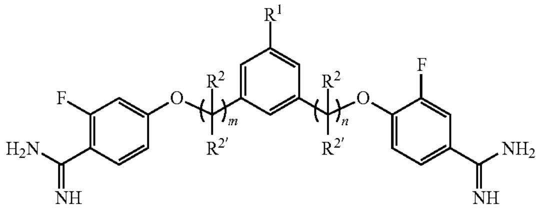
-continued
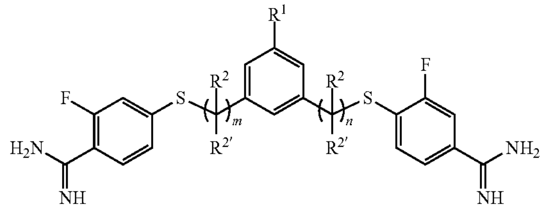
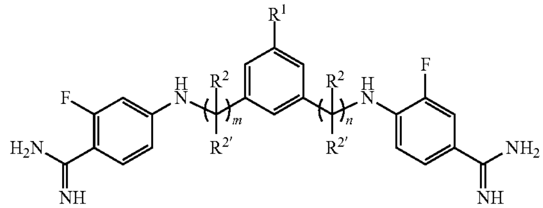
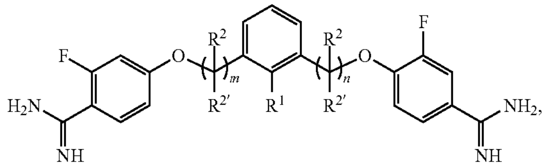
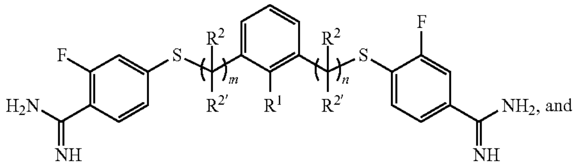
and
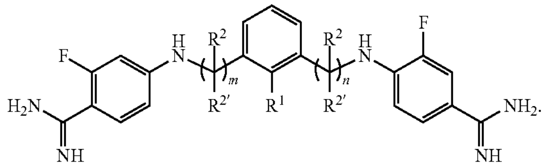
Non-limiting examples of compounds of Formula XIII include:
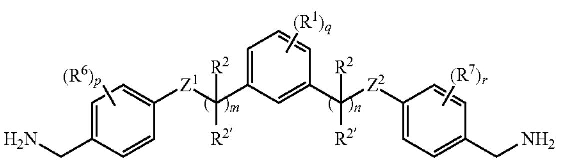
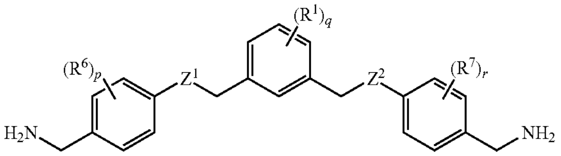
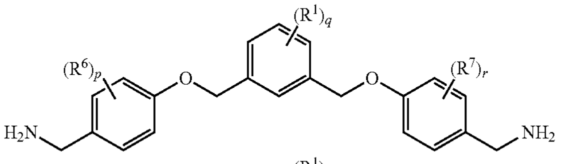
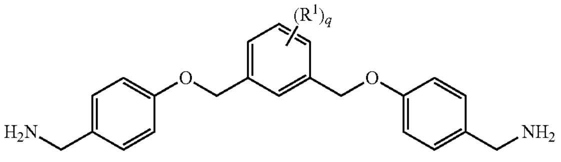

-continued
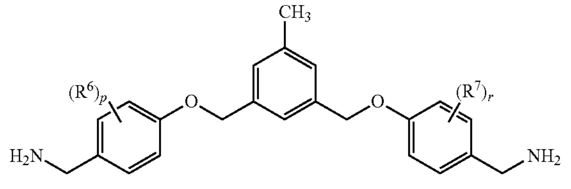
Non-limiting examples of compounds of Formula XIV include.
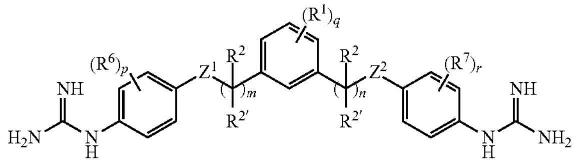
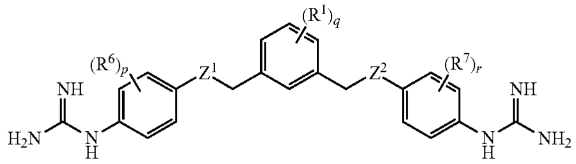
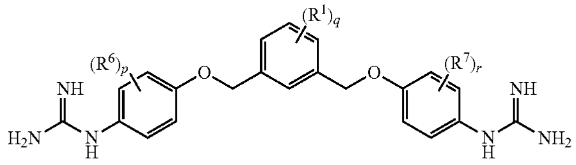
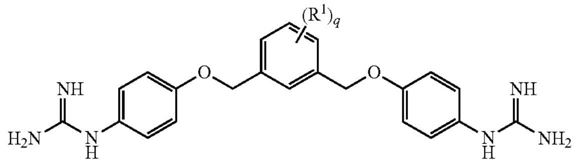
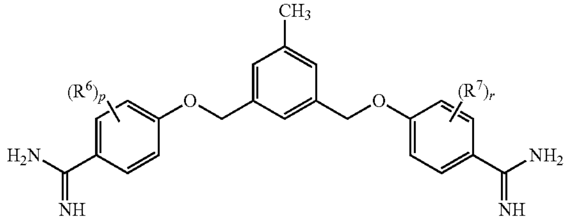
Examples of compounds of Formula I' include:
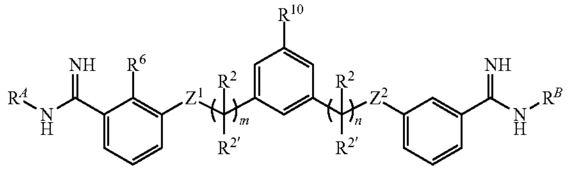
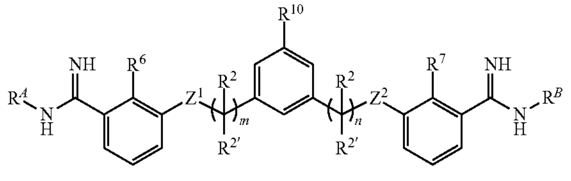
-continued
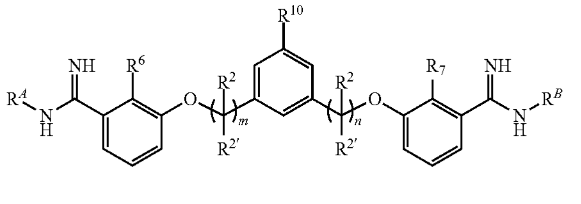
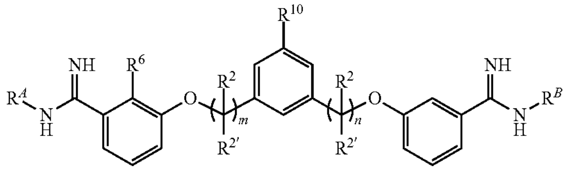
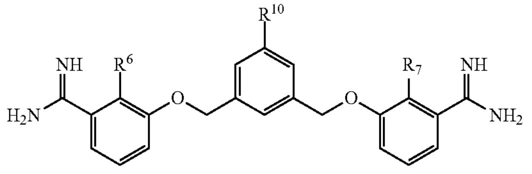
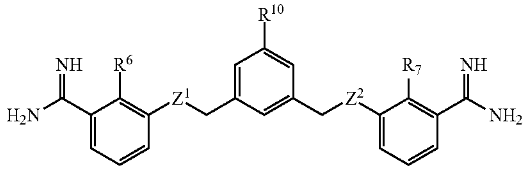
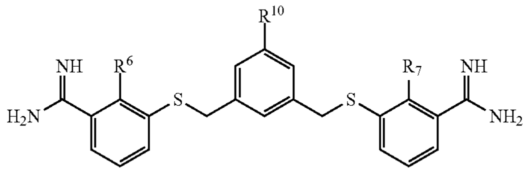
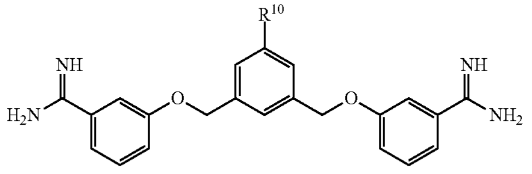
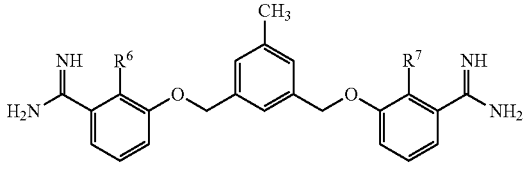
Non-limiting examples of compounds of Formula II include:
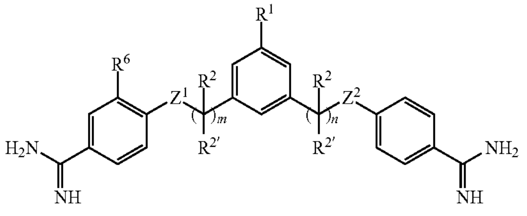
and -continued
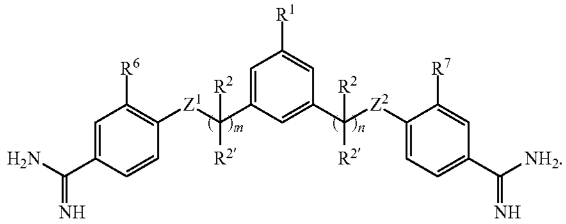
Non-limiting examples of compounds of Formula II include:
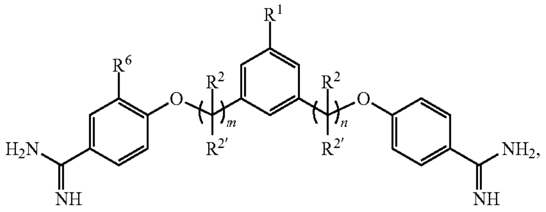
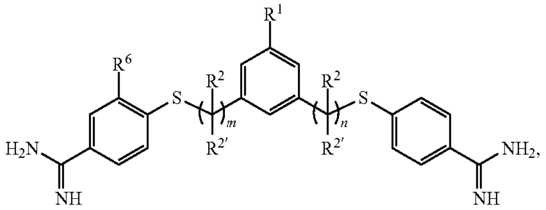
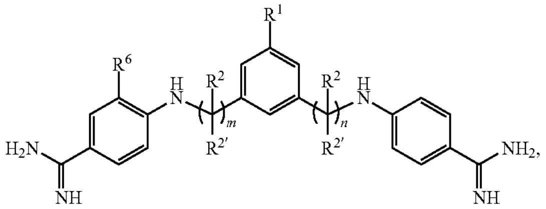
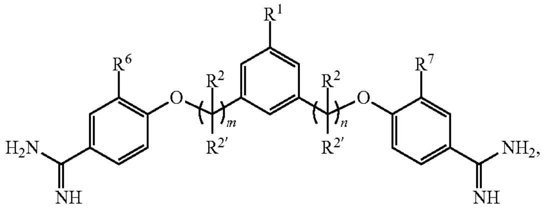
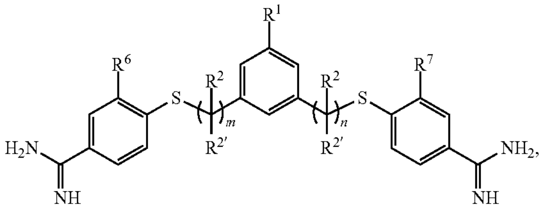
and
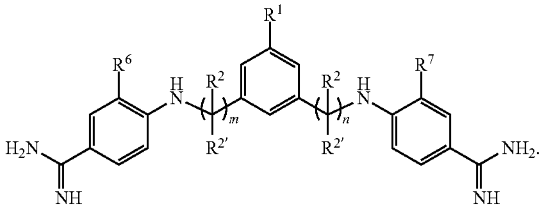
Non-limiting examples of compounds of Formula II include.
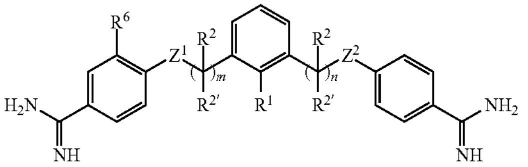
and
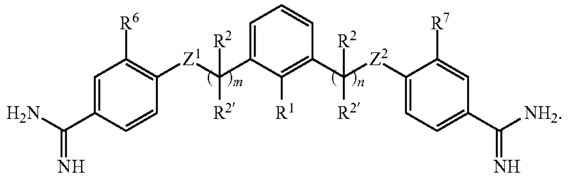
Non-limiting examples of compounds of Formula II include:
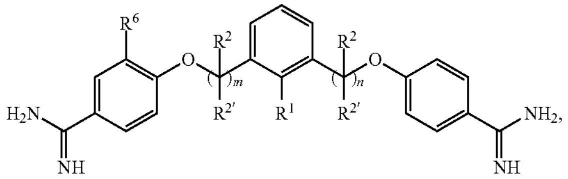
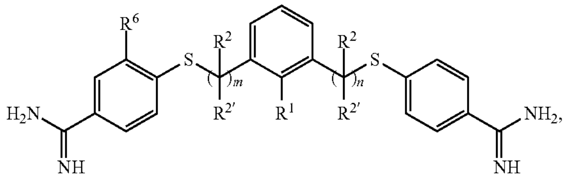
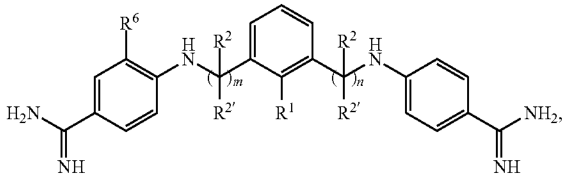
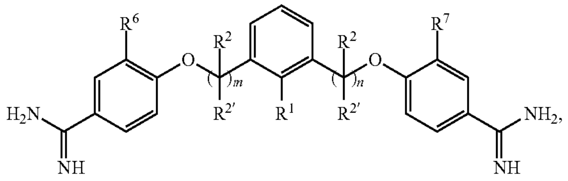
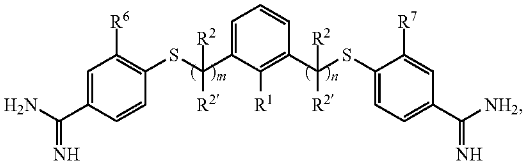
and
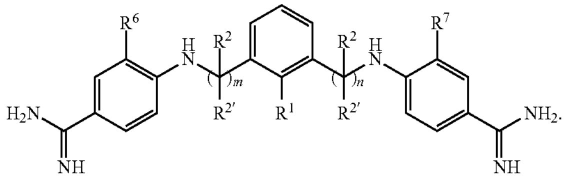

Non-limiting examples of compounds of Formula II include:
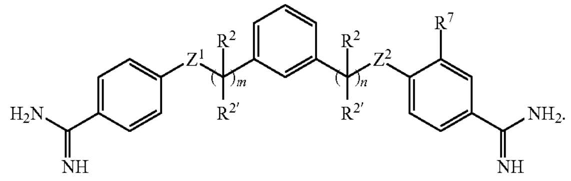
Non-limiting examples of compounds of Formula II include.
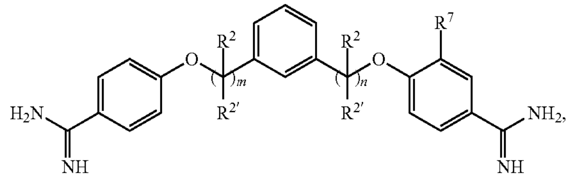
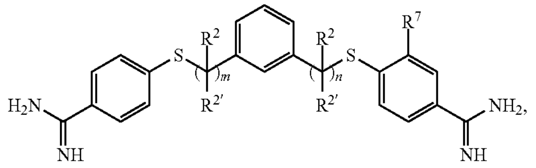
and
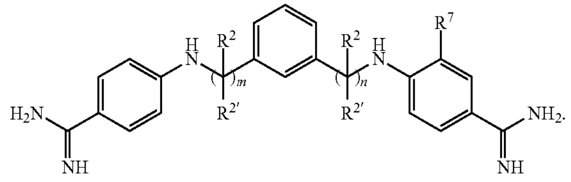
Examples of compounds of Formula II include:
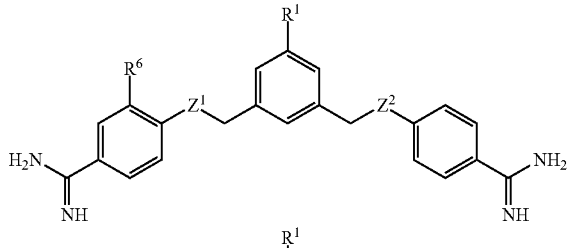
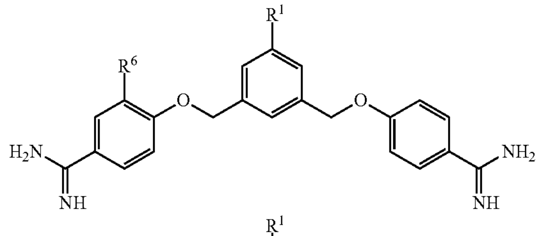
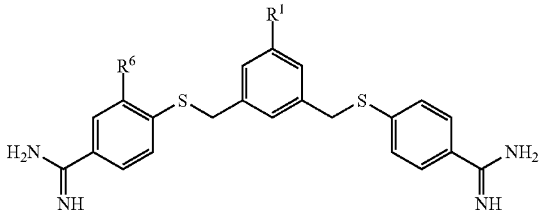
-continued
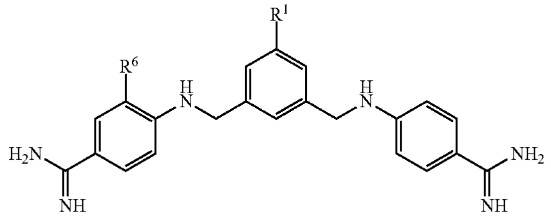
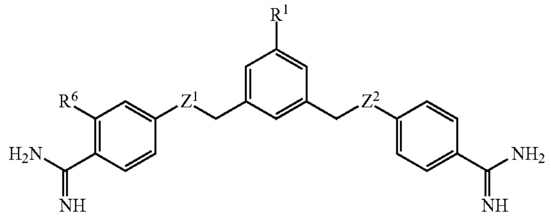
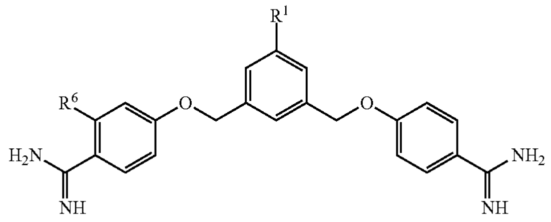
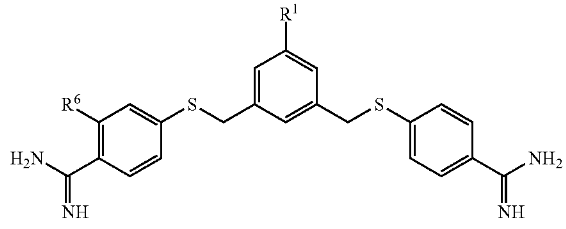
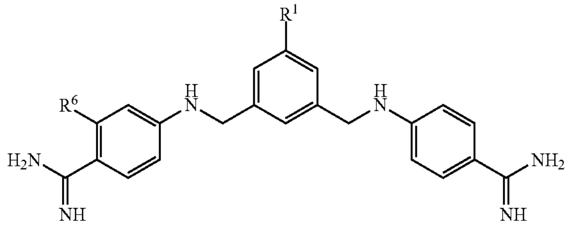
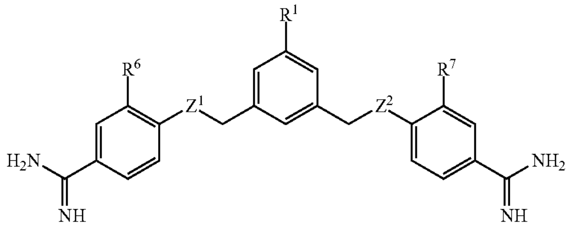
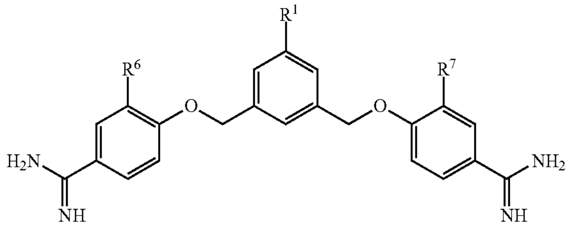

-continued
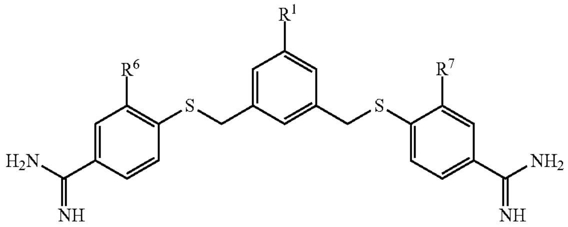
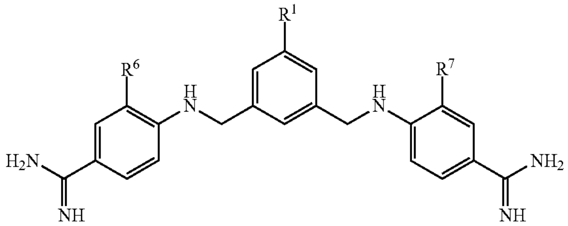
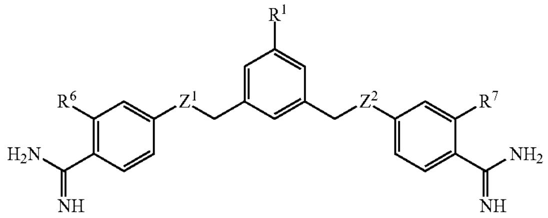
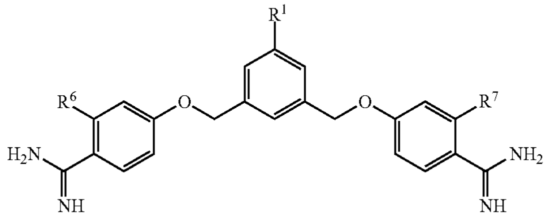
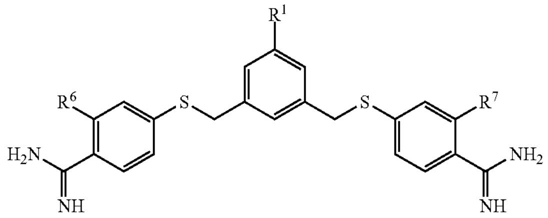
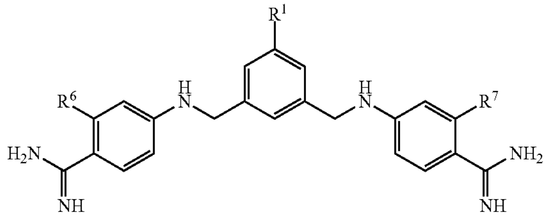
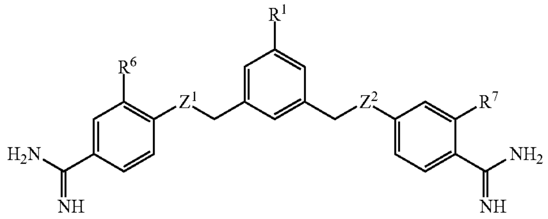
-continued
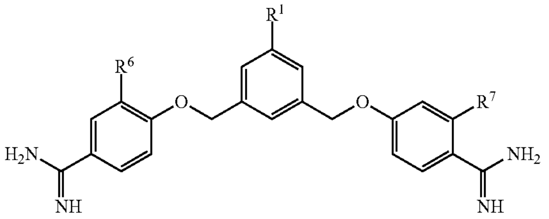
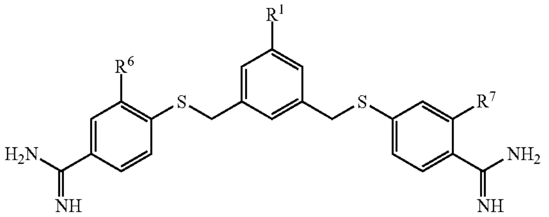
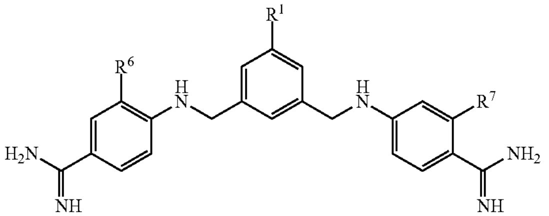
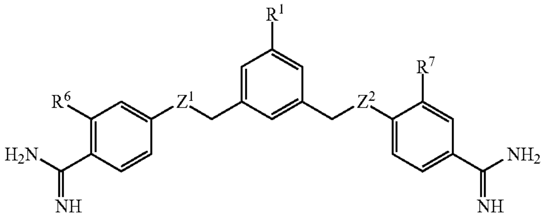
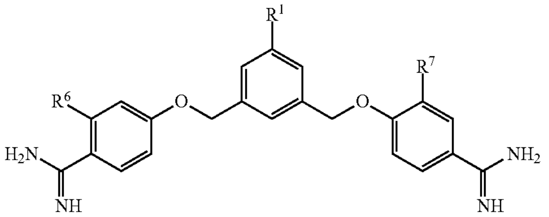
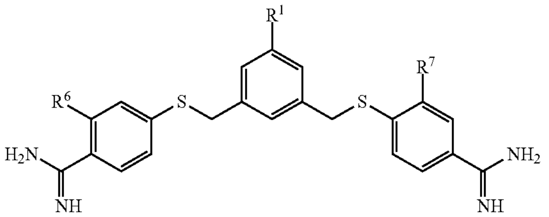
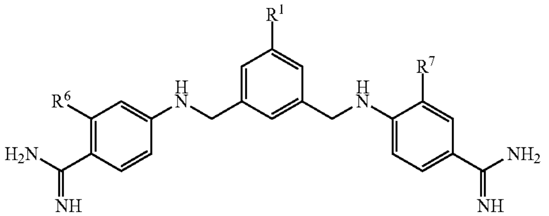
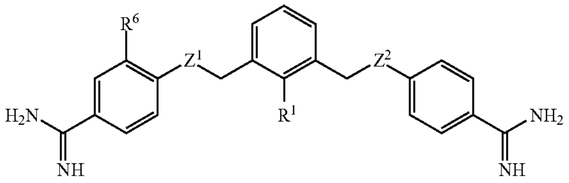

-continued
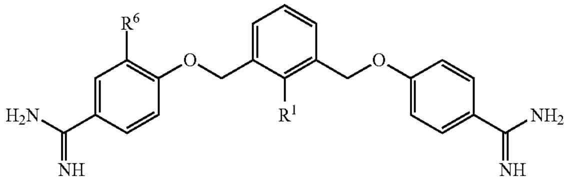
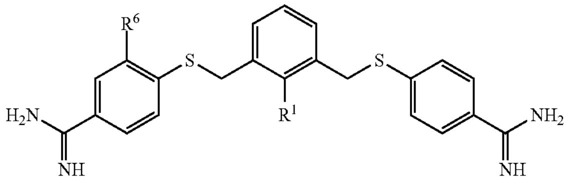
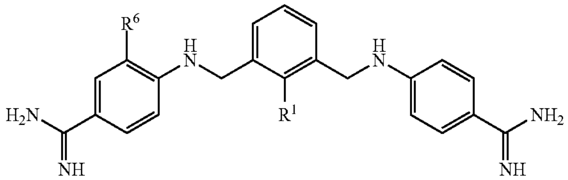
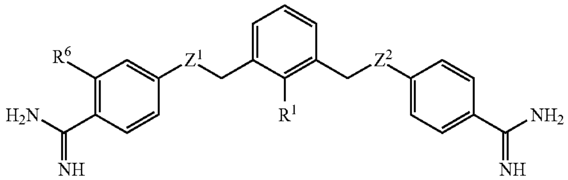
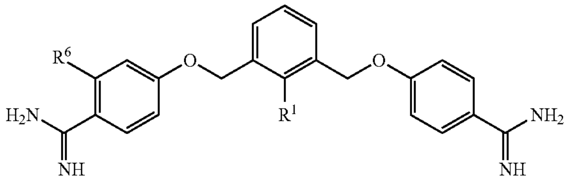
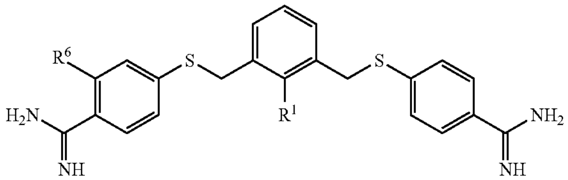
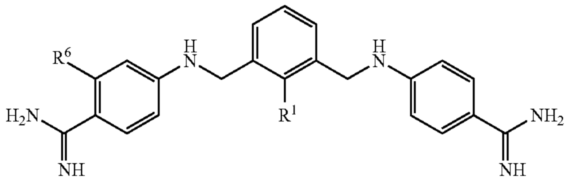
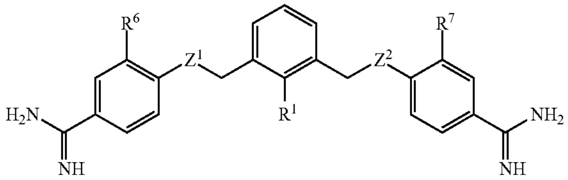
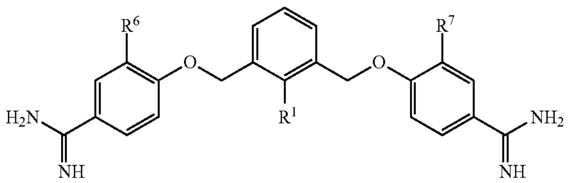
-continued
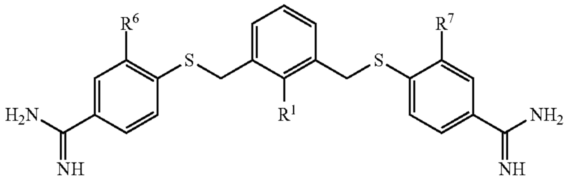
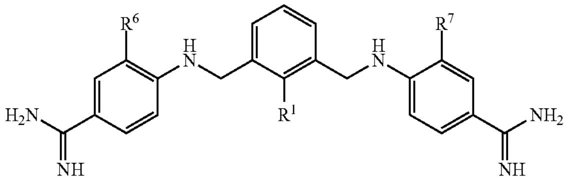
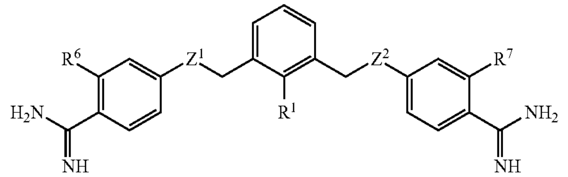
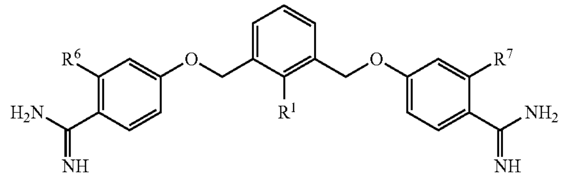
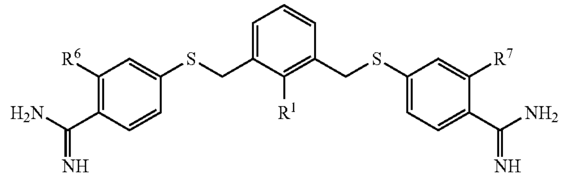
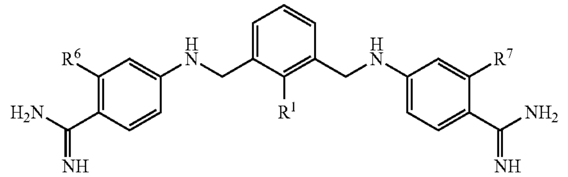
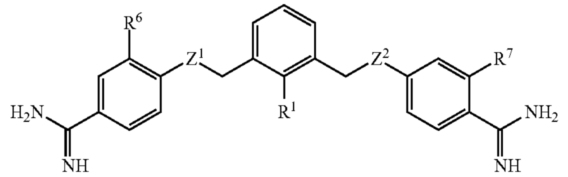
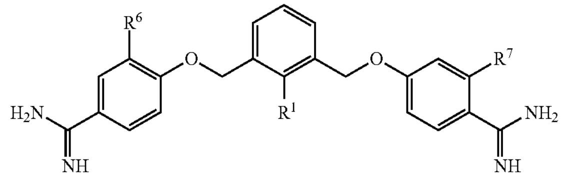
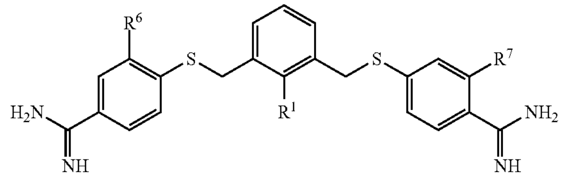

-continued
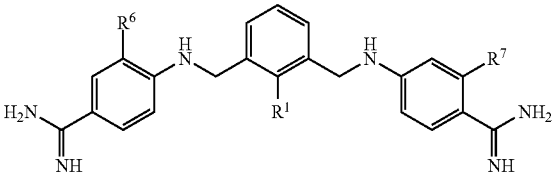
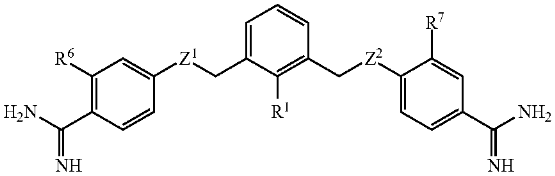
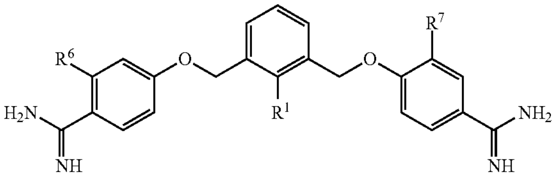
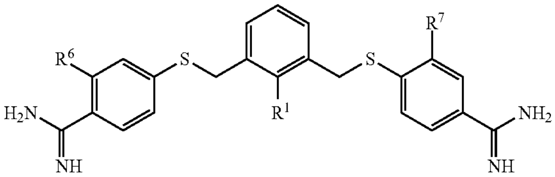
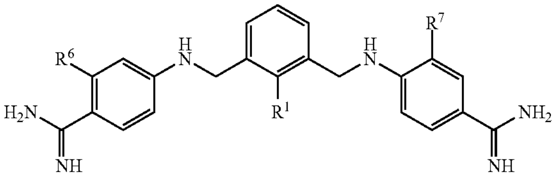
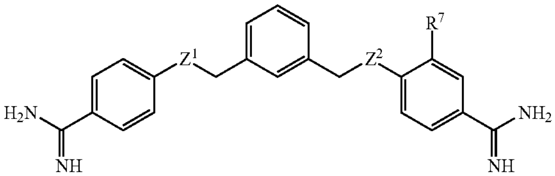
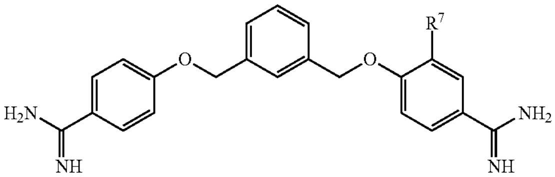
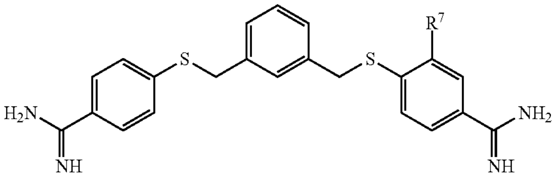
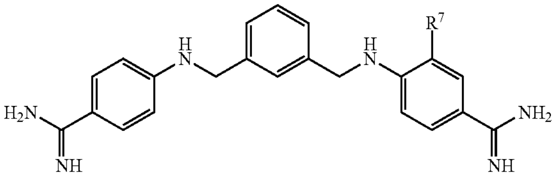
-continued
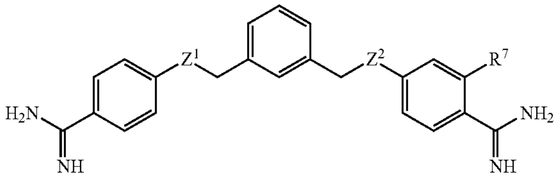
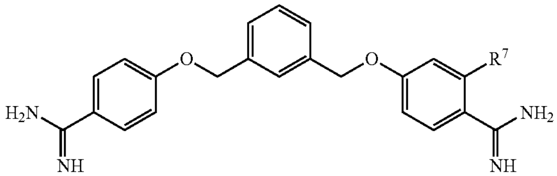
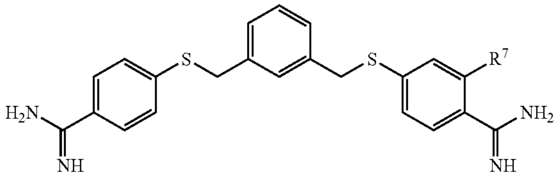
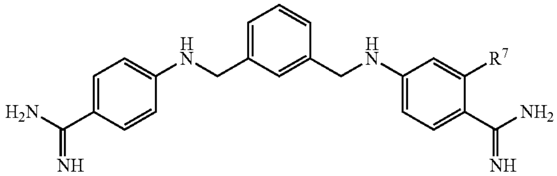
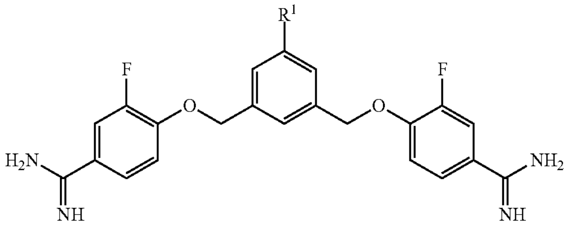
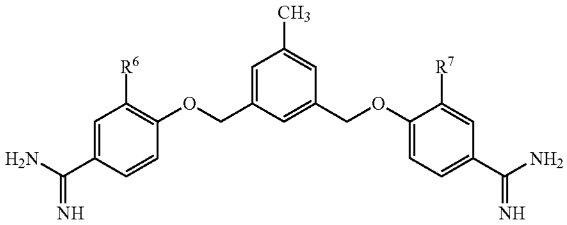
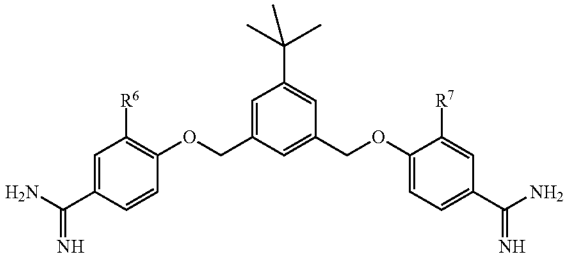

Non-limiting examples of compounds of Formula IT include:
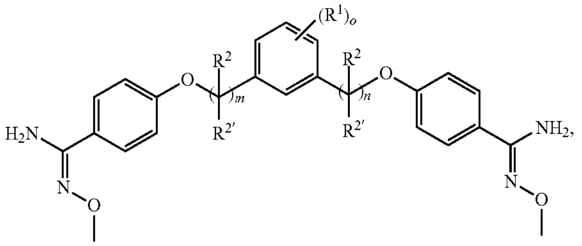
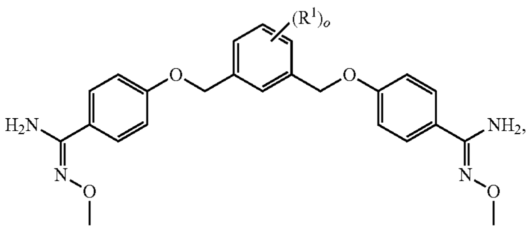
and
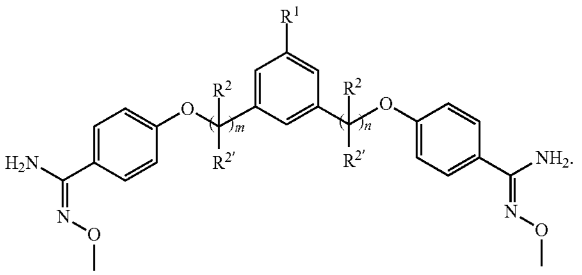
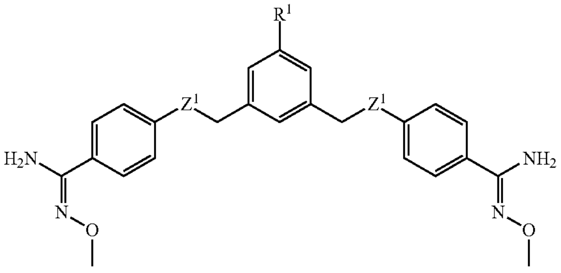
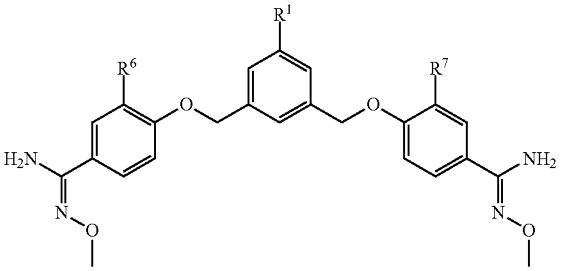
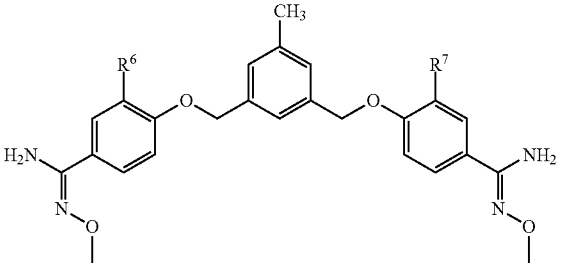
Non-limiting examples of compounds of Formula III include.
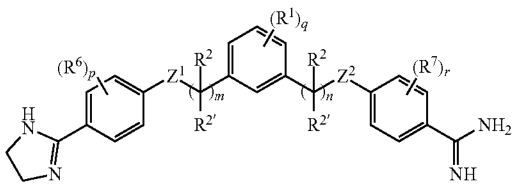
and
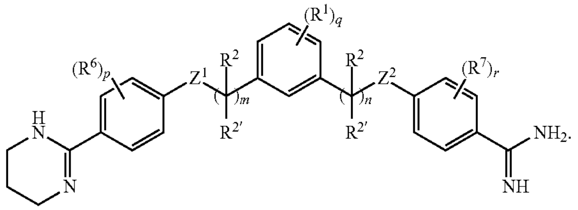
Non-limiting examples of compounds of Formula III include:
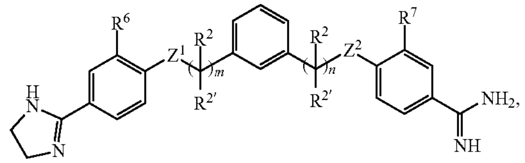
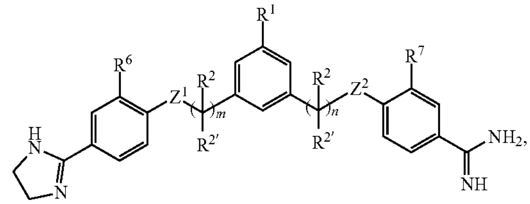
and
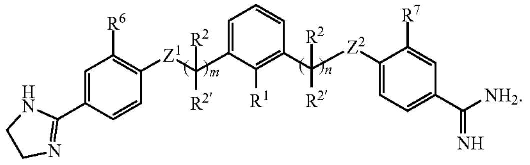
Non-limiting examples of compounds of Formula III include:
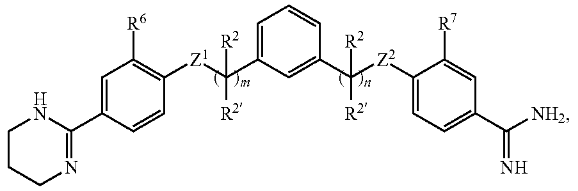
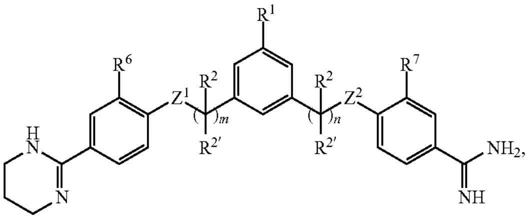
and -continued
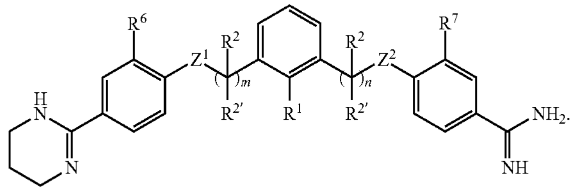
Additional examples of compounds of Formula III include:
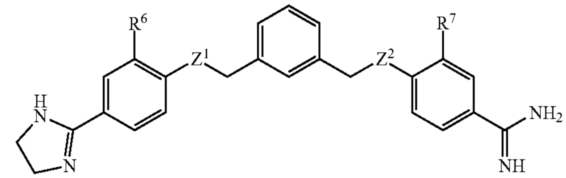
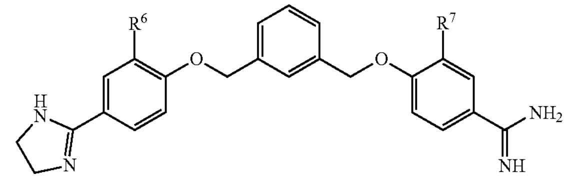
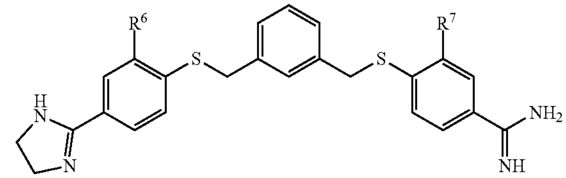
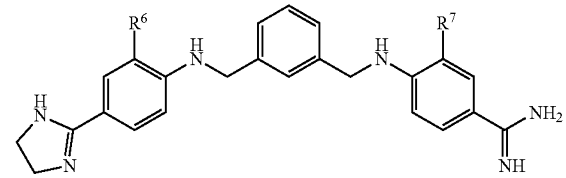
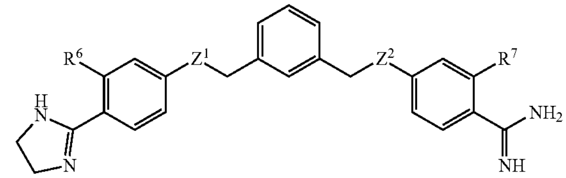
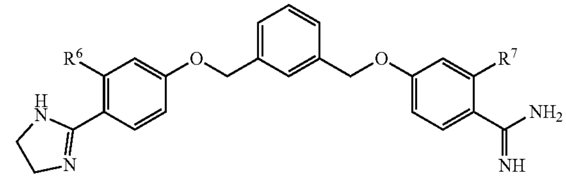
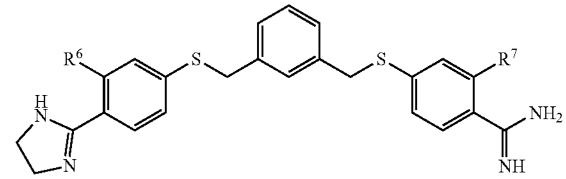
-continued
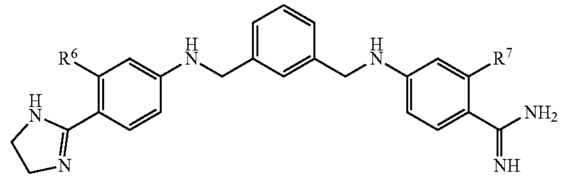
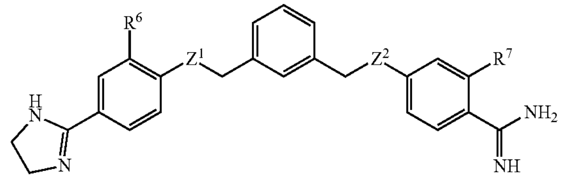
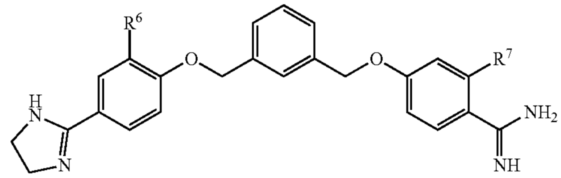
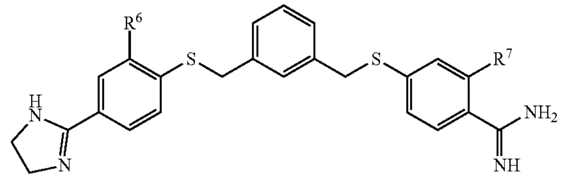
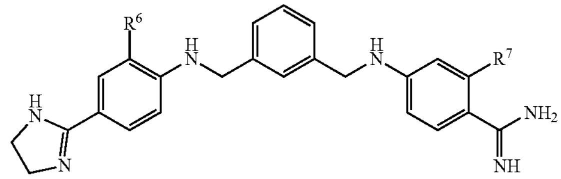
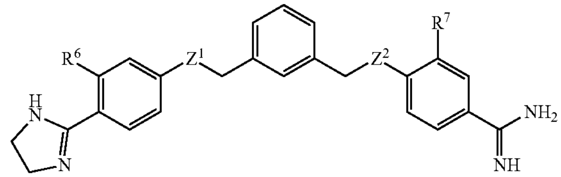
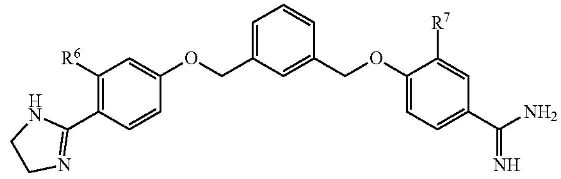
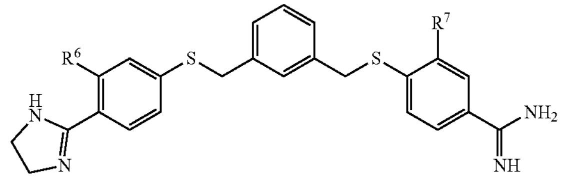
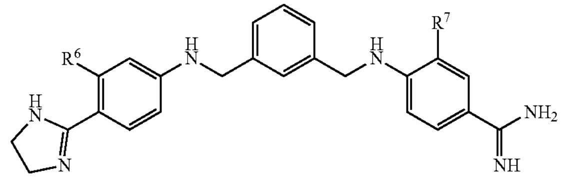

-continued
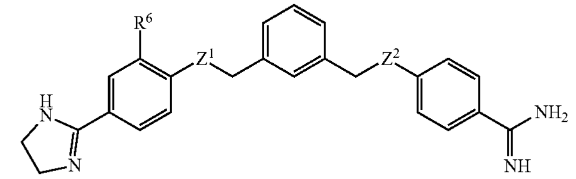
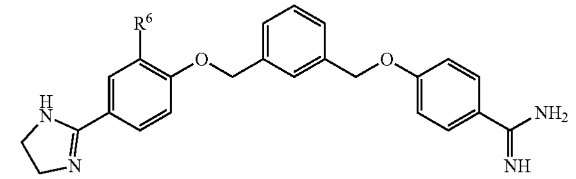
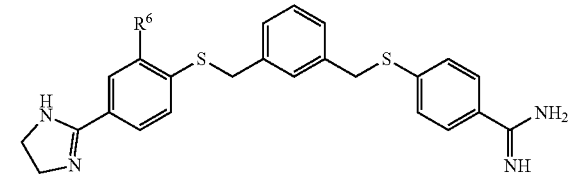
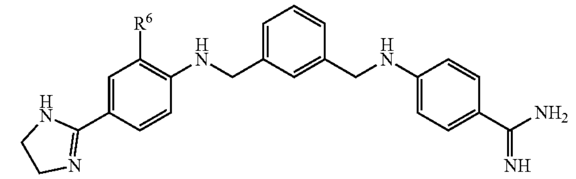
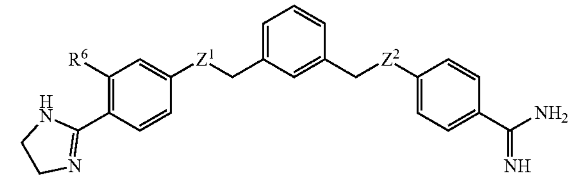
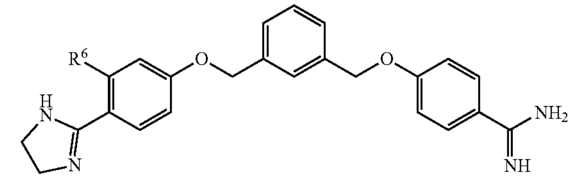
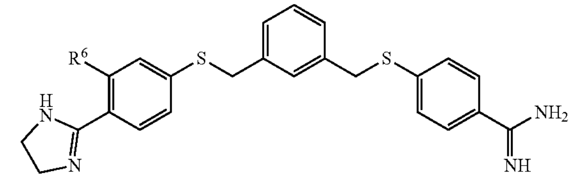
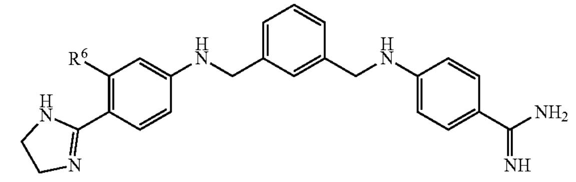
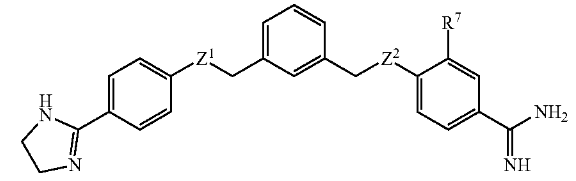
-continued
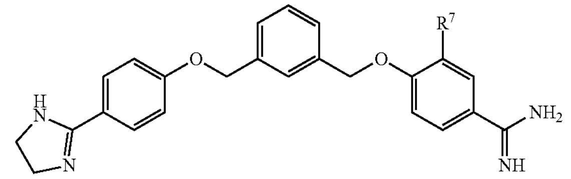
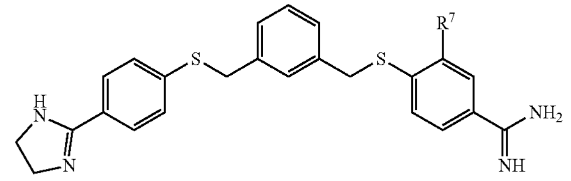
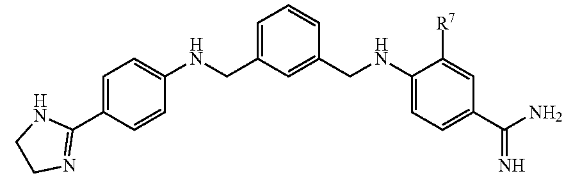
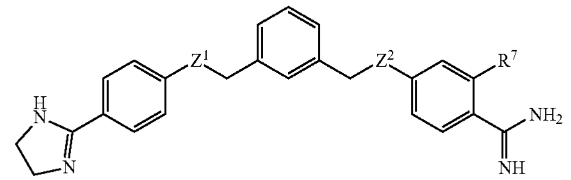
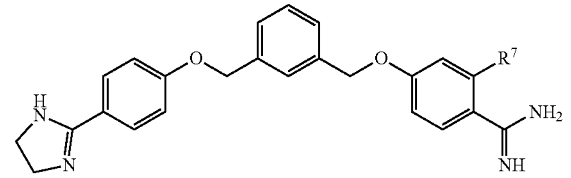
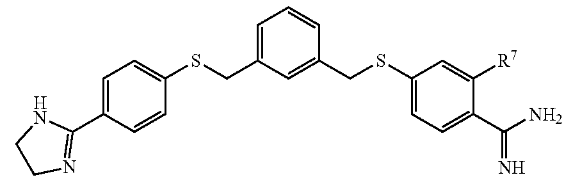
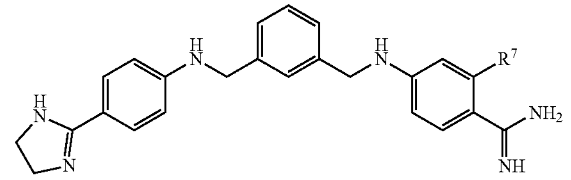
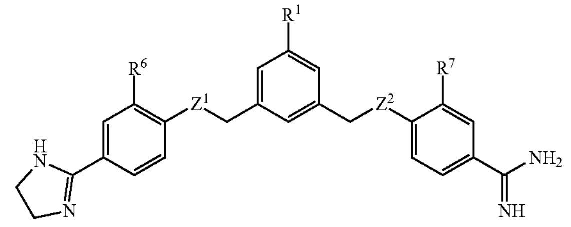
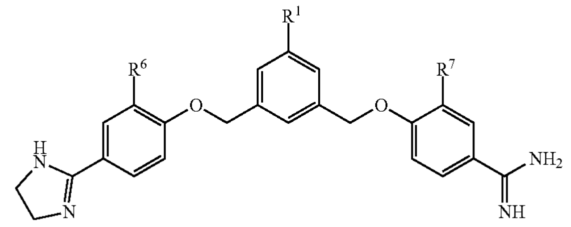

-continued
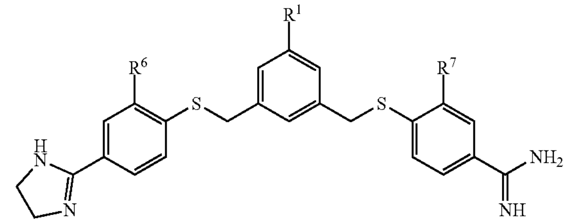
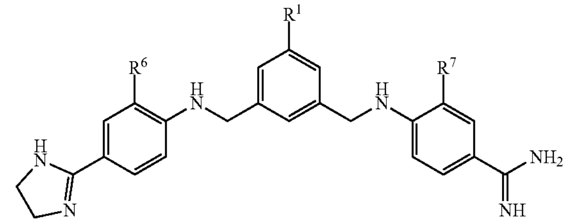
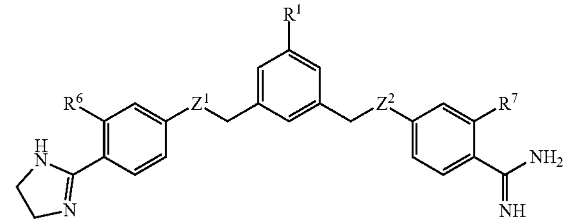
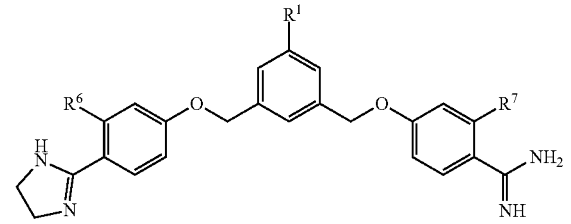
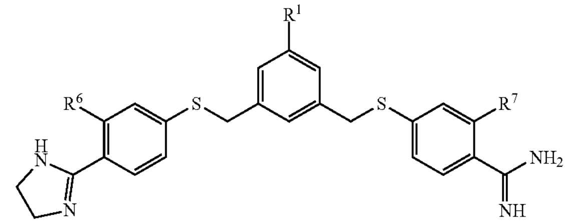
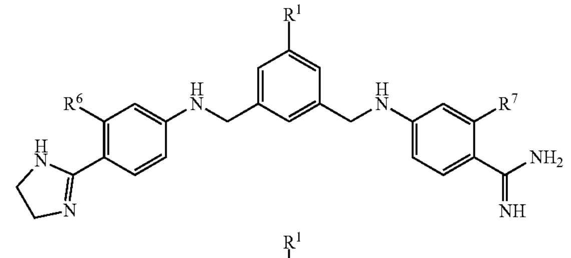
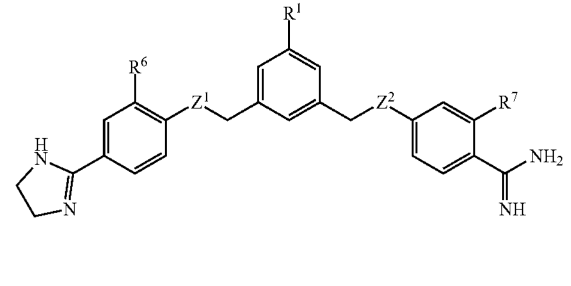
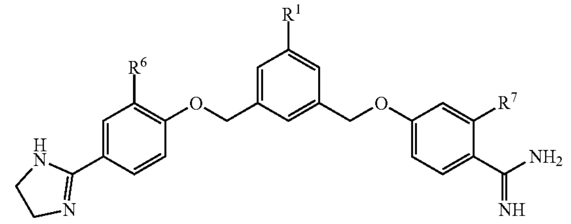
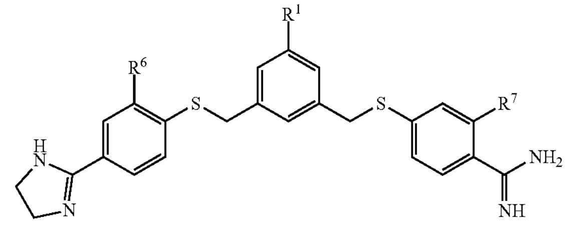
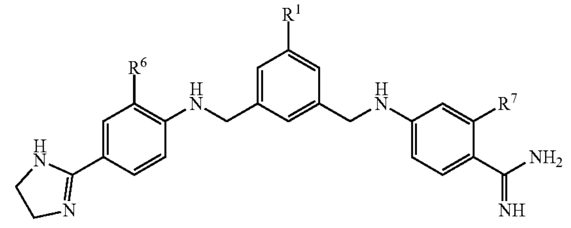
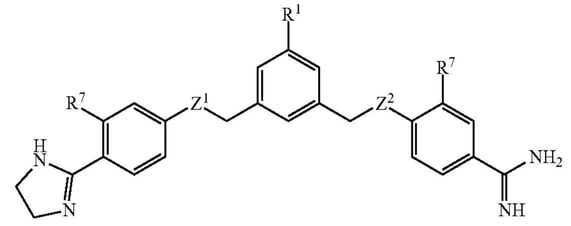
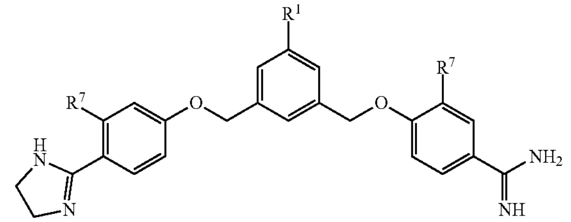
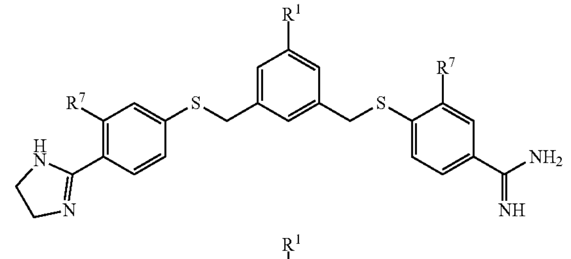
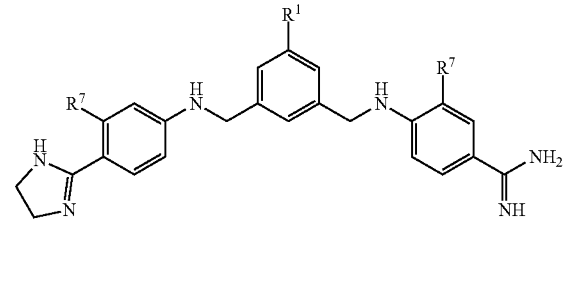
-continued -continued
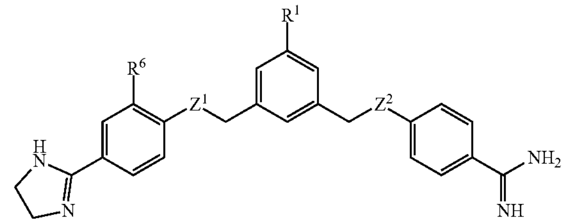
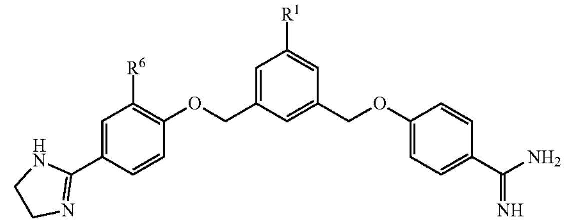
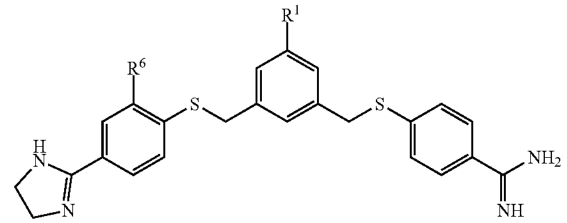
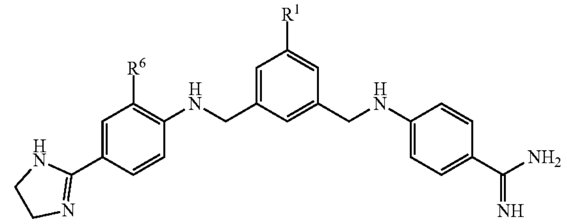
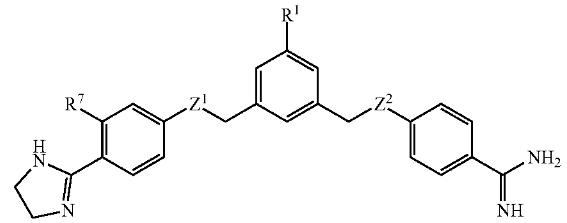
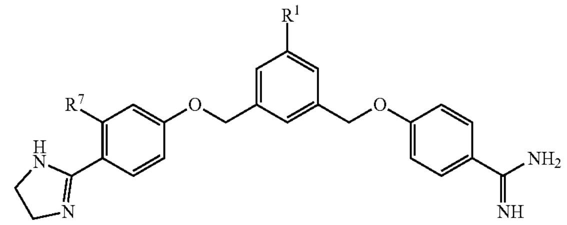
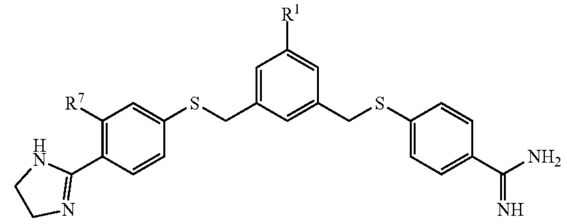
-continued
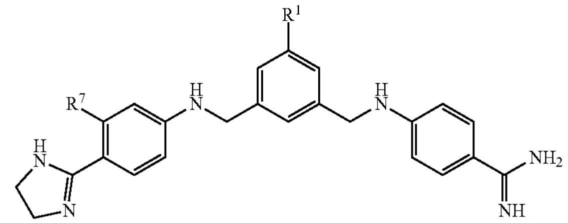
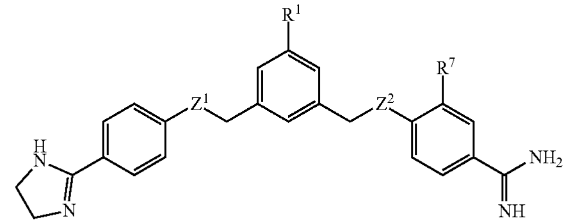
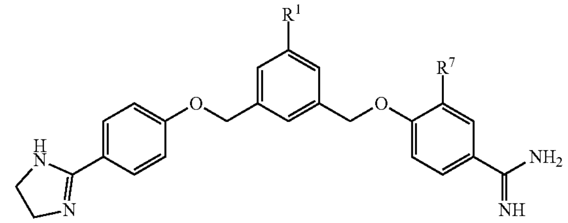
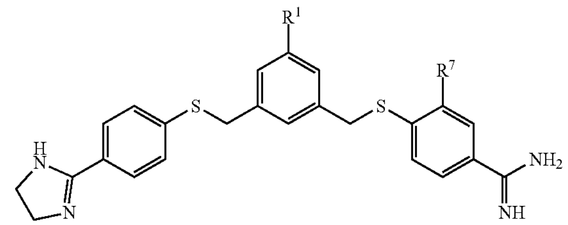
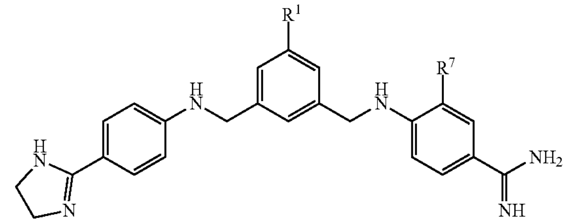
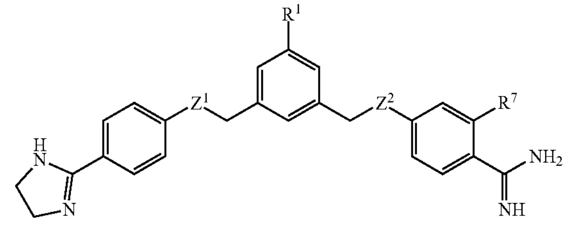
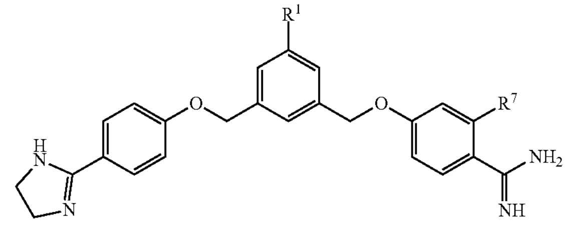

-continued
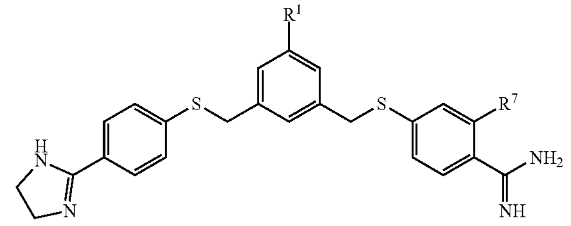
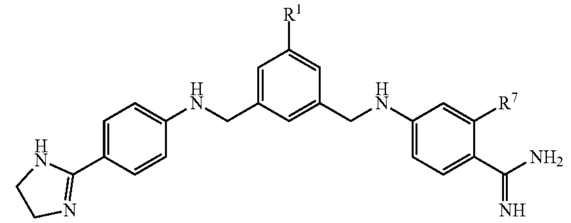
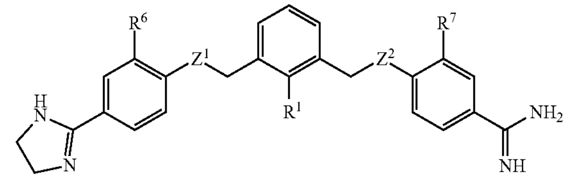
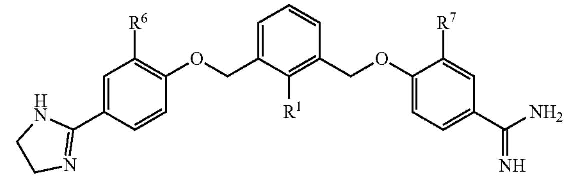
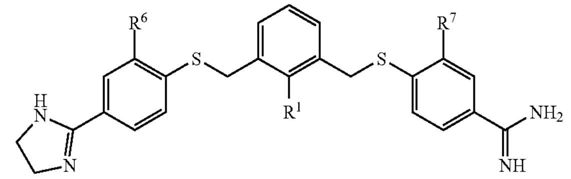
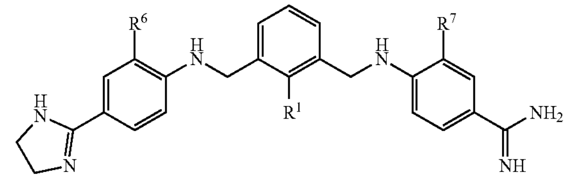
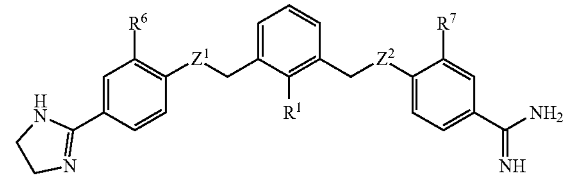
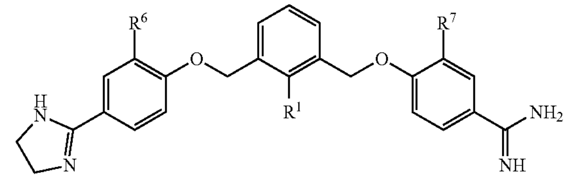
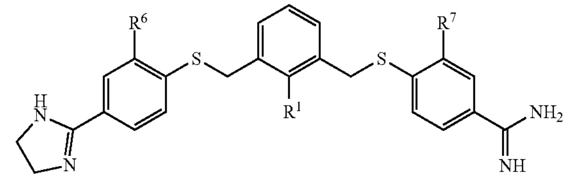
-continued
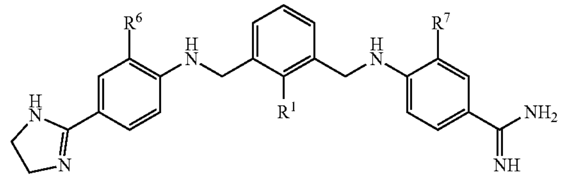
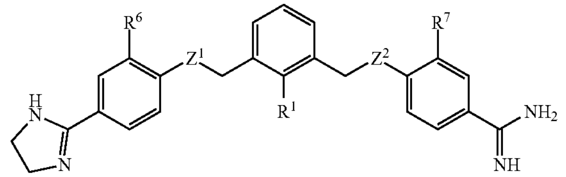
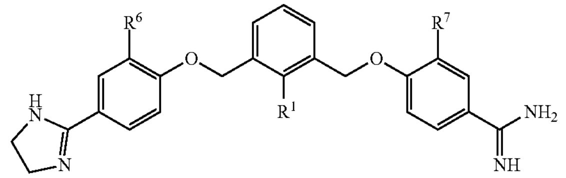
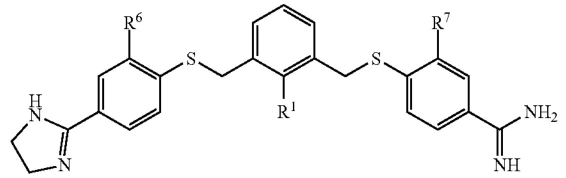
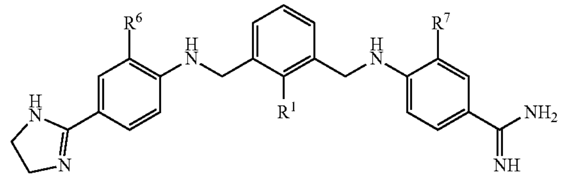
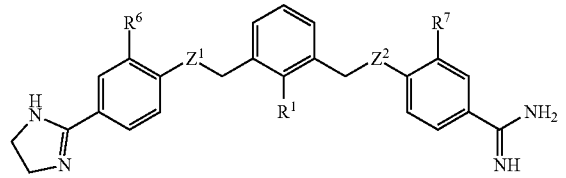
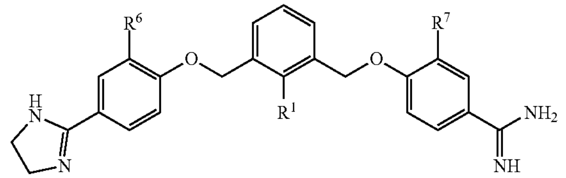
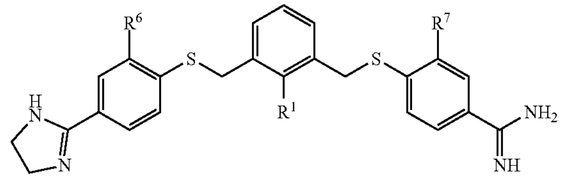
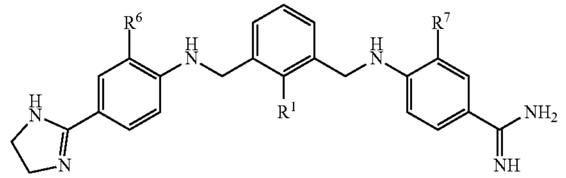

-continued
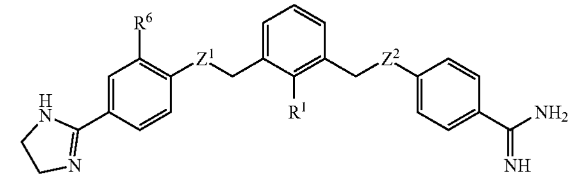
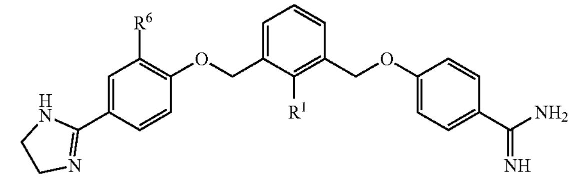
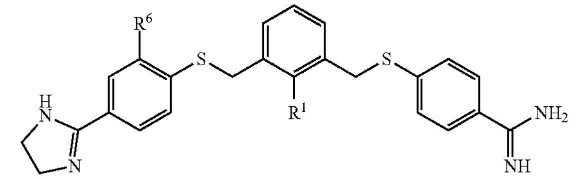
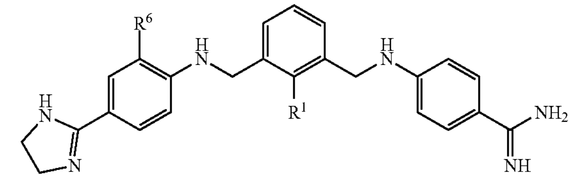
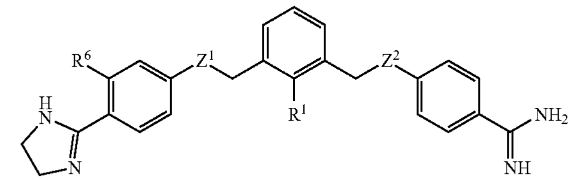
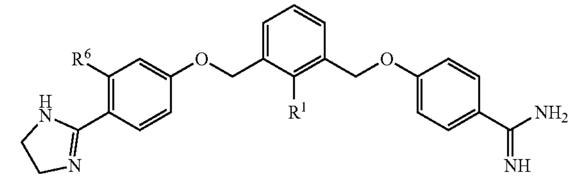
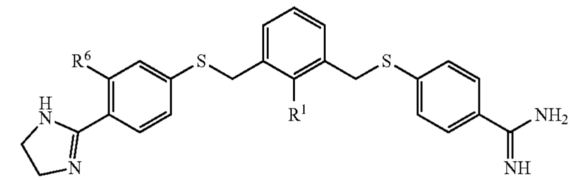
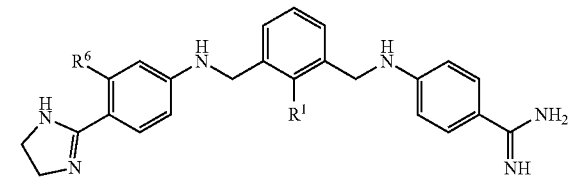
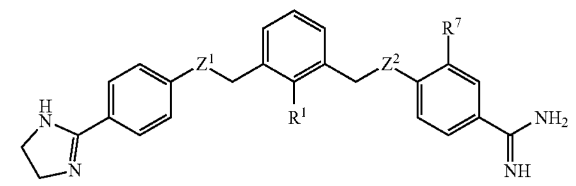
-continued
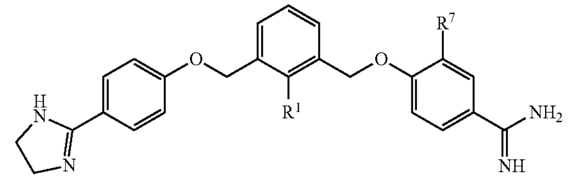
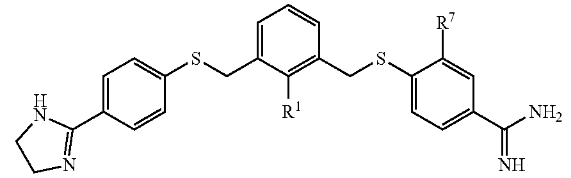
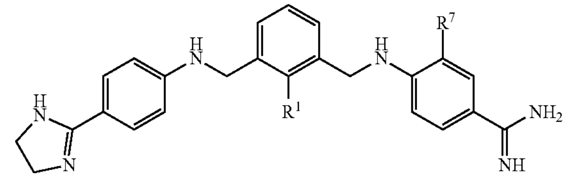
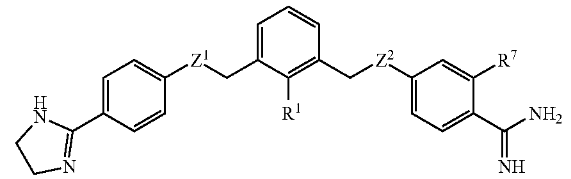
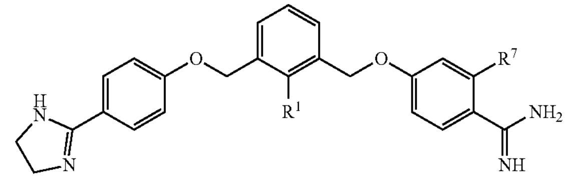
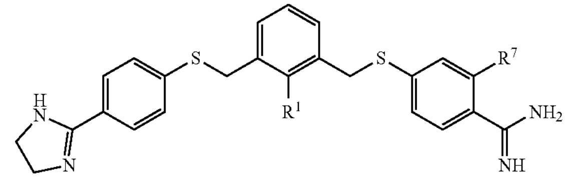
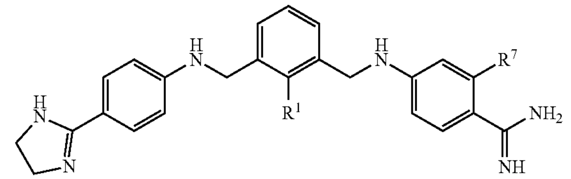
Additional examples of compounds of Formula III include:
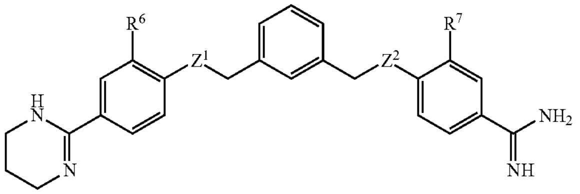

-continued
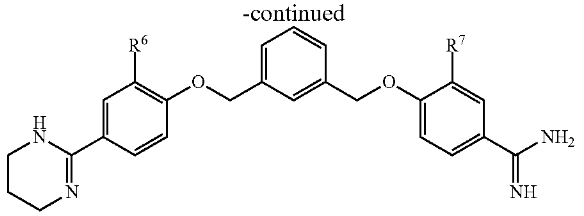
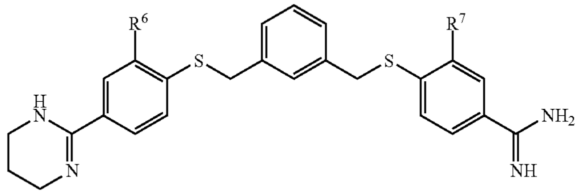
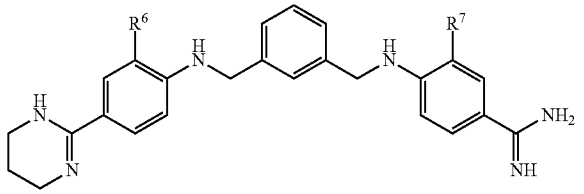
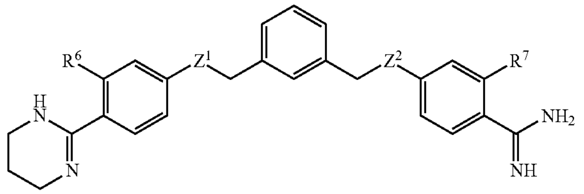
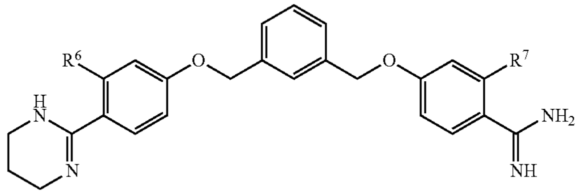
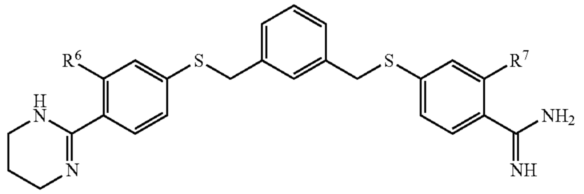
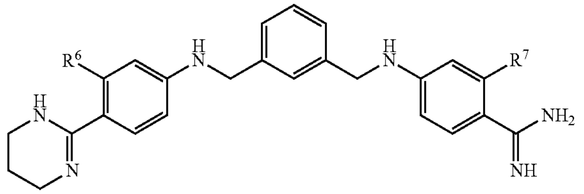
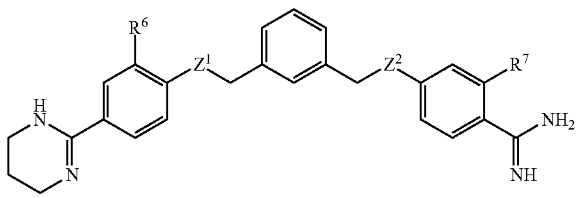
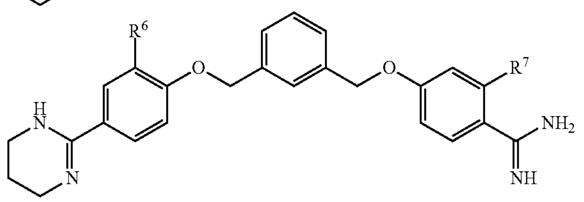
-continued
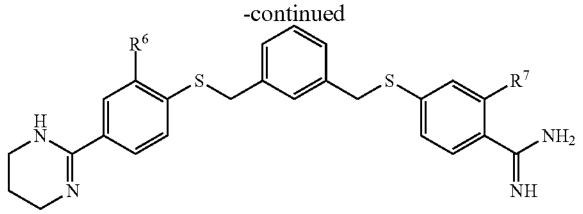
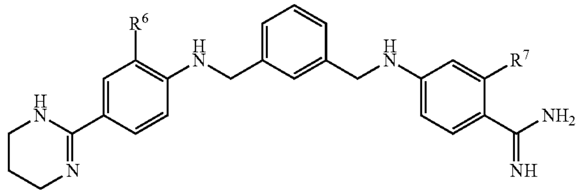
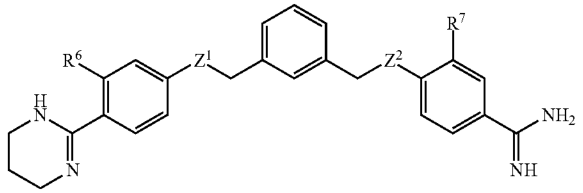
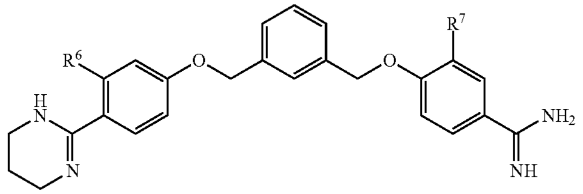
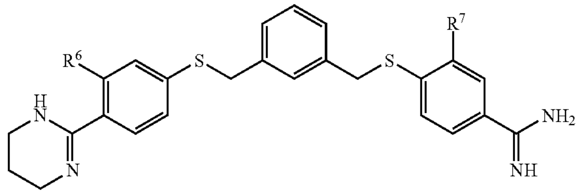
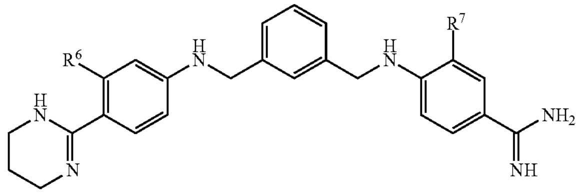
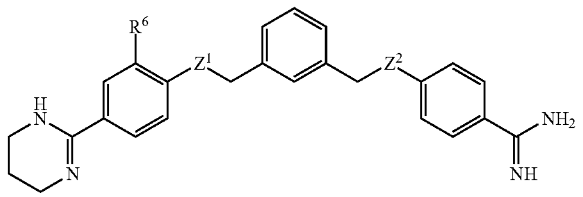
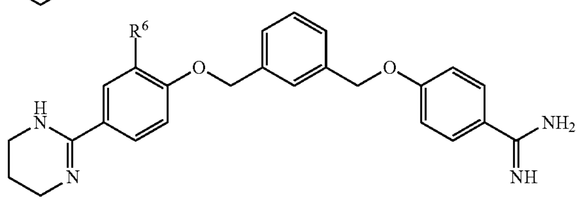
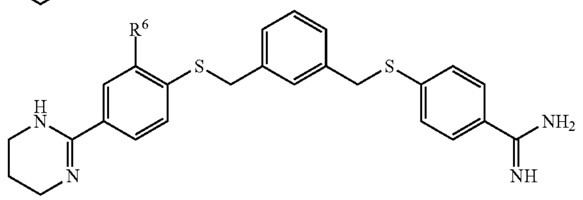

-continued
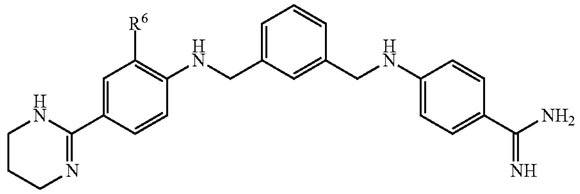
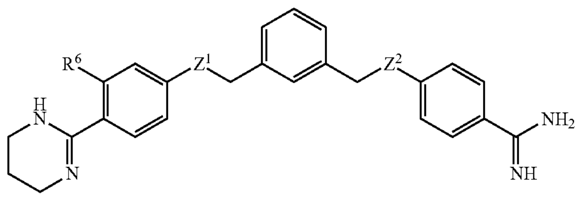
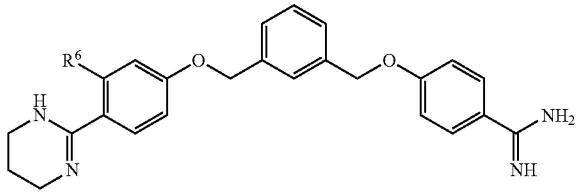
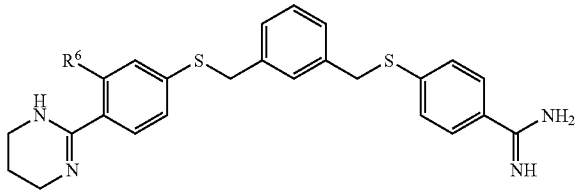
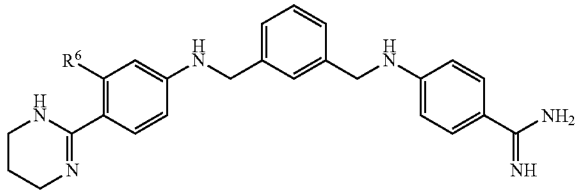
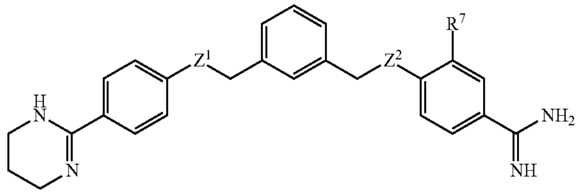
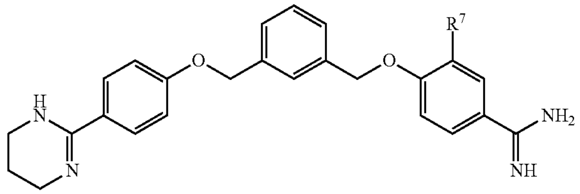
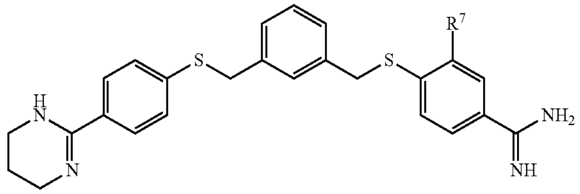
-continued
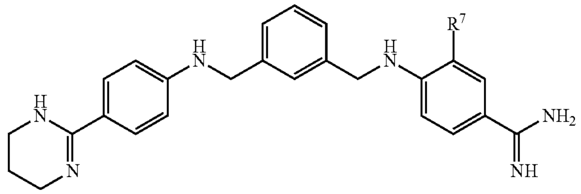
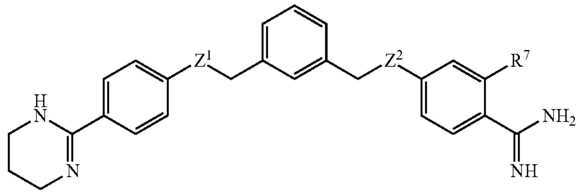
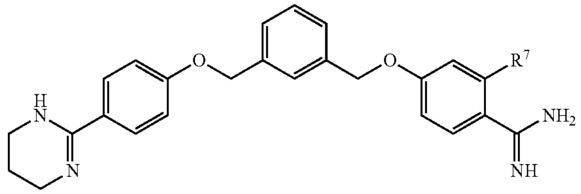
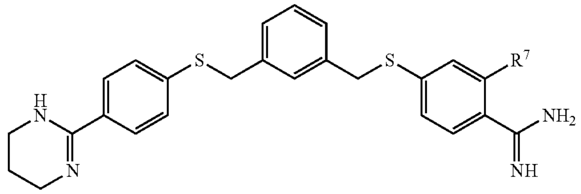
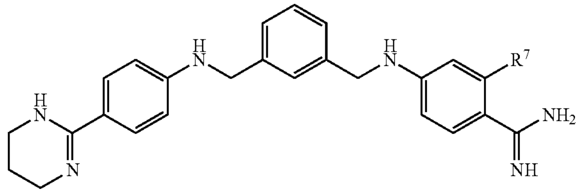
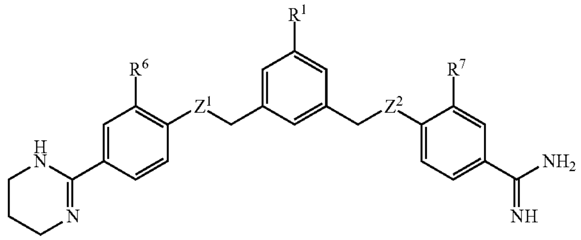
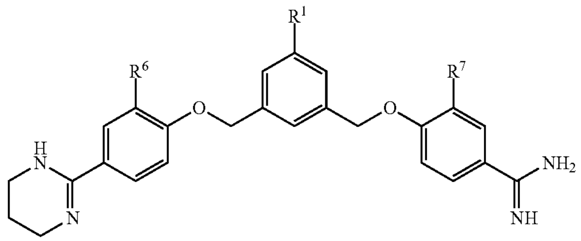
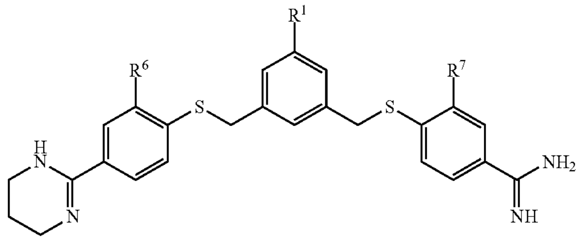

-continued
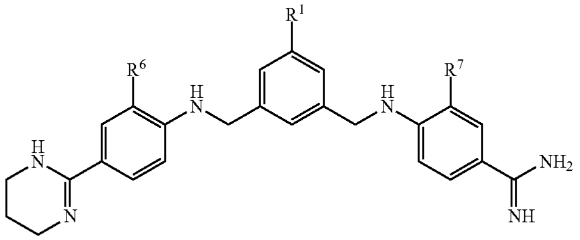
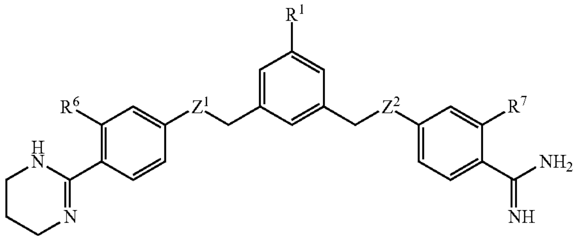
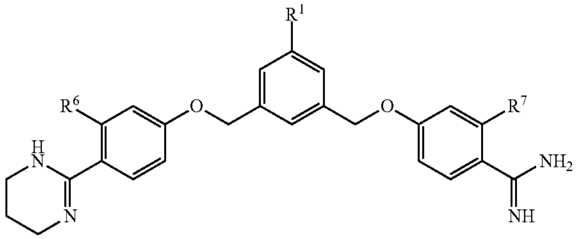
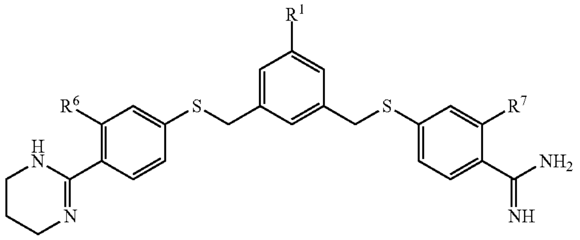
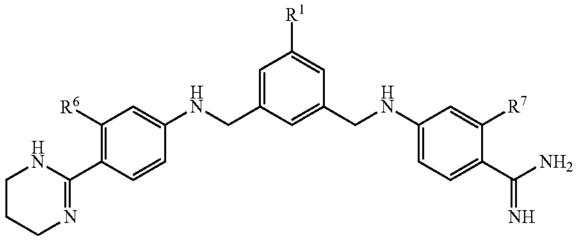
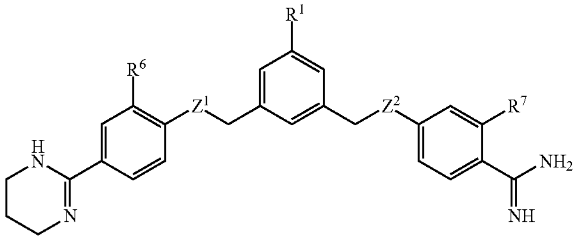
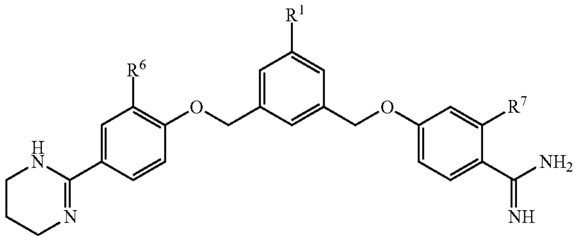
-continued
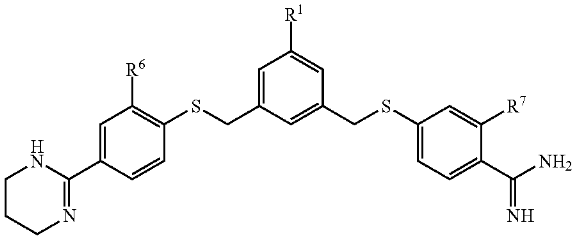
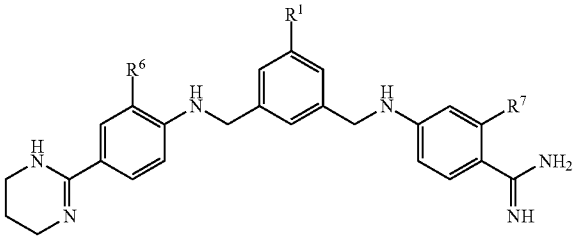
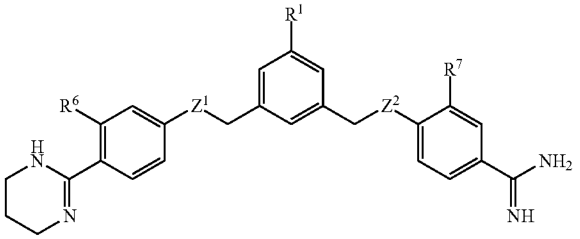
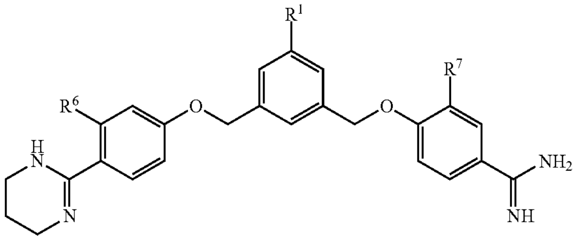
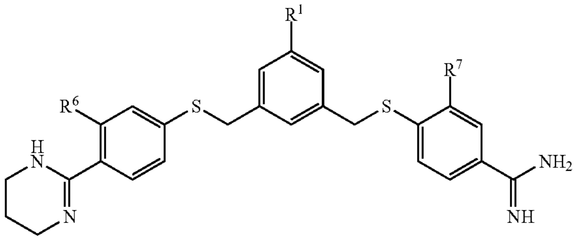
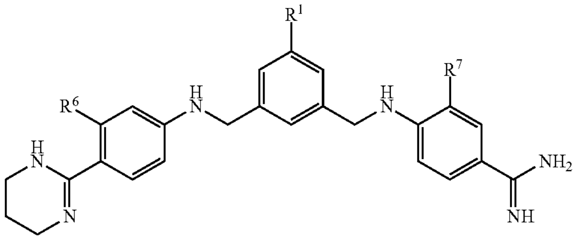
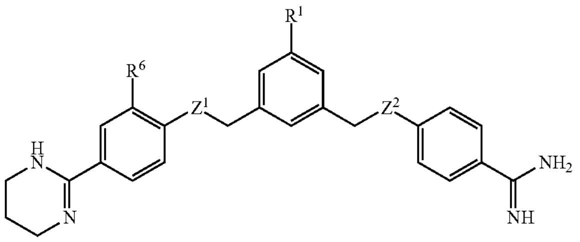

-continued
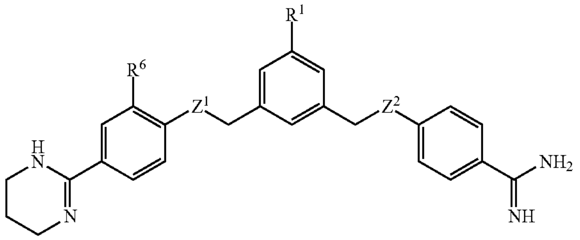
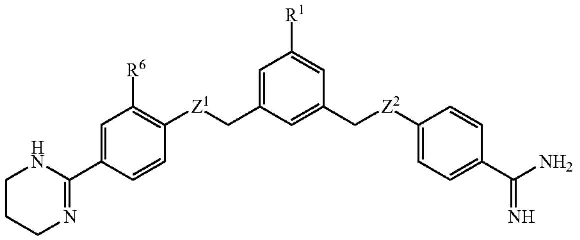
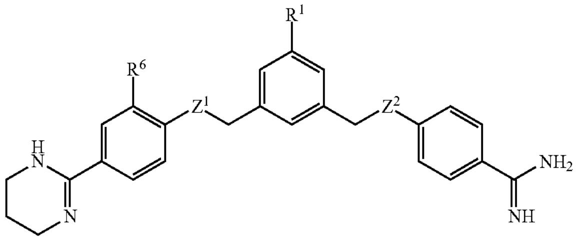
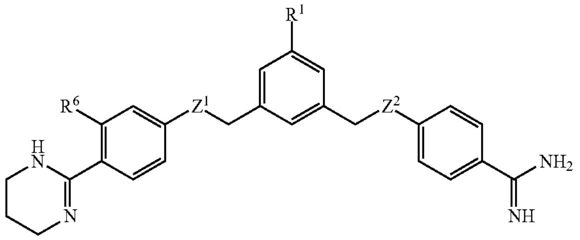
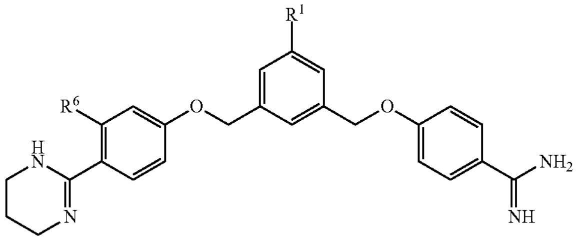
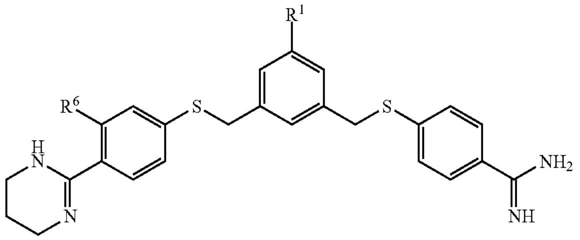
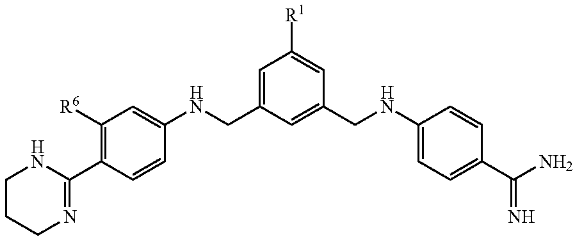
-continued
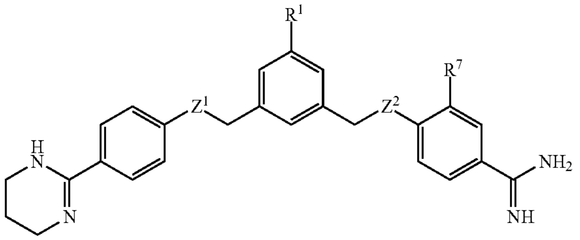
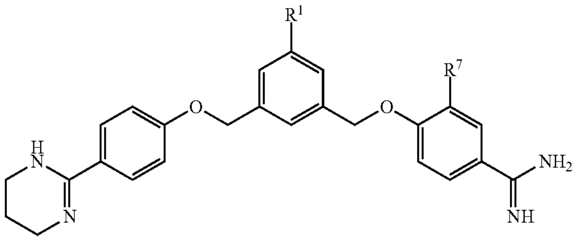
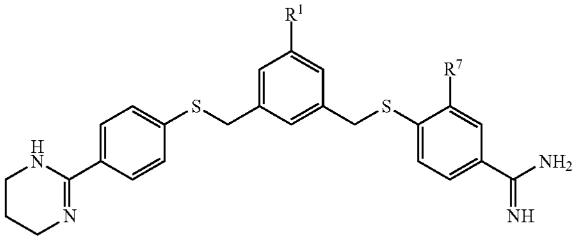
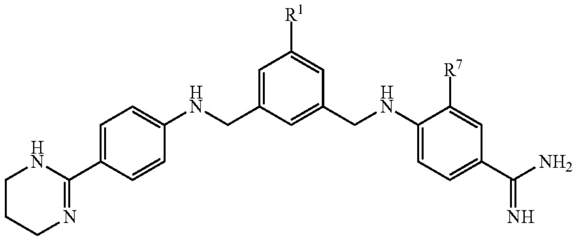
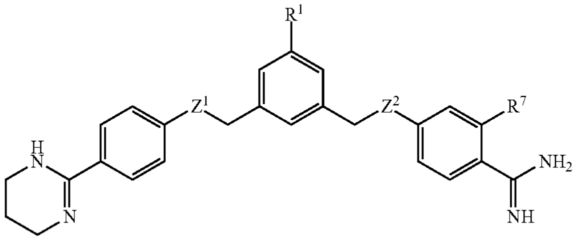
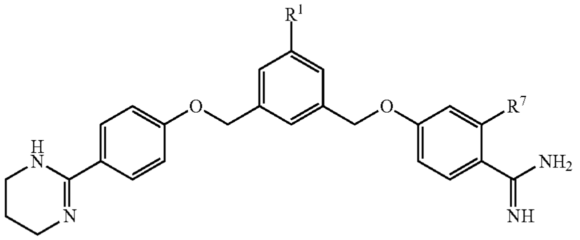
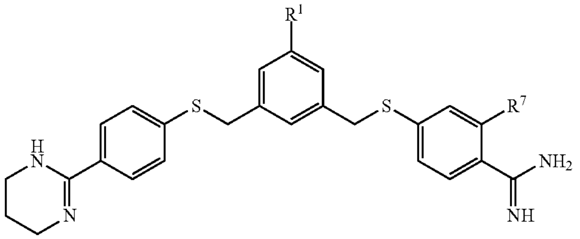

-continued
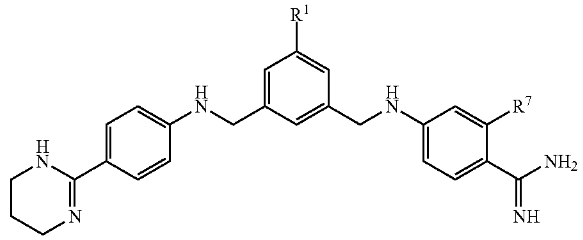
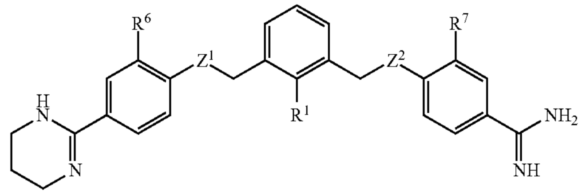
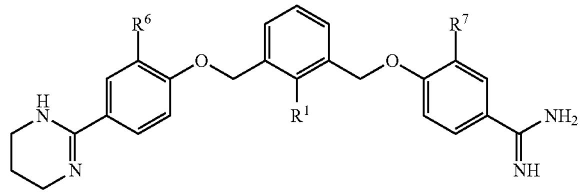
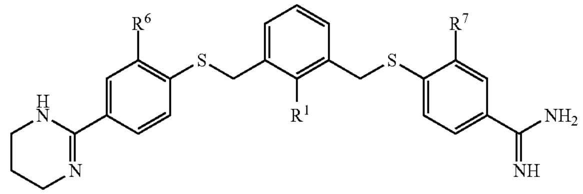
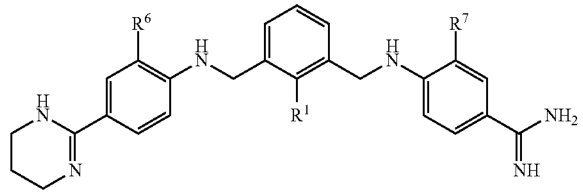
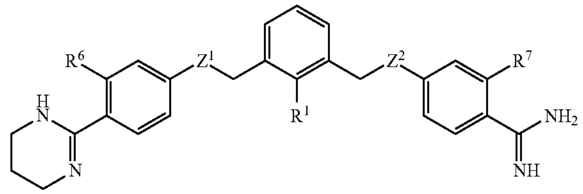
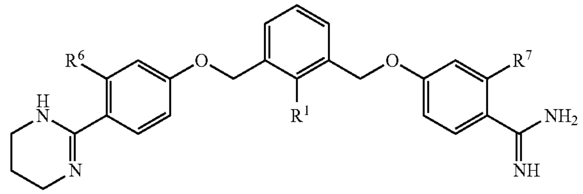
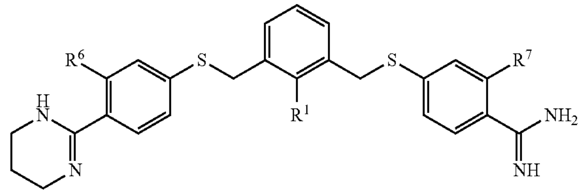
-continued
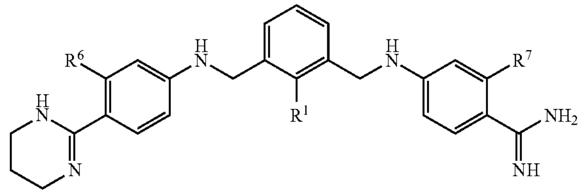
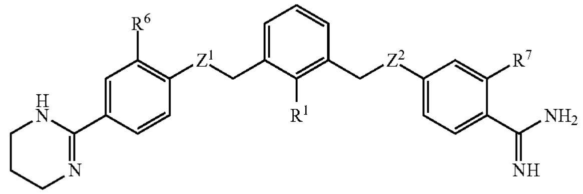
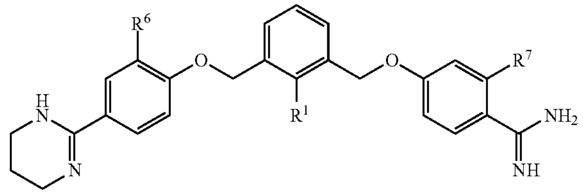
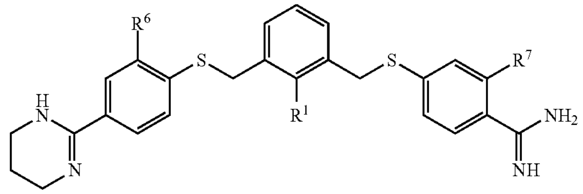
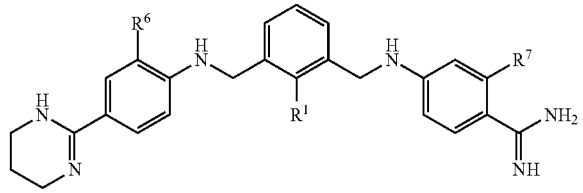
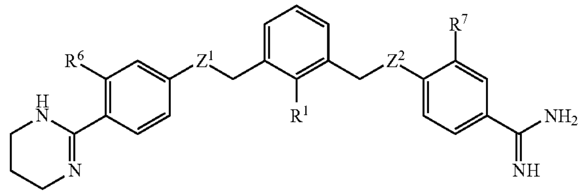
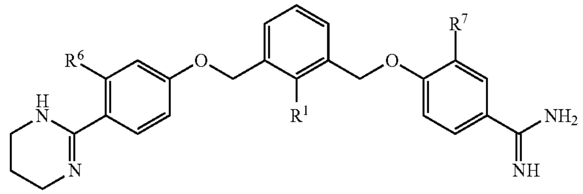
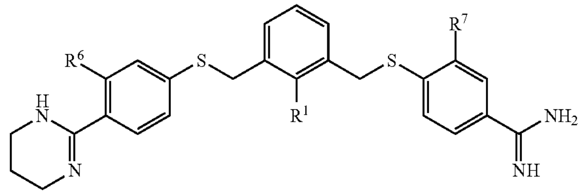

-continued
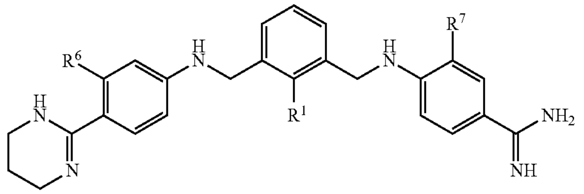
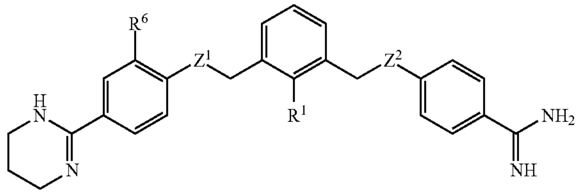
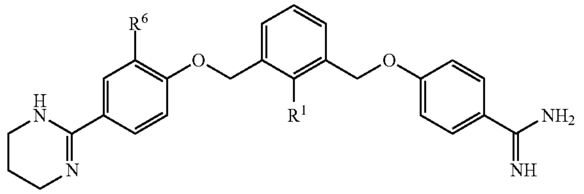
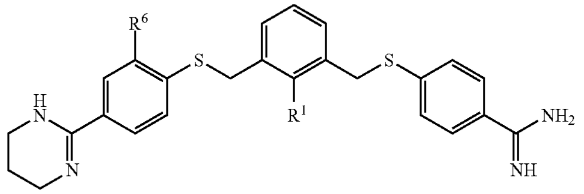
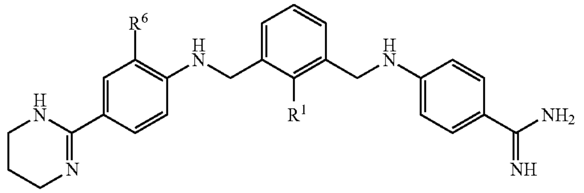
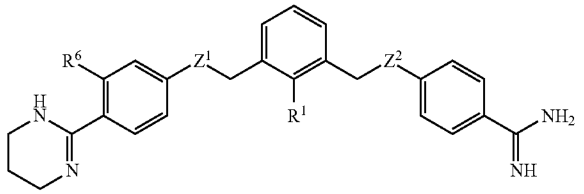
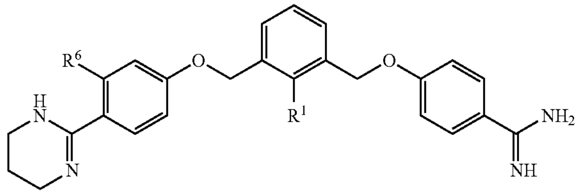
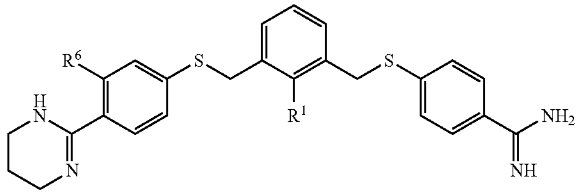
-continued
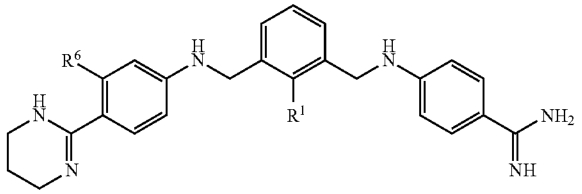
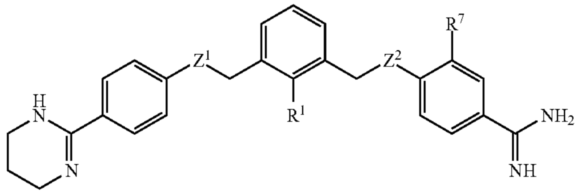
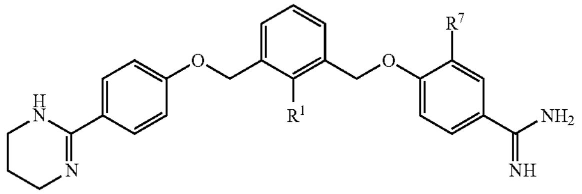
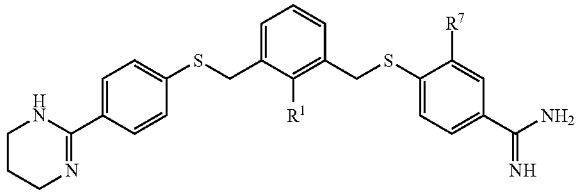
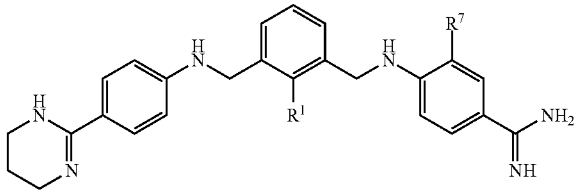
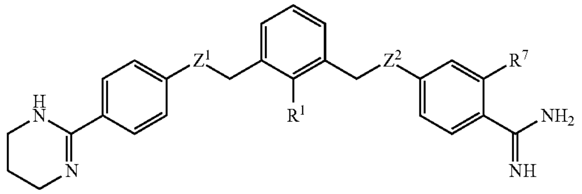
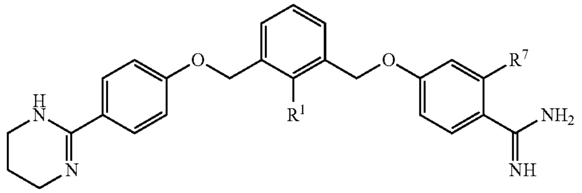
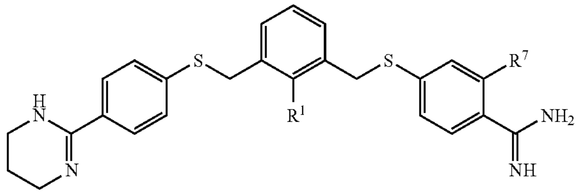

-continued
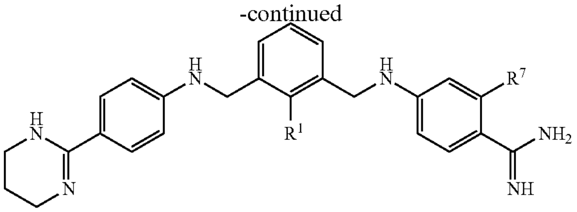
Non-limiting examples of compounds of Formula IV include:
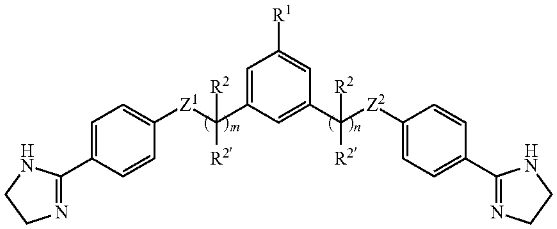
,
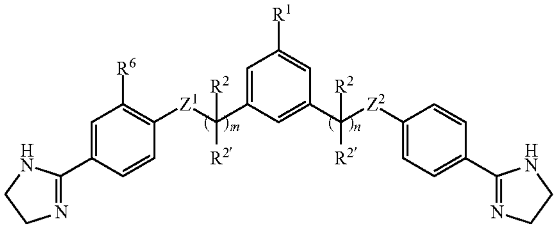
,
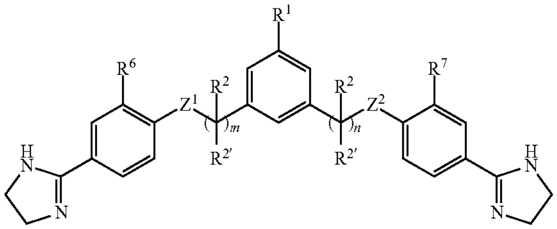
,
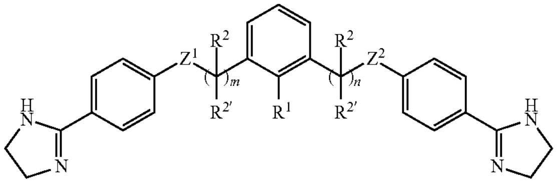
,
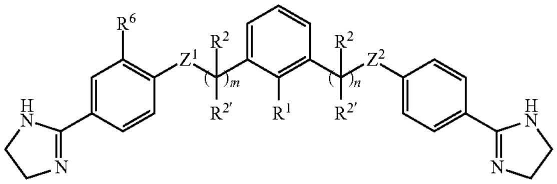
,
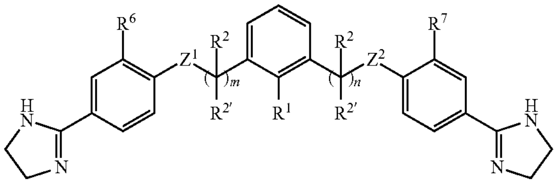
,
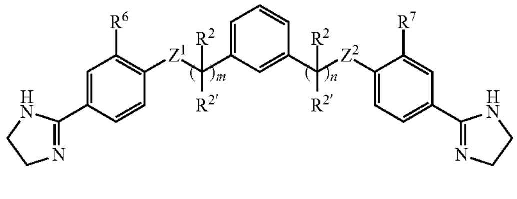
, and
-continued
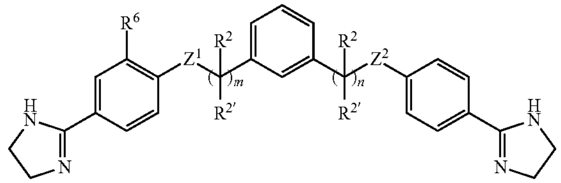
.
Non-limiting examples of compounds of Formula IV include:
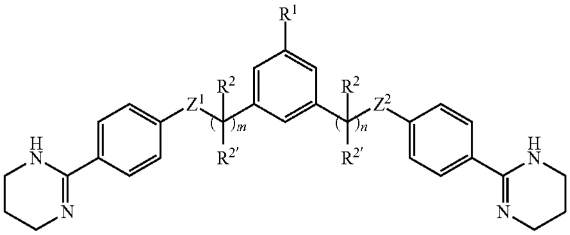
,
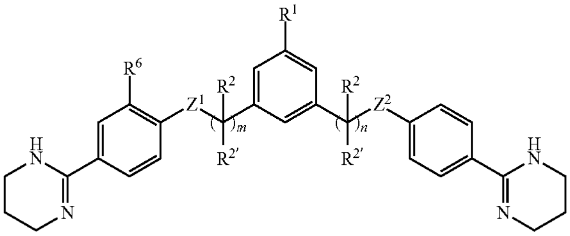
,
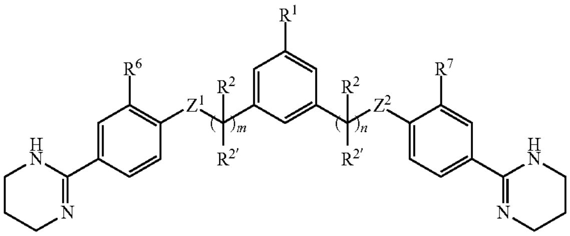
,
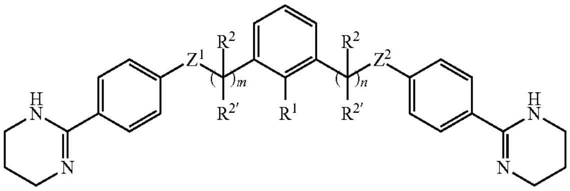
,
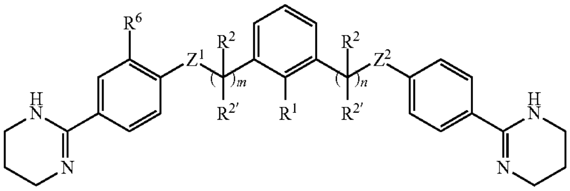
,
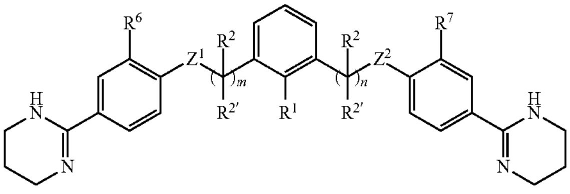
, -continued
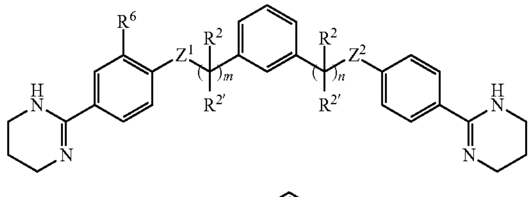
, and
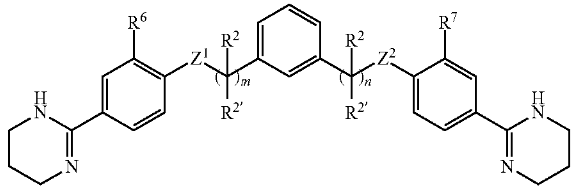
.
Non-limiting examples of compounds of Formula IV include:
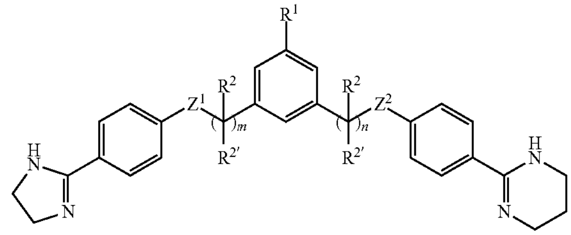
,
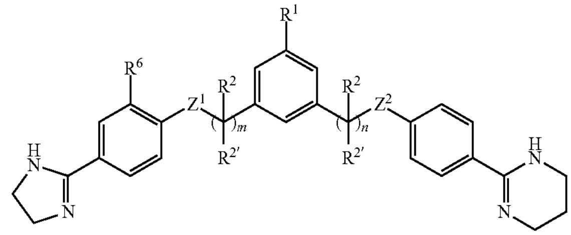
,
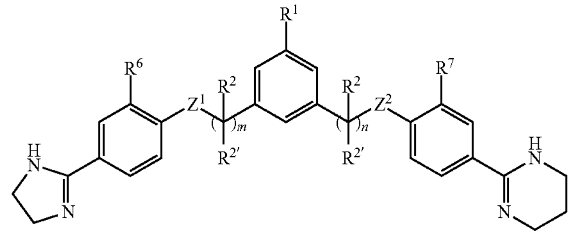
,
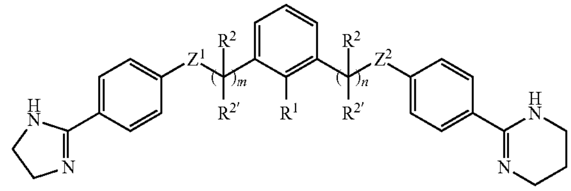
,
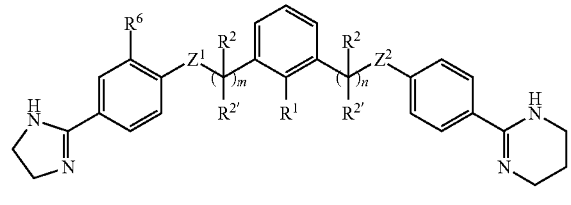
,
-continued
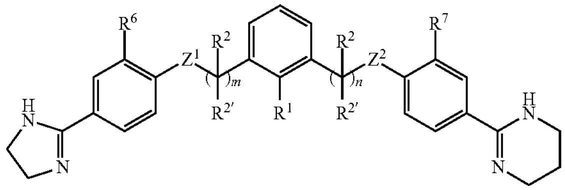
,
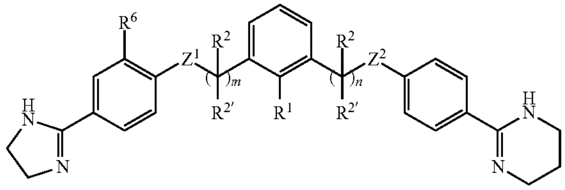
,
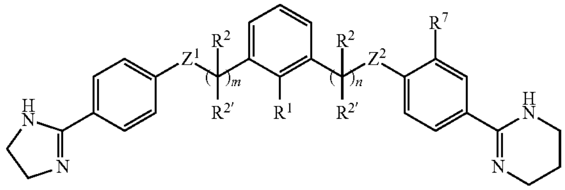
,
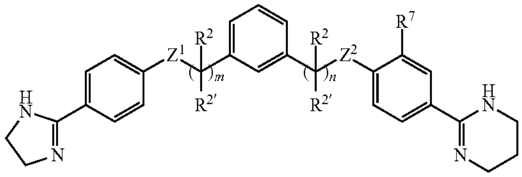
, and
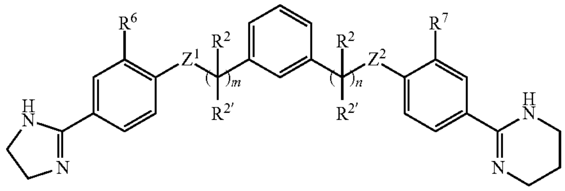
.
Additional examples of compounds of Formula IV include:
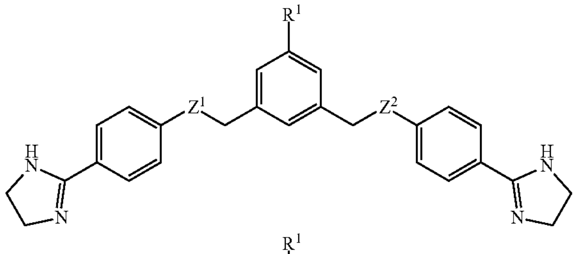
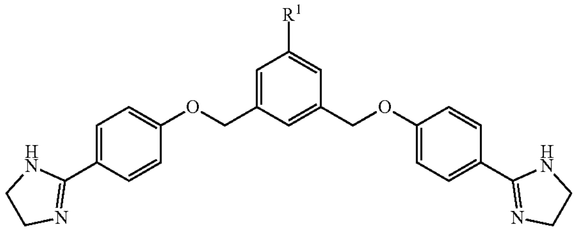

-continued
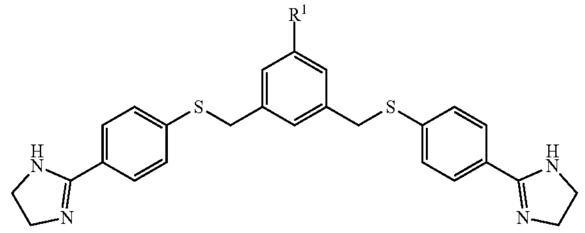
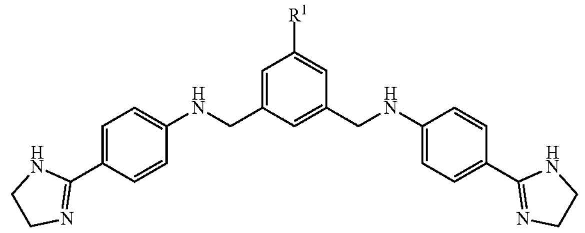
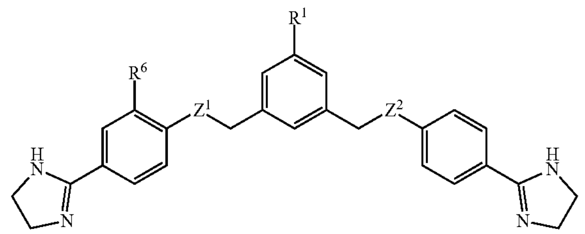
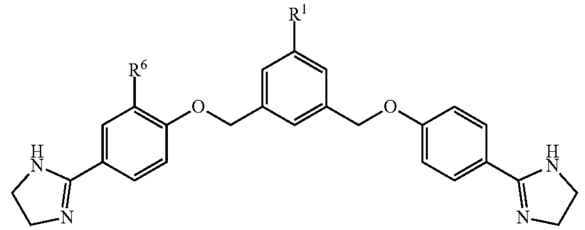
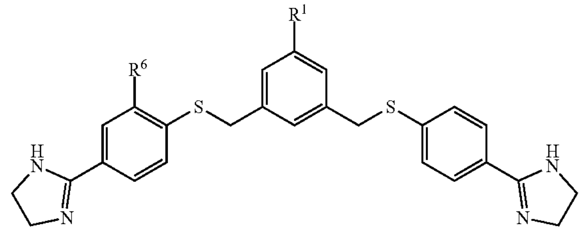
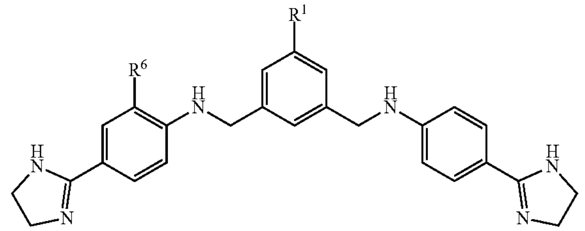
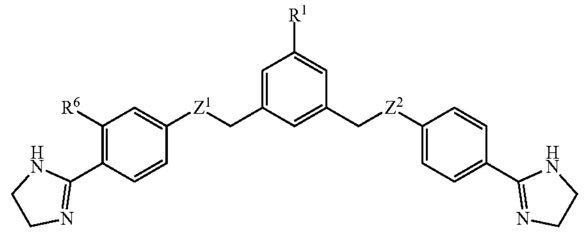
-continued
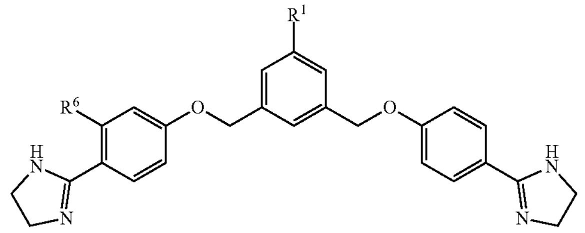
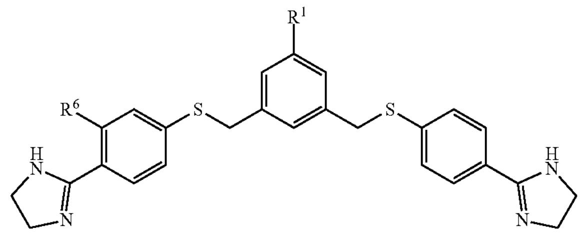
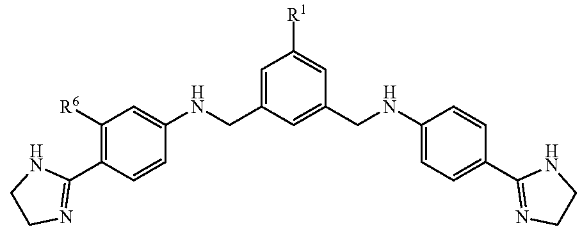
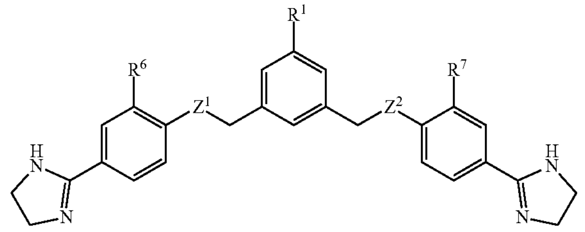
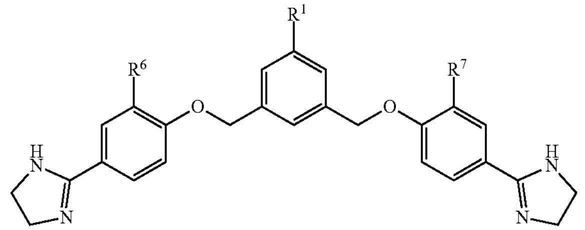
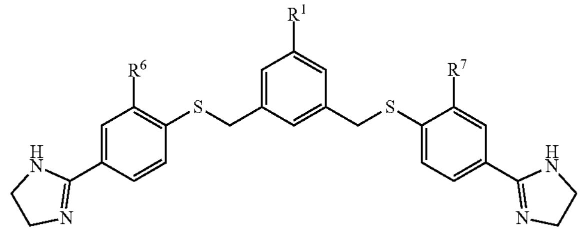
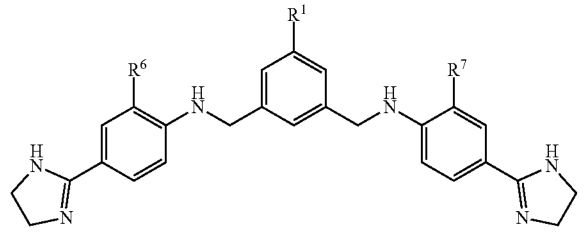

-continued
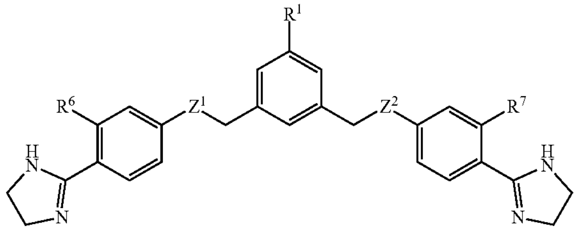
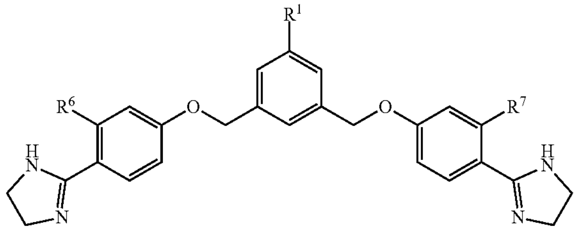
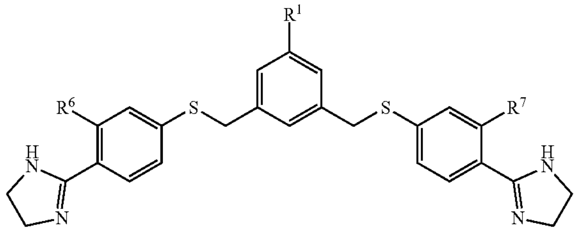
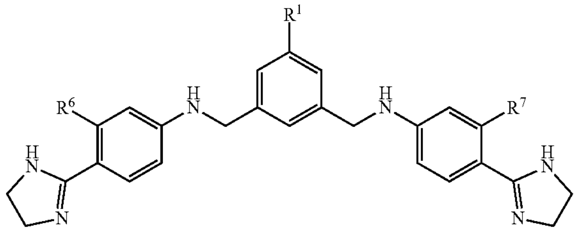
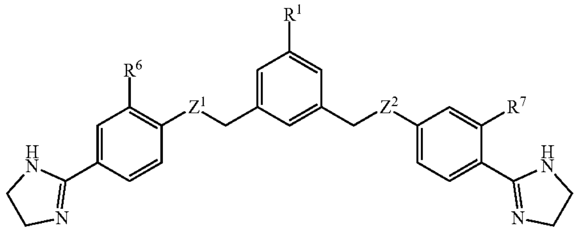
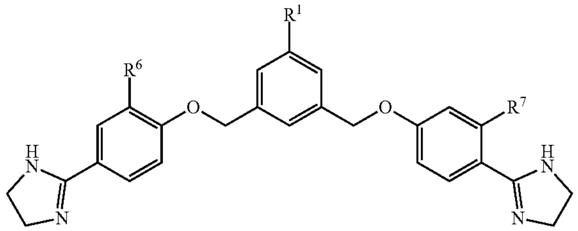
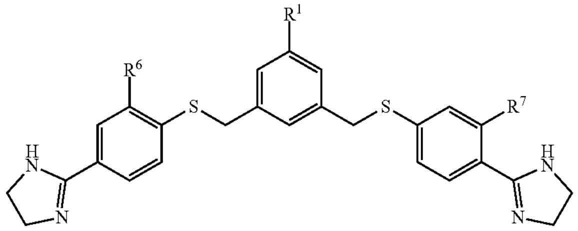
-continued
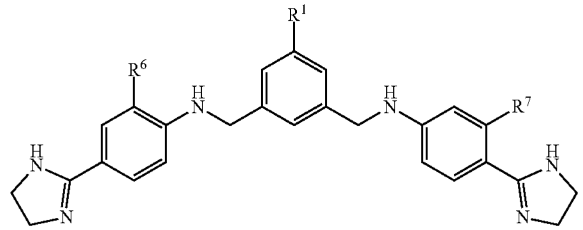
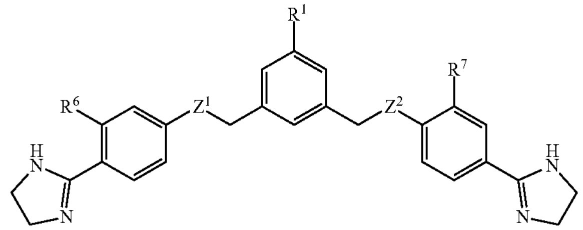
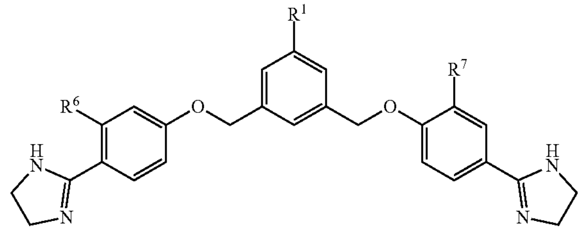
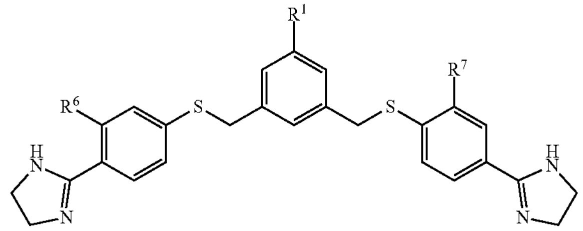
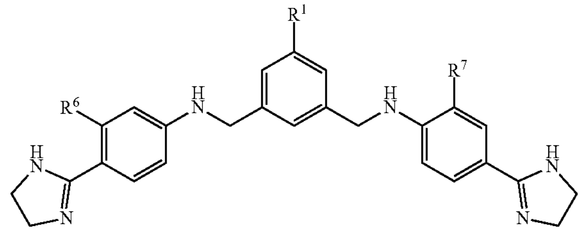
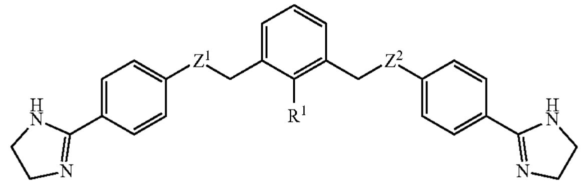
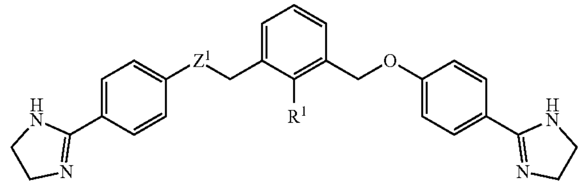
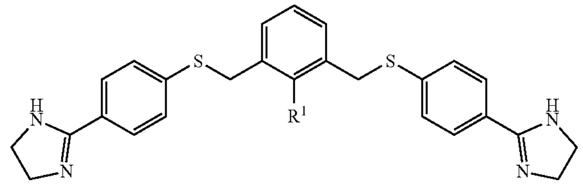

-continued
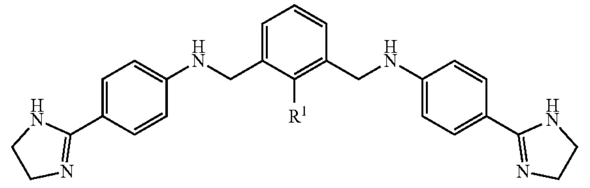
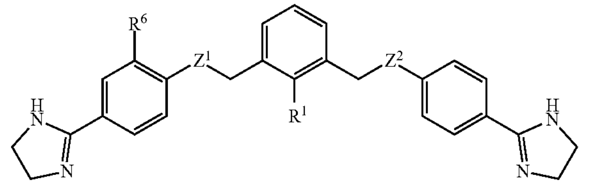
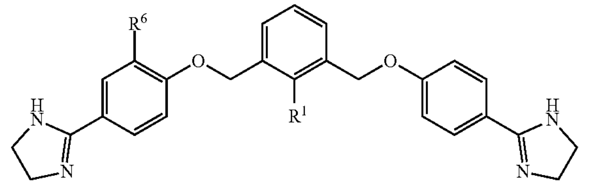
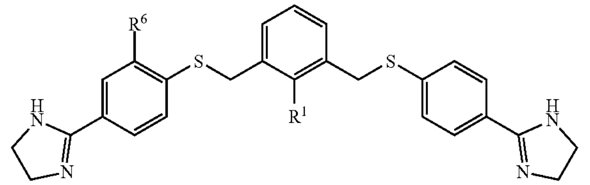
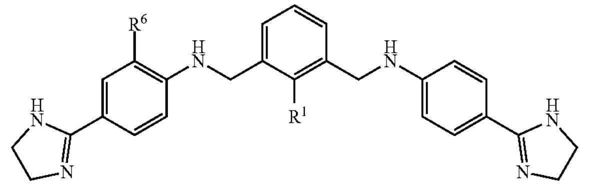
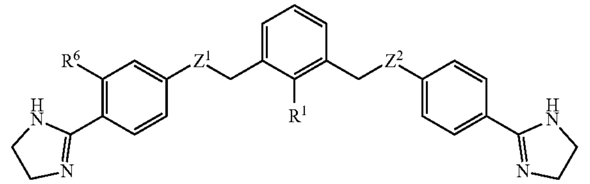
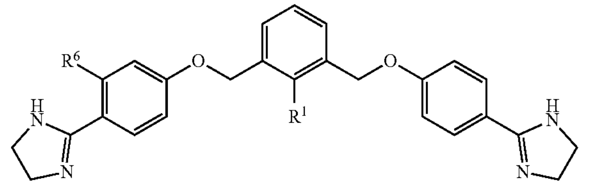
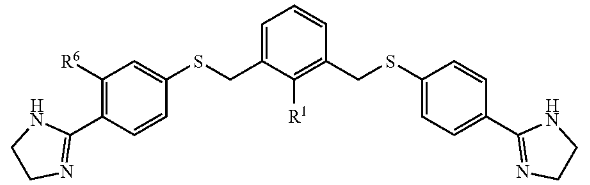
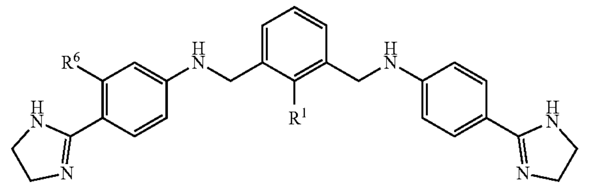
-continued
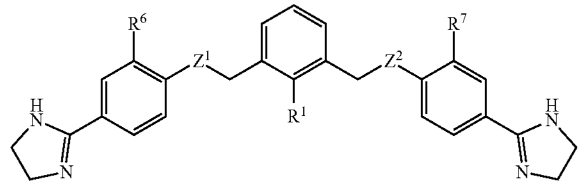
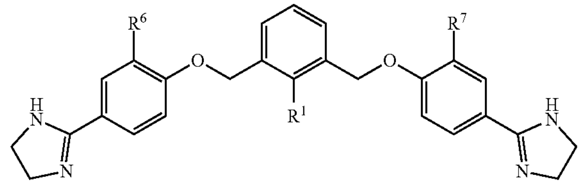
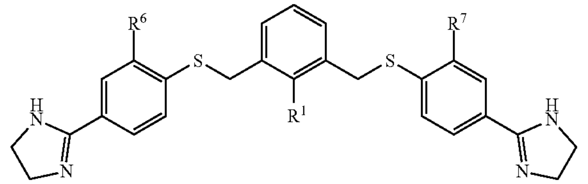
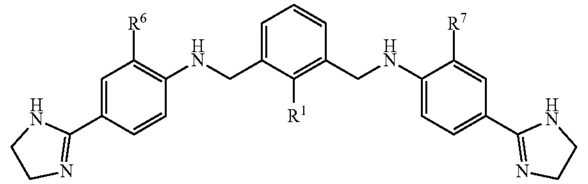
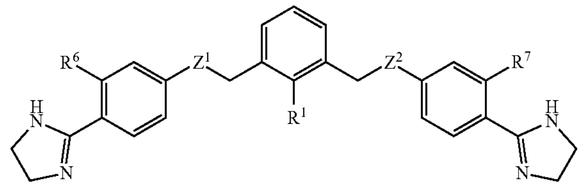
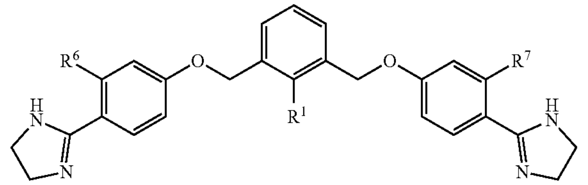
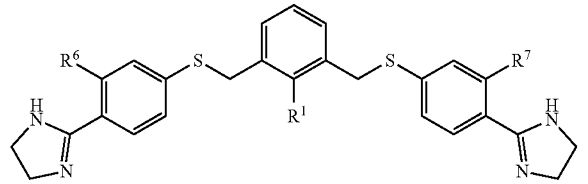
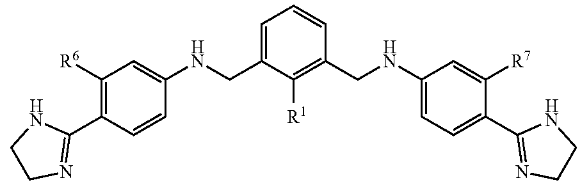
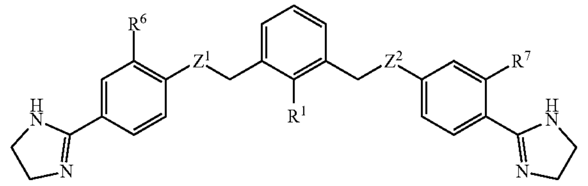

-continued
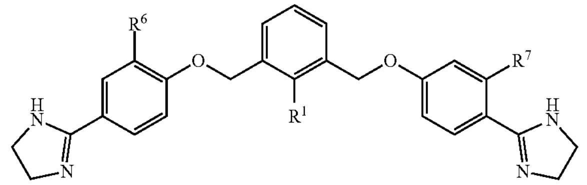
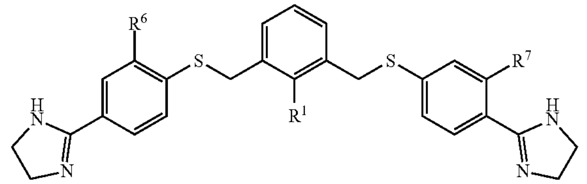
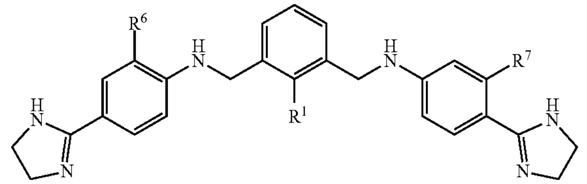
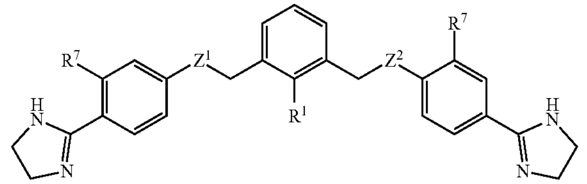
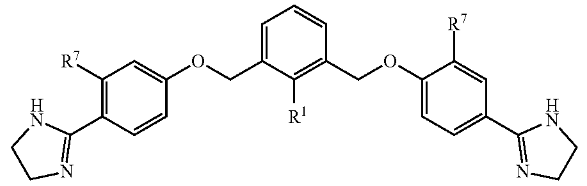
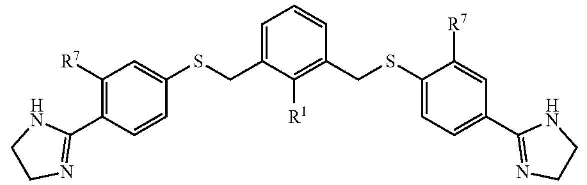
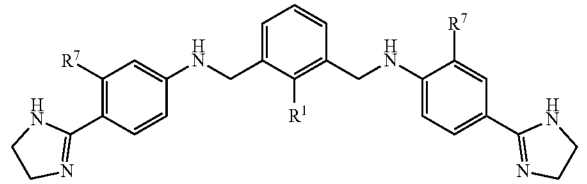
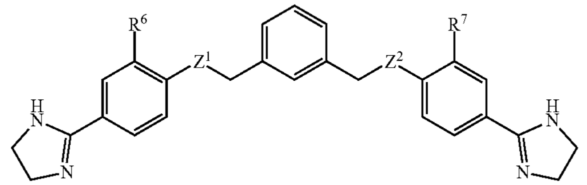
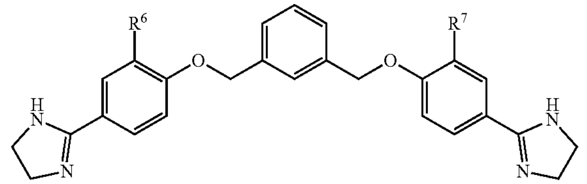
-continued
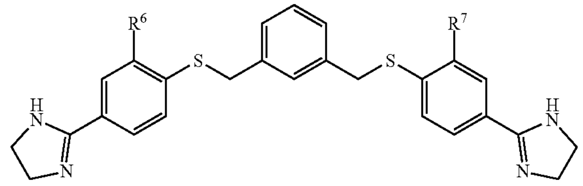
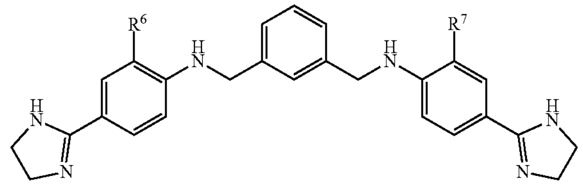
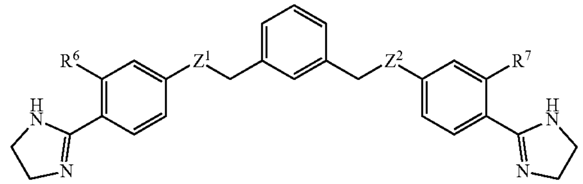
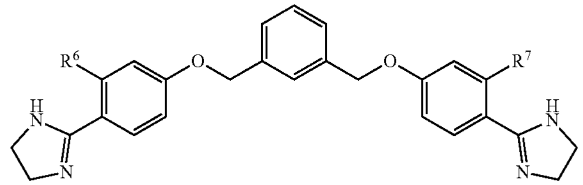
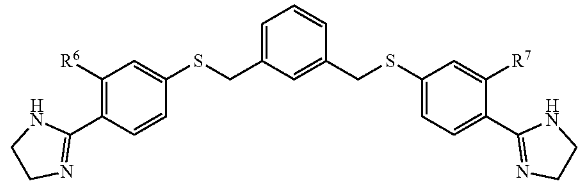
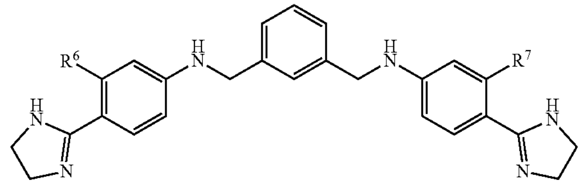
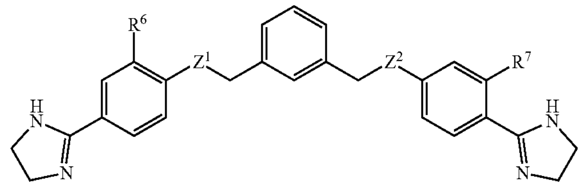
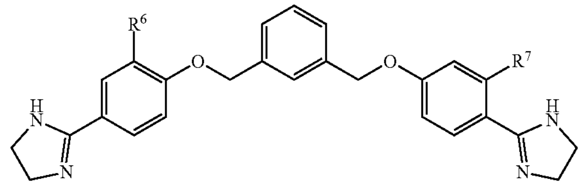
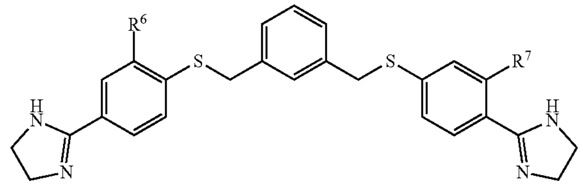

-continued
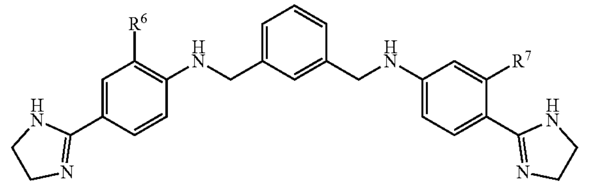
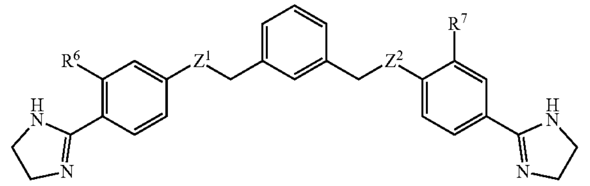
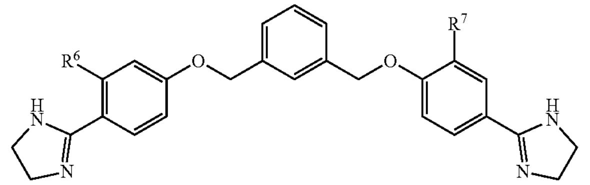
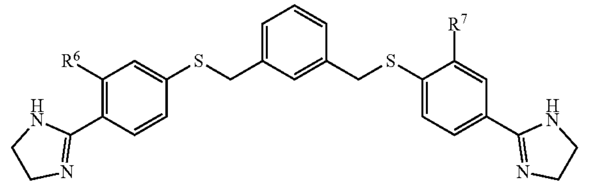
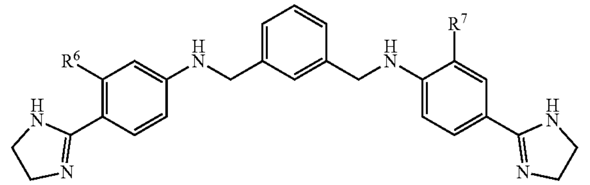
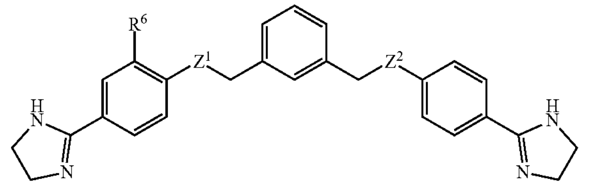
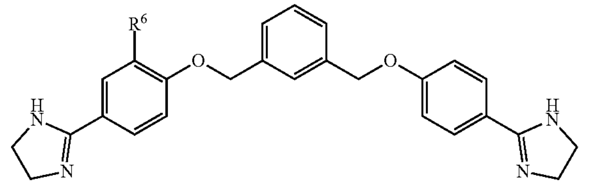
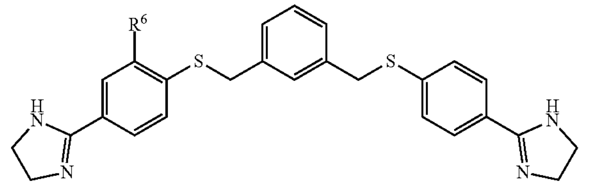
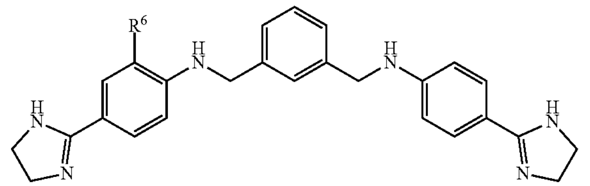
-continued
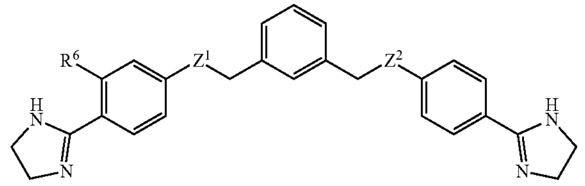
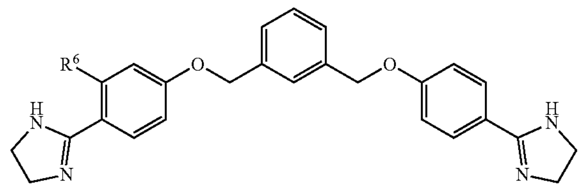
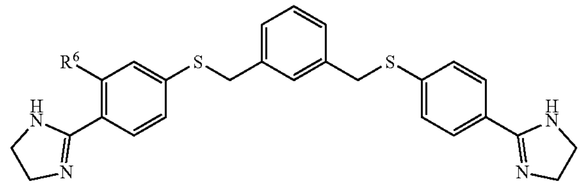
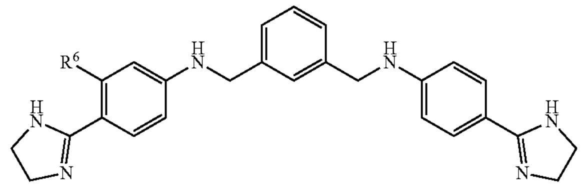
Additional examples of compounds of Formula IV include.
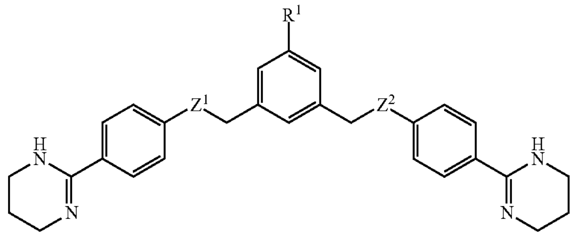
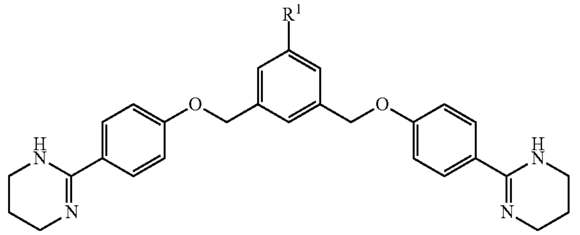
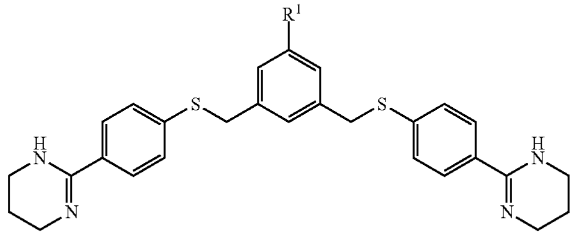

-continued
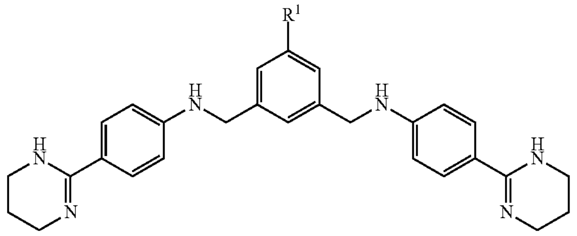
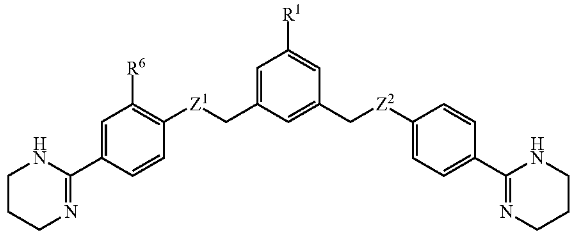
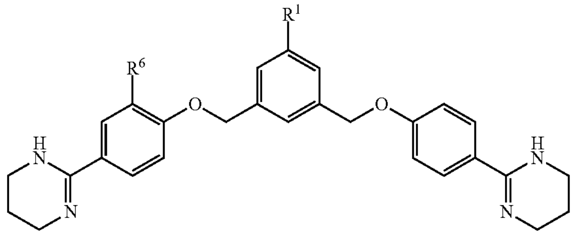
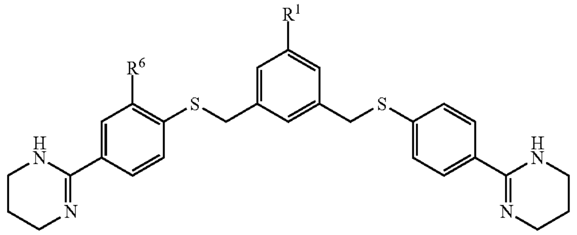
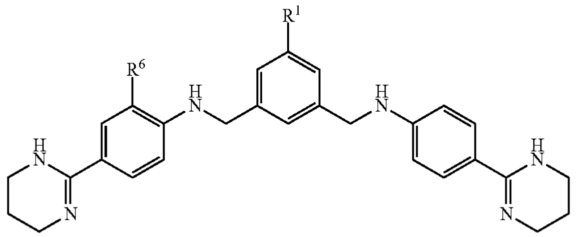
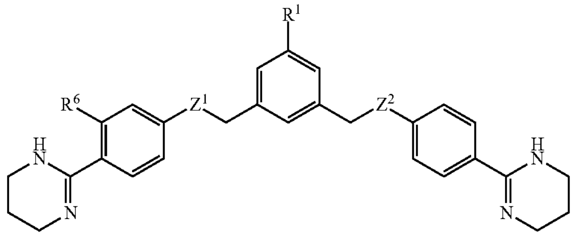
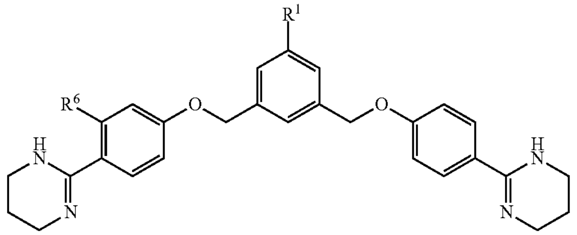
-continued
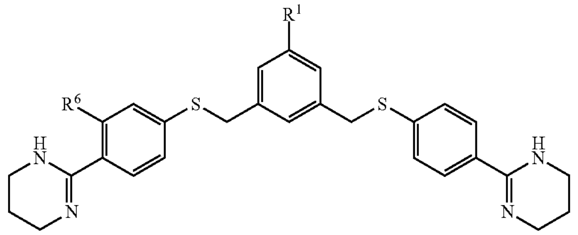
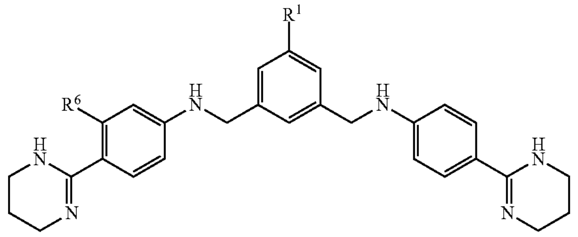
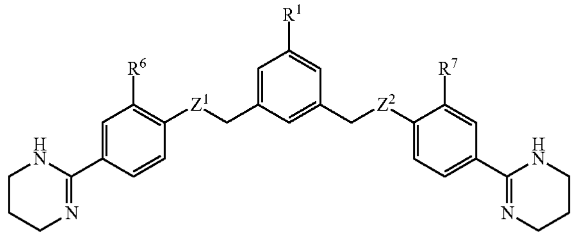
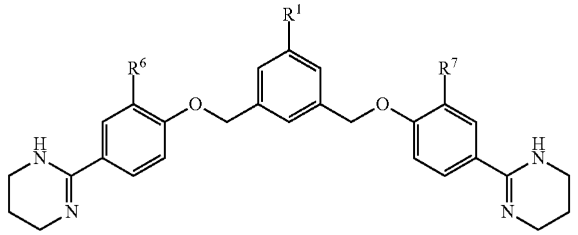
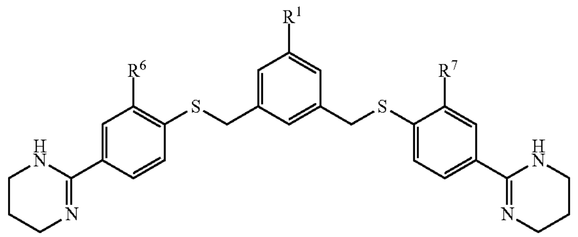
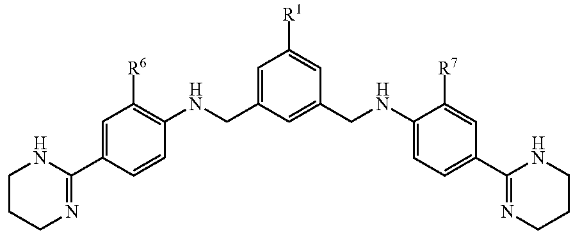
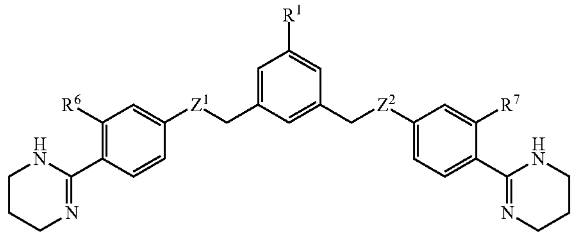

-continued
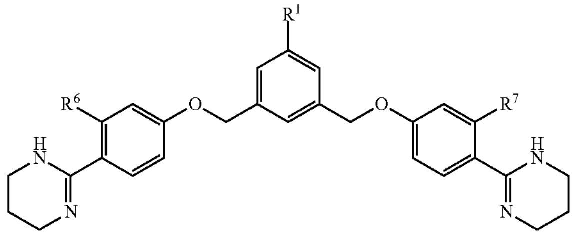
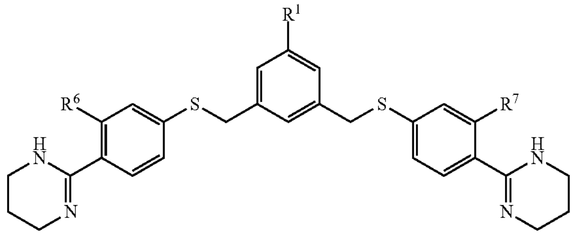
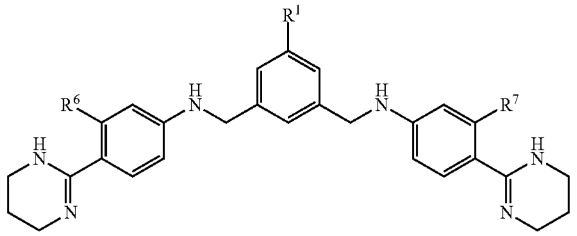
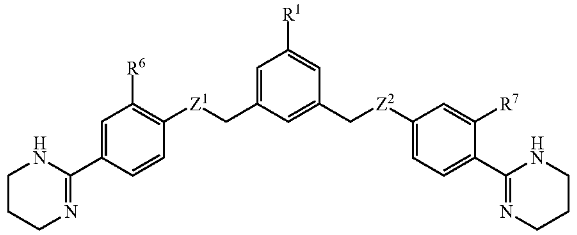
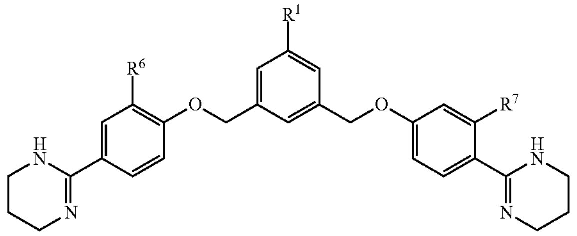
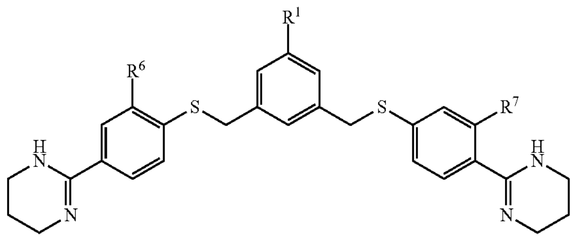
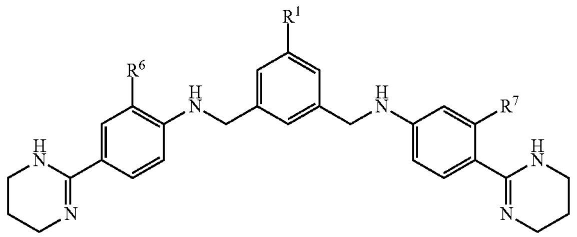
-continued
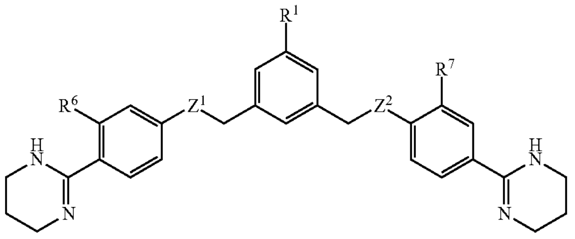
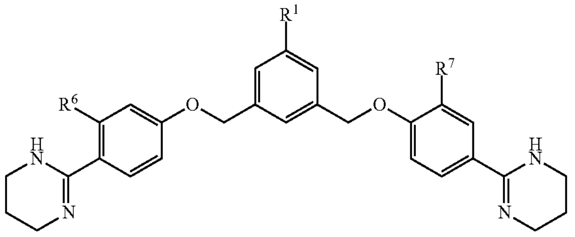
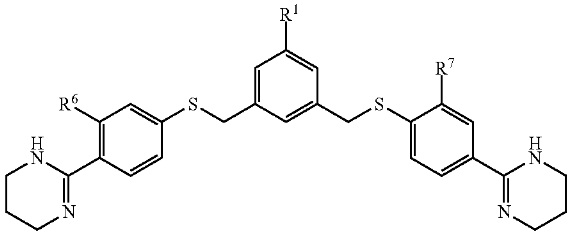
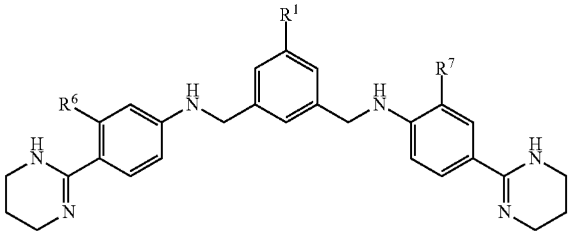
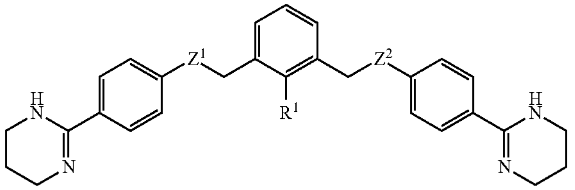
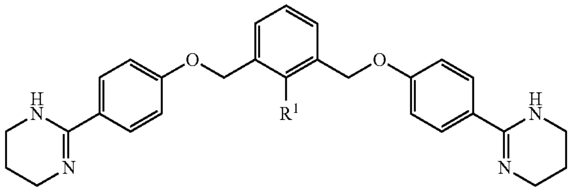
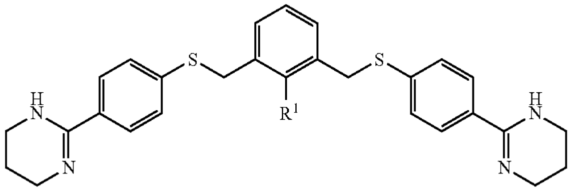
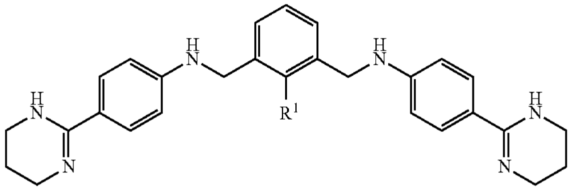

-continued
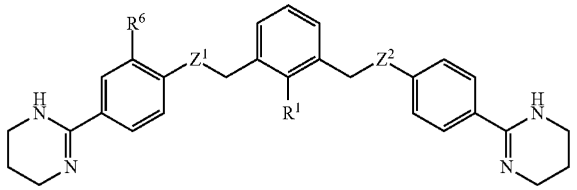
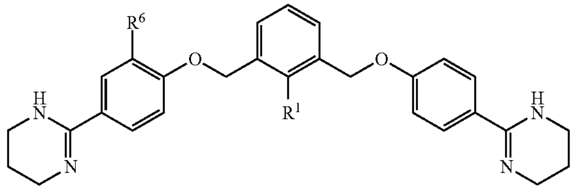
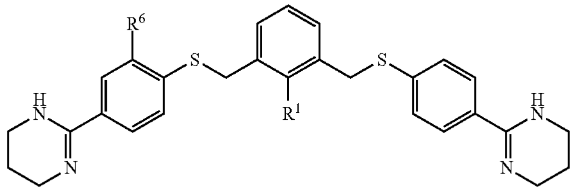
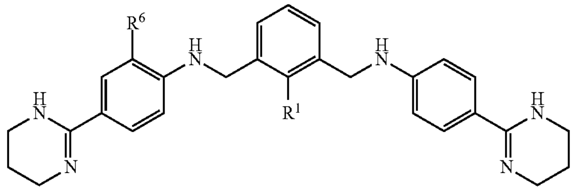
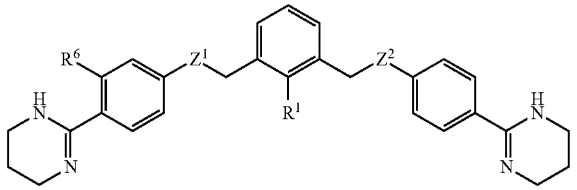
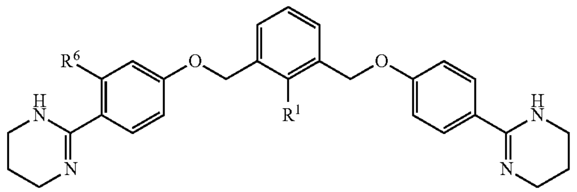
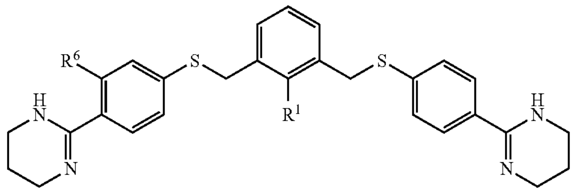
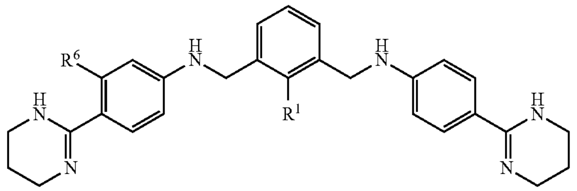
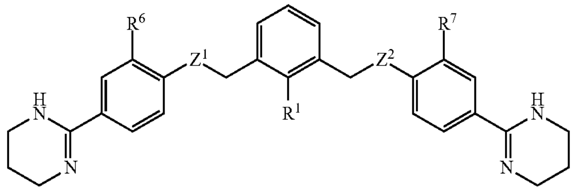
-continued
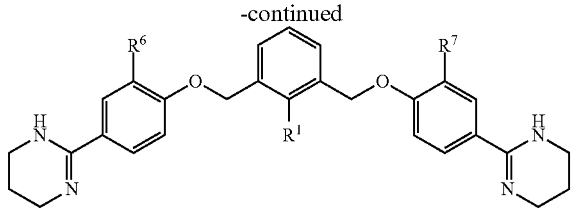
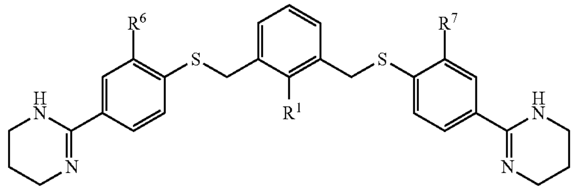
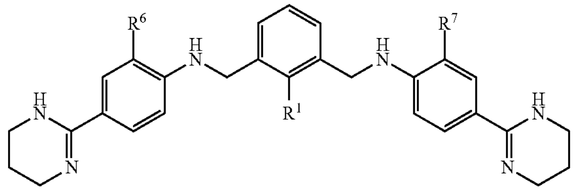
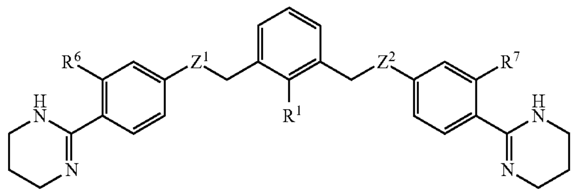
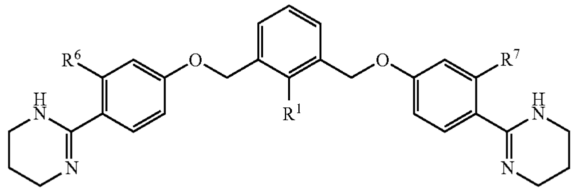
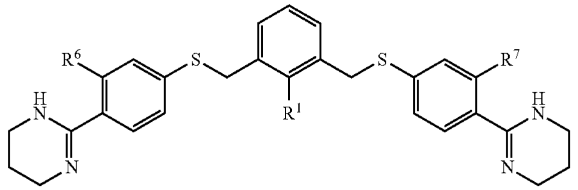
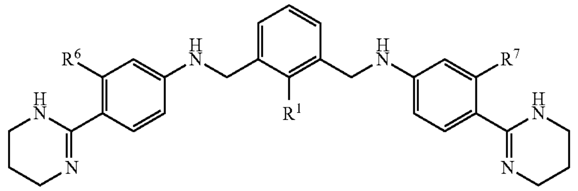
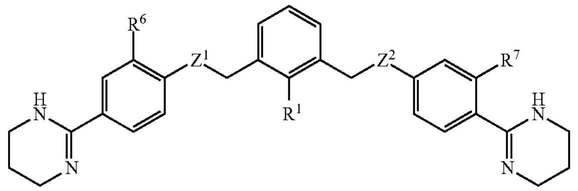
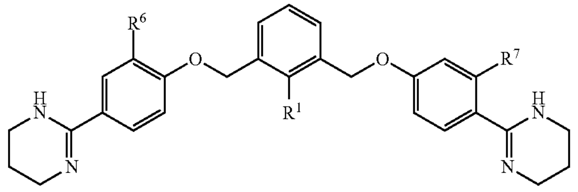

-continued
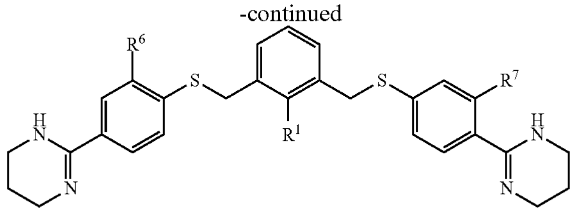
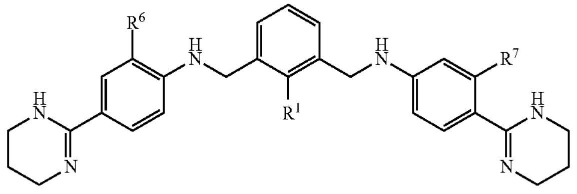
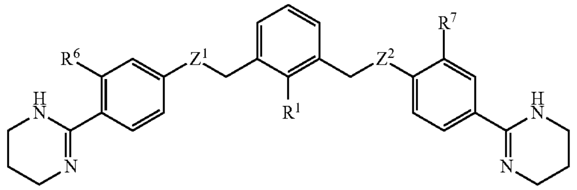
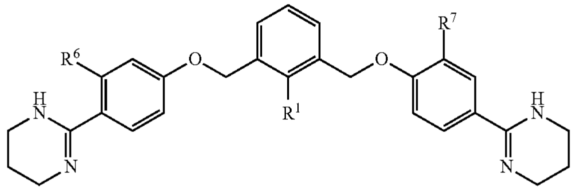
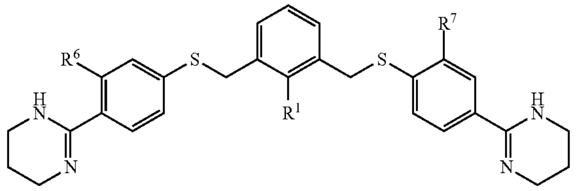
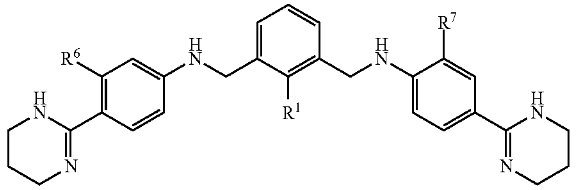
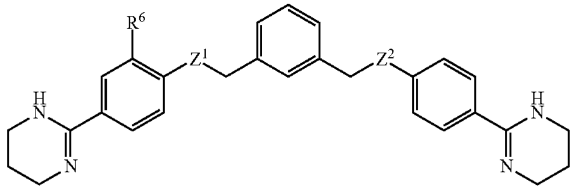
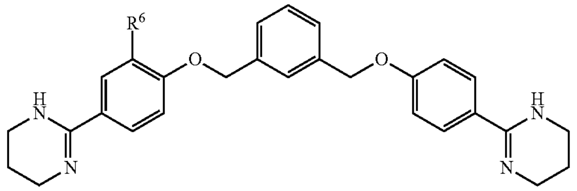
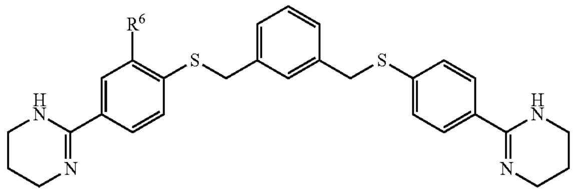
-continued
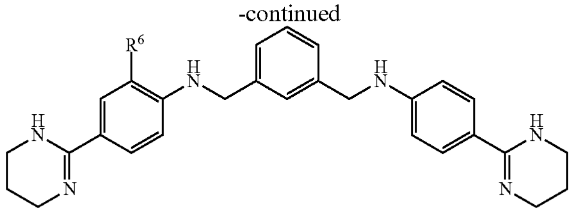
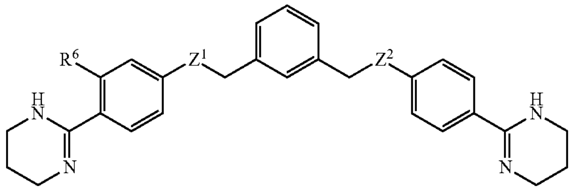
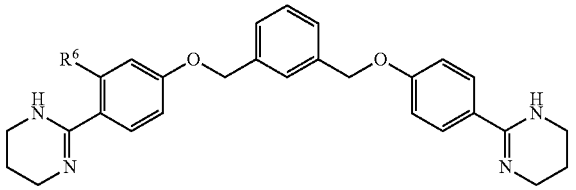
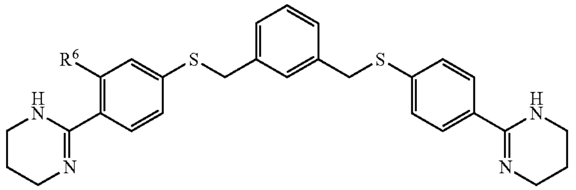
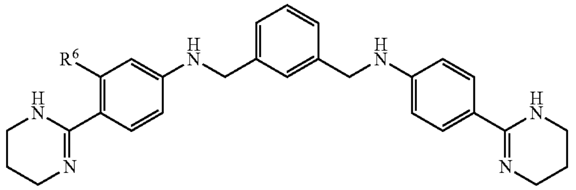
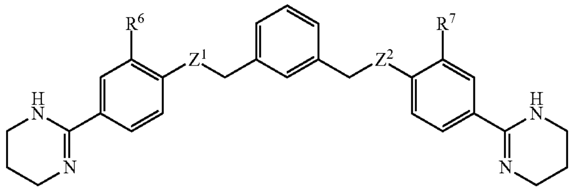
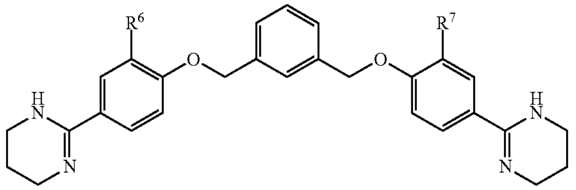
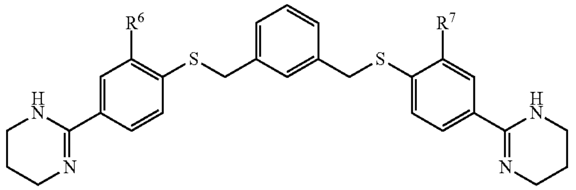
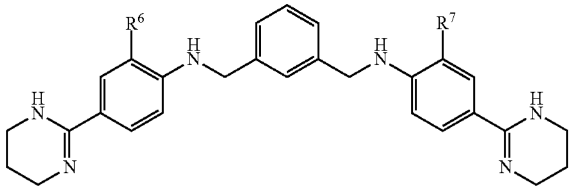

-continued
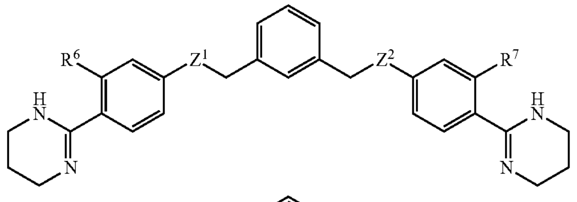
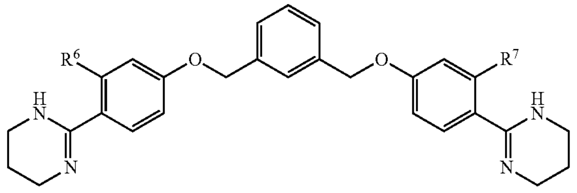
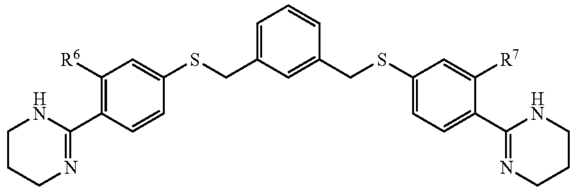
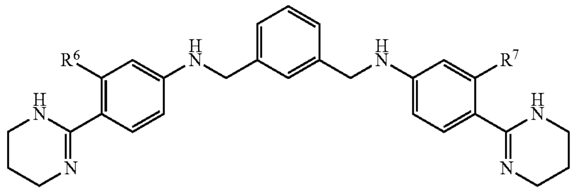
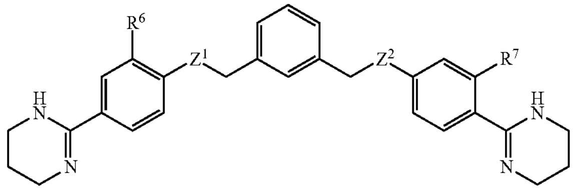
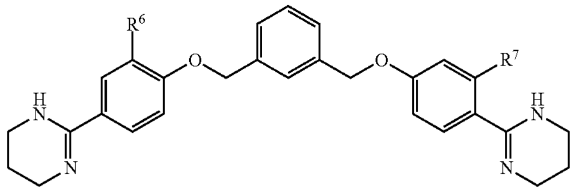
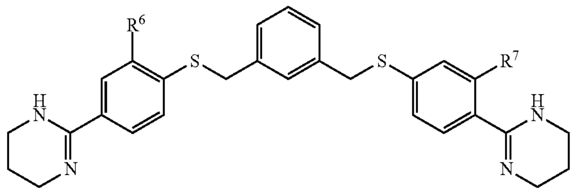
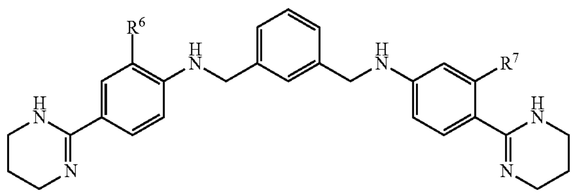
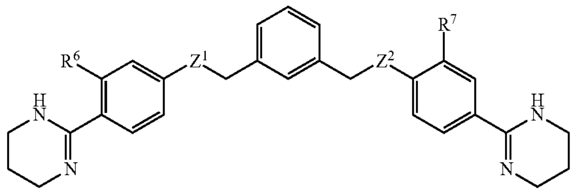
-continued
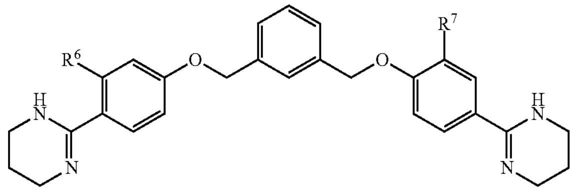
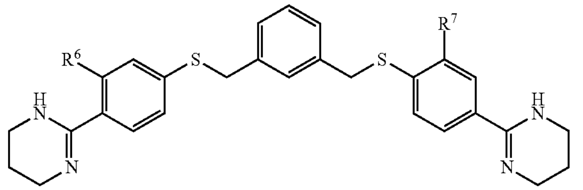
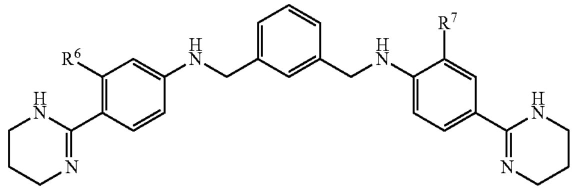
Additional examples of compounds of Formula IV include:
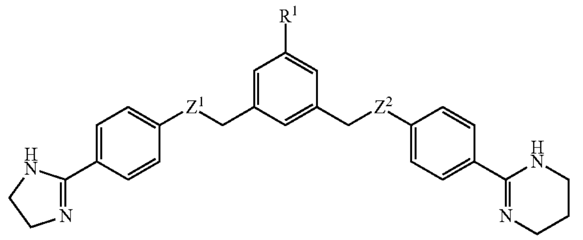
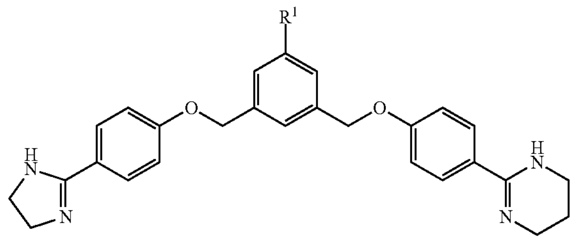
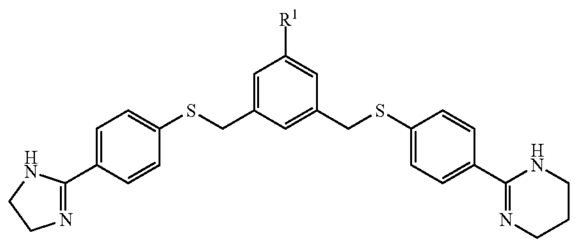
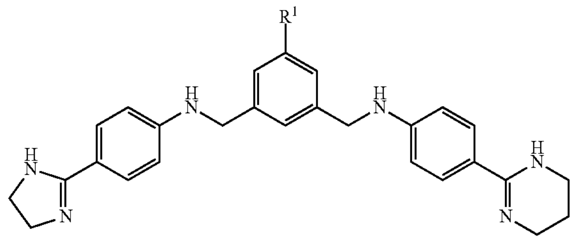

-continued
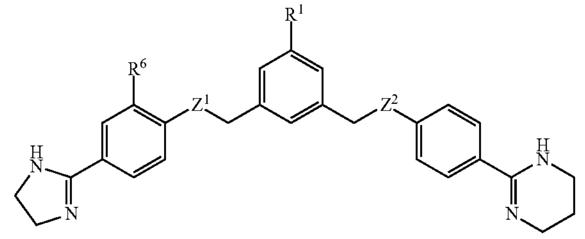
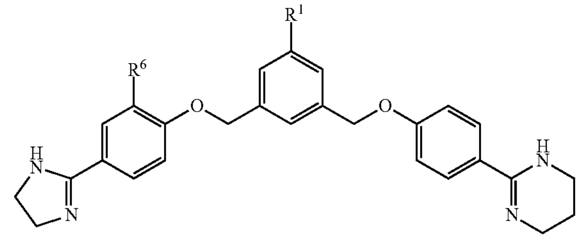
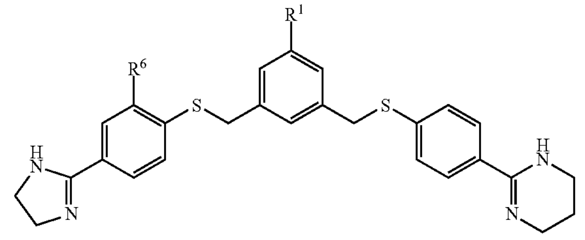
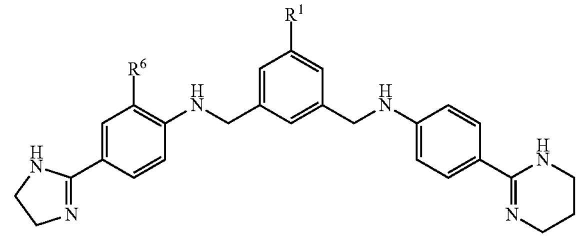
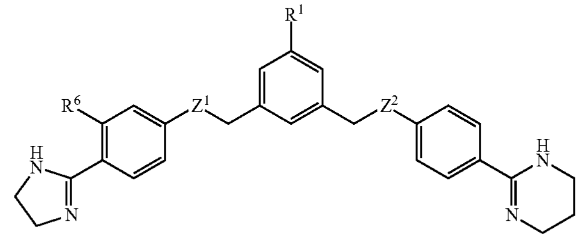
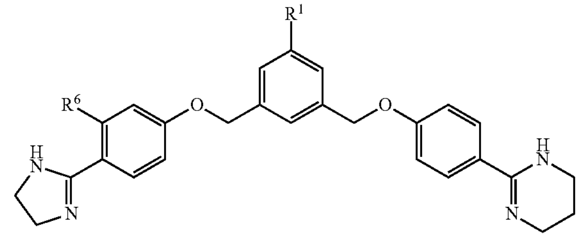
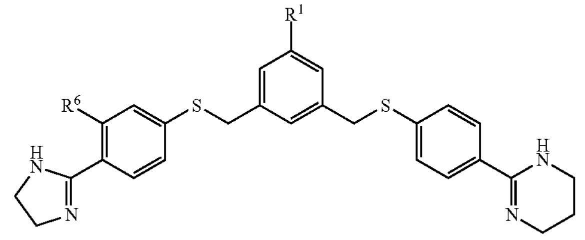
-continued
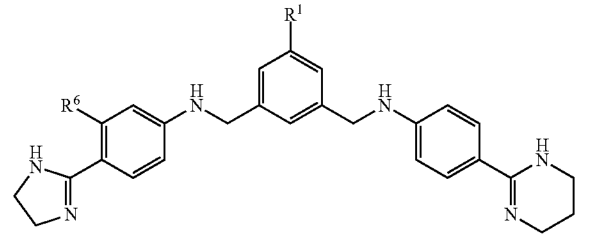
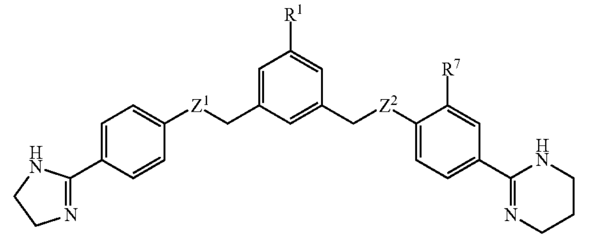
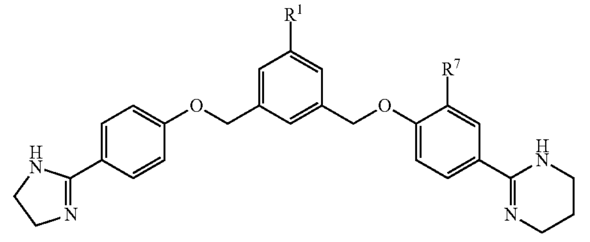
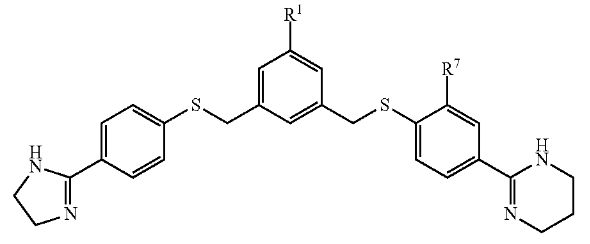
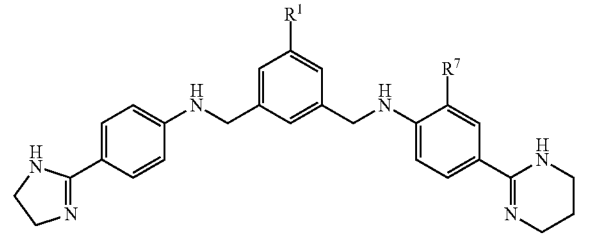
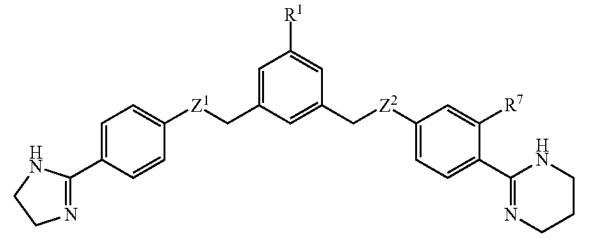
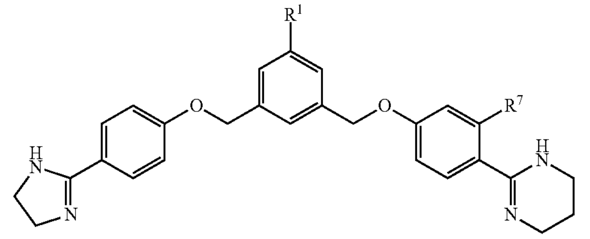

-continued
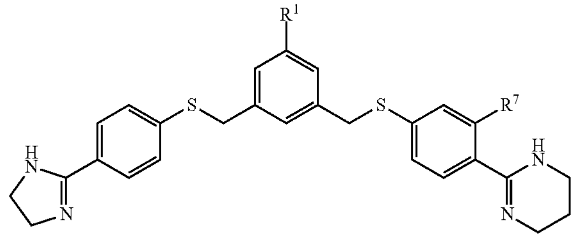
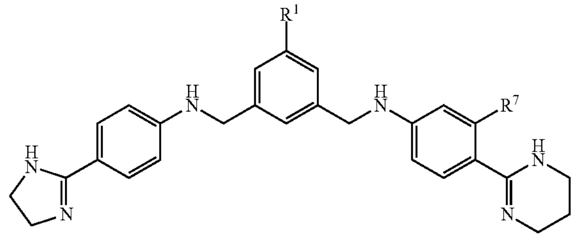
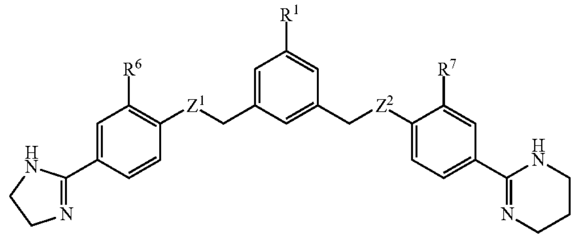
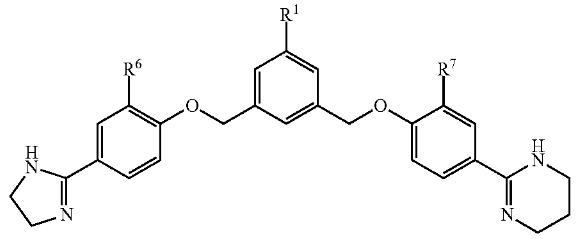
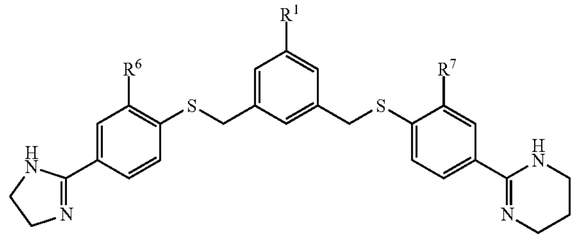
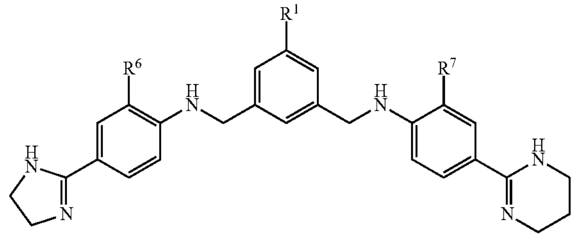
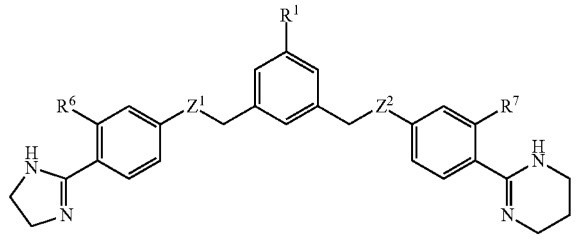
-continued
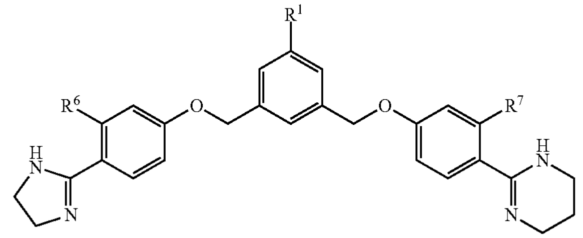
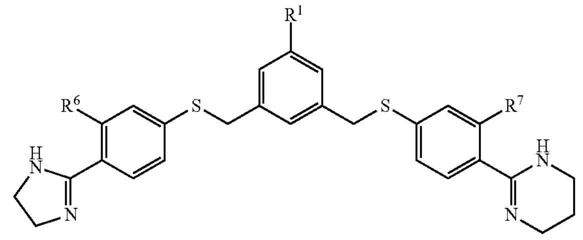
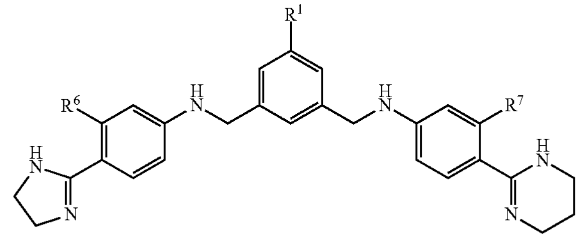
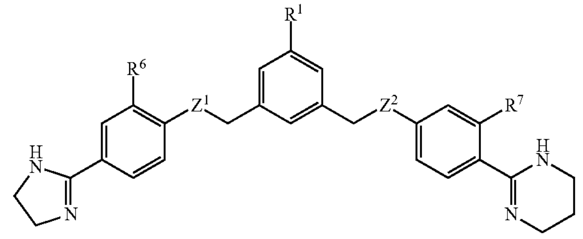
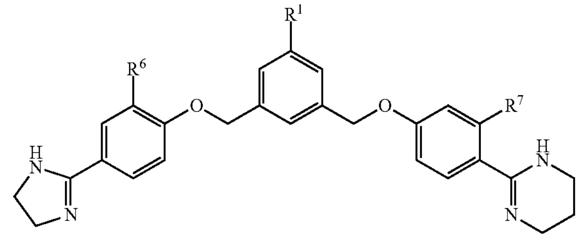
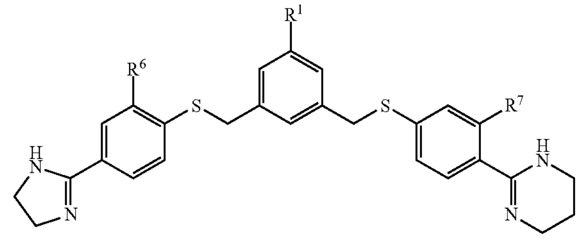
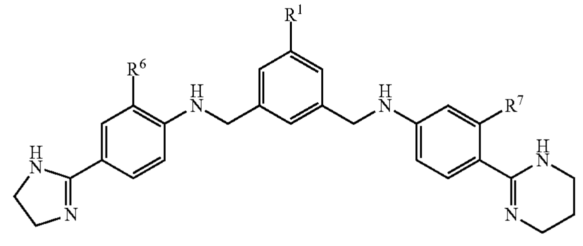

-continued
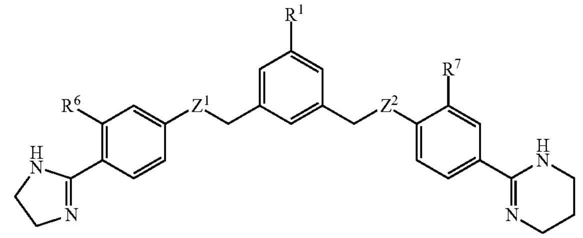
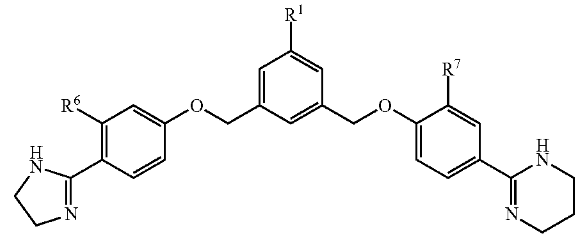
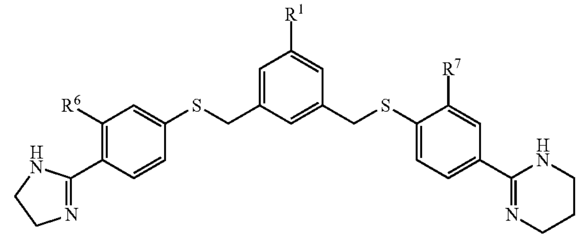
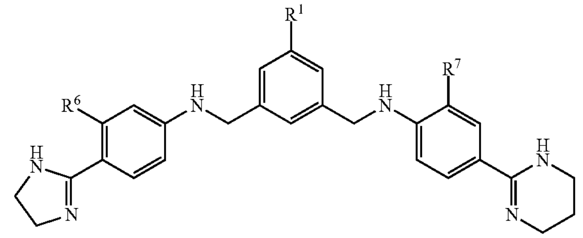
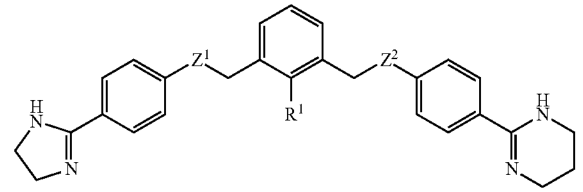
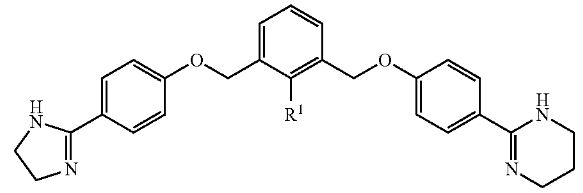
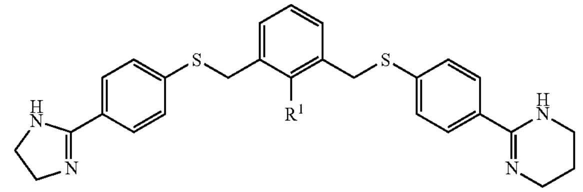
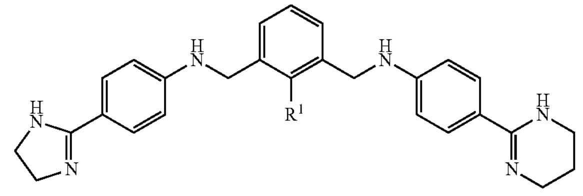
-continued
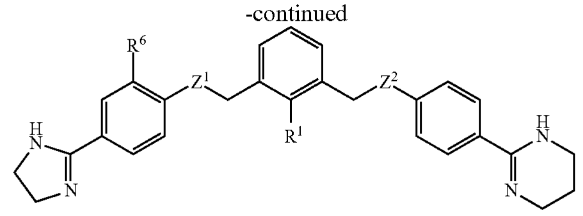
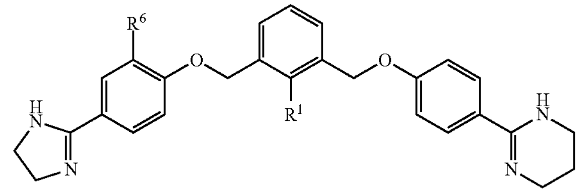
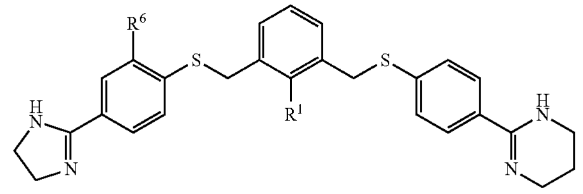
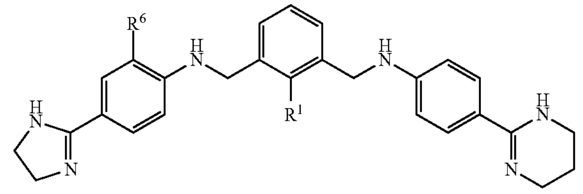
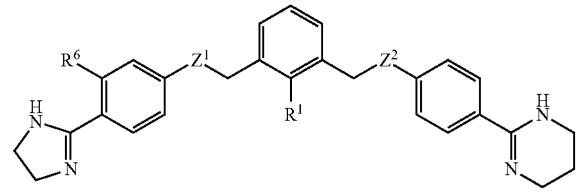
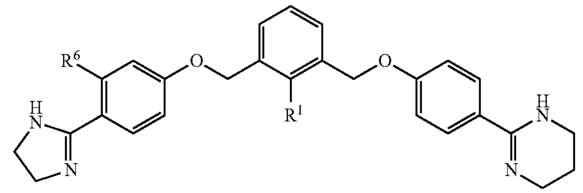
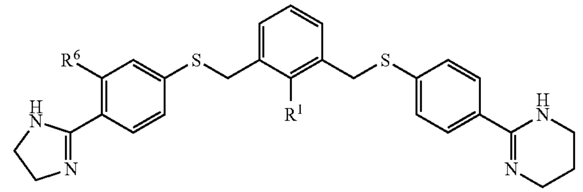
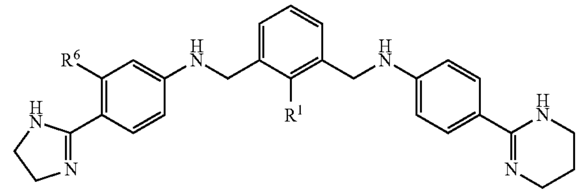
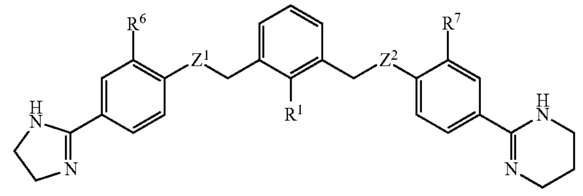

-continued
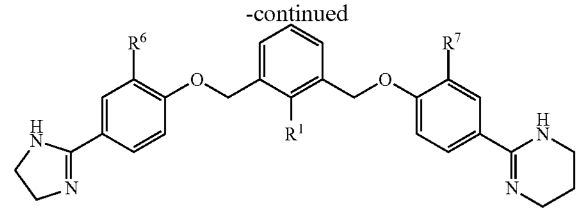
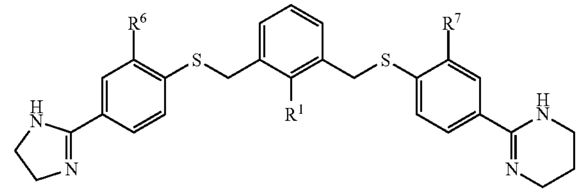
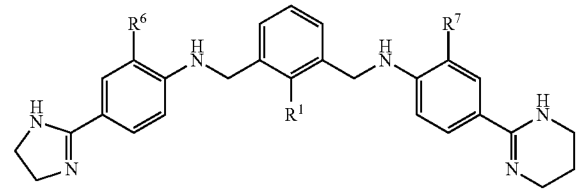
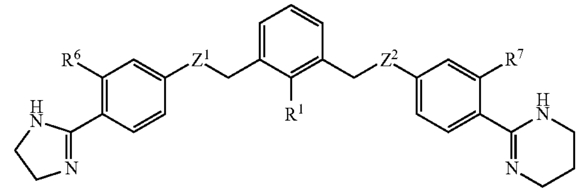
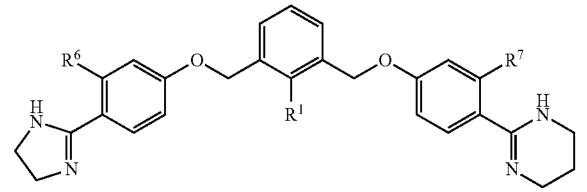
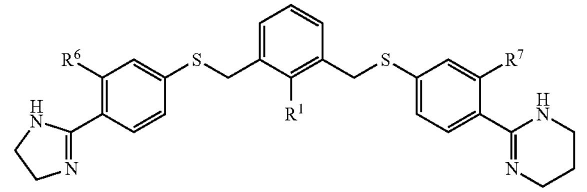
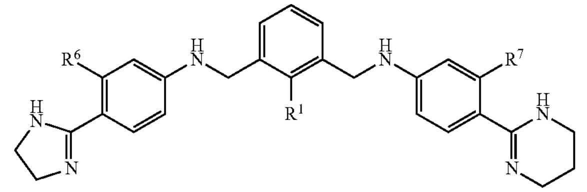
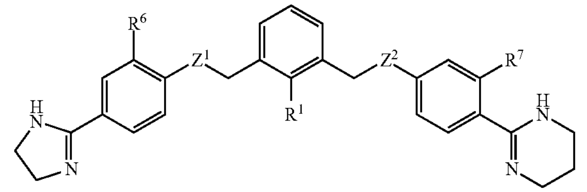
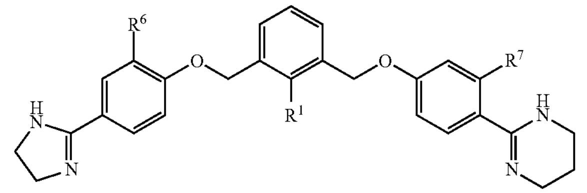
-continued
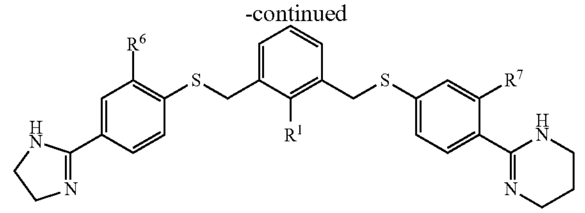
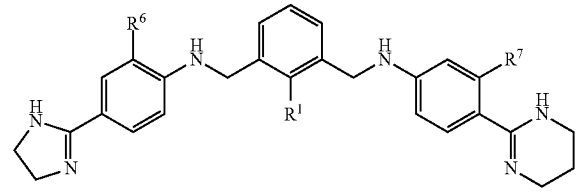
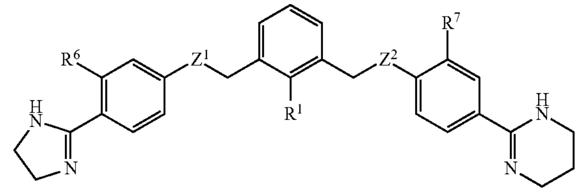
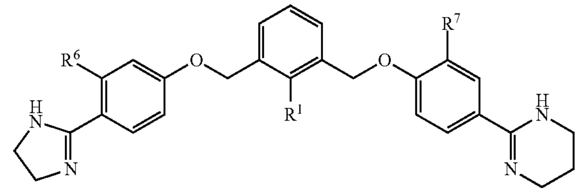
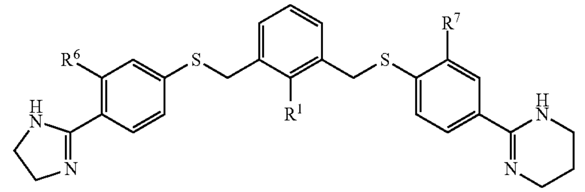
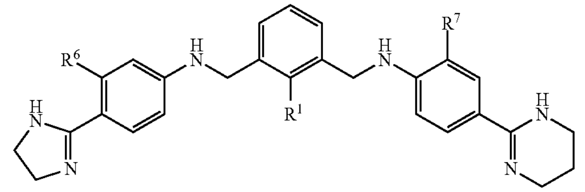
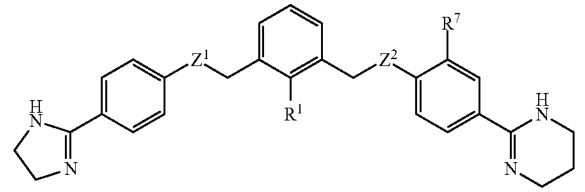
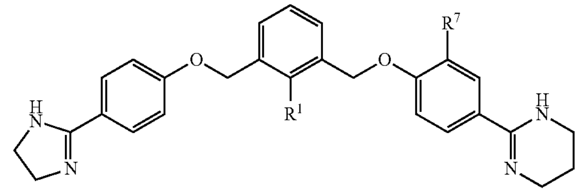
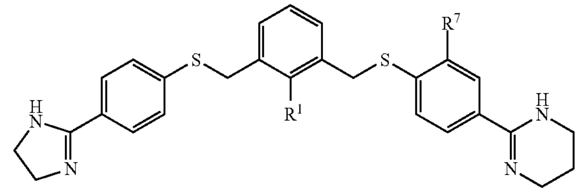

-continued
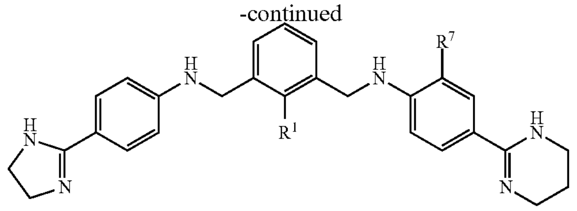
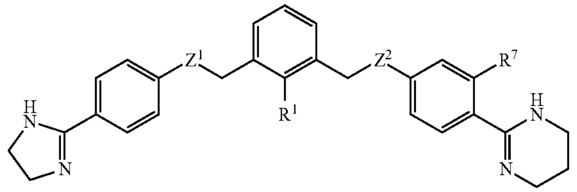
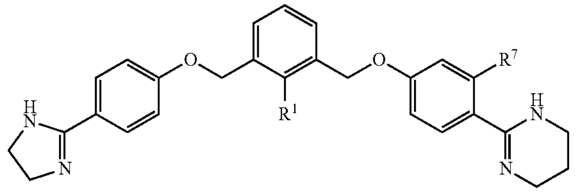
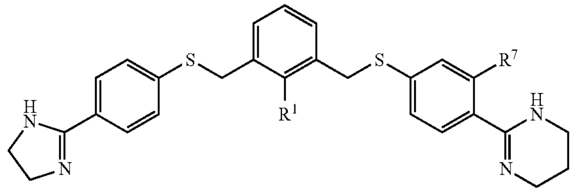
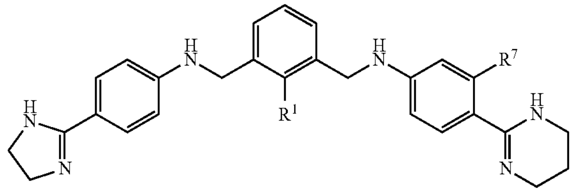
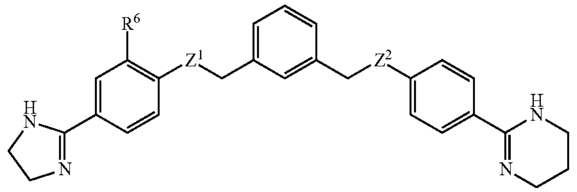
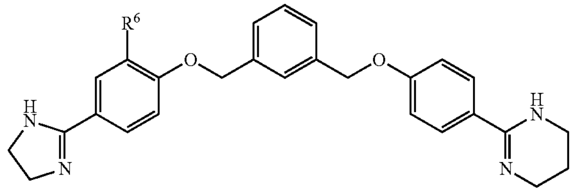
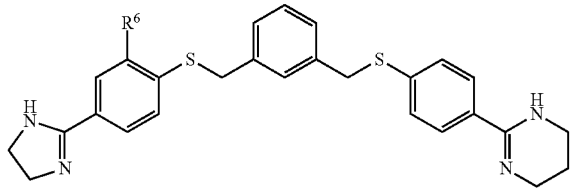
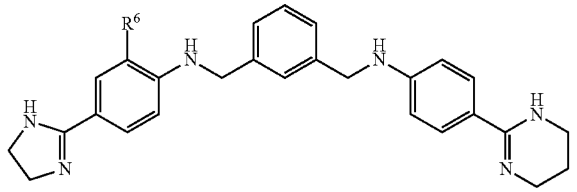
-continued
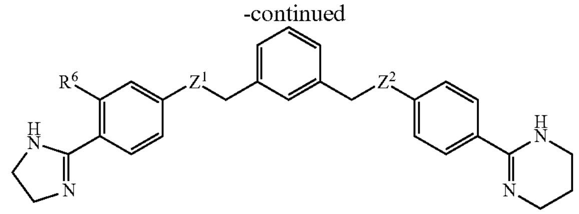
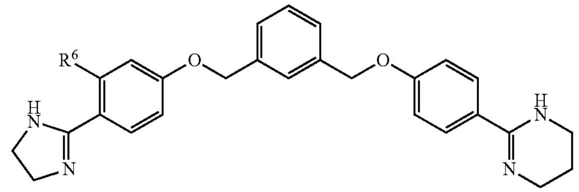
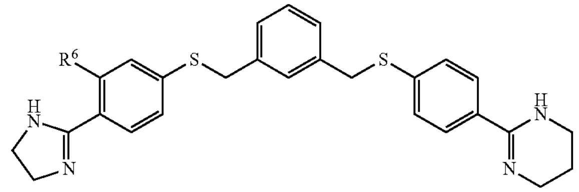
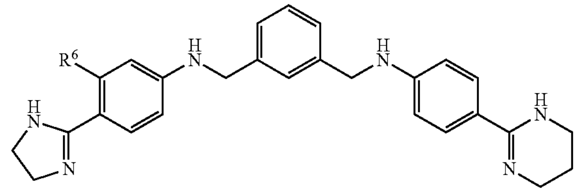
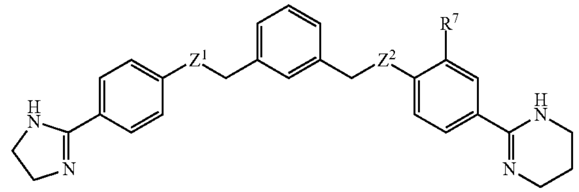
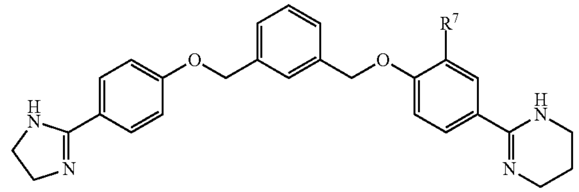
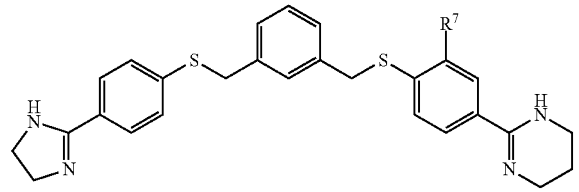
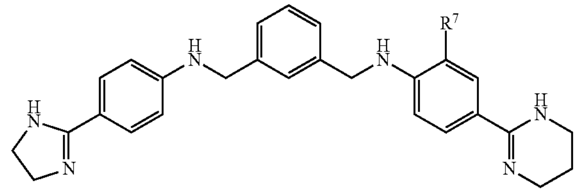
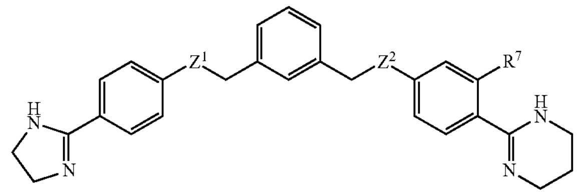

-continued
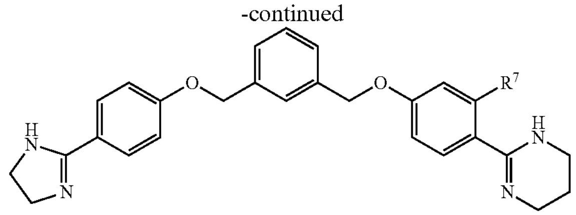
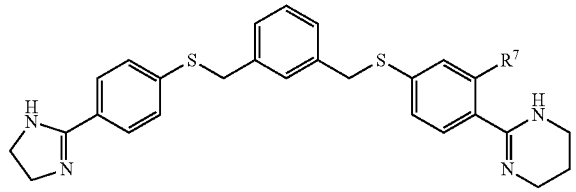
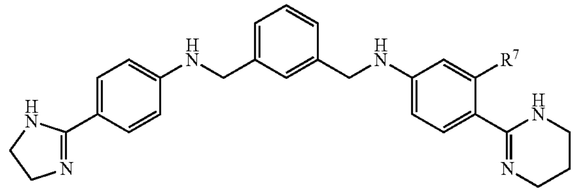
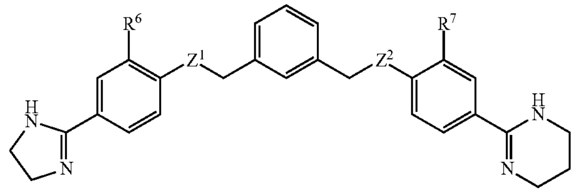
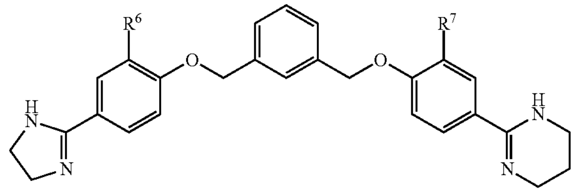
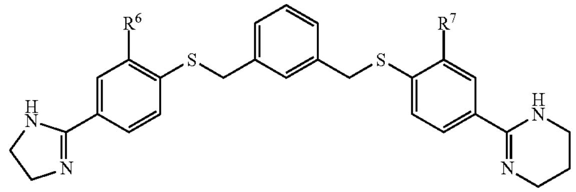
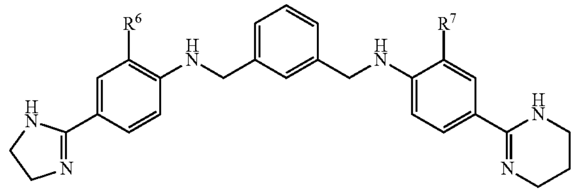
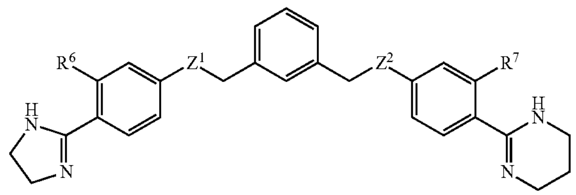
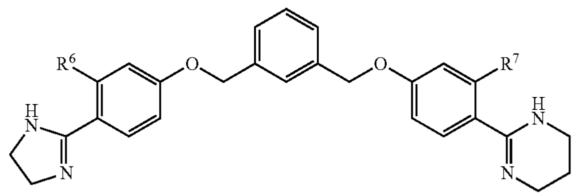
-continued
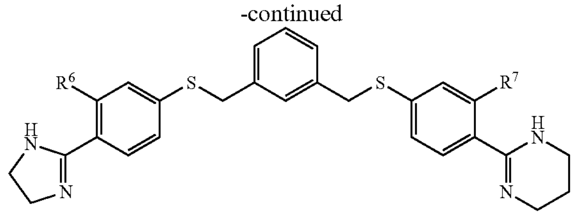
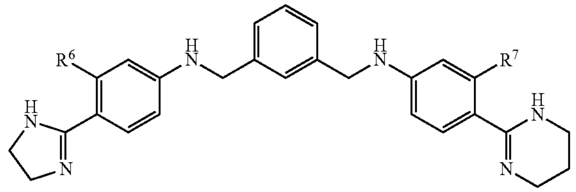
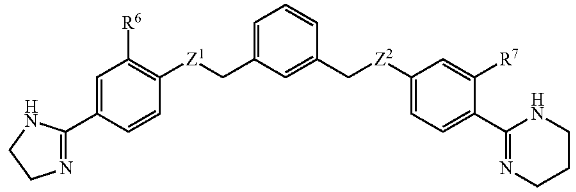
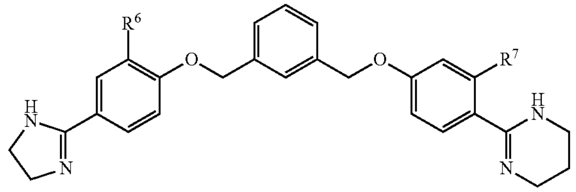
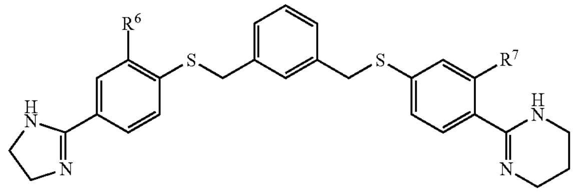
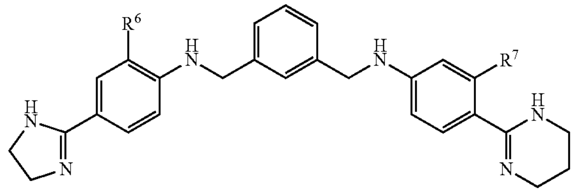
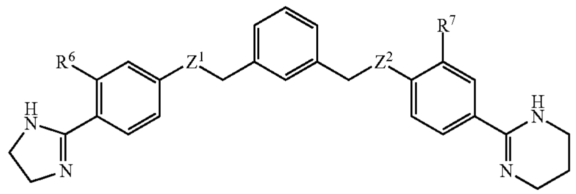
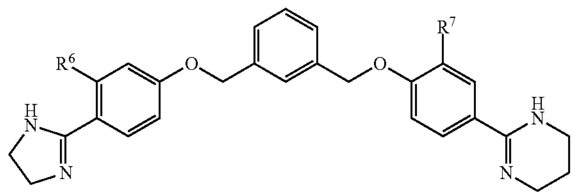
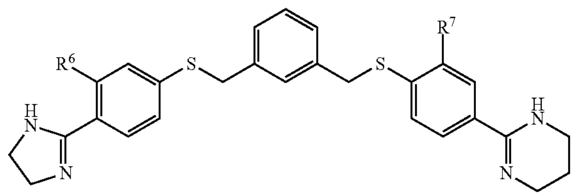

-continued
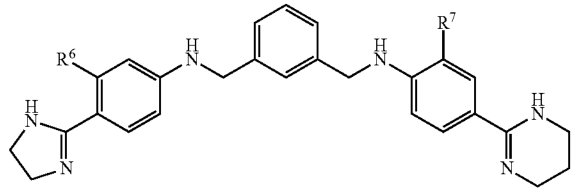
Non-limiting examples of compounds of Formula V include:
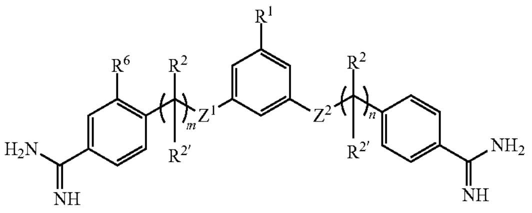
and
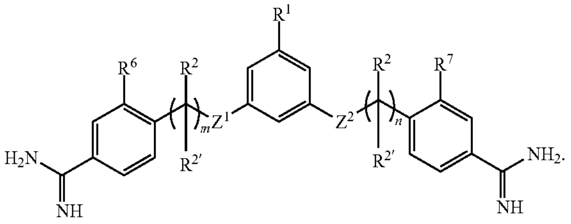
Non-limiting examples of compounds of Formula V include:
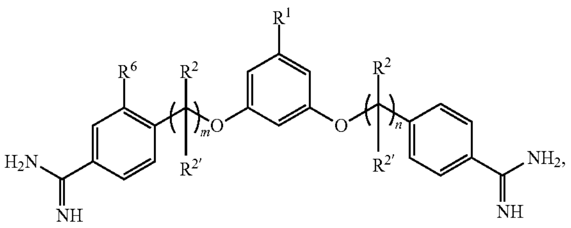
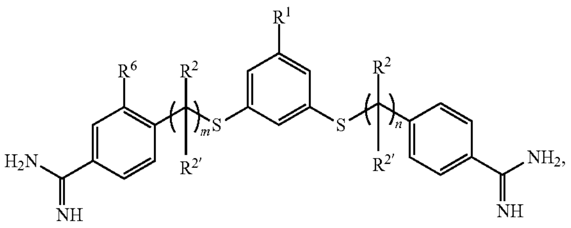
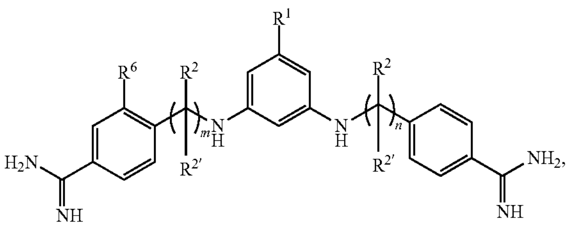
-continued
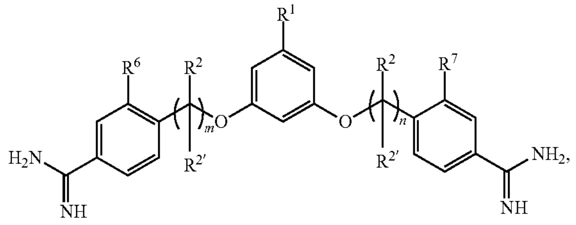
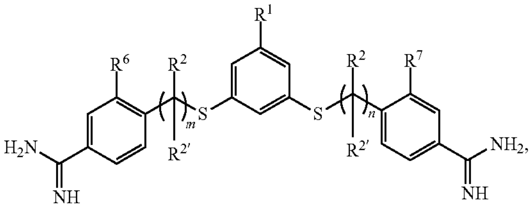
and
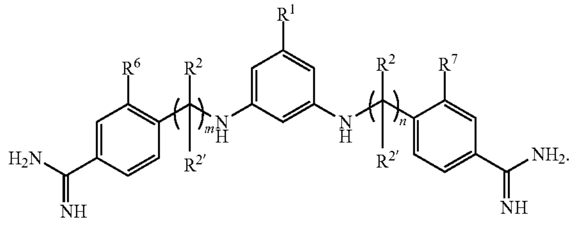
Non-limiting examples of compounds of Formula V include:
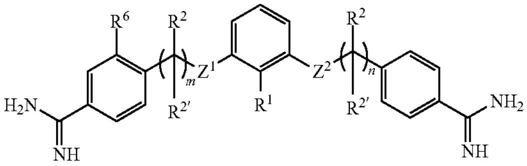
and
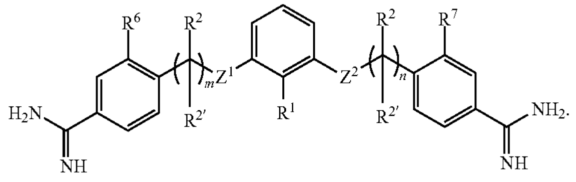
Non-limiting examples of compounds of Formula V include:
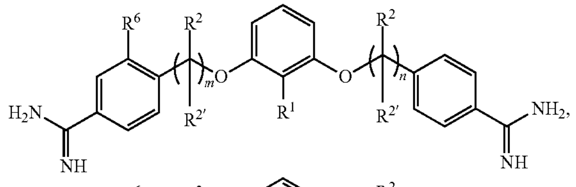
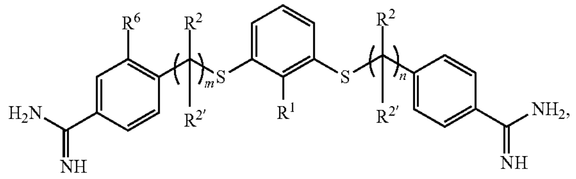

-continued
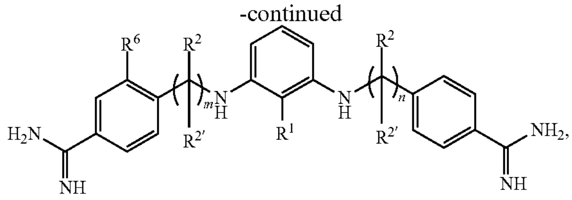
,
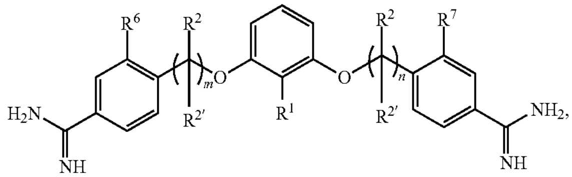
,
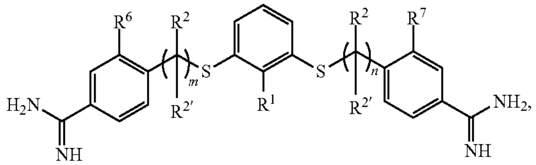
, and
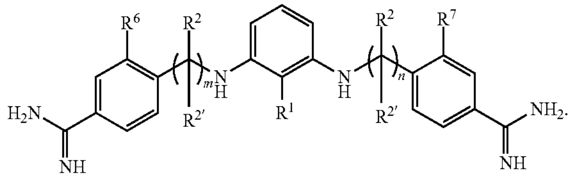
.
Examples of compounds of Formula V include:
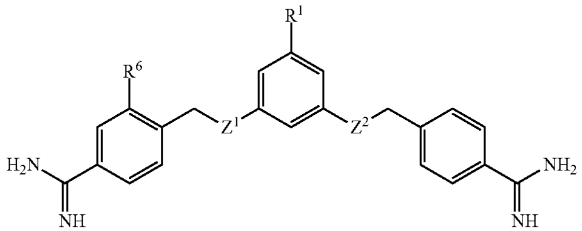
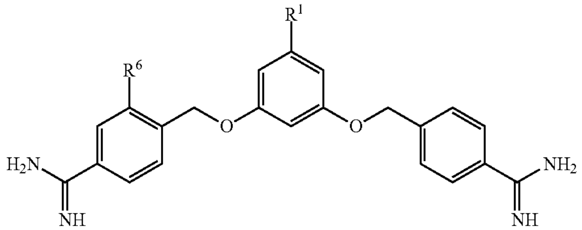
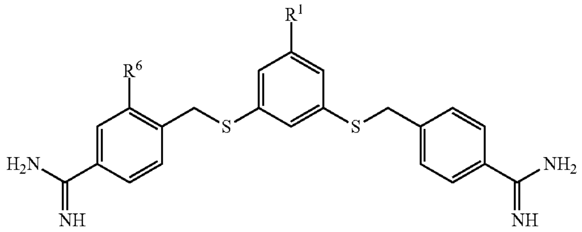
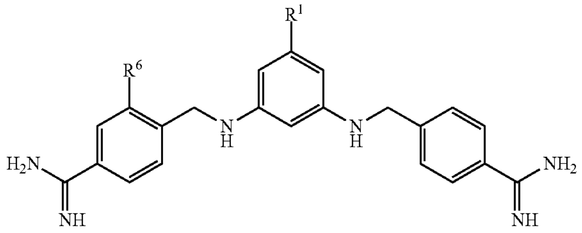
-continued
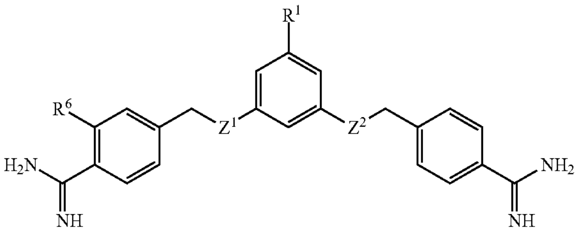
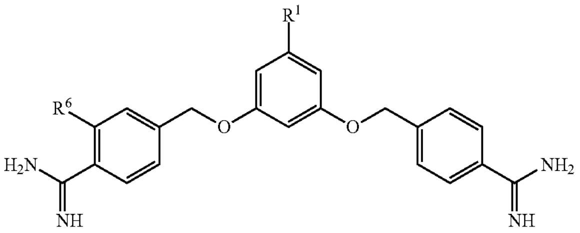
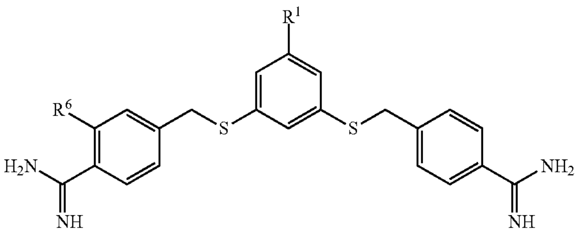
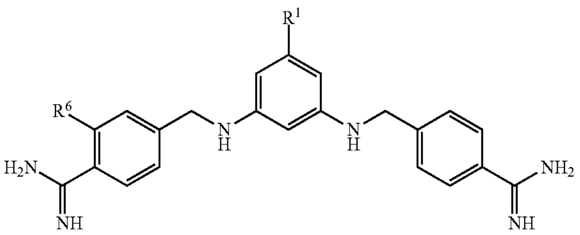
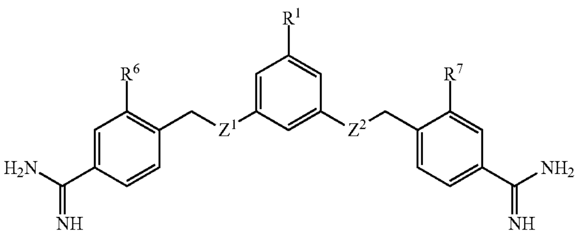
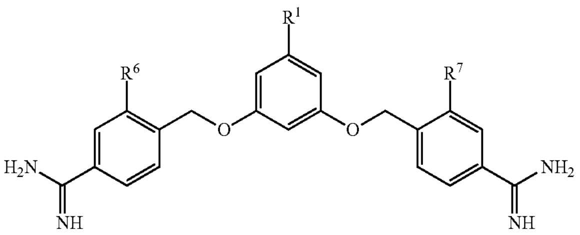
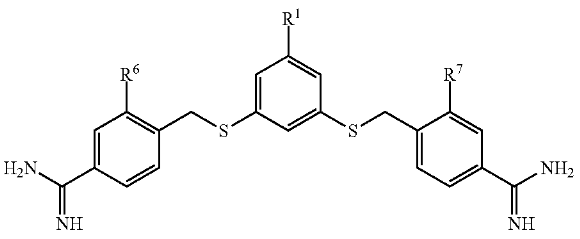

-continued
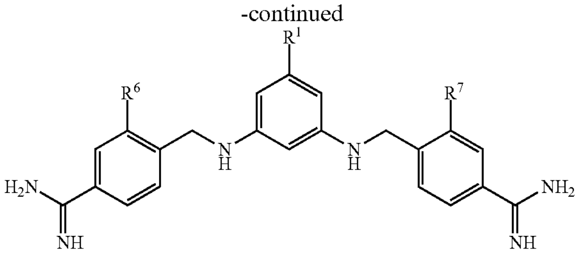
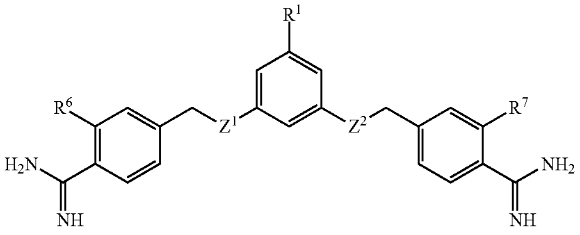
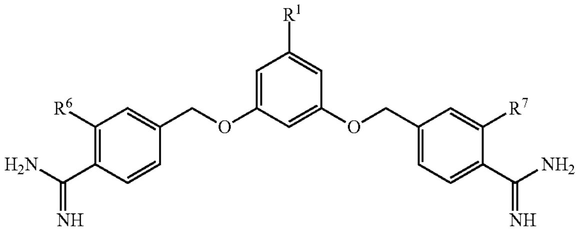
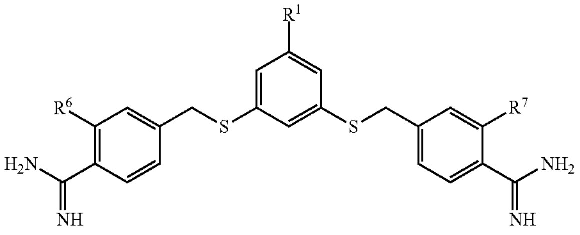
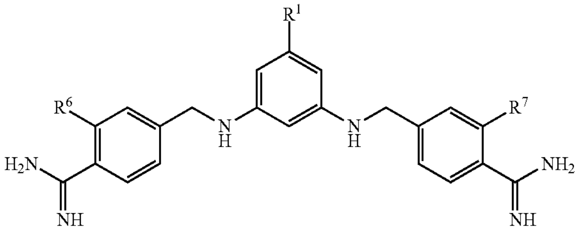
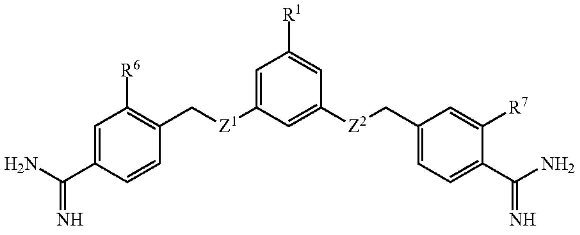
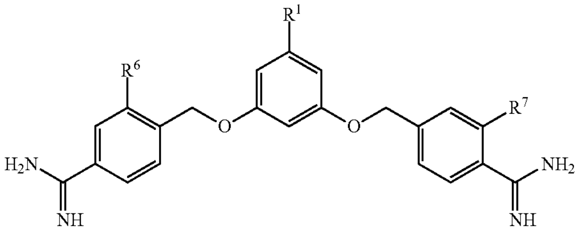
-continued
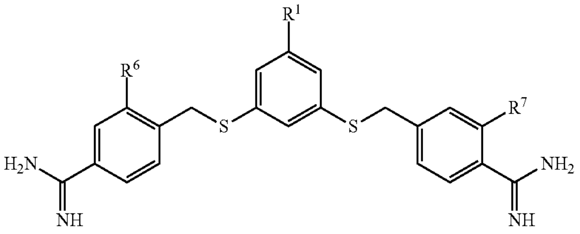
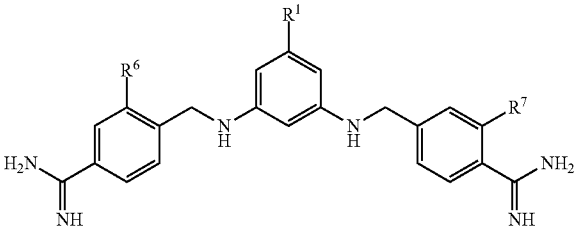
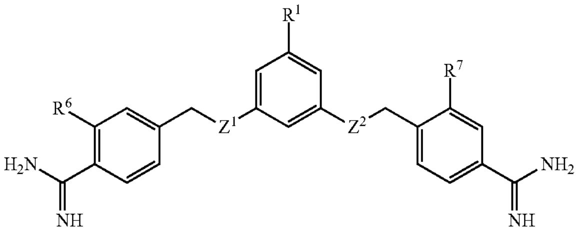
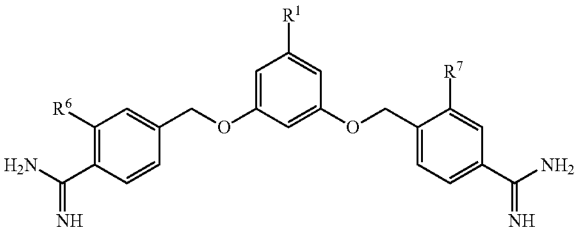
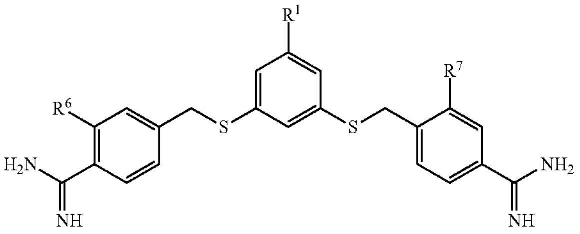
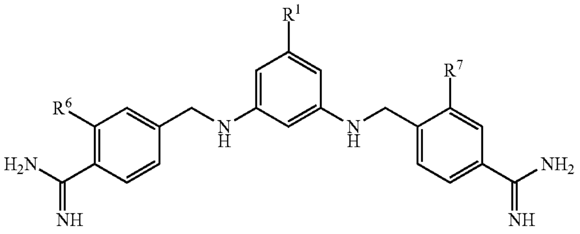
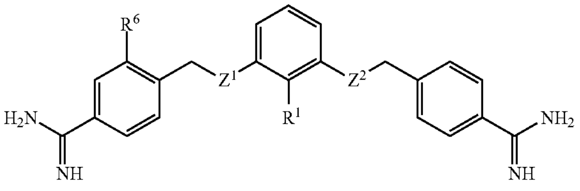

-continued
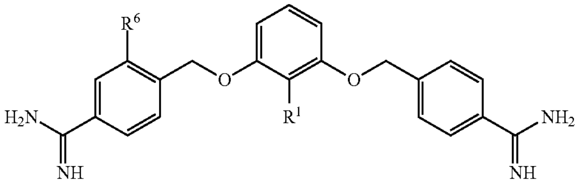
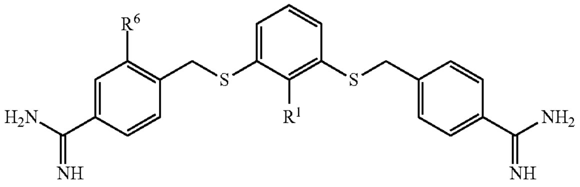
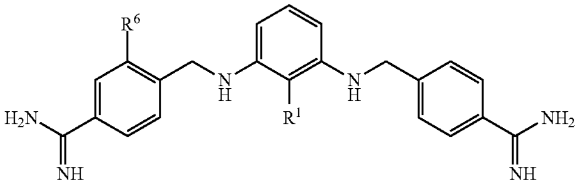
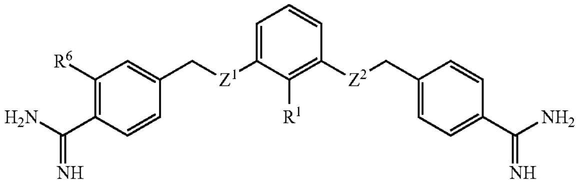
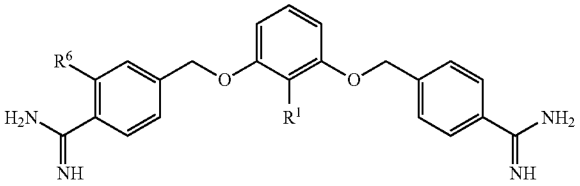
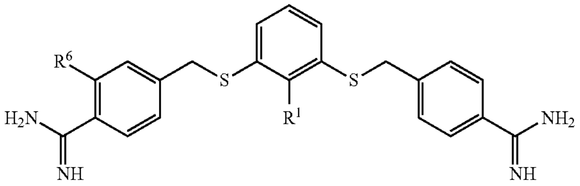
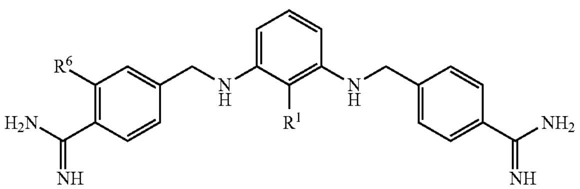
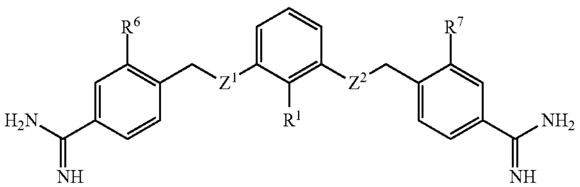
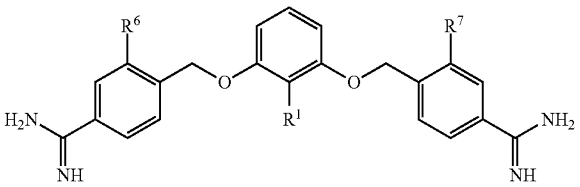
-continued
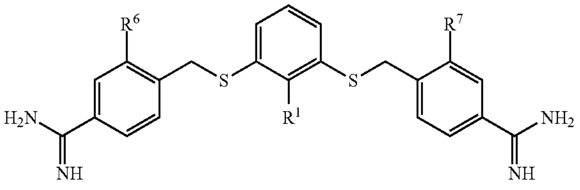
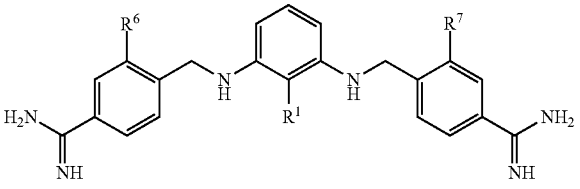
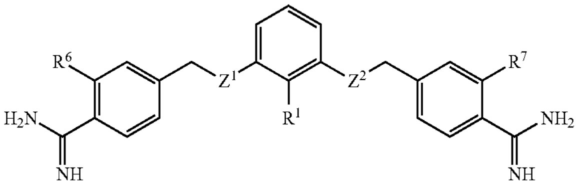
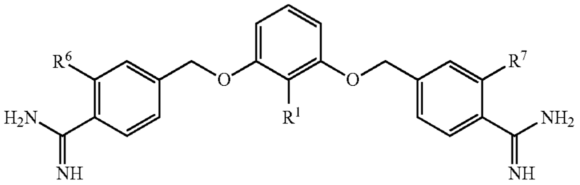
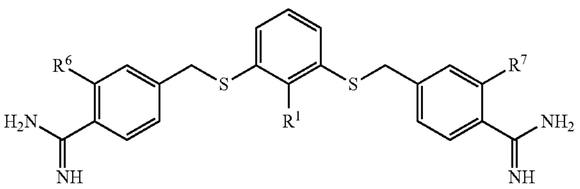
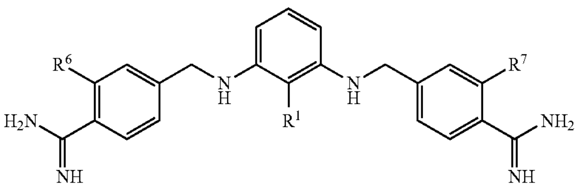
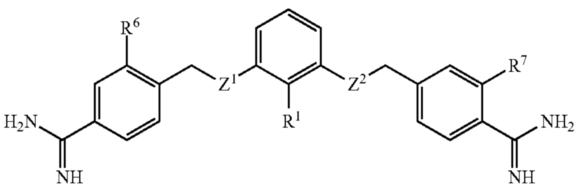
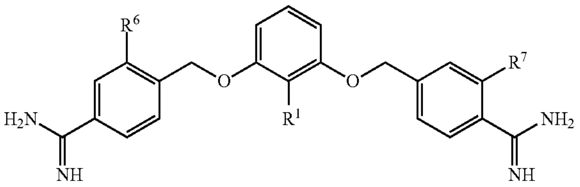
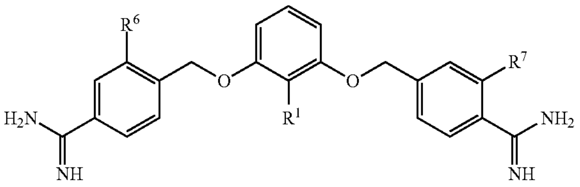

-continued
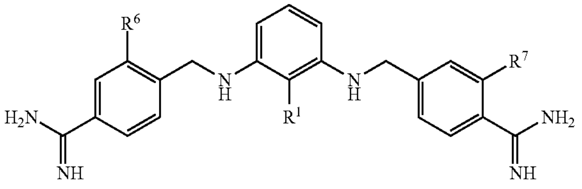
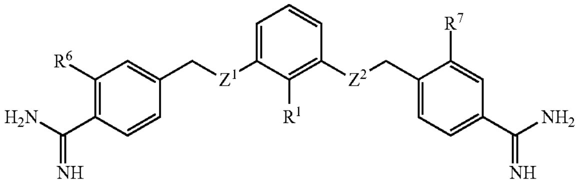
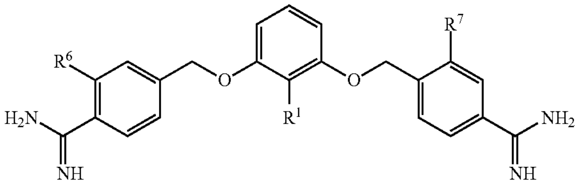
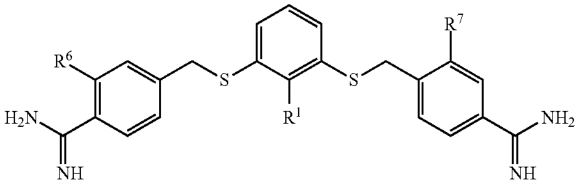
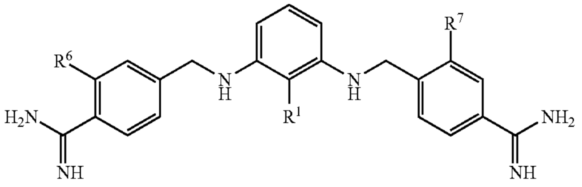
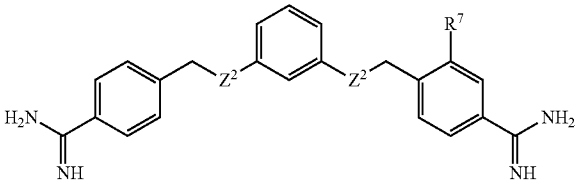
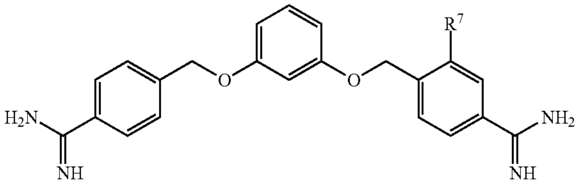
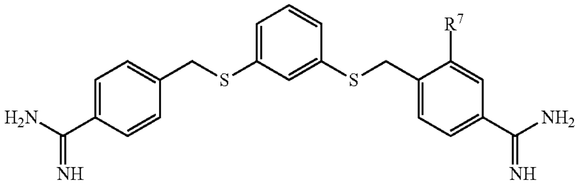
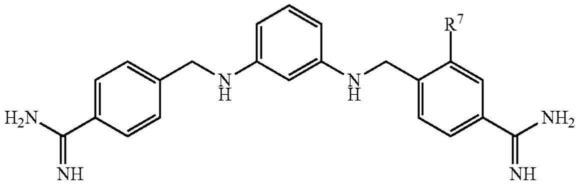
-continued
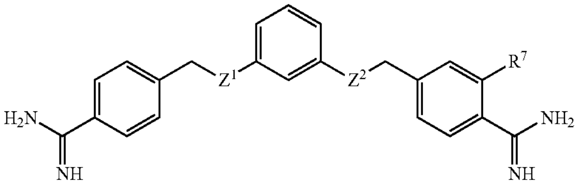
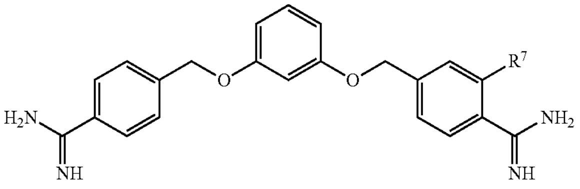
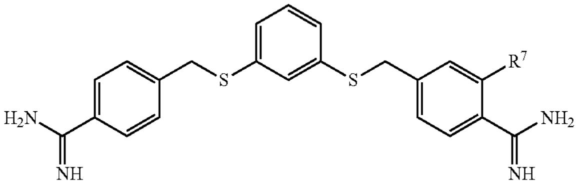
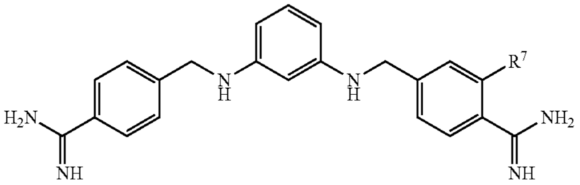
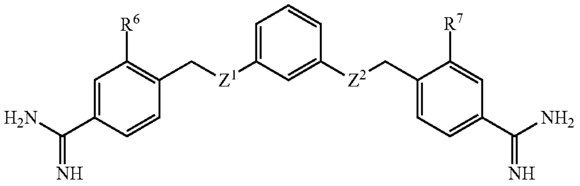
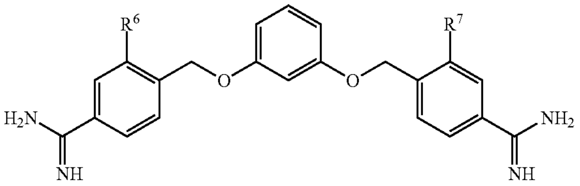
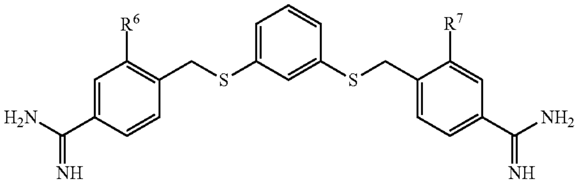
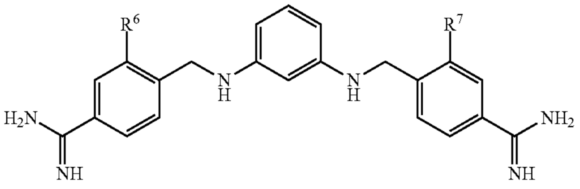
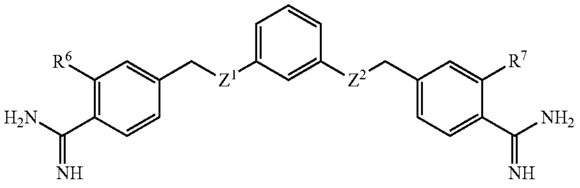

-continued
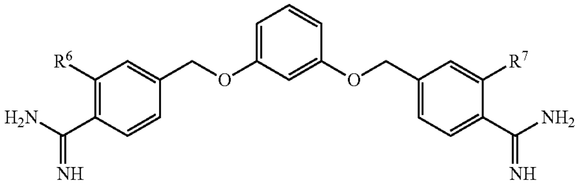
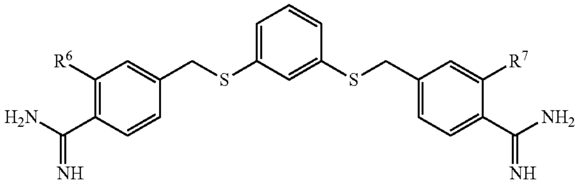
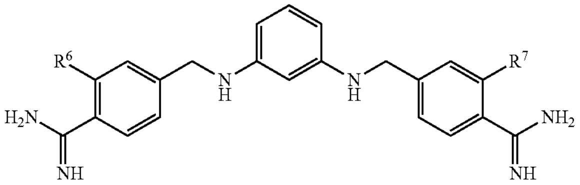
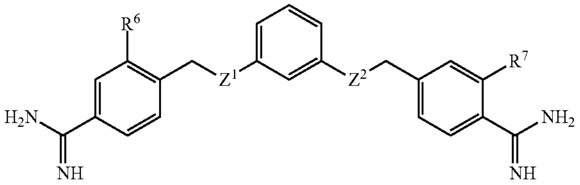
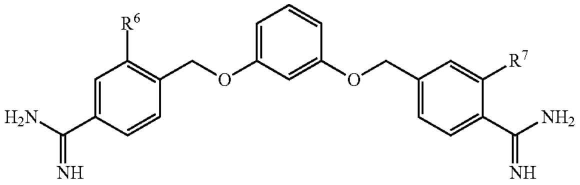
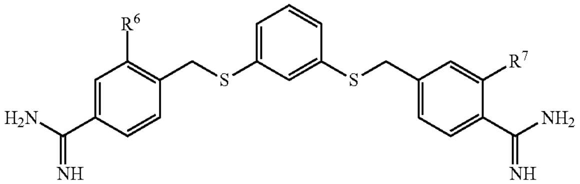
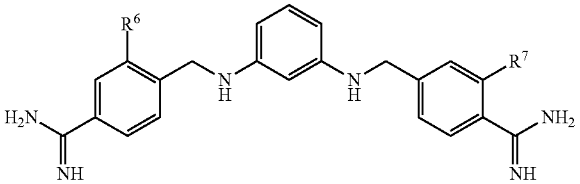
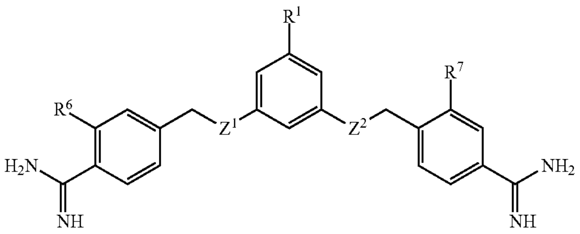
-continued
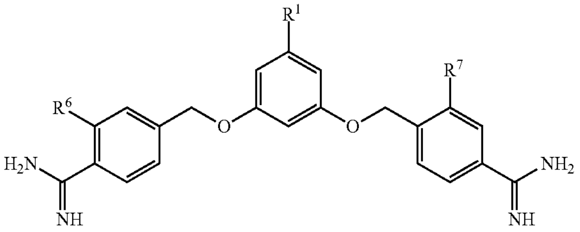
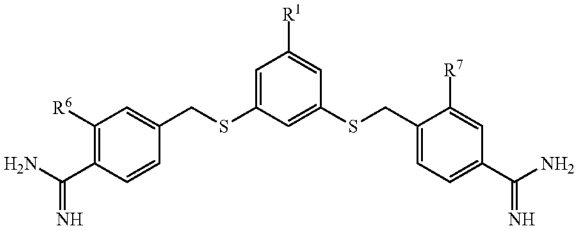
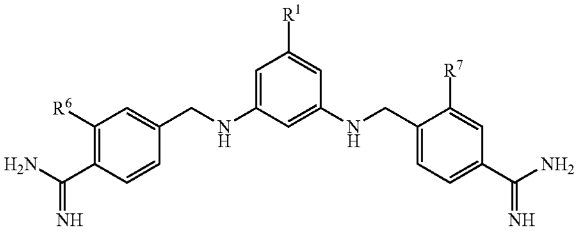
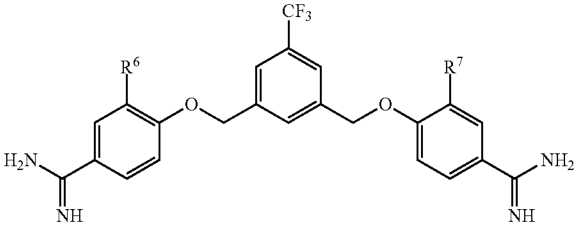
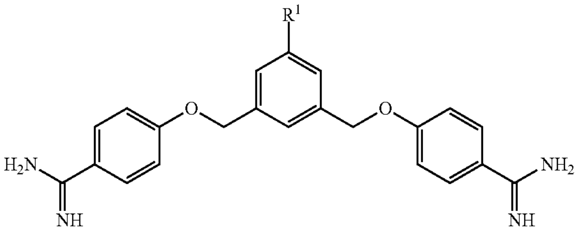
Non-limiting examples of compounds of Formula V' include:
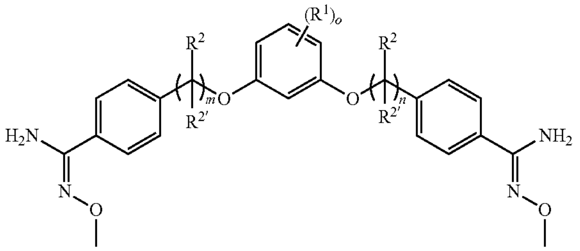

-continued
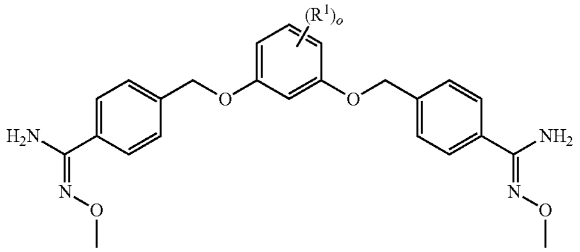
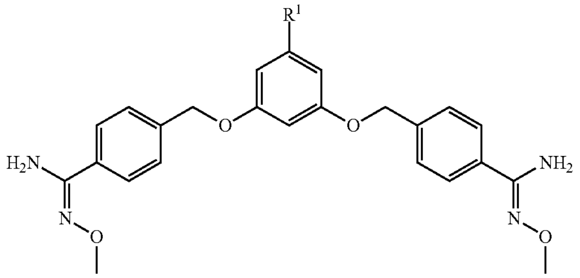
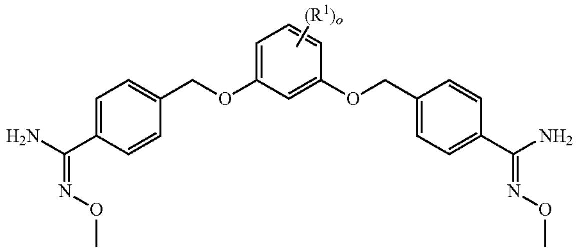
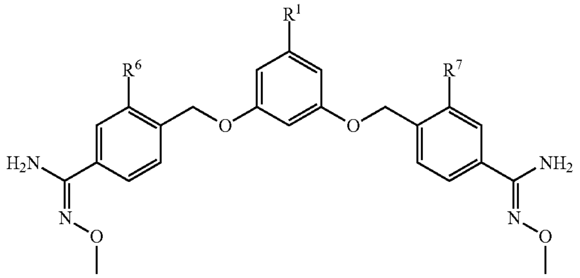
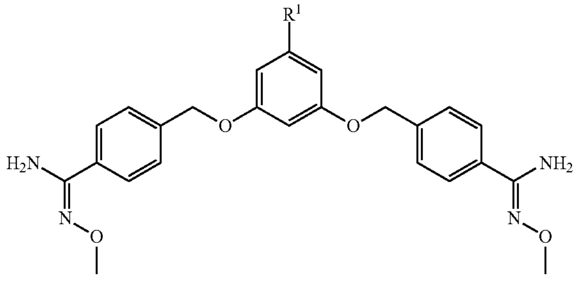
Non-limiting examples of compounds of Formula VI include:
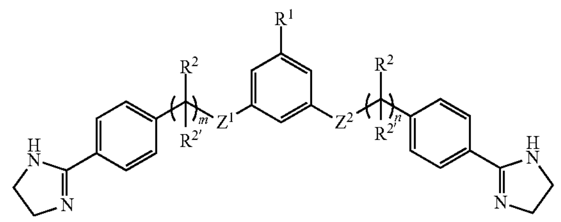
,
-continued
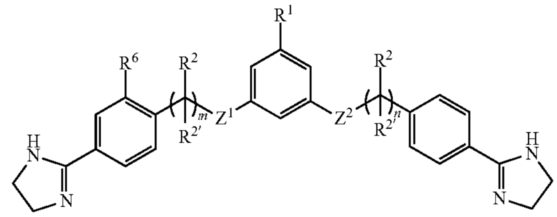
,
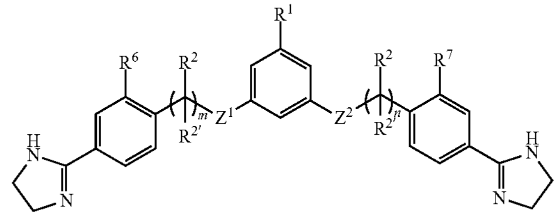
,
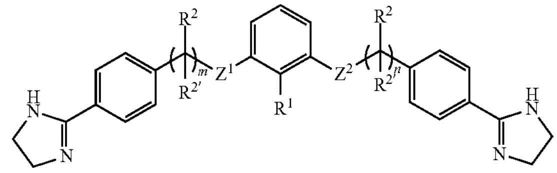
,
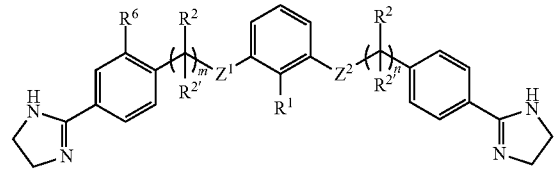
,
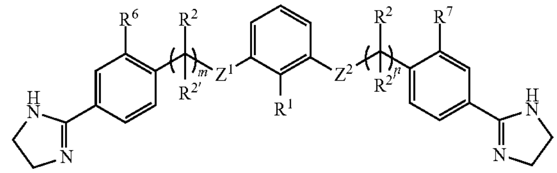
,
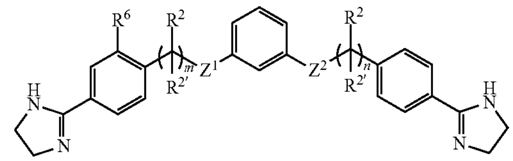
, and
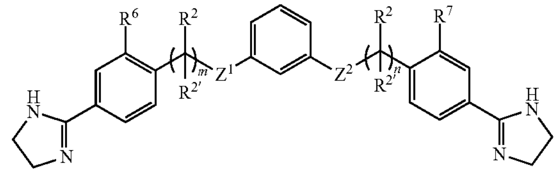
.
Non-limiting examples of compounds of Formula VI include.
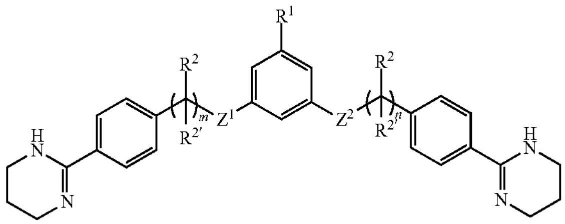
, -continued
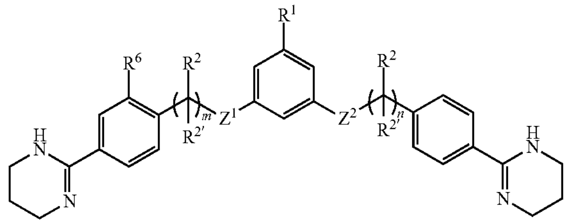
,
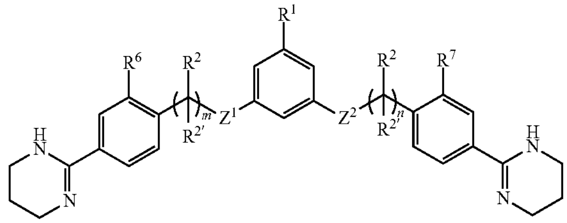
,
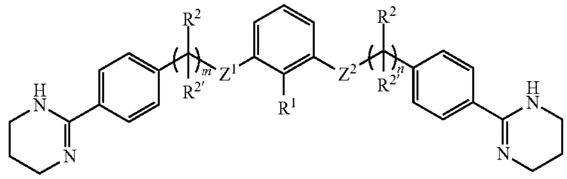
,
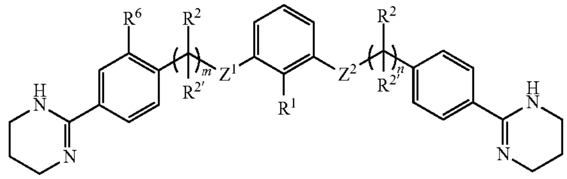
,
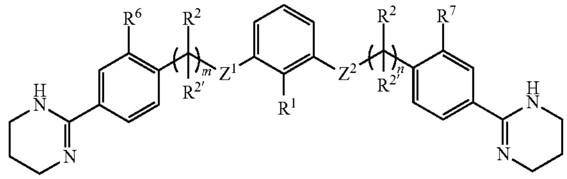
,
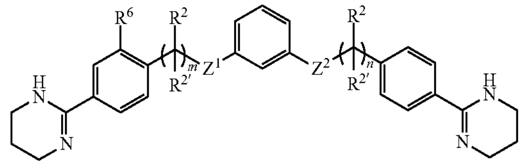
, and
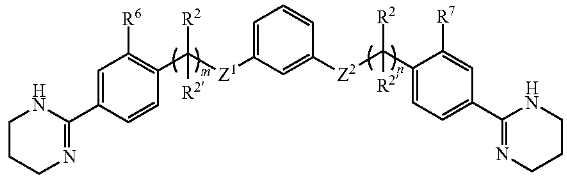
.
Additional examples of compounds of Formula VI include.
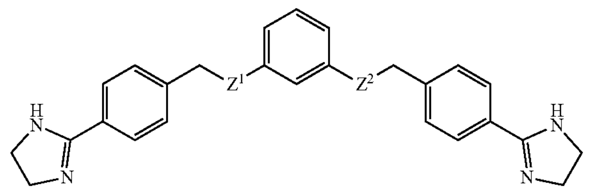
-continued
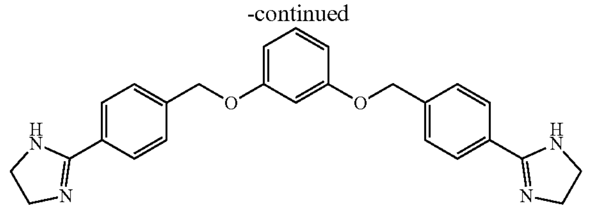
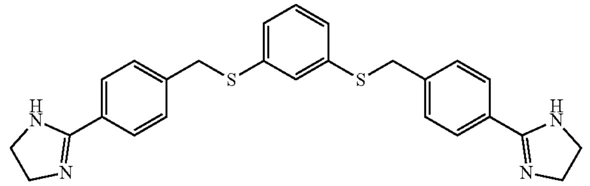
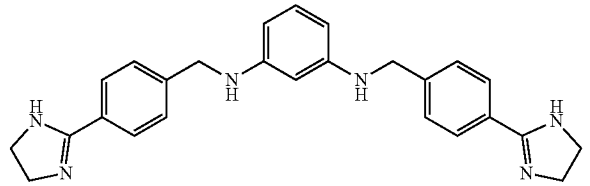
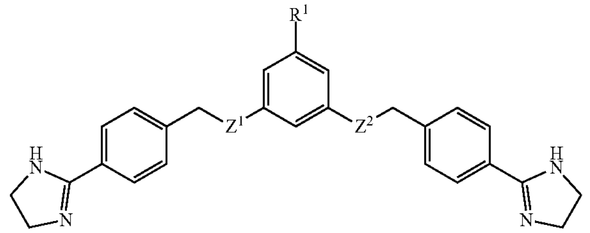
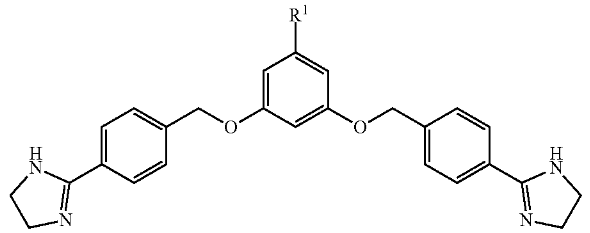
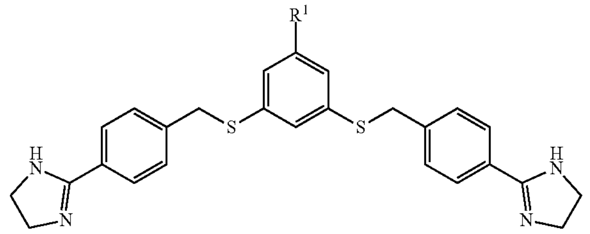
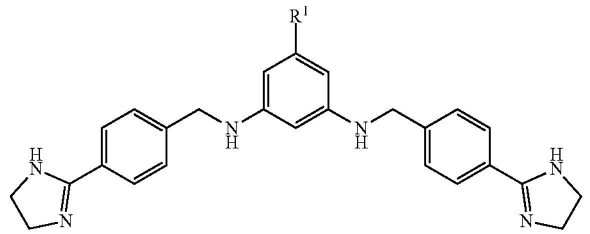
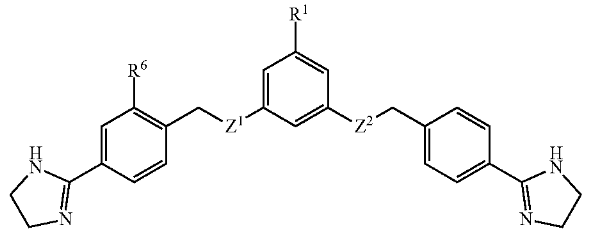

-continued
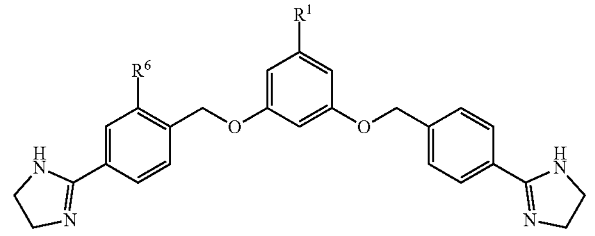
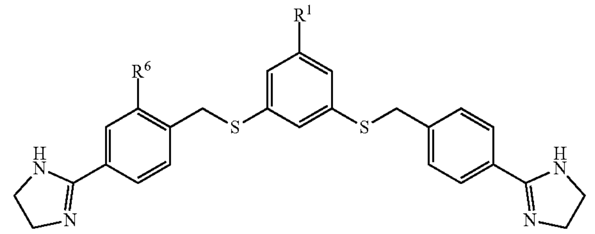
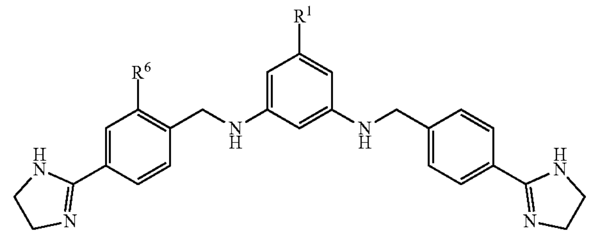
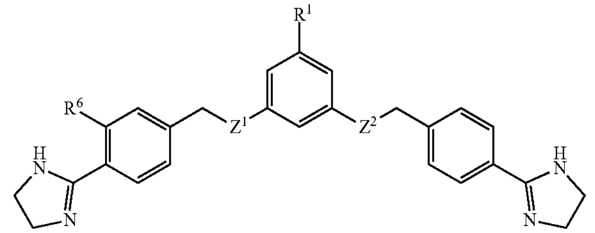
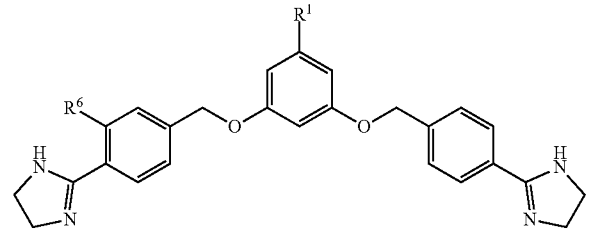
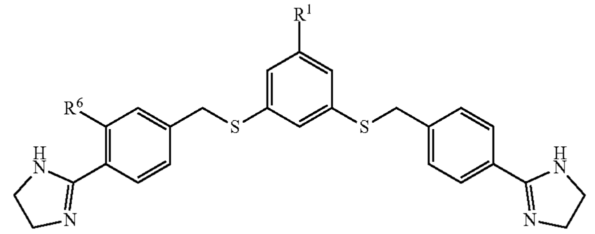
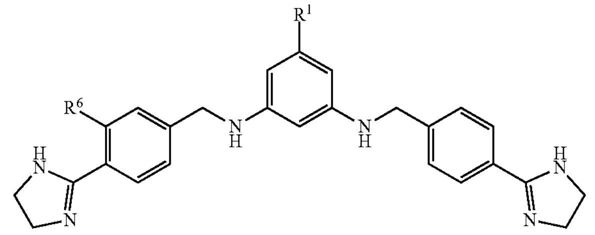
-continued
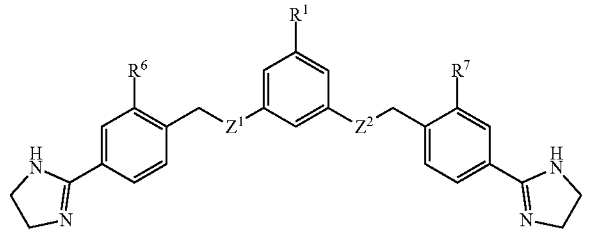
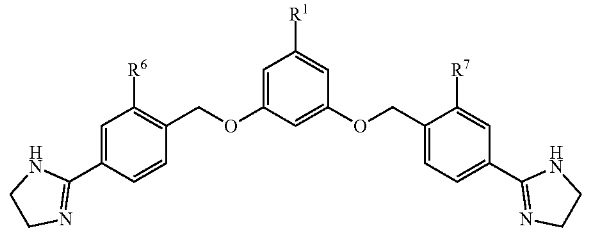
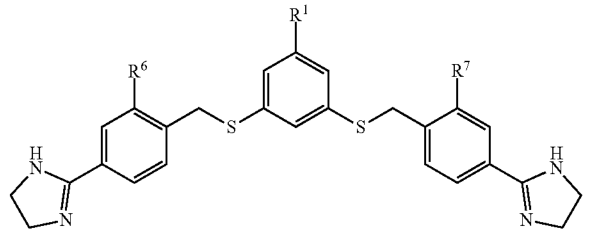
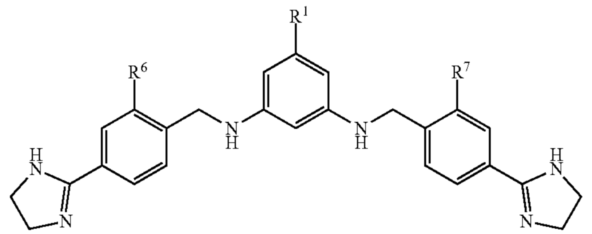
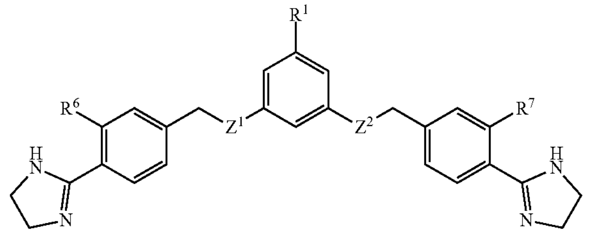
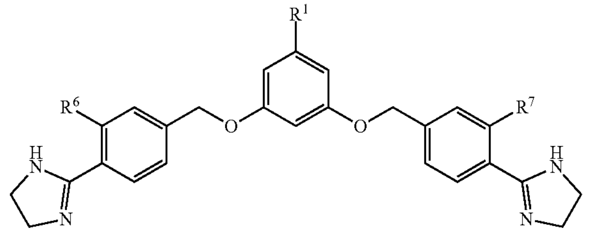
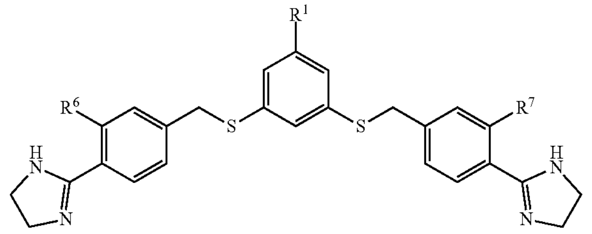

-continued
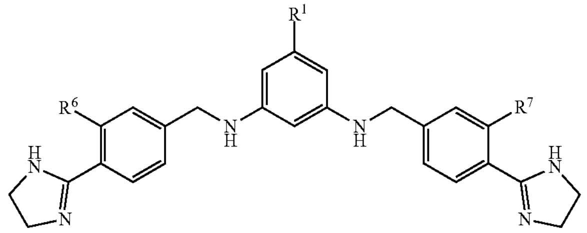
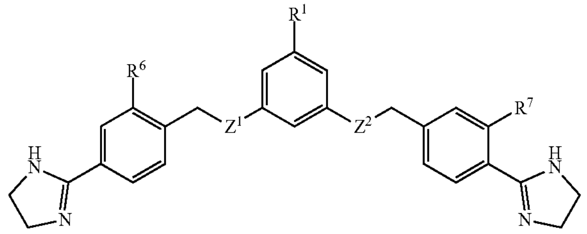
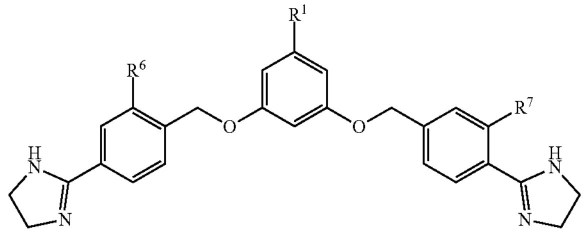
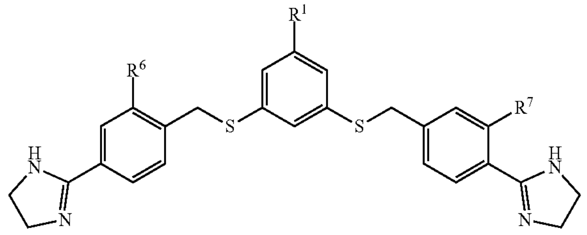
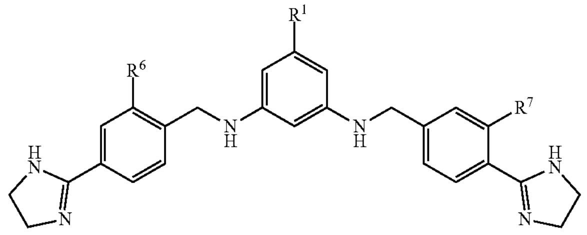
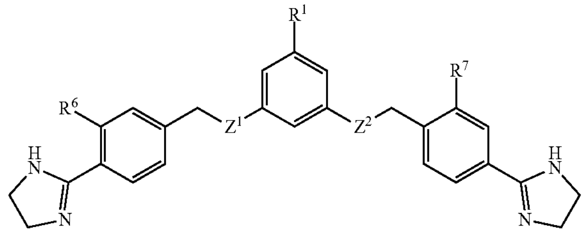
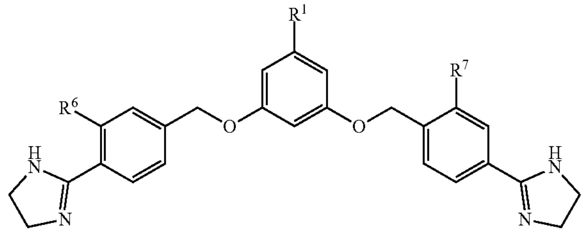
-continued
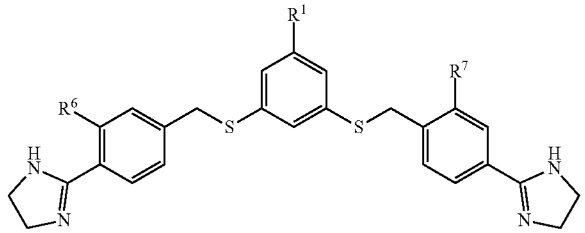
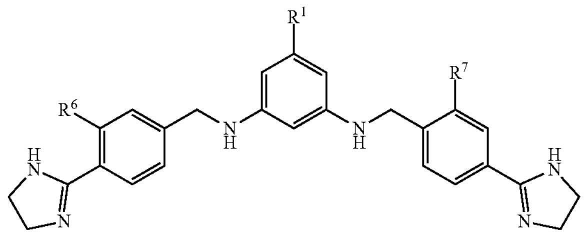
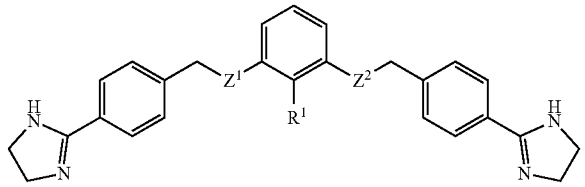
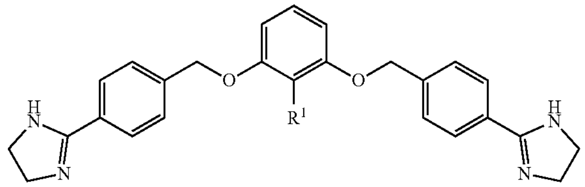
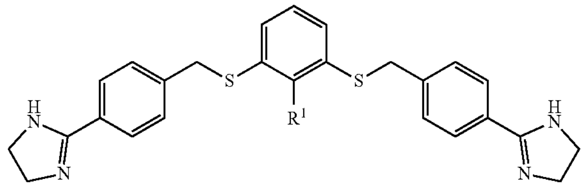
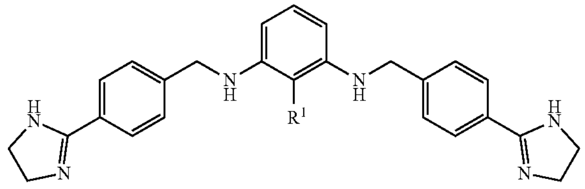
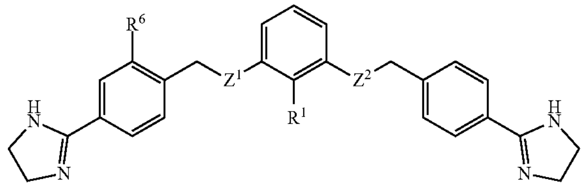
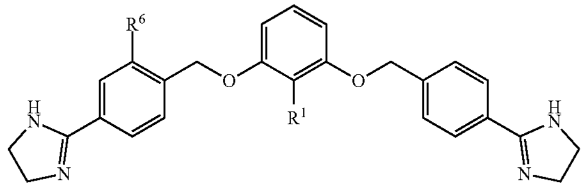

-continued
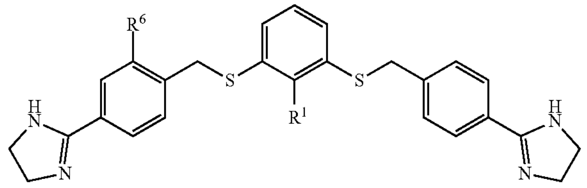
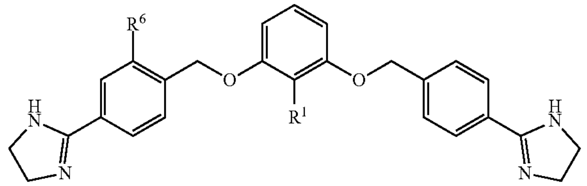
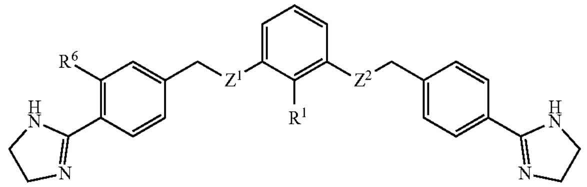
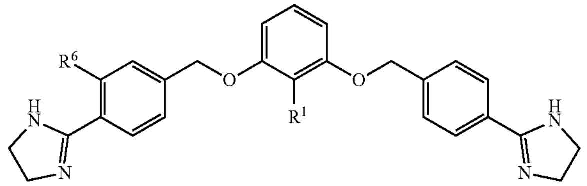
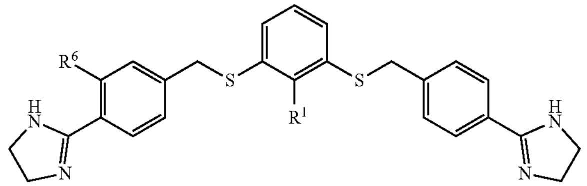
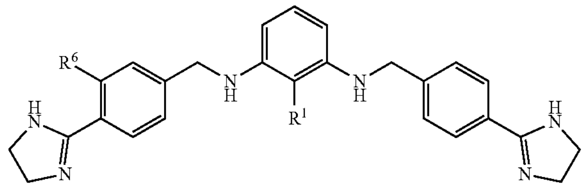
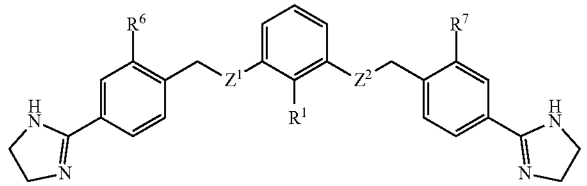
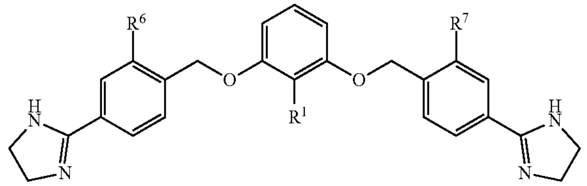
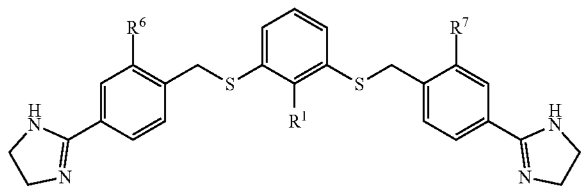
-continued
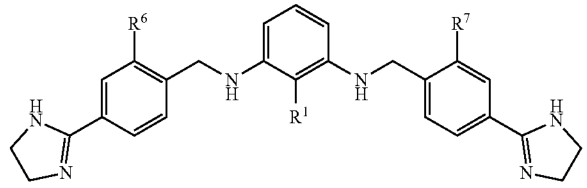
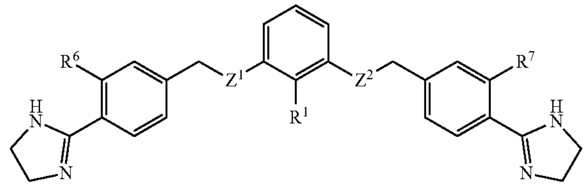
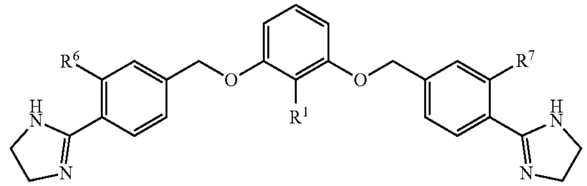
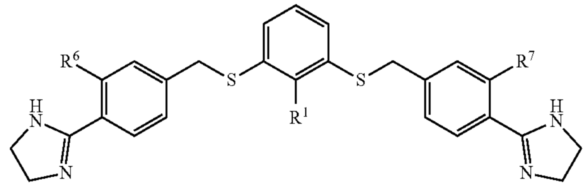
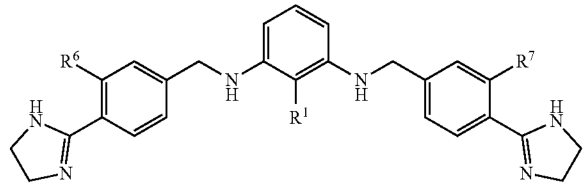
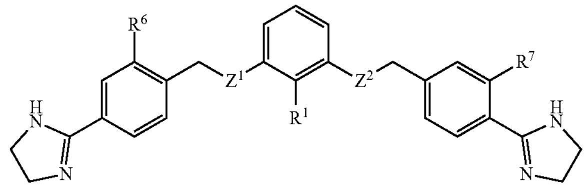
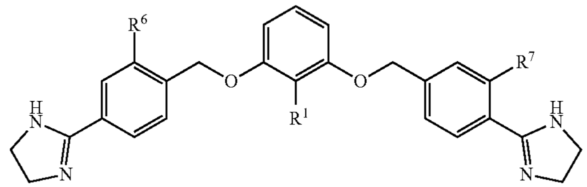
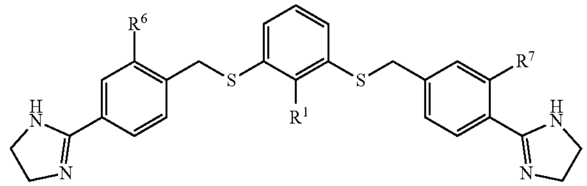
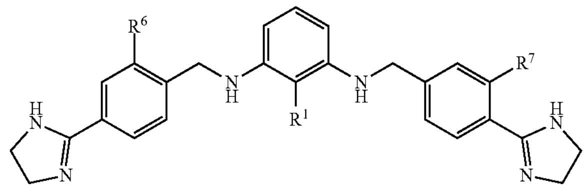

-continued
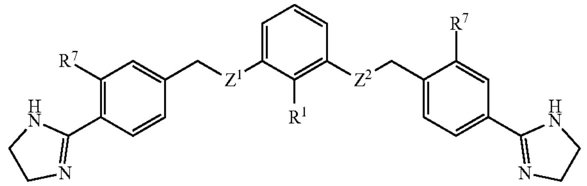
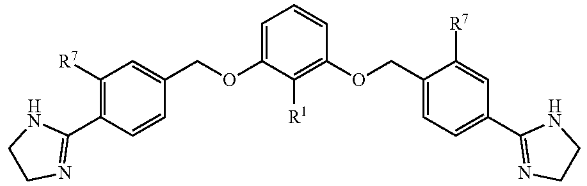
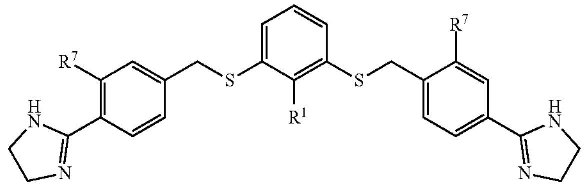
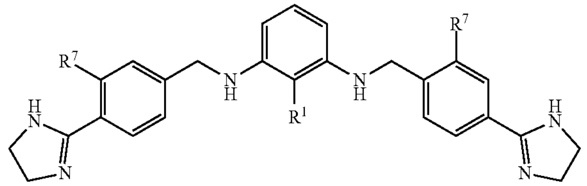
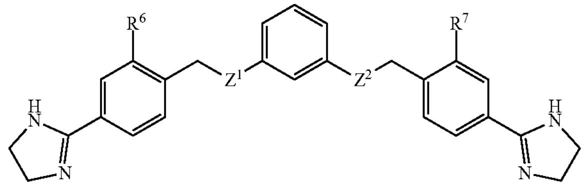
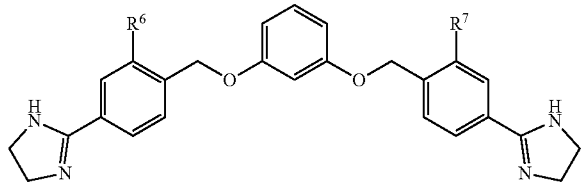
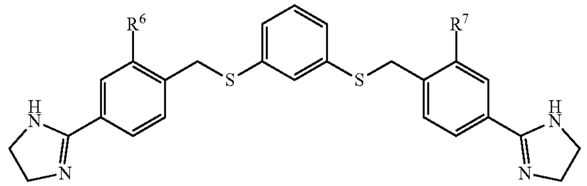
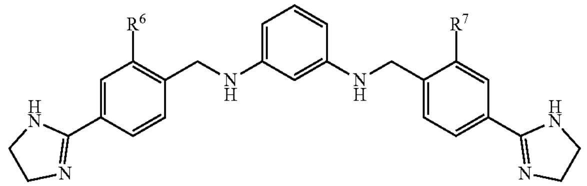
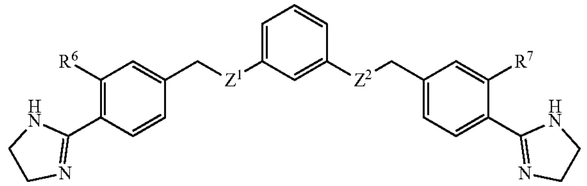
-continued
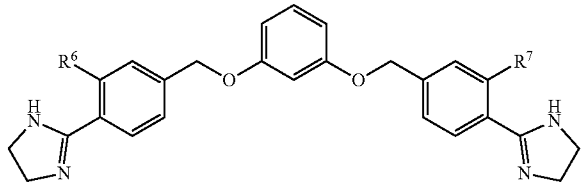
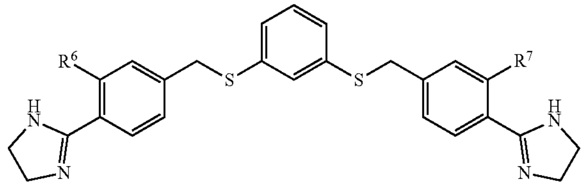
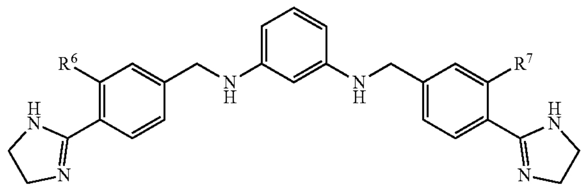
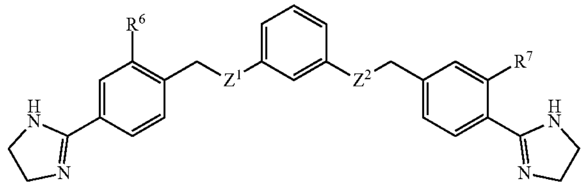
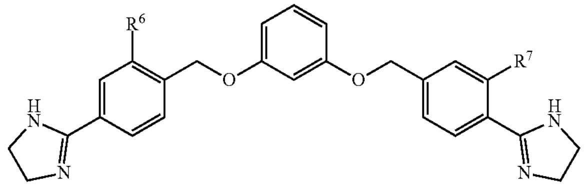
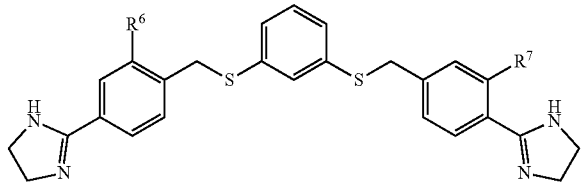
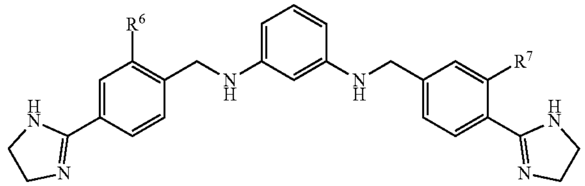
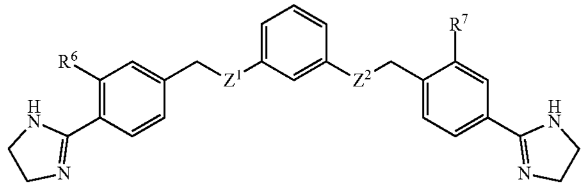
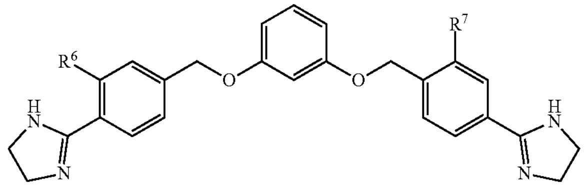

-continued
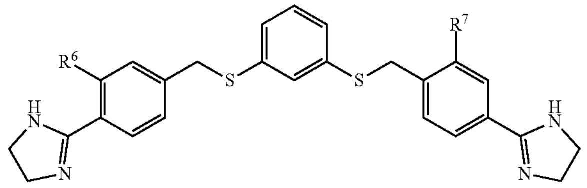
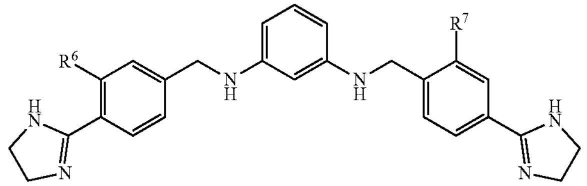
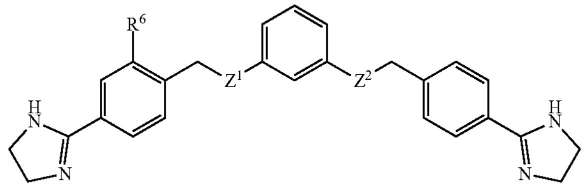
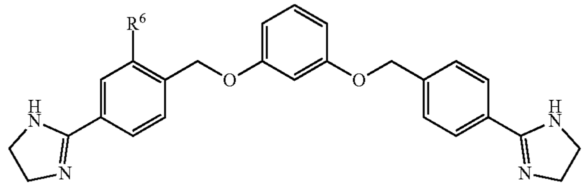
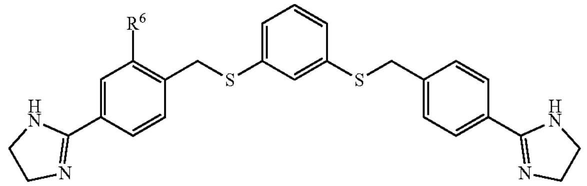
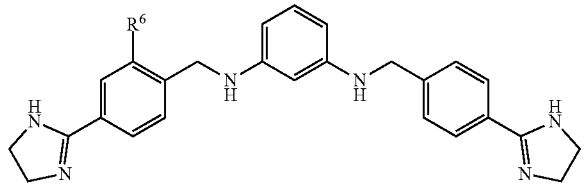
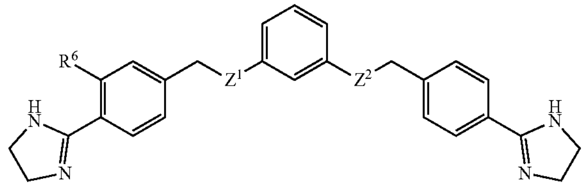
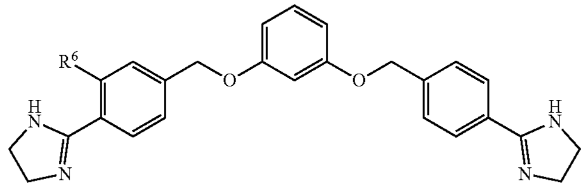
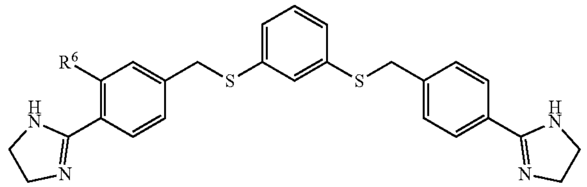
-continued
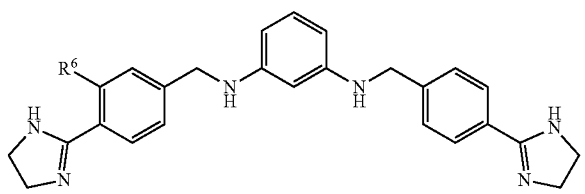
Additional examples of compounds of Formula VI include.
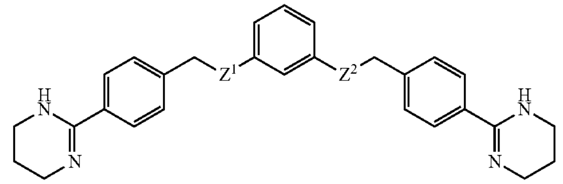
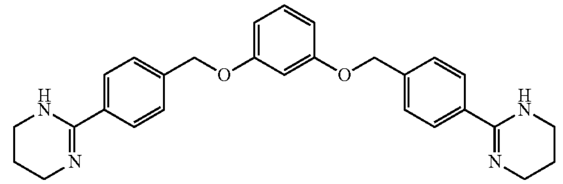
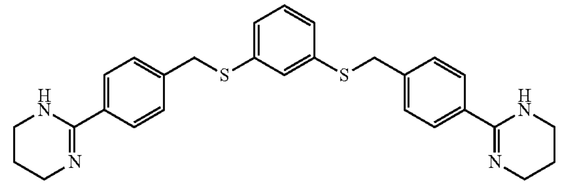
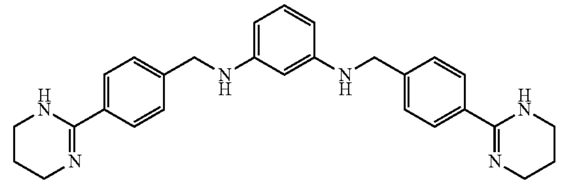
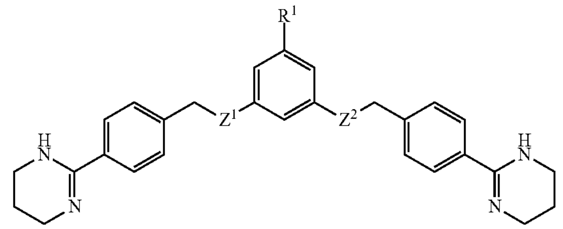
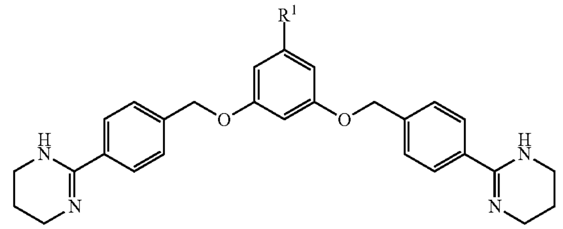

-continued
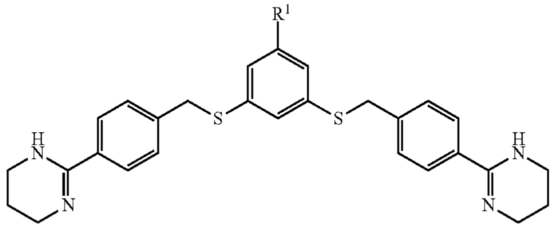
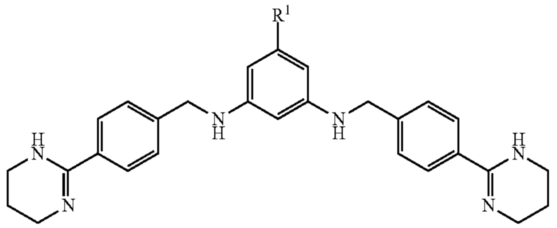
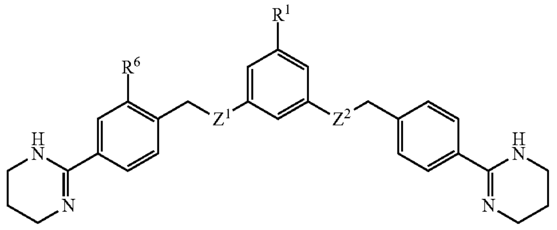
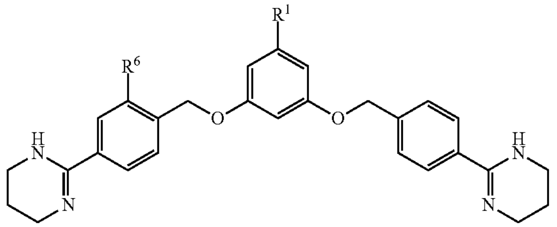
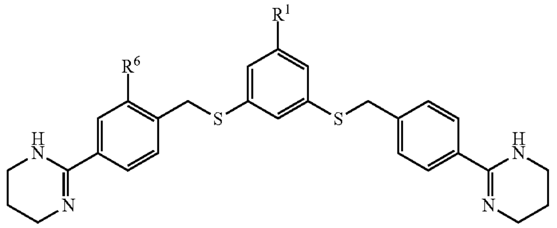
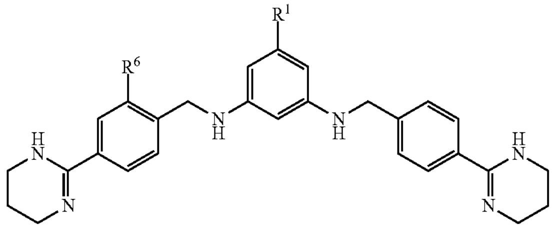
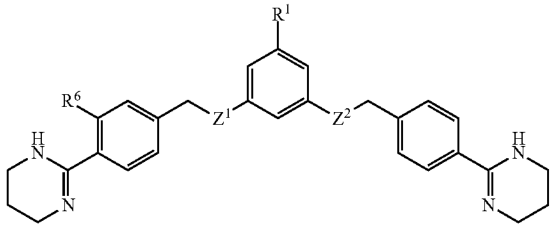
-continued
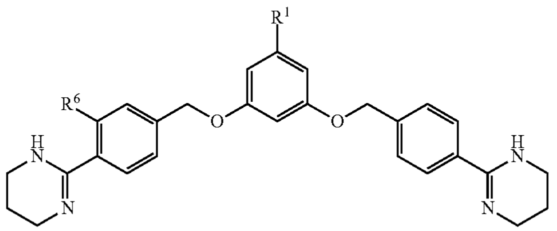
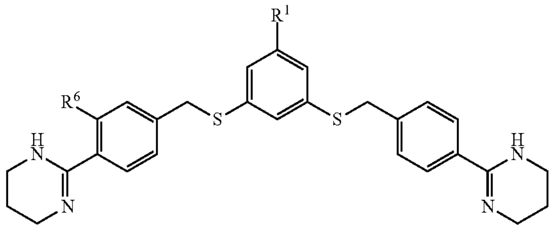
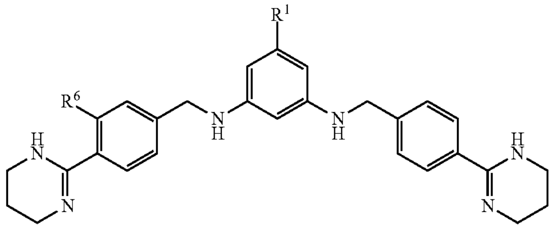
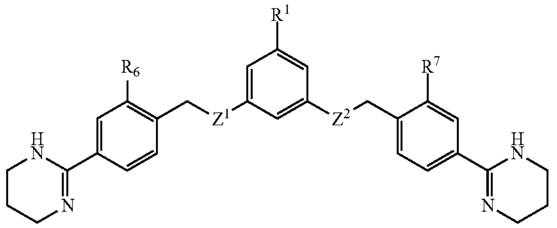
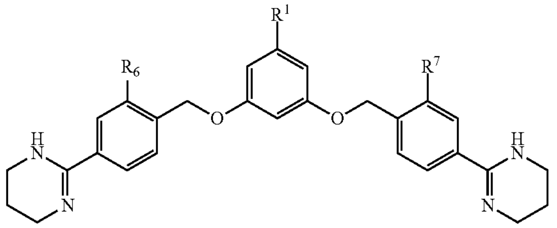
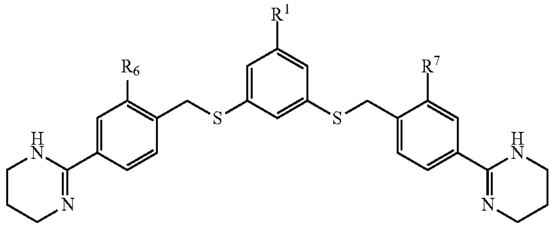
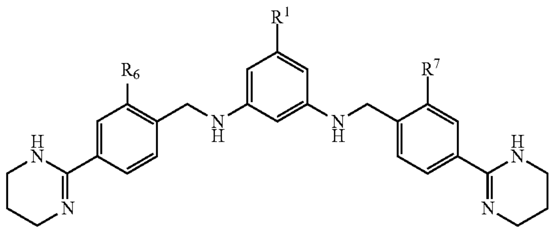

-continued
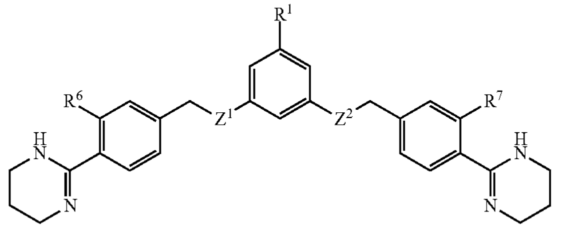
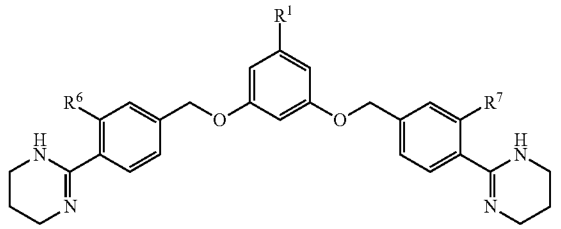
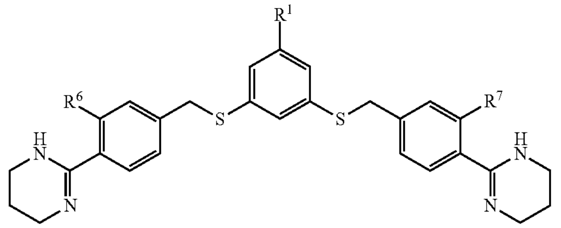
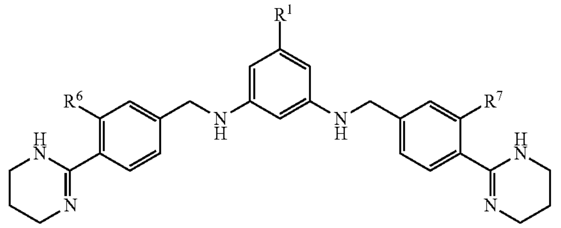
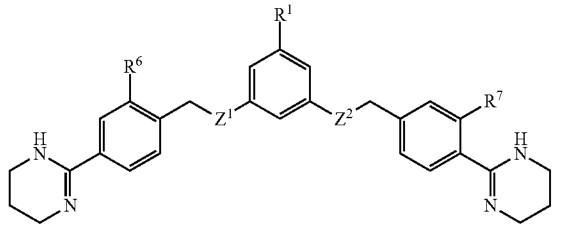
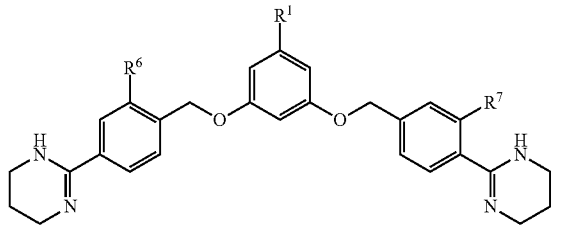
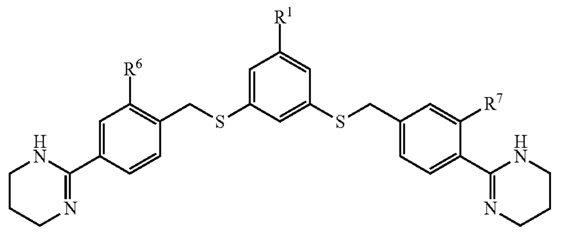
-continued
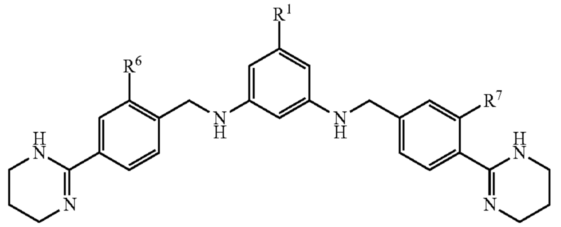
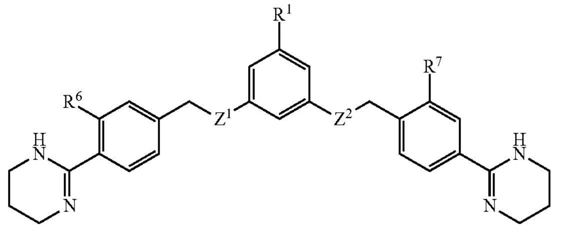
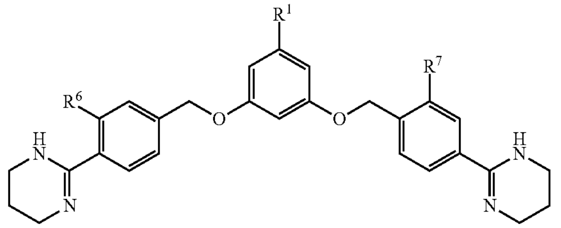
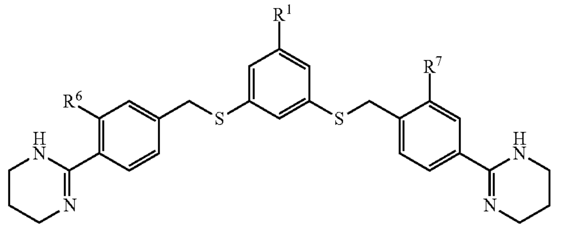
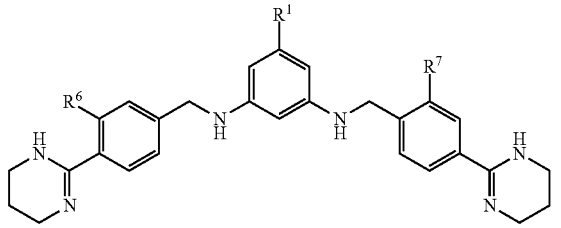
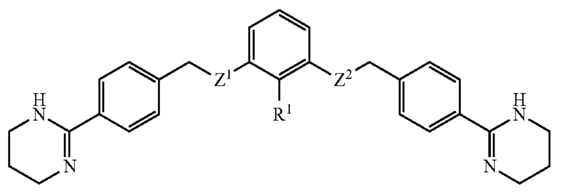
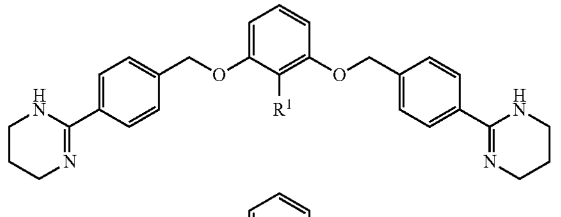
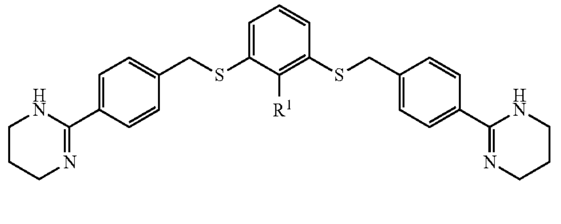

-continued
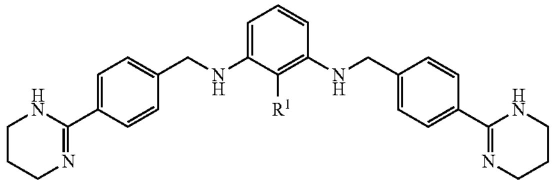
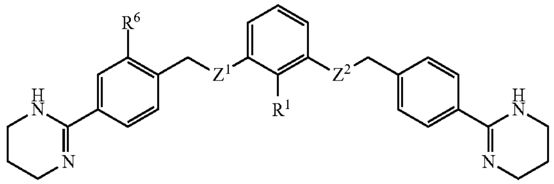
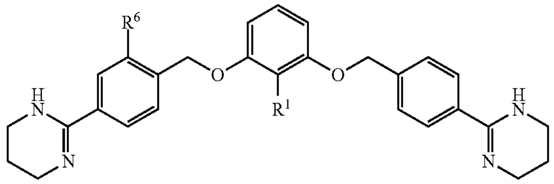
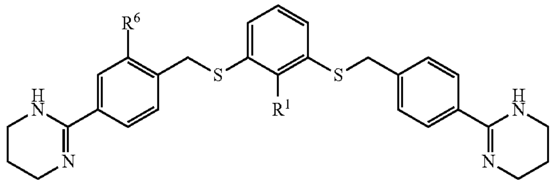
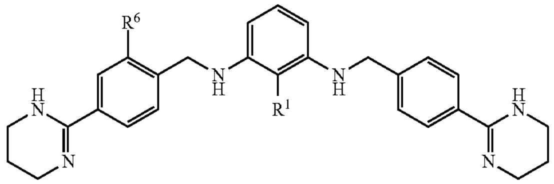
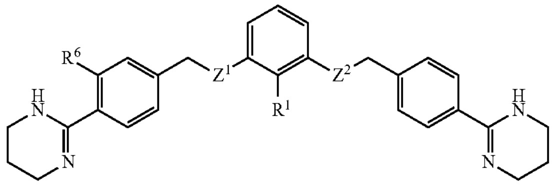
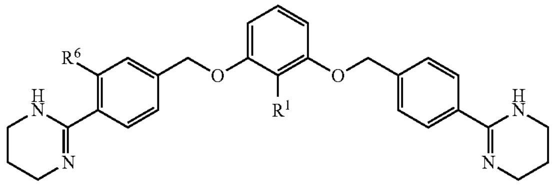
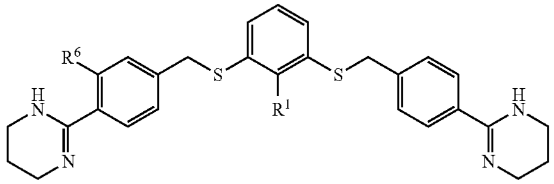
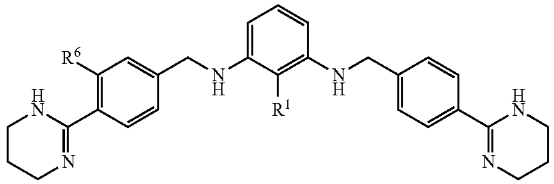
-continued
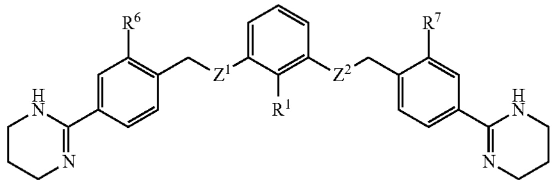
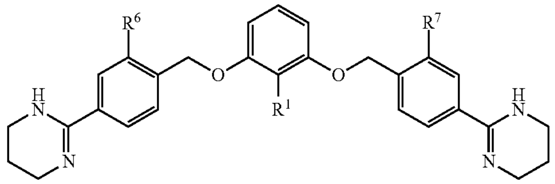
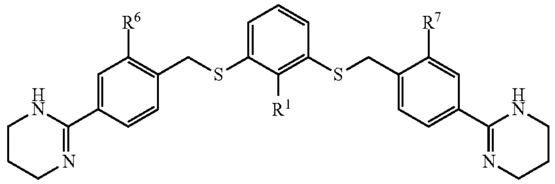
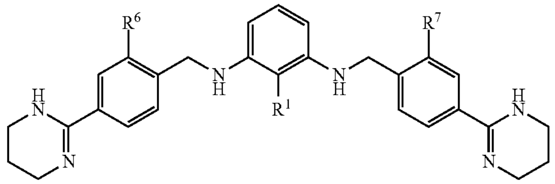
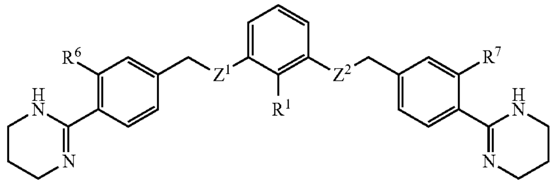
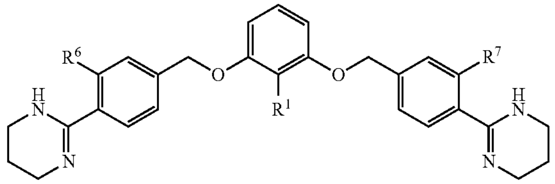
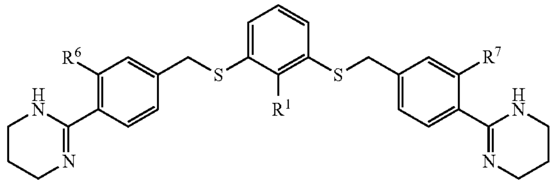
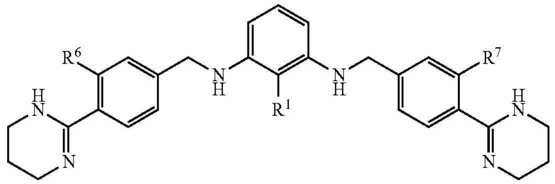
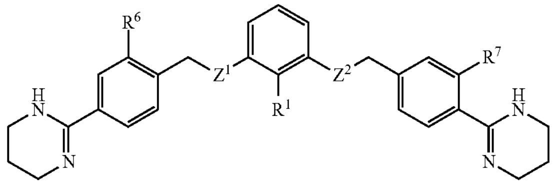

-continued
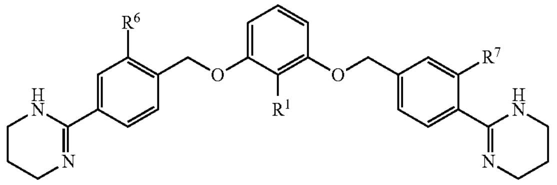
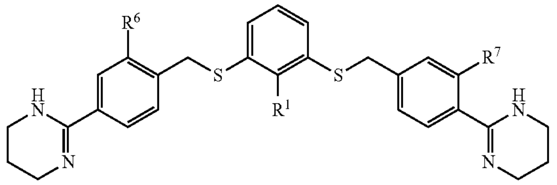
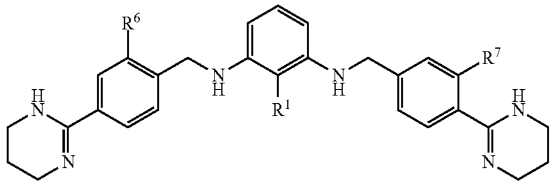
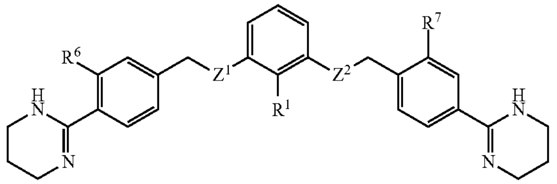
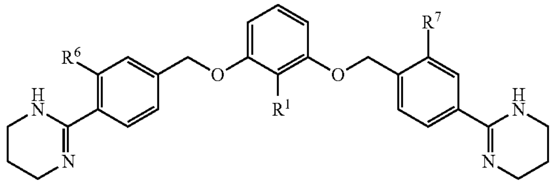
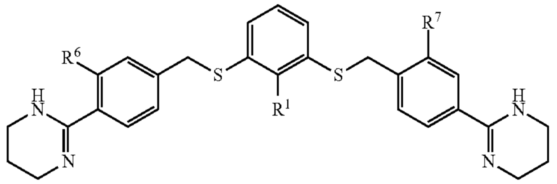
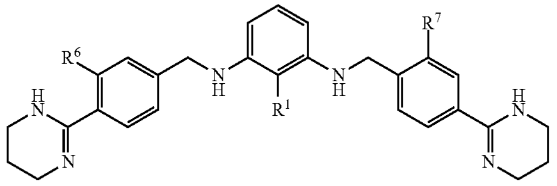
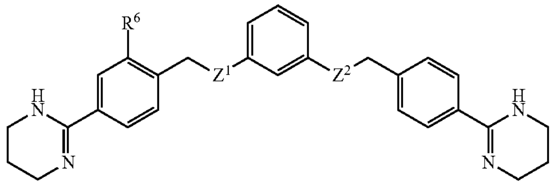
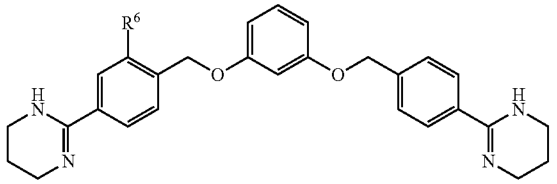
-continued
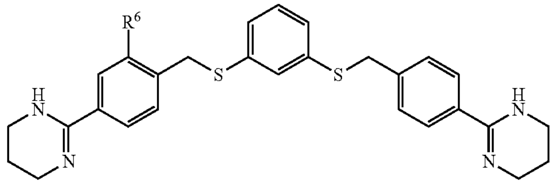
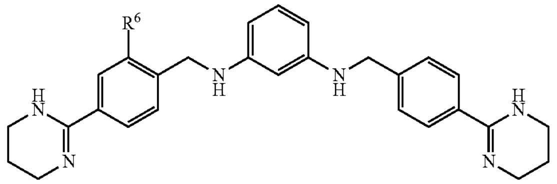
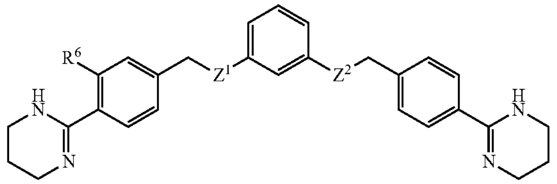
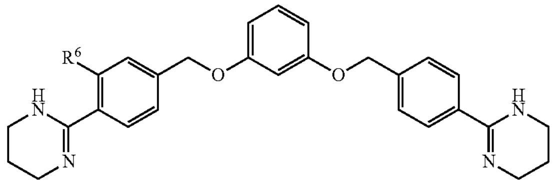
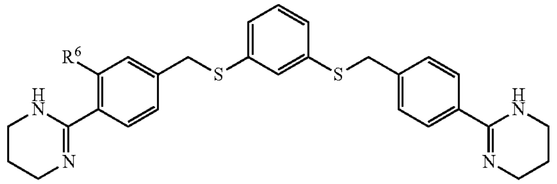
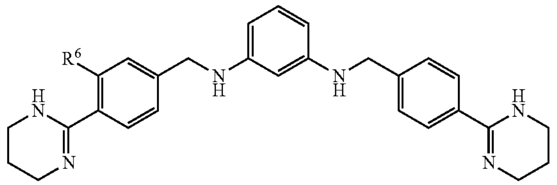
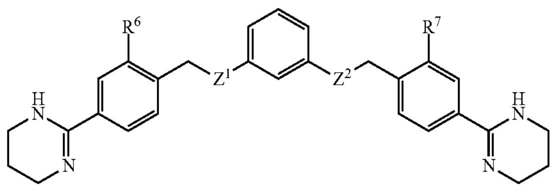
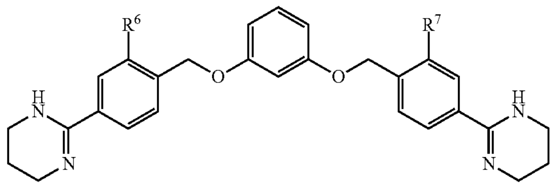
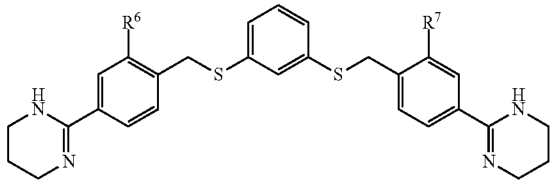

-continued
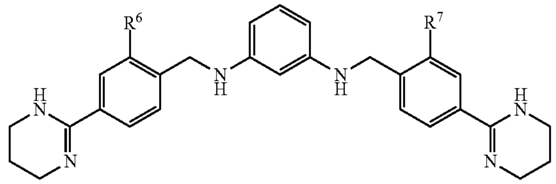
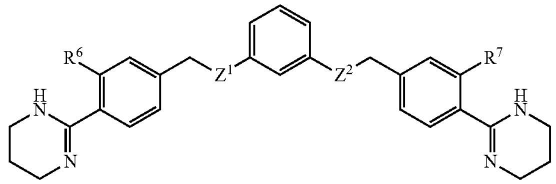
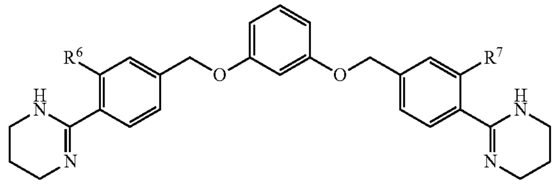
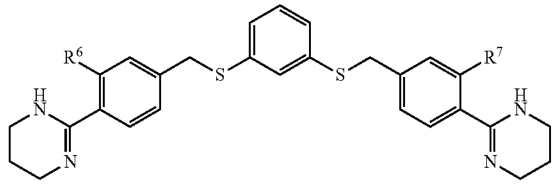
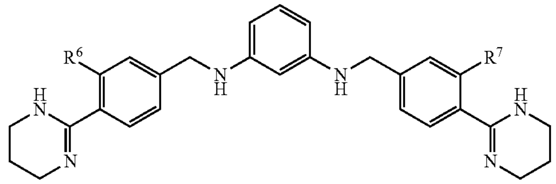
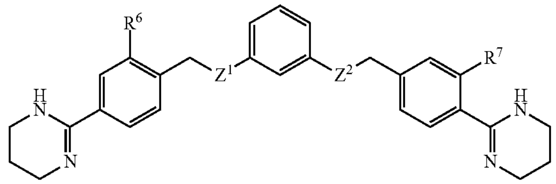
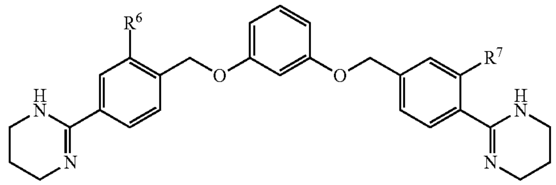
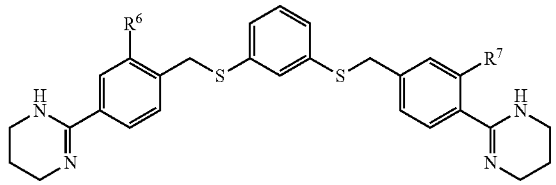
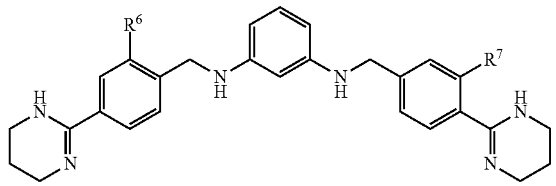
-continued
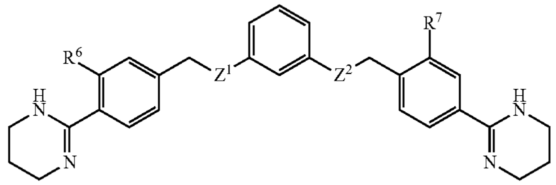
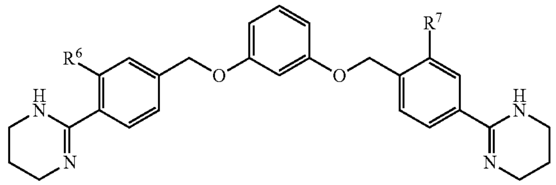
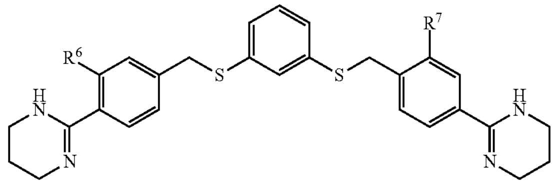
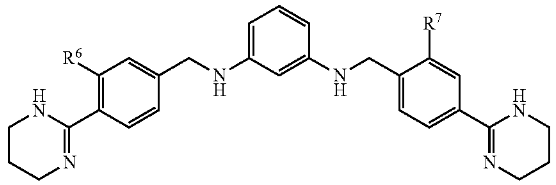
Additional examples of compounds of Formula VI include.
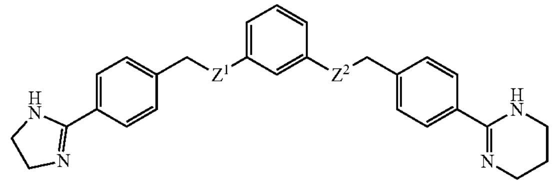
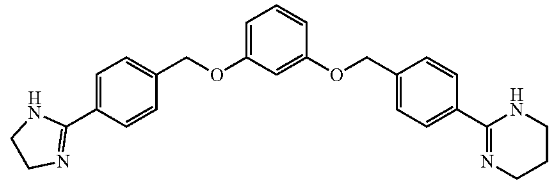
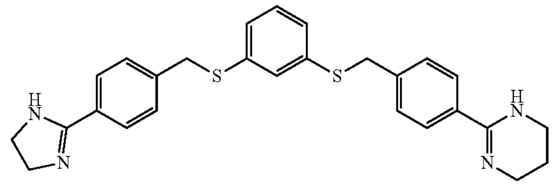
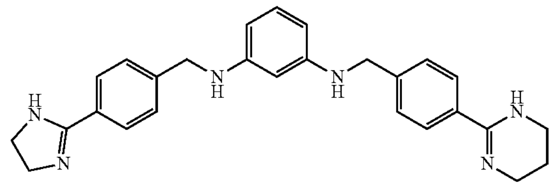

-continued
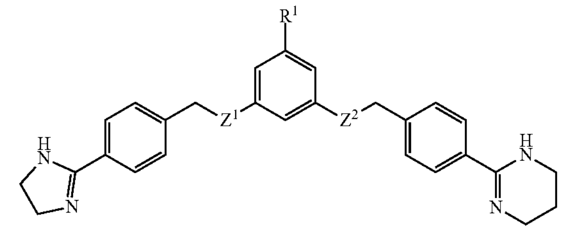
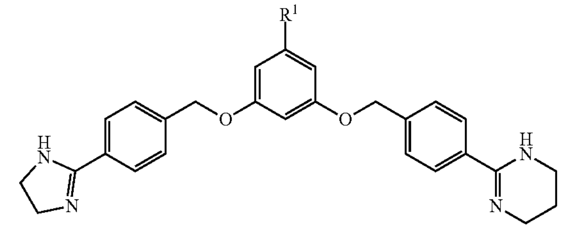
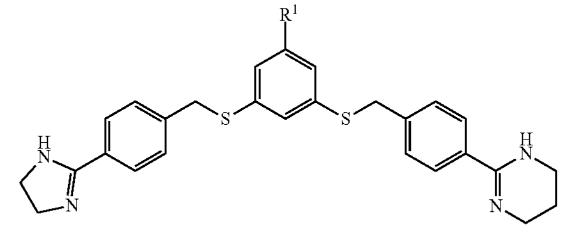
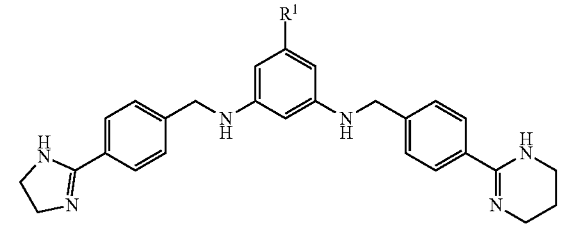
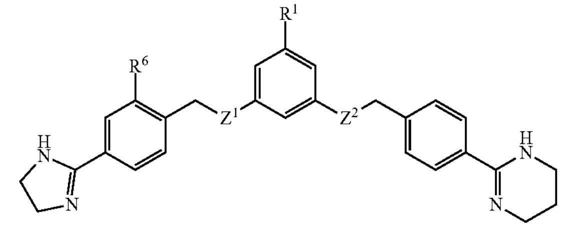
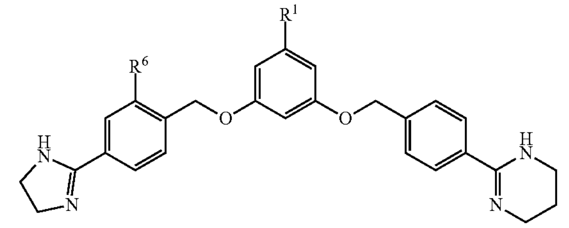
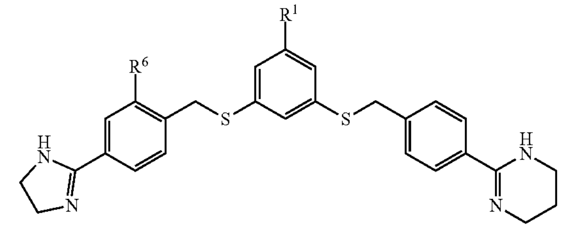
-continued
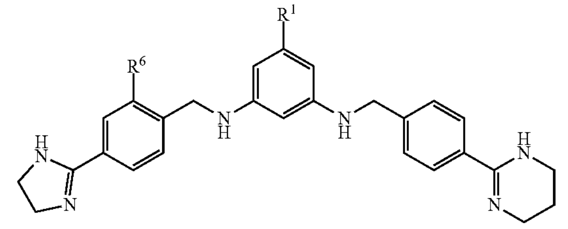
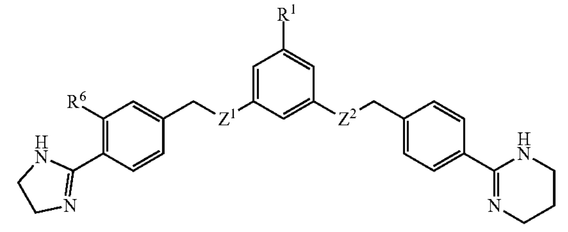
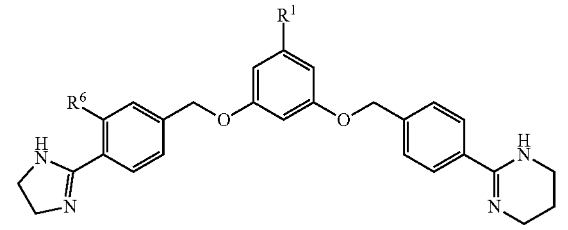
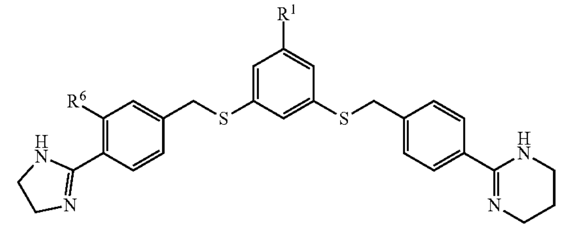
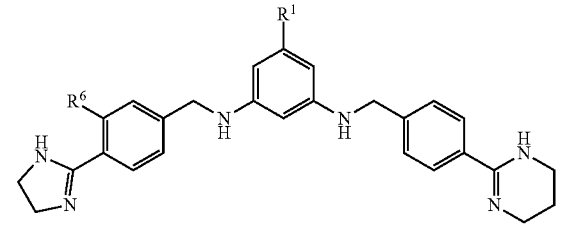
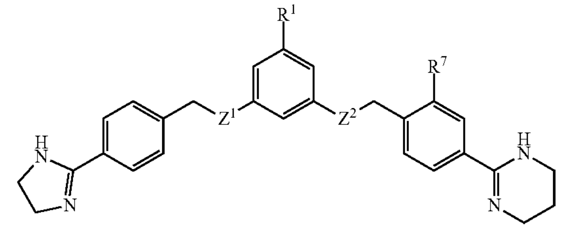
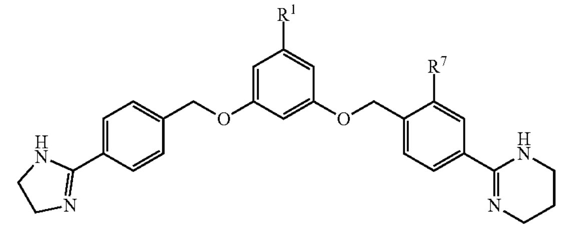

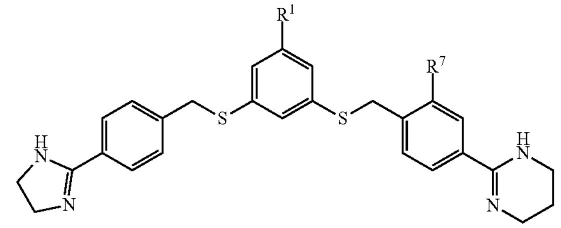
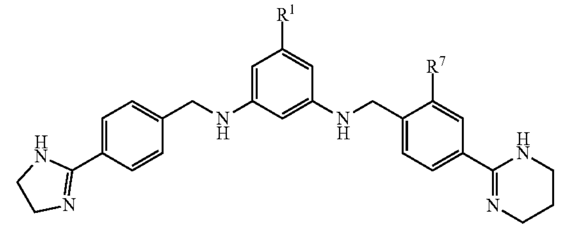
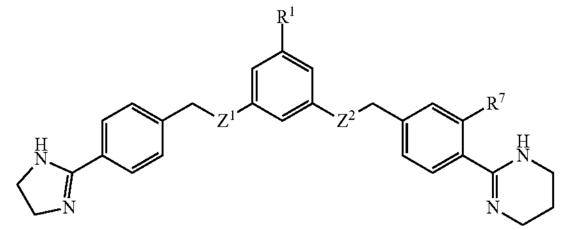
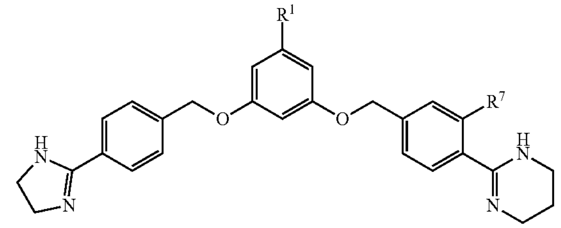
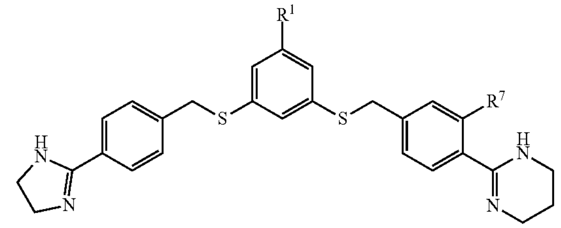
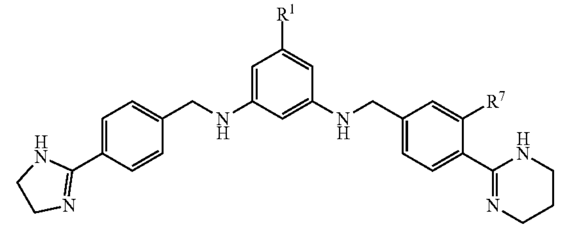
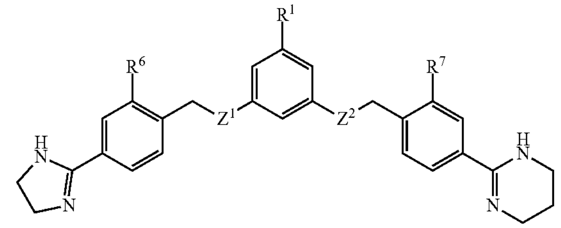
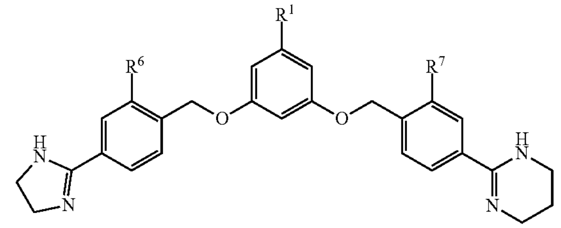
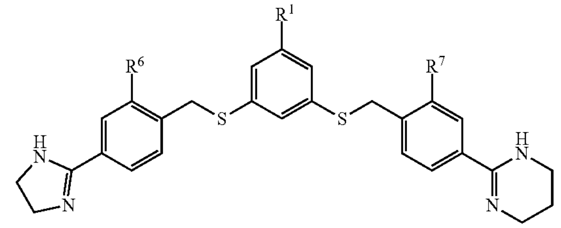
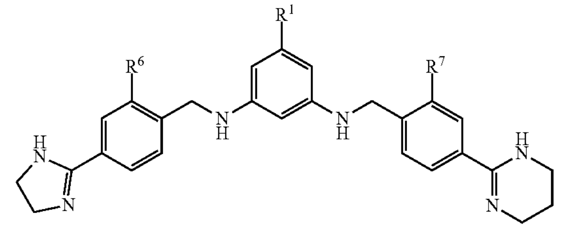
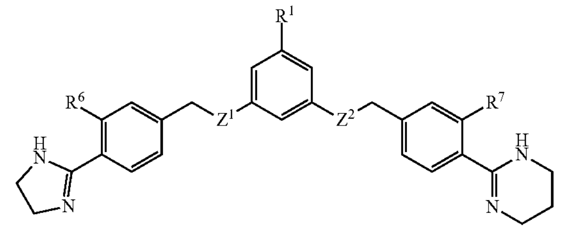
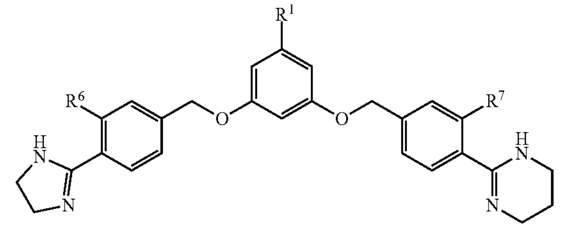
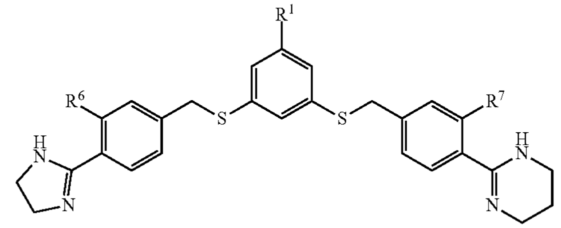
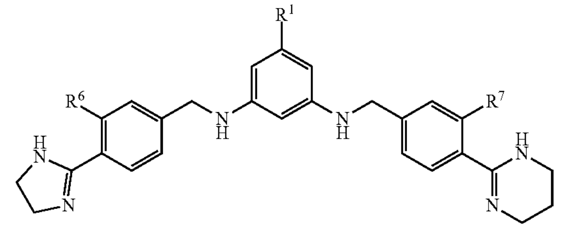

-continued
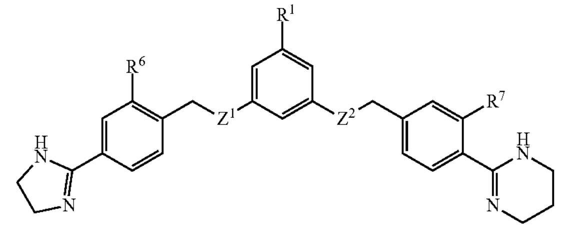
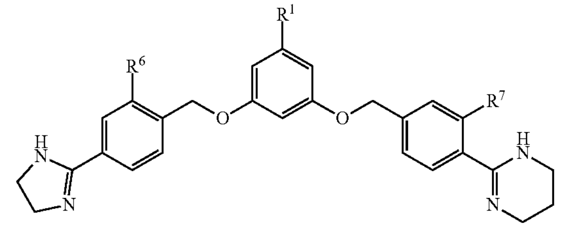
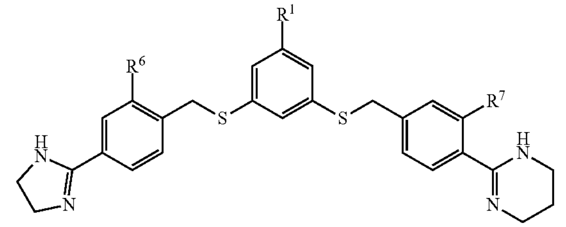
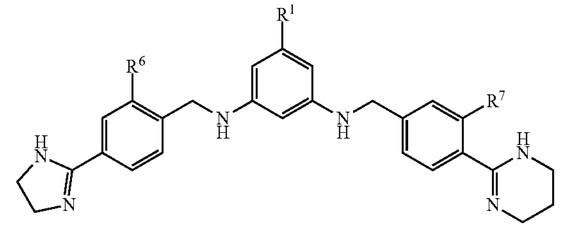
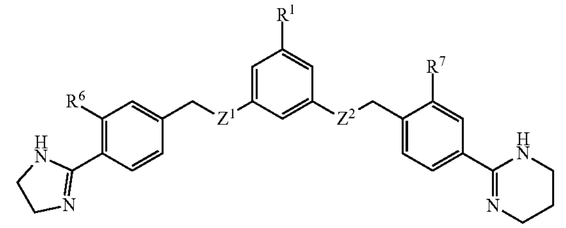
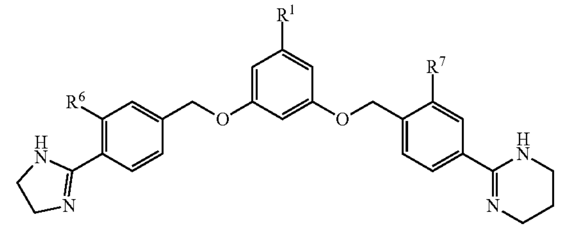
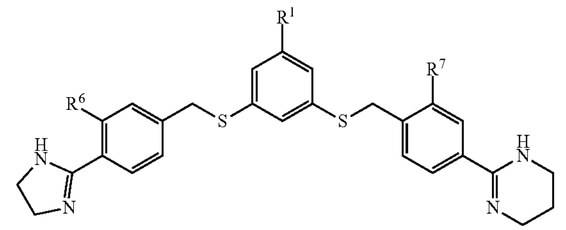
-continued
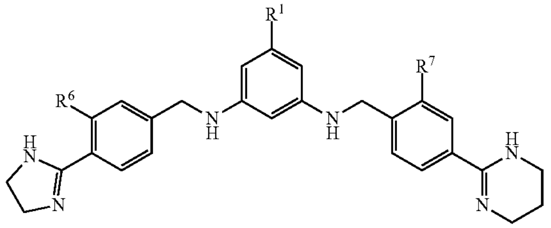
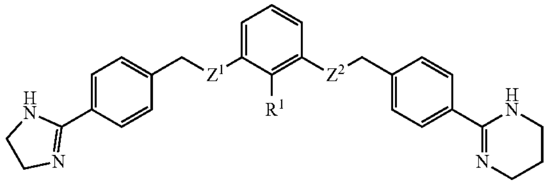
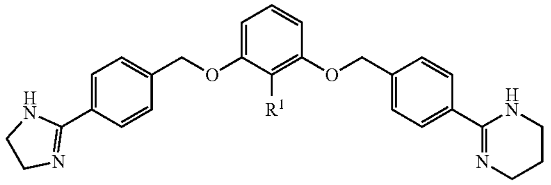
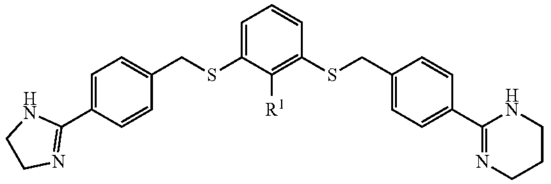
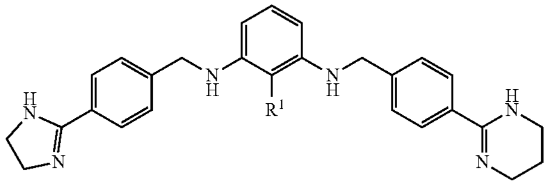
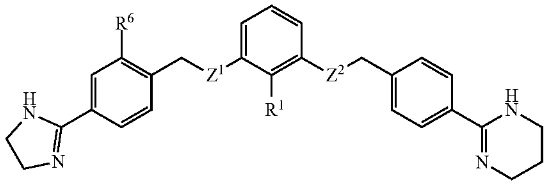
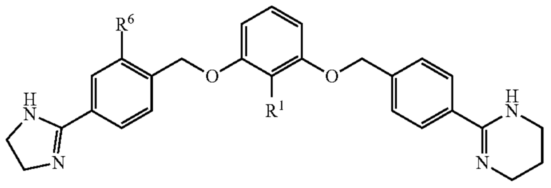
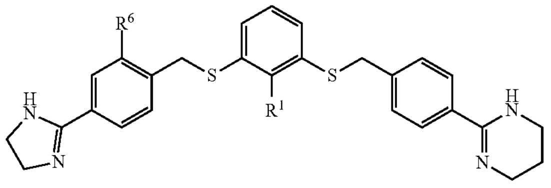
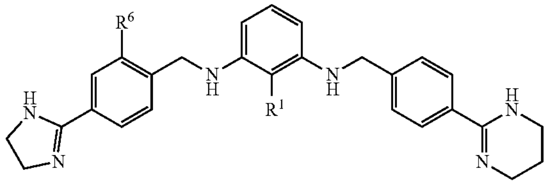

-continued
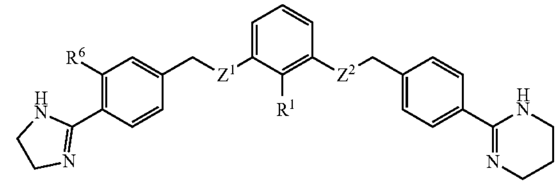
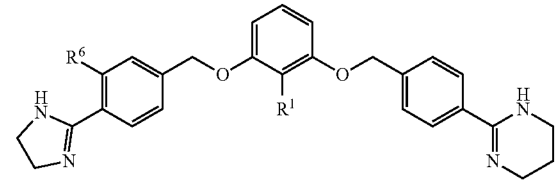
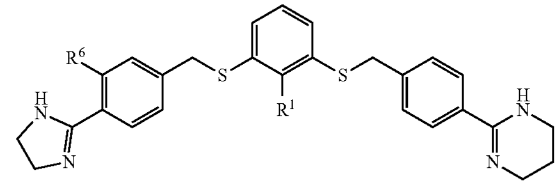
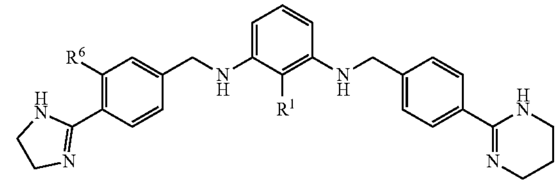
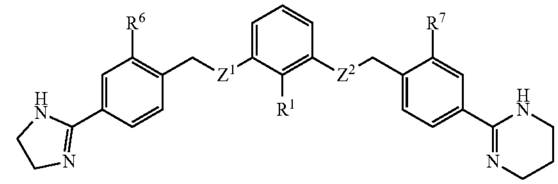
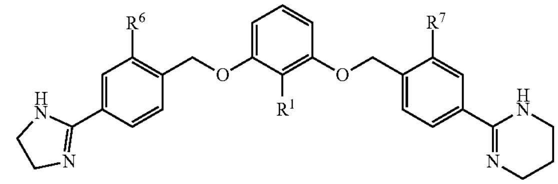
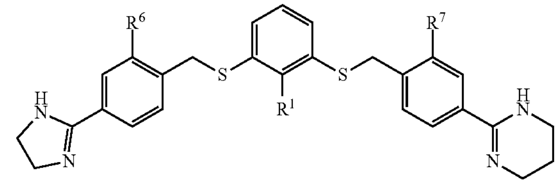
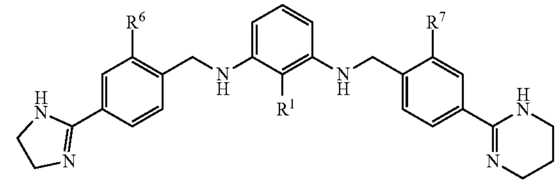
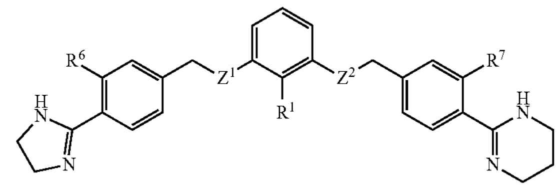
-continued
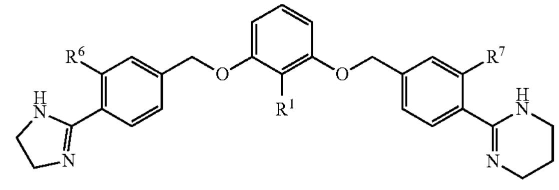
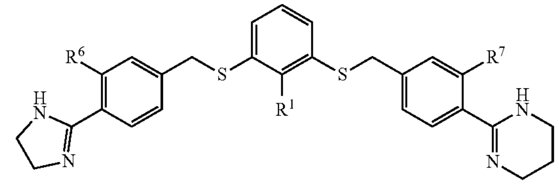
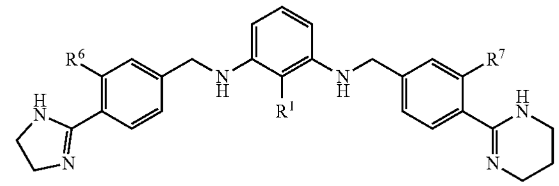
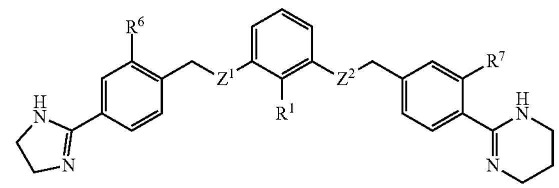
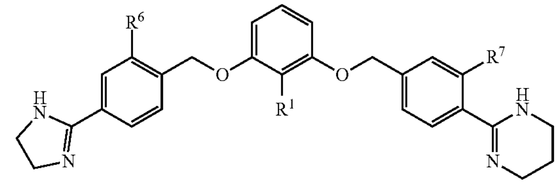
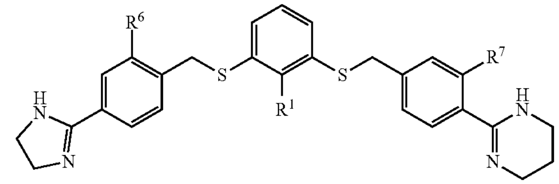
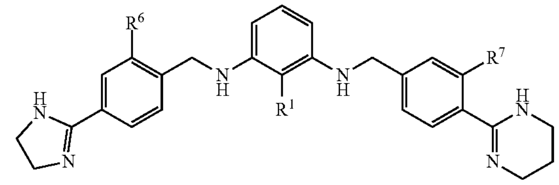
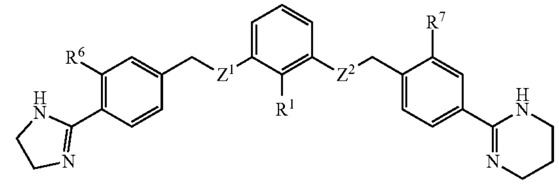
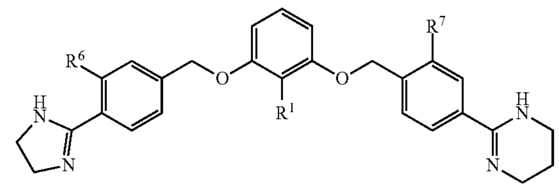

-continued
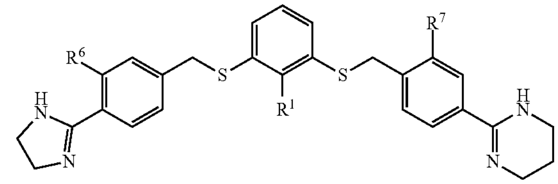
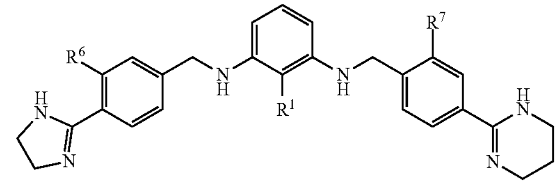
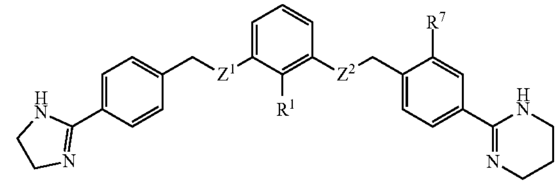
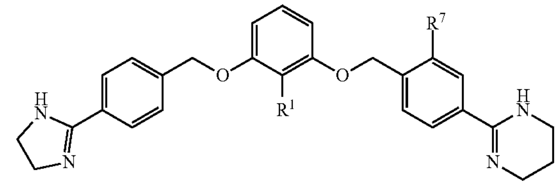
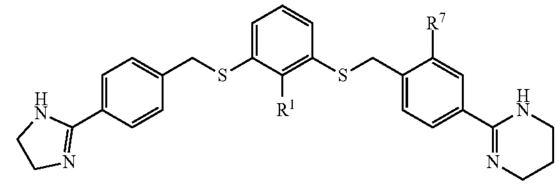
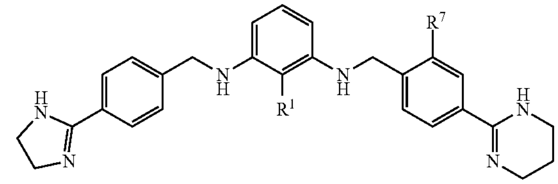
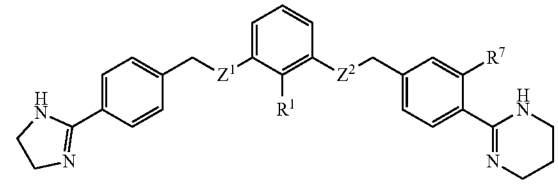
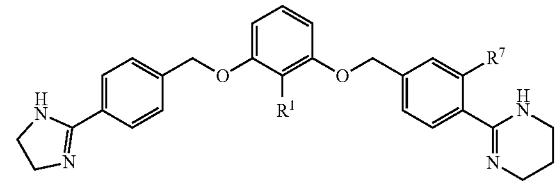
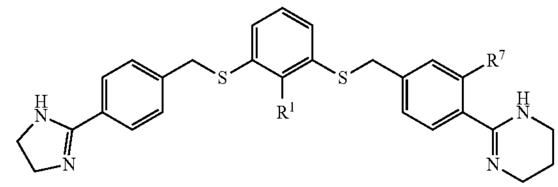
-continued
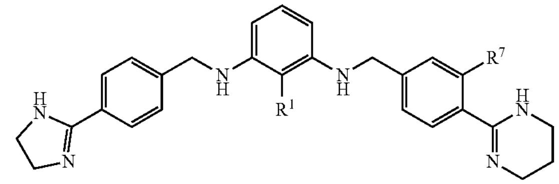
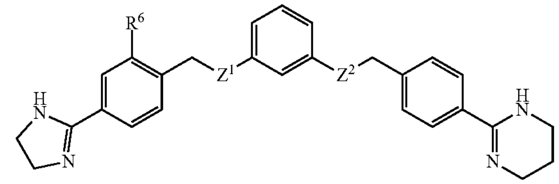
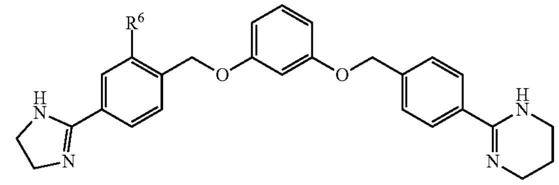
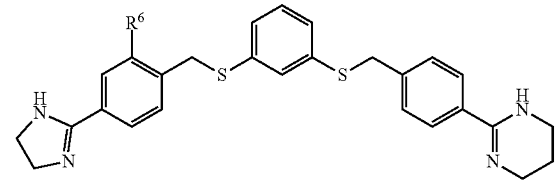
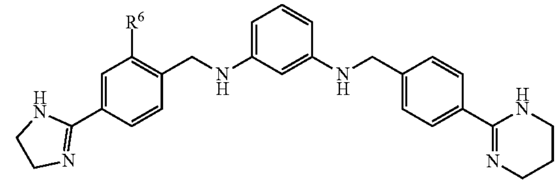
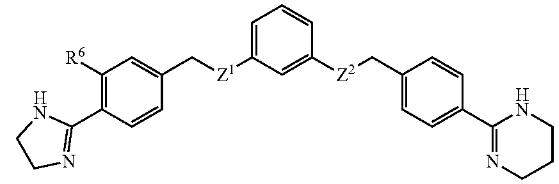
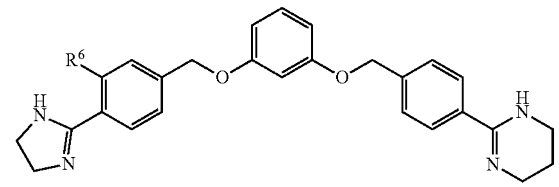
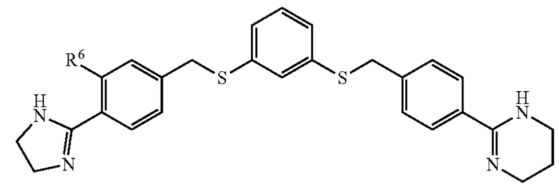
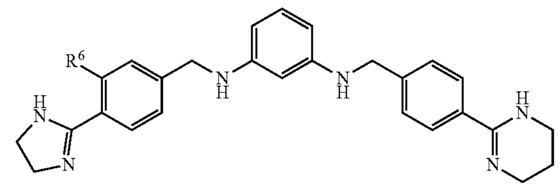

-continued
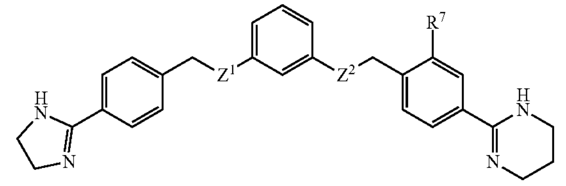
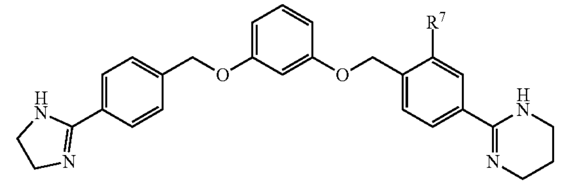
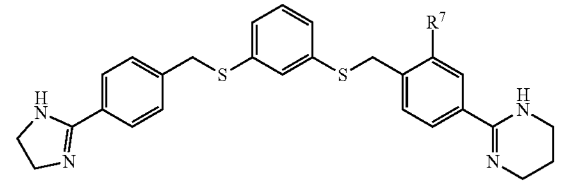
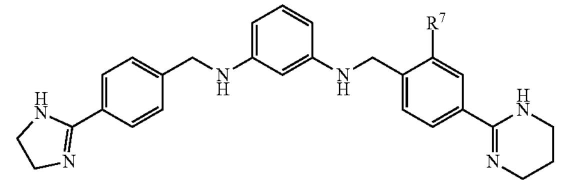
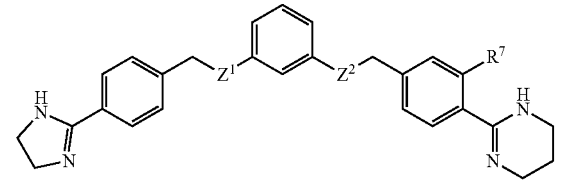
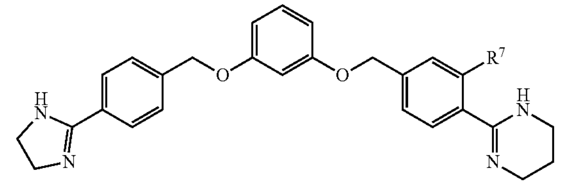
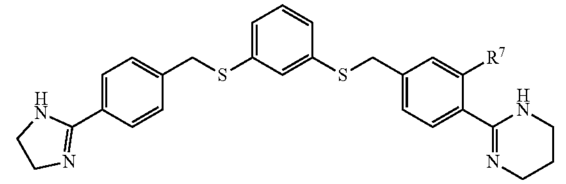
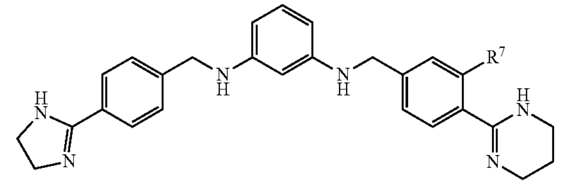
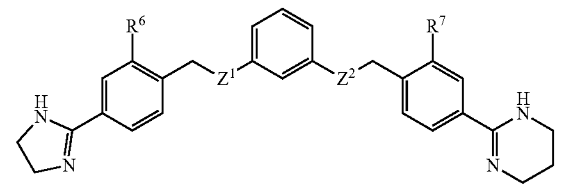
-continued
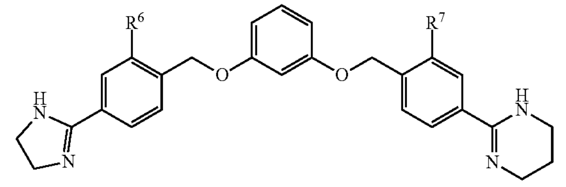
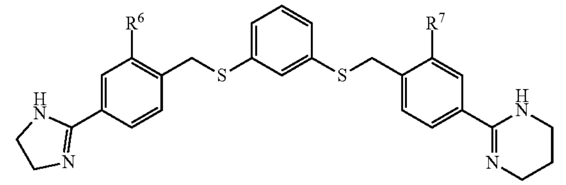
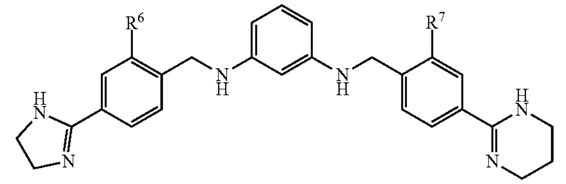
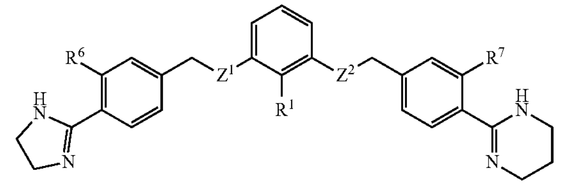
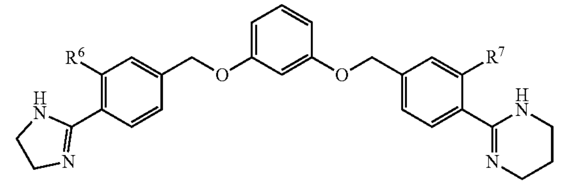
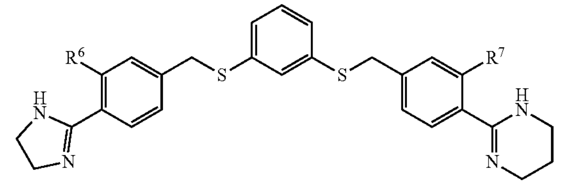
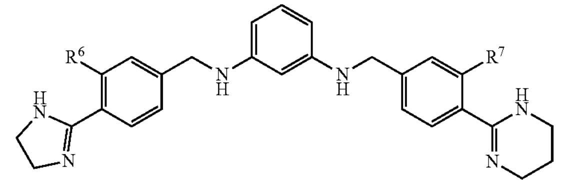
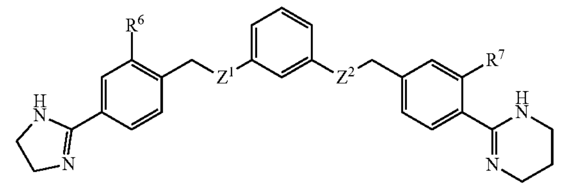
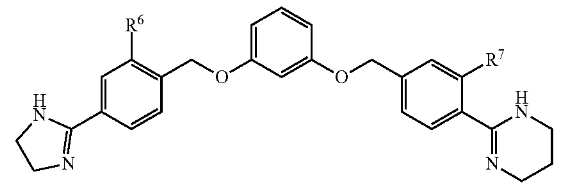

-continued
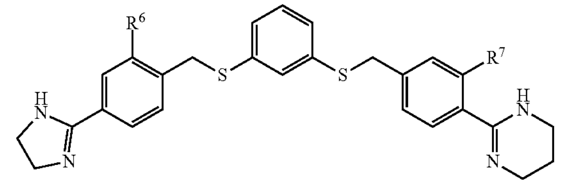
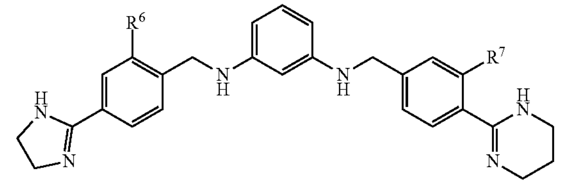
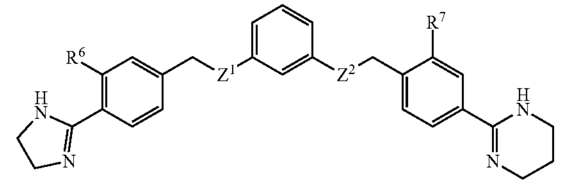
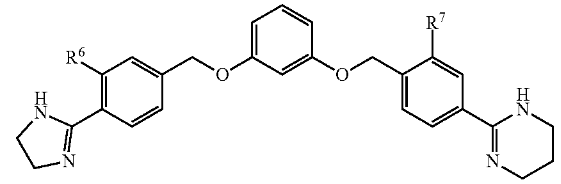
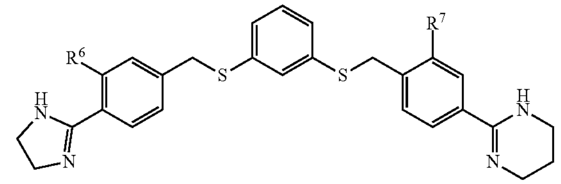
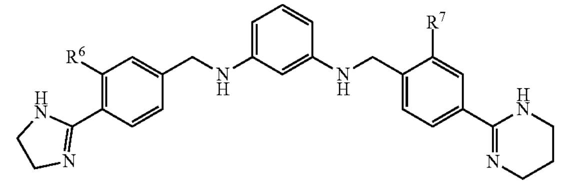
Non-limiting examples of compounds of Formula VII include.
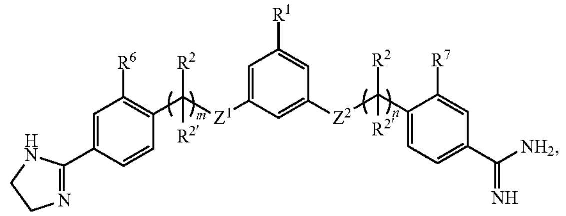
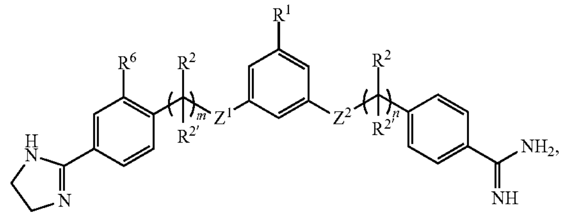
-continued
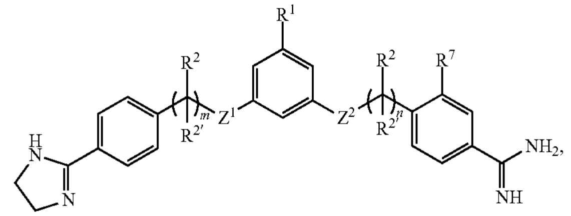
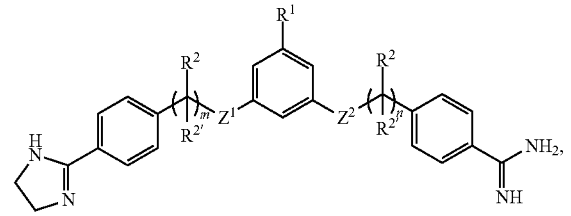
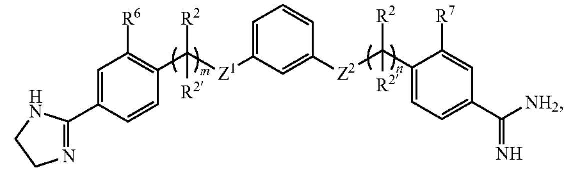
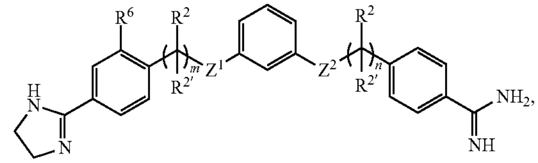
and
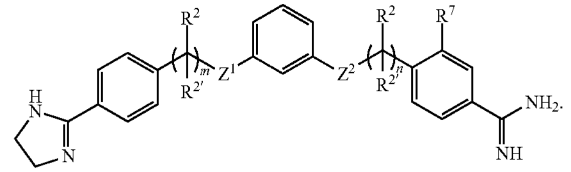
Non-limiting examples of compounds of Formula VII include.
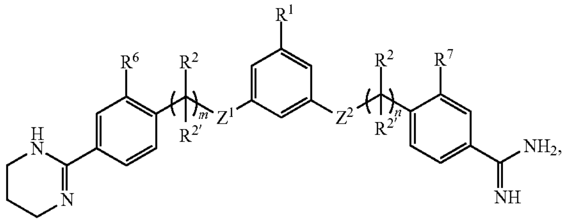
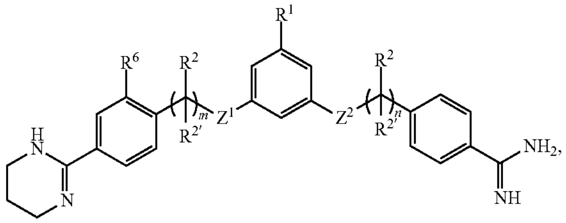

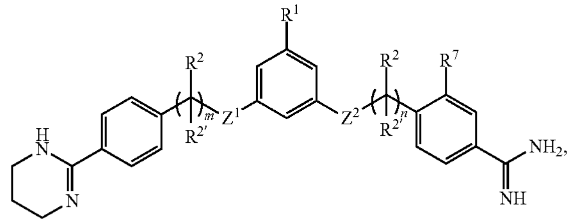
,
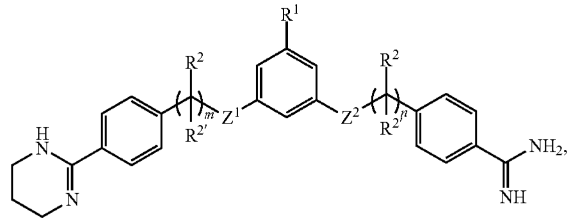
,
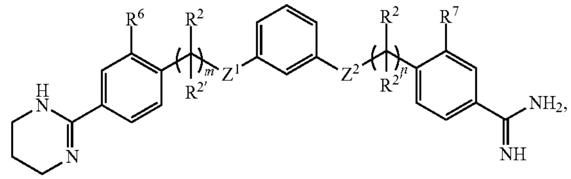
,
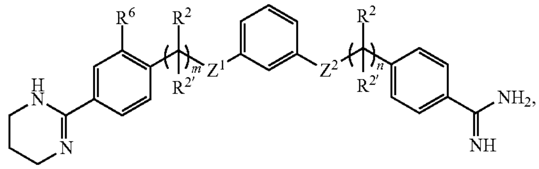
, and
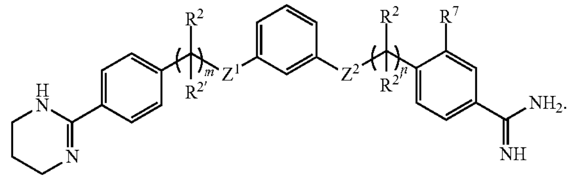
.
Additional examples of compounds of Formula VII include:
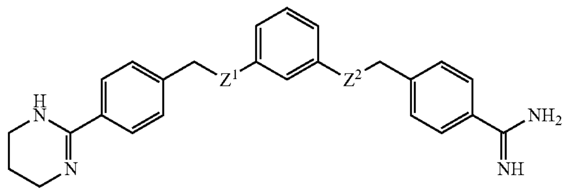
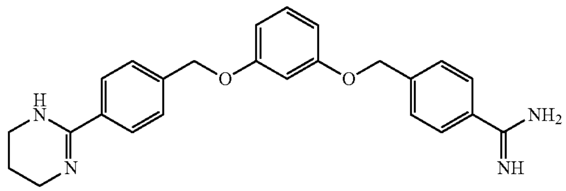
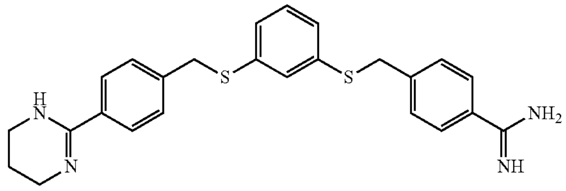
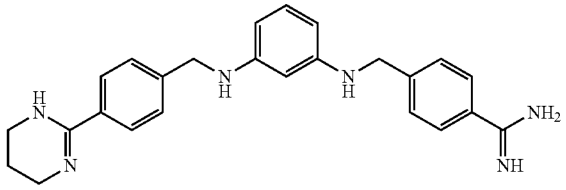
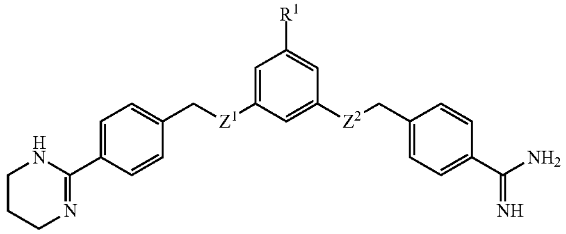
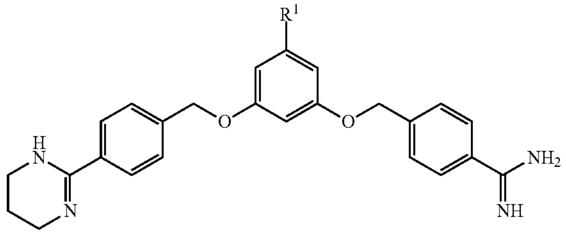
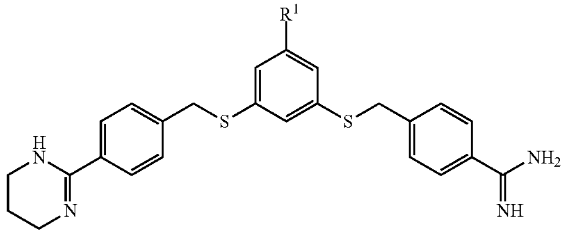
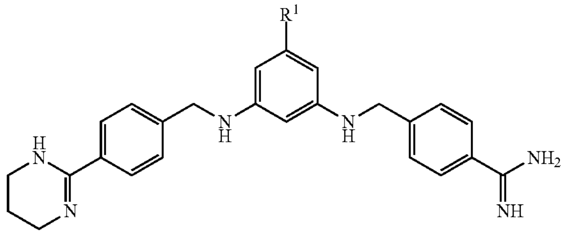
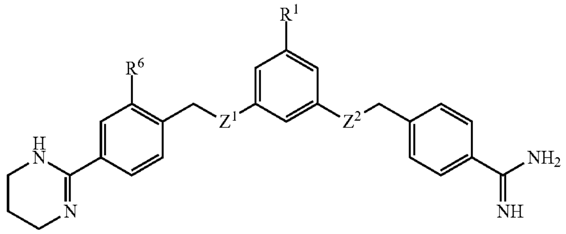
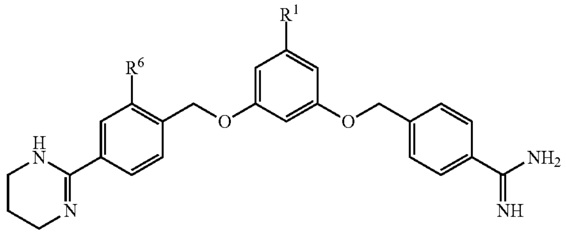

-continued
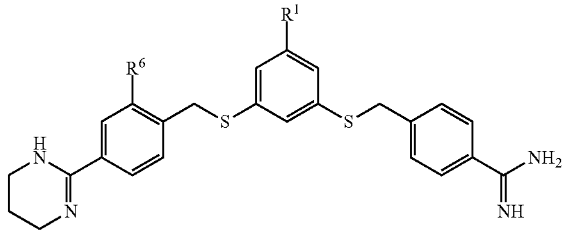
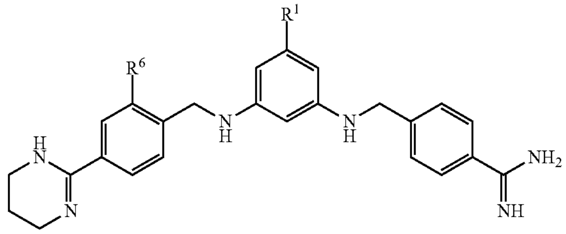
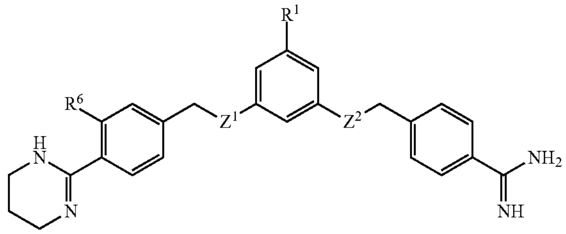
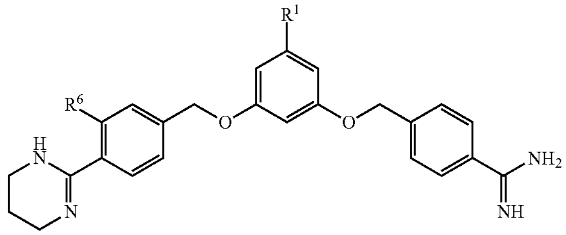
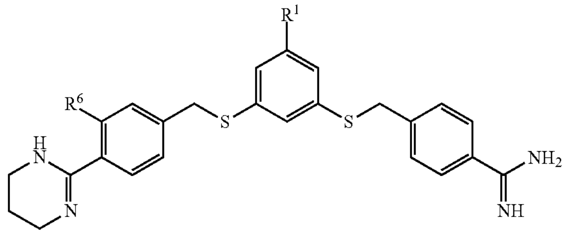
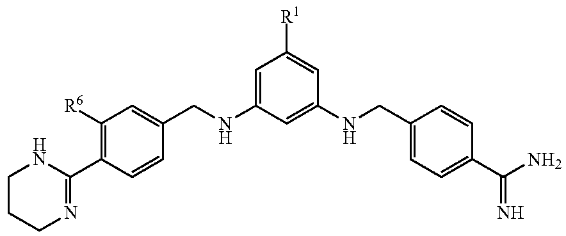
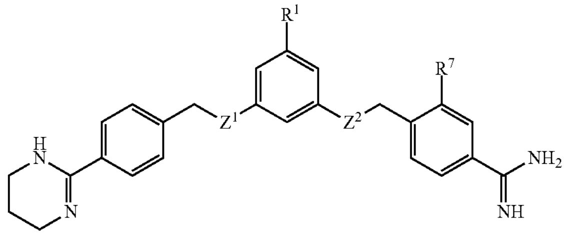
-continued
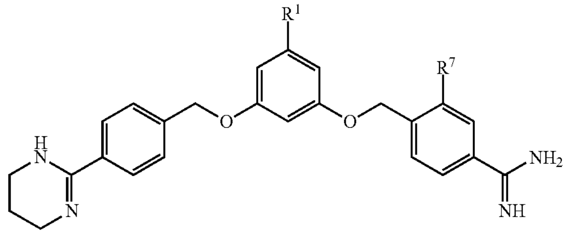
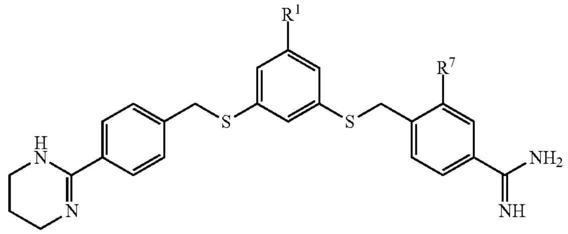
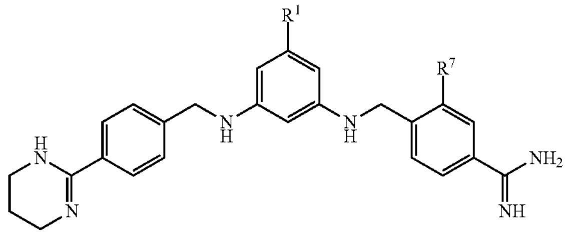
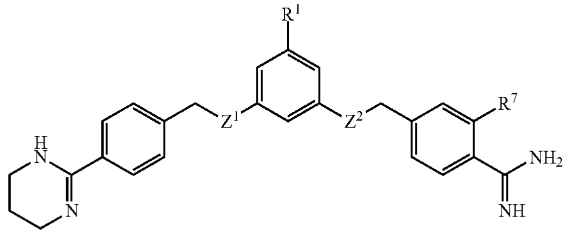
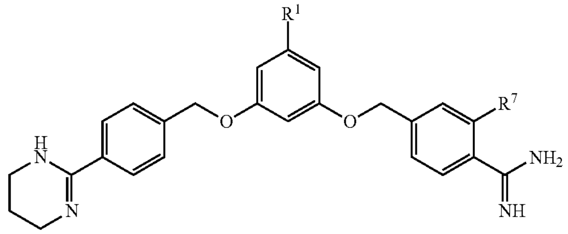
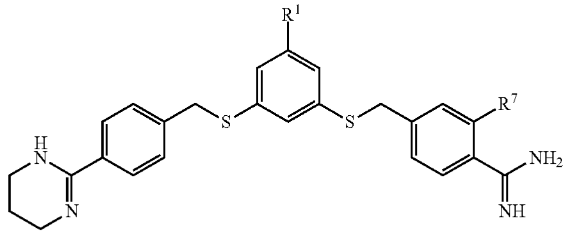
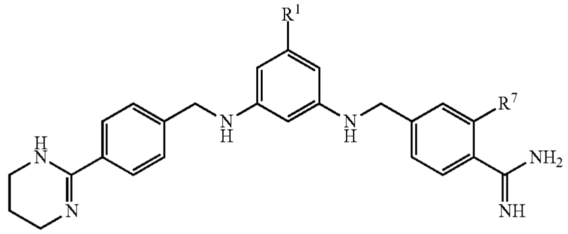

-continued
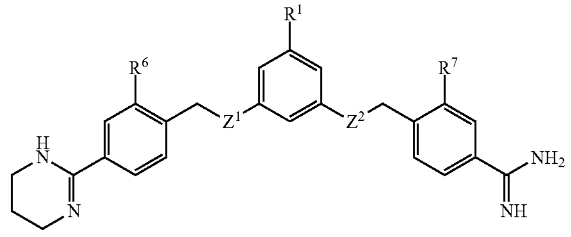
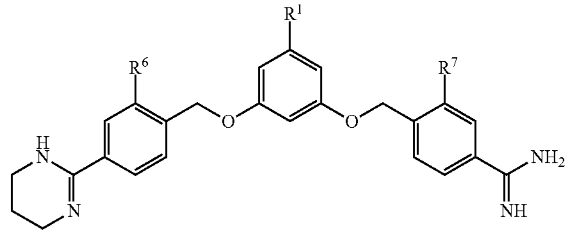
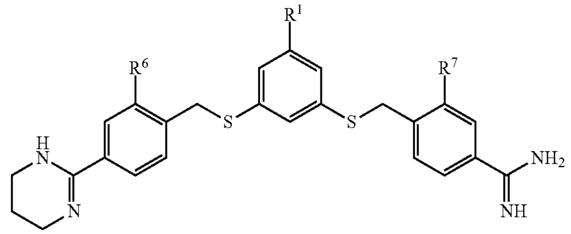
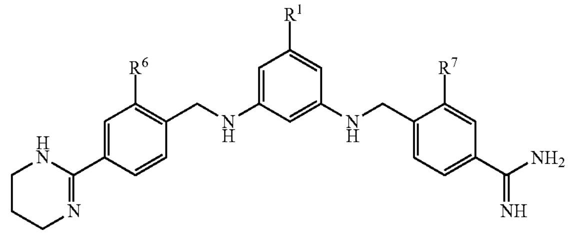
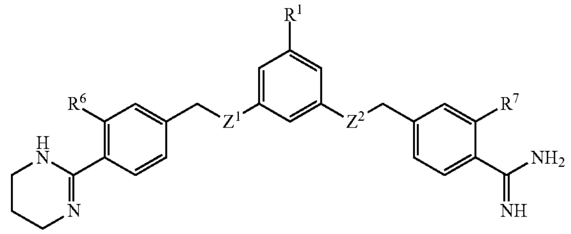
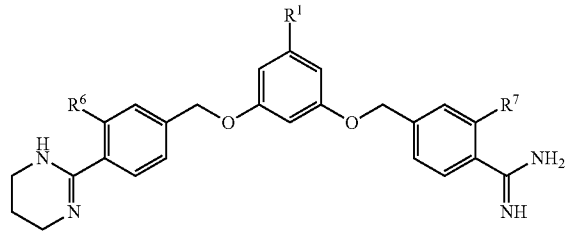
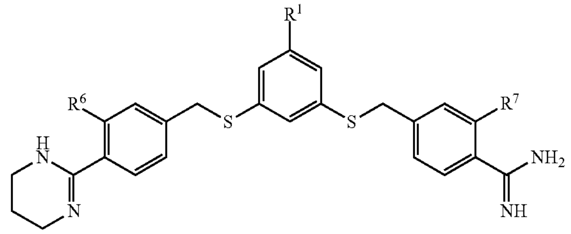
-continued
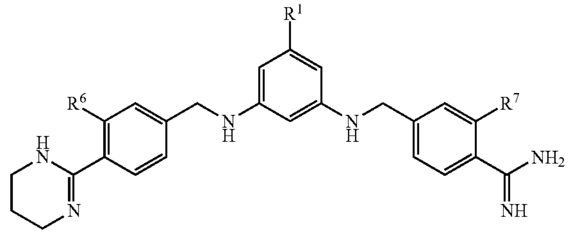
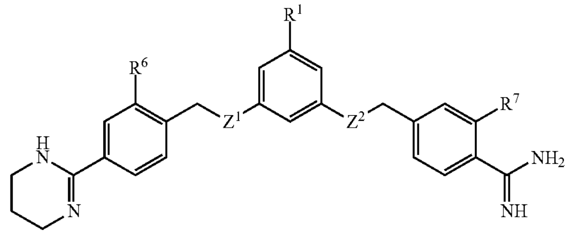
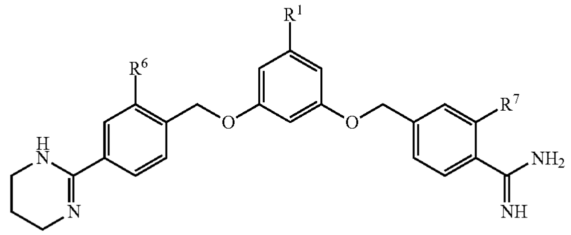
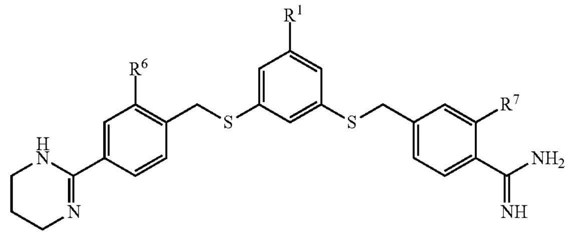
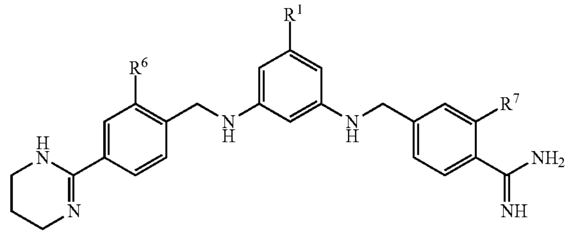
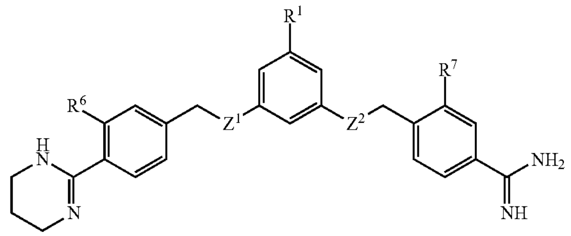
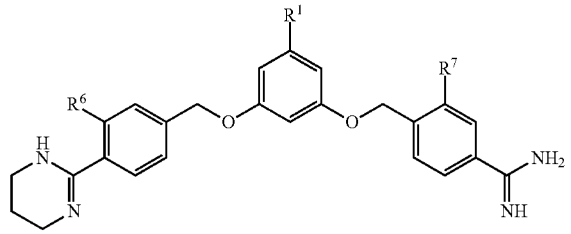

-continued
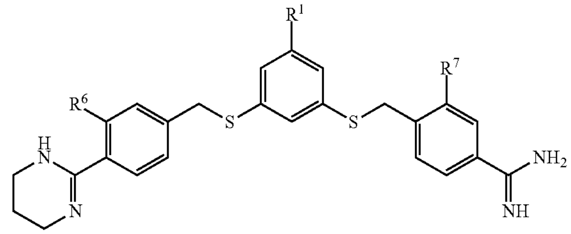
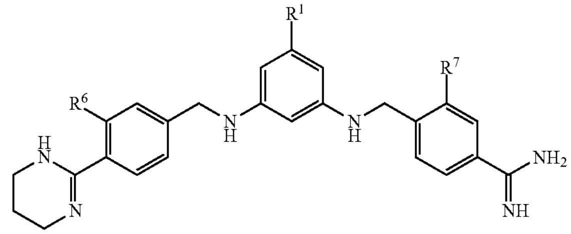
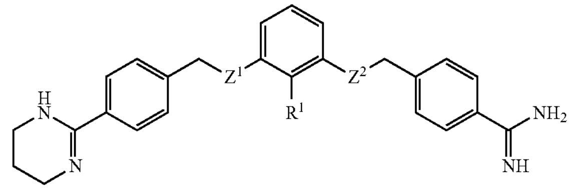
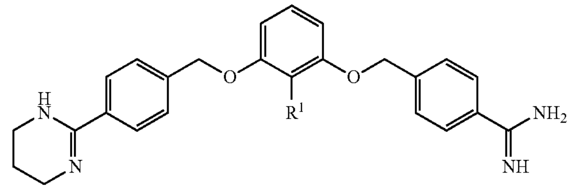
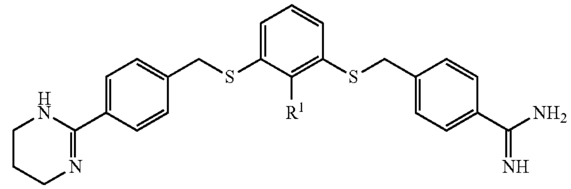
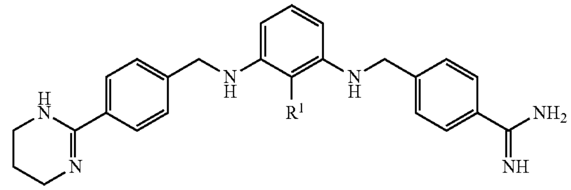
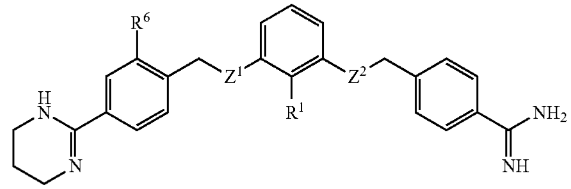
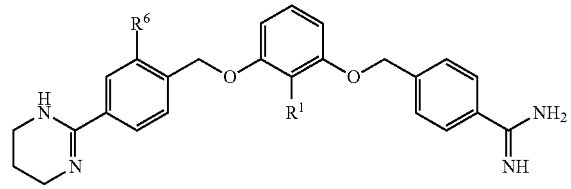
-continued
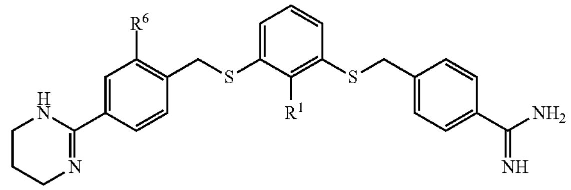
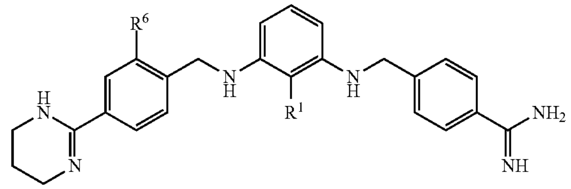
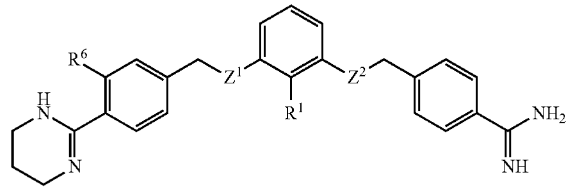
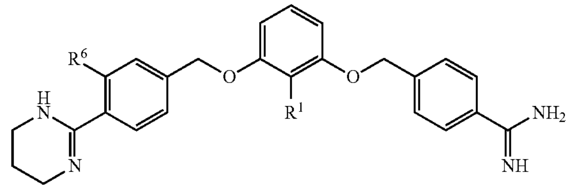
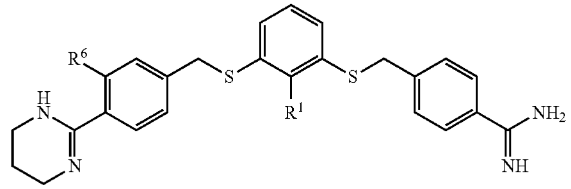
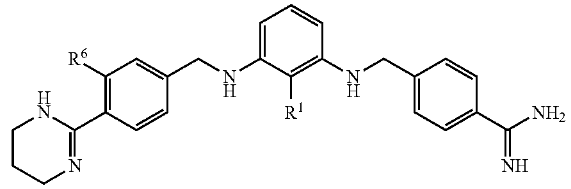
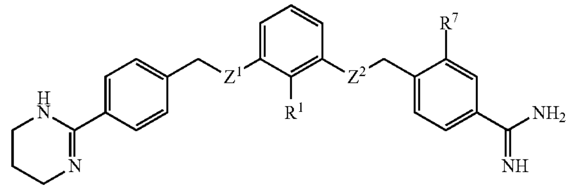
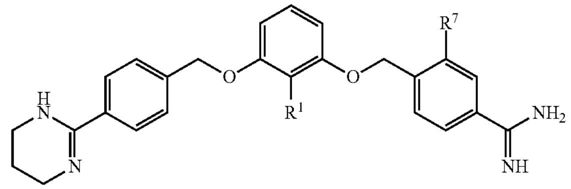
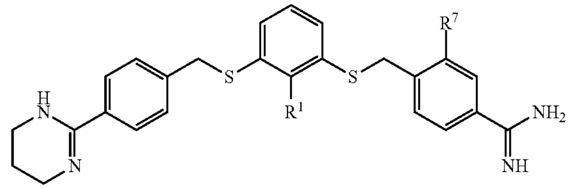

-continued
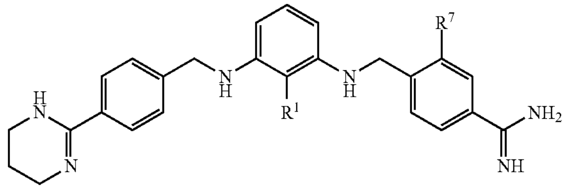
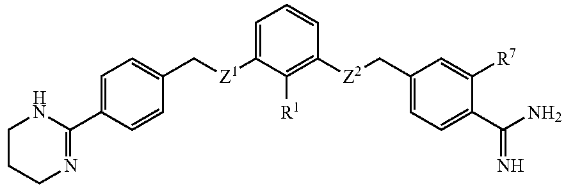
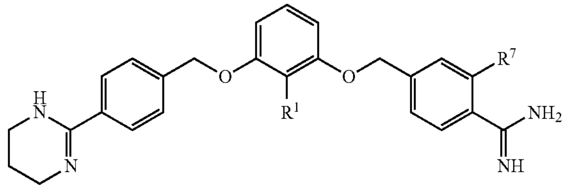
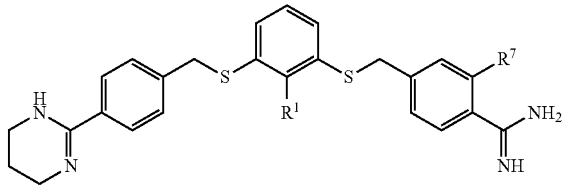
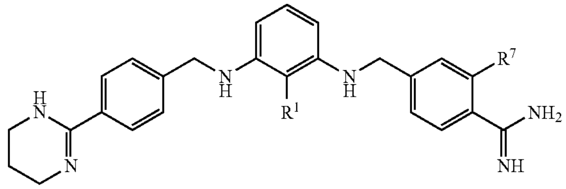
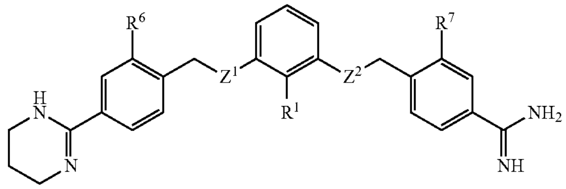
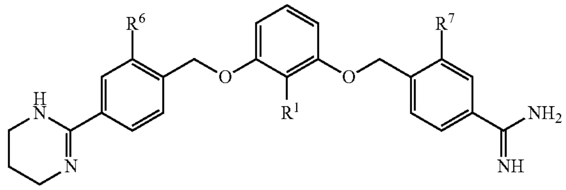
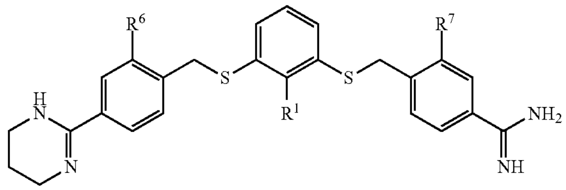
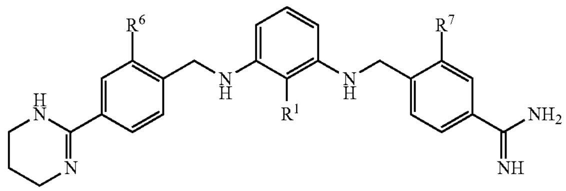
-continued
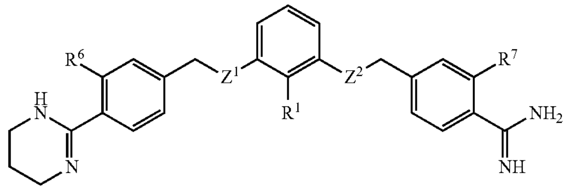
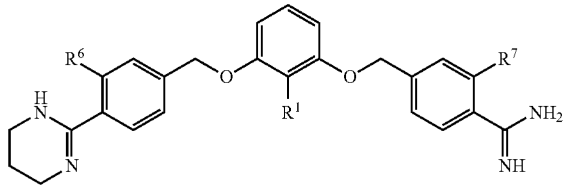
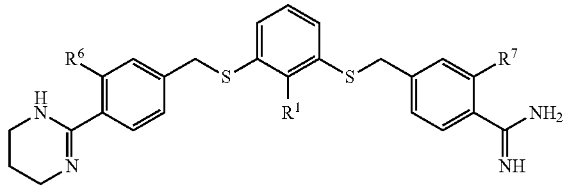
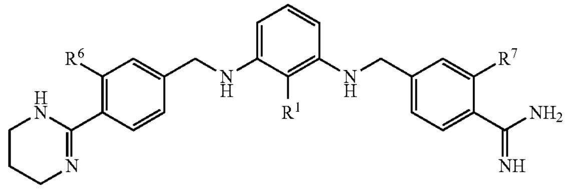
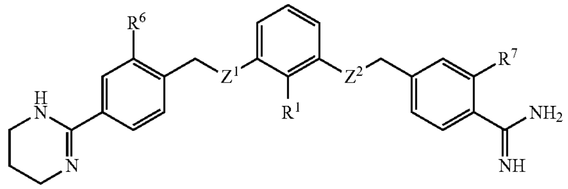
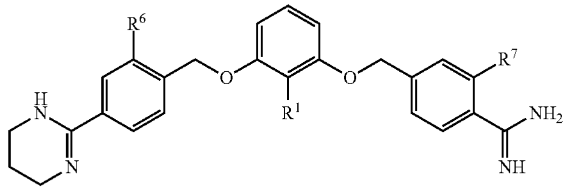
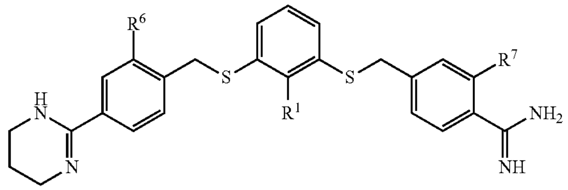
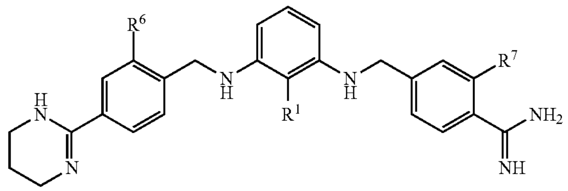
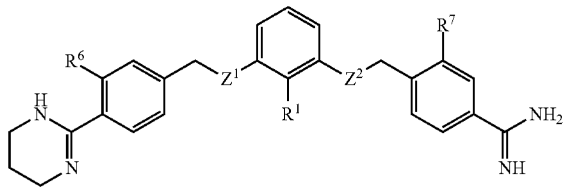

-continued
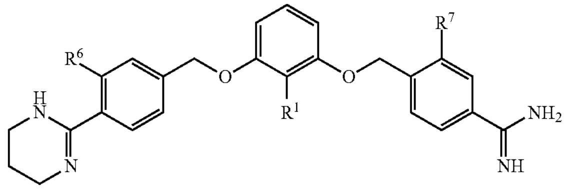
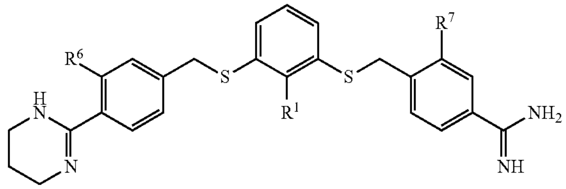
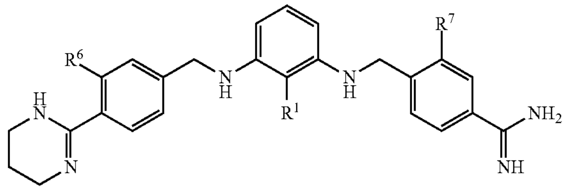
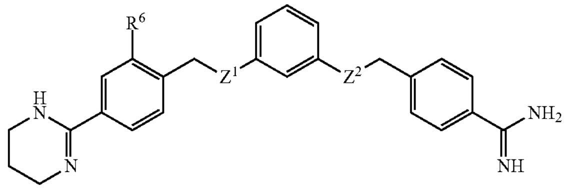
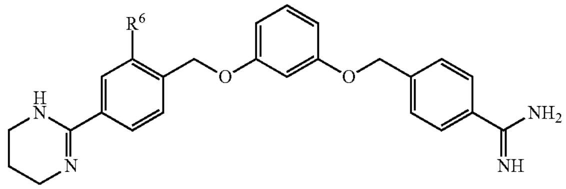
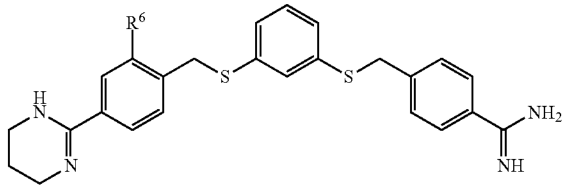
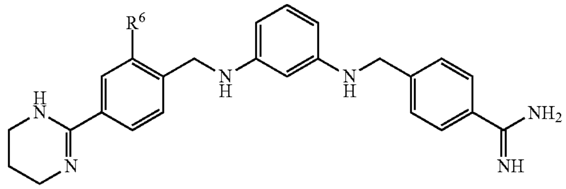
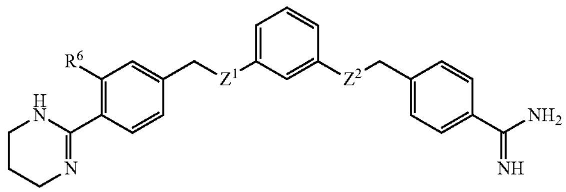
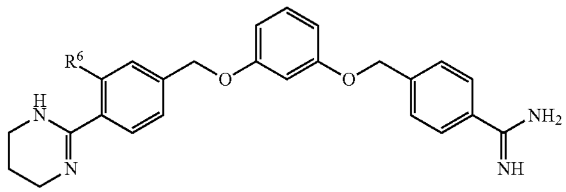
-continued
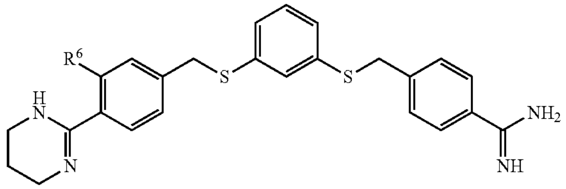
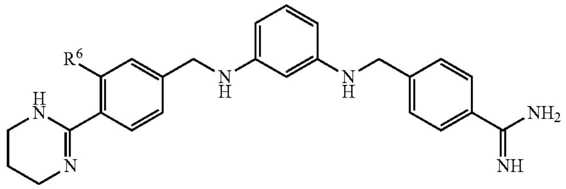
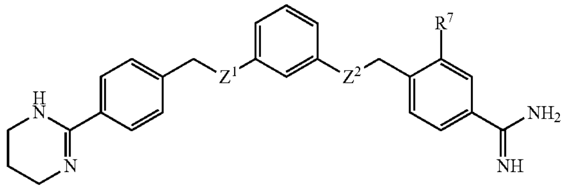
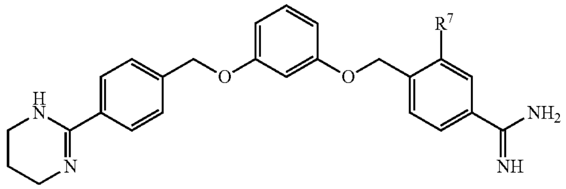
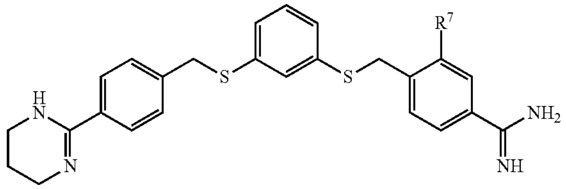
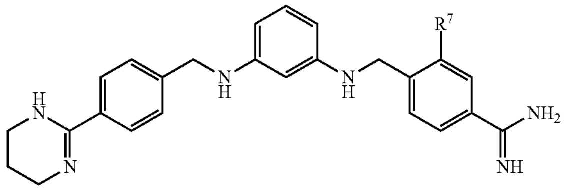
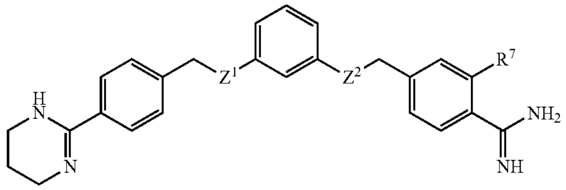
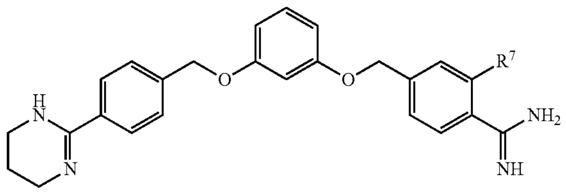
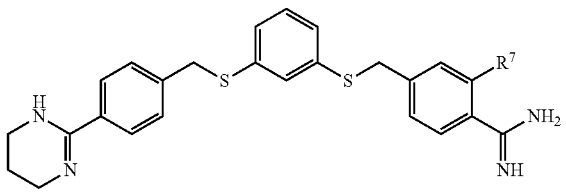

-continued
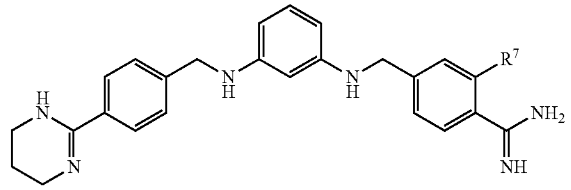
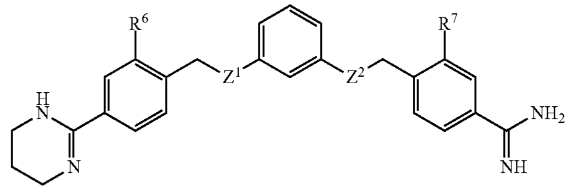
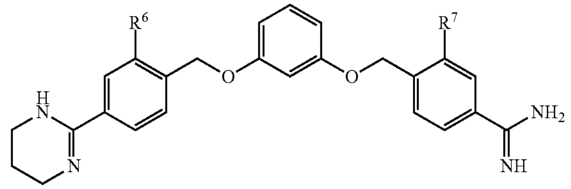
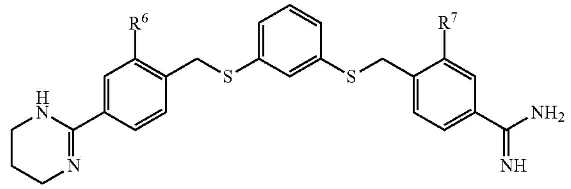
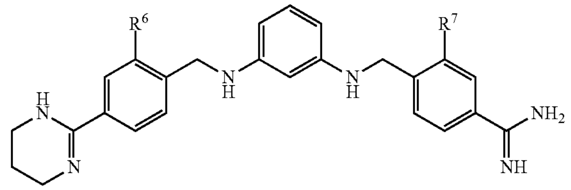
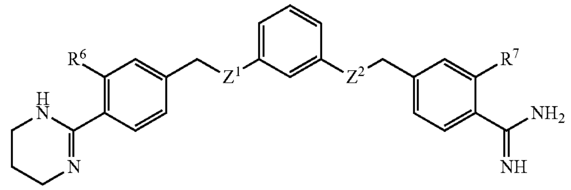
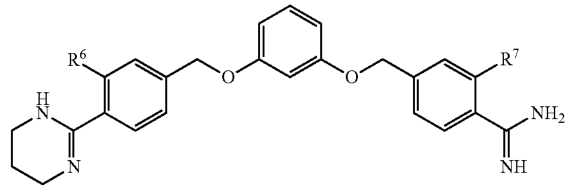
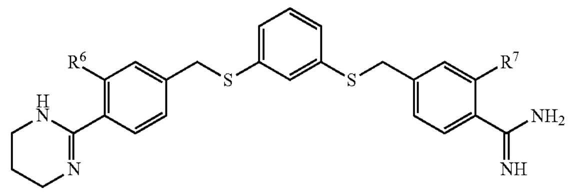
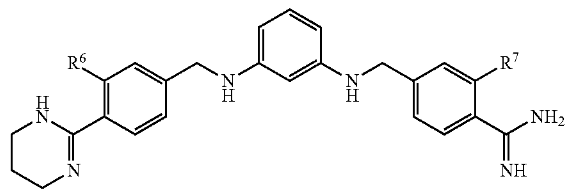
-continued
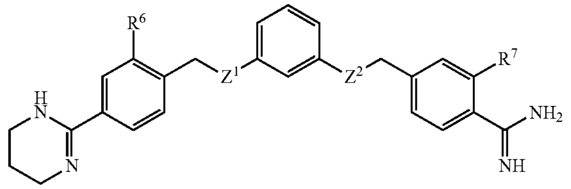
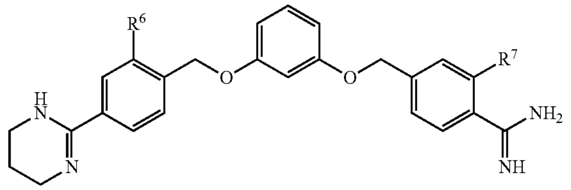
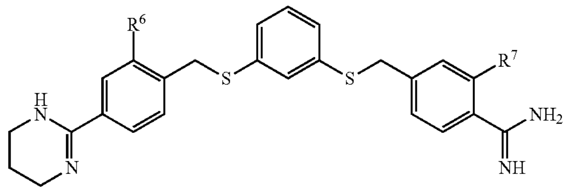
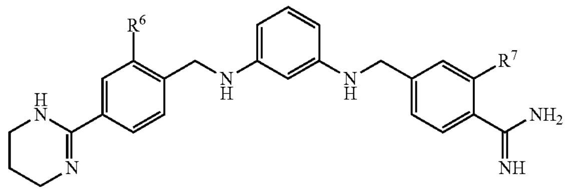
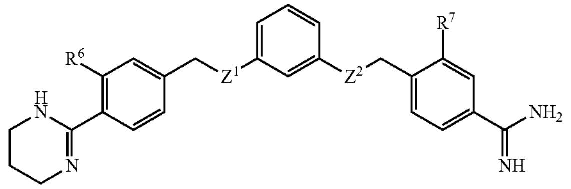
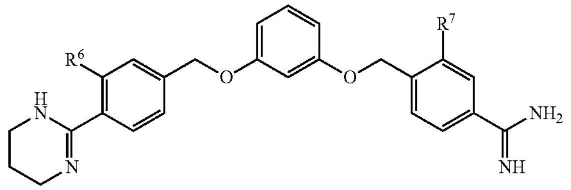
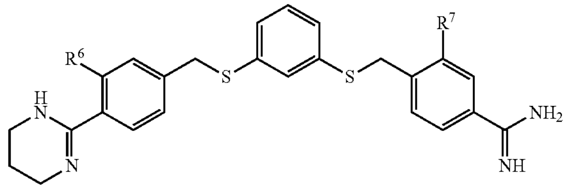
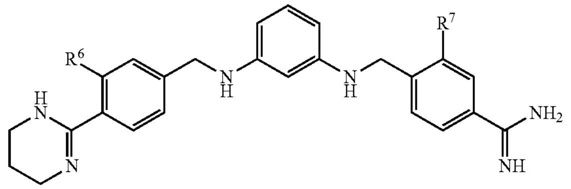
Additional examples of compounds of Formula VII include:

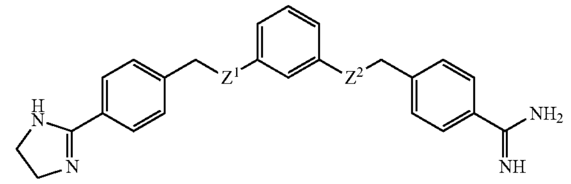
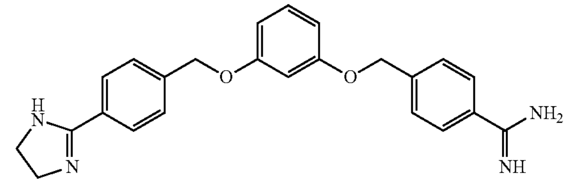
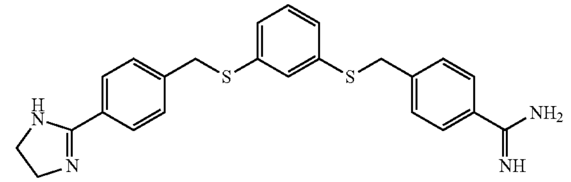
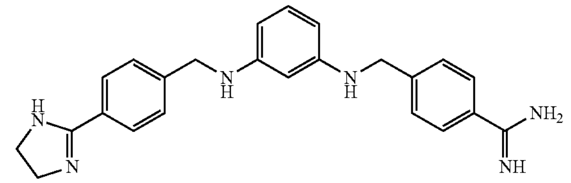
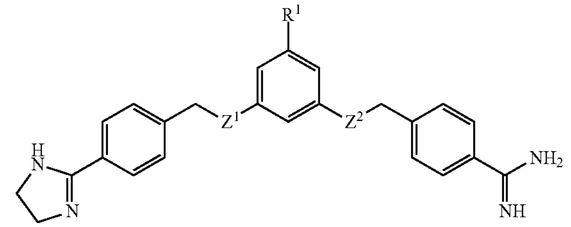
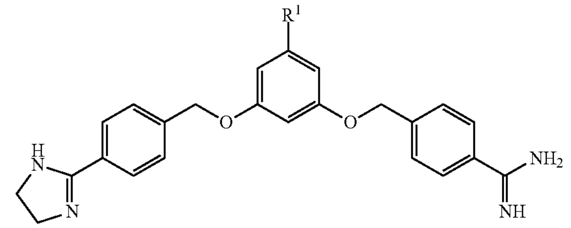
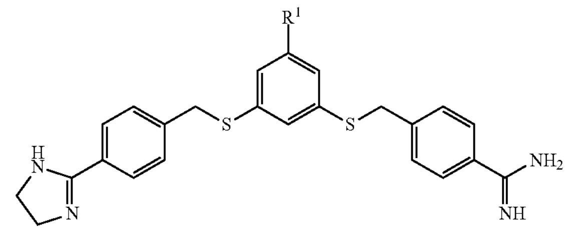
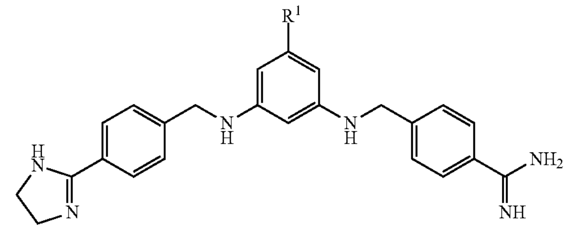
-continued
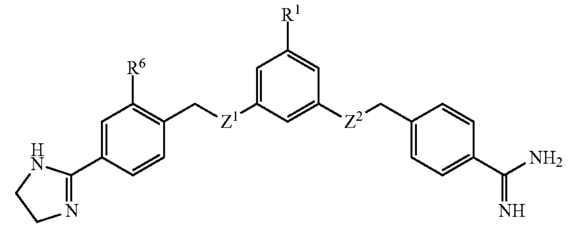
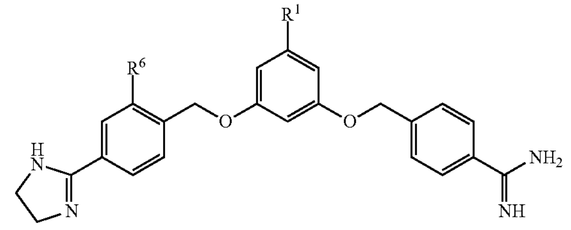
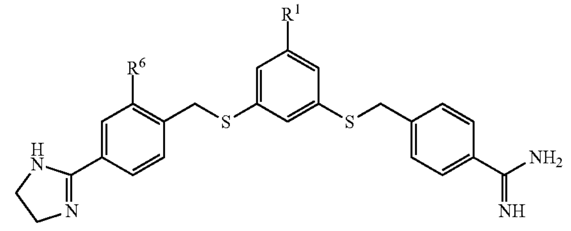
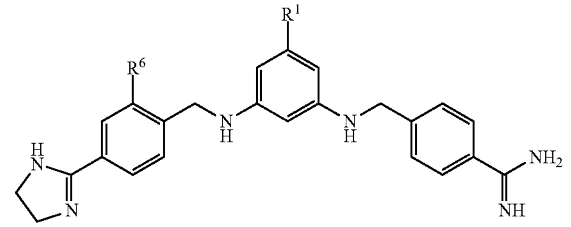
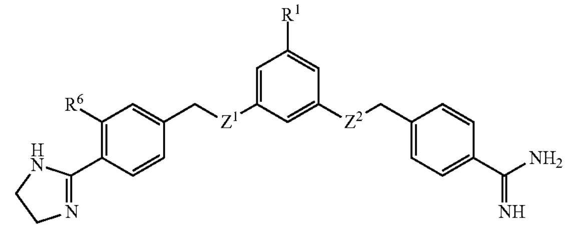
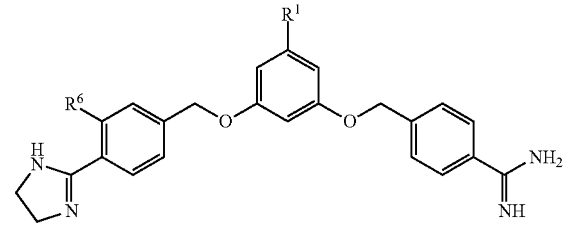
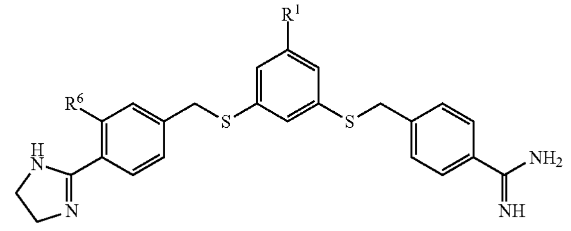

-continued
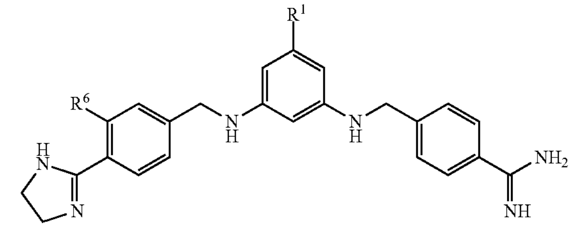
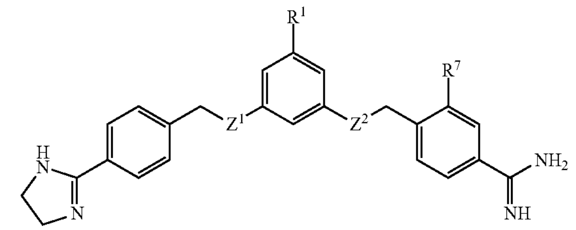
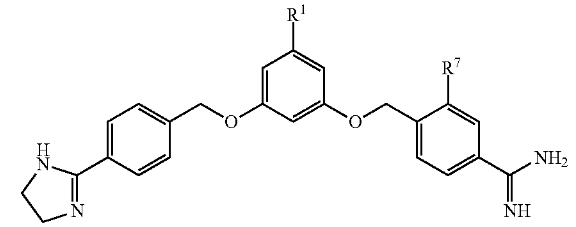
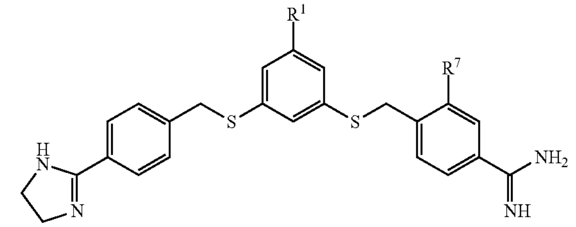
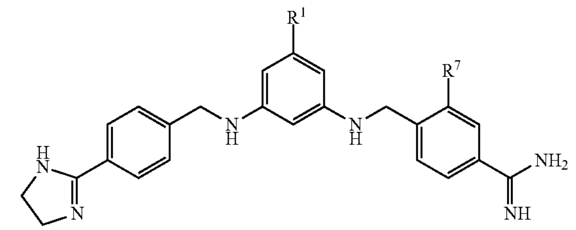
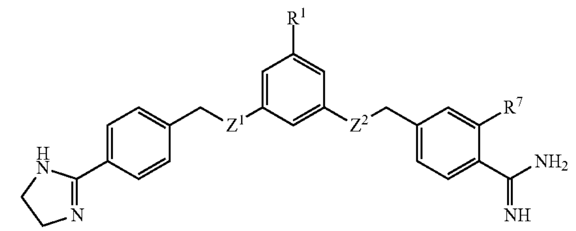
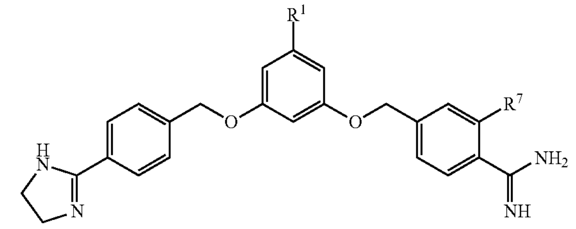
-continued
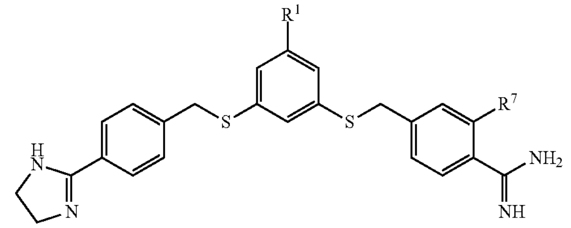
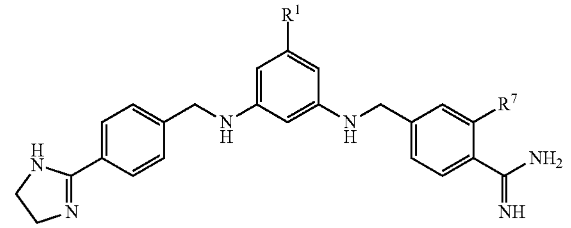
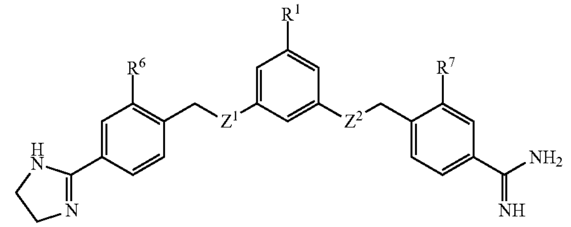
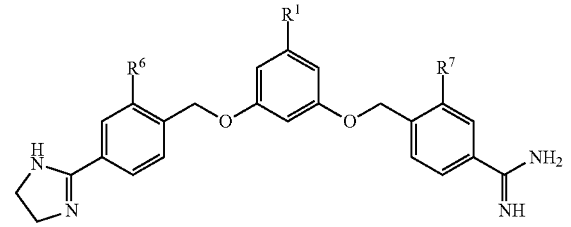
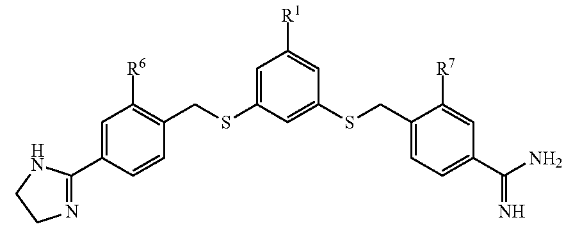
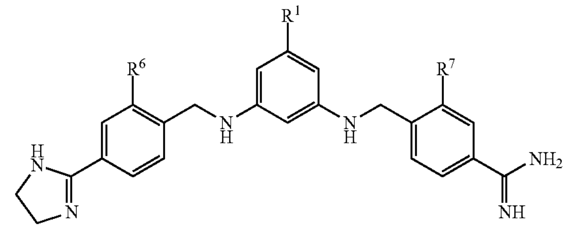
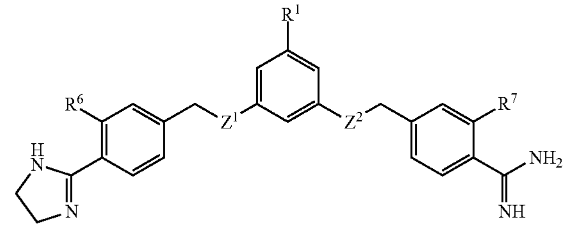

-continued
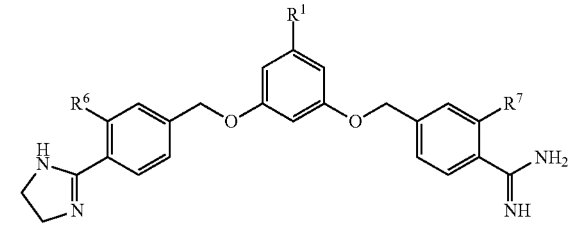
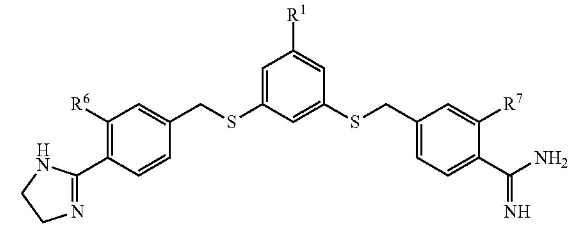
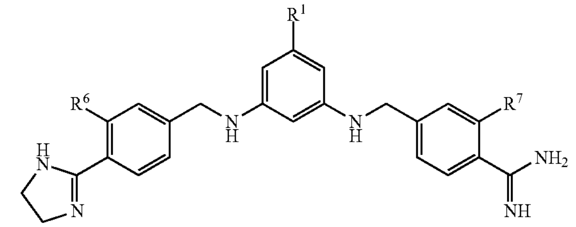
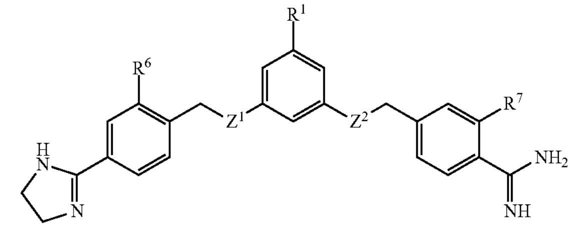
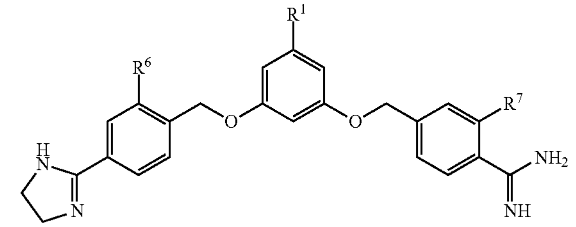
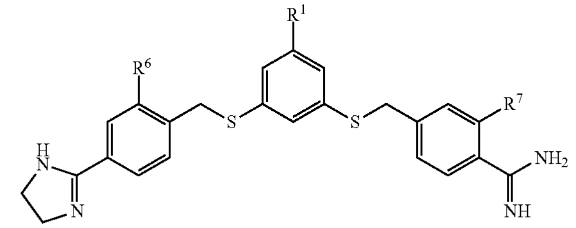
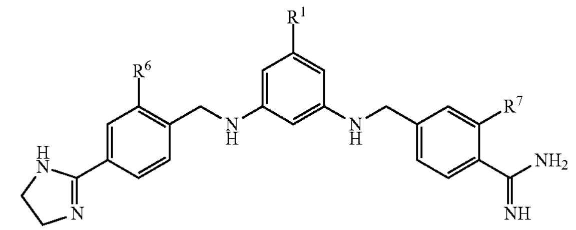
-continued
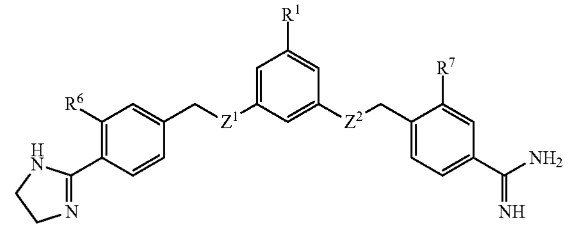
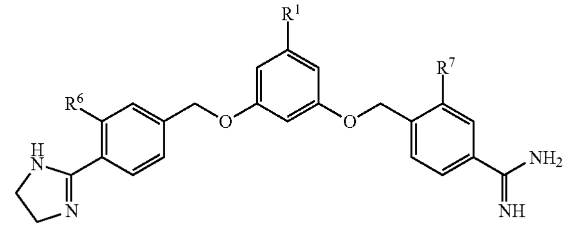
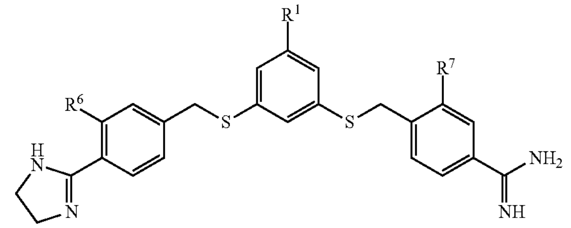
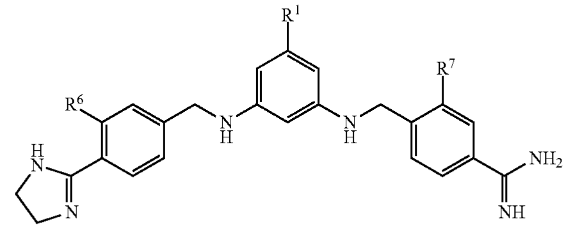
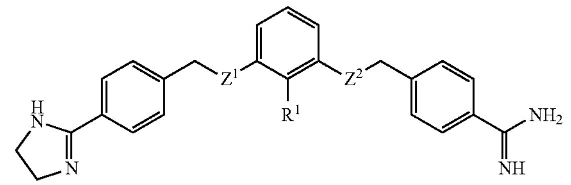
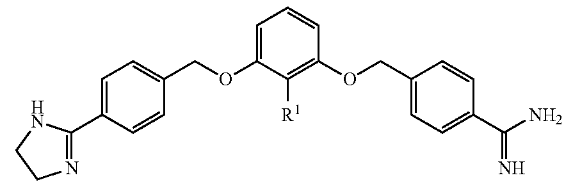
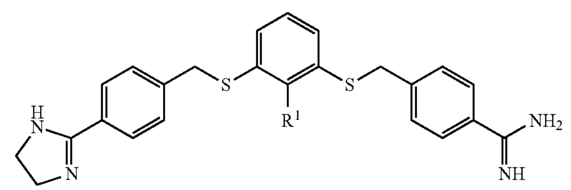
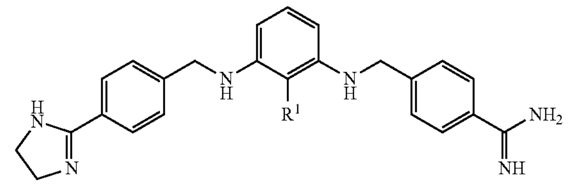

-continued
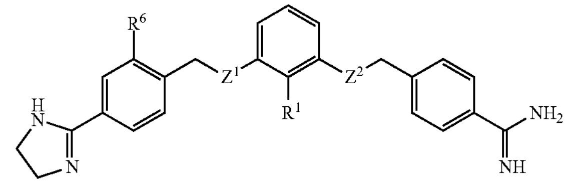
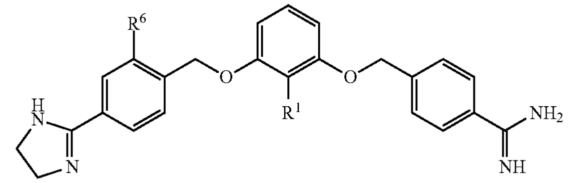
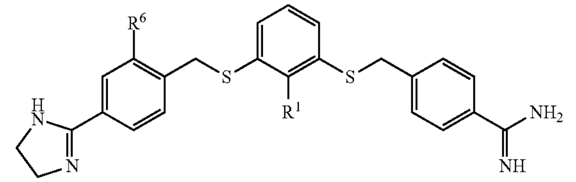
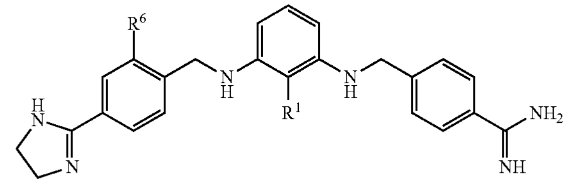
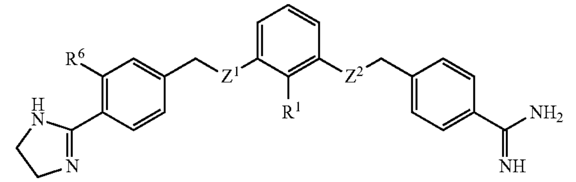
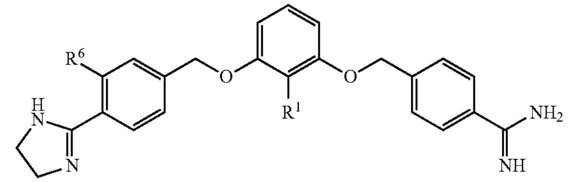
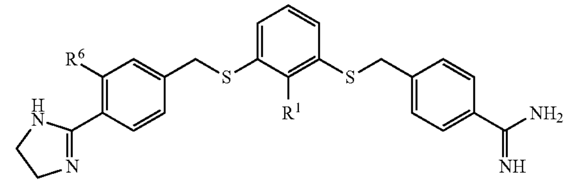
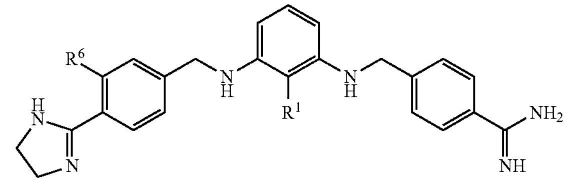
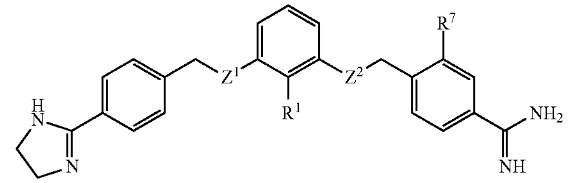
-continued
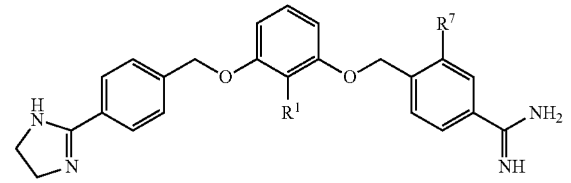
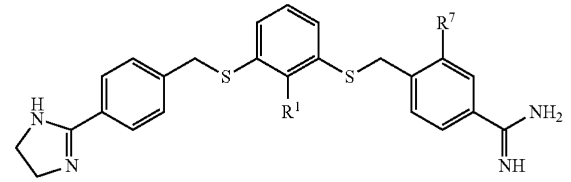
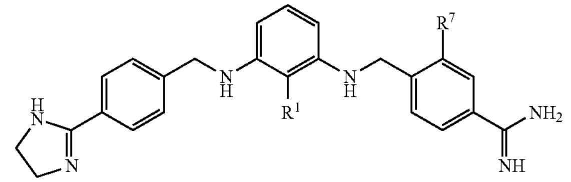
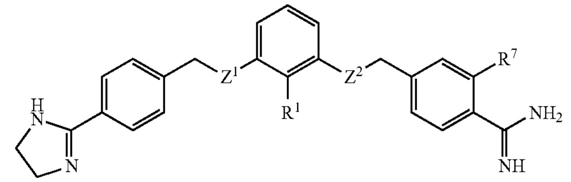
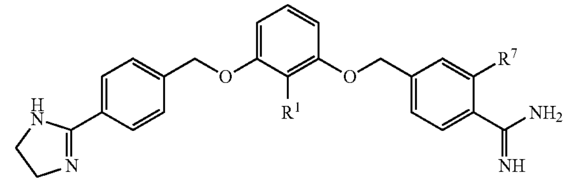
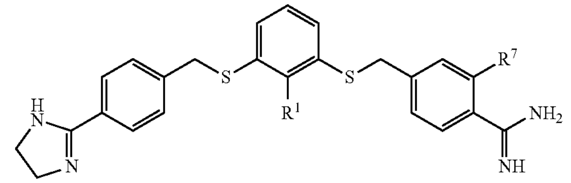
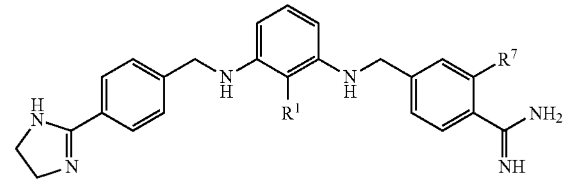
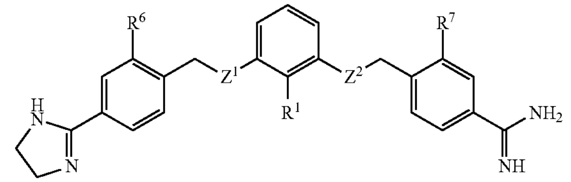
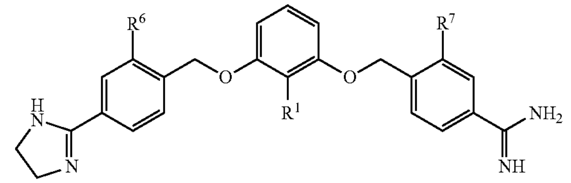

-continued
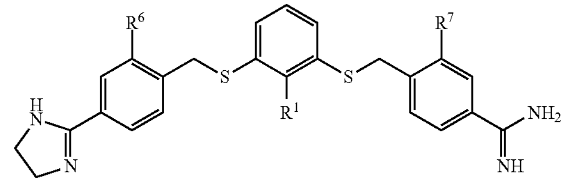
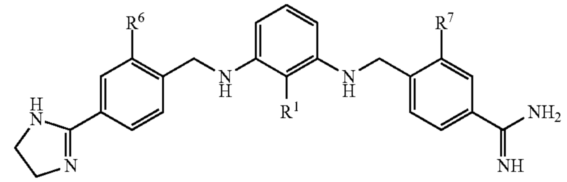
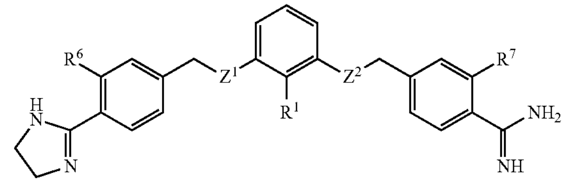
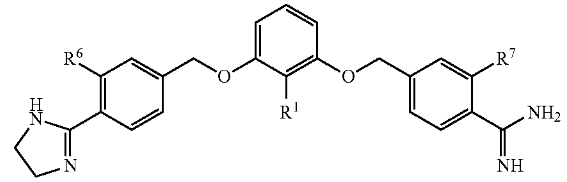
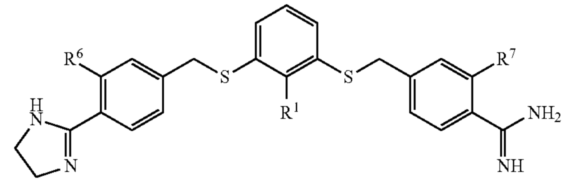
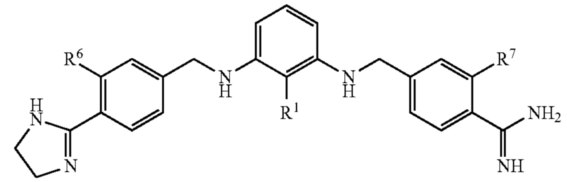
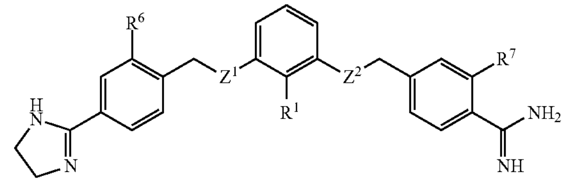
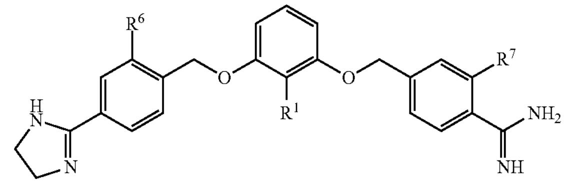
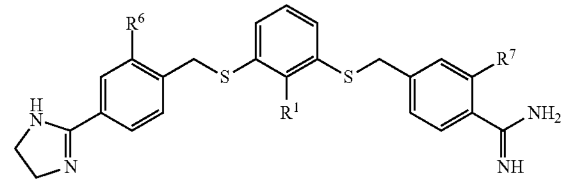
-continued
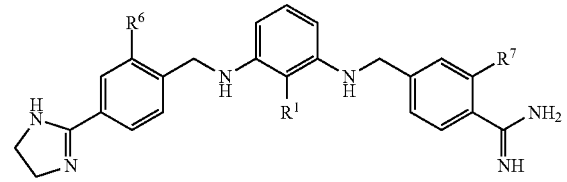
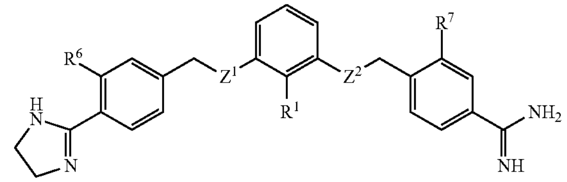
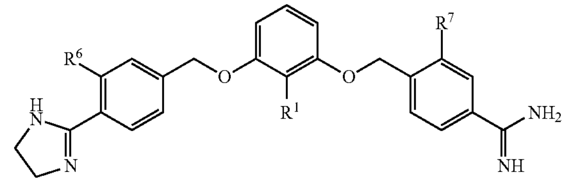
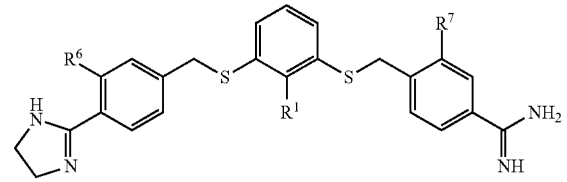
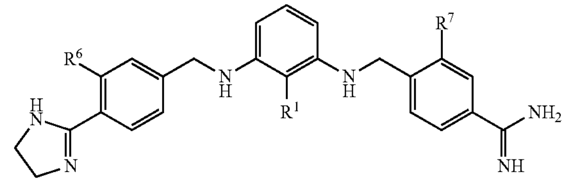
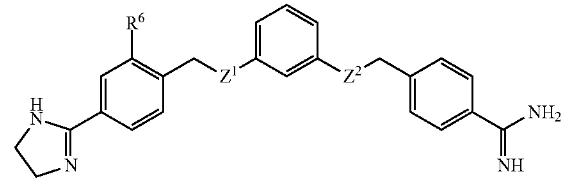
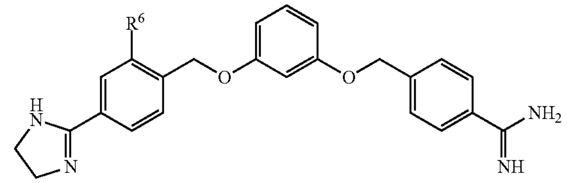
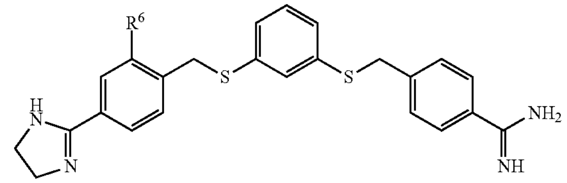
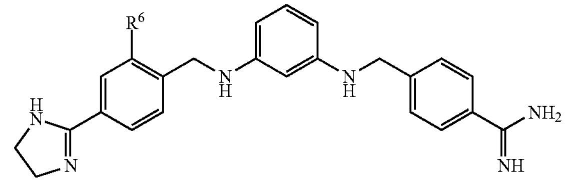

-continued
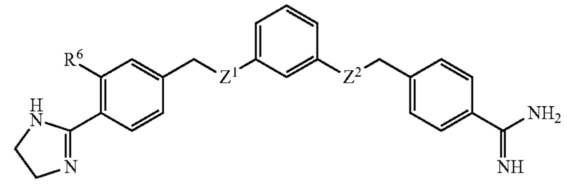
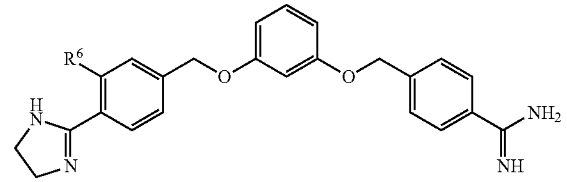
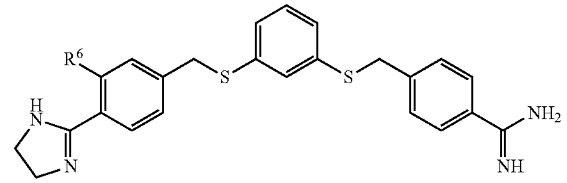
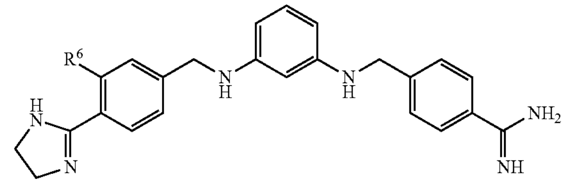
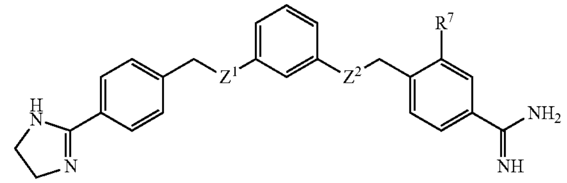
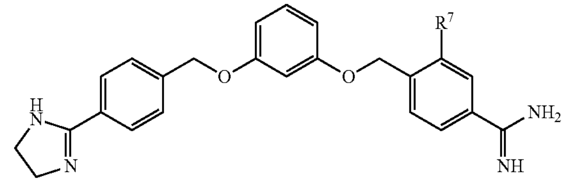
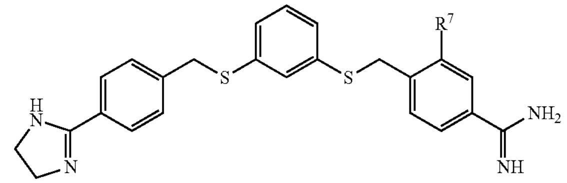
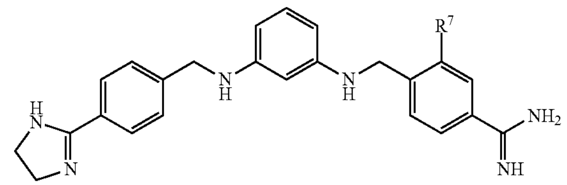
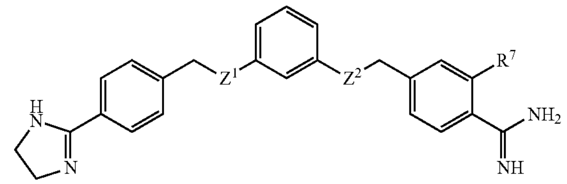
-continued
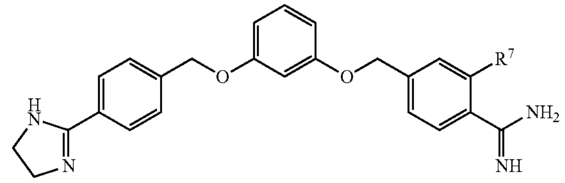
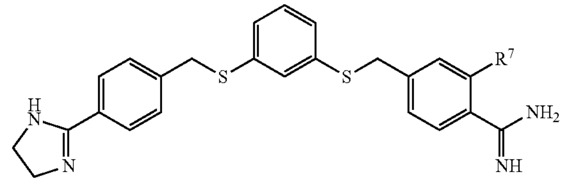
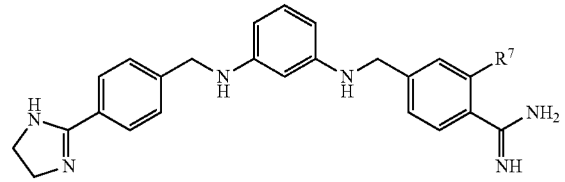
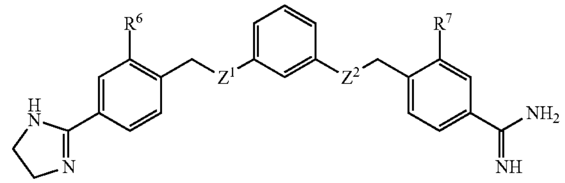
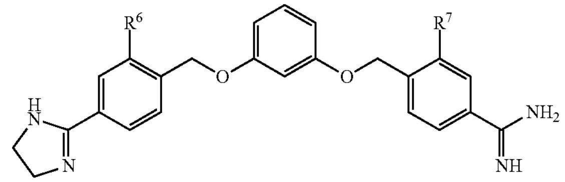
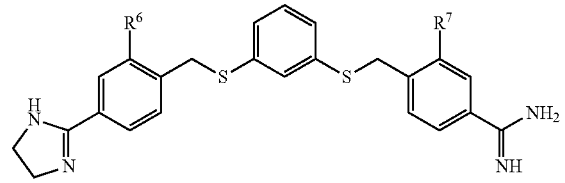
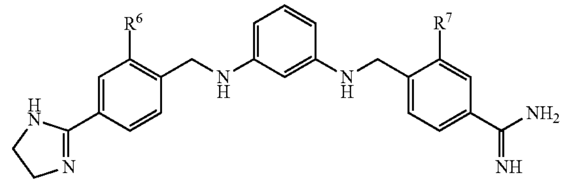
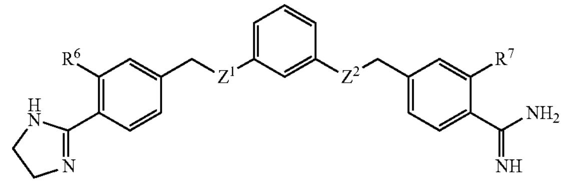
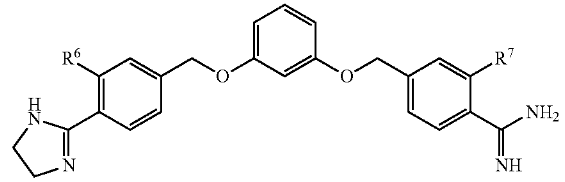

-continued
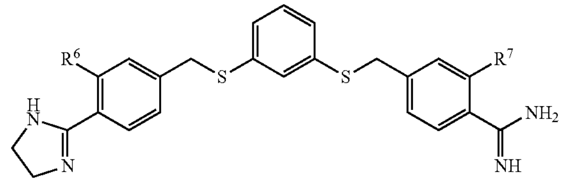
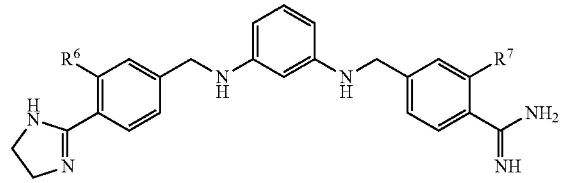
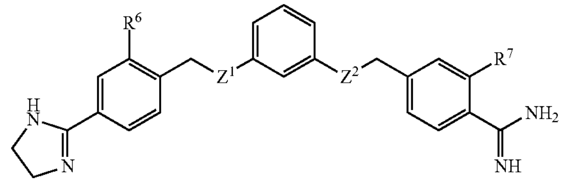
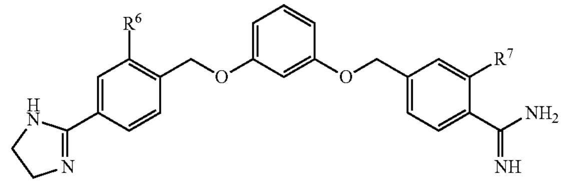
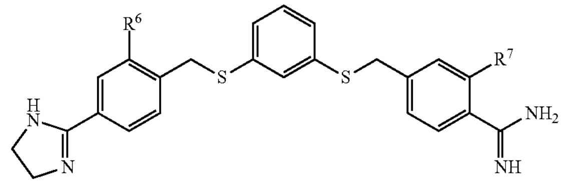
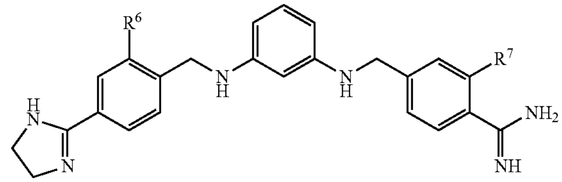
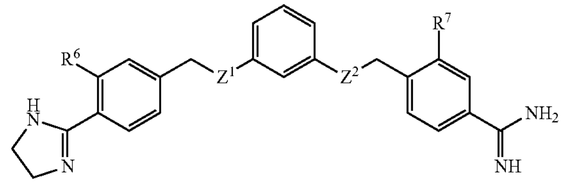
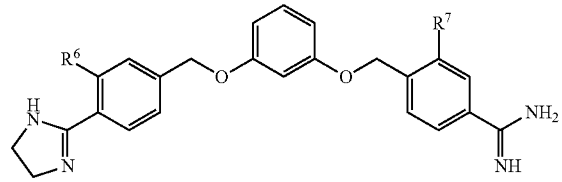
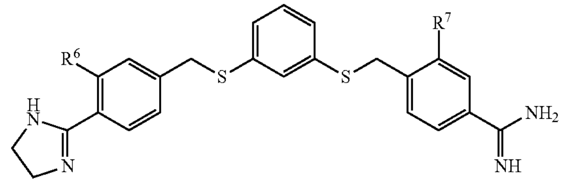
-continued
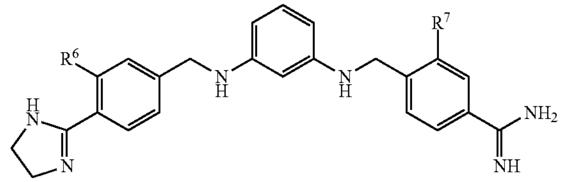
Non-limiting examples of compounds of Formula VIII include:
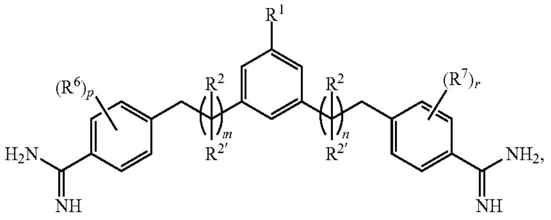
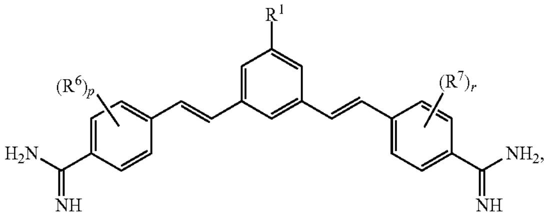
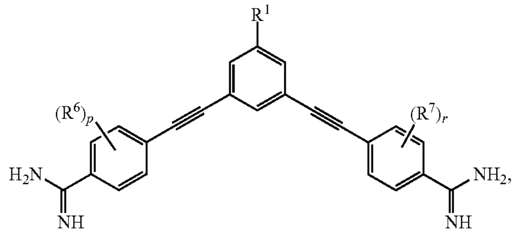
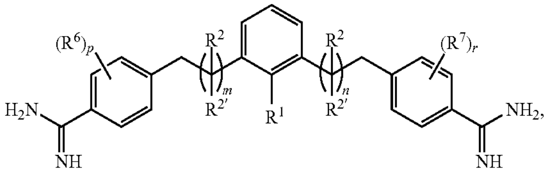
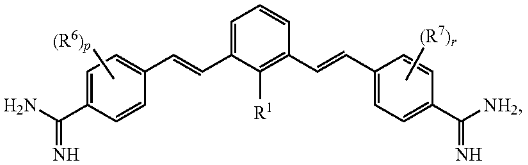
and
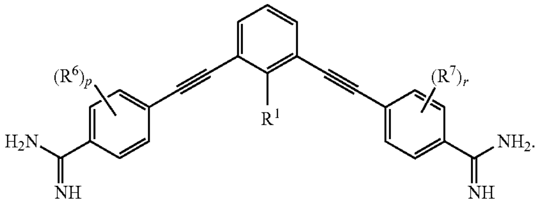
Non-limiting examples of compounds of Formula VIII' include:

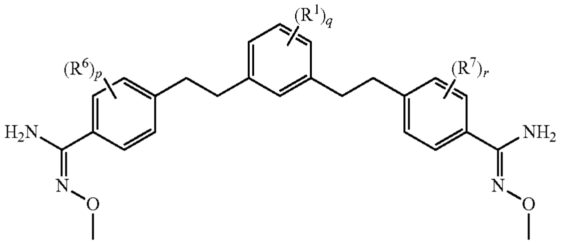
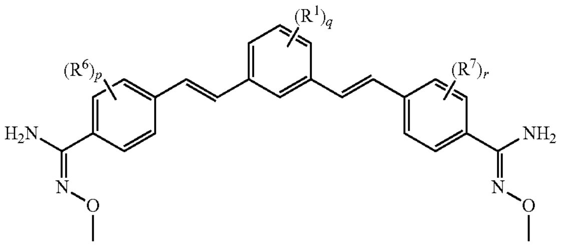
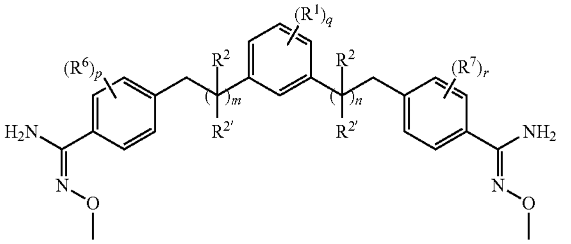
Additional examples of compounds of Formula VIII include:
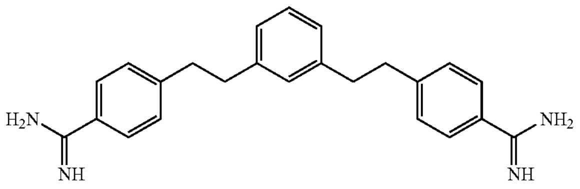
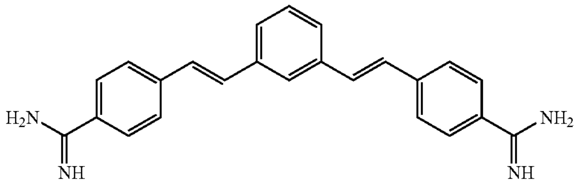
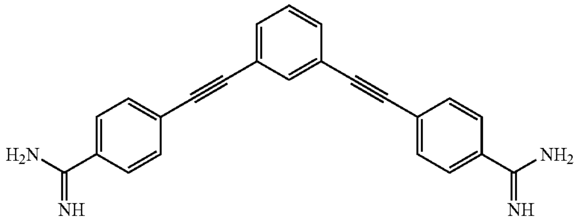
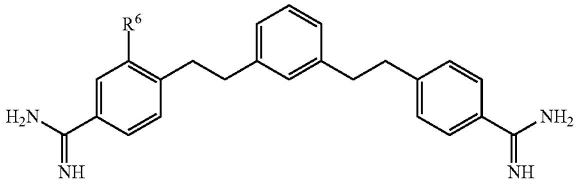
-continued
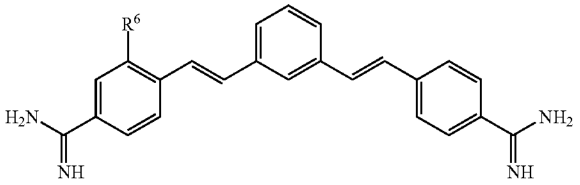
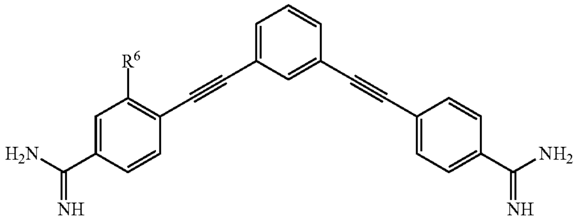
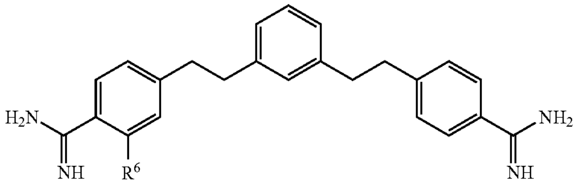
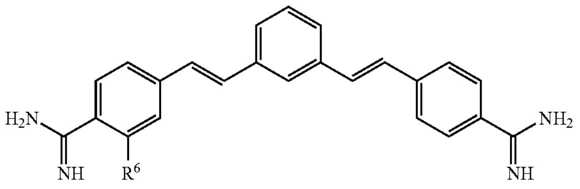
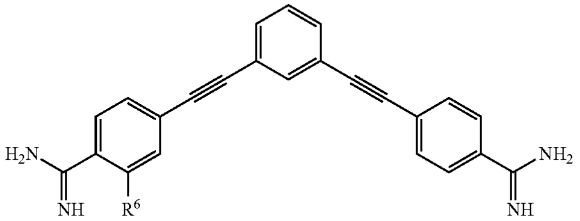
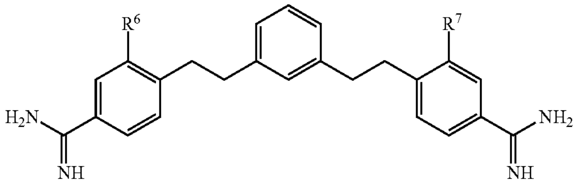
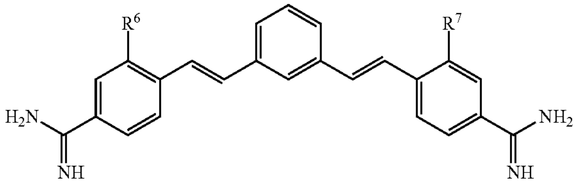
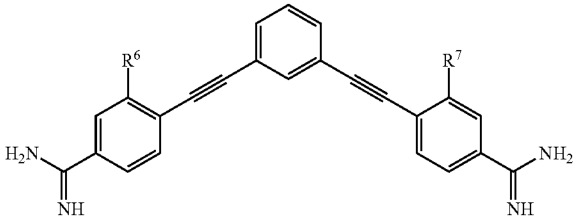

-continued
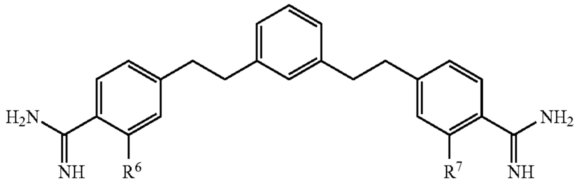
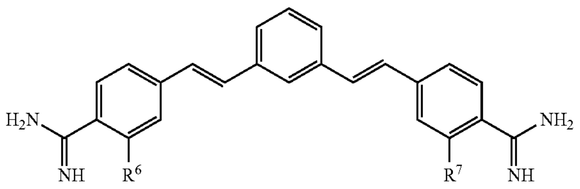
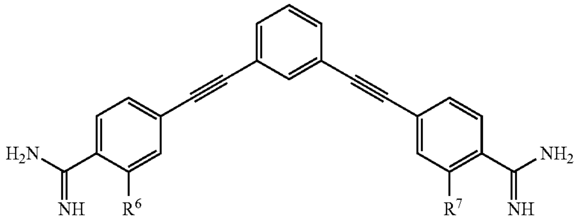
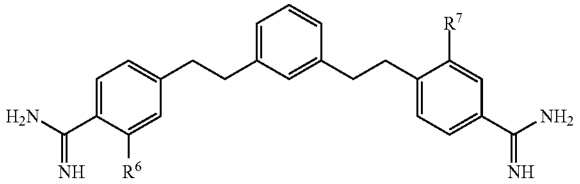
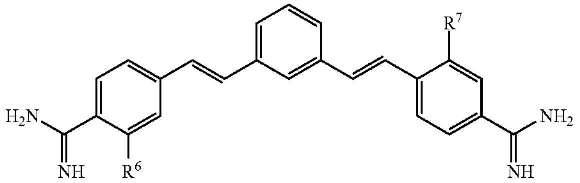
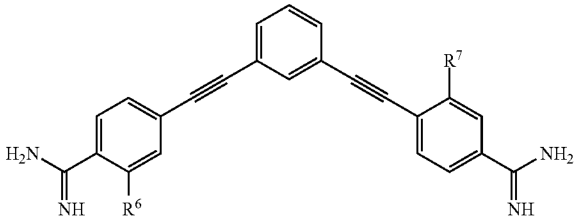
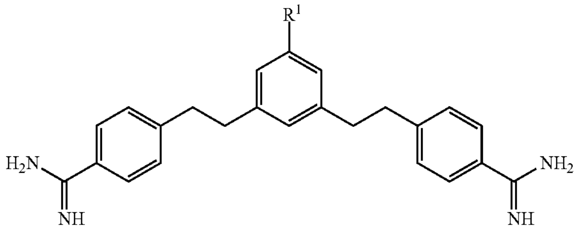
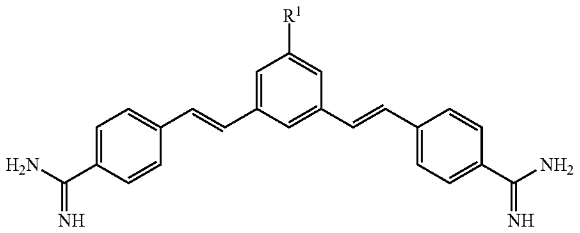
-continued
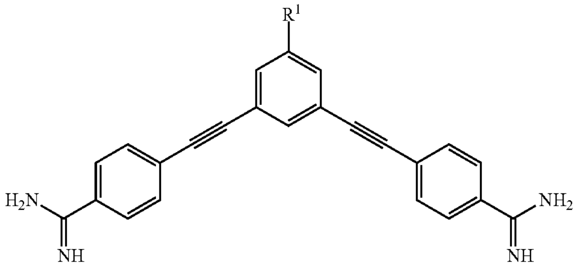
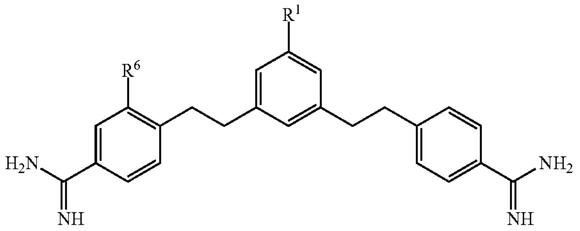
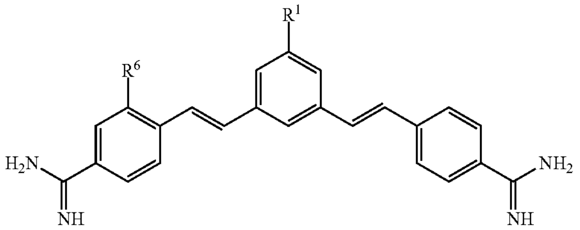
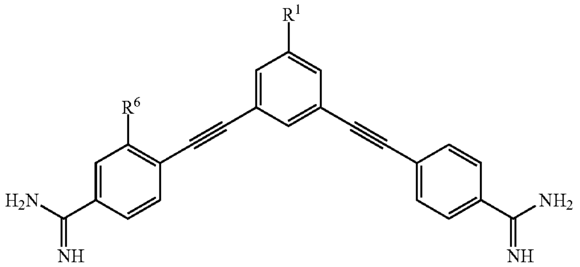
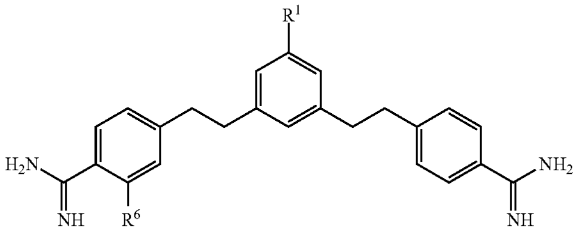
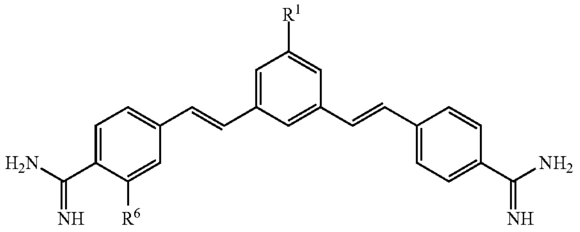
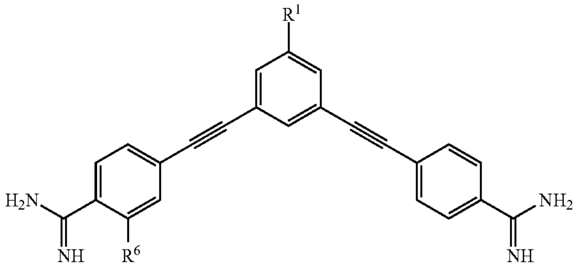

-continued
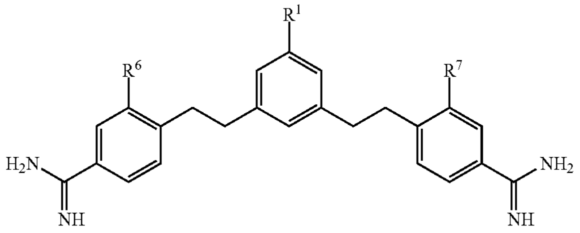
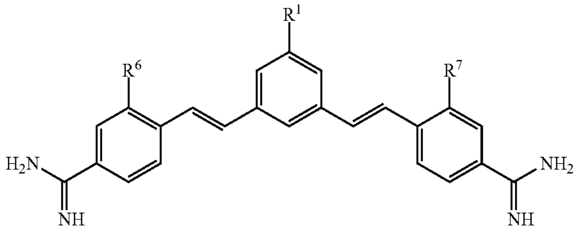
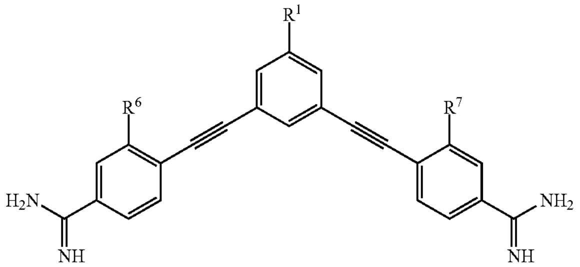
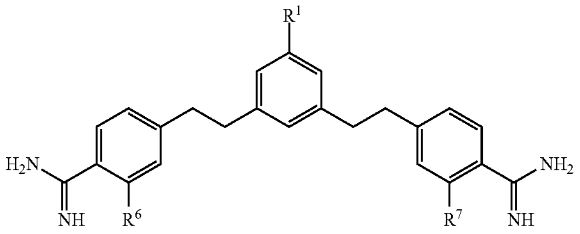
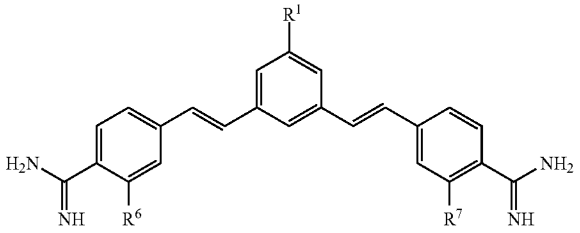
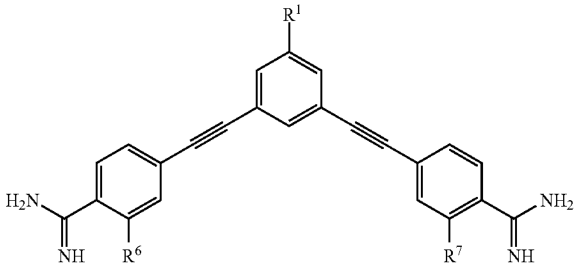
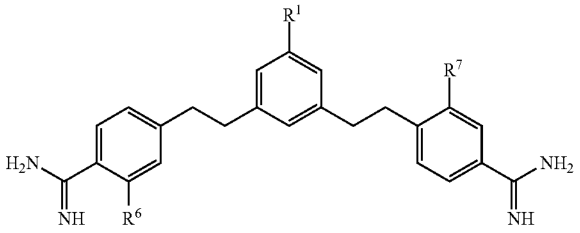
-continued
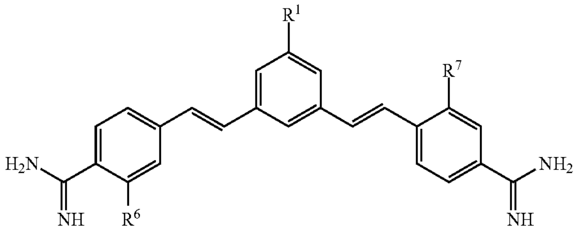
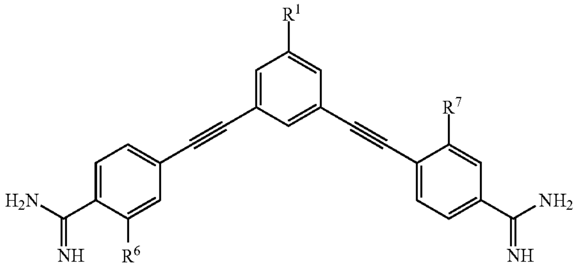
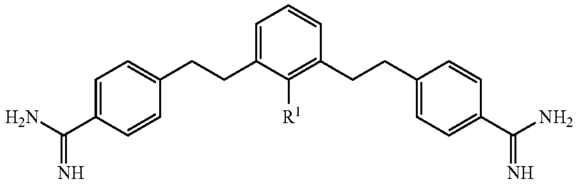
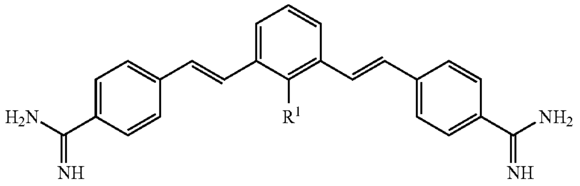
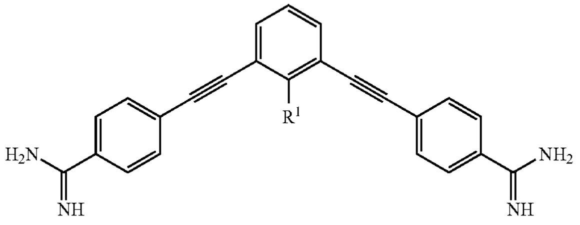
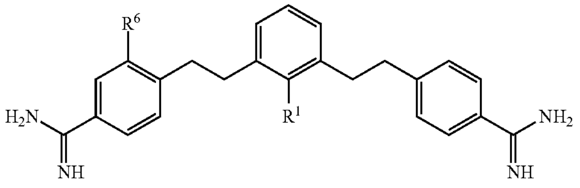
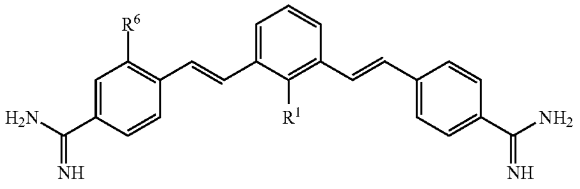
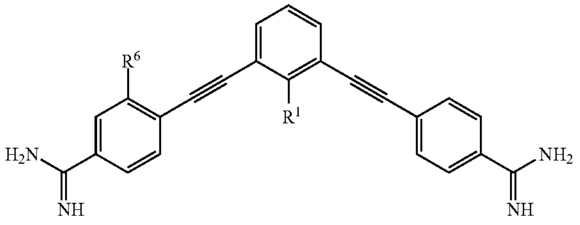

-continued
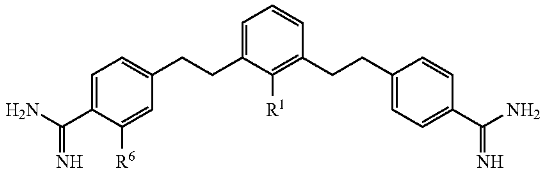
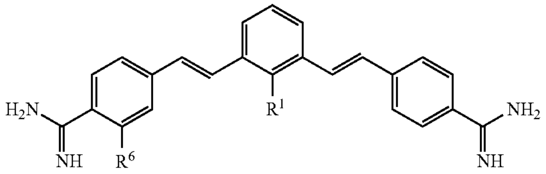
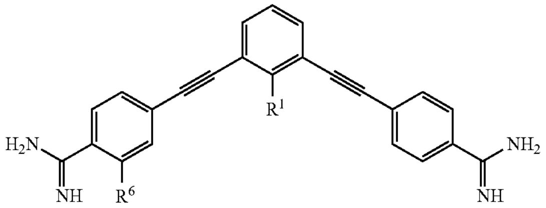
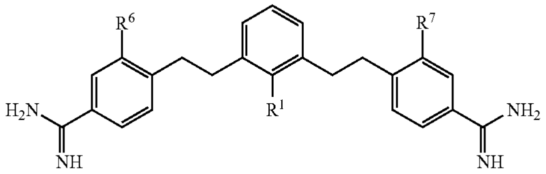
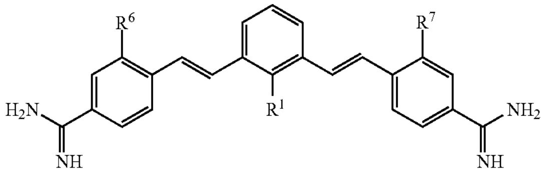
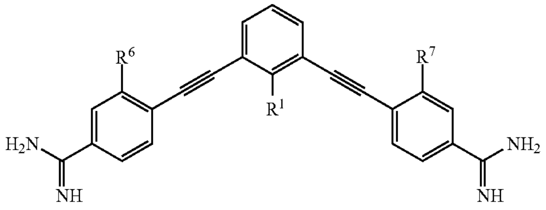
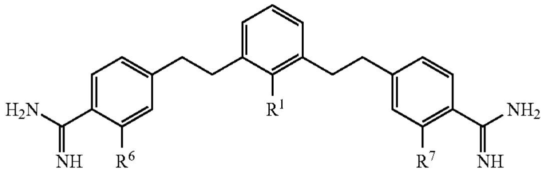
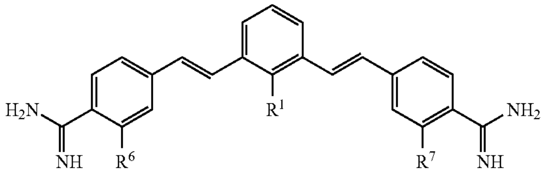
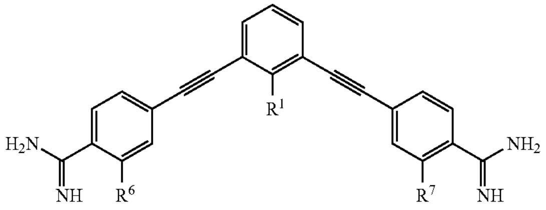
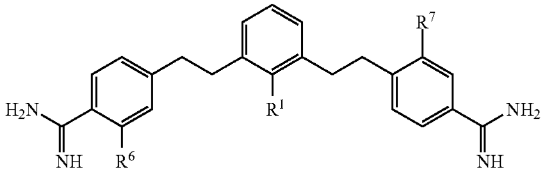
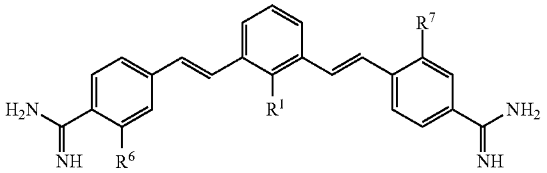
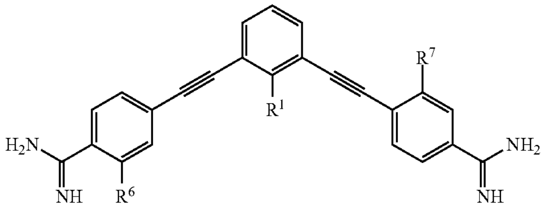
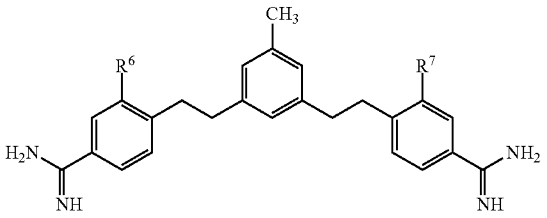
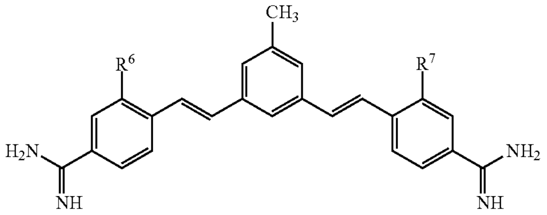
Non-limiting examples of compounds of Formula IX include:
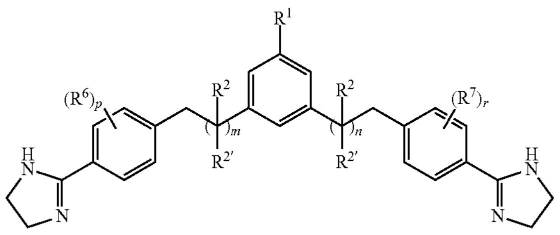
,
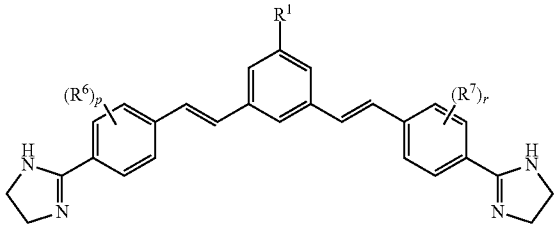
, -continued
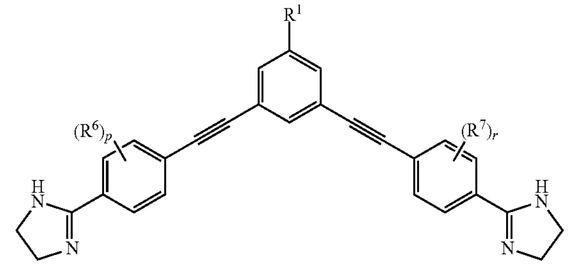
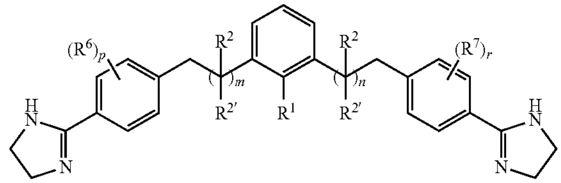
,
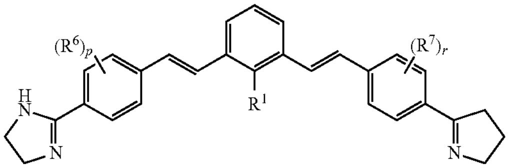
, and
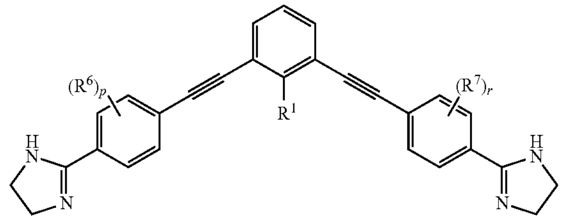
.
Non-limiting examples of compounds of Formula IX include.
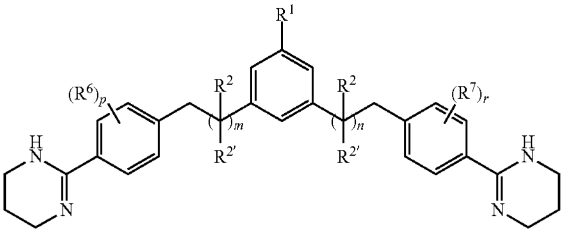
,
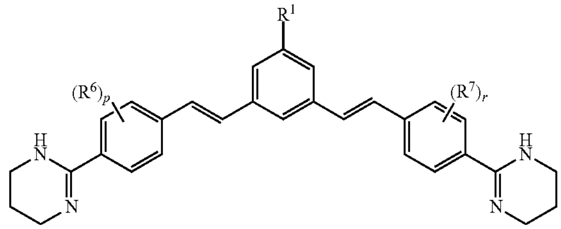
,
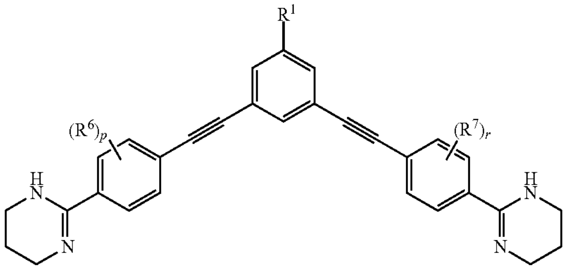
,
-continued
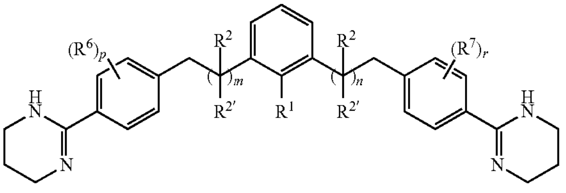
,
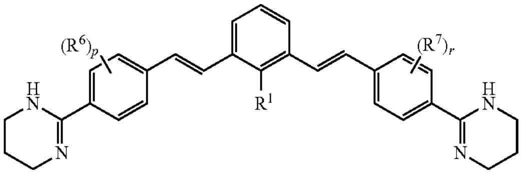
, and
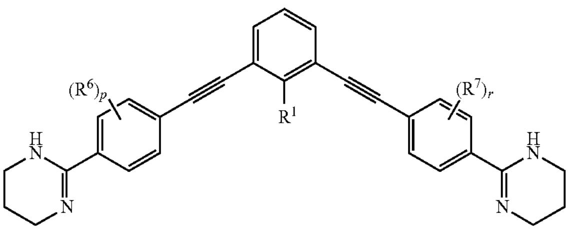
.
Non-limiting examples of compounds of Formula IX include:
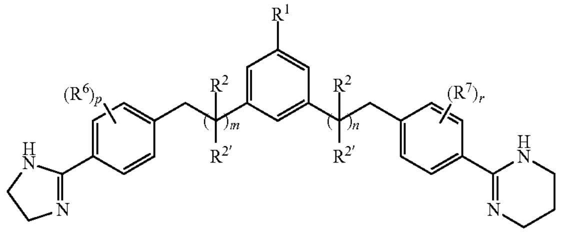
,
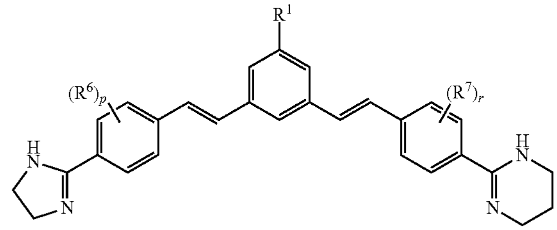
,
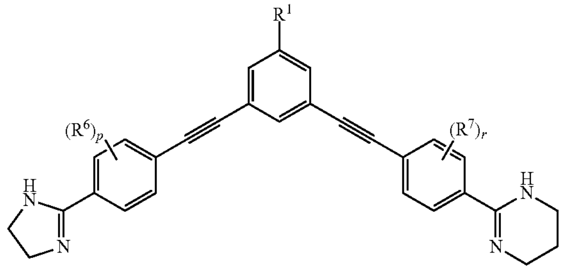
,
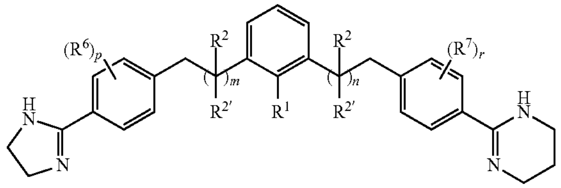
, -continued
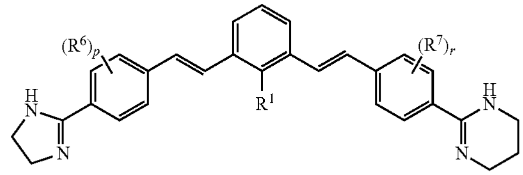
, and
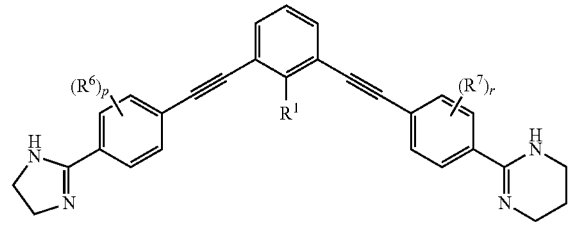
.
Additional examples of compounds of Formula IX include.
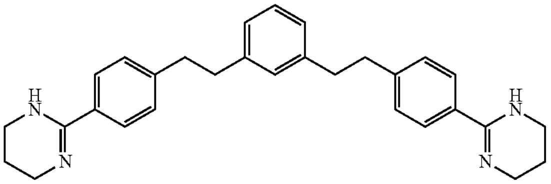
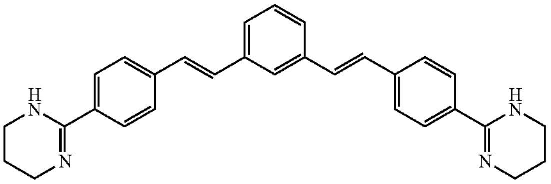
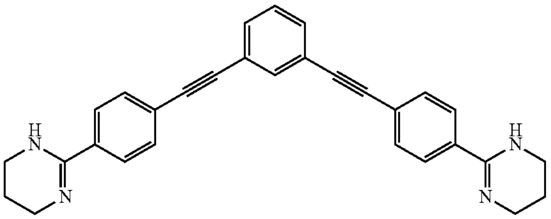
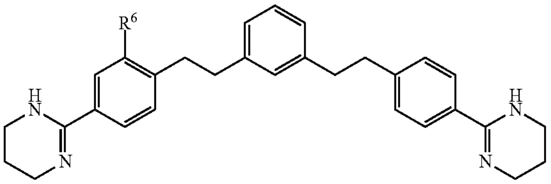
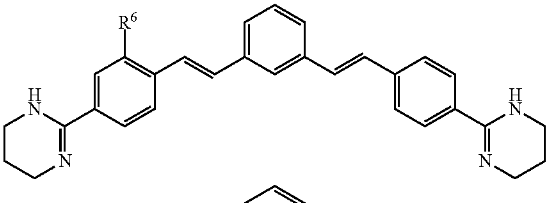
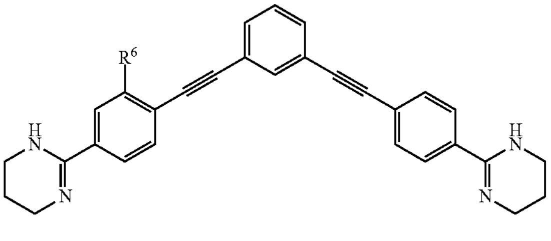
-continued
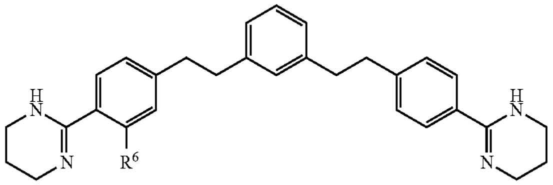
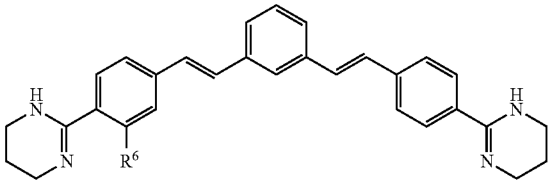
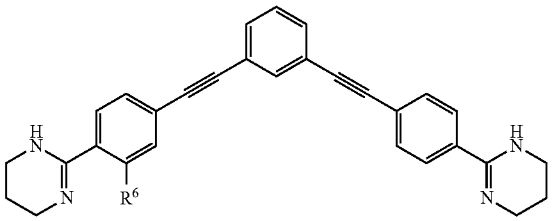
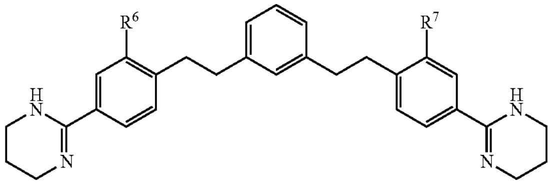
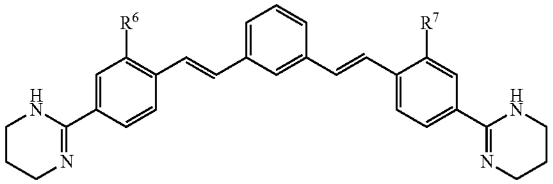
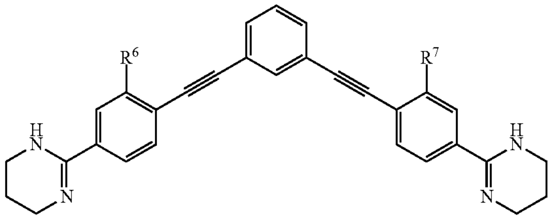
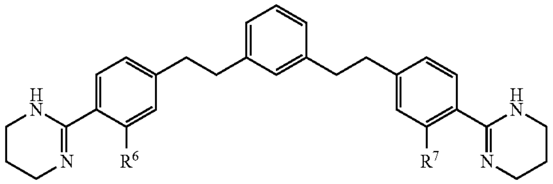
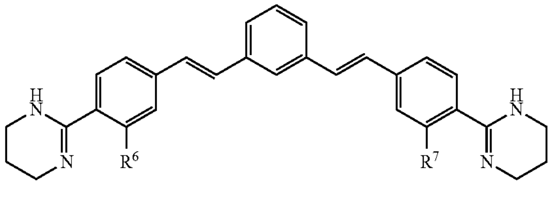

-continued
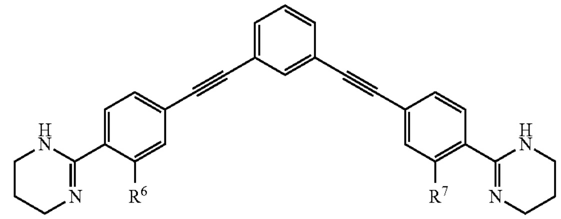
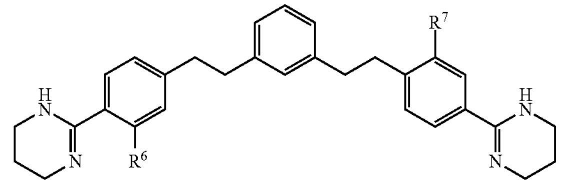
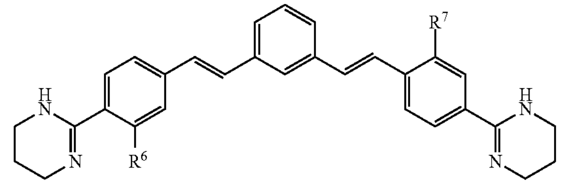
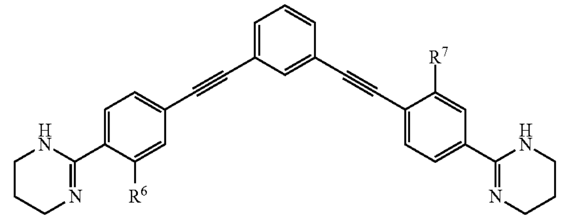
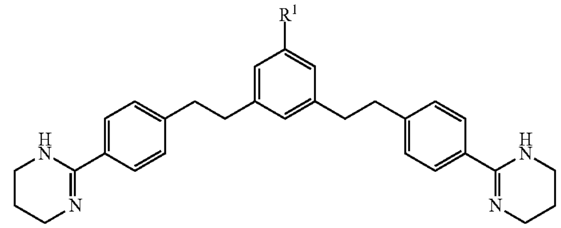
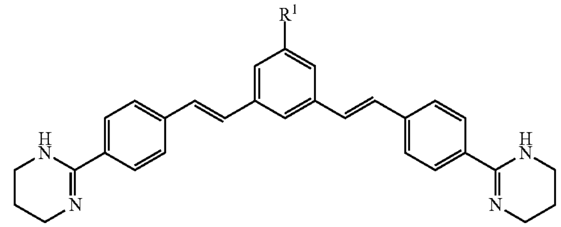
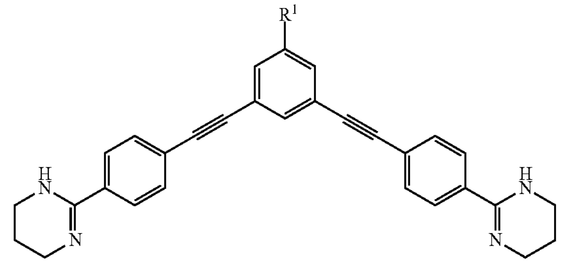
-continued
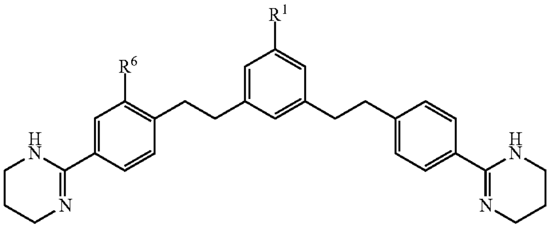
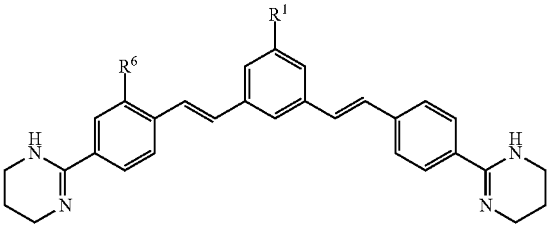
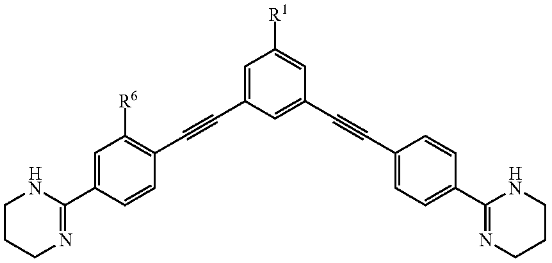
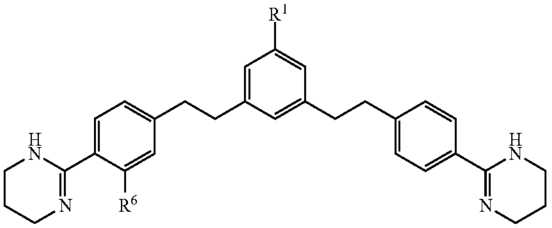
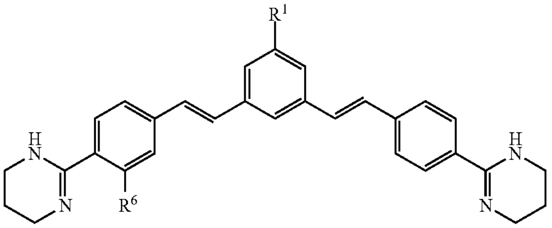
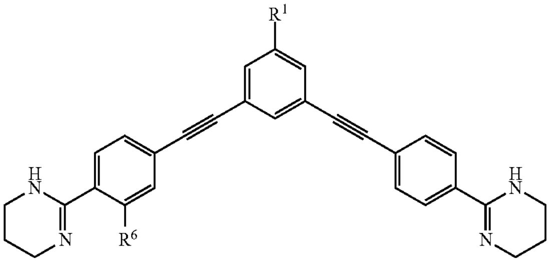
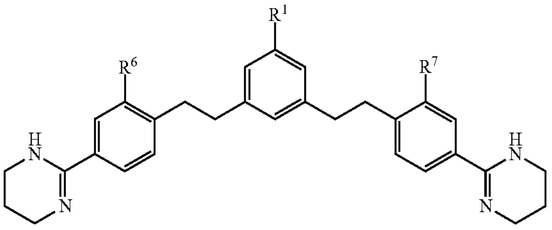

-continued
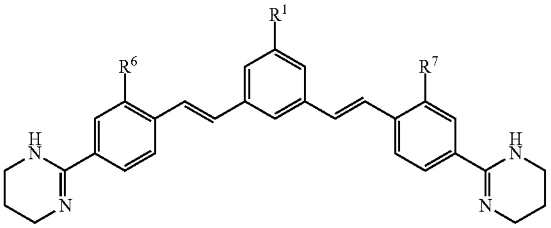
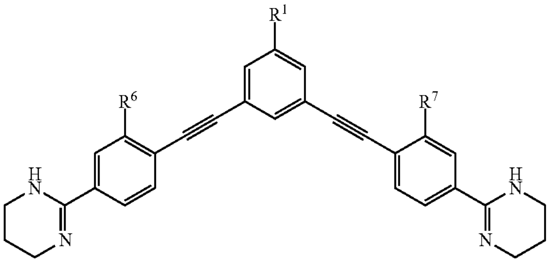
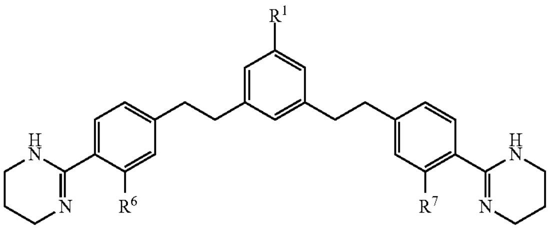
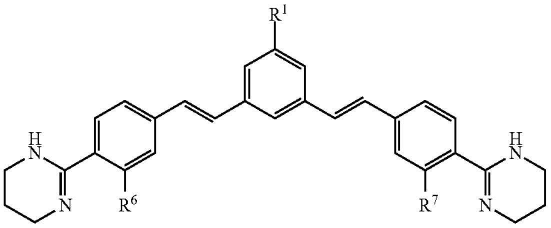
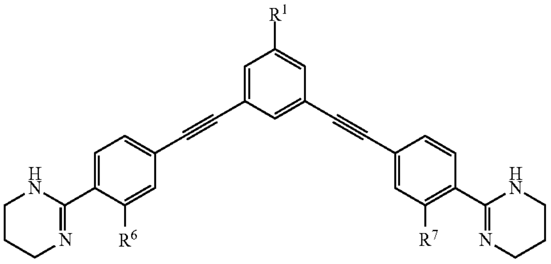
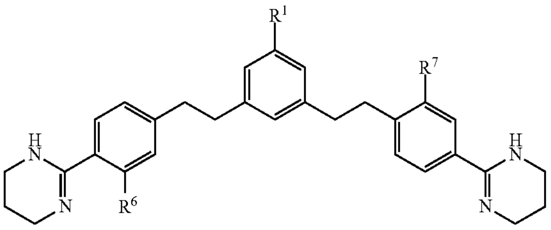
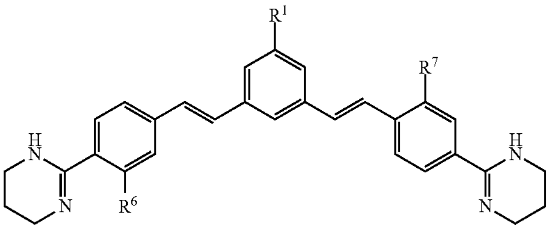
-continued
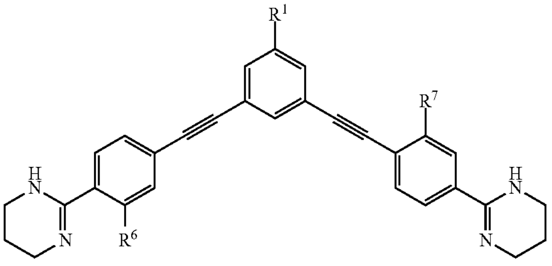
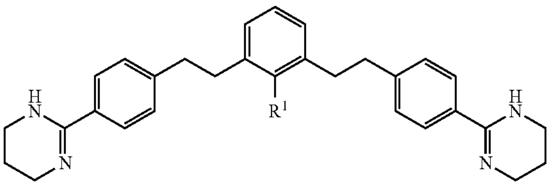
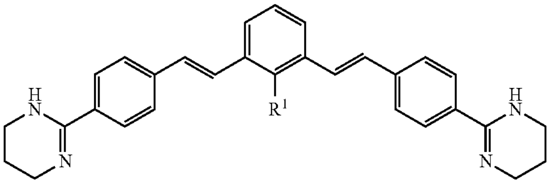
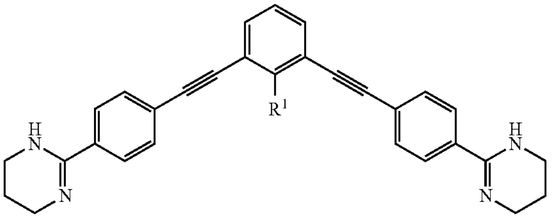
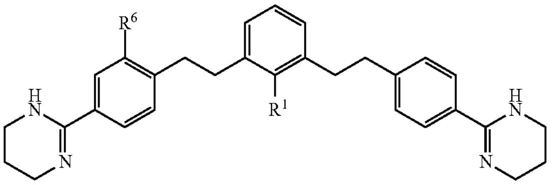
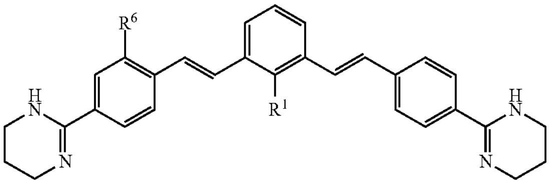
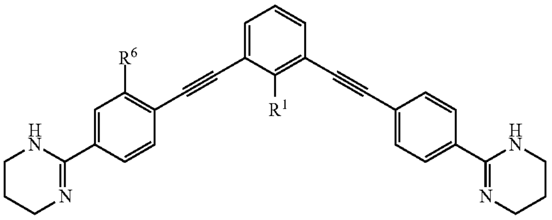
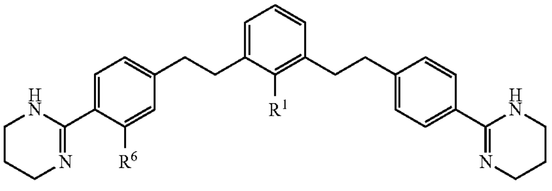

-continued
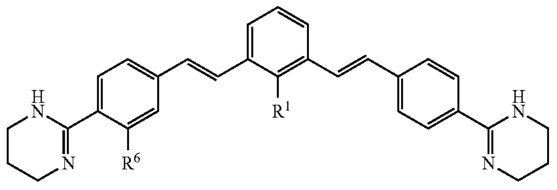
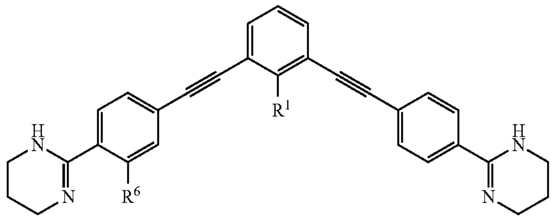
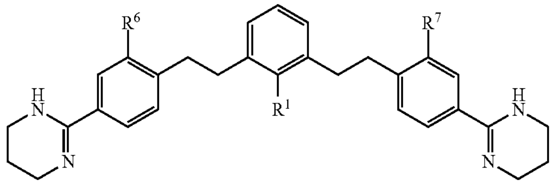
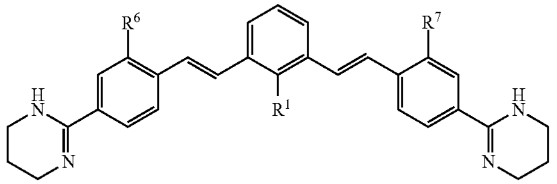
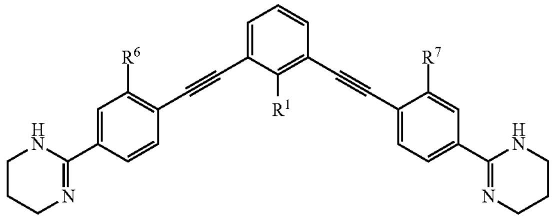
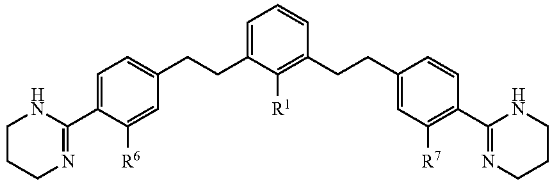
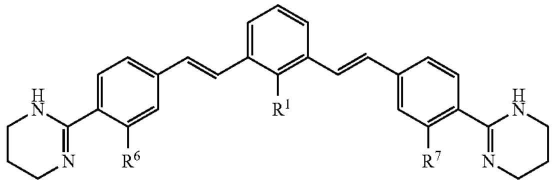
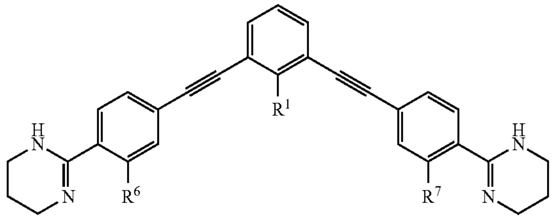
-continued
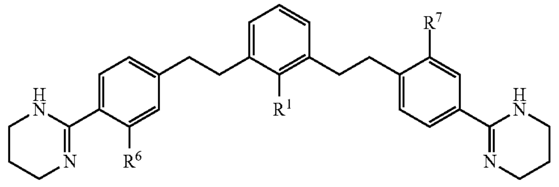
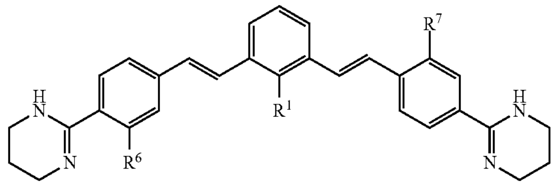
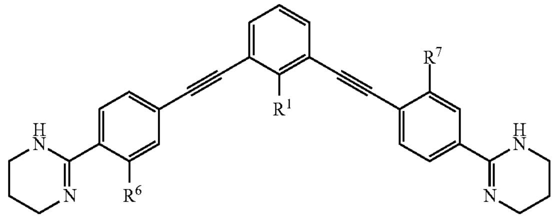
Additional examples of compounds of Formula IX include:
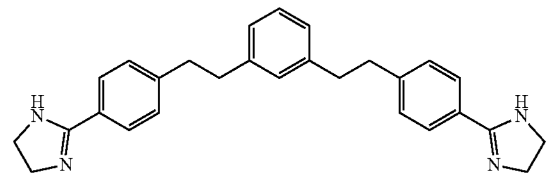
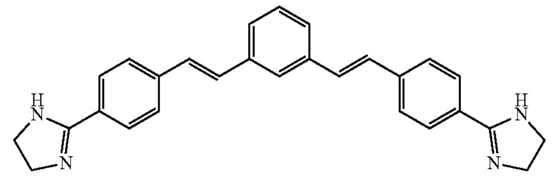
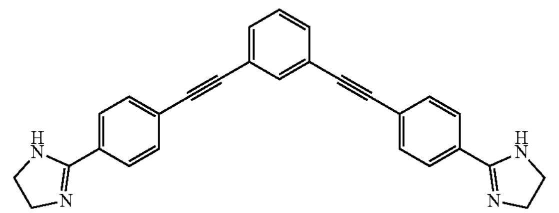
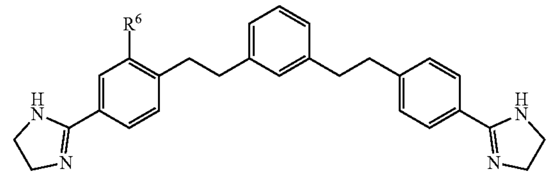
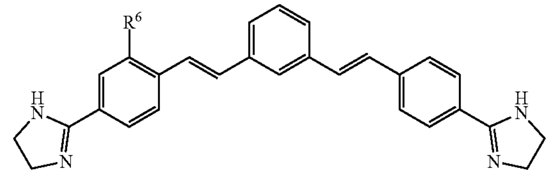

-continued
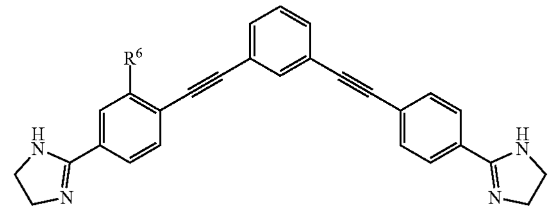
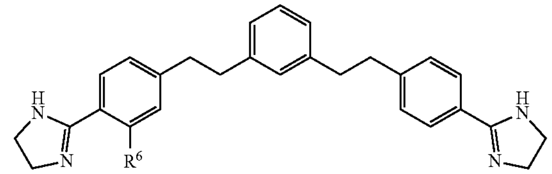
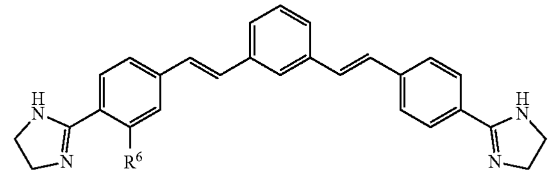
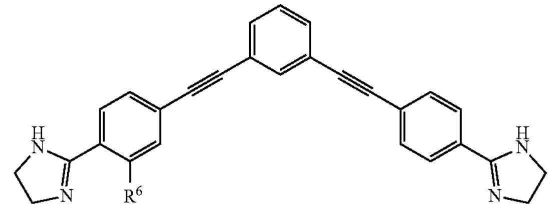
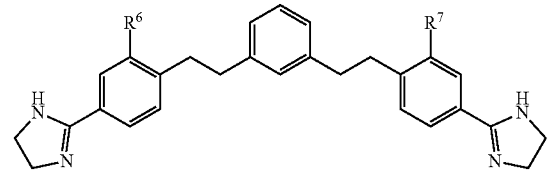
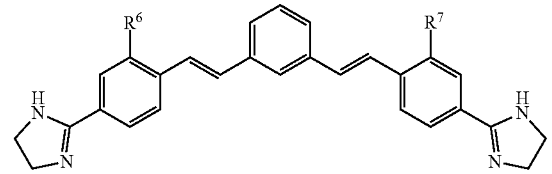
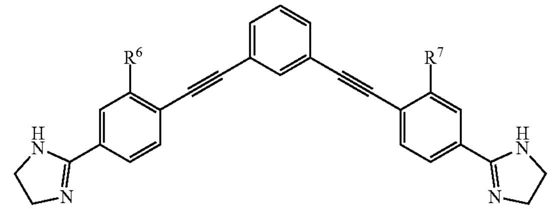
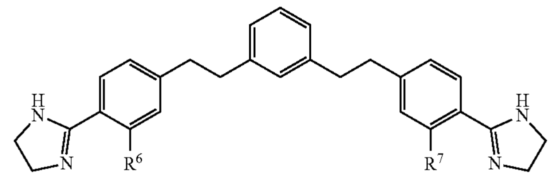
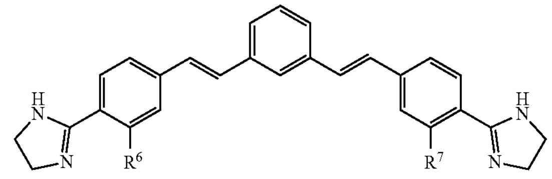
-continued
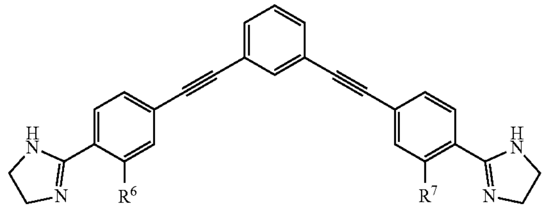
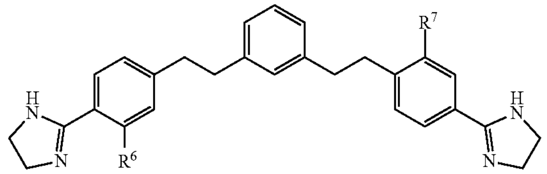
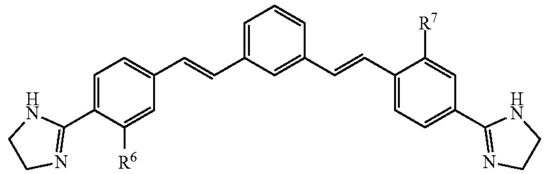
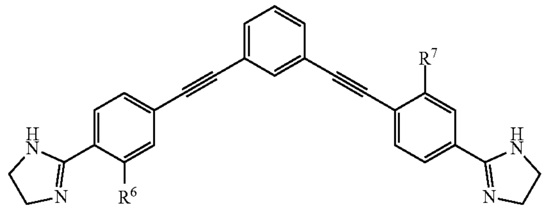
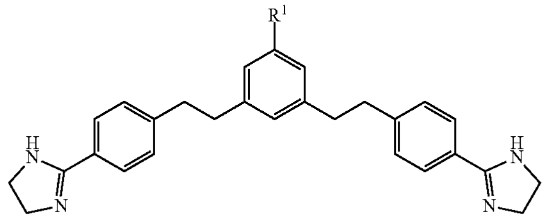
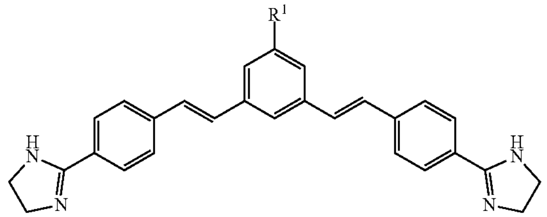
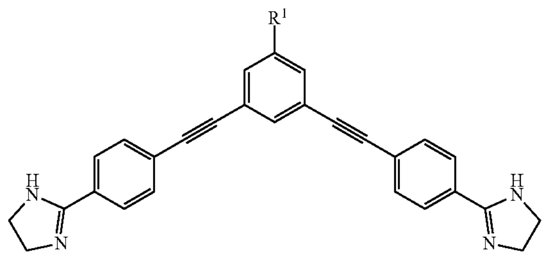
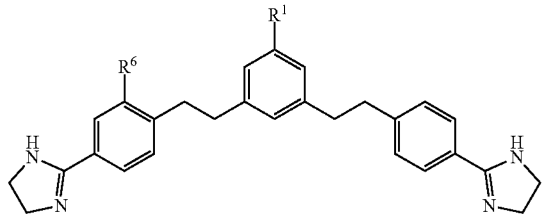

-continued
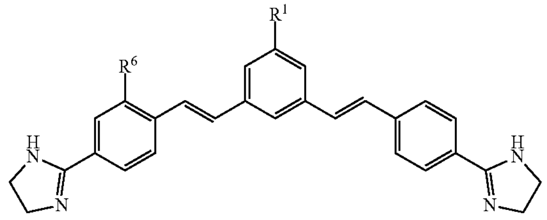
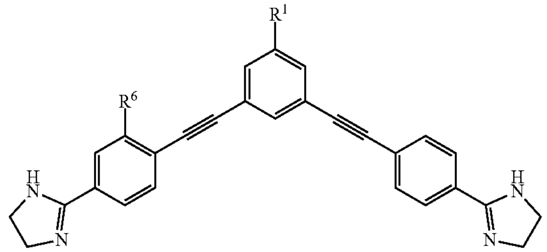
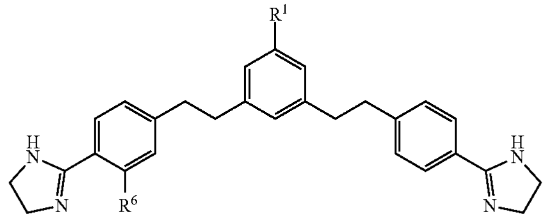
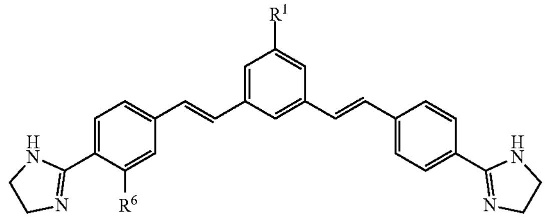
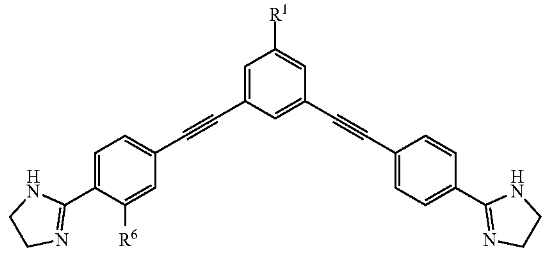
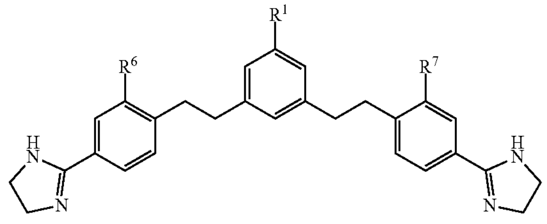
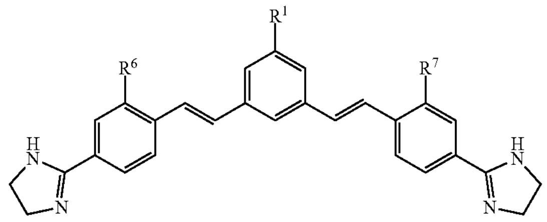
-continued
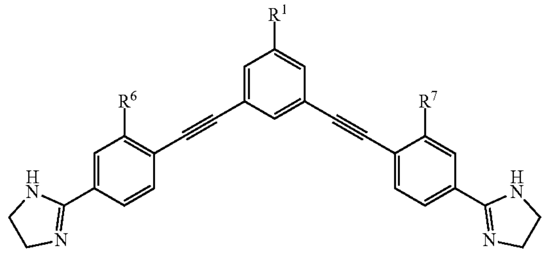
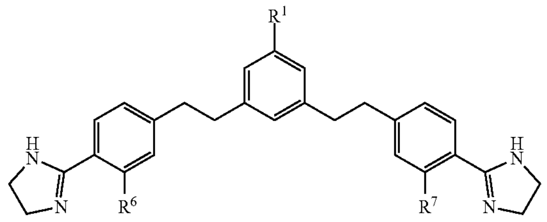
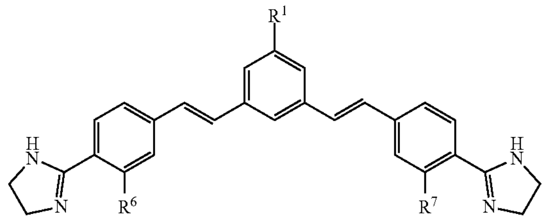
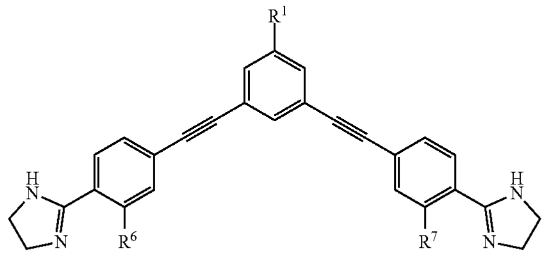
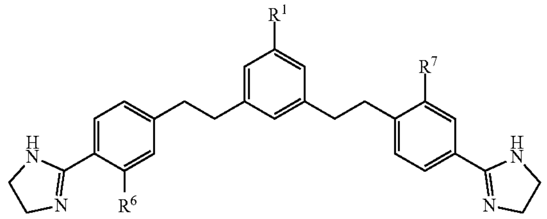
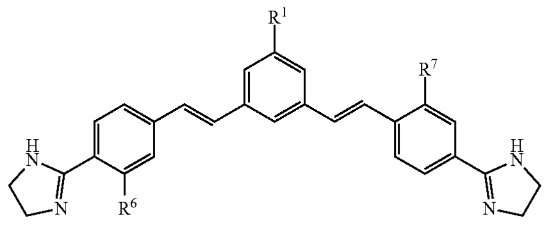
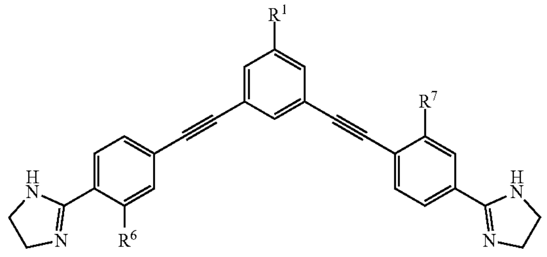

-continued
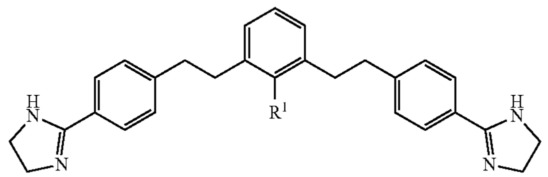
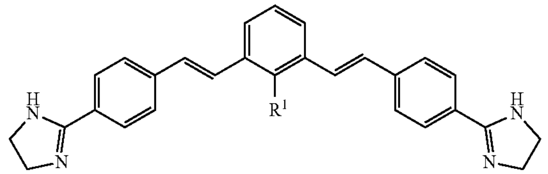
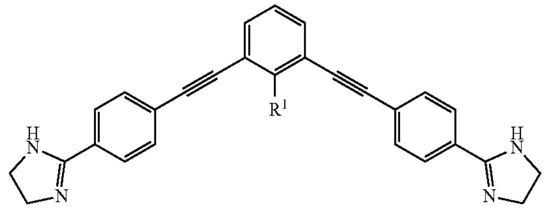
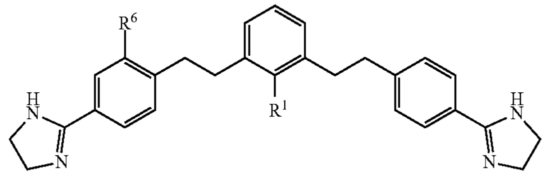
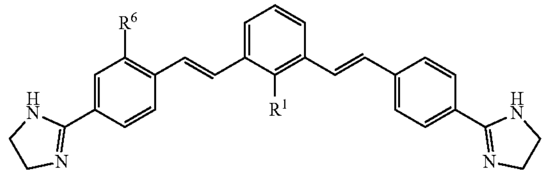
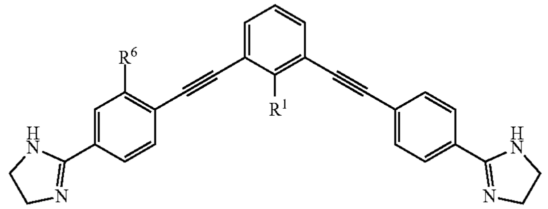
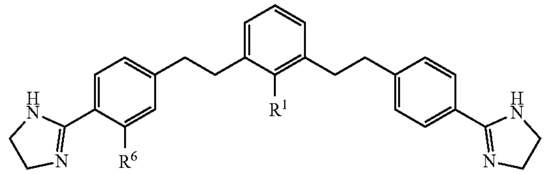
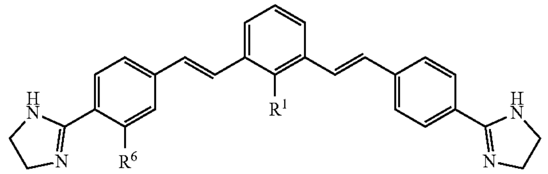
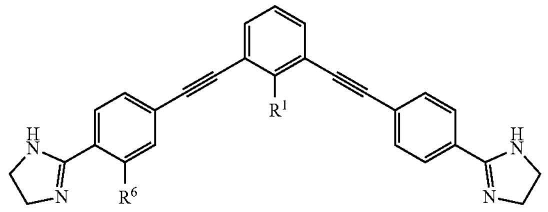
-continued
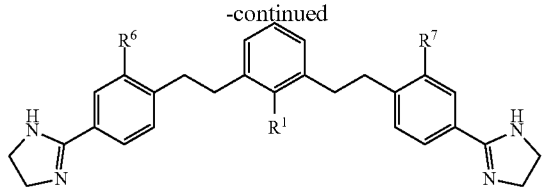
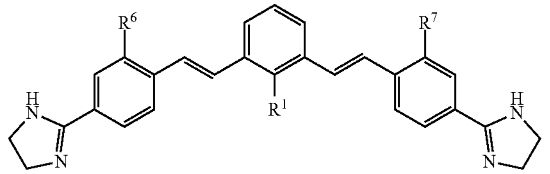
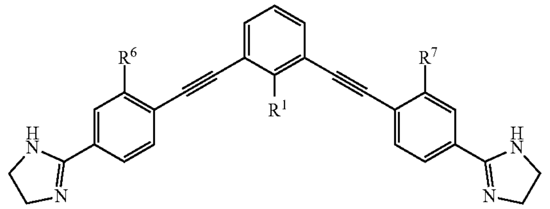
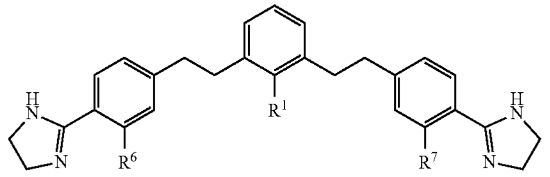
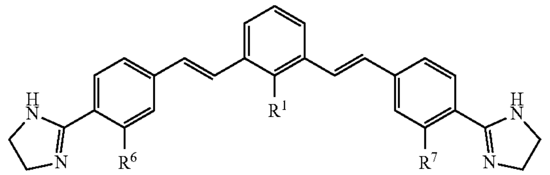
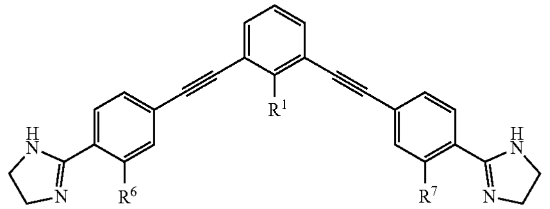
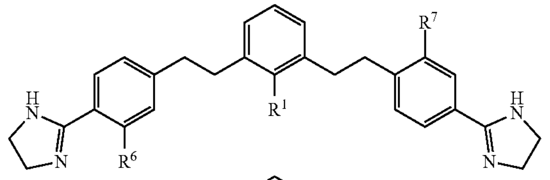
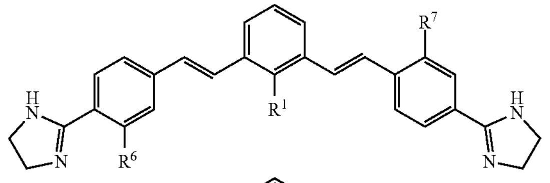
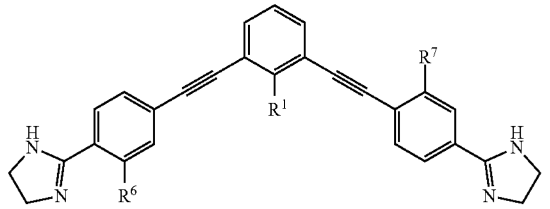
Additional examples of compounds of Formula IX include:

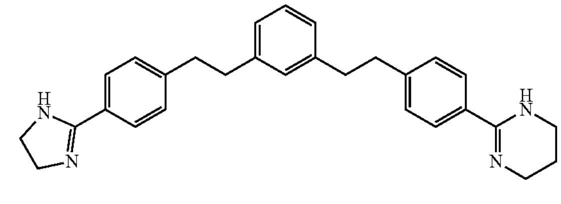
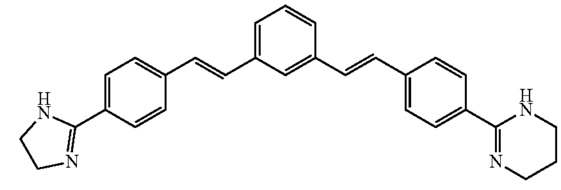
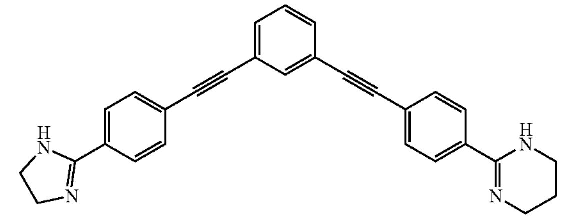
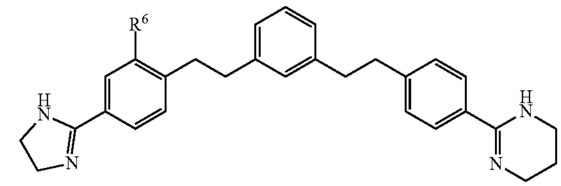
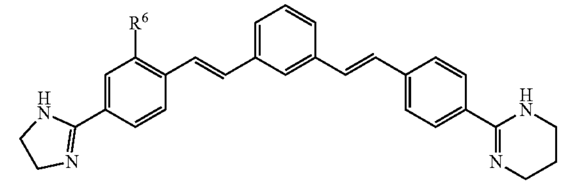
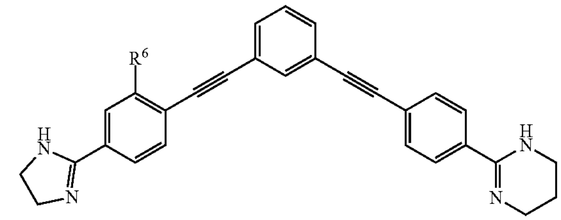
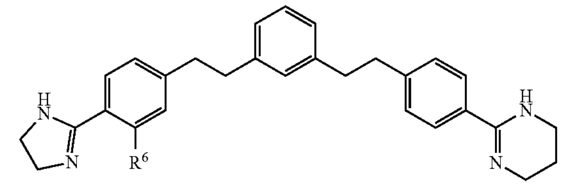
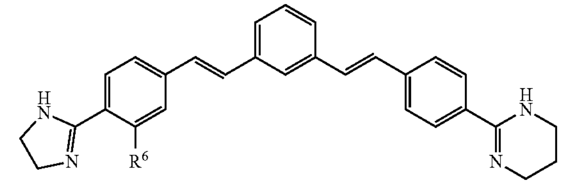
-continued
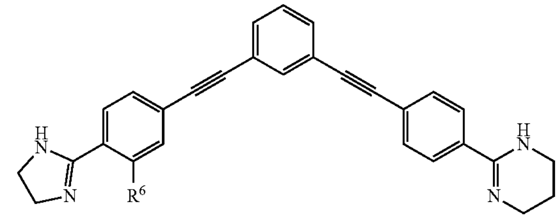
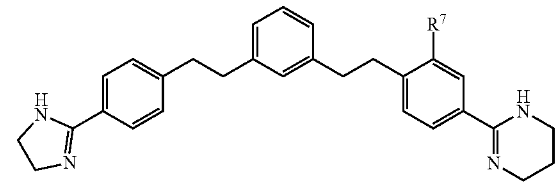
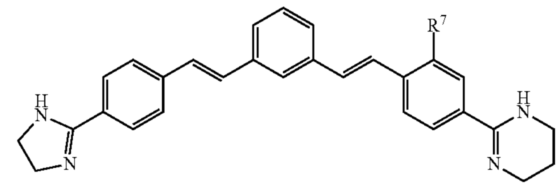
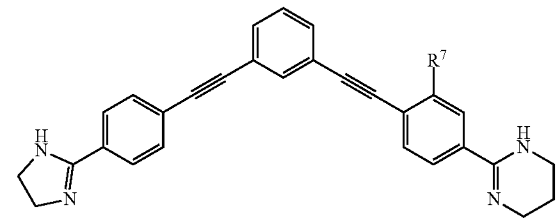
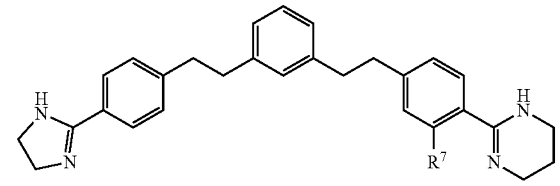
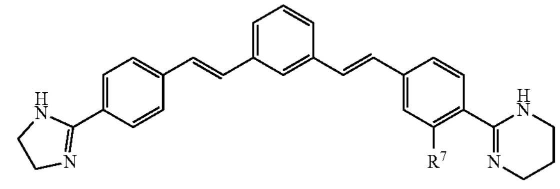
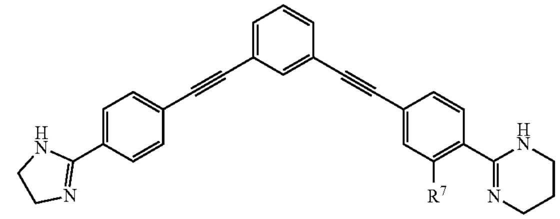
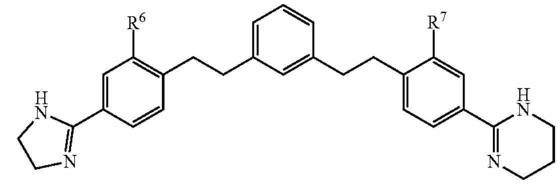

-continued
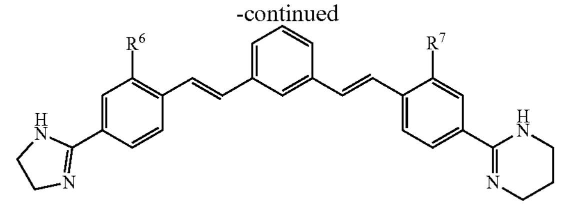
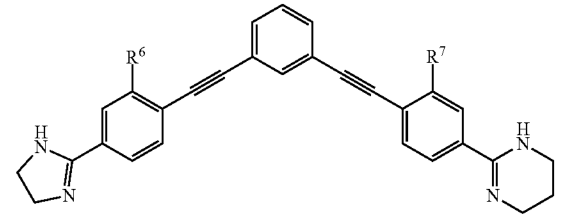
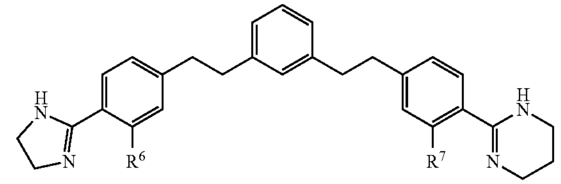
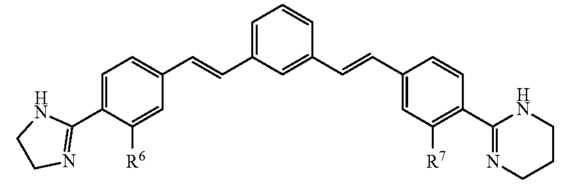
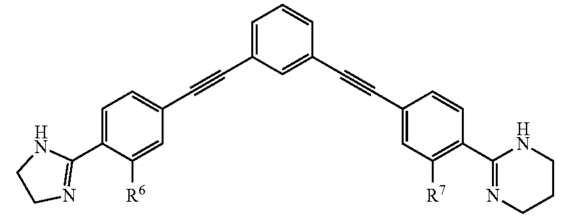
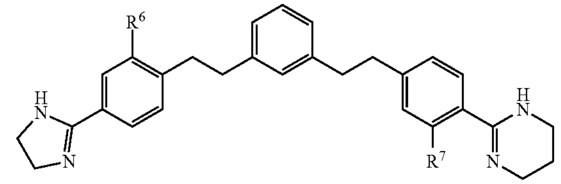
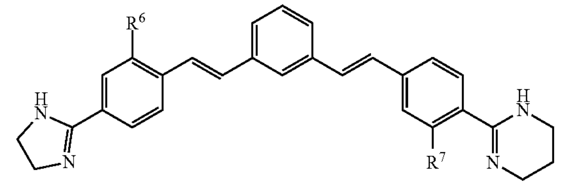
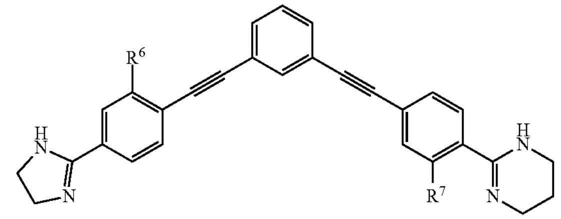
-continued
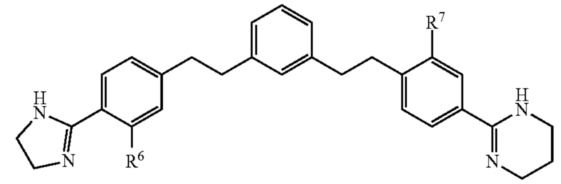
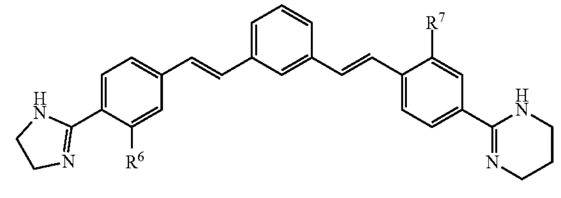
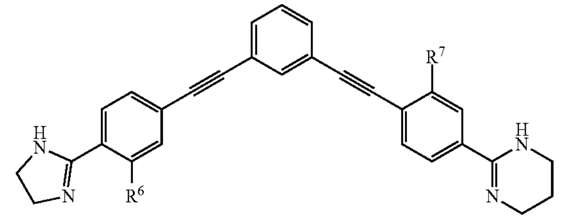
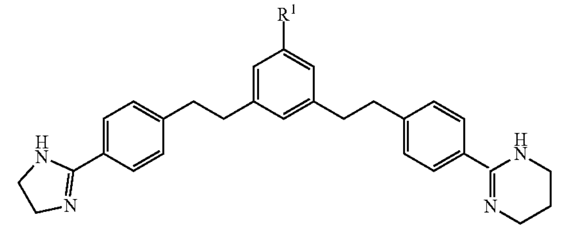
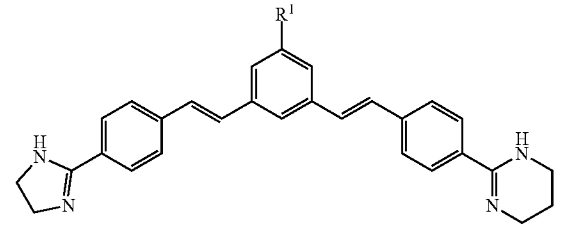
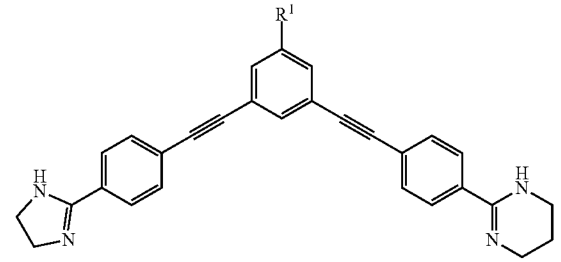
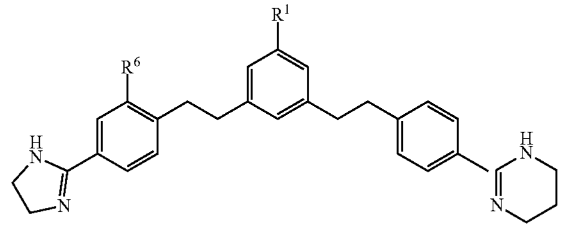

-continued
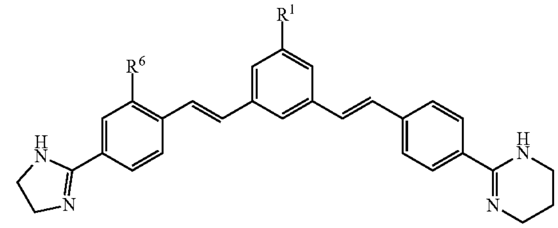
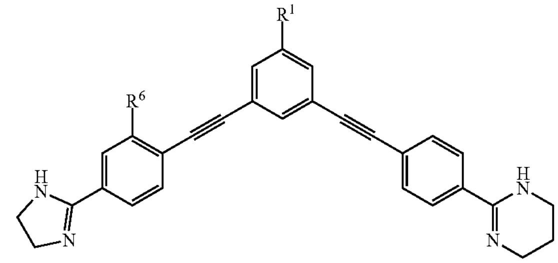
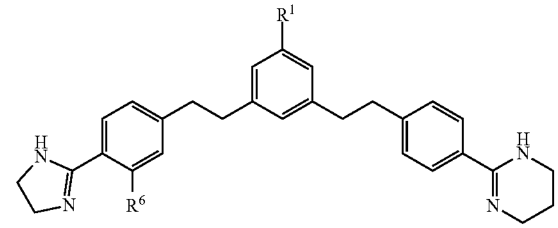
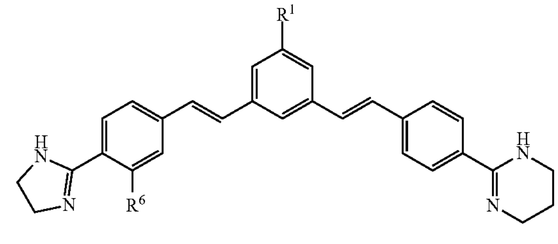
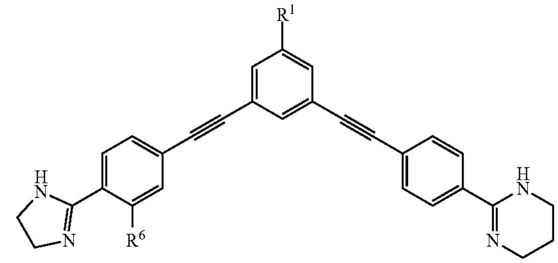
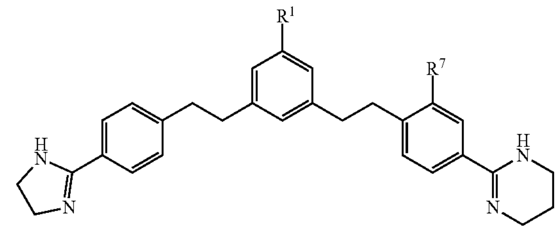
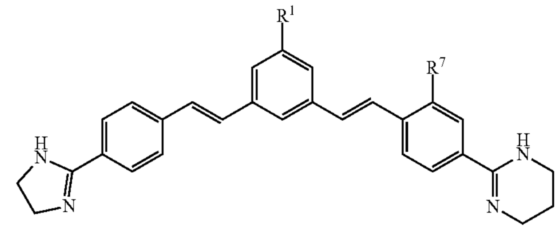
-continued
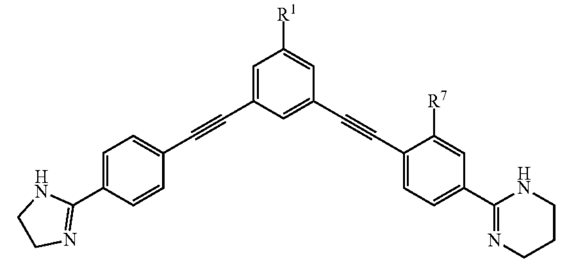
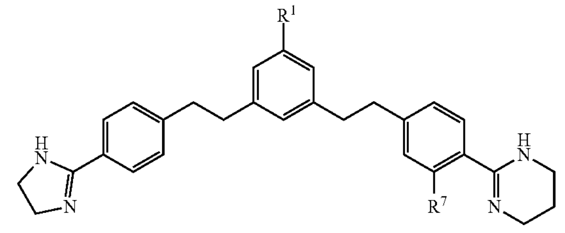
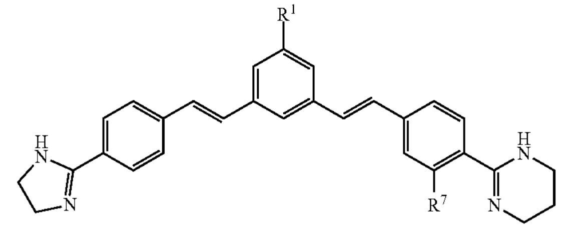
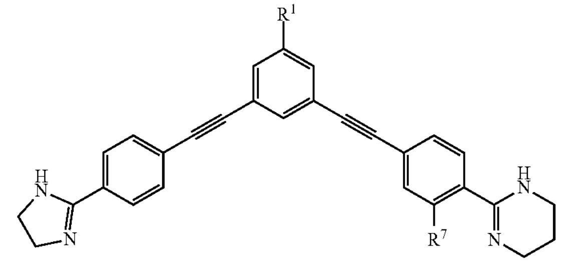
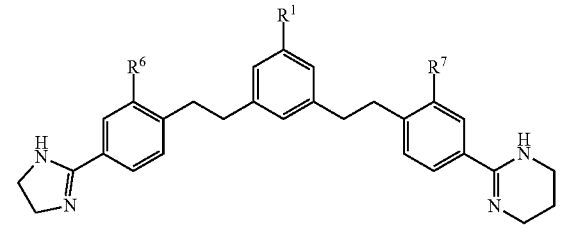
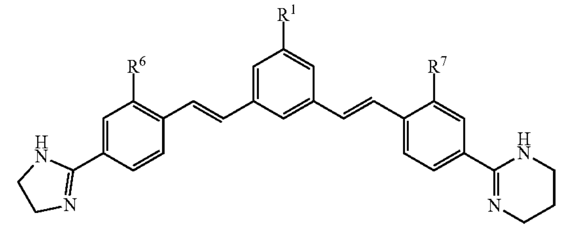
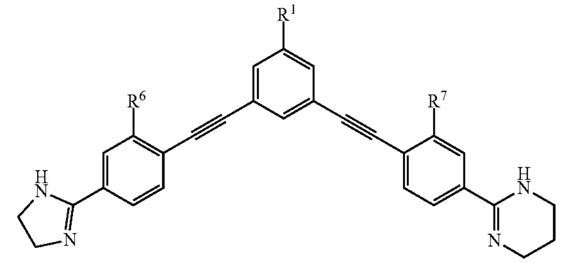

-continued
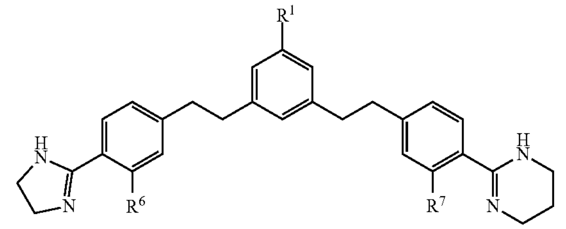
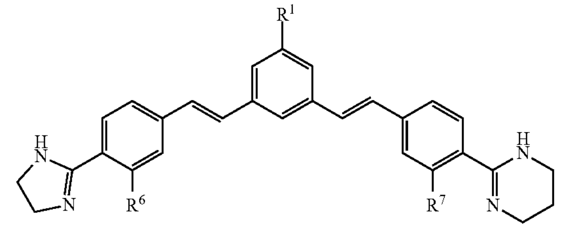
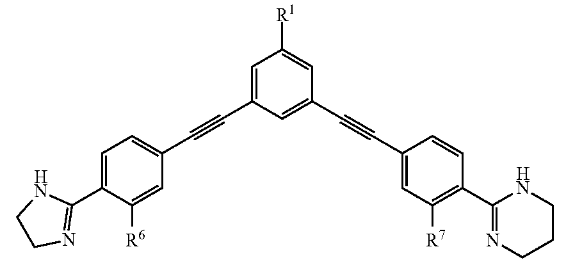
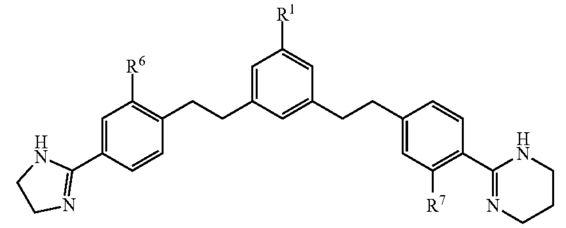
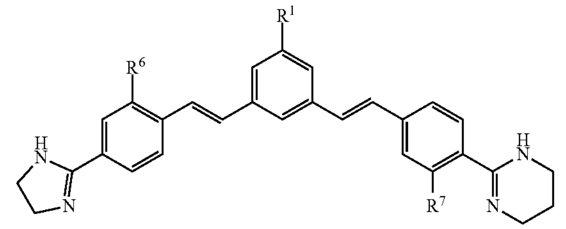
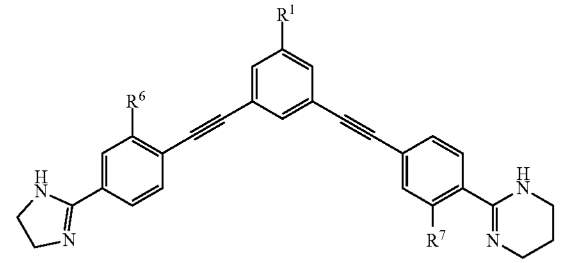
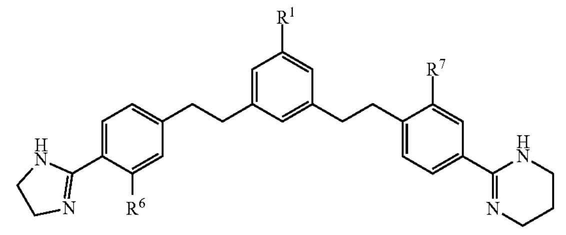
-continued
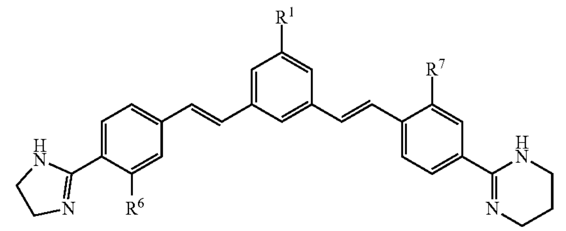
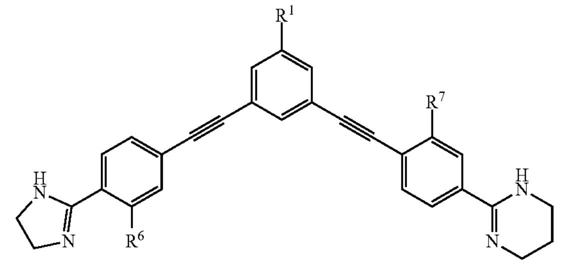
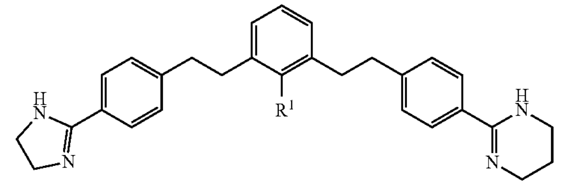
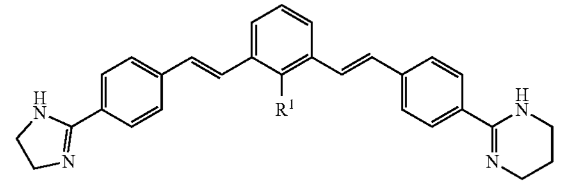
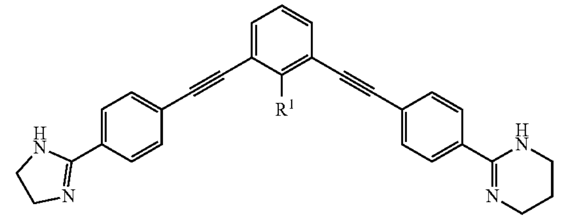
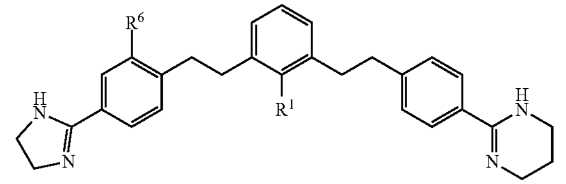
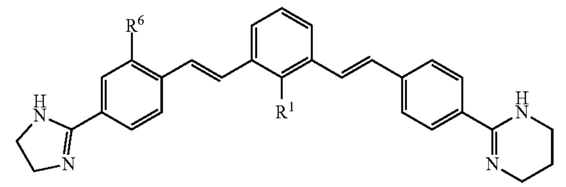
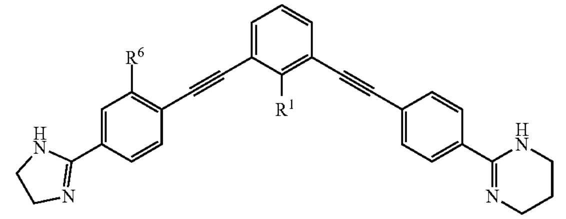

-continued
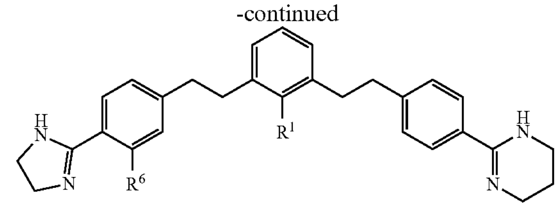
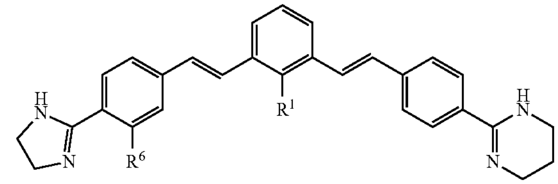
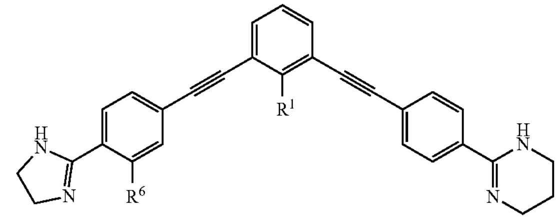
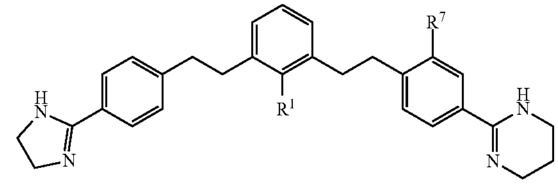
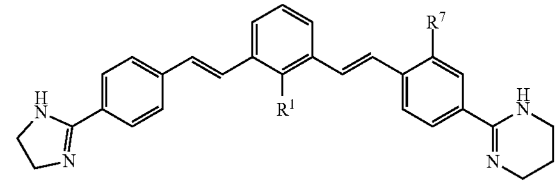
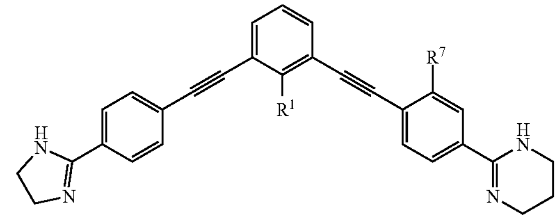
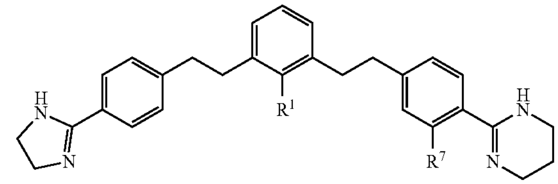
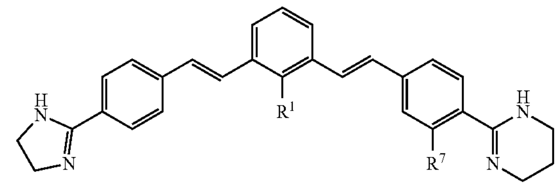
-continued
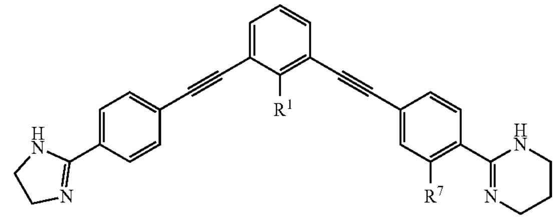
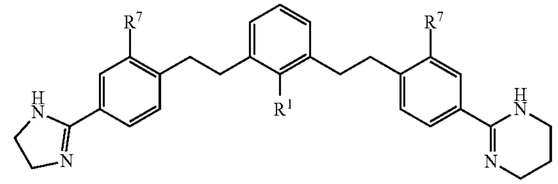
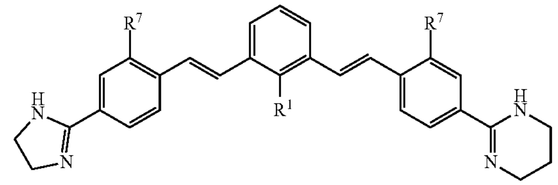
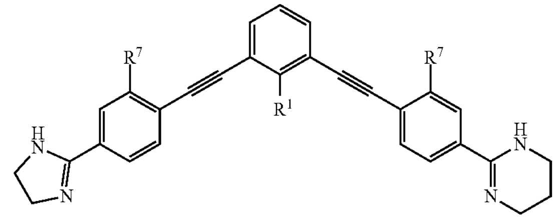
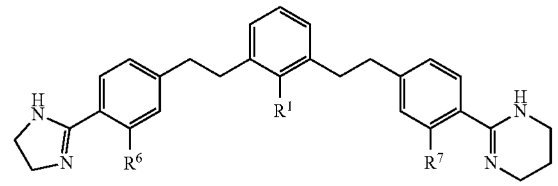
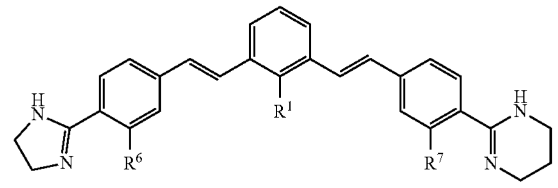
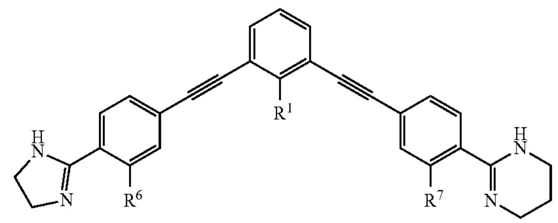
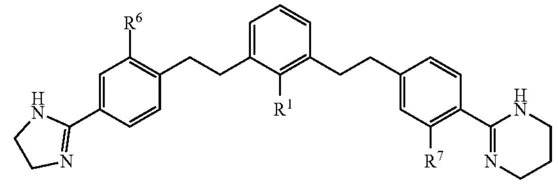

-continued
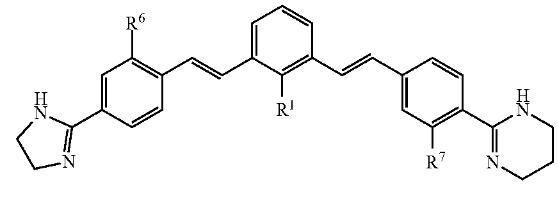
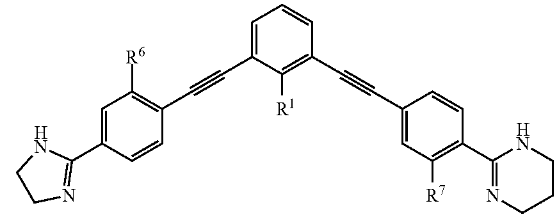
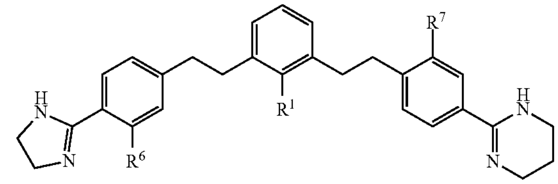
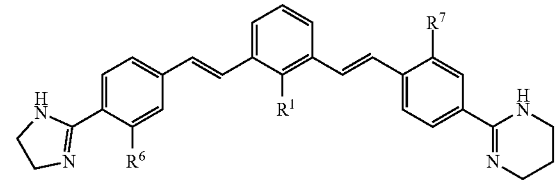
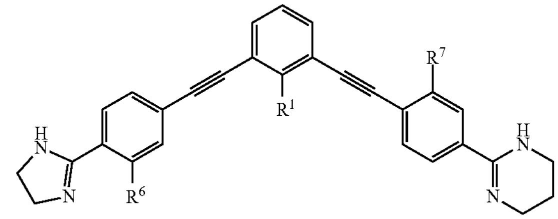
Non-limiting examples of compounds of Formula X include:
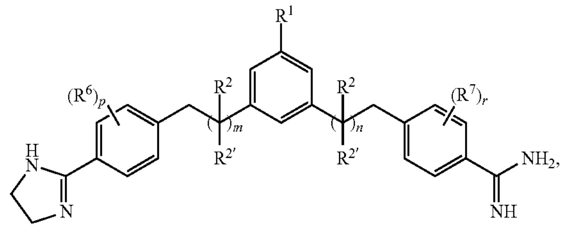
,
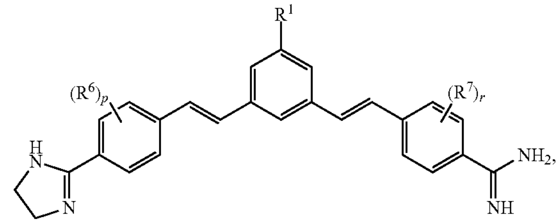
,
-continued
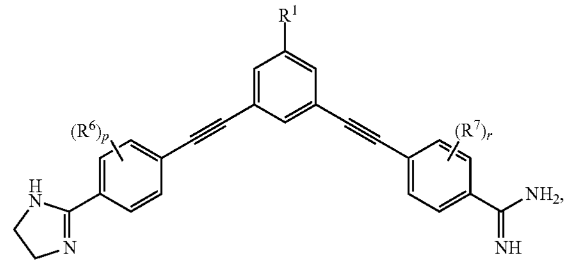
,
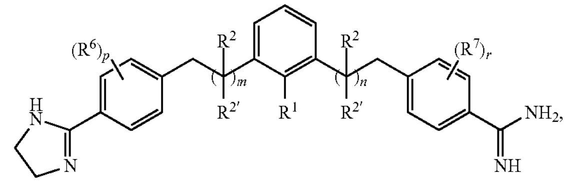
,
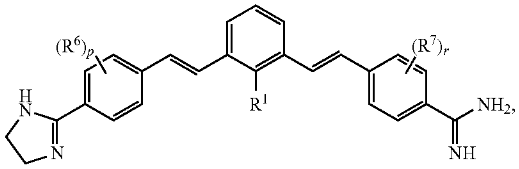
, and
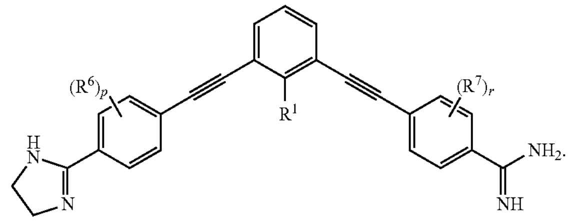
.
Non-limiting examples of compounds of Formula X include:
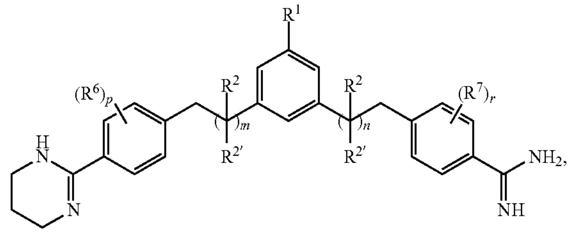
,
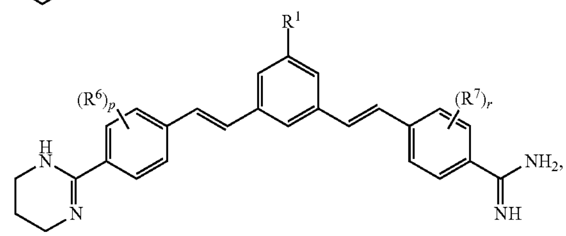
,
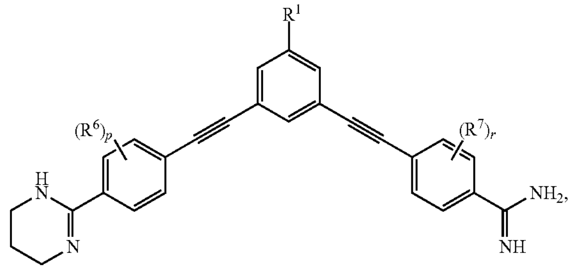
, -continued
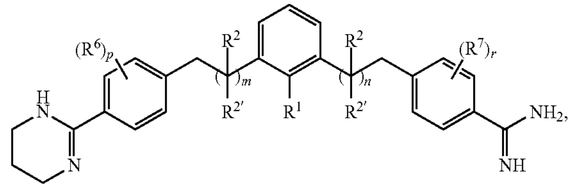
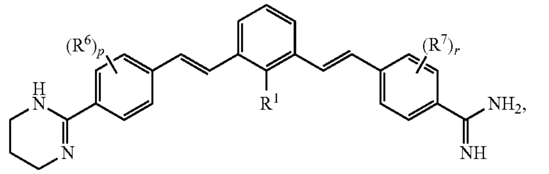
and
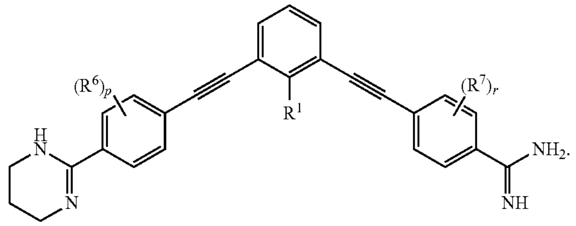
Additional examples of compounds of Formula X include.
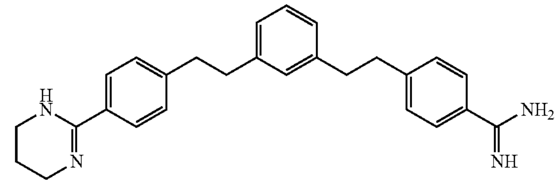
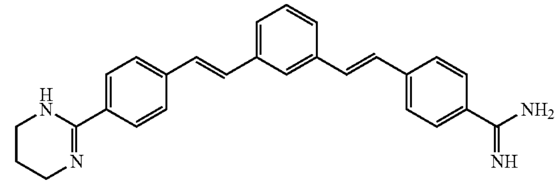
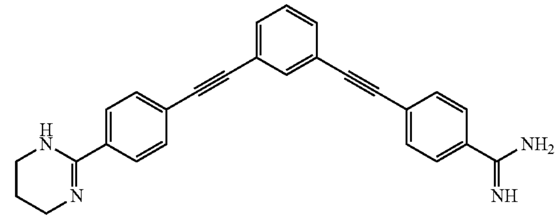
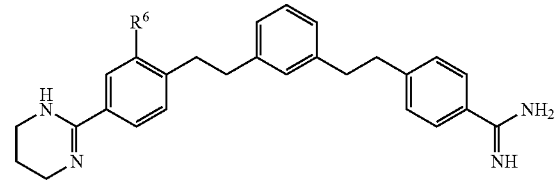
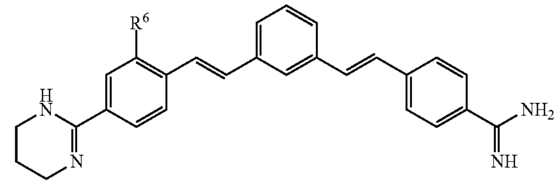
-continued
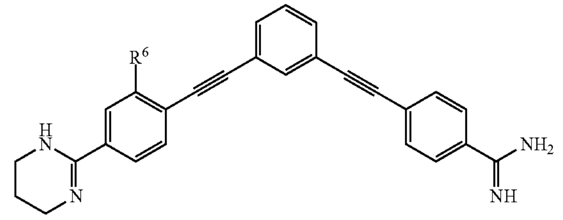
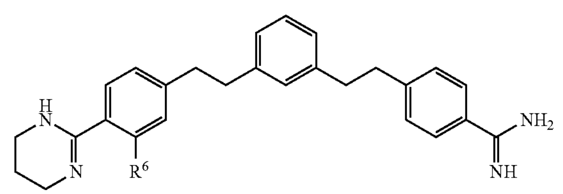
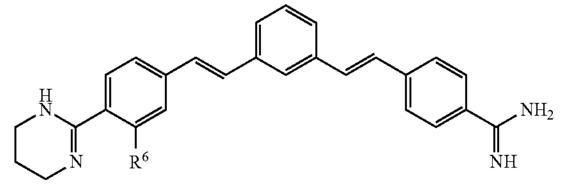
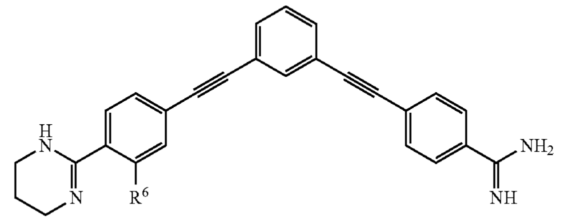
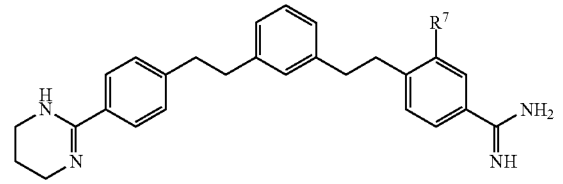
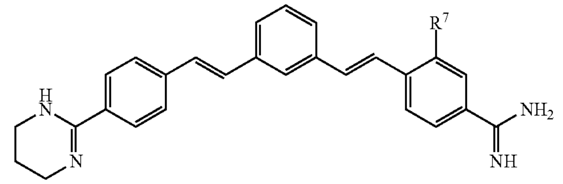
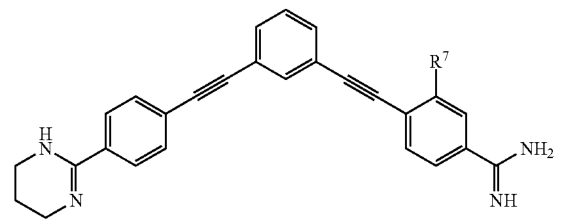
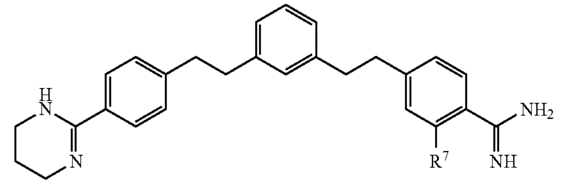

-continued
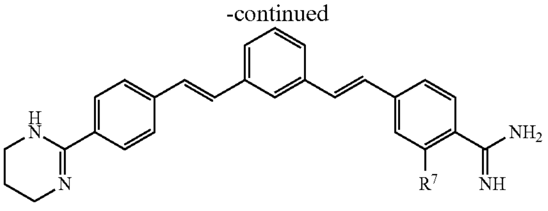
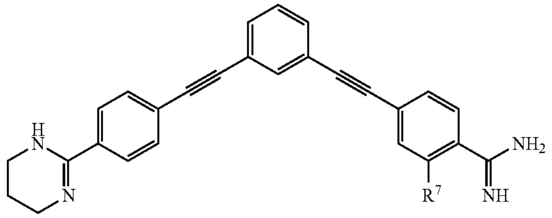
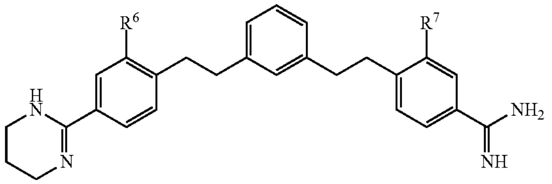
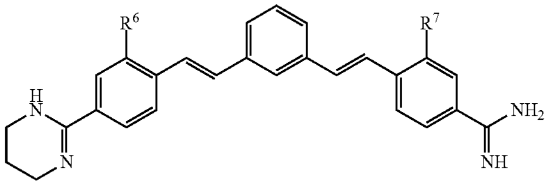
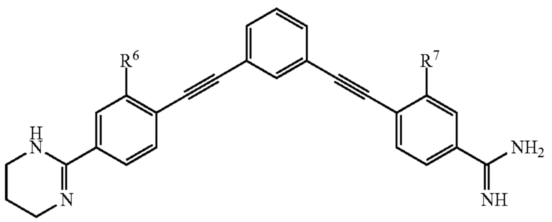
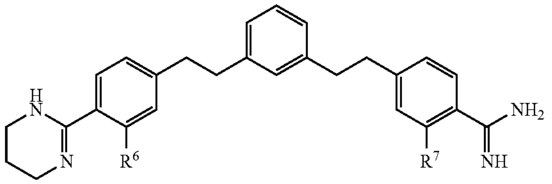
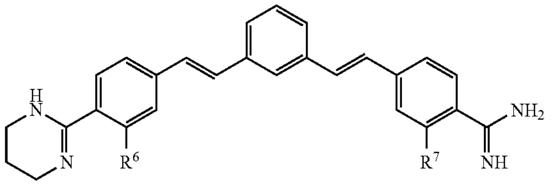
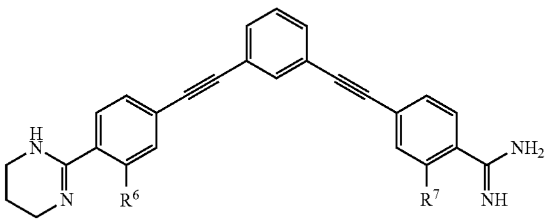
-continued
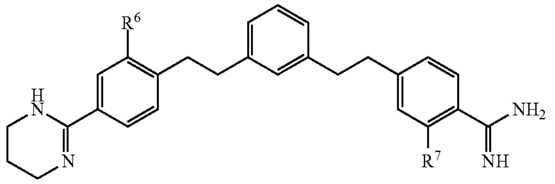
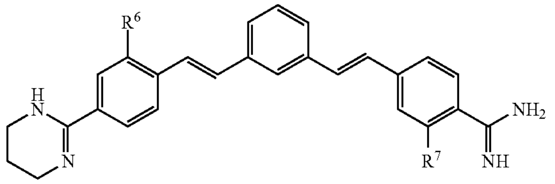
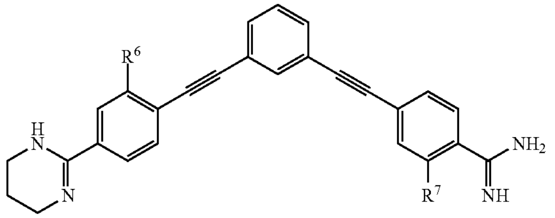
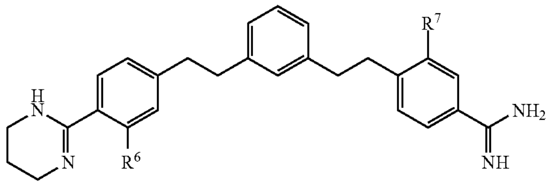
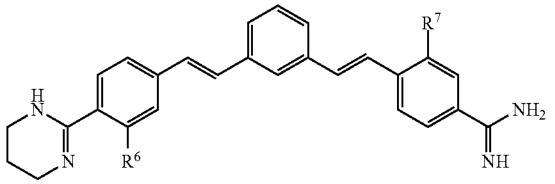
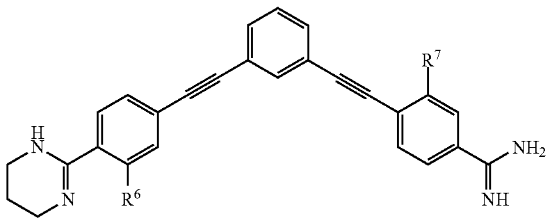
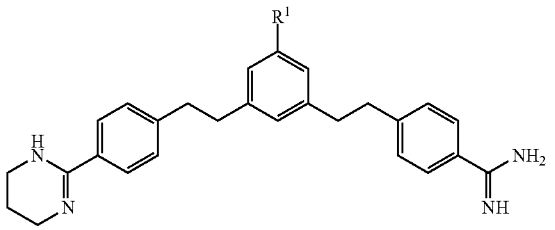
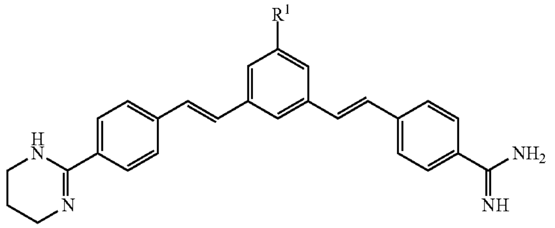

-continued
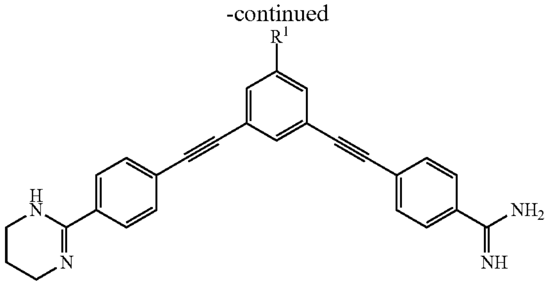
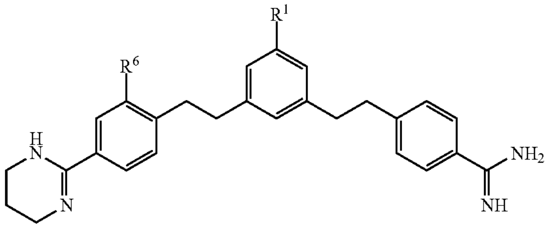
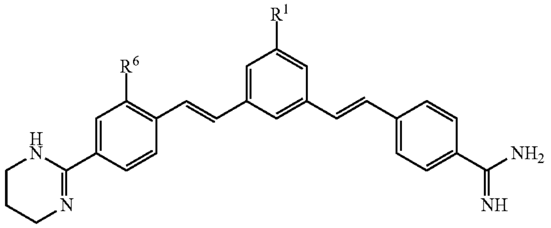
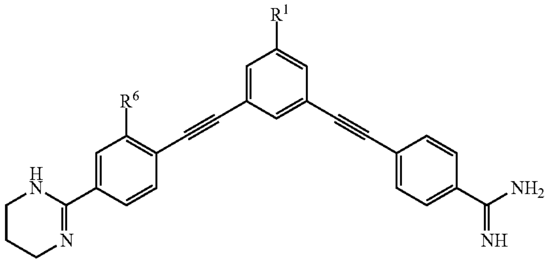
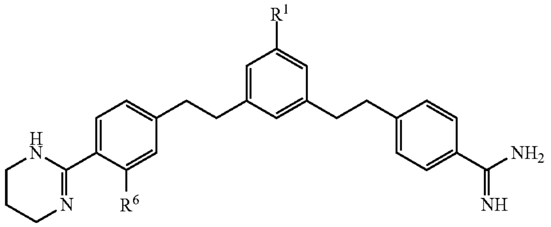
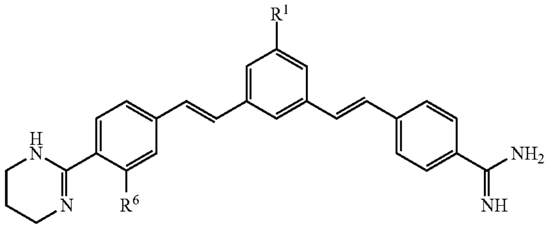
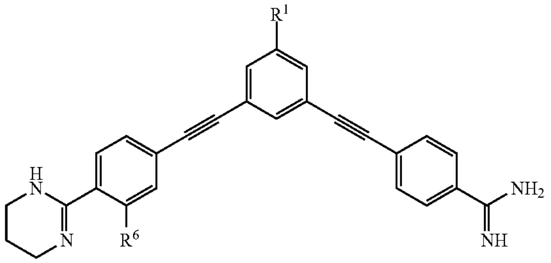
-continued
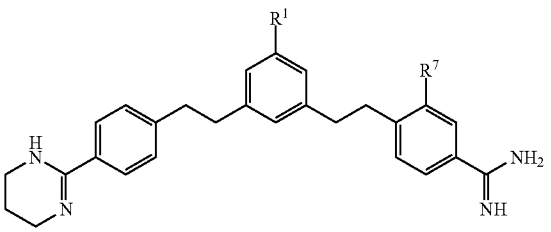
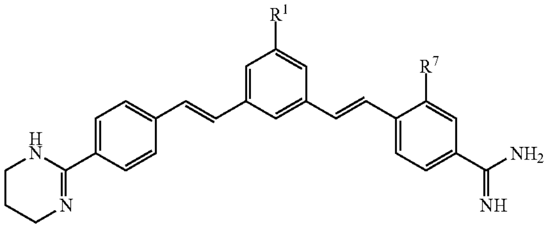
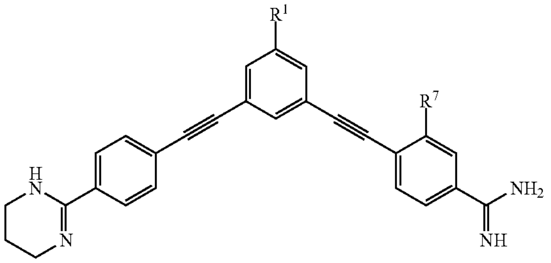
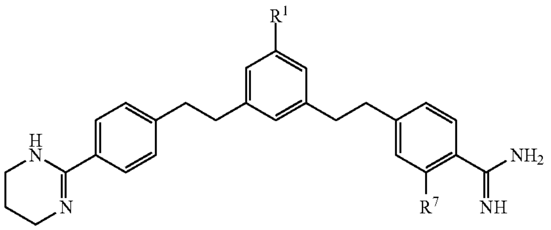
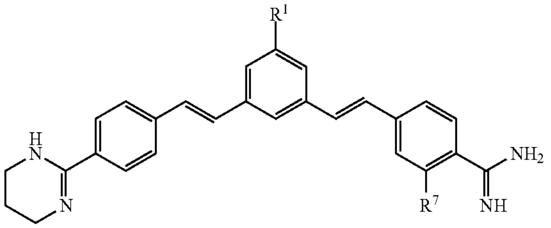
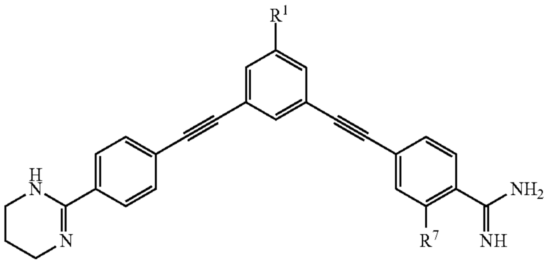
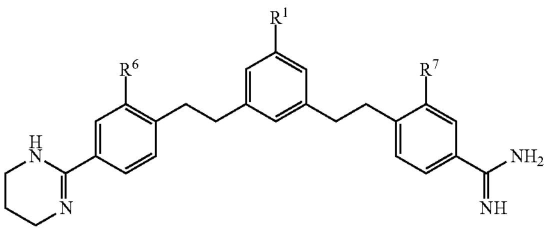

-continued
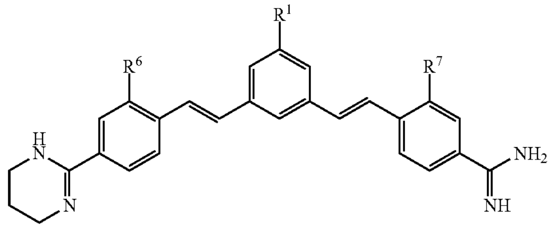
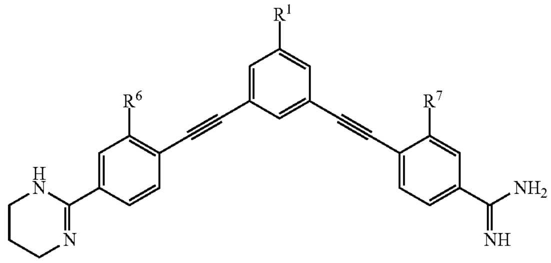
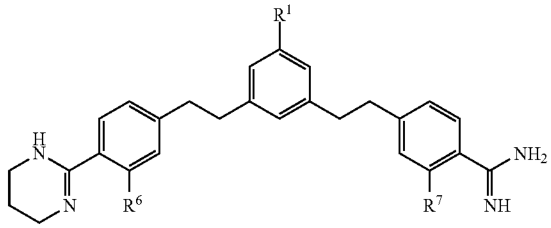
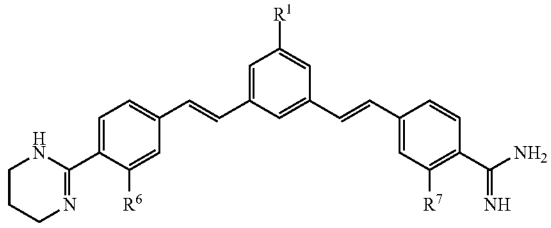
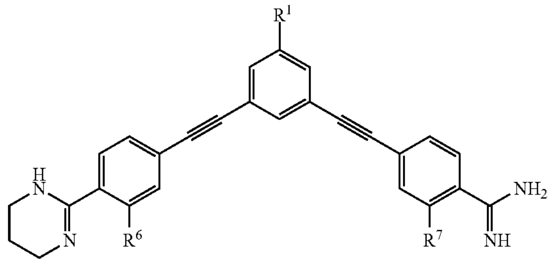
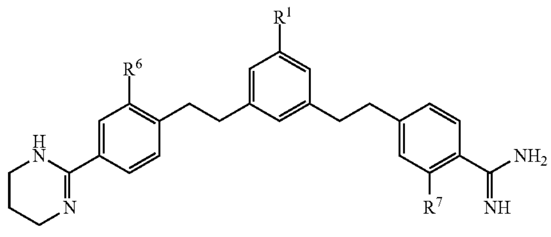
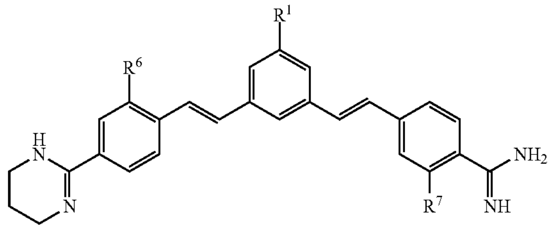
-continued
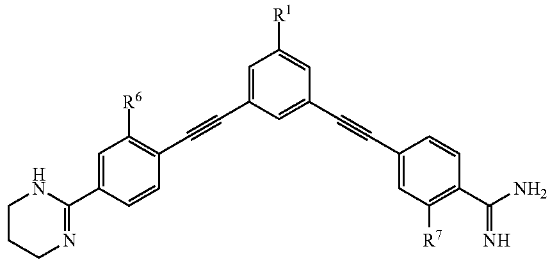
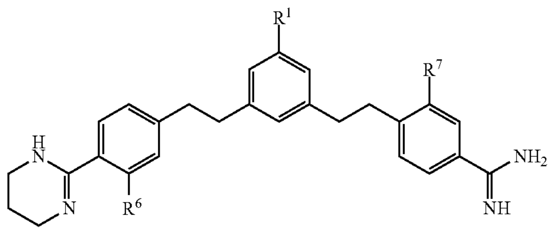
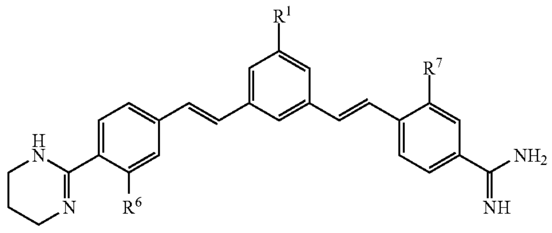
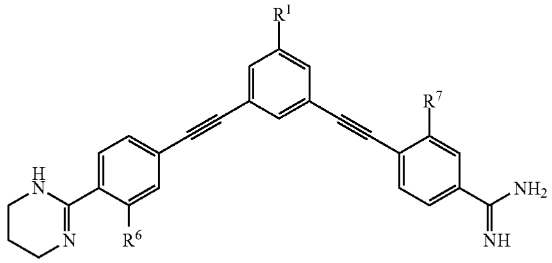
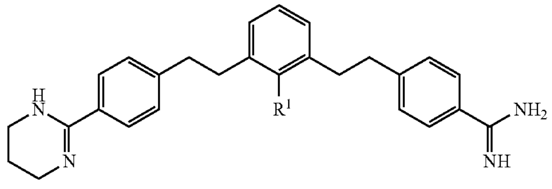
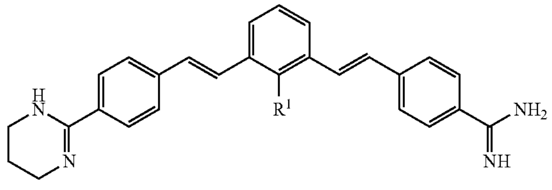
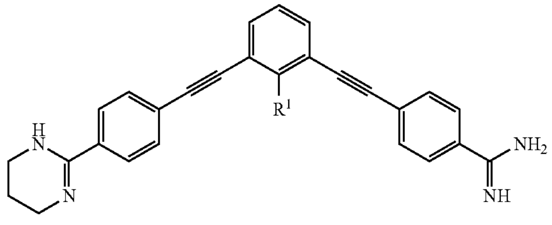

-continued
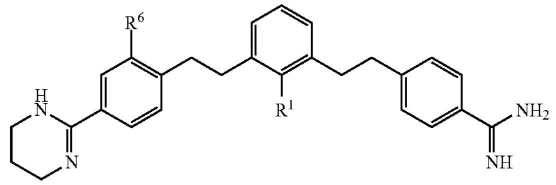
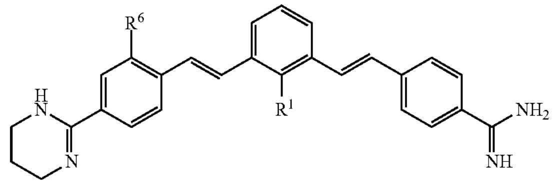
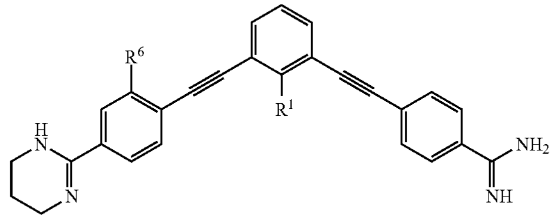
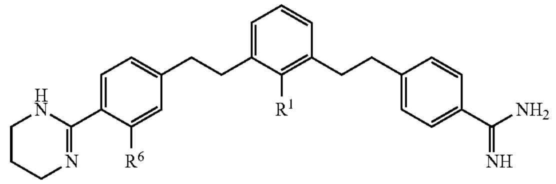
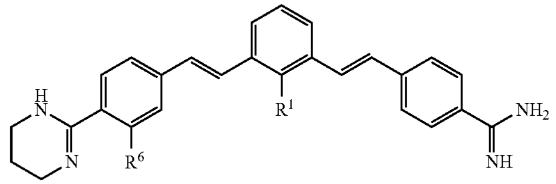
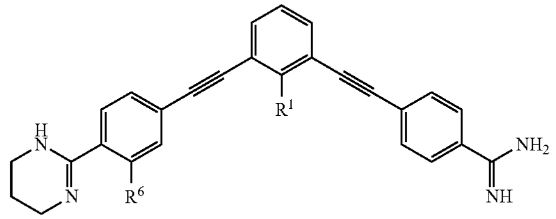
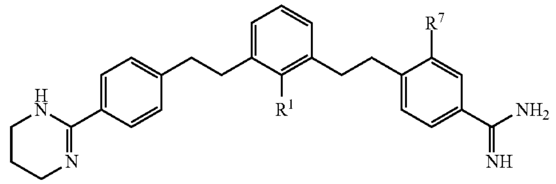
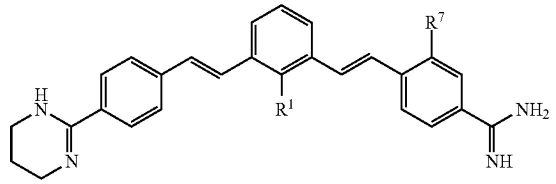
-continued
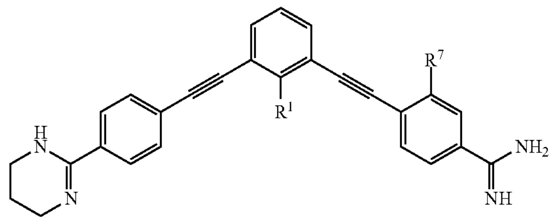
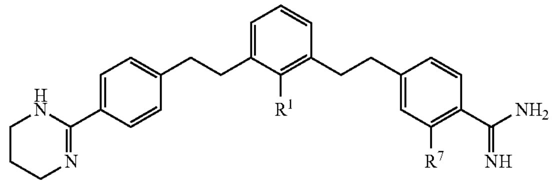
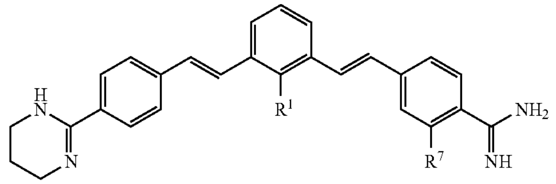
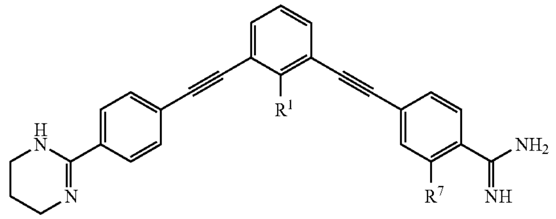
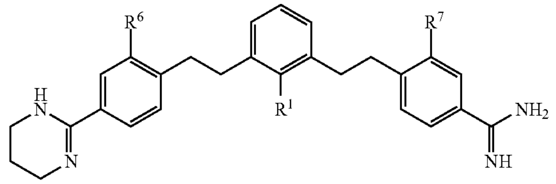
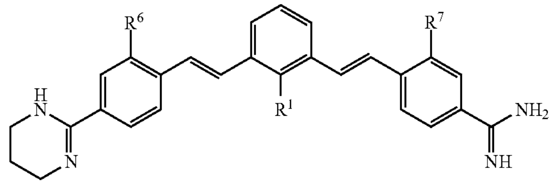
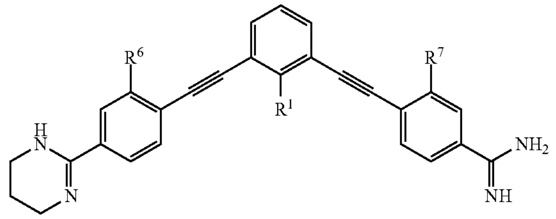
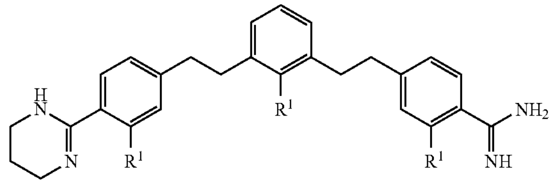

-continued
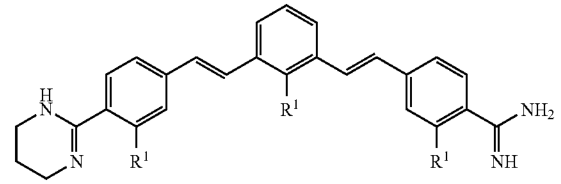
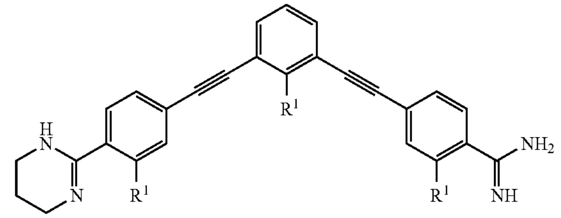
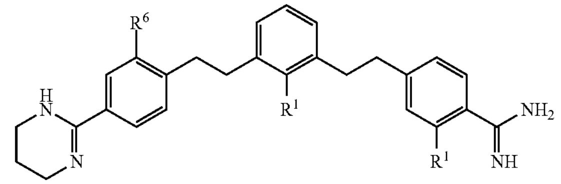
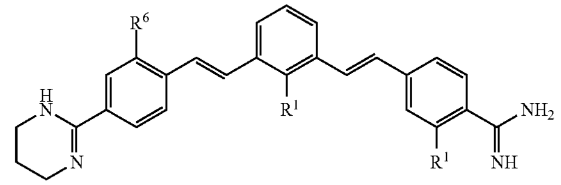
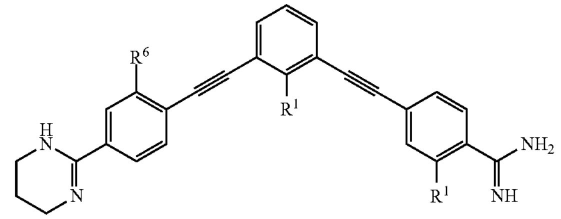
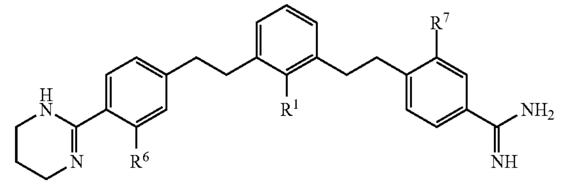
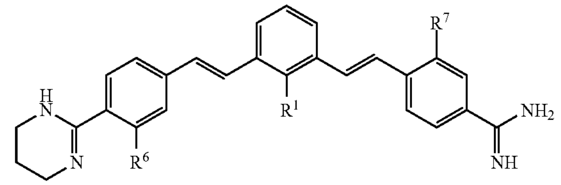
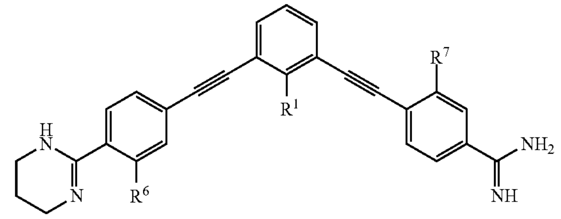
Additional examples of compounds of Formula X include:
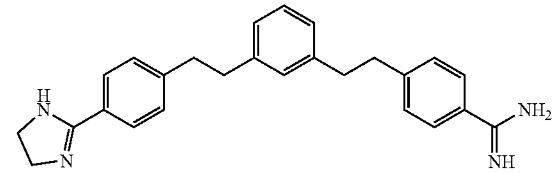
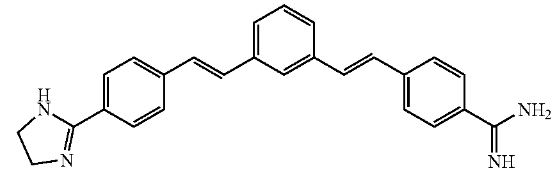
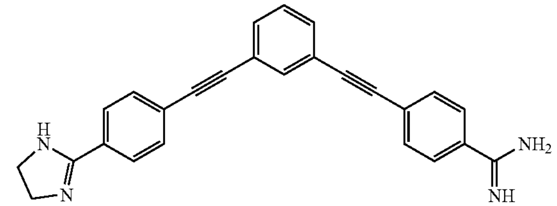
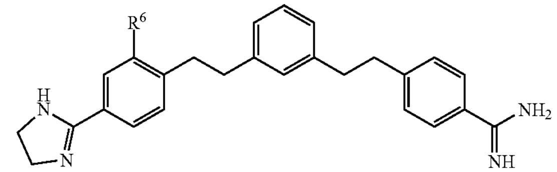
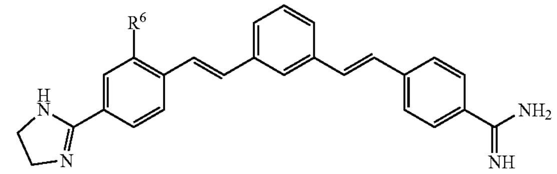
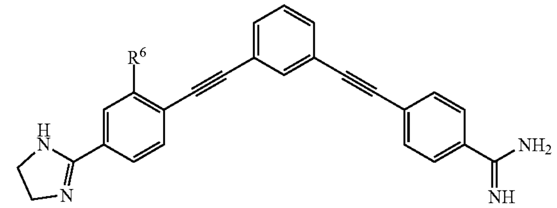
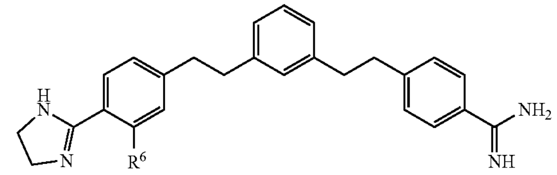
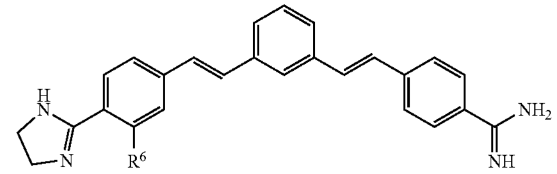
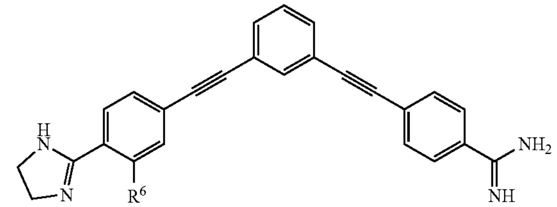

-continued
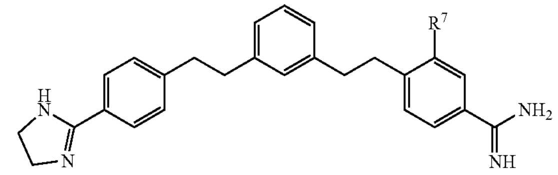
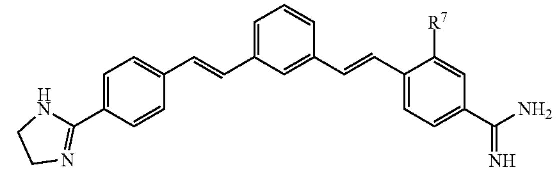
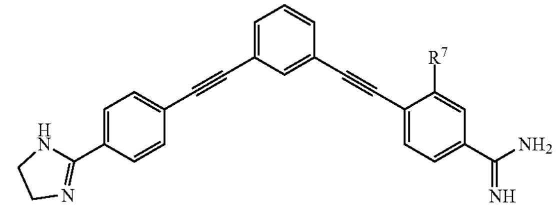
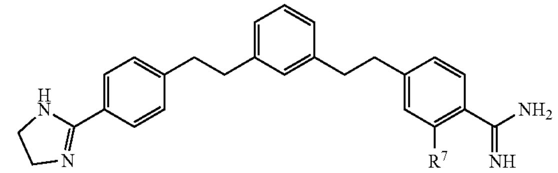
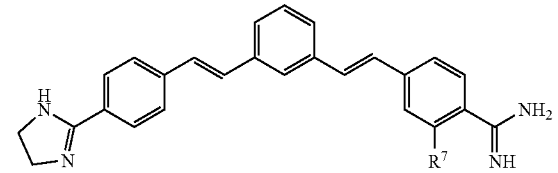
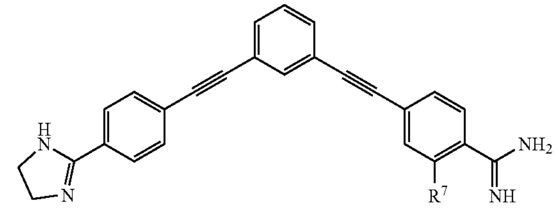
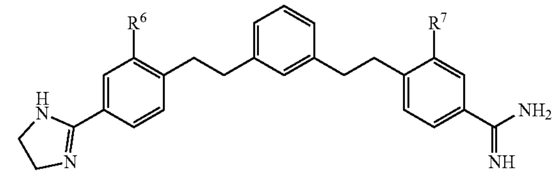
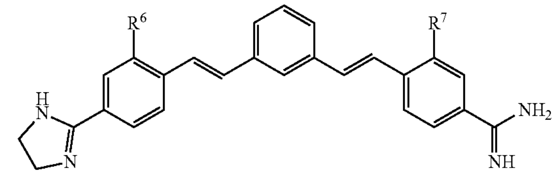
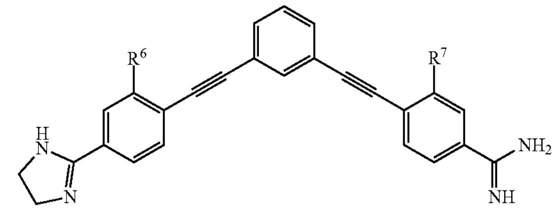
-continued
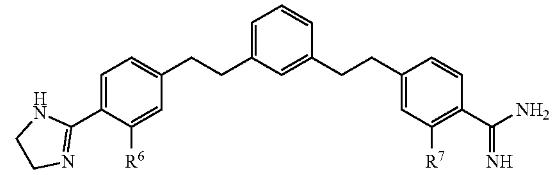
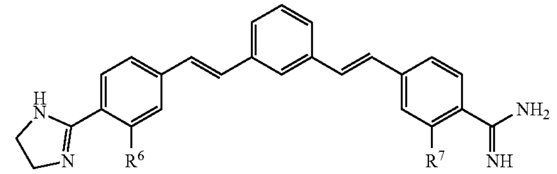
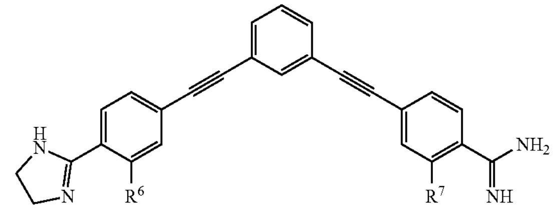
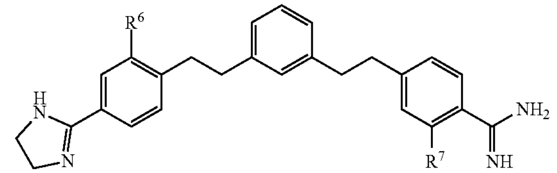
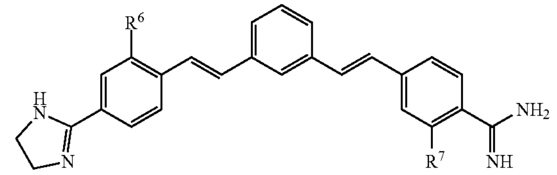
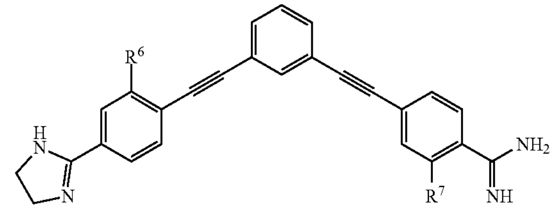
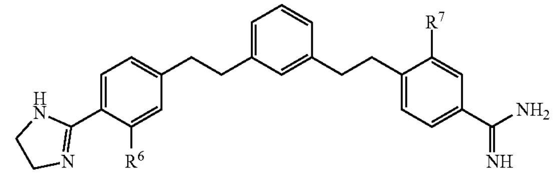
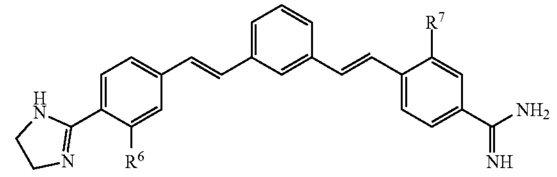
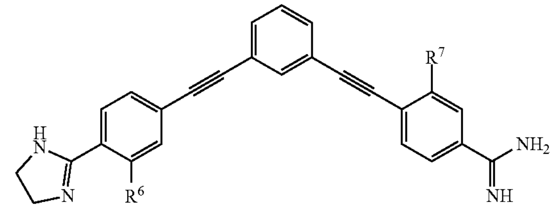

-continued
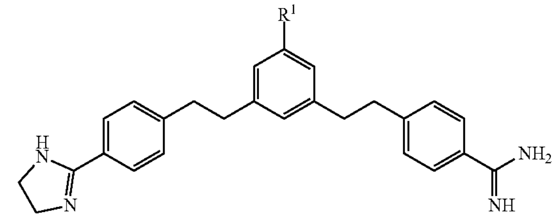
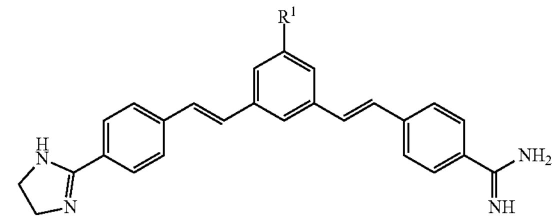
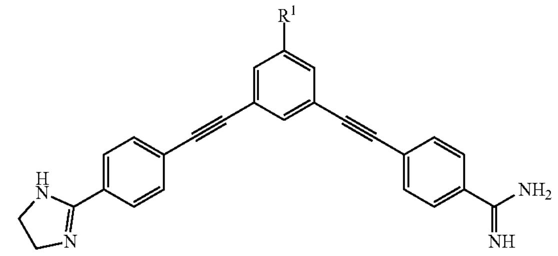
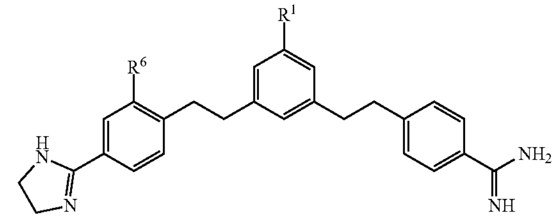
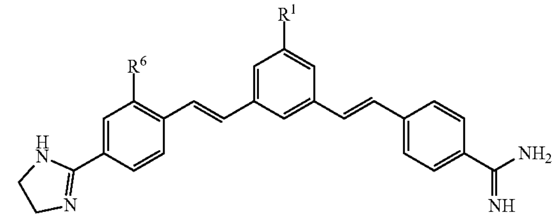
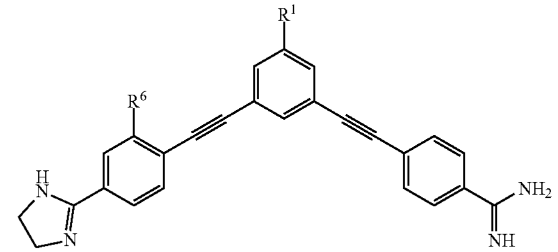
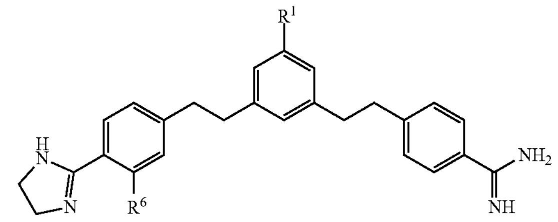
-continued
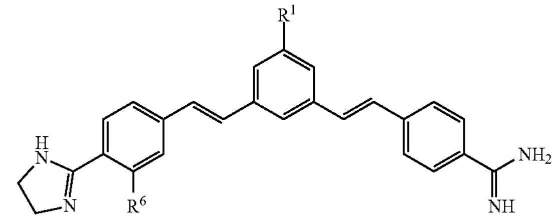
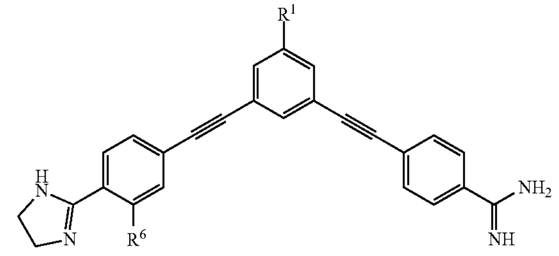
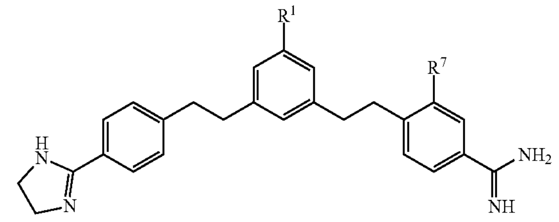
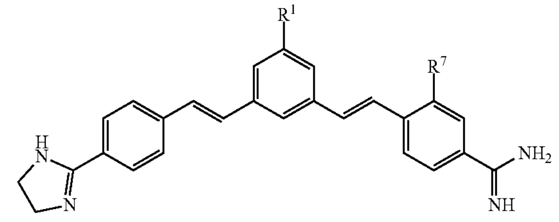
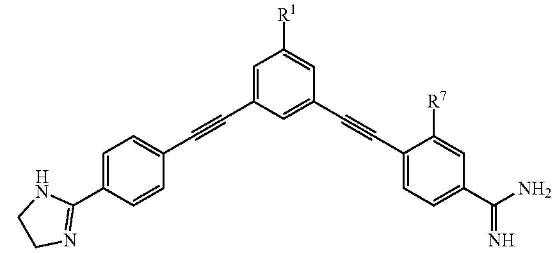
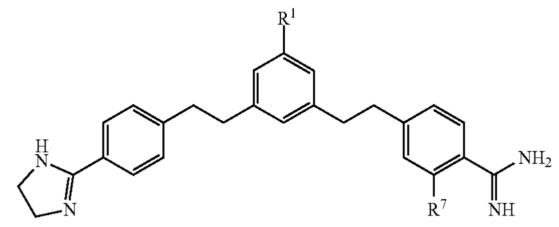
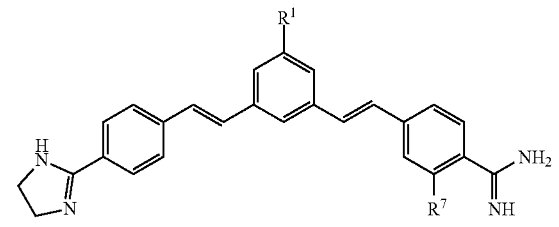

-continued
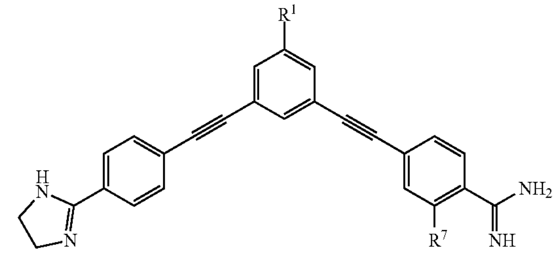
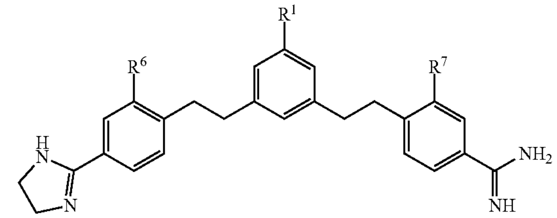
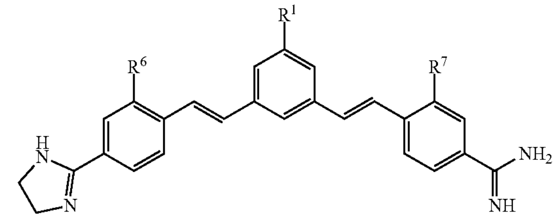
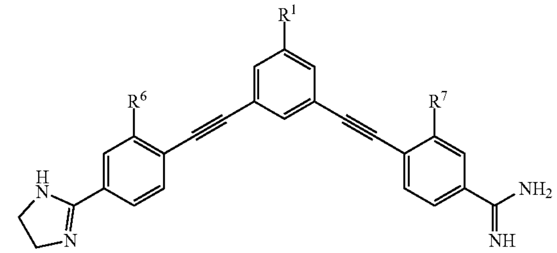
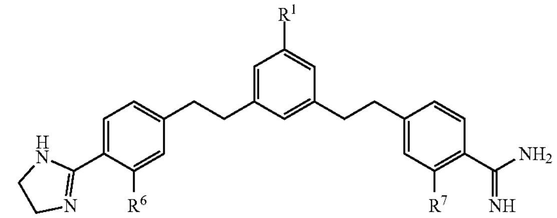
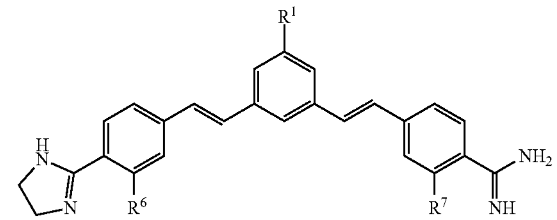
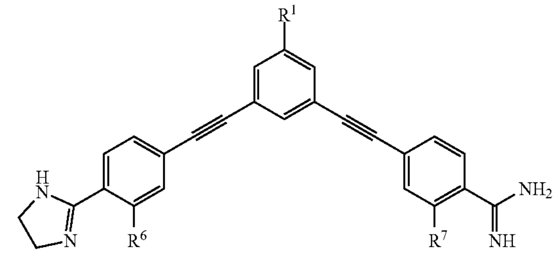
-continued
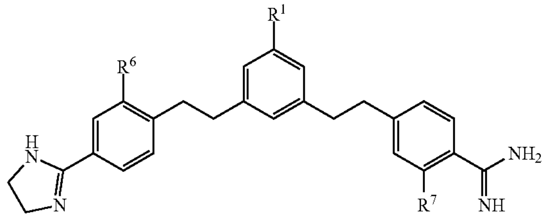
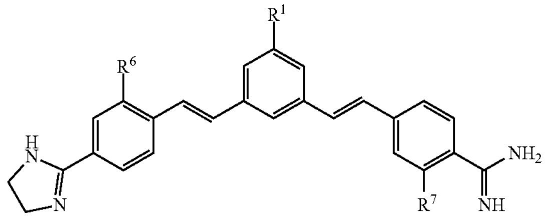
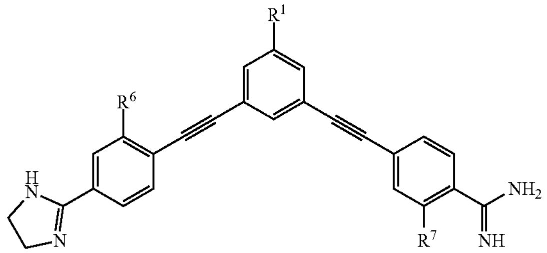
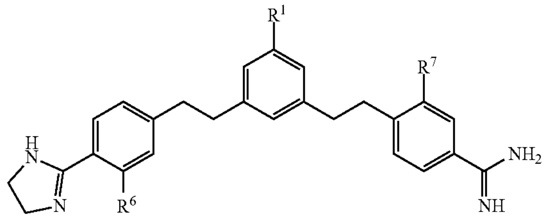
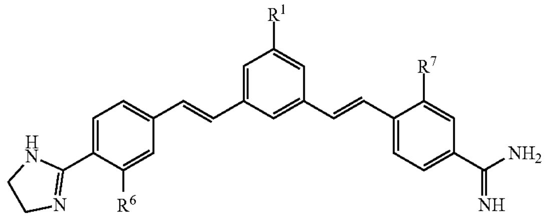
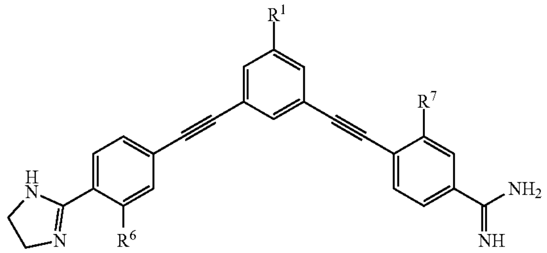
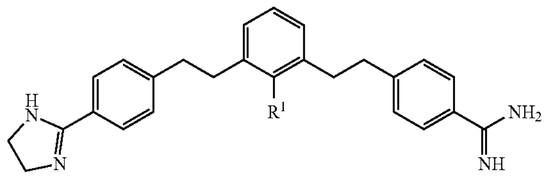
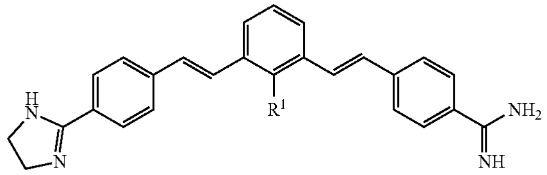

-continued
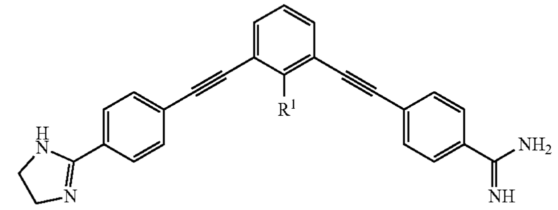
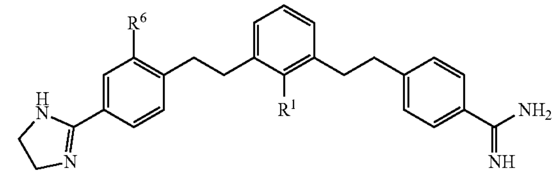
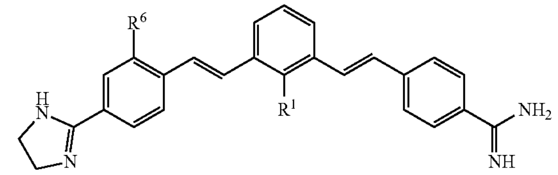
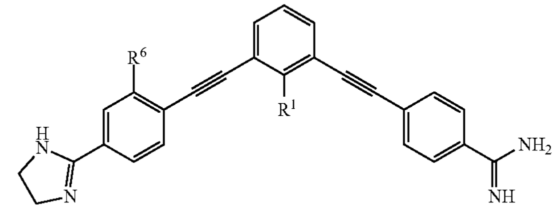
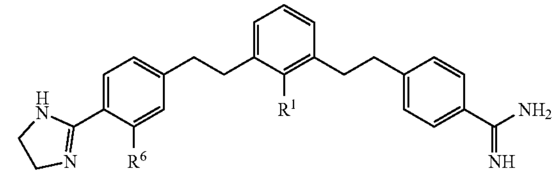
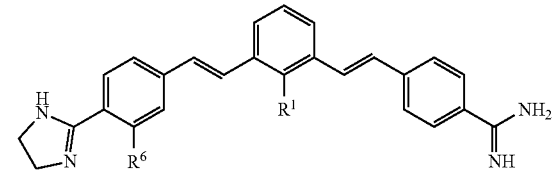
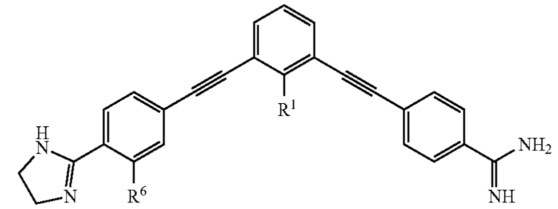
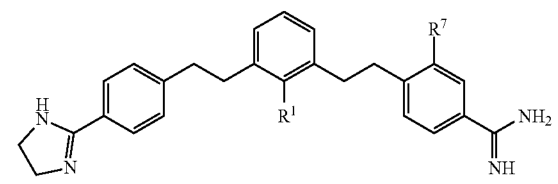
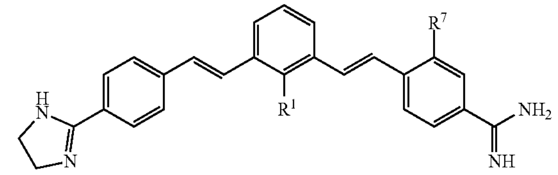
-continued
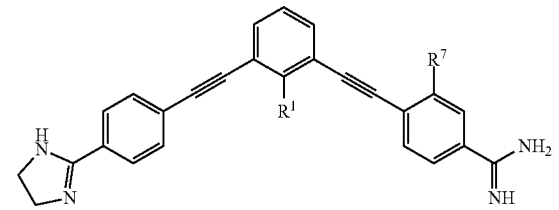
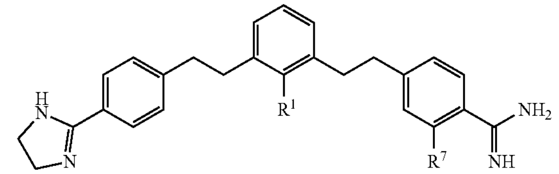
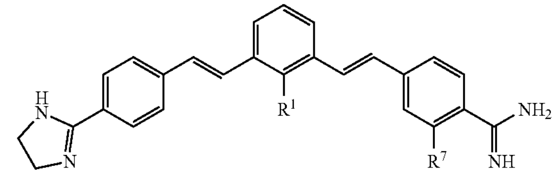
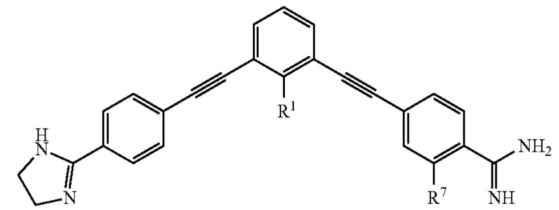
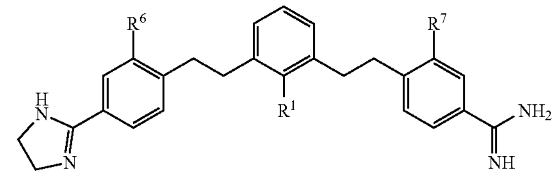
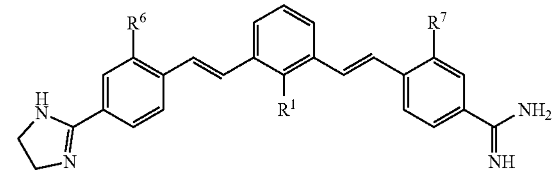
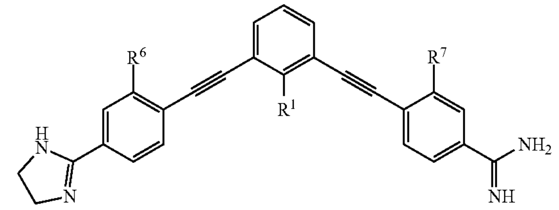
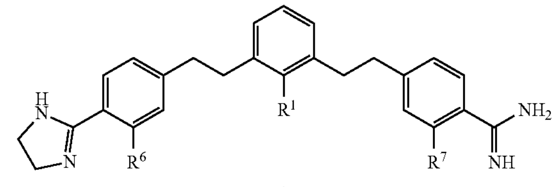
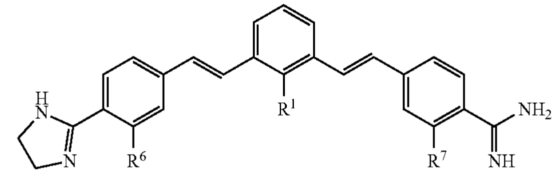

-continued
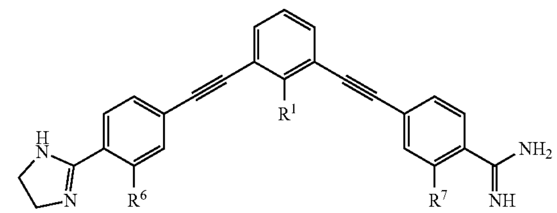
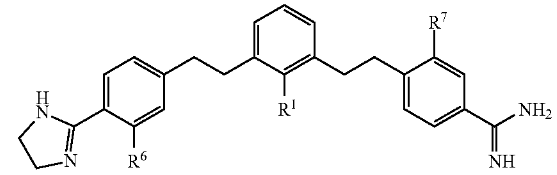
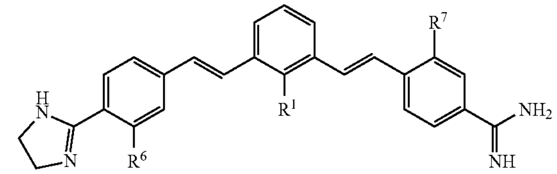
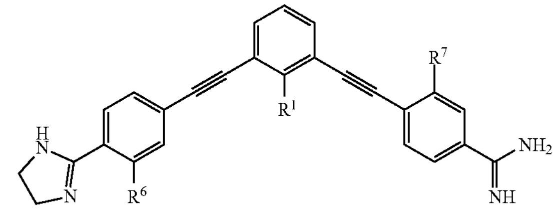
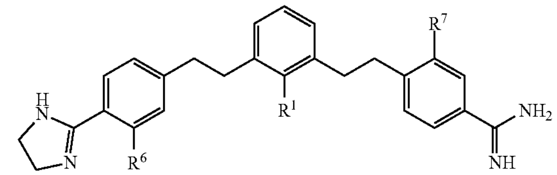
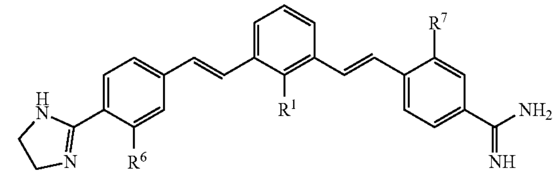
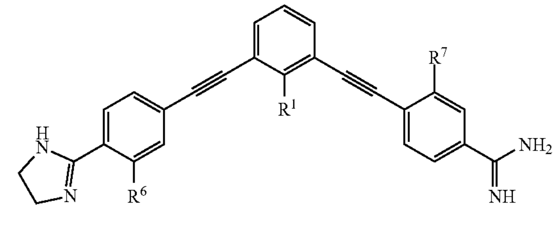
Examples of compounds of Formula XII include:
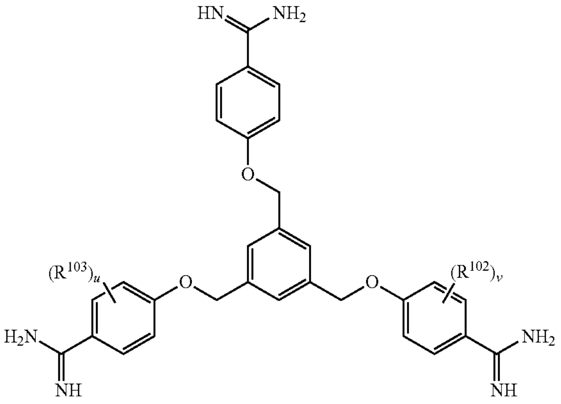
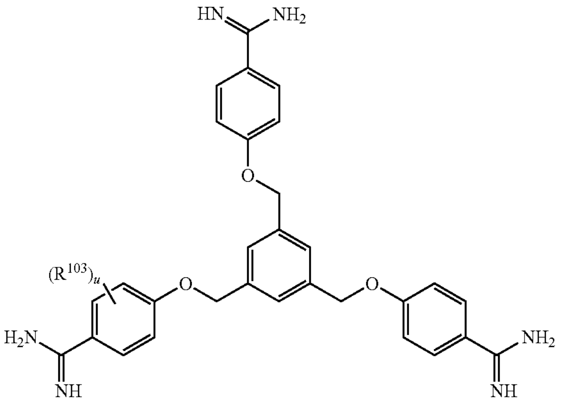
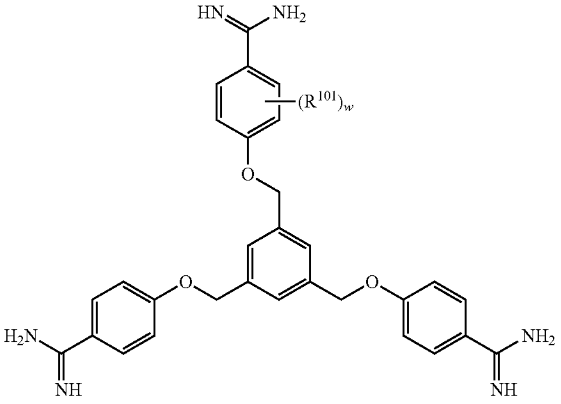
Preferred Compounds of the Present Invention include:
Compound M-1
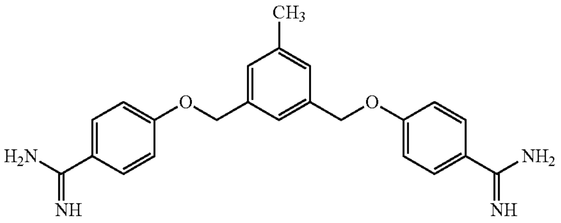

-continued

Compound A-8

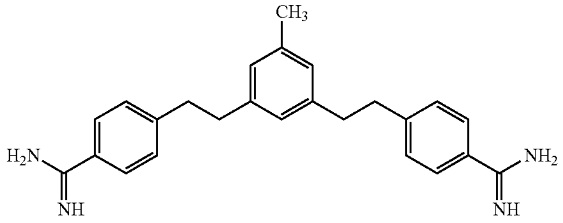

Compound C

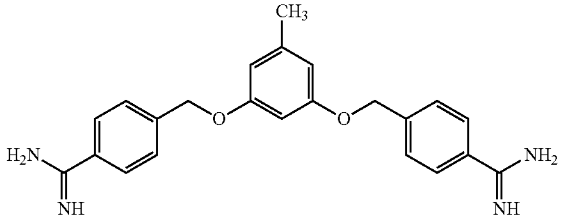

E-15

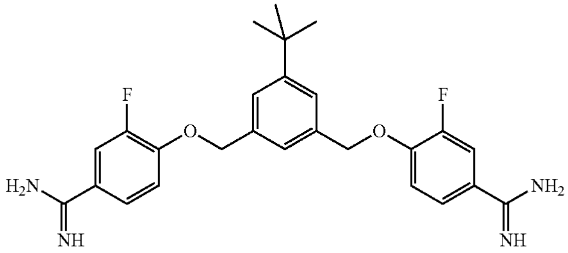

-continued

E-18

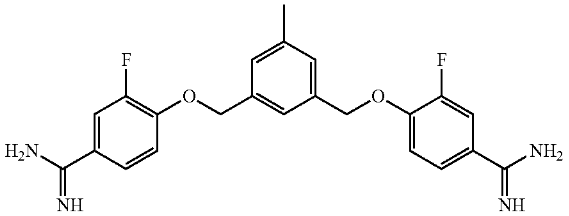

E-20

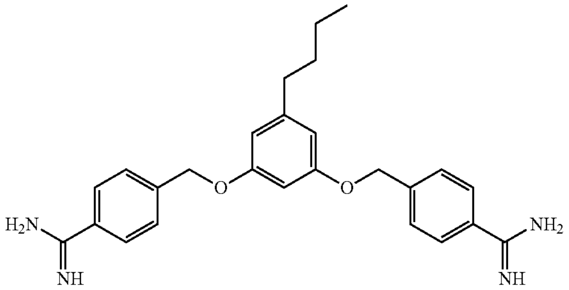

Additional examples of compounds of the present invention are provided in Table A, Table B, Table C, Table D, Table E, and Table F.

TABLE A

| Non-Limiting Examples of Compounds of Formula I-XII | |
|---|---|
| Cmpd # | Structure & Name |
| A-1 | 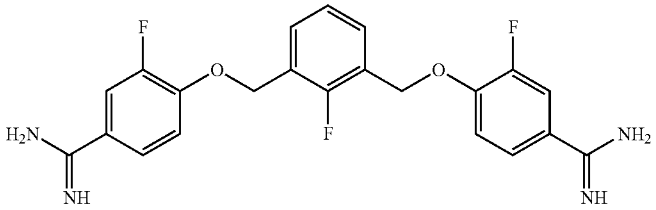 [SMILES: N=C(N)c1ccc(OCc2cccc(COc3ccc(C(=N)N)cc3F)c2F)c(F)c1] 4,4'-(((2-fluoro-1,3-phenylene)bis(methylene))bis(oxy))bis(3-fluorobenzimidamide) |
| A-2 | 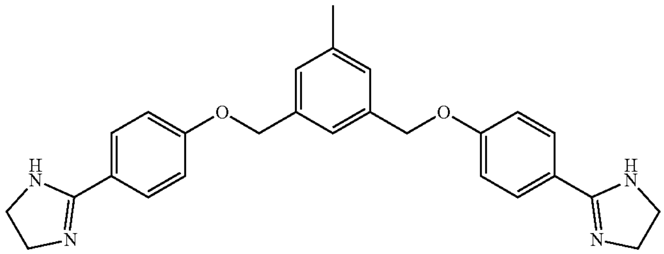 [SMILES: Cc1cc(COc2ccc(C3=NCCN3)cc2)cc(COc2ccc(C3=NCCN3)cc2)c1] 2,2'-((((5-methyl-1,3-phenylene)bis(methylene))bis(oxy))bis(4,1-phenylene))bis(4,5-dihydro-1H-imidazole) |

TABLE A-continued

| Cmpd # | Non-Limiting Examples of Compounds of Formula I-XII<br>Structure & Name |
|---|---|
| A-3 | 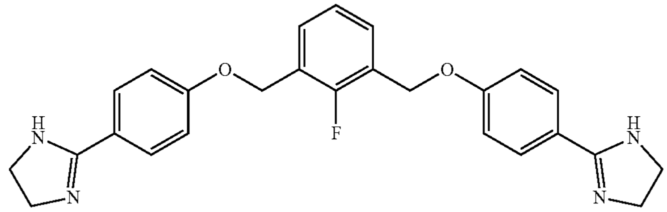 [SMILES: Fc1c(COc2ccc(C3=NCCN3)cc2)cccc1COc1ccc(C2=NCCN2)cc1]<br>2,2'-((((2-fluoro-1,3-phenylene)bis(methylene))bis(oxy))bis(4,1-phenylene))bis(4,5-dihydro-1H-imidazole) |
| A-4 | 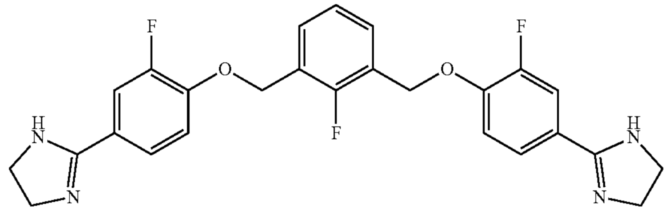 [SMILES: Fc1cc(C2=NCCN2)ccc1OCc1cccc(COc2ccc(C3=NCCN3)cc2F)c1F]<br>2,2'-((((2-fluoro-1,3-phenylene)bis(methylene))bis(oxy))bis(3-fluoro-4,1-phenylene))bis(4,5-dihydro-1H-imidazole) |
| A-5 | 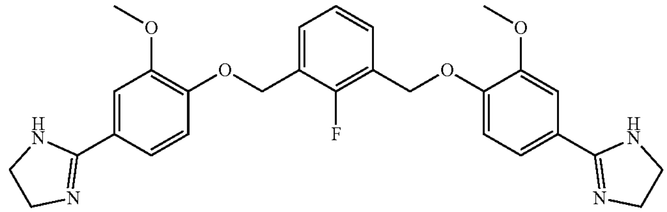 [SMILES: COc1cc(C2=NCCN2)ccc1OCc1cccc(COc2ccc(C3=NCCN3)cc2OC)c1F]<br>2,2'-((((2-fluoro-1,3-phenylene)bis(methylene))bis(oxy))bis(3-methoxy-4,1-phenylene))bis(4,5-dihydro-1H-imidazole) |
| A-6 | 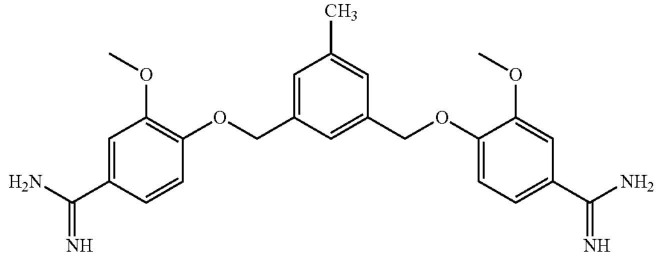 [SMILES: COc1cc(C(=N)N)ccc1OCc1cc(C)cc(COc2ccc(C(=N)N)cc2OC)c1]<br>4,4'-(((5-methyl-1,3-phenylene)bis(methylene))bis(oxy))bis(3-methoxybenzimidamide) |
| A-7 | 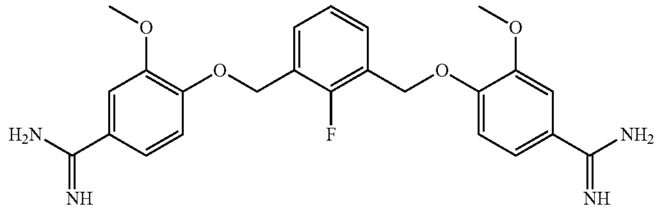 [SMILES: COc1cc(C(=N)N)ccc1OCc1cccc(COc2ccc(C(=N)N)cc2OC)c1F]<br>4,4'-(((2-fluoro-1,3-phenylene)bis(methylene))bis(oxy))bis(3-methoxybenzimidamide) |

TABLE A-continued

| Non-Limiting Examples of Compounds of Formula I-XII | |
|---|---|
| Cmpd # | Structure & Name |
| A-8 | 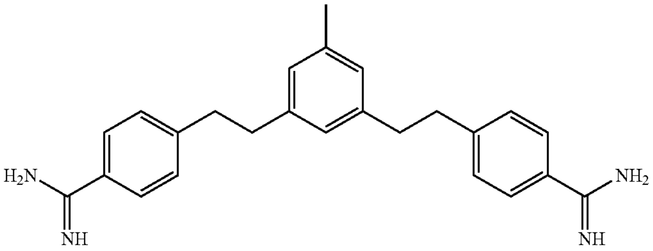 [SMILES: Cc1cc(CCc2ccc(C(=N)N)cc2)cc(CCc2ccc(C(=N)N)cc2)c1] 4,4'-((5-methyl-1,3-phenylene)bis(ethane-2,1-diyl))dibenzimidamide |

TABLE B

| Additional Non-Limiting Examples of Compounds of Formula I-X | |
|---|---|
| Cmpd # | Structure & Name |
| B-1 | 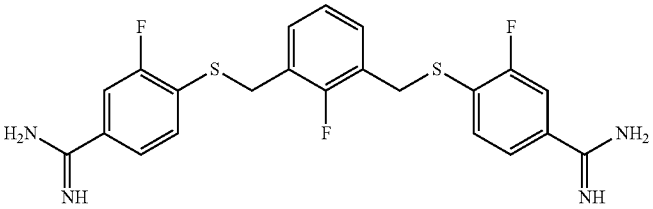 4,4'-(((2-fluoro-1,3-phenylene)bis(methylene))bis(sulfanediyl))bis(3-fluorobenzimidamide) |
| B-2 | 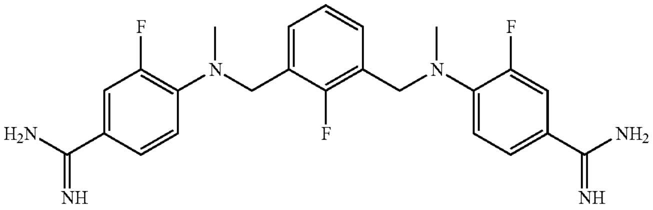 [SMILES: CN(Cc1cccc(CN(C)c2ccc(C(=N)N)cc2F)c1F)c1ccc(C(=N)N)cc1F] 4,4'-(((2-fluoro-1,3-phenylene)bis(methylene))bis(methylazanediyl))bis(3-fluorobenzimidamide) |
| B-3 | 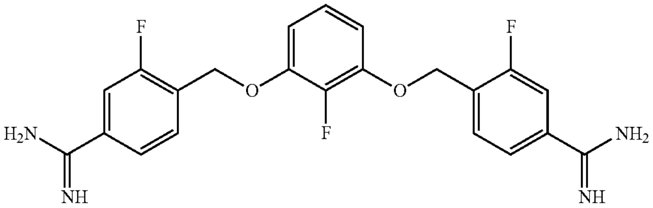 [SMILES: N=C(N)c1ccc(COc2cccc(OCc3ccc(C(=N)N)cc3F)c2F)c(F)c1] 4,4'-(((2-fluoro-1,3-phenylene)bis(oxy))bis(methylene))bis(3-fluorobenzimidamide) |

TABLE B-continued

| Additional Non-Limiting Examples of Compounds of Formula I-X | |
|---|---|
| Cmpd # | Structure & Name |
| B-4 | 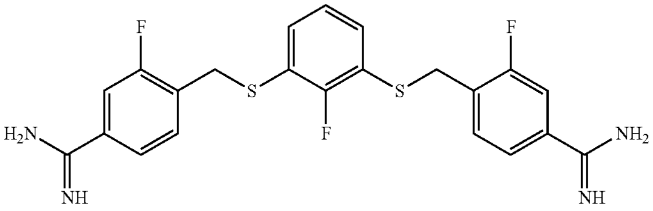 [SMILES: N=C(N)c1ccc(CSc2cccc(SCc3ccc(C(=N)N)cc3F)c2F)c(F)c1] 4,4'-(((2-fluoro-1,3-phenylene)bis(sulfanediyl))bis(methylene))bis(3-fluorobenzimidamide) |
| B-5 | 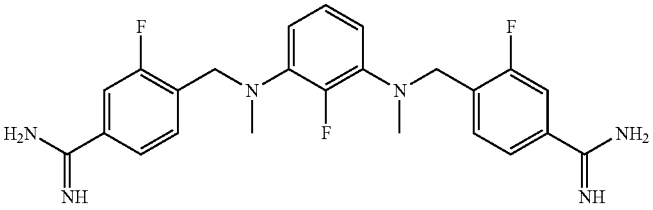 [SMILES: CN(Cc1ccc(C(=N)N)cc1F)c1cccc(N(C)Cc2ccc(C(=N)N)cc2F)c1F] 4,4'-(((2-fluoro-1,3-phenylene)bis(methylazanediyl))bis(methylene))bis(3-fluorobenzimidamide) |
| B-6 | 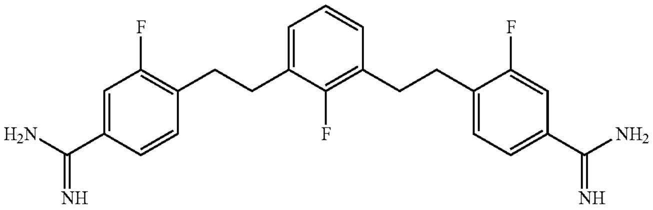 [SMILES: N=C(N)c1ccc(CCc2cccc(CCc3ccc(C(=N)N)cc3F)c2F)c(F)c1] 4,4'-((2-fluoro-1,3-phenylene)bis(ethane-2,1-diyl))bis(3-fluorobenzimidamide) |
| B-7 | 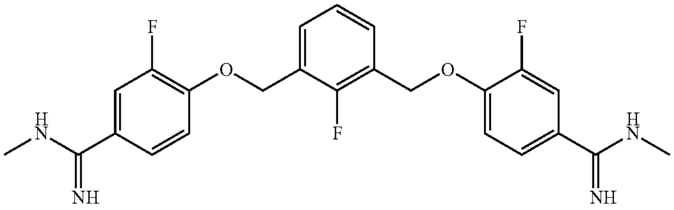 4,4'-(((2-fluoro-1,3-phenylene)bis(methylene))bis(oxy))bis(3-fluoro-N-methylbenzimidamide) |
| B-8 | 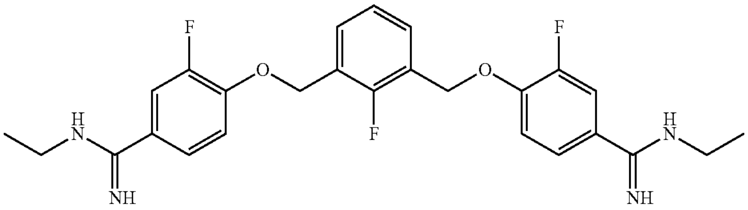 [SMILES: CCNC(=N)c1ccc(OCc2cccc(COc3ccc(C(=N)NCC)cc3F)c2F)c(F)c1] 4,4'-(((2-fluoro-1,3-phenylene)bis(methylene))bis(oxy))bis(N-ethyl-3-fluorobenzimidamide) |

TABLE B-continued

| Cmpd # | Additional Non-Limiting Examples of Compounds of Formula I-X<br>Structure & Name |
|---|---|
| B-9 | 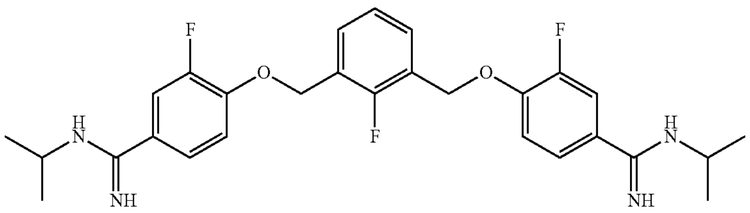 [SMILES: CC(C)NC(=N)c1ccc(OCc2cccc(COc3ccc(C(=N)NC(C)C)cc3F)c2F)c(F)c1]<br>4,4'-(((2-fluoro-1,3-phenylene)bis(methylene))bis(oxy))bis(3-fluoro-N-isopropylbenzimidamide) |
| B-10 | 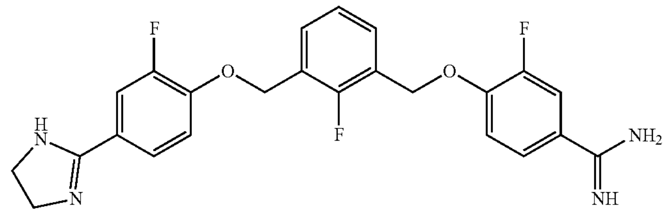 [SMILES: N=C(N)c1ccc(OCc2cccc(COc3ccc(C4=NCCN4)cc3F)c2F)c(F)c1]<br>4-((3-((4-(4,5-dihydro-1H-imidazol-2-yl)-2-fluorophenoxy)methyl)-2-fluorobenzyl)oxy)-3-fluorobenzimidamide |
| B-11 | 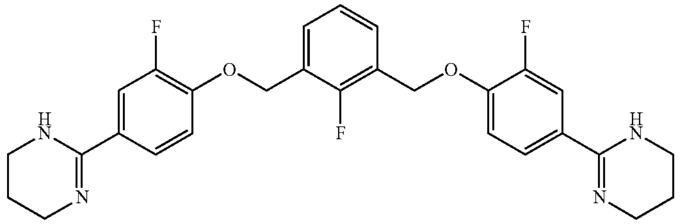 [SMILES: Fc1cc(C2=NCCCN2)ccc1OCc1cccc(COc2ccc(C3=NCCCN3)cc2F)c1F]<br>2,2'-((((2-fluoro-1,3-phenylene)bis(methylene))bis(oxy))bis(3-fluoro-4,1-phenylene))bis(1,4,5,6-tetrahydropyrimidine) |
| B-12 | 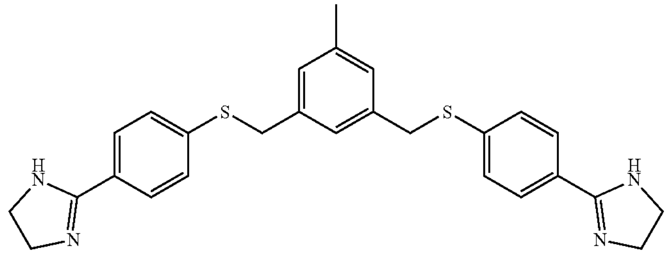<br>2,2'-((((5-methyl-1,3-phenylene)bis(methylene))bis(sulfanediyl)bis(4,1-phenylene))bis(4,5-dihydro-1H-imidazole) |
| B-13 | 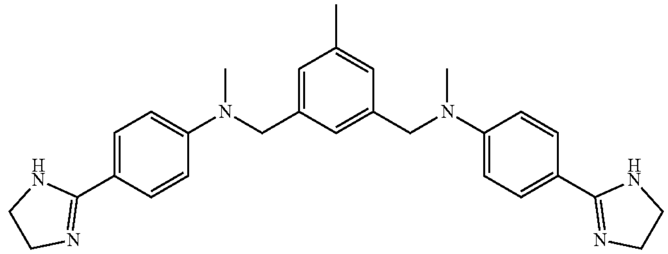 [SMILES: Cc1cc(CN(C)c2ccc(C3=NCCN3)cc2)cc(CN(C)c2ccc(C3=NCCN3)cc2)c1]<br>N,N'-((5-methyl-1,3-phenylene)bis(methylene))bis(4-(4,5-dihydro-1H-imidazol-2-yl)-N-methylaniline) |

TABLE B-continued

| Additional Non-Limiting Examples of Compounds of Formula I-X | |
|---|---|
| Cmpd # | Structure & Name |
| B-14 | 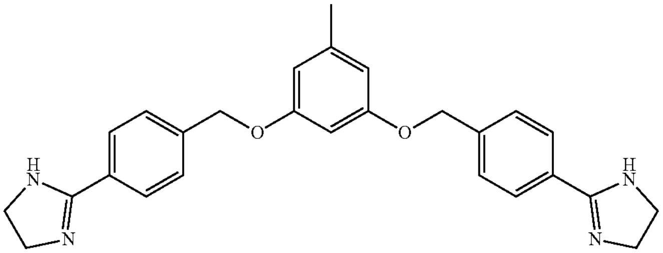 [SMILES: Cc1cc(OCc2ccc(C3=NCCN3)cc2)cc(OCc2ccc(C3=NCCN3)cc2)c1] 2,2'-((((5-methyl-1,3-phenylene)bis(oxy))bis(methylene))bis(4,1-phenylene))bis(4,5-dihydro-1H-imidazole) |
| B-15 | 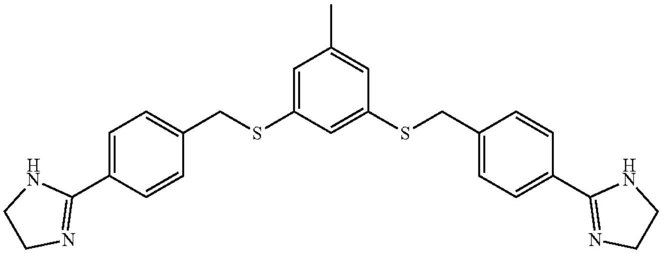 2,2'-((((5-methyl-1,3-phenylene)bis(sulfanediyl))bis(methylene))bis(4,1-phenylene))bis(4,5-dihydro-1H-imidazole) |
| B-16 | 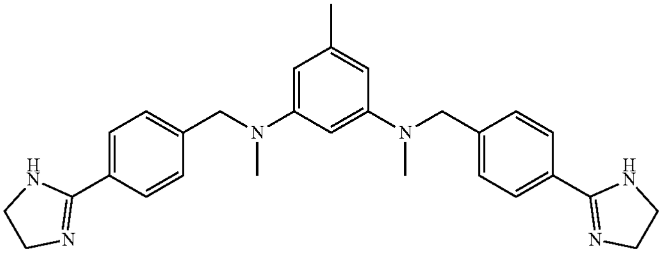 [SMILES: Cc1cc(N(C)Cc2ccc(C3=NCCN3)cc2)cc(N(C)Cc2ccc(C3=NCCN3)cc2)c1] N1,N3-bis(4-(4,5-dihydro-1H-imidazol-2-yl)benzyl)-N1,N3,5-trimethylbenzene-1,3-diamine |
| B-17 | 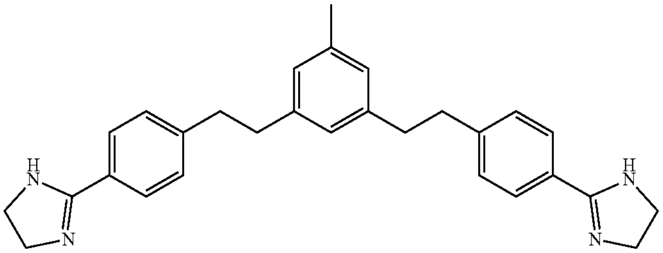 [SMILES: Cc1cc(CCc2ccc(C3=NCCN3)cc2)cc(CCc2ccc(C3=NCCN3)cc2)c1] 2,2'-(((5-methyl-1,3-phenylene)bis(ethane-2,1-diyl))bis(4,1-phenylene))bis(4,5-dihydro-1H-imidazole) |

TABLE B-continued

| Additional Non-Limiting Examples of Compounds of Formula I-X | |
|---|---|
| Cmpd # | Structure & Name |
| B-18 | 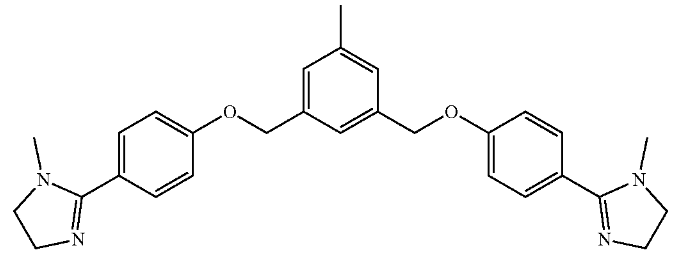 [SMILES: Cc1cc(COc2ccc(C3=NCCN3C)cc2)cc(COc2ccc(C3=NCCN3C)cc2)c1] 2,2'-((((5-methyl-1,3-phenylene)bis(methylene))bis(oxy))bis(4,1-phenylene))bis(1-methyl-4,5-dihydro-1H-imidazole) |
| B-19 | 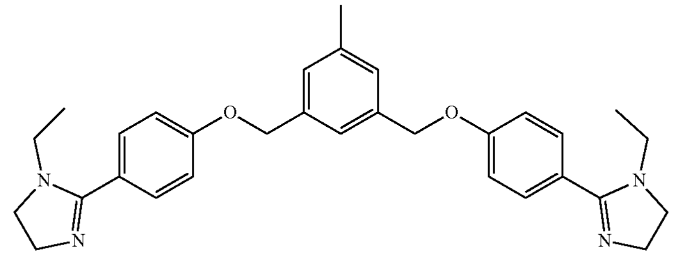 [SMILES: CCN1CCN=C1c1ccc(OCc2cc(C)cc(COc3ccc(C4=NCCN4CC)cc3)c2)cc1] 2,2'-((((5-methyl-1,3-phenylene)bis(methylene))bis(oxy)bis(4,1-phenylene))bis(1-ethyl-4,5-dihydro-1H-imidazole) |
| B-20 | 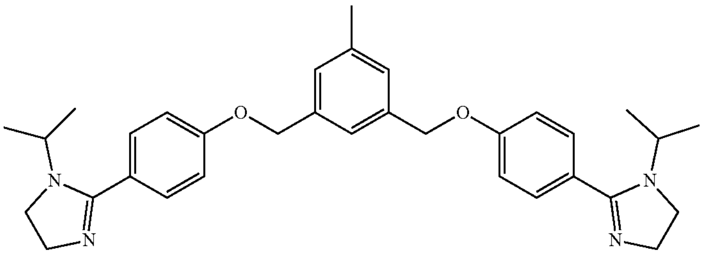 [SMILES: Cc1cc(COc2ccc(C3=NCCN3C(C)C)cc2)cc(COc2ccc(C3=NCCN3C(C)C)cc2)c1] 2,2'-((((5-methyl-1,3-phenylene)bis(methylene))bis(oxy))bis(4,1-phenylene))bis(1-isopropyl-4,5-dihydro-1H-imidazole) |
| B-21 | 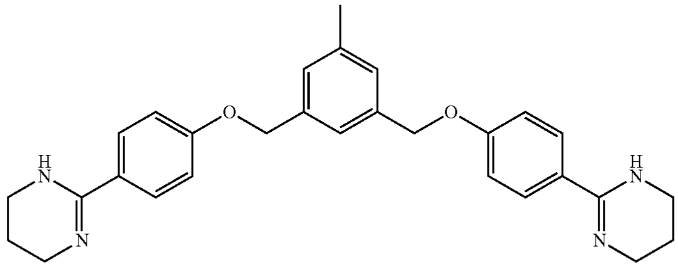 [SMILES: Cc1cc(COc2ccc(C3=NCCCN3)cc2)cc(COc2ccc(C3=NCCCN3)cc2)c1] 2,2'-((((5-methyl-1,3-phenylene)bis(methylene))bis(oxy))bis(4,1-phenylene))bis(1,4,5,6-tetrahydropyrimidine) |

TABLE B-continued

| Additional Non-Limiting Examples of Compounds of Formula I-X | |
|---|---|
| Cmpd # | Structure & Name |
| B-22 | 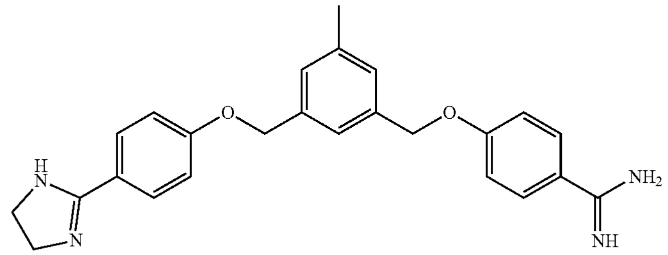 [SMILES: Cc1cc(COc2ccc(C(=N)N)cc2)cc(COc2ccc(C3=NCCN3)cc2)c1] 4-((3-((4-(4,5-dihydro-1H-imidazol-2-yl)phenoxy)methyl)-5-methylbenzyl)oxy)benzimidamide |
| B-23 | 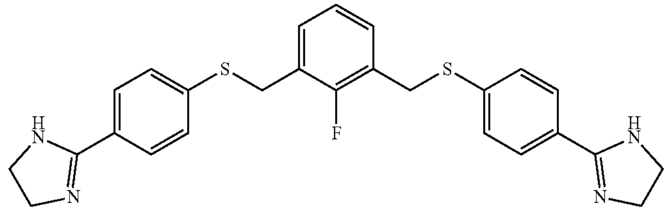 2,2'-((((2-fluoro-1,3-phenylene)bis(methylene))bis(sulfanediyl))bis(4,1-phenylene))bis(4,5-dihydro-1H-imidazole) |
| B-24 | 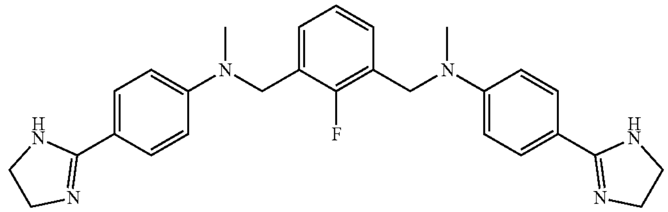 [SMILES: CN(Cc1cccc(CN(C)c2ccc(C3=NCCN3)cc2)c1F)c1ccc(C2=NCCN2)cc1] N,N'-((2-fluoro-1,3-phenylene)bis(methylene))bis(4-(4,5-dihydro-1H-imidazol-2-yl)-N-methylaniline) |
| B-25 | 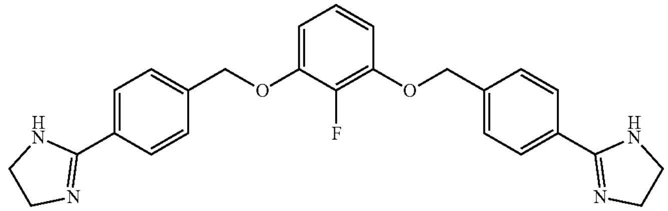 2,2'-((((2-fluoro-1,3-phenylene)bis(oxy))bis(methylene))bis(4,1-phenylene))bis(4,5-dihydro-1H-imidazole) |
| B-26 | 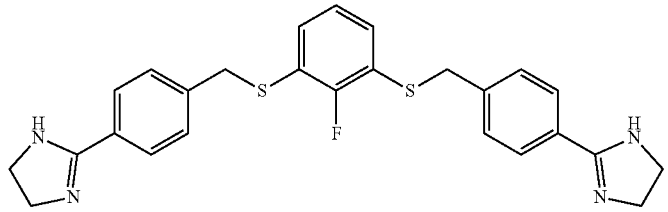 [SMILES: Fc1c(OCc2ccc(C3=NCCN3)cc2)cccc1OCc1ccc(C2=NCCN2)cc1] 2,2'-((((2-fluoro-1,3-phenylene)bis(sulfanediyl))bis(methylene))bis(4,1-phenylene))bis(4,5-dihydro-1H-imidazole) |

TABLE B-continued

| Additional Non-Limiting Examples of Compounds of Formula I-X | |
|---|---|
| Cmpd # | Structure & Name |
| B-27 | 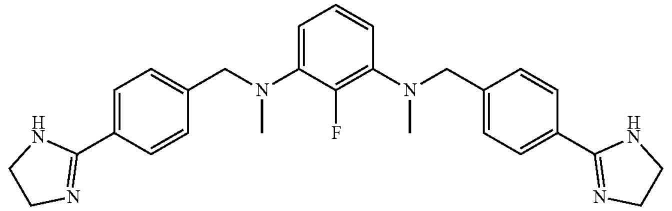 [SMILES: CN(Cc1ccc(C2=NCCN2)cc1)c1cccc(N(C)Cc2ccc(C3=NCCN3)cc2)c1F] N1,N3-bis(4-(4,5-dihydro-1H-imidazol-2-yl)benzyl)-2-fluoro-N1,N3-dimethylbenzene-1,3-diamine |
| B-28 | 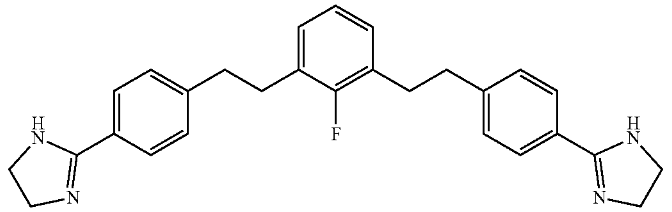 [SMILES: Fc1c(CCc2ccc(C3=NCCN3)cc2)cccc1CCc1ccc(C2=NCCN2)cc1] 2,2'-(((2-fluoro-1,3-phenylene)bis(ethane-2,1-diyl))bis(4,1-phenylene))bis(4,5-dihydro-1H-imidazole) |
| B-29 | 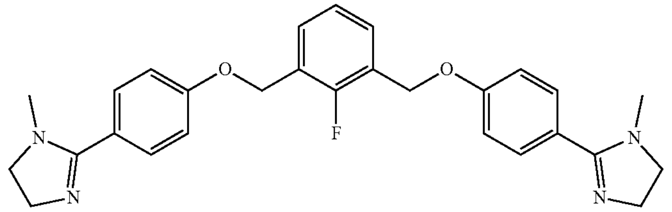 [SMILES: CN1CCN=C1c1ccc(OCc2cccc(COc3ccc(C4=NCCN4C)cc3)c2F)cc1] 2,2'-((((2-fluoro-1,3-phenylene)bis(methylene))bis(oxy))bis(4,1-phenylene))bis(1-methyl-4,5-dihydro-1H-imidazole) |
| B-30 | 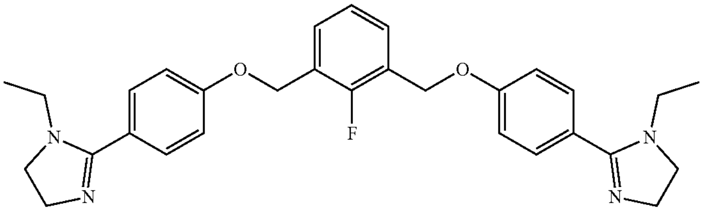 [SMILES: CCN1CCN=C1c1ccc(OCc2cccc(COc3ccc(C4=NCCN4CC)cc3)c2F)cc1] 2,2'-((((2-fluoro-1,3-phenylene)bis(methylene))bis(oxy))bis(4,1-phenylene))bis(1-ethyl-4,5-dihydro-1H-imidazole) |
| B-31 | 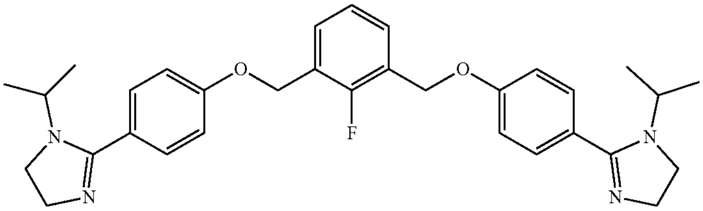 [SMILES: CC(C)N1CCN=C1c1ccc(OCc2cccc(COc3ccc(C4=NCCN4C(C)C)cc3)c2F)cc1] 2,2'-((((2-fluoro-1,3-phenylene)bis(methylene))bis(oxy))bis(4,1-phenylene))bis(1-isopropyl-4,5-dihydro-1H-imidazole) |

TABLE B-continued

| Cmpd # | Structure & Name |
|---|---|
| | Additional Non-Limiting Examples of Compounds of Formula I-X |
| B-32 | 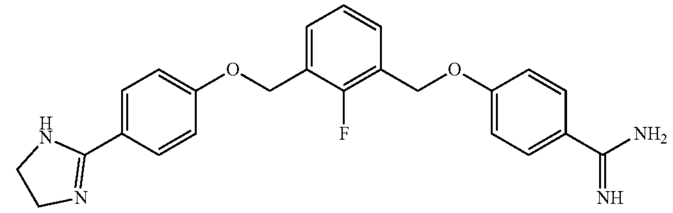 [SMILES: N=C(N)c1ccc(OCc2cccc(COc3ccc(C4=NCCN4)cc3)c2F)cc1]<br>4-((3-((4-(4,5-dihydro-1H-imidazol-2-yl)phenoxy)methyl)-2-fluorobenzyl)oxy)benzimidamide |
| B-33 | 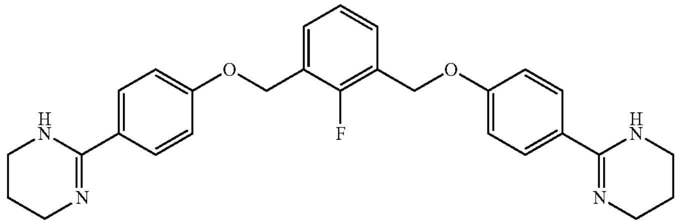 [SMILES: Fc1c(COc2ccc(C3=NCCCN3)cc2)cccc1COc1ccc(C2=NCCCN2)cc1]<br>2,2'-((((2-fluoro-1,3-phenylene)bis(methylene))bis(oxy))bis(4,1-phenylene))bis(1,4,5,6-tetrahydropyrimidine) |
| B-34 | 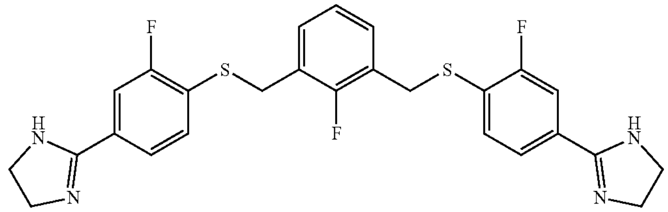 [SMILES: Fc1cc(C2=NCCN2)ccc1SCc1cccc(CSc2ccc(C3=NCCN3)cc2F)c1F]<br>2,2'-((((2-fluoro-1,3-phenylene)bis(methylene))bis(sulfanediyl))bis(3-fluoro-4,1-phenylene)bis(4,5-dihydro-IH-imidazole) |
| B-35 | 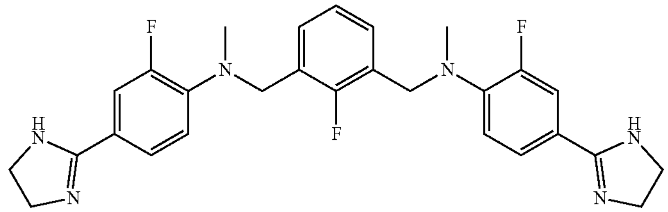 [SMILES: CN(Cc1cccc(CN(C)c2ccc(C3=NCCN3)cc2F)c1F)c1ccc(C2=NCCN2)cc1F]<br>N,N'-((2-fluoro-1,3-phenylene)bis(methylene))bis(4-(4,5-dihydro-1H-imidazol-2-yl)-2-fluoro-N-methylaniline) |
| B-36 | 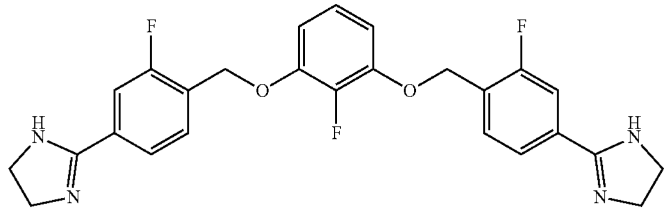 [SMILES: Fc1cc(C2=NCCN2)ccc1COc1cccc(OCc2ccc(C3=NCCN3)cc2F)c1F]<br>2,2'-((((2-fluoro-1,3-phenylene)bis(oxy))bis(methylene))bis(3-fluoro-4,1-phenylene))bis(4,5-dihydro-1H-imidazole) |

TABLE B-continued

| Additional Non-Limiting Examples of Compounds of Formula I-X | |
|---|---|
| Cmpd # | Structure & Name |
| B-37 | 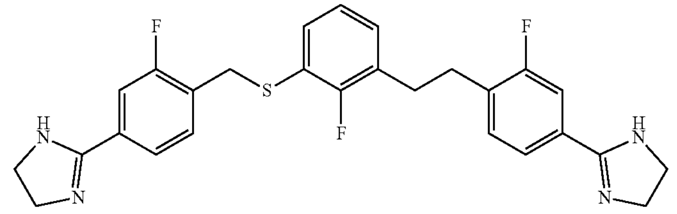<br>2,2'-((((2-fluoro-1,3-phenylene)bis(sulfanediyl))bis(methylene))bis(3-fluoro-4,1-phenylene))bis(4,5-dihydro-1H-imidazole) |
| B-38 | 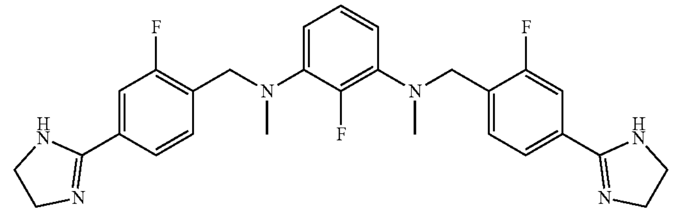<br>N1,N3-bis(4-(4,5-dihydro-1H-imidazol-2-yl)-2-fluorobenzyl)-2-fluoro-N1,N3-dimethylbenzene-1,3-diamine |
| B-39 | 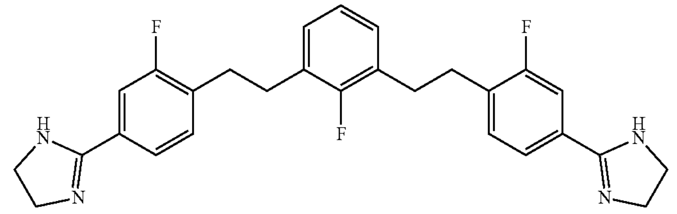 [SMILES: Fc1cc(C2=NCCN2)ccc1CCc1cccc(SCc2ccc(C3=NCCN3)cc2F)c1F]<br>2,2'-(((2-fluoro-1,3-phenylene)bis(ethane-2,1-diyl))bis(3-fluoro-4,1-phenylene))bis(4,5-dihydro-1H-imidazole) |
| B-40 | 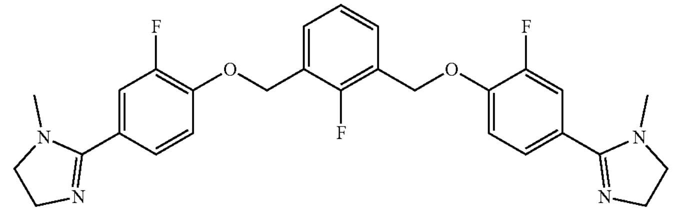 [SMILES: CN1CCN=C1c1ccc(OCc2cccc(COc3ccc(C4=NCCN4C)cc3F)c2F)c(F)c1]<br>2,2'-((((2-fluoro-1,3-phenylene)bis(methylene))bis(oxy))bis(3-fluoro-4,1-phenylene))bis(1-methyl-4,5-dihydro-1H-imidazole) |
| B-41 | 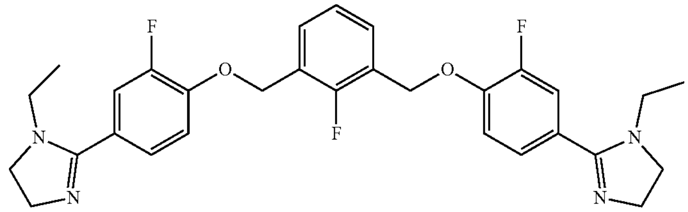 [SMILES: CCN1CCN=C1c1ccc(OCc2cccc(COc3ccc(C4=NCCN4CC)cc3F)c2F)c(F)c1]<br>2,2'-((((2-fluoro-1,3-phenylene)bis(methylene))bis(oxy))bis(3-fluoro-4,1-phenylene))bis(1-ethyl-4,5-dihydro-1H-imidazole) |

TABLE B-continued

| Additional Non-Limiting Examples of Compounds of Formula I-X | |
|---|---|
| Cmpd # | Structure & Name |
| B-42 | 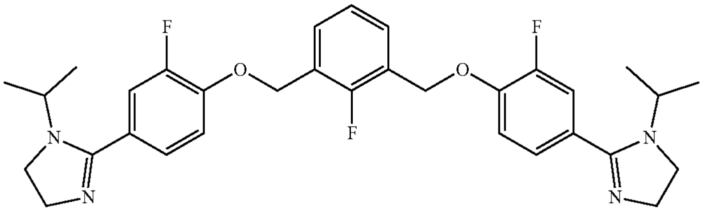 [SMILES: CC(C)N1CCN=C1c1ccc(OCc2cccc(COc3ccc(C4=NCCN4C(C)C)cc3F)c2F)c(F)c1] 2,2'-((((2-fluoro-1,3-phenylene)bis(methylene))bis(oxy))bis(3-fluoro-4,1-phenylene))bis(1-isopropyl-4,5-dihydro-1H-imidazole) |
| B-43 | 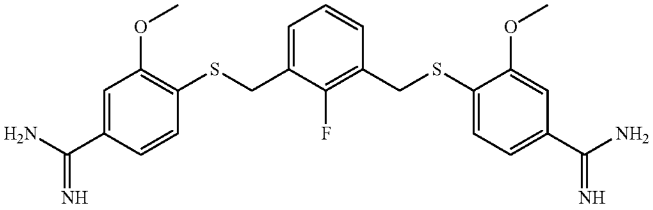 [SMILES: COc1cc(C(=N)N)ccc1SCc1cccc(CSc2ccc(C(=N)N)cc2OC)c1F] 4,4'-(((2-fluoro-1,3-phenylene)bis(methylene))bis(sulfanediyl))bis(3-methoxybenzimidamide) |
| B-44 | 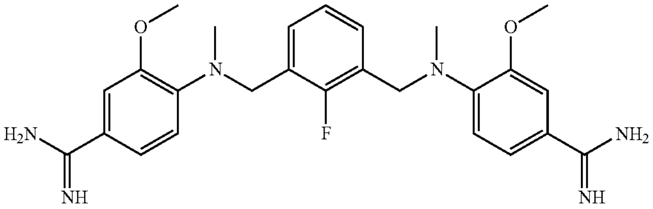 [SMILES: COc1cc(C(=N)N)ccc1N(C)Cc1cccc(CN(C)c2ccc(C(=N)N)cc2OC)c1F] 4,4'-(((2-fluoro-1,3-phenylene)bis(methylene))bis(methylazanediyl))bis(3-methoxybenzimidamide) |
| B-45 | 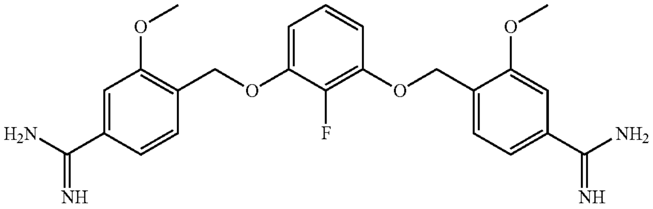 [SMILES: COc1cc(C(=N)N)ccc1CSc1cccc(SCc2ccc(C(=N)N)cc2OC)c1F] 4,4'-(((2-fluoro-1,3-phenylene)bis(oxy))bis(methylene))bis(3-methoxybenzimidamide) |
| B-46 | 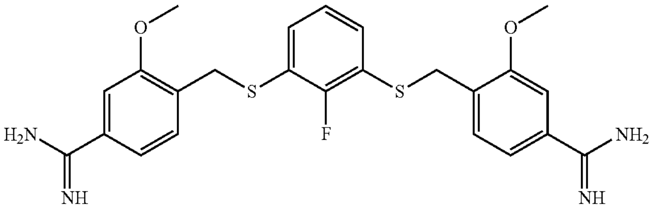 4,4'-(((2-fluoro-1,3-phenylene)bis(sulfanediyl))bis(methylene))bis(3-methoxybenzimidamide) |

TABLE B-continued

| Cmpd # | Structure & Name |
| --- | --- |
| | Additional Non-Limiting Examples of Compounds of Formula I-X |
| B-47 | 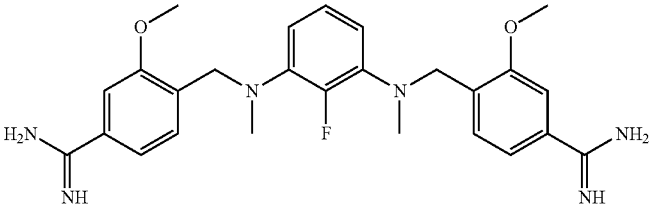 [SMILES: COc1cc(C(=N)N)ccc1CN(C)c1cccc(N(C)Cc2ccc(C(=N)N)cc2OC)c1F] 4,4'-(((2-fluoro-1,3-phenylene)bis(methylazanediyl))bis(methylene))bis(3-methoxybenzimidamide) |
| B-48 | 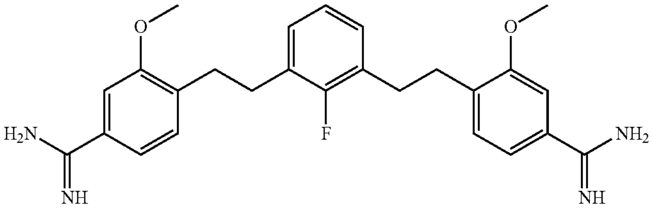 [SMILES: COc1cc(C(=N)N)ccc1CCc1cccc(CCc2ccc(C(=N)N)cc2OC)c1F] 4,4'-((2-fluoro-1,3-phenylene)bis(ethane-2,1-diyl))bis(3-methoxybenzimidamide) |
| B-49 | 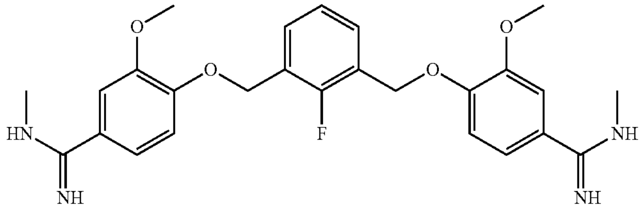 [SMILES: CNC(=N)c1ccc(OCc2cccc(COc3ccc(C(=N)NC)cc3OC)c2F)c(OC)c1] 4,4'-(((2-fluoro-1,3-phenylene)bis(methylene))bis(oxy))bis(3-methoxy-N-methylbenzimidamide) |
| B-50 | 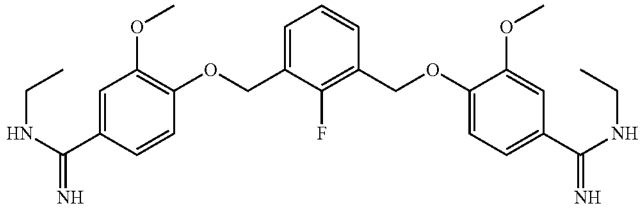 [SMILES: CCNC(=N)c1ccc(OCc2cccc(COc3ccc(C(=N)NCC)cc3OC)c2F)c(OC)c1] 4,4'-(((2-fluoro-1,3-phenylene)bis(methylene))bis(oxy))bis(N-ethyl-3-methoxybenzimidamide) |
| B-51 | 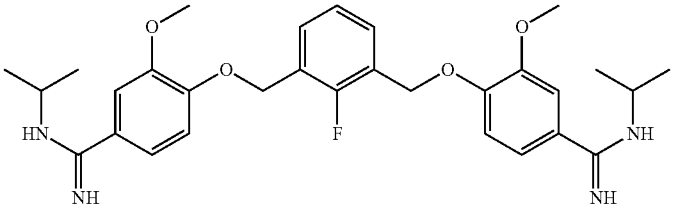 [SMILES: COc1cc(C(=N)NC(C)C)ccc1OCc1cccc(COc2ccc(C(=N)NC(C)C)cc2OC)c1F] 4,4'-(((2-fluoro-1,3-phenylene)bis(methylene))bis(oxy))bis(N-isopropyl-3-methoxybenzimidamide) |

TABLE B-continued

| Cmpd # | Structure & Name |
| --- | --- |
| | Additional Non-Limiting Examples of Compounds of Formula I-X |
| B-52 | 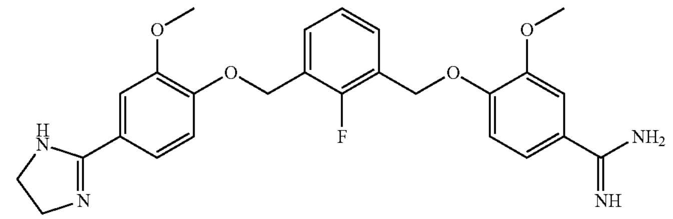 [SMILES: COc1cc(C(=N)N)ccc1OCc1cccc(COc2ccc(C3=NCCN3)cc2OC)c1F] 4-((3-((4-(4,5-dihydro-1H-imidazol-2-yl)-2-methoxyphenoxy)methyl)-2-fluorobenzyl)oxy)-3-methoxybenzimidamide |
| B-53 | 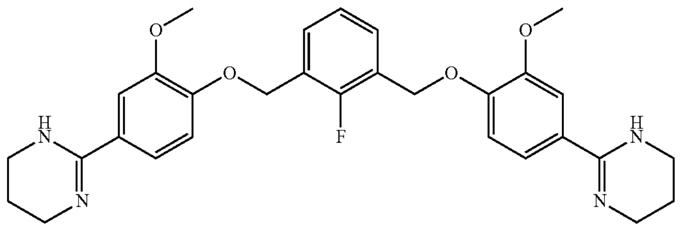 [SMILES: COc1cc(C2=NCCCN2)ccc1OCc1cccc(COc2ccc(C3=NCCCN3)cc2OC)c1F] 2,2'-((((2-fluoro-1,3-phenylene)bis(methylene))bis(oxy))bis(3-methoxy-4,1-phenylene))bis(1,4,5,6-tetrahydropyrimidine) |
| B-54 | 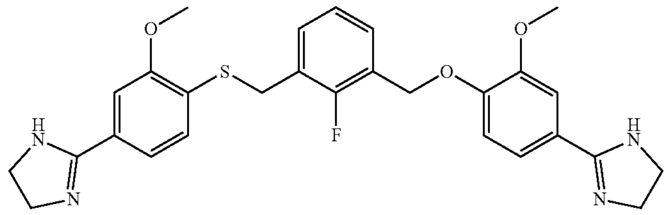 [SMILES: COc1cc(C2=NCCN2)ccc1OCc1cccc(CSc2ccc(C3=NCCN3)cc2OC)c1F] 2,2'-((((2-fluoro-1,3-phenylene)bis(methylene))bis(sulfanediyl))bis(3-methoxy-4,1-phenylene))bis(4,5-dihydro-1H-imidazole) |
| B-55 | 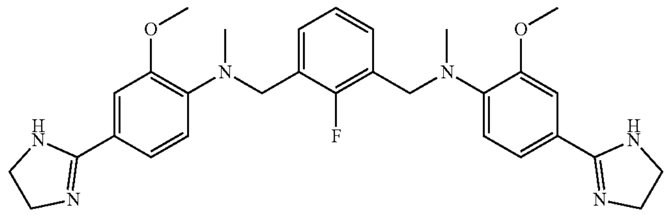 [SMILES: COc1cc(C2=NCCN2)ccc1N(C)Cc1cccc(CN(C)c2ccc(C3=NCCN3)cc2OC)c1F] N,N'-((2-fluoro-1,3-phenylene)bis(methylene))bis(4-(4,5-dihydro-1H-imidazol-2-yl)-2-methoxy-N-methylaniline) |
| B-56 | 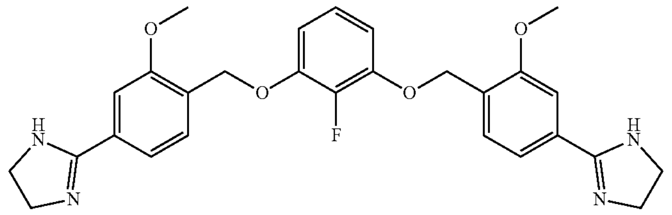 2,2'-((((2-fluoro-1,3-phenylene)bis(oxy))bis(methylene))bis(3-methoxy-4,1-phenylene))bis(4,5-dihydro-1H-imidazole) |

TABLE B-continued

| Cmpd # | Structure & Name |
|---|---|
| | Additional Non-Limiting Examples of Compounds of Formula I-X |
| B-57 | 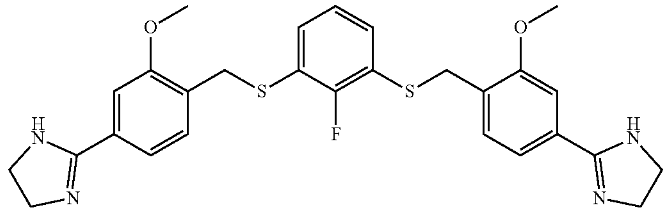 [SMILES: COc1cc(C2=NCCN2)ccc1COc1cccc(OCc2ccc(C3=NCCN3)cc2OC)c1F] 2,2'-((((2-fluoro-1,3-phenylene)bis(sulfanediyl))bis(methylene))bis(3-methoxy-4,1-phenylene))bis(4,5-dihydro-1H-imidazole) |
| B-58 | 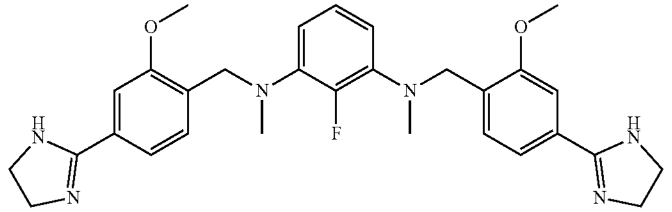 [SMILES: COc1cc(C2=NCCN2)ccc1CN(C)c1cccc(N(C)Cc2ccc(C3=NCCN3)cc2OC)c1F] N1,N3-bis(4-(4,5-dihydro-1H-imidazol-2-yl)-2-methoxybenzyl)-2-fluoro-N1,N3-dimethylbenzene-1,3-diamine |
| B-59 | 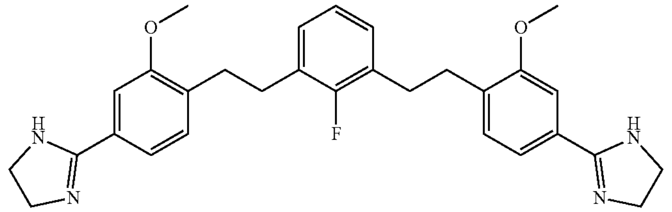 [SMILES: COc1cc(C2=NCCN2)ccc1CCc1cccc(CCc2ccc(C3=NCCN3)cc2OC)c1F] 2,2'-(((2-fluoro-1,3-phenylene)bis(ethane-2,1-diyl))bis(3-methoxy-4,1-phenylene))bis(4,5-dihydro-1H-imidazole) |
| B-60 | 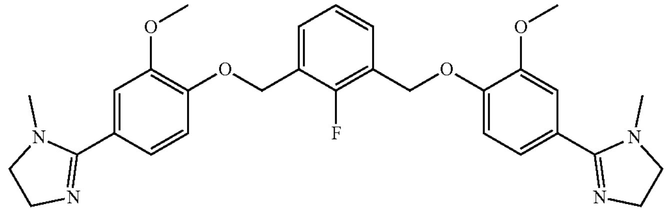 [SMILES: COc1cc(C2=NCCN2C)ccc1OCc1cccc(COc2ccc(C3=NCCN3C)cc2OC)c1F] 2,2'-((((2-fluoro-1,3-phenylene)bis(methylene))bis(oxy))bis(3-methoxy-4,1-phenylene))bis(1-methyl-4,5-dihydro-1H-imidazole) |
| B-61 | 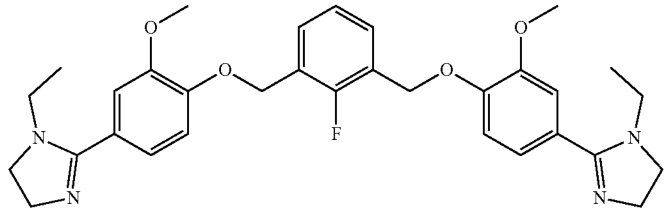 [SMILES: CCN1CCN=C1c1ccc(OCc2cccc(COc3ccc(C4=NCCN4CC)cc3OC)c2F)c(OC)c1] 2,2'-((((2-fluoro-1,3-phenylene)bis(methylene))bis(oxy))bis(3-methoxy-4,1-phenylene))bis(1-ethyl-4,5-dihydro-1H-imidazole) |

TABLE B-continued

| Cmpd # | Additional Non-Limiting Examples of Compounds of Formula I-X<br>Structure & Name |
|---|---|
| B-62 | 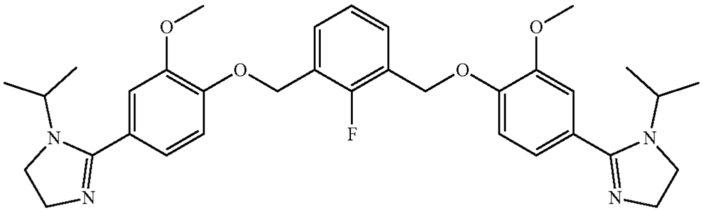 [SMILES: COc1cc(C2=NCCN2C(C)C)ccc1OCc1cccc(COc2ccc(C3=NCCN3C(C)C)cc2OC)c1F]<br>2,2'-((((2-fluoro-1,3-phenylene)bis(methylene))bis(oxy))bis(3-methoxy-4,1-phenylene))bis(1-isopropyl-4,5-dihydro-1H-imidazole) |
| B-63 | 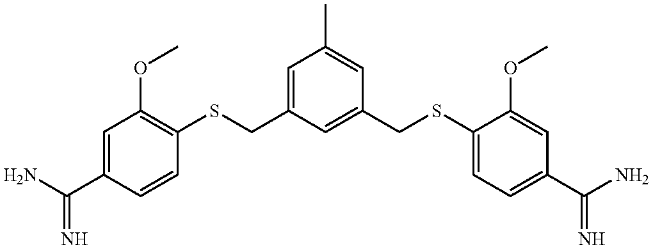 [SMILES: COc1cc(C(=N)N)ccc1SCc1cc(C)cc(CSc2ccc(C(=N)N)cc2OC)c1]<br>4,4'-(((5-methyl-1,3-phenylene)bis(methylene))bis(sulfanediyl))bis(3-methoxybenzimidamide) |
| B-64 | 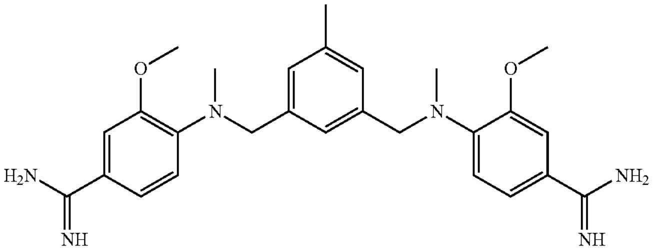 [SMILES: COc1cc(C(=N)N)ccc1N(C)Cc1cc(C)cc(CN(C)c2ccc(C(=N)N)cc2OC)c1]<br>4,4'-(((5-methyl-1,3-phenylene)bis(methylene))bis(methylazanediyl))bis(3-methoxybenzimidamide) |
| B-65 | 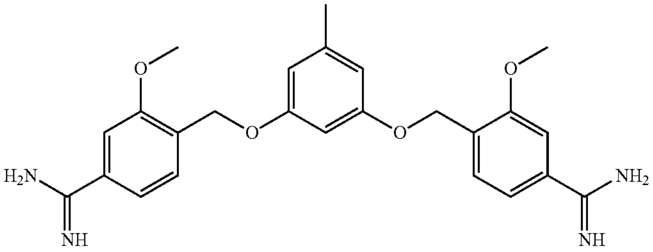 [SMILES: COc1cc(C(=N)N)ccc1COc1cc(C)cc(OCc2ccc(C(=N)N)cc2OC)c1]<br>4,4'-(((5-methyl-1,3-phenylene)bis(oxy))bis(methylene))bis(3-methoxybenzimidamide) |

TABLE B-continued

| Additional Non-Limiting Examples of Compounds of Formula I-X | |
|---|---|
| Cmpd # | Structure & Name |
| B-66 | 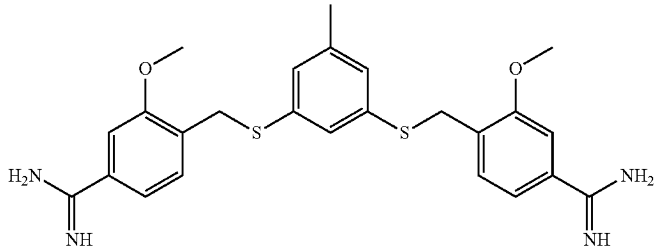 [SMILES: COc1cc(C(=N)N)ccc1CSc1cc(C)cc(SCc2ccc(C(=N)N)cc2OC)c1] 4,4'-(((5-methyl-1,3-phenylene)bis(sulfanediyl))bis(methylene))bis(3-methoxybenzimidamide) |
| B-67 | 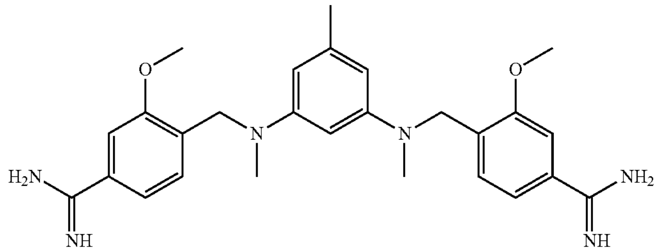 [SMILES: COc1cc(C(=N)N)ccc1CN(C)c1cc(C)cc(N(C)Cc2ccc(C(=N)N)cc2OC)c1] 4,4'-(((5-methyl-1,3-phenylene)bis(methylazanediyl))bis(methylene))bis(3-methoxybenzimidamide) |
| B-68 | 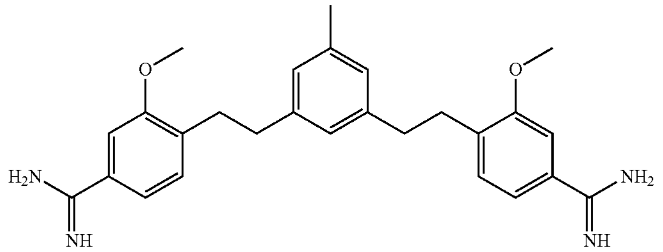 4,4'-((5-methyl-1,3-phenylene)bis(ethane-2,1-diyl))bis(3-methoxybenzimidamide) |
| B-69 | 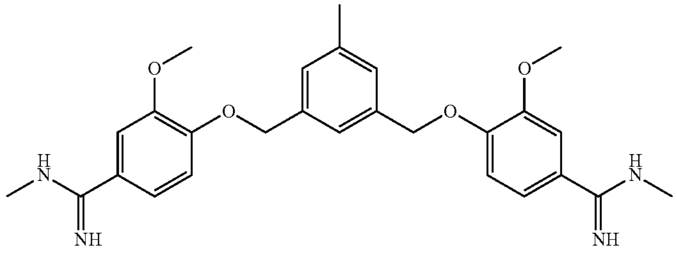 4,4'-(((5-methyl-1,3-phenylene)bis(methylene))bis(oxy))bis(3-methoxy-N-methylbenzimidamide) |

TABLE B-continued

| Cmpd # | Structure & Name |
|---|---|
| | Additional Non-Limiting Examples of Compounds of Formula I-X |
| B-70 | 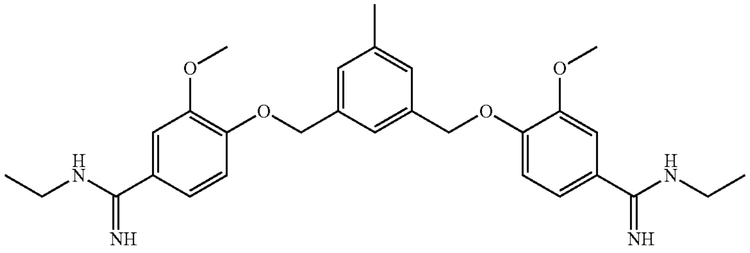 [SMILES: CCNC(=N)c1ccc(OCc2cc(C)cc(COc3ccc(C(=N)NCC)cc3OC)c2)c(OC)c1] 4,4'-(((5-methyl-1,3-phenylene)bis(methylene))bis(oxy))bis(N-ethyl-3-methoxybenzimidamide) |
| B-71 | 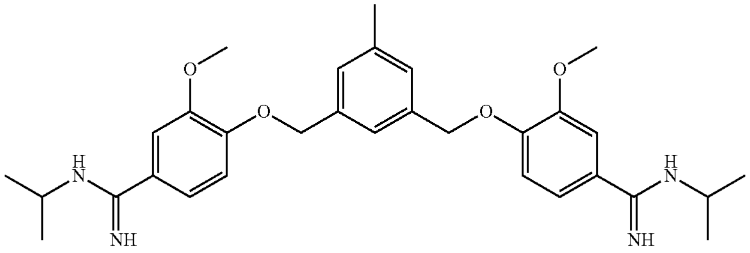 [SMILES: COc1cc(C(=N)NC(C)C)ccc1OCc1cc(C)cc(COc2ccc(C(=N)NC(C)C)cc2OC)c1] 4,4'-(((5-methyl-1,3-phenylene)bis(methylene))bis(oxy))bis(N-isopropyl-3-methoxybenzimidamide) |
| B-72 | 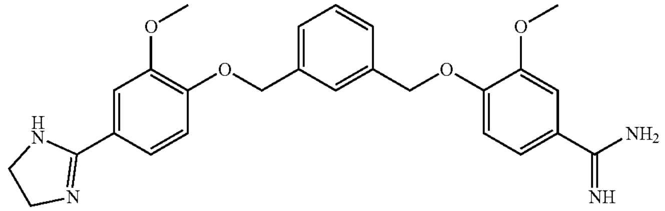 [SMILES: COc1cc(C(=N)N)ccc1OCc1cccc(COc2ccc(C3=NCCN3)cc2OC)c1] 4-((3-((4-(4,5-dihydro-1H-imidazol-2-yl)-2-methoxyphenoxy)methyl)-5-methylbenzyl)oxy)-3-methoxybenzimidamide |
| B-73 | 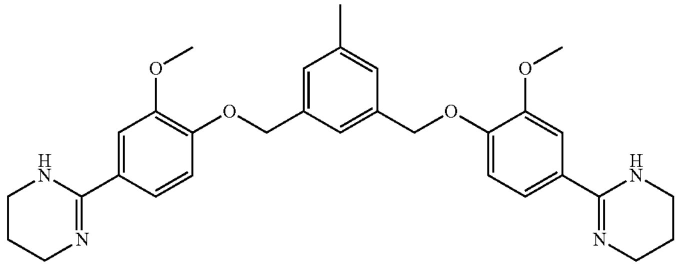 [SMILES: COc1cc(C2=NCCCN2)ccc1OCc1cc(C)cc(COc2ccc(C3=NCCCN3)cc2OC)c1] 2,2'-((((5-methyl-1,3-phenylene)bis(methylene))bis(oxy))bis(3-methoxy-4,1-phenylene))bis(1,4,5,6-tetrahydropyrimidine) |

TABLE B-continued

| Cmpd # | Structure & Name |
| --- | --- |
| | Additional Non-Limiting Examples of Compounds of Formula I-X |
| B-74 | 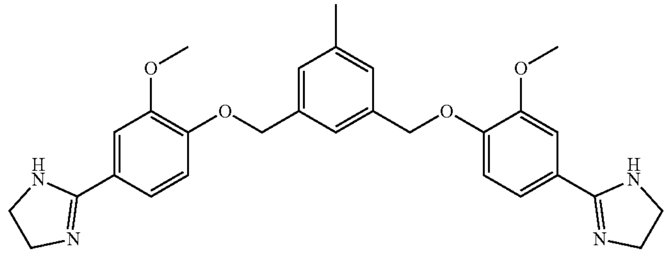 [SMILES: COc1cc(C2=NCCN2)ccc1SCc1cc(C)cc(CSc2ccc(C3=NCCN3)cc2OC)c1]<br>2,2'-((((5-methyl-1,3-phenylene)bis(methylene))bis(oxy))bis(3-methoxy-4,1-phenylene))bis(4,5-dihydro-1H-imidazole) |
| B-75 | 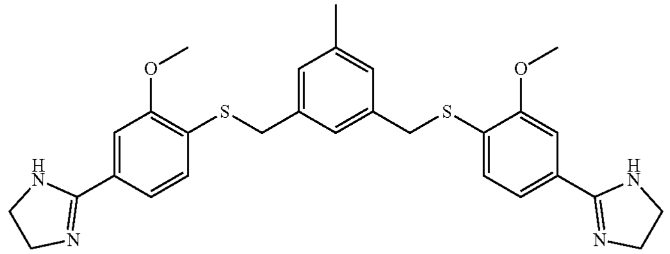<br>2,2'-((((5-methyl-1,3-phenylene)bis(methylene))bis(sulfanediyl))bis(3-methoxy-4,1-phenylene))bis(4,5-dihydro-1H-imidazole) |
| B-76 | 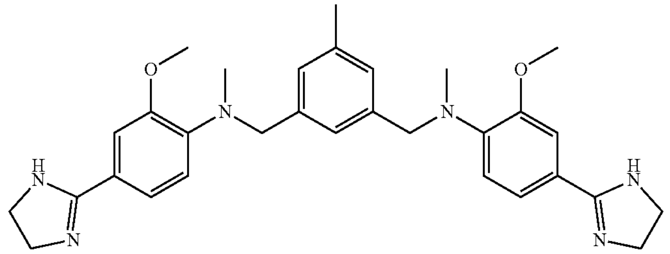 [SMILES: COc1cc(C2=NCCN2)ccc1N(C)Cc1cc(C)cc(CN(C)c2ccc(C3=NCCN3)cc2OC)c1]<br>N,N'-((5-methyl-1,3-phenylene)bis(methylene))bis(4-(4,5-dihydro-1H-imidazol-2-yl)-2-methoxy-N-methylaniline) |
| B-77 | 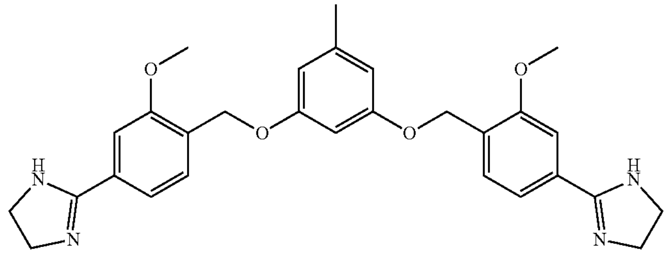<br>2,2'-((((5-methyl-1,3-phenylene)bis(oxy))bis(methylene))bis(3-methoxy-4,1-phenylene))bis(4,5-dihydro-1H-imidazole) |

TABLE B-continued

| Cmpd # | Structure & Name |
|---|---|
| | Additional Non-Limiting Examples of Compounds of Formula I-X |
| B-78 | 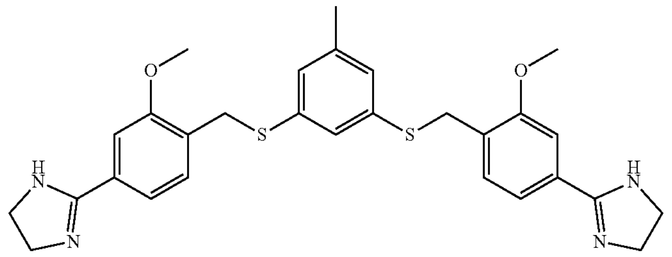 [SMILES: COc1cc(C2=NCCN2)ccc1COc1cc(C)cc(OCc2ccc(C3=NCCN3)cc2OC)c1] 2,2'-((((5-methyl-1,3-phenylene)bis(sulfanediyl))bis(methylene))bis(3-methoxy-4,1-phenylene))bis(4,5-dihydro-1H-imidazole) |
| B-79 | 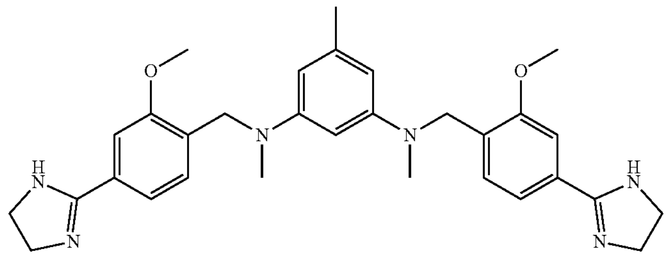 [SMILES: COc1cc(C2=NCCN2)ccc1CN(C)c1cc(C)cc(N(C)Cc2ccc(C3=NCCN3)cc2OC)c1] N1,N3-bis(4-(4,5-dihydro-1H-imidazol-2-yl)-2-methoxybenzyl)-N1,N3,5-trimethylbenzene-1,3-diamine |
| B-80 | 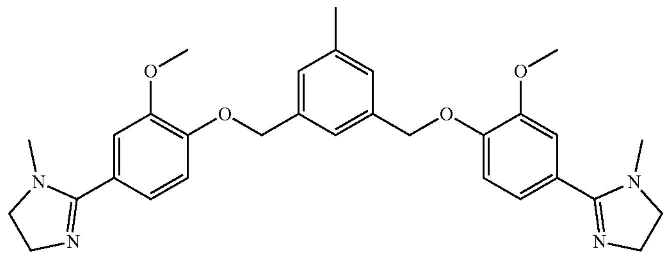 [SMILES: COc1cc(C2=NCCN2C)ccc1OCc1cc(C)cc(COc2ccc(C3=NCCN3C)cc2OC)c1] 2,2'-((((5-methyl-1,3-phenylene)bis(methylene))bis(oxy))bis(3-methoxy-4,1-phenylene))bis(1-methyl-4,5-dihydro-1H-imidazole) |
| B-81 | 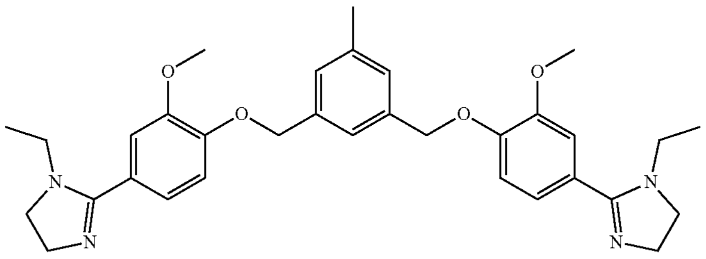 [SMILES: CCN1CCN=C1c1ccc(OCc2cc(C)cc(COc3ccc(C4=NCCN4CC)cc3OC)c2)c(OC)c1] 2,2'-((((5-methyl-1,3-phenylene)bis(methylene))bis(oxy))bis(3-methoxy-4,1-phenylene))bis(1-ethyl-4,5-dihydro-1H-imidazole) |

TABLE B-continued

| Additional Non-Limiting Examples of Compounds of Formula I-X | |
|---|---|
| Cmpd # | Structure & Name |
| B-82 | 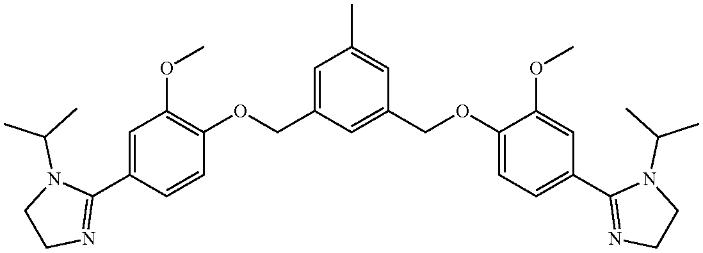 [SMILES: COc1cc(C2=NCCN2C(C)C)ccc1OCc1cc(C)cc(COc2ccc(C3=NCCN3C(C)C)cc2OC)c1]<br>2,2'-((((5-methyl-1,3-phenylene)bis(methylene))bis(oxy))bis(3-methoxy-4,1-phenylene))bis(1-isopropyl-4,5-dihydro-1H-imidazole) |
| B-83 | 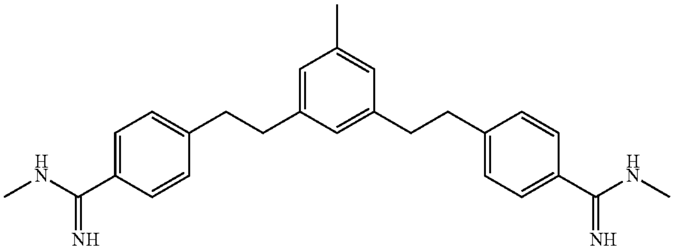<br>4,4'-((5-methyl-1,3-phenylene)bis(ethane-2,1-diyl))bis(N-methylbenzimidamide) |
| B-84 | 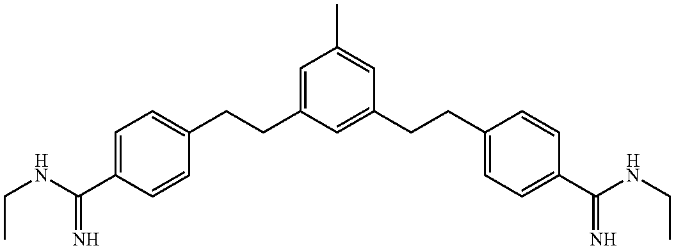 [SMILES: CCNC(=N)c1ccc(CCc2cc(C)cc(CCc3ccc(C(=N)NCC)cc3)c2)cc1]<br>4,4'-((5-methyl-1,3-phenylene)bis(ethane-2,1-diyl))bis(N-ethylbenzimidamide) |
| B-85 | 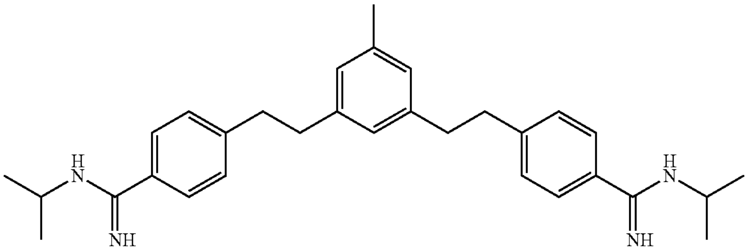 [SMILES: Cc1cc(CCc2ccc(C(=N)NC(C)C)cc2)cc(CCc2ccc(C(=N)NC(C)C)cc2)c1]<br>4,4'-((5-methyl-1,3-phenylene)bis(ethane-2,1-diyl))bis(N-isopropylbenzimidamide) |

TABLE B-continued

| Additional Non-Limiting Examples of Compounds of Formula I-X | |
|---|---|
| Cmpd # | Structure & Name |
| B-86 | 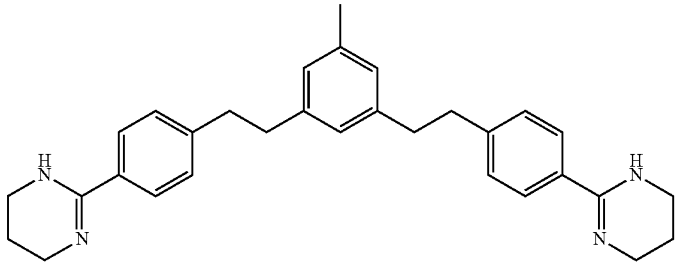 [SMILES: Cc1cc(CCc2ccc(C3=NCCCN3)cc2)cc(CCc2ccc(C3=NCCCN3)cc2)c1] 2,2'-(((5-methyl-1,3-phenylene)bis(ethane-2,1-diyl))bis(4,1-phenylene))bis(1,4,5,6-tetrahydropyrimidine) |
| B-87 | 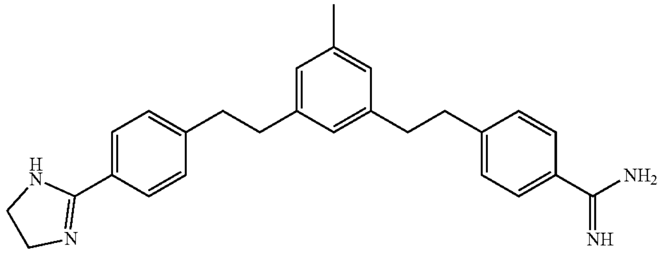 [SMILES: Cc1cc(CCc2ccc(C(=N)N)cc2)cc(CCc2ccc(C3=NCCN3)cc2)c1] 4-(3-(4-(4,5-dihydro-1H-imidazol-2-yl)phenethyl)-5-methylphenethyl)benzimidamide |
| B-88 | 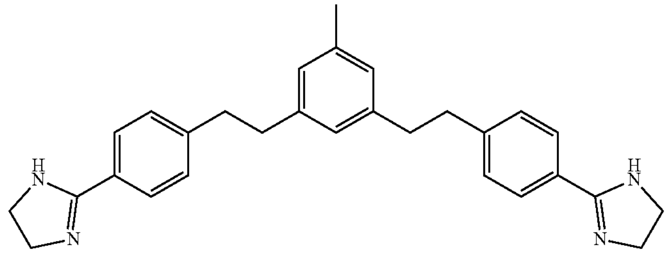 [SMILES: Cc1cc(CCc2ccc(C3=NCCN3)cc2)cc(CCc2ccc(C3=NCCN3)cc2)c1] 2,2'-(((5-methyl-1,3-phenylene)bis(ethane-2,1-diyl))bis(4,1-phenylene))bis(4,5-dihydro-1H-imidazole) |
| B-89 | 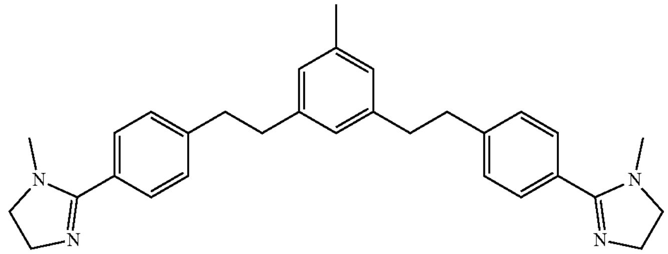 [SMILES: Cc1cc(CCc2ccc(C3=NCCN3C)cc2)cc(CCc2ccc(C3=NCCN3C)cc2)c1] 2,2'-(((5-methyl-1,3-phenylene)bis(ethane-2,1-diyl))bis(4,1-phenylene))bis(1-methyl-4,5-dihydro-1H-imidazole) |

TABLE B-continued

| Additional Non-Limiting Examples of Compounds of Formula I-X | |
|---|---|
| Cmpd # | Structure & Name |
| B-90 | 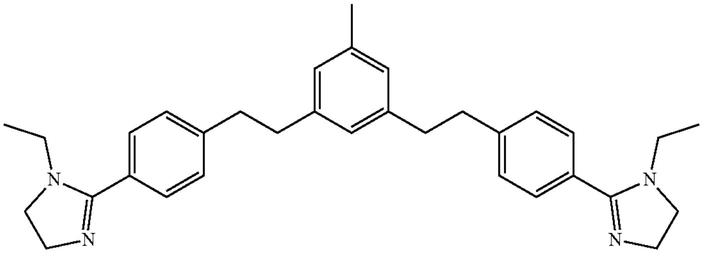 [SMILES: CCN1CCN=C1c1ccc(CCc2cc(C)cc(CCc3ccc(C4=NCCN4CC)cc3)c2)cc1] 2,2'-(((5-methyl-1,3-phenylene)bis(ethane-2,1-diyl))bis(4,1-phenylene))bis(1-ethyl-4,5-dihydro-1H-imidazole) |
| B-91 | 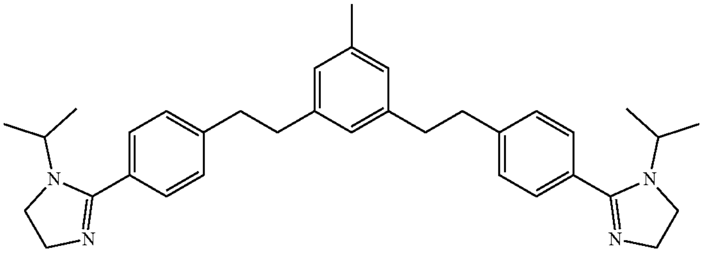 2,2'-(((5-methyl-1,3-phenylene)bis(ethane-2,1-diyl))bis(4,1-phenylene))bis(1-isopropyl-4,5-dihydro-1H-imidazole) |
| B-92 | 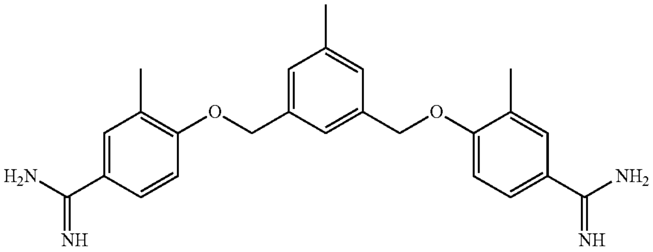 [SMILES: Cc1cc(COc2ccc(C(=N)N)cc2C)cc(COc2ccc(C(=N)N)cc2C)c1] 4,4'-(((5-methyl-1,3-phenylene)bis(methylene)bis(oxy))bis(3-methylbenzimidamide) |
| B-93 | 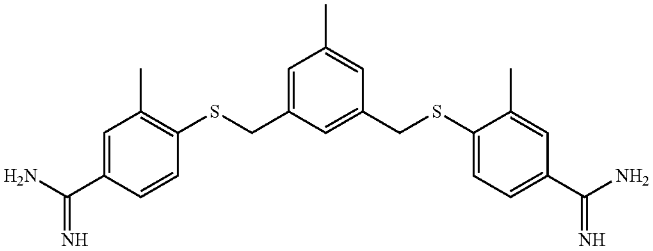 [SMILES: Cc1cc(CSc2ccc(C(=N)N)cc2C)cc(CSc2ccc(C(=N)N)cc2C)c1] 4,4'-(((5-methyl-1,3-phenylene)bis(methylene))bis(sulfanediyl))bis(3-methylbenzimidamide) |

TABLE B-continued

| Additional Non-Limiting Examples of Compounds of Formula I-X | |
|---|---|
| Cmpd # | Structure & Name |
| B-94 | 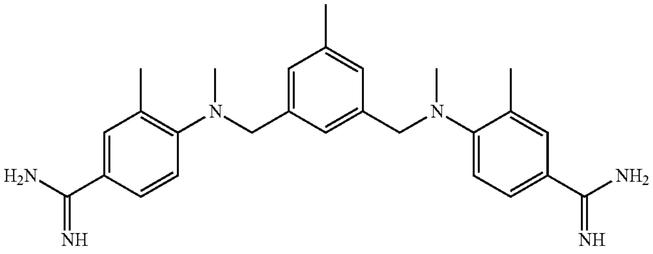 [SMILES: Cc1cc(CN(C)c2ccc(C(=N)N)cc2C)cc(CN(C)c2ccc(C(=N)N)cc2C)c1] 4,4'-(((5-methyl-1,3-phenylene)bis(methylene))bis(methylazanediyl))bis(3-methylbenzimidamide) |
| B-95 | 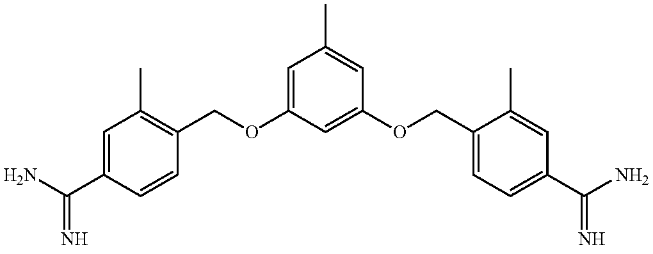 4,4'-(((5-methyl-1,3-phenylene)bis(oxy))bis(methylene))bis(3-methylbenzimidamide) |
| B-96 | 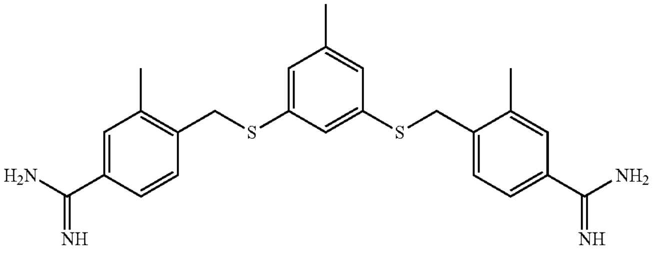 [SMILES: Cc1cc(SCc2ccc(C(=N)N)cc2C)cc(SCc2ccc(C(=N)N)cc2C)c1] 4,4'-(((5-methyl-1,3-phenylene)bis(sulfanediyl))bis(methylene))bis(3-methylbenzimidamide) |
| B-97 | 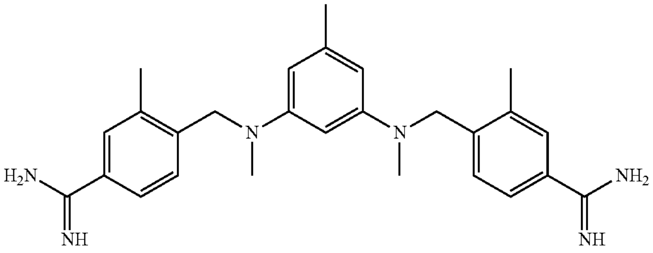 [SMILES: Cc1cc(N(C)Cc2ccc(C(=N)N)cc2C)cc(N(C)Cc2ccc(C(=N)N)cc2C)c1] 4,4'-(((5-methyl-1,3-phenylene)bis(methylazanediyl))bis(methylene))bis(3-methylbenzimidamide) |

TABLE B-continued

| Cmpd # | Additional Non-Limiting Examples of Compounds of Formula I-X<br>Structure & Name |
|---|---|
| B-98 | 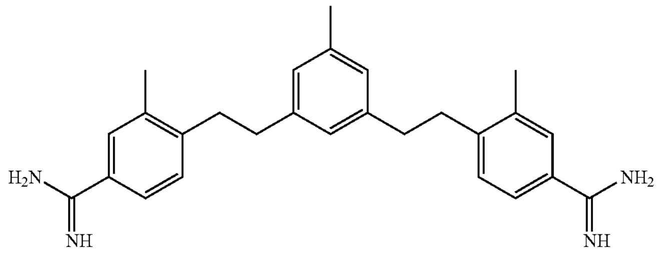 [SMILES: Cc1cc(CCc2ccc(C(=N)N)cc2C)cc(CCc2ccc(C(=N)N)cc2C)c1]<br>4,4'-((5-methyl-1,3-phenylene)bis(ethane-2,1-diyl))bis(3-methylbenzimidamide) |
| B-99 | 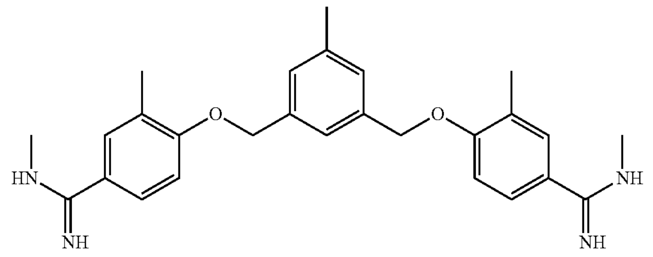 [SMILES: CNC(=N)c1ccc(OCc2cc(C)cc(COc3ccc(C(=N)NC)cc3C)c2)c(C)c1]<br>4,4'-(((5-methyl-1,3-phenylene)bis(methylene))bis(oxy))bis(N,3-dimethylbenzimidamide) |
| B-100 | 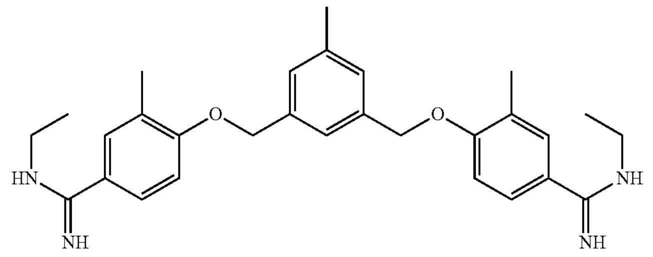 [SMILES: CCNC(=N)c1ccc(OCc2cc(C)cc(COc3ccc(C(=N)NCC)cc3C)c2)c(C)c1]<br>4,4'-(((5-methyl-1,3-phenylene)bis(methylene))bis(oxy))bis(N-ethyl-3-methylbenzimidamide) |
| B-101 | 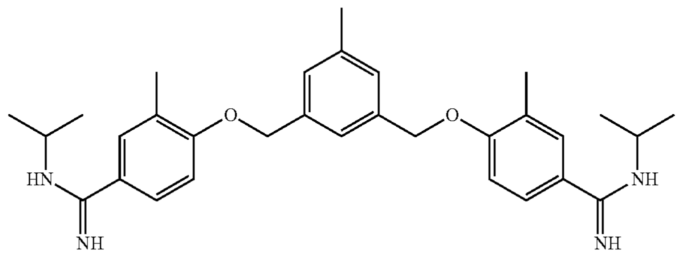 [SMILES: Cc1cc(COc2ccc(C(=N)NC(C)C)cc2C)cc(COc2ccc(C(=N)NC(C)C)cc2C)c1]<br>4,4'-(((5-methyl-1,3-phenylene)bis(methylene))bis(oxy))bis(N-isopropyl-3-methylbenzimidamide) |

TABLE B-continued

Additional Non-Limiting Examples of Compounds of Formula I-X

| Cmpd # | Structure & Name |
|---|---|
| B-102 | 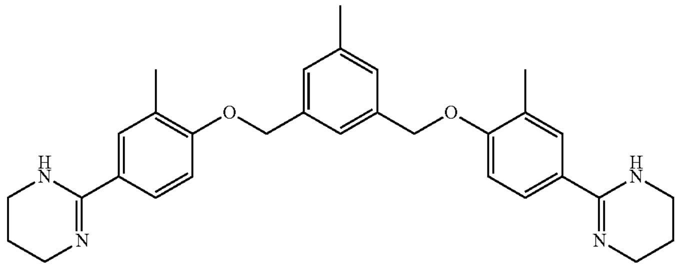 [SMILES: Cc1cc(COc2ccc(C3=NCCCN3)cc2C)cc(COc2ccc(C3=NCCCN3)cc2C)c1] 2,2'-((((5-methyl-1,3-phenylene)bis(methylene))bis(oxy))bis(3-methyl-4,1-phenylene))bis(1,4,5,6-tetrahydropyrimidine) |
| B-103 | 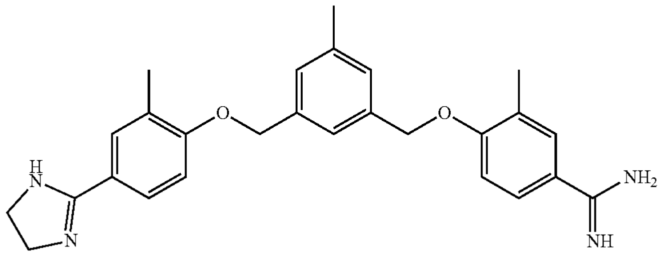 [SMILES: Cc1cc(COc2ccc(C(=N)N)cc2C)cc(COc2ccc(C3=NCCN3)cc2C)c1] 4-((3-((4-(4,5-dihydro-1H-imidazol-2-yl)-2-methylphenoxy)methyl)-5-methylbenzyl)oxy)-3-methylbenzimidamide |
| B-104 | 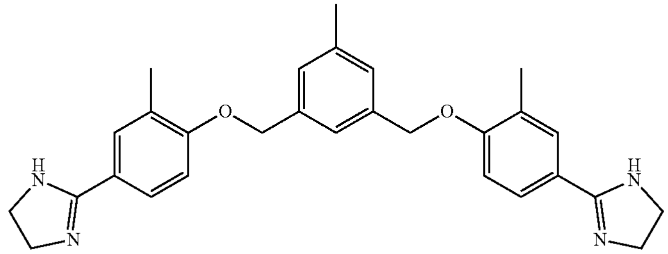 [SMILES: Cc1cc(COc2ccc(C3=NCCN3)cc2C)cc(COc2ccc(C3=NCCN3)cc2C)c1] 2,2'-((((5-methyl-1,3-phenylene)bis(methylene))bis(oxy))bis(3-methyl-4,1-phenylene))bis(4,5-dihydro-1H-imidazole) |
| B-105 | 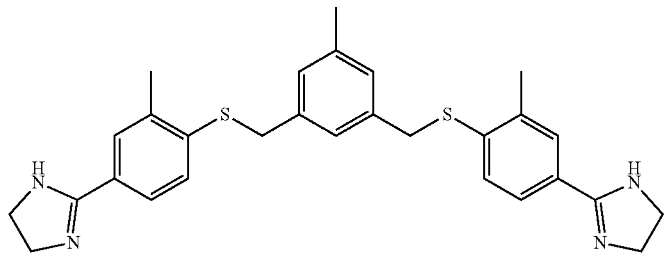 [SMILES: Cc1cc(CSc2ccc(C3=NCCN3)cc2C)cc(CSc2ccc(C3=NCCN3)cc2C)c1] 2,2'-((((5-methyl-1,3-phenylene)bis(methylene))bis(sulfanediyl))bis(3-methyl-4,1-phenylene))bis(4,5-dihydro-1H-imidazole) |

TABLE B-continued

| Additional Non-Limiting Examples of Compounds of Formula I-X | |
|---|---|
| Cmpd # | Structure & Name |
| B-106 | 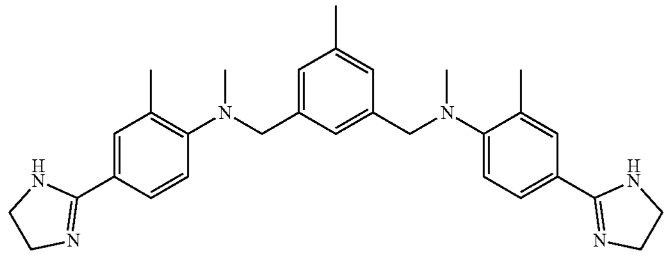 [SMILES: Cc1cc(CN(C)c2ccc(C3=NCCN3)cc2C)cc(CN(C)c2ccc(C3=NCCN3)cc2C)c1] N,N'-((5-methyl-1,3-phenylene)bis(methylene))bis(4-(4,5-dihydro-1H-imidazol-2-yl)-N,2-dimethylaniline) |
| B-107 | 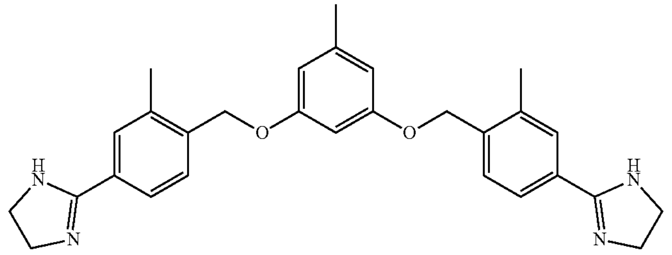 2,2'-((((5-methyl-1,3-phenylene)bis(oxy))bis(methylene))bis(3-methyl-4,1-phenylene))bis(4,5-dihydro-1H-imidazole) |
| B-108 | 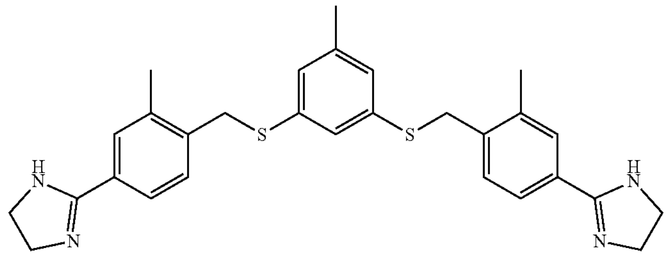 [SMILES: Cc1cc(OCc2ccc(C3=NCCN3)cc2C)cc(OCc2ccc(C3=NCCN3)cc2C)c1] 2,2'-((((5-methyl-1,3-phenylene)bis(sulfanediyl))bis(methylene))bis(3-methyl-4,1-phenylene))bis(4,5-dihydro-1H-imidazole) |
| B-109 | 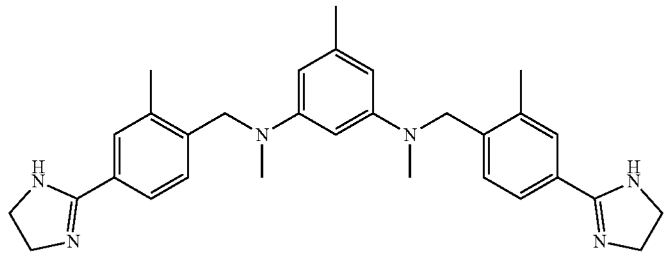 [SMILES: Cc1cc(N(C)Cc2ccc(C3=NCCN3)cc2C)cc(N(C)Cc2ccc(C3=NCCN3)cc2C)c1] N1,N3-bis(4-(4,5-dihydro-1H-imidazol-2-yl)-2-methylbenzyl)-N1,N3,5-trimethylbenzene-1,3-diamine |

TABLE B-continued

| Additional Non-Limiting Examples of Compounds of Formula I-X | |
|---|---|
| Cmpd # | Structure & Name |
| B-110 | 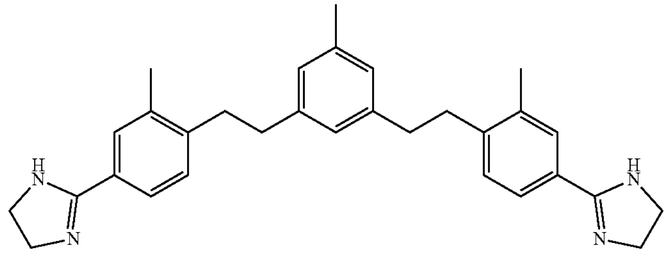 [SMILES: Cc1cc(CCc2ccc(C3=NCCN3)cc2C)cc(CCc2ccc(C3=NCCN3)cc2C)c1] 2,2'-(((5-methyl-1,3-phenylene)bis(ethane-2,1-diyl))bis(3-methyl-4,1-phenylene))bis(4,5-dihydro-1H-imidazole) |
| B-111 | 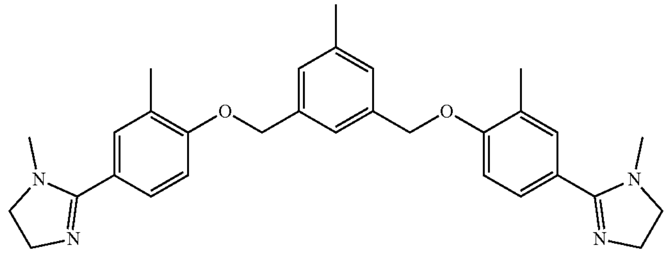 [SMILES: Cc1cc(COc2ccc(C3=NCCN3C)cc2C)cc(COc2ccc(C3=NCCN3C)cc2C)c1] 2,2'-((((5-methyl-1,3-phenylene)bis(methylene))bis(oxy))bis(3-methyl-4,1-phenylene))bis(1-methyl-4,5-dihydro-1H-imidazole) |
| B-112 | 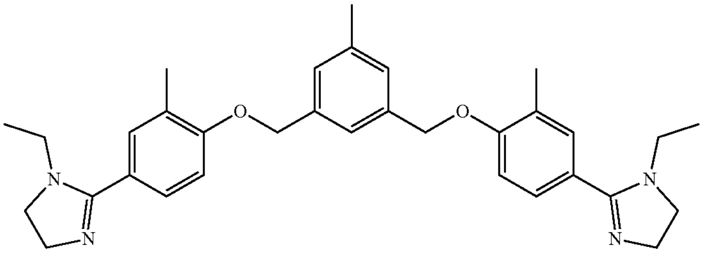 [SMILES: CCN1CCN=C1c1ccc(OCc2cc(C)cc(COc3ccc(C4=NCCN4CC)cc3C)c2)c(C)c1] 2,2'-((((5-methyl-1,3-phenylene)bis(methylene))bis(oxy)bis(3-methyl-4,1-phenylene))bis(1-ethyl-4,5-dihydro-1H-imidazole) |
| B-113 | 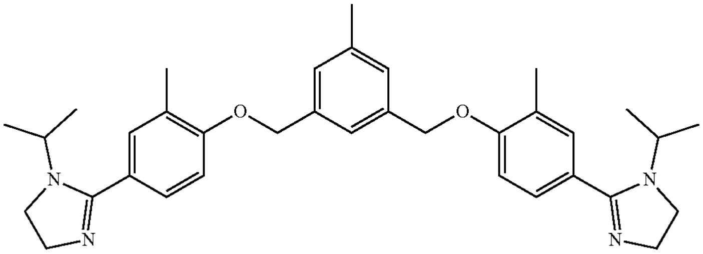 [SMILES: Cc1cc(COc2ccc(C3=NCCN3C(C)C)cc2C)cc(COc2ccc(C3=NCCN3C(C)C)cc2C)c1] 2,2'-((((5-methyl-1,3-phenylene)bis(methylene))bis(oxy))bis(3-methyl-4,1-phenylene))bis(1-isopropyl-4,5-dihydro-1H-imidazole) |

TABLE B-continued

| Cmpd # | Structure & Name |
|---|---|
| | Additional Non-Limiting Examples of Compounds of Formula I-X |
| B-114 | 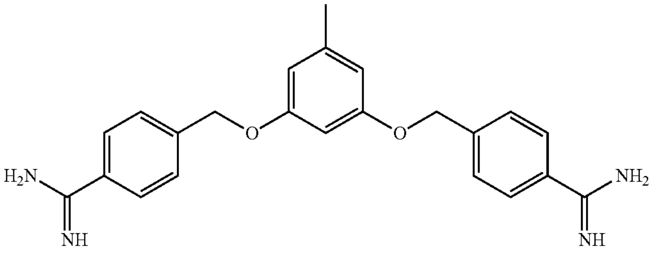 [SMILES: Cc1cc(SCc2ccc(C(=N)N)cc2)cc(SCc2ccc(C(=N)N)cc2)c1]<br>4,4'-(((5-methyl-1,3-phenylene)bis(oxy))bis(methylene))dibenzimidamide |
| B-115 | 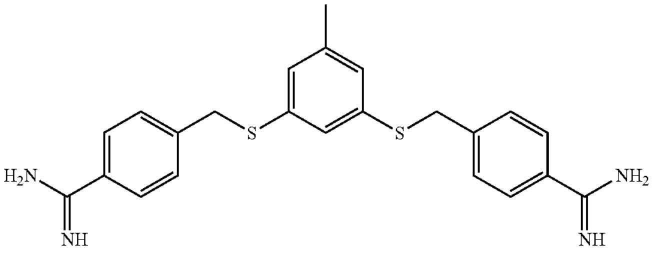<br>4,4'-(((5-methyl-1,3-phenylene)bis(sulfanediyl))bis(methylene))dibenzimidamide |
| B-116 | 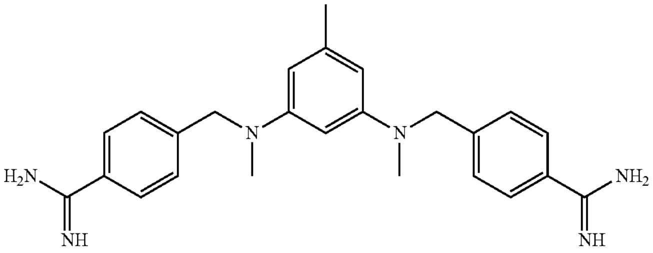 [SMILES: Cc1cc(N(C)Cc2ccc(C(=N)N)cc2)cc(N(C)Cc2ccc(C(=N)N)cc2)c1]<br>4,4'-(((5-methyl-1,3-phenylene)bis(methylazanediyl))bis(methylene))dibenzimidamide |

TABLE C

| Cmpd # | Structure & Name |
|---|---|
| | Additional Compounds of the Present Invention |
| C-1 | 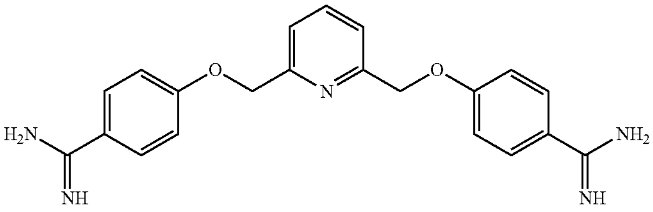<br>4-((6-((4-carbamimidoylphenoxy)methyl)pyridin-2-yl)methoxy)benzamide |

TABLE C-continued

| Additional Compounds of the Present Invention | |
|---|---|
| Cmpd # | Structure & Name |
| C-2 | 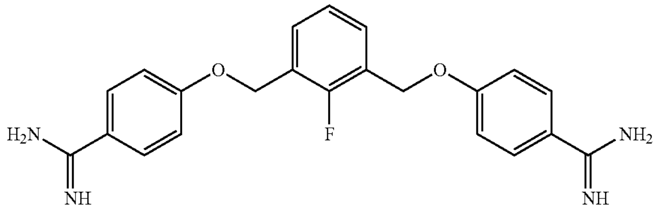 4,4′-(((2-fluoro-1,3-phenylene)bis(methylene))bis(oxy))dibenzimidamide |
| C-3 | 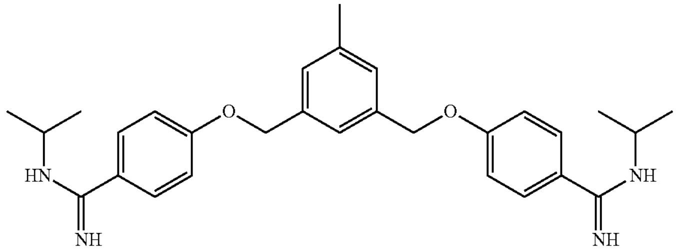 4,4′-(((5-methyl-1,3-phenylene)bis(methylene)bis(oxy)) bis(N-isopropylbenzimidamide) |
| C-4 | 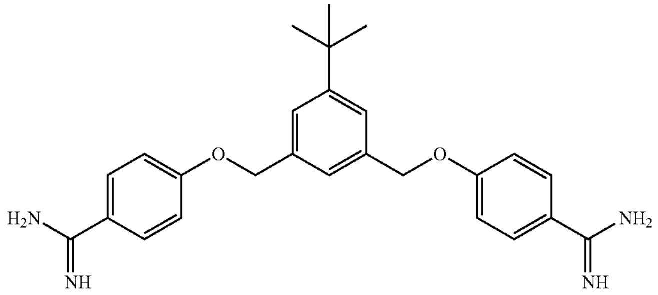 4,4′-(((5-tert-butyl)-1,3-phenylene)bis(methylene)bis(oxy)) dibenzimidamide) |
| C-5 | 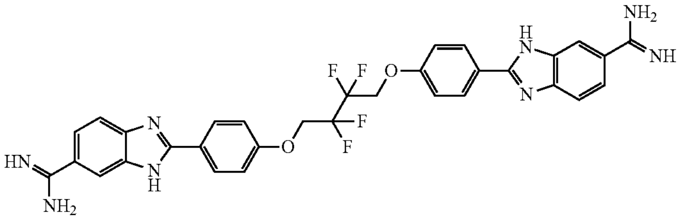 2,2′-(((2,2,3,3-tetrafluorobutane-1,4-diyl)bis(oxy))bis(4,1-phenylene)) bis(1H-benzo[d]imidazole-6-carboximidamide) |
| C-6 | 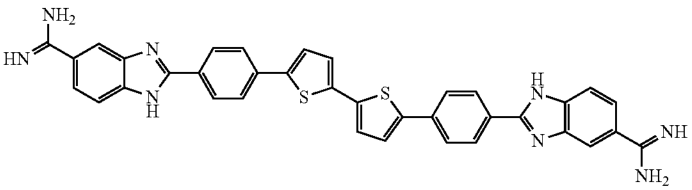 2,2′-([2,2′-bithiophene]-5,5′-diylbis(4,1-phenylene))bis(1H-benzo[d]imidazole-5-carboximidamide) |

TABLE C-continued
| Additional Compounds of the Present Invention | |
|---|---|
| Cmpd # | Structure & Name |
| C-7 | 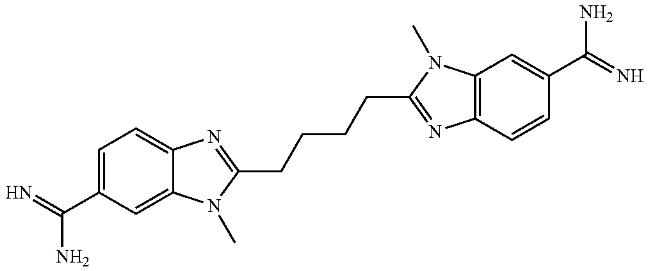 2,2′-(butane-1,4-diyl)bis(1-methyl-1H-benzo[d]imidazole-5-carboximidamide) |
| C-8 | 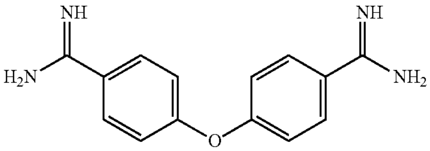 4,4′-oxydibenzimidamide |
| C-9 | 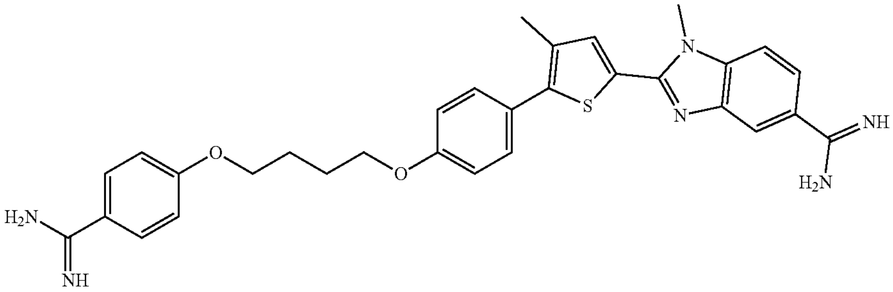 [SMILES: Cc1cc(-c2nc3cc(C(=N)N)ccc3n2C)sc1-c1ccc(OCCCCOc2ccc(C(=N)N)cc2)cc1] 2-(5-(4-(4-(4-carbamimidoylphenoxy)butoxy)phenyl)-4-methylthiophen-2-yl)-1-methyl-1H-benzo[d]imidazole-5-carboximidamide |
| C-10 | 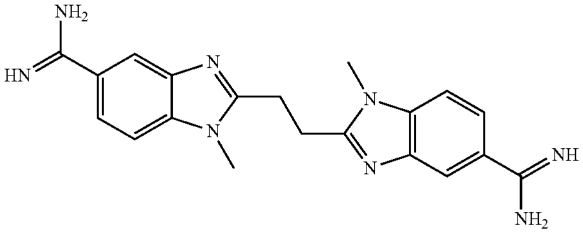 [SMILES: Cn1c(CCc2nc3cc(C(=N)N)ccc3n2C)nc2cc(C(=N)N)ccc21] 2,2'-(ethane-1,2-diyl)bis(1-methyl-1H-benzo[d]imidazole-5-carboximidamide) |

TABLE D

| Additional Compounds of the Present Invention | |
|---|---|
| Cmpd # | Structure & Name |
| D-1 | 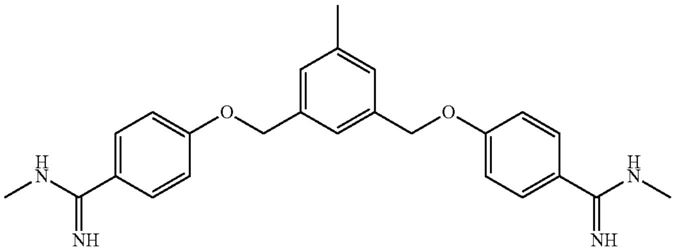 4,4'-(((5-methyl-1,3-phenylene)bis(methylene))bis(oxy))bis(N-methylbenzimidamide) |
| D-2 | 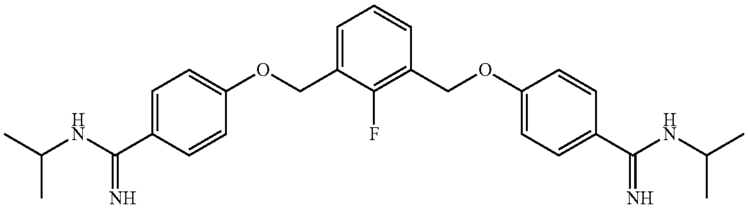 4,4'-(((2-fluoro-1,3-phenylene)bis(methylene))bis(oxy))bis(N-isopropylbenzimidamide) |
| D-3 | 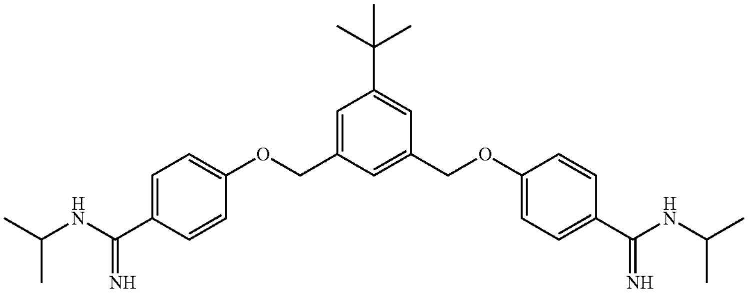 4,4'-(((5-(tert-butyl)-1,3-phenylene)bis(methylene))bis(oxy))bis(N-isopropylbenzimidamide) |
| D-4 | 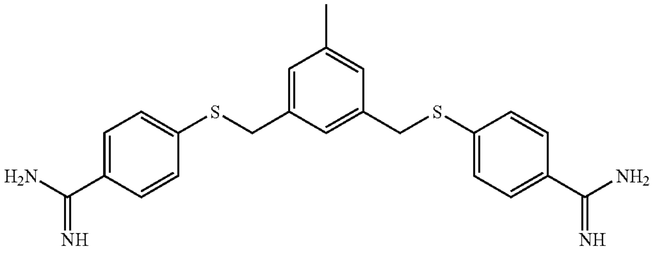 4,4'-(((5-methyl-1,3-phenylene)bis(methylene))bis(sulfanediyl))dibenzimidamide) |

TABLE D-continued
| Additional Compounds of the Present Invention | |
|---|---|
| Cmpd # | Structure & Name |
| D-5 | 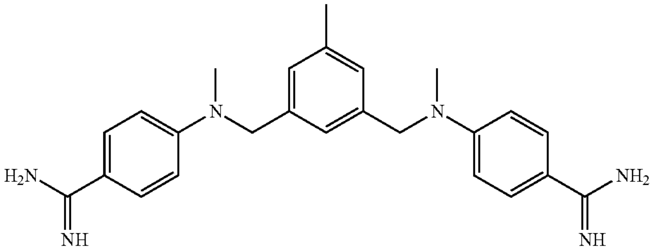 4,4′-(((5-methyl-1,3-phenylene)bis(methylene)) bis(methylazanediyl))dibenzimidamide) |
| D-6 | 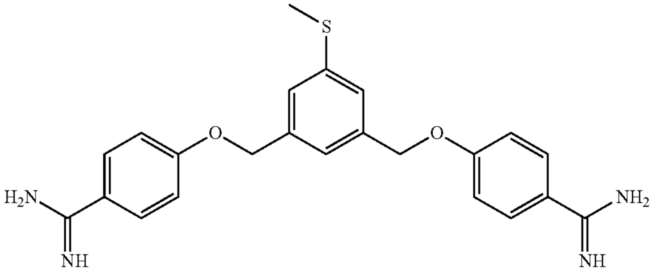 4,4′-(((5-methylthio)-1,3-phenylene)bis(methylene)) bis(oxy))dibenzimidamide) |
| D-7 | 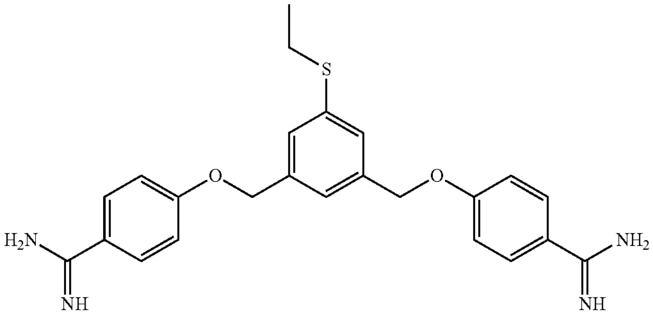 4,4′-(((5-ethylthio)-1,3-phenylene)bis(methylene)) bis(oxy))dibenzimidamide) |
| D-8 | 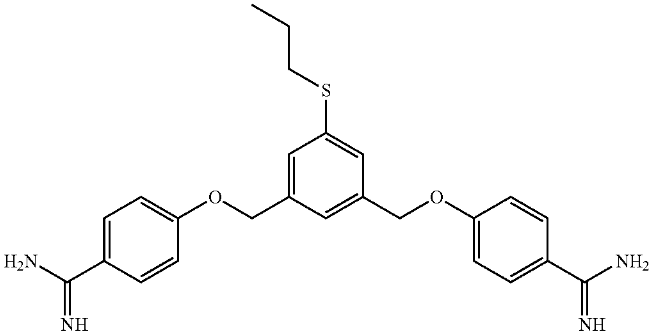 4,4′-(((5-(propylthio)-1,3-phenylene)bis(methylene)) bis(oxy))dibenzimidamide) |

TABLE D-continued
| Additional Compounds of the Present Invention | |
|---|---|
| Cmpd # | Structure & Name |
| D-9 | 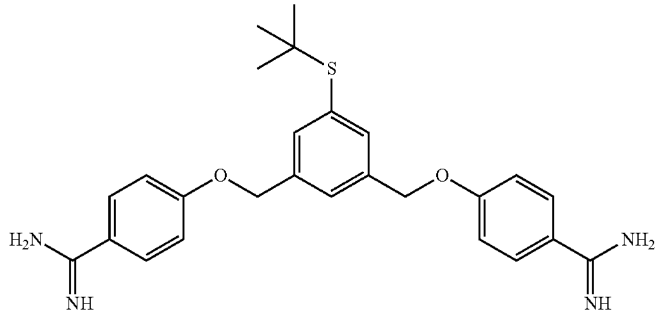 4,4′-(((5-(tert-buylthio)-1,3-phenylene)bis(methylene)) bis(oxy))dibenzimidamide) |
TABLE E
| Additional Compounds of the Present Invention | |
|---|---|
| E-1 | 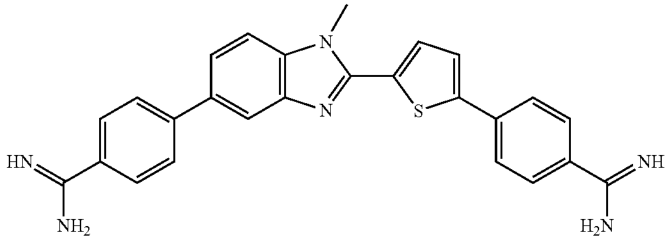 [SMILES: Cn1c(-c2ccc(-c3ccc(C(=N)N)cc3)s2)nc2cc(-c3ccc(C(=N)N)cc3)ccc21] |
| E-2 | 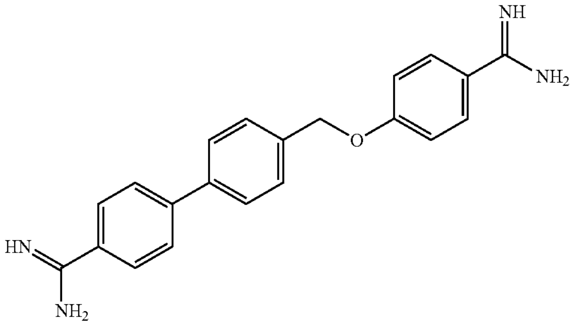 [SMILES: N=C(N)c1ccc(OCc2ccc(-c3ccc(C(=N)N)cc3)cc2)cc1] |
| E-3 | 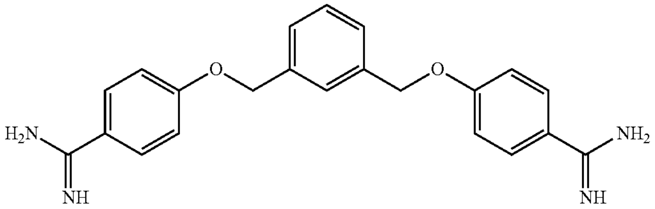 [SMILES: N=C(N)c1ccc(OCc2cccc(COc3ccc(C(=N)N)cc3)c2)cc1] |

TABLE E-continued
| Additional Compounds of the Present Invention |
|---|
| E-4 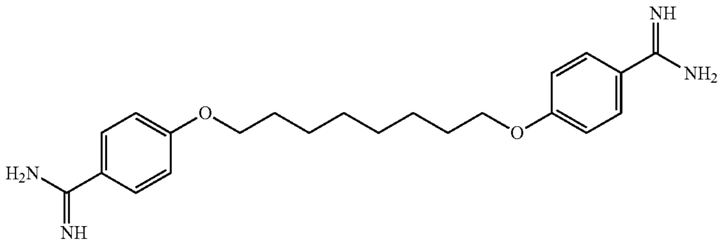 [SMILES: N=C(N)c1ccc(OCCCCCCCCOc2ccc(C(=N)N)cc2)cc1] |
| E-5 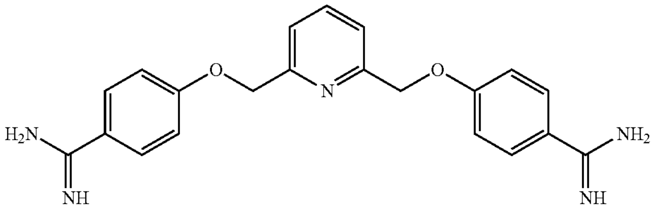 [SMILES: N=C(N)c1ccc(OCc2cccc(COc3ccc(C(=N)N)cc3)n2)cc1] |
| E-6 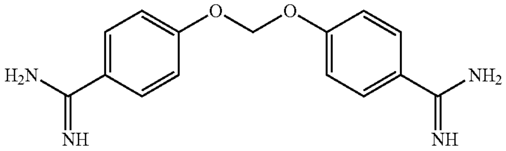 [SMILES: N=C(N)c1ccc(OCOc2ccc(C(=N)N)cc2)cc1] |
| E-7 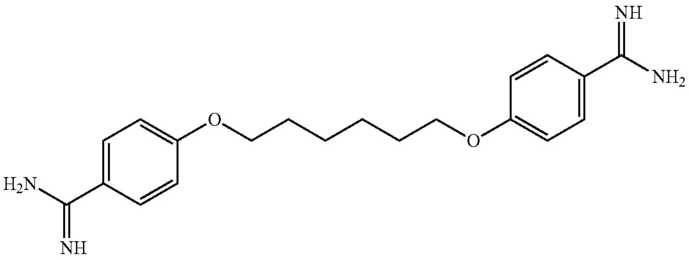 [SMILES: N=C(N)c1ccc(OCCCCCCOc2ccc(C(=N)N)cc2)cc1] |
| E-9 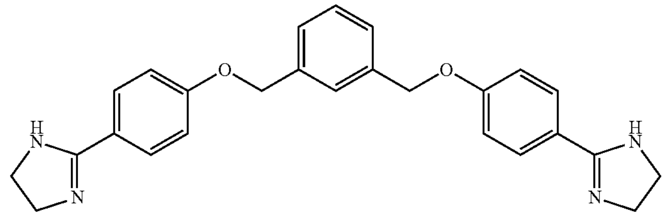 [SMILES: c1cc(COc2ccc(C3=NCCN3)cc2)cc(COc2ccc(C3=NCCN3)cc2)c1] |
| E-10 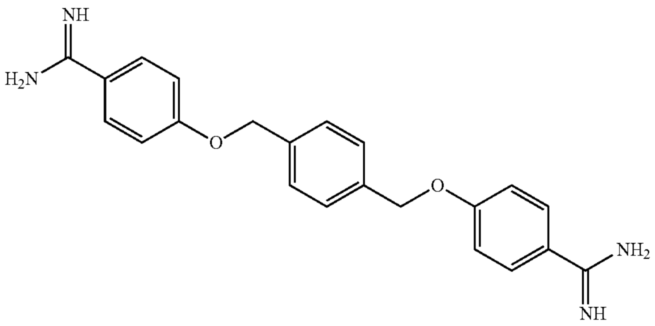 [SMILES: N=C(N)c1ccc(OCc2ccc(COc3ccc(C(=N)N)cc3)cc2)cc1] |

TABLE E-continued
| Additional Compounds of the Present Invention | |
|---|---|
| E-12 | 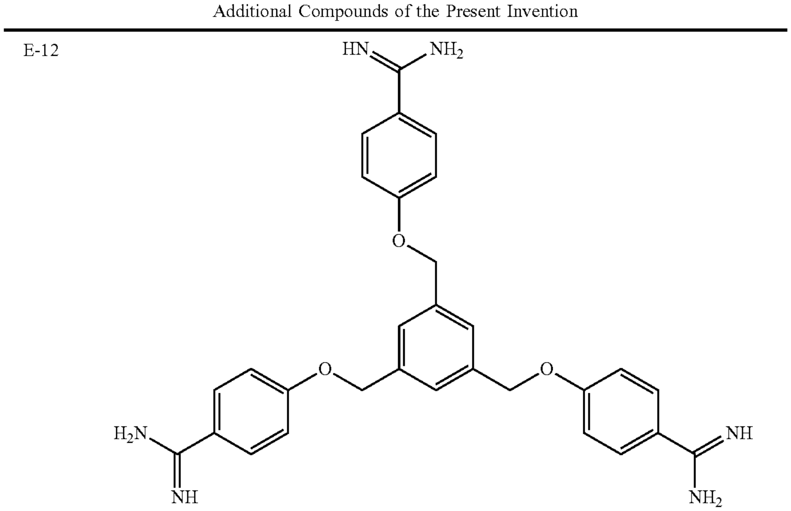 |
TABLE F
| Additional Compounds of the Present Invention | |
|---|---|
| E-11 | 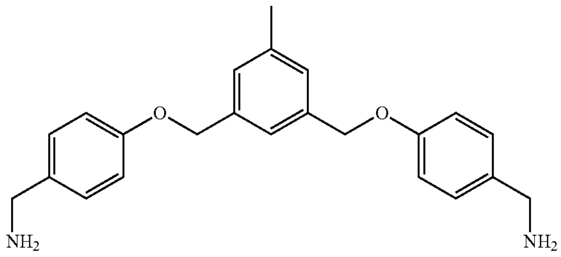 [SMILES: Cc1cc(COc2ccc(CN)cc2)cc(COc2ccc(CN)cc2)c1] |
| E-13 | 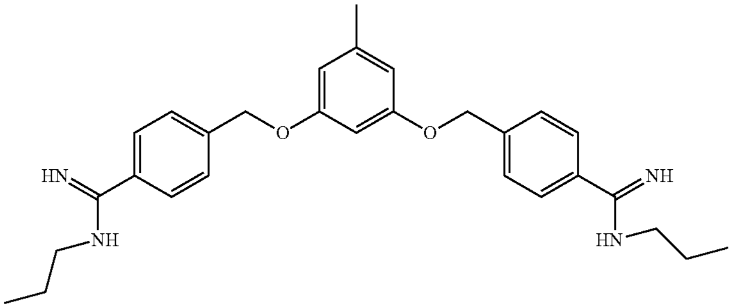 [SMILES: CCCNC(=N)c1ccc(COc2cc(C)cc(OCc3ccc(C(=N)NCCC)cc3)c2)cc1] |
| E-14 | 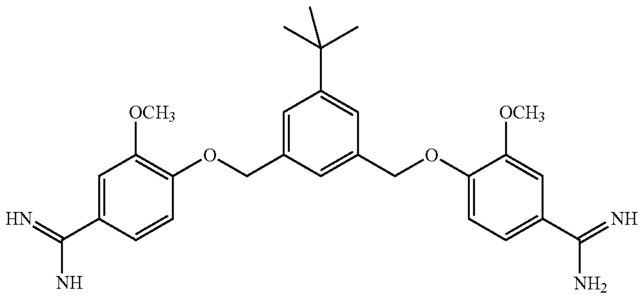 [SMILES: COc1cc(C(=N)N)ccc1OCc1cc(COc2ccc(C(=N)N)cc2OC)cc(C(C)(C)C)c1] |

TABLE F-continued
Additional Compounds of the Present Invention
E-15
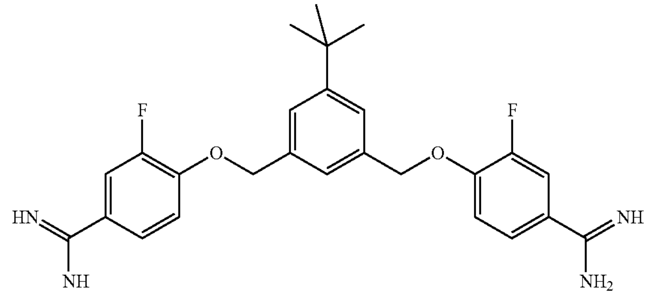 [SMILES: CC(C)(C)c1cc(COc2ccc(C(=N)N)cc2F)cc(COc2ccc(C(=N)N)cc2F)c1]
E-16
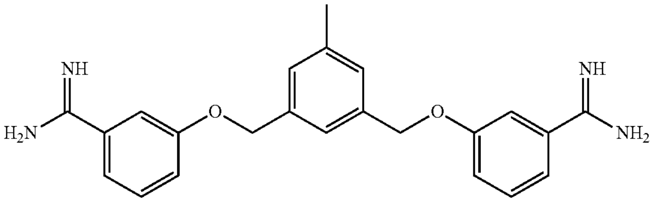 [SMILES: Cc1cc(COc2cccc(C(=N)N)c2)cc(COc2cccc(C(=N)N)c2)c1]
E-17
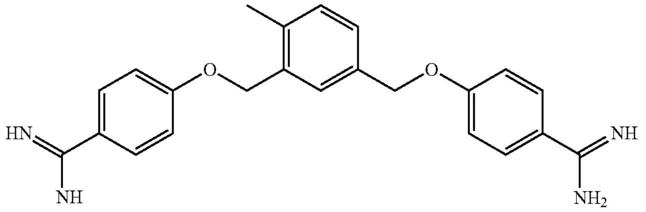 [SMILES: Cc1ccc(COc2ccc(C(=N)N)cc2)cc1COc1ccc(C(=N)N)cc1]
E-18
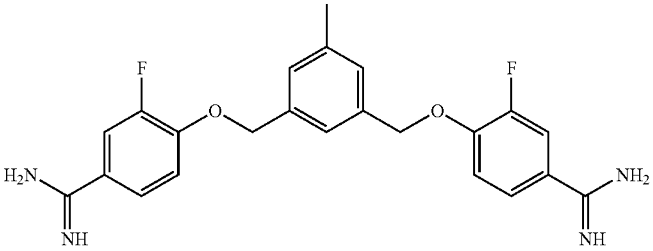 [SMILES: Cc1cc(COc2ccc(C(=N)N)cc2F)cc(COc2ccc(C(=N)N)cc2F)c1]
E-19
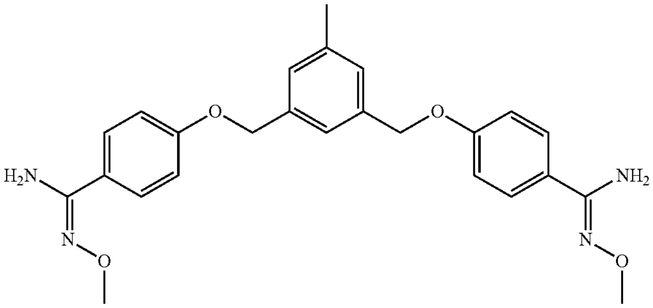 [SMILES: CO/N=C(\N)c1ccc(OCc2cc(C)cc(COc3ccc(/C(N)=N\OC)cc3)c2)cc1]

TABLE F-continued

Additional Compounds of the Present Invention

E-20

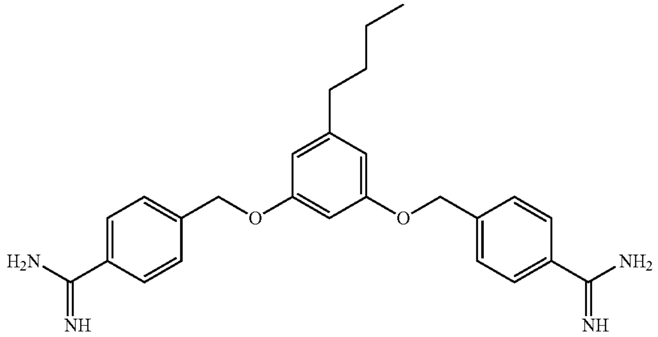 [SMILES: CCCCc1cc(OCc2ccc(C(=N)N)cc2)cc(OCc2ccc(C(=N)N)cc2)c1]

E-22

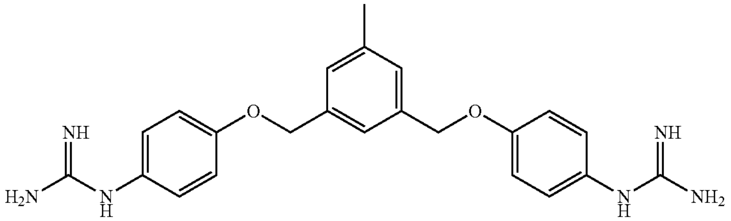 [SMILES: Cc1cc(COc2ccc(NC(=N)N)cc2)cc(COc2ccc(NC(=N)N)cc2)c1]

E-23

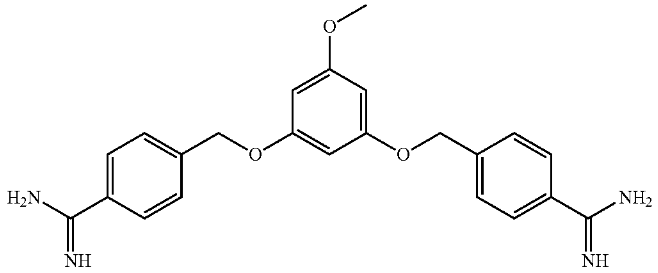 [SMILES: COc1cc(OCc2ccc(C(=N)N)cc2)cc(OCc2ccc(C(=N)N)cc2)c1]

E-24

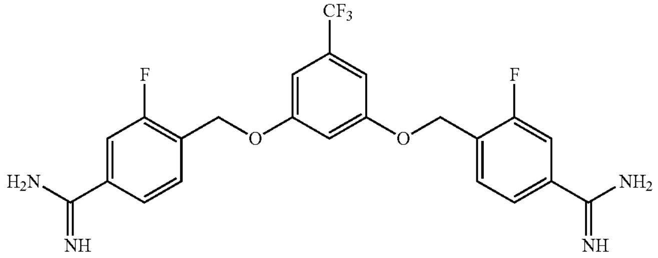 [SMILES: N=C(N)c1ccc(COc2cc(OCc3ccc(C(=N)N)cc3F)cc(C(F)(F)F)c2)c(F)c1]

E-25

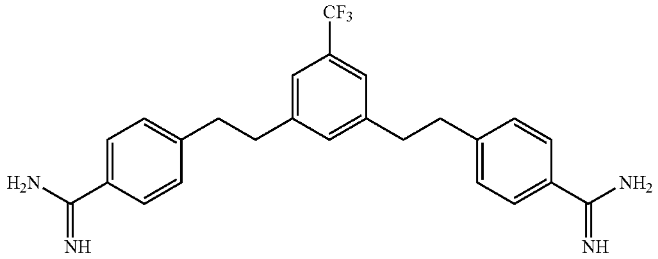 [SMILES: N=C(N)c1ccc(CCc2cc(CCc3ccc(C(=N)N)cc3)cc(C(F)(F)F)c2)cc1]

Pharmaceutical Compositions

Active compounds described herein can be administered to a host in need thereof as the neat chemical, but are more typically administered as a pharmaceutical composition that includes an effective amount for a host, typically a human, in need of such treatment of an active compound as described herein or its pharmaceutically acceptable salt thereof. Thus, in one embodiment, the disclosure provides pharmaceutical compositions comprising an effective amount of compound or pharmaceutically acceptable salt thereof together with at least one pharmaceutically acceptable carrier for any of the uses described herein. The pharmaceutical composition may contain a compound or salt as the only active agent, or, in an alternative embodiment, the compound and at least one additional active agent.

An effective amount of an active compound as described herein, or the active compound described herein in combination or alternation with, or preceded by, concomitant with or followed by another active agent, can be used in an amount sufficient to (a) inhibit the progression of a bacterial infection; (b) cause a regression of a bacterial infection; (c) cause a cure of a bacterial infection; or inhibit or prevent the development of a bacterial infection. Accordingly, an effective amount of an active compound or its salt or composition described herein will provide a sufficient amount of the active agent when administered to a patient to provide a clinical benefit.

The exact amount of the active compound or pharmaceutical composition described herein to be delivered to the host, typically a human, in need thereof, will be determined by the health care provider to achieve the desired clinical benefit.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.5, 1, 1.5, 2, 2.5, 3, 3.5, 4, 4.5, 5, 10, 15, 20, 25, 50, 75, 100, 150, 200, 250, 300, 350, 400, 450, 500, 550, 600, 650, 700, 750, 800, 900, 1000, 1100, 1200, 1250, 1300, 1400, 1500, or 1600 mg of active compound, or its salt or prodrug. In one embodiment, the dosage form has at least about 1 mg, 5 mg, 10 mg, 25 mg, 50 mg, 75 mg, 100 mg, 200 mg, 400 mg, 500 mg, 600 mg, 1000 mg, 1200 mg, or 1600 mg of active compound, or its salt. The amount of active compound in the dosage form is calculated without reference to the salt. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The pharmaceutical composition may for example include a molar ratio of the active compound and an additional active agent that achieves the desired result. For example, the pharmaceutical composition may contain a molar ratio of about 0.5:1, about 1:1, about 2:1, about 3:1 or from about 1.5:1 to about 4:1 of an additional active agent in combination with the active compound (additional active agent:active compound), or its salt, described herein. In one embodiment, the additional active agent is an antibiotic.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitoneal, subcutaneous, transnasal, sublingual, intrathecal, or rectal or by other means, in dosage unit formulations containing conventional pharmaceutically acceptable carriers. For ocular delivery, the compound can be administered, as desired, for example, as a solution, suspension, or other formulation via intravitreal, intrastromal, intracameral, subtenon, sub-retinal, retro-bulbar, peribulbar, suprachorodial, subchorodial, chorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device, injection, or topically administered formulation, for example a solution or suspension provided as an eye drop.

The pharmaceutical composition may be formulated as any pharmaceutically useful form, e.g., as an aerosol, a cream, a gel, a gel cap, a pill, a microparticle, a nanoparticle, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution or suspension. Some dosage forms, such as tablets and capsules, are subdivided into suitably sized unit doses containing appropriate quantities of the active components, e.g., an effective amount to achieve the desired purpose.

Pharmaceutical compositions, and methods of manufacturing such compositions, suitable for administration as contemplated herein are known in the art. Examples of known techniques include, for example, U.S. Pat. Nos. 4,983,593, 5,013,557, 5,456,923, 5,576,025, 5,723,269, 5,858,411, 6,254,889, 6,303,148, 6,395,302, 6,497,903, 7,060,296, 7,078,057, 7,404,828, 8,202,912, 8,257,741, 8,263,128, 8,337,899, 8,431,159, 9,028,870, 9,060,938, 9,211,261, 9,265,731, 9,358,478, and 9,387,252, incorporated by reference herein.

The pharmaceutical compositions contemplated here can optionally include a carrier. Carriers must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. Classes of carriers include, but are not limited to binders, buffering agents, coloring agents, diluents, disintegrants, emulsifiers, fillers, flavorants, glidents, lubricants, pH modifiers, preservatives, stabilizers, surfactants, solubilizers, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, colloidal silicon dioxide, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the compound of the present invention.

In certain embodiments, the pharmaceutical composition for administration further includes a compound or salt described herein and optionally comprises one or more of a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol) 5000-phosphatidylethanolamine; poly(ethylene glycol) 400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g. poly(1,3-dioxan-2one)), polyanhydride (e.g. poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g. poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), hydroxypropylmethyl cellulose acetate succinate (HPMCAS).

In some embodiments, the pharmaceutical preparation may include polymers for controlled delivery of the described compounds, including, but not limited to pluronic polymers, polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates. In some embodiments, polymers may be modified with polyethylene glycol (PEG), with a carbohydrate, and/or with acyclic polyacetals derived from polysaccharides. See, e.g., Papisov, 2001, ACS Symposium Series, 786:301, incorporated by reference herein.

The compounds of the present invention can be formulated as particles. In one embodiment the particles are or include microparticles. In an alternative embodiment the particles are or include nanoparticles.

Common techniques for preparing particles include, but are not limited to, solvent evaporation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

In one embodiment, the particles are derived through a solvent evaporation method. In this method, a compound described herein (or polymer matrix and one or more compounds described herein) is dissolved in a volatile organic solvent, such as methylene chloride. The organic solution containing a compound described herein is then suspended in an aqueous solution that contains a surface active agent such as poly(vinyl alcohol). The resulting emulsion is stirred until most of the organic solvent evaporated, leaving solid nanoparticles or microparticles. The resulting nanoparticles or microparticles are washed with water and dried overnight in a lyophilizer. Nanoparticles with different sizes and morphologies can be obtained by this method.

Pharmaceutical compositions which contain labile polymers, such as certain polyanhydrides, may degrade during the fabrication process due to the presence of water. For these polymers, methods which are performed in completely or substantially anhydrous organic solvents can be used to make the particles.

Solvent removal can also be used to prepare particles from a compound that is hydrolytically unstable. In this method, the compound (or polymer matrix and one or more compounds) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In one embodiment an active compound as described herein is administered to a patient in need thereof as particles formed by solvent removal. In another embodiment the present invention provides particles formed by solvent removal comprising a compound of the present invention and one or more pharmaceutically acceptable excipients as defined herein. In another embodiment the particles formed by solvent removal comprise a compound of the present invention and an additional therapeutic agent. In a further embodiment the particles formed by solvent removal comprise a compound of the present invention, an additional therapeutic agent, and one or more pharmaceutically acceptable excipients. In another embodiment any of the described particles formed by solvent removal can be formulated into a tablet and then coated to form a coated tablet. In an alternative embodiment the particles formed by solvent removal are formulated into a tablet but the tablet is uncoated.

In one embodiment, the particles are derived by spray drying. In this method, a compound (or polymer matrix and one or more compounds) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In one embodiment an active compound as described herein is administered to a patient in need thereof as a spray dried dispersion (SDD). In another embodiment the present invention provides a spray dried dispersion (SDD) comprising a compound of the present invention and one or more pharmaceutically acceptable excipients as defined herein. In another embodiment the SDD comprises a compound of the present invention and an additional therapeutic agent. In a further embodiment the SDD comprises a compound of the present invention, an additional therapeutic agent, and one or more pharmaceutically acceptable excipients. In another embodiment any of the described spray dried dispersions can be coated to form a coated tablet. In an alternative embodiment the spray dried dispersion is formulated into a tablet but is uncoated. Particles can be formed from the active compound as described herein using a phase inversion method. In this method, the compound (or polymer matrix and one or more active compounds) is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In one embodiment, an active compound as described herein is administered to a patient in need thereof as particles formed by phase inversion. In another embodiment the present invention provides particles formed by phase inversion comprising a compound of the present invention and one or more pharmaceutically acceptable excipients as defined herein. In another embodiment the particles formed by phase inversion comprise a compound of the present invention and an additional therapeutic agent. In a further embodiment the particles formed by phase inversion comprise a compound of the present invention, an additional therapeutic agent, and one or more pharmaceutically acceptable excipients. In another embodiment any of the described particles formed by phase inversion can be formulated into a tablet and then coated to form a coated tablet. In an alternative embodiment the particles formed by phase inversion are formulated into a tablet but the tablet is uncoated.

Techniques for particle formation using coacervation are known in the art, for example, as described in GB-B-929 406; GB-B-929 40 1; and U.S. Pat. Nos. 3,266,987, 4,794,000, and 4,460,563. Coacervation involves the separation of a compound (or polymer matrix and one or more compounds) solution into two immiscible liquid phases. One phase is a dense coacervate phase, which contains a high concentration of the compound, while the second phase contains a low concentration of the compound. Within the dense coacervate phase, the compound forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

In one embodiment an active compound as described herein is administered to a patient in need thereof as particles formed by coacervation. In another embodiment the present invention provides particles formed by coacervation comprising a compound of the present invention and one or more pharmaceutically acceptable excipients as defined herein. In another embodiment the particles formed by coacervation comprise a compound of the present invention and an additional therapeutic agent. In a further embodiment the particles formed by coacervation comprise a compound of the present invention, an additional therapeutic agent, and one or more pharmaceutically acceptable excipients. In another embodiment any of the described particles formed by coacervation can be formulated into a tablet and then coated to form a coated tablet. In an alternative embodiment the particles formed by coacervation are formulated into a tablet but the tablet is uncoated.

Methods for very low temperature casting of controlled release microspheres are described in U.S. Pat. No. 5,019,400 to Gombotz et al. In this method, the compound is dissolved in a solvent. The mixture is then atomized into a vessel containing a liquid non-solvent at a temperature below the freezing point of the drug solution which freezes the compound droplets. As the droplets and non-solvent for the compound are warmed, the solvent in the droplets thaws and is extracted into the non-solvent, hardening the microspheres.

In one embodiment, a compound of the present invention is administered to a patient in need thereof as particles formed by low temperature casting. In another embodiment the present invention provides particles formed by low temperature casting comprising a compound of the present invention and one or more pharmaceutically acceptable excipients as defined herein. In another embodiment the particles formed by low temperature casting comprise a compound of the present invention and an additional therapeutic agent. In a further embodiment the particles formed by low temperature casting comprise a compound of the present invention, an additional therapeutic agent, and one or more pharmaceutically acceptable excipients. In another embodiment any of the described particles formed by low temperature casting can be formulated into a tablet and then coated to form a coated tablet. In an alternative embodiment the particles formed by low temperature casting are formulated into a tablet but the tablet is uncoated.

In one aspect of the present invention, an effective amount of an active compound as described herein is incorporated into a nanoparticle, e.g. for convenience of delivery and/or extended release delivery. The use of materials in nanoscale provides one the ability to modify fundamental physical properties such as solubility, diffusivity, blood circulation half-life, drug release characteristics, and/or immunogenicity. A number of nanoparticle-based therapeutic and diagnostic agents have been developed for the treatment of cancer, diabetes, pain, asthma, allergy, and infections. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In addition, nanoparticle-based compound delivery can be used to release compounds at a sustained rate and thus lower the frequency of administration, deliver drugs in a targeted manner to minimize systemic side effects, or deliver two or more drugs simultaneously for combination therapy to generate a synergistic effect and suppress drug resistance. A number of nanotechnology-based therapeutic products have been approved for clinical use. Among these products, liposomal drugs and polymer-based conjugates account for a large proportion of the products. See, Zhang, L., et al., Nanoparticles in Medicine: Therapeutic Applications and Developments, Clin. Pharm. and Ther., 83 (5): 761-769, 2008.

Methods for producing nanoparticles are known in the art. For example, see Muller, R. H., et al., Solid lipid nanoparticles (SLN) for controlled drug delivery—a review of the state of the art, *Eur. H. Pharm. Biopharm.,* 50:161-177, 2000; U.S. Pat. No. 8,691,750 to Consien et al.; WO 2012/145801 to Kanwar. U.S. Pat. No. 8,580,311 to Armes, S. et al.; Petros, R. A. and DeSimone, J. M., Strategies in the design of nanoparticles for therapeutic applications, Nature Reviews/Drug Discovery, vol. 9:615-627, 2010; U.S. Pat. Nos. 8,465,775; 8,444,899; 8,420,124; 8,263,129; 8,158,728; 8,268,446; Pellegrino et al., 2005, Small, 1:48; Murray et al., 2000, Ann. Rev. Mat. Sci., 30:545; and Trindade et al., 2001, Chem. Mat., 13:3843; all incorporated herein by reference. Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5 (6): 843-853 (2010)), U.S. Pat. No. 5,543,158 to Gref et al., or WO publication WO2009/051837 by Von Andrian et al. Zauner et al., 1998, Adv. Drug Del. Rev., 30:97; and Kabanov et al., 1995, Bioconjugate Chem., 6:7; (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372; Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633; U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and U.S. Pat. No. 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181; Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732; C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5 (6): 843-853 (2010); U.S. Pat. No. 6,632,671 to Unger Oct. 14, 2003, all incorporated herein by reference.

In one embodiment, the polymeric particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In some embodiments, a compound described herein may be covalently coupled to a polymer used in the nanoparticle, for example a polystyrene particle, PLGA particle, PLA particle, or other nanoparticle.

The pharmaceutical compositions can be formulated for oral administration. These compositions can contain any amount of active compound that achieves the desired result, for example between 0.1 and 99 weight % (wt. %) of the compound and usually at least about 5 wt. % of the compound. Some embodiments contain at least about 10%, 15%, 20%, 25 wt. % to about 50 wt. % or from about 5 wt. % to about 75 wt. % of the compound.

Pharmaceutical compositions suitable for rectal administration are typically presented as unit dose suppositories. These may be prepared by admixing the active compound with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Pharmaceutical compositions suitable for transdermal administration may also be delivered by iontophoresis (see, for example, *Pharmaceutical Research* 3 (6): 318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Pharmaceutical compositions suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of inhalation drug delivery devices and methods include, for example, U.S.

Pat. No. 7,383,837 titled "Inhalation device" (SmithKline Beecham Corporation); WO/2006/033584 titled "Powder inhaler" (Glaxo SmithKline Pharmaceuticals SA); WO/2005/044186 titled "Inhalable pharmaceutical formulations employing desiccating agents and methods of administering the same" (Glaxo Group Ltd and SmithKline Beecham Corporation); U.S. Pat. No. 9,095,670 titled "Inhalation device and method of dispensing medicament", U.S. Pat. No. 8,205,611 titled "Dry powder inhaler" (Astrazeneca AB); WO/2013/038170 titled "Inhaler" (Astrazeneca AB and Astrazeneca UK Ltd.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Many methods and devices for drug delivery to the eye are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277,830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nano-particles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment". WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957,034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion". WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres". U.S. Pat. No. 8,465,778 titled "Method of making tyrosine kinase microspheres", U.S. Pat. No. 8,409,607 titled "Sustained release intraocular implants containing tyrosine kinase inhibitors and related methods". U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US20070071756 titled "Delivery of an agent to ameliorate inflammation" (Peyman); US20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

Methods of Treatment

In one embodiment, an effective amount of an active compound or its salt or composition as described herein is used to treat or to prevent a medical disorder which is mediated by the presence of a bacterium, for example a bacterial infection. In one embodiment, the compounds of the present invention may be used to treat a disorder, typically an infection, caused by a pathogenic bacterium. In one embodiment, a method is provided comprising administering an effective amount of a compound or a pharmaceutically acceptable salt or composition thereof described herein to a subject, typically a human, to treat an infection caused by a pathogenic bacterium.

In one embodiment, the compounds of the present invention may be used to treat a disorder, typically an infection, caused by a gram-positive bacterium. In one embodiment, a method is provided comprising administering an effective amount of a compound or a pharmaceutically acceptable salt or composition thereof described herein to treat an infection caused by a gram-positive bacterium. Non-limiting examples of gram-positive bacteria which may be treated using the compounds of the present invention either alone or in combination with another therapeutic include: *Actinomyces* species including *Actinomyces israelii, Actinomyces naeslundii, Actinomyces viscosus, Actinomyces odontolyticus*, and *Actinomyces pyogenes; Bacillus* species including *Bacillus anthracis, Bacillus cereus*, and *Bacillus subtilis; Clostridium* species including *Clostridium botulinum, Clostridium difficile, Clostridium perfringens, Clostridium sordellii*, and *Clostridium tetani; Corynebacterium* species including *Corynebacterium diphtheriae, Corynebacterium jeikeium, Corynebacterium minutissimum, Corynebacterium mucifaciens, Corynebacterium pseudotuberculosis, Corynebacterium striatum, Corynebacterium tenuis*, and *Corynebacterinon ulcerans; Enterococcus* species including *Enterococcus casseliflavus, Enterococcus faecalis, Enterococcus faecium, Enterococcus raffinosus*, and *Enterococcus hirae; Leuconostoc* species including *Leuconostoc pseudomesenteroides; Micrococcus* species such as *Micrococcus luteus; Nocardia* species including *Nocardia asteroides; Propionibacterium* species including *Propionibacterium acnes: Staphylococcus* species including *Staphylococcus aureus, Staphylococcus capitis, Staphylococcus epidermidis, Staphylococcus haemolyticus, Staphylococcus hominis, Staphylococcus lugdunensis, Staphyloccocus pasteuri*, and *Staphyloccocus saprophyticus*; and *Streptococcus* species including *Streptococcus agalactiae, Streptococcus anginosus, Streptococcus bovis, Streptococcus dysgalactiae, Streptococcus mitis, Streptococcus mutans, Streptococcus pneumoniae, Streptococcus pyogenes, Streptococcus sanguinis, Streptococcus suis*, and *Streptococcus viridans.*

In one embodiment, the compounds of the present invention may be used to treat a disorder, typically an infection, caused by a gram-negative bacterium. In one embodiment, a method is provided comprising administering an effective amount of a compound or a pharmaceutically acceptable salt or composition thereof described herein to treat an infection caused by a gram-negative bacterium. Non-limiting examples of gram-negative bacteria which may be treated using the compounds of the present invention either alone or in combination with another therapeutic include: *Acinetobacter* species including *Acinetobacter baumannii* and *Acinetobacter iwoffii; Aeromonas* species including *Aeromonas veronii* biovar *sobria* (previously *Aeromonas sobria*), *Aeromonas caviae*, and *Aeromonas hydrophila; Alcaligenes/Achromobacter* species including *Alcaligenes faecalis* and *Alcaligenes xylosoxidans; Bacteroides* species including *Bacteroides fragilis; Bartonella* species including *Bartonella bacilliformis, Bartonella clarridgeiae, Bartonella elizabethae, Bartonella henselae, Bartonella koehlerae, Bartonalla naantalienis, Bartonella quintana, Bartonella rochalimae, Bartonella vinsonii*, and *Bartonella washoensis; Bordetella* species including *Bordetella bronchispetica, Bordetella pertussis*, and *Bordetella parapertussis; Borrelia* species including *Borrelia afzelii, Borrelia burgdorferi, Borrelia crocidurae, Borrelia duttoni, Borrelia garinii, Borrelia hermsii, Borrelia hispanica, Borellia miyamotoi, Borrelia parkeri, Borrelia persica, Borrelia recurrentis, Borrelia turicatae*, and *Borrelia venezuelensis; Brevundimonas* species including *Brevundimonas diminuta* and *Brevundimonas vesicularis; Brucella* species including *Brucella abortus, Brucella canis, Brucella melitensis*, and *Brucella suis; Burkholderia* species including *Burkholderia cepacia, Burkholderia mallei*, and *Burkholderia pseudomallei, Campylobacter* species including *Campylobacter jejuni, Campylobacter coli, Campylobacter upsaliensis, Campylobacter lari*, and *Campylobacter coli; Chlamydia/Chlamidophila* species including *Chlamydophila pneumoniae, Chlamydophila psittaci, Chlamidophila pecorum*, and *Chlamydia trachomatis; Citrobacter* species including *Citrobacter amalonaticus, Citrobacter freundii, Citrobacter koseri*, and *Citrobacter diversus; Coxiella burnetti; Ehrlichia* species including *Ehrlichia canis* and *Ehrlichia chaffeensis; Enterobacter* species including *Enterobacter aerogenes* and *Enterobacter cloacae; Escherichia* species including *Escherichia coli; Francisella* species including *Francisella novicida, Francisella philomiragia*, and *Francisella tularensis; Haemophilus* species including *Haemophilus influenzae* and *Haemophilus ducreyi; Helicobacter* species including *Helicobacter pylori, Klebsiella* species including *Klebsiella granulomatis, Klebsiella oxytoca*, and *Klebsiella pneumoniae; Leclercia adecarboxylata; Legionella* species including *Legionella pneumophila; Leptospira* species including *Leptospira interrogans, Leptospira noguchii, Leptospira santarosai*, and *Leptospira weilii: Listeria* species including *Listeria monocytogenes; Moraxella* species including *Moraxella catarrhalis, Moraxella lacunata*, and *Moraxella bovis; Morganella* species including *Morganella morganii, Mycoplasma* species including *Mycoplasma amphoriforme, Mycoplasma buccale, Mycoplasma faucium, Mycoplasma fermentans, Mycoplasma genitalium, Mycoplasma hominis, Mycoplasma lipophilum, Mycoplasma orale, Mycoplasma penetrans, Mycoplasma pirun, Mycoplasma pneumoniae, Mycoplasma primatum, Mycoplasma salivarium*, and *Mycoplasma spermatophilum, Neisseria* species including *Neisseria meningitidis* and *Neisseria gonorrhoeae; Orientia* species including *Orientia tsutsugamushi* and *Orientia chuto; Pantoea* species including *Pantoea agglomerans; Paracoccus* species including *Paracoccus yeei; Prevotella* species including *Prevotella intermedia* and *Prevotella melaninogenica; Proteus* species including *Proteus mirabilis, Proteus penneri*, and *Proteus vulgaris; Providencia* species including *Providencia rettgeri* and *Providencia stuartii; Pseudomonas* species including *Pseudomonas aeruginoas, Pseudomonas oryzihabitans, Pseudomonas plecoglossidica*, and *Pseudomonas stutzeri; Ralstonia* species including *Ralstonia pickettii* and *Ralstonia insidiosa; Rickettsia* species including *Rickettsia africae, Rickettsia akari, Rickettsia australis, Rickettsia conorii, Rickettsia felis, Rickettsia japonica, Rickettsia prowazekii, Rickettsia rickettsia, Rickettsia sibirica*, and *Rickettsia typhi; Roseomonas* species including *Roseomonas gilardii; Salmonella* species including *Salmonella bongori, Salmonella enterica, Salmonella paratyphi, Salmonella typhi*, and *Salmonella typhimurium; Serratia* species including *Serratia marcescens, Serratia liquefaciens, Serratia rubidaea*, and *Serratia odoriferae; Shigella* species including *Shigella dysenteriae* and *Shigella sonnei: Sphingomonas* species including *Sphingomonas mucosissima* and *Sphingomonas paucimobilus; Stenotrophomas* species including *Stenotrophomas maltophilia, Treponema* species including *Treponema carateum, Treponema paraluiscuniculi*, and *Treponema pallidum; Ureaplasma* species including *Ureaplasma urealyticum; Vibrio* species including *Vibrio cholera, Vibrio parahaemolyticus*, and *Vibrio vulnificus*; and *Yersinia* species including *Yersinia enterocolitica, Yersinia pestis*, and *Yersinia pseudotuberculosis.*

In one embodiment, the compounds of the present invention may be used to treat a disorder, typically an infection, caused by a mycobacterium. In one embodiment, a method is provided comprising administering an effective amount of a compound or a pharmaceutically acceptable salt or composition thereof described herein to treat an infection caused by a mycobacterium. Non-limiting examples of mycobacteria which may be treated using the compounds of the present invention either alone or in combination with another therapeutic include *Mycobacterium abcessus, Mycobacterium africanum, Mycobacterium agri, Mycobacterium aichiense, Mycobacterium alvei, Mycobacterium arabiense, Mycobacterium aromaticivorans, Mycobacterium arosiense, Mycobacterium arupense, Mycobacterium aquaticum, Mycobacterium asiaticum, Mycobacterium aubagnese, Mycobacterium aurum, Mycobacterium austroafricamumm, Mycobacterium avium, Mycobacterium avium paratuberculosis, Mycobacterium avium silvaticum, Mycobacterium avium hominussuis, Mycobacterium bacteremicum, Mycobacterium barrassiae, Mycobacterium boenickei, Mycobacterium bohemicum, Mycobacterium bolletii, Mycobacterium botniense, Mycobacterium bovis, Mycobacterium branderi, Mycobacterium brisbanense, Mycobacterium brumae, Mycobacterium canariasense, Mycobacterium canettii, Mycobacterium caprae, Mycobacterium chimaera, Mycobacterium chelonae, Mycobacterium chitae, Mycobacterium chubuense, Mycobacterium colombiense, Mycobacterium conceptionense, Mycobacterium confluentis, Mycobacterium conspicuum, Mycobacterium cookii, Mycobacterium cosmeticum, Mycobacterium diernhoferi, Mycobacterium doricum, Mycobacterium duvalii, Mycobacterium elephantis, Mycobacterium fallax, Mycobacterium farcinogenes, Mycobacterium flavescens, Mycobacterium florentinum, Mycobacterium fortuitum, Mycobacterium frederikbergense, Mycobacterium gadium, Mycobacterium gastri, Mycobacterium genavense, Mycobacterium gilvum, Mycobacterium gordonae, Mycobacterium haemophiluscobacterium hassiacum, Mycobacterium heidelbergense,*

*Mycobacterium heckshornense; Mycobacterium hiberniae, Mycobacterium hodleri, Mycobacterium holsaticum, Mycobacterium houstonense, Mycobacterium icosiumassilensis, Mycobacterium immunogemmm, Mycobacterium indicus pranii, Mycobacterium intacellulare, Mycobacterium intracellulare, Mycobacterium interjectum, Mycobacterium intermedium, Mycobacterium iranicum, Mycobacterium kansasii, Mycobacterium komossense, Mycobacterium kubicae, Mycobacterium lentiflavum, Mycobacterium leprae, Mycobacterium lepraemurium, Mycobacterium lepromatosis, Mycobacterium liflandii, Mycobacterium Hatzerense, Mycobacterium madagascariense, Mycobacterium mageritense, Mycobacterium malmoense, Mycobacterium marinum, Mycobacterium massiliense, Mycobacterium massilipolynesiensis, Mycobacterium microti, Mycobacterium monacense, Mycobacterium montfiorense, Mycobacterium morokaense, Mycobacterium mucogenicum, Mycobacterium mungi, Mycobacterium murale, Mycobacterium nebraskense, Mycobacterium neoaurum, Mycobacterium neworleansense, Mycobacterium nonchromogenicum, Mycobacterium obuense, Mycobacterium orygis, Mycobacterium palustre, Mycobacterium parascofutlaceum, Mycobacterium parafortuitum, Mycobacterium perigrinum, Mycobacterium phlei, Mycobacteriin phocaicum, Mycobacterium pinnipedii, Mycobacterium porciman, Mycobacterium pseudoshottsii, Mycobacterium psychotolerans, Mycobacterium pulveris, Mycobacterium pyrenivorans, Mycobacterium saskatchewanense, Mycobacterium sediminis, Mycobacterium senegalense, Mycobacterium septicum, Mycobacterium shimoidei, Mycobacterium shottsii, Mycobacterium simiae, Mycobacterium smegmatis, Mycobacterium sphagni, Mycobacterium stephanolepidis, Mycobacterium suricattae, Mycobacterium szulgai, Mycobacterium talmoniae, Mycobacterium terrae, Mycobacterium thermoresistibile, Mycobacterium triplex, Mycobacterium triviale, Mycobacterium tuberculosis, Mycobacterhan tusciae, Mycobacterium ulcerans, Mycobacterium vaccae, Mycobacterium vanbaalenii, Mycobacterium xenopi, and Mycobacterium yongonense.*

In one embodiment, an effective amount of an active compound or its salt or composition as described herein is used to treat or to prevent a medical disorder which is mediated by the presence of an antibiotic-resistant bacterium. In one embodiment, the compounds of the present invention may be used to treat a disorder, typically an infection, caused by a pathogenic antibiotic-resistant bacterium. In one embodiment, a method is provided comprising administering an effective amount of a compound or a pharmaceutically acceptable salt or composition thereof described herein to a subject, typically a human, to treat an infection caused by a pathogenic antibiotic-resistant bacterium. Non-limiting examples of gram-positive antibiotic-resistant bacteria include: antibiotic-resistant *Clostridium difficile*, drug-resistant *Streptococcus pneumoniae*, clindamycin-resistant Group B *Streptococcus*, erythromycin-resistant Group A *Streptococcus*, methicillin-resistant *Staphylococcus aureus* (MRSA), vancomycin-resistant *Staphylococcus aureus* (VRSA), and vancomycin-resistant *Enterococcus* (VRE).

Non-limiting examples of gram-negative antibiotic-resistant bacteria include: antibiotic-resistant *Burkholderia cepacia*, carbapenem-resistant Enterobacteriaceae (CRE) gut bacteria, drug-resistant *Campylobacter*, drug-resistant non-typhoidal *Salmonella*, drug-resistant *Shigella*, multi-drug-resistant *Acinetobacter*, multi-drug-resistant *Escherichia coli*, multi-drug-resistant *Klebsiella pneumoniae*, multi-drug-resistant *Neisseria Gonorrhoeae*, and multidrug-resistant *Pseudomonas aeruginosa.*

In one embodiment, an effective amount of an active compound or its salt or composition as described herein is used to treat or to prevent a medical disorder which is mediated by the presence of an antibiotic-resistant mycobacterium. In one embodiment, the compounds of the present invention may be used to treat a disorder, typically an infection, caused by a pathogenic antibiotic-resistant mycobacterium. In one embodiment, a method is provided comprising administering an effective amount of a compound or a pharmaceutically acceptable salt or composition thereof described herein to a subject, typically a human, to treat an infection caused by a pathogenic antibiotic-resistant mycobacterium. In one embodiment, the antibiotic-resistant mycobacterium is multi-drug-resistant *Mycobacterium tuberculosis* (MDR-TB).

Non-limiting examples of disorders mediated by a bacterium that may be treated by the compounds of the present invention, either alone or in combination with another therapeutic, include actinomycosis, anaplasmosis, anthrax, bacillary angiomatosis, actinomycetoma, bacterial pneumonia, bacterial vaginosis, bacterial endocarditis, bartonellosis, botulism, boutenneuse fever, brucellosis, bejel, brucellosis spondylitis, bubonic plague, Buruli ulcer, Bairnsdale ulcer, bacillary dysentery, campylobacteriosis, Carrion's disease, cat-scratch disease, cellulitis, chancroid, chlamydia, chlamydia conjunctivitis, clostridial myonecrosis, cholera, *Clostridium difficile* colitis, diphtheria, Daintree ulcer, donavanosis, dysentery, erhlichiosis, epidemic typhus, fried rice syndrome, five-day fever, floppy baby syndrome, Far East scarlet-like fever, gas gangrene, glanders, gonorrhea, granuloma inguinale, human necrobacillosis, hemolytic-uremic syndrome, human ewingii ehrlichiosis, human monocytic ehrlichiosis, human granulocytic anaplasmosis, infant botulism, Izumi fever, Kawasaki disease, Kumusi ulder, lymphogranuloma venereum, Lemierre's syndrome, Legionellosis, leprosy, leptospirosis, listeriosis, Lyme disease, lymphogranuloma venereum, Malta fever, Mediterranean fever, myonecrosis, mycoburuli ulcer, mucocutaneous lymph node syndrome, meliodosis, meningococcal disease, murine typhus, *Mycoplasma* pneumonia, mycetoma, neonatal conjunctivitis, nocardiosis, Oroya fever, ophthalmia neonatorum, ornithosis, Pontiac fever, peliosis hepatis, pneumonic plague, postanginal shock including sepsis, pasteurellosis, pelvic inflammatory disease, pertussis, plague, pneumococcal infection, pneumonia, psittacosis, parrot fever, pseudotuberculosis, Q fever, quintan fever, rabbit fever, relapsing fever, rickettsialpox, Rocky Mountain spotted fever, rat-bite fever, Reiter syndrome, rheumatic fever, salmonellosis, scarlet fever, sepsis, septicemic plague, Searls ulcer, shigellosis, soft chancre, syphilis, streptobacillary fever, scrub typhus, Taiwan acute respiratory agent, Trench fever, trachoma, tuberculosis, tularemia, typhoid fever, typhus, tetanus, toxic shock syndrome, undulant fever, ulcus molle, *Vibrio parahaemolyticus* enteritis, Whitmore's disease, walking pneumonia, Waterhouse-Friderichsen syndrome, yaws, and yersiniosis.

In one embodiment, the compounds of the present invention may be used to treat an inflammatory disorder caused by the presence of a bacterial infection. Non-limiting examples of such inflammatory disorders include adenoiditis, appendicitis, arteritis, ascending cholangitis, balanitis, blepharitis, bronchitis, bursitis, cellulitis, cerebral vasculitis, cervicitis, chemosis, cholecystitis, chondritis, choroioamnionitis, colitis, conjunctivitis, constrictive pericarditis, cryptitis, dacryoadenitis, dermatitis, duodenal lymphocytosis, encephalitis, endocarditis, endometritis, endotheliitis, enteritis, enterocolitis, eosinophilis fasciitis, epididymitis, esophagitis, folliculitis, gastritis, gingivitis, glomerulonephritis, glossitis, hepatitis, infectious arthritis, ileitis, intertrigo, keratitis, keratoconjunctivitis, labyrithitis, lymphadenitis, mastitis, mastoiditis, myocarditis, myopericarditis, myositis, necrotizing fasciitis, nephritis, omaphalitis, oophoritis, ophthalmitis, orchitis, osteitis, osteomyelitis, pancreatitis, paraproctitis, parotitis, pericarditis, perichondritis, perifolliculitis, periodontitis, peritonitis, pharyngitis, phlebitis, pleurisy, pneumonitis, pulmonitis, proctitis, prostatitis, pulpitis, pyelonephritis, pyomyositis, retinal vasculitis, rheumatic fever, rhinitis, scleritis, salpingitis, sialadenitis, sinusitis, stomatitis, synovitis, septicemia, tenosynovitis, thyroiditis, tonsillitis, tularemia, urethritis, uveitis, vaginitis, vasculitis, and vulvitus.

In another embodiment, a method is provided for treating a bacterial infection in a host, typically a human, comprising administering to the host an effective amount of an antibiotic in combination with an effective amount of a compound of Formula XI:

(XI)

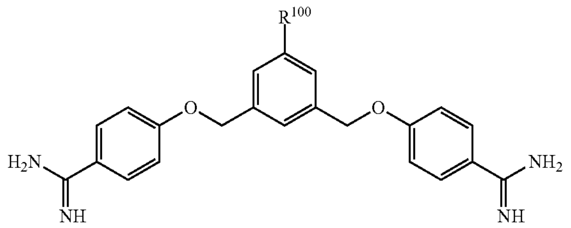

or a pharmaceutically acceptable salt thereof, optionally in a pharmaceutically acceptable carrier to form a pharmaceutical composition;

wherein $R^{100}$ is selected from halogen, cyano, —COOH, —COO($C_1$-$C_6$alkyl), trifluoromethyl, —$SO_3H$, $C_1$-$C_6$alkyl, hydroxyl, $C_1$-$C_6$alkoxy, amino, and —N($C_1$-$C_6$alkyl) 2. In one embodiment, the bacterial infection is caused by a gram-positive bacterium. In one embodiment, the bacterial infection is caused by a gram-negative bacterium. In one embodiment, the bacterial infection is caused by a mycobacterium.

Non-limiting examples of compounds of Formula XI that may be used in the above method include:

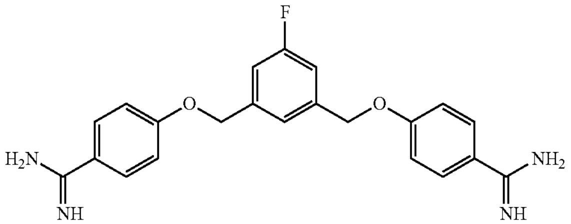

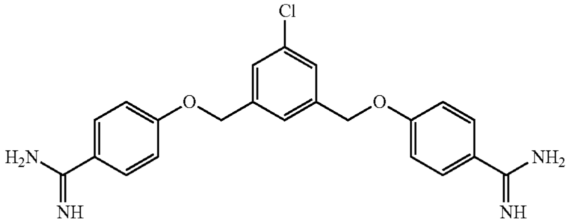

-continued

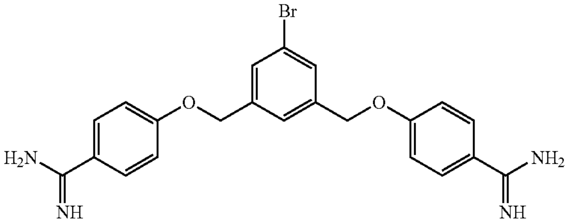

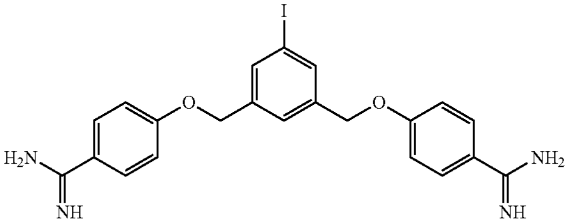

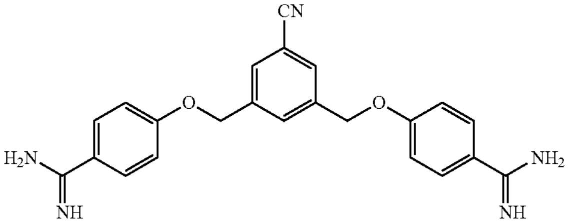

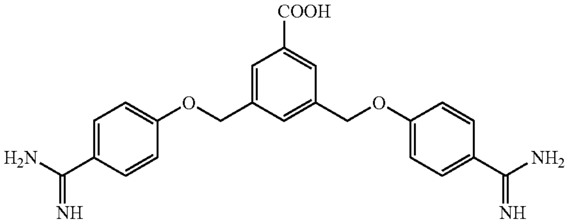

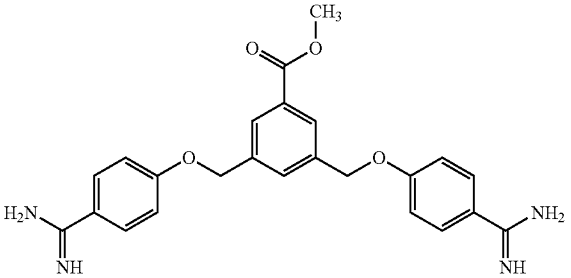

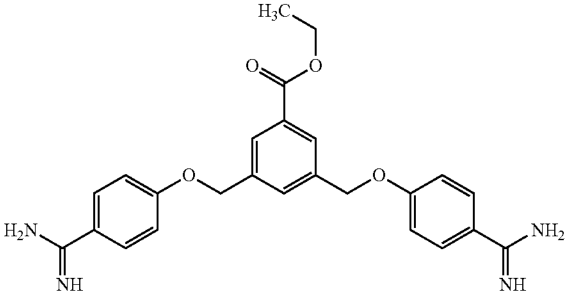

-continued
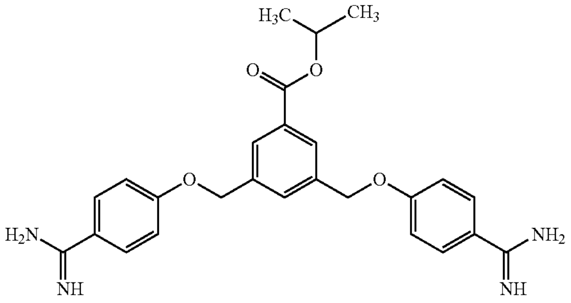
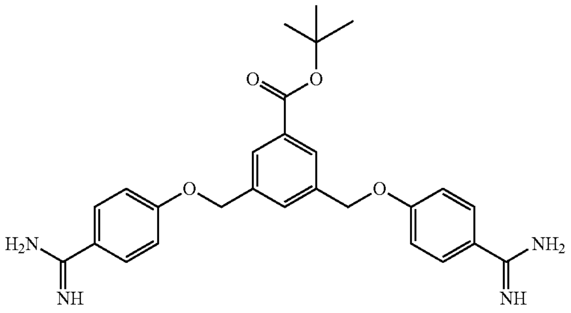
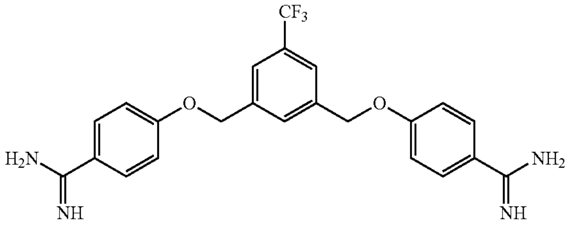
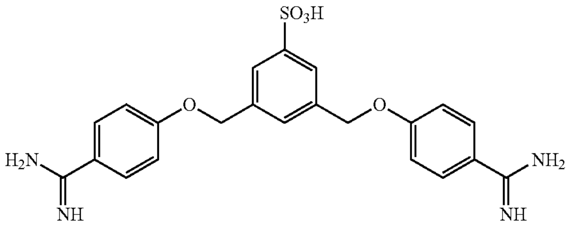
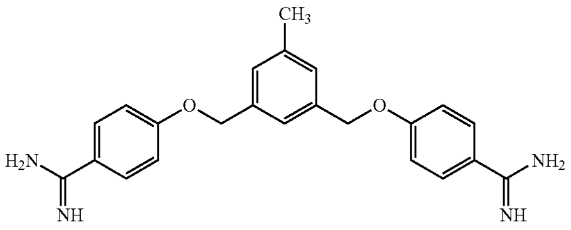
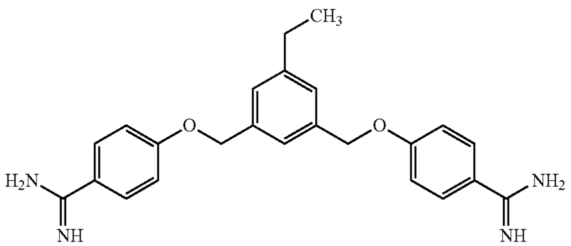
-continued
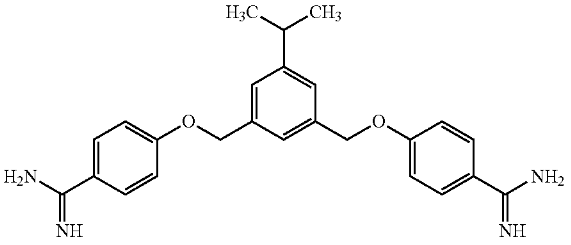
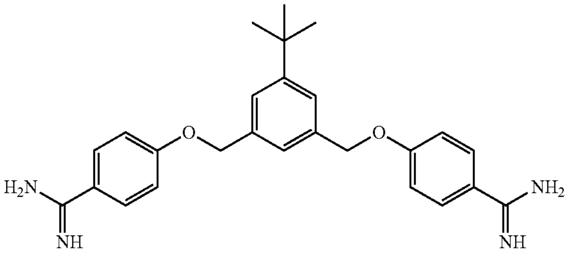
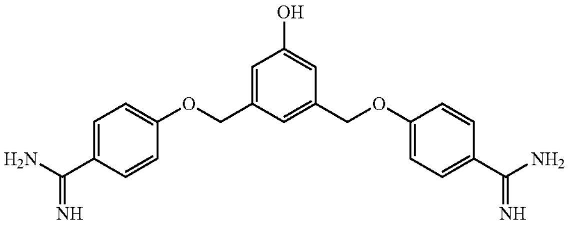
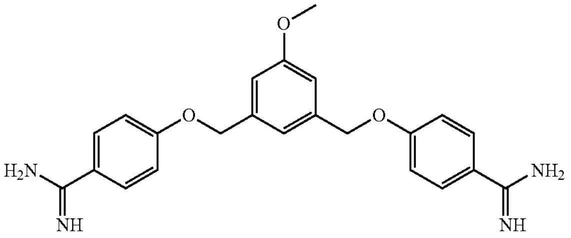
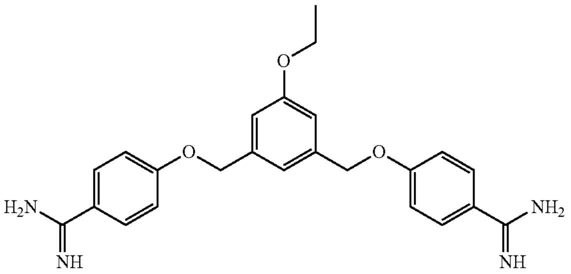
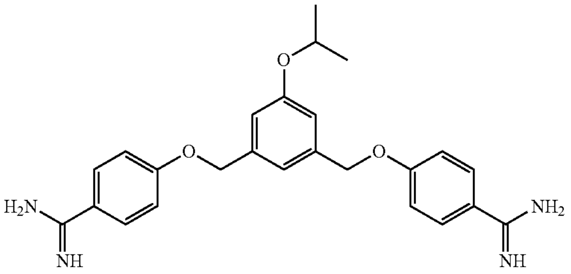

-continued

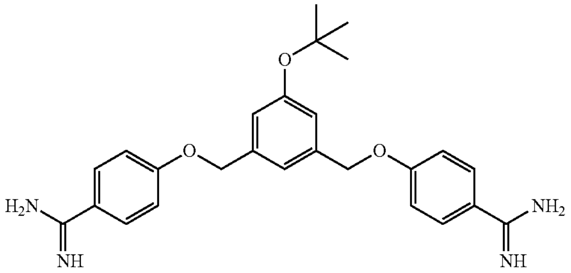

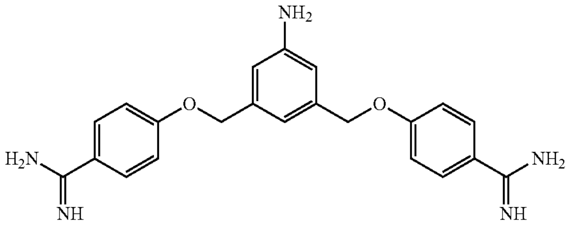

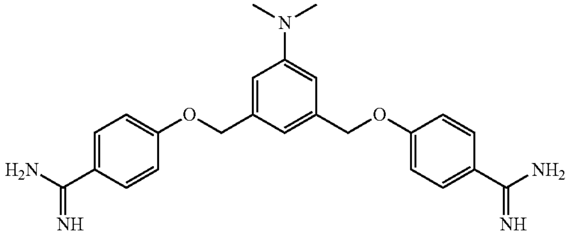

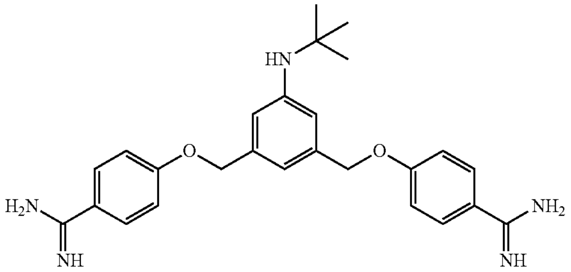

Additional non-limiting examples of Formula XI include:

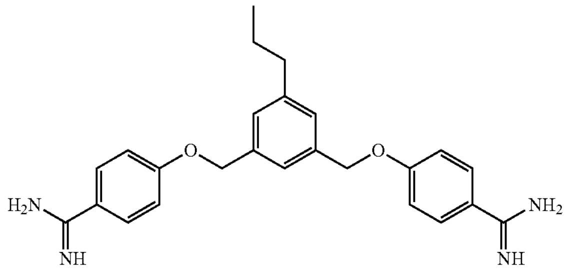

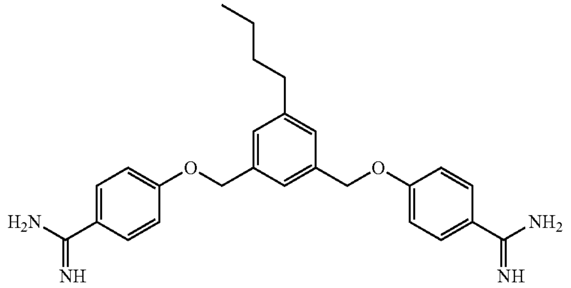

-continued

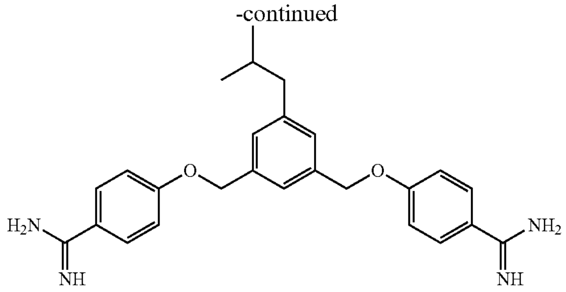

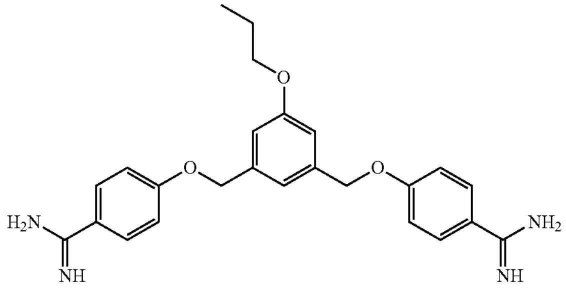

Non-limiting examples of compounds of Formula XI' that may be used in the above method include:

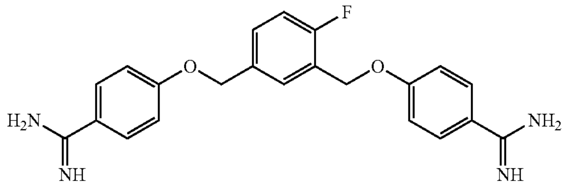

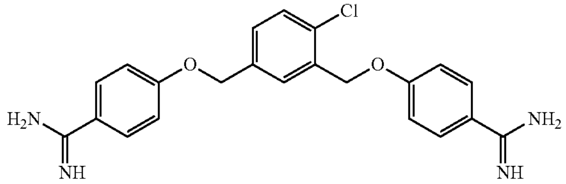

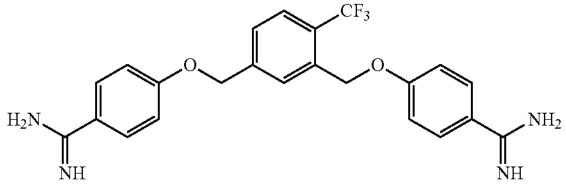

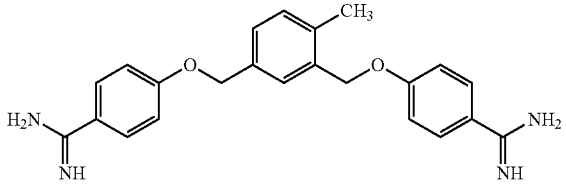

In yet another aspect, provided is a method for potentiating the effect of an antibiotic in the treatment of a bacterial infection in a host, typically a human, comprising administering to the host an effective amount of the antibiotic in combination with an effective amount of a compound of Formula XI or Formula XI' or a pharmaceutically acceptable salt thereof, optionally in a pharmaceutically acceptable carrier to form a pharmaceutical composition. In one embodiment, the bacterial infection is caused by a gram-positive bacterium. In one embodiment, the bacterial infection is caused by a gram-negative bacterium. In one embodiment, the bacterial infection is caused by a mycobacterium.

Combination Therapy

In one embodiment, an active compounds or its salt or composition as described herein may be provided in combination or alternation with or preceded by, concomitant with or followed by, an effective amount of at least one additional therapeutic agent, for example, for treatment of a disorder listed herein. Non-limiting examples of additional active agents for such combination therapy are provided below. In the described below and herein generally, whenever any of the terms referring to an active compound or its salt or composition as described herein are used, it should be understood that pharmaceutically acceptable salt, prodrugs, or compositions are considered included, unless otherwise stated or inconsistent with the text.

In one embodiment, an active compound of its salt or composition as described herein may be used in combination or alternation with an antibiotic. In one embodiment, the antibiotic is an aminoglycoside. In one embodiment, the antibiotic is selected from amikacin, gentamicin, kanamycin, neomycin, netilmicin, tobramycin, paromomycin, streptomycin, and spectinomycin. In one embodiment, the antibiotic is an ansamycin. In one embodiment, the antibiotic is selected from geldanamycin, herbimycin, and rifaximin. In one embodiment, the antibiotic is a carbapenem. In one embodiment, the antibiotic is selected from ertapenem, doripenem, imipenem, panipenem, biapenem, tebipenem, and meropenem. In one embodiment, the antibiotic is a cephalosporin. In one embodiment, the antibiotic is selected from cefacetrile, cefadroxil, cephalexin, cefaloglycin, cefalonium, cefaloridine, cefalotin, cefapirin, cefatrizine, cefazaflur, cefazedone, cefazolin, cefradrine, cefroxadine, and ceftezole. In one embodiment, the antibiotic is selected from cefaclor, cefonicid, cefprozil, cefuroxime, cefuzonam, cefmetazole, cefotetan, cefoxitin, loracarbef, cefbuperazone, cefminox, cefoxitin, and cefotiam. In one embodiment, the antibiotic is selected from cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, and latamoxef. In one embodiment, the antibiotic is selected from cefclidine, cefepime, cefluprenam, cefoselis, cefozopran, cefpirome, cefquinome, and flomoxef. In one embodiment, the antibiotic is selected from ceftobiprole, ceftaroline, and ceftolozane. In one embodiment, the antibiotic is a glycopeptide. In one embodiment, the antibiotic is selected from teicoplanin, vancomycin, telavancin, dalbavancin, ramoplanin, decaplanin, and oritavancin. In one embodiment, the antibiotic is a lincosamide. In one embodiment, the antibiotic is selected from lincomycin, clindamycin, and pirlimycin. In one embodiment, the antibiotic is daptomycin. In one embodiment, the antibiotic is a macrolide. In one embodiment, the antibiotic is selected from azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin. In one embodiment, the antibiotic is a ketolide. In one embodiment, the antibiotic is selected from telithromycin, cethromycin, and solithromycin. In one embodiment, the antibiotic is a monobactam. In one embodiment, the antibiotic is selected from aztreonam. In one embodiment, the antibiotic is a nitrofuran. In one embodiment, the antibiotic is selected from diruazone, furazolidone, nifurfoline, nifuroxazide, nifurquinazol, nifurtoinol, nifurzide, nitrofural, and nitrofurantoin. In one embodiment, the antibiotic is an oxazolidinone. In one embodiment, the antibiotic is selected from linezolid, posizolid, tedizolid, radezolid, torezolid, and cycloserine. In one embodiment, the antibiotic is a penicillin. In one embodiment, the antibiotic is selected from penicillin G, penicillin K, penicillin N, penicillin O, and penicillin V. In one embodiment, the antibiotic is selected from meticillin, nafcillin, oxacillin, cloxacillin, dicloxacillin, and flucoxacillin. In one embodiment, the antibiotic is selected from ampicillin, amoxicillin, pivampicillin, hetacillin, bacampicillin, metampicillin, talampicillin, and epicillin. In one embodiment, the antibiotic is selected from carbenicilin, ticarcillin, and temocillin. In one embodiment, the antibiotic is selected from mezlocillin and piperacillin. In one embodiment, the antibiotic is selected from clavulanic acid, sulbactam, and tazobactam. In one embodiment, the antibiotic is a polypeptide antibiotic. In one embodiment, the antibiotic is selected from bacitracin, colistin, and polymyxin B. In one embodiment, the antibiotic is a quinolone or fluoroquinolone antibiotic. In one embodiment, the antibiotic is selected from flumequine, oxolinic acid, rosoxacin, cinoxacin, nalidixic acid, and piromidic acid. In one embodiment, the antibiotic is selected from ciprofloxacin, fleroxacin, lomefloxacin, nadifloxacin, norfloxacin, ofloxacin, pefloxacin, rufloxacin, and enoxacin. In one embodiment, the antibiotic is selected from balofloxacin, grepafloxacin, levofloxacin, pazufloxacin, sparfloxacin, temafloxacin, and tosufloxacin. In one embodiment, the antibiotic is selected from clinafloxacin, gatifloxacin, moxifloxacin, sitafloxacin, prulifloxacin, besifloxacin, gemifloxacin, trovafloxacin, delafloxacin, and ozenoxacin. In one embodiment, the antibiotic is a sulfonamide. In one embodiment, the antibiotic is selected from sulfacetamide, sulfadiazine, sulfadimidine, sulfafurazole, sulfisomidine, sulfadoxine, sulfamethoxazole, sulfamoxole, sulfanitran, sulfadimethoxine, sulfamethoxypyridazine, sulfametoxydiazine, sulfadoxine, sulfametopyrazine, terephtyl, mafenide, sulfanilamide, sulfasalazine, sulfisoxazole, and sulfonamicochrysoidine. In one embodiment, the antibiotic is a tetracycline. In one embodiment, the antibiotic is selected from tetracycline, chlortetracycline, oxytetracycline, demeclocycline, lymecycline, meclocycline, metacycline, minocycline, and rolitetracycline.

In one embodiment, the antibiotic is selected from clofazimine, dapsone, capreomycin, cycloserine, ethambutol, ethionamide, isoniazid, pyrazinamide, rifampicin, rifabutin, rifapentine, and streptomycin. In another embodiment, the antibiotic is selected from arsphenamide, chloramphenicol, fosfomycin, fusidic acid, metronidazole, mupirocin, platensimycin, quinupristin, dalfopristin, thiamphenicol, tigecycline, and trimethoprim.

Topical Formulations for the Treatment of Acne Vulgaris

Acne vulgaris is a skin disease caused in part by excessive outgrowth of *Propionibacterium acnes* bacteria and inflammation induced in response to the *P. acnes* bacteria. Acne, a common skin disease, occurs when hair follicles become clogged with dead skin cells and oil from the skin. Acne develops due to blockages that occur through increased sebum production influenced by androgens, excessive deposition of keratin in the hair follicle leading to comedo formation. The earliest pathological change involves the formation of a microcomedone due to the accumulation of skin cells in the hair follicle, which mix with oily sebum to block the follicle, a process further exacerbated by the presence of the *P. acnes* biofilm. If the microcomedone is superficial, melanin within the plug oxidizes upon exposure to air, forming a blackhead or open comedo. If the microcomedone is deeper within the hair follicle, a whitehead or closed comedo forms.

*Propionibacterium acnes* (reclassified as *Cutibacterium acnes* in 2016) is a Gram-positive bacterium (rod) linked to acne that belongs to the *Cutibacterium* Genus and the Propionibacteriaceae Family. Typically slow-growing, it is aerotolerant anaerobe, meaning that it can tolerate the presence of oxygen, but does not utilize oxygen for its growth. While the bacteria is involved in the maintenance of healthy skin, it can also cause many common skin disorders such as acne vulgaris. The bacteria predominately lives deep within follicles and pores, where it uses sebum, cellular debris, and metabolic byproducts from surrounding skin tissue as a source of energy and nutrients. Elevated production of sebum or blockage of follicles can cause the bacteria to grow and this rapid growth can trigger inflammation that can led to the symptoms of common skin disorders, such as folliculitis and acne vulgaris.

While less common, *Staphylococcus epidermidis* can also cause acne. It is a Gram-positive bacterium belonging to the *Staphylococcus* Genus and the Staphylococcaceae Family that is part of the normal human flora and typically skin flora or mucosal flora. It is a facultative anaerobic bacteria and can therefore grow with or without oxygen. It is usually not pathogenic, but in patients with comprised immune systems, the bacteria can cause an infection. *Staphylococcus epidermidis* has ability to form biofilms on plastic and its infections are generally related to catheters or surgical implants.

The presence of *P. acnes* induces skin inflammation due to the bacteria's ability to bind to toll-like receptors (TLRs), especially TLR2 and TLR4 and by altering the fatty composition of the oily sebum by oxidizing squalene. The subsequent inflammatory cascades lead to the formation of inflammatory acne lesions such as papules, pustules, or nodules. If the inflammatory reaction is very severe, the follicle will break into the dermis and subcutaneous tissue as a deep nodule, leading to local tissue destruction and scarring.

Traditionally, acne is classified as either non-inflammatory (open/closed comedones) or inflammatory (papules, pustules, or nodules). Mounting evidence indicates that inflammation exists throughout the entire duration of the acne lesion lifecycle, establishing the critical role of inflammation in the pathology of acne. In the earliest stages of acne lesion development, CD3+ T cell, CD4+ T cell, and macrophage populations are elevated, while the levels of the pro-inflammatory cytokine interleukin-1 are also upregulated. Initiation of inflammatory events have been documented even before clinical detection of acne lesions.

The active compounds described herein can be administered to a human in need thereof as a neat chemical or as a topical formulation that includes an effective amount of a compound described herein, or its pharmaceutically acceptable salt, for a human in need of treatment of acne vulgaris. Thus, in one embodiment, the disclosure provides topical formulations comprising an effective amount of a compound described herein, or its pharmaceutically acceptable salt, together with at least one topically acceptable carrier for any of the uses described herein. The topical formulation may contain a compound or salt as the only active ingredient, or, in an alternative embodiment, the compound and at least one additional active agent.

An effective amount of a compound as described herein, or the compound described herein in combination or alternation with, or preceded by, concomitant with or followed by another active agent, can be used in an amount sufficient to (a) inhibit the progression of acne vulgaris; (b) cause a regression of acne vulgaris; (c) cause a cure of acne vulgaris; or inhibit or prevent the development of acne vulgaris. Accordingly, an effective amount of a compound or its salt or composition described herein will provide a sufficient amount of the agent when administered to human to provide a desired benefit.

Topical formulations are classified into three major categories: solid forms (such as dusting powders); liquid forms (such as lotions and liniments); and semi-liquid forms (such as ointments, pastes, creams, and gels). Additives or excipients are used as inactive ingredients in topical formulations for structuring. The main use of topical formulation additives are to control the extent of absorption of the active compound, maintaining the viscosity, improving the stability and organoleptic properties, and increasing the bulk of the formulation. The main goal of topical formulations is to confine the desired effect to the skin or within the skin. Such formulations are preferred because they are protective, emollient, and deliver the active agent to exert local activity when applied to the skin or mucous membranes.

In one embodiment, the topical formulation is a solid formulation such as a dusting powder. A dusting powder is a finely divided insoluble powder containing ingredients used on skin especially for allaying irritation or absorbing moisture, discouraging bacterial growth and providing lubricant properties. Easy powder flow ability and spreadability are important parameters that are considered in the manufacture and evaluation of a dusting powder formulation. The dusting powder should adhere to the skin, provide good coverage and skin adsorption, should be free of irritant properties, and should protect the skin from drying and irritation. Representative examples of excipients that can be used in dusting powder formulations include, but are not limited to, talc, starch (such as corn starch, wheat starch, or potato starch), kaolin, zinc stearate, zinc oxide, aluminum chlorohydrate, aluminum zirconium chlorhydrex, micronized wax, and chlorhexidine (as the acetate, gluconate, or hydrochloride salt).

In one embodiment, the topical formulation is a cream formulation. Creams are semisolid emulsion formulation for application to the skin or mucous membranes. Creams may be formulated as water in oil (w/o) emulsions or as oil in water (o/w) emulsions. Water in oil emulsion creams are less greasy and provide good spreadability compared to ointments. Oil in water emulsion creams, often called vanishing creams, readily rub into the skin and are easily removed by water.

Water in oil emulsion formulations typically consist of a hydrophilic component, e.g. water or other hydrophilic diluent, and a hydrophobic component, e.g. a lipid, oil, or oily material. The hydrophilic component is typically dispersed, i.e. exists as small particles and droplets, within the hydrophobic component. Water in oil emulsions typically comprise from about 1% to about 98% of the dispersed hydrophilic phase and from about 1% to about 50% of the hydrophobic phase. Additives commonly used in water in oil emulsion formulations include wool fat (containing sterols, cholesterol, oxycholesterol, triterpene, or aliphatic alcohols), waxes, bivalent soaps, sorbitan esters, borax, and oleic acid. In some embodiments, the water in oil emulsion refers to a water in silicone emulsion.

Oil in water emulsion formulations typically consist of a hydrophilic component, e.g. water or other hydrophilic diluent, and a hydrophobic component, e.g. a lipid, oil, or oily material. The hydrophobic component is typically dispersed, i.e. exists as small particles and droplets, within the hydrophilic component. Water in oil emulsions typically comprise from about 1% to about 98% of the hydrophilic phase and from about 1% to about 50% of the dispersed hydrophobic phase. Additives commonly used in oil in water emulsion formulations include polysorbates (such as Tween 80, Tween 21, and Tween 40), methylcellulose, acacia, tragacanth, triethanolamine oleate, arachis oil, and cetostearyl alcohol.

In one embodiment, the topical formulation is an ointment formulation. Ointments are greasy semisolid preparations of a dissolved or dispersed active compound. Ointment bases often influence topical drug bioavailability due to their occlusive properties of the stratum corneum, which enhances the flux of drug across the skin and affects drug dissolution or partitioning within and from the ointment to the skin. Ointments usually are moisturizing and are good for dry skin, as well as having a low risk of sensitization or irritation due to having few ingredients beyond the base oil or fat. The vehicle for an ointment formulation, known as an ointment base, may be an oleaginous base, an absorption base, or a water-soluble base.

Oleaginous bases are composed entirely of lipophilic materials. They are anhydrous, insoluble in water, and not easily removable with water. Oleaginous bases are inexpensive, non-reactive, nonirritating, are good emollients, have protective and occlusive properties, and are not water washable. Representative examples of oleaginous bases include hydrocarbons (such as petrolatum, paraffin wax, liquid paraffin, microcrystalline wax, plastibase, or Ceresi), vegetable oils and animal fat (such as coconut oil, bees wax, olive oil, lanolin, peanut oil, spermacetic wax, sesame oil, or almond oil), hydrogenated and sulfated oils (such as hydrogenated castor oil, hydrogenated cotton seed oil, hydrogenated soya bean oil, hydrogenated corn oil, or hydrogenated sulfated castor oils), alcohols/acids/esters (such as cetyl alcohol, stearic acid, stearyl alcohol, oleic acid, olelyl alcohol, palmitic acid, lauryl alcohol, lauraic acid, myristyl alcohol, ethyl oleate, isopropyl myristicate, or ethylene glycol), and silicones (such as dimethylpropylsiloxanes, methyl phenyl polysiloxanes, and steryl esters of dimethyl polysiloxanes).

Absorption bases are known to take up several times their own weights in water but not permit absorption of medicament form the base. The advantages of absorption bases are their protective, occlusive, and emollient properties, their ability to absorb liquids, and that they do not wash off easily so they hold the incorporated compound with sufficient contact with the skin. Representative examples of absorption bases include hydrophilic petrolatum and anhydrous lanolin.

Water-soluble bases, also known as greaseless ointment bases, consists of water soluble ingredients such as polyethylene glycol polymer (carbowax). Polyethylene glycol is water soluble, nonvolatile, and inert. Other water-soluble bases include glyceryl monostearate, cellulose derivatives, sodium alginate, bentonite, and carbopol 934.

In one embodiment, the topical formulation is a gel formulation. Gels are transparent or translucent semisolid preparations of one or more active ingredients in suitable hydrophilic or hydrophobic bases. Gels may be clear or opaque, and polar hydroalcoholic or nonpolar. Gels are prepared by either a fusion process or a special procedure necessitated by the gelling agents, humectants, and preservatives. Gelling agents exhibit pseudoplastic properties that give the formulation a thixotropic consistency. Gelling agents are typically used in concentrations of 0.5-10% to allow for easy addition of the active drug before the gel is formed. Representative examples of agents used in gel formulations include tragacanth, fenugreek mucilage, methyl cellulose, hydroxy ethyl cellulose, hydroxy propyl cellulose, hydroxy propyl methyl cellulose, carboxy methylcellulose, carbopol, pectin, poloxamers, alginates (such as sodium, potassium, or ammonium alginates), gelatin, starch, polyvinyl alcohol, povidone, propylene glycol, and ethyldiamine tetraacetic acid.

In one embodiment, the topical formulation is a paste formulation. Pastes are stiff preparations containing a high proportion of a finely powdered solid such as starch, zinc oxide, calcium carbonate, or talc. Pastes are often less greasy than ointment formulations.

In one embodiment, the topical formulation is a lotion formulation. Lotions are low- to medium-viscosity preparations intended for application to unbroken skin. Lotions are applied to external skin with bare hands, a clean cloth, cotton wool or gauze. Lotions provide cooling effects to the skin by the evaporation of solvents formulated therein. Typical additives in lotion formulations include bentonite, sodium carboxymethylcellulose, alcohols, and glycerin.

In one embodiment, the topical formulation is a liniment formulation. Liniments are liquid or semiliquid preparations meant for application to the skin with friction or rubbing. They act as a rubefacient, soother, or stimulant. Typical vehicles for liniment formulations are alcohol, oil, or soap based. Typical additives in a liniment formulation include castor oil, cotton seed oil, peanut oil, sesame oil, and oleic acid.

A wide variety of optional components/ingredients may be included in the topical formulations including, but not limited to, absorbents, abrasives, anticaking agents, antifoaming agents, antimicrobial agents, binders, biological actives, buffering agents, bulking agents, chemical additives, cosmetic biocides, denaturants, cosmetic astringents, drug astringents, external analgesics, film formers, humectants, opacifying agents, fragrances, pigments, colorings, essential oils, skin sensates, emollients, skin soothing agents, skin healing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, oil/sebum control agents, sweat control agents, sequestrants, anti-inflammatory agents, anti-androgens, depilation agents, desquamation agents/exfoliants, organic hydroxy acids, vitamins and derivatives thereof, and natural extracts.

An effective amount of an active compound or its salt or composition as described herein can also be used to treat or prevent acne vulgaris in a human, due to any bacteria that causes such acne, including *P. acnes* and *S. epidermis*. In one embodiment, a method is provided comprising administering to a human an effective amount of a compound or its pharmaceutically acceptable salt or composition either alone or in combination with an effective amount of an additional active agent, for example an antibiotic or anti-inflammatory agent, to treat acne vulgaris.

Acne vulgaris severity may be classified as mild, moderate, or severe. Mild acne is classically defined by the presence of clogged skin follicle (known as comedones) limited to the face with occasional inflammatory lesions. Moderate acne occurs when a higher number of inflammatory papules and pustules occur on the face, with some being found on the trunk of the body. Severe acne occurs when nodules are the characteristic facial lesions and involvement of the trunk is extensive.

The present method includes identifying a target portion of skin affected with acne vulgaris and in need of treatment and applying a compound or its salt or composition as described herein to the target portion of skin. In some instances, the target portion of skin may not appear to be suffering from acne vulgaris, i.e. the compound or its salt or composition as described herein may be used as a preventative therapy for acne vulgaris. The compound or its salt or composition may be applied to the target skin portion and, if desired, to the surrounding skin at least once a day, twice a day, or on a more frequent daily basis during the treatment period. Typically, the compound or its salt or composition is applied in the morning and/or in the evening before bed.

The treatment period is ideally sufficient time for the active compound to reduce or eliminate the appearance of acne vulgaris on the target portion of skin. The treatment period may last for at least 1 week, about two weeks, about 4 weeks, about 8 weeks, or about 12 weeks. The treatment period may extend over multiple months (about 3-12 months) or multiple years. The step of applying the compound or its salt or composition may be accomplished by localized application, i.e. by applying to the targeted area while minimizing delivery to skin surfaces where treatment is not desired, or by applying more generally or broadly to one or more skin surfaces.

*Propionibacterium acnes* (reclassified as *Cutibacterium acnes* in 2016) is a Gram-positive bacterium (rod) linked to acne that belongs to the *Cutibacterium* Genus and the Propionibacteriaceae Family. Typically slow-growing, it is aerotolerant anaerobe, meaning that it can tolerate the presence of oxygen, but does not utilize oxygen for its growth. While the bacteria is involved in the maintenance of healthy skin, it can also cause many common skin disorders such as acne vulgaris. The bacteria predominately lives deep within follicles and pores, where it uses sebum, cellular debris, and metabolic byproducts from surrounding skin tissue as a source of energy and nutrients. Elevated production of sebum or blockage of follicles can cause the bacteria to grow and this rapid growth can trigger inflammation that can led to the symptoms of common skin disorders, such as folliculitis and acne vulgaris.

*Staphylococcus epidermidis* is a Gram-positive bacterium belonging to the *Staphylococcus* Genus and the Staphylococcaceae Family that is part of the normal human flora and typically skin flora or mucosal flora. It is a facultative anaerobic bacteria and can therefore grow with or without oxygen. It is usually not pathogenic, but in patients with comprised immune systems, the bacteria can cause an infection. *Staphylococcus epidermidis* has ability to form biofilms on plastic and its infections are generally related to catheters or surgical implants.

In one embodiment, an active compound or its salt or composition as described herein may be used in combination or alternation with benzoyl peroxide. In the skin follicle, benzoyl peroxide kills *P. acnes* by oxidizing its proteins through the formation of oxygen free radicals and benzoic acid. These radicals are believed to interfere with the bacterium's metabolism and ability to make proteins. Additionally, benzoyl peroxide is mildly effective at breaking down comedones and inhibiting inflammation. In one embodiment, an active compound or its salt is formulated in combination with benzoyl peroxide in a topical formulation as described herein.

In one embodiment, an active compound or its salt or composition as described herein may be used in combination or alternation with a retinoid. Retinoids are medications which reduce inflammation, normalize the follicle cell life cycle, and reduce sebum production. They are structurally related to vitamin A. The retinoids appear to influence the cell life cycle in the follicle lining; this helps prevent the accumulation of skin cells within the hair follicle that can create a blockage. Frequently used topical retinoids include adapalene, isotretinoin, retinol, tazarotene, and tretinoin. In one embodiment, an active compound or its salt is formulated in combination with a retinoid in a topical formulation as described herein.

In one embodiment, an active compound or its salt or composition as described herein may be used in combination or alternation with an antibiotic. Antibiotics are frequently applied to the skin or taken orally to treat acne and are thought to work due to their antimicrobial activity against *P. acnes* and their ability to reduce inflammation. Commonly used antibiotics, either applied to the skin or taken orally, include clindamycin, erythromycin, metronidazole, sulfacetamide, and tetracyclines such as doxycycline and minocycline. Other representative topical antibiotics include bacitracin, polymycin b, neomycin, retapamulin, mupirocin, pramoxine, gentamicin, mafenide, and ozenoxacin. The compounds described herein are particularly effective in combination with antibiotics due to their potentiation of the antimicrobial effect of the antibiotic. In one embodiment, an active compound or its salt is formulated in combination with an antibiotic in a topical formulation as described herein.

In one embodiment, an active compound or its salt or composition as described herein may be used in combination or alternation with azelaic acid. Azelaic acid is thought to be an effective acne treatment due to its ability to reduce skin cell accumulation in the follicle, along with its antibacterial and anti-inflammatory properties. In one embodiment, an active compound or its salt is formulated in combination with an antibiotic in a topical formulation as described herein.

In one embodiment, an active compound or its salt or composition as described herein may be used in combination or alternation with salicyclic acid. Salicyclic acid is a topically applied beta-hydroxy acid that has keratolytic properties in addition to stopping bacterial reproduction. In one embodiment, an active compound or its salt is formulated in combination with salicyclic acid in a topical formulation as described herein.

In one embodiment, an active compound or its salt or composition as described herein may be used in combination or alternation with niacinamide. Niacinamide can improve acne by decreasing inflammation, suppressing sebum production, and promoting wound healing. In one embodiment, an active compound or its salt is formulated in combination with salicyclic acid in a topical formulation as described herein.

Process of Preparation of Compounds of the Present Invention

The compounds described herein can be prepared by methods known to those skilled in the art. In one non-limiting example, the disclosed compounds can be made using the routes provided below.

Compounds of the present invention with stereocenters may be drawn without stereochemistry for convenience. One skilled in the art will recognize that pure enantiomers and diastereomers can be prepared by methods known in the art. Example of methods to obtain optically active materials include at least the following.

i. physical separation of crystals—a technique whereby macroscopic crystals of the individual enantiomers are manually separated. This technique can be used if crystals of the separate enantiomers exist, i.e., the material is a conglomerate, and the crystals are visually distinct;

ii. simultaneous crystallization—a technique whereby the individual enantiomers are separately crystallized from a solution of the racemate, possible only if the enantiomer is a conglomerate in the solid state;

iii. enzymatic resolutions—a technique whereby partial or complete separation of a racemate by virtue of differing rates of reaction for the enantiomers with an enzyme;

iv. enzymatic asymmetric synthesis—a synthetic technique whereby at least one step in the synthesis uses an enzymatic reaction to obtain an enantiomerically pure or enriched synthetic precursor of the desired enantiomer;

v. chemical asymmetric synthesis—a synthetic technique whereby the desired enantiomer is synthesized from an achiral precursor under conditions that produce asymmetry (i.e. chirality) in the product, which may be achieved by chiral catalysts or chiral auxiliaries;

vi. diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer;

vii. first- and second-order asymmetric transformations—a technique whereby diastereomers from the racemate quickly equilibrate to yield a preponderance in solution of the diastereomer from the desired enantiomer of where preferential crystallization of the diastereomer from the desired enantiomer perturbs the equilibrium such that eventually in principle all the material is converted to the crystalline diastereomer from the desired enantiomers. The desired enantiomer is then released from the diastereomer;

viii. kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix. enantiospecific synthesis from non-racemic precursors—a synthetic technique whereby the desired enantiomer is obtained from non-chiral starting materials and where the stereochemical integrity is not or is only minimally compromised over the course of the synthesis;

x. chiral liquid chromatography—a technique whereby the enantiomers of a racemate are separated in a liquid mobile phase by virtue of their differing interactions with a stationary phase (including vial chiral HPLC). The stationary phase can be made of chiral material or the mobile phase can contain an additional chiral material to provoke the differing interactions;

xi. chiral gas chromatography—a technique whereby the racemate is volatilized and enantiomers are separated by virtue of their differing interactions in the gaseous mobile phase with a column containing a fixed non-racemic chiral adsorbent phase;

xii. extraction with chiral solvents—a technique whereby the enantiomers are separated by virtue of preferential dissolution of one enantiomer into a particular chiral solvent;

xiii. transport across chiral membranes—a technique whereby a racemate is place in contact with a thin 5 membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through; and xiv. simulated moving bed chromatography is used in one embodiment. A wide variety of chiral stationary phases are commercially available.

General Routes of Synthesis

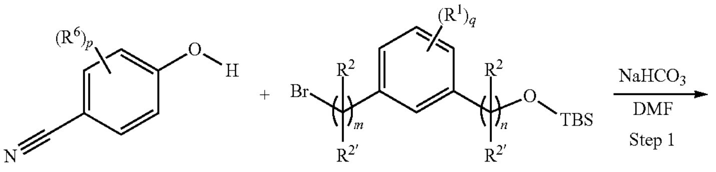

S-1 S-2

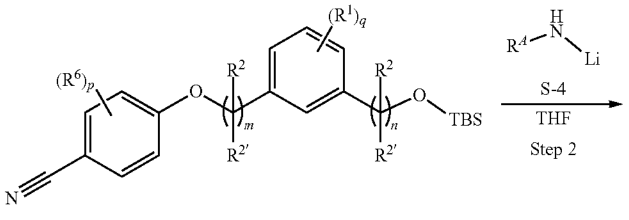

S-3

-continued

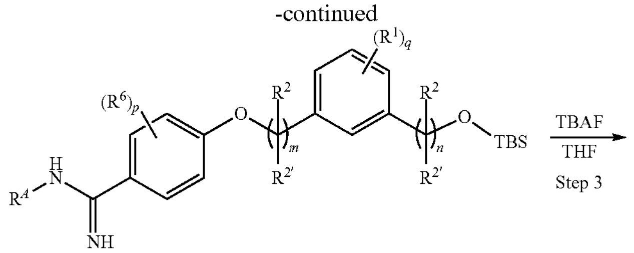

S-5

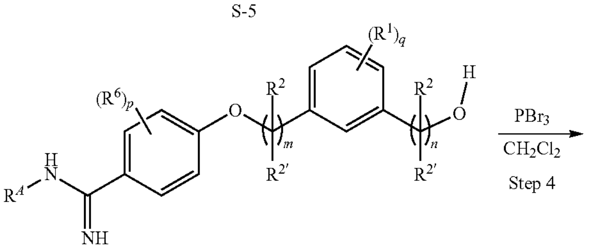

S-6

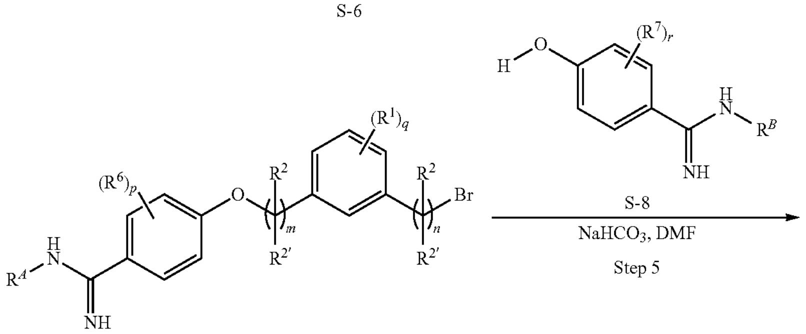

S-7

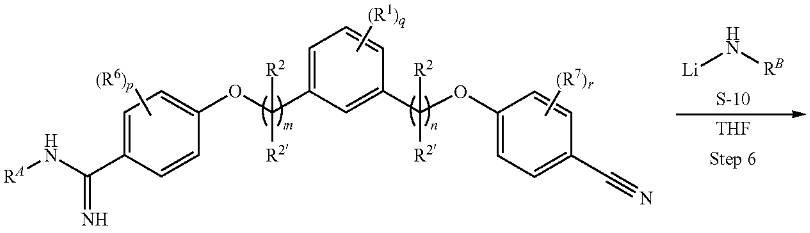

S-9

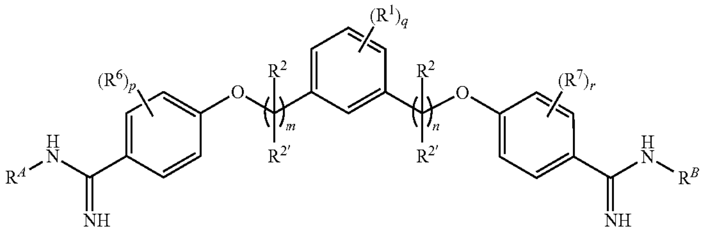

S-11

Route 1

In one embodiment, for example, a compound of Formula II can be made by the process shown in Route 1. In Step 1, the alcohol group in S-1 performs a nucleophilic substitution on the bromide group in S-2 in the presence of base, for example sodium bicarbonate, to provide the phenol ether S-3. In Step 2, the lithium salt of $R^A$—$NH_2$ S-4 adds to the nitrile group in S-3 to provide amidine S-5. In Step 3, the tert-butyldimethylsilyl ether group in S-5 is cleaved with tetrabutylammonium chloride to provide alcohol S-6. In Step 4, the alcohol group in S-6 is converted to a bromide group in S-7 using phosphorous tribromide. In Step 5, the alcohol group in S-8 preforms a nucleophilic substitution on the bromide group in S-7 to provide phenol ether S-9. In Step 6, the lithium salt of $R^B$—$NH_2$ S-10 adds to the nitrile group in S-9 to provide diamidine S-11. Variations of this route can also be used for compounds wherein $Z^1$ and $Z^2$ are S or $N(R^5)$ with appropriate modifications that would be known to those having skill in the art.

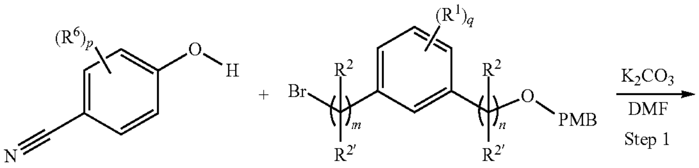
S-12 S-13
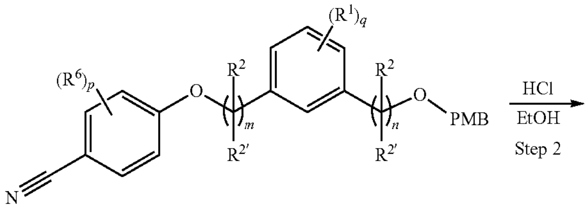
S-14
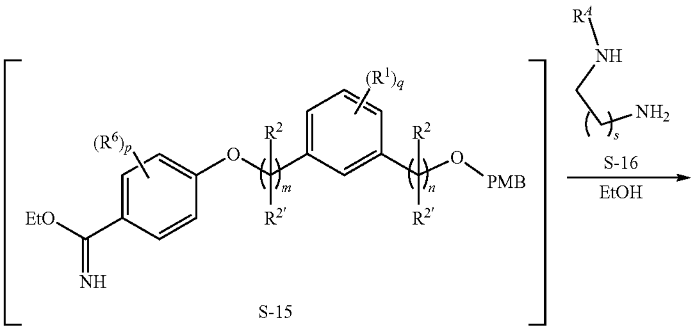
S-15
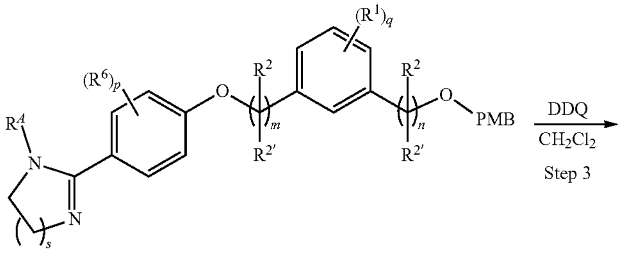
S-17
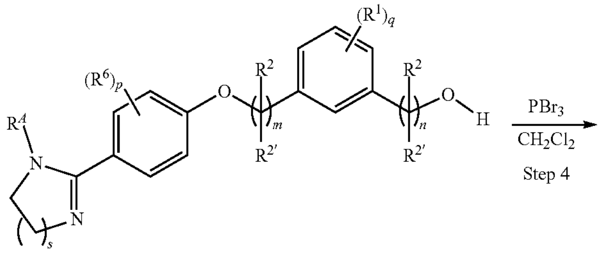
S-18
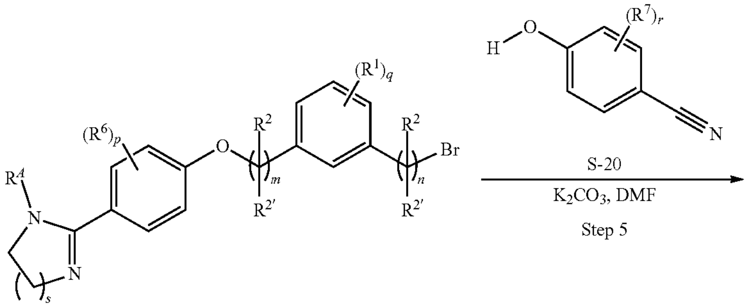
S-19

-continued

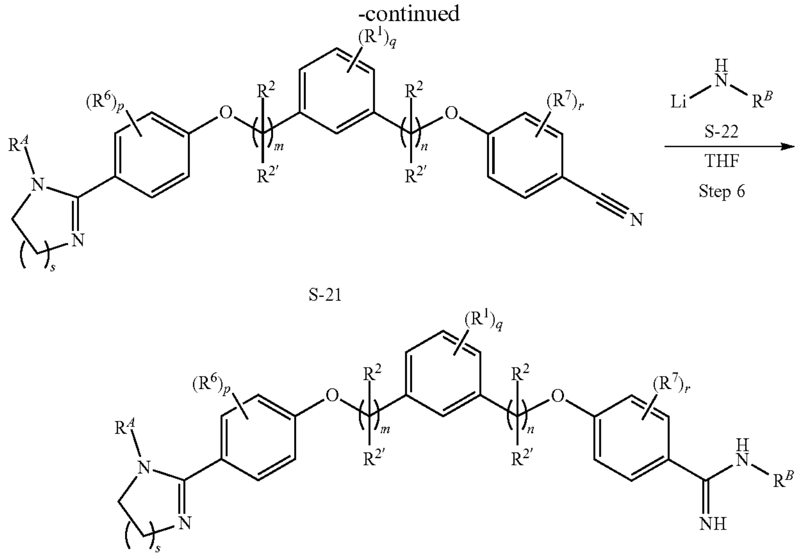

S-21

S-23

Route 2

In one embodiment, for example, a compound of Formula III can be made by the process shown in Route 2. In Step 1, the alcohol group in S-12 performs a nucleophilic substitution of the bromide group in S-13 in the presence of base, for example potassium carbonate, to provide phenol ether S-14. In Step 2, the nitrile group in S-14 is reacted with ethanol in the presence of an acid, for example hydrogen chloride, to provide an intermediate benzimidate S-15, which is then immediately reacted with diamine S-16 to provide cyclic amidine S-17. In Step 3, the 4-methoxybenzyl ether in S-17 is cleaved using an oxidant, for example DDQ, to provide the alcohol S-18. In step 4, the alcohol group in S-18 is converted to a bromide group in S-19 using phosphorous tribromide. In Step 5, the alcohol group in S-20 performs a nucleophilic substitution on the bromide group of S-19 to provide the phenol ether S-21. In Step 6, the lithium salt of $R^B$—$NH_2$ S-22 is added to the nitrile group of S-21 to provide the amidine S-23. Variations of this route can also be used for compounds wherein $Z^1$ and $Z^2$ are S or $N(R^5)$ with appropriate modifications that would be known to those having skill in the art.

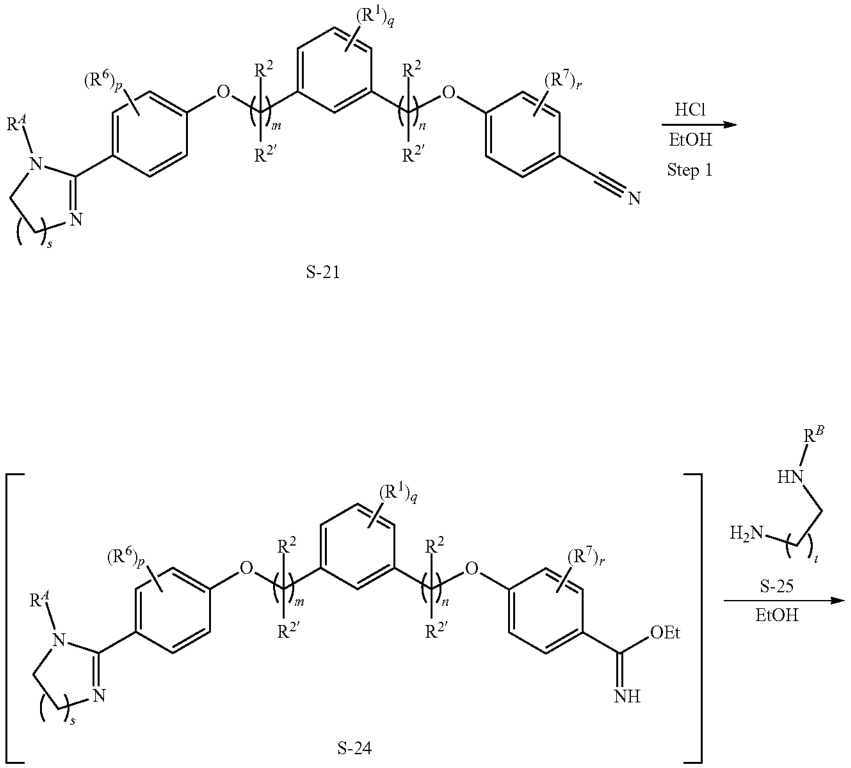

S-21

S-24

-continued

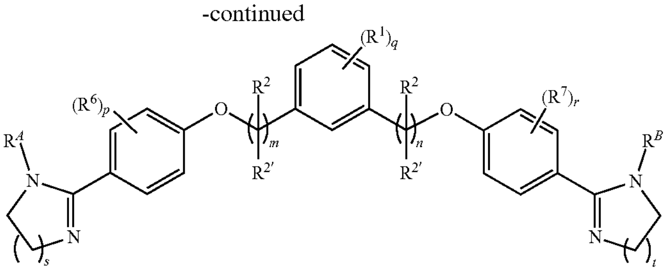

S-26

Route 3

In one embodiment, for example, a compound of Formula IV can be made by the process shown in Route 3. The intermediate S-21 can be made using the same sequence of steps shown in Route 2 above. In Step 1, S-21 is reacted with ethanol in the presence of an acid, for example hydrogen chloride, to provide intermediate benzimidate S-24, which is then immediately reacted with diamine S-25 to provide amidine S-26. Variations of this route can also be used for compounds wherein $Z^1$ and $Z^2$ are independently S or $N(R^5)$ with appropriate modifications that would be known to those having skill in the art.

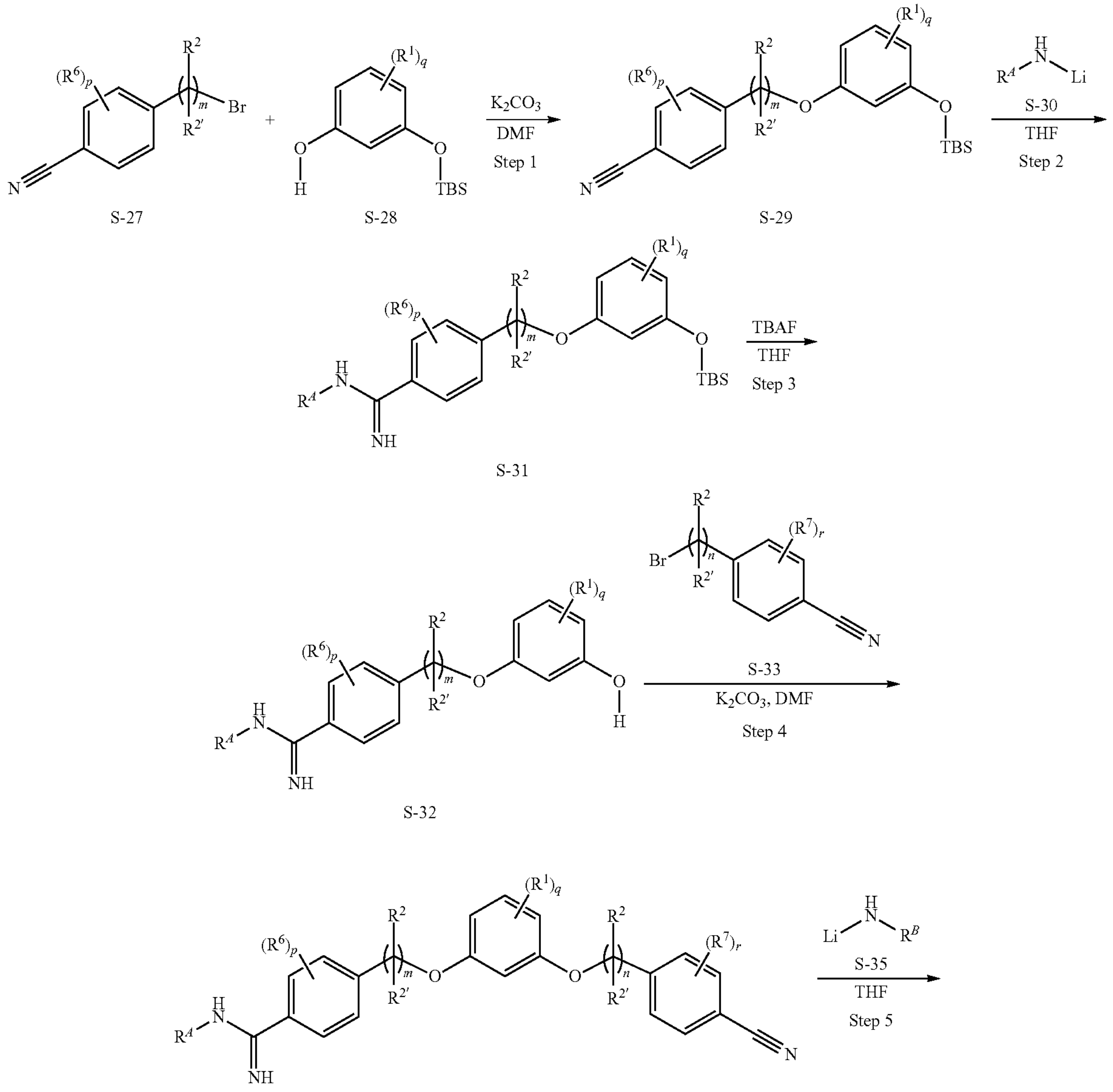

S-27 S-28 S-29 S-31 S-32 S-34

-continued

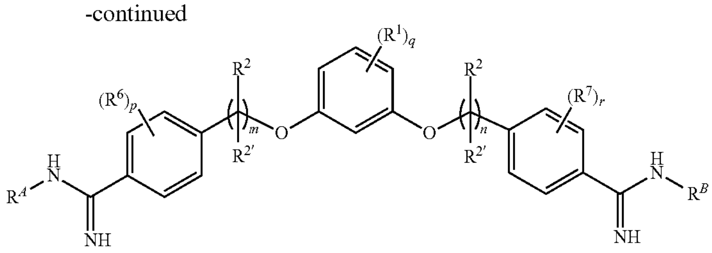

S-36

Route 4

In one embodiment, for example, a compound of Formula V can be made by the process shown in Route 4. In step 1, the benzylic bromide group of S-27 is reacted with the phenol group of S-28 in the presence of base, for example potassium carbonate, to provide the benzylic ether S-29. In Step 2, the nitrile group of S-29 is reacted with the lithium salt of $R^A$—$NH_2$ S-30 to provide the amidine S-31. In Step 3, the tert-butyldimethylsilyl ether S-31 is cleaved using tetrabutylammonium fluoride to provide the phenol S-32. In Step 4, the phenol group of S-32 is reacted with the benzylic bromide group of S-33 to provide the benzylic ether S-34. In Step 5, the nitrile group of S-34 is reacted with the lithium salt of $R^B$—$NH_2$ S-35 to provide the amidine S-36. Variations of this route can also be used for compounds wherein $Z^1$ and $Z^2$ are independently S or $N(R^5)$ with appropriate modifications that would be known to those having skill in the art. Compounds of Formula VI can be made using a similar route by exchanging Step 2 of Route 4 with a variation of Step 2 of Route 2 using appropriate modifications that would be known to those having skill in the art. Compounds of Formula VII can be made using a similar route by exchanging Step 2 of Route 4 with a variation of Step 2 of Route 2 and exchanging Step 5 of route 4 with a variation of Step 1 of Route 3, with each step using appropriate modifications that would be known to those having skill in the art.

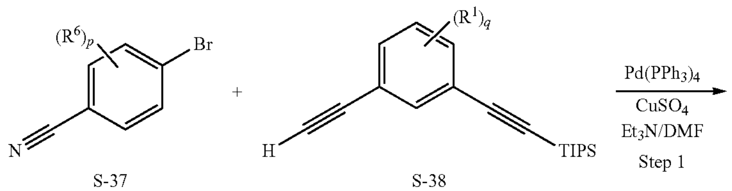

S-37 S-38

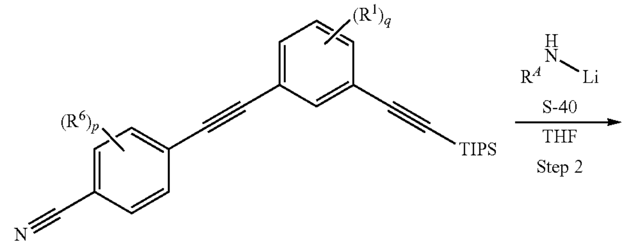

S-39

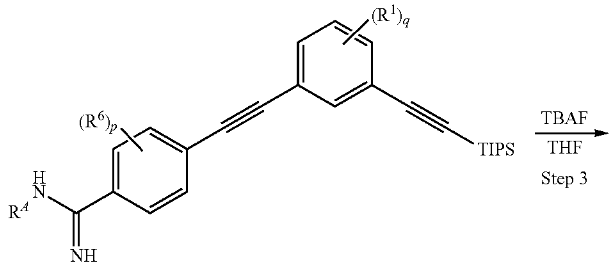

S-41

-continued

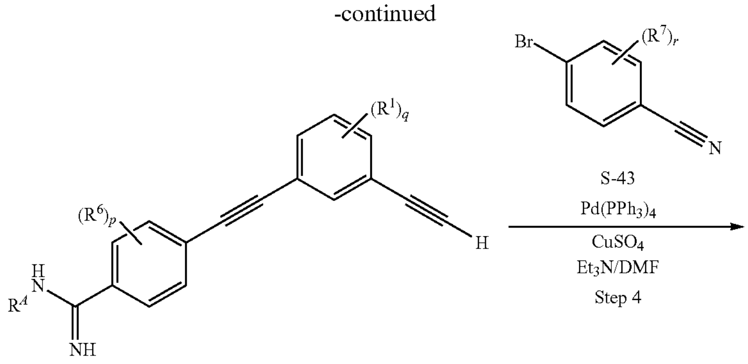

S-42

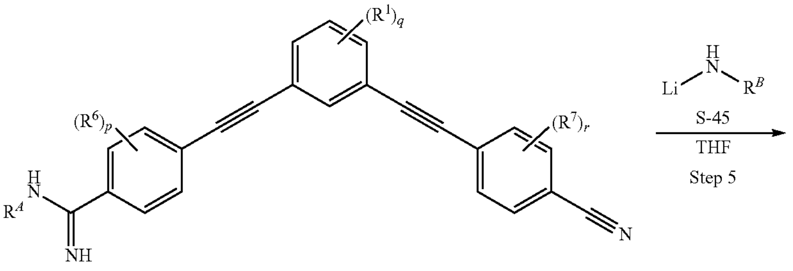

S-44

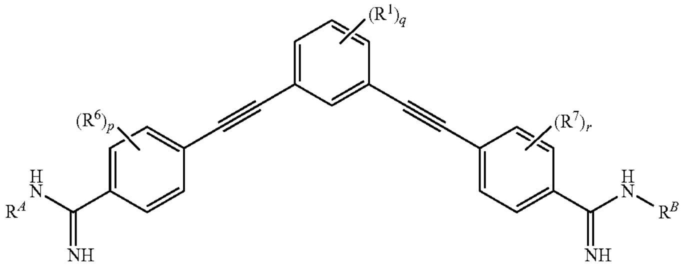

S-46

Route 5

In one embodiment, for example, a compound of Formula VIII can be made by a process shown in Route 5. In Step 1, the aryl bromide group of S-37 is coupled to the terminal alkyne group of S-38 using a palladium catalyst, for example $Pd(PPh_3)_4$, and a copper catalyst, for example copper (II) sulfate, in the presence of an amine base, for example triethylamine, to provide arylalkyne S-39. In Step 2, the nitrile group of S-39 is reacted with the lithium salt of $R^A$—$NH_2$ S-40 to provide amidine S-41. In Step 3, the triisopropylsilyl group of S-41 is removed using tetrabutylammonium fluoride to provide terminal alkyne S-42. In Step 4, the aryl bromide group of S-43 is coupled to the terminal alkyne group of S-42 using a palladium catalyst, for example $Pd(PPh_3)_4$, and a copper catalyst, for example copper (II) sulfate, in the presence of an amine base, for example triethylamine, to provide arylalkyne S-44. Compounds of Formula X can be made using a similar route by exchanging Step 2 of Route 5 with a variation of Step 2 of Route 2 using appropriate modifications that would be known to those having skill in the art. Compounds of Formula IX can be made using a similar route by exchanging Step 2 of Route 5 with a variation of Step 2 of Route 2 and exchanging Step 5 of route 5 with a variation of Step 1 of Route 3, with each step using appropriate modifications that would be known to those having skill in the art.

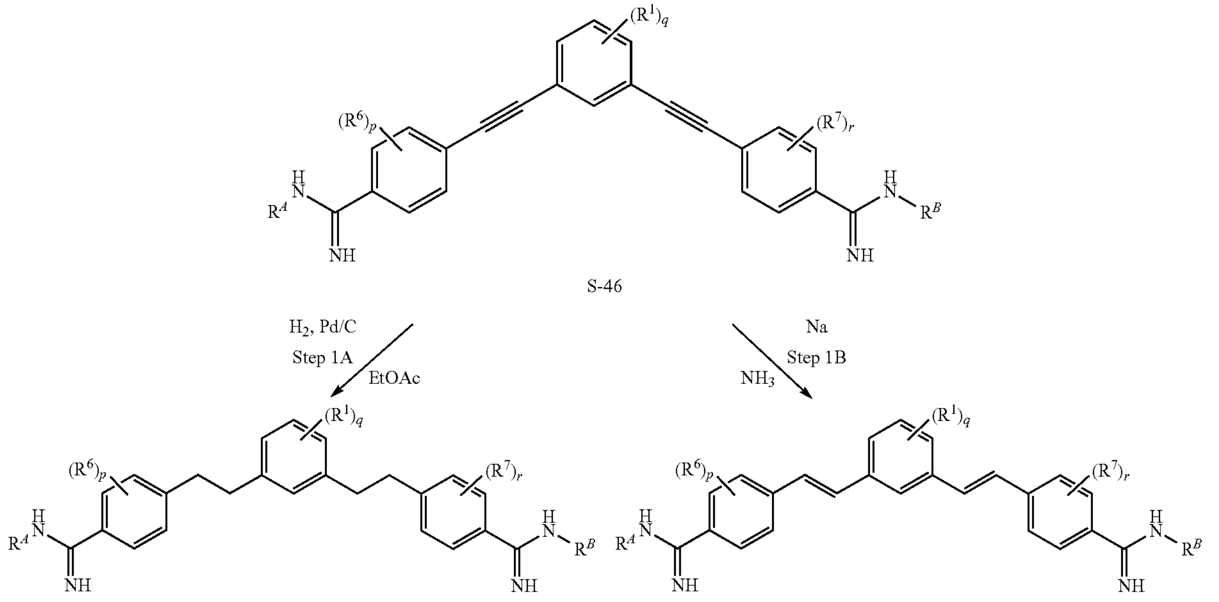

S-46

S-47

S-48

Route 6

In one embodiment, for example, additional compounds of Formula VIII can be made by a process shown in Route 6. The intermediate S-47 can be made using the same sequence of steps shown in Route 5 above. In Step 1A, the alkyne groups in S-46 are reduced using hydrogen gas with catalytic Pd/C to provide the alkane derivative S-47. Alternatively in Step 1B, the alkyne groups in S-46 can be reduced using sodium metal in liquid ammonium to provide the alkene derivative S-48. Compounds of Formula IX or X can be made using this route by selecting the appropriate variation of Route 5 to produce intermediate S-46 as would be apparent to those having skill in the art.

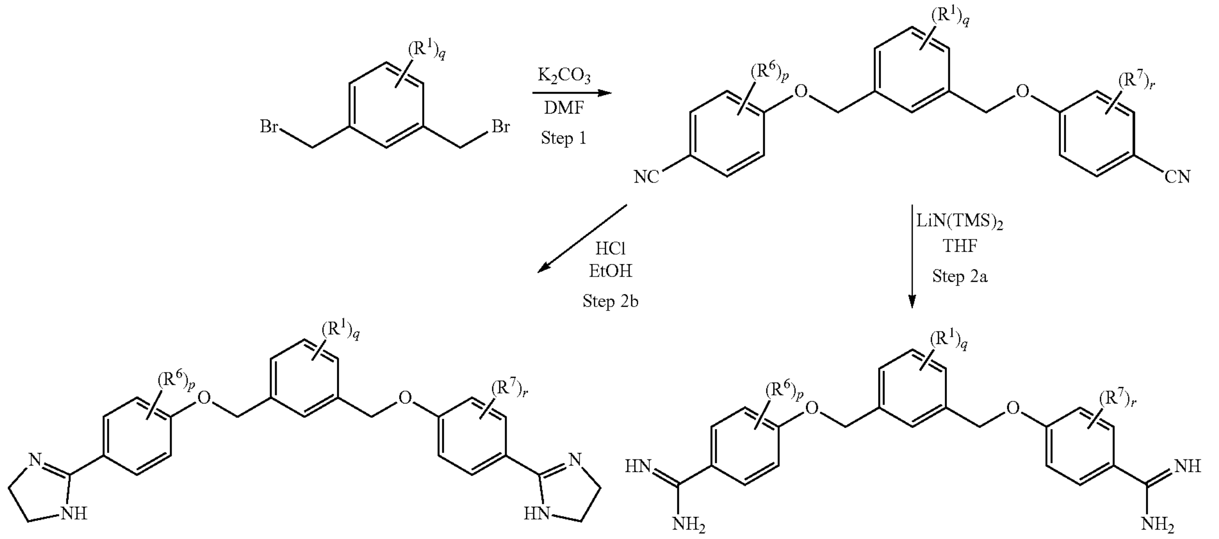

Route 7

General Procedure for synthesis of dinitrile compounds, Step 1: A mixture of 1,3-bis (bromomethyl)-benzene/substituted benzene (5 mmol), 4-hydroxybenzonitrile or 4-hydroxy substituted benzonitrile (10 mmol) and anhydrous $K_2CO_3$ (2.07 g, 15 mmol) in 10 ml DMF was heated at 45° C. for 4 hours [TLC (Hex:EtOAc 4:1) monitored the reaction]. Then the reaction mixture was diluted with ice water (70 ml) and stirred for 30 minutes. The white precipitate was filtered, washed with water, and dried. Then the white solid was dissolved in a solvent (75 ml) (DCM, methanol or THF), dried over anhydrous MgSO4, filtered, concentrated with rotavapor, triturated with hexane, filtered and dried in vacuum to yield white solid in 70-76% yield.

General Procedure for synthesis of dihydrochloride diamidines, Step 2a: To a cold and stirred suspension of di-nitrile (1 mmol) in 15 ml dry THF was added 6.0 ml (6 mmol) of $LiN(TMS)_2$ (1 M in THF). The reaction was stirred for 24 hours at room temperature, cooled, acidified carefully with saturated ethanolic-HCl to form a white solid. The mixture was stirred for 2 hours, after which all solvents were removed under vacuum to afford a crude product. The crude product was then diluted with ether and filtered and collected as a white solid. The white solid was then diluted with 10 mL ice water, basified with 2 M NaOH to afford a white precipitate that was filtered, washed with water and air dried. The solid was suspended in anhydrous ethanol (15 ml) and 5 mL saturated ethanolic HCl for 6 hours. Then ethanol was distilled off and the product was triturated with dry ether and filtered. The solid was dried in vacuum at 80° C. for 12 hours to yield (65-75%) diamidine dihydrochloride as white solid.

General procedure for synthesis of dihydrochloride isopropyl amidines and imidazolines, Step 2b: The nitrile was added to anhydrous EtOH saturated with hydrogen chloride at 0° C. in a dry flask. The reaction mixture was then sealed, slowly warmed to ambient temperature, and stirred until the nitrile was no longer detectable by TLC. The reaction mixture was diluted with anhydrous ether. The precipitated imidate ester dihydrochloride was filtered off under nitrogen and dried under high vacuum. The imidate was then reacted immediately with the appropriate amine in EtOH (refluxing for imidazoline and room temperature for isopropyl amidines). The reaction mixture was concentrated in vacuum. Then ether was added, and the product was filtered. The solid was suspended in 10 ml ice-water and basified with 2 M NaOH. The resulting white precipitate was filtered, washed with water, and air dried. The free base was converted to its dihydrochloride salt using saturated ethanolic HCl as white solid, which was dried in vacuum at 80° C. for 12 h to yield (65-75%).

EXPERIMENTAL EXAMPLES OF THE PRESENT INVENTION

Example 1. Synthesis of Select Compounds of the Present Invention

Synthesis 1. Synthesis of 4,4'-(((5-Methyl-1,3-phenylene)bis(methylene))bis(oxy))dibenzimidamide Hydrochloride (Compound M-1 Dihydrochloride)

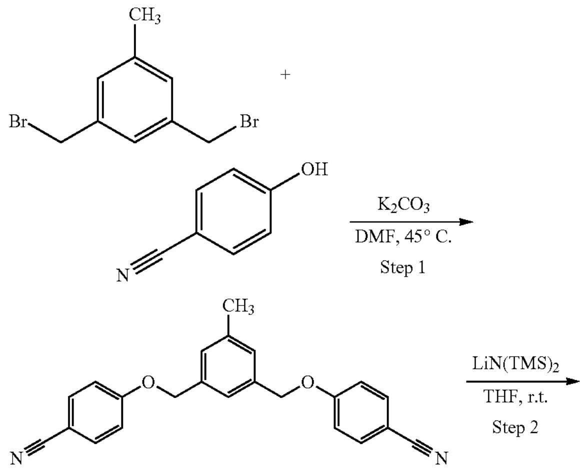

-continued

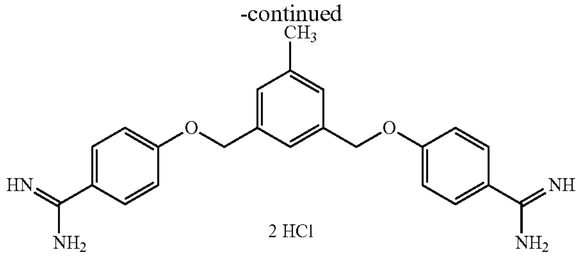

Step 1. Preparation of 4,4'-(((5-Methyl-1,3-phenylene)bis(methylene))bis(oxy))dibenzonitrile A mixture of 1,3-bis(bromomethyl)-5-methylbenzene (1.38 g, 5 mmol), 4-hydroxybenzonitrile (1.19 g, 10 mmol), and $K_2CO_3$ (2.07 g, 15 mmol) in DMF (10 mL) was heated at 45° C. for 4 hours (monitored by TLC, 4:1 hexanes/EtOAc). The reaction was then diluted with ice water (70 mL) and stirred for 30 minutes. The resulting white precipitate was filtered, washed with water, and dried in air. The isolated white precipitate was dissolved in dichloromethane, dried over anhydrous magnesium sulfate, filtered, and concentrated under reduced pressure. The residue was triturated with hexane, filtered, and dried under vacuum to yield 4,4'-(((5-methyl-1,3-phenylene)bis(methylene))bis(oxy))dibenzonitrile (2.54 g, 72%) as a white solid. mp: 135-137° C.; $^1$H NMR (DMSO-$d_6$): 7.67 (d, 4H, J=8.8 Hz), 7.34 (s, 1H), 7.26 (s, 2H), 7.17 (d, 4H, J=8.8 Hz), 5.18 (s, 4H), 2.34 (s, 3H); $^{13}$C NMR (DMSO-$d_6$): 163.7, 138.1, 136.4, 134.2, 128.2, 124.3, 119.1, 115.8, 103.0, 69.5, 20.9: MS: HRMS-ESI-POS.: calc. for $C_{23}H_{18}N_2O_2Na$ m/z 377.1266 ($M^+$+1), found m/z 377.1269.

Step 2. Preparation of 4,4'-(((5-Methyl-1,3-phenylene)bis(methylene))bis(oxy))dibenzimidamide Hydrochloride To a suspension of 4,4'-(((5-methyl-1,3-phenylene)bis(methylene))bis(oxy))dibenzonitrile (0.354 g, 1 mmol) in dry THF (15 mL) stirred over an ice bath was added lithium bis(trimethylsilyl)amide solution (1 M in THF, 6.0 mL), and the reaction was stirred at room temperature for 24 hours. The reaction mixture was cooled over an ice bath and then acidified by the slow addition of saturated ethanolic HCl solution until a white solid formed. The mixture was stirred for two hours and then all solvents were removed under vacuum. The crude residue was brought up in ether and filtered. The filter cake was brought up in ice water (10 mL) and basified with 2 M NaOH solution until a white precipitate formed. The solid was filtered, washed with water, and air dried. The isolated solid was suspended in anhydrous ethanol (15 mL) and saturated ethanolic HCl solution (5 mL) for 6 hours. The solvent was removed by distillation, and the resulting white solid was triturated with dry diethyl ether and filtered. The isolated white solid was dried at 80° C. under vacuum for 12 hours to provide 4,4'-(((5-methyl-1,3-phenylene)bis(methylene))bis(oxy))dibenzimidamide hydrochloride (0.33 g, 71%) as a white solid. mp. 269-71° C.; $^1$H NMR (DMSO-$d_6$): 9.47 (s, 4H), 9.29 (s, 4H), 7.88 (d, 4H, J=8.0 Hz), 7.65 (d, 4H, J=8.0 Hz), 6.51 (s, 1H), 6.49 (s, 2H), 5.21 (s, 4H), 2.24 (s, 3H); $^{13}$C NMR (DMSO-$d_6$): 165.4, 159.0, 143.3, 139.9, 128.3, 127.6, 127.3, 108.2, 99.3, 68.2, 21.4; MS: HRMS-ESI-POS.: calc. for $C_{23}H_{25}N_4O_2$ m/z 389.1972 ($M^+$+1), found m/z 389.1976; analysis calc.

for $C_{23}H_{24}N_4O_2{\cdot}2HCl{\cdot}0.25H_2O$: C, 59.21; H, 5.73; N, 12.02, Found: C, 59.41; H, 5.66; N, 11.55.

Synthesis 2. Synthesis of 2,2'-((((5-Methyl-1,3-phenylene)bis(methylene))bis(oxy))bis(4,1-phenylene)) bis(4,5-dihydro-1H-imidazole) Dihydrochloride (Compound A-2 Dihydrochloride)

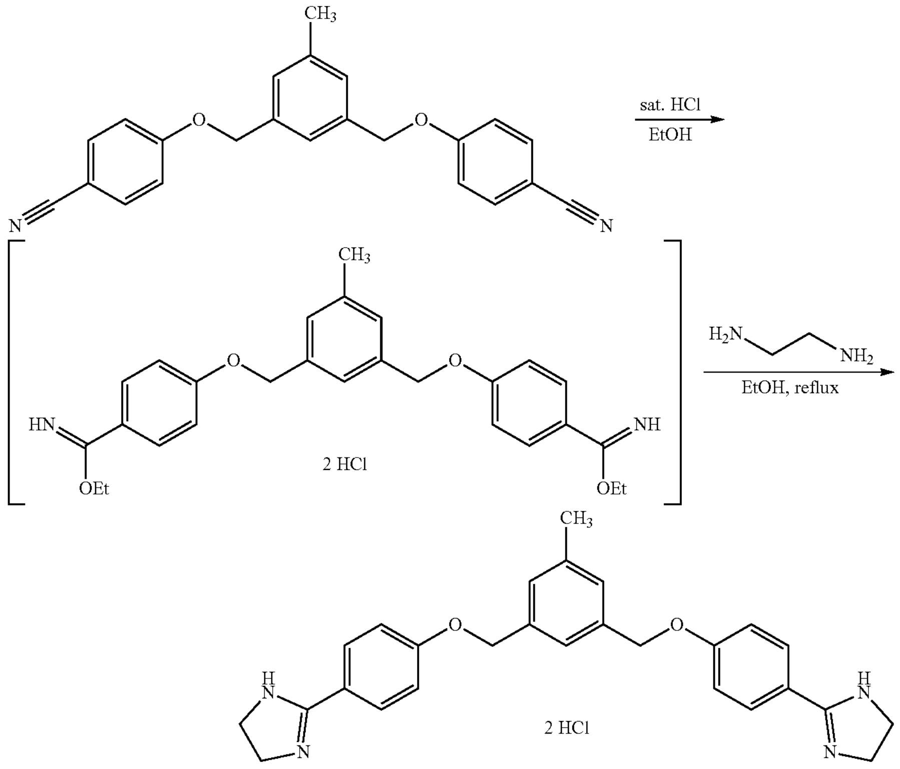

4,4'-(((5-Methyl-1,3-phenylene)bis(methylene))bis(oxy)) dibenzonitrile (0.354 g, 1 mmol) was added to anhydrous EtOH saturated with hydrogen chloride at 0° C. in a dry flask. The reaction mixture was sealed, slowly warmed to room temperature, and stirred until complete consumption of the starting material. The reaction mixture was diluted with anhydrous diethyl ether, and the resulting precipitate was filtered under nitrogen and dried under high vacuum to provide crude diethyl 4,4'-(((5-methyl-1,3-phenylene)bis (methylene))bis(oxy))dibenzimidate dihydrochloride, which was used immediately without further purification.

The crude imidate was brought up in ethanol, and ethane-1,2-diamine was added. The reaction mixture was heated to reflux and stirred until complete consumption of the starting material. The reaction mixture was concentrated under reduced pressure. Diethyl ether was added, and the resulting precipitate was filtered. The solid was suspended in 10 mL of ice water and basified with 2 M NaOH. The resulting white precipitate was filtered, washed with water, and air dried. The solid was brought up in saturated ethanolic HCl solution and stirred for 6 hours. The ethanol was distilled, and the resulting precipitate was triturated with diethyl ether and filtered. The resulting solid was dried under vacuum at 80° C. for 12 hours to provide 2,2'-((((5-methyl-1,3-phenylene)bis(methylene))bis(oxy))bis(4,1-phenylene))bis(4,5-dihydro-1H-imidazole) dihydrochloride (0.38 g, 72%) as a white solid. mp 274-6° C.; $^1$H NMR (DMSO-$d_6$): 10.9 (s, 4H), 8.09 (d, 4H, J=8.0 Hz), 7.68 (d, 4H, J=8.0 Hz), 6.52 (s, 1H), 6.49 (s, 2H), 5.22 (s, 4H), 4.0 (s, 8H), 2.42 (s, 3H); $^{13}$C NMR (DMSO-$d_6$): 164.4, 159.0, 144.1, 128.9, 127.7, 121.4, 108.3, 99.3, 68.2, 44.2, 21.4; MS: HRMS-ESI-POS.: calc. for $C_{27}H_{29}N_4O_2$ m/z 441.2291 ($M^+$+1), found m/z 441.2292; analysis calc. for $C_{27}H_{24}N_4O_2{\cdot}2HCl{\cdot}1.55H_2O$: C, 60.09; H, 6.17; N, 10.39, Found: C,60.38; H, 5.99; N, 10.33.

Synthesis 3. Synthesis of 2,2'-((((5-Methyl-1,3-phenylene)bis(methylene))bis(oxy))bis(4,1-phenylene)) bis(1,4,5,6-tetrahydropyrimidine) dihydrochloride (Compound B-21 dihydrochloride)

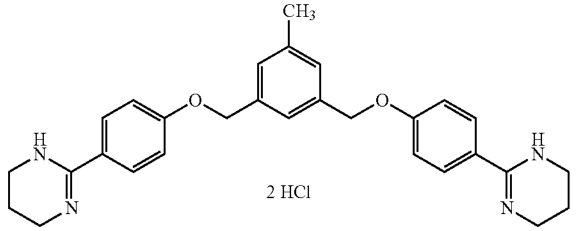 [SMILES: Cc1cc(COc2ccc(C3=NCCCN3)cc2)cc(COc2ccc(C3=NCCCN3)cc2)c1]

The corresponding dinitrile (0.4 g, 1.12 mmol) was converted to 1, 3-Bis {(4-(2-tetrahydropyrimidyl)-benzyloxy}-5-methylbenzene dihydrochloride as white solid following Step 2b of General Route 7 (0.48 g, 75%) using 1,3-diaminopropane (0.25 g, 3.4 mmol); $^1$H NMR (DMSO-$d_6$) 10.23 (s, 4H), 7.82 (d, J=8.1 Hz, 4H), 7.64 (d, J=8.1 Hz, 4H), 6.51 (s, 1H), 6.49 (s, 2H), 5.19 (s, 4H), 3.49 (s, 8H), 2.24 (s, 3H), 1.97 (s, 4H); $^{13}C$ NMR (DMSO-$d_6$) 159.08, 158.50, 142.57, 139.92, 127.93, 127.56, 127.54, 108.26, 99.22, 68.25, 38.88, 38.64, 21.41, 17.69; MS: HRMS-ESI-POS.: calc. for $C_{29}H_{32}N_4O_2$ m/z 469.2604 ($M^+$+1), found m/z 469.2617; analysis calc. for $C_{29}H_{32}N_4O_2$·2HCl·1$H_2O$; C, 61.26; H, 6.55; N, 9.85, Found: C, 61.32; H, 6.36; N, 9.80.

Synthesis 4. Synthesis of 4,4'-(((2-Fluoro-1,3-phenylene)bis(methylene))bis(oxy))dibenzimidamide Dihydrochloride (Compound C-2 Dihydrochloride)

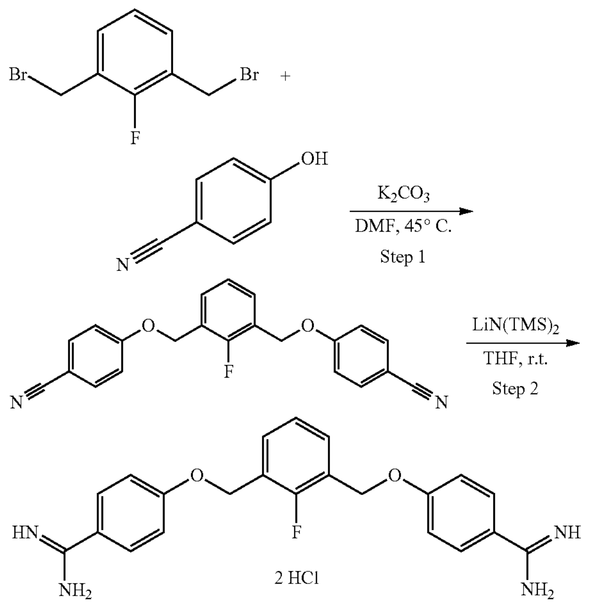

Step 1. Preparation of 4,4'-(((2-Fluoro-1,3-phenylene)bis(methylene))bis(oxy))dibenzonitrile A mixture of 1,3-bis(bromomethyl)-2-fluorobenzene (1.4 g, 5 mmol), 4-hydroxybenzonitrile (1.19 g, 10 mmol), and $K_2CO_3$ (2.07 g, 15 mmol) in DMF (10 mL) was heated at 45° C. for 4 hours (monitored by TLC, 4:1 hexanes/EtOAc). The reaction was then diluted with ice water (70 mL) and stirred for 30 minutes. The resulting white precipitate was filtered, washed with water, and dried in air. The isolated white precipitate was dissolved in dichloromethane, dried over anhydrous magnesium sulfate, filtered, and concentrated under reduced pressure. The residue was triturated with hexane, filtered, and dried under vacuum to yield 4,4'-(((2-Fluoro-1,3-phenylene)bis(methylene))bis(oxy)) dibenzonitrile (2.53 g, 70%) as a white solid. mp 173-5° C.; $^1H$ NMR (DMSO-$d_6$): 7.78 (d, 4H, J=8.4 Hz), 7.59 (t, 2H, J=7.2 Hz), 7.29 (t, 1H, J=7.2 Hz), 7.23 (d, 4H, J=8.4 Hz), 5.3 (s, 4H); $^{13}C$ NMR (DMSO-$d_6$): 161.4, 158.4 (d, $J_{C-F}$=248 Hz), 134.0, 130.7 (d, $J_{C-F}$=4.1 Hz), 124.2 (d, $J_{C-F}$=4.1 Hz), 123.1 (d, $J_{C-F}$=13.5 Hz), 118.7, 115.6, 103.3, 63.8 (d, $J_{C-F}$=3.3 Hz); MS: HRMS-ESI-POS.: calc. for $C_{22}H_{15}FN_2O_2Na$ m/z 381.1015 ($M^+$+Na), found m/z 381.1005.

Step 2. Preparation of 4,4'-(((2-Fluoro-1,3-phenylene)bis(methylene))bis(oxy))dibenzimidamide Dihydrochloride To a suspension of 4,4'-(((2-Fluoro-1,3-phenylene)bis (methylene))bis(oxy))dibenzonitrile (0.358 g, 1 mmol) in dry THF (15 mL) stirred over an ice bath was added lithium bis(trimethylsilyl)amide solution (1 M in THF, 6.0 mL), and the reaction was stirred at room temperature for 24 hours. The reaction mixture was cooled over an ice bath and then acidified by the slow addition of saturated ethanolic HCl solution until a white solid formed. The mixture was stirred for two hours and then all solvents were removed under vacuum. The crude residue was brought up in ether and filtered. The filter cake was brought up in ice water (10 mL) and basified with 2 M NaOH solution until a white precipitate formed. The solid was filtered, washed with water, and air dried. The isolated solid was suspended in anhydrous ethanol (15 mL) and saturated ethanolic HCl solution (5 mL) for 6 hours. The solvent was removed by distillation, and the resulting white solid was triturated with dry diethyl ether and filtered. The isolated white solid was dried at 80° C. under vacuum for 12 hours to provide 4,4'-(((2-fluoro-1,3-phenylene)bis(methylene))bis(oxy))dibenzimidamide Dihydrochloride (0.36 g, 71%) as a white solid. mp. 175-7° C.; $^1H$ NMR (DMSO-$d_6$): 9.22 (s, 4H), 8.95 (s, 4H), 7.87 (d, 4H, J=9.2 Hz), 7.64 (t, 2H, J=7.6 Hz), 7.31 (t, 1H, J=7.6 Hz), 7.29 (d, 4H, J=9.2 Hz), 5.31 (s, 4H); $^{13}C$ NMR (DMSO-$d_6$): 164.7, 162.4, 158.8 (d, $J_{C-F}$=248 Hz), 131.2 (d, $J_{C-F}$=3.7 Hz), 130.3, 124.6 (d, $J_{C-F}$=3.7 Hz), 123.4 (d, $J_{C-F}$=14.5 Hz), 119.9, 115.0, 64.1 (d, $J_{C-F}$=2.98 Hz), MS: HRMS-ESI-POS.: calc. for $C_{22}H_{22}FN_4O_2$ m/z 393.1721 ($M^+$+1), found m/z 393.1707; analysis calc. for $C_{22}H_{21}FN_4O_2$·2HCl·1.5$H_2O$. 0.2$C_4H_{10}O$ (ether): C, 54.07; H, 5.57; N, 11.07, Found: C, 54.38; H, 5.27; N, 10.89.

Synthesis 5. Synthesis of 4,4'-(((2-Fluoro-1,3-phenylene)bis(methylene))bis(sulfanediyl))dibenzimidamide dihydrochloride

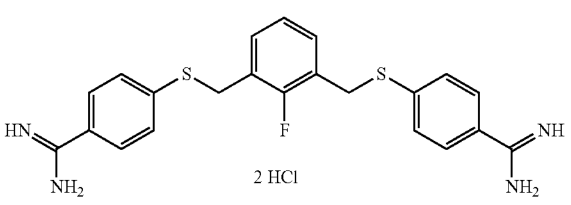 [SMILES: N=C(N)c1ccc(SCc2cccc(CSc3ccc(C(=N)N)cc3)c2F)cc1]

4,4'-(((2-Fluoro-1,3-phenylene)bis(methylene))bis(sulfanediyl))dibenzimidamide dihydrochloride can be synthesized by the same procedure by substituting 4-hydroxybenzonitrile with 4-mercaptobenzonitrile in Step 1.

Synthesis 6. Synthesis of 4,4'-(((2-fluoro-1,3-phenylene)bis(methylene))bis(methylazanediyl))dibenzimidamide dihydrochloride

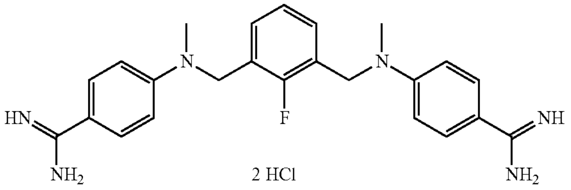 [SMILES: CN(Cc1cccc(CN(C)c2ccc(C(=N)N)cc2)c1F)c1ccc(C(=N)N)cc1]

4,4'-(((2-fluoro-1,3-phenylene)bis(methylene))bis(methylazanediyl))dibenzimidamide dihydrochloride can be synthesized by the same procedure by substituting 4-hydroxybenzonitrile with 4-(methylamino)benzonitrile in Step 1.

Synthesis 7. Synthesis of 2,2'-((((2-Fluoro-1,3-phenylene)bis(methylene))bis(oxy))bis(4,1-phenylene))bis(4,5-dihydro-1H-imidazole) Dihydrochloride (Compound A-3 Dihydrochloride)

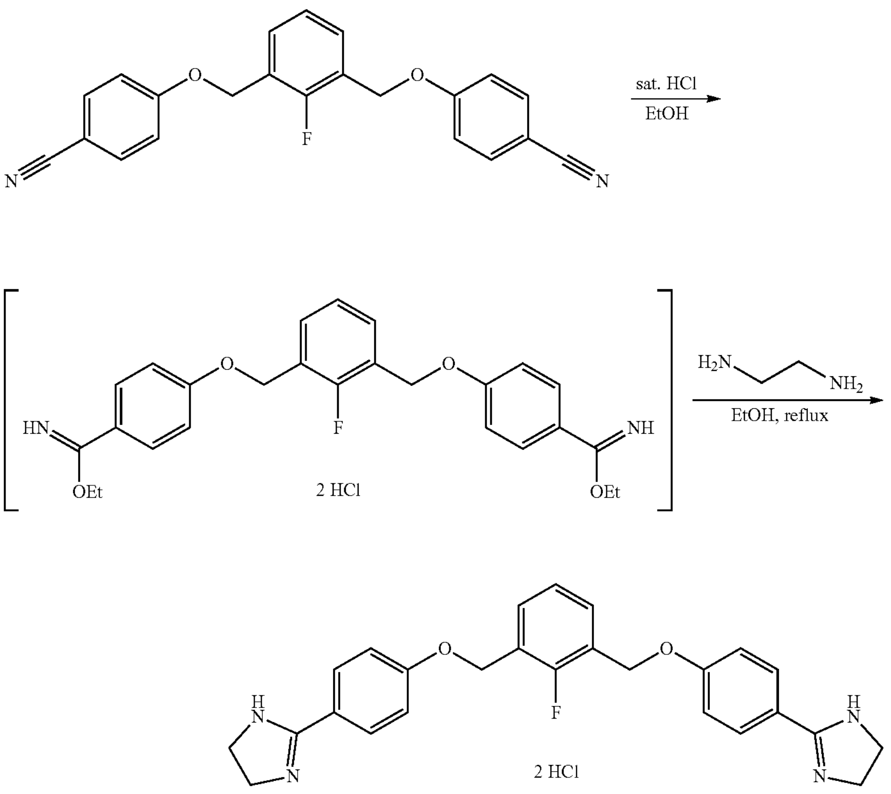

4,4'-(((2-Fluoro-1,3-phenylene)bis(methylene))bis(oxy))dibenzonitrile (0.358 g, 1 mmol) was added to anhydrous EtOH saturated with hydrogen chloride at 0° C. in a dry flask. The reaction mixture was sealed, slowly warmed to room temperature, and stirred until complete consumption of the starting material. The reaction mixture was diluted with anhydrous diethyl ether, and the resulting precipitate was filtered under nitrogen and dried under high vacuum to provide crude diethyl 4,4'-(((2-fluoro-1,3-phenylene)bis(methylene))bis(oxy))dibenzimidate dihydrochloride, which was used immediately without further purification.

The crude imidate was brought up in ethanol, and ethane-1,2-diamine was added. The reaction mixture was heated to reflux and stirred until complete consumption of the starting material. The reaction mixture was concentrated under reduced pressure. Diethyl ether was added, and the resulting precipitate was filtered. The solid was suspended in 10 mL of ice water and basified with 2 M NaOH. The resulting white precipitate was filtered, washed with water, and air dried. The solid was brought up in saturated ethanolic HCl solution and stirred for 6 hours. The ethanol was distilled, and the resulting precipitate was triturated with diethyl ether and filtered. The resulting solid was dried under vacuum at 80° C. for 12 hours to provide 2,2'-((((2-fluoro-1,3-phenylene)bis(methylene))bis(oxy))bis(4,1-phenylene))bis(4,5-dihydro-1H-imidazole) dihydrochloride (0.38 g, 70%) as a white solid. mp 250-252° C.; $^{1}H$ NMR (DMSO-$d_6$): 10.81 (s, 4H), 8.15 (d, 4H, J=7.6 Hz), 7.64 (t, 2H, J=7.2 Hz), 7.33-7.30 (m, 5H), 5.23 (s, 4H), 3.39 (s. 8H); $^{13}C$ NMR (DMSO-$d_6$): 163.8, 162.7, 154.6 (d, $J_{C-F}$=248 Hz), 130.0 (d, $J_{C-F}$=4.2 Hz), 124.4 (d, $J_{C-F}$=2.25 Hz), 123.2 (d, $J_{C-F}$=15.2 Hz), 115.2, 114.4, 64.5 (d, $J_{C-F}$=3.5 Hz), 43.9; MS: HRMS-ESI-POS.: calc. for $C_{26}H_{26}FN_4O_2$ m/z 445.2034 ($M^{+}$+1), found m/z 445.2047; analysis calc. for $C_{26}H_{25}FN_4O_2 \cdot 2HCl \cdot 1.75H_2O$: C, 56.88; H, 5.60; N, 10.20, Found: C, 58.99; H, 5.63; N, 10.41.

Synthesis 8. Synthesis of 2,2'-((((2-fluoro-1,3-phenylene)bis(methylene))bis(oxy))bis(4,1-phenylene))bis(1,4,5,6-tetrahydropyrimidine) dihydrochloride (Compound B-33 dihydrochloride)

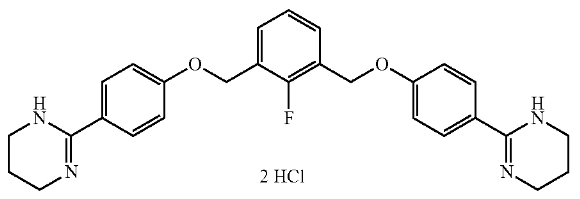 [SMILES: Fc1c(COc2ccc(C3=NCCCN3)cc2)cccc1COc1ccc(C2=NCCCN2)cc1]

2,2'-((((2-fluoro-1,3-phenylene)bis(methylene))bis(oxy))bis(4,1-phenylene))bis(1,4,5,6-tetrahydropyrimidine) dihydrochloride (Compound B-33 dihydrochloride) can be synthesized by the same procedure by substituting ethane-1,2-diamine with propane-1,3-diamine.

Synthesis 9. Synthesis of 4,4'-(((2-Fluoro-1,3-phenylene)bis(methylene))bis(oxy))bis(3-fluorobenzimidamide) Dihydrochloride (Compound A-1 Dihydrochloride)

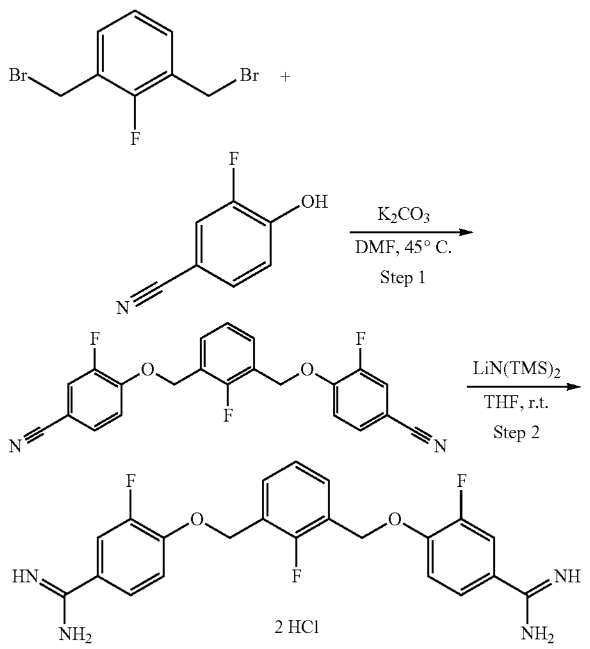

Step 1. Preparation of 4,4'-(((2-Fluoro-1,3-phenylene)bis(methylene))bis(oxy))bis(3-fluorobenzonitrile)

A mixture of 1,3-bis(bromomethyl)-2-fluorobenzene (1.4 g, 5 mmol), 3-fluoro-4-hydroxybenzonitrile (1.37 g, 10 mmol), and $K_2CO_3$ (2.07 g, 15 mmol) in DMF (10 mL) was heated at 45° C. for 4 hours (monitored by TLC, 4:1 hexanes/EtOAc). The reaction was then diluted with ice water (70 mL) and stirred for 30 minutes. The resulting white precipitate was filtered, washed with water, and dried in air. The isolated white precipitate was dissolved in dichloromethane, dried over anhydrous magnesium sulfate, filtered, and concentrated under reduced pressure. The residue was triturated with hexane, filtered, and dried under vacuum to yield 4,4'-(((2-fluoro-1,3-phenylene)bis(methylene))bis(oxy))bis(3-fluorobenzonitrile) (2.8 g. 71%) as a white solid. mp 185-7° C.; $^1H$ NMR (DMSO-$d_6$): 7.88 (d, 2H, J=8.4 Hz), 7.72 (d, 8.4 Hz), 7.64 (t, 2H, J=7.6 Hz), 7.54 (t, 2H, J=7.6 Hz), 7.33 (t, 1H, J=7.6 Hz), 7.23 (d, 4H, J=8.4 Hz), 5.37 (s, 4H); $^{13}C$ NMR (DMSO-$d_6$): 158.50 (d, $J_{C-F}$=250 Hz), 151.0 (d, $J_{C-F}$=248 Hz), 150.1 (d, $J_{C-F}$=11.0 Hz), 131.1 (d, $J_{C-F}$=4.4 Hz), 130.1 (d, $J_{C-F}$=3.75 Hz), 124.4 (d, $J_{C-F}$=4.28 Hz), 122.7 (d, $J_{C-F}$=15.4 Hz), 119.6 (d, $J_{C-F}$=21.4 Hz), 117.6 (d, $J_{C-F}$=3.4 Hz), 115.91 (d, $J_{C-F}$=2.25 Hz), 103.3 (d, $J_{C-F}$=8.73 Hz), 64.84 (d, $J_{C-F}$=4.21 Hz); MS: HRMS-ESI-POS.: calc. for $C_{22}H_{13}F_3N_2O_2Na$ m/z 417.0827 ($M^+$+Na), found m/z 417.0832.

Step 2. Preparation of 4,4'-(((2-Fluoro-1,3-phenylene)bis(methylene))bis(oxy))bis(3-fluorobenzimidamide) Dihydrochloride To a suspension of 4,4'-(((2-fluoro-1,3-phenylene)bis(methylene))bis(oxy))bis(3-fluorobenzonitrile) (0.394 g, 1 mmol) in dry THF (15 mL) stirred over an ice bath was added lithium bis(trimethylsilyl)amide solution (1 M in THF, 6.0 mL), and the reaction was stirred at room temperature for 24 hours. The reaction mixture was cooled over an ice bath and then acidified by the slow addition of saturated ethanolic HCl solution until a white solid formed. The mixture was stirred for two hours and then all solvents were removed under vacuum. The crude residue was brought up in ether and filtered. The filter cake was brought up in ice water (10 mL) and basified with 2 M NaOH solution until a white precipitate formed. The solid was filtered, washed with water, and air dried. The isolated solid was suspended in anhydrous ethanol (15 mL) and saturated ethanolic HCl solution (5 mL) for 6 hours. The solvent was removed by distillation, and the resulting white solid was triturated with dry diethyl ether and filtered. The isolated white solid was dried at 80° C. under vacuum for 12 hours to provide 4,4'-(((2-fluoro-1,3-phenylene)bis(methylene))bis(oxy))bis(3-fluorobenzimidamide) dihydrochloride (0.303 g, 71%) as a white solid. mp. 2255-7° C.; $^1H$ NMR (DMSO-$d_6$): 9.27 (br, 8H), 7.88 (dd, 2H, J=2.4 Hz, J=12.0 Hz), 7.78 (dd, 2H, J=1.6 Hz, J=8.4 Hz), 7.66 (t, 2H, J=7.6 Hz), 7.61 (d, 2H, J=8.8 Hz), 7.34 (d, 1H, J=7.6 Hz), 5.40 (s, 4H); $^{13}C$ NMR (DMSO-$d_6$): 164.3, 159.35 (d, $J_{C-F}$=249 Hz), 151.31 (d, $J_{C-F}$=245 Hz), 150.88 (d, $J_{C-F}$=11.0 Hz), 152.1 (d, $J_{C-F}$=4.5 Hz), 126.33 (d, $J_{C-F}$=3.0 Hz), 125.14 (d, $J_{C-F}$=3.0 Hz), 123.44 (d, $J_{C-F}$=14.0 Hz), 120.65 (d, $J_{C-F}$=7 Hz), 116.71 (d, $J_{C-F}$=21.0 Hz), 115.5, 65.42 (d, $J_{C-F}$=2.98 Hz), MS: HRMS-ESI-POS.: calc. for $C_{22}H_{20}F_3N_4O_2$ m/z 429.1533 ($M^+$+1), found m: 429.1536; analysis calc. for $C_{22}H_{19}F_3N_4O_2\cdot 2HCl\cdot 0.75H_2O$; C, 51.32; H, 4.40; N, 10.88, Found: C, 51.47; H, 4.39; N, 10.69.

Synthesis 10. Synthesis of 4,4'-(((2-Fluoro-1,3-phenylene)bis(methylene))bis(sulfanediyl))bis(3-fluorobenzimidamide) dihydrochloride (Compound B-1 dihydrochloride)

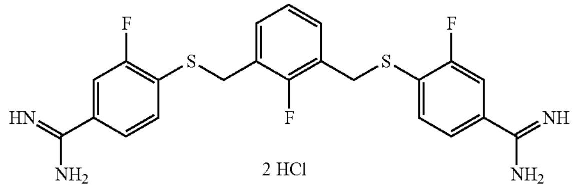 [SMILES: N=C(N)c1ccc(SCc2cccc(CSc3ccc(C(=N)N)cc3F)c2F)c(F)c1]

4,4'-(((2-Fluoro-1,3-phenylene)bis(methylene))bis(sulfanediyl))bis(3-fluorobenzimidamide) dihydrochloride (Compound B-1 dihydrochloride) can be synthesized by the same procedure by substituting 3-fluoro-4-hydroxybenzonitrile with 3-fluoro-4-mercaptobenzonitrile in Step 1.

Synthesis 11. Synthesis of 4,4'-(((2-Fluoro-1,3-phenylene)bis(methylene))bis(methylazanediyl))bis(3-fluorobenzimidamide) dihydrochloride (Compound B-2 dihydrochloride)

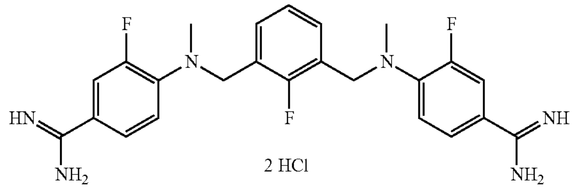 [SMILES: CN(Cc1cccc(CN(C)c2ccc(C(=N)N)cc2F)c1F)c1ccc(C(=N)N)cc1F]

4,4'-(((2-Fluoro-1,3-phenylene)bis(methylene))bis(methylazanediyl))bis(3-fluorobenzimidamide) dihydrochloride (Compound B-2 dihydrochloride) can be synthesized by the same procedure by substituting 3-fluoro-4-hydroxybenzonitrile with 3-fluoro-4-(methylamino)benzonitrile in Step 1.

Synthesis 12. Synthesis of 2,2'-((((2-Fluoro-1,3-phenylene)bis(methylene))bis(oxy))bis(3-fluoro-4,1-phenylene))bis(4,5-dihydro-1H-imidazole) Dihydrochloride (Compound A-4 Dihydrochloride)

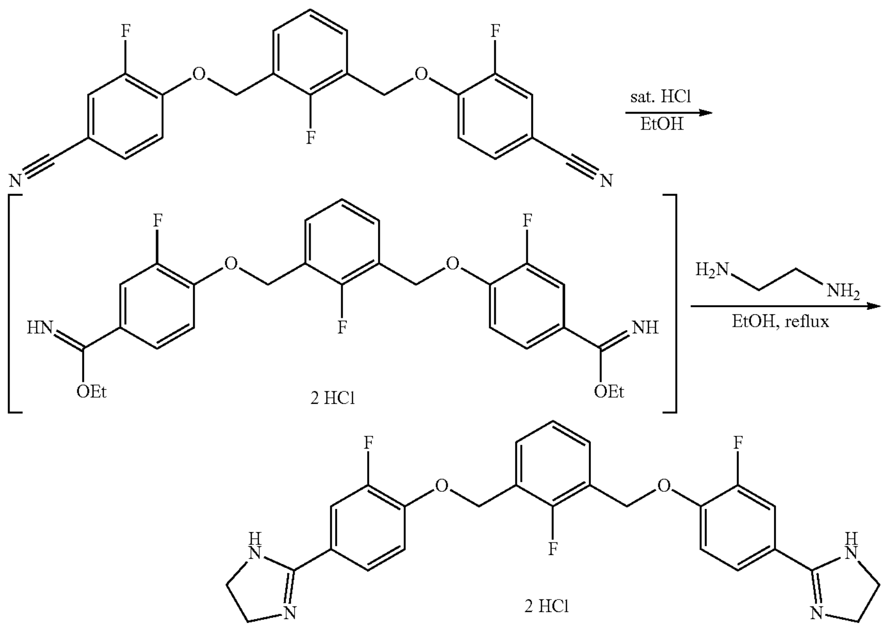

4,4'-(((2-Fluoro-1,3-phenylene)bis(methylene))bis(oxy))bis(3-fluorobenzonitrile) (0.394 g. 1 mmol) was added to anhydrous EtOH saturated with hydrogen chloride at 0° C. in a dry flask. The reaction mixture was sealed, slowly warmed to room temperature, and stirred until complete consumption of the starting material. The reaction mixture was diluted with anhydrous diethyl ether, and the resulting precipitate was filtered under nitrogen and dried under high vacuum to provide crude diethyl 4,4'-(((2-fluoro-1,3-phenylene)bis(methylene))bis(oxy))bis(3-fluorobenzimidate) dihydrochloride, which was used immediately without further purification.

The crude imidate was brought up in ethanol, and ethane-1,2-diamine was added. The reaction mixture was heated to reflux and stirred until complete consumption of the starting material. The reaction mixture was concentrated under reduced pressure. Diethyl ether was added, and the resulting precipitate was filtered. The solid was suspended in 10 mL of ice water and basified with 2 M NaOH. The resulting white precipitate was filtered, washed with water, and air dried. The solid was brought up in saturated ethanolic HCl solution and stirred for 6 hours. The ethanol was distilled, and the resulting precipitate was triturated with diethyl ether and filtered. The resulting solid was dried under vacuum at 80° C. for 12 hours to provide 2,2'-((((2-fluoro-1,3-phenylene)bis(methylene))bis(oxy))bis(3-fluoro-4,1-phenylene))bis(4,5-dihydro-1H-imidazole) dihydrochloride (0.4 g, 70%) as a white solid. mp. 218-20° C.; $^{1}H$ NMR (DMSO-$d_6$): 10.78 (br, 4H), 8.12 (d, 2H, J=12.0 Hz), 8.02 (d, 2H, J=9.2 Hz), 7.63 (t, 2H, J=7.6 Hz), 7.58 (t, 2H, J=8.4 Hz), 7.32 (t, 1H, J=7.6 Hz), 5.43 (s, 4H), 3.99 (s, 8H); $^{13}C$ NMR (DMSO-$d_6$): 164.2, 159.12 (d, $J_{C-F}$=250 Hz), 151.68 (d, $J_{C-F}$=247 Hz), 151.3 (d, $J_{C-F}$=10.5 Hz), 131.74 (d, $J_{C-F}$=4.5 Hz), 126.6 (d, $J_{C-F}$=3.3 Hz), 124.91 (d, $J_{C-F}$=4.5 Hz), 123.18 (d, $J_{C-F}$=14.5 Hz), 116.61 (d, $J_{C-F}$=21.0 Hz), 116.3, 115.18 (d, $J_{C-F}$=7.5 Hz), 65.73 (d, $J_{C-F}$=4.0 Hz), MS: HRMS-ESI-POS.: calc. for $C_{26}H_{24}F_3N_4O_2$ m/z 481.1846 ($M^{+}$+1), found m/z 481.1857; analysis calc. for $C_{26}H_{23}F_3N_4O_2$·2HCl·1.1$H_2O$; C, 54.47; H, 4.78; N, 9.77, Found: C, 54.10; H, 4.76; N, 9.65.

Synthesis 13. Synthesis of 2,2'-((((2-Fluoro-1,3-phenylene)bis(methylene))bis(oxy))bis(3-fluoro-4,1-phenylene))bis(1,4,5,6-tetrahydropyrimidine) dihydrochloride (Compound B-11 dihydrochloride)

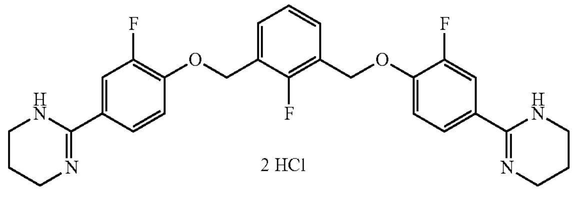 [SMILES: Fc1cc(C2=NCCCN2)ccc1OCc1cccc(COc2ccc(C3=NCCCN3)cc2F)c1F]

2,2'-((((2-Fluoro-1,3-phenylene)bis(methylene))bis(oxy))bis(3-fluoro-4,1-phenylene))bis(1,4,5,6-tetrahydropyrimidine) dihydrochloride (Compound B-11 dihydrochloride) can be synthesized by the same procedure by substituting ethane-1,2-diamine with propane-1,3-diamine.

Synthesis 14. Synthesis of 2,2'-((((2-Fluoro-1,3-phenylene)bis(methylene))bis(oxy))bis(3-methoxy-4,1-phenylene))bis(4,5-dihydro-1H-imidazole) Dihydrochloride (Compound A-5 Dihydrochloride)

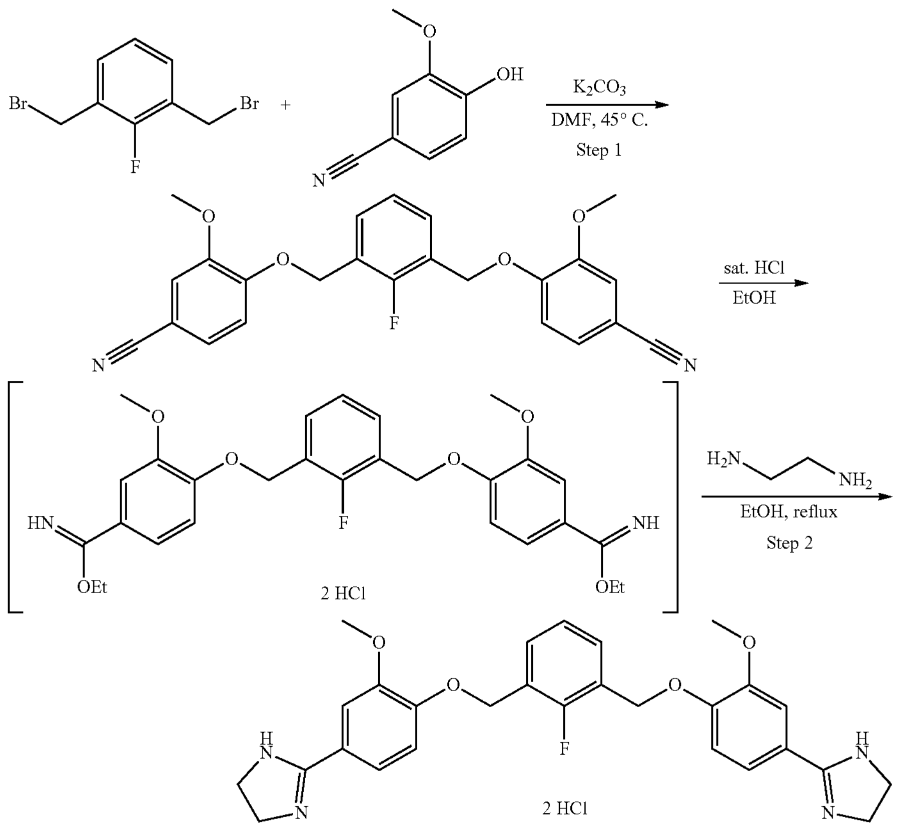

Step 1. Preparation of 4,4'-(((2-Fluoro-1,3-phenylene)bis(methylene))bis(oxy))bis(3-methoxybenzonitrile)

A mixture of 1,3-bis(bromomethyl)-2-fluorobenzene (1.4 g, 5 mmol), 4-hydroxy-3-methoxybenzonitrile (1.37 g, 10 mmol), and $K_2CO_3$ (2.07 g, 15 mmol) in DMF (10 mL) was heated at 45° C. for 4 hours (monitored by TLC, 4:1 hexanes/EtOAc). The reaction was then diluted with ice water (70 mL) and stirred for 30 minutes. The resulting white precipitate was filtered, washed with water, and dried in air. The isolated white precipitate was dissolved in dichloromethane, dried over anhydrous magnesium sulfate, filtered, and concentrated under reduced pressure. The residue was triturated with hexane, filtered, and dried under vacuum to yield 4,4'-(((2-fluoro-1,3-phenylene)bis(methylene))bis(oxy))bis(3-methoxybenzonitrile) (2.8 g, 71%) as a white solid. mp 187-9° C.; $^1$H NMR (DMSO-$d_6$): 7.59 (t, 2H, J=7.2 Hz), 7.45-7.41 (m, 4H), 731-7.27 (m 3H), 5.25 (s, 4H), 3.82 (s, 6H); $^{13}$C NMR (DMSO-$d_6$): 158.8 (d, $J_{C-F}$=251 Hz), 151.5, 149.1, 131.4 (d, $J_{C-F}$=3.8 Hz), 126.3, 124.5 (d, $J_{C-F}$=4.0 Hz), 123.3 (d, $J_{C-F}$=14.8 Hz), 119.2, 114.7, 113.4, 110.1, 64.2 (d, $J_{C-F}$=4.5 Hz), 55.9; MS: HRMS-ESI-POS.: calc. for $C_{24}H_{19}FN_2O_4Na$ m/z 441.1226 ($M^+$+Na), found m/z 441.1237.

Step 2. Preparation of 2,2'-((((2-Fluoro-1,3-phenylene)bis(methylene))bis(oxy))bis(3-methoxy-4,1-phenylene))bis(4,5-dihydro-1H-imidazole) Dihydrochloride 4,4'-(((2-fluoro-1,3-phenylene)bis(methylene))bis(oxy))bis(3-methoxybenzonitrile) (0.418 g, 1 mmol) was added to anhydrous EtOH saturated with hydrogen chloride at 0° C. in a dry flask. The reaction mixture was sealed, slowly warmed to room temperature, and stirred until complete consumption of the starting material. The reaction mixture was diluted with anhydrous diethyl ether, and the resulting precipitate was filtered under nitrogen and dried under high vacuum to provide crude diethyl 4,4'-(((2-fluoro-1,3-phenylene)bis(methylene))bis(oxy))bis(3-methoxybenzimidate) dihydrochloride, which was used immediately without further purification.

The crude imidate was brought up in ethanol, and ethane-1,2-diamine was added. The reaction mixture was heated to reflux and stirred until complete consumption of the starting material. The reaction mixture was concentrated under reduced pressure. Diethyl ether was added, and the resulting precipitate was filtered. The solid was suspended in 10 mL of ice water and basified with 2 M NaOH. The resulting white precipitate was filtered, washed with water, and air dried. The solid was brought up in saturated ethanolic HCl solution and stirred for 6 hours. The ethanol was distilled, and the resulting precipitate was triturated with diethyl ether and filtered. The resulting solid was dried under vacuum at 80° C. for 12 hours to provide 2,2'-((((2-fluoro-1,3-phenylene)bis(methylene))bis(oxy))bis(3-methoxy-4,1-phenylene))bis(4,5-dihydro-1H-imidazole) dihydrochloride (0.43 g, 70%) as a white solid. mp. 237-9° C.; $^1$H NMR (DMSO-$d_6$): 10.79 (s, 4H), 7.84 (d, 2H, J=2.0 Hz), 7.77 (dd, 2H, J=2.0 Hz, J=8.4 Hz), 7.62 (t, 2H, J=7.6 Hz), 7.40 (d, J=8.4 Hz), 7.32 (t, 1H, J=7.6 Hz), 5.29 (s, 4H), 3.97 (s, 8H), 3.86 (s, 6H); $^{13}$C NMR (DMSO-$d_6$): 164.1, 159.01 (d, $J_{C-F}$=250 Hz), 152.4, 148.9, 131.5 (d, $J_{C-F}$=3.0 Hz), 124.9 (d, $J_{C-F}$=4.0 Hz), 123.0 (d, $J_{C-F}$=15.0 Hz), 122.8, 114.4, 112.8, 112.1, 64.4 (d, $J_{C-F}$=3.5 Hz), 56.2, 44.1; MS: HRMS-ESI-POS.: calc. for $C_{28}H_{30}FN_4O_4$ m/z 505.2246 (M$^+$+1), found m/z 505.2248; analysis calc. for $C_{28}H_{29}F_3N_4O_4$·2HCl·1.85$H_2O$; C, 54.83; H, 5.83; N, 8.90, Found: C, 55.01; H, 5.67; N, 9.02.

Synthesis 15. Synthesis of 2,2'-((((2-fluoro-1,3-phenylene)bis(methylene))bis(oxy))bis(3-methoxy-4,1-phenylene))bis(1,4,5,6-tetrahydropyrimidine) dihydrochloride (Compound B-53 dihydrochloride)

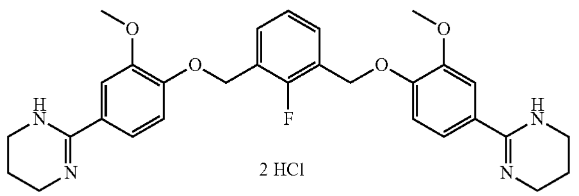 [SMILES: COc1cc(C2=NCCCN2)ccc1OCc1cccc(COc2ccc(C3=NCCCN3)cc2OC)c1F]

2,2'-((((2-fluoro-1,3-phenylene)bis(methylene))bis(oxy)) bis(3-methoxy-4,1-phenylene))bis(1,4,5,6-tetrahydropyrimidine) dihydrochloride (Compound B-53 dihydrochloride) can be synthesized by the same procedure by substituting ethane-1,2-diamine with propane-1,3-diamine in Step 2.

Synthesis 16. Synthesis of 4,4'-(((5-Methyl-1,3-phenylene)bis(methylene))bis(oxy))bis(3-methoxybenzimidamide) Dihydrochloride (Compound A-6 Dihydrochloride)

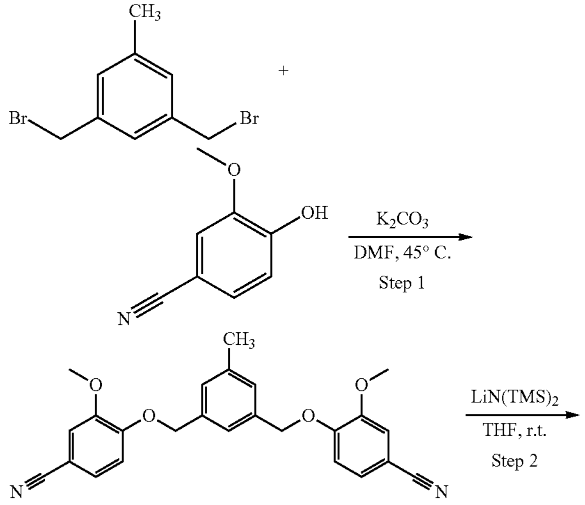

-continued

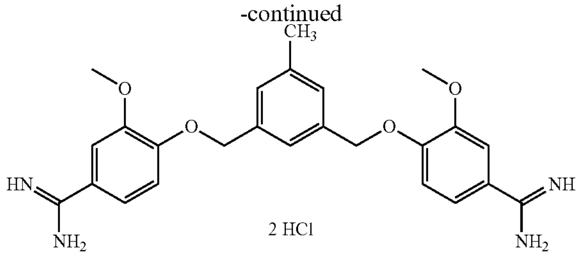

Step 1. Preparation of 4,4'-(((5-Methyl-1,3-phenylene)bis(methylene))bis(oxy))bis(3-methoxybenzonitrile)

A mixture of 1,3-bis(bromomethyl)-5-methylbenzene (1.4 g, 5 mmol), 4-hydroxy-3-methoxybenzonitrile (1.37 g, 10 mmol), and $K_2CO_3$ (2.07 g, 15 mmol) in DMF (10 mL) was heated at 45° C. for 4 hours (monitored by TLC, 4:1 hexanes/EtOAc). The reaction was then diluted with ice water (70 mL) and stirred for 30 minutes. The resulting white precipitate was filtered, washed with water, and dried in air. The isolated white precipitate was dissolved in dichloromethane, dried over anhydrous magnesium sulfate, filtered, and concentrated under reduced pressure. The residue was triturated with hexane, filtered, and dried under vacuum to yield 4,4'-(((5-methyl-1,3-phenylene)bis(methylene))bis(oxy))bis(3-methoxybenzonitrile) (1.57 g, 76%) as a white solid. $^1$H NMR (DMSO-$d_6$): 7.40 (m, 4H), 7.30 (s, 1H), 7.25 (s, 2H), 7.19 (d, J=8.6 Hz, 2H), 5.15 (s, 4H), 3.81 (s, 6H), 2.34 (s, 3H). $^{13}$C NMR (DMSO-$d_6$): 152.2, 149.6, 138.6, 136.9, 128.9, 126.7, 125.1, 119.8, 115.2, 113.9, 103.4, 70.3, 56.4, 21.4; MS: HRMS-ESI-POS.: calc. for $C_{25}H_{35}N_2O_4$ m/z 415.1652 (M$^+$+1), found m/z 415.1643.

Step 2. Preparation of 4,4'-(((5-Methyl-1,3-phenylene)bis(methylene))bis(oxy))bis(3-methoxybenzimidamide) Dihydrochloride To a suspension of 4,4'-(((5-methyl-1,3-phenylene)bis(methylene))bis(oxy))bis(3-methoxybenzonitrile) (0.41 g, 1 mmol) in dry THF (15 mL) stirred over an ice bath was added lithium bis(trimethylsilyl)amide solution (1 M in THF, 6.0 mL), and the reaction was stirred at room temperature for 24 hours. The reaction mixture was cooled over an ice bath and then acidified by the slow addition of saturated ethanolic HCl solution until a white solid formed. The mixture was stirred for two hours and then all solvents were removed under vacuum. The crude residue was brought up in ether and filtered. The filter cake was brought up in ice water (10 mL) and basified with 2 M NaOH solution until a white precipitate formed. The solid was filtered, washed with water, and air dried. The isolated solid was suspended in anhydrous ethanol (15 mL) and saturated ethanolic HCl solution (5 mL) for 6 hours. The solvent was removed by distillation, and the resulting white solid was triturated with dry diethyl ether and filtered. The isolated white solid was dried at 80° C. under vacuum for 12 hours to provide 4,4'-(((5-methyl-1,3-phenylene)bis(methylene))bis(oxy))bis(3-methoxybenzimidamide) dihydrochloride (0.39 g, 76%) as a white solid. $^1$H NMR (DMSO-$d_6$): 9.28 (s, 4H), 8.98 (s, 4H), 7.49 (dd, J=4.3, 2.3 Hz, 4H), 7.34 (s, 1H), 7.26 (m, 4H), 5.19 (s, 4H), 3.86 (s, 6H), 2.35 (s, 6H): $^{13}$C NMR (DMSO-$d_6$) 165.1, 152.7, 149.2, 138.5, 137.1, 128.9, 125.04, 122.3, 119.9, 113.2, 112.0, 70.4, 56.4, 21.4;

MS: HRMS-ESI-POS.: calc. for $C_{25}H_{30}N_4O_4$ m/z 225.1128 ($M/2^{+}+2$), found m/z 225.1119; analysis calc. for C25H28N4O4·2HCl·1.8H2O; C, 54.21; H, 6.11; N, 10.11, Found: C, 54.05; H, 5.98; N, 9.70.

Synthesis 17. Synthesis of 4,4'-(((5-Methyl-1,3-phenylene)bis(methylene))bis(sulfanediyl))bis(3-methoxybenzimidamide) dihydrochloride (Compound B-63 dihydrochloride)

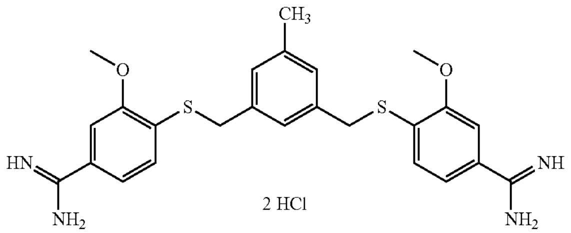 [SMILES: COc1cc(C(=N)N)ccc1SCc1cc(C)cc(CSc2ccc(C(=N)N)cc2OC)c1]

4,4'-(((5-Methyl-1,3-phenylene)bis(methylene))bis(sulfanediyl))bis(3-methoxybenzimidamide) dihydrochloride (Compound B-63 dihydrochloride) can be prepared by the same procedure by substituting 4-hydroxy-3-methoxybenzonitrile with 4-mercapto-3-methoxybenzonitrile in Step 1.

Synthesis 18. Synthesis of 4,4'-(((5-methyl-1,3-phenylene)bis(methylene))bis(methylazanediyl))bis(3-methoxybenzimidamide) dihydrochloride (Compound B-64 dihydrochloride)

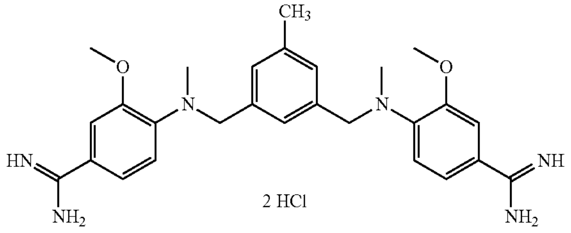 [SMILES: COc1cc(C(=N)N)ccc1N(C)Cc1cc(C)cc(CN(C)c2ccc(C(=N)N)cc2OC)c1]

4,4'-(((5-methyl-1,3-phenylene)bis(methylene))bis(methylazanediyl))bis(3-methoxybenzimidamide) dihydrochloride (Compound B-64 dihydrochloride) can be prepared by the same procedure by substituting 4-hydroxy-3-methoxybenzonitrile with 3-methoxy-4-(methylamino)benzonitrile in Step 1.

Synthesis 19. Synthesis of 4,4'-(((2-Fluoro-1,3-phenylene)bis(methylene))bis(oxy))bis(3-methoxybenzimidamide) Dihydrochloride (Compound A-7 Dihydrochloride)

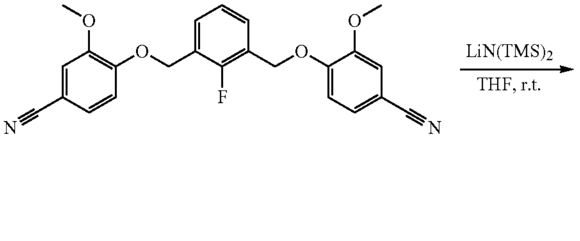

-continued

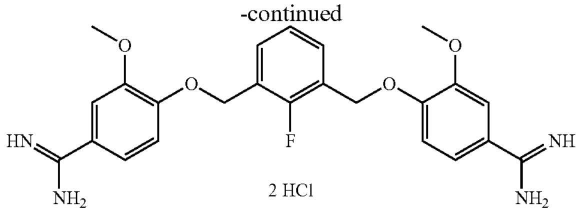

Synthesis of 1, 3-Bis {(4-cyano-2-methoxy)-phenoxy methyl}-2-fluorobenzene: Reaction of 1,3-bis(bromomethyl)-2-fluorobenzenel (1.4 g, 5 mmol) and 4-hydroxy-2-methoxybenzonitrile (1.37 g, 10 mmol) following Step 1 of General Route 7 yielded 1, 3-bis {(4-cyano-2-methoxy)-phenoxy methyl}-2-fluorobenzene as white solid (2.8 g, 71%); mp 185-7° C.; 1H NMR (DMSO-d6): 7.59 (t, 2H, J=7.2 Hz), 7.45-7.41 (m, 4H), 731-7.27 (m 3H), 5.25 (s, 4H), 3.82 (s, 6H); 13C NMR (DMSO-d6): 159.2 (d, JC-F=247 Hz), 152.01, 149.59, 131.91 (d, JC-F=3 Hz) 126.74, 125.02 (d, JC-F=4.0 Hz), 123.77 (d, JC-F=14 Hz), 119.64, 115.22, 113.88, 103.69, 64.76, 56.41; MS: HRMS-ESI-POS.: calc. for $C_{24}H_{19}FN_2O_4Na$ m/z 441.1226 ($M^{+}+Na$), found m/z 441.1237.

Synthesis of 4,4'-(((2-fluoro-1,3-phenylene)bis(methylene))bis(oxy))bis(3-methoxybenzimidamide) dihydrochloride (Compound A-7 dihydrochloride): To a suspension of 4,4'-(((2-fluoro-1,3-phenylene)bis(methylene))bis(oxy))bis (3-methoxybenzonitrile) (0.41 g, 1 mmol) in dry THF (15 mL) stirred over an ice bath was added lithium bis(trimethylsilyl)amide solution (1 M in THF, 6.0 mL), and the reaction was stirred at room temperature for 24 hours. The reaction mixture was cooled over an ice bath and then acidified by the slow addition of saturated ethanolic HCl solution until a white solid formed. The mixture was stirred for two hours and then all solvents were removed under vacuum. The crude residue was brought up in ether and filtered. The filter cake was brought up in ice water (10 mL) and basified with 2 M NaOH solution until a white precipitate formed. The solid was filtered, washed with water, and air dried. The isolated solid was suspended in anhydrous ethanol (15 mL) and saturated ethanolic HCl solution (5 mL) for 6 hours. The solvent was removed by distillation, and the resulting white solid was triturated with dry diethyl ether and filtered. The isolated white solid was dried at 80° C. under vacuum for 12 hours to provide 4,4'-(((2-fluoro-1,3-phenylene)bis(methylene))bis(oxy))bis(3-methoxybenzimidamide) dihydrochloride (0.37 g, 72%) as a white solid. $^{1}H$ NMR (DMSO-$d_6$): 9.32 (s, 4H), 9.04 (s, 4H), 7.61 (t, 2H, J=7.2 Hz), 7.53 (m, 4H), 7.39-7.28 (m, 4H), 5.27 (s, 4H), 3.863 (s, 6H); $^{13}C$ NMR (DMSO-$d_6$): 165.3, 159.3 (d, $J_{C-F}$=250 Hz), 152.6, 149.2, 131.9 (d, $J_{C-F}$=2.9 Hz), 125.0 (d, $J_{C-F}$=3.6 Hz), 123.9 (d, $J_{C-F}$=14.7 Hz), 122.2, 120.3, 113.2, 112.0, 64.8 (d, $J_{C-F}$=3.2 Hz), 56.4; MS: HRMS-ESI-POS.: calc. for $C_{24}H_{27}FN_4O_4$ m/z 237.1003 ($M/2^{+}+2$), found m/z 237.0995; analysis calc. for C24H25FN4O4·2HCl·1.8H2O; C, 51.67; H, 5.53; N, 10.04; Found: C, 51.10; H, 5.14; N, 8.86.

Synthesis 20. Synthesis of 4,4'-(((5-(tert-Butyl)-1,3-phenylene)bis(methylene))bis(oxy))dibenzimidamide Dihydrochloride (Compound C-4 Dihydrochloride)

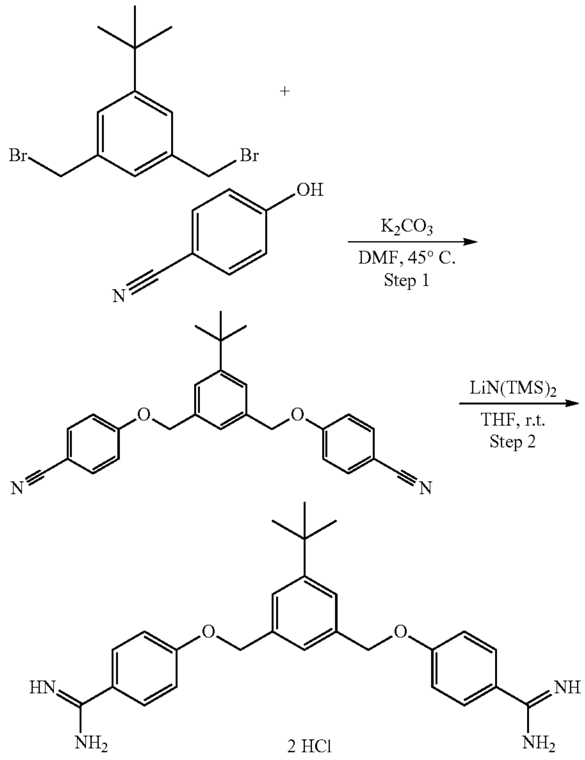

Synthesis of 1,3-bis(bromomethyl)-5-(tert-butyl)benzene: 5-tert-Butylisophthalic acid (4 g, 18 mmol) in THF (100 ml) was added dropwise under ice-bath conditions in a solution of lithium aluminium hydride (1.5 g, 38 mmol) in THF (100 ml). The reaction was stirred for 1 h at 0° C. and then heated at 60° C. for 24 h. The reaction was monitored by TLC. Upon completion, the reaction mixture was cooled to 0° C. and quenched with methanol and water. The quenched reaction was filtered through Celite and washed with EtOAc (100 mL). The solvent was removed under reduced pressure and was extracted with EtOAc (3×100 mL), dried over $MgSO_4$ and concentrated to afford the required diol (5-(tert-butyl)-1,3-phenylene)dimethanol (3.2 g. 94%); 1H NMR (CDCl3): 7.32 (d, 2H, J=1.3 Hz), 7.19 (s, 1H), 4.69 (s, 4H), 1.33 (s, 6H); 13C NMR (CDCl3) 152.04, 140.93, 123.45, 122.94, 65.60, 34.79, 31.39; MS: HRMS-ESI-POS.: calc. for C12H17O m/z 177.1274 (M+−H2O), found m/z 177.1274.

$PBr_3$ (2.5 mL, 26 mmol) was added dropwise to a solution of diol (5-(tert-butyl)-1,3-phenylene)dimethanol (2.3 g, 11.8 mmol) in DCM maintained at 0° C. The reaction mixture was stirred at room temperature for 4 h and then quenched with ice water. The solution was extracted with $CH_2Cl_2$ (3×100 mL), dried over $MgSO_4$ and concentrated to afford the required dibromo compound as a white solid (3.4 g, 90%); 1H NMR (CDCl3): 7.36 (d, J=1.4 Hz, 2H), 7.28 (s, 1H), 4.51 (s, 4H), 1.36 (s, 9H); 13C NMR (CDCl3): 152.06, 138.02, 126.88, 126.29, 34.82, 33.49, 31.25.

Step 1. Preparation of 4,4'-(((5-(tert-Butyl)-1,3-phenylene)bis(methylene))bis(oxy))dibenzonitrile A mixture of 1,3-bis(bromomethyl)-5-(tert-butyl)benzene (1.6 g, 5 mmol), 4-hydroxybenzonitrile (1.19 g, 10 mmol), and $K_2CO_3$ (2.07 g, 15 mmol) in DMF (10 mL) was heated at 45° C. for 4 hours (monitored by TLC, 4:1 hexanes/EtOAc). The reaction was then diluted with ice water (70 mL) and stirred for 30 minutes. The resulting white precipitate was filtered, washed with water, and dried in air. The isolated white precipitate was dissolved in dichloromethane, dried over anhydrous magnesium sulfate, filtered, and concentrated under reduced pressure. The residue was triturated with hexane, filtered, and dried under vacuum to yield 4,4'-(((5-(tert-butyl)-1,3-phenylene)bis(methylene))bis(oxy))dibenzonitrile (1.54 g, 78%) as a white solid. $^1$H NMR (DMSO-$d_6$): 7.81-7.77 (m, 4H), 7.48 (d, J=1.1 Hz, 2H), 7.36 (s, 1H), 7.22-7.18 (m, 4H), 5.21 (2, 4H), 1.29 (s, 9H); $^{13}$C NMR ($CDCl_3$) 162.0, 152.5, 136.0, 134.0, 124.8, 124.0, 119.2, 115.6, 104.3, 70.4, 34.9, 31.3; MS: HRMS-ESI-POS.: calc. for $C_{26}H_{25}N_2O_2$ m/z 397.1911 ($M^+$+1), found m/z 397.1912.

Step 2. Preparation of 4,4'-(((5-(tert-Butyl)-1,3-phenylene)bis(methylene))bis(oxy))dibenzimidamide Dihydrochloride To a suspension of 4,4'-(((5-(tert-butyl)-1,3-phenylene)bis(methylene))bis(oxy))dibenzonitrile (0.370 g, 1 mmol) in dry THF (15 mL) stirred over an ice bath was added lithium bis(trimethylsilyl)amide solution (1 M in THE, 6.0 mL), and the reaction was stirred at room temperature for 24 hours. The reaction mixture was cooled over an ice bath and then acidified by the slow addition of saturated ethanolic HCl solution until a white solid formed. The mixture was stirred for two hours and then all solvents were removed under vacuum. The crude residue was brought up in ether and filtered. The filter cake was brought up in ice water (10 mL) and basified with 2 M NaOH solution until a white precipitate formed. The solid was filtered, washed with water, and air dried. The isolated solid was suspended in anhydrous ethanol (15 mL) and saturated ethanolic HCl solution (5 mL) for 6 hours. The solvent was removed by distillation, and the resulting white solid was triturated with dry diethyl ether and filtered. The isolated white solid was dried at 80° C. under vacuum for 12 hours to provide 4,4'-(((5-(tert-butyl)-1,3-phenylene)bis(methylene))bis(oxy))dibenzimidamide dihydrochloride (0.35 g, 70%) as a white solid. $^1$H NMR (DMSO-$d_6$): 9.43 (s, 4H), 9.21 (s, 2H), 7.94 (d, J=8.4 Hz, 4H), 7.49 (s, 2H), 7.39 (s, 1H), 7.23 (d, J=8.4 Hz, 4H), 5.23 (s, 4H), 1.29 (s, 9H); $^{13}$C NMR (DMSO-$d_6$): 165.3, 163.1, 152.1, 136.5, 130.5, 125.2, 125.1, 119.9, 115.7, 70.3, 34.8, 31.4; MS: HRMS-ESI-POS.: calc. for $C_{26}H_{31}N_4O_2$ m/z 431.2442 ($M^+$+1), found m/z 431.2425; analysis calc. for $C_{26}H_{30}N_4O_2$·2HCl·1.5$H_2O$·0.8CH; OH; C, 57.88; H, 6.92; N, 10.07, Found: C, 57.83; H, 6.50; N, 8.86.

Synthesis 21. Synthesis of 4,4'-(((5-(tert-Butyl)-1,3-phenylene)bis(methylene))bis(sulfanediyl))dibenzimidamide dihydrochloride

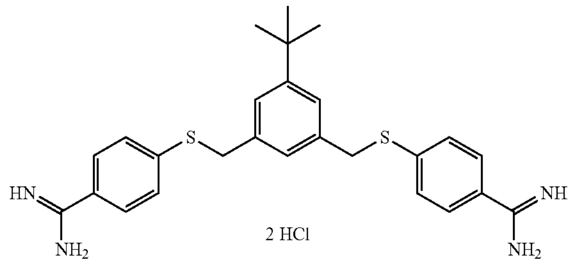

4,4'-(((5-(tert-Butyl)-1,3-phenylene)bis(methylene))bis(sulfanediyl))dibenzimidamide dihydrochloride can be prepared by the same procedure by substituting 4-hydroxybenzonitrile with 4-mercaptobenzonitrile in Step 1.

Synthesis 22. Synthesis of 4,4'-(((5-(tert-Butyl)-1,3-phenylene)bis(methylene))bis(methylazanediyl)) dibenzimidamide dihydrochloride

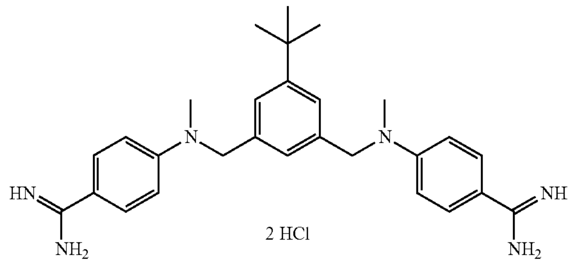 [SMILES: CN(Cc1cc(CN(C)c2ccc(C(=N)N)cc2)cc(C(C)(C)C)c1)c1ccc(C(=N)N)cc1]

4,4'-(((5-(tert-Butyl)-1,3-phenylene)bis(methylene))bis(methylazanediyl)) dibenzimidamide dihydrochloride can be prepared by the same procedure by substituting 4-hydroxybenzonitrile with 4-(methylamino)benzonitrile in Step 1.

Synthesis 23. Synthesis of 4,4'-((5-Methyl-1,3-phenylene)bis(ethane-2,1-diyl))dibenzimidamide Dihydrochloride (Compound A-8 Dihydrochloride)

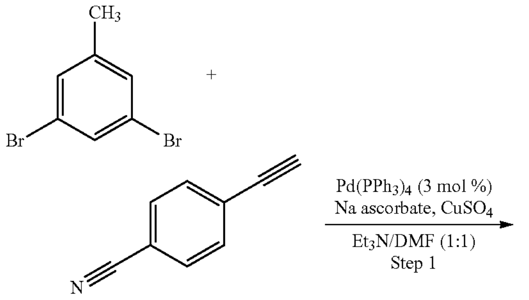

-continued

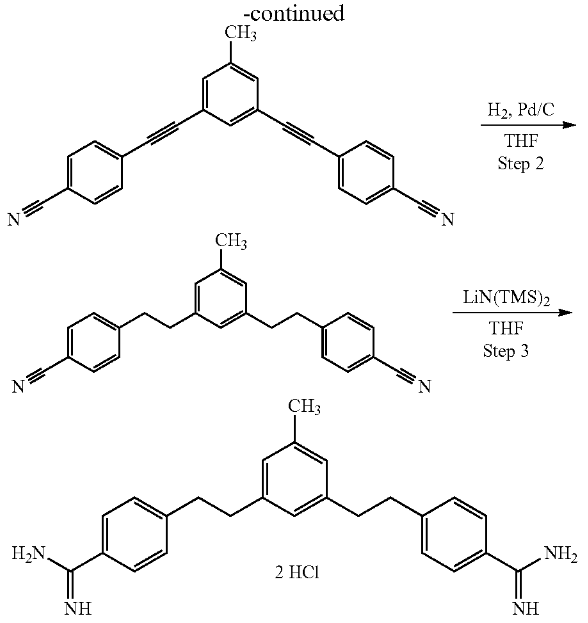

Step 1. Preparation of 4,4'-((5-Methyl-1,3-phenylene)bis(ethyne-2,1-diyl))dibenzonitrile To a solution of 1,3-dibromo-5-methylbenzene (0.98 g, 3.9 mmol) in DMF/$Et_3N$ (1:1, 6 mL) was added $Pd(PPh_3)_4$ (3 mol %) and 4-ethynylbenzonitrile (1 g, 7.8 mmol), and the mixture was stirred for 5 minutes. Sodium ascorbate (6 mol % in DMF) and $CuSO_4$ (1 mol % in DMF) were the added, and the reaction was stirred at 80° C. for 4 hours. The reaction was diluted with EtOAc and washed with saturated $NH_4Cl$ solution and brine. The organic layer was dried over anhydrous $Na_2SO_4$, filtered, and concentrated under reduced pressure. The crude residue was purified by column chromatography on silica gel (5:1 hexanes/EtOAc) to provide 4,4'-((5-methyl-1,3-phenylene)bis(ethyne-2,1-diyl))dibenzonitrile (0.67 g, 50%) as a white solid. $^1H$ NMR ($CDCl_3$) 7.70-7.60 (m, 8H), 7.57 (s, 1H), 7.40 (s, 2H), 2.41 (s, 3H); $^{13}C$ NMR ($CDCl_3$) $^{13}C$ NMR ($CDCl_3$) δ 138.78, 132.99, 132.13, 132.09, 127.91, 122.64, 118.46, 111.76, 92.75, 88.16, 21.07.

Step 2. Preparation of 4,4'-((5-Methyl-1,3-phenylene)bis(ethane-2,1-diyl))dibenzonitrile To a suspension of 10% Pd/C in THF (30 mL) under argon was added 4,4'-((5-methyl-1,3-phenylene)bis(ethyne-2,1-diyl))dibenzonitrile (0.5 g. 1.46 mmol). The argon was exchanged for $H_2$ gas, and the reaction mixture was stirred overnight. The reaction mixture was diluted with DCM and filtered through celite. The organic phase was washed with water, dried over anhydrous $Na_2SO_4$, filtered, and concentrated under reduced pressure to provide 4,4'-((5-methyl-1,3-phenylene)bis(ethane-2,1-diyl))dibenzonitrile (0.45 g, 88%) as a pale yellow solid. $^1H$ NMR ($CDCl_3$) 7.59 (d, 4H, J=8.3 Hz), 7.27 (d, 4H, J=8.2 Hz), 6.85 (s, 2H), 6.71 (s, 1H), 3.00-2.92 (m, 4H), 2.90-2.83 (m, 4H), 2.32 (s, 3H); $^{13}C$ NMR ($CDCl_3$) 147.34, 140.83, 138.28, 132.16, 129.31, 127.18, 125.62, 119.08, 109.86, 38.02, 37.14, 21.33.

Step 3. Preparation of 4,4'-((5-Methyl-1,3-phenylene)bis(ethane-2,1-diyl))dibenzimidamide Dihydrochloride To a suspension of 44,4'-((5-methyl-1,3-phenylene)bis(ethane-2,1-diyl))dibenzonitrile (0.35 g, 1 mmol) in dry THF (15 mL) stirred over an ice bath was added lithium bis(trimethylsilyl)amide solution (1 M in THF, 6.0 mL), and the reaction was stirred at room temperature for 24 hours. The reaction mixture was cooled over an ice bath and then acidified by the slow addition of saturated ethanolic HCl solution until a white solid formed. The mixture was stirred for two hours and then all solvents were removed under vacuum. The crude residue was brought up in ether and filtered. The filter cake was brought up in ice water (10 mL) and basified with 2 M NaOH solution until a white precipitate formed. The solid was filtered, washed with water, and air dried. The isolated solid was suspended in anhydrous ethanol (15 mL) and saturated ethanolic HCl solution (5 mL) for 6 hours. The solvent was removed by distillation, and the resulting white solid was triturated with dry diethyl ether and filtered. The isolated white solid was dried at 80° C. under vacuum for 12 hours to provide 4,4'-((5-methyl-1,3-phenylene)bis(ethane-2,1-diyl))dibenzimidamide (0.32 g, 70%) as a white solid. $^1$H NMR (DMSO-$d_6$) 9.34 (s, 4H), 9.12 (s, 4H), 7.78 (d, 4H, J=8.3 Hz), 7.49 (d, 4H, J=8.3 Hz), 6.94 (s, 1H), 6.90 (s, 2H), 2.96 (dd, 4H, J=9.6, 6.1 Hz), 2.83 (dd, 4H, J=9.7, 6.1 Hz), 2.24 (s, 3H); $^{13}$C NMR (DMSO-$d_6$) 165.84, 148.82, 141.37, 137.69, 129.47, 128.55, 127.27, 126.01, 125.89, 37.23, 36.95, 21.46; MS: HRMS-ESI-POS.: calc. for $C_{22}H_{30}N_4$ m/z 193.1230 ($M/2^{+}$+2), found m/z 193.1222; analysis calc. for $C_{25}H_{28}N_4\cdot 2HCl\cdot 1.8H_2O$; C, 61.29; H, 6.91; N, 11.43, Found: C, 61.61; H, 6.71; N, 14.36.

Synthesis 24. Synthesis of 4,4'-((2-Fluoro-1,3-phenylene)bis(ethane-2,1-diyl))bis(3-fluorobenzimidamide) Dihydrochloride (Compound B-6 Dihydrochloride)

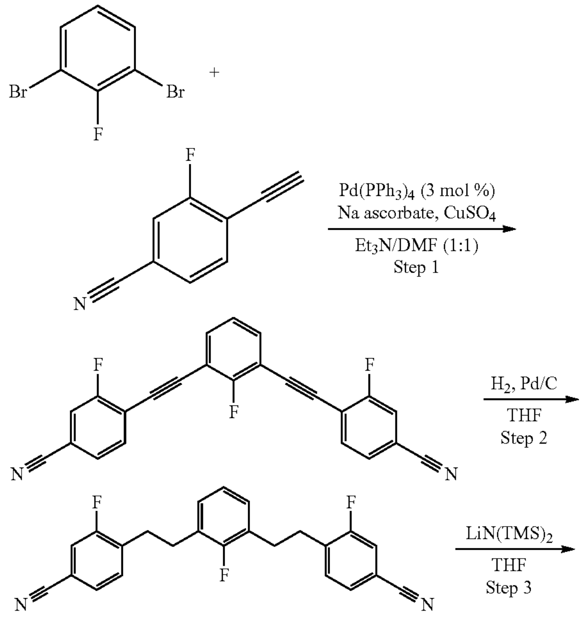

-continued

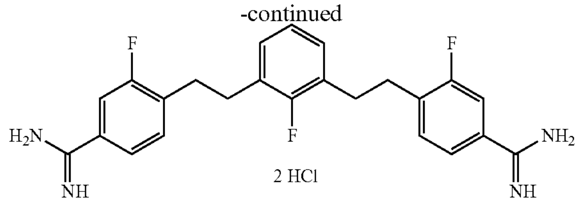

Step 1. Preparation of 4,4'-((2-Fluoro-1,3-phenylene)bis(ethyne-2,1-diyl))bis(3-fluorobenzonitrile)

To a solution of 1,3-dibromo-2-fluorobenzene (1 equiv) in DMF/$Et_3N$ (1:1) is added $Pd(PPh_3)_4$ (3 mol %) and 4-ethynyl-3-fluorobenzonitrile (2 equiv), and the mixture is stirred for 5 minutes. Sodium ascorbate (6 mol % in DMF) and $CuSO_4$ (1 mol % in DMF) are then added, and the reaction is stirred at 80° C. for 4 hours. The reaction is diluted with EtOAc and washed with saturated $NH_4Cl$ solution and brine. The organic layer is dried over anhydrous $Na_2SO_4$, filtered, and concentrated under reduced pressure. The crude residue is purified by column chromatography on silica gel to provide 4,4'-((2-fluoro-1,3-phenylene)bis(ethyne-2,1-diyl))bis(3-fluorobenzonitrile).

Step 2. Preparation of 4,4'-((2-Fluoro-1,3-phenylene)bis(ethane-2,1-diyl))bis(3-fluorobenzonitrile)

To a suspension of 10% Pd/C in THE is added 4,4'-((2-fluoro-1,3-phenylene)bis(ethyne-2,1-diyl))bis(3-fluorobenzonitrile). The argon is exchanged for $H_2$ gas, and the reaction is stirred overnight. The reaction mixture is diluted with DCM and filtered through celite. The organic phase is washed with water, dried over anhydrous $Na_2SO_4$, filtered, and concentrated under reduced pressure to provide 4,4'-((2-fluoro-1,3-phenylene)bis(ethane-2,1-diyl))bis(3-fluorobenzonitrile).

Step 3. Preparation of 4,4'-((2-Fluoro-1,3-phenylene)bis(ethane-2,1-diyl))bis(3-fluorobenzimidamide) Dihydrochloride To a suspension of 4,4'-((2-fluoro-1,3-phenylene)bis(ethane-2,1-diyl))bis(3-fluorobenzonitrile) (1 equiv) in dry THF stirred over an ice bath is added lithium bis(trimethylsilyl)amide solution (1.0 M in THE, 6 equiv), and the reaction is stirred at room temperature for 24 hours. The reaction mixture is cooled over an ice bath and then acidified by the slow addition of saturated ethanolic HCl solution until a solid forms. The mixture is stirred for two hours and then all solvents are removed under vacuum. The crude residue is brought up in ether and filtered. The filter cake is brought up in ice water and basified with 2 M NaOH solution until a precipitate forms. The solid is filtered, washed with water, and air dried. The isolated solid is suspended in a 3:1 mixture of anhydrous ethanol and saturated ethanolic HCl solution for 6 hours. The solvent is removed by distillation, and the resulting solid is triturated with dry diethyl ether and filtered. The isolated solid is dried at 80° C. under vacuum for 12 hours to provide 4,4'-((2-fluoro-1,3-phenylene)bis(ethane-2,1-diyl))bis(3-fluorobenzimidamide) dihydrochloride.

Synthesis 25. Synthesis of 4-((3-((4-(4,5-Dihydro-1H-imidazol-2-yl)phenoxy)methyl)-5-methylbenzyl)oxy)benzimidamide Dihydrochloride (Compound B-22 Dihydrochloride)

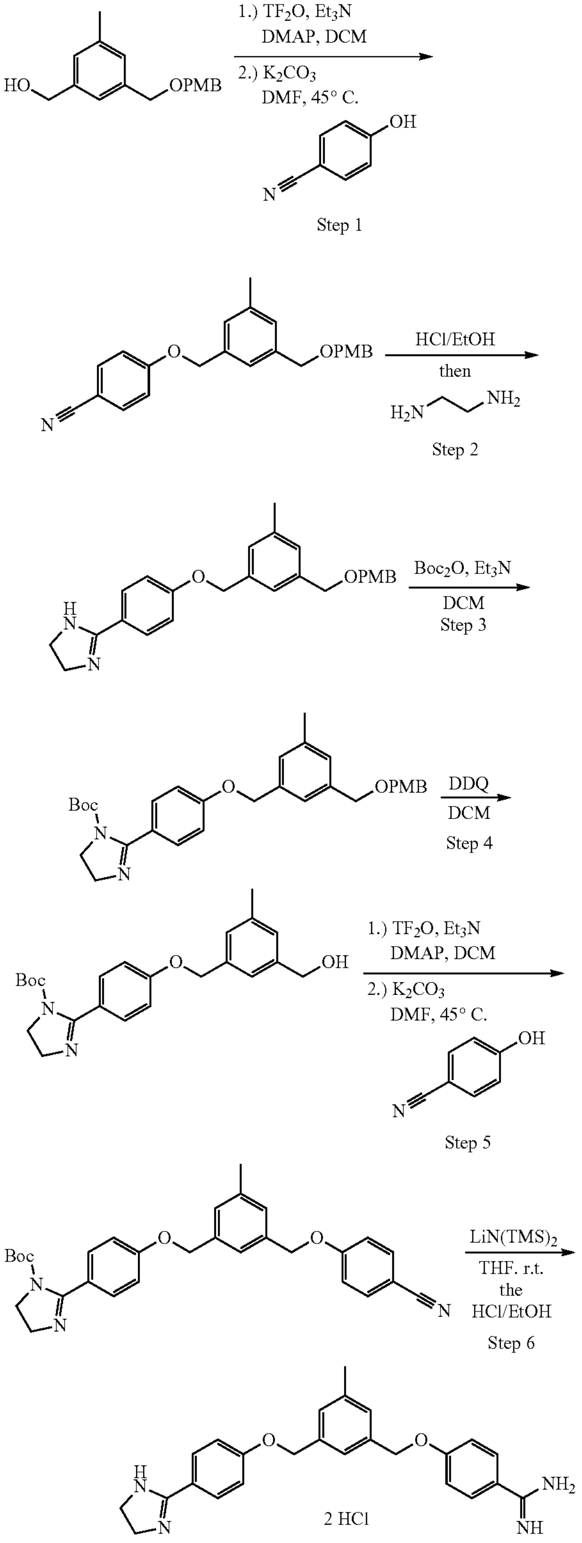

Step 1. Preparation of 4-((3-(((4-Methoxybenzyl)oxy)methyl)-5-methylbenzyl)oxy)benzonitrile To a solution of (3-(((4-methoxybenzyl)oxy)methyl)-5-methylphenyl) methanol (1 equiv) and 4-dimethylamino-pyridine (0.1 equiv) in DCM is added triethylamine (1 equiv) followed by triflic anhydride (1 equiv) at 0° C., and the reaction is stirred at room temperature for 4 hours. The reaction is concentrated under reduced pressure to provide the crude triflate, which is used without further purification.

The crude triflate is brought up in DMF, and 4-hydroxy-benzonitrile (1 equiv) and $K_2CO_3$ (3 equiv) are added. The reaction mixture is heated up to 45° C. and stirred for 4 hours. The reaction is then diluted with ice water and stirred for 30 minutes. The resulting reaction mixture is extracted with 3×DCM. The combined organic layer is dried over anhydrous magnesium sulfate, filtered, and concentrated under reduced pressure. Purification by column chromatography on silica gel provides 4-((3-(((4-methoxybenzyl)oxy)methyl)-5-methylbenzyl)oxy)benzonitrile.

Step 2. Preparation of 2-(4-((3-(((4-Methoxybenzyl)oxy)methyl)-5-methylbenzyl)oxy)phenyl)-4,5-dihydro-1H-imidazole 4-((3-(((4-Methoxybenzyl)oxy)methyl)-5-methylbenzyl)oxy)benzonitrile is added to anhydrous EtOH saturated with hydrogen chloride at 0° C. in a dry flask. The reaction mixture is sealed, slowly warmed to room temperature, and stirred until complete consumption of the starting material. The reaction mixture is diluted with anhydrous diethyl ether, and the resulting precipitate is filtered under nitrogen and dried under vacuum to provide the crude ethyl imidate hydrochloride, which is used immediately without further purification.

The crude imidate is brought up in ethanol, and ethane-1,2-diamine is added. The reaction mixture is heated to reflux and stirred until complete consumption of the starting material. The reaction mixture is concentrated under reduced pressure, and DCM and water are added. The layers are separated, and the aqueous layer is extracted with 3×DCM. The combined organic layer is dried over anhydrous sodium sulfate, filtered, and concentrated under reduced pressure. Purification by column chromatography on silica gel provides 2-(4-((3-(((4-methoxybenzyl)oxy)methyl)-5-methylbenzyl)oxy)phenyl)-4,5-dihydro-1H-imidazole.

Step 3. Preparation of tert-Butyl 2-(4-((3-(((4-Methoxybenzyl)oxy)methyl)-5-methylbenzyl)oxy)phenyl)-4,5-dihydro-1H-imidazole-1-carboxylate To a solution of 2-(4-((3-(((4-methoxybenzyl)oxy)methyl)-5-methylbenzyl)oxy)phenyl)-4,5-dihydro-1H-imidazole (1 equiv) in DCM is added triethylamine (2 equiv) and di tert-butyl dicarbonate (1 equiv) at 0° C., and the reaction is warmed up to room temperature and stirred for two hours. The reaction mixture is quenched by the addition of saturated ammonium chloride, and the layers are separated. The aqueous layer is extracted with 3×DCM. The combined organic layer is dried over anhydrous sodium sulfate, filtered, and concentrated under reduced pressure. Purification by column chromatography on silica gel provides tert-butyl 2-(4-((3-(((4-methoxybenzyl)oxy)methyl)-5-methylbenzyl)oxy)phenyl)-4,5-dihydro-1H-imidazole-1-carboxylate.

Step 4. Preparation of tert-Butyl 2-(4-((3-(Hydroxymethyl)-5-methylbenzyl)oxy)phenyl)-4,5-dihydro-1H-imidazole-1-carboxylate To a solution of tert-butyl 2-(4-((3-(((4-methoxybenzyl)oxy)methyl)-5-methylbenzyl)oxy)phenyl)-4,5-dihydro-1H-imidazole-1-carboxylate (1 equiv) in DCM is added 4,5-dichloro-3,6-dioxocyclohexa-1,4-diene-1,2-dicarbonitrile (1 equiv), and the reaction is stirred at room temperature until complete consumption of the starting material. Methanol and sodium borohydride (5 equiv) is then added in portions, and the reaction mixture is stirred for 24 hours. The reaction mixture is concentrated under reduced pressure and brought up in dichloromethane and water. The layers are separated, and the aqueous layer is extracted with 3×DCM. The combined organic layer is dried over anhydrous sodium sulfate, filtered, and concentrated under reduced pressure. Purification by column chromatography on silica gel provides tert-butyl 2-(4-((3-(hydroxymethyl)-5-methylbenzyl)oxy)phenyl)-4,5-dihydro-1H-imidazole-1-carboxylate.

Step 5. Preparation of tert-Butyl 2-(4-((3-((4-Cyanophenoxy)methyl)-5-methylbenzyl)oxy)phenyl)-4,5-dihydro-1H-imidazole-1-carboxylate To a solution of tert-butyl 2-(4-((3-(hydroxymethyl)-5-methylbenzyl)oxy)phenyl)-4,5-dihydro-1H-imidazole-1-carboxylate (1 equiv) and 4-dimethylaminopyridine (0.1 equiv) in DCM is added triethylamine (1 equiv) followed by triflic anhydride (1 equiv) at 0° C., and the reaction is stirred at room temperature for 4 hours. The reaction is concentrated under reduced pressure to provide the crude triflate, which is used without further purification.

The crude triflate is brought up in DMF, and 4-hydroxybenzonitrile (1 equiv) and $K_2CO_3$ (3 equiv) are added. The reaction mixture is heated up to 45° C. and stirred for 4 hours. The reaction is then diluted with ice water and stirred for 30 minutes. The resulting reaction mixture is extracted with 3×DCM. The combined organic layer is dried over anhydrous magnesium sulfate, filtered, and concentrated under reduced pressure. Purification by column chromatography on silica gel provides tert-butyl 2-(4-((3-((4-cyanophenoxy)methyl)-5-methylbenzyl)oxy)phenyl)-4,5-dihydro-1H-imidazole-1-carboxylate.

Step 6. Preparation of 4-((3-((4-(4,5-Dihydro-1H-imidazol-2-yl)phenoxy)methyl)-5-methylbenzyl)oxy)benzimidamide Dihydrochloride To a solution of tert-butyl 2-(4-((3-((4-cyanophenoxy)methyl)-5-methylbenzyl)oxy)phenyl)-4,5-dihydro-1H-imidazole-1-carboxylate (1 equiv) in dry THF stirred over an ice bath is added lithium bis(trimethylsilyl)amide (1 M in THF, 1 equiv), and the reaction is stirred at room temperature for 24 hours. The reaction mixture is cooled over an ice bath and then acidified by the slow addition of saturated ethanolic HCL solution until a solid forms. The mixture is stirred for two hours and then all solvents are removed under vacuum. The crude residue is brought up in ether and filtered. The filter cake is brought up in ice water and basified with 2 M NaOH solution until a precipitate forms. The solid is filtered, washed with water, and air dried. The isolated solid is suspended in a 3:1 mixture of anhydrous ethanol and saturated ethanolic HCl solution for 6 hours. The solvent is removed by distillation, and the resulting solid is triturated with dry diethyl ether and filtered. The solvent is removed by distillation, and the resulting solid is dried at 80° C. for 12 hours to provide 4-((3-((4-(4,5-dihydro-1H-imidazol-2-yl)phenoxy)methyl)-5-methylbenzyl)oxy)benzimidamide dihydrochloride.

Synthesis 26. Synthesis of 4-((3-Methyl-5-((4-(1,4,5,6-tetrahydropyrimidin-2-yl)phenoxy)methyl)benzyl)oxy)benzimidamide dihydrochloride

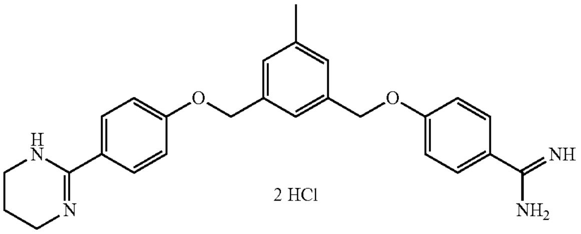 [SMILES: Cc1cc(COc2ccc(C(=N)N)cc2)cc(COc2ccc(C3=NCCCN3)cc2)c1]

4-((3-Methyl-5-((4-(1,4,5,6-tetrahydropyrimidin-2-yl)phenoxy)methyl)benzyl)oxy)benzimidamide dihydrochloride can be prepared by the same procedure by substituting ethane-1,2-diamine with propane-1,3-diamine in Step 2.

Synthesis 27. Synthesis of N,N'-((2-Fluoro-1,3-phenylene)bis(methylene))bis(4-(4,5-dihydro-1H-imidazol-2-yl)-N-methylaniline) Dihydrochloride (Compound B-24 Dihydrochloride)

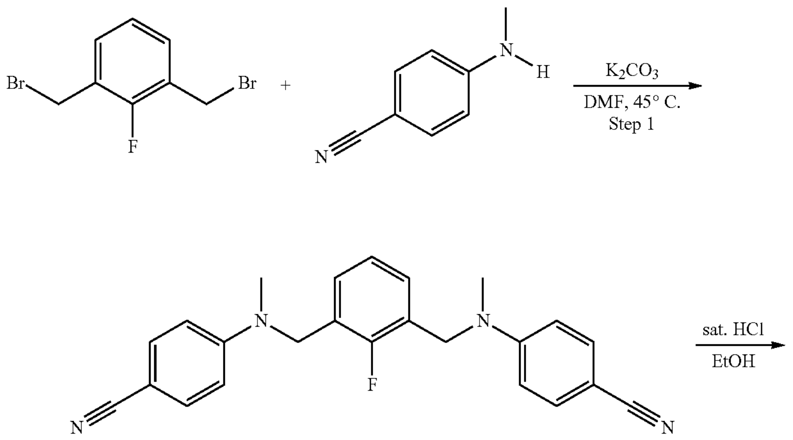

-continued

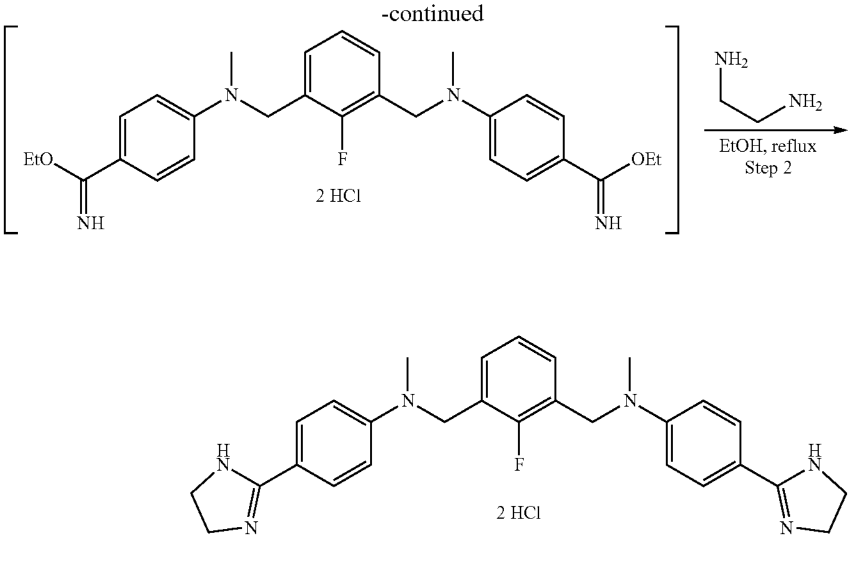

Step 1. Preparation of 4,4'-(((2-Fluoro-1,3-phenylene)bis(methylene))bis(methylazanediyl))dibenzonitrile A mixture of 1,3-bis(bromomethyl)-2-fluorobenzene (1 equiv), 4-(methylamino)benzonitrile (2 equiv), and $K_2CO_3$ (3 equiv) in DMF is heated at 45° C. for 4 hours. The reaction is then diluted with ice water and stirred for 30 minutes. The resulting precipitate is filtered, washed with water, and dried in air. The isolated precipitate is dissolved in DCM, dried over anhydrous magnesium sulfate, filtered, and concentrated under reduced pressure. The residue is triturated with hexane, filtered, and dried under vacuum to provide 4,4'-(((2-fluoro-1,3-phenylene)bis(methylene))bis(methylazanediyl))dibenzonitrile.

Step 2. Preparation of N,N'-((2-Fluoro-1,3-phenylene)bis(methylene))bis(4-(4,5-dihydro-1H-imidazol-2-yl)-N-methylaniline) Dihydrochloride 4,4'-(((2-Fluoro-1,3-phenylene)bis(methylene))bis(methylazanediyl))dibenzonitrile (1 equiv) is added to saturated ethanolic hydrogen chloride at 0° C. in a dry flask. The reaction mixture is sealed, slowly warmed to room temperature, and stirred until complete consumption of the starting material. The reaction mixture is diluted with anhydrous diethyl ether, and the resulting precipitate is filtered under nitrogen and dried under high vacuum to provide crude diethyl 4,4'-(((2-fluoro-1,3-phenylene)bis(methylene))bis(methylazanediyl))dibenzimidate dihydrochloride, which was used immediately without further purification.

The crude imidate is brought up in ethanol, and ethane-1,2-diamine is added. The reaction mixture is heated to reflux and stirred until complete consumption of the starting material. The reaction mixture is concentrated under reduced pressure. Diethyl ether is added, and the resulting precipitate is filtered. The solid is suspended in ice water and basified with 2 M NaOH. The resulting precipitate is filtered, washed with water, and air dried. The solid is brought up in saturated ethanolic HCl solution and stirred for 6 hours. The ethanol is removed by distillation, and the resulting precipitate is triturated with diethyl ether and filtered. The resulting solid is dried under vacuum at 80° C. for 12 hours to provide N,N'-((2-dluoro-1,3-phenylene)bis(methylene))bis(4-(4,5-dihydro-1H-imidazol-2-yl)-N-methylaniline) dihydrochloride.

Synthesis 28. Synthesis of N,N'-((2-Fluoro-1,3-phenylene)bis(methylene))bis(N-methyl-4-(1,4,5,6-tetrahydropyrimidin-2-yl)aniline) dihydrochloride

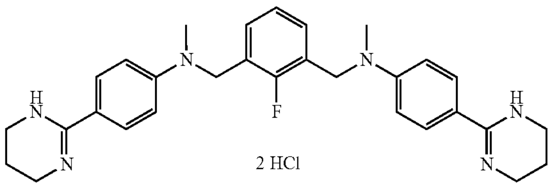 [SMILES: CN(Cc1cccc(CN(C)c2ccc(C3=NCCCN3)cc2)c1F)c1ccc(C2=NCCCN2)cc1]

N,N'-((2-Fluoro-1,3-phenylene)bis(methylene))bis(N-methyl-4-(1,4,5,6-tetrahydropyrimidin-2-yl)aniline) dihydrochloride can be synthesized by the same procedure by substituting ethane-1,2-diamine with propane-1,3-diamine in Step 2

Synthesis 29. Synthesis of 2,2'-((((2-Fluoro-1,3-phenylene)bis(sulfanediyl))bis(methylene))bis(4,1-phenylene))bis(4,5-dihydro-1H-imidazole) Dihydrochloride (Compound B-26 Dihydrochloride)

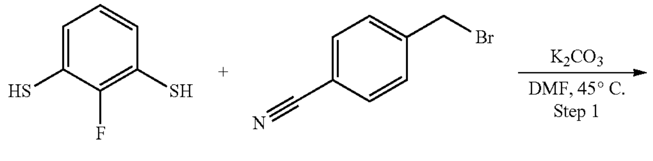

-continued

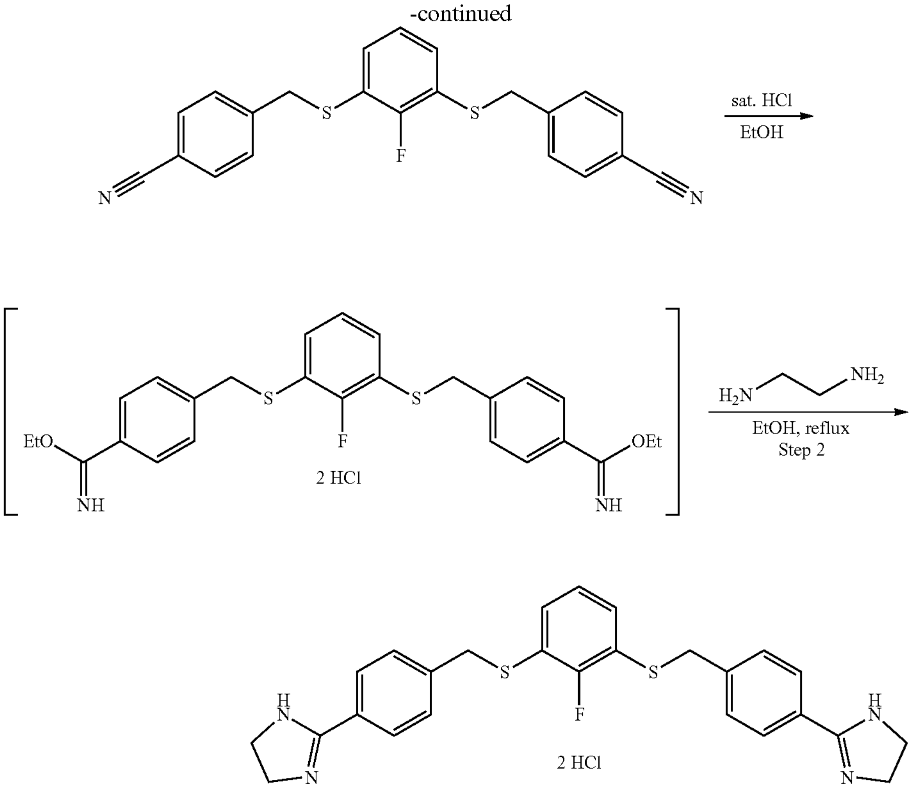

Step 1. Preparation of 4,4'-(((2-Fluoro-1,3-phenylene)bis(sulfanediyl))bis(methylene))dibenzonitrile A mixture of 2-fluorobenzene-1,3-dithiol (1 equiv), 4-(bromomethyl)benzonitrile (2 equiv), and $K_2CO_3$ (3 equiv) in DMF is heated at 45° C. for 4 hours. The reaction is then diluted with ice water and stirred for 30 minutes. The resulting precipitate is filtered, washed with water, and dried in air. The isolated precipitate is dissolved in DCM, dried over anhydrous magnesium sulfate, filtered, and concentrated under reduced pressure. The residue is triturated with hexane, filtered, and dried under vacuum to provide 4,4'-(((2-fluoro-1,3-phenylene)bis(sulfanediyl))bis(methylene))dibenzonitrile.

Step 2. Preparation of N,N'-((2-Fluoro-1,3-phenylene)bis(methylene))bis(4-(4,5-dihydro-1H-imidazol-2-yl)-N-methylaniline) Dihydrochloride 4,4'-(((2-Fluoro-1,3-phenylene)bis(sulfanediyl))bis(methylene))dibenzonitrile (1 equiv) is added to saturated ethanolic hydrogen chloride at 0° C. in a dry flask. The reaction mixture is sealed, slowly warmed to room temperature, and stirred until complete consumption of the starting material. The reaction mixture is diluted with anhydrous diethyl ether, and the resulting precipitate is filtered under nitrogen and dried under high vacuum to provide crude diethyl 4,4'-(((2-fluoro-1,3-phenylene)bis(sulfanediyl))bis(methylene))dibenzimidate dihydrochloride, which was used immediately without further purification.

The crude imidate is brought up in ethanol, and ethane-1,2-diamine is added. The reaction mixture is heated to reflux and stirred until complete consumption of the starting material. The reaction mixture is concentrated under reduced pressure. Diethyl ether is added, and the resulting precipitate is filtered. The solid is suspended in ice water and basified with 2 M NaOH. The resulting precipitate is filtered, washed with water, and air dried. The solid is brought up in saturated ethanolic HCl solution and stirred for 6 hours. The ethanol is removed by distillation, and the resulting precipitate is triturated with diethyl ether and filtered. The resulting solid is dried under vacuum at 80° C. for 12 hours to provide N,N'-((2-fluoro-1,3-phenylene)bis(methylene))bis(4-(4,5-dihydro-1H-imidazol-2-yl)-N-methylaniline) dihydrochloride.

Synthesis 30. Synthesis of 2,2'-((((2-fluoro-1,3-phenylene)bis(sulfanediyl))bis(methylene))bis(4,1-phenylene))bis(1,4,5,6-tetrahydropyrimidine) dihydrochloride

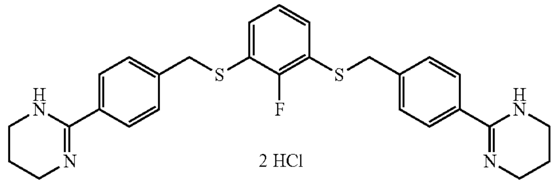 [SMILES: Fc1c(SCc2ccc(C3=NCCCN3)cc2)cccc1SCc1ccc(C2=NCCCN2)cc1]

2,2'-((((2-fluoro-1,3-phenylene)bis(sulfanediyl))bis(methylene))bis(4,1-phenylene))bis(1,4,5,6-tetrahydropyrimidine) dihydrochloride can be synthesized using the same procedure by substituting ethane-1,2-diamine with propane-1,3-diamine in Step 2.

Synthesis 31. Synthesis of 2,2'-(((2-Fluoro-1,3-phenylene)bis(ethane-2,1-diyl))bis(4,1-phenylene))bis(4,5-dihydro-1H-imidazole) Dihydrochloride (Compound B-28 Dihydrochloride)

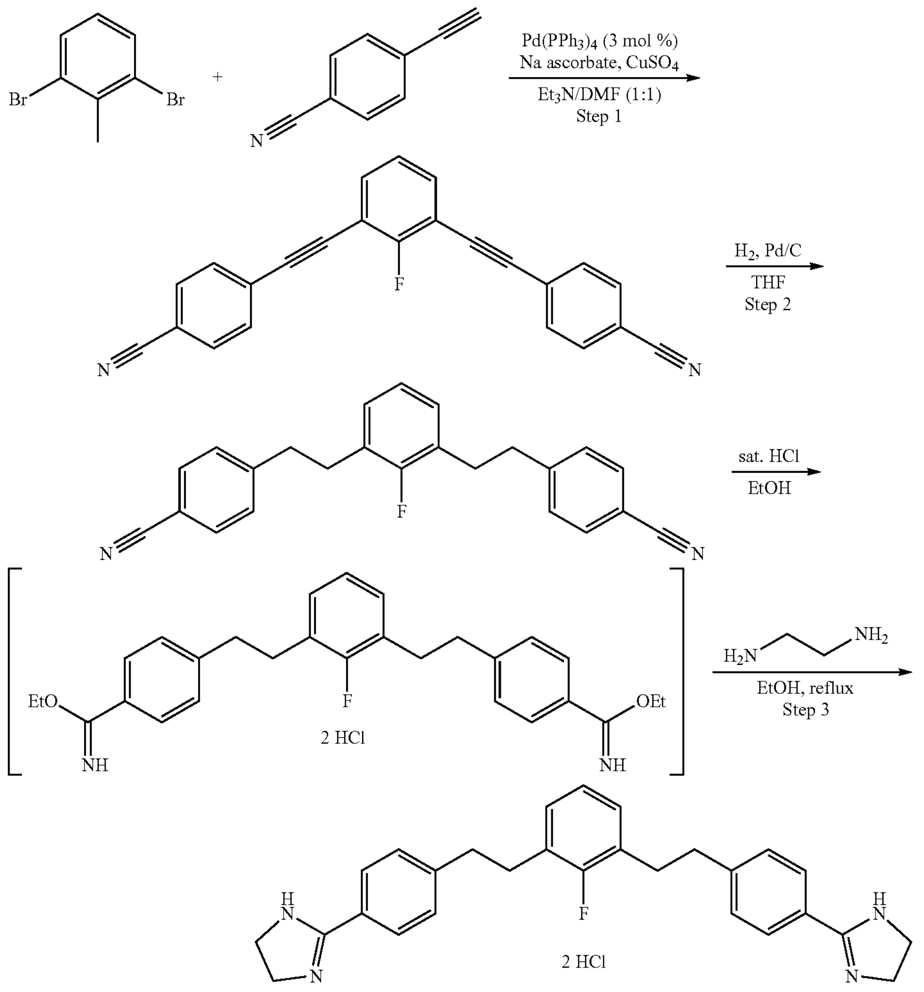

Step 1. Preparation of 4,4'-((2-Fluoro-1,3-phenylene)bis(ethyne-2,1-diyl))dibenzonitrile To a solution of 1,3-dibromo-2-methylbenzene (1 equiv) in DMF/$Et_3N$ (1:1) is added $Pd(PPh_3)_4$ (3 mol %) and 4-ethynylbenzonitrile (2 equiv), and the mixture is stirred for 5 minutes. Sodium ascorbate (6 mol % in DMF) and $CuSO_4$ (1 mol % in DMF) are then added, and the reaction is stirred at 80° C. for 4 hours. The reaction is diluted with EtOAc and washed with saturated $NH_4Cl$ solution and brine. The organic layer is dried over anhydrous $Na_2SO_4$, filtered, and concentrated under reduced pressure. The crude residue is purified by column chromatography on silica gel to provide 4,4'-((2-fluoro-1,3-phenylene)bis(ethyne-2,1-diyl))dibenzonitrile.

Step 2. Preparation of 4,4'-((2-Fluoro-1,3-phenylene)bis(ethane-2,1-diyl))dibenzonitrile To a suspension of 10% Pd/C in THF is added 4,4'-((2-fluoro-1,3-phenylene)bis(ethyne-2,1-diyl))dibenzonitrile. The argon is exchanged for $H_2$ gas, and the reaction is stirred overnight. The reaction mixture is diluted with DCM and filtered through celite. The organic phase is washed with water, dried over anhydrous $Na_2SO_4$, filtered, and concentrated under reduced pressure to provide 4,4'-((2-fluoro-1,3-phenylene)bis(ethane-2,1-diyl))dibenzonitrile.

Step 3. Preparation of 2,2'-(((2-Fluoro-1,3-phenylene)bis(ethane-2,1-diyl))bis(4,1-phenylene))bis(4,5-dihydro-1H-imidazole) Dihydrochloride 4,4'-((2-fluoro-1,3-phenylene)bis(ethane-2,1-diyl))dibenzonitrile (1 equiv) is added to saturated ethanolic hydrogen chloride at 0° C. in a dry flask. The reaction mixture is sealed, slowly warmed to room temperature, and stirred until complete consumption of the starting material. The reaction mixture is diluted with anhydrous diethyl ether, and the resulting precipitate is filtered under nitrogen and dried under high vacuum to provide crude diethyl 4,4'-((2-fluoro-1,3-phenylene)bis(ethane-2,1-diyl))dibenzimidate dihydrochloride, which was used immediately without further purification.

The crude imidate is brought up in ethanol, and ethane-1,2-diamine is added. The reaction mixture is heated to reflux and stirred until complete consumption of the starting material. The reaction mixture is concentrated under reduced pressure. Diethyl ether is added, and the resulting precipitate is filtered. The solid is suspended in ice water and basified with 2 M NaOH. The resulting precipitate is filtered, washed with water, and air dried. The solid is brought up in saturated ethanolic HCl solution and stirred for 6 hours. The ethanol is removed by distillation, and the resulting precipitate is triturated with diethyl ether and filtered. The resulting solid is dried under vacuum at 80° C. for 12 hours to provide 2,2'-(((2-fluoro-1,3-phenylene)bis(ethane-2,1-diyl))bis(4,1-phenylene))bis(4,5-dihydro-1H-imidazole) dihydrochloride.

Synthesis 32. Synthesis of 2,2'-(((2-Fluoro-1,3-phenylene)bis(ethane-2,1-diyl))bis(4,1-phenylene))bis(1,4,5,6-tetrahydropyrimidine) dihydrochloride

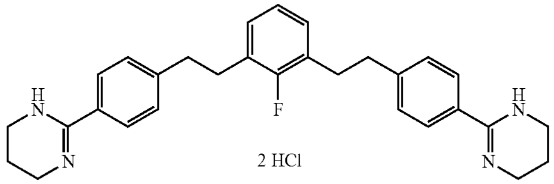 [SMILES: Fc1c(CCc2ccc(C3=NCCCN3)cc2)cccc1CCc1ccc(C2=NCCCN2)cc1]

2 HCl 2,2'-(((2-Fluoro-1,3-phenylene)bis(ethane-2,1-diyl))bis(4,1-phenylene))bis(1,4,5,6-tetrahydropyrimidine) dihydrochloride can be synthesized using the same procedure by substitutingf ethane-1,2-diamine with propane-1,3-diamine in Step 3.

Synthesis 33. Synthesis of 4,4'-((2-Fluoro-1,3-phenylene)bis(ethane-2,1-diyl))bis(3-methoxybenzimidamide) Dihydrochloride (Compound B-48 Dihydrochloride)

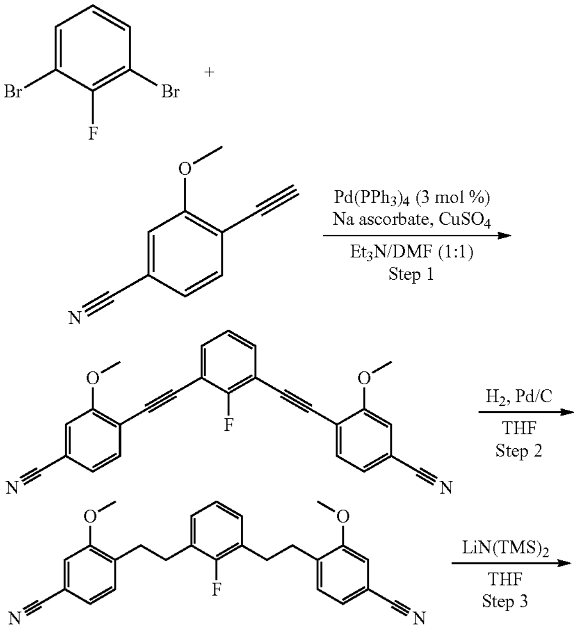

-continued

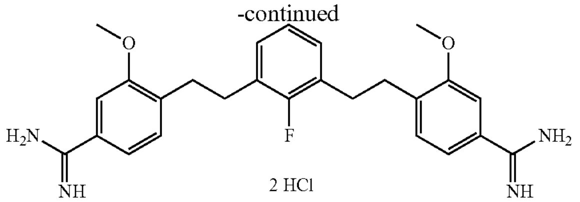

2 HCl

Step 1. Preparation of 4,4'-((2-Fluoro-1,3-phenylene)bis(ethyne-2,1-diyl))bis(3-methoxybenzonitrile)

To a solution of 1,3-dibromo-2-fluorobenzene (1 equiv) in DMF/$Et_3N$ (1:1) is added $Pd(PPh_3)_4$ (3 mol %) and 4-ethynyl-3-methoxybenzonitrile (2 equiv), and the mixture is stirred for 5 minutes. Sodium ascorbate (6 mol % in DMF) and $CuSO_4$ (1 mol % in DMF) are then added, and the reaction is stirred at 80° C. for 4 hours. The reaction is diluted with EtOAc and washed with saturated $NH_4Cl$ solution and brine. The organic layer is dried over anhydrous $Na_2SO_4$, filtered, and concentrated under reduced pressure. The crude residue is purified by column chromatography on silica gel to provide 4,4'-((2-fluoro-1,3-phenylene)bis(ethyne-2,1-diyl))bis(3-methoxybenzonitrile).

Step 2. Preparation of 4,4'-((2-Fluoro-1,3-phenylene)bis(ethane-2,1-diyl))bis(3-methoxybenzonitrile)

To a suspension of 10% Pd/C in THE is added 4,4'-((2-fluoro-1,3-phenylene)bis(ethyne-2,1-diyl))bis(3-methoxybenzonitrile). The argon is exchanged for $H_2$ gas, and the reaction is stirred overnight. The reaction mixture is diluted with DCM and filtered through celite. The organic phase is washed with water, dried over anhydrous $Na_2SO_4$, filtered, and concentrated under reduced pressure to provide 4,4'-((2-fluoro-1,3-phenylene)bis(ethane-2,1-diyl))bis(3-methoxybenzonitrile).

Step 3. Preparation of 4,4'-((2-Fluoro-1,3-phenylene)bis(ethane-2,1-diyl))bis(3-methoxybenzimidamide) Dihydrochloride To a suspension of 4,4'-((2-fluoro-1,3-phenylene)bis(ethane-2,1-diyl))bis(3-methoxybenzonitrile) (1 equiv) in dry THE stirred over an ice bath is added lithium bis(trimethylsilyl)amide solution (1.0 M in THF, 6 equiv), and the reaction is stirred at room temperature for 24 hours. The reaction mixture is cooled over an ice bath and then acidified by the slow addition of saturated ethanolic HCl solution until a solid forms. The mixture is stirred for two hours and then all solvents are removed under vacuum. The crude residue is brought up in ether and filtered. The filter cake is brought up in ice water and basified with 2 M NaOH solution until a precipitate forms. The solid is filtered, washed with water, and air dried. The isolated solid is suspended in a 3:1 mixture of anhydrous ethanol and saturated ethanolic HCl solution for 6 hours. The solvent is removed by distillation, and the resulting solid is triturated with dry diethyl ether and filtered. The isolated solid is dried at 80° C. under vacuum for 12 hours to 4,4'-((2-fluoro-1,3-phenylene)bis(ethane-2,1-diyl))bis(3-methoxybenzimidamide) dihydrochloride.

Synthesis 34. Preparation of N1,N3-Bis(4-(4,5-dihydro-1H-imidazol-2-yl)-2-methoxybenzyl)-2-fluoro-N1,N3-dimethylbenzene-1,3-diamine Dihydrochloride (Compound B-58 Dihydrochloride)

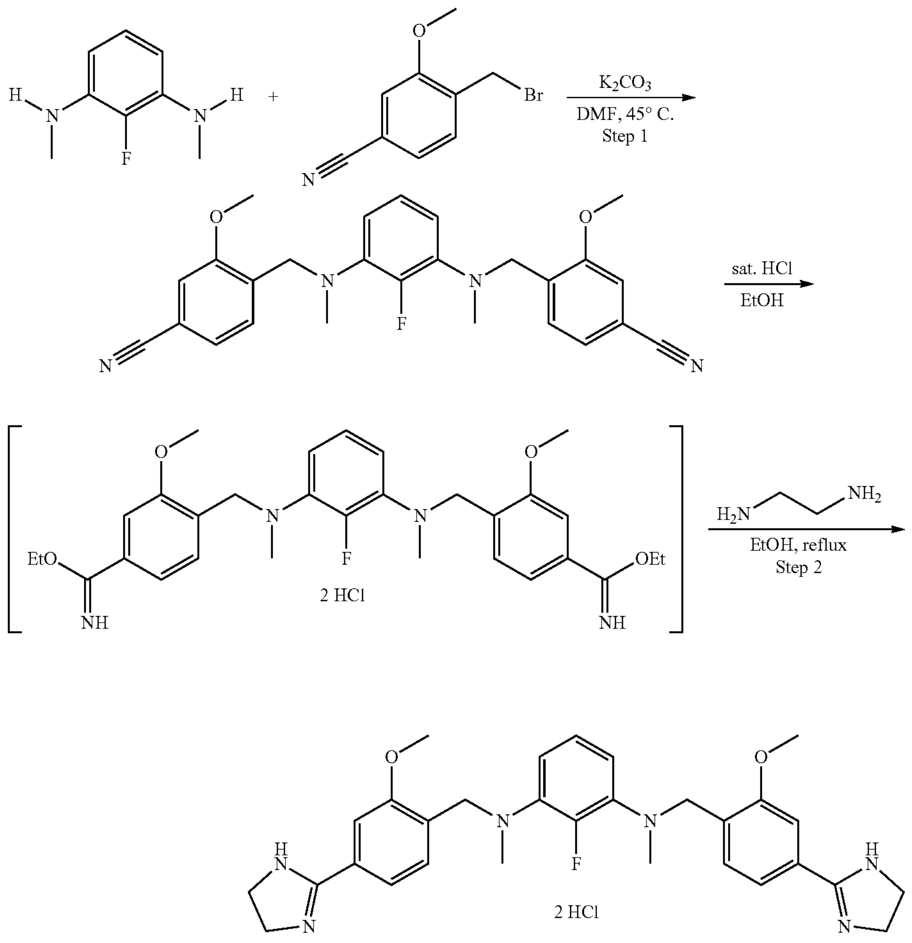

Step 1. Preparation of 4,4'-(((2-Fluoro-1,3-phenylene)bis(methylazanediyl))bis(methylene))bis(3-methoxybenzonitrile)

A mixture of 2-fluoro-N1,N3-dimethylbenzene-1,3-diamine (1 equiv), 4-(bromomethyl)-3-methoxybenzonitrile (2 equiv), and $K_2CO_3$ (3 equiv) in DMF is heated at 45° C. for 4 hours. The reaction is then diluted with ice water and stirred for 30 minutes. The resulting precipitate is filtered, washed with water, and dried in air. The isolated precipitate is dissolved in DCM, dried over anhydrous magnesium sulfate, filtered, and concentrated under reduced pressure. The residue is triturated with hexane, filtered, and dried under vacuum to provide 4,4'-(((2-fluoro-1,3-phenylene)bis(methylazanediyl))bis(methylene))bis(3-methoxybenzonitrile).

Step 2. Preparation of N1,N3-Bis(4-(4,5-dihydro-1H-imidazol-2-yl)-2-methoxybenzyl)-2-fluoro-N1,N3-dimethylbenzene-1,3-diamine Dihydrochloride 4,4'-(((2-Fluoro-1,3-phenylene)bis(sulfanediyl))bis(methylene))dibenzonitrile (1 equiv) is added to saturated ethanolic hydrogen chloride at 0° C. in a dry flask. The reaction mixture is sealed, slowly warmed to room temperature, and stirred until complete consumption of the starting material. The reaction mixture is diluted with anhydrous diethyl ether, and the resulting precipitate is filtered under nitrogen and dried under high vacuum to provide crude diethyl 4,4'-(((2-fluoro-1,3-phenylene)bis(methylazanediyl))bis(methylene))bis(3-methoxybenzimidate) dihydrochloride, which was used immediately without further purification.

The crude imidate is brought up in ethanol, and ethane-1,2-diamine is added. The reaction mixture is heated to reflux and stirred until complete consumption of the starting material. The reaction mixture is concentrated under reduced pressure. Diethyl ether is added, and the resulting precipitate is filtered. The solid is suspended in ice water and basified with 2 M NaOH. The resulting precipitate is filtered, washed with water, and air dried. The solid is brought up in saturated ethanolic HCl solution and stirred for 6 hours. The ethanol is removed by distillation, and the resulting precipitate is triturated with diethyl ether and filtered. The resulting solid is dried under vacuum at 80° C. for 12 hours to provide N1, N3-bis(4-(4,5-dihydro-1H-imidazol-2-yl)-2-methoxybenzyl)-2-fluoro-N1,N3-dimethylbenzene-1,3-diamine dihydrochloride.

Synthesis 35. Synthesis of 2-Fluoro-N1,N3-bis(2-methoxy-4-(1,4,5,6-tetrahydropyrimidin-2-yl)benzyl)-N1,N3-dimethylbenzene-1,3-diamine

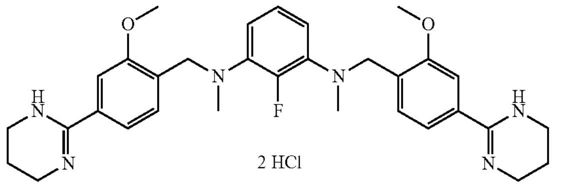 [SMILES: COc1cc(C2=NCCCN2)ccc1CN(C)c1cccc(N(C)Cc2ccc(C3=NCCCN3)cc2OC)c1F]

2-Fluoro-N1,N3-bis(2-methoxy-4-(1,4,5,6-tetrahydropyrimidin-2-yl)benzyl)-N1,N3-dimethylbenzene-1,3-diamine can be synthesized by the same procedure by substituting ethane-1,2-diamine with propane-1,3-diamine in Step 2.

Synthesis 36. Synthesis of 4,4'-(((5-Methyl-1,3-phenylene)bis(methylazanediyl))bis(methylene))bis(3-methoxybenzimidamide) Dihydrochloride (Compound B-67 Dihydrochloride)

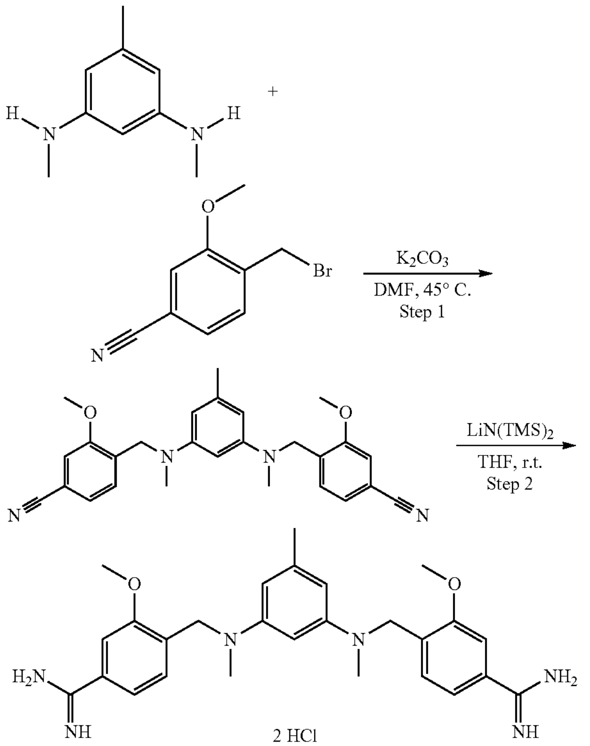

Step 1. Preparation of 4,4'-(((5-Methyl-1,3-phenylene)bis(methylazanediyl))bis(methylene))bis(3-methoxybenzonitrile)

A mixture of N1,N3,5-trimethylbenzene-1,3-diamine (1 equiv), 4-(bromomethyl)-3-methoxybenzonitrile (2 equiv), and $K_2CO_3$ (3 equiv) in DMF is heated at 45° C. for 4 hours. The reaction is then diluted with ice water and stirred for 30 minutes. The resulting precipitate is filtered, washed with water, and dried in air. The isolated precipitate is dissolved in dichloromethane, dried over anhydrous magnesium sulfate, filtered, and concentrated under reduced pressure. The residue is triturated with hexane, filtered, and dried under vacuum to yield 4,4'-(((5-methyl-1,3-phenylene)bis(methylazanediyl))bis(methylene))bis(3-methoxybenzonitrile).

Step 2. Preparation of 4,4'-(((5-Methyl-1,3-phenylene)bis(methylazanediyl))bis(methylene))bis(3-methoxybenzimidamide) Dihydrochloride To a suspension of 4,4'-(((5-methyl-1,3-phenylene)bis(methylazanediyl))bis(methylene))bis(3-methoxybenzonitrile) (1 equiv) in dry THF (15 mL) stirred over an ice bath is added lithium bis(trimethylsilyl)amide solution (1 M in THF, 6 equiv), and the reaction is stirred at room temperature for 24 hours. The reaction mixture is cooled over an ice bath and then acidified by the slow addition of saturated ethanolic HCl solution until a solid forms. The mixture is stirred for two hours and then all solvents are removed under vacuum. The crude residue is brought up in ether and filtered. The filter cake is brought up in ice water and basified with 2 M NaOH solution until a precipitate forms. The solid is filtered, washed with water, and air dried. The isolated solid is suspended in a 3:1 mixture of anhydrous ethanol and saturated ethanolic HCl solution for 6 hours. The solvent is removed by distillation, and the resulting solid is triturated with dry diethyl ether and filtered. The isolated solid is dried at 80° C. under vacuum for 12 hours to provide 4,4'-(((5-methyl-1,3-phenylene)bis(methylazanediyl))bis(methylene))bis(3-methoxybenzimidamide) dihydrochloride.

Synthesis 37. Synthesis of 4,4'-(((5-Methyl-1,3-phenylene)bis(oxy))bis(methylene))bis(3-methoxybenzimidamide) dihydrochloride (Compound B-65 dihydrochloride)

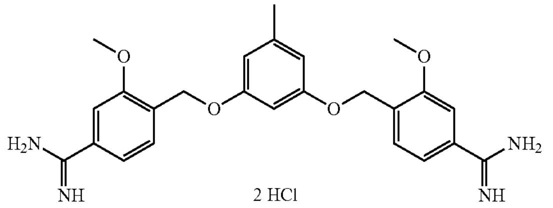 [SMILES: COc1cc(C(=N)N)ccc1COc1cc(C)cc(OCc2ccc(C(=N)N)cc2OC)c1]

4,4'-(((5-Methyl-1,3-phenylene)bis(oxy))bis(methylene))bis(3-methoxybenzimidamide) dihydrochloride (Compound B-65 dihydrochloride) can be synthesized by the same procedure by substituting N1,N3,5-trimethylbenzene-1,3-diamine with 5-methylbenzene-1,3-diol in Step 1.

Synthesis 38. Synthesis of 4,4'-(((5-Methyl-1,3-phenylene)bis(sulfanediyl))bis(methylene))bis(3-methoxybenzimidamide) dihydrochloride (Compound B-66 dihydrochloride)

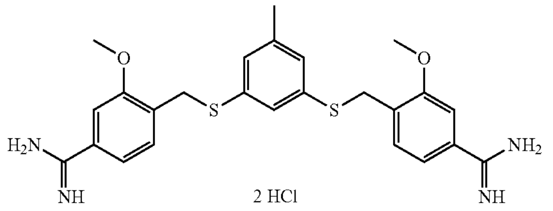 [SMILES: COc1cc(C(=N)N)ccc1CSc1cc(C)cc(SCc2ccc(C(=N)N)cc2OC)c1]

4,4'-(((5-Methyl-1,3-phenylene)bis(sulfanediyl))bis(methylene))bis(3-methoxybenzimidamide) dihydrochloride (Compound B-66 dihydrochloride) can be synthesized by the same procedure by substituting N1, N3,5-trimethylbenzene-1,3-diamine with 5-methylbenzene-1,3-dithiol in Step 1.

Synthesis 39. Synthesis of 4,4'-(((5-Methyl-1,3-phenylene)bis(methylene))bis(oxy))bis(3-methoxy-N-methylbenzimidamide) Dihydrochloride (Compound B-69 Dihydrochloride)

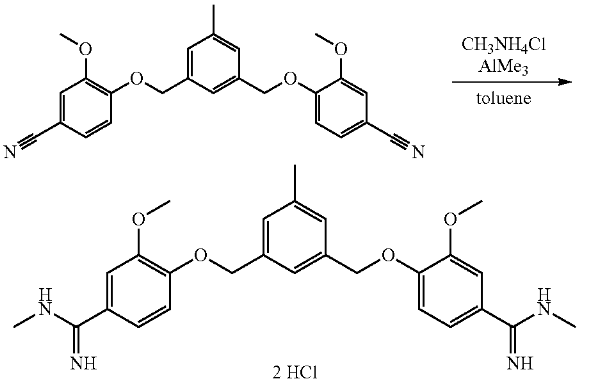

To a solution of methylamine hydrochloride (3 equiv) in toluene at 0° C. is added trimethylaluminum (2.0 M in toluene, 3 equiv), and the result mixture is warmed up to room temperature and stirred for 2 hours. A solution of 4,4'-(((5-methyl-1,3-phenylene)bis(methylene))bis(oxy))bis(3-methoxybenzonitrile) (1 equiv) in toluene is then added, and the reaction mixture is heated to 80° C. and stirred for 24 hours. The reaction mixture is cooled to room temperature and slowly poured into ice water. DCM is added, and the mixture is filtered through celite. The layers are separated, and the aqueous layer is extracted with DCM (3×). The combined organic layer is washed with brine, dried over anhydrous sodium sulfate, filtered, and concentrated under reduced pressure. The isolated solid is suspended in a 3:1 mixture of anhydrous ethanol and saturated ethanolic HCl solution for 6 hours. The solvent is removed by distillation, and the resulting solid is triturated with dry diethyl ether and filtered. The isolated solid is dried at 80° C. under vacuum for 12 hours to provide 4,4'-(((5-methyl-1,3-phenylene)bis(methylene))bis(oxy))bis(3-methoxy-N-methylbenzimidamide) dihydrochloride.

Synthesis 40. Synthesis of 4,4'-(((5-Methyl-1,3-phenylene)bis(methylene))bis(oxy))bis(N-ethyl-3-methoxybenzimidamide) dihydrochloride (Compound B-70 dihydrochloride)

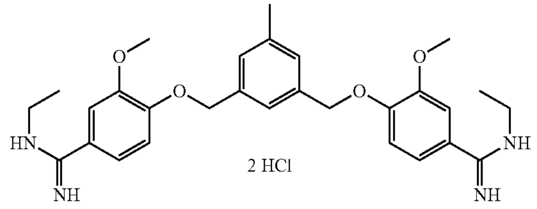 [SMILES: CCNC(=N)c1ccc(OCc2cc(C)cc(COc3ccc(C(=N)NCC)cc3OC)c2)c(OC)c1]

4,4'-(((5-Methyl-1,3-phenylene)bis(methylene))bis(oxy))bis(N-ethyl-3-methoxybenzimidamide) dihydrochloride (Compound B-70 dihydrochloride) can be synthesized by the same procedure by substituting methylamine hydrochloride with ethylamine.

Synthesis 41. Synthesis of 4,4'-(((5-Methyl-1,3-phenylene)bis(methylene))bis(oxy))bis(N-isopropyl-3-methoxybenzimidamide) dihydrochloride (Compound B-71 dihydrochloride)

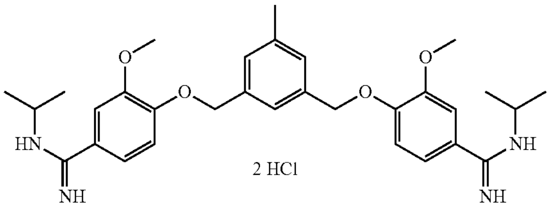 [SMILES: COc1cc(C(=N)NC(C)C)ccc1OCc1cc(C)cc(COc2ccc(C(=N)NC(C)C)cc2OC)c1]

4,4'-(((5-Methyl-1,3-phenylene)bis(methylene))bis(oxy))bis(N-isopropyl-3-methoxybenzimidamide) dihydrochloride (Compound B-71 dihydrochloride) can be synthesized by the same procedure by substituting methylamine hydrochloride with isopropylamine.

Synthesis 42. Synthesis of 2,2'-((((5-Methyl-1,3-phenylene)bis(oxy))bis(methylene))bis(3-methoxy-4,1-phenylene))bis(4,5-dihydro-1H-imidazole) Dihydrochloride (Compound B-77 Dihydrochloride)

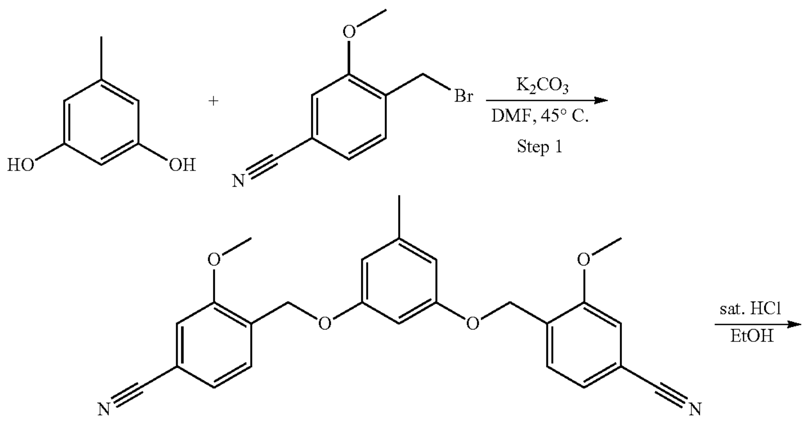

-continued

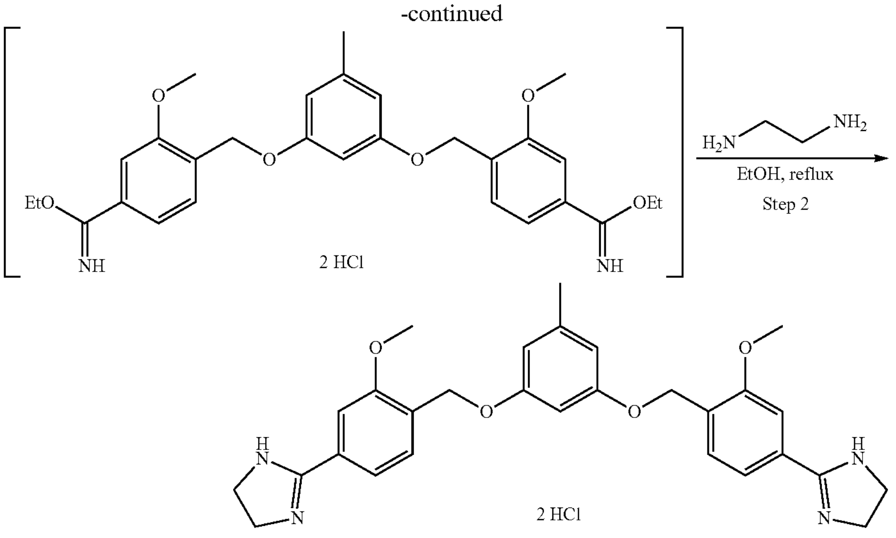

Step 1. Preparation of 4,4'-(((5-Methyl-1,3-phenylene)bis(oxy))bis(methylene))bis(3-methoxybenzonitrile)

A mixture of 5-methylbenzene-1,3-diol (1 equiv), 4-(bromomethyl)-3-methoxybenzonitrile (2 equiv), and $K_2CO_3$ (3 equiv) in DMF is heated at 45° C. for 4 hours. The reaction is then diluted with ice water and stirred for 30 minutes. The resulting precipitate is filtered, washed with water, and dried in air. The isolated precipitate is dissolved in DCM, dried over anhydrous magnesium sulfate, filtered, and concentrated under reduced pressure. The residue is triturated with hexane, filtered, and dried under vacuum to provide 4,4'-(((5-methyl-1,3-phenylene)bis(oxy))bis(methylene))bis(3-methoxybenzonitrile).

Step 2. Preparation of 2,2'-((((5-Methyl-1,3-phenylene)bis(oxy))bis(methylene))bis(3-methoxy-4,1-phenylene))bis(4,5-dihydro-1H-imidazole) Dihydrochloride 4,4'-(((5-Methyl-1,3-phenylene)bis(oxy))bis(methylene))bis(3-methoxybenzonitrile) (1 equiv) is added to saturated ethanolic hydrogen chloride at 0° C. in a dry flask. The reaction mixture is sealed, slowly warmed to room temperature, and stirred until complete consumption of the starting material. The reaction mixture is diluted with anhydrous diethyl ether, and the resulting precipitate is filtered under nitrogen and dried under high vacuum to provide crude diethyl 4,4'-(((5-methyl-1,3-phenylene)bis(oxy))bis(methylene))bis(3-methoxybenzimidate) dihydrochloride, which was used immediately without further purification.

The crude imidate is brought up in ethanol, and ethane-1,2-diamine is added. The reaction mixture is heated to reflux and stirred until complete consumption of the starting material. The reaction mixture is concentrated under reduced pressure. Diethyl ether is added, and the resulting precipitate is filtered. The solid is suspended in ice water and basified with 2 M NaOH. The resulting precipitate is filtered, washed with water, and air dried. The solid is brought up in saturated ethanolic HCl solution and stirred for 6 hours. The ethanol is removed by distillation, and the resulting precipitate is triturated with diethyl ether and filtered. The resulting solid is dried under vacuum at 80° C. for 12 hours to provide 2,2'-((((5-methyl-1,3-phenylene)bis(oxy))bis(methylene))bis(3-methoxy-4,1-phenylene))bis(4,5-dihydro-1H-imidazole) dihydrochloride.

Synthesis 43. Synthesis of 2,2'-((((5-Methyl-1,3-phenylene)bis(oxy))bis(methylene))bis(3-methoxy-4,1-phenylene))bis(1,4,5,6-tetrahydropyrimidine) dihydrochloride

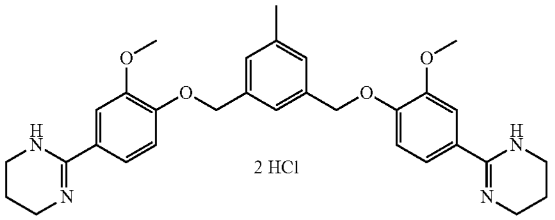 [SMILES: COc1cc(C2=NCCCN2)ccc1OCc1cc(C)cc(COc2ccc(C3=NCCCN3)cc2OC)c1]

2,2'-((((5-Methyl-1,3-phenylene)bis(oxy))bis(methylene))bis(3-methoxy-4,1-phenylene))bis(1,4,5,6-tetrahydropyrimidine) dihydrochloride can be prepared by the same procedure by substituting ethane-1,2-diamine with propane-1,3-diamine in Step 2.

Synthesis 44. Synthesis of 4,4'-((5-Methyl-1,3-phenylene)bis(ethane-2,1-diyl))bis(N-methylbenzimidamide) Dihydrochloride (Compound B-83 Dihydrochloride)

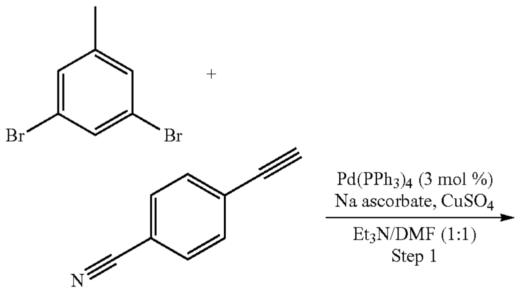

-continued

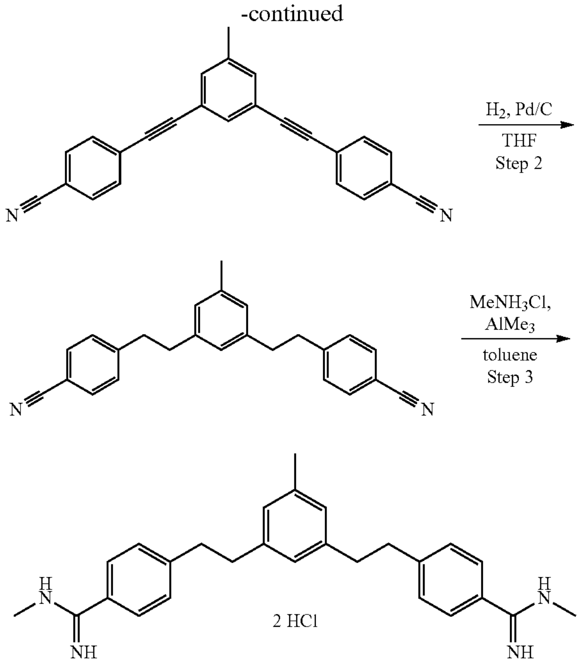

Step 1. Preparation of 4,4'-((5-Methyl-1,3-phenylene)bis(ethyne-2,1-diyl))dibenzonitrile To a solution of 1,3-dibromo-5-methylbenzene (1 equiv) in DMF/$Et_3N$ (1:1) is added $Pd(PPh_3)_4$ (3 mol %) and 4-ethynylbenzonitrile (2 equiv), and the mixture is stirred for 5 minutes. Sodium ascorbate (6 mol % in DMF) and $CuSO_4$ (1 mol % in DMF) are then added, and the reaction is stirred at 80° C. for 4 hours. The reaction is diluted with EtOAc and washed with saturated $NH_4Cl$ solution and brine. The organic layer is dried over anhydrous $Na_2SO_4$, filtered, and concentrated under reduced pressure. The crude residue is purified by column chromatography on silica gel to provide 4,4'-((5-methyl-1,3-phenylene)bis(ethyne-2,1-diyl))dibenzonitrile.

Step 2. Preparation of 4,4'-((5-Methyl-1,3-phenylene)bis(ethane-2,1-diyl))dibenzonitrile To a suspension of 10% Pd/C in THF is added 4,4'-((5-methyl-1,3-phenylene)bis(ethyne-2,1-diyl))dibenzonitrile. The argon is exchanged for $H_2$ gas, and the reaction is stirred overnight. The reaction mixture is diluted with DCM and filtered through celite. The organic phase is washed with water, dried over anhydrous $Na_2SO_4$, filtered, and concentrated under reduced pressure to provide 4,4'-((5-methyl-1,3-phenylene)bis(ethane-2,1-diyl))dibenzonitrile.

Step 3. Preparation of 4,4'-((5-Methyl-1,3-phenylene)bis(ethane-2,1-diyl))bis(N-methylbenzimidamide) Dihydrochloride To a solution of methylamine hydrochloride (3 equiv) in toluene at 0° C. is added trimethylaluminum (2.0 M in toluene, 3 equiv), and the result mixture is warmed up to room temperature and stirred for 2 hours. A solution of 4 4,4'-((5-methyl-1,3-phenylene)bis(ethane-2,1-diyl))dibenzonitrile (1 equiv) in toluene is then added, and the reaction mixture is heated to 80° C. and stirred for 24 hours. The reaction mixture is cooled to room temperature and slowly poured into ice water. DCM is added, and the mixture is filtered through celite. The layers are separated, and the aqueous layer is extracted with DCM (3×). The combined organic layer is washed with brine, dried over anhydrous sodium sulfate, filtered, and concentrated under reduced pressure. The isolated solid is suspended in a 3:1 mixture of anhydrous ethanol and saturated ethanolic HCl solution for 6 hours. The solvent is removed by distillation, and the resulting solid is triturated with dry diethyl ether and filtered. The isolated solid is dried at 80° C. under vacuum for 12 hours to provide 4,4'-((5-methyl-1,3-phenylene)bis(ethane-2,1-diyl))bis(N-methylbenzimidamide) dihydrochloride.

Synthesis 45. Synthesis of 4,4'-((5-Methyl-1,3-phenylene)bis(ethane-2,1-diyl))bis(N-ethylbenzimidamide) dihydrochloride (Compound B-84 dihydrochloride)

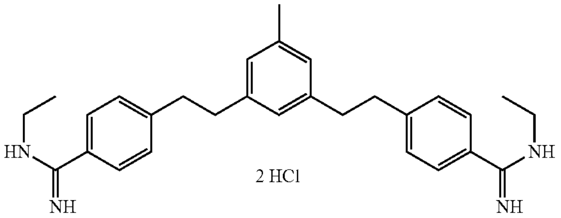 [SMILES: CCNC(=N)c1ccc(CCc2cc(C)cc(CCc3ccc(C(=N)NCC)cc3)c2)cc1]

4,4'-((5-Methyl-1,3-phenylene)bis(ethane-2,1-diyl))bis(N-ethylbenzimidamide) dihydrochloride (Compound B-84 dihydrochloride) can be prepared by the same procedure by substituting methylamine hydrochloride with ethylamine in Step 3.

Synthesis 46. Synthesis of 4,4'-((5-Methyl-1,3-phenylene)bis(ethane-2,1-diyl)bis(N-isopropylbenzimidamide) dihydrochloride (Compound B-85 dihydrochloride)

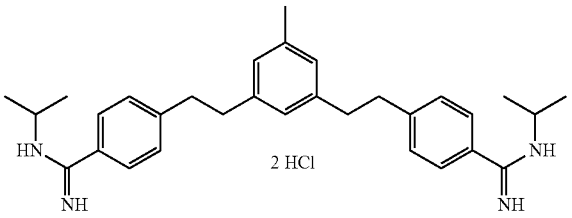 [SMILES: Cc1cc(CCc2ccc(C(=N)NC(C)C)cc2)cc(CCc2ccc(C(=N)NC(C)C)cc2)c1]

4,4'-((5-Methyl-1,3-phenylene)bis(ethane-2,1-diyl))bis(N-isopropylbenzimidamide) dihydrochloride (Compound B-85 dihydrochloride) can be prepared by the same procedure by substituting methylamine hydrochloride with isopropylamine in Step 3.

Synthesis 47. Synthesis of 2,2'-(((5-Methyl-1,3-phenylene)bis(ethane-2,1-diyl))bis(4,1-phenylene))bis(1-ethyl-4,5-dihydro-1H-imidazole) Dihydrochloride (Compound B-90 Dihydrochloride)

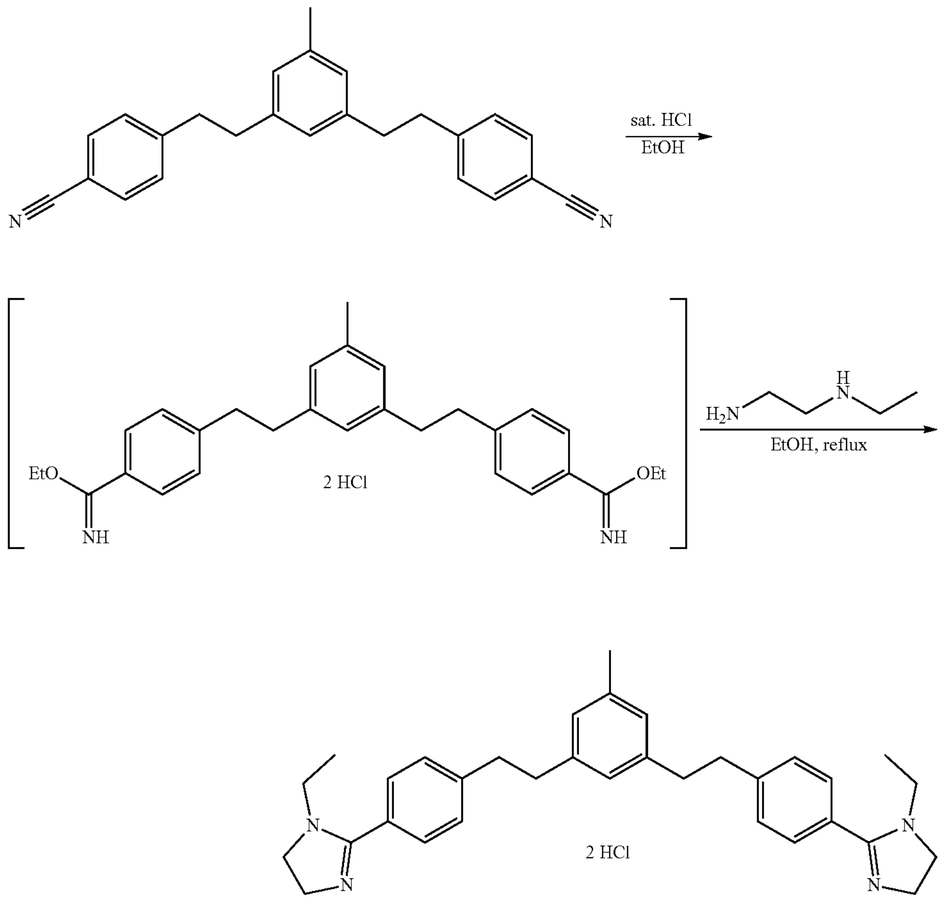

4,4'-((5-Methyl-1,3-phenylene)bis(ethane-2,1-diyl))dibenzonitrile (1 equiv) is added to saturated ethanolic hydrogen chloride at 0° C. in a dry flask. The reaction mixture is sealed, slowly warmed to room temperature, and stirred until complete consumption of the starting material. The reaction mixture is diluted with anhydrous diethyl ether, and the resulting precipitate is filtered under nitrogen and dried under high vacuum to provide crude diethyl 4,4'-((5-methyl-1,3-phenylene)bis(ethane-2,1-diyl))dibenzimidate dihydrochloride, which was used immediately without further purification.

The crude imidate is brought up in ethanol, and N1-ethylethane-1,2-diamine is added. The reaction mixture is heated to reflux and stirred until complete consumption of the starting material. The reaction mixture is concentrated under reduced pressure. Diethyl ether is added, and the resulting precipitate is filtered. The solid is suspended in ice water and basified with 2 M NaOH. The resulting precipitate is filtered, washed with water, and air dried. The solid is brought up in saturated ethanolic HCl solution and stirred for 6 hours. The ethanol is removed by distillation, and the resulting precipitate is triturated with diethyl ether and filtered. The resulting solid is dried under vacuum at 80° C. for 12 hours to provide 2,2'-(((5-methyl-1,3-phenylene)bis(ethane-2,1-diyl))bis(4,1-phenylene))bis(1-ethyl-4,5-dihydro-1H-imidazole) dihydrochloride.

Synthesis 48. Synthesis of 2,2'-(((5-Methyl-1,3-phenylene)bis(ethane-2,1-diyl))bis(4,1-phenylene))bis(4,5-dihydro-1H-imidazole) dihydrochloride (Compound B-17 dihydrochloride)

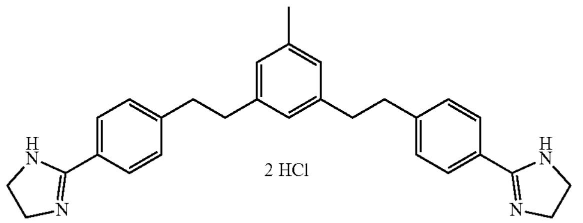 [SMILES: Cc1cc(CCc2ccc(C3=NCCN3)cc2)cc(CCc2ccc(C3=NCCN3)cc2)c1]

2,2'-(((5-Methyl-1,3-phenylene)bis(ethane-2,1-diyl))bis(4,1-phenylene))bis(4,5-dihydro-1H-imidazole) dihydrochloride (Compound B-17 dihydrochloride) can be prepared by the same procedure by substituting N1-ethylethane-1,2-diamine with ethane-1,2-diamine.

Synthesis 49. Synthesis of 2,2'-(((5-Methyl-1,3-phenylene)bis(ethane-2,1-diyl))bis(4,1-phenylene))bis(1-methyl-4,5-dihydro-1H-imidazole) dihydrochloride (Compound B-89 dihydrochloride)

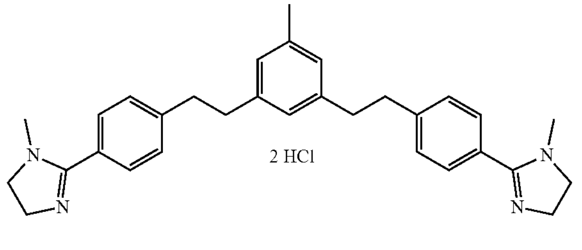 [SMILES: Cc1cc(CCc2ccc(C3=NCCN3C)cc2)cc(CCc2ccc(C3=NCCN3C)cc2)c1]

2,2'-(((5-Methyl-1,3-phenylene)bis(ethane-2,1-diyl))bis(4,1-phenylene))bis(1-methyl-4,5-dihydro-1H-imidazole) dihydrochloride (Compound B-89 dihydrochloride) can be prepared by the same procedure by substituting N1-ethylethane-1,2-diamine with N1-methylethane-1,2-diamine.

Synthesis 50. Synthesis of 2,2'-(((5-Methyl-1,3-phenylene)bis(ethane-2,1-diyl))bis(4,1-phenylene))bis(1-isopropyl-4,5-dihydro-1H-imidazole) dihydrochloride (Compound B-91 dihydrochloride)

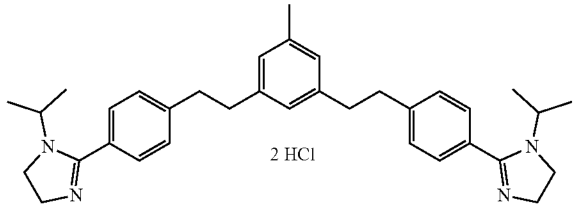 [SMILES: Cc1cc(CCc2ccc(C3=NCCN3C(C)C)cc2)cc(CCc2ccc(C3=NCCN3C(C)C)cc2)c1]

2,2'-(((5-Methyl-1,3-phenylene)bis(ethane-2,1-diyl))bis(4,1-phenylene))bis(1-isopropyl-4,5-dihydro-1H-imidazole) dihydrochloride (Compound B-91 dihydrochloride) can be prepared by the same procedure by substituting N1-ethylethane-1,2-diamine with N1-isopropylethane-1,2-diamine.

Synthesis 51. Synthesis of 4,4'-(((5-Methyl-1,3-phenylene)bis(oxy))bis(methylene))bis(3-methylbenzimidamide) Dihydrochloride (Compound B-95 Dihydrochloride)

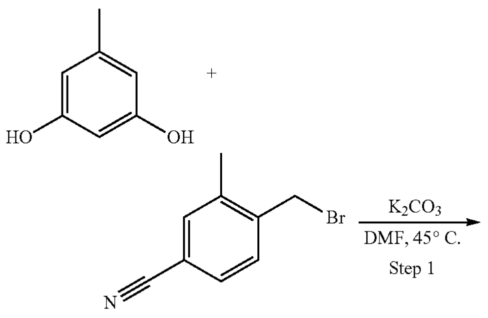

-continued

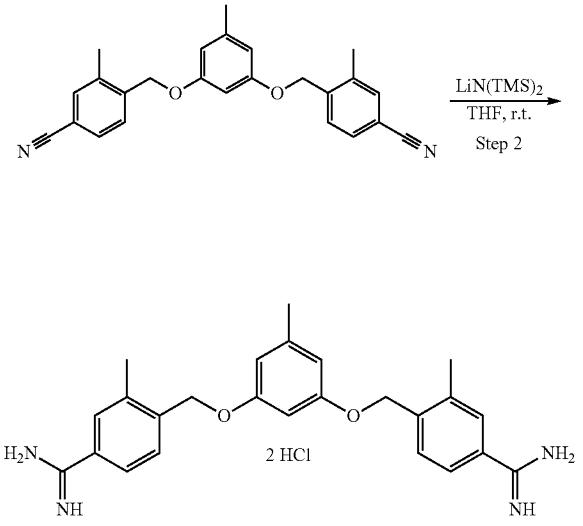

Step 1. Preparation of 4,4'-(((5-Methyl-1,3-phenylene)bis(oxy))bis(methylene))bis(3-methylbenzonitrile)

A mixture of 5-methylbenzene-1,3-diol (1 equiv), 4-(bromomethyl)-3-methylbenzonitrile (2 equiv), and $K_2CO_3$ (3 equiv) in DMF is heated at 45° C. for 4 hours. The reaction is then diluted with ice water and stirred for 30 minutes. The resulting precipitate is filtered, washed with water, and dried in air. The isolated precipitate is dissolved in dichloromethane, dried over anhydrous magnesium sulfate, filtered, and concentrated under reduced pressure. The residue is triturated with hexane, filtered, and dried under vacuum to yield 4,4'-(((5-methyl-1,3-phenylene)bis(oxy))bis(methylene))bis(3-methylbenzonitrile).

Step 2. Preparation of 4,4'-(((5-Methyl-1,3-phenylene)bis(oxy))bis(methylene))bis(3-methylbenzimidamide) Dihydrochloride To a suspension of 4,4'-(((5-methyl-1,3-phenylene)bis(oxy))bis(methylene))bis(3-methylbenzonitrile) (1 equiv) in dry THF (15 mL) stirred over an ice bath is added lithium bis(trimethylsilyl)amide solution (1 M in THF, 6 equiv), and the reaction is stirred at room temperature for 24 hours. The reaction mixture is cooled over an ice bath and then acidified by the slow addition of saturated ethanolic HCl solution until a solid forms. The mixture is stirred for two hours and then all solvents are removed under vacuum. The crude residue is brought up in ether and filtered. The filter cake is brought up in ice water and basified with 2 M NaOH solution until a precipitate forms. The solid is filtered, washed with water, and air dried. The isolated solid is suspended in a 3:1 mixture of anhydrous ethanol and saturated ethanolic HCl solution for 6 hours. The solvent is removed by distillation, and the resulting solid is triturated with dry diethyl ether and filtered. The isolated solid is dried at 80° C. under vacuum for 12 hours to provide 4,4'-(((5-methyl-1,3-phenylene)bis(oxy))bis(methylene))bis(3-methylbenzimidamide) dihydrochloride.

Synthesis 52. Synthesis of 4,4'-(((5-Methyl-1,3-phenylene)bis(sulfanediyl))bis(methylene))bis(3-methylbenzimidamide) dihydrochloride (Compound B-96 dihydrochloride)

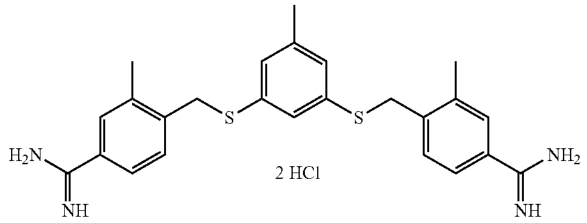 [SMILES: Cc1cc(SCc2ccc(C(=N)N)cc2C)cc(SCc2ccc(C(=N)N)cc2C)c1]

4,4'-(((5-Methyl-1,3-phenylene)bis(sulfanediyl))bis(methylene))bis(3-methylbenzimidamide) dihydrochloride (Compound B-96 dihydrochloride) can be prepared by the same procedure by substituting 5-methylbenzene-1,3-diol with 5-methylbenzene-1,3-dithiol in Step 1.

Synthesis 53. Synthesis of 4,4'-(((5-Methyl-1,3-phenylene)bis(methylazanediyl))bis(methylene))bis(3-methylbenzimidamide) dihydrochloride (Compound B-97 dihydrochloride)

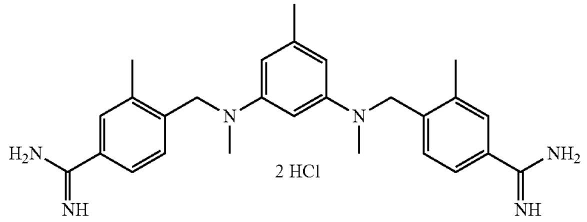 [SMILES: Cc1cc(N(C)Cc2ccc(C(=N)N)cc2C)cc(N(C)Cc2ccc(C(=N)N)cc2C)c1]

4,4'-(((5-Methyl-1,3-phenylene)bis(methylazanediyl))bis(methylene))bis(3-methylbenzimidamide) dihydrochloride (Compound B-97 dihydrochloride) can be prepared by the same procedure by substituting 5-methylbenzene-1,3-diol with N1,N3,5-trimethylbenzene-1,3-diamine in Step 1.

Synthesis 54. Synthesis of 4,4'-(((5-Methyl-1,3-phenylene)bis(methylene))bis(oxy))bis(N-isopropyl-3-methylbenzimidamide) Dihydrochloride (Compound B-101 Dihydrochloride)

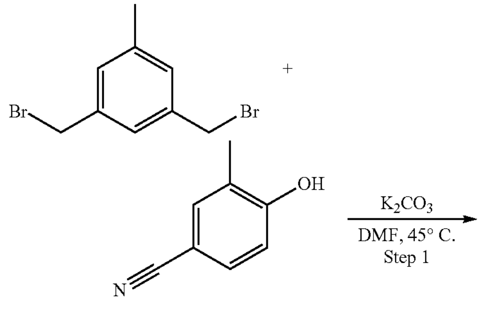

-continued

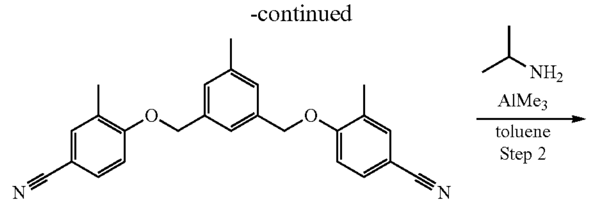

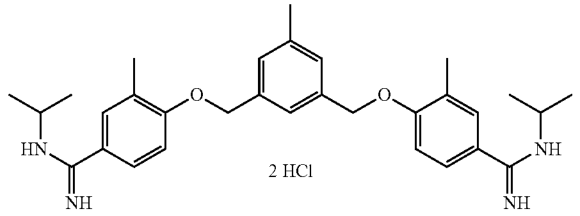

Step 1. Preparation of 4,4'-(((5-Methyl-1,3-phenylene)bis(methylene))bis(oxy))bis(3-methylbenzonitrile)

A mixture of 1,3-bis(bromomethyl)-5-methylbenzene (1 equiv), 4-hydroxy-3-methylbenzonitrile (2 equiv), and $K_2CO_3$ (3 equiv) in DMF is heated at 45° C. for 4 hours. The reaction is then diluted with ice water and stirred for 30 minutes. The resulting precipitate is filtered, washed with water, and dried in air. The isolated precipitate is dissolved in dichloromethane, dried over anhydrous magnesium sulfate, filtered, and concentrated under reduced pressure. The residue is triturated with hexane, filtered, and dried under vacuum to yield 4,4'-(((5-methyl-1,3-phenylene)bis(methylene))bis(oxy))bis(3-methylbenzonitrile).

Step 2. Preparation of 4,4'-(((5-Methyl-1,3-phenylene)bis(methylene))bis(oxy))bis(N-isopropyl-3-methylbenzimidamide) Dihydrochloride To a solution of isopropylamine (3 equiv) in toluene at 0° C. is added trimethylaluminum (2.0 M in toluene, 3 equiv), and the result mixture is warmed up to room temperature and stirred for 2 hours. A solution of 4,4'-(((5-methyl-1,3-phenylene)bis(methylene))bis(oxy))bis(3-methylbenzonitrile) (1 equiv) in toluene is then added, and the reaction mixture is heated to 80° C. and stirred for 24 hours. The reaction mixture is cooled to room temperature and slowly poured into ice water. DCM is added, and the mixture is filtered through celite. The layers are separated, and the aqueous layer is extracted with DCM (3×). The combined organic layer is washed with brine, dried over anhydrous sodium sulfate, filtered, and concentrated under reduced pressure. The isolated solid is suspended in a 3:1 mixture of anhydrous ethanol and saturated ethanolic HCl solution for 6 hours. The solvent is removed by distillation, and the resulting solid is triturated with dry diethyl ether and filtered. The isolated solid is dried at 80° C. under vacuum for 12 hours to provide 4,4'-(((5-methyl-1,3-phenylene)bis(methylene))bis(oxy))bis(N-isopropyl-3-methylbenzimidamide) dihydrochloride.

Synthesis 55. Synthesis of 4,4'-(((5-Methyl-1,3-phenylene)bis(methylene))bis(oxy))bis(N-ethyl-3-methylbenzimidamide) dihydrochloride (Compound B-100 dihydrochloride)

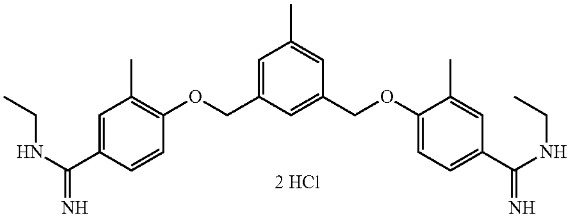 [SMILES: CCNC(=N)c1ccc(OCc2cc(C)cc(COc3ccc(C(=N)NCC)cc3C)c2)c(C)c1]

4,4'-(((5-Methyl-1,3-phenylene)bis(methylene))bis(oxy))bis(N-ethyl-3-methylbenzimidamide) dihydrochloride (Compound B-100 dihydrochloride) can be prepared by the same procedure by substituting isopropylamine with ethylamine in Step 2.

Synthesis 56. Synthesis of 4,4'-(((5-Methyl-1,3-phenylene)bis(methylene))bis(oxy))bis(N,3-dimethylbenzimidamide) dihydrochloride (Compound B-99 dihydrochloride)

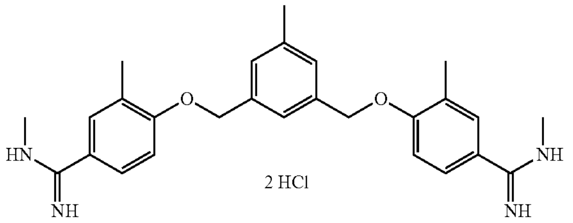 [SMILES: CNC(=N)c1ccc(OCc2cc(C)cc(COc3ccc(C(=N)NC)cc3C)c2)c(C)c1]

4,4'-(((5-Methyl-1,3-phenylene)bis(methylene))bis(oxy))bis(N,3-dimethylbenzimidamide) dihydrochloride (Compound B-99 dihydrochloride) can be prepared by the same procedure by substituting isopropylamine with methylamine hydrochloride in Step 2.

Synthesis 57. Synthesis of 2,2'-(((5-Methyl-1,3-phenylene)bis(ethane-2,1-diyl))bis(3-methyl-4,1-phenylene))bis(4,5-dihydro-1H-imidazole) Dihydrochloride (Compound B-110 Dihydrochloride)

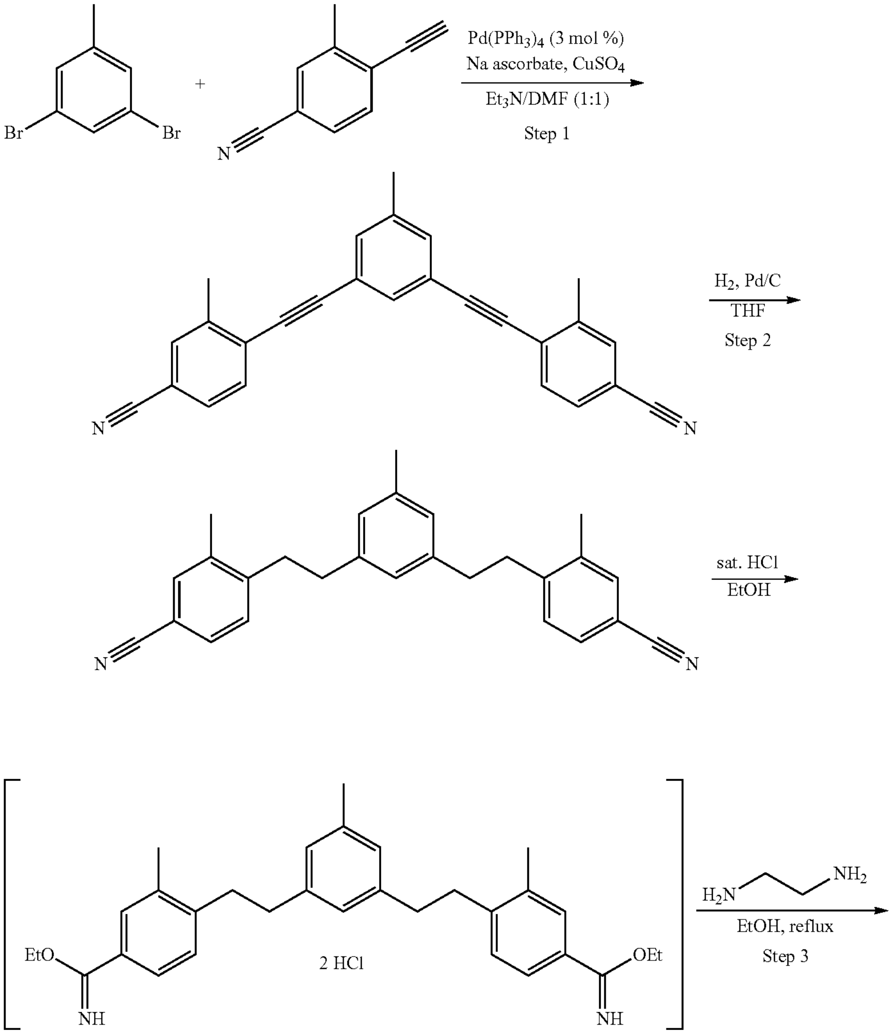

-continued

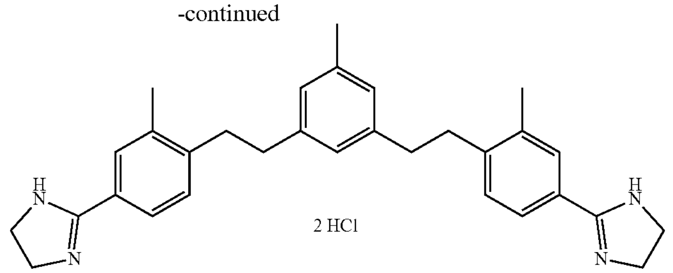

Step 1. Preparation of 4,4'-((5-Methyl-1,3-phenylene)bis(ethyne-2,1-diyl))bis(3-methylbenzonitrile)

To a solution of 1,3-dibromo-5-methylbenzene (1 equiv) in DMF/$Et_3N$ (1:1) is added $Pd(PPh_3)_4$ (3 mol %) and 4-ethynyl-3-methylbenzonitrile (2 equiv), and the mixture is stirred for 5 minutes. Sodium ascorbate (6 mol % in DMF) and $CuSO_4$ (1 mol % in DMF) are then added, and the reaction is stirred at 80° C. for 4 hours. The reaction is diluted with EtOAc and washed with saturated $NH_4Cl$ solution and brine. The organic layer is dried over anhydrous $Na_2SO_4$, filtered, and concentrated under reduced pressure. The crude residue is purified by column chromatography on silica gel to provide 4,4'-((5-methyl-1,3-phenylene)bis(ethyne-2,1-diyl))bis(3-methylbenzonitrile).

Step 2. Preparation of 44,4'-((5-Methyl-1,3-phenylene)bis(ethane-2,1-diyl))bis(3-methylbenzonitrile)

To a suspension of 10% Pd/C in THF is added 4,4'-((5-methyl-1,3-phenylene)bis(ethyne-2,1-diyl))bis(3-methylbenzonitrile). The argon is exchanged for $H_2$ gas, and the reaction is stirred overnight. The reaction mixture is diluted with DCM and filtered through celite. The organic phase is washed with water, dried over anhydrous $Na_2SO_4$, filtered, and concentrated under reduced pressure to provide 4,4'-((5-methyl-1,3-phenylene)bis(ethane-2,1-diyl))bis(3-methylbenzonitrile).

Step 3. Preparation of 2,2'-(((5-Methyl-1,3-phenylene)bis(ethane-2,1-diyl))bis(3-methyl-4,1-phenylene))bis(4,5-dihydro-1H-imidazole) Dihydrochloride 4,4'-((5-Methyl-1,3-phenylene)bis(ethane-2,1-diyl))bis(3-methylbenzonitrile) (1 equiv) is added to saturated ethanolic hydrogen chloride at 0° C. in a dry flask. The reaction mixture is sealed, slowly warmed to room temperature, and stirred until complete consumption of the starting material. The reaction mixture is diluted with anhydrous diethyl ether, and the resulting precipitate is filtered under nitrogen and dried under high vacuum to provide crude diethyl 4,4'-((5-methyl-1,3-phenylene)bis(ethane-2,1-diyl))bis(3-methylbenzimidate) dihydrochloride, which was used immediately without further purification.

The crude imidate is brought up in ethanol, and N1-ethylethane-1,2-diamine is added. The reaction mixture is heated to reflux and stirred until complete consumption of the starting material. The reaction mixture is concentrated under reduced pressure. Diethyl ether is added, and the resulting precipitate is filtered. The solid is suspended in ice water and basified with 2 M NaOH. The resulting precipitate is filtered, washed with water, and air dried. The solid is brought up in saturated ethanolic HCl solution and stirred for 6 hours. The ethanol is removed by distillation, and the resulting precipitate is triturated with diethyl ether and filtered. The resulting solid is dried under vacuum at 80° C. for 12 hours to provide 2,2'-(((5-methyl-1,3-phenylene)bis(ethane-2,1-diyl))bis(3-methyl-4,1-phenylene))bis(4,5-dihydro-1H-imidazole) dihydrochloride.

Synthesis 58. Synthesis of 2,2'-(((5-methyl-1,3-phenylene)bis(ethane-2,1-diyl))bis(3-methyl-4,1-phenylene))bis(1-methyl-4,5-dihydro-1H-imidazole) dihydrochloride

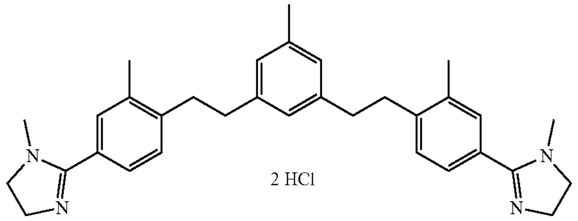 [SMILES: Cc1cc(CCc2ccc(C3=NCCN3C)cc2C)cc(CCc2ccc(C3=NCCN3C)cc2C)c1]

2,2'-(((5-methyl-1,3-phenylene)bis(ethane-2,1-diyl))bis(3-methyl-4,1-phenylene))bis(1-methyl-4,5-dihydro-1H-imidazole) dihydrochloride can be prepared by the same procedure by substituting ethane-1,2-diamine with N1-methylethane-1,2-diamine in Step 3.

Synthesis 59. Synthesis of 2,2'-(((5-Methyl-1,3-phenylene)bis(ethane-2,1-diyl))bis(3-methyl-4,1-phenylene))bis(1-ethyl-4,5-dihydro-1H-imidazole) dihydrochloride

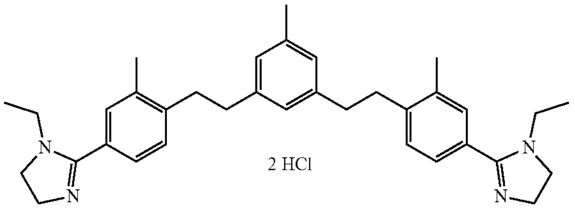 [SMILES: CCN1CCN=C1c1ccc(CCc2cc(C)cc(CCc3ccc(C4=NCCN4CC)cc3C)c2)c(C)c1]

2,2'-(((5-Methyl-1,3-phenylene)bis(ethane-2,1-diyl))bis(3-methyl-4,1-phenylene))bis(1-ethyl-4,5-dihydro-1H-imidazole) dihydrochloride can be prepared by the same procedure by substituting ethane-1,2-diamine with N1-ethylethane-1,2-diamine.

Synthesis 60. Synthesis of 2,2'-(((5-Methyl-1,3-phenylene)bis(ethane-2,1-diyl))bis(3-methyl-4,1-phenylene))bis(1-isopropyl-4,5-dihydro-1H-imidazole) dihydrochloride

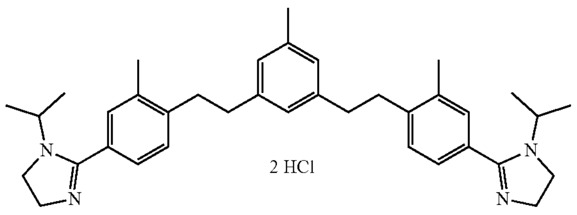 [SMILES: Cc1cc(CCc2ccc(C3=NCCN3C(C)C)cc2C)cc(CCc2ccc(C3=NCCN3C(C)C)cc2C)c1]

2,2'-(((5-Methyl-1,3-phenylene)bis(ethane-2,1-diyl))bis(3-methyl-4,1-phenylene))bis(1-isopropyl-4,5-dihydro-1H-imidazole) dihydrochloride can be prepared by the same procedure by substituting ethane-1,2-diamine with N1-isopropylethane-1,2-diamine.

Synthesis 61. Synthesis of 2,2'-(((5-Methyl-1,3-phenylene)bis(ethane-2,1-diyl))bis(3-methyl-4,1-phenylene))bis(1,4,5,6-tetrahydropyrimidine) dihydrochloride

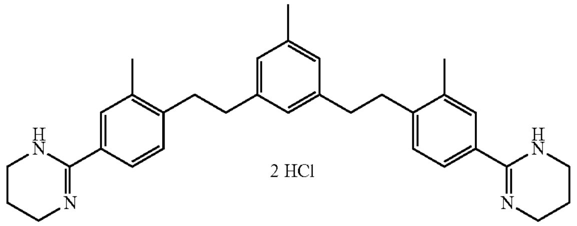 [SMILES: Cc1cc(CCc2ccc(C3=NCCCN3)cc2C)cc(CCc2ccc(C3=NCCCN3)cc2C)c1]

2,2'-(((5-Methyl-1,3-phenylene)bis(ethane-2,1-diyl))bis(3-methyl-4,1-phenylene))bis(1,4,5,6-tetrahydropyrimidine) dihydrochloride can be prepared by the same procedure by substituting ethane-1,2-diamine with propane-1,3-diamine.

Synthesis 62. Synthesis of 4,4'-(((5-Methyl-1,3-phenylene)bis(sulfanediyl))bis(methylene))dibenzimidamide Dihydrochloride (Compound B-115 Dihydrochloride)

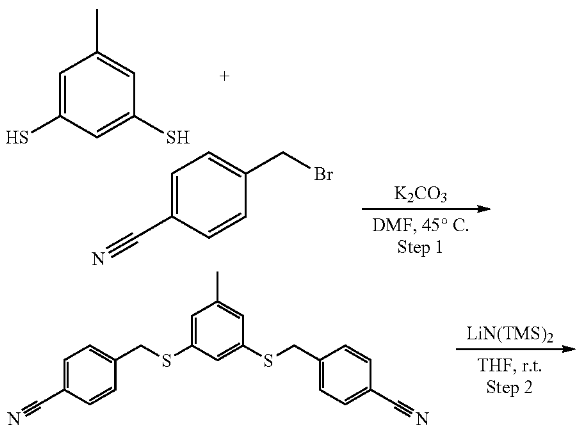

-continued

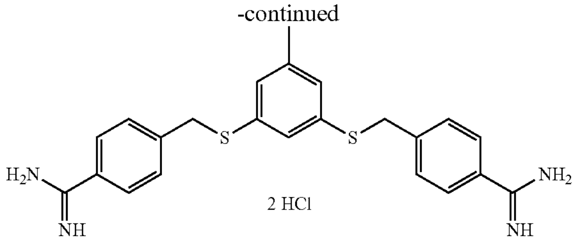

Step 1. Preparation of 4,4'-(((5-Methyl-1,3-phenylene)bis(sulfanediyl))bis(methylene))dibenzonitrile Dihydrochloride A mixture of 5-methylbenzene-1,3-dithiol (1 equiv), 4-(bromomethyl)benzonitrile (2 equiv), and $K_2CO_3$ (3 equiv) in DMF is heated at 45° C. for 4 hours. The reaction is then diluted with ice water and stirred for 30 minutes. The resulting precipitate is filtered, washed with water, and dried in air. The isolated precipitate is dissolved in dichloromethane, dried over anhydrous magnesium sulfate, filtered, and concentrated under reduced pressure. The residue is triturated with hexane, filtered, and dried under vacuum to yield 4,4'-(((5-methyl-1,3-phenylene)bis(sulfanediyl))bis(methylene))dibenzonitrile.

Step 2. Preparation of 4,4'-(((5-Methyl-1,3-phenylene)bis(sulfanediyl))bis(methylene))dibenzimidamide Dihydrochloride To a suspension of 4,4'-(((5-methyl-1,3-phenylene)bis(sulfanediyl))bis(methylene))dibenzonitrile (1 equiv) in dry THF (15 mL) stirred over an ice bath is added lithium bis(trimethylsilyl)amide solution (1 M in THF, 6 equiv), and the reaction is stirred at room temperature for 24 hours. The reaction mixture is cooled over an ice bath and then acidified by the slow addition of saturated ethanolic HCl solution until a solid forms. The mixture is stirred for two hours and then all solvents are removed under vacuum. The crude residue is brought up in ether and filtered. The filter cake is brought up in ice water and basified with 2 M NaOH solution until a precipitate forms. The solid is filtered, washed with water, and air dried. The isolated solid is suspended in a 3:1 mixture of anhydrous ethanol and saturated ethanolic HCl solution for 6 hours. The solvent is removed by distillation, and the resulting solid is triturated with dry diethyl ether and filtered. The isolated solid is dried at 80° C. under vacuum for 12 hours to provide 4,4'-(((5-methyl-1,3-phenylene)bis(sulfanediyl))bis(methylene))dibenzimidamide dihydrochloride.

Synthesis 63. Synthesis of 4,4'-(((5-Methyl-1,3-phenylene)bis(oxy))bis(methylene))dibenzimidamide dihydrochloride (Compound B-114 dihydrochloride)

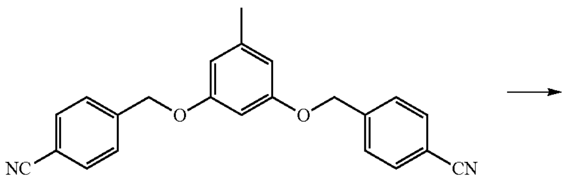

-continued

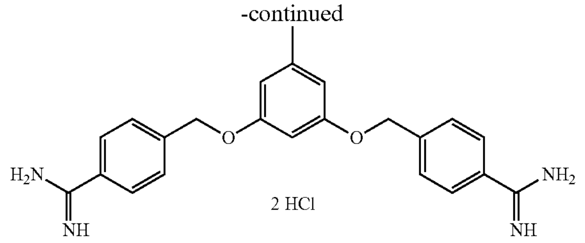

Synthesis of 1, 3-Bis {(4-cyano)-benzyloxy}-5-methylbenzene: A mixture of orcinol (0.5 g, 4.1 mmol), 4-cyanobenzyl bromide (1.65 g, 8.4 mmol) and anhydrous $K_2CO_3$ (1.66 g, 12 mmol) in 10 ml DMF was stirred at room temperature overnight [TLC (Hex:EtOAc 4:1) monitored the reaction]. Then the reaction mixture was diluted with ice water (70 ml) and stirred for 30 min. The yellow precipitate was filtered, washed with water, and dried in air. Then the yellow solid was dissolved in a dichloromethane (100 ml), dried over anhydrous $MgSO_4$, filtered, concentrated with rotavapor, triturated with hexane, filtered and dried in vacuum to yield 1, 3-Bis {(4-cyano)-benzyloxy}-5-methylbenzene as a yellow solid (0.97 g, 66.5%); 1H NMR (CDCl3): 7.70 (d, 4H, J=8.3 Hz), 7.55 (d, 4H, J=8.2 Hz), 6.45 (d, 2H, J=2.0 Hz), 6.41 (d, 1H, J=2.1 Hz), 5.11 (s, 4H), 2.33 (s, 3H); 13C NMR (CDCl3) 159.35, 142.42, 140.78, 132.43, 127.54, 118.70, 111.75, 108.54, 99.36, 68.89, 21.87; MS: HRMS-ESI-POS.: calc. for $C_{23}H_{18}N_2O_2Na$ m/z 377.1260 (M++Na), found m/z 377.1245.

Synthesis of 1, 3-Bis {(4-amidino)-benzyloxy}-5-methylbenzene dihydrochloride: The dinitrile (0.33 g, 0.93 mmol) was converted to 1, 3-Bis {(4-amidino)-benzyloxy}-5-methylbenzene dihydrochloride as white solid following Step 2b of General Route 7 (0.3 g, 75%); mp. 280-81° C.; $^1$H NMR (DMSO-$d_6$) 9.46 (s, 4H), 9.25 (s, 4H), 7.87 (d, 4H, J=7.8 Hz), 7.65 (d, 4H, J=8.2 Hz), 6.51 (s, 1H), 6.49 (s, 2H), 5.20 (s, 4H), 2.24 (s, 3H); $^{13}$C NMR (DMSO-d6) 165.92, 159.53, 143.81, 140.43, 128.80, 128.05, 127.69, 108.74, 99.77, 68.69, 21.88; analysis calc. for $C_{23}H_{24}N_4$ O2·2HCl·1$H_2$O: C, 57.62; H, 5.88; N, 11.68, Found: C, 57.98; H, 5.49; N, 11.34.

Synthesis 64. Synthesis of 4,4'-(((5-Methyl-1,3-phenylene)bis(methylazanediyl))bis(methylene))dibenzimidamide dihydrochloride (Compound B-116 dihydrochloride)

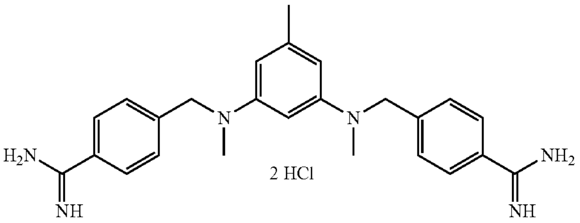 [SMILES: Cc1cc(N(C)Cc2ccc(C(=N)N)cc2)cc(N(C)Cc2ccc(C(=N)N)cc2)c1]

4,4'-(((5-Methyl-1,3-phenylene)bis(methylazanediyl))bis(methylene))dibenzimidamide dihydrochloride (Compound B-116 dihydrochloride) can be prepared by the same procedure by substituting 5-methylbenzene-1,3-dithiol with N1,N3,5-trimethylbenzene-1,3-diamine in Step 1.

Synthesis 65. Synthesis of 4-((3-((4-(4,5-Dihydro-1H-imidazol-2-yl)-2-fluorobenzyl)oxy)-2-fluorophenoxy)methyl)-3-fluorobenzimidamide Dihydrochloride

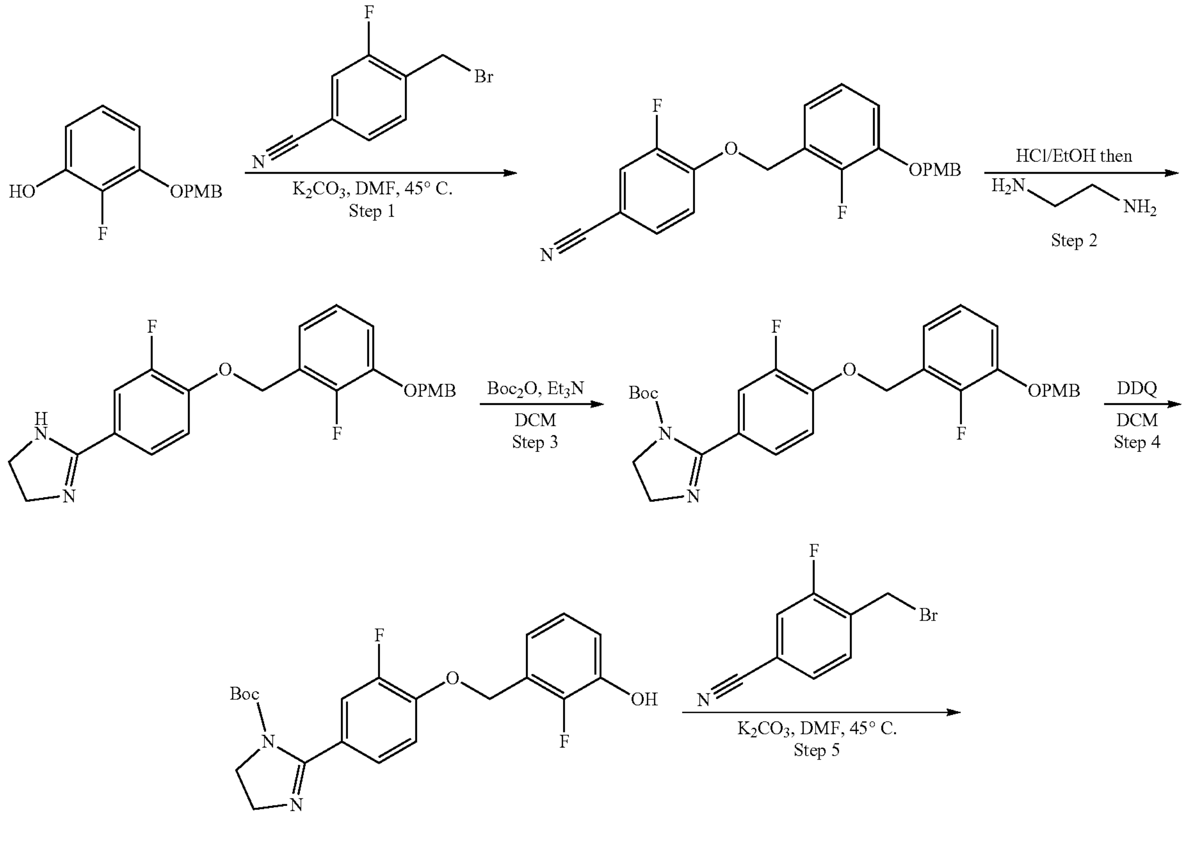

-continued

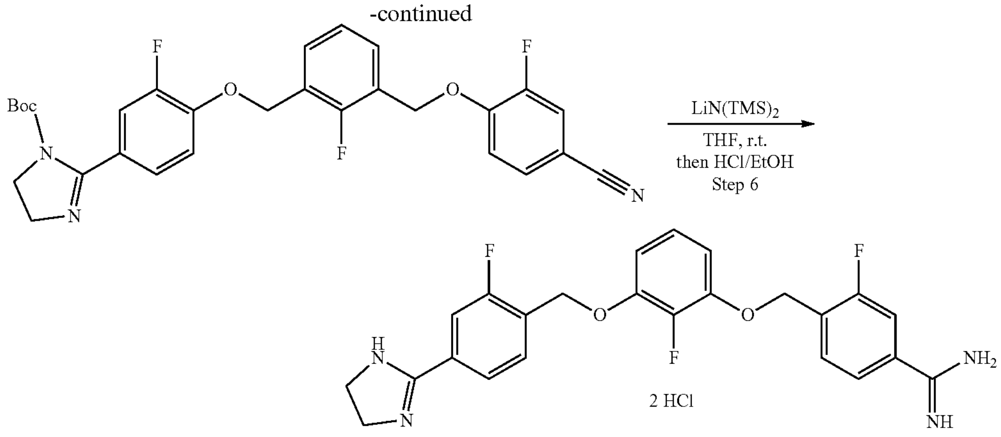

Step 1. Preparation of 3-Fluoro-4-((2-fluoro-3-((4-methoxybenzyl)oxy)phenoxy)methyl)benzonitrile A mixture of 2-fluoro-3-((4-methoxybenzyl)oxy) phenol (1 equiv), 4-(bromomethyl)-3-fluorobenzonitrile (1 equiv), and potassium carbonate (2 equiv) in DMF is heated at 45° C. for 4 hours. The reaction is then diluted with ice water and stirred for 30 minutes. The resulting precipitate is filtered, washed with water, and dried in air. The isolated precipitate is dissolved in dichloromethane, dried over anhydrous magnesium sulfate, filtered, and concentrated under reduced pressure. The residue is triturated with hexane, filtered, and dried under vacuum to provide 3-fluoro-4-((2-fluoro-3-((4-methoxybenzyl)oxy) phenoxy)methyl)benzonitrile.

Step 2. Preparation of 2-(3-Fluoro-4-((2-fluoro-3-((4-methoxybenzyl)oxy)phenoxy)methyl)phenyl)-4,5-dihydro-1H-imidazole 3-Fluoro-4-((2-fluoro-3-((4-methoxybenzyl)oxy)phenoxy)methyl)benzonitrile is added to anhydrous EtOH saturated with hydrogen chloride at 0° C. in a dry flask. The reaction mixture is sealed, slowly warmed to room temperature, and stirred until complete consumption of the starting material. The reaction mixture is diluted with anhydrous diethyl ether, and the resulting precipitate is filtered under nitrogen and dried under vacuum to provide the crude ethyl imidate hydrochloride, which is used immediately without further purification.

The crude imidate is brought up in ethanol, and ethane-1,2-diamine is added. The reaction mixture is heated to reflux and stirred until complete consumption of the starting material. The reaction mixture is concentrated under reduced pressure, and DCM and water are added. The layers are separated, and the aqueous layer is extracted with 3×DCM. The combined organic layer is dried over anhydrous sodium sulfate, filtered, and concentrated under reduced pressure. Purification by column chromatography on silica gel provides 2-(3-fluoro-4-((2-fluoro-3-((4-methoxybenzyl)oxy)phenoxy)methyl)phenyl)-4,5-dihydro-1H-imidazole.

Step 3. Preparation of tert-Butyl 2-(3-Fluoro-4-((2-fluoro-3-((4-methoxybenzyl)oxy)phenoxy)methyl)phenyl)-4,5-dihydro-1H-imidazole-1-carboxylate To a solution of 2-(3-fluoro-4-((2-fluoro-3-((4-methoxybenzyl)oxy)phenoxy)methyl)phenyl)-4,5-dihydro-1H-imidazole (1 equiv) in DCM is added triethylamine (2 equiv) and di tert-butyl dicarbonate (1 equiv) at 0° C., and the reaction is warmed up to room temperature and stirred for two hours. The reaction mixture is quenched by the addition of saturated ammonium chloride, and the layers are separated. The aqueous layer is extracted with 3×DCM. The combined organic layer is dried over anhydrous sodium sulfate, filtered, and concentrated under reduced pressure. Purification by column chromatography on silica gel provides tert-butyl 2-(3-fluoro-4-((2-fluoro-3-((4-methoxybenzyl)oxy)phenoxy)methyl)phenyl)-4,5-dihydro-1H-imidazole-1-carboxylate.

Step 4. Preparation of tert-Butyl 2-(3-Fluoro-4-((2-fluoro-3-hydroxyphenoxy)methyl)phenyl)-4,5-dihydro-1H-imidazole-1-carboxylate To a solution of tert-butyl 2-(3-fluoro-4-((2-fluoro-3-((4-methoxybenzyl)oxy)phenoxy)methyl)phenyl)-4,5-dihydro-1H-imidazole-1-carboxylate (1 equiv) in DCM is added 4,5-dichloro-3,6-dioxocyclohexa-1,4-diene-1,2-dicarbonitrile (1 equiv), and the reaction is stirred at room temperature until complete consumption of the starting material. Methanol and sodium borohydride (5 equiv) is then added in portions, and the reaction mixture is stirred for 24 hours. The reaction mixture is concentrated under reduced pressure and brought up in dichloromethane and water. The layers are separated, and the aqueous layer is extracted with 3×DCM. The combined organic layer is dried over anhydrous sodium sulfate, filtered, and concentrated under reduced pressure. Purification by column chromatography on silica gel provides tert-butyl 2-(3-fluoro-4-((2-fluoro-3-hydroxyphenoxy)methyl)phenyl)-4,5-dihydro-1H-imidazole-1-carboxylate.

Step 5. Preparation of tert-Butyl 2-(4-((3-((4-Cyano-2-fluorobenzyl)oxy)-2-fluorophenoxy)methyl)-3-fluorophenyl)-4,5-dihydro-1H-imidazole-1-carboxylate A mixture of tert-butyl 2-(3-fluoro-4-((2-fluoro-3-hydroxyphenoxy)methyl)phenyl)-4,5-dihydro-1H-imidazole-1-carboxylate (1 equiv), 4-(bromomethyl)-3-fluorobenzonitrile (1 equiv), and potassium carbonate (2 equiv) in DMF is heated at 45° C. for 4 hours. The reaction is then diluted with ice water and stirred for 30 minutes. The resulting precipitate is filtered, washed with water, and dried in air. The isolated precipitate is dissolved in dichloromethane, dried over anhydrous magnesium sulfate, filtered, and concentrated under reduced pressure. The residue is triturated with hexane, filtered, and dried under vacuum to provide tert-butyl 2-(4-((3-((4-cyano-2-fluorobenzyl)oxy)-2-fluorophenoxy)methyl)-3-fluorophenyl)-4,5-dihydro-1H-imidazole-1-carboxylate.

Step 6. Preparation of 4-((3-((4-(4,5-Dihydro-1H-imidazol-2-yl)-2-fluorobenzyl)oxy)-2-fluorophenoxy)methyl)-3-fluorobenzimidamide Dihydrochloride To a solution of tert-butyl 2-(4-((3-((4-cyano-2-fluorobenzyl)oxy)-2-fluorophenoxy)methyl)-3-fluorophenyl)-4,5-dihydro-1H-imidazole-1-carboxylate (1 equiv) in dry THF stirred over an ice bath is added lithium bis(trimethylsilyl) amide (1 M in THF, 1 equiv), and the reaction is stirred at room temperature for 24 hours. The reaction mixture is cooled over an ice bath and then acidified by the slow addition of saturated ethanolic HCL solution until a solid forms. The mixture is stirred for two hours and then all solvents are removed under vacuum. The crude residue is brought up in ether and filtered. The filter cake is brought up in ice water and basified with 2 M NaOH solution until a precipitate forms. The solid is filtered, washed with water, and air dried. The isolated solid is suspended in a 3:1 mixture of anhydrous ethanol and saturated ethanolic HCl solution for 6 hours. The solvent is removed by distillation, and the resulting solid is triturated with dry diethyl ether and filtered. The solvent is removed by distillation, and the resulting solid is dried at 80° C. for 12 hours to provide 4-((3-((4-(4,5-dihydro-1H-imidazol-2-yl)-2-fluorobenzyl)oxy)-2-fluorophenoxy)methyl)-3-fluorobenzimidamide dihydrochloride.

Synthesis 66. Synthesis of 3-Fluoro-4-((2-fluoro-3-((2-fluoro-4-(1,4,5,6-tetrahydropyrimidin-2-yl)benzyl)oxy)phenoxy)methyl)benzimidamide dihydrochloride

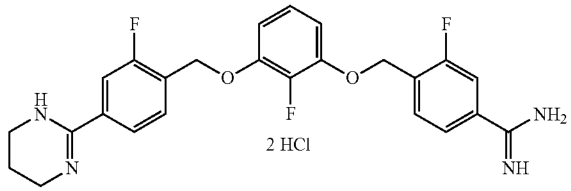 [SMILES: N=C(N)c1ccc(COc2cccc(OCc3ccc(C4=NCCCN4)cc3F)c2F)c(F)c1]

3-Fluoro-4-((2-fluoro-3-((2-fluoro-4-(1,4,5,6-tetrahydropyrimidin-2-yl)benzyl)oxy)phenoxy)methyl)benzimidamide dihydrochloride can be prepared by the same procedure by substituting ethane-1,2-diamine with propane-1,3-diamine in Step 2.

Synthesis 67. Synthesis of 3-Methyl-4-(3-methyl-5-(2-methyl-4-(1,4,5,6-tetrahydropyrimidin-2-yl)phenethyl)phenethyl)benzimidamide Dihydrochloride

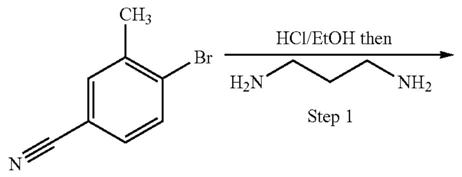

-continued

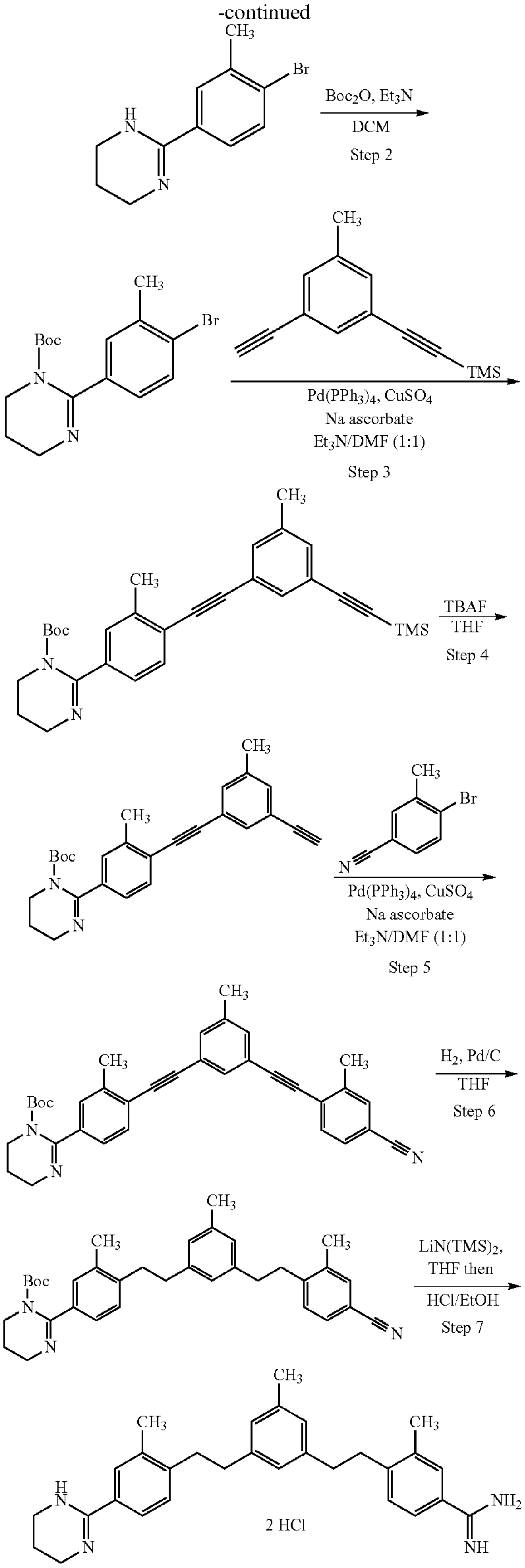

Step 1. Preparation of 2-(4-Bromo-3-methylphenyl)-1,4,5,6-tetrahydropyrimidine 4-bromo-3-methylbenzonitrile is added to anhydrous EtOH saturated with hydrogen chloride at 0° C. in a dry flask. The reaction mixture is sealed, slowly warmed to room temperature, and stirred until complete consumption of the starting material. The reaction mixture is diluted with anhydrous diethyl ether, and the resulting precipitate is filtered under nitrogen and dried under vacuum to provide the crude ethyl imidate hydrochloride, which is used immediately without further purification.

The crude imidate is brought up in ethanol, and propane-1,3-diamine is added. The reaction mixture is heated to reflux and stirred until complete consumption of the starting material. The reaction mixture is concentrated under reduced pressure, and DCM and water are added. The layers are separated, and the aqueous layer is extracted with 3×DCM. The combined organic layer is dried over anhydrous sodium sulfate, filtered, and concentrated under reduced pressure. Purification by column chromatography on silica gel provides 2-(4-bromo-3-methylphenyl)-1,4,5,6-tetrahydropyrimidine.

Step 2. Preparation of tert-Butyl 2-(4-Bromo-3-methylphenyl)-5,6-dihydropyrimidine-1 (4H)-carboxylate To a solution of 2-(4-bromo-3-methylphenyl)-1,4,5,6-tetrahydropyrimidine (1 equiv) in DCM is added triethylamine (2 equiv) and di tert-butyl dicarbonate (1 equiv) at 0° C., and the reaction is warmed up to room temperature and stirred for two hours. The reaction mixture is quenched by the addition of saturated ammonium chloride, and the layers are separated. The aqueous layer is extracted with 3×DCM. The combined organic layer is dried over anhydrous sodium sulfate, filtered, and concentrated under reduced pressure. Purification by column chromatography on silica gel provides tert-butyl 2-(4-bromo-3-methylphenyl)-5,6-dihydropyrimidine-1 (4H)-carboxylate.

Step 3. Preparation of tert-Butyl 2-(3-methyl-4-((3-methyl-5-((trimethylsilyl)ethynyl)phenyl)ethynyl)phenyl)-5,6-dihydropyrimidine-1 (4H)-carboxylate To a solution of tert-butyl 2-(4-bromo-3-methylphenyl)-5,6-dihydropyrimidine-1 (4H)-carboxylate (1 equiv) in DMF/$Et_3N$ (1:1) is added $Pd(PPh_3)_4$ (3 mol %) and ((3-ethynyl-5-methylphenyl)ethynyl)trimethylsilane (1 equiv), and the mixture is stirred for five minutes. Sodium ascorbate (6 mol % in DMF) and $CuSO_4$ (1 mol % in DMF) are then added, and the reaction is stirred at 80° C. for 4 hours. The reaction is diluted with EtOAc and washed with saturated $NH_4Cl$ solution and brine. The organic layer is dried over anhydrous $Na_2SO_4$, filtered, and concentrated under reduced pressure. The crude residue is purified by column chromatography on silica gel to provide tert-Butyl 2-(3-methyl-4-((3-methyl-5-((trimethylsilyl) ethynyl)phenyl) ethynyl)phenyl)-5,6-dihydropyrimidine-1 (4H)-carboxylate.

Step 4. Preparation of tert-Butyl 2-(4-((3-Ethynyl-5-methylphenyl)ethynyl)-3-methylphenyl)-5,6-dihydropyrimidine-1 (4H)-carboxylate To a solution of tert-Butyl 2-(3-methyl-4-((3-methyl-5-((trimethylsilyl) ethynyl)phenyl) ethynyl)phenyl)-5,6-dihydropyrimidine-1 (4H)-carboxylate (1 equiv) in THE is added TBAF (1 M in THF, 2 equiv), and the reaction is stirred at room temperature for 6 hours. The reaction is quenched with saturated $NH_4Cl$ solution and diethyl ether, and the layers are separated. The aqueous layer is extracted with 3× diethyl ether. The combined organic layer is washed with brine, dried over anhydrous magnesium sulfate, filtered, and concentrated under reduced pressure. Purification by column chromatography on silica gel provides tert-butyl 2-(4-((3-ethynyl-5-methylphenyl)ethynyl)-3-methylphenyl)-5,6-dihydropyrimidine-1 (4H)-carboxylate.

Step 5. Preparation of tert-Butyl 2-(4-((3-((4-Cyano-2-methylphenyl)ethynyl)-5-methylphenyl) ethynyl)-3-methylphenyl)-5,6-dihydropyrimidine-1 (4H)-carboxylate To a solution of tert-butyl 2-(4-((3-ethynyl-5-methylphenyl) ethynyl)-3-methylphenyl)-5,6-dihydropyrimidine-1 (4H)-carboxylate (1 equiv) in DMF/$Et_3N$ (1:1) is added $Pd(PPh_3)_4$ (3 mol %) and 4-bromo-3-methylbenzonitrile (1 equiv), and the mixture is stirred for five minutes. Sodium ascorbate (6 mol % in DMF) and $CuSO_4$ (1 mol % in DMF) are then added, and the reaction is stirred at 80° C. for 4 hours. The reaction is diluted with EtOAc and washed with saturated $NH_4Cl$ solution and brine. The organic layer is dried over anhydrous $Na_2SO_4$, filtered, and concentrated under reduced pressure. The crude residue is purified by column chromatography on silica gel to provide tert-butyl 2-(4-((3-((4-cyano-2-methylphenyl) ethynyl)-5-methylphenyl) ethynyl)-3-methylphenyl)-5,6-dihydropyrimidine-1 (4H)-carboxylate.

Step 6. Preparation of tert-Butyl 2-(4-(3-(4-Cyano-2-methylphenethyl)-5-methylphenethyl)-3-methylphenyl)-5,6-dihydropyrimidine-1 (4H)-carboxylate To a suspension of 10% Pd/C in THF is added tert-butyl 2-(4-((3-((4-cyano-2-methylphenyl)ethynyl)-5-methylphenyl)ethynyl)-3-methylphenyl)-5,6-dihydropyrimidine-1 (4H)-carboxylate. The argon atmosphere is exchanged for $H_2$ gas, and the reaction is stirred overnight. The reaction mixture is diluted with DCM and diltered through celite. The organic phase is washed with water, dried over anhydrous $Na_2SO_4$, filtered, and concentrated under reduced pressure to provide tert-butyl 2-(4-(3-(4-cyano-2-methylphenethyl)-5-methylphenethyl)-3-methylphenyl)-5,6-dihydropyrimidine-1 (4H)-carboxylate.

Step 7. Preparation of 3-Methyl-4-(3-methyl-5-(2-methyl-4-(1,4,5,6-tetrahydropyrimidin-2-yl)phenethyl)phenethyl)benzimidamide Dihydrochloride To a solution of tert-butyl 2-(4-(3-(4-cyano-2-methylphenethyl)-5-methylphenethyl)-3-methylphenyl)-5,6-dihydropyrimidine-1 (4H)-carboxylate (1 equiv) in dry THF stirred over an ice bath is added lithium bis(trimethylsilyl) amide (1 M in THE, 1 equiv), and the reaction is stirred at room temperature for 24 hours. The reaction mixture is cooled over an ice bath and then acidified by the slow addition of saturated ethanolic HCL solution until a solid forms. The mixture is stirred for two hours and then all solvents are removed under vacuum. The crude residue is brought up in ether and filtered. The filter cake is brought up in ice water and basified with 2 M NaOH solution until a precipitate forms. The solid is filtered, washed with water, and air dried. The isolated solid is suspended in a 3:1 mixture of anhydrous ethanol and saturated ethanolic HCl solution for 6 hours. The solvent is removed by distillation, and the resulting solid is triturated with dry diethyl ether and filtered. The solvent is removed by distillation, and the resulting solid is dried at 80° C. for 12 hours to provide 3-methyl-4-(3-methyl-5-(2-methyl-4-(1,4,5,6-tetrahydropyrimidin-2-yl) phenethyl) phenethyl)benzimidamide dihydrochloride.

Synthesis 68. Synthesis of 4-(3-(4-(4,5-Dihydro-1H-imidazol-2-yl)-2-methylphenethyl)-5-methylphenethyl)-3-methylbenzimidamide dihydrochloride

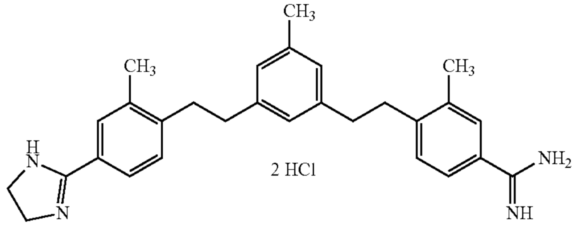 [SMILES: Cc1cc(CCc2ccc(C(=N)N)cc2C)cc(CCc2ccc(C3=NCCN3)cc2C)c1]

4-(3-(4-(4,5-Dihydro-1H-imidazol-2-yl)-2-methylphenethyl)-5-methylphenethyl)-3-methylbenzimidamide dihydrochloride can be prepared by the same procedure by substituting propane-1,3-diamine with ethane-1,2-diamine in Step 1.

Synthesis 69. Synthesis of 1, 3-Bis {(4-amidino)-phenoxy methyl}-benzene dihydrochloride (Compound E-3 dihydrochloride)

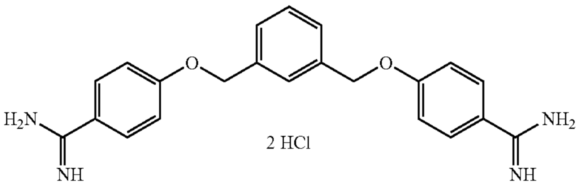 [SMILES: N=C(N)c1ccc(OCc2cccc(COc3ccc(C(=N)N)cc3)c2)cc1]

Step 1: A mixture of 1,3-bis(bromomethyl)-benzene (1.30 g, 5 mmol) and 4-hydroxybenzonitrile (1.19, 10 mmol) using the procedure of Step 1 of General Route 7 to yield 1, 3-bis {(4-cyano)-phenoxy methyl}-benzene as white solid (2.6 g, 76%); 1H NMR (DMSO-d6): 7.78 (d, 4H, J=8.8 Hz), 7.55 (s, 1H), 7.45 (s, 3H), 7.19 (d, 4H, J=8.8 Hz), 5.23 (s, 4H); 13C NMR (DMSO-d6): 161.7, 136.5, 134.2, 128.8, 127.6, 127.2, 119.1, 115.9, 103.1, 69.5; MS: HRMS-ESI-POS.: calc. for C22H22N4O2Na m/z 363.1109 (M++Na), found m/z 363.1105.

Step 2: 1, 3-Bis {(4-cyano)-phenoxy methyl}-benzene (0.34 g, 1 mmol) was converted to 1, 3-bis {(4-amidino) phenoxy methyl}-benzene dihydrochloride as a white solid (0.35 g, 74%) following the procedure of Step 2a of General Route 7; mp 168-70° C.; $^{1}$H NMR (DMSO-d6): 9.35 (s, 4H), 9.18 (s, 4H), 7.91 (d, 4H, J=8.8 Hz), 7.59 (s, 1H), 7.46 (s, 3H), 7.23 (d, 4H, J=8.8 Hz), 5.27 (s, 4H); $^{13}$C NMR (DMSO-d6): 164.7, 162.5, 136.7, 130.2, 128.8, 127.6, 127.1, 119.7, 115.1, 69.5; MS: HRMS-ESI-POS.: calc. for $C_{22}H_{23}N_4O_2$ m/z 375.1816 (M++1), found m/z 375.1816; analysis calc. for $C_{22}H_{22}N_4O2{\cdot}2HCl{\cdot}1.25H_2O$: C, 56.23; H, 5.68; N, 11.92, Found: C, 56.48; H, 5.66; N, 11.85.

Synthesis 70. Synthesis of 1, 3-Bis {(4-(2-imidazolino))-phenoxy methyl}-benzene dihydrochloride (Compound E-9 dihydrochloride)

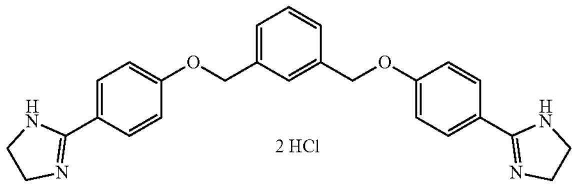 [SMILES: c1cc(COc2ccc(C3=NCCN3)cc2)cc(COc2ccc(C3=NCCN3)cc2)c1]

1, 3-Bis {(4-cyano)-phenoxy methyl}-benzene (0.34 g, 10 mmol) was converted to the imidate dihydrochloride, which was reacted with 1,2-diamino ethane to yield the diimidazoline dihydrochloride as white solid (0.36 g, 72%) following Step 2b of General Route 7; mp 245-7° C.; $^{1}$H NMR (DMSO-d6): 10.73 (s, 4H), 8.12 (d, 4H, J=8.4 Hz), 7.58 (s, 1H), 7.46 (s, 3H), 7.26 (d, 4H, J=8.4 Hz), 5.28 (s, 4H), 3.96 (s, 8H); $^{13}$C NMR (DMSO-d6): 163.9, 162.9, 136.6, 131.0, 128.8, 127.7, 127.2, 115.4, 114.3, 69.5, 44.0; MS: HRMS-ESI-POS.: calc. for C26H27N4O2 m/z 427.2148 ($M^{+}$+1), found m/z 427.2134; analysis calc. for $C_{26}H_{26}N_4O_2{\cdot}2HCl{\cdot}0.75H_2O$: C, 60.97; H, 5.81; N, 10.97, Found: C, 60.88; H, 5.89; N, 10.90.

Synthesis 71. Synthesis of 1, 3-Bis {(4-isopropylamidino)-phenoxy methyl}-5-methylbenzene dihydrochloride (Compound C-3 dihydrochloride)

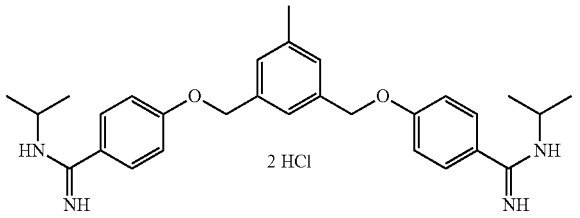 [SMILES: Cc1cc(COc2ccc(C(=N)NC(C)C)cc2)cc(COc2ccc(C(=N)NC(C)C)cc2)c1]

Step 1: Reaction of 1,3-bis(bromomethyl)-5-methylbenzene (1.38 g, 5 mmol) and 4-hydroxybenzonitrile (1.19 g, 10 mmol) yielded 1, 3-bis(4-cyano-phenoxy methyl)-5-methylbenzene as white solid (2.54 g, 72%), using Step 1 of General Route 7; $^{1}$H NMR (DMSO-d6): 7.67 (d, 4H, J=8.8 Hz), 7.34 (s, 1H), 7.26 (s, 2H), 7.17 (d, 4H, J=8.8 Hz), 5.18 (s, 4H), 2.34 (s, 3H); $^{13}$C NMR (DMSO-d6): 163.7, 138.1, 136.4, 134.2, 128.2, 124.3, 119.1, 115.8, 103.0, 69.5, 20.9: MS: HRMS-ESI-POS.: calc. for $C_{23}H_{19}N_2O_2$ m/z 355.1441 (M++1), found m/z 355.1430.

Step 2: 1, 3-Bis (4-cyano-phenoxy methyl)-5-methylbenzene (0.35 g, 1 mmol) was converted to 1, 3-bis {4-isopropylamidino (phenoxy methyl)-5-methyl-benzene dihydrochloride as a pale yellow solid following Step 2b of General Route 7 (0.27 g, 50%) using isopropylamine (0.25 ml, 3 mmol). 1H NMR (DMSO-d6): 9.43 (d, J=8.0 Hz, 2H), 9.31 (d, J=14.2 Hz, 2H), 8.99 (s, 2H), 7.73 (d, J=8.7 Hz, 4H), 7.37 (s, 1H), 7.27 (s, 2H), 7.21 (d, J=8.8 Hz, 4H), 5.21 (s, 4H), 4.06 (m, 2H), 2.34 (s, 3H), 1.26 (d, J=6.3 Hz, 12H); 13C NMR (DMSO-d6): 162.52, 161.61, 138.58, 137.14, 130.77, 128.58, 124.71, 121.62, 115.38, 69.94, 45.36, 21.76, 21.41; MS: HRMS-ESI-POS.: calc. for C29H38N4O2 m/z 237.1492 (M/2++2), found m/z 237.1482; analysis calc. for $C_{29}H_{36}N_4O_2 \cdot 2HCl \cdot 2H_2O$; C, 59.89; H, 7.27; N, 9.6, Found: C, 59.98; H, 6.97; N, 9.02.

Synthesis 72. Synthesis of 1, 4-Bis {(4-amidino)-phenoxy methyl}benzene dihydrochloride (Compound E-10 dihydrochloride)

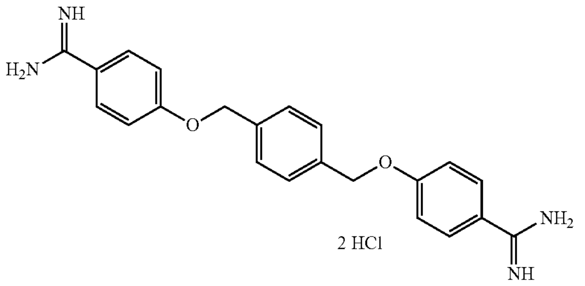 [SMILES: N=C(N)c1ccc(OCc2ccc(COc3ccc(C(=N)N)cc3)cc2)cc1]

Step 1: The reaction of 1,4-bis(bromomethyl)lbenzene (1.32 g, 5 mmol) and 4-hydroxybenzonitrile (1.19 g, 10 mmol) yielded 1, 4-bis(4-cyano-phenoxy methyl)benzene as white solid (1.74 g, 78%), using Step 1 of General Route 7; 1H NMR ($CDCl_3$): 7.59 (d, 4H, J=8.9 Hz), 7.45 (s, 4H), 7.02 (d, J=8.9 Hz, 4H), 5.13 (s, 4H); $^{13}C$ NMR ($CDCl_3$): 161.82, 136.01, 134.07, 127.86, 119.10, 115.57, 104.45, 69.88; MS: HRMS-ESI-POS.: calc. for $C_{22}H_{17}N_2O_2$ m/z 341.1285 ($M^+$+1), found m/z 341.1283.

Step 2: 1, 4-Bis (4-cyano-phenoxy methyl)benzene (0.340 g, 1 mmol) was converted to 1, 4-bis {4-amidino (phenoxy methyl)benzene dihydrochloride as a pale yellow solid following Step 2a of General Route 7 (0.33 g, 76%). $^1H$ NMR (DMSO-d6): 9.25 (s, 4H), 9.02 (s, 4H), 7.85 (d, J=8.9 Hz, 4H), 7.51 (s, 4H), 7.23 (d, J=9.0 Hz, 4H), 5.26 (s, 4H); 13C NMR (DMSO-d6): 165.16, 163.12, 136.67, 130.67, 128.49, 120.12, 115.64, 69.79; MS: HRMS-ESI-POS.: calc. for $C_{22}H_{24}N_4O_2$ m/z 188.0944 ($M/2^+$+2), found m/z 188.0936; analysis calc. for $C_{22}H_{22}N_4O_2 \cdot 2HCl \cdot 1.3H_2O$; C, 56.31; H, 5.69; N, 11.90, Found: C, 56.78; H, 5.40; N, 11.21.

Synthesis 73: Synthesis of 1, 3-Bis {(4-methanamine)-phenoxy methyl}-5-methylbenzene dihydrochloride (Compound E-11 dihydrochloride)

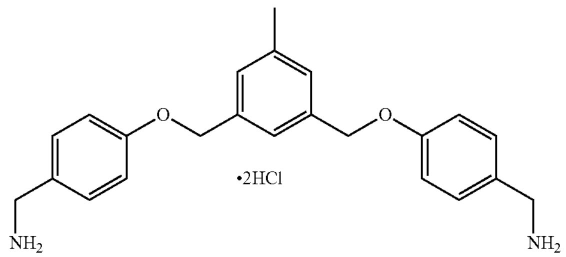 [SMILES: Cc1cc(COc2ccc(CN)cc2)cc(COc2ccc(CN)cc2)c1]

A solution of 1,3-bis(4-cyano-phenoxy methyl)-5-methylbenzene (1.0 g, 2.8 mmol) in THF (20 ml) was added dropwise to a suspension of $LiAlH_4$ (0.32 g, 7.4 mmol) in THE under argon gas at 0° C. and stirred at room temperature for 16 h. The reaction was quenched with addition of $H_2O$ (5 ml) at 0° C. followed by the addition of 16% NaOH solution (2 ml). The mixture was stirred at room temperature for approximately 2 hours after which it was filtered through celite. The solution was then concentrated in vacuo to obtain the free diamine. The product residue was then dissolved in ethanol followed by addition of HCl in ethanol (2 ml) for salt formation. The reaction mixture was evaporated in vacuo followed by ether precipitation to obtain the product as a green solid. (1.0 g, 87%). $^1H$ NMR (DMSO-d6) 8.45 (s, 6H), 7.43 (d, 4H, J=8.2 Hz), 7.32 (s, 1H), 7.22 (s, 2H), 7.03 (d, 4H, J=8.2 Hz), 5.09 (s, 4H), 2.32 (s, 3H); $^{13}C$ NMR (DMSO-d6) 158.85, 138.37, 137.62, 131.02, 128.25, 126.70, 124.48, 115.26, 69.61, 42.09, 21.43; MS: HRMS-ESI-POS.: calc. for C23H27N2O2 m/z 363.2079 (M++1), found m/z 363.2067.; analysis calc. for $C_{23}H_{26}N_2O_2 \cdot 2HCl \cdot 1.3H_2O$; C, 60.21; H, 6.72; N, 6.10, Found: C, 60.67; H, 6.29; N, 5.48.

Synthesis 74. Synthesis of 1, 3, 5-Tris {(4-amidino)-phenethyl}-5-methylbenzene trihydrochloride (Compound E-12 trihydrochloride)

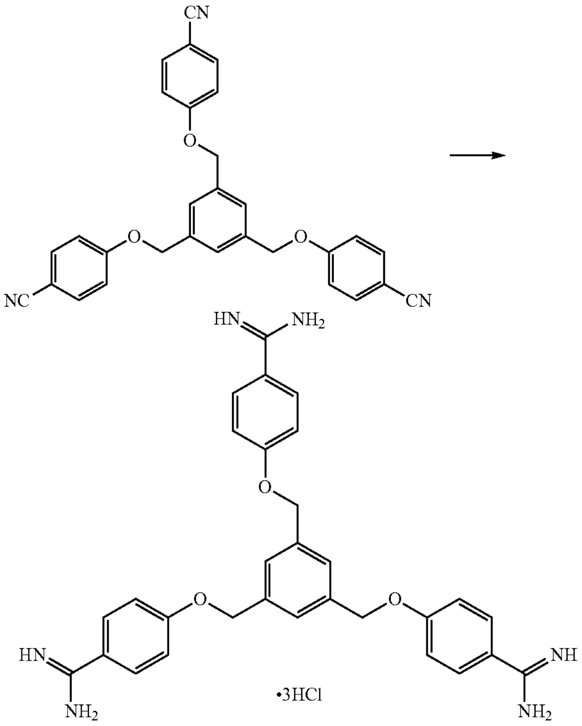

Synthesis of 1,3,5-tris(4-cyano-phenoxy methyl)-5-methyl-benzene: Reaction of 1,3,5-tris (bromomethyl)benzene (1.54 g, 4.3 mmol) and 4-hydroxybenzonitrile (1.64 g, 14 mmol) yielded 1,3,5-tris(4-cyano-phenoxy methyl)-5-methyl-benzene as white solid (1.69 g, 84%), using Step 1 of General Route 7: 1H NMR (DMSO-d6) 7.78 (d, 6H, J=8.9 Hz), 7.53 (s, 3H), 7.18 (d, 6H, J=8.9 Hz), 5.24 (s, 6H); 13C NMR (DMSO-d6) 162.13, 137.44, 134.69, 127.39, 119.55, 116.36, 103.60, 69.80; MS: HRMS-ESI-POS.: calc. for $C_{30}H_{21}N_3O_3Na$ m/z 494.1481 ($M^+$+Na), found m/z 494.1481.

Synthesis of 1,3,5-tris {4-amidino (phenoxy methyl)-5-methyl-benzene trihydrochloride: The tinitrile (0.56 g, 1.2 mmol) was converted to 1,3,5-tris {4-amidino (phenoxy methyl)-5-methyl-benzene trihydrochloride as brown solid following Step 2a of General Route 7 (0.58 g, 78%). 1H NMR (DMSO-d6) 9.46 (s, 6H), 9.25 (s, 6H), 7.96 (d, 6H, J=8.2 Hz), 7.57 (s, 3H), 7.23 (d, 6H, J=8.4 Hz, 1H), 5.28 (s, 6H), 3.50 (s, 9H); 13C NMR (DMSO-d6) 165.17, 163.01, 137.58, 130.76, 127.30, 120.08, 115.58, 69.87; MS: HRMS-ESI-POS.: calc. for C30H32N6O3 m/z 262.1262 (M/2++2), found m/z 262.1258; analysis calc. for $C_{30}H_{30}N_6O_3\cdot 3HCl\cdot 8.5H_2O$; C, 45.89; H, 6.42; N, 10.70, Found: C, 45.42; H, 5.71; N, 10.12.

Synthesis 75. Synthesis of 1, 3-Bis {(4-isopropylamidino)-phenoxy methyl}-2-fluorobenzene dihydrochloride (Compound D-10 dihydrochloride)

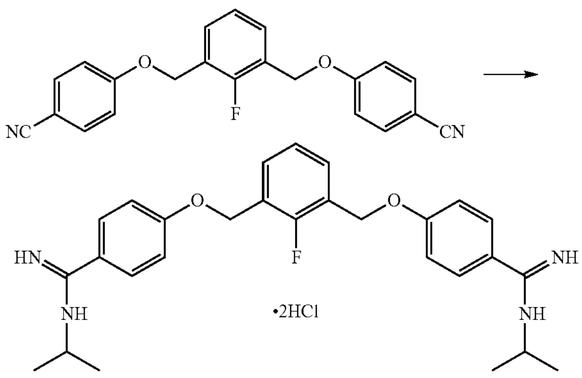

Synthesis of 1,3-bis(4-cyano-phenoxy methyl)-2-fluorobenzene: Reaction of 1,3-bis (bromomethyl)-2-fluorobenzene1 (1.4 g, 5 mmol) and 4-hydroxybenzonitrile (1.19 g, 10 mmol) yielded 1, 3-bis(4-cyano-phenoxy methyl)-2-fluorobenzene as white solid (2.53 g, 70%), following Step 1 of General Route 7; mp 173-5° C.; $^1$H NMR (DMSO-d6): 7.78 (d, 4H, J=8.4 Hz), 7.59 (t, 2H, J=7.2 Hz), 7.29 (t, 1H, J=7.2 Hz), 7.23 (d, 4H, J=8.4 Hz), 5.3 (s, 4H); $^{13}$C NMR (DMSO-d6): 161.4, 158.4 (d, $J_{C\text{-}F}$=248 Hz), 134.0, 130.7 (d, $J_{C\text{-}F}$=4.1 Hz), 124.2 (d, $J_{C\text{-}F}$=4.1 Hz), 123.1 (d, $J_{C\text{-}F}$=13.5 Hz), 118.7, 115.6, 103.3, 63.8 (d, $J_{C\text{-}F}$=3.3 Hz); MS: HRMS-ESI-POS.: calc. for C22H15FN2O2Na m/z 381.1015 ($M^+$+Na), found m/z 381.1005.

Synthesis 1, 3-bis {4-isopropylamidino (phenoxy methyl)-2-fluorobenzene of dihydrochloride: The dinitrile (0.35 g, 0.97 mmol) was converted to 1, 3-bis {4-isopropylamidino (phenoxy methyl)-2-fluorobenzene dihydrochloride as white solid following Step 2b of General Route 7 (0.38 g, 73%) with isopropylamine (0.17 g, 2.92 mmol); mp. 269-70° C.; $^1$H NMR (DMSO-d6): 9.48 (d, 2H, J=8.0 Hz), 9.37 (s, 2H), 9.06 (s, 2H), 7.76 (d, 4H, J=8.7 Hz), 7.62 (t, 2H, J=7.2 Hz), 7.30 (t, 1H, J=7.6 Hz), 7.25 (d, 4H, J=8.7 Hz), 5.30 (s, 4H), 4.10 (dd, 2H, J=13.6, 6.6 Hz), 1.27 (d, 12H, J=6.3 Hz); $^{13}$C NMR (DMSO-d6): 162.31, 161.55, 159.23 (d, $J_{C\text{-}F}$=249.7 Hz), 131.66 (d, $J_{C\text{-}F}$=3.4 Hz), 130.85, 125.01 (d, $J_{C\text{-}F}$=3.6 Hz), 123.93 (d, $J_{C\text{-}F}$=14.6 Hz), 121.86, 115.28, 64.45 (d, JC-F=3.5 Hz), 45.42, 21.76; MS: HRMS-ESI-POS.: calc. for C28H34FN4O2 m/z 477.2660 ($M^+$+1), found m/z 477.2643; analysis calc. for $C_{28}H_{34}FN_4O_2\cdot 2HCl\cdot 1.19H_2O$): C, 58.79; H, 6.76; N, 9.79, Found: C, 58.49; H, 6.05; N, 9.85.

Synthesis 76. Synthesis of 3-Bis {(4-isopropylamidino-2-fluoro)-phenoxy methyl}-2-fluorobenzene dihydrochloride (Compound B-9 dihydrochloride)

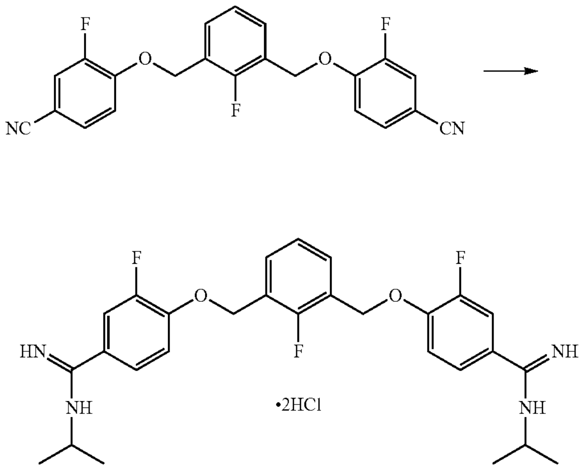

Synthesis of 1,3-bis(2-fluoro-4-cyano-phenoxymethyl)-2-fluorobenzene: Reaction of 1,3-bis(bromomethyl)-2-fluorobenzene1 (1.4 g, 5 mmol) and 2-fluoro-4-hydroxybenzonitrile (1.37 g, 10 mmol) following Step 1 of General Route 7 yielded 1, 3-bis(2-fluoro-4-cyano-phenoxymethyl)-2-fluorobenzene as white solid (2.8 g, 71%); mp 185-7° C.; 1H NMR (DMSO-d6): 7.88 (d, 2H, J=8.4 Hz), 7.72 (d, 8.4 Hz), 7.64 (t, 2H, J=7.6 Hz), 7.54 (t, 2H, J=7.6 Hz), 7.33 (t, 1H, J=7.6 Hz), 7.23 (d, 4H, J=8.4 Hz), 5.37 (s, 4H); 13C NMR (DMSO-d6): 158.50 (d, $J_{C\text{-}F}$=250 Hz), 151.0 (d, $J_{C\text{-}F}$=248 Hz), 150.1 (d, $J_{C\text{-}F}$=11.0 Hz), 131.1 (d, $J_{C\text{-}F}$=4.4 Hz), 130.1 (d, $J_{C\text{-}F}$=3.75 Hz), 124.4 (d, $J_{C\text{-}F}$=4.28 Hz), 122.7 (d, $J_{C\text{-}F}$=15.4 Hz), 119.6 (d, $J_{C\text{-}F}$=21.4 Hz), 117.6 (d, $J_{C\text{-}F}$=3.4 Hz), 115.91 (d, $J_{C\text{-}F}$=2.25 Hz), 103.3 (d, $J_{C\text{-}F}$=8.73 Hz), 64.84 (d, $J_{C\text{-}F}$=4.21 Hz); MS: HRMS-ESI-POS.: calc. for $C_{22}H_{13}F_3N_2O_2Na$ m/z 417.0827 ($M^+$+Na), found m/z 417.0832.

Synthesis of 1,3-bis(4-isopropylamidino-2-fluoro-phenoxy methyl)-2-fluorobenzene dihydrochloride: The dinitrile (0.32 g, 0.81 mmol) was converted to 1, 3-bis(4-isopropylamidino-2-fluoro-phenoxy methyl)-2-fluorobenzene dihydrochloride as white solid following Step 2b of General Route 7 (0.28 g, 70%) using isopropylamine (0.14 g, 2.43 mmol); mp. 193-5° C.; 1H NMR (DMSO-d6): 9.50 (s, 2H), 9.21 (s, 2H), 7.77 (dd, 2H, J=11.9, 2.2 Hz), 7.69-7.62 (m, 4H), 7.57 (t, 2H, J=8.6 Hz), 7.33 (t, 1H, J=7.6 Hz), 5.39 (s, 4H), 4.10 (dt, 2H, J=13.0, 6.5 Hz), 1.27 (d, 12H, J=6.4 Hz); 13C NMR (DMSO-d6): 160.01, 158.90 (d, $J_{C\text{-}F}$=250.6 Hz), 151.95, 149.85, 149.63 (d, $J_{C\text{-}F}$=24.1 Hz), 131.56 (d, $J_{C\text{-}F}$=2.5 Hz), 125.91 (d, $J_{C\text{-}F}$=2.9 Hz), 124.68 (d, $J_{C\text{-}F}$=3.8 Hz), 123.08 (d, $J_{C\text{-}F}$=14.5 Hz), 121.60 (d, $J_{C\text{-}F}$=7.2 Hz), 116.63 (d, $J_{C\text{-}F}$=20.9 Hz), 114.91, 64.89 (d, $J_{C\text{-}F}$=3.7 Hz), 45.13, 21.25, MS: HRMS-ESI-POS.: calc. for $C_{28}H_{32}F_3N_4O_2$ m/z 513.2472 ($M^+$+1), found m/z 513.2450; analysis calc. for $C_{22}H_{19}F_3N_4O_2\cdot 2HCl\cdot 1.25H_2O$; C, 55.31; H, 5.88; N, 9.21, Found: C, 55.39; H, 5.85; N, 8.95.

Synthesis 77. Synthesis of 1, 3-Bis {(4-n-propyl-amidino)-benzyloxy}-5-methylbenzene dihydrochloride (Compound E-13 dihydrochloride)

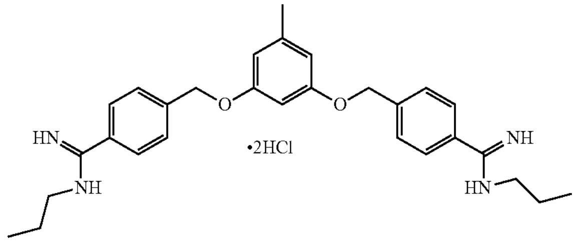 [SMILES: CCCNC(=N)c1ccc(COc2cc(C)cc(OCc3ccc(C(=N)NCCC)cc3)c2)cc1]

The corresponding dinitrile (0.35 g, 0.98 mmol) was converted to 1, 3-Bis {(4-n-propylamidino)-benzyloxy}-5-methylbenzene dihydrochloride as white solid following Step 2b of General Route 7 (0.37 g, 70%) using n-propylamine (0.17 g, 3 mmol); $^1$H NMR (DMSO-$d_6$) 9.91 (s, 2H), 9.54 (s, 2H), 9.19 (s, 2H), 7.80 (d, J=8.3 Hz, 4H), 7.64 (d, 4H, J=8.3 Hz), 6.51 (d, J=1.9 Hz, 2H), 6.49 (s, 1H), 5.20 (s, 4H), 3.44-3.38 (m, 2H), 2.24 (s, 3H), 1.66 (dd, J=14.5, 7.3 Hz, 4H), 0.95 (d, J=7.4 Hz, 6H); $^{13}$C NMR (DMSO-$d_6$) 162.52, 159.09, 142.67, 140.21, 128.45, 128.27, 127.54, 108.26, 99.44, 68.25, 44.17, 21.43, 20.85, 11.18; MS: HRMS-ESI-POS.: calc. for $C_{29}H_{36}N_4O_2$ m/z 473.2917 ($M^+$+1), found m/z 473.2940; analysis calc. for $C_{29}H_{36}N_4O_2$·2HCl·1$H_2O$; C, 62.00; H, 7.14; N, 9.97, Found: C, 61.97; H, 7.13; N, 9.78.

Synthesis 78. Synthesis of 3-Bis {[4-amidino-2-methoxy)-phenoxy methyl]}-5-(tert-butyl)benzene dihydrochloride (Compound E-14 dihydrochloride)

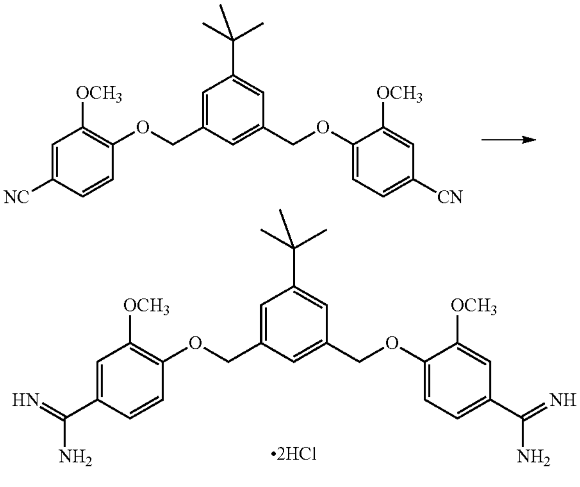

Synthesis of 1,3-bis(2-methoxy-4-cyano-phenoxy methyl)-5-(tert-butyl)benzene: Reaction of 1,3-bis(bromomethyl)-5-(tert-butyl)benzene (1.2 g, 3.75 mmol) and 2-methoxy-4-hydroxybenzonitrile (1.2 g, 7.5 mmol) yielded yielded 1, 3-bis(2-methoxy-4-cyano-phenoxy methyl)-5-(tert-butyl)benzene as white solid (1.35 g, 79%) following Step 1 of General Route 7. $^1$H NMR ($CDCl_3$): 7.41 (s, 2H), 7.31 (s, 1H), 7.23 (dd, J=8.3, 1.5 Hz, 2H), 7.11 (d, J=1.4 Hz, 2H), 6.93 (d, J=8.4 Hz, 2H), 5.19 (s, 4H), 3.90 (s, 6H), 1.32 (s, 9H); $^{13}$C NMR ($CDCl_3$): 152.36, 152.05, 149.70, 136.07, 126.26, 124.48, 123.58, 119.18, 114.46, 113.45, 104.31, 71.17, 56.21, 34.81, 31.29; MS: HRMS-ESI-POS.: calc. for $C_{28}H_{28}N_2O_4$Na m/z 479.1947 ($M^+$+Na), found m/z 479.1942.

Synthesis of 1,3-bis(2-methoxy-4-cyano-phenoxy methyl)-5-(tert-butyl)benzene dihydrochloride: The dinitrile (0.35 g, 0.76 mmol) was converted to yield 1, 3-bis(2-methoxy-4-cyano-phenoxy methyl)-5-(tert-butyl)benzene dihydrochloride as white solid following Step 2a of General Route 7 (0.30 g, 72%); $^1$H NMR (DMSO-$d_6$): 9.33 (s, 4H), 9.04 (s, 4H), 7.55-7.46 (m, 6H), 7.35 (s, 1H), 7.28 (d, J=9.2 Hz, 2H), 5.21 (s, 4H), 3.86 (s, 6H), 1.29 (s, 9H); $^{13}$C NMR (DMSO-$d_6$): 165.11, 152.79. 151.78, 149.26, 136.74, 125.39, 122.29, 119.97, 113.35, 111.94, 70.80, 56.45, 34.91, 31.55; MS: HRMS-ESI-POS.: calc. for $C_{28}H_{35}N_4O_4$ m/z 479.1947 ($M^+$+1) 491.2658, found m/z 491.2645.

Synthesis 79. 1, 3-bis {[4-amidino-2-fluoro]-phenoxy methyl]}-5-(tert-butyl)benzene dihydrochloride (Compound E-15 dihydrochloride)

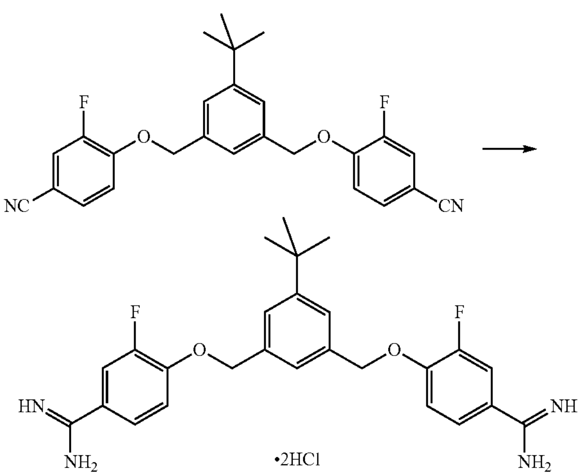

Synthesis of 1,3-bis(2-fluoro-4-cyano-phenoxy methyl)-5-(tert-butyl)benzene: Reaction of 1,3-bis(bromomethyl)-5-(tert-butyl)benzene (1.5 g, 4.7 mmol) and 2-fluoro-4-hydroxybenzonitrile (1.3 g, 9.4 mmol) yielded 1, 3-bis(2-fluoro-4-cyano-phenoxy methyl)-5-(tert-butyl)benzene as white solid (1.52 g, 75%) following Step 1 of General Route 7. $^1$H NMR (DMSO-$d_6$): 7.86 (dd, J=11.3, 1.9 Hz, 2H), 7.68 (d, J=8.5 Hz, 2H), 7.50 (s, 2H), 7.45 (t, J=8.6 Hz, 2H), 7.37 (s, 1H), 5.30 (s, 4H), 1.29 (s, 9H); $^{13}$C NMR (DMSO-$d_6$) 152.23 (d, $J_{C-F}$=241.4 Hz), 151.86 (d, $J_{C-F}$=186.48 Hz), 135.65, 129.74, 129.70, 124.96, 123.90, 120.00 (d, $J_{C-F}$=21.34 Hz), 118.04 (d, $J_{C-F}$=2.48 Hz), 115.42 (d, $J_{C-F}$=2.21 Hz), 104.62 (d, $J_{C-F}$=8.21 Hz), 71.50, 34.98, 31.40; MS: MS: HRMS-ESI-POS.: calc. for $C_{24}H_{27}FN_4O_4$ m/z 455.1547 (M++Na), found m/z 455.1541.

Synthesis of 1,3-bis (2-fluoro-4-cyano-phenoxy methyl)-5-(tert-butyl)benzene dihydrochloride: The dinitrile (0.35 g, 0.8 mmol) was converted to yielded 1, 3-bis(2-fluoro-4-cyano-phenoxy methyl)-5-(tert-butyl)benzene dihydrochloride as brown solid following Step 2a of General Route 7 (0.30 g, 70.1%); $^1$H NMR (DMSO-$d_6$): 9.50 (s, 4H), 9.26 (s, 4H), 7.91 (dd, J=12.1 Hz, 2H), 7.84-7.91 (m, 2H), 7.56-7.48 (m, 4H), 7.40 (s, 1H), 5.32 (s, 4H), 1.28 (d, J=7.8 Hz, 9H); $^{13}$C NMR (DMSO-$d_6$): 164.25, 152.62, 151.14 (d, $J_{C-F}$=10.4

Hz), 151.07 (d, $J_{C-F}$=178.7 Hz), 136.33, 126.32 (d, $J_{C-F}$=3.0 Hz), 125.51, 125.23, 120.25 (d, $J_{C-F}$=7.2 Hz), 116.59 (d, $J_{C-F}$=21.0 Hz), 115.62, 71.15, 34.93, 31.51; MS: HRMS-ESI-POS.: calc. for $C_{26}H_{29}N_4O_2F_2$ m/z 467.2272 ($M^+$+1), found m/z 467.2271.

Synthesis 80. Synthesis of 1, 3-Bis {(3-amidino)-phenoxy methyl}benzene dihydrochloride (Compound E-16 dihydrochloride)

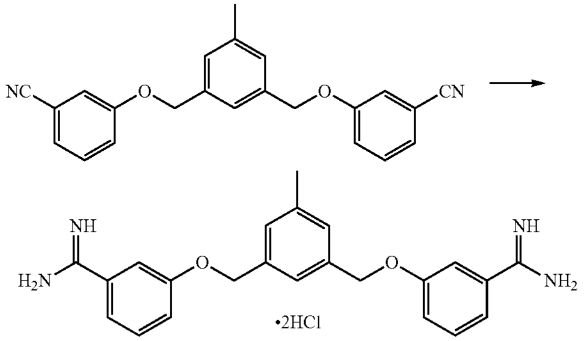

Synthesis of 1,3-bis(3-cyano-phenoxy methyl)-5-methyl-benzene: Reaction of 1,3-bis (bromomethyl)-5-methylbenzene (2.13 g, 7.7 mmol) and 3-cyanophenol (2.05 g, 17 mmol) yielded 1, 3-bis(3-cyano-phenoxy methyl)-5-methyl-benzene as white solid (2.6 g, 91%), using Step 1 of General Route 7; $^1$H NMR ($CDCl_3$): 7.45-7.37 (m, 2H), 7.32-7.26 (s, 3H), 7.25-7.19 (m, 6H), 5.09 (s, 4H), 2.43 (s, 3H); $^{13}$C NMR ($CDCl_3$): 158.70, 139.23, 136.47, 130.45, 128.17, 124.88, 123.53, 120.13, 118.69, 117.81, 113.29, 70.13, 21.42; MS: HRMS-ESI-POS.: calc. for $C_{23}H_{18}N_2O_2$ m/z 377.1266 (M+Na), found m/z 377.1250.

Synthesis of 1,3-bis {3-amidino (phenoxy methyl)benzene dihydrochloride: The dinitrile (0.32 g, 0.9 mmol) was converted to 1, 3-bis {3-amidino (phenoxy methyl)benzene dihydrochloride as white solid following Step 2a of General Route 7 (0.32 g, 76%). $^1$H NMR (DMSO-$d_6$): 9.41 (s, 4H), 9.08 (s, 4H), 7.54 (t, J=8.0 Hz, 2H), 7.48 (s, 2H), 7.43-7.33 (m, 5H), 7.27 (s, 2H), 5.17 (s, 4H), 2.34 (s, 3H); $^{13}$C NMR (DMSO-$d_6$): 165.75, 158.84, 138.67, 137.18, 130.96, 130.08, 129.67, 128.63, 124.74, 120.83, 120.69, 114.69, 70.06, 21.39; MS: HRMS-ESI-POS.: calc. for $C_{23}H_{24}N_4O_2$ m/z 389.1978 ($M^+$+1), found m/z 389.1980.

Synthesis 81. Synthesis of 1, 3-Bis {(4-amidino)-thiophenoxy methyl}-5-methylbenzene dihydrochloride (Compound D-4 dihydrochloride)

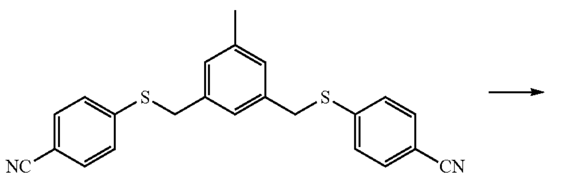

-continued

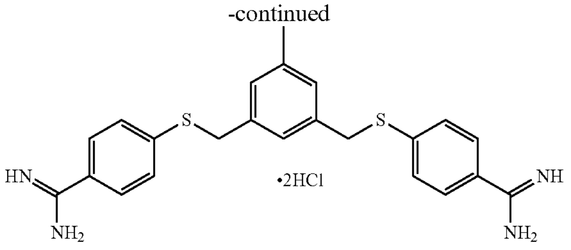

Synthesis of 1,3-bis(4-cyano-thiophenoxy methyl)-5-methyl-benzene: Reaction of 1,3-bis (bromomethyl)-5-methylbenzene (0.93 g, 3.3 mmol) and 4-mercaptobenzonitrile (1.0 g. 7.3 mmol) yielded 1, 3-bis(4-cyano-thiophenoxy methyl)-5-methyl-benzene as white solid (1.12 g, 85%), using Step 1 of General Route 7; $^1$H NMR ($CDCl_3$): 7.52 (d, J=8.4 Hz, 4H), 7.30 (d. J=8.4 Hz, 4H), 7.16 (s, 1H), 7.11 (s, 2H), 4.15 (s, 4H), 5.18 (s, 4H), 2.34 (s, 3H); $^{13}$C NMR (DMSO-$d_6$): 144.34, 139.20, 136.26, 132.27, 128.96, 127.33, 126.17, 118.80, 108.67, 36.90, 21.30; MS: HRMS-ESI-POS.: calc. for $C_{23}H_{19}N_2S_2$ m/z 387.0984 ($M^+$+1), found m/z 387.1003.

Synthesis of 1,3-bis {4-amidino (thiophenoxy methyl)-5-methyl-benzene dihydrochloride: Dinitrile (0.30 g, 0.74 mmol) was converted to 1, 3-bis {4-amidino (thiophenoxy methyl)-5-methyl-benzene dihydrochloride as green solid following Step 2b of General Route 7 (0.19 g, 50%) using ammonia gas. $^1$H NMR (DMSO-$d_6$): 9.31 (s, 4H), 9.04 (s, 4H), 7.75 (d, J=8.6 Hz, 4H), 7.52 (d, J=8.59 Hz, 4H), 7.32 (s, 1H), 7.17 (s, 2H), 4.34 (s, 4H), 2.26 (s, 3H); $^{13}$C NMR (DMSO-$d_6$): 159.28, 139.92, 137.35, 133.65, 129.13, 127.76, 108.13, 99.20, 68.72, 41.86, 21.43; MS: HRMS-ESI-POS.: calc. for $C_{23}H_{25}N_4S_2$ m/z 421.1521 (M++1), found m/z 421.1532.

Synthesis 82. Synthesis of 1, 3-Bis {(4-(2-imidazolino))-thiophenoxy methyl}-5-methylbenzene dihydrochloride (Compound B-12 dihydrochloride)

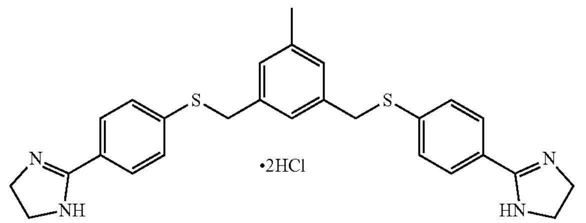 [SMILES: Cc1cc(CSc2ccc(C3=NCCN3)cc2)cc(CSc2ccc(C3=NCCN3)cc2)c1]

The corresponding dinitrile (0.386 g, 1 mmol) was converted to 1, 3-Bis {(4-(2-imidazolino))-thiophenoxy methyl}-5-methylbenzene dihydrochloride as a brown solid following Step 2b of General Route 7 (0.39 g, 72%) by refluxing imidate ester with 1,2 diaminoethane. $^1$H NMR (DMSO-$d_6$): 10.73 (s, 4H), 7.96 (d, 4H, J=8.6 Hz), 7.54 (d, 4H, J=8.6 Hz), 7.32 (s, 1H), 7.16 (s, 2H), 4.36 (s, 4H), 3.98 (s, 8H), 2.26 (s, 3H); $^{13}$C NMR (DMSO-$d_6$): 164.00, 145.86, 138.05, 136.70, 129.01, 128.61, 126.32, 118.23, 44.19, 34.77, 20.88; MS: HRMS-ESI-POS.: calc. for $C_{27}H_{29}N_4S_2$ m/z 473.1834 (M+1), found m/z 473.1842.

Synthesis 83. Synthesis of 1, 3-Bis {(4-amidino)-phenoxy methyl}-6-methylbenzene dihydrochloride (E-17 dihydrochloride)

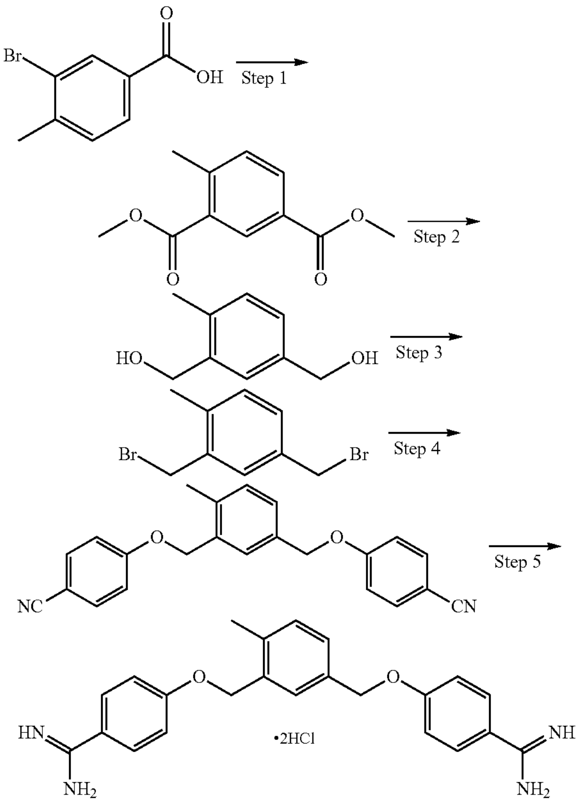

Step 1:3-bromo-4 methylbenzoic acid (5 g, 23.25 mmol) was added to 50 ml dry THF in a three neck round bottom flask under Ar gas atmosphere. The temperature of the reaction mixture was cooled to 0° C. and a solution of 3.0 M methyl magnesium bromide (8.5 ml, 25.57 mmol) was added and stirred for 2 hrs. The temperature was further lowered to −65° C. and 1.6 M n-butyl lithium solution (29 mL, 46.5 mmol) in hexane was added with constant stirring. After 4 h of reaction time, dry ice was added and the reaction mixture was sealed and stirred overnight. Upon completion of the reaction, mixture was acidified and then filtered. This residue was taken with catalytic amounts of conc. $H_2SO_4$ in methanol and refluxed overnight to form the methyl ester. The reaction mixture was cooled to room temperature on completion, 10 ml water was added to it and extracted with ethyl acetate (3×50 mL). The organic layer was dried with anhydrous $Na_2SO_4$ and concentrated in vacuo to yield Dimethyl 4-methylisophthalate as white solid (3.92 g, 81%). $^1$H NMR ($CDCl_3$): 8.57 (d, J=1.7 Hz, 1H), 8.04 (dd, J=8.0, 1.8 Hz, 1H), 7.33 (d, J=8.0 Hz 1H), 3.92 (d, J=3.2 Hz, 6H), 2.66 (s, 3H); $^{13}$C NMR ($CDCl_3$): 167.34, 166.50, 145.73, 132.79, 132.12, 132.04, 129.90, 128.11, 52.36, 52.20, 22.03; MS: HRMS-ESI-POS.: calc. for $C_{11}H_{12}O_4$ m/z 231.0633 ($M^+$+Na), found m/z 231.0642.

Step 2: Dimethyl 4-methylisophthalate (1 g, 4.8 mmol) in THF (20 ml) was added dropwise under ice-bath condition in a solution of lithium aluminium hydride (0.73 g, 19.2 mmol) in THF (30 ml). The reaction was stirred for 1 h at 0° C. and then overnight at room temperature. The reaction was monitored by TLC. Upon completion, the reaction mixture was cooled to 0° C. and quenched with methanol and water. The quenched reaction was filtered through Celite and washed with EtOAc (50 mL). The solvent was removed under reduced pressure and was extracted with EtOAc (3×50 mL), dried over $MgSO_4$ and concentrated to afford the required diol (4-methyl-1,3-phenylene)dimethanol (0.62 g, 85%) as a white solid. %). $^1$H NMR ($CDCl_3$): 7.32 (s, 1H), 7.14 (d, J=1.8 Hz, 2H), 4.60 (d, J=14.4 Hz, 4H), 2.29 (s, 3H); $^{13}$C NMR ($CDCl_3$): 139.13, 138.71, 135.34, 130.50, 126.45, 126.24, 65.14, 63.21, 18.45; MS: HRMS-ESI-POS.: calc. for $C_9H_{12}O_2$ m/z 175.0735 ($M^+$+Na), found m/z 175.0730.

Step 3: $PBr_3$ (0.7 mL, 7.38 mmol) was added dropwise to a solution of diol (0.511 g, 3.35 mmol) in DCM maintained at 0° C. The reaction mixture was stirred at room temperature for 4 h and then quenched with ice water. The solution was extracted with $CH_2Cl_2$ (3×25 mL), dried over $MgSO_4$ and concentrated to afford the required dibromo compound as a white solid (0.93 g, 90%). $^1$H NMR ($CDCl_3$): 7.34 (d, J=1.6 Hz, 1H), 7.28-7.24 (m, 1H), 7.17 (d, J=7.8 Hz, 1H), 4.48 (d, J=12.6 Hz, 4H), 2.41 (s, 3H); $^{13}$C NMR ($CDCl_3$): 137.81, 136.37, 136.10, 131.47, 130.64, 129.66, 33.10, 31.82, 18.70;

Step 4: Reaction of 2,4-bis(bromomethyl)-1-methylbenzene (0.9 g, 3.2 mmol) and 4-hydroxybenzonitrile (0.84 g, 7 mmol) yielded 1, 3-bis(4-cyano-phenoxy methyl)-6-methylbenzene as white solid (0.81 g, 72%), using Step 1 of General Route 7; $^1$H NMR ($CDCl_3$): 7.59 (dd, J=11.2, 8.9 Hz, 4H), 7.44 (s, 1H), 7.36-7.27 (m, 2H), 7.08-6.96 (m, 4H), 5.09 (d, J=1.6 Hz, 4H), 2.38 (s, 3H); $^{13}$C NMR ($CDCl_3$): 162.05, 162.01, 137.10, 134.28, 134.21, 134.15, 133.81, 131.18, 128.02, 127.87, 119.24, 115.68, 115.59, 104.59, 104.44, 70.08, 68.74, 18.83; MS: HRMS-ESI-POS.: calc. for $C_{23}H_{18}N_2O_2$ m/z 377.1266 (M++Na), found m/z 377.1256.

Step 5: Dinitrile (0.35 g, 1 mmol) was converted to 1, 3-bis {4-amidino (phenoxy methyl)-6-methyl-benzene dihydrochloride as brown solid following Step 2a of General Route 7 (0.32 g, 70%); $^1$H NMR (DMSO-$d_6$): 9.33 (d, J=9.8 Hz, 4H), 9.14 (d, J=6.6 Hz, 4H), 7.90 (dd, J=12.8, 8.9 Hz, 4H), 7.55 (s, 1H), 7.41-7.35 (m, 1H), 7.31-7.18 (m, 5H),), 5.23 (d, J=7.0 Hz, 4H), 2.34 (s, 3H); $^{13}$C NMR (DMSO-$d_6$): 164.73, 162.73, 162.61, 136.74, 134.52, 133.87, 130.45, 130.24, 130.20, 128.21, 127.95, 119.70, 119.59, 115.15, 115.08, 69.45, 68.36, 18.29; MS: HRMS-ESI-POS.: calc. for $C_{23}H_{24}N_4O_2$ m/z 389.1978 ($M^+$+1), found m/z 389.1971.

Synthesis 84. Synthesis of 1, 3-Bis {[4-amidino-2-fluoro)-phenoxy methyl]}-5-methyl-benzene dihydrochloride (Compound E-18 dihydrochloride)

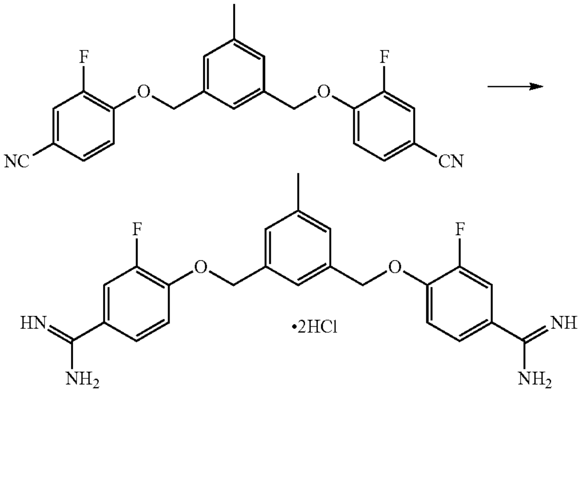

Characterization of dinitile compound: $^{1}$H NMR ($CDCl_3$): 7.45-7.38 (m, 4H), 7.31 (s, 1H), 7.26 (s, 2H), 7.08 (t, J=8.4 Hz, 2H), 5.2 (s. 4H), 2.35 (s, 3H); $^{13}$C NMR ($CDCl_3$): 152.01 (d, JC-F=250.69 Hz), 150.79 (d, $J_{C-F}$=10.32 Hz), 139.2, 135.84, 129.72 (d, $J_{C-F}$=4.0 Hz), 128.37, 123.47, 119.97 (d, $J_{C-F}$=21.4 Hz), 118.02 (d, $J_{C-F}$=2.27 Hz), 115.31 (d, $J_{C-F}$=2.2 Hz), 104.58 (d, $J_{C-F}$=8.2 Hz), 70.99, 21.41; MS: HRMS-ESI-POS.: calc. for $C_{23}H_{16}F_2N_2O_2$ m/z 413.1078 ($M^+$+Na), found m/z 413.1087.

Characterization of 1, 3-Bis {[4-amidino-2-fluoro)-phenoxy methyl]}-5-methyl-benzene dihydrochloride: $^{1}$H NMR (DMSO-$d_6$): 9.43 (s, 4H), 9.25 (s, 4H), 7.90 (dd, J=12.1, 2.2 Hz, 2H), 7.77 (d, J=1.1, 2H), 7.50 (t, J=8.7 Hz, 2H), 7.39 (s, 1H), 7.30 (s, 2H), 5.31 (s, 4H), 2.36 (s, 3H); $^{13}$C NMR (DMSO-$d_6$): 163.81, 151.35 (d, $J_{C-F}$=159.65 Hz), 150.13 (d, $J_{C-F}$=85.8 Hz), 138.31, 136.19, 128.51, 125.83 (d, $J_{C-F}$=2.9 Hz), 124.47, 119.97 (d, $J_{C-F}$=7.2 Hz), 116.19 (d. $J_{C-F}$=21.0 Hz), 115.10 (d, $J_{C-F}$=0.92 Hz), 70.33, 20.96; MS: HRMS-ESI-POS.: calc. for $C_{23}H_{22}F_2N_4O_2$ m/z 425.1789 (M++1), found m/z 425.1777.

Synthesis 85. Synthesis of 1, 3-Bis {(4-N-methoxy-amidino)-phenoxy methyl}-5-methylbenzene (Compound E-19)

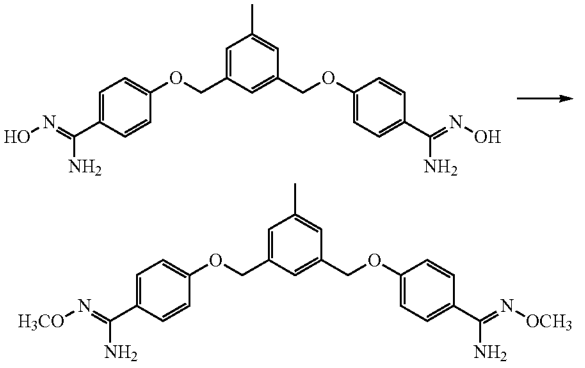

Synthesis of 1, 3-Bis {(4-N-hydroxyamidino)-phenoxy methyl}-5-methylbenzene: A suspension of hydroxylamine hydrochloride (1.50 g, 21.58 mmol) in anhydrous DMSO (50 ml) was cooled to 5° C. and potassium t-butoxide (2.98 g, 21.58 mmol) was added slowly to this suspension. The mixture was stirred at this temperature for 30 min. 1, 3-bis(4-cyano-phenoxy methyl)-5-methyl-benzene (0.956 g, 2.69 mmol) was added and the reaction mixture was stirred overnight at room temperature. Ice water was used to quench the reaction and stirred for about 30 min. The precipitate was collected, washed with water, dichloromethane ether and hexane and dried under vacuum to yield 1, 3-Bis {(4-N-hydroxyamidino)-phenoxy methyl}-5-methylbenzene as a white solid (0.9 g, 80%). $^{1}$H NMR (DMSO-$d_6$) 9.47 (br s, 2H), 7.60 (d, 4H, J=8.8 Hz), 7.33 (s, 1H), 7.23 (s, 2H), 7.00 (d, 4H, J=8.9 Hz), 5.73 (s, 4H), 5.00 (s, 4H), 2.33 (s, 3H); $^{13}$C NMR (DMSO-$d_6$) 158.89, 150.55, 137.91, 137.18, 127.82, 126.73, 125.98, 124.09, 114.32, 69.15, 20.97; MS: HRMS-ESI-POS.: calc. for $C_{23}H_{24}N_4O_4$ m/z 421.1876 (M++1), found m/z 421.1875.

Synthesis of 1, 3-Bis {(4-N-methoxyamidino)-phenoxy methyl}-5-methylbenzene: To a solution of bis-hydroxyamidine (0.1 g, 0.24 mmol) in DMF was added LiOH hydrate (0.12 g, 2.85 mmol) and dimethylsulfate (0.23 ml, 2.38 mmol). The reaction mixture was stirred at room temperature for 72 hours following which it was diluted with water and stirred for 30 minutes. The precipitate was filtered and washed with hexane to yield 1, 3-Bis {(4-N-methoxyamidino)-phenoxy methyl}-5-methylbenzene as a white solid (0.06 g, 56%). $^{1}$H NMR ($CDCl_3$): 7.55 (d, 4H, J=8.8 Hz), 7.26 (s, 1H), 7.19 (s, 2H), 6.95 (d, 4H, J=8.8 Hz), 5.06 (s, 4H), 4.77 (br s, 4H), 3.90 (s, 6H), 2.39 (s, 3H); $^{13}$C NMR ($CDCl_3$): 160.13, 151.86, 138.98, 137.14, 128.00, 127.40, 125.29, 123.70, 115.04, 123.70, 115.04, 69.98, 61.49, 21.51; MS: HRMS-ESI-POS.: calc. for $C_{25}H_{25}N_4O_4$ m/z 449.2189 (M++1), found m: 449.2180.

Synthesis 86. Synthesis of 1, 3-Bis {(4-amidino)-benzyloxy}-5-(n-pentyl)benzene dihydrochloride (Compound E-20 dihydrochloride)

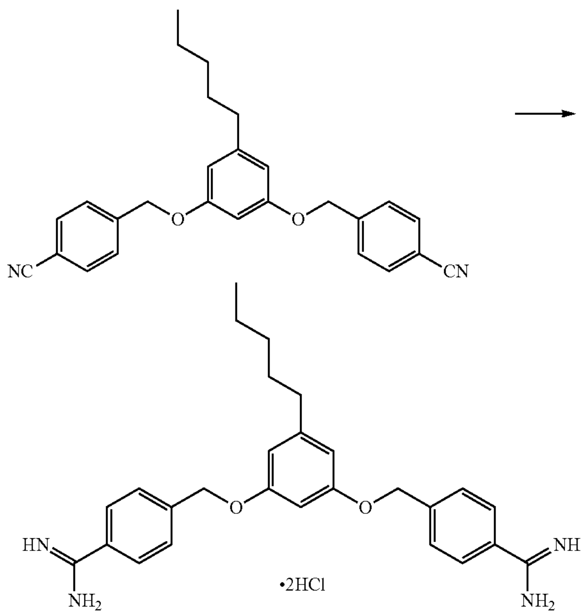

Synthesis of 1, 3-Bis {(4-cyano)-benzyloxy}-5-trifluoromethylbenzene: A mixture of olivetol (1.4 g, 8.2 mmol), 4-cyanobenzyl bromide (3.53 g, 18 mmol) and anhydrous $K_2CO_3$ (3.4 g, 24.6 mmol) in 100 ml DMF was stirred at room temperature overnight [TLC (Hex:EtOAc 4:1) monitored the reaction]. Then the reaction mixture was diluted with ice water (50 ml) and extracted with ethyl acetate (3×100 ml) followed by water and brine wash. The combined organic layer was dried over anhydrous $Na_2SO_4$, filtered, concentrated with rotavapor to yield 1, 3-Bis {(4-cyano)-benzyloxy}-5-trifluoromethylbenzene as a orange solid (3.2 g, 95.0%); $^{1}$H NMR ($CDCl_3$): 7.67 (d, 4H, J=8.3 Hz), 7.53 (d, 4H, J=8.2 Hz), 6.44 (d, 2H, J=2.2 Hz), 6.40 (t, 1H, J=2.2 Hz), 5.09 (s, 4H), 2.65-2.49 (m, 2H), 1.66-1.52 (m, 2H), 1.45-1.28 (m, 4H), 0.89 (t, 1H, J=6.9 Hz); $^{13}$C NMR ($CDCl_3$): 159.39, 145.99, 142.53, 132.47, 127.66, 118.78, 111.76, 107.98, 99.49, 68.97, 36.29, 31.50, 30.95, 22.61, 14.12; MS: HRMS-ESI-POS.: calc. for $C_{27}H_{27}N_2O_2Na$ m/z 433.1892 ($M^+$+1), found m/z 433.1873.

Synthesis of 1, 3-Bis {(4-amidino)-benzyloxy}-5-(n-pentyl)benzene dihydrochloride: The dinitrile (0.32 g, 0.78 mmol) was converted to 1, 3-Bis {(4-amidino)-benzyloxy}-

5-(n-pentyl)benzene dihydrochloride as white solid following Step 2b of General Route 7 (0.32 g, 80%) using ammonia gas. $^1$H NMR (DMSO-d$_6$): 9.47 (s, 4H), 9.28 (s, 4H), 7.88 (d, J=8.3 Hz, 4H), 7.65 (d, J=8.3 Hz, 4H), 6.51 (d, 1H, J=1.9 Hz), 6.48 (d, 1H, J=1.8 Hz), 5.20 (s, 4H), 2.47 (m, 1H), 1.65-1.38 (m, 2H), 1.38-1.20 (m, 4H), 0.84 (t, 3H, J=7.0 Hz); $^{13}$C NMR (DMSO-d$_6$): 165.44, 159.10, 145.03, 143.39, 128.34, 127.68, 127.28, 107.64, 99.62, 68.29, 35.43, 30.91, 30.37, 21.99, 13.96; MS: HRMS-ESI-POS.: calc. for $C_{27}H_{32}N_4O_2$ m/z 445.2604 (M$^+$+1), found m/z 445.2624.

Synthesis 87. Synthesis of 1, 3-Bis {(4-amidino)-benzyloxy}-5-trifluoromethylbenzene dihydrochloride (Compound C dihydrochloride)

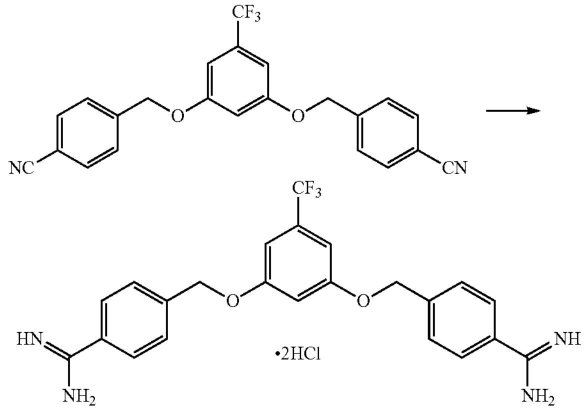

Synthesis of 1, 3-Bis {(4-cyano)-benzyloxy}-5-trifluoromethylbenzene: A mixture of 5-(trifluoromethyl)-1,3-diol (0.7 g, 4.2 mmol), 4-cyanobenzyl bromide (1.80 g, 9.21 mmol) and anhydrous $K_2CO_3$ (1.73 g, 12.6 mmol) in 20 ml DMF was stirred at room temperature overnight [TLC (Hex:EtOAc 4:1) monitored the reaction]. Then the reaction mixture was diluted with ice water (50 ml) and stirred for 30 min. The grey precipitate was filtered, washed with water, and dried in air. Then the yellow solid was dissolved in a dichloromethane (100 ml), dried over anhydrous $Na_2SO_4$, filtered, concentrated with rotavapor, triturated with hexane, filtered and dried in vacuum to yield 1, 3-Bis {(4-cyano)-benzyloxy}-5-trifluoromethylbenzene as a grey solid (1.48 g, 87.0%); $^1$H NMR (CDCl$_3$): 7.70 (d, 4H, J=8.3 Hz), 7.54 (d, 4H, J=8.3 Hz), 6.85 (d, 2H, J=2.1 Hz), 6.71 (t, 1H, J=2.2 Hz), 5.13 (s, 4H); $^{13}$C NMR (CDCl$_3$): 159.75, 141.48, 132.66, 127.76, 118.65, 112.25, 105.39, 104.85, 69.40; MS: HRMS-ESI-POS.: calc. for $C_{23}H_{15}N_2O_2F_3Na$ m/z 431.0961 (M$^+$+Na), found m/z 431.0983.

Synthesis of 1, 3-Bis {(4-amidino)-benzyloxy}-5-trifluoromethylbenzene dihydrochloride: The dinitrile (0.35 g, 0.85 mmol) was converted to 1, 3-Bis {(4-amidino)-benzyloxy}-5-trifluoromethylbenzene dihydrochloride as green solid following Step 2b of General Route 7 (0.3 g, 70%) using ammonia gas. $^1$H NMR (DMSO-d$_6$): 9.44 (s, 4H), 9.21 (s, 4H), 7.88 (d, J=8.2 Hz, 4H), 7.69 (d, J=8.3 Hz, 4H), 7.03 (s, 1H), 7.00 (s, 2H), 5.33 (s, 4H); $^{13}$C NMR (DMSO-d$_6$): 165.43, 159.75, 142.61, 128.47, 127.90, 127.74, 105.97, 104.51, 68.94, 26.70.; MS: HRMS-ESI-POS.: calc. for $C_{23}H_{21}F_3N_4O_2$ m/z 443.1695 (M$^+$+1), found m/z 443.1687.

Synthesis 88. Synthesis of 1, 3-Bis {(4-guadino)-phenoxy methyl}-5-methylbenzene di(trifluoroacetate) salt (Compound E-22 di(trifluoroacetate) salt)

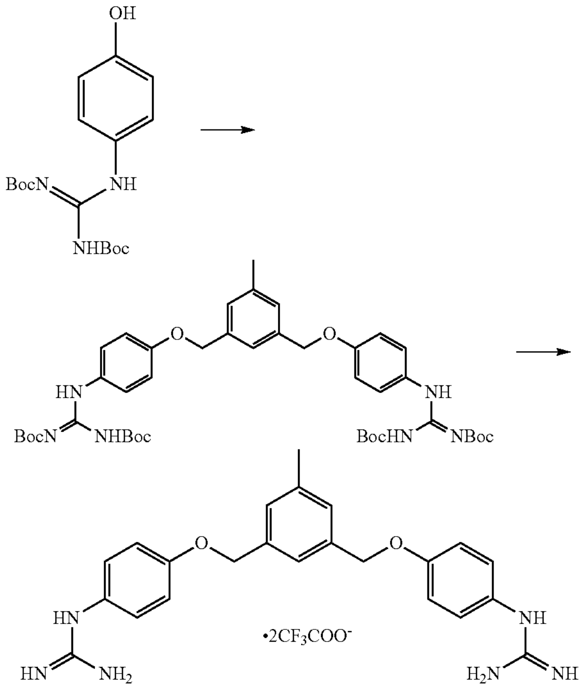

Synthesis of p-[N',N"-Di(Boc)guanidino]phenol: p-aminophenol (1.64 g, 15.0 mmol, 1.5 equiv) and N,N'-Di(Boc)-S-methylisothiourea (2.90 g, 10.0 mmol, 1 equiv) were stirred in THF (100 ml) for 10 minutes after which the reaction was cooled to 0° C. $HgCl_2$ (2.99 g, 11.0 mmol, 1.1 equiv) was added slowly to this solution and stirred for 20 h. The reaction mixture was concentrated and purified with column chromatography using 5:1 Hexane:EA as eluant to give p-[N',N"-Di(Boc)guanidino]phenol as a white solid (3.16 g, 60%). $^1$H NMR (CDCl$_3$): 11.61 (s, NH), 9.96 (s, NH), 7.01 (d, J=8.8 Hz, 2H), 6.58 (d, J=8.8 Hz, 2H), 1.53 (s, 9H), 1.44 (s, 9H); $^{13}$C NMR (CDCl$_3$): 156.05, 155.67, 153.29, 126.68, 116.41, 84.02, 80.35, 28.25, 28.21; MS: HRMS-ESI-POS.: calc. for $C_{17}H_{26}N_3O_5$ m/z 352.1872 (M$^+$+1), found m/z 352.1863.

Sythesis of 1, 3-Bis {(4-N',N"-Di(Boc)guanidino)-phenoxy methyl}-5-methylbenzene: Reaction of 1,3-bis(bromomethyl)-5-methylbenzene (0.36 g, 1.3 mmol), p-[N',N"-Di(Boc)guanidino]phenol (1.0 g, 2.84 mmol) and $K_2CO_3$ (0.54 g, 3.9 mmol) yielded 1, 3-Bis {(4-N',N"-Di(Boc) guanidino)-phenoxy methyl}-5-methylbenzene as white solid (0.74 g, 70%), following Step 1 of Route 7. $^1$H NMR (CDCl$_3$): 11.65 (s, 2H), 10.22 (s, 2H), 7.48 (d, J=8.9 Hz, 2H), 7.26 (s, 1H), 7.19 (s, 2H), 6.93 (d, J=9.0 Hz, 4H), 5.02 (s, 4H), 2.38 (s, 3H), 1.53 (s, 9H), 1.49 (s, 5H); MS: HRMS-ESI-POS.: calc. for $C_{43}H_{59}N_6O_{10}$ m/z 819.4293 (M$^+$+1), found m/z 819.4326.

Synthesis of 1, 3-Bis {(4-guadino)-phenoxy methyl}-5-methylbenzene di(trifluoroacetate) salt: 1, 3-Bis {(4-N',N"-Di(Boc)guanidino)-phenoxy methyl}-5-methylbenzene (32 mg, 0.039 mmol) was in DCM (2 ml) was treated with TFA (1 ml) for 2 hours. The solvent was removed in vacuo to yield 1, 3-Bis {(4-guadino)-phenoxy methyl}-5-methylbenzene di(trifluoroacetate) salt as a white solid. (20 mg, 80%). $^{1}$H NMR (MeOD): 7.33 (s, 1H), 7.23 (s, 2H), 7.22-7.19 (m, 4H), 7.11-7.06 (m, 4H), 5.09 (s, 4H), 2.36 (s, 3H); $^{13}$C NMR (MeOD): 159.77, 158.51, 139.83, 138.72, 128.83, 128.76, 128.57, 124.79, 117.16, 71.06, 21.39; MS: HRMS-ESI-POS.: calc. for $C_{23}H_{26}N_6O_2$ m/z 419.2195 (M++1), found m/z 419.2212.

Synthesis 89. Synthesis of 1, 3-Bis {(4-amidino)-benzyloxy}-5-(methoxy)benzene dihydrochloride (Compound E-23 dihydrochloride)

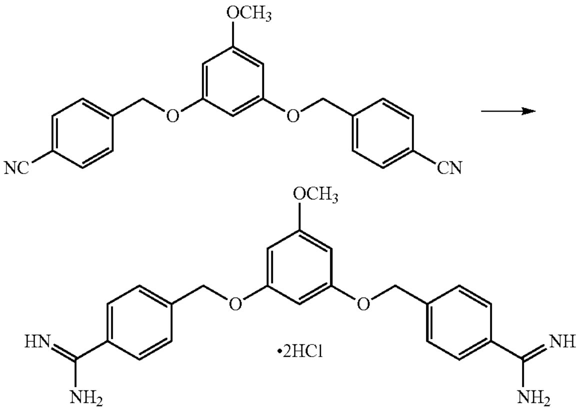

Syntheis of 1, 3-Bis {(4-cyano)-benzyloxy}-5-(methoxy) benzene: A mixture of 5-methoxyresorcinol (1. g, 8.7 mmol), 4-cyanobenzyl bromide (3.74 g, 18 mmol) and anhydrous $K_2CO_3$ (3.6 g, 26.02 mmol) in 100 ml DMF was stirred at room temperature overnight [TLC (Hex:EtOAc 4:1) monitored]. Then the reaction mixture was diluted with ice water (50 ml) and extracted with ethyl acetate (3×100 ml) followed by water and brine wash. The combined organic layer is dried over anhydrous $Na_2SO_4$, filtered, concentrated with rotavapor and purified with column chromatography using 5:1 hexane:EA as elutant to yield 1, 3-Bis {(4-cyano)-benzyloxy}-5-(methoxy)benzene as a white solid (2.94 g, 71.0%); $^{1}$H NMR (CDCl$_3$): 7.64 (d, 4H, J=8.1 Hz), 7.51 (d, 4H, J=8.2 Hz), 6.20-6.18 (m, 1H), 6.16 (d 2H, J=2.0 Hz), 5.06 (s, 4H), 3.75 (s, 3H); $^{13}$C NMR (CDCl$_3$): 161.82, 160.27, 142.30, 132.57, 127.71, 118.78, 111.94, 94.66, 94.47, 69.11; MS: HRMS-ESI-POS.: calc. for $C_{23}H_{18}N_2O_3$Na m/z 393.1215 (M$^+$+Na), found m/z 393.1201.

Synthesis of 1, 3-Bis {(4-amidino)-benzyloxy}-5-(methoxy)benzene dihydrochloride: The dinitrile (0.37 g, 0.99 mmol) was converted to 1, 3-Bis {(4-amidino)-benzyloxy}-5-(methoxy)benzene dihydrochloride as yellow solid following Step 2b of Route 7 (0.35 g, 75%) using ammonia gas. $^{1}$H NMR (DMSO-d$_6$): 9.45 (s, 4H), 9.24 (s, 4H), 7.87 (d, J=8.0 Hz, 4H), 7.65 (d. J=8.1 Hz, 4H), 6.32 (s, 1H), 6.23 (s, 2H), 5.21 (s, 4H), 3.71 (s, 3H); $^{13}$C NMR (DMSO-d$_6$): 165.42, 161.19, 159.84, 143.19, 128.33, 127.62, 94.73, 94.13, 68.36, 55.28; MS: HRMS-ESI-POS.: calc. for $C_{23}H_{25}N_4O_3$ m/z 405.1927 (M$^+$+1), found m/z 405.1923.

Synthesis 90. Synthesis of 1, 3-Bis {(4-amidino-2-fluoro)-benzyloxy}-5-(methoxy)benzene dihydrochloride (Compound E-24)

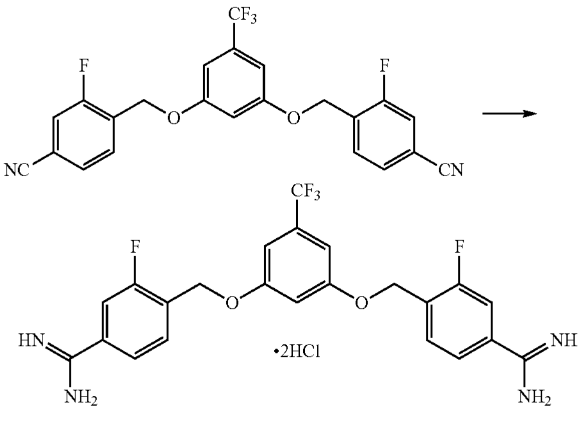

Synthesis of 1, 3-Bis {(4-cyano 2-fluoro)-benzyloxy}-5-trifluoromethylbenzene: A mixture of 5-(Trifluoromethyl)-1,3-diol (0.42 g, 2.4 mmol), 4-cyano2-fluorobenzyl bromide (1.07 g. 5.04 mmol) and anhydrous $K_2CO_3$ (0.99 g, 7.2 mmol) in 20 ml DMF was stirred at 45° C. for 4 h [TLC (Hex:EtOAc 4:1) monitored]. Then the reaction mixture was diluted with ice water (30 ml) and stirred for 30 min. The white precipitate was filtered, washed with water, and dried in air. Then the grey white was dissolved in a dichloromethane (50 ml), dried over anhydrous $Na_2SO_4$, filtered, concentrated with rotavapor and dried in vacuum to yield 1, 3-Bis {(4-cyano 2-fluoro)-benzyloxy}-5-trifluoromethylbenzene as a white solid (0.73 g, 70%); $^{1}$H NMR (CDCl$_3$): 7.67 (t, J=7.5 Hz, 2H), 7.51 (s, 2H), 7.42 (d, J=9.3 Hz, 2H), 6.89 (s, 2H), 6.75 (s, 1H), 5.19 (s, 4H); $^{13}$C NMR (DMSO-d$_6$): 159.53 (d, $J_{C-F}$=251.1 Hz), 159.45, 130.13 (d, $J_{C-F}$=4.4 Hz), 129.29 (d, $J_{C-F}$=14.0 Hz), 128.54 (d, $J_{C-F}$=4.1 Hz), 119.16 (d, $J_{C-F}$=24.4 Hz), 117.30 (d, $J_{C-F}$=2.8 Hz), 113.58 (d, $J_{C-F}$=9.4 Hz), 105.06, 104.97 (d, $J_{C-F(CF3)}$=4.0 Hz), 63.42 (d, $J_{C-F}$=4.4 Hz); MS: HRMS-ESI-POS.: calc. for $C_{23}H_{13}N_2O_2F_5$Na m/z 467.077 (M$^+$+Na), found m/z 467.0468.

Synthesis of 1, 3-Bis {(4-amidino2-fluoro)-benzyloxy}-5-trifluoromethylbenzene dihydrochloride: The dinitrile (0.30 g. 0.68 mmol) was added to anhydrous EtOH saturated with hydrogen chloride (20 mL) at 0° C. in a dry flask. The reaction mixture was then sealed, slowly warmed to ambient temperature, and stirred for 7 days. Ethanol was removed using rotary evaporator. Anhydrous diethyl ether (20 mL) was added to the reaction mixture and the precipitated imidate ester dihydrochloride was filtered off and dried under high vacuum. Ammonia gas (using a cylinder) was passed through imidate ester in EtOH (10 mL) and stirred for a day. The reaction mixture was concentrated in vacuum. Then anhydrous ether was added, and the product was filtered and dried in the oil pump. The free base was converted to its dihydrochloride salt by stirring the diamidine with saturated ethanolic HCl (2 mL) for 2-3 h. The solvent was removed thoroughly and the obtained product was dried in vacuum at 80° C. for 12 h to yield 1, 3-Bis {(4-amidino2-fluoro)-benzyloxy}-5-trifluoromethylbenzene dihydrochloride as a white solid (0.3 g, 60%). $^{1}$H NMR (DMSO-d$_6$); $^{1}$H NMR (DMSO-d$_6$): 9.42 (s, 4H), 9.23 (s, 4H), 7.83 (t, J=7.2 Hz, 4H), 7.76 (d, J=10.5 Hz, 2H), 7.70

(d, J=7.9 Hz, 2H), 7.08 (s, 1H), 7.04 (s, 2H), 5.35 (s, 4H); MS: HRMS-ESI-POS.: calc. for $C_{23}H_{20}N_4O_2F_5$ m/z 479.1506 ($M^+$+1), found m/z 479.1512.

Synthesis 91. Synthesis of 1, 3-Bis {(4-amidino)-phenethyl}-5-trifluoromethylbenzene dihydrochloride (Compound E-25 dihydrochloride)

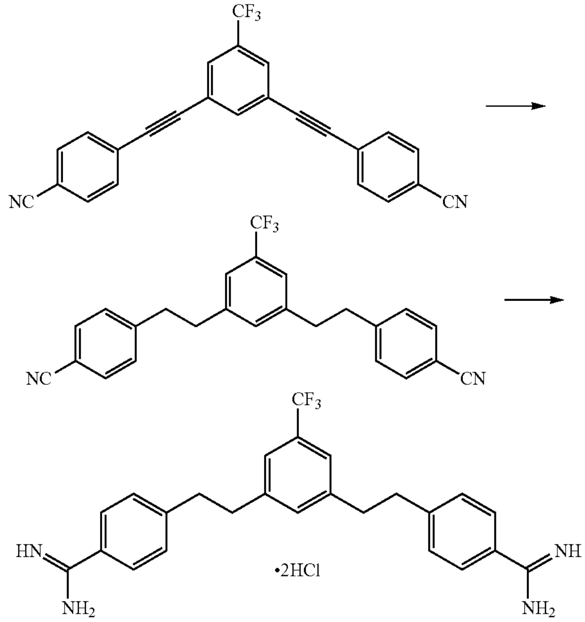

Synthesis of 4,4'-((5-(trifluoromethyl)-1,3-phenylene)bis(ethyne-2,1-diyl))dibenzonitrile: To 3,5-dibromobenzotrifluoride (1.57 g, 5.2 mmol) was added 1:1 DMF-$Et_3N$ (10 ml). To this solution, 3 mole % $Pd(PPh_3)_4$ and 4-Ethynylbenzonitrile (1.32 g, 10.4 mmol) were added and stirred for 5 minutes. Further, 6 mol % Na ascorbate solution, 1 mol % $CuSO_4$ solution in DMF were added to the reaction mixture and stirred for 4 h at 80° C. The reaction mixture was extracted with ethyl acetate followed by ammonium chloride and brine wash. The combined organic layer was dried over anhydrous $Na_2SO_4$ and then concentrated invacuo. The product was purified using column chromatography and obtained using 5:1 Hexane:Ethyl acetate system as a white solid (1.23 g, 60%). $^1$H NMR ($CDCl_3$) 7.88 (s, 1H), 7.79 (s, 2H), 7.70-7.61 (m, 8H); $^{13}$C NMR ($CDCl_3$): δ 137.70, 132.39, 132.36, 128.79, 127.19, 124.06, 118.40, 112.55, 90.90, 90.03; MS: HRMS-ESI-POS.: calc. for $C_{25}H_{11}N_2F_3Na$ m/z 419.0772 (M+Na), found m/z 419.0771.

Synthesis of 4,4'-((5-(trifluoromethyl)-1,3-phenylene)bis(ethane-2,1-diyl))dibenzonitrile: To 10% Pd//0 C in THF (30 ml) under argon gas was added 4,4'-((5-trifluoromethyl-1, 3-phenylene)bis(ethyne-2,1-diyl))dibenzonitrile (1.23 g, 3.1 mmol). The argon gas was exchanged for $H_2$ gas and the reaction mixture was stirred overnight. The reaction mixture was quenched with $CH_2Cl_2$ and filtered through celite. Extraction was carried out with $CH_2Cl_2$ followed by water wash. The combined organic layer was dried over anhydrous $Na_2SO_4$ and then concentrated invacuo to give the product as a white solid (1.22 g, 97.3%). $^1$H NMR ($CDCl_3$) δ 7.58 (d, J=8.2 Hz, 4H), 7.22 (d, J=8.3 Hz, 6H), 7.00 (s, 1H), 2.94 (s, 8H);); $^{13}$C NMR (DMSO-$d_6$): 146.56, 141.85, 132.40, 132.18, 129.40, 123.38 (dd, $J_{C-F(CF3)}$=7.7, 3.5 Hz), 123.19, 123.15, 123.12, 119.04, 110.30, 37.78, 37.03); MS: HRMS-ESI-POS.: calc. for $C_{25}H_{19}N_2F_3Na$ m/z 427.1377 ($M^+$+Na), found m/z 427.1398.

Synthesis of 1, 3-Bis {(4-amidino)-benzyloxy}-5-trifluoromethylbenzene dihydrochloride: Dinitrile (0.31 g, 0.76 mmol) was added to anhydrous EtOH saturated with hydrogen chloride (20 mL) at 0° C. in a dry flask. The reaction mixture was then sealed, slowly warmed to ambient temperature, and stirred for 7 days. Ethanol was removed using rotary evaporator. Anhydrous diethyl ether (20 mL) was added to the reaction mixture and the precipitated imidate ester dihydrochloride was filtered off and dried under high vacuum. Ammonia gas (using a cylinder) was passed through imidate ester in EtOH (10 mL) and stirred for a day. The reaction mixture was concentrated in vacuum. Then anhydrous ether was added, and the product was filtered and dried in the oil pump. The free base was converted to its dihydrochloride salt by stirring the diamidine with saturated ethanolic HCl (2 mL) for 2-3 h. The solvent was removed thoroughly and the obtained product was dried in vacuum at 80° C. for 12 h to yield 1, 3-Bis {(4-amidino)-benzyloxy}-5-trifluoromethylbenzene dihydrochloride as a white solid (0.31 g, 62%). $^1$H NMR (DMSO-$d_6$): $^1$H NMR (DMSO-$d_6$) δ 9.24 (s, 4H), 9.12 (s, 4H), 7.76 (d, J=8.2 Hz, 4H), 7.51 (m, 5H), 7.46 (s, 2H), 2.99 (s, 8H); NMR ($CDCl_3$) δ 7.58 (d, J=8.2 Hz, 4H), 7.22 (d, J=8.3 Hz, 6H), 7.00 (s, 1H), 2.94 (s, 8H);); $^{13}$C NMR (DMSO-$d_6$): 165.40, 147.92, 142.59, 132.70, 129.05, 128.13, 125.75, 122.75, 36.46, 56.13; MS: HRMS-ESI-POS.: calc. for $C_{25}H_{26}N_4F_3$ m/z 439.2110 ($M^+$+1), found m/z 439.2111.

Example 2. Sensitization of *Escherichia Coli* (Gram Negative Bacterium) and *Bacillus Subtilis* (Gram Positive Bacterium) to Erythromycin

*E. coli* bacteria were cultured in Miller's broth at 37° C. overnight prior to treatment. *B. subtilis* bacteria were cultured in nutrient broth at 37° C. overnight prior to treatment. Bacteria were then incubated with various concentrations of erythromycin with or without the compounds shown below for 20 hours. Bacterial density was measured based on $OD_{600}$. Magnitude of the sensitization (sensitization fold) was calculated based on the $IC_{90}$ of erythromycin using the following formula:

Sensitization fold(SF)=$IC_{90}$ of erythromycin without compounds/$IC_{90}$ of erythromycin with compounds The results of the erythromycin sensitization studies for *E. coli* and *B. subtilis* are provided in Table 1A and Table 1B. NA=no activity; --=not tested; T=toxic TABLE 1A
| Sensitization of *E. coli* and *B. subtilis* Bacteria to Erythromycin | | |
|---|---|---|
| Compound | SF (*E. coli*) | SF (*B. subtilis*) |
| 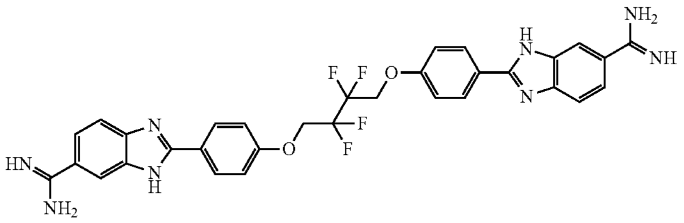 C-5 | <2 | NA at 12.5 and 25 μM |
| 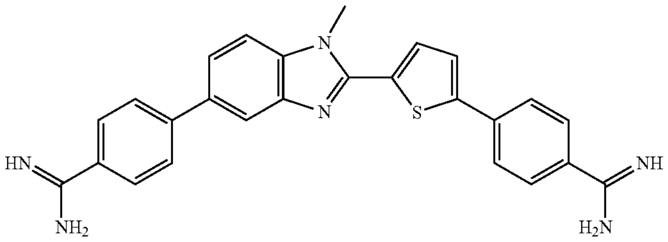 E-1 | NA | NA |
| 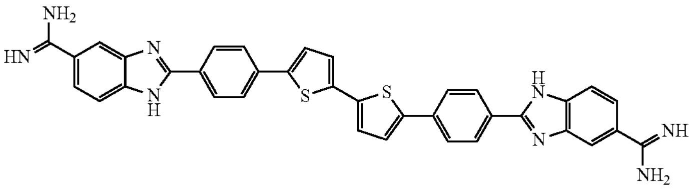 C-6 | NA | NA |
| 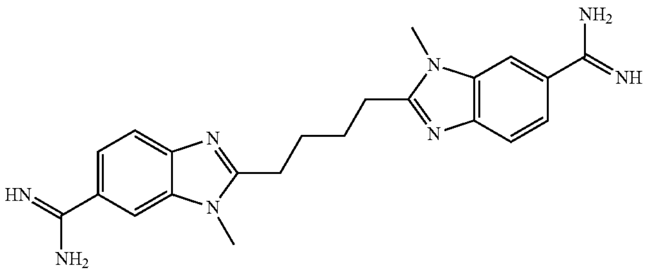 C-7 | NA | NA at 12.5 and 25 μM |
| 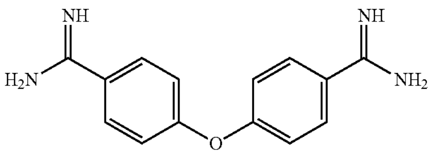 C-8 | NA | NA at 12.5 and 25 μM |

TABLE 1A-continued
Sensitization of *E. coli* and *B. subtilis* Bacteria to Erythromycin
| Compound | SF (*E. coli*) | SF (*B. subtilis*) |
|---|---|---|
| 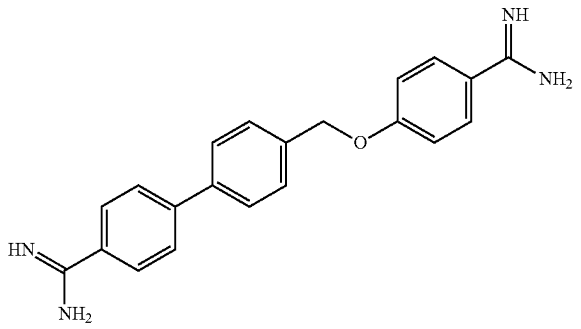 E-2 | <2 | NA |
| 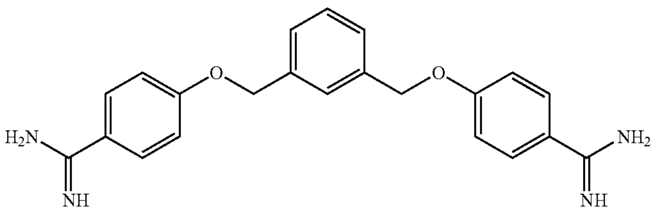 E-3 | <2 | NA |
| 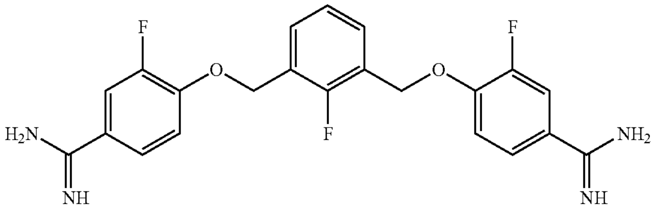 A-1 | 6 | NA |
| 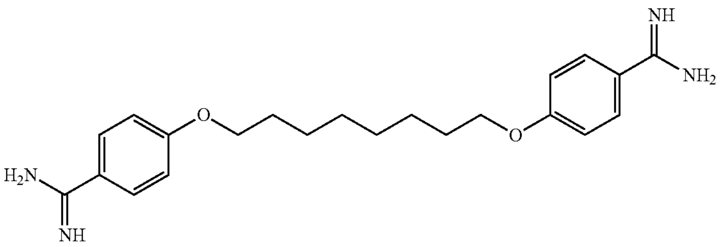 E-4 | T | NA |
| 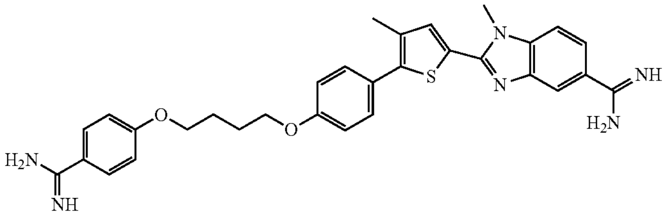 C-9 | <2 | NA |

TABLE 1A-continued
Sensitization of *E. coli* and *B. subtilis* Bacteria to Erythromycin
| Compound | SF (*E. coli*) | SF (*B. subtilis*) |
|---|---|---|
| 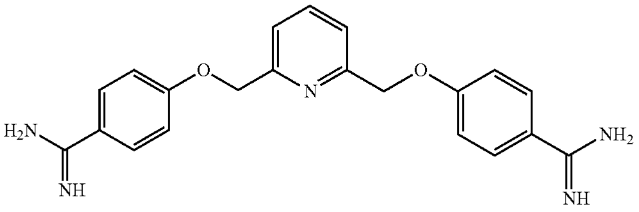 E-5 | NA | NA |
| 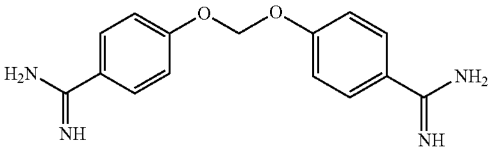 E-6 | NA | NA |
| 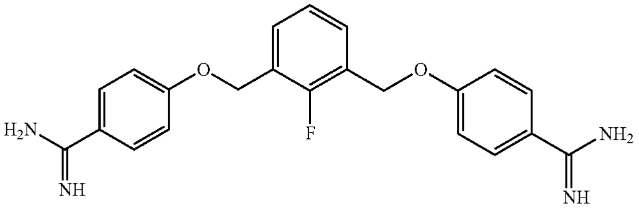 C-2 | <2 | NA |
| 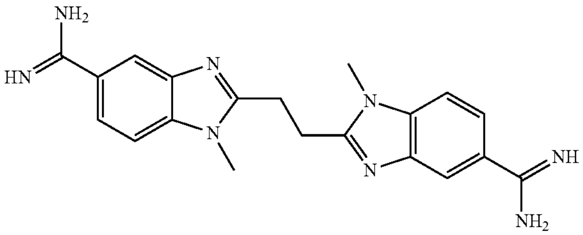 C-10 | NA | NA at 12.5 and 25 μM |
| 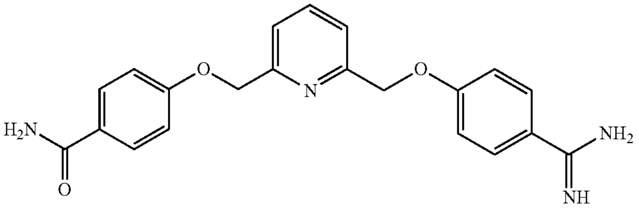 C-1 | NA | NA at 12.5 and 25 μM |
| 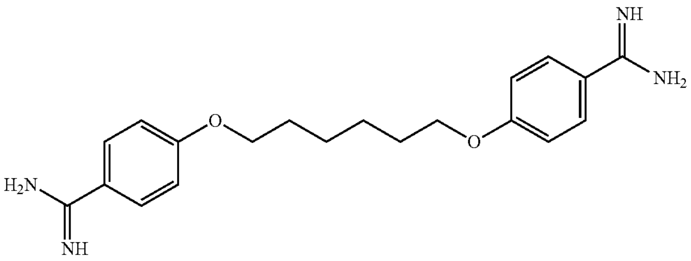 E-7 | NA | NA |

TABLE 1A-continued
| Sensitization of *E. coli* and *B. subtilis* Bacteria to Erythromycin | | |
|---|---|---|
| Compound | SF (*E. coli*) | SF (*B. subtilis*) |
| 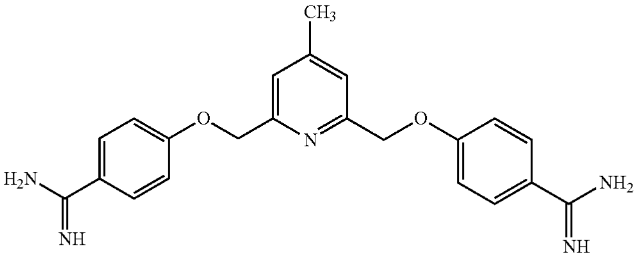 Compound M-1 | 33 (32-fold at 25 μM; 8-fold at 12.5 μM) | >30 (32-fold at 12 μM; 8-fold at 6 μM) |
| 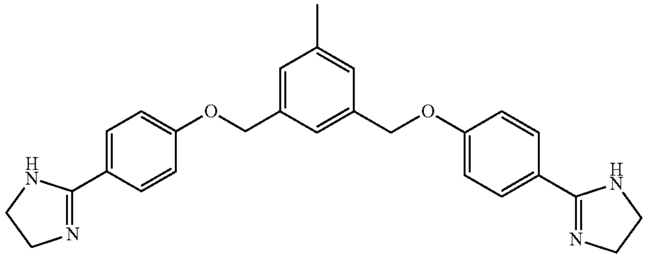 A-2 | NA at 12.5 and 25 μM | >4 |
| 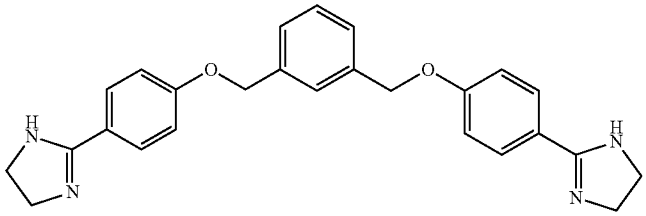 E-9 | NA at 12.5 and 25 μM | — |
| 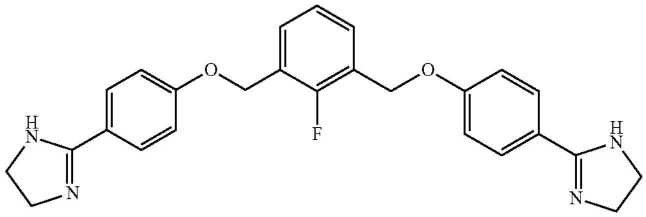 A-3 | NA at 12.5 and 25 μM | — |
| 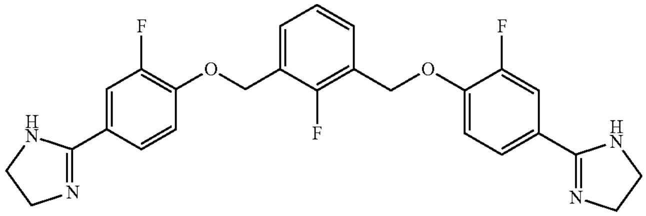 A-4 | NA at 12.5 and 25 μM | — |

TABLE 1A-continued
Sensitization of *E. coli* and *B. subtilis* Bacteria to Erythromycin
| Compound | SF (*E. coli*) | SF (*B. subtilis*) |
| --- | --- | --- |
| 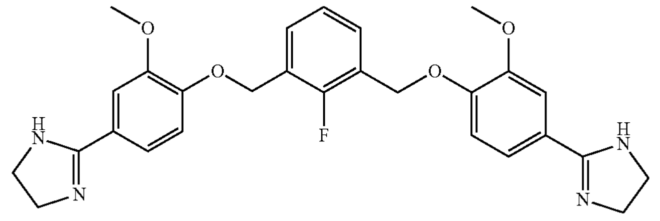 A-5 | NA at 12.5 and 25 μM | — |
| 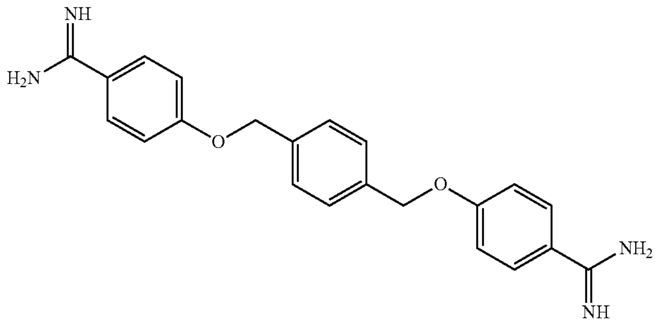 E-10 | NA at 12.5 and 25 μM | <2 |
| 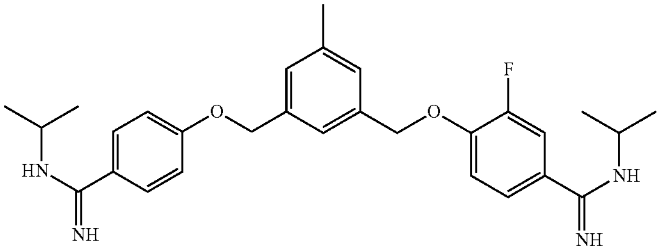 C-3 | NA at 12.5 and 25 μM | T |
| 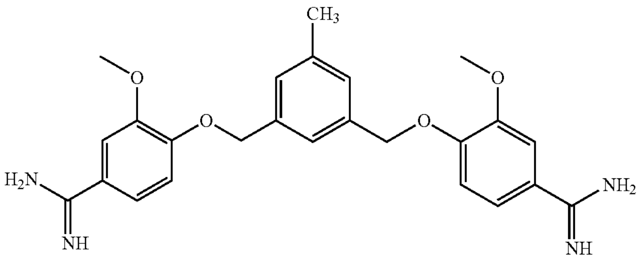 A-6 | NA | NA |
| 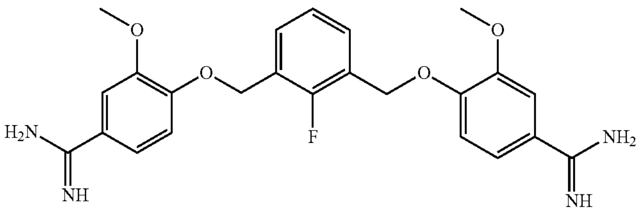 A-7 | NA at 12.5 and 25 μM | 4-fold at 6 μM |

TABLE 1A-continued
| Sensitization of *E. coli* and *B. subtilis* Bacteria to Erythromycin | | |
|---|---|---|
| Compound | SF (*E. coli*) | SF (*B. subtilis*) |
| 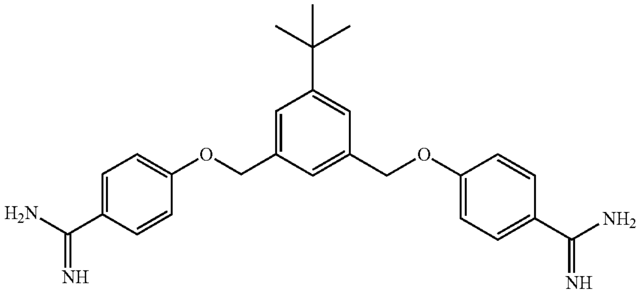 C-4 | 4-fold at 12.5 μM | NA |
| 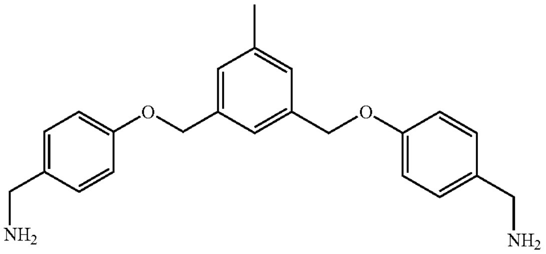 E-11 | 4-fold at 25 μM | 16-fold at 12.5 μM |
| 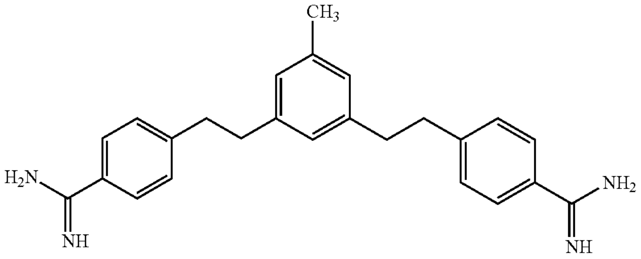 A-8 | 32-fold at 25 μM; 8-fold at 12.5 μM | 32-fold at 6 μM |

TABLE 1B
| Sensitization of *E. coli* and *B. subtilis* Bacteria to Erythromycin | | |
|---|---|---|
| Compound | SF (*E. coli*) | SF (*B. subtilis*) |
| 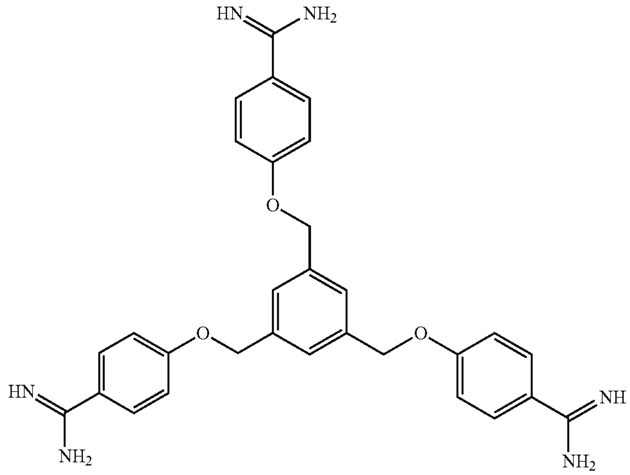 E-12 | NA | T |
| 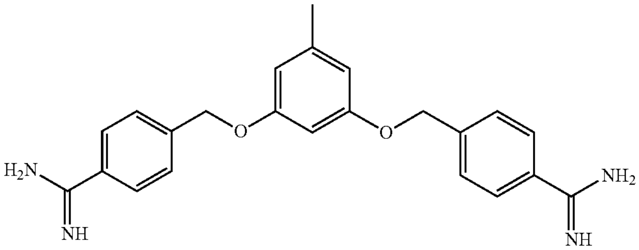 B-114 | 32-fold at 25 μM | 32-fold at 12 μM |
| 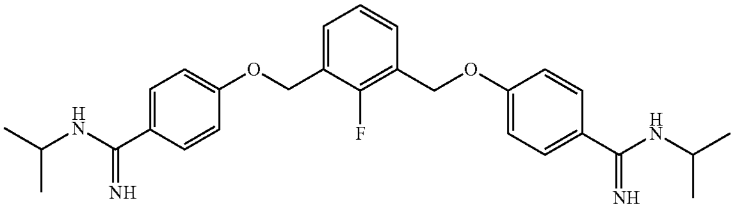 D-2 | NA at 12 and 25 μM | NA at 6 μM |
| 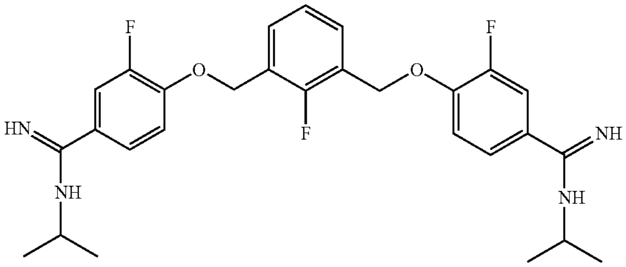 B-9 | NA at 12 and 25 μM | NA at 12 and 6 μM |

TABLE 1B-continued
Sensitization of *E. coli* and *B. subtilis* Bacteria to Erythromycin
| Compound | SF (*E. coli*) | SF (*B. subtilis*) |
|---|---|---|
| 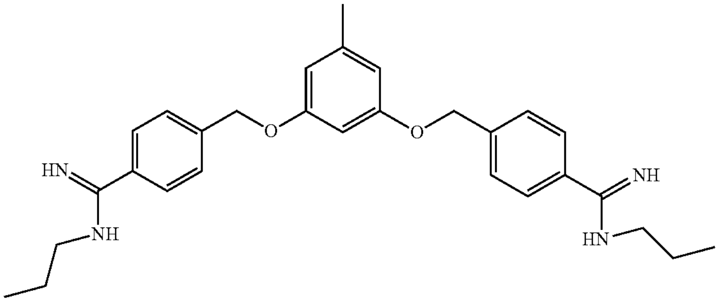 E-13 | NA at 12.5 and 25 μM | NA at 12 and 6 μM |
| 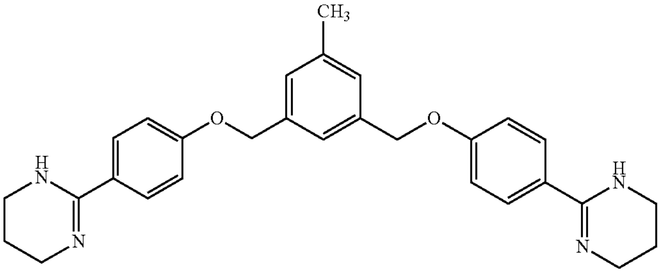 B-21 | NA at 12.5 and 25 μM | NA at 12 and 6 μM |
| 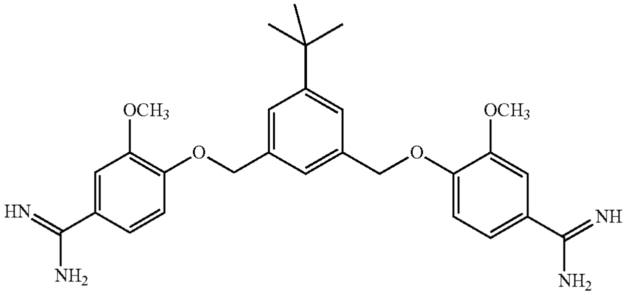 E-14 | 8-fold at 12.5 μM; 2-fold at 6 μM | 8-fold at 12 μM; 2-fold at 6 μM |
| 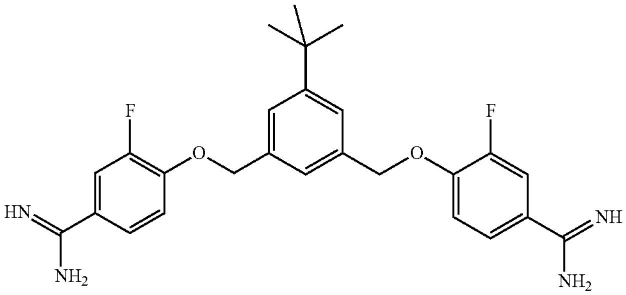 E-15 | 32-fold at 12 μM; 4-fold at 6 μM | 8-fold at 6 μM; 2-fold at 3 μM |

TABLE 1B-continued
Sensitization of *E. coli* and *B. subtilis* Bacteria to Erythromycin
| Compound | SF (*E. coli*) | SF (*B. subtilis*) |
| --- | --- | --- |
| 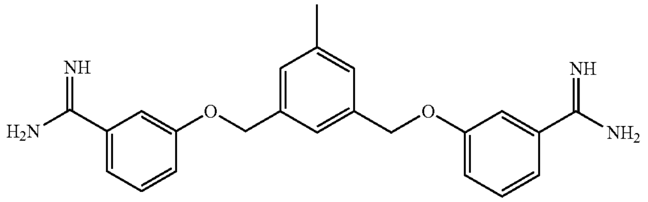 E-16 | 8-fold at 25 μM; 2-fold at 12 μM | 32-fold at 12 μM; 8-fold at 6 μM |
| 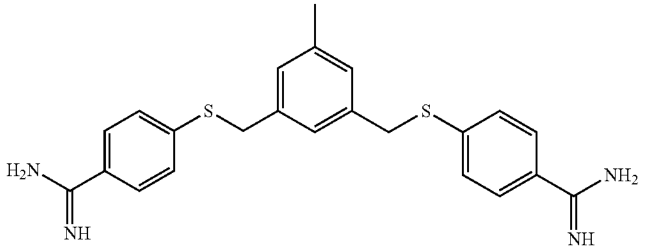 D-4 | 32-fold at 12.5 μM; 4- to 8-fold at 6 μM | 32-fold at 6 μM; 4- to 8-fold at 3 μM |
| 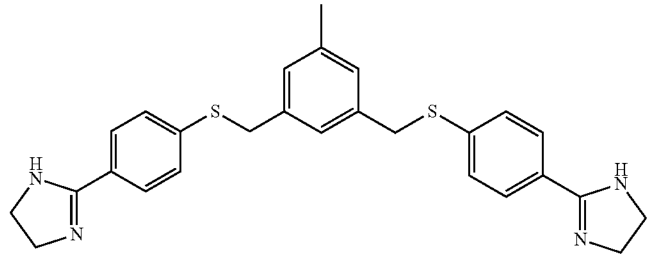 B-12 | NA at 12.5 and 6 μM | 16-fold at 6 μM; 4-fold at 3 μM |
| 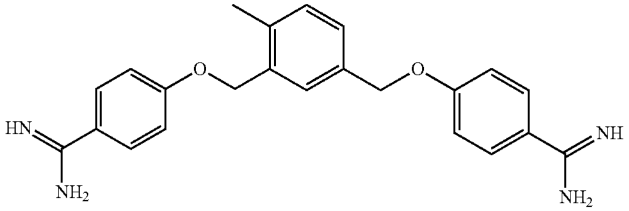 E-17 | 32-fold at 25 μM; 4- fold at 12.5 μM | 32-fold at 12 μM; 16-fold at 6 μM |
| 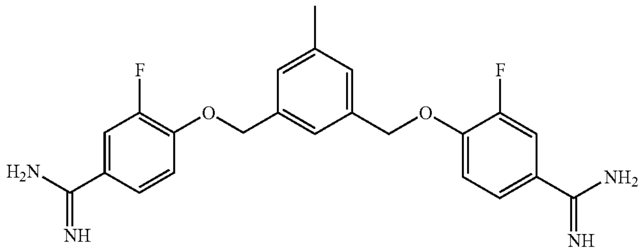 E-18 | 64-fold at 25 μM | — |

TABLE 1B-continued
| Sensitization of *E. coli* and *B. subtilis* Bacteria to Erythromycin | | |
|---|---|---|
| Compound | SF (*E. coli*) | SF (*B. subtilis*) |
| 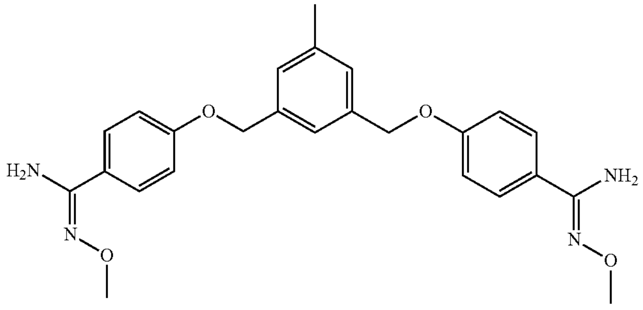 E-19 | 4-fold at 20 μM | — |
| 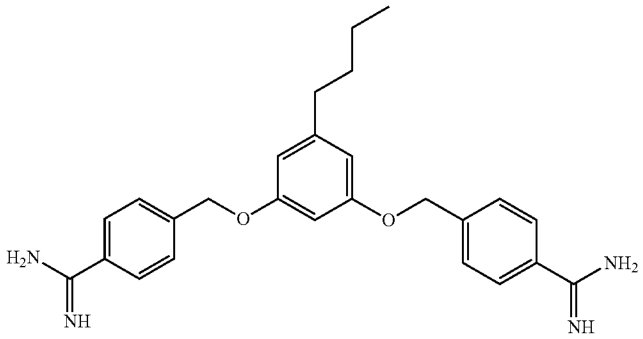 E-20 | 10 μM > 32 fold | — |
| 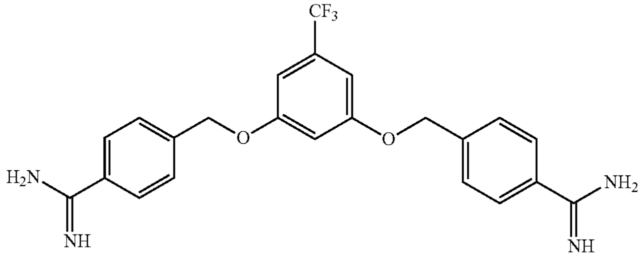 Compound C | 10 μM > 32 fold | — |
| 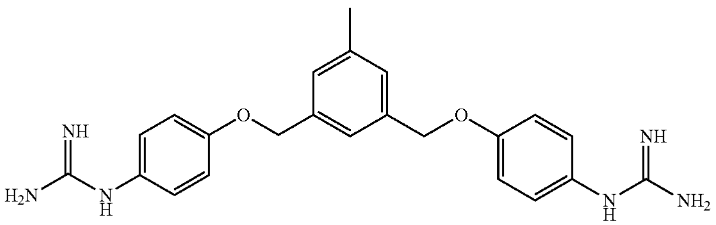 E-22 | Similar to Compd M-1 | — |

TABLE 1B-continued

| Sensitization of *E. coli* and *B. subtilis* Bacteria to Erythromycin | | |
|---|---|---|
| Compound | SF (*E. coli*) | SF (*B. subtilis*) |
| 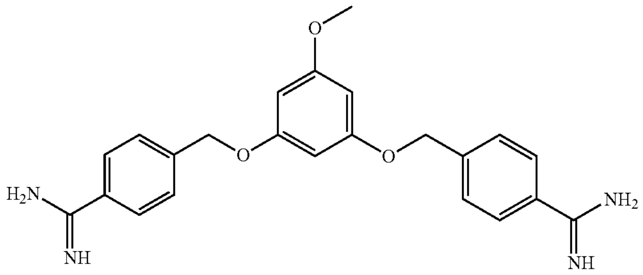 E-23 | No effect at 20 μM | — |

To determine the MIC for each compound against *E. coli*, *E. coli* bacteria were cultured in Miller's broth or Mueller Hinton Broth at 37° C. overnight prior to treatment. Bacteria were then cultured with varying concentration of the compounds shown below for 48 hours, and then bacterial density was measured based on OD600. The minimum inhibitory concentration (MIC, 90% growth inhibition) was calculated for each compound, as shown in Table 2. The procedure to determine the MIC for each compound against *B. subtilis* was the same except that the bacteria was cultured in nutrient broth. The MIC of each compound against *B. subtilis* is shown in Table 2 (NA=no activity, --=not tested).

TABLE 2

| MIC of Select Compounds Against *E. coli* and *B. subtilis* | | |
|---|---|---|
| Compound | MIC (*E. coli*) | MIC (*B. subtilis*) |
| 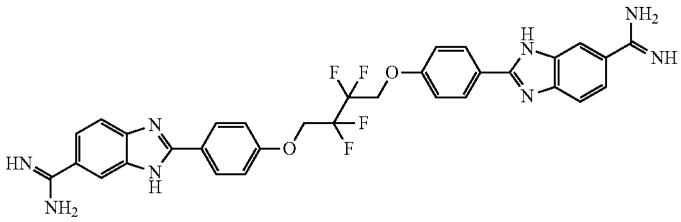 C-5 | 25 μM inhibit 50% | 25 μM inhibit 20%; 12.5 inhibit 10% |
| 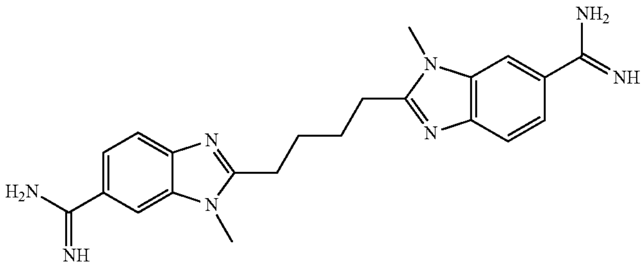 C-7 | NA | 25 μM inhibit 20%; 12.5 result in NA |
| 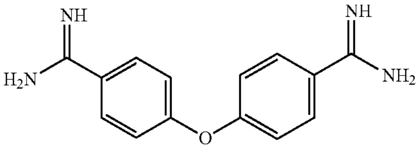 C-8 | NA | 25 μM inhibit 70%; 12.5 inhibit 60% |

TABLE 2-continued
| MIC of Select Compounds Against *E. coli* and *B. subtilis* | | |
|---|---|---|
| Compound | MIC (*E. coli*) | MIC (*B. subtilis*) |
| 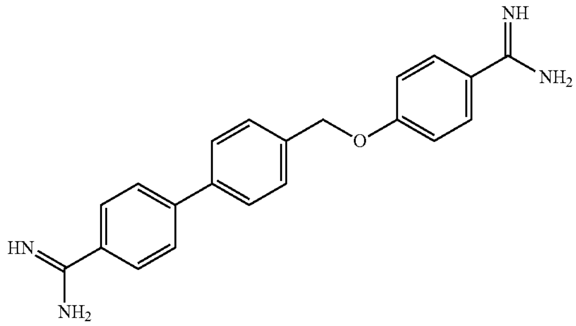 E-2 | 25 μM inhibit 50% | 12.5 μM reach MIC; 2 μM inhibit 30% |
| 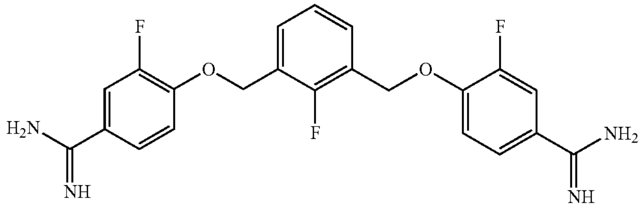 A-1 | 50 μM inhibit 90%; 25 μM inhibit 70%; 12 μM inhibit 40% | 12.5 μM reach MIC; 2 μM inhibit 10% |
| 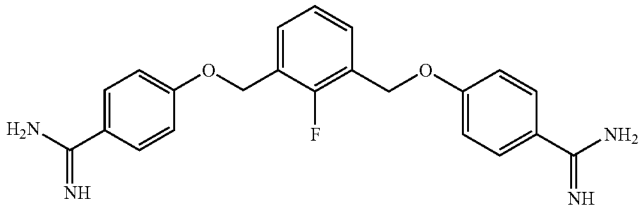 C-2 | 12 μM inhibit 80%; 6 μM inhibit 60% | 12 μM inhibit 60%; 6 μM inhibit 50% |
| 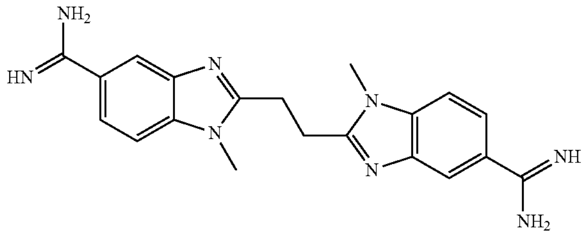 C-10 | 50 μM inhibit 10% | 25 PM inhibit 70%; 12.5 μM inhibit 20% |
| 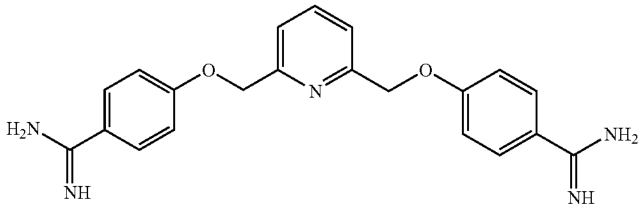 C-1 | 50 μM results in NA | 25 μM inhibit 10%; 12.5 μM results in NA |

TABLE 2-continued
MIC of Select Compounds Against *E. coli* and *B. subtilis*
| Compound | MIC (*E. coli*) | MIC (*B. subtilis*) |
|---|---|---|
| 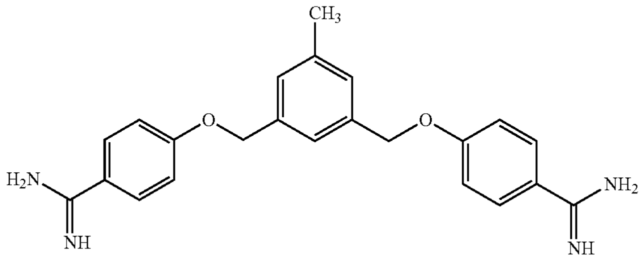 Compound M-1 | 25 μM inhibit 25%; 12 μM inhibit 15% | 25 μM inhibit 50%; 12 μM inhibit 20% |
| 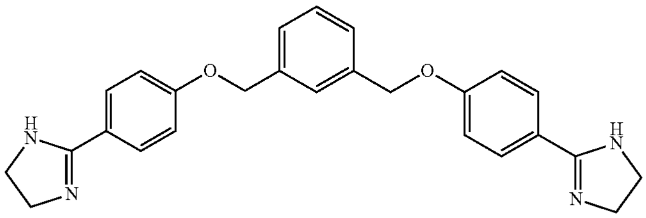 E-9 | 25 μM inhibit 50%; 12 μM inhibit 25% | — |
| 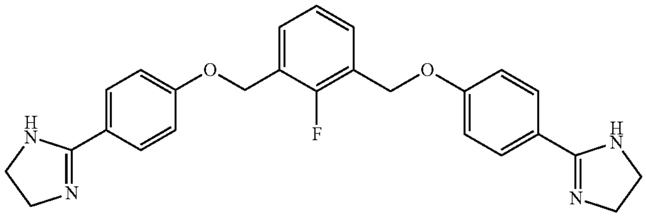 A-3 | 25 μM inhibit 20%; 12 μM results in NA | — |
| 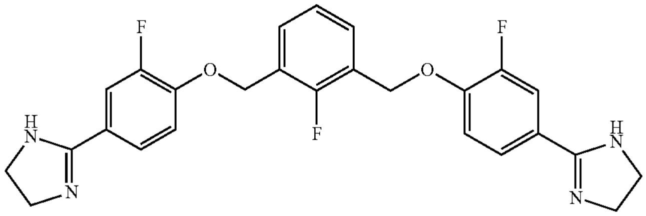 A-4 | NA at 25 and 12 μM | — |
| 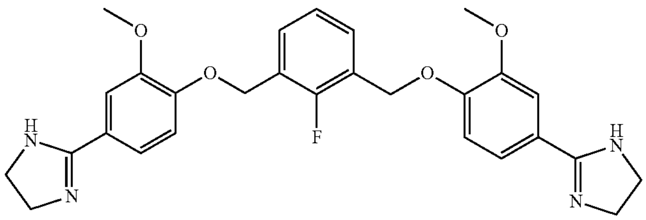 A-5 | NA at 25 and 12 μM | — |

TABLE 2-continued

| MIC of Select Compounds Against *E. coli* and *B. subtilis* | | |
|---|---|---|
| Compound | MIC (*E. coli*) | MIC (*B. subtilis*) |
| 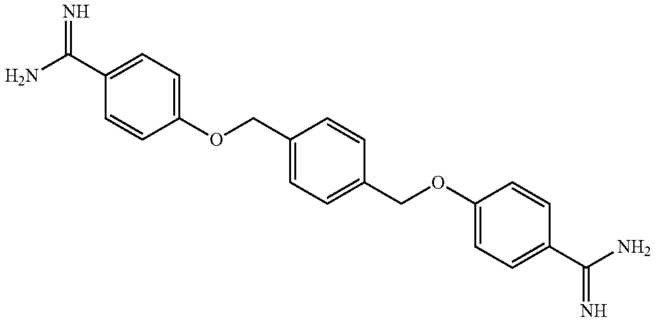 E-10 | 25 μM inhibit 20%; 12 μM inhibit 10% | 12 μM inhibit 70%; 6 μM inhibit 60% |
| 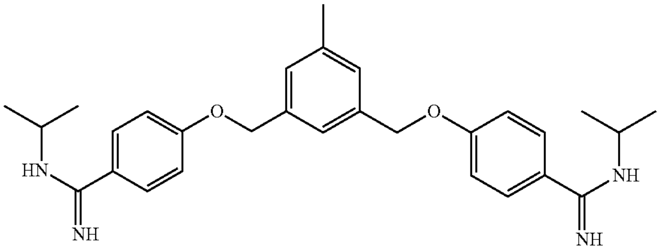 C-3 | 25 μM inhibit 50%; 12 u.M inhibit 40% | 6 μ.M reach MIC; 2 μM inhibit 70%; 1 μM inhibit 60% |
| 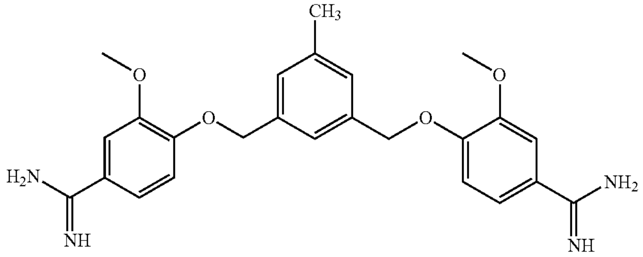 A-6 | 25 μM inhibit 50%; 12 μM inhibit 25% | 6 μ.M reach MIC; 2 μM inhibit 50%; 1 μM inhibit 10% |
| 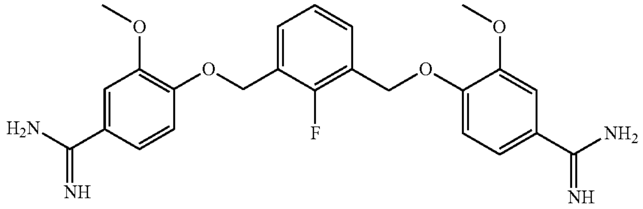 A-7 | 25 μM inhibit 50%; 12 μM inhibit 30% | 12 μM inhibit 50%; 6 μM inhibit 25% |
| 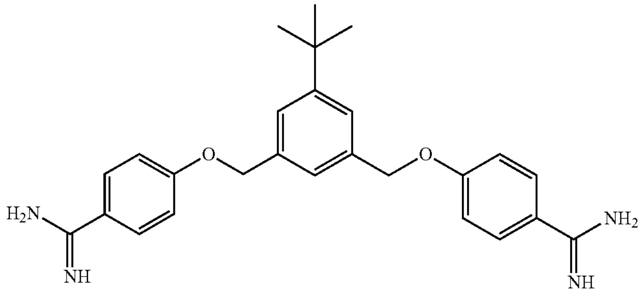 C-4 | 25 μM inhibit 90%; 12 μM inhibit 40% | 6 μM reach MIC; 2 μM inhibit 70%; 1 μM inhibit 10% |

TABLE 2-continued
MIC of Select Compounds Against *E. coli* and *B. subtilis*
| Compound | MIC (*E. coli*) | MIC (*B. subtilis*) |
|---|---|---|
| 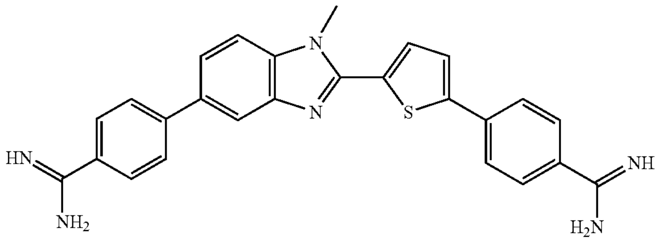 E-1 | 25 μM inhibit 15% | 12 μM reach MIC; 6 μM inhiit 50%; 2 μM 20% |
| 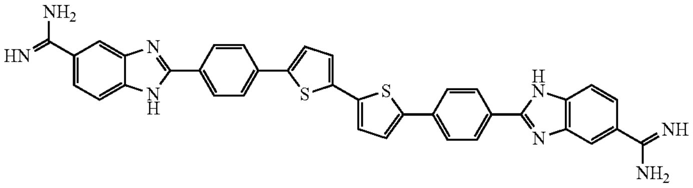 C-6 | 50 μM inhibit 10% | 12 and 6 μM inhibit 20% |
| 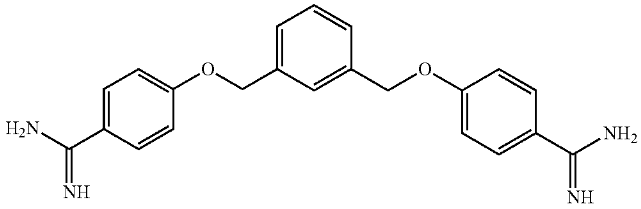 E-3 | 50 μM inhibit 60%: 25 μM inhibit 50%; 12 μM inhibit 35% | 12 μM inhibit 70%; 6 μM inhibit 60%; 2 μM inhibit 30% |
| 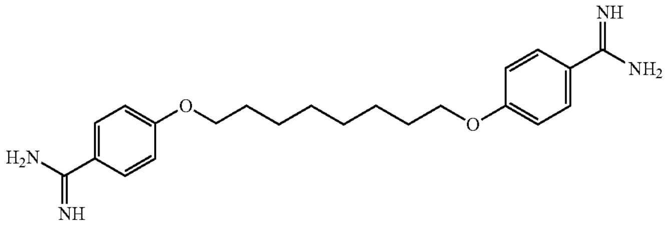 E-4 | 25 μM | — |
| 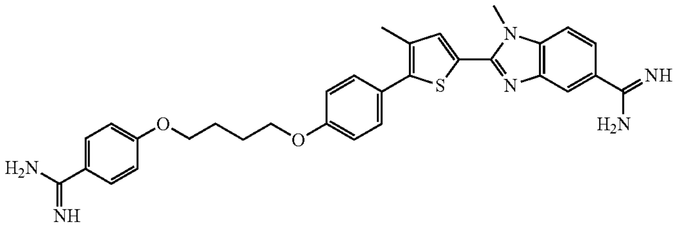 C-9 | 25 μM inhibit 30% | 12 μM inhibit 70%; 6 μM results in NA |
| 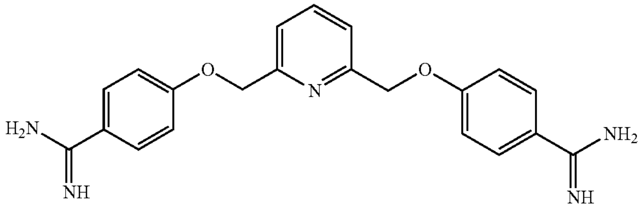 E-5 | 50 μM inhibit 50% | 12.5 μM reach MIC; 2 μM inhibit 40% |

TABLE 2-continued
| MIC of Select Compounds Against *E. coli* and *B. subtilis* | | |
|---|---|---|
| Compound | MIC (*E. coli*) | MIC (*B. subtilis*) |
| 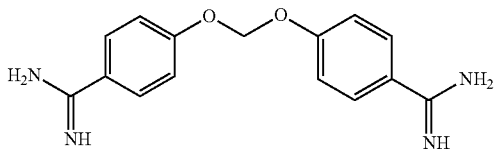 E-6 | 50 μM results in NA | 12.5 μM inhibit 80%; 6 μM inhibit 10% |
| 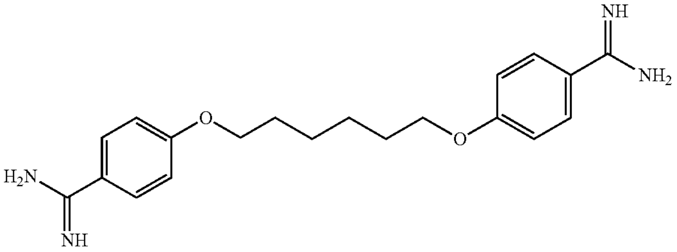 E-7 | 25 μM inhibit 70%; 12 μM inhibit 40% | 12 μM reach MIC; 6 μM inhibit 40%; 2 μM inhibit 30% |
| 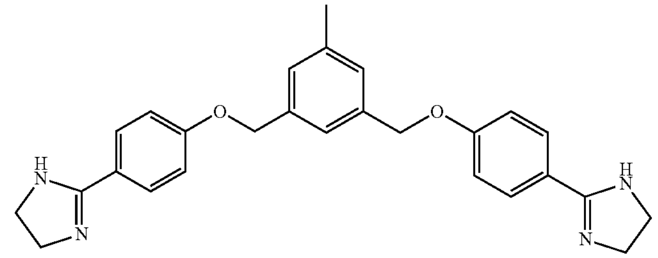 A-2 | 25 μM inhibit 25%; 12 μM inhibit 10% | 12 μM inhibit 25%; 6 μM inhibit 20% |
| 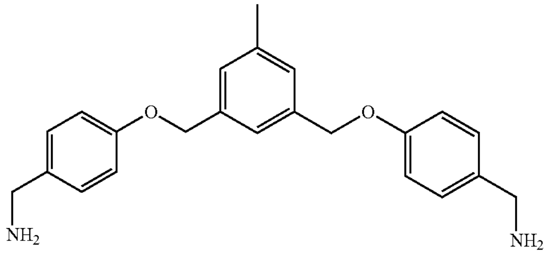 E-11 | 25 μM inhibit 30%; 12 μM inhibit 10% | 12 μM inhibit 10% |

TABLE 2-continued
| MIC of Select Compounds Against *E. coli* and *B. subtilis* | | |
|---|---|---|
| Compound | MIC (*E. coli*) | MIC (*B. subtilis*) |
| 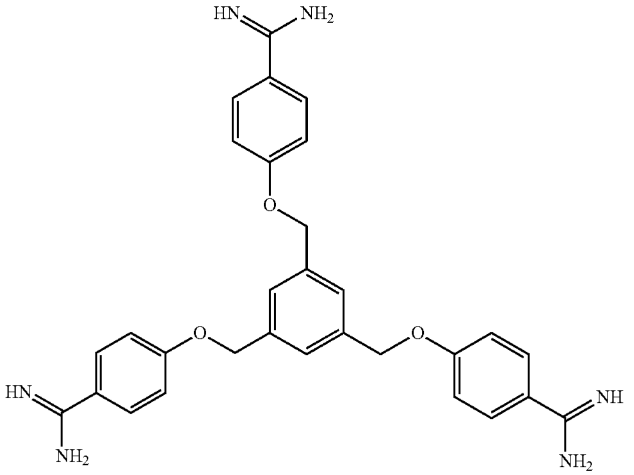 E-12 | 25 µM inhibit 60%; 12 µM inhibit 40% | 12 µM reach MIC; 6 µM inhibit 80% |
| 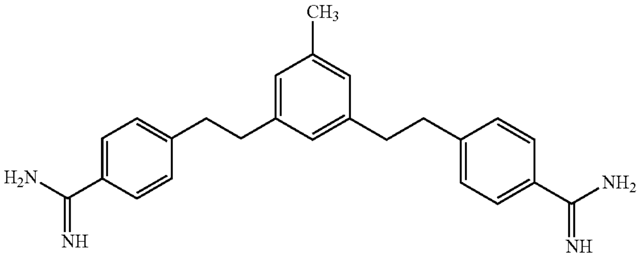 A-8 | 25 µM inhibit 20%; 12 µM inhibit 10% | 12 µM inhibit 80%; 6 µM inhibit 30% |
| 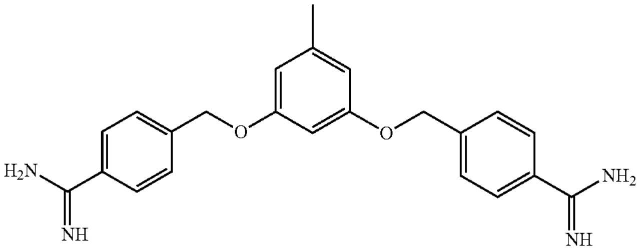 B-114 | 25 u.M inhibit 30% | 12 µM inhibit 20% |
| 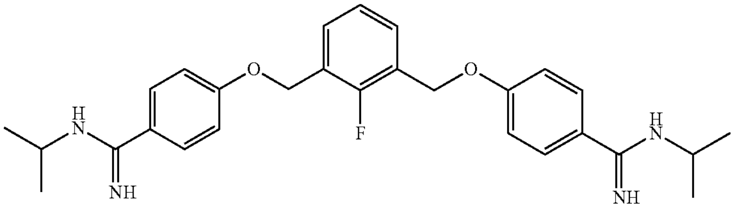 D-2 | 25 µM inhibit 80%; 12 µM inhibit 60% | 12 µM inhibit 80%; 6 µM inhibit 70% |

TABLE 2-continued
| MIC of Select Compounds Against *E. coli* and *B. subtilis* | | |
|---|---|---|
| Compound | MIC (*E. coli*) | MIC (*B. subtilis*) |
| 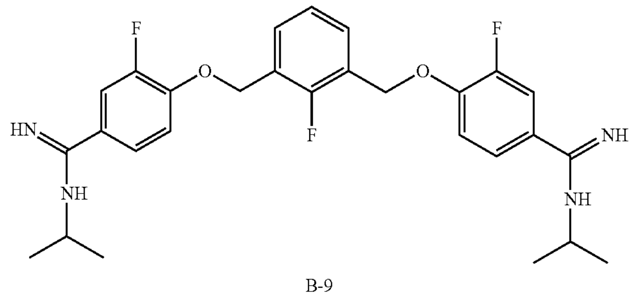 B-9 | 25 μM inhibit 50%; 12 μM inhibit 40% | 12 μM inhibit 70%; 6 inhibit 60% |
| 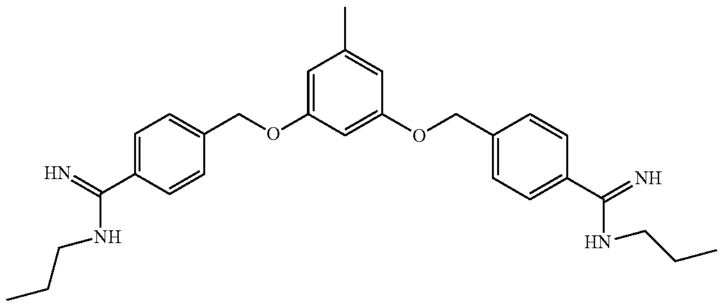 E-13 | NA at 50 μM | 50 μM reach MIC; 25 μM inhibit 50%; 12.5 μM inhibit 30% |
| 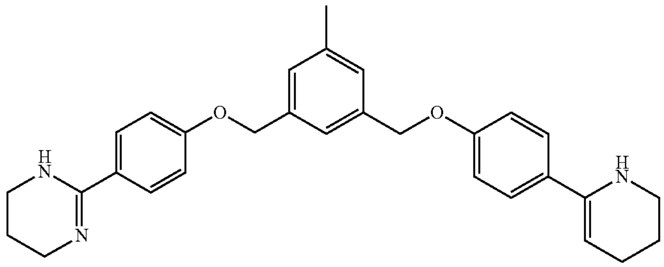 B-21 | NA at 50 μM | 50 pM reach MIC; 25 μM inhibit 50%; NA at 12.5 μM |
| 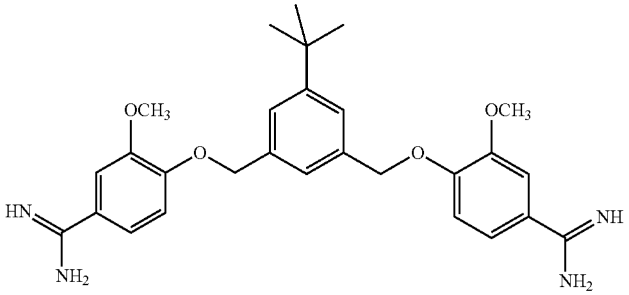 E-14 | 50 μM inhibit 80% | 6 μM inhibit 40%; 3 μM inhibit 30% |

TABLE 2-continued
| MIC of Select Compounds Against *E. coli* and *B. subtilis* | | |
|---|---|---|
| Compound | MIC (*E. coli*) | MIC (*B. subtilis*) |
| 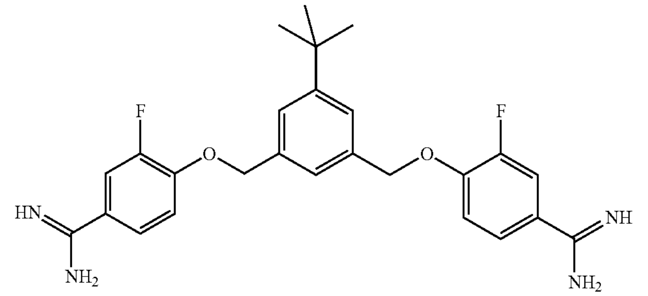 E-15 | 50 μM | 50 μM reach MIC |
| 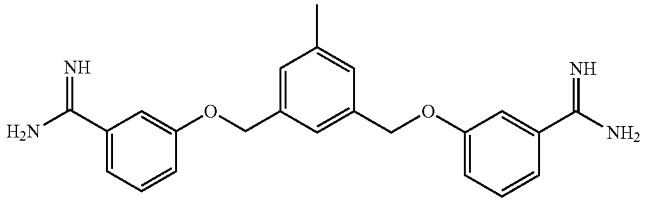 E-16 | 50 μM inhibit 80% | 50 μM to reach MIC |
| 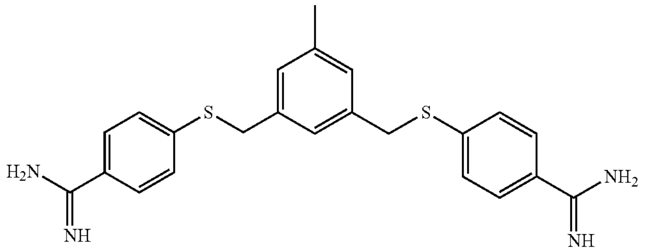 D-4 | 12 u.M inhibit 15% | 6 μM inhibit 40%; 3 μM inhibit 10% |
| 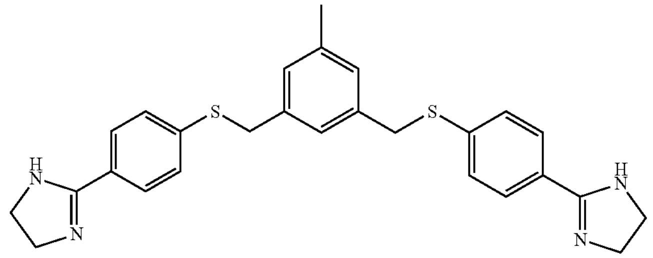 B-12 | 12.5 μM inhibit 10% | NA at 6 and 3 μM |
| 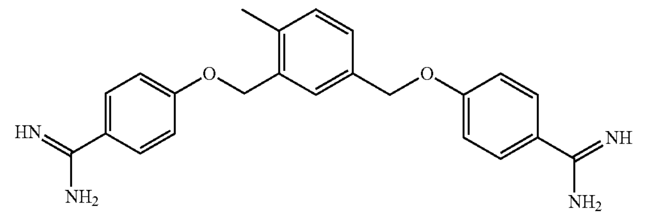 E-17 | — | 12 μM inhibit 60%; 6 μM inhibit 40% |

TABLE 2-continued
| MIC of Select Compounds Against *E. coli* and *B. subtilis* | | |
|---|---|---|
| Compound | MIC (*E. coli*) | MIC (*B. subtilis*) |
| 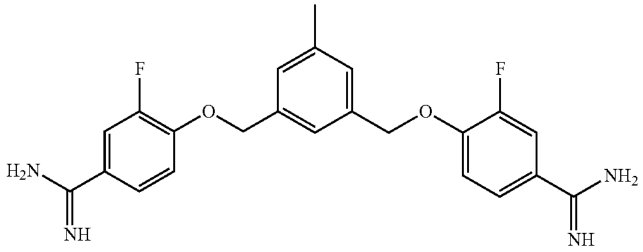 E-18 | 25 u.M inhibit 30% | — |
| 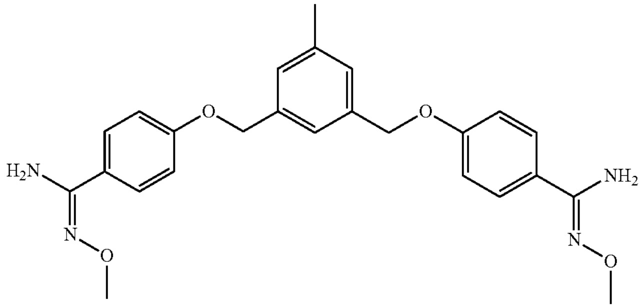 E-19 | 100 μM | — |
| 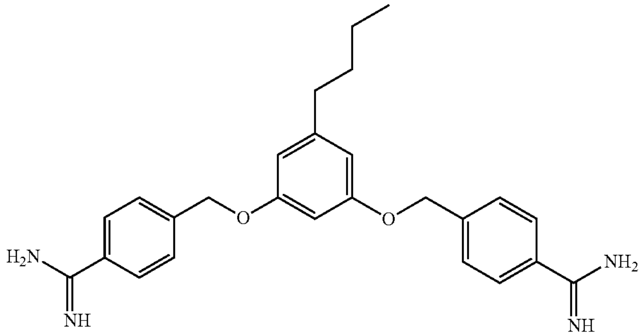 E-20 | 10 μM inhibit 20% | — |
| 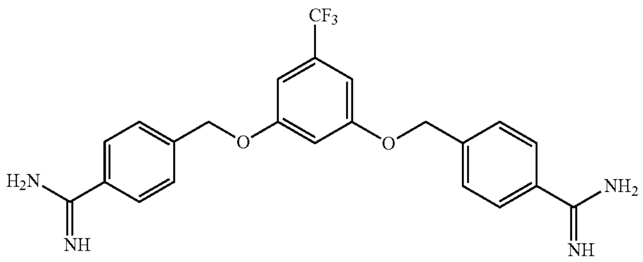 Compound C | NA at 50 μM | — |

TABLE 2-continued
| MIC of Select Compounds Against *E. coli* and *B. subtilis* | | |
|---|---|---|
| Compound | MIC (*E. coli*) | MIC (*B. subtilis*) |
| 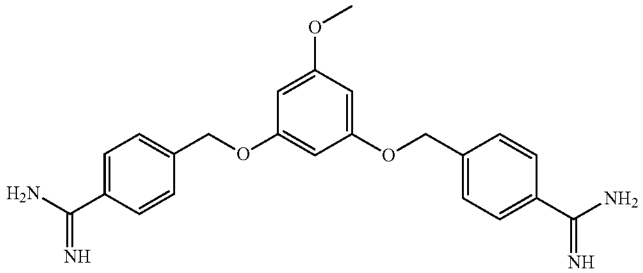 E-23 | NA at 20 μM | — |
| 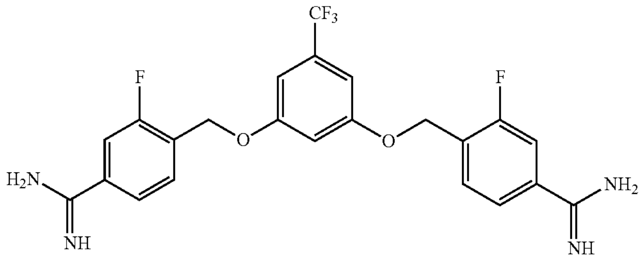 E-24 | Similar to Compd C | — |
| 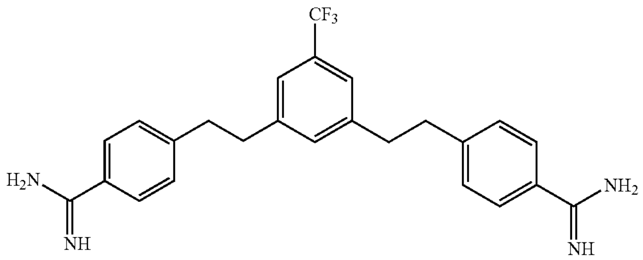 E-25 | Similar to Compd C | — |

Example 3. Antibacterial Activity Against *Mycobacterium Smegmatis*

*M. smegmatis* bacteria were cultured in 7H9 media at 37° C. overnight prior to treatment. Bacteria were then cultured with varying concentration of the compounds shown below for 48 hours, and then bacterial density was measured based on OD600. The minimum inhibitory concentration (MIC, 90% growth inhibition) was calculated for each compound, as shown in Table 3A and Table 3B (NA=no activity).

TABLE 3A

Antibacterial Activity Against *M. Smegmatis*

| Compound | MIC |
|---|---|
| 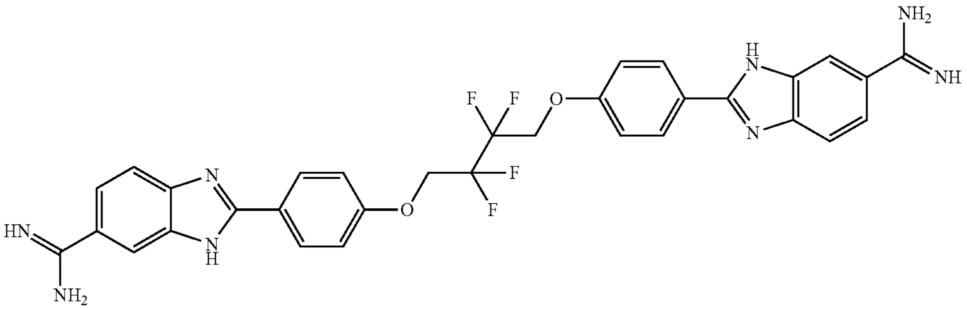<br>C-5 | 6 μM |
| 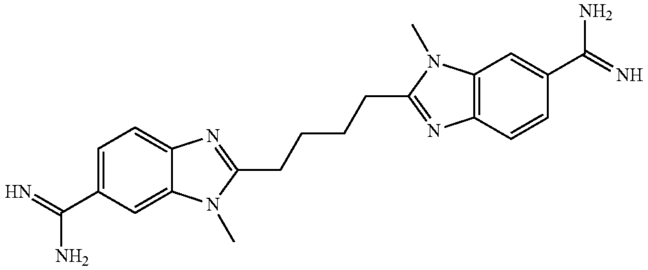<br>C-7 | NA |
| 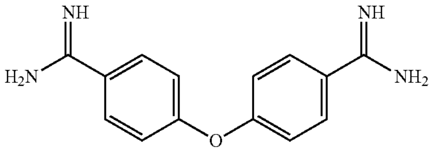<br>C-8 | NA |
| 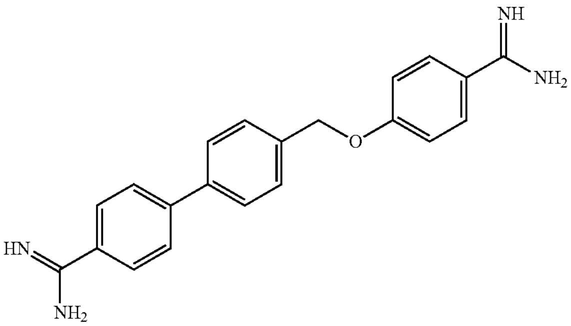<br>E-2 | 6 μM |

TABLE 3A-continued
| Antibacterial Activity Against *M. Smegmatis* | |
|---|---|
| Compound | MIC |
| 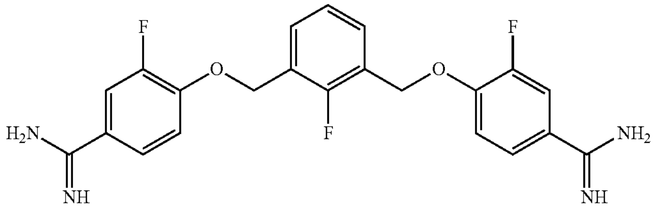 A-1 | 12 μM |
| 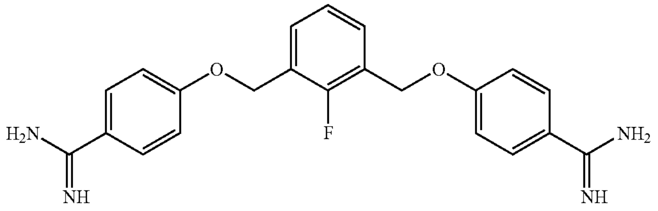 C-2 | 12 μM |
| 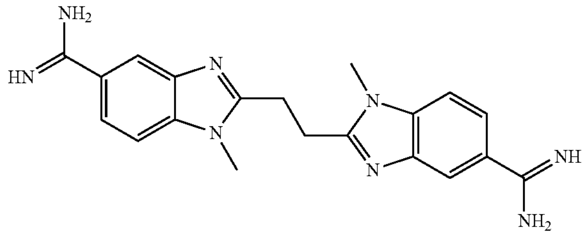 C-10 | NA |
| 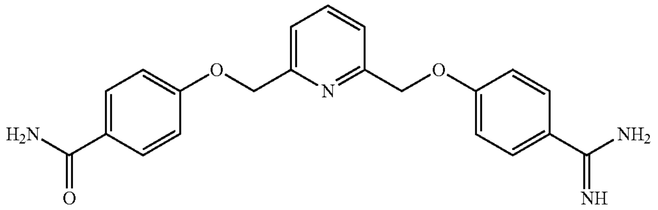 C-1 | NA |
| 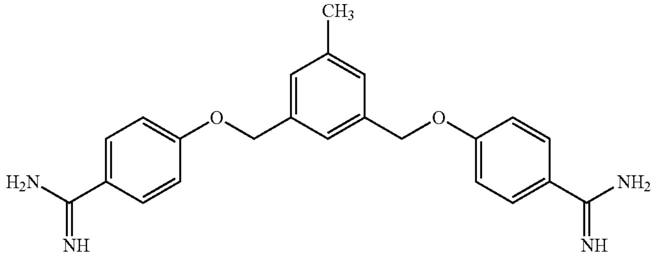 Compound M-1 | 12 μM |
| 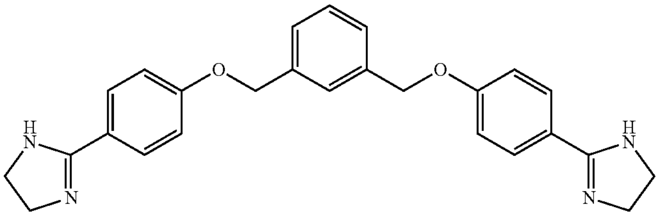 E-9 | 12 μM |

TABLE 3A-continued
| Antibacterial Activity Against *M. Smegmatis* | |
|---|---|
| Compound | MIC |
| 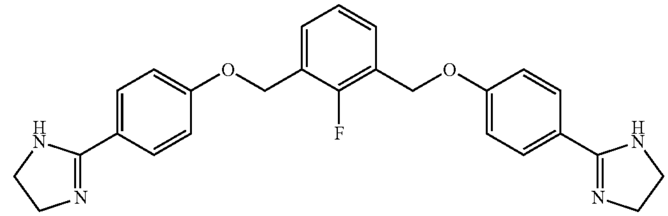 A-3 | 25 μM |
| 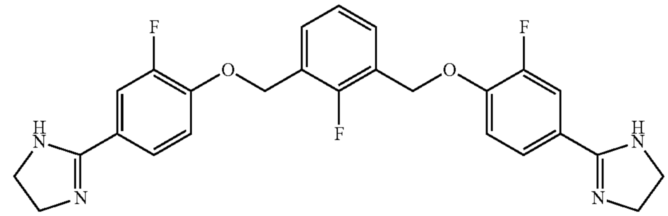 A-4 | NA |
| 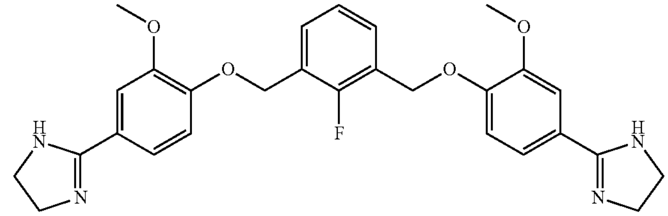 A-5 | 25 μM |
| 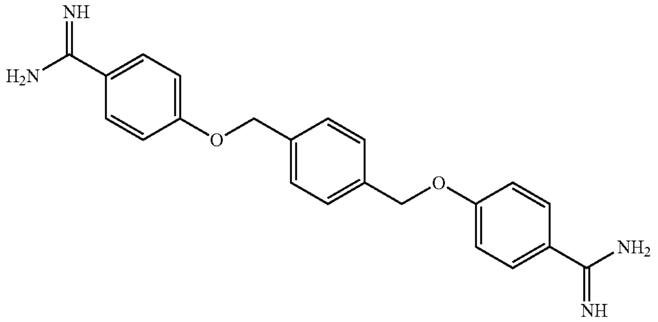 E-10 | 3 μM |
| 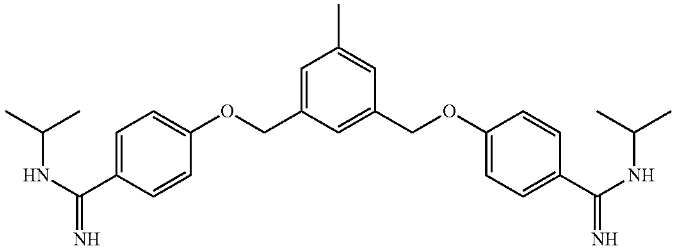 C-3 | 3 μM |

TABLE 3A-continued
| Antibacterial Activity Against *M. Smegmatis* | |
|---|---|
| Compound | MIC |
| 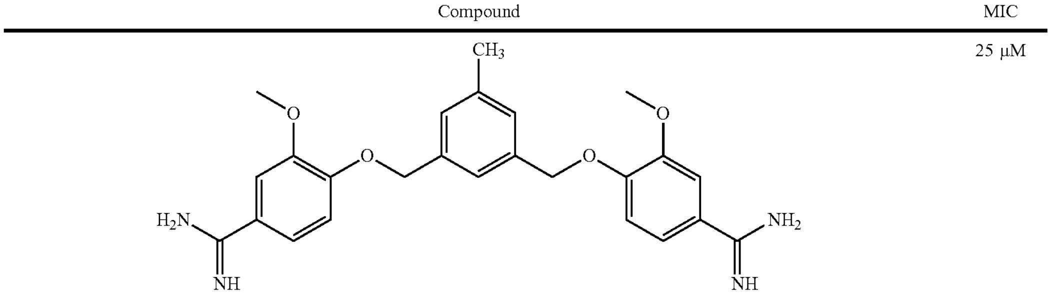 A-6 | 25 μM |
| 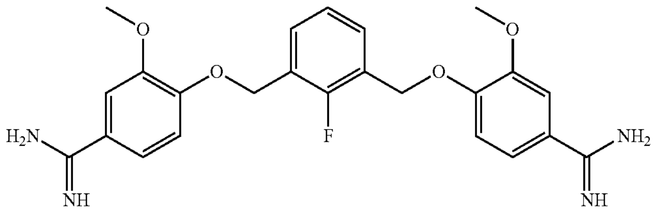 A-7 | 6 μM |
| 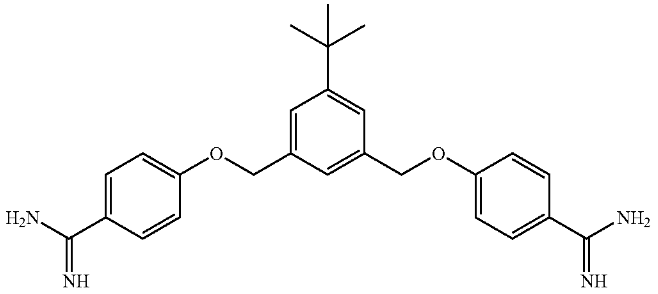 C-4 | 6 μM |
TABLE 3B
| Antibacterial Activity Against *M. Smegmatis* | |
|---|---|
| Compound | MIC |
| 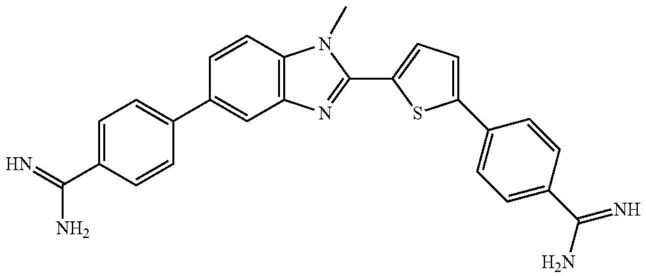 E-1 | 6 μM |

TABLE 3B-continued
| Antibacterial Activity Against *M. Smegmatis* | |
|---|---|
| Compound | MIC |
| 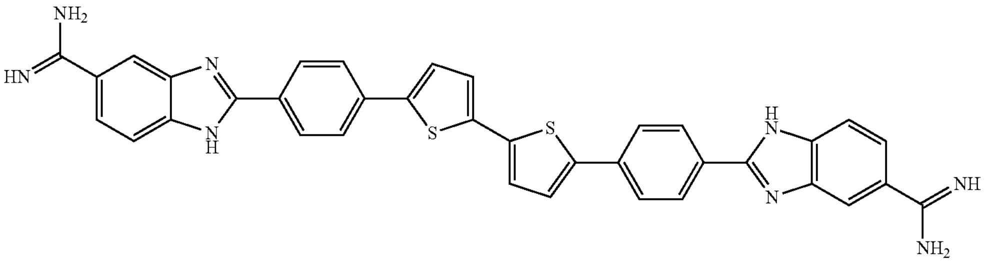 C-6 | NA |
| 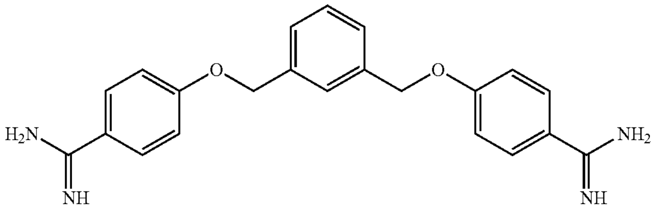 E-3 | 12 μM |
| 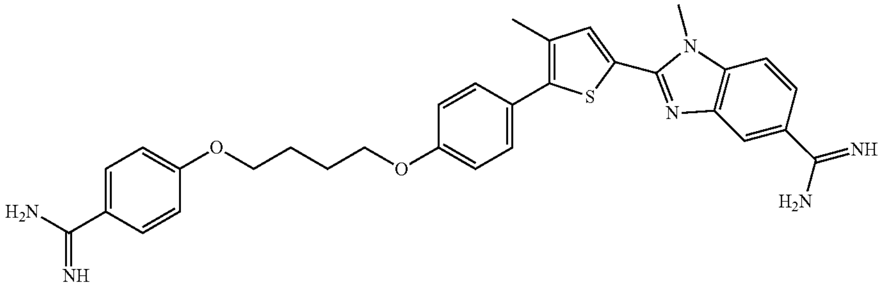 C-9 | 3-6 μM |
| 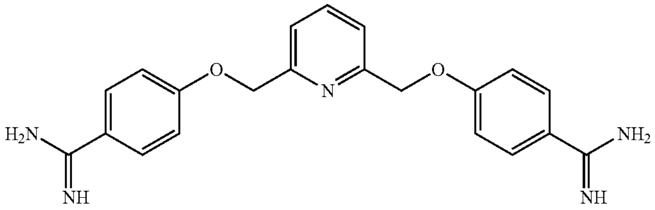 E-5 | 12 μM |
| 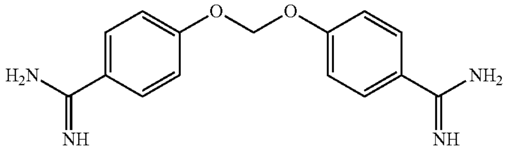 E-6 | NA |

TABLE 3B-continued
| Antibacterial Activity Against *M. Smegmatis* | |
|---|---|
| Compound | MIC |
| 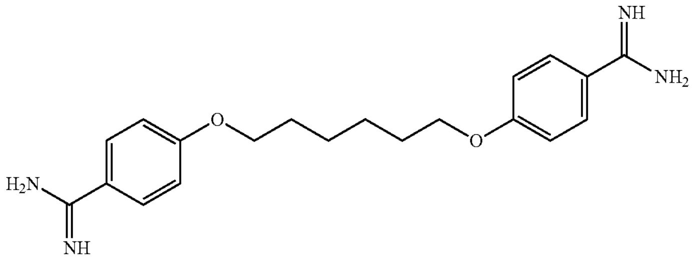 E-7 | 6 μM |
| 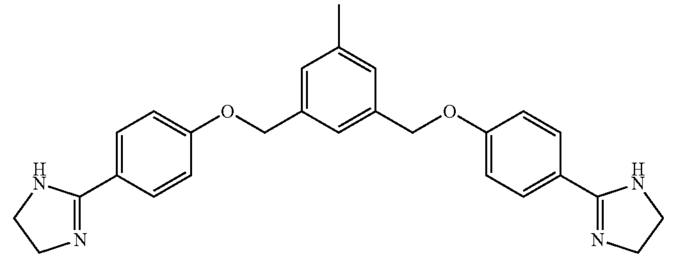 A-2 | 25 μM |
| 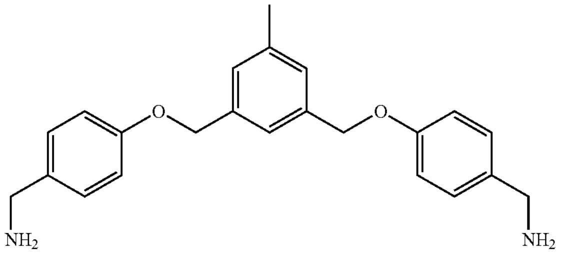 E-11 | NA |
| 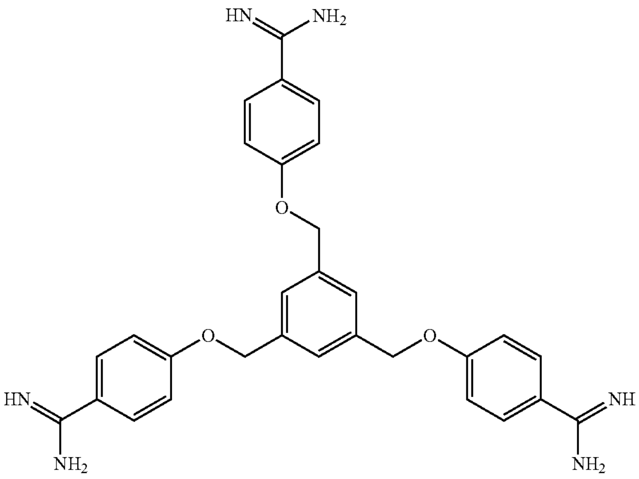 E-12 | 3-6 μM |

TABLE 3B-continued

| Antibacterial Activity Against *M. Smegmatis* | |
|---|---|
| Compound | MIC |
| 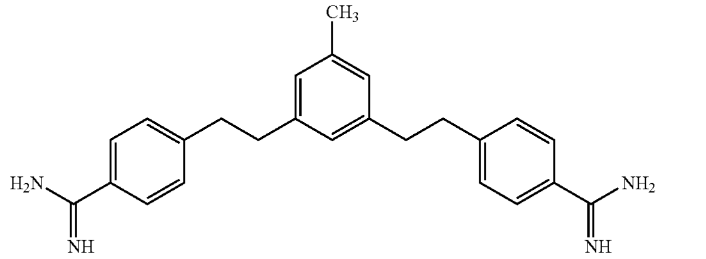 Compound A-8 | 6-12 μM |
| 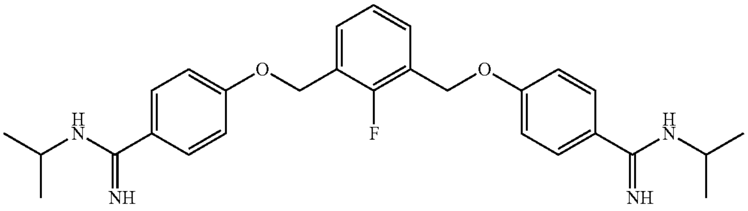 D-2 | 3 μM |
| 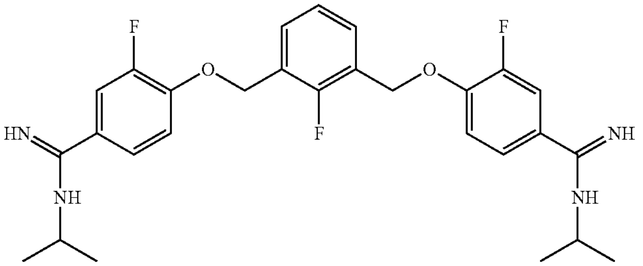 B-9 | 12 μM |

Example 4. Diamidine Compound M-1 Sensitizes the Gram-Positive Bacterium *Bacillus subtilis* to Erythromycin, Novobiocin, and Tetracycline (M-1)

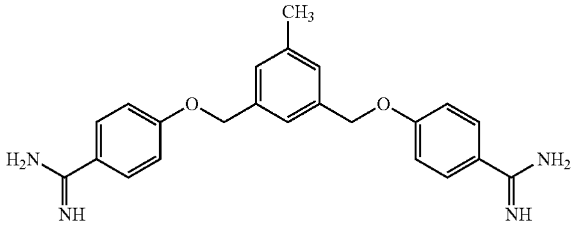

Figure 2:
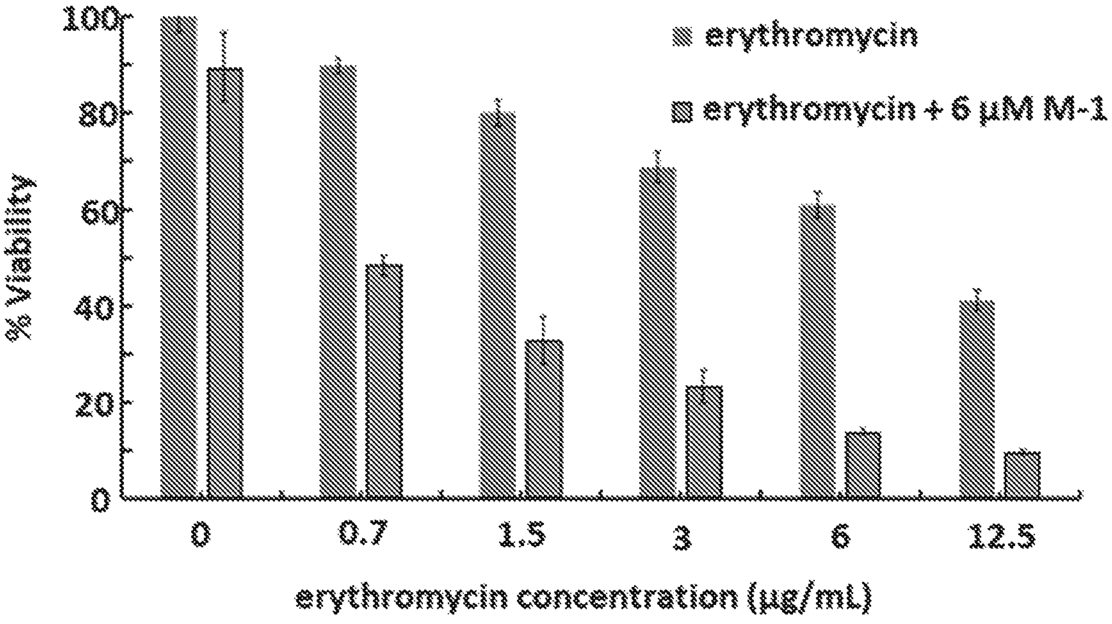
FIG. 2 is a bar graph showing the growth inhibitory effect on *B. subtilus* by the combination of 6 μM compound M-1 with erythromycin. *B. subtilis* was cultured with erythromycin at varying concentrations (0, 0.7, 1.5, 3, 6 or 12.5 μg/mL) either alone or in combination with 6 μM M-1. The y-axis is bacterial viability measured in percent. The x-axis is erythromycin concentration measured in micrograms per milliliter.
Figure 4:
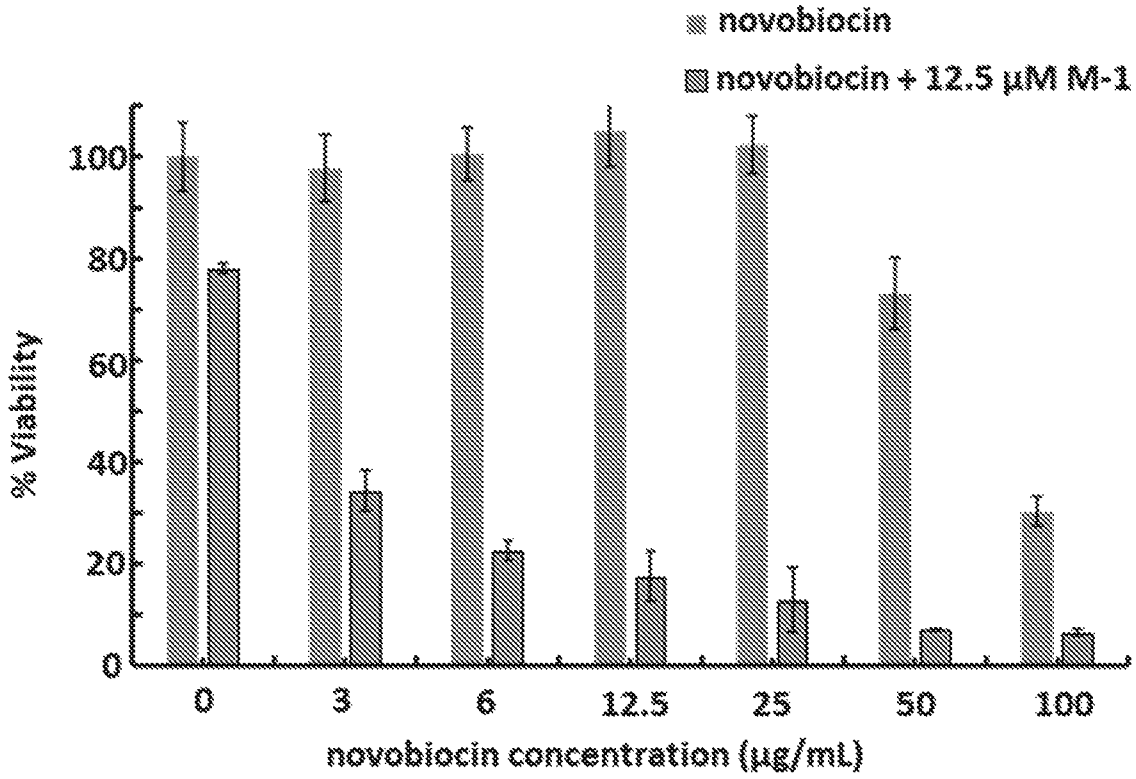
FIG. 4 is a bar graph showing the growth inhibitory effect on *B. subtilus* by the combination of 12.5 μM compound M-1 with novobiocin. *B. subtilis* was cultured with novobiocin at varying concentrations (0, 3, 6, 12.5, 25, 50, or 100 μg/mL) either alone or in combination with 12.5 μM M-1. The y-axis is bacterial viability measured in percent. The x-axis is novobiocin concentration measured in micrograms per milliliter.
Figure 5:
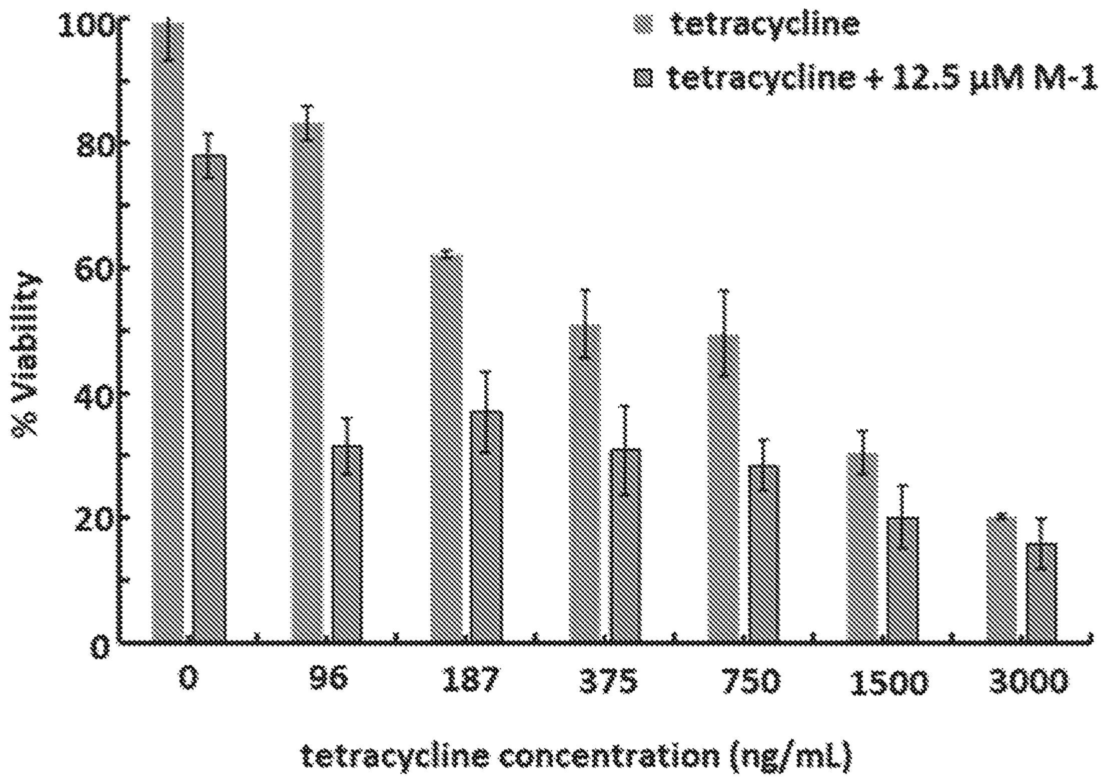
FIG. 5 is a bar graph showing the growth inhibitory effect on *B. subtilus* by the combination of 12.5 μM compound M-1 with tetracycline. *B. subtilis* was cultured with tetracycline at varying concentrations (0, 96, 187, 375, 750, 1500 or 3000 ng/mL) either alone or in combination with 12.5 μM M-1. The y-axis is bacterial viability measured in percent. The x-axis is tetracycline concentration measured in nanograms per milliliter.
Figure 6:
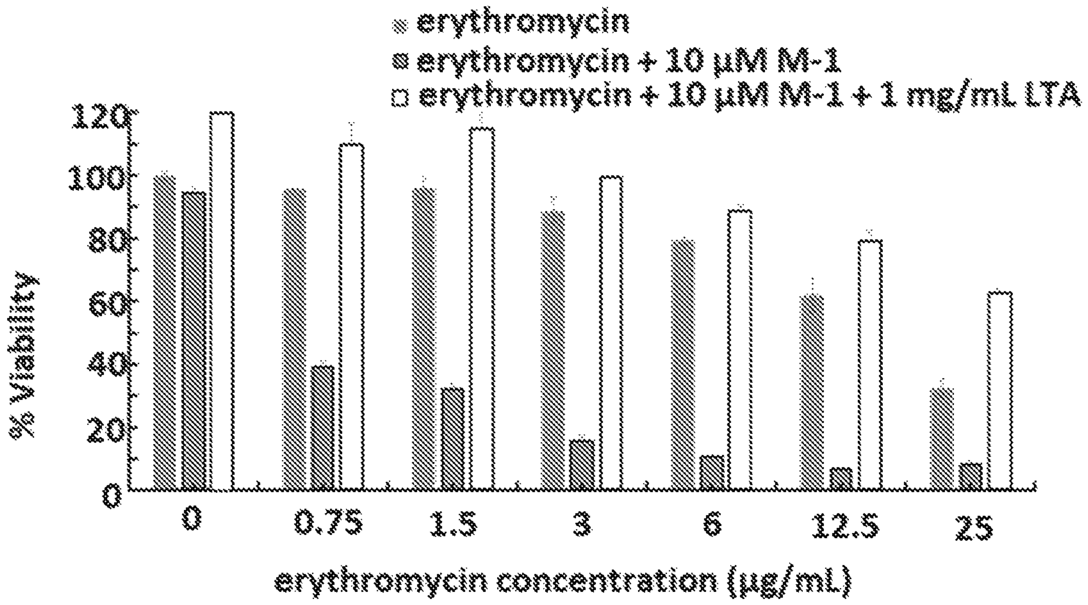
FIG. 6 is a bar graph showing the growth inhibitory effect on *B. subtilus* by the combination of 10 μM M-1 with erythromycin in the presence or absence of lipoteichoic acid (LTA). *B. subtilis* was cultured with erythromycin at varying concentrations (0, 0.75, 1.5, 3, 6, 12.5 or 25 μg/mL) either alone, in combination with 10 μM M-1, or in combination with 10 μM M-1 in the presence of 1 mg/mL lipoteichoic acid. The y-axis is bacterial viability measured in percent. The x-axis is erythromycin concentration measured in micrograms per milliliter.

*B. subtilis* was cultured with erythromycin at varying concentrations in the absence or presence of compound M-1 (12.5 or 6 μM) for 20 hours. Bacterial viability was then determined by measuring density using OD600. As shown in FIG. 1 and FIG. 2, compound M-1 in combination with erythromycin showed significant bacterial growth inhibition than erythromycin alone, while compound M-1 alone only showed a small inhibitory effect on bacterial growth (80% viability at 12.5 μM concentration). *B. subtilis* was also cultured with either novobiocin or tetracycline at varying concentrations either in the absence or presence of compound M-1 (12.5 μM) for 20 hours. Bacterial viability was subsequently determined by measuring density using OD600. Similar to what was observed with the combination of erythromycin and compound M-1, the combination of novobiocin or tetracycline and compound M-1 also showed significant bacterial growth inhibition as shown in FIG. 4 and FIG. 5. As shown in FIG. 6, the growth inhibitory effect of the combination of erythromycin and M-1 could be inhibited by co-culturing with lipoteichoic acid (LTA) at 1 mg/mL concentration. This suggests that a possible mechanism for activity of Compound M-1 is by binding to teichoic acid, a key component in bacterial cell membrane synthesis.

Example 5. Diamidine Compounds M-1 and A-1 Sensitize the Gram-Negative Bacterium *Escherichia Coli* to Erythromycin

Figure 7:
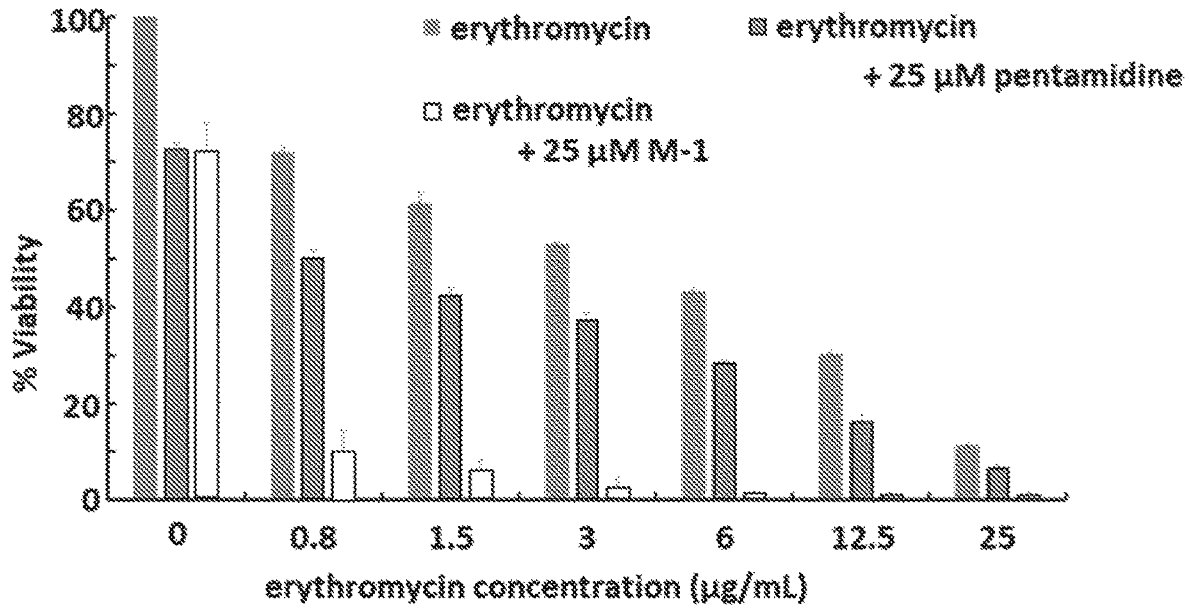
FIG. 7 is a bar graph showing the growth inhibitory effect on *E. coli* by the combination of 25 μM compound M-1 or pentamidine with erythromycin. *E. coli* was cultured with erythromycin at varying concentrations (0, 0.8, 1.5, 3, 6, 12.5 or 25 μg/mL) either alone or in combination with 25 μM compound M-1 or pentamidine. The y-axis is bacterial viability measured in percent. The x-axis is erythromycin concentration measured in micrograms per milliliter.
Figure 8:
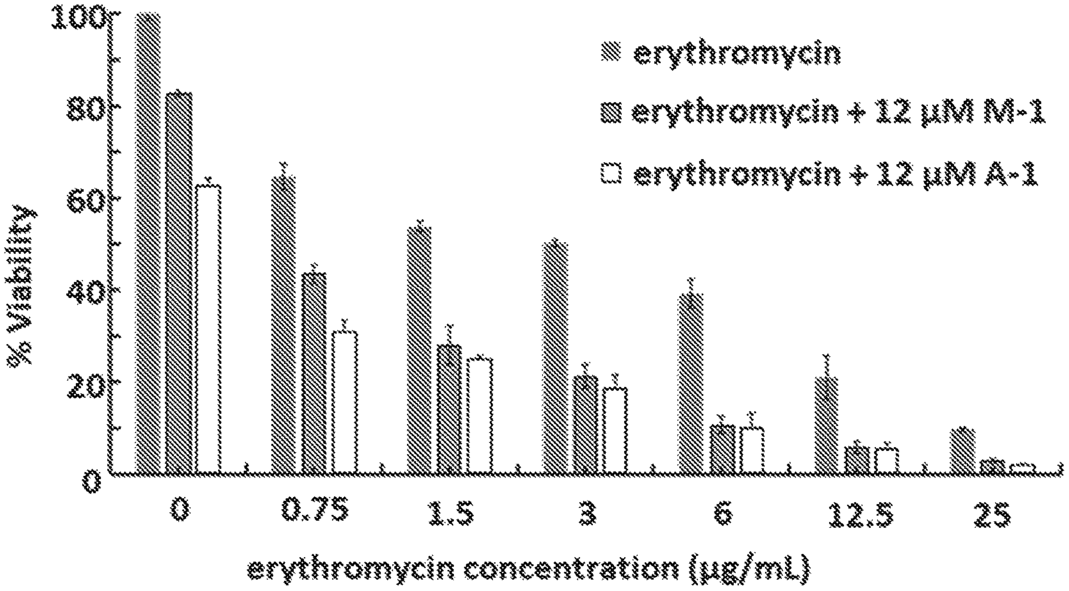
FIG. 8 is a bar graph showing the growth inhibitory effect on *E. coli* by the combination of 12 μM compound M-1 or A-1 with erythromycin. *E. coli* was cultured with erythromycin at varying concentrations (0, 0.75, 1.5, 3, 6, 12.5 or 25 μg/mL) either alone or in combination with 12 μM compound M-1 or A-1. The y-axis is bacterial viability measured in percent. The x-axis is erythromycin concentration measured in micrograms per milliliter.
Figure 9:
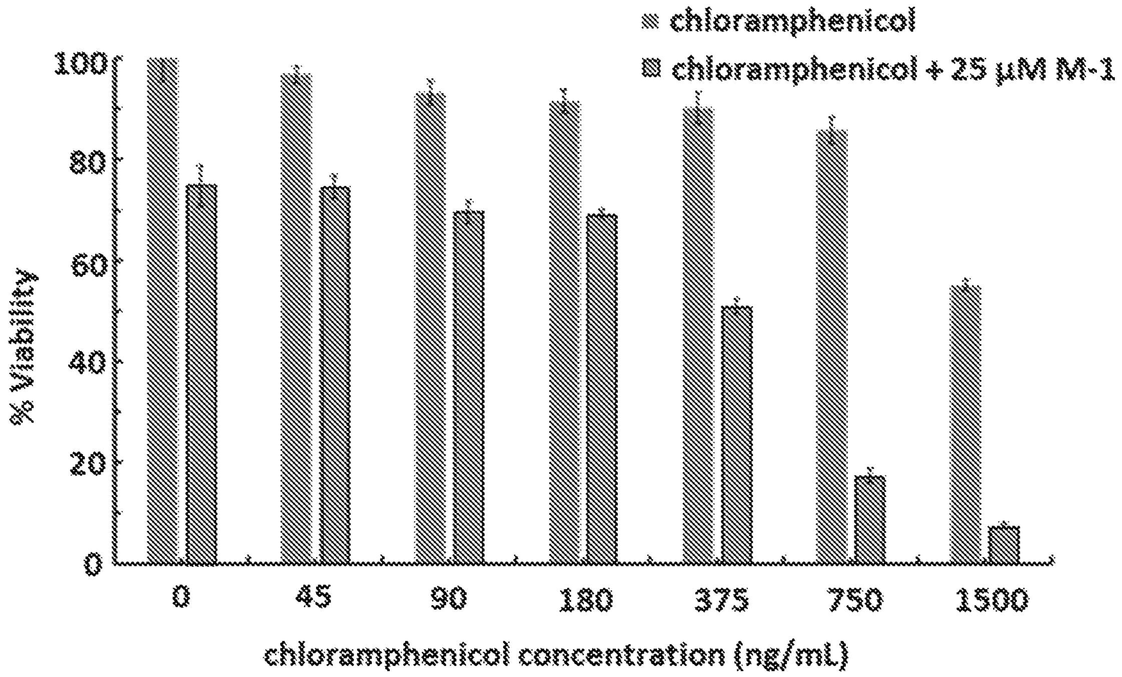
FIG. 9 is a bar graph showing the growth inhibitory effect on *E. coli* by the combination of 25 μM compound M-1 with chloramphenicol. *E. coli* was cultured with chloramphenicol at varying concentrations (0, 45, 90, 180, 375, 750 or 1500 ng/ml) either alone or in combination with 25 μM compound M-1. The y-axis is bacterial viability measured in percent. The x-axis is chloramphenicol concentration measured in nanograms per milliliter.
Figure 10:
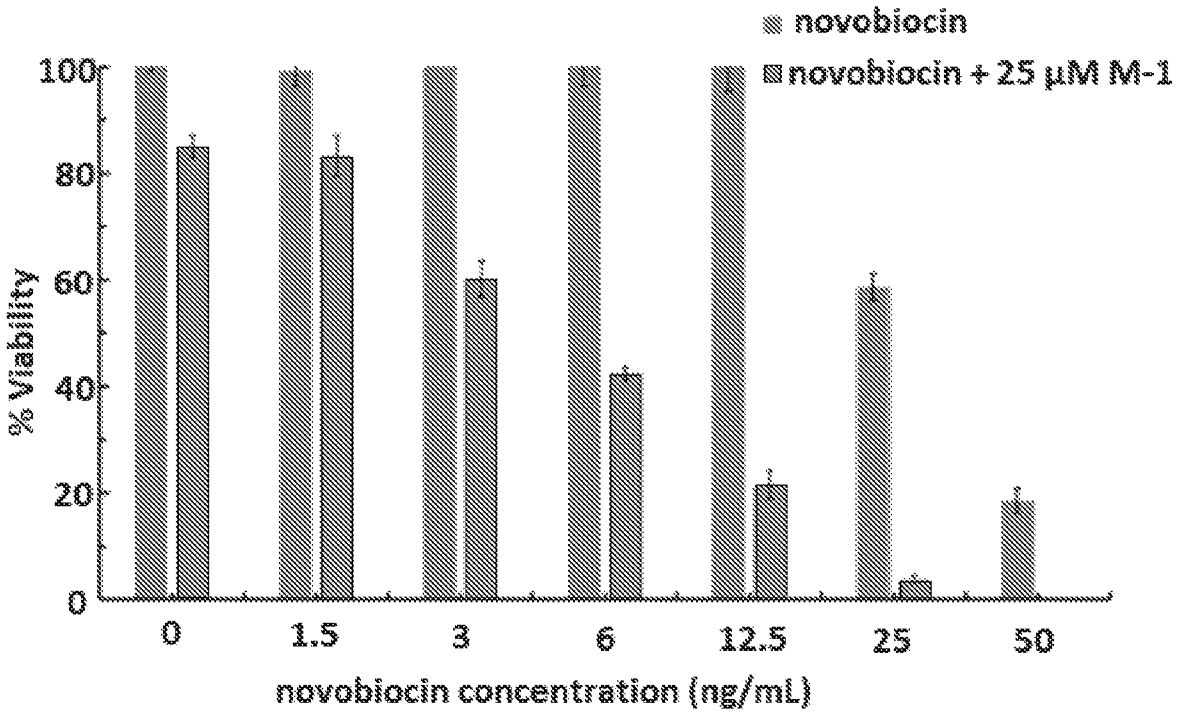
FIG. 10 is a bar graph showing the growth inhibitory effect on *E. coli* by the combination of 25 μM compound M-1 with novobiocin. *E. coli* was cultured with novobiocin at varying concentrations (0, 1.5, 3, 6, 12.5, 25 or 90 ng/mL) either alone or in combination with 25 μM compound M-1. The y-axis is bacterial viability measured in percent. The x-axis is novobiocin concentration measured in nanograms per milliliter.
Figure 11:
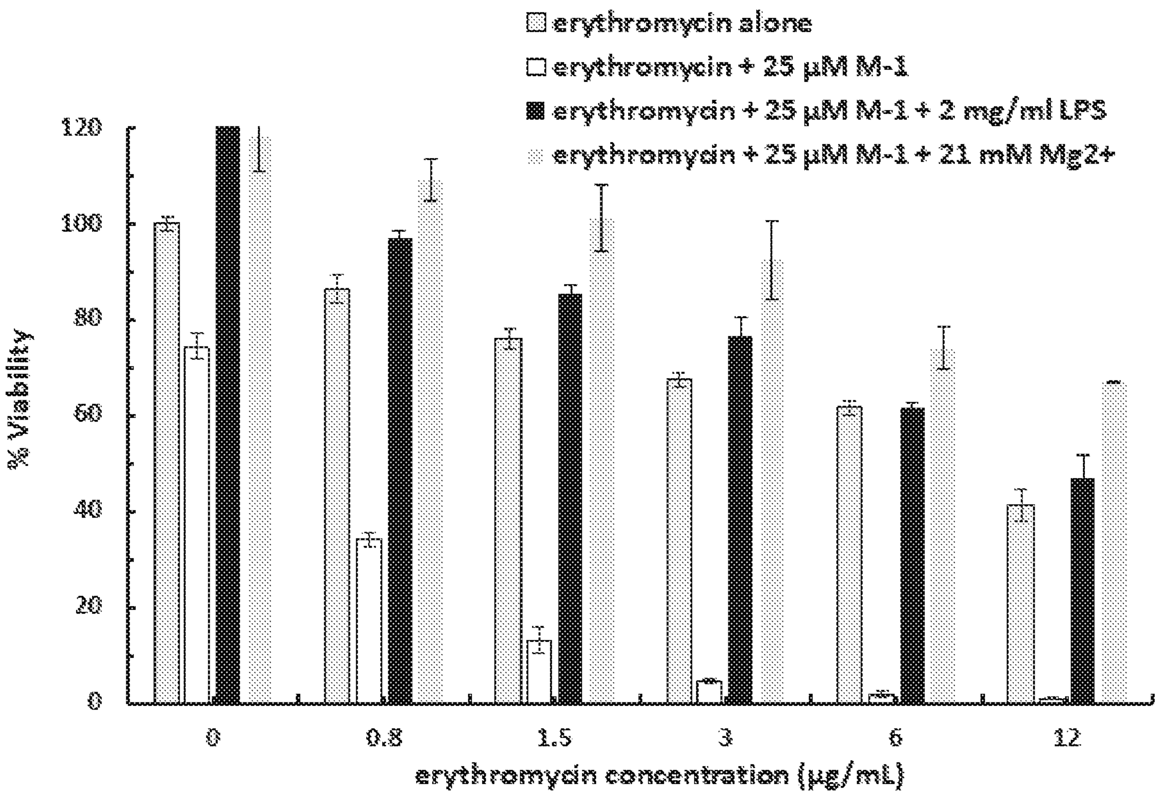
FIG. 11 is a bar graph showing the growth inhibitory effect on *E. coli* by the combination of 12 μM compound M-1 with erythromycin in the presence or absence or lipopolysaccharides (LPS) or magnesium ion ($Mg^{2+}$). *E. coli* was cultured with erythromycin at varying concentrations (0, 0.8, 1.5, 3, 6 or 12 μg/mL) either alone, in combination with 12 μM compound M-1, in combination with 12 μM compound M-1 in the presence of 2 mg/mL LPS, or in combination with 12 μM compound M-1 in the presence of 21 mM $Mg^{2+}$. The y-axis is bacterial viability measured in percent. The x-axis is erythromycin concentration measured in micrograms per milliliter.

*E. coli* was cultured with erythromycin at varying concentrations in the absence or presence of M-1 (25 μM) or pentamidine (25 μM) for 20 hours. Bacterial viability was then determined by measuring density using OD600. As shown in FIG. 7, compound M-1 in combination with erythromycin showed significant bacterial growth inhibition than erythromycin alone or in combination with pentamidine. As shown in FIG. 8, compound A-1 (12 μM) also showed a similar growth inhibitory effect in combination with erythromycin as that displayed by compound M-1 (12 μM). As shown in FIG. 9 and FIG. 10, a similar synergistic effect on growth inhibition of *E. coli* was seen with compound M-1 in combination with chloramphenicol and novobiocin, respectfully. As shown in FIG. 11, the sensitization effect of compound M-1 with erythromycin was inhibited by co-culturing with 2 mg/mL lipopolysaccharides (LPS) extracted from *E. coli* or 21 mM $Mg^{2+}$, suggesting that at least one of the possible sensitization mechanisms is through lipopolysaccharide binding.

Example 6. Diamidine Compound A-2 Sensitizes *B. subtilis* and Diamidine Compound A-8 Sensitizes Both *B. subtilis* and *E. coli* to Erythromycin

Figure 3:
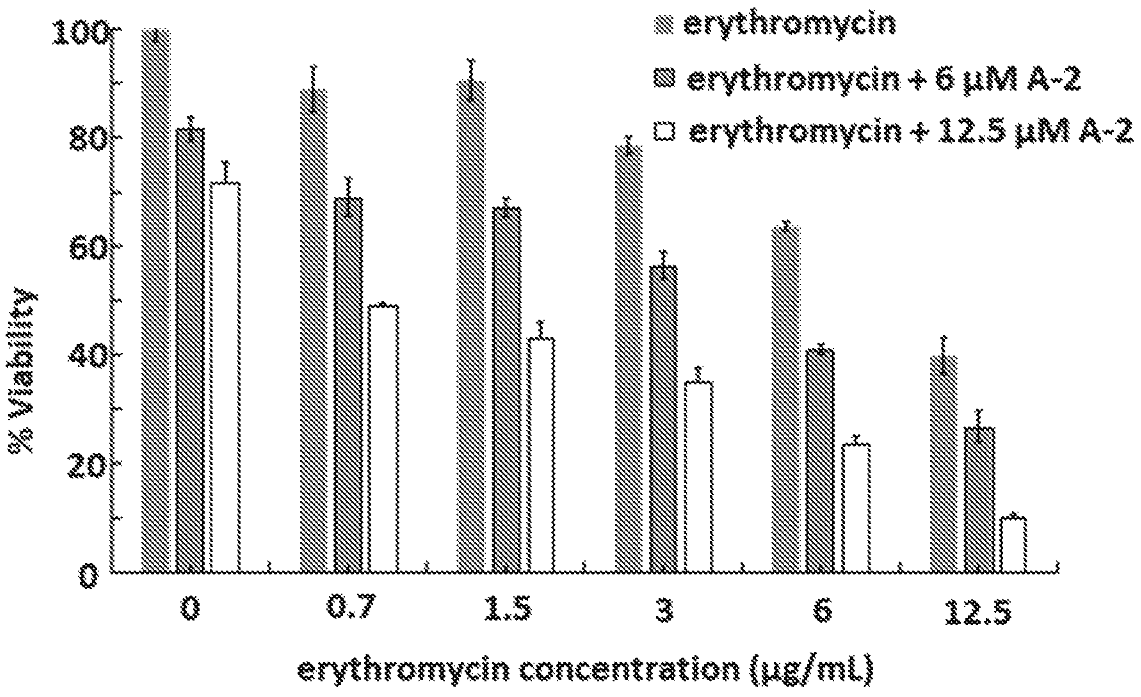
FIG. 3 is a bar graph showing the growth inhibitory effect on *B. subtilus* by the combination of 6 or 12.5 μM compound A-2 with erythromycin. *B. subtilis* was cultured with erythromycin at varying concentrations (0, 0.7, 1.5, 3, 6 or 12.5 μg/mL) either alone or in combination with 6 or 12.5 μM A-2. The y-axis is bacterial viability measured in percent. The x-axis is erythromycin concentration measured in micrograms per milliliter.
Figure 12:
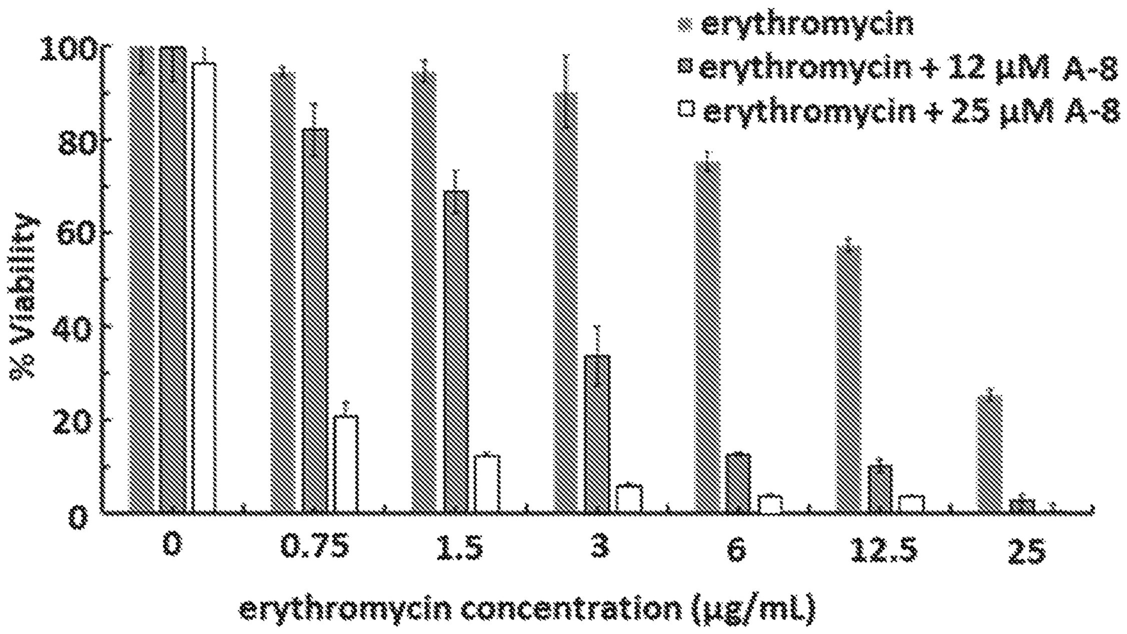
FIG. 12 is a bar graph showing the growth inhibitory effect on *E. coli* by the combination of 12 or 25 μM compound A-8 with erythromycin. *E. coli* was cultured with erythromycin at varying concentrations (0, 0.75, 1.5, 3, 6, 12.5 or 25 μg/mL) either alone or in combination with 12 or 25 μM compound A-8. The y-axis is bacterial viability measured in percent. The x-axis is erythromycin concentration measured in micrograms per milliliter.
Figure 13:
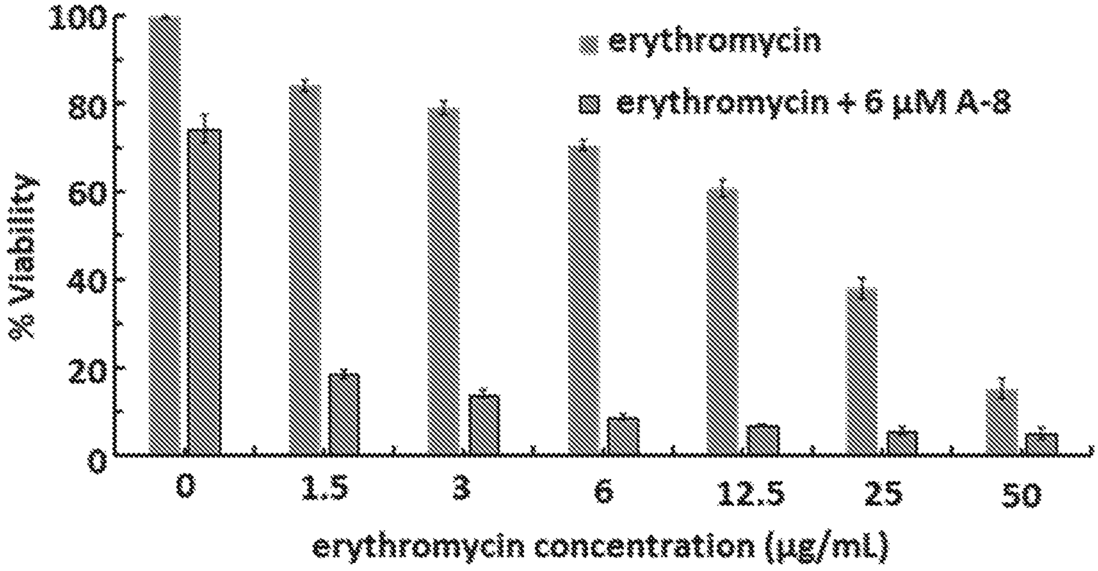
FIG. 13 is a bar graph showing the growth inhibitory effect on *B. subtilus* by the combination of 6 μM compound A-8 with erythromycin. *B. subtilis* was cultured with erythromycin at varying concentrations (0, 0.75, 1.5, 3, 6, 12.5 or 25 μg/mL) either alone or in combination with 6 μM A-8. The y-axis is bacterial viability measured in percent. The x-axis is erythromycin concentration measured in micrograms per milliliter.

*B. subtilis* was cultured with erythromycin at varying concentrations in the absence or presence of A-2 (6 or 12.5 μM) or A-8 (12 or 25 μM) for 20 hours. *E. coli* was cultured with erythromycin at varying concentrations in the absence or presence of A-8 (6 μM) for 20 hours. Bacterial viability was then determined by measuring density using OD600. As shown in FIG. 3 and FIG. 12, compound A-2 or A-8, respectfully, in combination with erythromycin showed significant bacterial growth inhibition for *B. subtilis* compared to erythromycin alone. As shown in FIG. 13, growth inhibition was also observed for *E. coli* by compound A-8 in combination with erythromycin.

Example 7. Compound C is a Potent Bacterial Sensitizer

Figure 14A:
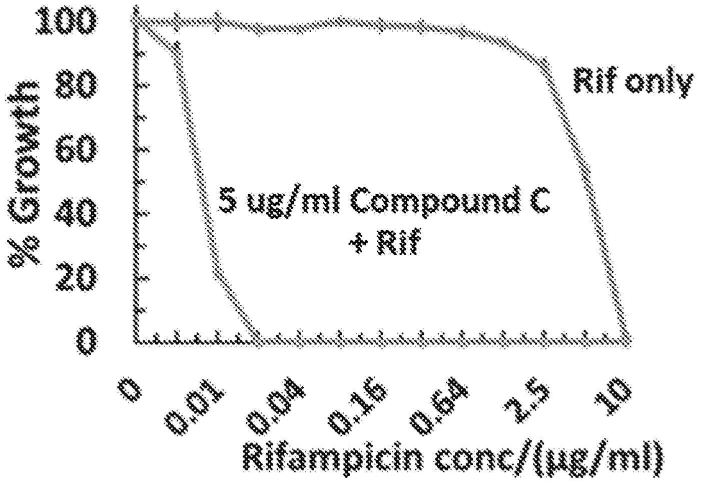
FIG. 14A is a line graph that demonstrates that Compound C sensitizes *E. coli* to rifampicin as discussed in Example 7. Bacteria were cultured with the antibiotic at various concentrations in the presence or absence of bacterial sensitizer for 24 hours at 37° C. Bacterial growth density was determined by measuring $OD_{600}$ (absorbance measured at a wavelength of 600 nm). The x-axis is the rifampicin concentration measured in μg/ml and the y-axis is the growth measured in percent.
Figure 14B:
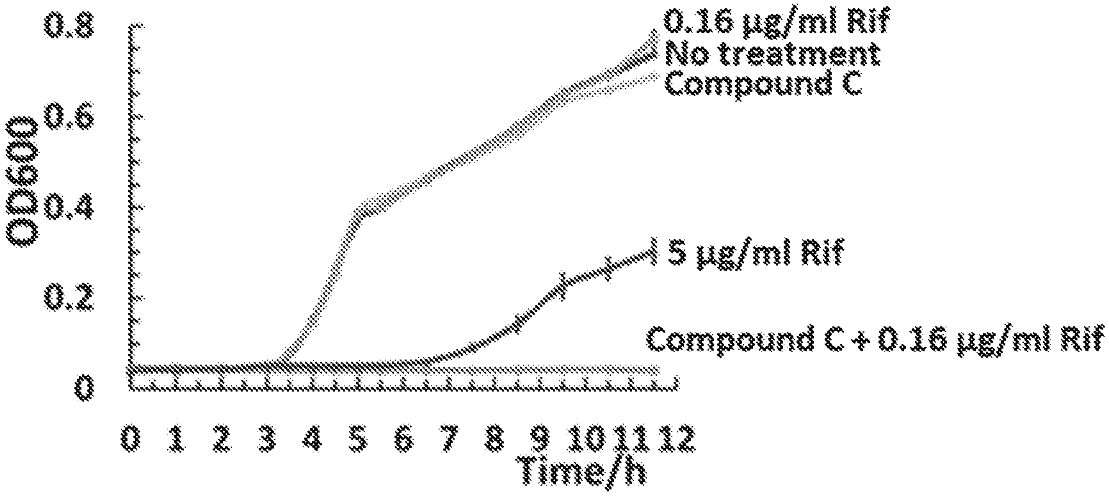
FIG. 14B is a line graph that demonstrates that Compound C sensitizes *E. coli* to rifampicin as discussed in Example 7. Bacteria were cultured with rifampicin in the presence and absence of 5 mcg/mL of Compound C at 37° C. (Compound C concentration alone was 5 μg). Bacterial growth density was determined by measuring $OD_{600}$ at different time points. The x-axis is time measured in hours and the y-axis is $OD_{600}$ (absorbance measured at wavelength of 600 nm).
Figure 15:
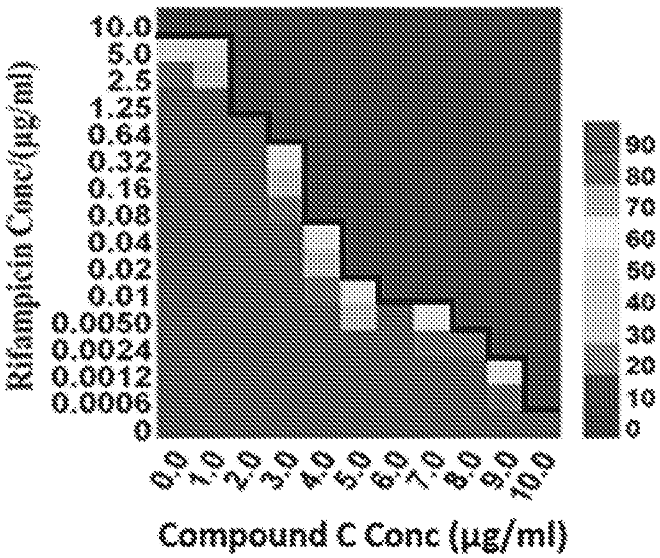
FIG. 15 is a concentration plot that demonstrates the sensitization of *E. coli* to rifampicin in the presence of Compound C in a concentration-dependent manner as discussed in Example 7. The scale 0 to 100 represents increasing bacteria growth intensity compared with non-treatment group. Area above the thick black bar represents no visible bacteria growth. The x-axis is Compound C concentration measured in μg/ml and the y-axis is rifampicin concentraton measured in ng/ml.
Figures 16, 17:
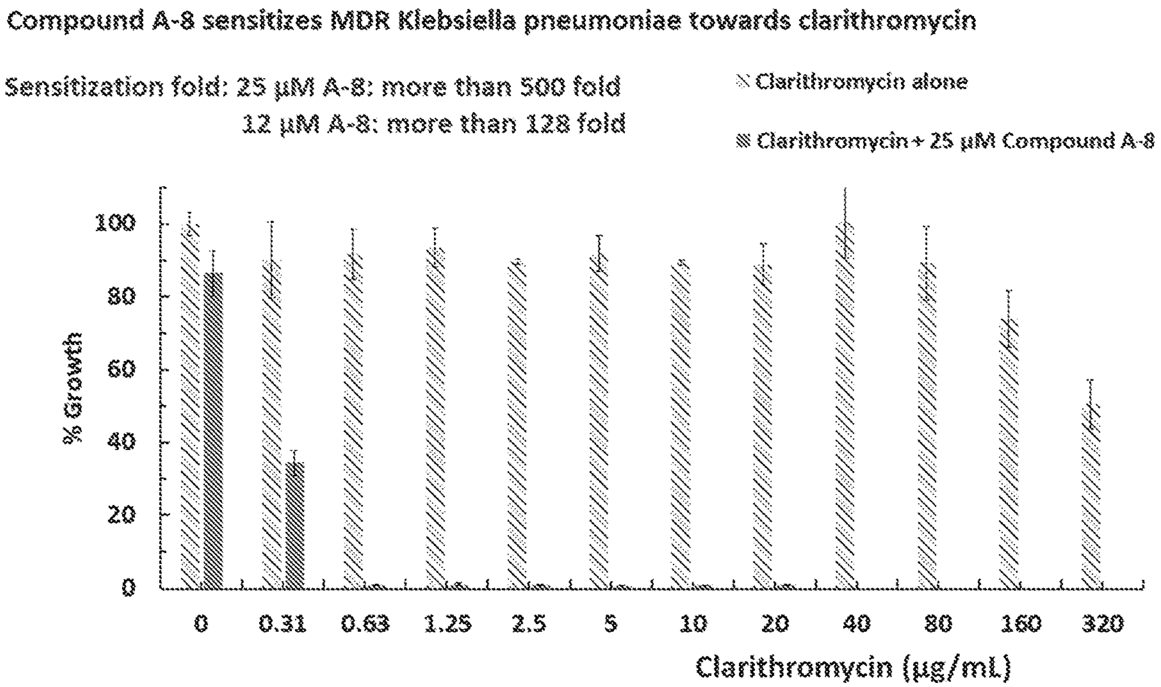
FIG. 16 is a bar graph that demonstrates the sensitization of *Klebsiella pneumoniae* to clarithromycin when exposed to Compound A-8. The x-axis is clarithromycin measured in μg/ml and the y-axis is growth measured in percent.
FIG. 17 is a table demonstrating a reduction in the frequency of the development of bacterial resistance to trovafloxacin, novobiocin, chloramphenicol, and polymycin B when concurrently exposed to Compound M-1.

Compound C sensitizes Gram-negative bacteria *E. coli* toward both narrow-spectrum and broad-spectrum antibiotics. At 5 μg/mL, Compound C sensitizes *E. coli* toward rifampicin by 512-fold, lowering the MIC of rifampicin from 10 to 0.02 μg/mL (FIG. 14A). The sensitization effect is concentration-dependent (FIG. 14B), reaching over 16,000-fold when 10 μg/ml Compound Cis used (Table 3).

TABLE 3

MIC of rifampicin on *E. coli* with different concentrations of Compound C

| Compound C Concentration (μg/ml) | Sensitization fold | MIC (μg/ml) |
|---|---|---|
| 2 | 8 | 1.25 |
| 4 | 128 | 0.08 |
| 6 | 1024 | 0.01 |
| 8 | 2,048 | 0.005 |
| 10 | 16,384 | 0.0006 |

Similarly, the MIC of clarithromycin is lowered from 50 to 0.2 μg/mL to achieve a 256-fold sensitization. For antibiotics traditionally intended for treating Gram-negative bacterial infections, Compound C further lowers their MIC. For example, the MIC of broad-spectrum trovafloxacin against *E. coli* changes from 0.05 when alone to 0.0015 μg/ml in the presence of 5 μg/mL Compound C. Similarly, the MIC of polymyxin B is lowered from 1.2 to 0.04 μg/mL to achieve a 32-fold sensitization by Compound C. Polymyxin B is a last-resort antibiotic with severe toxicity. By increasing its potency, Compound C should be able to drastically reduce the toxicity of polymyxin B (Table 4). Further, the fractional inhibitory concentration (FIC) values are all below 0.5, indicating strong synergy between the sensitizer and antibiotic. The formula for calculating FIC is shown below:

$$FIC = \frac{MIC \text{ of antibiotics with } MD}{MIC \text{ of antibiotics only}} + \frac{MIC \text{ of } MD \text{ in the presence of antibiotics}}{MIC \text{ of MD only}}$$

TABLE 4

Compound C sensitizes wild-type *E. Coli* towards various antibiotics

| Antibiotics (AB) (μg/ml) | MIC of AB only | MIC of AB with Compound C (5 μg/ml) | Sensitization fold | FIC |
|---|---|---|---|---|
| Rifampicin | 10 | 0.019 | 516 | 0.11 |
| Clarithromycin | 50 | 0.2 | 256 | 0.11 |
| Novobiocin | 100 | 1.5 | 64 | 0.12 |
| Erythromycin | 50 | 0.4 | 128 | 0.11 |
| Clindamycin | 250 | 4 | 64 | 0.12 |
| Chloramphenicol | 12.5 | 1.5 | 8 | 0.22 |
| Trovafloxacin | 0.05 | 0.0015 | 32 | 0.13 |
| Polymyxin B | 1.2 | 0.04 | 32 | 0.13 |

Sensitization fold = MIC of antibiotics only/MIC of antibiotics with Membrane disruptor (MD)

In another aspect, such sensitizers convert many narrow-spectrum antibiotics to broad-spectrum ones (Table 5), significantly increasing the arsenal of available antibiotics for treating bacterial infection. For example, rifampicin, clarithromycin and novobiocin are normally not considered active against Gram-negative bacteria such as *E. coli*. However, 5 μg/ml Compound C sensitizes *E. coli* toward these antibiotics by 64- to 512-fold, bringing their MIC to 0.02 to 1.5 μg/ml, respectively.

TABLE 5

Compound C converts narrow-spectrum antibiotics to broad-spectrum

| Antibiotics (AB) (μg/ml) | MIC of AB only | MIC of AB with Compound C (5 μg/ml) | Sensitization fold | FIC |
|---|---|---|---|---|
| Rifampicin | 10 | 0.019 | 512 | 0.10 |
| Clarithromycin | 50 | 0.2 | 256 | 0.10 |
| Erythromycin | 50 | 0.4 | 128 | 0.11 |
| Novobiocin | 100 | 1.5 | 64 | 0.12 |

Bacterial strain: wild type *E. coli*

Example 8. The Potentialization of Drug-Resistant Strains Towards Existing Antibiotics In addition to its effect on wild-type bacteria, Compound C restores sensitivity of drug-resistant strains toward existing antibiotics and broadens the spectrum of usage for antibiotics against drug-resistant strains. Carbapenem-resistant strains pose a grave threat to public health and are listed as Priority 1 Pathogens by the WHO. New Delhi metallo-beta-lactamase 1 (NDM-1) is an enzyme that makes bacteria resistant to a broad range of beta-lactam antibiotics, including the antibiotics of the carbapenem family. A NDM-1 over-expressing *E. coli* strain was constructed following a literature-reported protocol. The constructed strains showed 50 to 100-fold increase of MIC towards several beta-lactam antibiotics such as ampicillin, ceftazidime and meropenem. Compound C sensitizes this NDM-1 over-expressing strain towards various antibiotics similarily to the way it sensitizes wild-type strain. The results are summarized in Table 6, which shows that Compound C sensitizes Carbapenem-resistant *E. coli* towards various antibiotics. Compound C sensitizes Carbapenem-resistant *E. coli* towards rifampicin in a concentration dependent manner (Table 7).

TABLE 6

Compound C sensitizes NDM-1 over-expressing *E. coli* towards various antibiotics

| Antibiotics (AB) (μg/ml) | MIC of AB only | MIC of AB with Compound C (5 μg/ml) | Sensitization fold | FIC |
|---|---|---|---|---|
| Rifampicin | 10 | 0.019 | 516 | 0.11 |
| Clarithromycin | 24 | 0.4 | 64 | 0.12 |
| Novobiocin | 50 | 1.6 | 32 | 0.13 |
| Clindamycin | 250 | 4 | 64 | 0.12 |
| Chloramphenicol | 6.25 | 0.8 | 8 | 0.22 |
| Trovafloxacin | 0.025 | 0.0008 | 32 | 0.13 |

Sensitization fold = MIC of antibiotics only/MIC of antibiotics with Membrane disruptor (MD)

Figure 18:
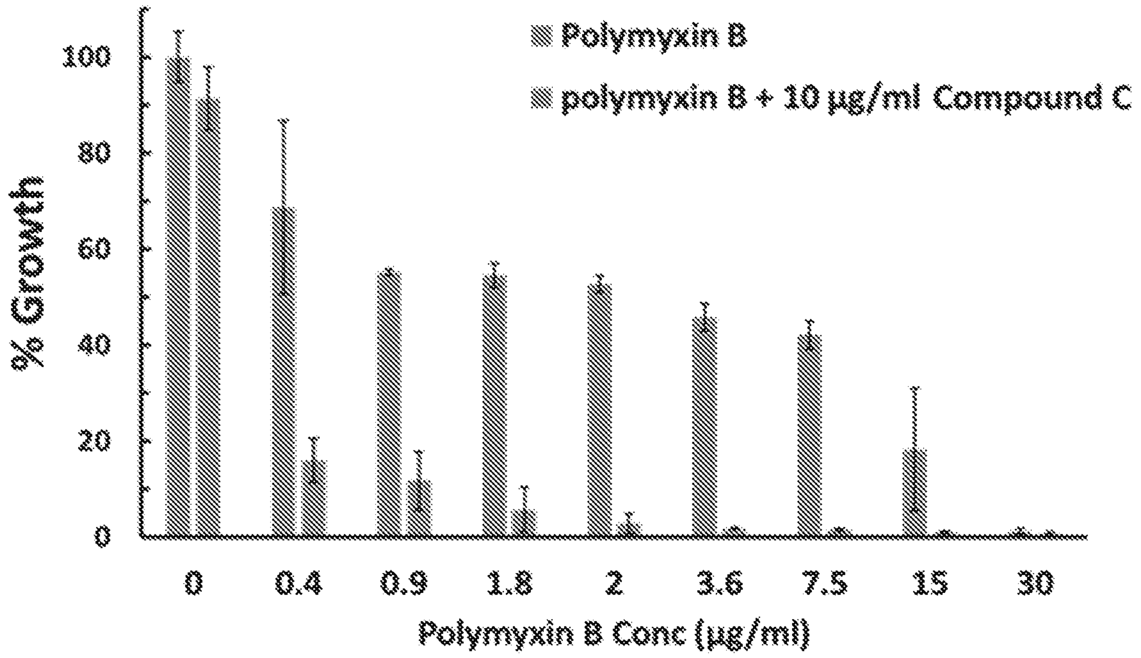
FIG. 18 is a bar graph showing that Compound C sensitizes MCR-1 overexpressing *E. coli* towards polymyxin B as described in Example 8. Bacteria were cultured with antibiotics at various concentrations in the presence or absence of Compound C (10 μg/ml) for 24 h at 37° C. and bacterial growth density was determined by measuring OD600. The y-axis is bacterial viability measured in percent. The x-axis is polymyxin B concentration measured in micrograms per milliliter.

Gram-negative strains that over-express MCR-1 gene show resistance towards colistin, a last resort antibiotic. Those strains modify Lipid A and reduce surface negative charge, which leads to decreased binding affinity towards colistin family antibiotics. We constructed a MCR-1 over-expressing *E. coli* strain following a literature reported protocol. The MIC of polymyxin B on this strain is 30 μg/ml, and the MIC of polymyxin B on wild type is 1.6 μg/ml. In the presence of 10 mcg/ml of Compound C, the MIC (based on $IC_{90}$) was lowered to 1.8 μg/ml (FIG. 18).

TABLE 7

MIC of rifampicin on NDM-1 over-expressing *E. coli* with different concentrations of Compound C

| Compound C Concentration (μg/ml) | Sensitization fold | MIC (μg/ml) |
|---|---|---|
| 2 | 2 | 5 |
| 4 | 64 | 0.16 |
| 6 | 1,024 | 0.01 |
| 8 | 4,048 | 0.0024 |
| 9 | 9,096 | 0.0012 |

Example 9. Bacterial Sensitizers are Among the Most Potent Known with Reduced Levels of Toxicity Pentamidine and PMBN achieved a 10-fold sensitization of *E. coli* toward erythromycin at a minimal concentration of 40 and 20 μg/ml, respectively, consistent with literature reported values. However, just 2.5 μg/ml of Compound C afforded a 10-fold sensitization. Pentamidine is reported to sensitize colistin-resistant Gram-negative bacteria toward novobiocin in a mouse infection model and the in vitro activity of Compound C is in the same range as colistin.

We also compared the activity of the various diamidines (Table 8). Compared with the initial lead, Compound M-1 (8 sensitization fold at 5 μg/ml), several compounds such as Compound E-18, Compound E-15 and Compound C showed increased activity, leading to 32, 256, 512 sensitization fold respectively. Compound C is thus far the most potent bacterial sensitizer in its class.

TABLE 8

Activity of various compounds of the present invention

| Compound | Sensitization fold |
|---|---|
| Compound M-1 | 8 |
| Compound A-1 | 8 |
| Compound A-8 | 16 |
| Compound E-18 | 32 |
| Compound E-15 | 256 |
| Compound C | 512 |

Example 10. Mechanism of Action for Compounds of the Present Invention

The antibiotic concentration inside *E. coli* with and without Compound M-1 was measured. The inactivated form of antibiotic was used because the active antibiotic would kill the bacteria or inhibit bacterial growth and this would lead to results that cannot be compared against other control experiments. O-Methyl novobiocin is an inactivated form of novobiocin that was used for this experiment.

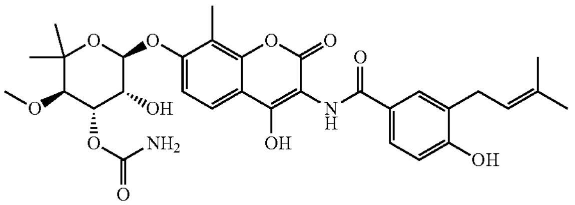

Novobiocin

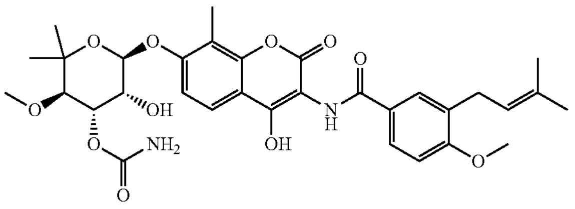

O-Methyl Novobiocin

Figure 19:
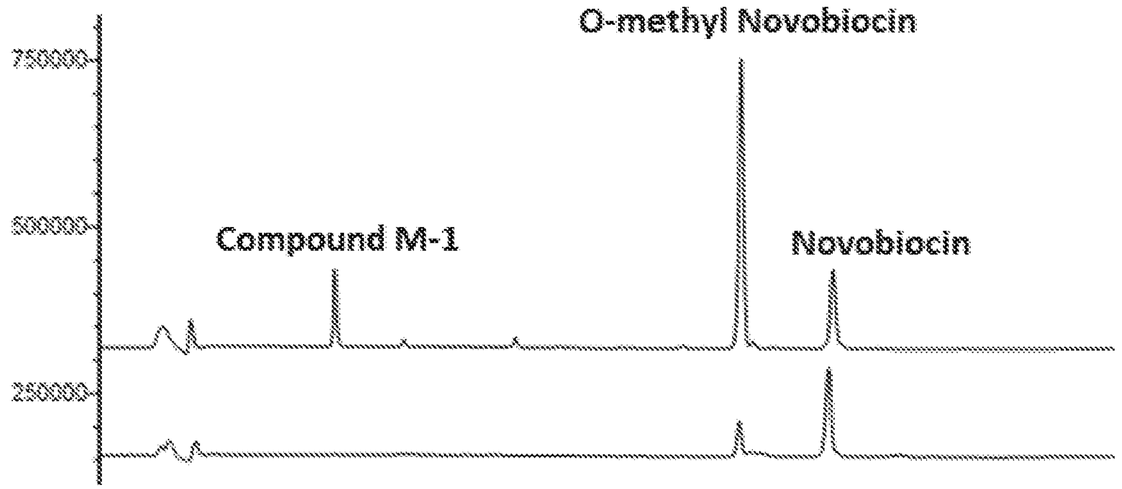
FIG. 19 is the HPLC analysis of O-methyl novobiocin in the *E. coli* lysis as described in Example 10. The upper line is O-methyl novobiocin in the *E. coli* lysis in the presence of 10 μg/ml Compound M-1 and the lower line is O-methyl novobiocin in the *E. coli* lysis without Compound M-1. Novobiocin was added as an internal standard.

*E. coli* was cultured with 50 μg/ml O-methyl novobiocin for 24 hours at 37° C. with continuous shaking in the absence and presence of 10 μg/ml Compound M-1. *E. coli* was then centrifuged and the supernatant was removed. To the precipitation that contained *E. coli*, PBS and novobiocin were added as internal standard and the resulting mixture was sonicated to lyse the cell. The mixture was diluted with acetonitrile (3×) and centrifuged. The supernatant, which contained O-methyl novobiocin, was analyzed by HPLC. The O-methyl novobiocin concentrations inside the bacteria increased 9.1-fold in *E. coli* in the presence of 10 μg/ml Compound M-1 (FIG. 19). Such results correlate well with the fact that 10 μg/ml Compound M-1 can sensitize *E. coli* towards novobiocin 8-fold.

Figure 20:
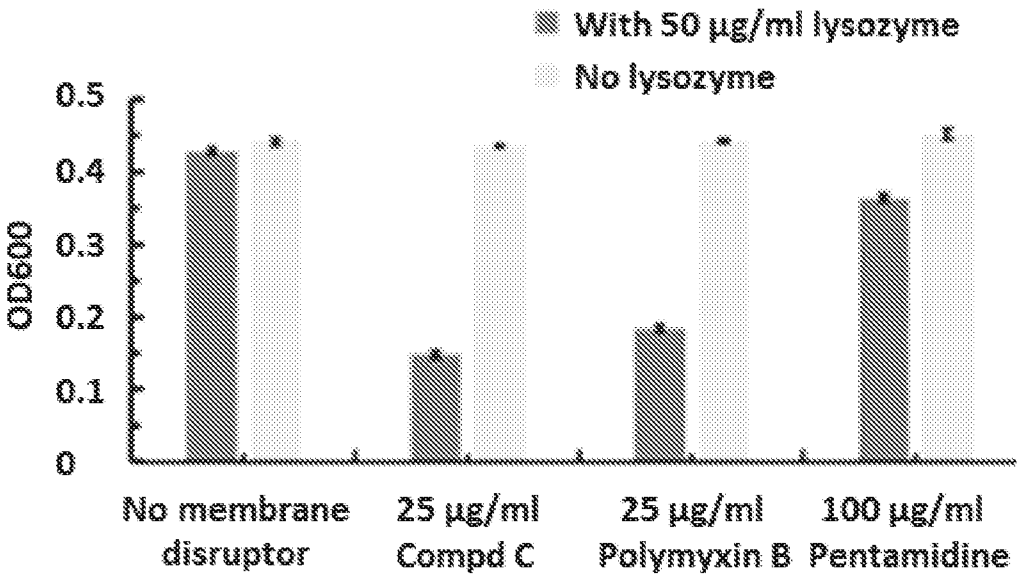
FIG. 20 is a graph of the *E. coli* outer membrane integrity measurement using the lysosomal lysis assay as described in Example 10. *E. coli* (OD600 measurement of about 0.5) was treated with Compound C with or without lysozyme for 10 minutes at room temperature. *E. coli* with impaired outer membrane caused by Compound C lead to decreased OD600 measurements. The x-axis is labeled with the compound and the y-axis is *E. coli* growth density determined by measuring OD600, Polymyxin B and pentamidine were used as positive controls.

The mechanism of action was also elucidated using a well-recognized lysosome assay that allows for assessment of membrane permeability. Specifically, lysozyme (about 14 KDa) breaks down bacterial cell wall and leads to bacterial lysis. However, lysozyme cannot penetrate intact Gram-negative bacterial outer membrane. With impaired Gram-negative bacterial membrane, lysozyme is able to diffuse across the disrupted membrane and enzymatically cleave peptidoglycan, which leads to bacterial lysis. Lysozyme (50

μg/ml) induced quick bacterial lysis in the presence of 25 μg/ml of Compound C (FIG. 20). In the absence of the sensitizer, no cell lysis was observed. No lysis was observed in the absence of lysosome as well. These results indicate that Compound C disrupts membrane integrity and is more potent than pentamidine (Polymyxin B and pentamidine were used as positive controls).

Figure 21:
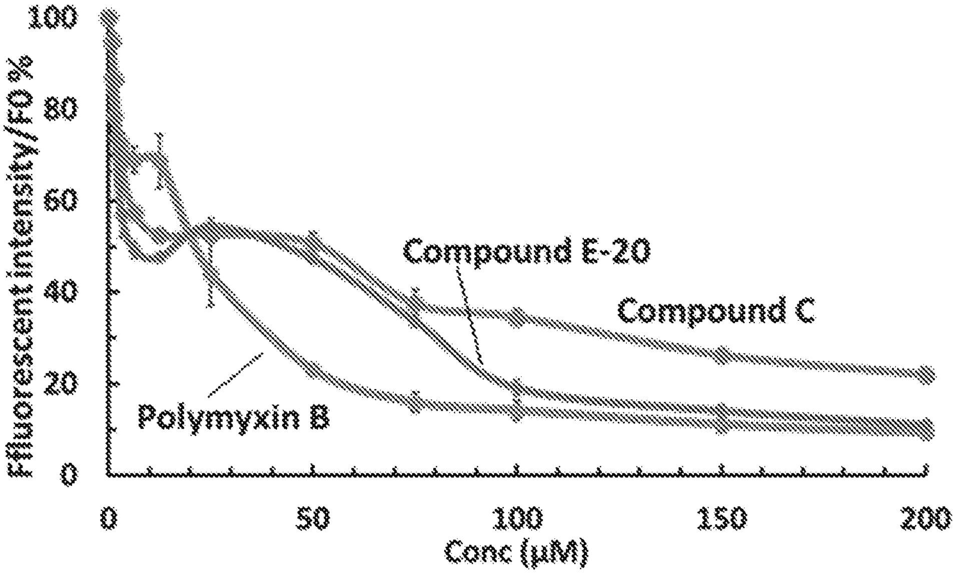
FIG. 21 is a graph describing the in vivo lipid A binding assay using Dansyl-PMBN as described in Example 11. Dansyl-PMBN (10 μM) was added to *E. coli* (OD600 measurement of about 0.5) and the fluorescent intensity at this time was recorded as F0. Sensitizers (Compound C, Compound E-20, and Polymyxin B) were added gradually and the fluorescent intensity was recorded 30 seconds later to determine the fluorescent intensity as a percent. The x-axis is concentration of the sensitizers measured in μM and the y-axis is the fluorescent intensity measured as a percent.

Example 11. Lipid A is the Molecular Target of Compounds of the Present Invention Lipid A is a key component of the outer membrane of Gram-negative bacteria and is responsible for maintaining its integrity of the outer membrane. The binding affinity of the compounds of the present invention to Lipid A was measured following literature procedures using a fluorescent conjugate of a polymyxin-B derivative (Dansyl-PMBN). Dansyl-PMBN binds to the lipid A part of LPS and leads to increased fluorescent intensity. In the presence of another component that can bind to lipid A, the Dansyl-PMBN will be replaced and show decreased fluorescent intensity. When 10 μM of Dansyl-PMBN was added to *E. coli* stock (OD600 measurement around 0.5), the fluorescent intensity increased 10-fold. With the gradual adding of Compound E-20 or Compound C (FIG. 21), the fluorescent intensity of Dansyl-PMBN continued to decrease, indicating that these compounds bind to lipid A.

Example 12. Bacteria Show Low Resistance Frequency towards Compounds of the Present Invention Resistance frequency is an important issue to consider when developing new antimicrobial agents. Using a standard resistance frequency analysis procedure, the resistance frequency was determined. Briefly, *E. coli* was challenged with different antibiotics such as novobiocin, trovafloxacin, polymyxin B, and chloramphenicol at a concentration that is 2 to 6-fold that of the MIC with or without 10 μg/ml Compound M-1 on agar plates for 48 hours. Colonies that survived the antibiotic and Compound M-1 combination were considered resistant mutant strains toward this combinational treatment. As a representative example, from $6*10^8$ CFU *E. coli,* 16 colonies were observed to be resistant to antibiotic-Compound M-1 combinations while >200 colonies were resistant to antibiotic only. Compound M-1 lowers the resistance frequency of bacteria toward antibiotics. The component in the combination responsible for the resistance was next determined. The 16 resistant colonies were challenged with another combination-rifampicin and Compound M-1. Compound M-1 was still able to sensitize these 16 colonies towards rifampicin, indicating the continuing susceptibility of these strains toward Compound M-1 sensitization and indicating that the resistance found in the combination is not toward Compound M-1 itself. *E. coli* showed low resistance frequency toward Compound M-1 and the resistance frequency of *E. coli* towards 10 μg/ml Compound M-1 was $<1/6*10^8$ CFU (the resistance in the example is not defined based on direct inhibition/bactericidal effect of Compound M-1 but based on the sensitization effect of Compound M-1).

Example 13. Compounds of the Present Invention Sensitize Gram-Positive Strains

Figure 22A:
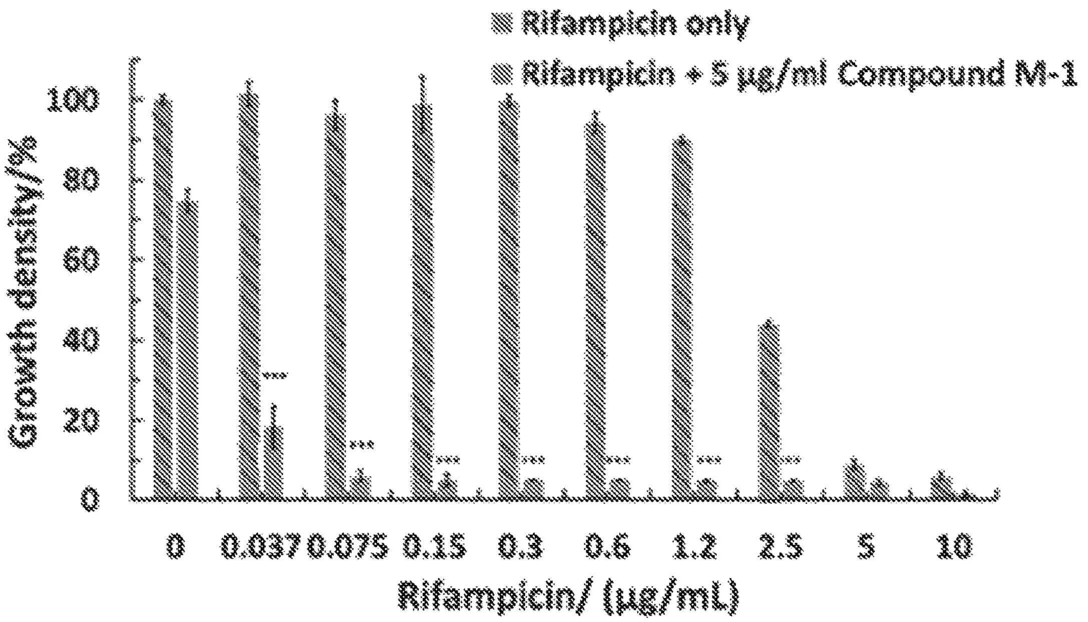
FIG. 22A is a bar graph showing that Compound M-1 sensitizes *B. subtilis* towards rifampicin as described in Example 13. Bacteria was cultured with rifampicin at various concentrations in the presence or absence of Compound M-1 for 24 hours at 37° C. and bacterial growth density was determined by measuring OD600. The y-axis is growth density measured in percent. The x-axis is rifampicin concentration measured in micrograms per milliliter (***: $p<0.01$).
Figure 22B:
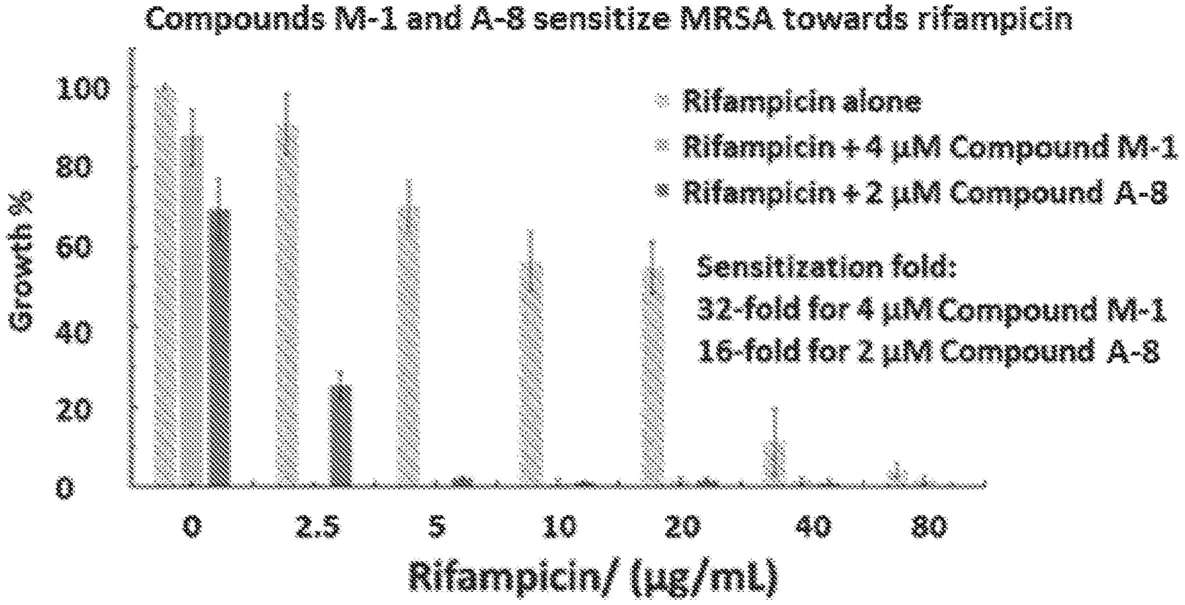
FIG. 22B is a bar graph showing that Compound M-1 and Compound A-8 sensitize MRSA towards rifampicin as described in Example 13. Bacteria was cultured with rifampicin at various concentrations in the presence or absence of Compound M-1 for 24 hours at 37° C. and bacterial growth density was determined by measuring $OD_{600}$. The y-axis is growth density measured in percent. The x-axis is rifampicin concentration measured in micrograms per milliliter (***: $p<0.01$).

Compound M-1 can sensitize Gram-positive bacteria such as *B. subtilis* towards traditional antibiotics. The MIC of Compound M-1 on wild type *B. subtilis* is 50 μg/ml. As shown in FIG. 22A and FIG. 22B, 5.5 μg/ml of Compound M-1 by itself does not affect the bacterial growth much (80% growth density compared with no-treatment group). The MIC of rifampicin on *B. subtilis* in the presence of 5.5 μg/ml of Compound M-1 is 0.037 μg/ml, a concentration at which rifampicin barely has any inhibition effect. The sensitization fold and FIC index is 256-fold and 0.11. The MIC of erythromycin in the presence of and absence of Compound M-1 is 1.5 and 50 μg/mL. The sensitization fold is 32-fold for Compound M-1 and the FIC index is 0.14. Compound M-1 (5.5 μg/ml) sensitizes *B. subtilis* towards a wide range of antibiotics with distinct anti-microbial mechanisms such as clindamycin (16-fold), clarithromycin (32-fold), novobiocin (4-fold), methicillin (4-fold), entrapenem (4-fold), trovafloxacin (8-fold).

Compound M-1 (2.7 μg/ml) sensitizes MRSA towards existing antibiotics such as rifampicin (32-fold) (FIG. 22B) and trovafloxacin (16-fold). Rifampicin is the first line of defense against MRSA and many MRSA stains grow resistance to rifampicin through overexpression of efflux pump and other mechanisms. Combined with Compound M-1, rifampicin can be used more effectively against MRSA.

Example 14. Compounds of the Present Invention Achieve Selectivity for Gram-Positive Bacteria Over Gram-Negative Bacteria Compound A-8 can also sensitize a wide range of bacteria strains to achieve broad-spectrum activity. The structure difference between lipid A from Gram-negative bacteria and wall teichoic acid from Gram-positive bacteria means that Gram-negative and -positive bacteria can be targeted separately. This is important because severe damage to the human body can result from an imbalance of gut microbiota caused by improper antibiotics usage. Substitution on the amidine group such as butyl (Compound E-13) or t-butyl (Compound C-3) or the restraint of the amidine group in a five (Compound A-2) or six-member (Compound B-21) ring can change the amidine to an amine and greatly decrease, or even abolish, the ability to sensitize Gram-negative bacteria while preserving the ability to sensitize some Gram-positive bacteria. Certain compounds can selectively work on Gram-positive bacteria over Gram-negative bacteria and even selectively work on certain Gram-positive bacteria. Compound E-11 sensitizes *B. subtilis* towards erythromycin 32-fold, but has no effect on MRSA at 5 μg/ml. Compound E-13 and Compound B-21 at 10 μg/ml can sensitize MRSA 16-fold towards rifampicin, but have no effect on *B. subtilis.*

Compound A-8 and Compound M-1, broad-spectrum sensitizers, can also achieve some selectivity because the concentration required to achieve the same sensitization fold varies from strain to strain. For example, the concentration of Compound A-8 required to sensitive wild type *E. coli, B. subtilis* and MRSA towards rifampicin 32-fold is 7 μg/ml, 3 μg/ml and 1.5 μg/ml. When using a relatively low dosage like 1.5 μg/ml, Compound A-8 will prefer to sensitize MRSA over *E. coli* and *B. subtilis.*

Figure 23A:
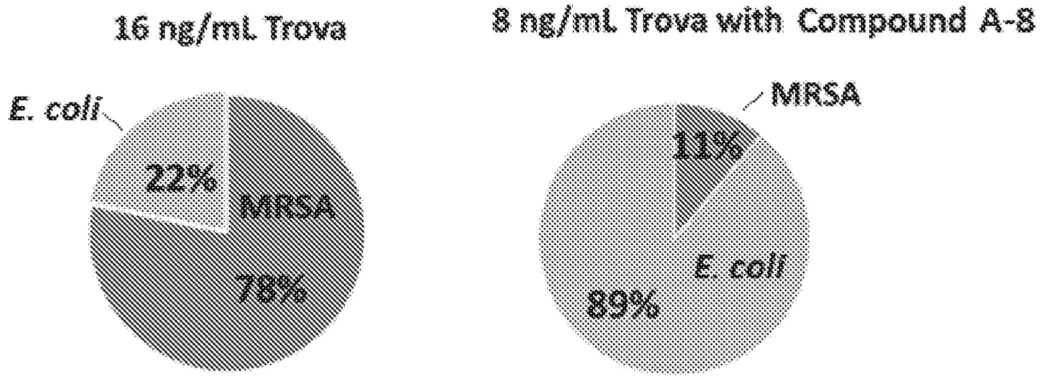
FIG. 23A is a comparison of the relative ratio of *E. coli* and MRSA treated with the antibiotic trovafloxacin in the absence (pie chart on the left) and in the presence (pie chart on the right) of Compound A-8 as described in Example 14. In the absence of Compound A-8, trovafloxacin preferred to inhibit *E. coli* and the bacterial population was 78% MRSA. However, Compound A-8 sensitizes trovafloxacin to MRSA. In presence of Compound A-8, trovafloxacin preferred the inhibition of MRSA and the MRSA population was only 11%.
Figure 23B:
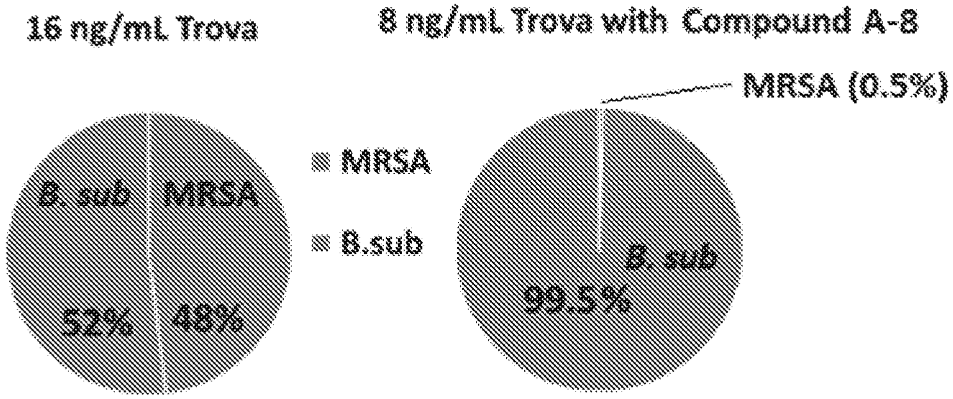
FIG. 23B is a comparison of the relative ratio of *B. sub* and MRSA treated with the antibiotic trovafloxacin in the absence (pie chart on the left) and in the presence (pie chart on the right) of Compound A-8 as described in Example 14. In the absence of Compound A-8, trovafloxacin approximately equally inhibited *B. sub* and MRSA. However, Compound A-8 sensitizes trovafloxacin to MRSA. In presence of Compound A-8, trovafloxacin preferred the inhibition of MRSA and the MRSA population was only 0.5%.

The MIC of many antibiotics such as erythromycin, rifampicin and trovafloxacin on MRSA is significantly higher than wild type *E. coli*, meaning that even narrow-spectrum antibiotic such as rifampicin, a first-line of defense of MRSA, can cause severe collateral damage to benign Gram-negative bacteria like *E. coli* before it can kill MRSA. As a proof of concept, the relative ratio of *E. coli* and MRSA (FIG. 23A) or *B. subtilis* and MRSA (FIG. 23 B) was measured with and without Compound A-8. As shown in FIG. 23A, trovafloxacin (16 ng/ml) alone only inhibits *E. coli*, leaving MRSA as the dominant species (78% of the bacteria population). However, when trovafloxacin (8 ng/ml) is supplied with 1.5 μg/ml of Compound A-8, MRSA inhibition was achieved and *E. coli* was the dominant species (89% of the bacteria population). As shown in FIG. 23B, the relative survival ratio between *B. subtilis* and MRSA is 1:1 when treated with 16 ng/ml trovafloxacin, but the dominant composition (99.5%) is *B. subtilis* when the bacteria population is treated with 8 ng/ml trovafloxacin and 1.5 μg/ml of Compound A-8.

All publications and patent applications cited in this specification are herein incorporated by reference as if each individual publication or patent application were specifically and individually indicated to be incorporated by reference.

Example 15. Antibacterial Activity Against MRSA

MRSA bacteria were cultured in nutrient broth at 37° C. overnight prior to treatment. Bacteria were then incubated with various concentrations of erythromycin with or without the compounds shown below for 20 hours. Bacterial density was measured based on $OD_{600}$. Magnitude of the sensitization (sensitization fold) was calculated based on the $IC_{90}$ of erythromycin using the following formula:

Sensitization fold(SF)=$IC_{90}$ of erythromycin without compounds/$IC_{90}$ of erythromycin with compounds The results of the erythromycin sensitization studies for MRSA are provided in Table 4.

To determine the MIC for each compound against MRSA, MRSA bacteria were cultured in nutrient broth at 37° C. overnight prior to treatment. Bacteria were then cultured with varying concentration of the compounds shown below for 48 hours, and then bacterial density was measured based on OD600. The minimum inhibitory concentration (MIC, 90% growth inhibition) was calculated for each compound, as shown in Table 4 (NA=no activity; --=not measured).

TABLE 4

Sentization fold and MIC of Select Compounds Against MRSA

| Compound | SF (MRSA) | MIC (MRSA) |
|---|---|---|
| 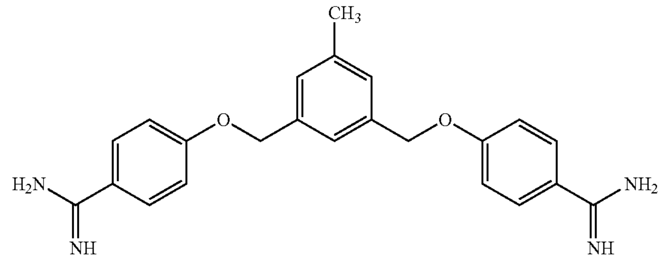 Compound M-1 | 32-fold at 6 μM | 25 μM reach MIC |
| 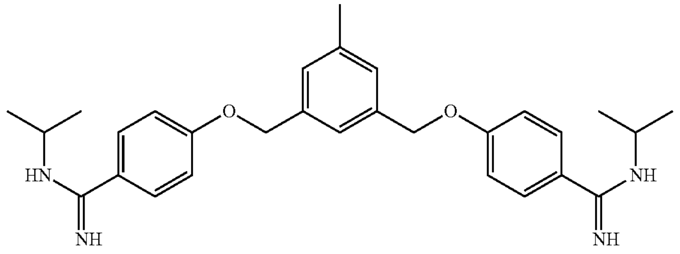 C-3 | 32-fold at 4 μM | 25 μM reach MIC |
| 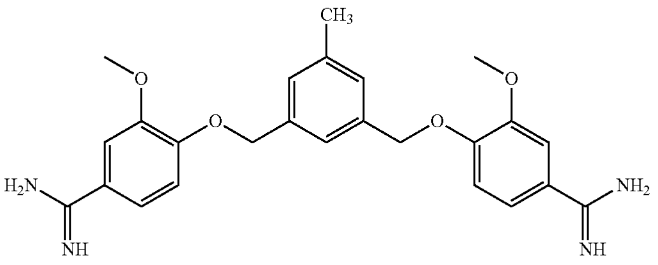 A-6 | 8-16-fold at 12 μM; 2-4 fold at 6 μM | 12 μM inhibit 10%; 25 μM reach MIC |

TABLE 4-continued
| Sentization fold and MIC of Select Compounds Against MRSA | | |
|---|---|---|
| Compound | SF (MRSA) | MIC (MRSA) |
| 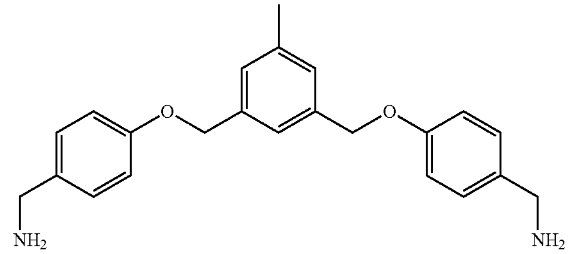 E-11 | NA at 12 and 25 μM | NA at 12 and 25 μM |
| 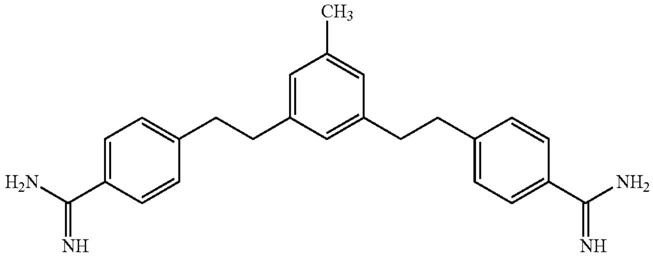 Compound A-8 | 16-fold at 3 μM | 12 μM reach MIC |
| 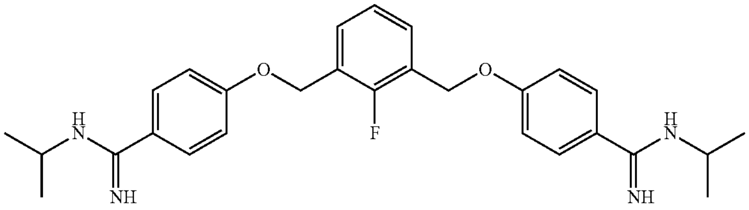 D-2 | 16-fold at 4 μM | 12.5 μM reach MIC |
| 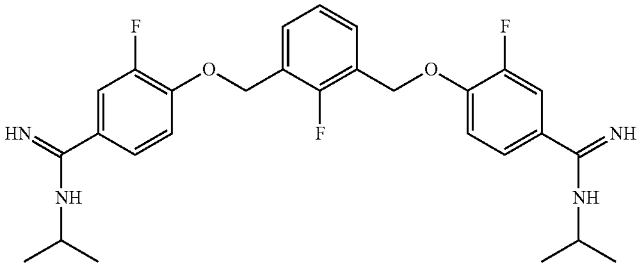 B-9 | 8-16-fold at 12 μM; 8-fold at 6 μM | 12 μM inhibit 30%; NA at 6 μM |
| 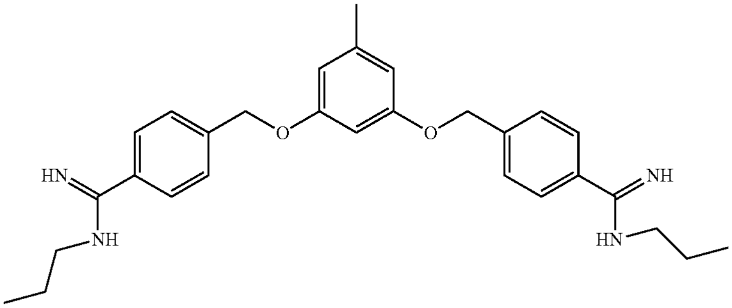 E-13 | 8-16-fold at 25 μM; 8-fold at 12 μM | 25 μM inhibit 30% |

TABLE 4-continued
| Compound | SF (MRSA) | MIC (MRSA) |
|---|---|---|
| 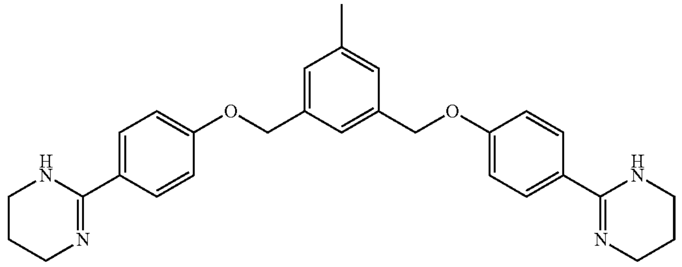 B-21 | 8-fold at 25 μM; 4-fold at 12 μM | NA at 25 μM |
| 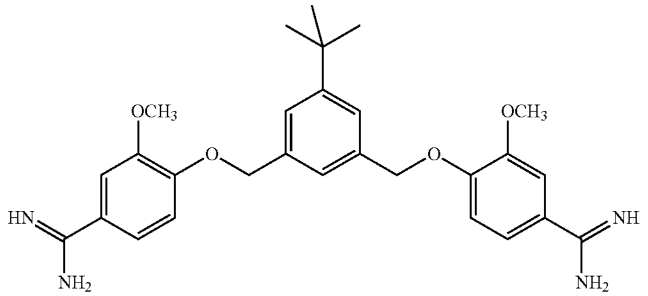 E-14 | — | 12 μM reach MIC |
| 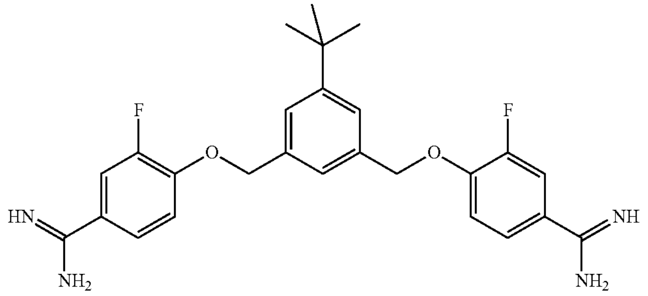 E-15 | — | 6 μM inhibit 60% |
| 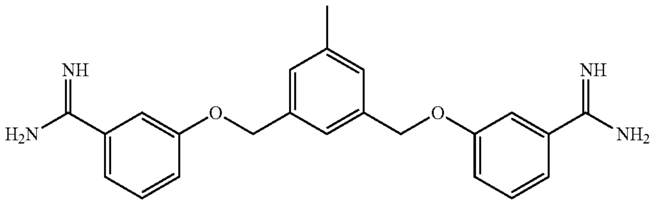 E-16 | 4-fold at 12.5 μM | 12.5 μM inhibit 30%; 25 μM reach MIC |
| 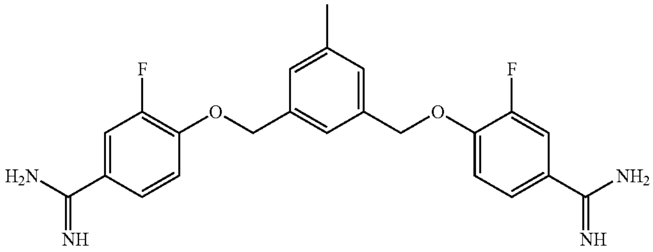 E-18 | — | 6 μM inhibit 20%; 12 μM reach MIC |
Sentization fold and MIC of Select Compounds Against MRSA Example 16. Cytotoxicity of Select Compounds of the Present Invention H9c2 (ATCC®R-1446™) cells Were used in the studies. The H9c2 cells were maintained in DMEM (Dulbeccoa's Modified Eagle's Medium) supplemented with 10% fetal bovine serum (Mid Sci; S01520HI) and 1% penicillin-streptomycin (Sigma-Aldrich; P4333) at 37° C. with 5% $CO_2$. The H9c2 cells were seeded in 96-well plate one day before the experiment. Different concentrations of di-amidine compounds were added into the H9c2 cells. The cells were then incubated with the compounds for 24 h at 37° C. with 5% $CO_2$. The cell viability was tested by the CCK-8. Specifically, after 24 h incubation, 10 μL CCK-8 was added to each well. After 3 h incubation at 37° C., the absorbance at 450 nm was recorded by a plate reader. The cytotoxicity in HEK293 and 3T3 cells was measured using the same procedure. Data is shown in Table 5 (NT=not toxic; --=not tested).

TABLE 5

Cytotoxicity against H9c2, HEK293, and 3T3 Cells

| Compound | H9c2 $CC^{50}$ | HEK293 $CC^{50}$ | 3T3 $CC^{50}$ |
|---|---|---|---|
| 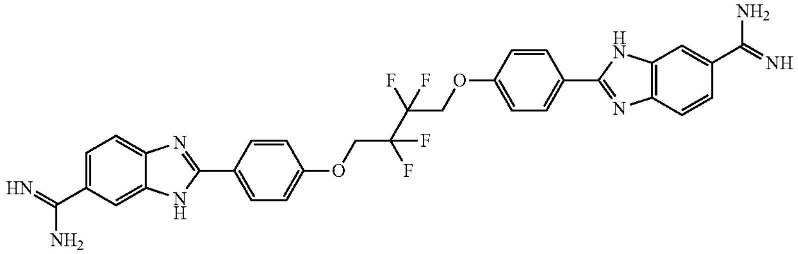 C-5 | 50 μM | — | — |
| 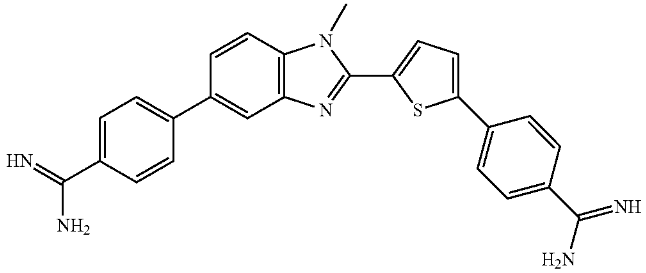 E-1 | 50 μM | — | — |
| 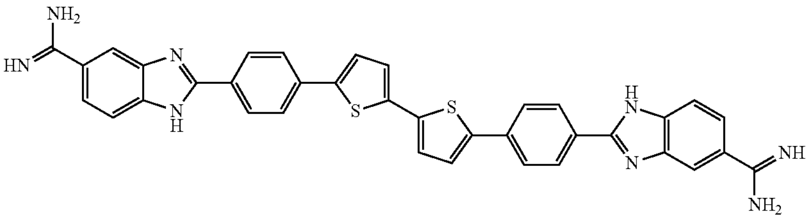 C-6 | 50 μM | — | — |
| 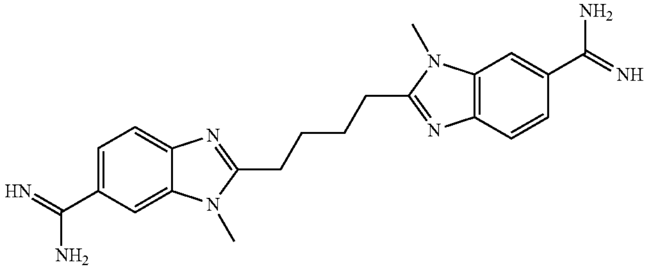 C-7 | 50 μM | — | — |

TABLE 5-continued
| Cytotoxicity against H9c2, HEK293, and 3T3 Cells | | | |
|---|---|---|---|
| Compound | H9c2 CC50 | HEK293 CC50 | 3T3 CC50 |
| 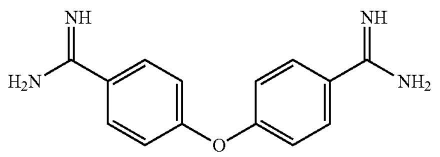 C-8 | 50 μM | — | — |
| 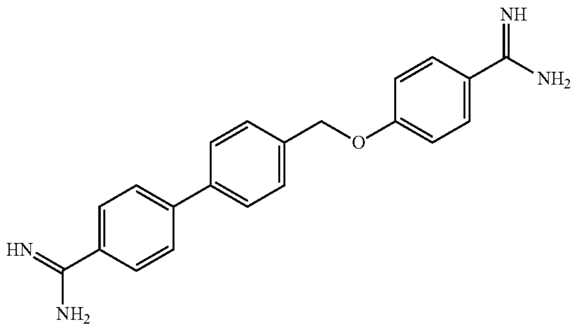 E-2 | 50 μM | — | — |
| 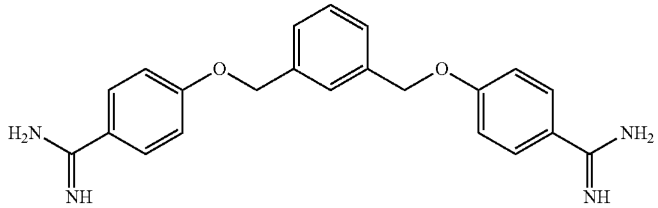 E-3 | 50 μM | — | — |
| 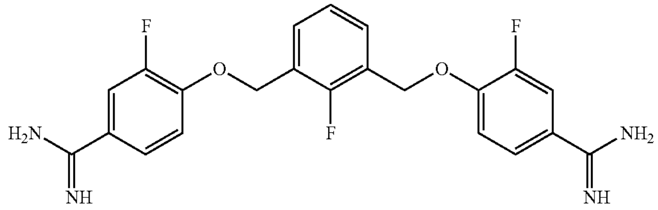 A-1 | 50 μM | 100 μM | 100 μM result in 30% |
| 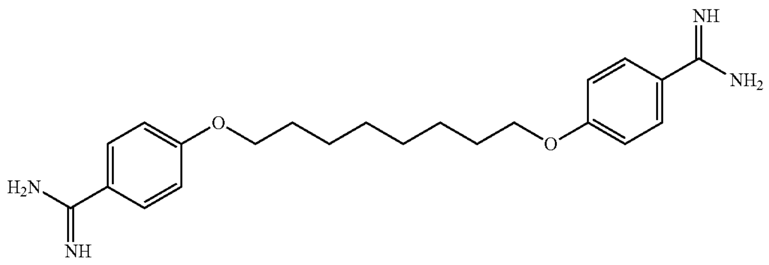 E-4 | <5 μM | — | — |

TABLE 5-continued
Cytotoxicity against H9c2, HEK293, and 3T3 Cells
| Compound | H9c2 $CC^{50}$ | HEK293 $CC^{50}$ | 3T3 $CC^{50}$ |
|---|---|---|---|
| 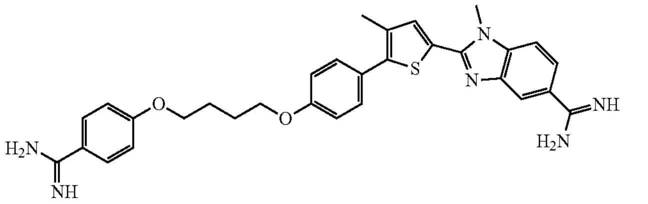 C-9 | 50 μM | — | — |
| 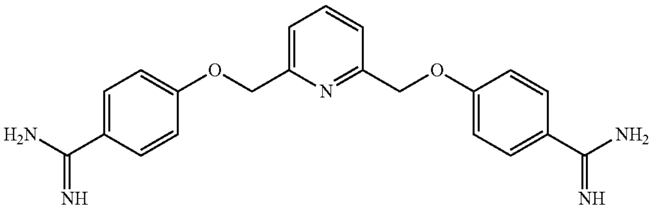 E-5 | 50 μM | — | — |
| 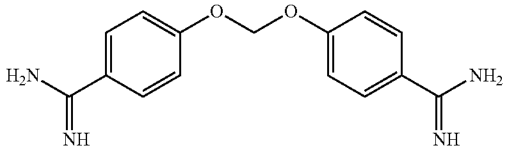 E-6 | 50 μM | — | — |
| 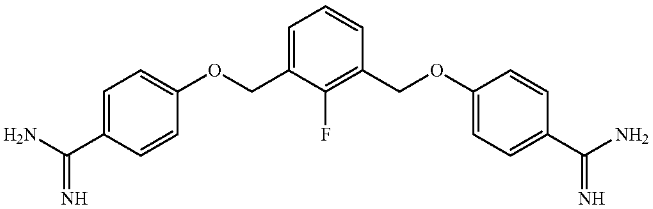 C-2 | 50 μM | — | — |
| 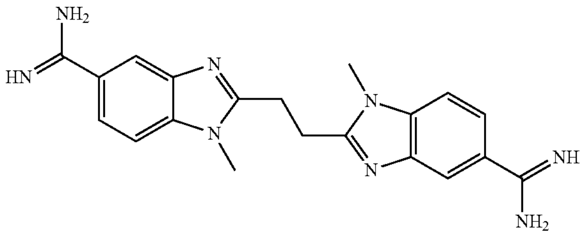 C-10 | 50 μM | — | — |
| 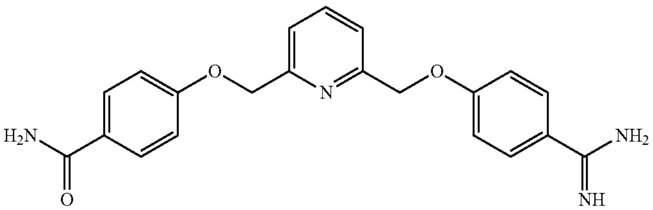 C-1 | 50 μM | — | — |

TABLE 5-continued
| Cytotoxicity against H9c2, HEK293, and 3T3 Cells | | | |
|---|---|---|---|
| Compound | H9c2 $CC^{50}$ | HEK293 $CC^{50}$ | 3T3 $CC^{50}$ |
| 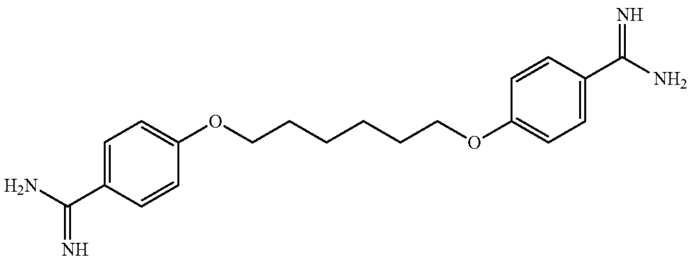 E-7 | <5 μM | — | — |
| 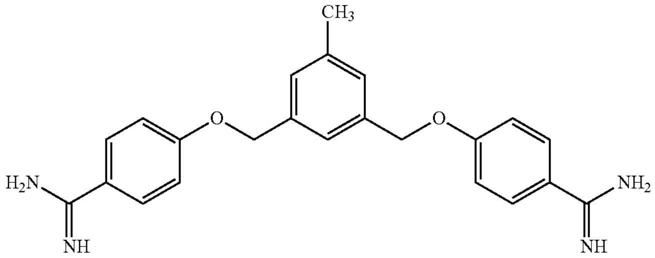 Compound M-1 | 50 μM | 100 μM result in 20% | 100 μM result in 20% |
| 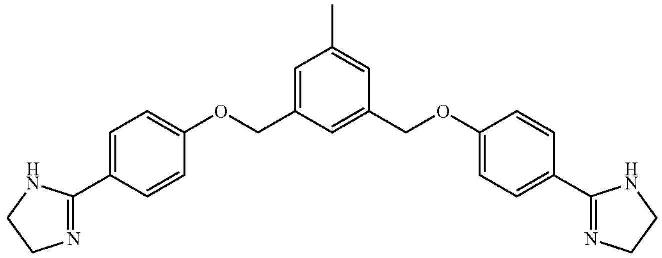 A-2 | 25 μM | 12 μM < $CC_{50}$ < 25 μM | 25 μM |
| 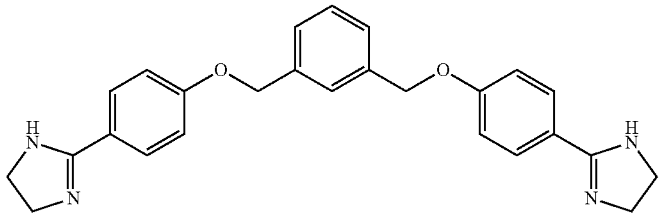 E-9 | <12 μM | — | — |
| 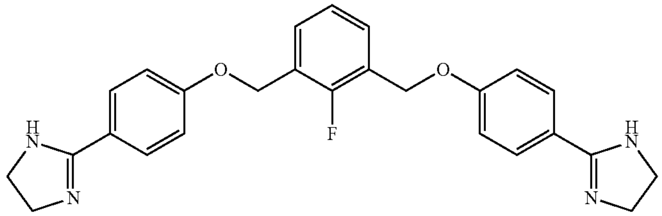 A-3 | 25 μM | — | — |

TABLE 5-continued
Cytotoxicity against H9c2, HEK293, and 3T3 Cells
| Compound | H9c2 $CC^{50}$ | HEK293 $CC^{50}$ | 3T3 $CC^{50}$ |
|---|---|---|---|
| 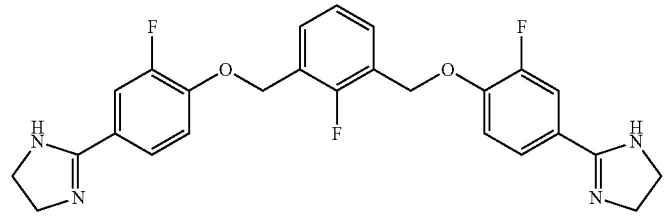 A-4 | 50 μM | — | — |
| 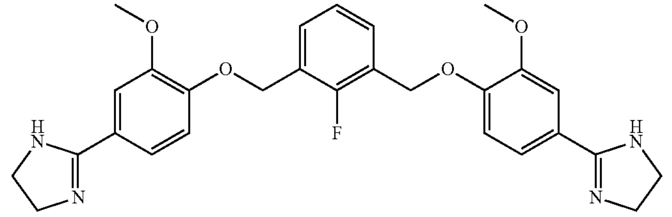 A-5 | 50 μM | — | — |
| 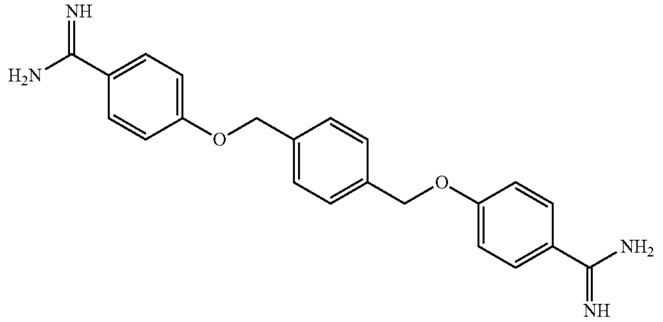 E-10 | 50 μM | 100 μM result in 30% | 100 result in 10% |
| 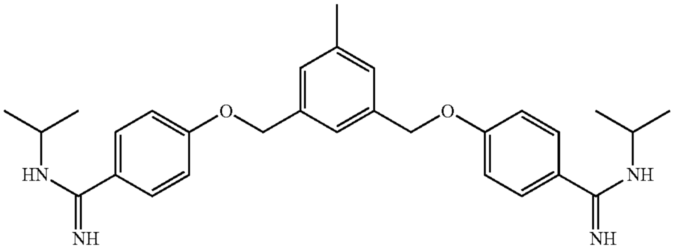 C-3 | NT at 100 μM | NT at 100 μM | NT at 100 μM |
| 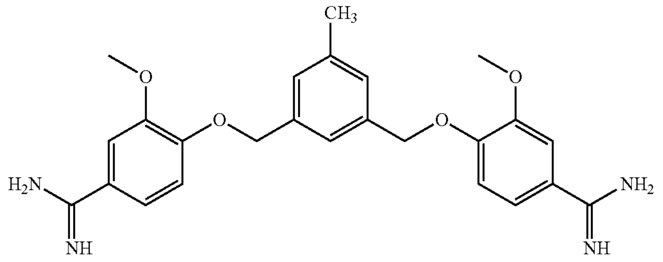 A-6 | NT at 100 μM | 100 μM result in 10% | NT at 100 μM |

TABLE 5-continued
| Cytotoxicity against H9c2, HEK293, and 3T3 Cells | | | |
|---|---|---|---|
| Compound | H9c2 CC50 | HEK293 CC50 | 3T3 CC50 |
| 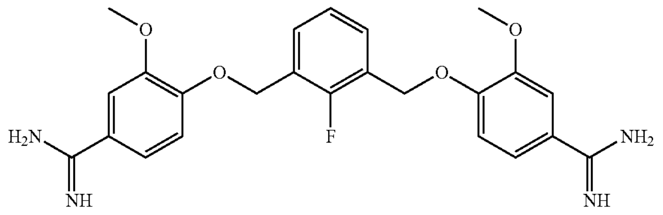 A-7 | 12.5 µM | — | — |
| 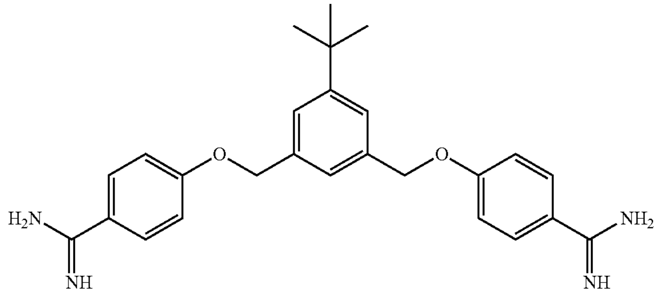 C-4 | 25 µM | — | — |
| 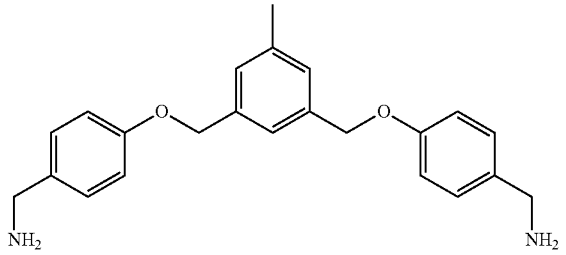 E-11 | — | 25 µM | 25 µM |
| 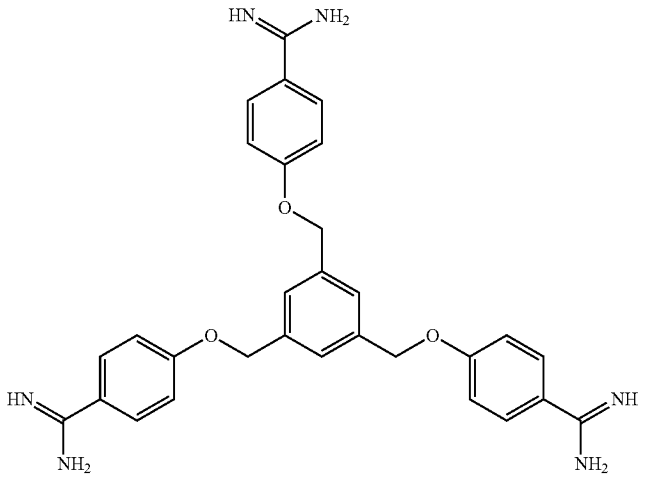 E-12 | — | 100 µM result in 10% | NT at 100 µM |

TABLE 5-continued
| Cytotoxicity against H9c2, HEK293, and 3T3 Cells | | | |
|---|---|---|---|
| Compound | H9c2 $CC^{50}$ | HEK293 $CC^{50}$ | 3T3 $CC^{50}$ |
| 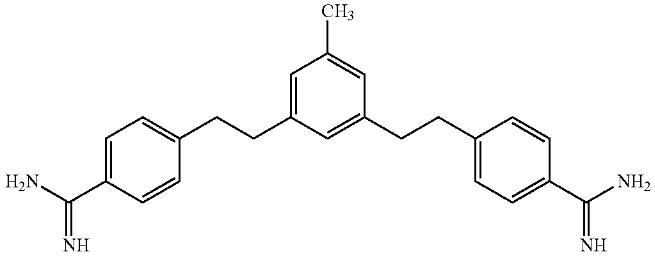 A-8 | 12.5 μM < $CC_{50}$ < 25 μM | 50 μM | 50 μM |
| 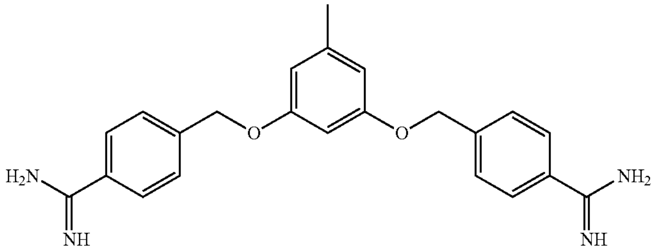 B-114 | — | NT at 100 μM | 100 UM result in 10% |
| 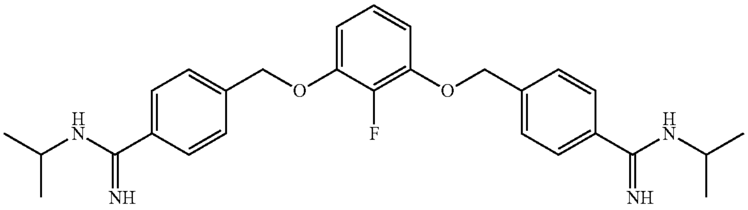 D-2 | — | NT at 100 μM | NT at 100 μM |
| 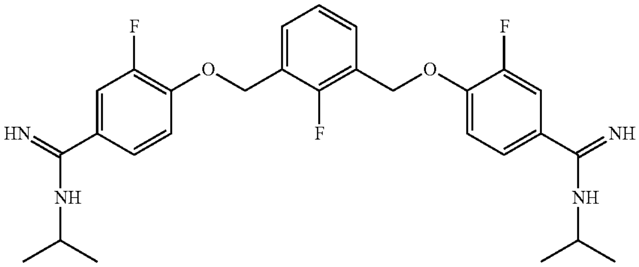 B-9 | — | NT at 100 μM | NT at 100 μM |
| 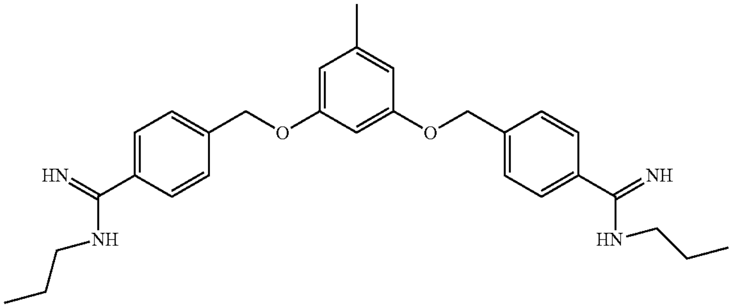 E-13 | — | NT at 100 μM | NT at 100 μM |

TABLE 5-continued
| Cytotoxicity against H9c2, HEK293, and 3T3 Cells | | | |
|---|---|---|---|
| Compound | H9c2 $CC^{50}$ | HEK293 $CC^{50}$ | 3T3 $CC^{50}$ |
| 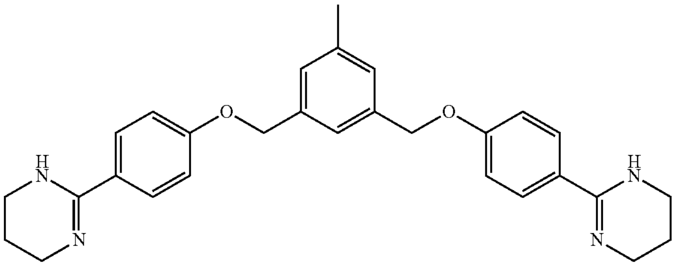 B-21 | — | NT at 100 μM | NT at 100 μM |
| 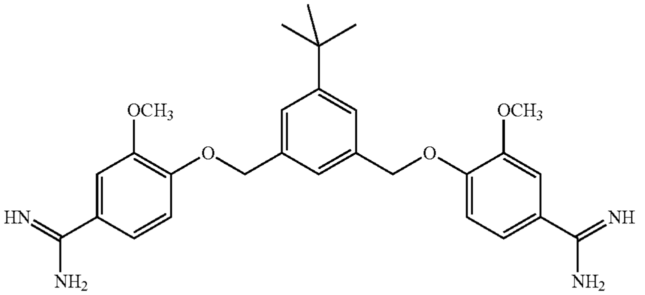 E-14 | — | 100 μM result in 20% | 50 μM < $CC_{50}$ < 100 μM |
| 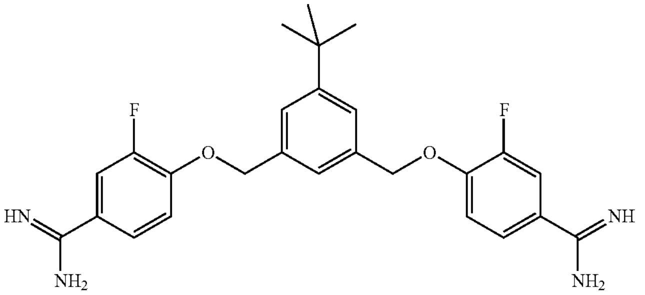 E-15 | 25 μM | 25 μM < $CC_{50}$ < 50 μM | 25 μM < $CC_{50}$ < 50 μM |
| 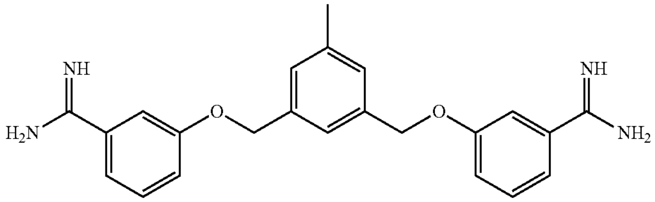 E-16 | — | 100 μM result in 20% | NT at 100 μM |
| 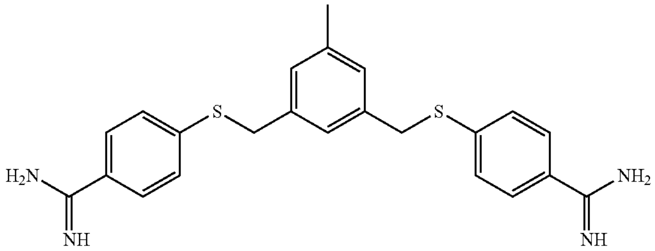 D-4 | — | 25 μM < $CC_{50}$ < 50 μM | 25 μM < CC50 < 50 μM |

TABLE 5-continued
Cytotoxicity against H9c2, HEK293, and 3T3 Cells
| Compound | H9c2 CC50 | HEK293 CC50 | 3T3 CC50 |
|---|---|---|---|
| 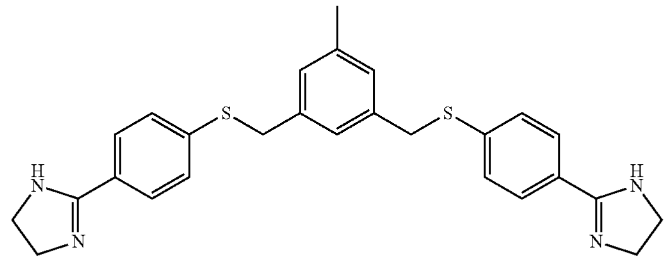 B-12 | — | 12.5 μM < $CC_{50}$ < 25 μM | 6 μM < $CC_{50}$ < 12.5 μM |
| 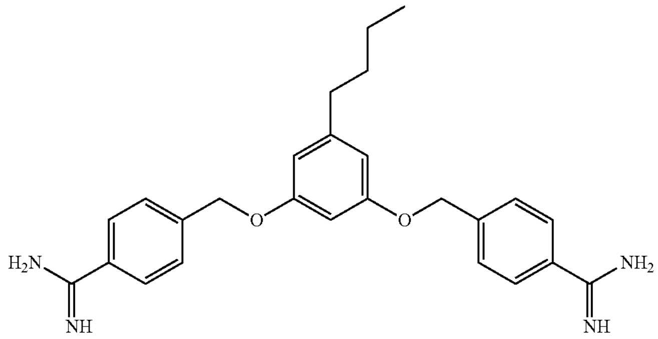 E-20 | 25 μM | — | — |
| 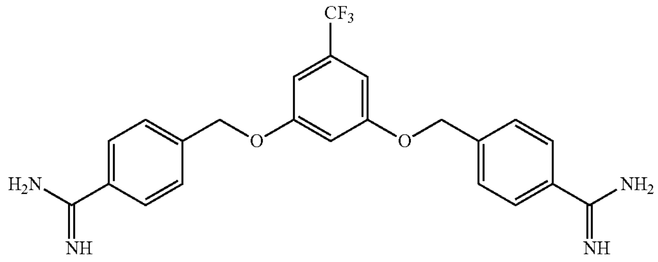 Compound C | 50 μM | — | — |
| 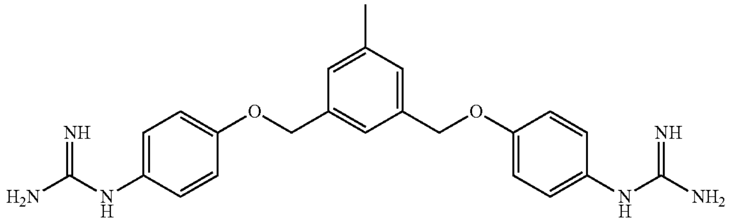 E-22 | 100 μM | — | — |

Although the foregoing invention has been described in some detail by way of illustration and example for the purposes of clarity of understanding, it will be readily apparent to one of ordinary skill in the art in light of the teaching of this invention that certain changes and modifications may be made thereto without departing from the spirit and scope of the invention as defined in the appended.

What is claimed is:

1. A compound of Formula V:

(V)

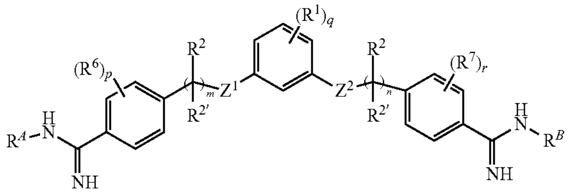

or a pharmaceutically acceptable salt thereof;

wherein:

$R^1$ is independently selected at each occurrence from halogen, hydroxyl, $C_1$-$C_6$alkoxy, $C_1$-$C_6$haloalkoxy, $C_2$-$C_6$alkanoyl, cyano, azido, nitro, —COOH, —$CONH_2$, —$P(O)(OH)_2$, —$N(R^5)(R^{5'})$, —$S(O)R^5$, —$SO_2R^5$, —$SO_3R^5$, —$SO_2N(R^5)(R^{5'})$, —$OSO_2R^5$, —$N(R^{5'})SO_2R^5$, $C_1$-$C_6$alkyl, $C_3$-$C_6$cycloalkyl, $C_2$-$C_6$alkenyl, $C_2$-$C_6$alkynyl, $C_1$-$C_6$haloalkyl, $C_1$-$C_6$aliphatic, thiol, $C_1$-$C_6$alkylthiol, and ($C_1$-$C_6$haloalkyl)thiol;

$Z^1$ and $Z^2$ are independently selected from O, S, $N(R^5)$, and C═O;

$R^2$ and $R^{2'}$ are independently selected at each occurrence from hydrogen, $C_1$-$C_6$alkyl, $C_3$-$C_6$cycloalkyl, $C_1$-$C_6$haloalkyl, and $C_1$-$C_6$aliphatic;

$R^5$ and $R^{5'}$ are independently selected at each occurrence from hydrogen, $C_1$-$C_6$alkyl, $C_3$-$C_6$cycloalkyl, $C_1$-$C_6$haloalkyl, and $C_1$-$C_6$aliphatic;

$R^A$ and $R^B$ are independently selected from hydrogen and $C_1$-$C_6$alkyl;

$R^6$ and $R^7$ is independently selected at each occurrence from hydrogen, halogen, hydroxyl, $C_1$-$C_6$alkoxy, $C_1$-$C_6$haloalkoxy, $C_1$-$C_6$alkanoyl, cyano, azido, nitro, —COOH, —$CONH_2$, —$P(O)(OH)_2$, —$N(R^5)(R^{5'})$, —$S(O)R^5$, —$SO_2R^5$, —$SO_3R^5$, —$SO_2N(R^5)(R^{5'})$, —$OSO_2R^5$, —$N(R^{5'})SO_2R^5$, $C_1$-$C_6$alkyl, $C_3$-$C_6$cycloalkyl, $C_2$-$C_6$alkenyl, $C_2$-$C_6$alkynyl, $C_1$-$C_6$haloalkyl, $C_1$-$C_6$aliphatic, thiol, $C_1$-$C_6$alkylthiol, and ($C_1$-$C_6$haloalkyl)thiol;

m and n are independently selected from 1, 2, 3, and 4;

p and r are independently selected from 1, 2, 3, and 4; and q is 0, 1, 2, 3, or 4;

wherein if q is 0, then at least one of $R^6$ and $R^7$ is not hydrogen.

2. The compound of claim 1, of the formula:

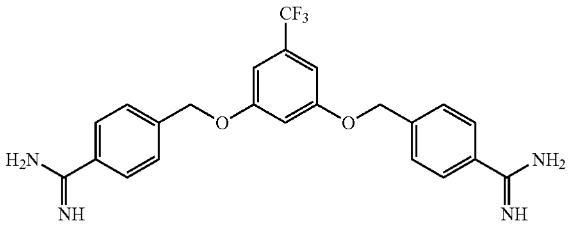 [SMILES: N=C(N)c1ccc(COc2cc(OCc3ccc(C(=N)N)cc3)cc(C(F)(F)F)c2)cc1]

or a pharmaceutically acceptable salt thereof.

3. The compound of claim 1, of the formula

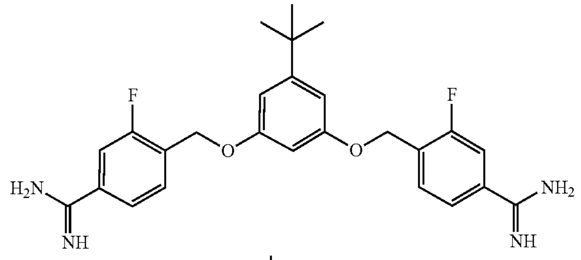

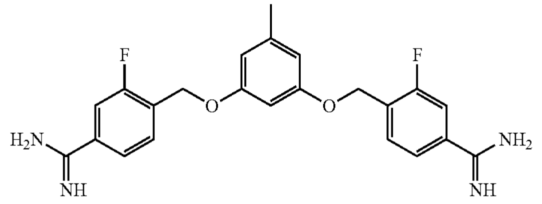

or

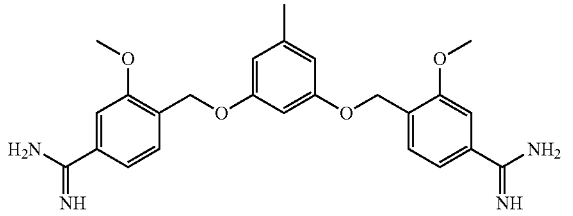

or a pharmaceutically acceptable salt thereof.

4. A pharmaceutical composition comprising a compound of claim 1 in a pharmaceutically acceptable carrier.

5. A method of treating a bacterial infection in a host in need thereof, comprising administering to the host an effective amount of a compound of claim 1 optionally in a pharmaceutically acceptable carrier and optionally in combination with an effective amount of an antibiotic.

6. A method of potentiating the therapeutic effect of an antibiotic during the treatment of a bacterial infection in a host in need thereof, comprising administering to the host an effective amount of a compound of claim 1 optionally in a pharmaceutically acceptable carrier in combination with the antibiotic.

7. The method of claim 5, wherein the bacterial infection is caused by a gram-positive bacterium, a gram-negative bacterium, or a mycobacterium.

8. The method of claim 7, wherein the gram-positive bacterium, the gram-negative bacterium, or the mycobacterium is antibiotic-resistant.

9. The compound of claim 1, wherein the compound is:
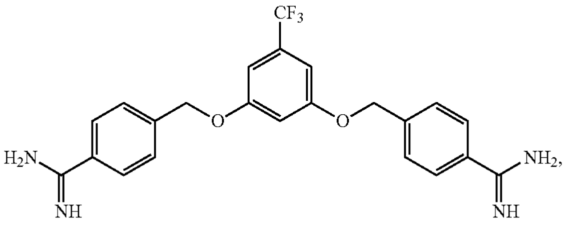 [SMILES: N=C(N)c1ccc(COc2cc(OCc3ccc(C(=N)N)cc3)cc(C(F)(F)F)c2)cc1]
or a pharmaceutically acceptable salt thereof.
10. The compound of claim 1, wherein the compound is selected from:
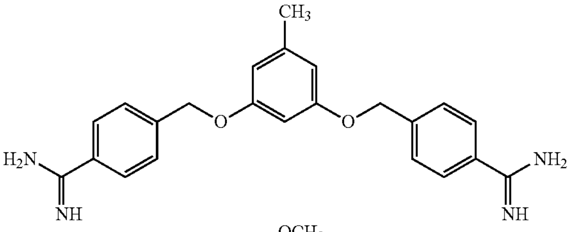
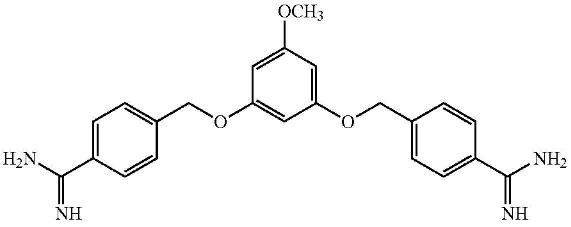
-continued
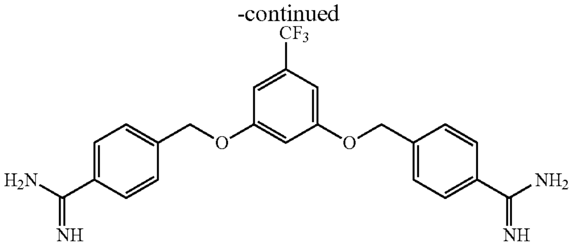
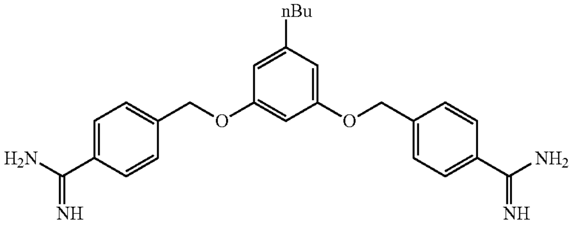
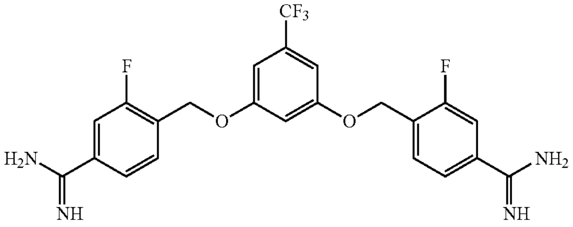
or a pharmaceutically acceptable salt thereof.
* * * * *